(12) United States Patent
Michon et al.

(10) Patent No.: US 10,964,415 B2
(45) Date of Patent: *Mar. 30, 2021

(54) AUTOMATED SYSTEMS AND METHODS FOR OBTAINING, STORING, PROCESSING AND UTILIZING IMMUNOLOGIC INFORMATION OF AN INDIVIDUAL OR POPULATION FOR VARIOUS USES

(71) Applicant: Wellstat Vaccines, LLC, Rockville, MD (US)

(72) Inventors: Francis Michon, Bethesda, MD (US); Samuel L. Moore, Sykesville, MD (US); Samuel J. Wohlstadter, Madison, VA (US); Charles Quentin Davis, Frederick, MD (US); Glen Otero, Del Mar, CA (US); Aaron S. Haleva, Oakhurst, NJ (US)

(73) Assignee: Wellstat Vaccines, LLC, Rockville, MD (US)

( * ) Notice: Subject to any disclaimer, the term of this patent is extended or adjusted under 35 U.S.C. 154(b) by 571 days.

This patent is subject to a terminal disclaimer.

(21) Appl. No.: 15/657,800

(22) Filed: Jul. 24, 2017

(65) Prior Publication Data

US 2017/0323078 A1 Nov. 9, 2017

Related U.S. Application Data

(60) Continuation of application No. 13/950,741, filed on Jul. 25, 2013, now abandoned, which is a division of
(Continued)

(51) Int. Cl.
*G06F 19/00* (2018.01)
*G16H 10/60* (2018.01)
(Continued)

(52) U.S. Cl.
CPC ............. *G16H 10/60* (2018.01); *G06Q 50/22* (2013.01); *G06Q 50/24* (2013.01)

(58) Field of Classification Search
CPC ........ G16H 50/70; G16H 10/60; G16H 50/80; G16H 50/30; G06Q 50/24
See application file for complete search history.

(56) References Cited

U.S. PATENT DOCUMENTS

| 4,636,385 A | 1/1987 | Plotkin et al. |
| 5,658,744 A | 8/1997 | Ochoa et al. |

(Continued)

FOREIGN PATENT DOCUMENTS

| EP | 0887759 A1 | 12/1998 |
| EP | 0917078 A1 | 5/1999 |

(Continued)

OTHER PUBLICATIONS

Reid, et al., "Adult immunizations: recommendations for practice", Mayo Clin Proc 1999; 74:377-384.

(Continued)

*Primary Examiner* — Maroun P Kanaan
(74) *Attorney, Agent, or Firm* — Lewis J. Kreisler

(57) ABSTRACT

A system and method for assessing the immunological status of one or more individuals in a patient population is presented. The method includes establishing a database comprising a plurality of records of information each representative of the immune status of an individual in the population, each of said records including (1) current information from one or more assays for the presence of a biochemical, and (2) individual specific information comprising one or more of said individual's medical history, said individual's doctors' observations and historical, demographic, lifestyle, and familial information relating to said individual. The method further includes processing the
(Continued)

information in said database to find trends or patterns relating to the immune status of individuals in said patient population; and using the said trends or patterns as part of a health care related decision making process.

4 Claims, 688 Drawing Sheets

Related U.S. Application Data application No. 12/291,529, filed on Nov. 10, 2008, now Pat. No. 8,498,879, which is a continuation-in-part of application No. 11/796,727, filed on Apr. 27, 2007, now Pat. No. 8,234,129.

(60) Provisional application No. 61/002,704, filed on Nov. 8, 2007, provisional application No. 60/796,266, filed on Apr. 27, 2006.

(51) Int. Cl.
*G06Q 50/22* (2018.01)
*G06Q 50/24* (2012.01)

(56) References Cited

U.S. PATENT DOCUMENTS

| | | |
|---|---|---|
| 5,660,176 A | 8/1997 | Iliff |
| 5,692,220 A | 11/1997 | Diamond et al. |
| 5,692,501 A | 12/1997 | Mintum |
| 5,732,397 A | 3/1998 | Detore et al. |
| 5,839,438 A | 11/1998 | Graettinger et al. |
| 5,860,917 A | 1/1999 | Comanor et al. |
| 5,960,443 A | 9/1999 | Young et al. |
| 6,151,581 A | 11/2000 | Kraftson et al. |
| 6,266,645 B1 | 7/2001 | Simpson |
| 6,287,254 B1 | 9/2001 | Dodds |
| 7,908,155 B2 | 3/2011 | Fuerst et al. |
| 8,234,129 B2 | 7/2012 | Michon et al. |
| 8,498,878 B2 | 7/2013 | Michon et al. |
| 2002/0059030 A1 | 5/2002 | Otworth et al. |
| 2002/0095585 A1 | 7/2002 | Scott |
| 2002/0188480 A1 | 12/2002 | Liebeskind et al. |
| 2003/0065535 A1 | 4/2003 | Karlov et al. |
| 2003/0208382 A1 | 11/2003 | Westfall |
| 2003/0212027 A1 | 11/2003 | Barbera-Guillem et al. |
| 2004/0003132 A1 | 1/2004 | Stanley et al. |
| 2004/0015337 A1 | 1/2004 | Thomas et al. |
| 2004/0122705 A1 | 6/2004 | Sabol et al. |
| 2004/0122706 A1 | 6/2004 | Walker et al. |
| 2004/0143461 A1 | 7/2004 | Watkins |
| 2004/0267568 A1 | 12/2004 | Chandler et al. |
| 2005/0071204 A1 | 3/2005 | Parankirinathan |
| 2006/0002949 A1 | 1/2006 | Glenn et al. |
| 2006/0030006 A1 | 2/2006 | Druilhe |
| 2006/0059145 A1 | 3/2006 | Henschke et al. |
| 2006/0074719 A1 | 4/2006 | Horner |
| 2006/0218010 A1 | 9/2006 | Michon et al. |
| 2006/0275844 A1 | 12/2006 | Linke et al. |
| 2008/0091471 A1 | 4/2008 | Michon et al. |

FOREIGN PATENT DOCUMENTS

| | | |
|---|---|---|
| WO | 9728445 A1 | 8/1997 |
| WO | 9933390 A2 | 7/1999 |
| WO | 0065472 A1 | 11/2000 |
| WO | 0237232 A2 | 5/2002 |
| WO | 2002088903 A2 | 11/2002 |
| WO | 2003057011 A2 | 7/2003 |
| WO | 2006045004 A2 | 4/2006 |
| WO | 2007127490 A2 | 11/2007 |
| WO | 2008040005 A1 | 4/2008 |

OTHER PUBLICATIONS

Van Loveren et al., "Vaccine-induced antibody responses as parameters of the influence of endogenous and environmental factors", RIVM report 640800 001 (May 2000) 36 pages. <URL:https://rivm.openrepository.com/rivm/bitstream/10029/9627/1/640800001.pdf>.

Carter, et al., "Developing and Testing a Decision Model for Predicting Influenza Vaccination Compliance", Health Services Research, 1986, 20(6): 897-932. <URL:http://www.ncbi.nlm.nih.gov/pubmed/3949541>.

Martin, K.E., et al.; "Health-Based Risk Assessment: Risk Adjusted Payments and Beyond"; Changes in Health Care Financing & Organization; Academy Health; (Jan. 2004).

Miller, P.L., et al.; "Combining Tabular, Rule-Based, and Procedural Knowledge in Computer-Based Guidelines for Childhood Immunization," Computers and Biomedical Research 30:211-231 (1997).

Taylor, J.A., et al.; "The Influence of Provider Behavior, Parental Characteristics, and a Public Policy Initiative on the Immunization Status of Children Followed by Private Pediatricians: A Study From Pediatric Research in Office Settings"; Pediatrics; vol. 99:2; pp. 209-215 (1997).

Pending (as of Nov. 1, 2017) Claims from U.S. Appl. No. 11/255,161.

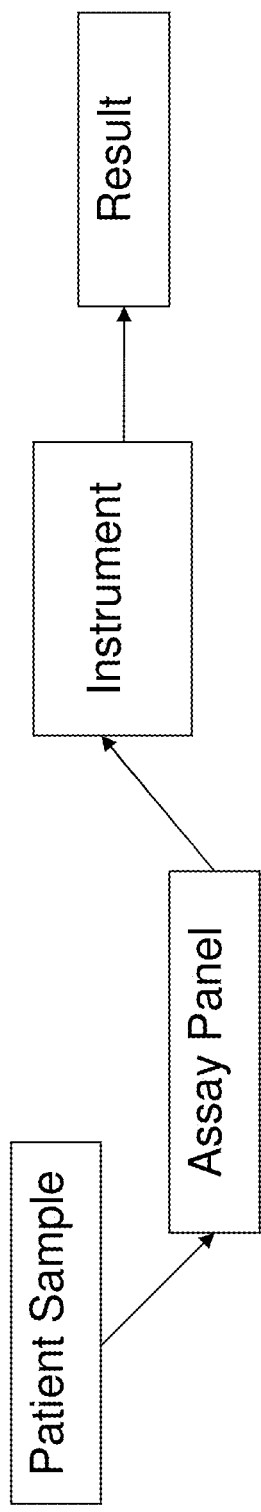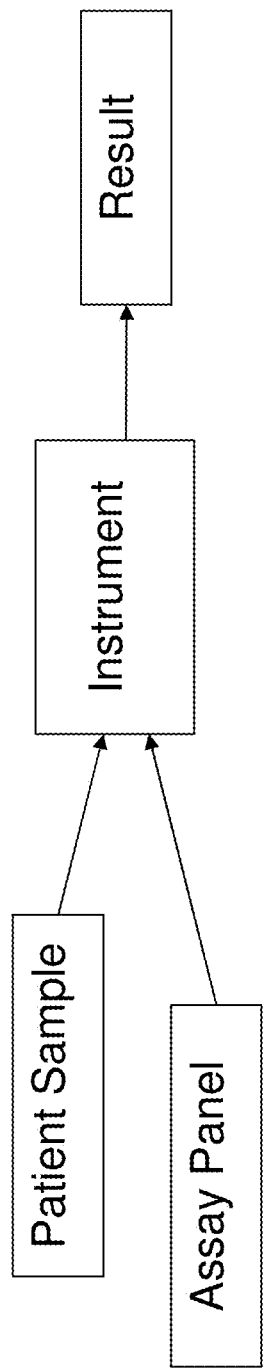
FIG. 3
FIG. 4

Additional Section I Figs.

FIG. 5F - Development of the immune response in schitosome infection (Pearce and MacDonald, 2002).
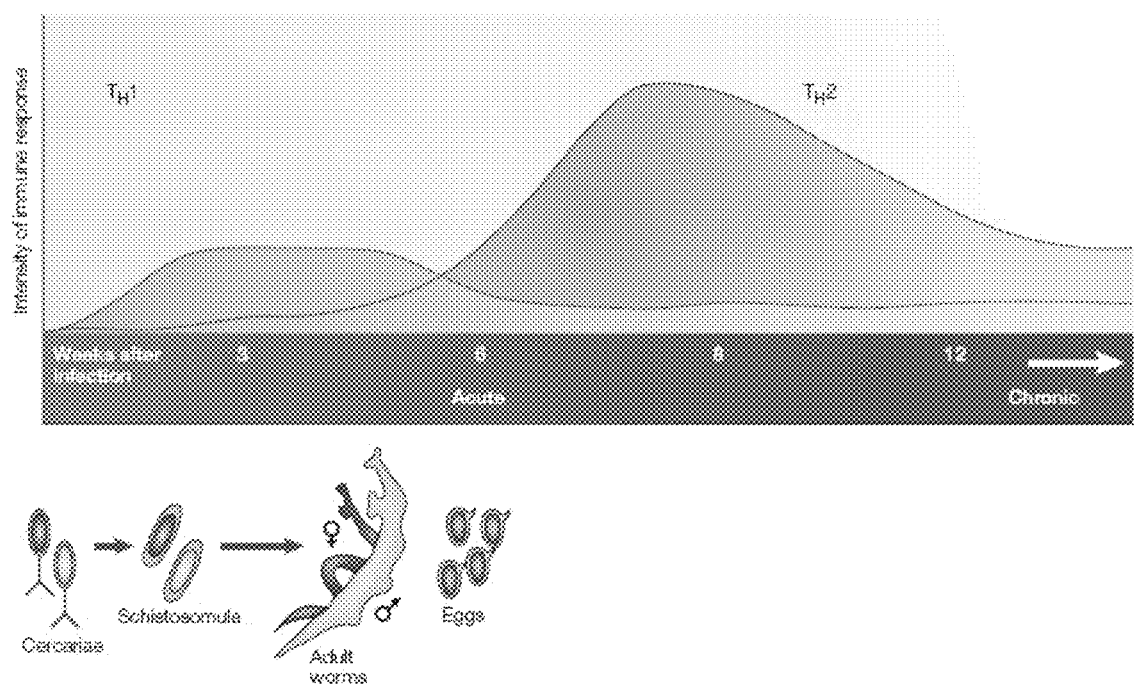

| | |
|---|---|
| IMMUNOSCORE | ANTIBODYHBS |
| GAMP | ANTIBODYDIPHTHERIA |
| GAMPACTIVITY | ANTIBODYTETANUS |
| GCMP | ANTIBODYPT1 |
| GCMPACTIVITY | ANTIBODYPRN1 |
| GWMP | ANTIBODYFHA1 |
| GWMPACTIVITY | ANTIBODYFIMBRIAE |
| GYMP | ANTIBODYPRP |
| GYMPACTIVITY | ANTIBODYPOLIO1 |
| GBMP | ANTIBODYPOLIO2 |
| GBMPACTIVITY | ANTIBODYPOLIO3 |
| C5 | ANTIBODYMEASLES |
| C6 | ANTIBODYRUBELLA |
| C7 | ANTIBODYVARICELLA |
| C8 | ANTIBODYPNEUMOCOCCALSEROTYPES |
| C9 | ANTIBODYIGG |
| PROPERDIN | ANTIBODYIGA |
| MBL | ANTIBODYIGM |
| FCYRLLA | ANTIBODYHSVIGG |
| IL_1 | ANTIBODYHSV1 |
| IL_1R | ANTIBODYHSV2 |
| IL_6 | ANTIBODYGONORRHOEAE |
| IL_10 | ANTIBODYPALLIDUM |
| | TCELLPALLIDUM |
| | ANTIBODYHIV |
| | TCELLHIV |
| | ANTIBODYGBS1 |
| | ANTIBODYGBS2 |
| | ANTIBODYGBS3 |
| | ANTIBODYTH1CYTOKINE |
| | ANTIBODYTH2CYTOKINE |

FIG. 6: Assay Results in Example Database

| |
|---|
| Vaccinate patient with vaccine X |
| Do not vaccinate the patient with vaccine X |
| Retest patient immediately |
| Retest patient in X days |
| Monitor patient for symptom X |
| Administer additional test X; rerun analysis in light of new test results |
| Make an entry into patient's medical history of X |
| Treat patient for condition X |

FIG. 7: Diagnostic Module Recommendation Types

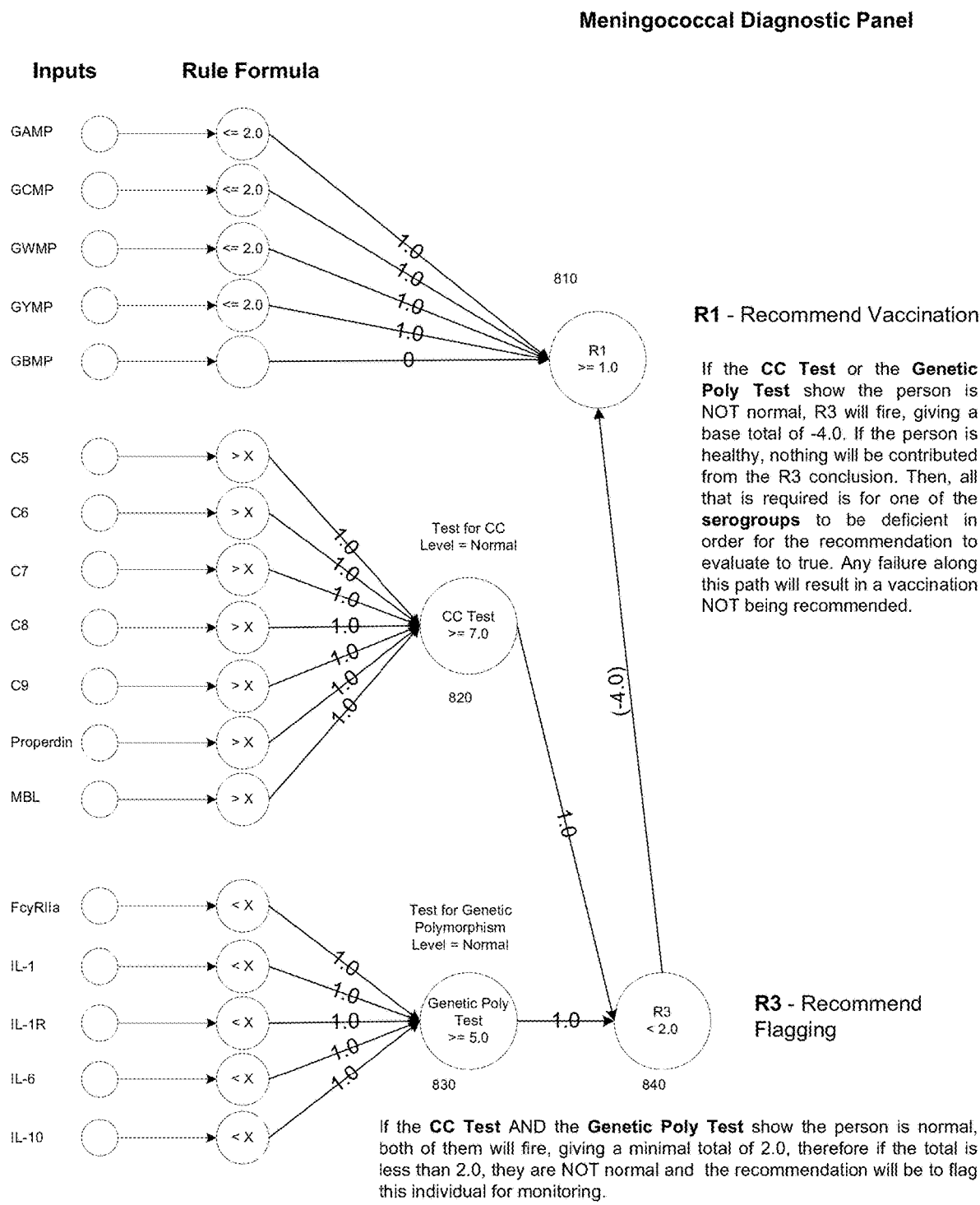
FIG. 8: Example Perceptron Network

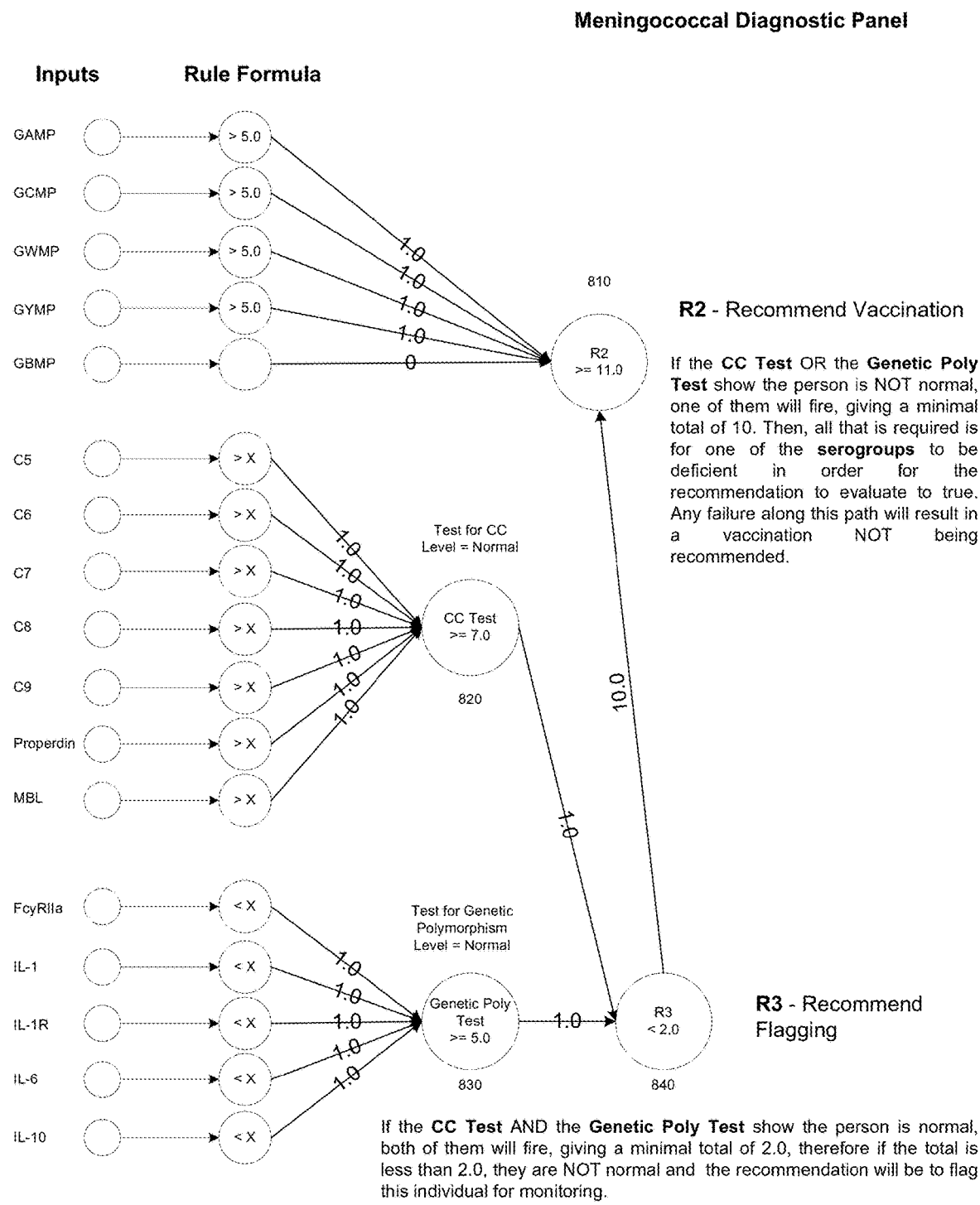
FIG. 8A: Example Perceptron Network

FIG. 9A: XML Representation of Perceptron Network

```xml
<?xml version="1.0" ?>
<TestRule>
  <Name>SerumIgGVPS</Name>
  <InputNeurons>
    <InputNeuron id="ruleR1_1" field="serumIgGLevelA" operator="lessThan" value="2.0" />
    <InputNeuron id="ruleR1_2" field="serumIgGLevelC" operator="lessThan" value="2.0" />
    <InputNeuron id="ruleR1_3" field="serumIgGLevelW" operator="lessThan" value="2.0" />
    <InputNeuron id="ruleR1_4" field="serumIgGLevelY" operator="lessThan" value="2.0" />
    <InputNeuron id="ruleR2_1" field="serumIgGLevelA" operator="lessThan" value="5.0" />
    <InputNeuron id="ruleR2_2" field="serumIgGLevelC" operator="lessThan" value="5.0" />
    <InputNeuron id="ruleR2_3" field="serumIgGLevelW" operator="lessThan" value="5.0" />
    <InputNeuron id="ruleR2_4" field="serumIgGLevelY" operator="lessThan" value="5.0" />
    <InputNeuron id="ruleCC_1" field="C5" operator="greaterThan" value="1.0" />
    <InputNeuron id="ruleCC_2" field="C6" operator="greaterThan" value="1.0" />
    <InputNeuron id="ruleCC_3" field="C7" operator="greaterThan" value="1.0" />
    <InputNeuron id="ruleCC_4" field="C8" operator="greaterThan" value="1.0" />
    <InputNeuron id="ruleCC_5" field="C9" operator="greaterThan" value="1.0" />
    <InputNeuron id="ruleCC_6" field="Properdin" operator="greaterThan" value="1.0" />
    <InputNeuron id="ruleCC_7" field="MBL" operator="greaterThan" value="1.0" />
    <InputNeuron id="ruleGP_1" field="FcyRIIa" operator="greaterThan" value="1.0" />
    <InputNeuron id="ruleGP_2" field="IL1" operator="greaterThan" value="1.0" />
    <InputNeuron id="ruleGP_3" field="IL1R" operator="greaterThan" value="1.0" />
    <InputNeuron id="ruleGP_4" field="IL6" operator="greaterThan" value="1.0" />
    <InputNeuron id="ruleGP_5" field="IL10" operator="greaterThan" value="1.0" />
  </InputNeurons>
  <InputDefinitions>
    <IntputDefinition>
      <Name>serumIgGLevelA</Name>
      <Units>ug/mL</Units>
      <Definition>The Serum IgG Levels for vaccine-preventable serogroups A of Neisseria meningitidis</Definition>
    </IntputDefinition>
    <IntputDefinition>
      <Name>serumIgGLevelC</Name>
      <Units>ug/mL</Units>
      <Definition>The Serum IgG Levels for vaccine-preventable serogroups C of Neisseria meningitidis</Definition>
    </IntputDefinition>
```

FIG. 9B: XML Representation of Perceptron Network
(Continued #1)

```xml
<IntputDefinition>
  <Name>serumIgGLevelW</Name>
  <Units>ug/mL</Units>
  <Definition>The Serum IgG Levels for vaccine-preventable serogroups W-135 of Neisseria
    meningitidis</Definition>
</IntputDefinition>
<IntputDefinition>
  <Name>serumIgGLevelY</Name>
  <Units>ug/mL</Units>
  <Definition>The Serum IgG Levels for vaccine-preventable serogroups Y of Neisseria
    meningitidis</Definition>
</IntputDefinition>
<IntputDefinition>
  <Name>C5</Name>
  <Units>ug/mL</Units>
  <Definition>Serum level of the complement component C5</Definition>
</IntputDefinition>
<IntputDefinition>
  <Name>C6</Name>
  <Units>ug/mL</Units>
  <Definition>Serum level of the complement component C6</Definition>
</IntputDefinition>
<IntputDefinition>
  <Name>C7</Name>
  <Units>ug/mL</Units>
  <Definition>Serum level of the complement component C7</Definition>
</IntputDefinition>
<IntputDefinition>
  <Name>C8</Name>
  <Units>ug/mL</Units>
  <Definition>Serum level of the complement component C8</Definition>
</IntputDefinition>
<IntputDefinition>
  <Name>C9</Name>
  <Units>ug/mL</Units>
  <Definition>Serum level of the complement component C9</Definition>
</IntputDefinition>
<IntputDefinition>
  <Name>Properdin</Name>
  <Units>ug/mL</Units>
  <Definition>Serum level of the complement component Properdin</Definition>
</IntputDefinition>
<IntputDefinition>
  <Name>MBL</Name>
  <Units>ug/mL</Units>
```

FIG. 9C: XML Representation of Perceptron Network
(Continued #2)

```xml
      <Definition>Serum level of the complement component Mannose-binding lectin
         (MBL)</Definition>
      </IntputDefinition>
   <IntputDefinition>
      <Name>FcyRIIa</Name>
      <Units>ug/mL</Units>
      <Definition>Measurement of genetic polymorphism for FcyRIIa receptor</Definition>
      </IntputDefinition>
   <IntputDefinition>
      <Name>IL1</Name>
      <Units>ug/mL</Units>
      <Definition>Measurement of genetic polymorphism for IL-1 receptor</Definition>
      </IntputDefinition>
   <IntputDefinition>
      <Name>IL1R</Name>
      <Units>ug/mL</Units>
      <Definition>Measurement of genetic polymorphism for IL-1R receptor</Definition>
      </IntputDefinition>
   <IntputDefinition>
      <Name>IL6</Name>
      <Units>ug/mL</Units>
      <Definition>Measurement of genetic polymorphism for IL-6 receptor</Definition>
      </IntputDefinition>
   <IntputDefinition>
      <Name>IL10</Name>
      <Units>ug/mL</Units>
      <Definition>Measurement of genetic polymorphism for IL-10 receptor</Definition>
      </IntputDefinition>
      </InputDefinitions>
   <HiddenNeurons>
   <NeuronDefinition id="CCTest" operator="greaterOrEqual" value="7.0" function="SUM">
      <Definition>Measurement of the serum levels of complement components.</Definition>
      <Result>Patient is deficient in the Complement Components</Result>
   <OutputDefinitionRules>
      <OutputDefinitionRule formulaid="ruleCC_1" weight="1.0" />
      <OutputDefinitionRule formulaid="ruleCC_2" weight="1.0" />
      <OutputDefinitionRule formulaid="ruleCC_3" weight="1.0" />
      <OutputDefinitionRule formulaid="ruleCC_4" weight="1.0" />
      <OutputDefinitionRule formulaid="ruleCC_5" weight="1.0" />
      <OutputDefinitionRule formulaid="ruleCC_6" weight="1.0" />
      <OutputDefinitionRule formulaid="ruleCC_7" weight="1.0" />
         </OutputDefinitionRules>
         </NeuronDefinition>
```

**FIG. 9D: XML Representation of Perceptron Network
(Continued #3)**

```xml
<NeuronDefinition id="GeneticPolyTest" operator="greaterOrEqual" value="5.0" function="SUM">
  <Definition>Measurement of genetic polymorphisms.</Definition>
  <Result>Patient has Genetic Polymorphisms present.</Result>
  <OutputDefinitionRules>
    <OutputDefinitionRule formulaid="ruleGP_1" weight="1.0" />
    <OutputDefinitionRule formulaid="ruleGP_2" weight="1.0" />
    <OutputDefinitionRule formulaid="ruleGP_3" weight="1.0" />
    <OutputDefinitionRule formulaid="ruleGP_4" weight="1.0" />
    <OutputDefinitionRule formulaid="ruleGP_5" weight="1.0" />
  </OutputDefinitionRules>
</NeuronDefinition>
<NeuronDefinition id="R3" operator="lessThan" value="2.0" function="SUM">
  <Definition>If the CC Test AND the Genetic Poly Test show the person is normal, both of them will fire, giving us a minimal total of 2.0, therefore if the total is less than 2.0, they are NOT normal and the recommendation will be to flag this individual for monitoring.</Definition>
  <Result>Flag patient for monitoring</Result>
  <OutputDefinitionRules>
    <OutputDefinitionRule formulaid="CCTest" weight="1.0" />
    <OutputDefinitionRule formulaid="GeneticPolyTest" weight="1.0" />
  </OutputDefinitionRules>
</NeuronDefinition>
</HiddenNeurons>
<OutputNeurons>
<NeuronDefinition id="R1" operator="greaterOrEqual" value="1.0" function="SUM">
  <Definition>If the CC Test or the Genetic Poly Test show the person is NOT normal, R3 will fire, giving us a base total of -4.0. If the person is healthy, nothing will be contributed from the R3 conclusion. Then, all that is required is for one of the serogroups to be deficient in order for the recommendation to evaluate to true. Any failure along this path will result in a vaccination NOT being recommended.</Definition>
  <Result>Vaccination Recommended</Result>
  <OutputDefinitionRules>
    <OutputDefinitionRule formulaid="ruleR1_1" weight="1.0" />
    <OutputDefinitionRule formulaid="ruleR1_2" weight="1.0" />
    <OutputDefinitionRule formulaid="ruleR1_3" weight="1.0" />
    <OutputDefinitionRule formulaid="ruleR1_4" weight="1.0" />
    <OutputDefinitionRule formulaid="R3" weight="-4.0" />
  </OutputDefinitionRules>
</NeuronDefinition>
<NeuronDefinition id="R2" operator="greaterOrEqual" value="11.0" function="SUM">
```

FIG. 9E: XML Representation of Perceptron Network
(Continued #4)

```xml
<Definition>If the CC Test OR the Genetic Poly Test show the person is NOT normal, one of
    them will fire, giving us a minimal total of 10. Then, all that is required is for one of the
    serogroups to be deficient in order for the recommendation to evaluate to true. Any
    failure along this path will result in a vaccination NOT being recommended.</Definition>
  <Result>Vaccination Recommended</Result>
  <OutputDefinitionRules>
    <OutputDefinitionRule formulaid="ruleR2_1" weight="1.0" />
    <OutputDefinitionRule formulaid="ruleR2_2" weight="1.0" />
    <OutputDefinitionRule formulaid="ruleR2_3" weight="1.0" />
    <OutputDefinitionRule formulaid="ruleR2_4" weight="1.0" />
    <OutputDefinitionRule formulaid="R3" weight="10.0" />
    </OutputDefinitionRules>
    </NeuronDefinition>
    </OutputNeurons>
    </TestRule>
```

| | |
|---|---|
| ~ | not |
| C(x) | cost of x |
| CD$_X$ | contracting disease X |
| D | death |
| IS | immune status |
| P( x \| y and z) | the probability of x occurring given y and z |
| T(x) | treating x |
| V$_X$ | vaccinate against disease X (more broadly, intervene against disease X) |

FIG. 10: Symbology for Diagnostic Goals

FIG. 11A: Diagnostic Goals

1.1 Conventional Approaches

1.1.1 Vaccinate/intervene against disease X if will reduce occurrence disease X not taking into account patient's IS if
$$P(CD_X \mid V_X) < P(CD_X \mid \sim V_X)$$
then $V_X$.

1.1.2 Vaccinate/intervene against disease X if will reduce health care costs directly related to disease X, not taking into account patient's IS if
$$P(CD_X \mid V_X) * C(T_X \mid CD_X \text{ and } V_X) + C(V_X) < P(CD_X \mid \sim V_X) * C(T_X \mid CD_X \text{ and } \sim V_X)$$
then $V_X$.

1.2 Optimize welfare of the patient

1.2.1 Vaccinate/intervene against disease X if will reduce occurrence disease X if
$$P(CD_X \mid V_X \text{ and } IS) < P(CD_X \mid \sim V_X \text{ and } IS)$$
then $V_X$.

1.2.2 Vaccinate/intervene against disease X if will reduce occurrence of any disease if
$$P(CD \mid V_X \text{ and } IS) < P(CD \mid \sim V_X \text{ and } IS)$$
then $V_X$.

1.3 Optimize health care costs

1.3.1 Vaccinate/intervene against disease X if will reduce health care costs directly related to disease X if
$$P(CD_X \mid V_X \text{ and } IS) * C(T_X \mid CD_X \text{ and } V_X \text{ and } IS) + C(V_X) < P(CD_X \mid \sim V_X \text{ and } IS) * C(T_X \mid CD_X \text{ and } \sim V_X \text{ and } IS)$$
then $V_X$.

1.3.2 Vaccinate/intervene against disease X if will reduce overall disease-related health care costs if
$$\sum_{i=alldiseases, includingX} [P(CD_i \mid V_X \text{ and } IS) * C(T_i \mid CD_i \text{ and } V_X \text{ and } IS)] + C(V_X) < \sum_{i=alldiseases, includingX} [P(CDi \mid \sim V_X \text{ and } IS) * C(Ti \mid CD_i \text{ and } \sim V_X \text{ and } IS)]$$
then $V_X$.

FIG. 11B: Diagnostic Goals

1.4 Optimize life-insurance costs 1.4.1 Vaccinate/intervene against disease X if will increase life-expectancy if
$$P(CD_X \mid V_X \text{ and } IS) * P(D \mid CD_X \text{ and } V_X \text{ and } IS) +$$
$$P(\sim CD_X \mid V_X \text{ and } IS) * P(D \mid \sim CD_X \text{ and } V_X \text{ and } IS)$$
$$<$$
$$P(CD_X \mid \sim V_X \text{ and } IS) * P(D \mid CD_X \text{ and } \sim V_X \text{ and } IS) +$$
$$P(\sim CD_X \mid \sim V_X \text{ and } IS) * P(D \mid \sim CD_X \text{ and } \sim V_X \text{ and } IS)$$
then $V_X$.

FIG. 12A: Example Database Schema, Patient Info

```
create table Patient_Info (
       PT_ID   NUMBER(9)
              CONSTRAINT ptid_nn NOT NULL ,
       PT_FT_NM   VARCHAR2(100),
       PT_LT_NM   VARCHAR2(100),
       PT_BIRTH_DT  DATE
              CONSTRAINT birthdate_nn NOT NULL,
       PT_GENDER  CHAR(1)
              CONSTRAINT gender_nn NOT NULL ,
       PT_ADDRESS1   VARCHAR2(200) ,
       PT_ADDRESS2   VARCHAR2(200) ,
       PT_CITY   VARCHAR2(50) ,
       PT_ZIP_CODE   NUMBER(5),
       PT_STATE   CHAR(2) ,
       PT_COUNTRY   VARCHAR2(200) ,
       PT_RES_TEL   NUMBER(9) ,
       PT_IS_LATINO   NUMBER(1) ,
       PT_IS_WHITE   NUMBER(1) ,
       PT_IS_BLACK   NUMBER(1) ,
       PT_IS_AFRCN_AMRCN   NUMBER(1) ,
       PT_IS_ASIAN   NUMBER(1) ,
       PT_IS_NTV_HAWAI   NUMBER(1) ,
       PT_IS_PAC_ISLNDR   NUMBER(1) ,
       PT_IS_AMRN_INDN   NUMBER(1) ,
       PT_IS_NTV_ALSK   NUMBER(1)
       )

TABLESPACE IMMUNOPRINT_PROD;

create table VISIT_INFO (
       VT_ID NUMBER(10)
              CONSTRAINT vtid_nn NOT NULL ,
       PT_ID   NUMBER(9),
       VT_DT     DATE
              CONSTRAINT vtDate_nn NOT NULL ,
       PT_AGE_AT_VISIT       NUMBER(5,2),
       PT_IS_PREG         NUMBER(1) ,
       PT_LAST_GESTATION   DATE ,
       PT_TOBACCO_USE      NUMBER(1) ,
       PT_TOBACCO_FREQ        NUMBER(10) ,
       PAYMENT_SRC        NUMBER(10) ,
       VT_ADVERSE_REASON   NUMBER(10) ,
       VT_REASON1          VARCHAR2(200) ,
       VT_REASON2          VARCHAR2(200) ,
```

FIG. 12B: Example Database Schema, Patient Info (Continued #1)

```
VT_REASON3              VARCHAR2(200),
VT_MAJOR_REASON         NUMBER(10),
PT_HEIGHT               NUMBER(5,2),
PT_WEIGHT               NUMBER(5,2),
PT_TEMPERATURE          NUMBER(5,2),
PT_S_BLD_PRESSURE       NUMBER(5,2),
PT_D_BLD_PRESS          NUMBER(5,2),
VT_DURATION             FLOAT(3),
VT_DISP_FOLLOW_UP_REQ   NUMBER(1),
VT_DISP_RETURN_IF_NEEDED NUMBER(1),
VT_DISP_REFER_OTHR_PHY  NUMBER(1),
VT_DISP_RETURN_AT_SPEC_TIME NUMBER(1),
VT_DISP_TEL_FOLLOW_UP   NUMBER(1),
VT_DISP_REFER_EMERGENCY NUMBER(1),
VT_DISP_ADMIT_TO_HOSPITAL NUMBER(1),
VT_DISP_OTHER           NUMBER(1),
VT_DISP_OTHER_DETAIL    VARCHAR2(300),
PT_PRIMARY_PHY          NUMBER(1),
PT_IS_REFERAL           NUMBER(1),
PT_IS_ESTABLISHED       NUMBER(1),
PT_NUM_PREV_VISITS      NUMBER(3),
PT_PRIMARY_DIAG         VARCHAR2(300),
PT_DIAG2                VARCHAR2(300),
PT_DIAG3                VARCHAR2(300),
PT_PRE_AIDS             NUMBER(1),
PT_PRE_ANAPHYLAXSIS     NUMBER(1),
PT_PRE_ANEMIA           NUMBER(1),
PT_PRE_ARTHRITIS        NUMBER(1),
PT_PRE_ARTIFICIAL_HEART_VALS NUMBER(1),
PT_PRE_ARTIFICIAL_JOINT NUMBER(1),
PT_PRE_ASTHMA           NUMBER(1),
PT_PRE_ALLERGIES        NUMBER(1),
PT_PRE_ALLERGIES_DET    VARCHAR2(200),
PT_PRE_BACK_PROBLEM     NUMBER(1),
PT_PRE_BLD_DIS          NUMBER(1),
PT_PRE_CANCER           NUMBER(1),
PT_PRE_CANCER_DET       NUMBER(1),
PT_PRE_CHEMO            NUMBER(1),
PT_PRE_CIRCULATRY_PROB  NUMBER(1),
PT_PRE_CHF              NUMBER(1),
PT_PRE_CHRONIC_RENAL_FAIL NUMBER(1),
PT_PRE_COLD             NUMBER(1),
PT_PRE_COPD             NUMBER(1),
PT_PRE_CORTISONE        NUMBER(1),
```

FIG. 12C: Example Database Schema, Patient Info (Continued #2)

```
PT_PRE_CON_HEART_LESIONS      NUMBER(1),
PT_PRE_COUGH_PRESISTENT       NUMBER(1),
PT_PRE_COUGH_UP_BLD           NUMBER(1),
PT_PRE_DEPRESSION             NUMBER(1),
PT_PRE_DIABETES               NUMBER(1),
PT_PRE_DRASTIC_WGT_LOSS       NUMBER(1),
PT_PRE_DRUG_DEP               NUMBER(1),
PT_PRE_EPILEPSY               NUMBER(1),
PT_PRE_EXCESSIVE_BLEEDING     NUMBER(1),
PT_PRE_FAINTING               NUMBER(1),
PT_PRE_FOOD_ALLERGIES         NUMBER(1),
PT_PRE_FEN_PHEN_USED          NUMBER(1),
PT_PRE_REDUX_USED             NUMBER(1),
PT_PRE_HEART_PROB_DET         VARCHAR2(300),
PT_PRE_HEMOPHILIA             NUMBER(1),
PT_PRE_HERPES                 NUMBER(1),
PT_PRE_HEP                    NUMBER(1),
PT_PRE_HEP_TYP1               VARCHAR2(4),
PT_PRE_HEP_TYP2               VARCHAR2(4),
PT_PRE_HYPERLIPIDEMIA         NUMBER(1),
PT_PRE_HYPERTENSION           NUMBER(1),
PT_PRE_INCEST                 NUMBER(1),
PT_PRE_CHILD_ABUSE            NUMBER(1),
PT_PRE_JAUNDICE               NUMBER(1),
PT_PRE_HIV_POS                NUMBER(1),
PT_PRE_KIDNEY_DIS_MAL         NUMBER(1),
PT_PRE_LATEX_ALLERGY          NUMBER(1),
PT_PRE_LIVER_DIS              NUMBER(1),
PT_PRE_MITRAL_VALVE_PROLAPSE  NUMBER(1),
PT_PRE_NERV_PROB              NUMBER(1),
PT_PRE_OBESITY                NUMBER(1),
PT_PRE_OSTEOPOROSIS           NUMBER(1),
PT_PRE_PACEMAKER              NUMBER(1),
PT_PRE_PERSIST_DIARRHEA       NUMBER(1),
PT_PRE_PSYCHIATIC_CARE        NUMBER(1),
PT_PRE_RAPID_WGT_LOSS         NUMBER(1),
PT_PRE_RADIATION_TREAT        NUMBER(1),
PT_PRE_RADIATION_DET          VARCHAR2(200),
PT_PRE_REPLACE_SURG           NUMBER(1),
PT_PRE_REPLACE_SURG_DET       VARCHAR2(200),
PT_PRE_RESPIRATORY_DIS        NUMBER(1),
PT_PRE_SKIN_RASH              NUMBER(1),
PT_PRE_SP_DIET                NUMBER(1),
```

FIG. 13: Example Database Schema, Visit Info

```
PT_PRE_SP_DIET_DESC          VARCHAR2(200),
PT_PRE_SPINA_BIFIDA          NUMBER(1),
PT_PRE_STRESS                NUMBER(1),
PT_PRE_STROKE                NUMBER(1),
PT_PRE_SURGICAL_IMPLANTS     NUMBER(1),
PT_PRE_SURGICAL_IMPLANTS_DET VARCHAR2(200),
PT_PRE_SWELLING_FEET_ANKLES  NUMBER(1),
PT_PRE_THYROID_DIS           NUMBER(1),
PT_PRE_TONSILLITIS           NUMBER(1),
PT_PRE_TUBERCULOSIS          NUMBER(1),
PT_PRE_ULCER                 NUMBER(1),
PT_PRE_COLITIS               NUMBER(1),
PT_PRE_VENERIAL_DIS          NUMBER(1),
PT_PRE_CONDITION_DET         VARCHAR2(400),
PT_PRE_DIS_MANG_ENROLL       NUMBER(1),
DIGNOSTIC_SRV_PERF           NUMBER(1),
BREAST_EXAM                  NUMBER(1),
PELVIC_EXAM                  NUMBER(1),
RECTAL_EXAM                  NUMBER(1),
SKIN_EXAM                    NUMBER(1),
DEPRESSION_SCREEN            NUMBER(1),
BONE_MATERIAL_DENSITY        NUMBER(1),
MAMMOGRAPHY                  NUMBER(1),
MRI                          NUMBER(1),
CT                           NUMBER(1),
PET                          NUMBER(1),
ULTRASOUND                   NUMBER(1)
) TABLESPACE IMMUNOPRINT_PROD;
```

FIG. 14A: Example Database Schema, Test Results

```
create table VISIT_TEST_RESULTS (
    VT_ID   NUMBER(10)
            CONSTRAINT tvtid_nn NOT NULL ,
    PT_ID   NUMBER(9)
            CONSTRAINT tptid_nn NOT NULL ,
    IMMUNOSCORE             Number(10,4),
    GAMP            Number(10,4),
    GAMPActivity            Number(10,4),
    GCMP            Number(10,4),
    GCMPActivity    Number(10,4),
    GWMP            Number(10,4),
    GWMPActivity            Number(10,4),
    GYMP            Number(10,4),
    GYMPActivity            Number(10,4),
    GBMP            Number(10,4),
    GBMPActivity            Number(10,4),
    C5              Number(10,4),
    C6              Number(10,4),
    C7              Number(10,4),
    C8              Number(10,4),
    C9              Number(10,4),
    PROPERDIN   Number(10,4),
    MBL             Number(10,4),
    FCYRLLA                 Number(10,4),
    IL_1            Number(10,4),
    IL_1R           Number(10,4),
    IL_6            Number(10,4),
    IL_10           Number(10,4),
    antibodyHBs             Number(10,4),
    antibodyDiphtheria      Number(10,4),
    antibodyTetanus         Number(10,4),
    antibodyPT1             Number(10,4),
    antibodyPRN1            Number(10,4),
    antibodyFHA1            Number(10,4),
    antibodyFimbriae        Number(10,4),
    antibodyPRP             Number(10,4),
    antibodyPolio1          Number(10,4),
    antibodyPolio2          Number(10,4),
    antibodyPolio3          Number(10,4),
    antibodyMeasles         Number(10,4),
    antibodyRubella         Number(10,4),
    antibodyVaricella       Number(10,4),
    antibodyPneumococcalSerotypes   Number(10,4),
```

FIG. 14B: Example Database Schema, Test Results (Continued)

```
    antibodyIgG          Number(10,4),
    antibodyIgA          Number(10,4),
    antibodyIgM          Number(10,4),
    antibodyHSVIgG           Number(10,4),
    antibodyHSV1             Number(10,4),
    antibodyHSV2             Number(10,4),
    antibodyGonorrhoeae Number(10,4),
    antibodyPallidum     Number(10,4),
    tCellPallidum        Number(10,4),
    antibodyHIV          Number(10,4),
    tCellHIV             Number(10,4),
    antibodyGBS1         Number(10,4),
    antibodyGBS2         Number(10,4),
    antibodyGBS3         Number(10,4),
    antibodyTh1Cytokine Number(10,4),
    antibodyTh2Cytokine Number(10,4)
)       TABLESPACE IMMUNOPRINT_PROD;
```

FIG. 15: Patient Age Intervals

| Pt Age At Visit (Age in years) |
|---|
| 0.17 |
| 0.5 |
| 1 |
| 2 |
| 5 |
| 12 |
| 16 |
| 21 |

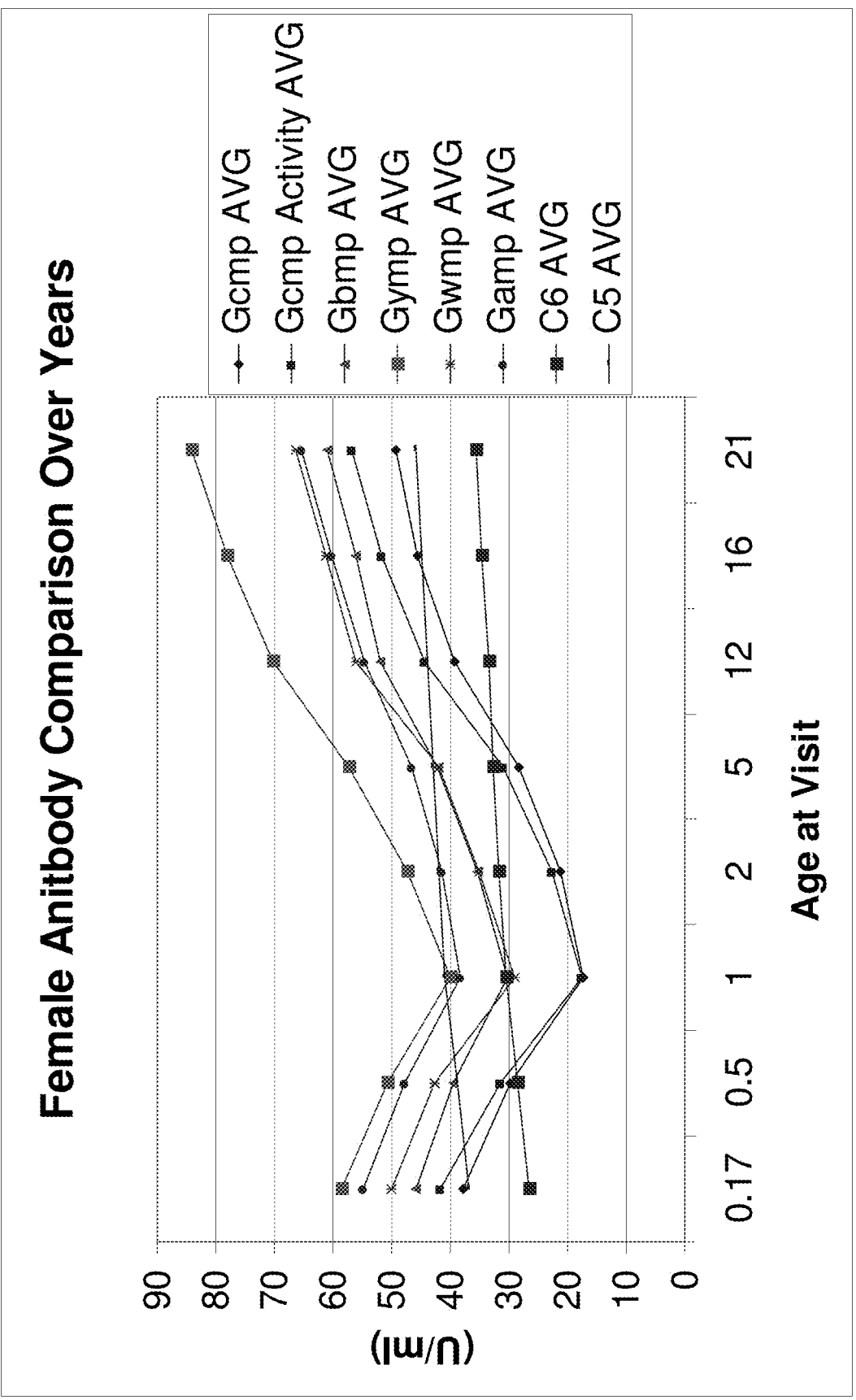
FIG. 16: Example of Levels of Various Antibodies in Female Simulated Population

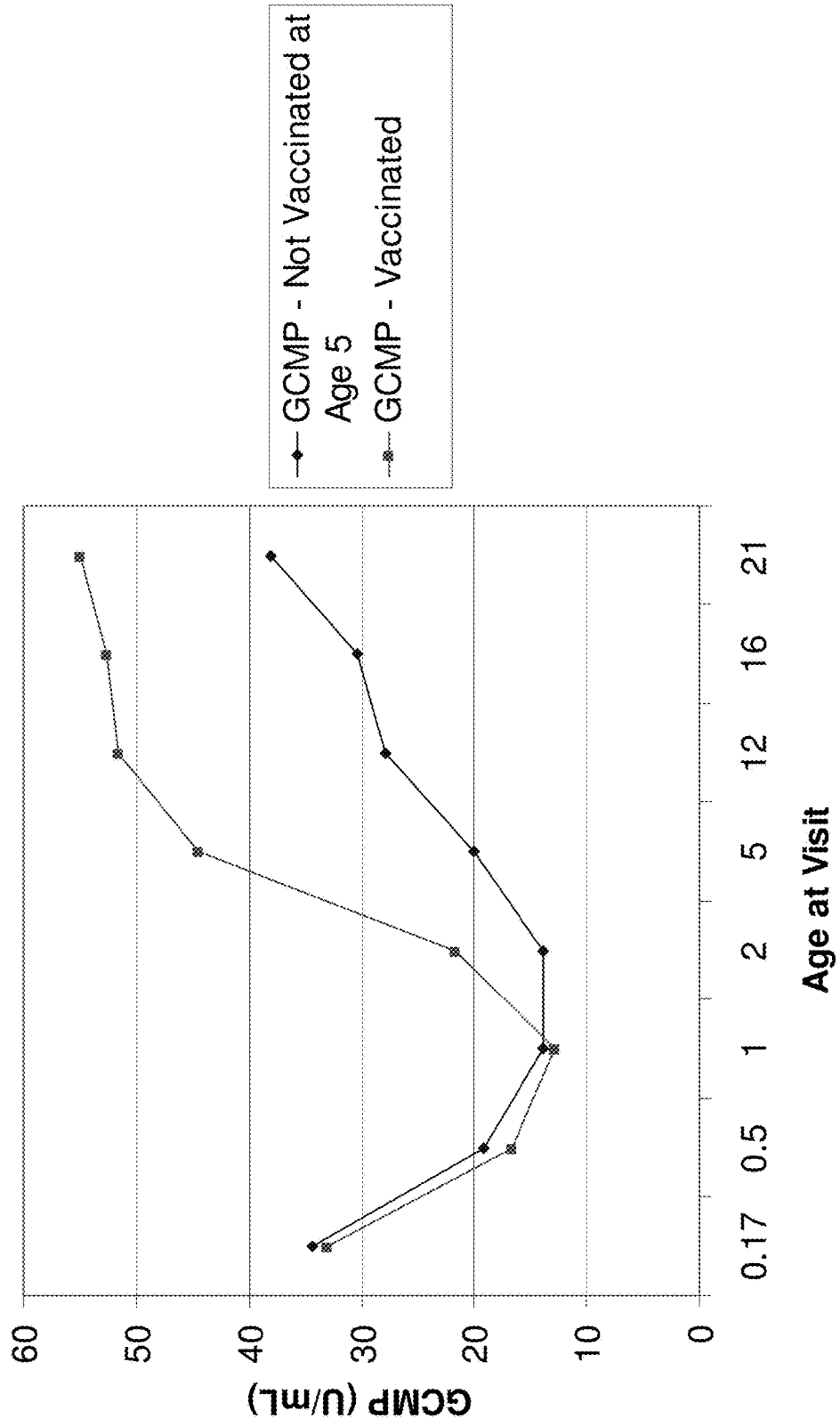
FIG. 17: Example of Comparison between Vaccinated and Non-Vaccinated Individuals

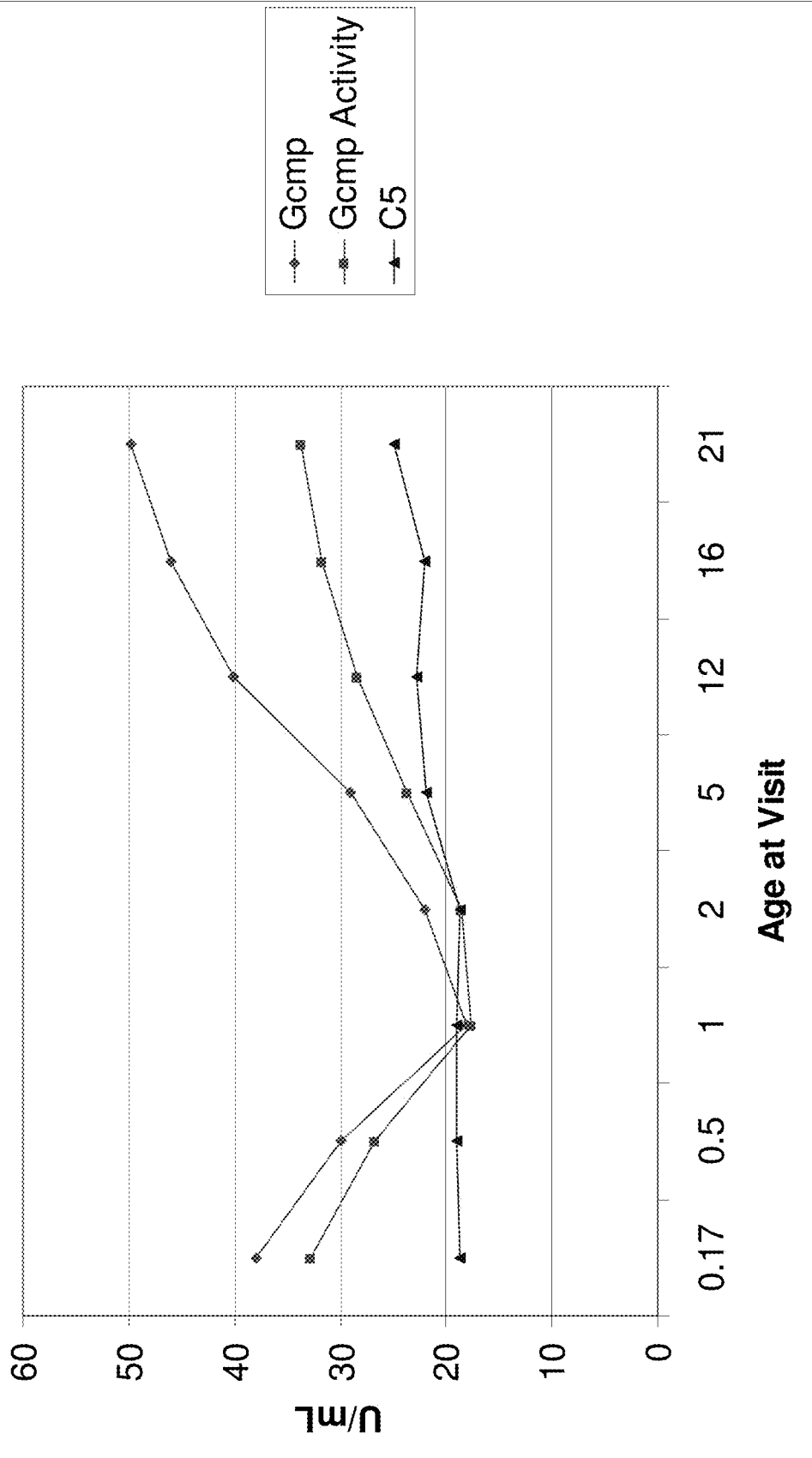
FIG. 18: Antibody Levels in a Complement-Deficient Individual

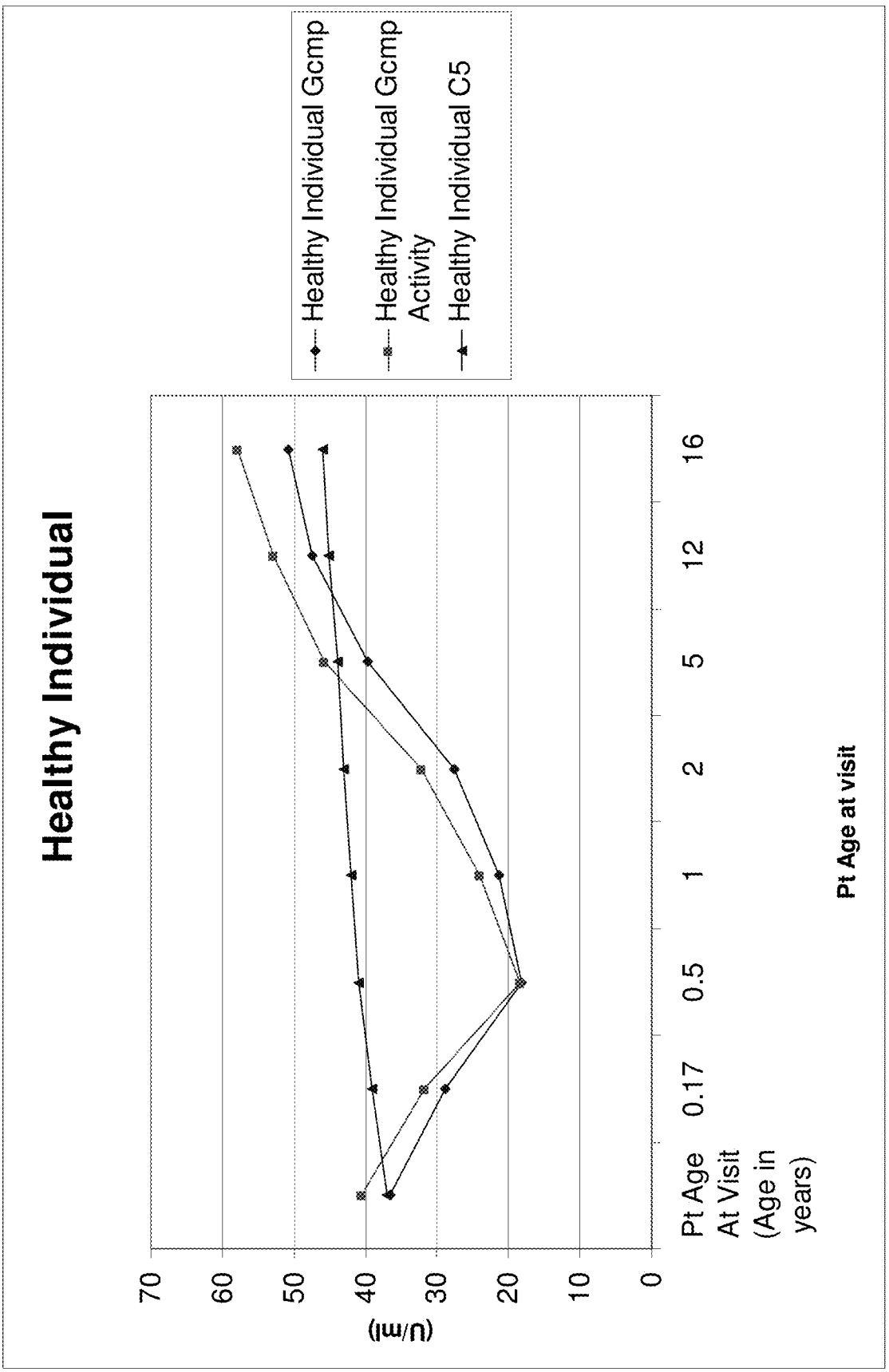
FIG.19: Antibody Levels in an Individual With No Complement Deficiency

```
SELECT * FROM PATIENT_INFO
WHERE PT_LT_NM LIKE "SMITH" AND
PT_GENDER = 0;
```

FIG. 19A: Example SQL Query

| Pt Age At Visit (Age in years) | Activity Vs Gcmp | Gamp Vs Gcmp | Gbmp Vs Gcmp | Gwmp Vs Gcmp | Gymp Vs Gcmp | C5 Vs Gcmp | C6 Vs Gcmp |
|---|---|---|---|---|---|---|---|
| 0.17 | | | | | | | |
| 0.5 | 0.99277579 | 0.630974777 | 0.848328143 | 0.771686375 | 0.829087982 | 0.6619765 | 0.0634558 |
| 1 | 0.75627538 | 0.760620792 | 0.782187342 | 0.779572654 | 0.784921088 | 0.7689116 | 0.0005239 |
| 2 | 0.753314684 | 0.807785412 | 0.809991603 | 0.752287188 | 0.706625551 | 0.5747302 | 0.0946182 |
| 5 | 0.661289901 | 0.769878799 | 0.763862956 | 0.730078492 | 0.618853492 | 0.3573768 | 0.1401185 |
| 12 | 0.673390454 | 0.787933834 | 0.817882396 | 0.711657244 | 0.641775362 | 0.0380292 | 0.1086897 |
| 16 | 0.7418404 | 0.823973559 | 0.8802667384 | 0.753366227 | 0.761504743 | 0.0301347 | 0.0305234 |
| 21 | 0.78471377 | 0.862998692 | 0.912548481 | 0.791712354 | 0.826684706 | 0.1550324 | 0.0034005 |

FIG. 19B: Correlation Among Antibody Levels in Female Population

All

| Field | All Regions | SS Africa | North Africa | Latin America | SE Asia | East Europe | Asia |
|---|---|---|---|---|---|---|---|
| Rubella Antibody Level | 0.01696 | 0.01725 | 0.02820 | 0.02087 | 0.01259 | 0.04209 | -0.00071 |
| Hep A Optical Density | 0.00289 | -0.01292 | -0.00383 | 0.00548 | 0.00428 | 0.01470 | 0.01250 |
| Measles Dade | 0.05962 | 0.02176 | 0.02851 | 0.04458 | 0.01731 | 0.05282 | 0.05664 |
| Measles Zeus | -0.00011 | -0.00678 | 0.00019 | 0.00005 | -0.04094 | -0.01052 | -0.00276 |
| Measles Ratios (Zeus) | -0.01871 | 0.00109 | 0.00262 | 0.00396 | -0.02531 | 0.01040 | 0.01574 |
| Measles Titre (Dade) | 0.00311 | 0.01208 | 0.03572 | 0.03274 | 0.00604 | 0.04483 | 0.02312 |
| Mumps Optical Density (Dade) | 0.04576 | 0.01728 | 0.02362 | 0.04142 | 0.01191 | 0.01783 | 0.02968 |
| Mumps Titration Dilution | -0.01614 | 0.01365 | 0.01055 | 0.00607 | -0.00101 | 0.00922 | -0.00684 |
| Varicella Titration Dilution | 0.58748 | 0.20802 | 0.20782 | 0.38211 | 0.34543 | 0.19549 | 0.44194 |

Males

| Field | All Regions | SS Africa | North Africa | Latin America | SE Asia | East Europe | Asia |
|---|---|---|---|---|---|---|---|
| Rubella Antibody Level | 0.00934 | 0.00894 | 0.04803 | -0.00329 | 0.09510 | 0.08321 | -0.00672 |
| Hep A Optical Density | 0.03123 | -0.00313 | -0.04762 | 0.03915 | 0.02641 | 0.07062 | 0.13102 |
| Measles Dade | 0.06740 | 0.09839 | -0.00457 | 0.05990 | 0.02038 | 0.08383 | 0.07644 |
| Measles Zeus | -0.00961 | 0.00902 | -0.02355 | 0.00266 | -0.02102 | 0.05920 | -0.03069 |
| Measles Ratios (Zeus) | -0.02176 | 0.01126 | -0.03130 | -0.02775 | -0.03309 | 0.03816 | 0.08083 |
| Measles Titre (Dade) | -0.01926 | -0.03419 | 0.06316 | 0.00003 | -0.04670 | 0.04905 | -0.03836 |
| Mumps Optical Density (Dade) | 0.08632 | 0.10904 | 0.05878 | 0.03885 | 0.00055 | 0.01187 | 0.08915 |
| Mumps Titration Dilution | -0.06019 | -0.05772 | 0.06635 | -0.03401 | -0.03514 | -0.01228 | 0.06619 |
| Varicella Titration Dilution | 0.66187 | 0.65630 | 0.32436 | 0.46052 | 0.70381 | 0.34140 | 0.72795 |

Females

| Field | All Regions | SS Africa | North Africa | Latin America | SE Asia | East Europe | Asia |
|---|---|---|---|---|---|---|---|
| Rubella Antibody Level | 0.01442 | 0.04756 | 0.02948 | 0.04313 | 0.02369 | 0.00416 | -0.08200 |
| Hep A Optical Density | 0.02049 | 0.00261 | 0.04691 | 0.01933 | 0.04588 | 0.01965 | -0.00638 |
| Measles Dade | 0.05086 | 0.03566 | 0.05466 | 0.00542 | 0.07098 | 0.05822 | 0.08963 |
| Measles Zeus | -0.00056 | -0.00007 | -0.00366 | -0.00014 | -0.01859 | -0.04096 | -0.02937 |
| Measles Ratios (Zeus) | -0.03599 | -0.01193 | 0.00604 | -0.04593 | -0.03991 | -0.00520 | -0.03539 |
| Measles Titre (Dade) | 0.01452 | 0.02839 | 0.09569 | 0.04440 | -0.01764 | 0.04325 | 0.00504 |
| Mumps Optical Density (Dade) | 0.10831 | 0.03880 | 0.05131 | 0.10664 | 0.01757 | 0.01200 | 0.05186 |
| Mumps Titration Dilution | -0.06906 | 0.00698 | -0.02306 | -0.00748 | 0.00162 | 0.01922 | 0.04560 |
| Varicella Titration Dilution | 0.70476 | 0.38696 | 0.51598 | 0.70693 | 0.42507 | 0.42465 | 0.68231 |

FIG. 20
Correlations of Various DB Variables With Varicella OD

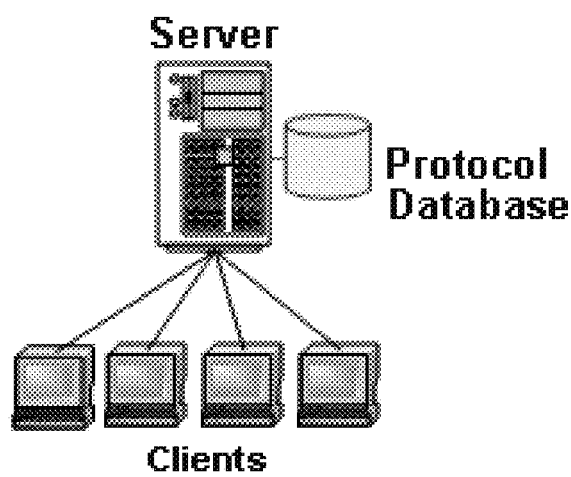
FIG. 21D-1 - Client-server model

FIG. 21D-2. Data Mining Tool form.

| Parameters | |
|---|---|
| Full Data Source | data\WellStat\CIP_data.xls ... |

Figure 21D-2:
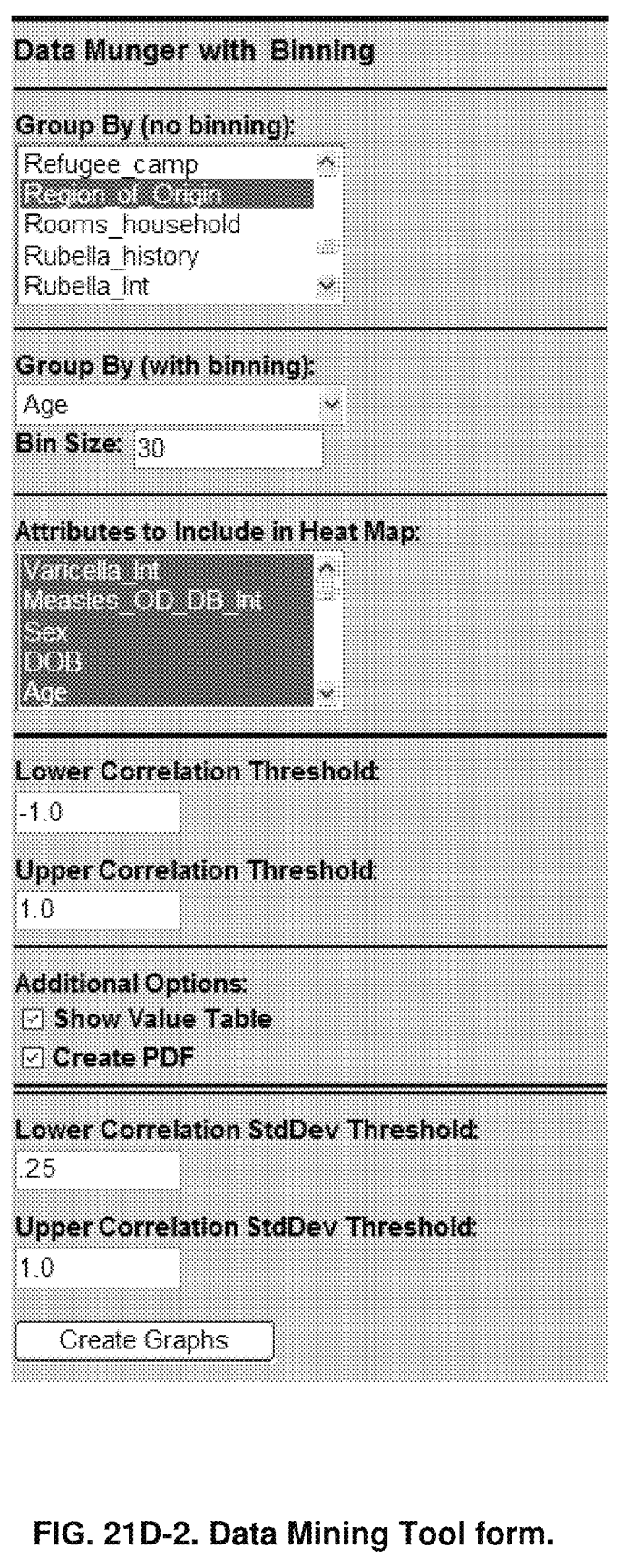
Figure 21D-5:
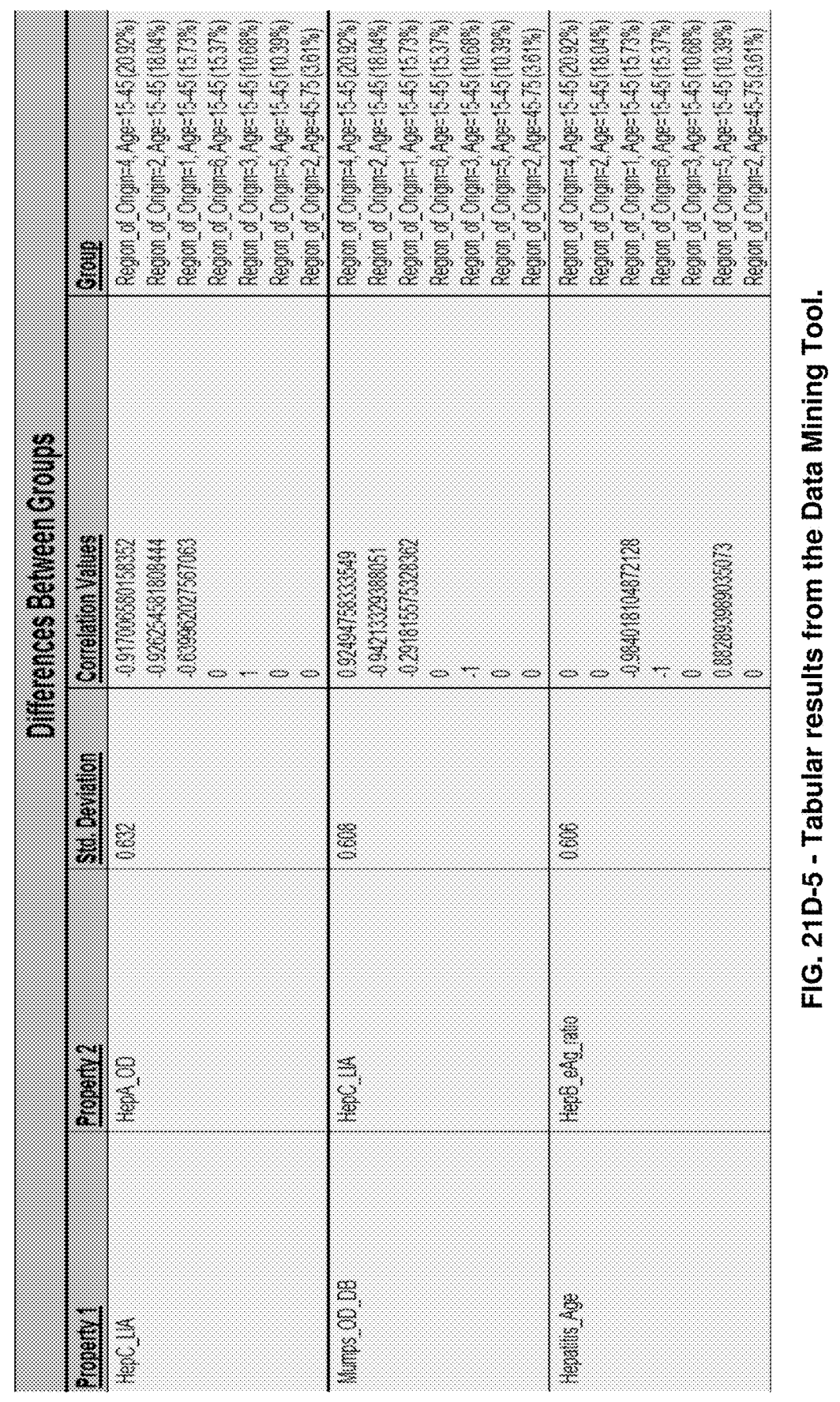

FIG. 21D-3 - Top level data source parameter.

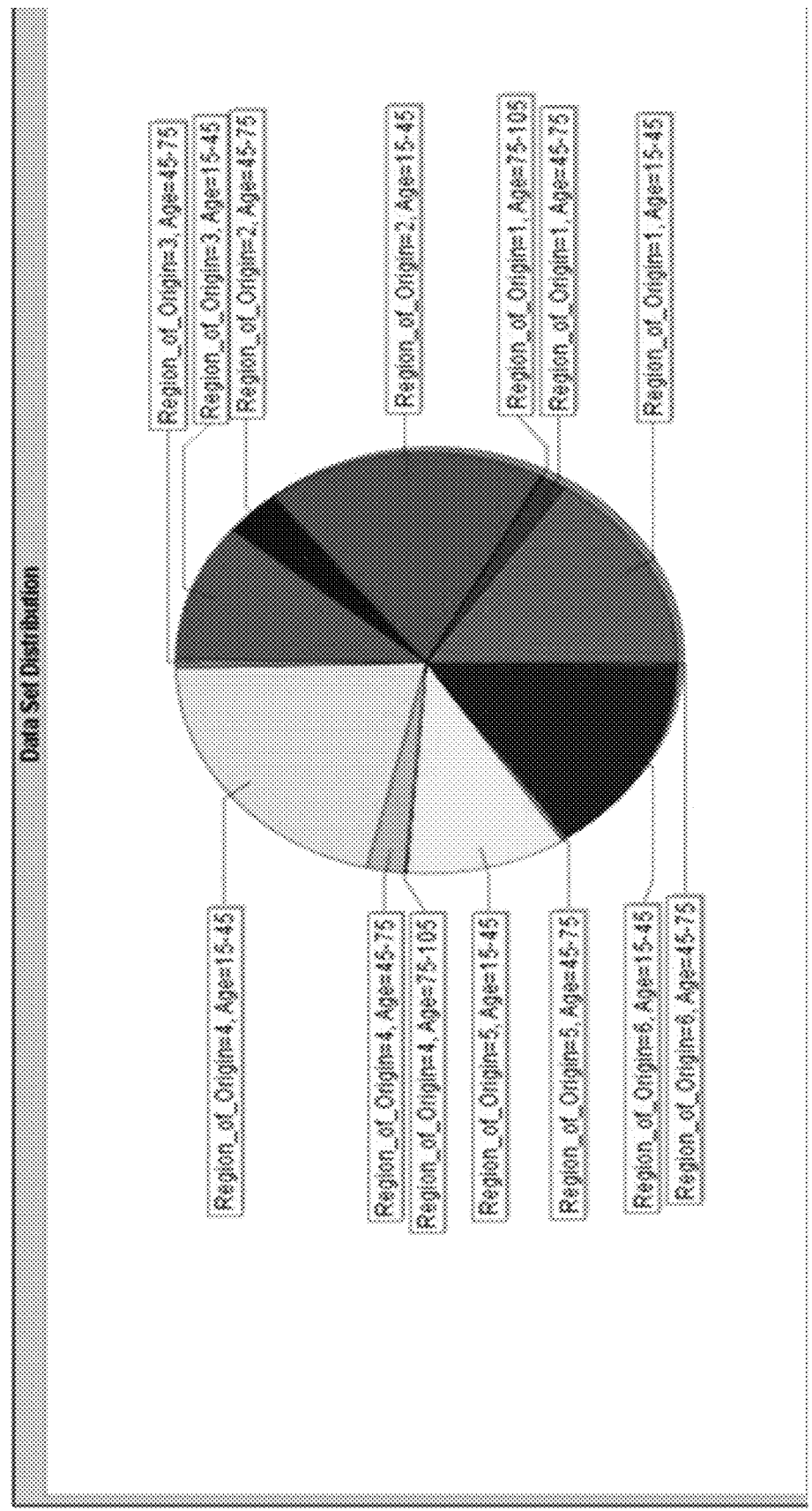
FIG. 21D-4A - Graphical results from the Data Mining Tool.

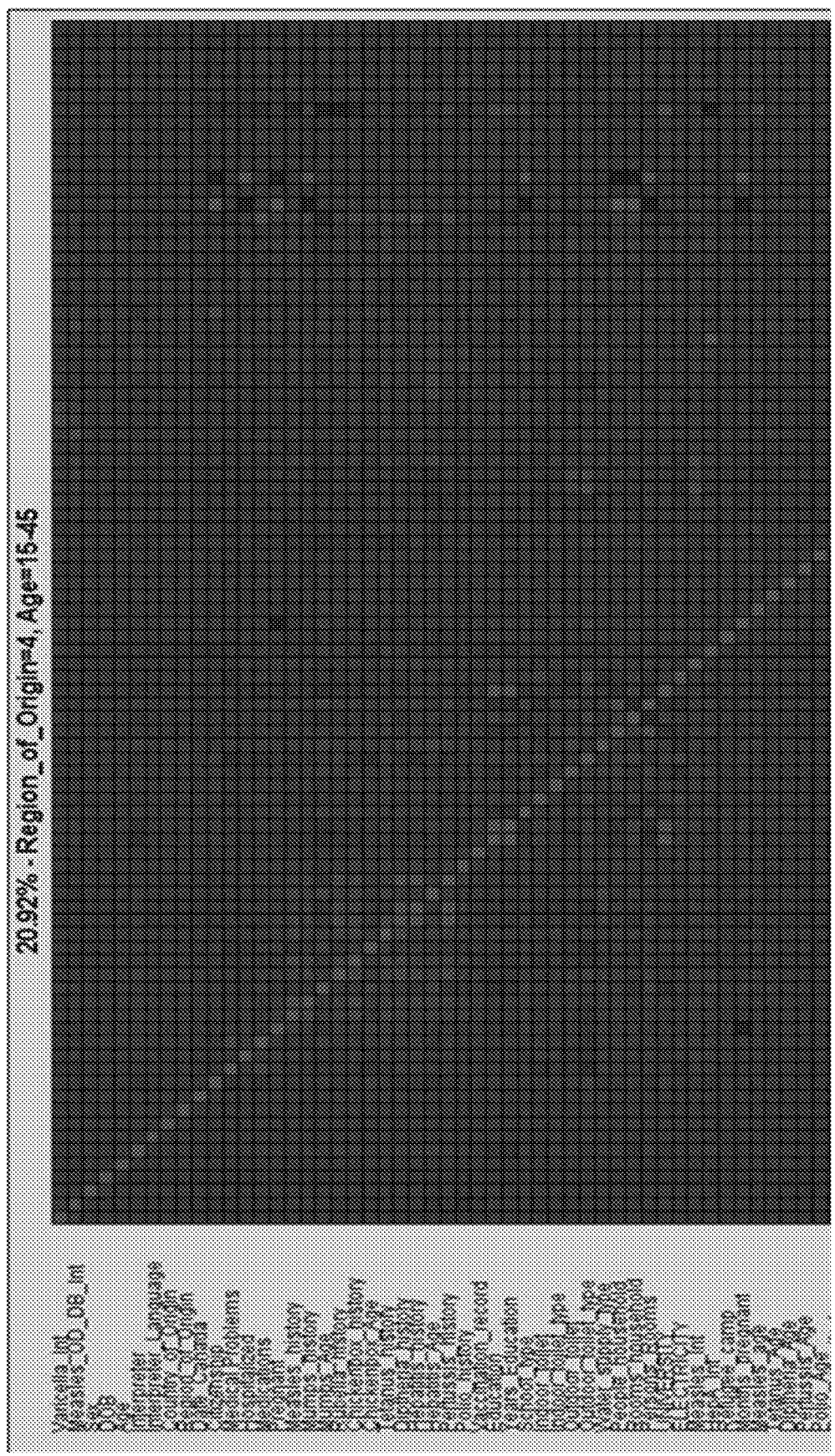
FIG. 21D-4B - Graphical results from the Data Mining Tool.

| 20.92% - Region_of_Origin=4, Age=15-45 | | |
|---|---|---|
| Property1 | Property2 | Corr Coefficient |
| Varicella_Int | Varicella_Int | 1.000 |
| Varicella_Int | Measles_OD_DB_Int | 0.128 |
| Varicella_Int | Sex | 0.000 |
| Varicella_Int | DOB | 0.000 |
| Varicella_Int | Age | 0.000 |
| Varicella_Int | Interpreter | -0.019 |
| Varicella_Int | Interpreter_Language | 0.000 |
| Varicella_Int | Country_of_Origin | 0.000 |
| Varicella_Int | Region_of_Origin | 0.000 |
| Varicella_Int | Date_Canada | 0.000 |
| Varicella_Int | Citizenship | 0.018 |
| Varicella_Int | Medical Problems | -0.100 |
| Varicella_Int | Hospitalized | -0.083 |
| Varicella_Int | Medications | -0.021 |
| Varicella_Int | Pregnant | -0.082 |
| Varicella_Int | Measles_history | 0.014 |
| Varicella_Int | Mumps_history | -0.078 |
| Varicella_Int | Mumps_Age | 0.132 |
| Varicella_Int | Rubella_history | -0.083 |
| Varicella_Int | Chickenpox_history | 0.023 |
| Varicella_Int | Chickenpox_Age | 0.091 |
| Varicella_Int | Tetanus_history | 0.082 |
| Varicella_Int | Diptheria_history | -0.158 |
| Varicella_Int | Hepatitis_history | -0.102 |
| Varicella_Int | Hepatitis_Age | -0.023 |
| Varicella_Int | Pertussis_history | -0.194 |
| Varicella_Int | Polio_history | 0.038 |
| Varicella_Int | Vaccination_record | 0.000 |

FIG. 21D-4C - Graphical results from the Data Mining Tool.

FIG. 21D-5 - Tabular results from the Data Mining Tool.

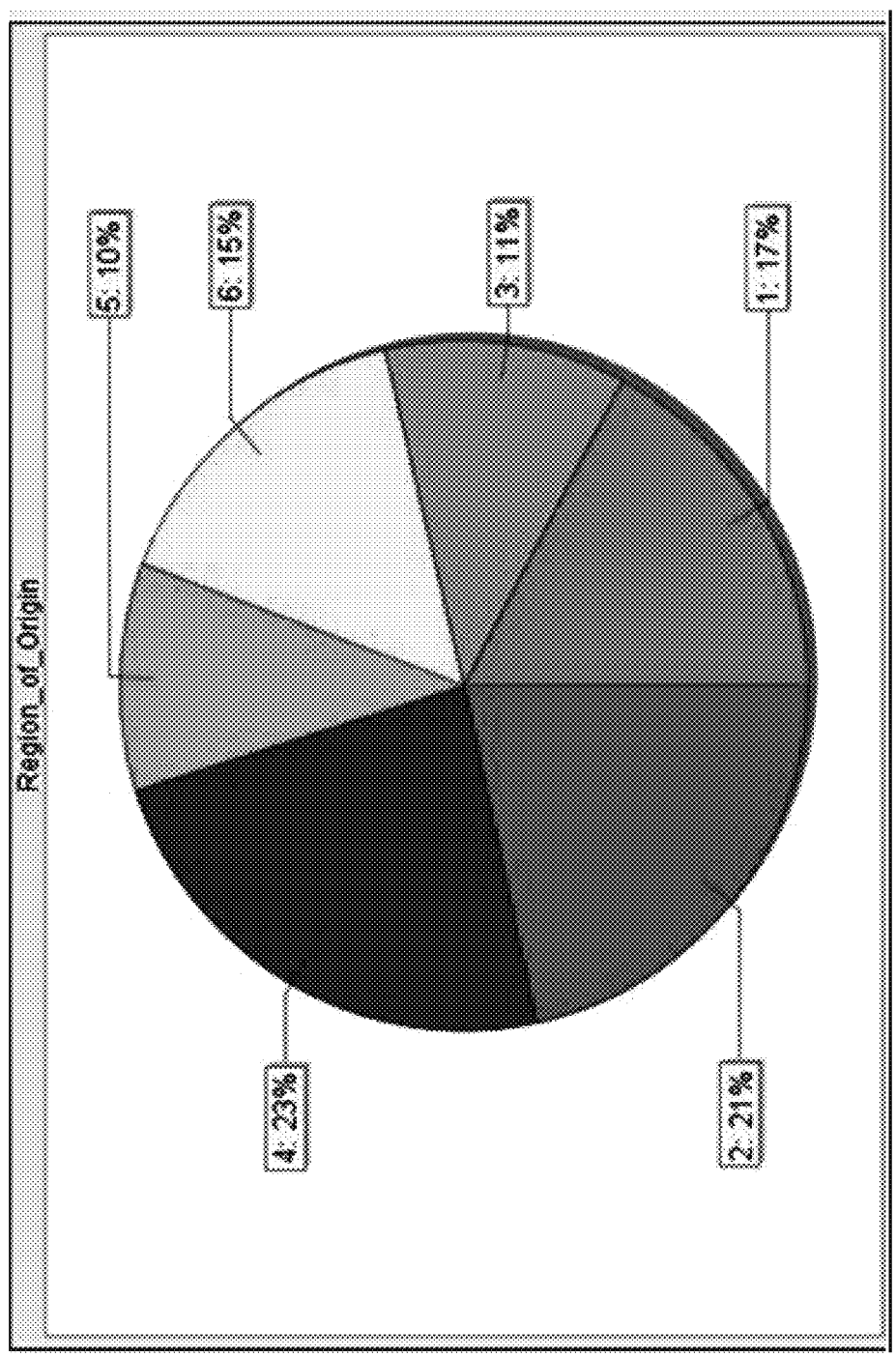
FIG. 21D-6A - Pie chart results of grouping properties from the Data Mining Tool.

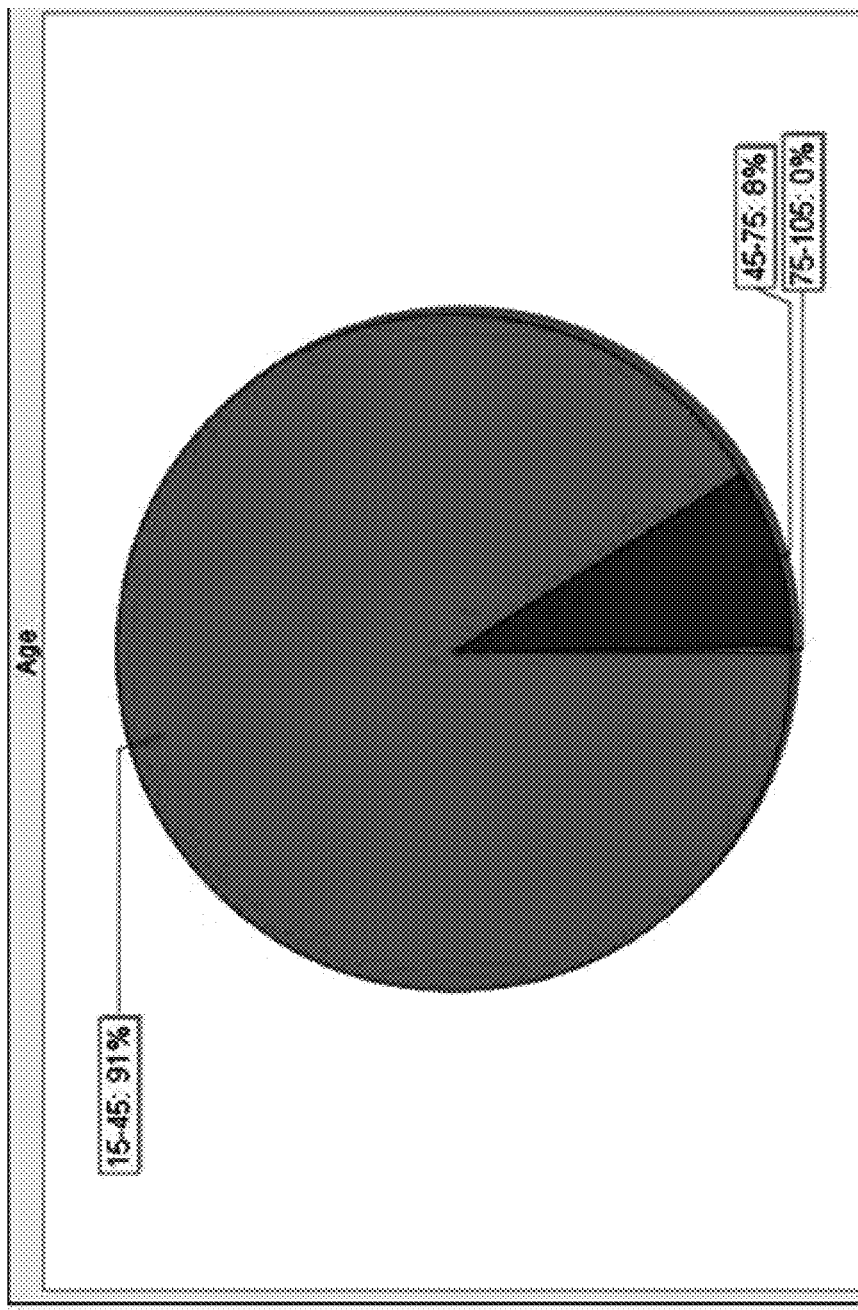
FIG. 21D-6B - Pie chart results of grouping properties from the Data Mining Tool. (continued)

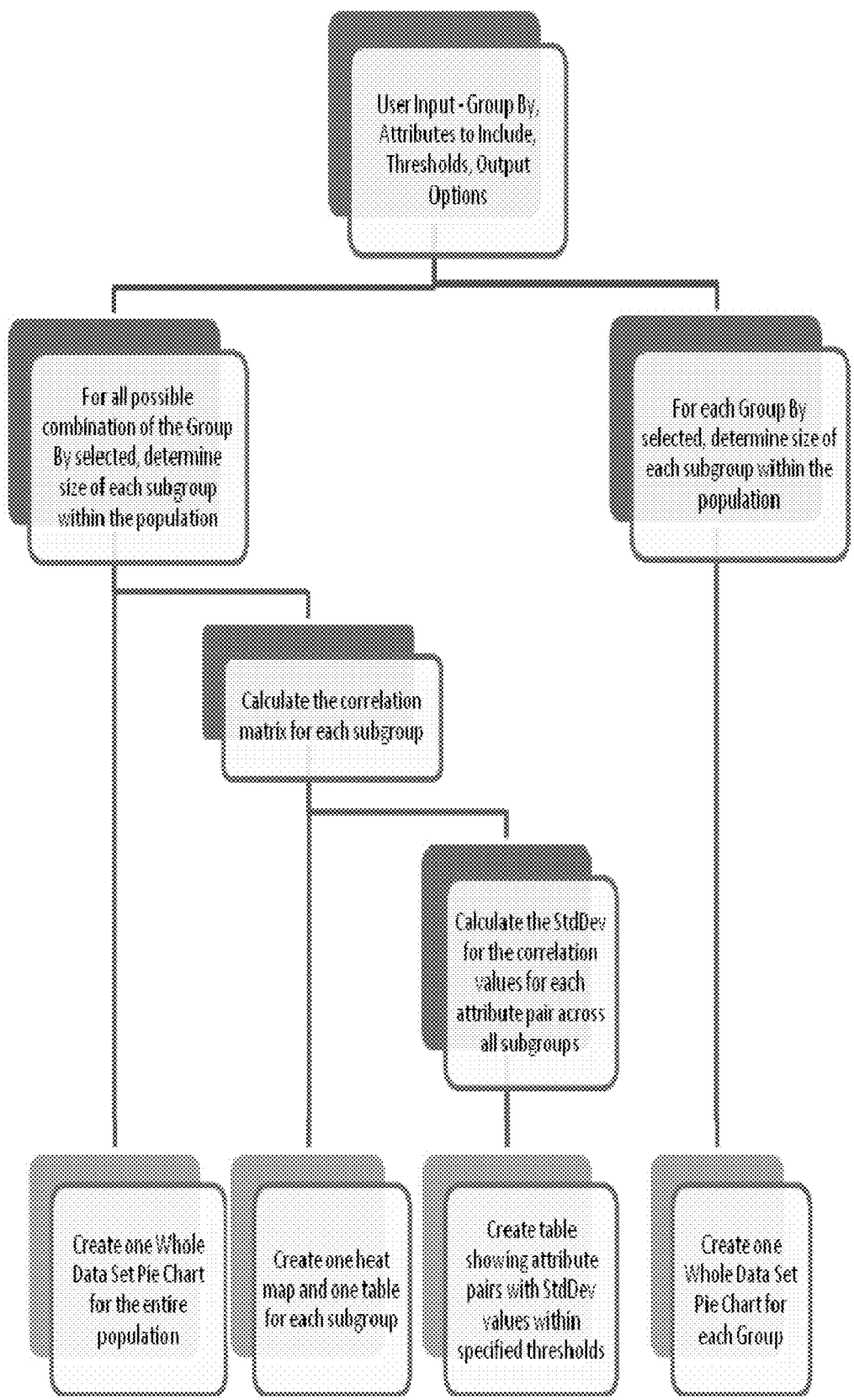
FIG. 21D-7 - Data Mining Tool flow chart.

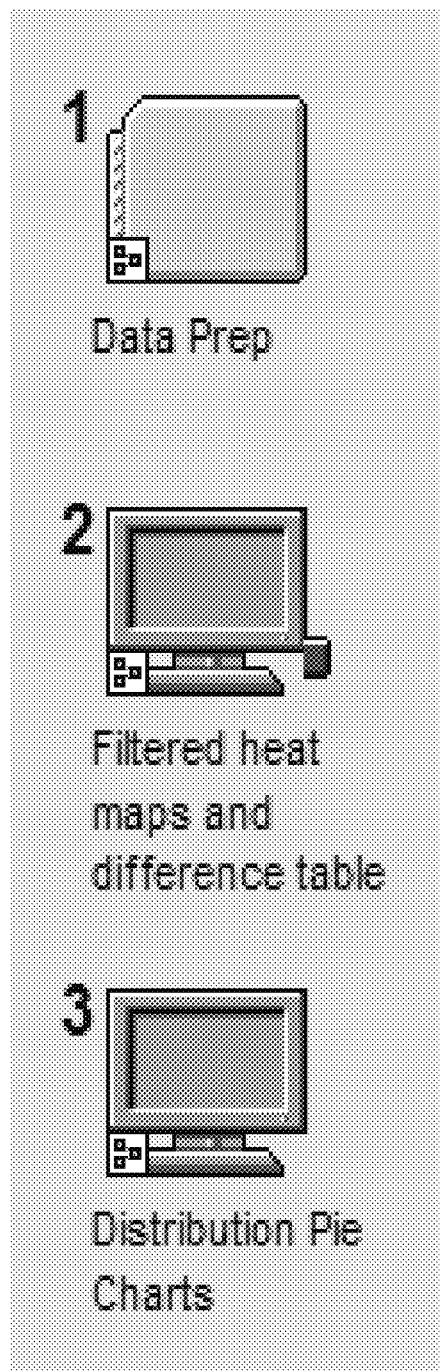
FIG. 21D-8 - Data Mining Tool protocol.

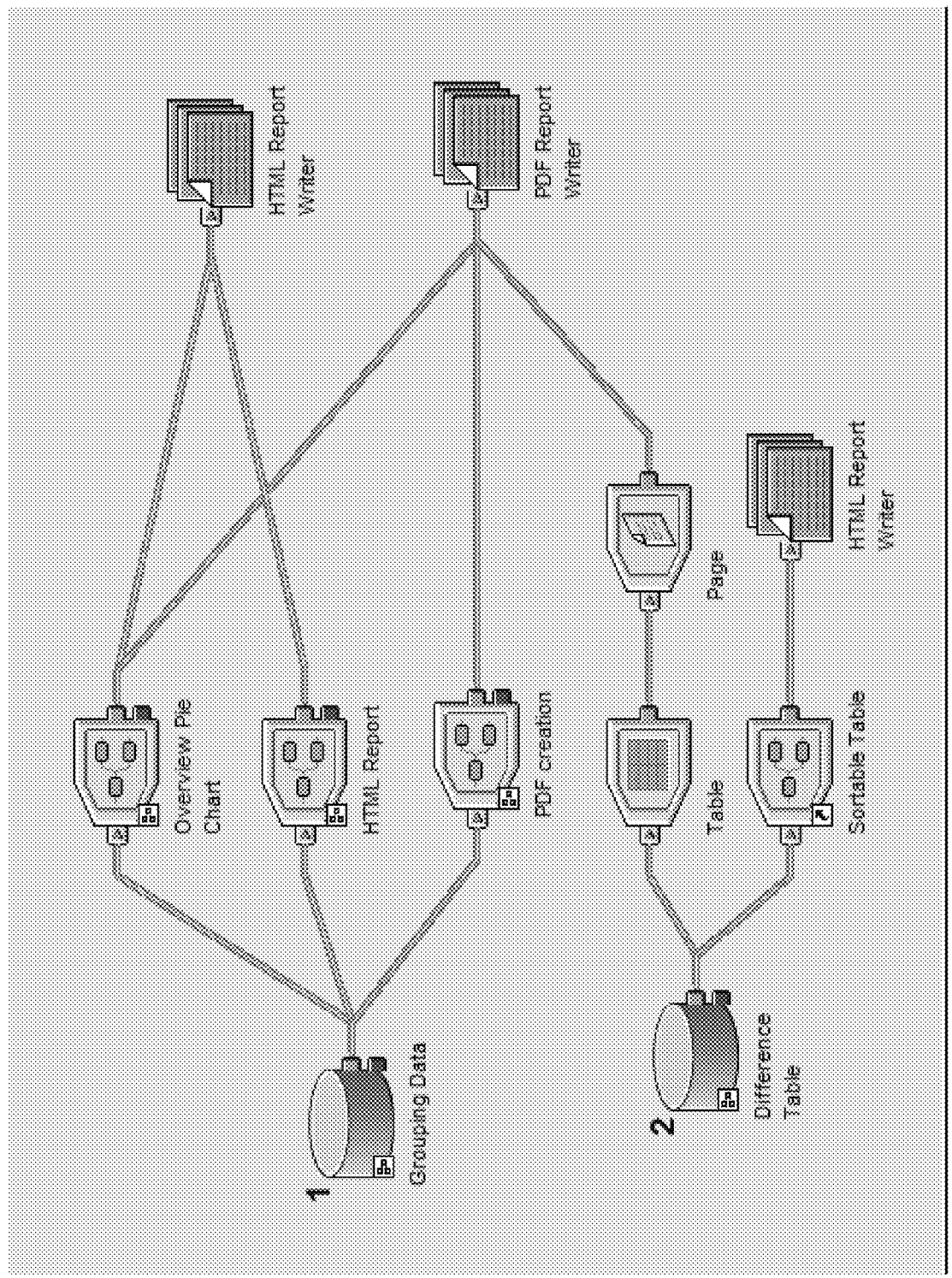
FIG. 21D-9 - Data Mining Tool subprotocols.

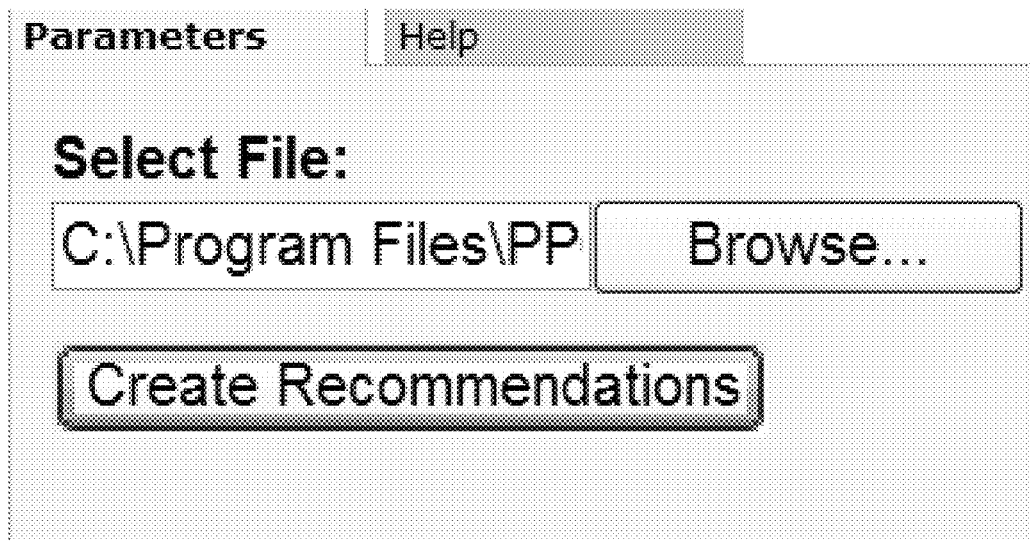
FIG. 21D-10 - Single Patient Vaccine Recommendations user interface.

| Parameters | |
|---|---|
| Rules Definition Source | data\WellStat\Rule_Definition.xls |
| Conditions Source | data\WellStat\Conditions.xls |
| Rules Source | data\WellStat\Rules.xls |
| Full Data Source | data\WellStat\CIP_data.xls |
| Literature Source | data\WellStat\Literature.xls |
| Keyword Source | data\WellStat\Rules_keywords.xls |

FIG. 21D-11 - Single Patient Vaccine Recommendations top level parameter list.

Results

Patient:1

| Conditions | Suggested Action | Internal References | External References |
|---|---|---|---|
| Filaria_Int_eq_eq | Re-test after several weeks to determine if they are in the early stages of infection. | | |
| Strongyloides_Int eq + | Examination of stool samples. Microscopic examination of stool specimens is insensitive; estimates for a single positive stool examination in cases of uncomplicated infection range from 0 to 66%. To overcome this lack of sensitivity, investigators have recommended examination of up to seven stool specimens; use of more sensitive and labor-intensive methods of stool examination; use of agar plate cultures; and collection of alternate specimens, such as duodenal aspirates. Due to these difficulties in diagnosing the progress of strongyloides infections, reported efficacies of drugs used to treat strongyloides infection vary widely. Chemotherapy is advocated and considered an effective control measure for the reduction of morbidity resulting from intestinal nematode infection. The current drug of choice for strongyloides is the benzimidazole compound, thiabendazole. This drug requires a three day regimen. Another drug being considered is ivermectin, which may be preferable, because it requires only one dose. Post-treatment follow-up testing recommendations would require stool sampling 30 days post-treatment. | Satoh, M. et al., Predictive markers for development of strongyloidiasis in patients infected with Both Strongyloides stercoralis and HTLV-1. Clin. Exp. Immunol. 133: 391-96 (2003). Atkins, N.S. et al., L3 antigen-specific antibody isotype responses in human strongyloidiasis: correlations with larval output. Parasite Immunology 21: 517-25 (1999). | |

FIG. 21D-12A - Single Patient Vaccine Recommendations results table.

| Patient Data | | | | | |
|---|---|---|---|---|---|
| Attribute | Value | Percentile Total | Percentile Sex = 1 | Percentile Age = 30-50 | Percentile Region = 2 |
| Age | 35 | | | | |
| Chickenpox_Age | | | | | |
| Chickenpox_history | 0 | | | | |
| Citizenship | 0 | | | | |
| CMV_Int | Reactive | | | | |
| CMV_OD | 245.10 | 50.72 | 50.00 | 48.13 | 37.00 |
| Country_of_Origin | 1 | | | | |
| Country_of_Origin_name | India | | | | |
| Date_recruited | 16049 | | | | |
| Date_Canada | 01-Jul-01 | | | | |
| Diptheria_Ab | 0.248 | | | | |
| Diptheria_Age | 91 | | | | |
| Diptheria_history | 0 | | | | |
| Diptheria_OD | 0.433 | 64.79 | 70.46 | 65.47 | 58.67 |
| DOB | 02-Sep-68 | | | | |
| Education | 2 | | | | |
| ELECTRICITY | 1 | | | | |
| Filaria_Ab_OD | 0.284 | 88.53 | 90.49 | 88.40 | 78.00 |
| Filaria_Int | eq | | | | |
| HepA_Int | Reactive | | | | |
| HepA_OD | 0.091 | 62.77 | 58.19 | 64.53 | 78.00 |

FIG. 21D-12B - Single Patient Vaccine Recommendations results table. (continued)

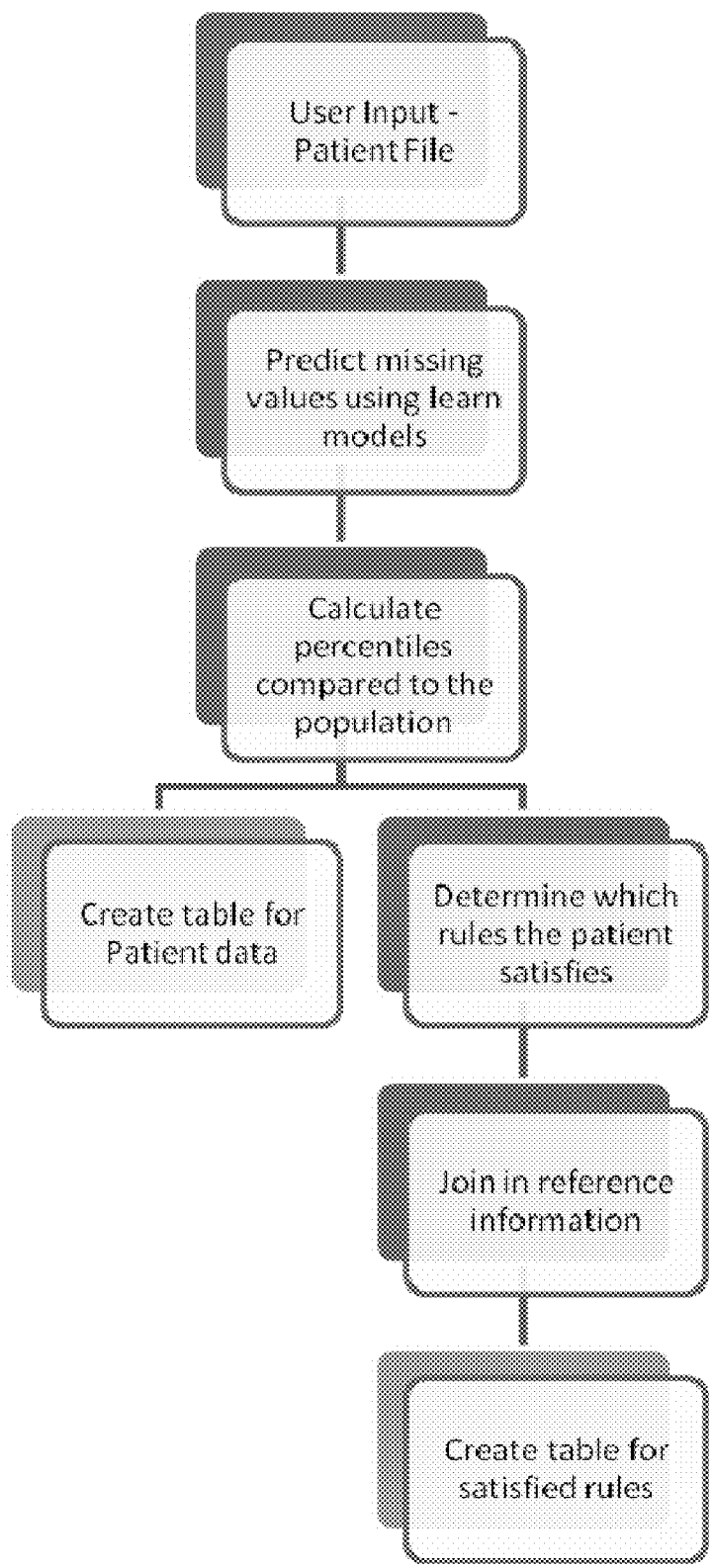
FIG. 21D-13 - Single Patient Vaccine Recommendations flow chart.

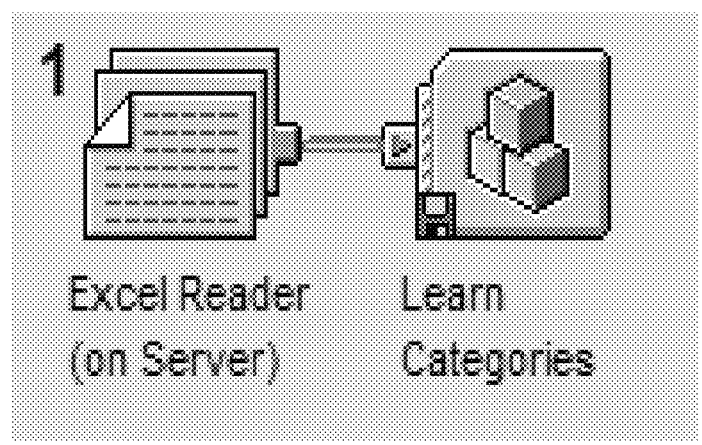
FIG. 21D-14 - Learn Models subprotocol.

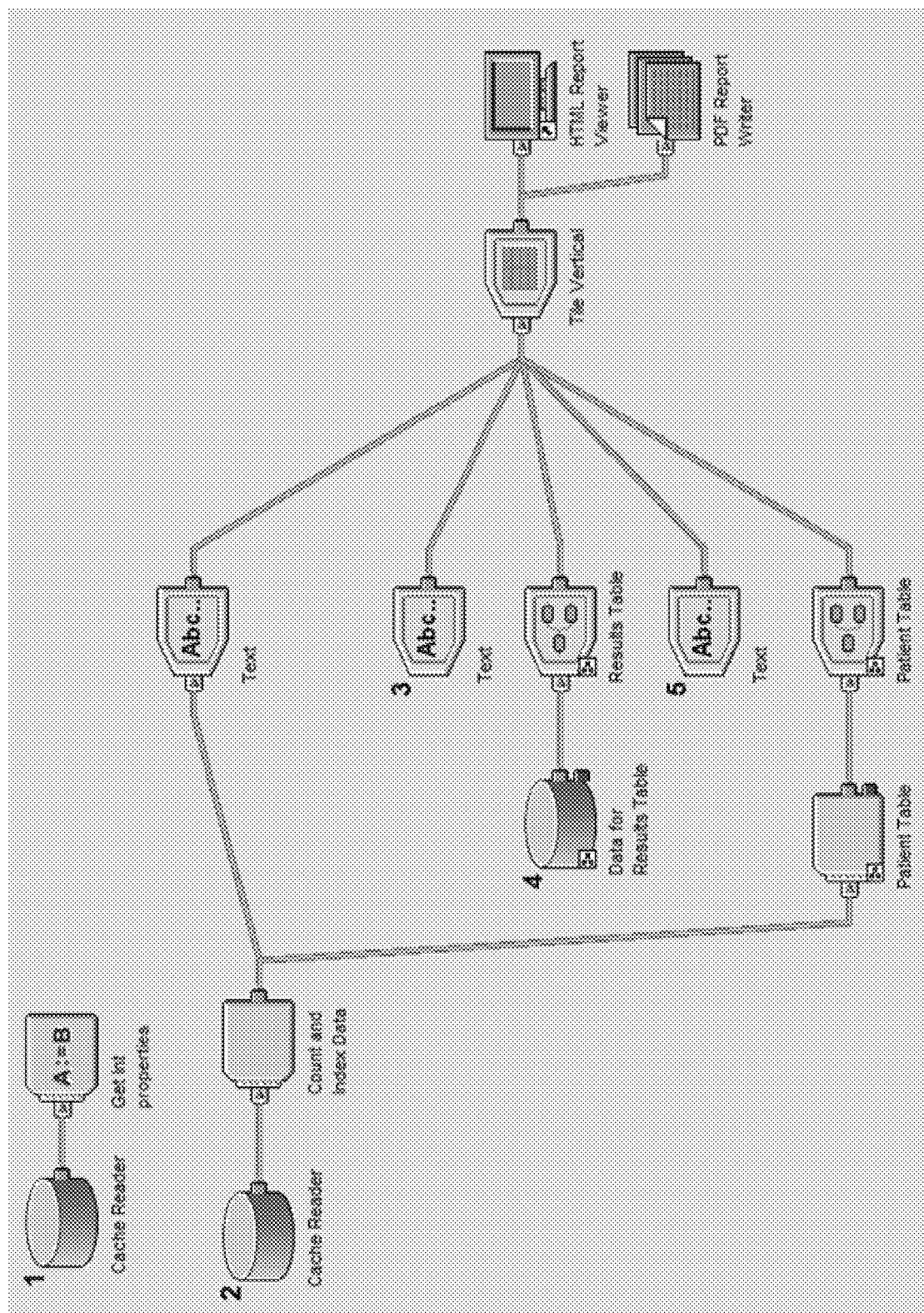
FIG. 21D-15 - Protocol for generating the Single Patient Vaccine Recommendations results table.

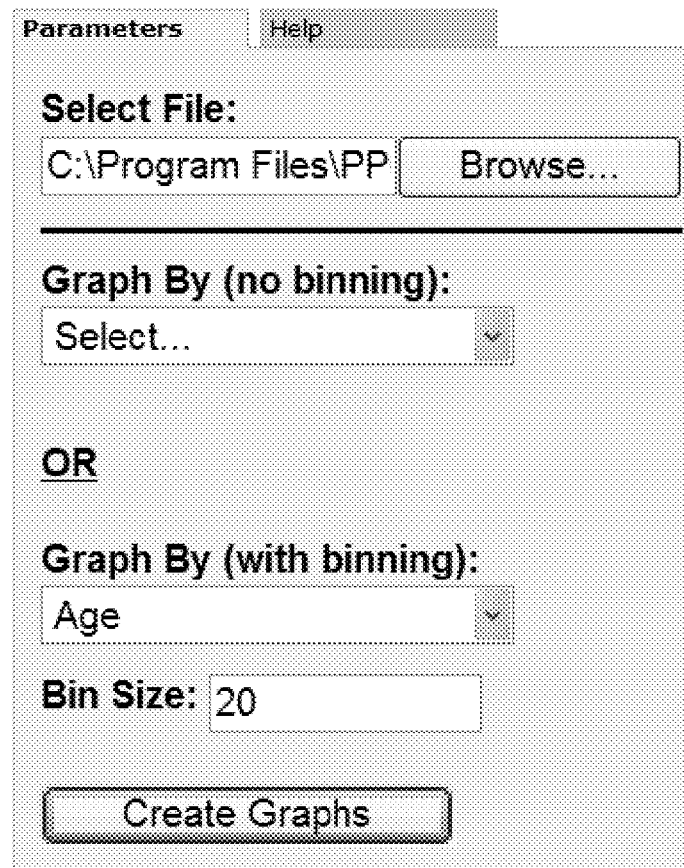
FIG. 21D-16 - Patient Population Rule Mining form.

| | |
|---|---|
| Rules Definition Source | data\WellStat\Rule_Definition.xls |
| Conditions Source | data\WellStat\Conditions.xls |
| Rules Source | data\WellStat\Rules.xls |

FIG. 21D-17 - Patient Population Rule Mining top level parameter list.

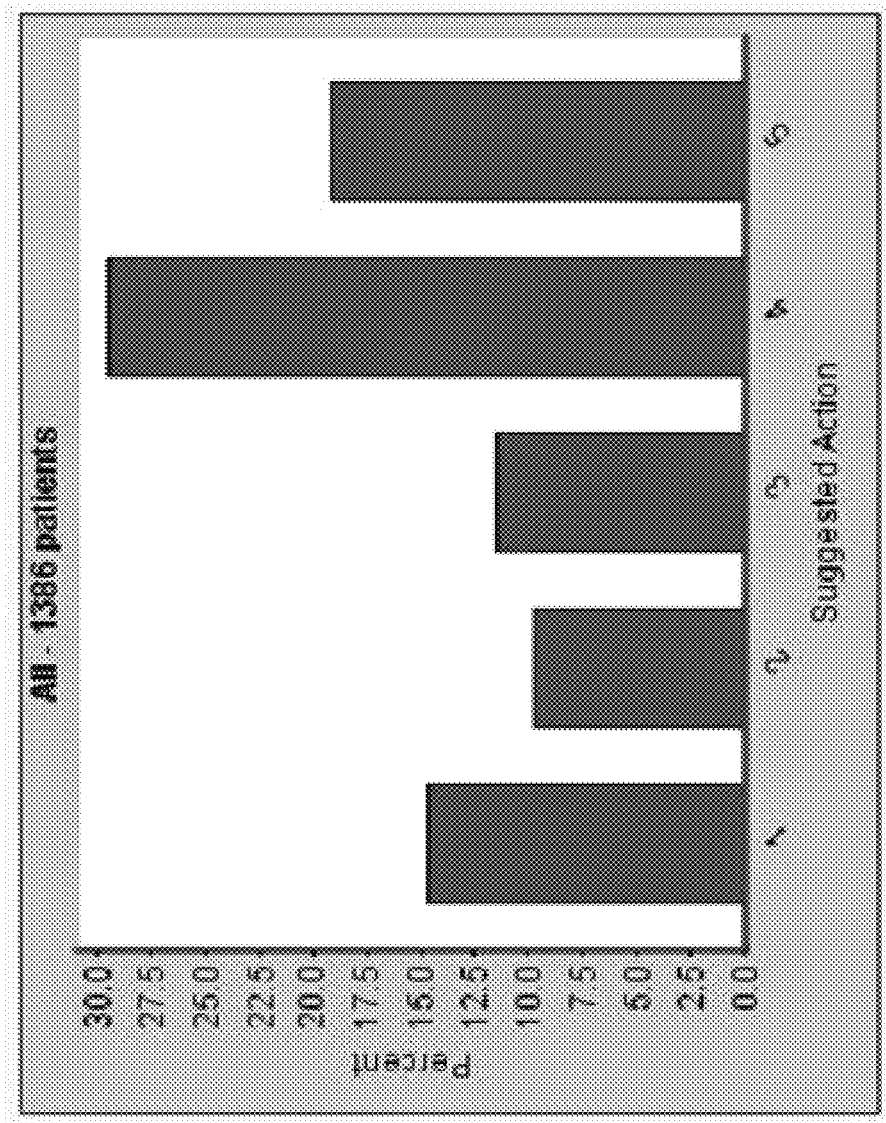
FIG. 21D-18A - Patient Population Rule Mining results

Percent Deviation Between Groups

| Rule ID | Suggested Action | StdDev |
|---|---|---|
| 1 | Praziquantel is used to treat all forms of schistosomiasis. Oxamniquine is used exclusively to treat intestinal schistosomiasis, and metrifonate is effective for the treatment of urinary schistosomiasis. According to the World Health Organization (WHO), treatment of schistosomiasis must be accompanied by health education to preclude re-infection. | 0.23 |
| 2 | Treatment with a combination of albendazole with either diethylcarbamazine or ivermectin. | 4.17 |
| 3 | Re-test after several weeks to determine if they are in the early stages of infection. | 9.30 |
| 4 | Examination of stool samples. Microscopic examination of stool specimens is insensitive, estimates for a single passive stool examination in cases of uncomplicated infection range from 0 to 66%. To overcome this lack of sensitivity, investigators have recommended examination of up to seven stool specimens; use of more sensitive and labor-intensive methods of stool examination; use of agar plate cultures; and collection of alternate specimens, such as duodenal aspirates. Due to these difficulties in diagnosing the progress of strongyloides infections, reported efficacies of drugs used to treat strongyloides infection vary widely. Chemotherapy is advocated and considered an effective control measure for the reduction of morbidity resulting from intestinal nematode infection. The current drug of choice for strongyloides is the benzimidazole compound thiabendazole. This drug requires a three day regimen. Another drug being considered is ivermectin, which may be preferable, because it requires only one dose. Post-treatment follow-up testing recommendations would require stool sampling 30 days post-treatment. | 9.71 |
| None | No Action Suggested | 6.04 |

FIG. 21D-18A1 - Patient Population Rule Mining results (Continued)

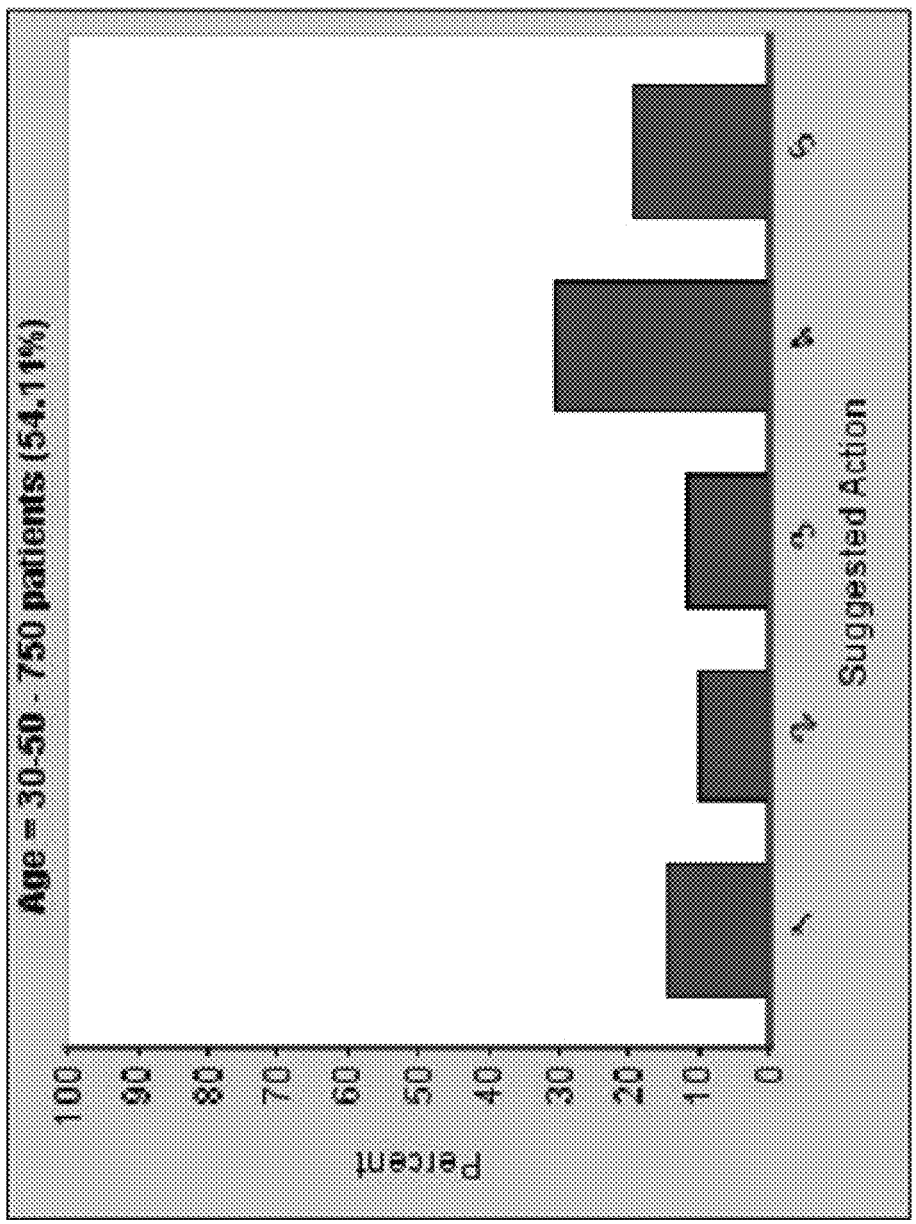
FIG. 21D-18B - Patient Population Rule Mining results.

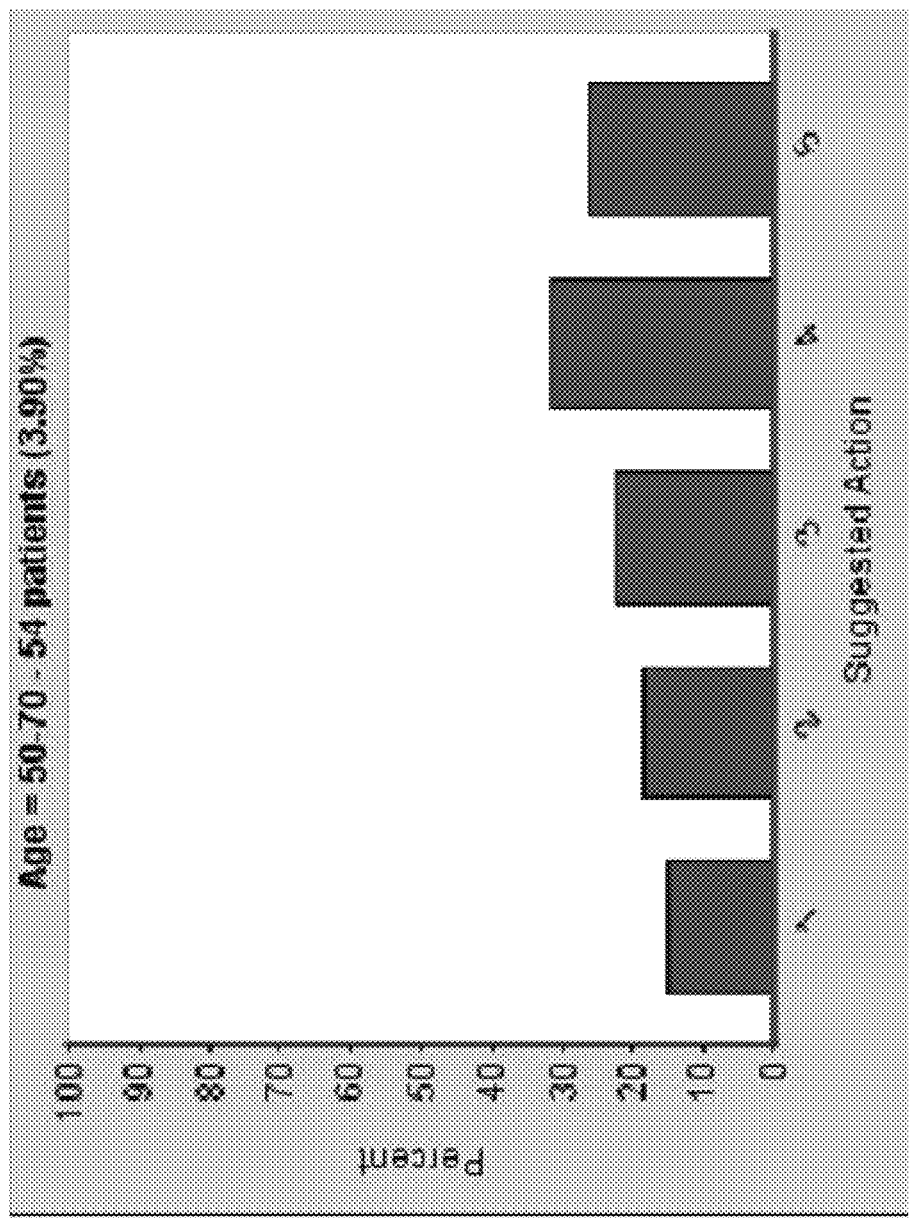
FIG. 21D-18B1 - Patient Population Rule Mining results (continued)

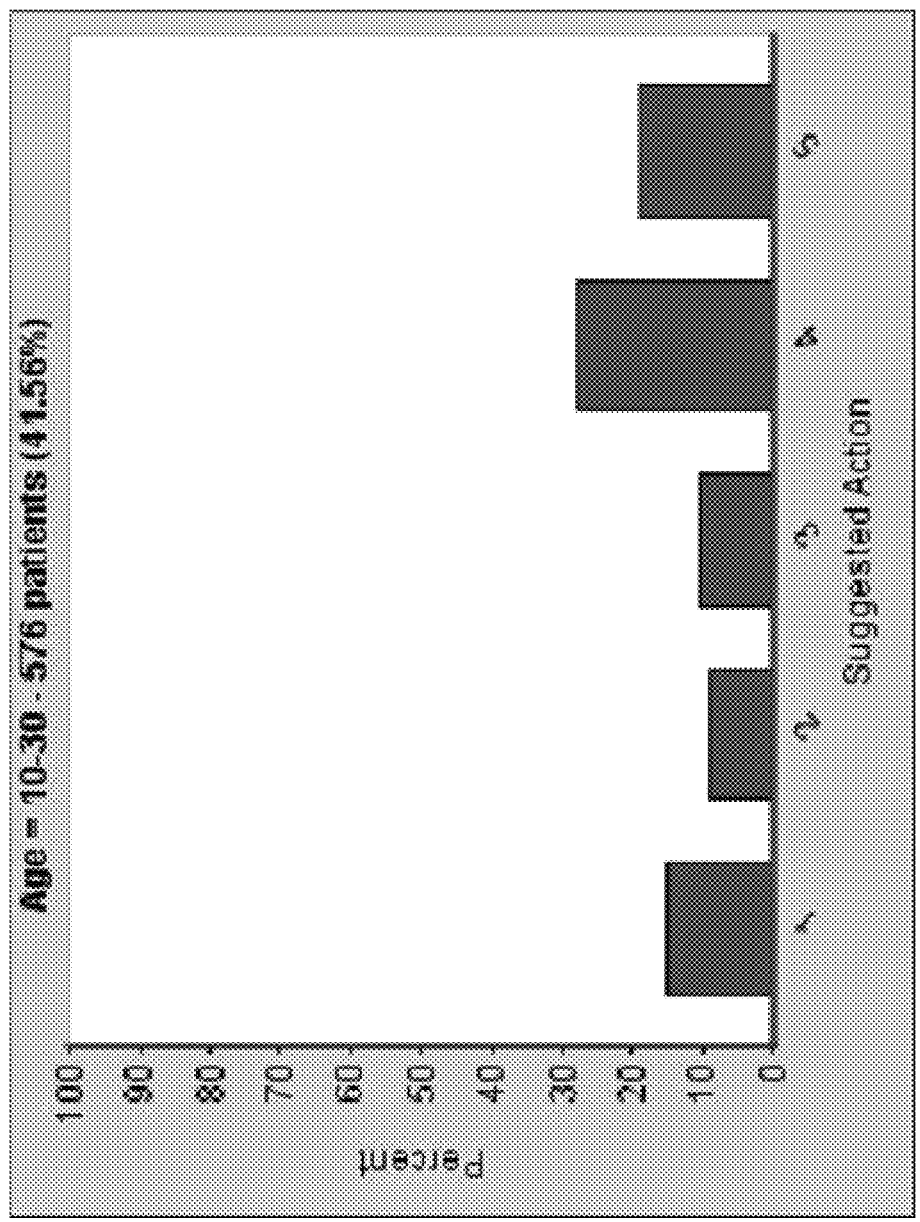
FIG. 21D-18B2 - Patient Population Rule Mining results (continued)

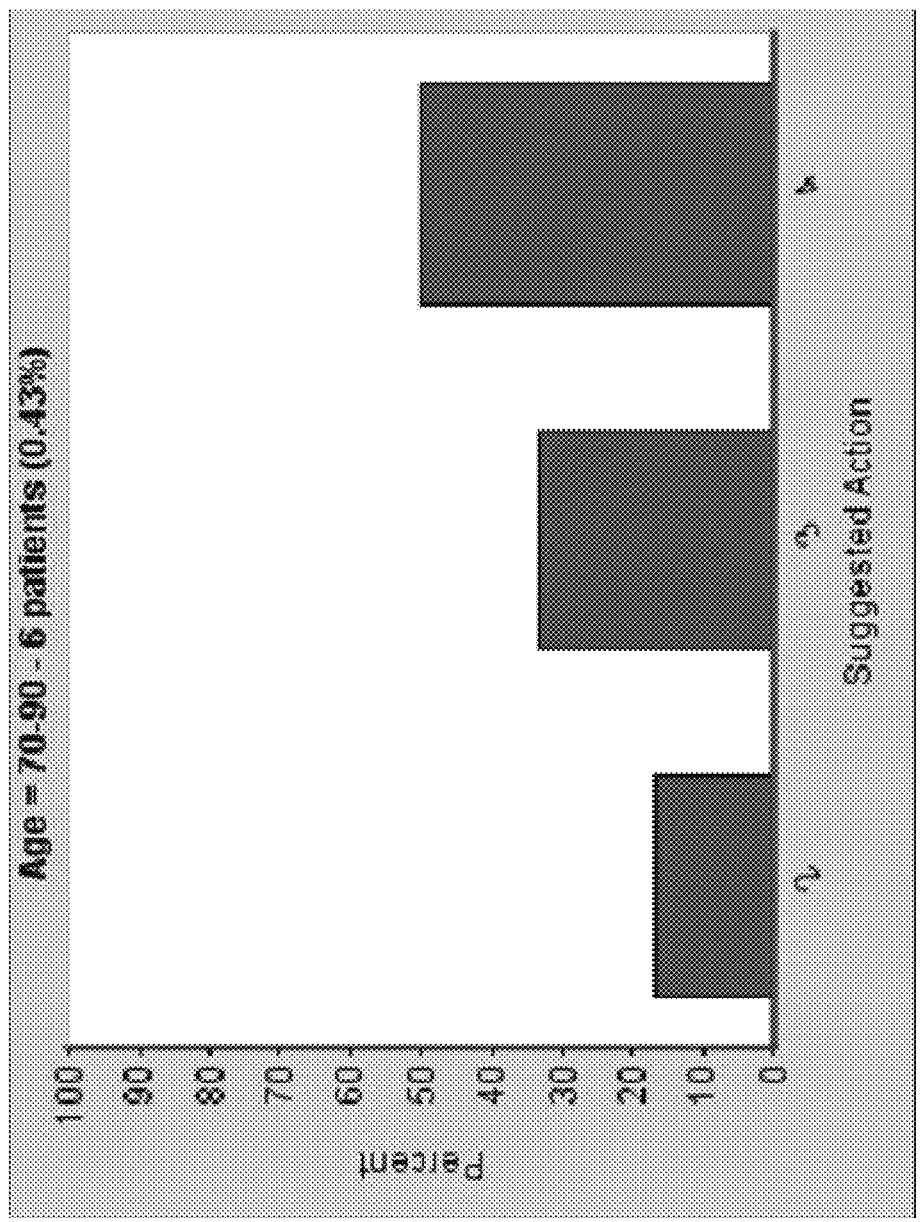
FIG. 21D-18B3 - Patient Population Rule Mining results (continued)

| ID | Select... | Conditions_Satisfied | Age | Interpreter | Interpreter_Language | Country_of_Origin |
|---|---|---|---|---|---|---|
| 2 | | Schistosoma_Int eq + Filaria_Int eq + Strongyloides_Int eq + | 31 | 0 | | Other |
| 15 | | Filaria_Int eq + Strongyloides_Int eq + | 30 | 0 | | Other |
| 44 | | Schistosoma_Int eq + Filaria_Int eq + Strongyloides_Int eq + | 31 | 0 | | Other |

| Region_of_Origin | Date_Canada | Citizenship | Medical Problems | Hospitalized | Medications | Pregnant |
|---|---|---|---|---|---|---|
| 2 | 22-May-02 | 0 | 0 | 0 | 0 | 0 |
| 2 | 25-May-99 | 3 | 0 | 0 | 0 | 0 |
| 4 | 22-Mar-02 | 0 | 0 | 1 | 0 | 0 |

FIG. 21D-19 - Table of data records used to create the bar graph in Figure 18.

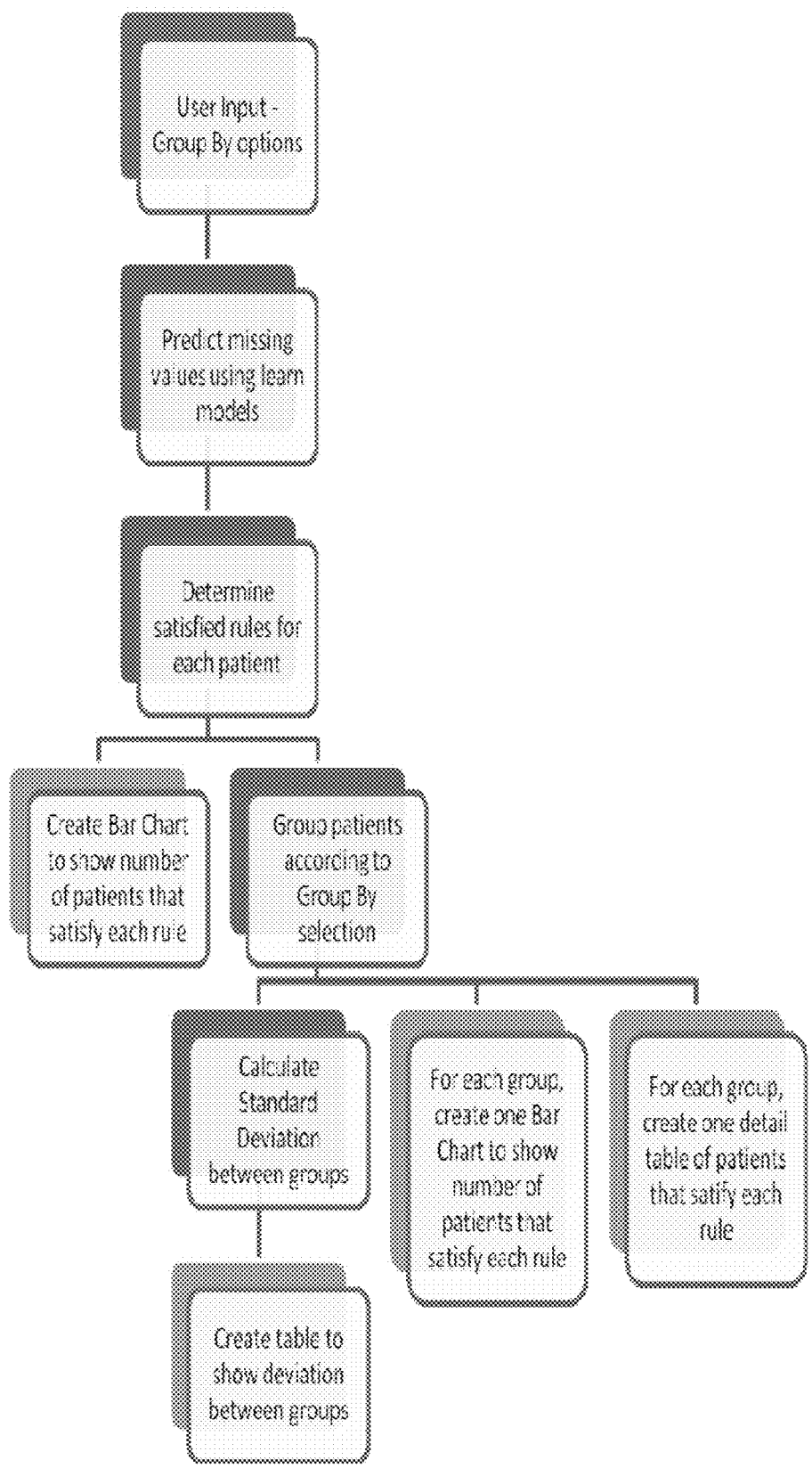
FIG. 21D-20 - Patient Population Rule Mining flow chart.

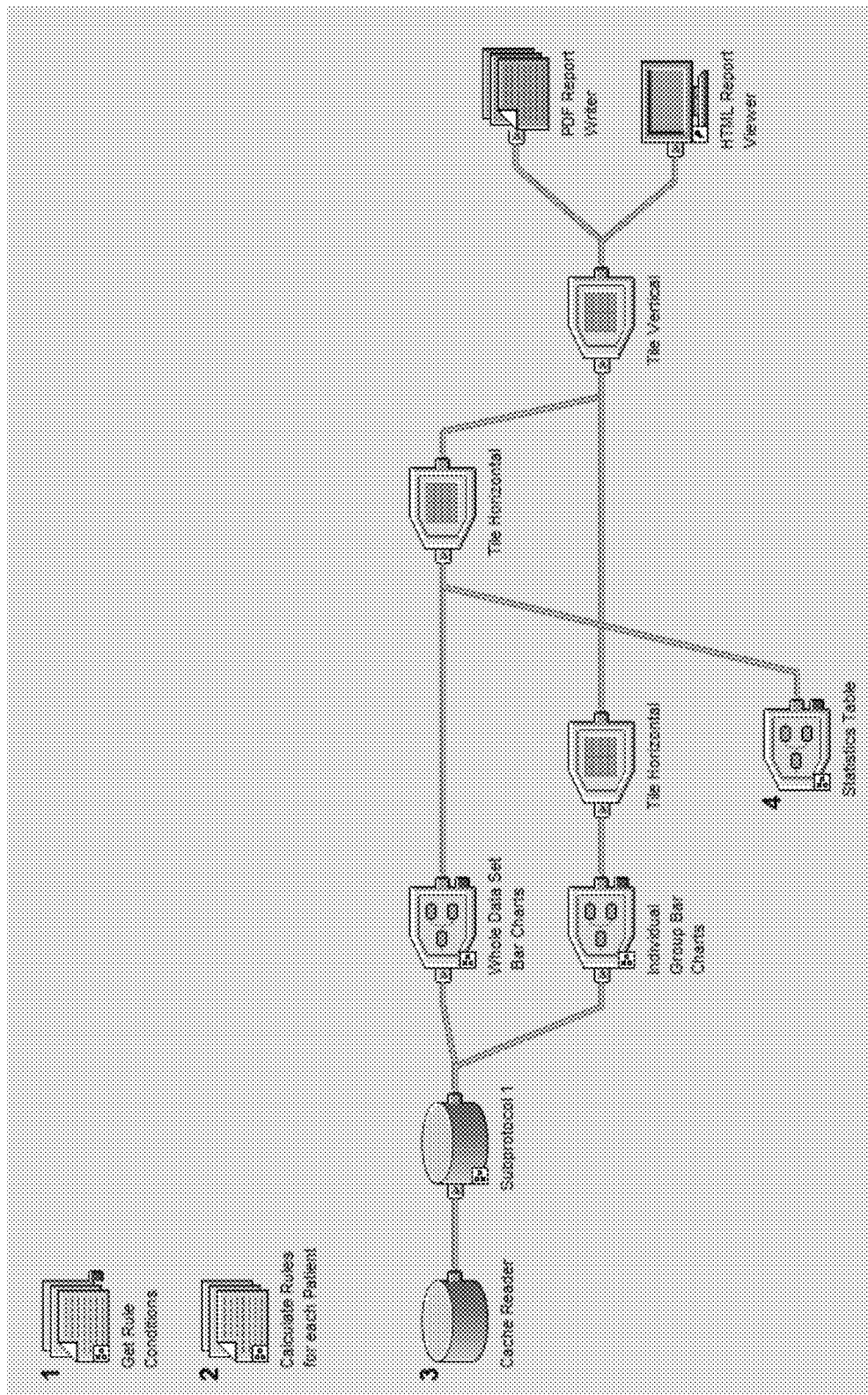
FIG. 21D-21 - Patient Population Rule Mining Protocol.

| Parameters | |
|---|---|
| Full Data Source | data\WellStat\CIP_data.xls |
| prop_list_bin | age |
| bin_size | 5 |
| stddev_upper_threshold | 2 |
| stddev_lower_threshold | .5 |

FIG. 21D-22 - Age Binned with Differences top level parameters.

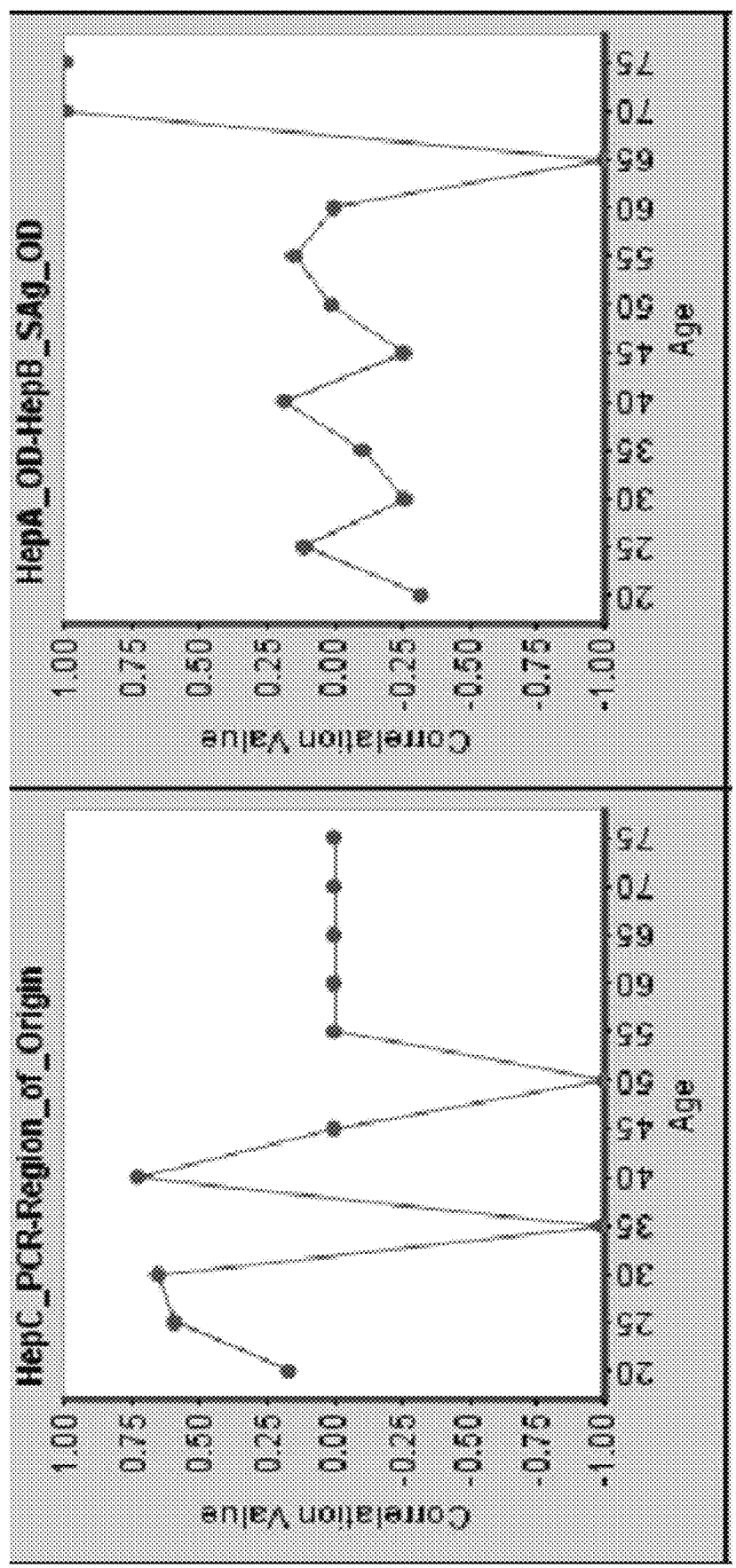
Fig. 21D-23A - Age Binned with Differences results.

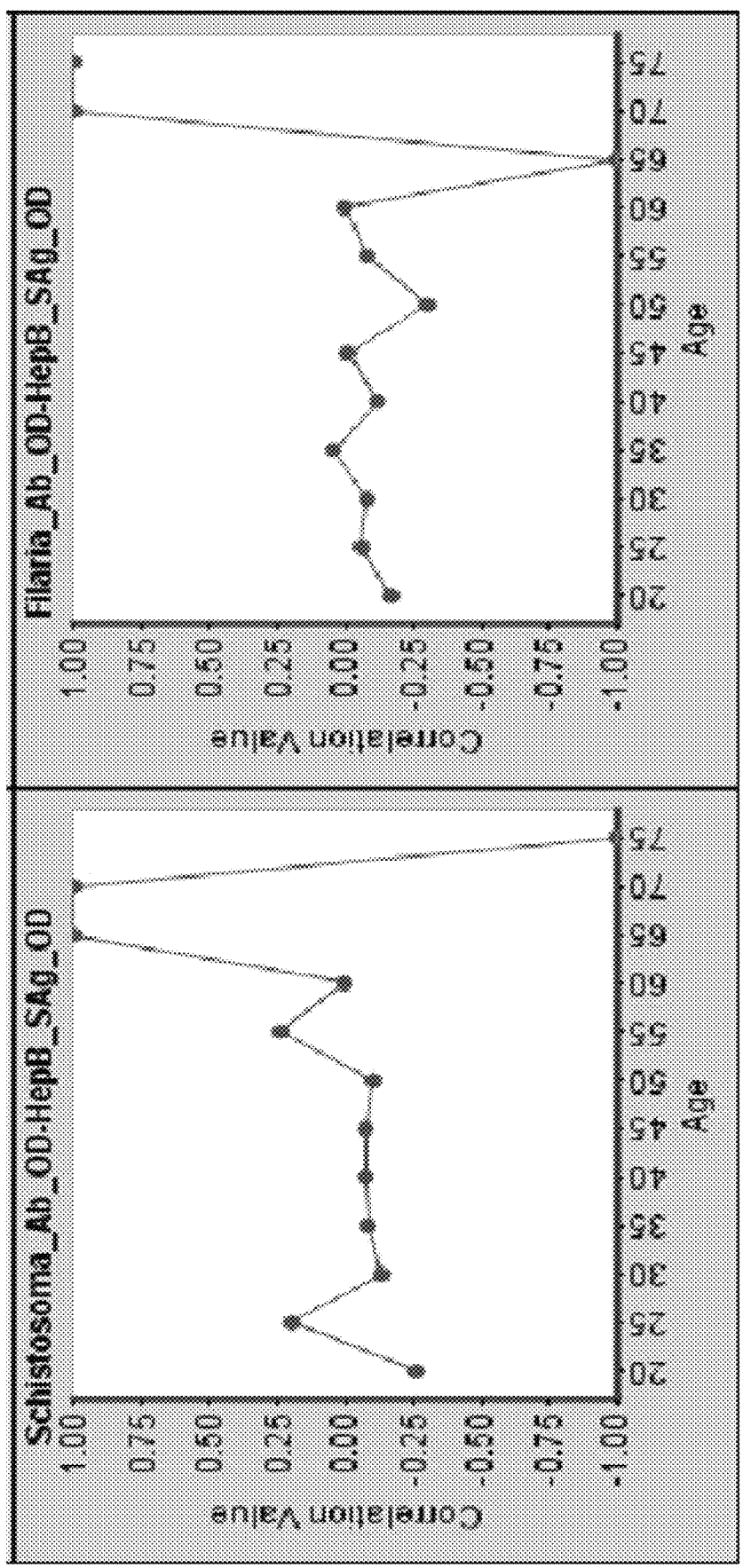
Fig. 21D-23B - Age Binned with Differences results (continued).

| Property | Prop_2 | value_StdDev | list |
|---|---|---|---|
| HepB_SAg_OD | Months_CA | 0.6069 | age=17.5-22.5 (9.31%)<br>age=22.5-27.5 (22.73%)<br>age=27.5-32.5 (27.34%)<br>age=32.5-37.5 (20.92%)<br>age=37.5-42.5 (8.08%)<br>age=42.5-47.5 (5.70%)<br>age=47.5-52.5 (2.96%)<br>age=52.5-57.5 (1.44%)<br>age=57.5-62.5 (0.58%)<br>age=62.5-67.5 (0.43%)<br>age=67.5-72.5 (0.22%)<br>age=72.5-77.5 (0.29%) |
| HepB_SAg_OD | HepC_Ab_OD | 0.6041 | age=17.5-22.5 (9.31%)<br>age=22.5-27.5 (22.73%)<br>age=27.5-32.5 (27.34%)<br>age=32.5-37.5 (20.92%)<br>age=37.5-42.5 (8.08%)<br>age=42.5-47.5 (5.70%)<br>age=47.5-52.5 (2.96%)<br>age=52.5-57.5 (1.44%)<br>age=57.5-62.5 (0.58%)<br>age=62.5-67.5 (0.43%)<br>age=67.5-72.5 (0.22%)<br>age=72.5-77.5 (0.29%) |

Fig. 21D-24A - Age Binned with Differences property correlation values.

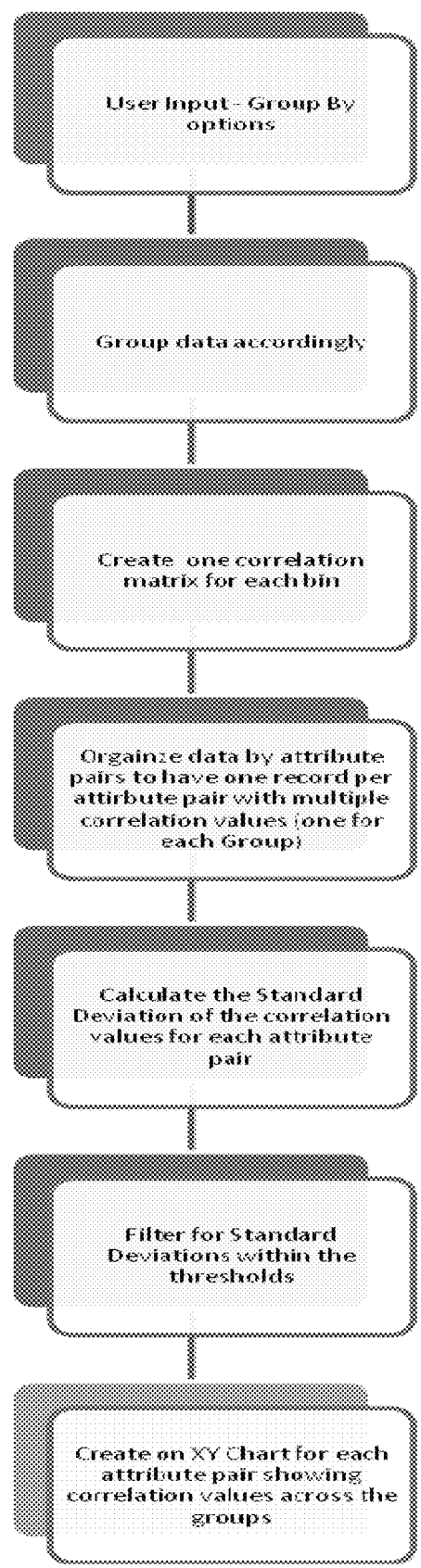
Fig. 21D-24B - Age Binned with Differences flow chart.

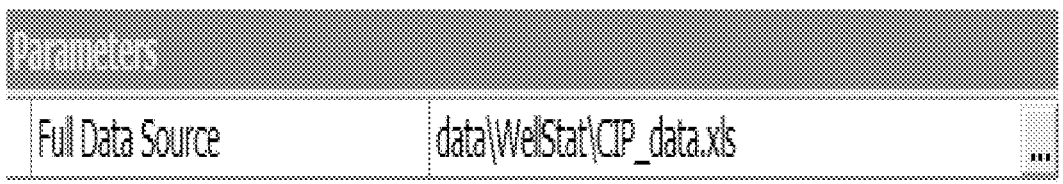
FIG. 21D-25 - Automated Run – Parallel top level parameters.

| HepB_eAb_ratio - Measles_OD_DB | |
|---|---|
| Group | Correlation Value |
| Measles_OD_DB_Int=0, Pregnant=0 (12.84%) | -1.000 |
| Measles_OD_DB_Int=0, Pregnant=1 (1.37%) | -1.000 |
| Measles_OD_DB_Int=0, Measles_history=0 (6.06%) | 1.000 |
| Measles_OD_DB_Int=0, Mumps_history=0 (8.08%) | 1.000 |
| Measles_OD_DB_Int=0, Rubella_history=2 (10.75%) | -1.000 |
| Measles_OD_DB_Int=0, Rubella_history=0 (3.17%) | -1.000 |
| Measles_OD_DB_Int=0, Chickenpox_history=2 (4.76%) | -1.000 |
| Measles_OD_DB_Int=0, Chickenpox_history=0 (4.26%) | -1.000 |
| Measles_OD_DB_Int=0, Diptheria_history=2 (7.36%) | -1.000 |
| Measles_OD_DB_Int=0, Diptheria_history=0 (7.22%) | 1.000 |
| Measles_OD_DB_Int=0, Medical Problems=0 (12.55%) | -0.933 |
| Measles_OD_DB_Int=0, Medications=0 (11.26%) | -0.933 |
| Measles_OD_DB_Int=0 (14.57%) | -0.918 |

| Measles_titre_DB - HepB_eAb_ratio | |
|---|---|
| Group | Correlation Value |
| Measles_OD_DB_Int=0, Pregnant=0 (12.84%) | -1.000 |
| Measles_OD_DB_Int=0, Pregnant=1 (1.37%) | -1.000 |
| Measles_OD_DB_Int=0, Measles_history=0 (6.06%) | -1.000 |
| Measles_OD_DB_Int=0, Mumps_history=0 (8.08%) | -1.000 |
| Measles_OD_DB_Int=0, Rubella_history=2 (10.75%) | -1.000 |
| Measles_OD_DB_Int=0, Rubella_history=0 (3.17%) | -1.000 |
| Measles_OD_DB_Int=0, Chickenpox_history=2 (4.76%) | -1.000 |
| Measles_OD_DB_Int=0, Chickenpox_history=0 (4.26%) | -1.000 |
| Measles_OD_DB_Int=0, Diptheria_history=2 (7.36%) | -1.000 |
| Measles_OD_DB_Int=0, Diptheria_history=0 (7.22%) | -1.000 |
| Measles_OD_DB_Int=0, Medical Problems=0 (12.55%) | -1.000 |
| Measles_OD_DB_Int=0, Medications=0 (11.26%) | -1.000 |
| Measles_OD_DB_Int=0 (14.57%) | -0.883 |

FIG. 21D-26A - Automated Run – Parallel output.

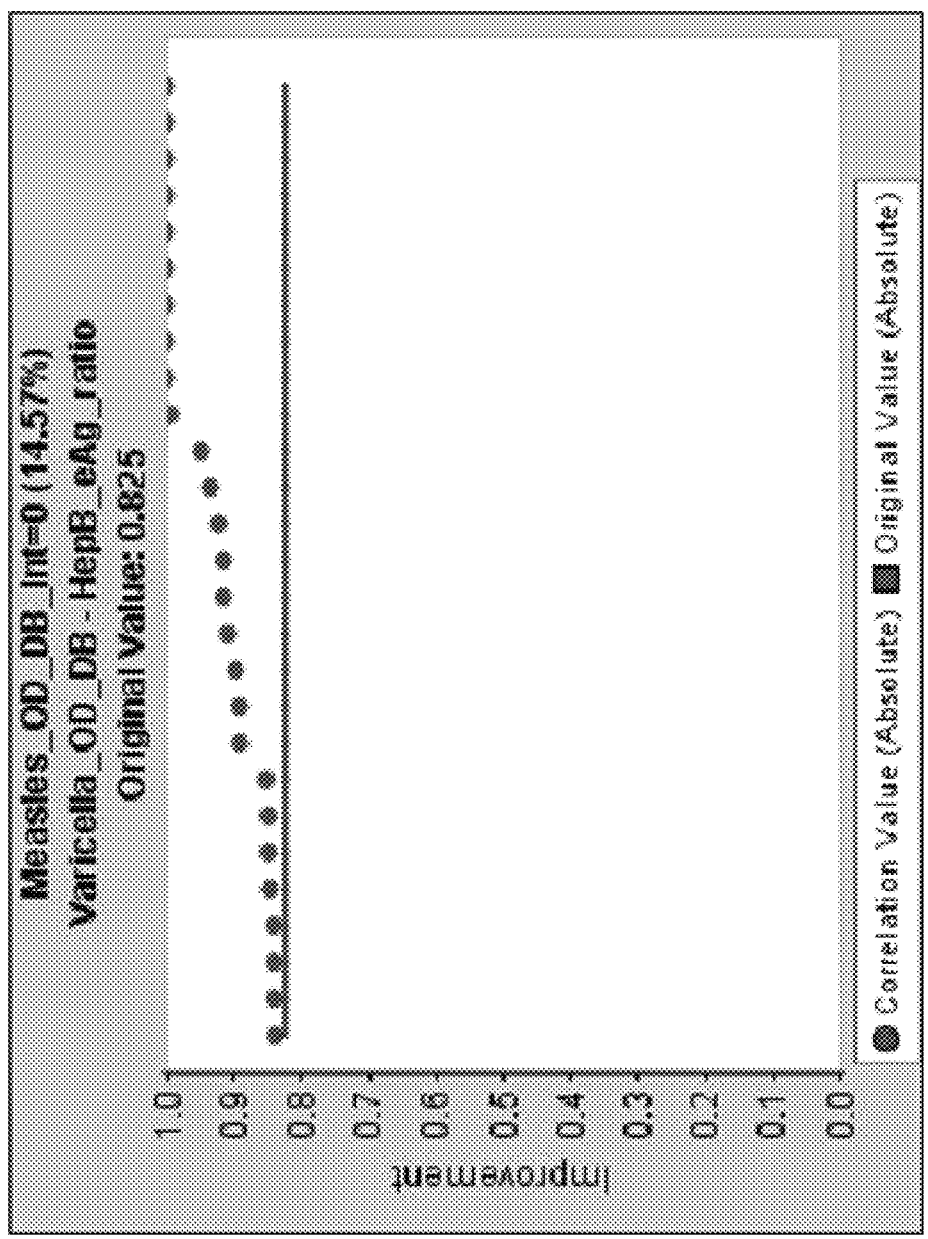
FIG. 21D-26B1 - Automated Run – Parallel output.

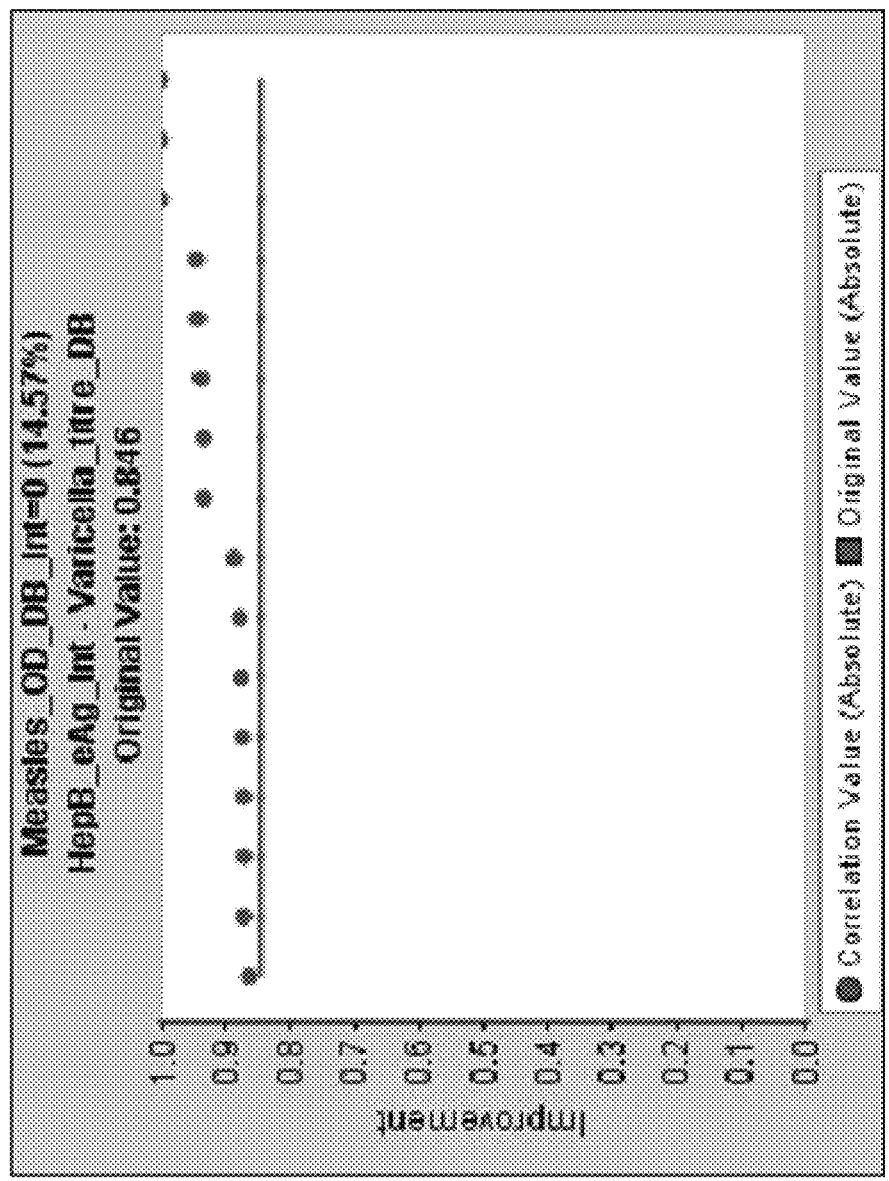
FIG. 21D-26B2 - Automated Run – Parallel output (continued).

| property | prop_2 | list | value |
|---|---|---|---|
| | | Varicella_Int=1 (92.35%) | |
| | | Months_pregnant - Pregnant | |
| | | Original Value: -0.954 | |
| Months_pregnant | Pregnant | Varicella_Int=1, Chickenpox_Age=20-60 (3.75%) | 1 |
| Months_pregnant | Pregnant | Varicella_Int=1, Mumps_titre_DB=5000-7000 (1.01%) | 1 |
| Months_pregnant | Pregnant | Varicella_Int=1, Strongyloides_Ab_OD=2.5-3.5 (0.65%) | 0.999999999999999 |
| Months_pregnant | Pregnant | Varicella_Int=1, Pertussis_history=1 (1.59%) | 0.9999999999999999 |
| Months_pregnant | Pregnant | Varicella_Int=1, Mumps_OD_DB=0-0.5 (66.16%) | -0.9845239656665312 |
| Months_pregnant | Pregnant | Varicella_Int=1, Measles_age=80-100 (69.77%) | -0.9652655742031199 |
| Months_pregnant | Pregnant | Varicella_Int=1, Measles_history=2 (34.56%) | -0.9667671542182 |
| Months_pregnant | Pregnant | Varicella_Int=1, Strongyloides_Int=-1 (37.52%) | -0.9679924921956688 |
| Months_pregnant | Pregnant | Varicella_Int=1, Medical_Problems=0 (76.77%) | -0.9684706596495 |
| Months_pregnant | Pregnant | Varicella_Int=1, Strongyloides_Int=1 (26.77%) | -0.9692831441869977 |
| Months_pregnant | Pregnant | Varicella_Int=1, Medications=1 (19.84%) | -0.9697422680999075 |
| Months_pregnant | Pregnant | Varicella_Int=1, Hepatitis_history=0 (59.09%) | -0.9704657170826 |
| Months_pregnant | Pregnant | Varicella_Int=1, Rubella_Ab=0-100 (63.28%) | -0.9712761477254 |
| Months_pregnant | Pregnant | Varicella_Int=1, Mumps_history=2 (25.83%) | -0.9736524083292 |
| Months_pregnant | Pregnant | Varicella_Int=1, Measles_OD_DB=0-0.5 (53.82%) | -0.9744464708173.6 |
| Months_pregnant | Pregnant | Varicella_Int=1, Tetanus_history=2 (30.42%) | -0.9760098012546.3 |
| Months_pregnant | Pregnant | Varicella_Int=1, Pertussis_history=0 (51.59%) | -0.984535556889996 |
| Months_pregnant | Pregnant | Varicella_Int=1, CMV_OD=50-150 (11.76%) | -0.999091748560.66 |
| Months_pregnant | Pregnant | Varicella_Int=1, Mumps_titre_DB=1000-3000 (30.74%) | -0.9992734586165.81 |
| Months_pregnant | Pregnant | Varicella_Int=1, CMV_OD=150-250 (19.12%) | -0.9994841929934.71 |
| Months_pregnant | Pregnant | Varicella_Int=1, Indoor_toilet_type=2 (4.76%) | -0.9995213649369.53 |
| Months_pregnant | Pregnant | Varicella_Int=1, Chickenpox_history=2 (25.32%) | -0.999596784923.23 |
| Months_pregnant | Pregnant | Varicella_Int=1, Region_of_Origin=6 (14.50%) | -0.9996334259107.32 |
| Months_pregnant | Pregnant | Varicella_Int=1, Citizenship=3 (44.08%) | -0.9996628700166.05 |
| Months_pregnant | Pregnant | Varicella_Int=1, Polio_history=2 (2.16%) | -0.999664228465.148 |
| Months_pregnant | Pregnant | Varicella_Int=1, Filaria_Int=0 (10.32%) | -0.9997240536519.13 |

FIG. 21D-26B3 - Automated Run – Parallel output (continued).

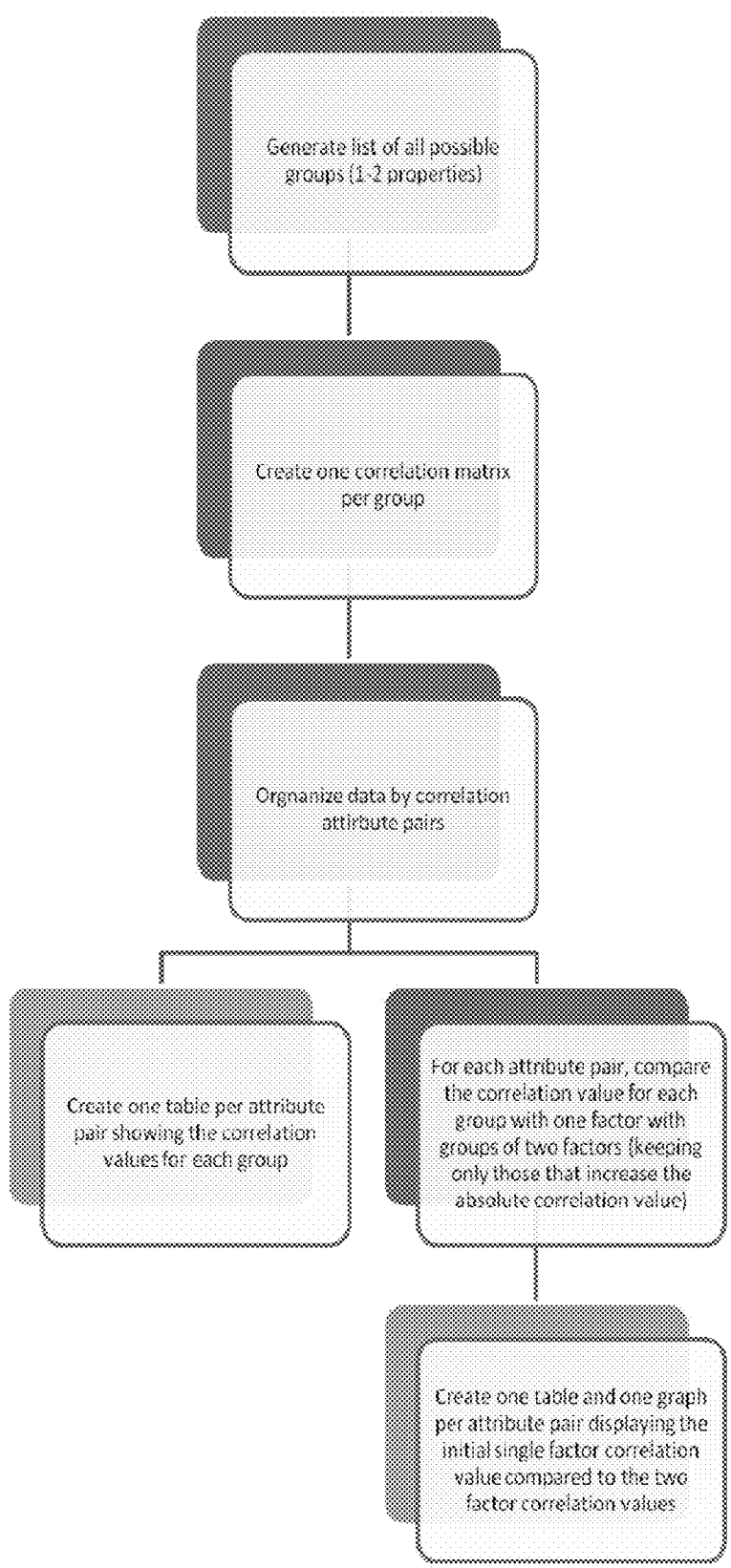
FIG. 21D-27 - Automated Run – Parallel flow chart.

```
for #i in 1 .. numvalues(prop_list)
loop
    for #j in (#i + 1) .. numvalues(prop_list)
    loop
        append(new_list, prop_list[#i].'.'.prop_list[#j]);
        append(bin_list, bin_size[#i].'.'.bin_size[#j]);
        for #k in (#i + 2) .. numvalues(prop_list)
        loop
            append(new_list, prop_list[#i].'.'.prop_list[#j].'.'.prop_list[#k]);
            append(bin_list, bin_size[#i].'.'.bin_size[#j].'.'.bin_size[#k]);
        end loop;
    end loop;
end loop;
```

FIG. 21D-28 - Automated Run – Parallel For loop.

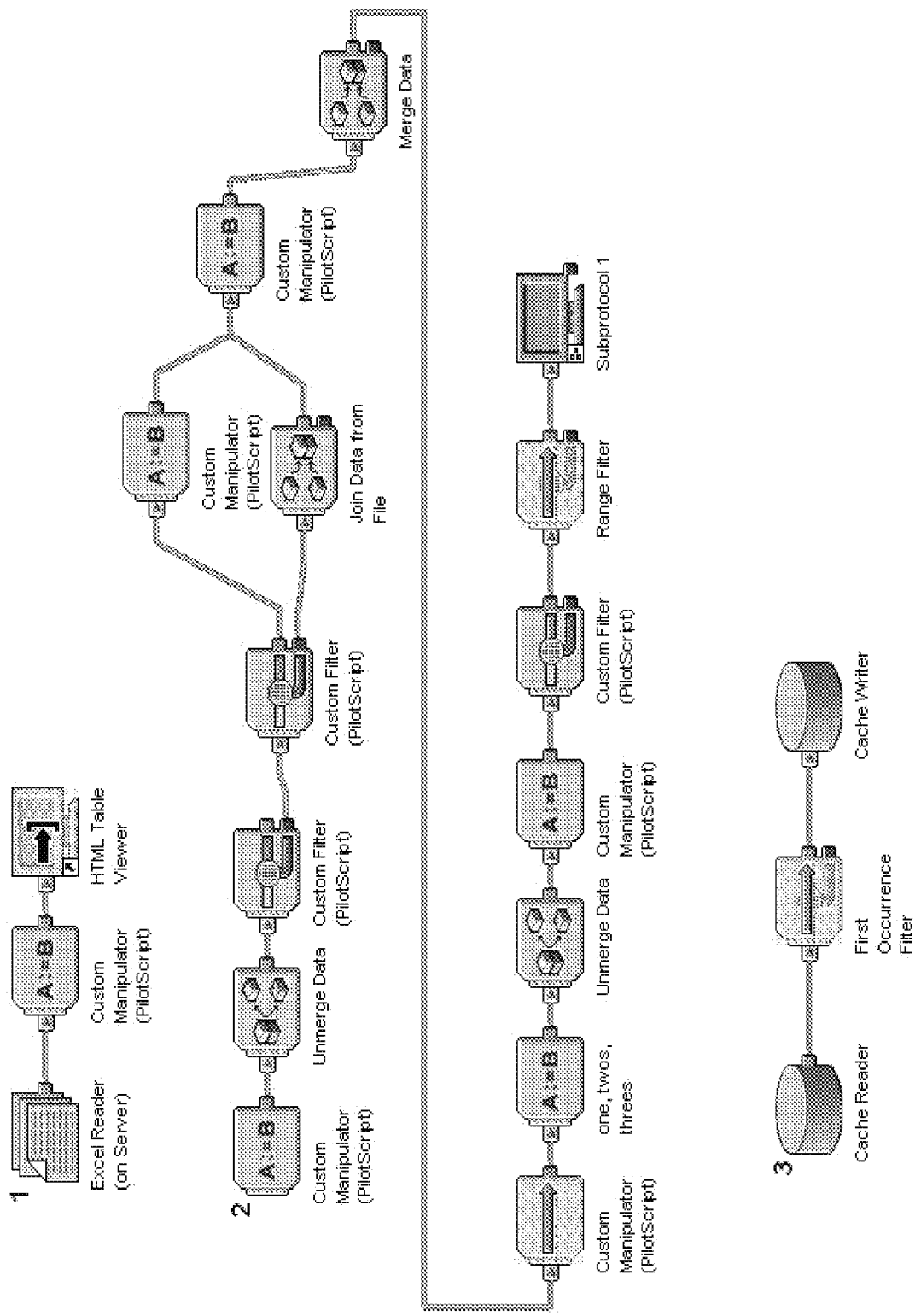
FIG. 21D-29 - Automated Run – Parallel Protocol.

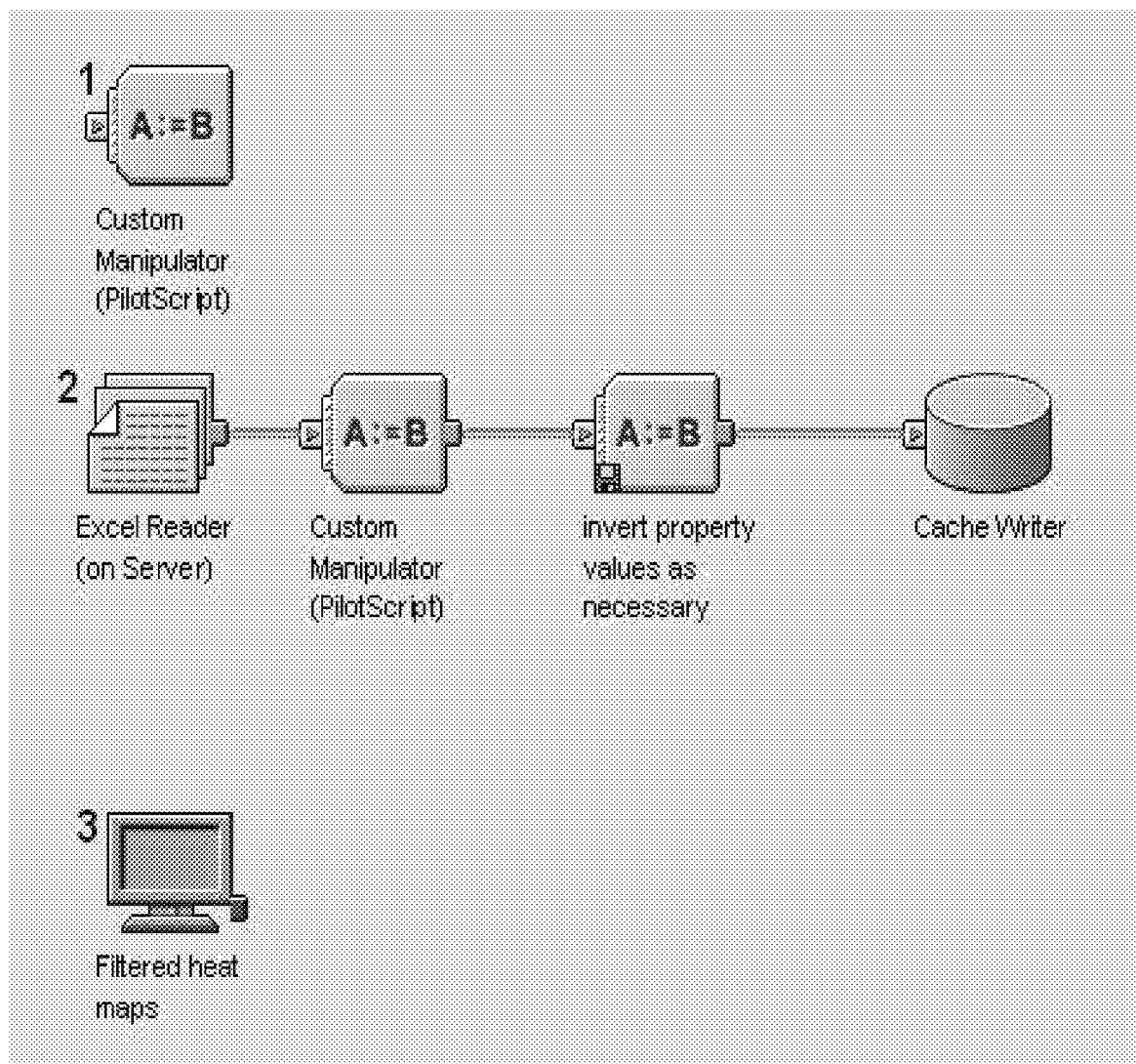
FIG. 21D-30 - Automated Run – Parallel Subprotocol 1.

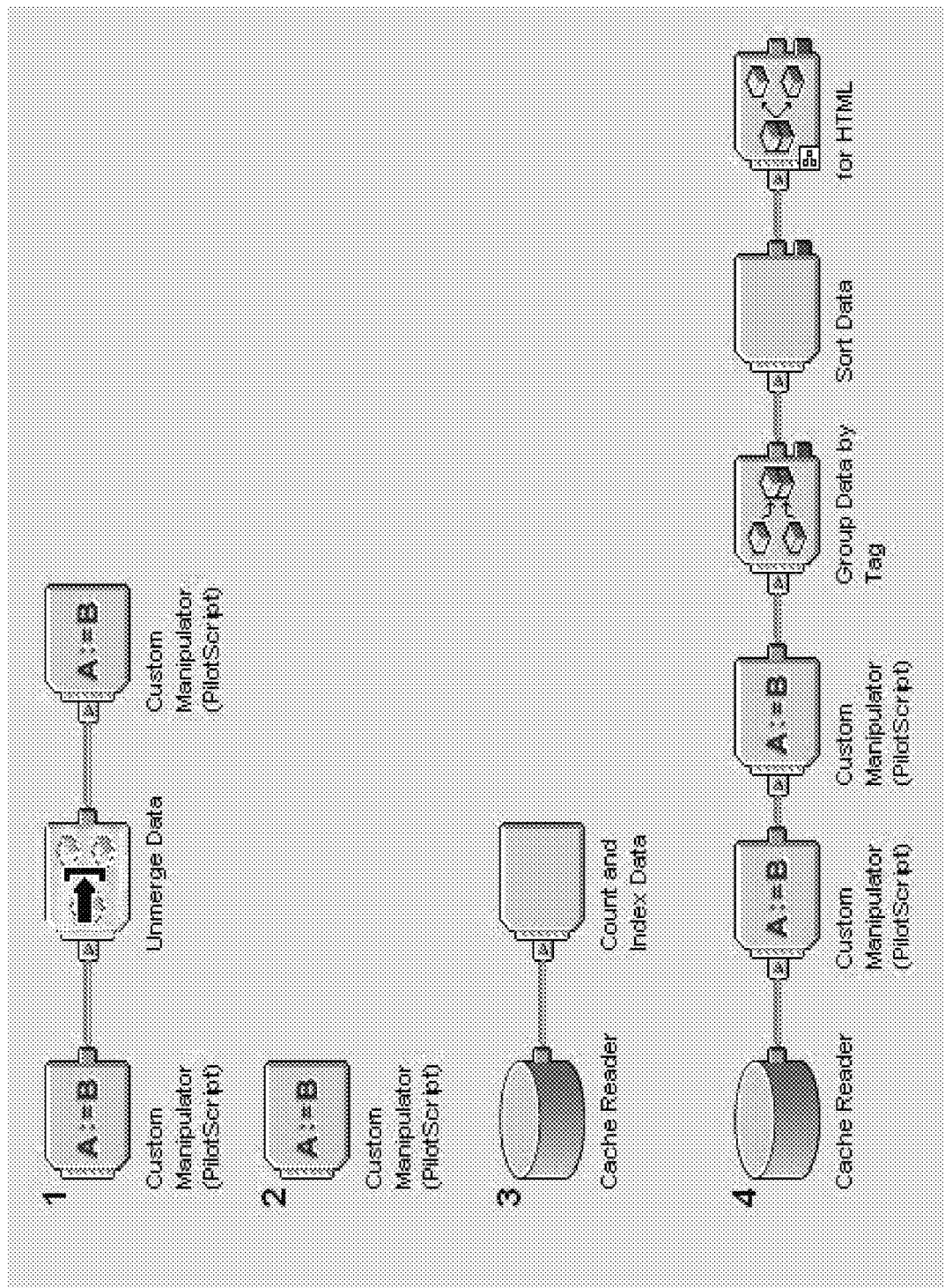
FIG. 21D-31 - Filtered Heat Maps Subprotocol.

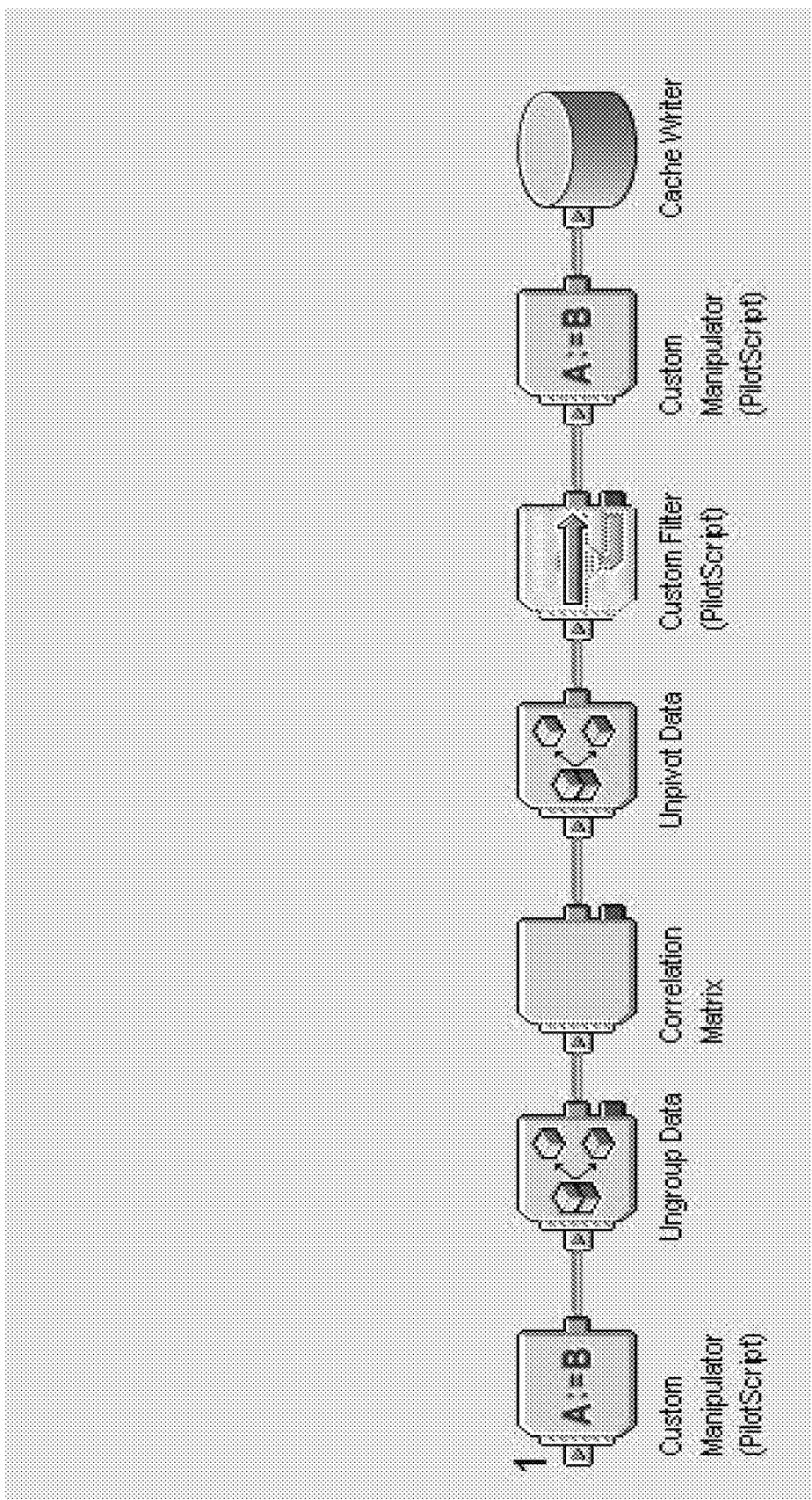
FIG. 21D-32 - Filtered Heat Maps "for HTML" subprotocol.

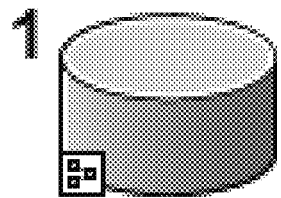
Data prep
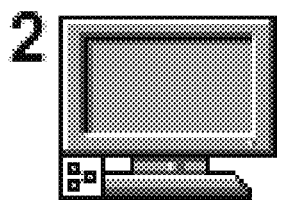
Create Graphs
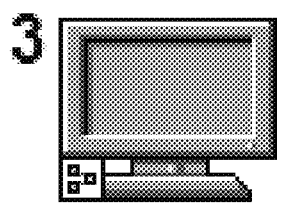
Create Tables
FIG. 21D-33 - Automated Run – Parallel Automated Data Mining Protocol.

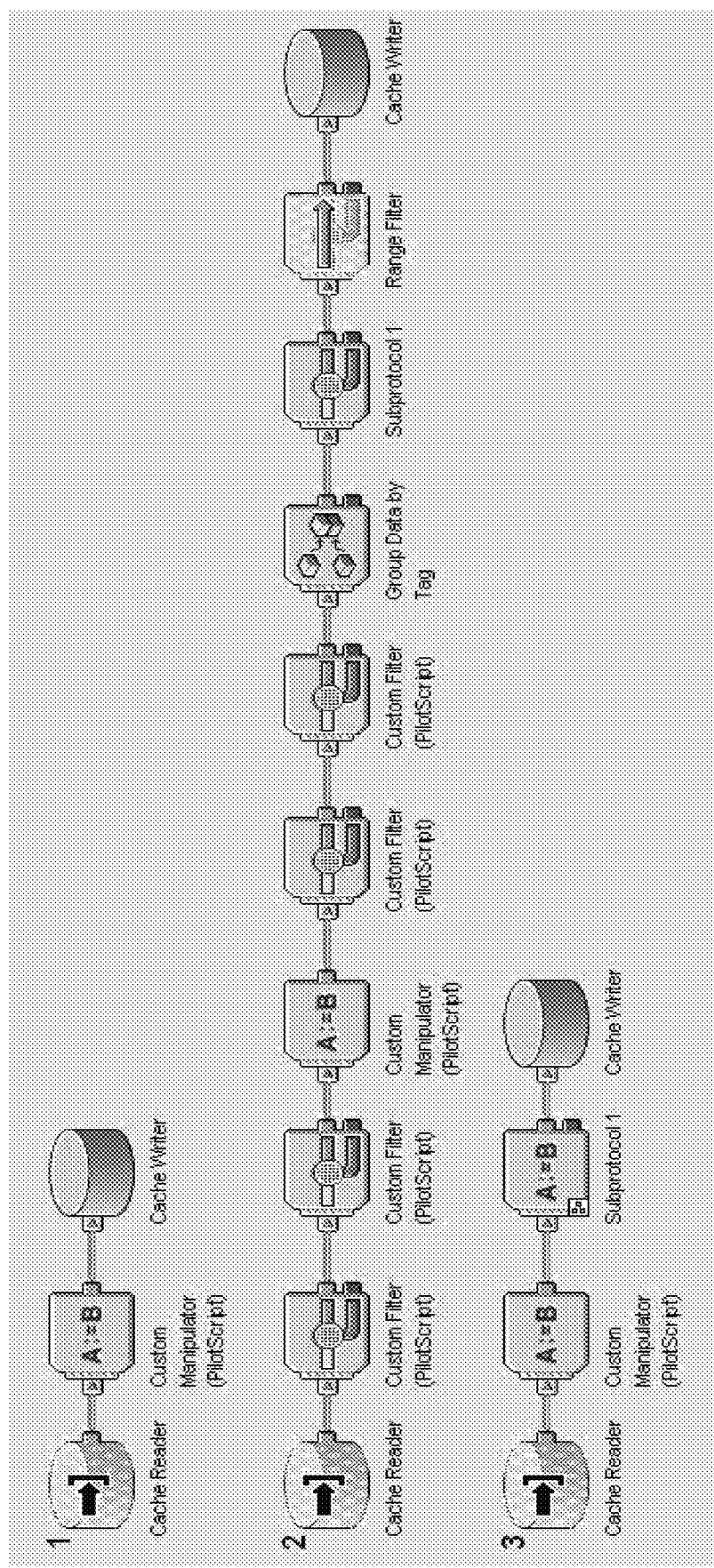
FIG. 21D-34 - Automated Data Mining Data Prep subprotocol.

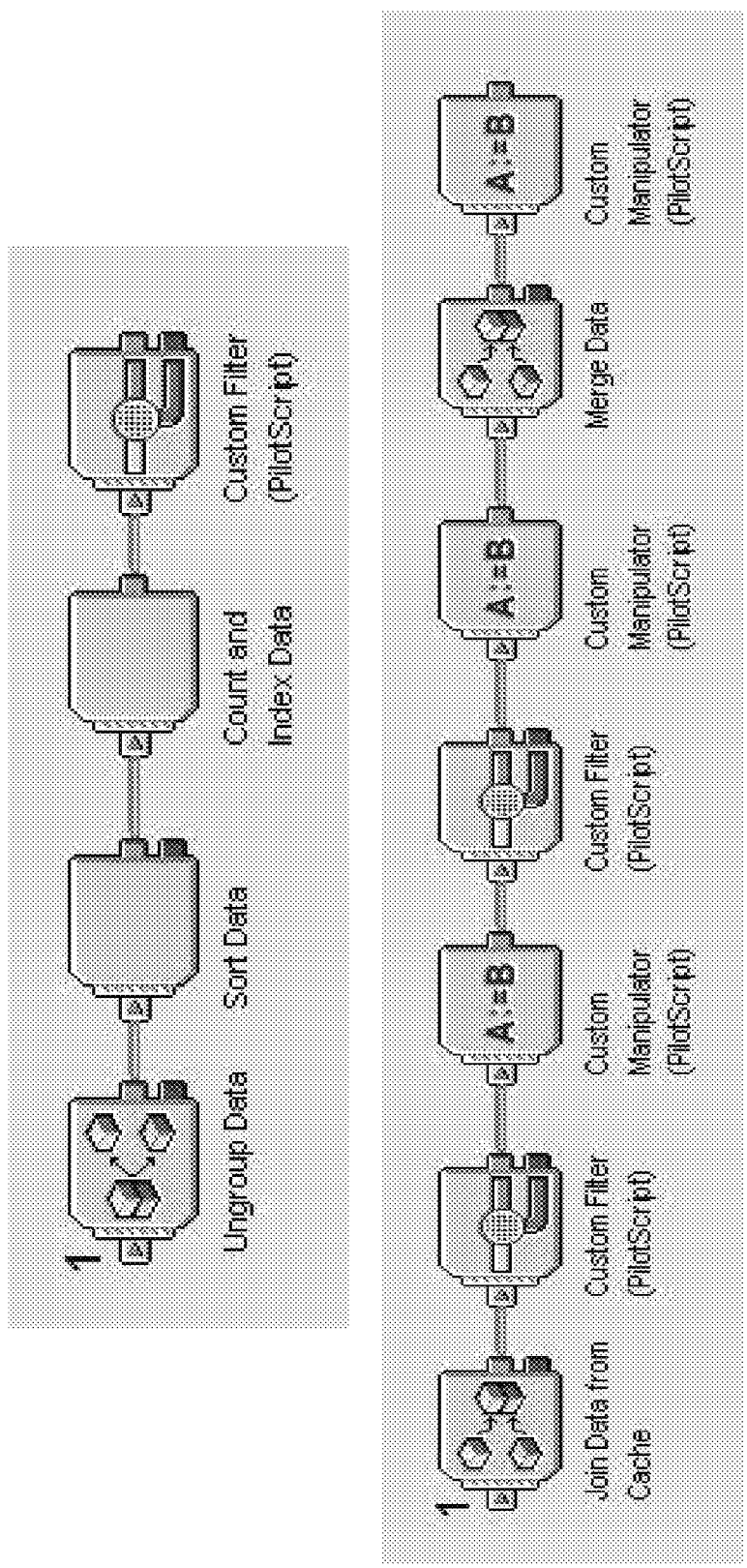
FIG. 21D-35 - The two sub-protocols belonging to the Data Prep sub-protocol.

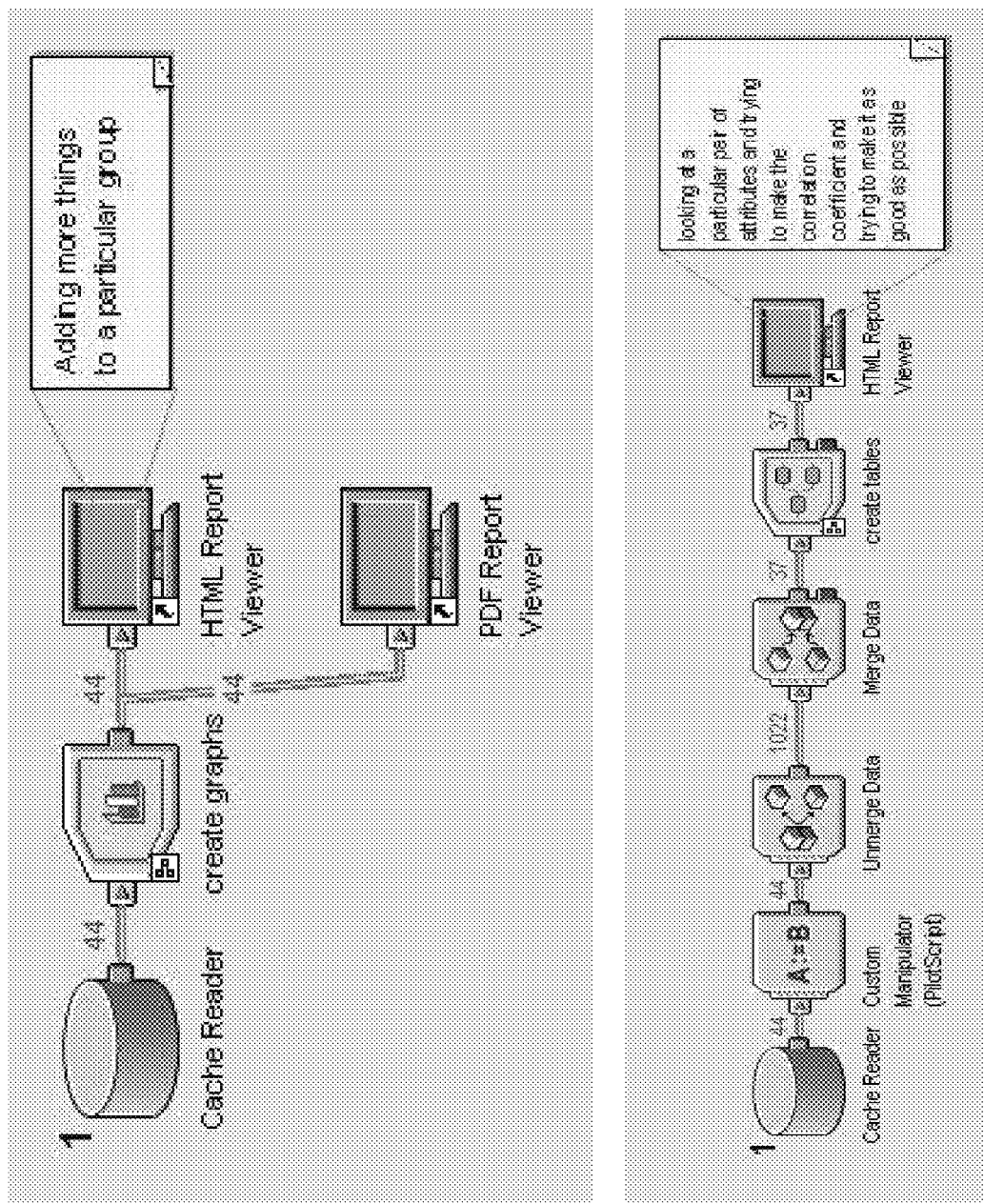
FIG. 21D-36 - The Create Graphs and Create Tables subprotocols of Automated Data Mining.

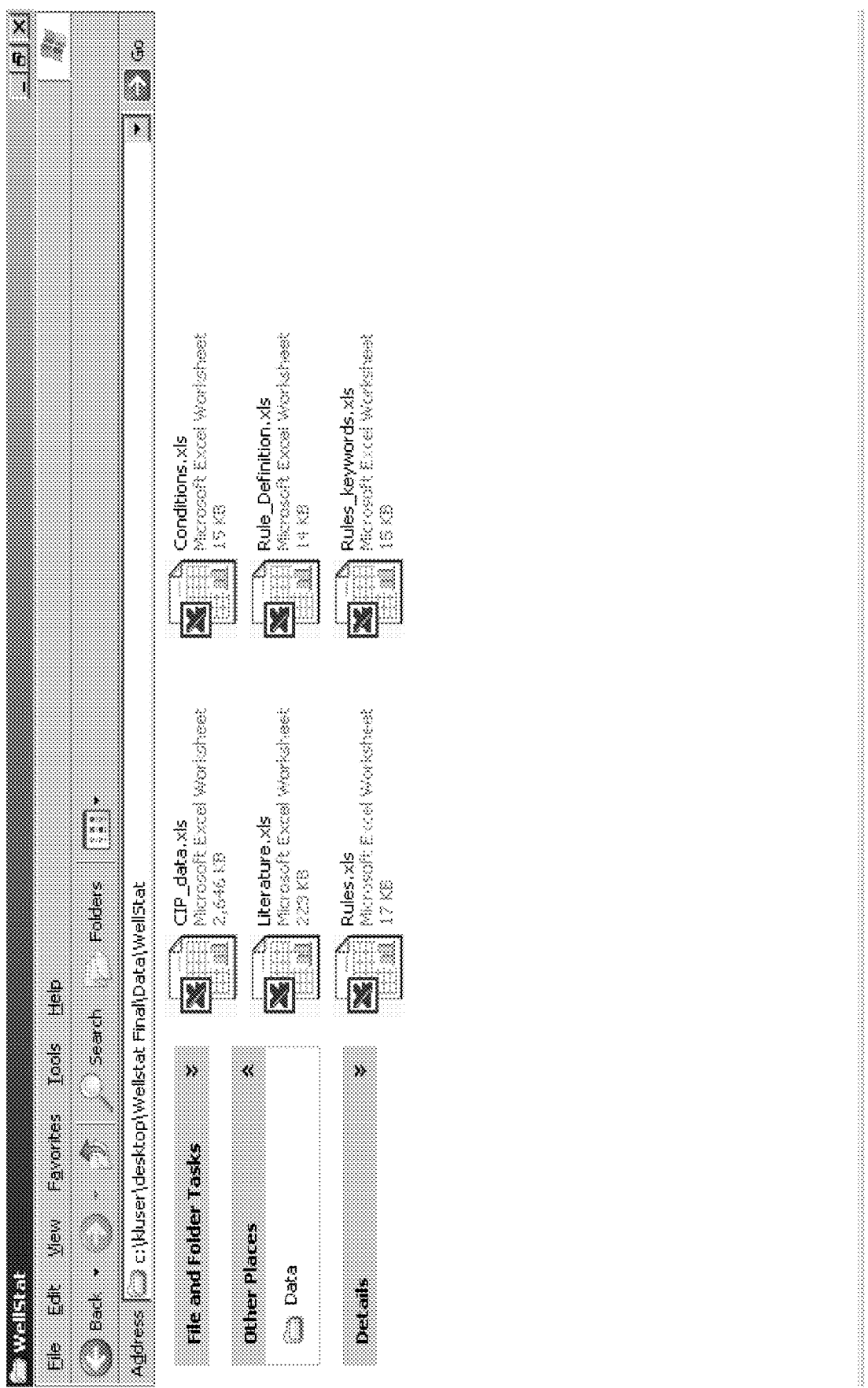
FIG. 21D-37 - Protocol data spreadsheets.

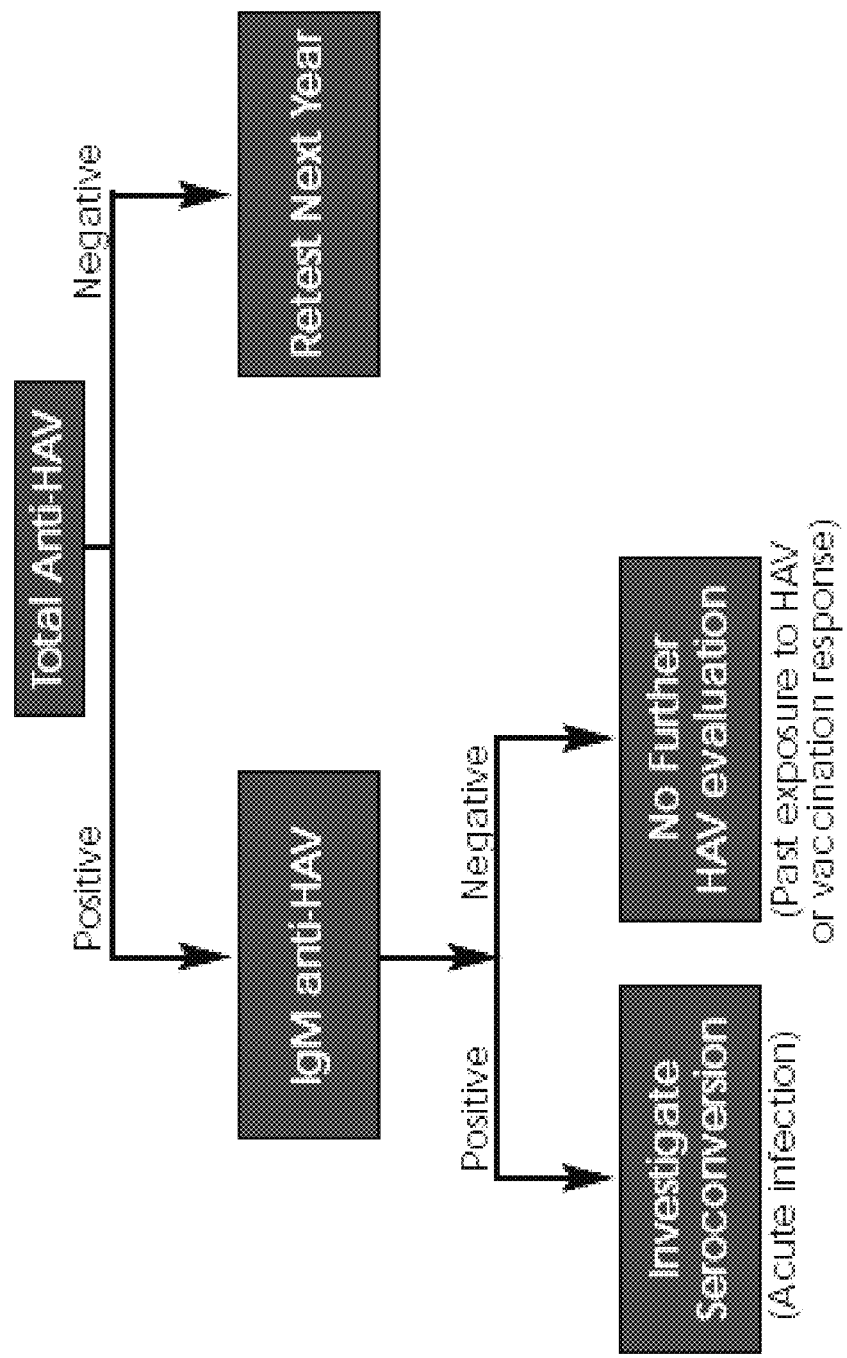
FIG. 21D-38 - Exemplary Algorithm for Hepatitis A Virus (HAV) Testing

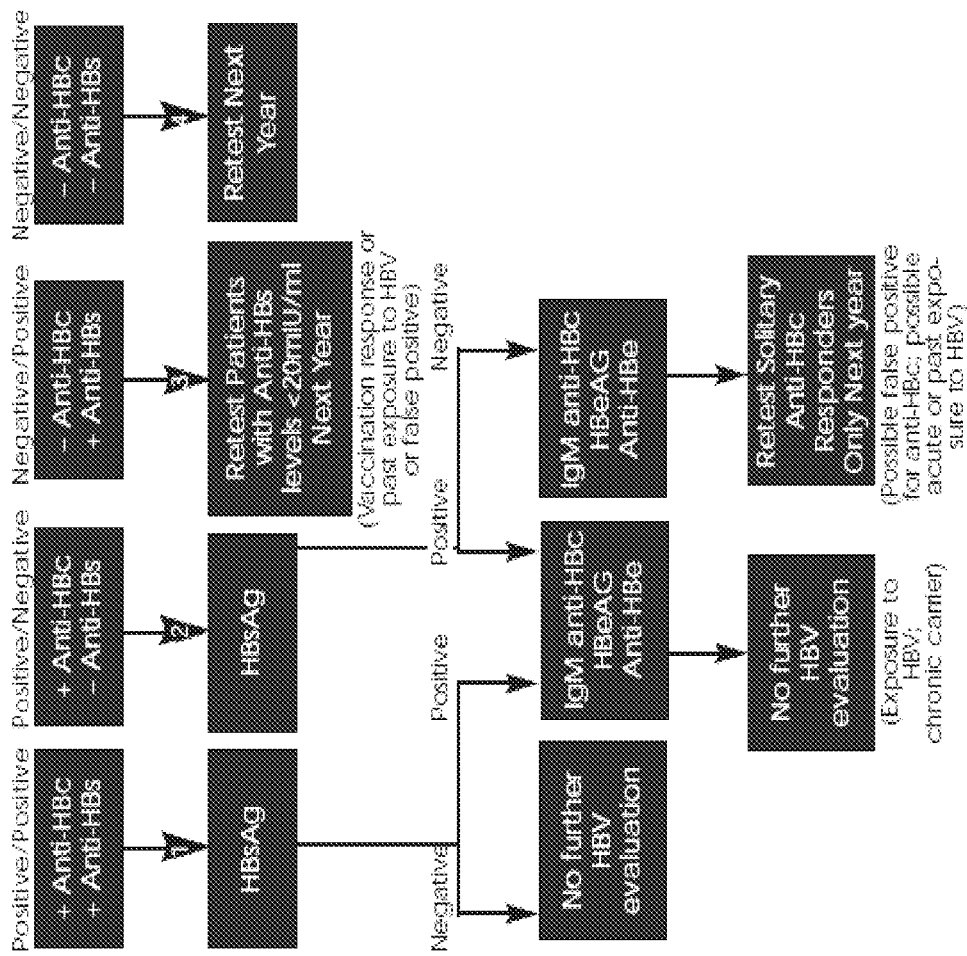
FIG. 21D-39 - Exemplary Algorithm for Hepatitis B Virus Testing

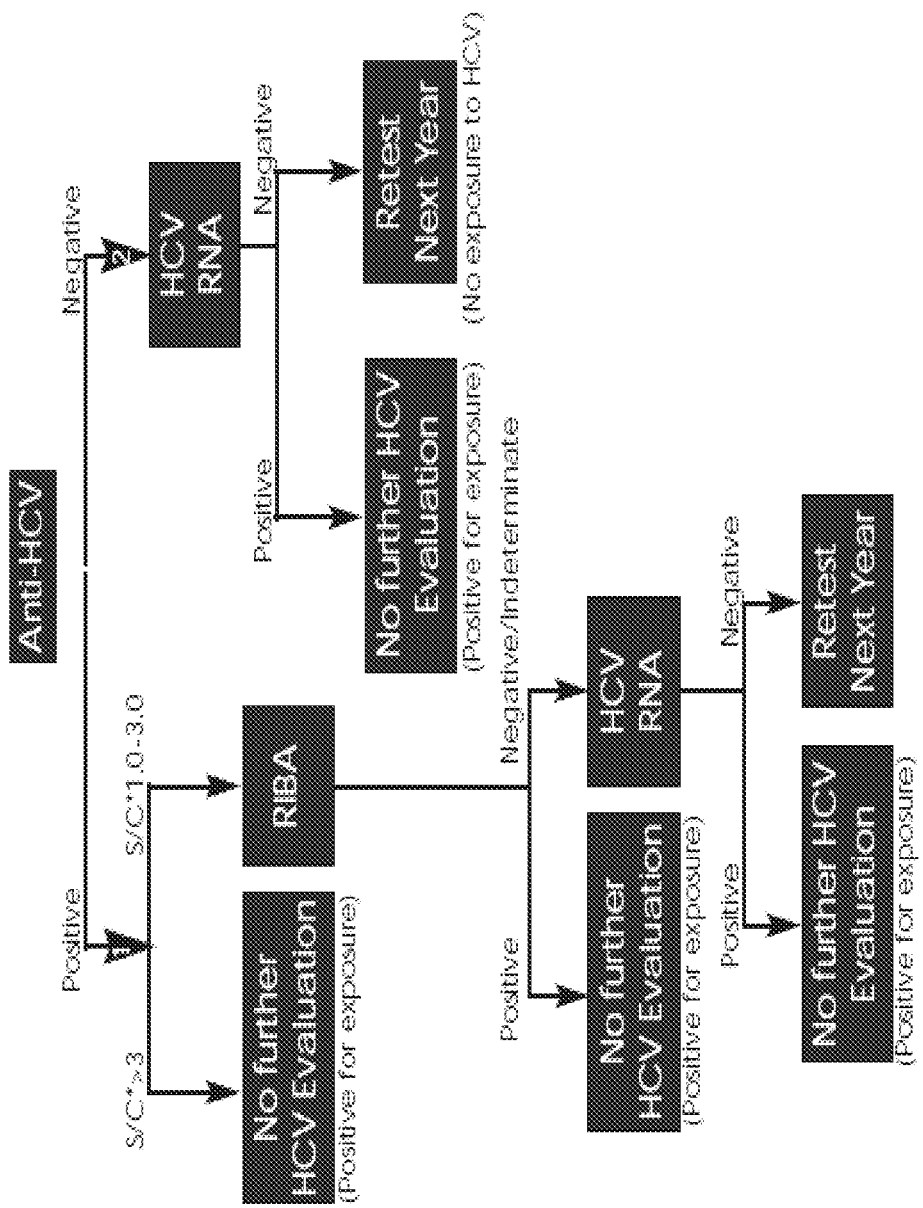

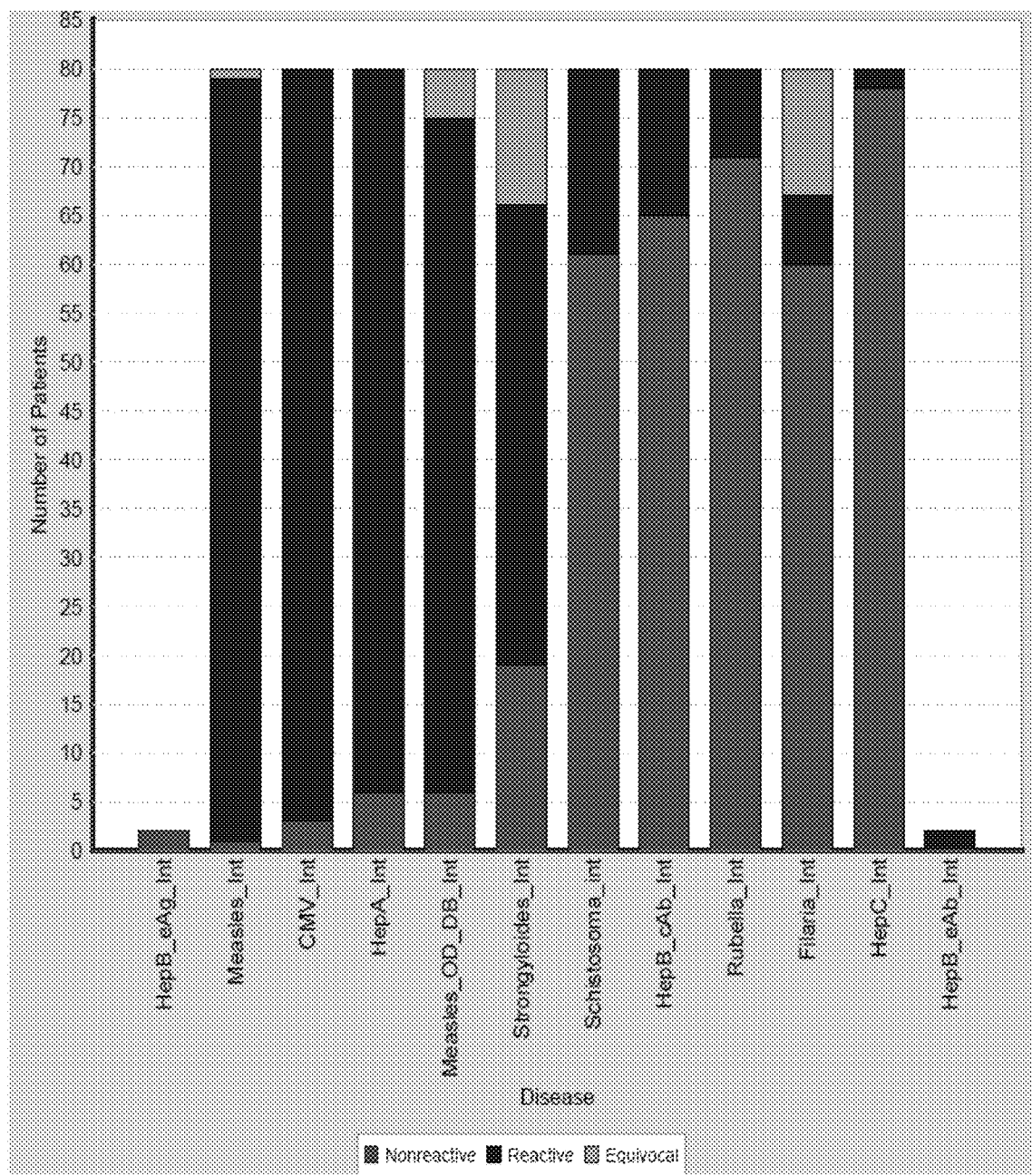
FIG. 21E-1: Interpretation of immunoassay results of random sampling of CIP.

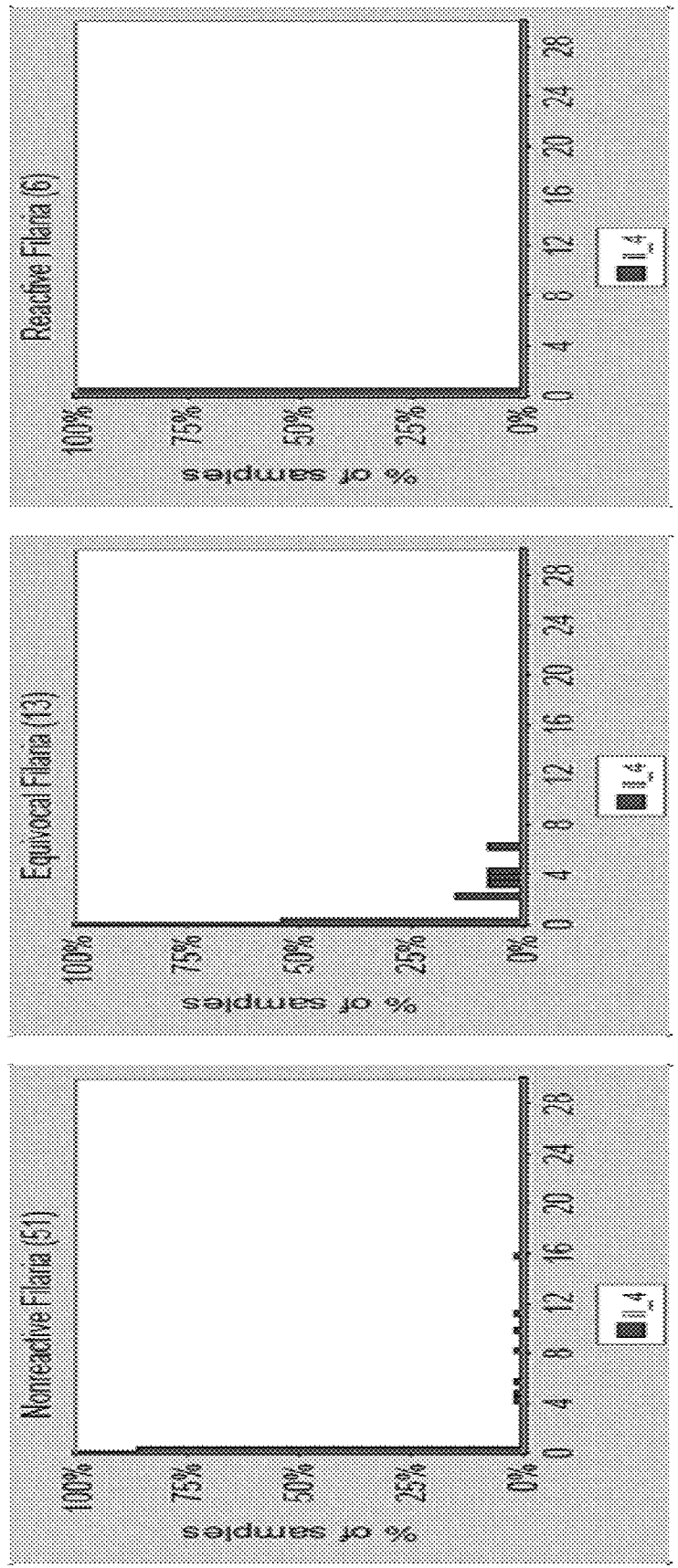
FIG. 21E-2a-IL-4 and IL-5 cytokine assay compared with filaria assay results.

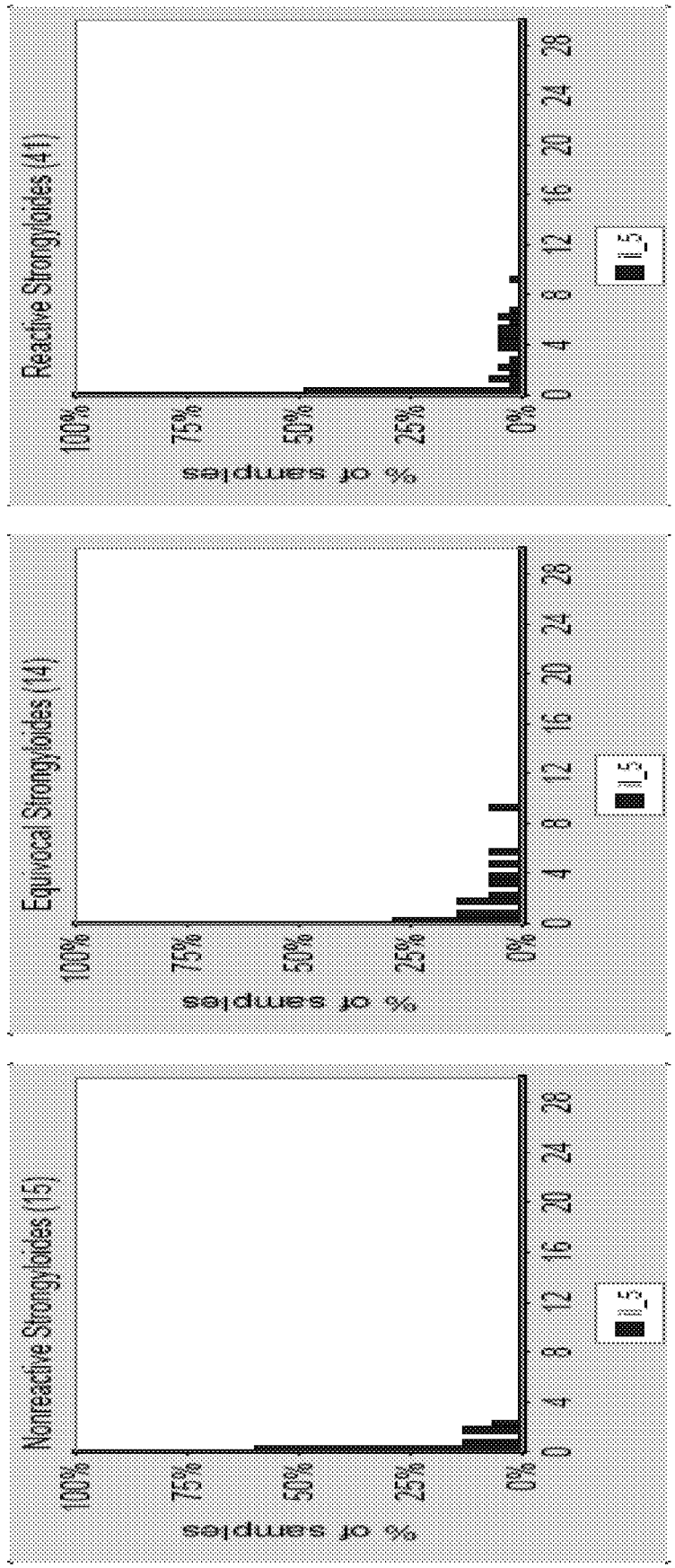
FIG. 21E-2b: IL-5 cytokine assay compared with strongyloides assay results.

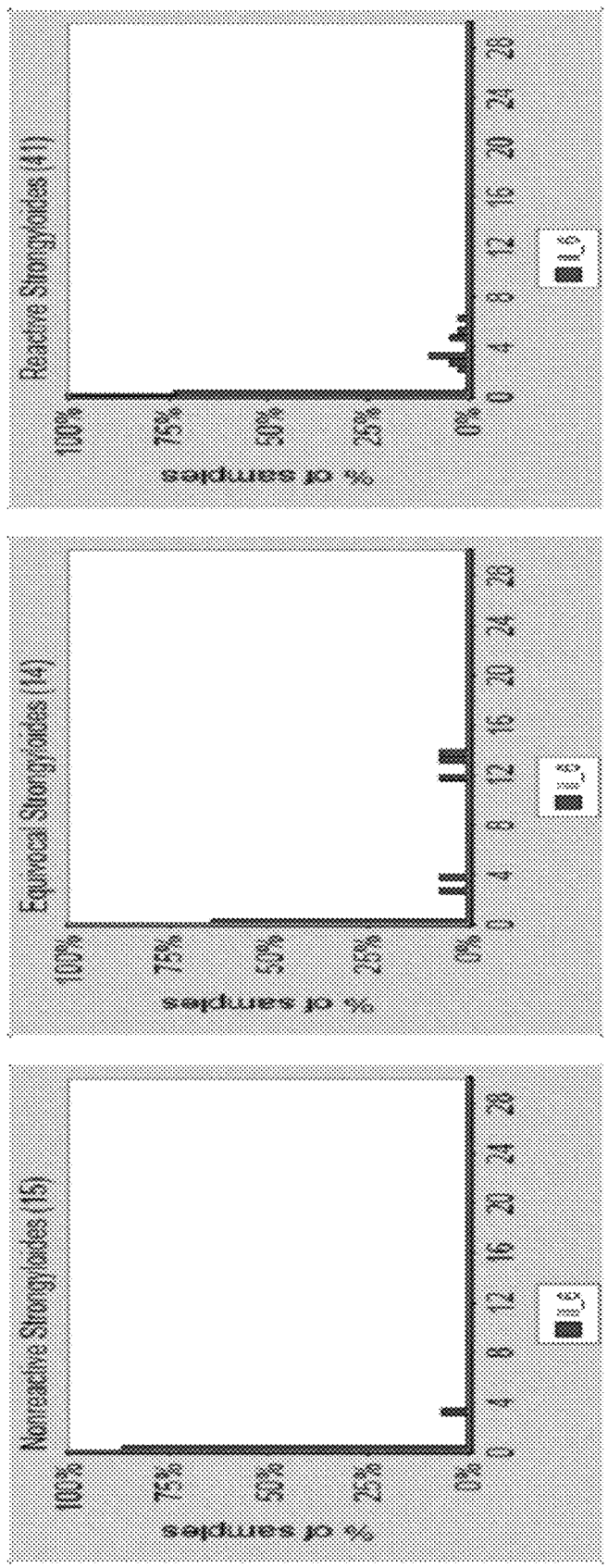
FIG. 21E-2c1: Inflammatory cytokine assays for IL-6 and TNFα compared with strongyloides assay results.

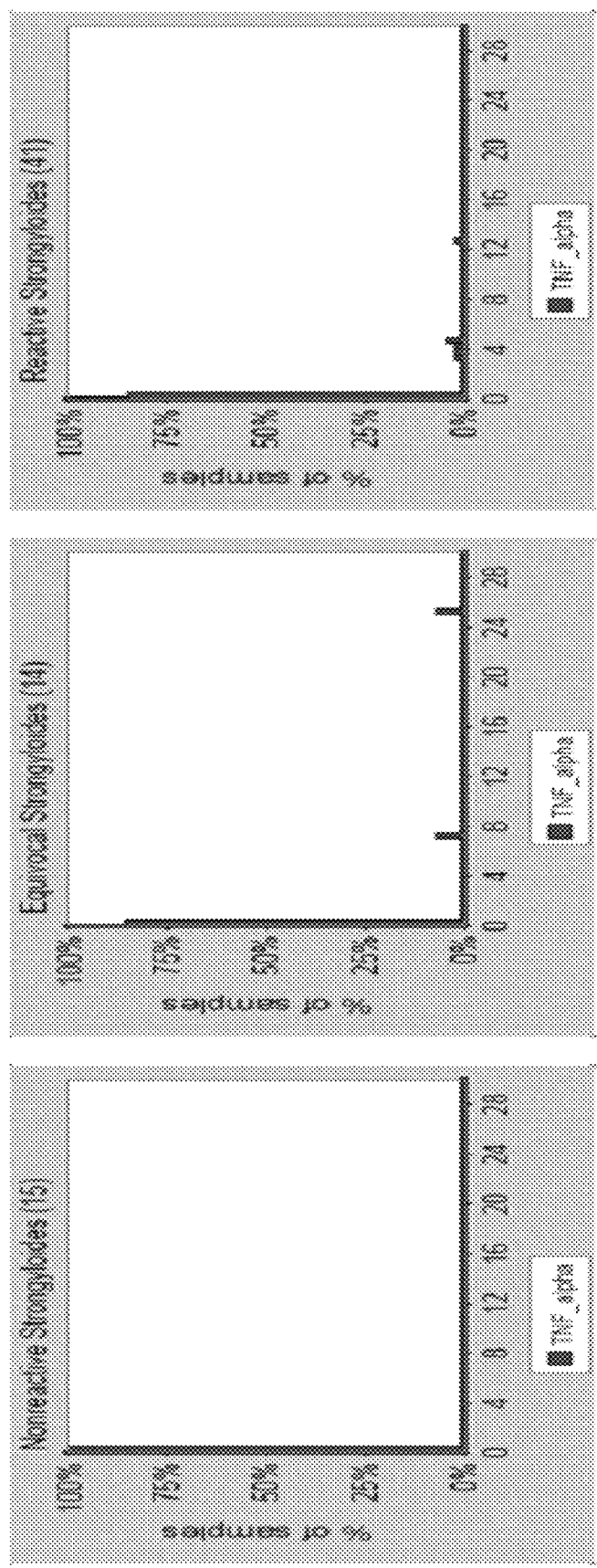
FIG. 21E-2c2: Inflammatory cytokine assays for IL-6 and TNFα compared with strongyloides assay results.

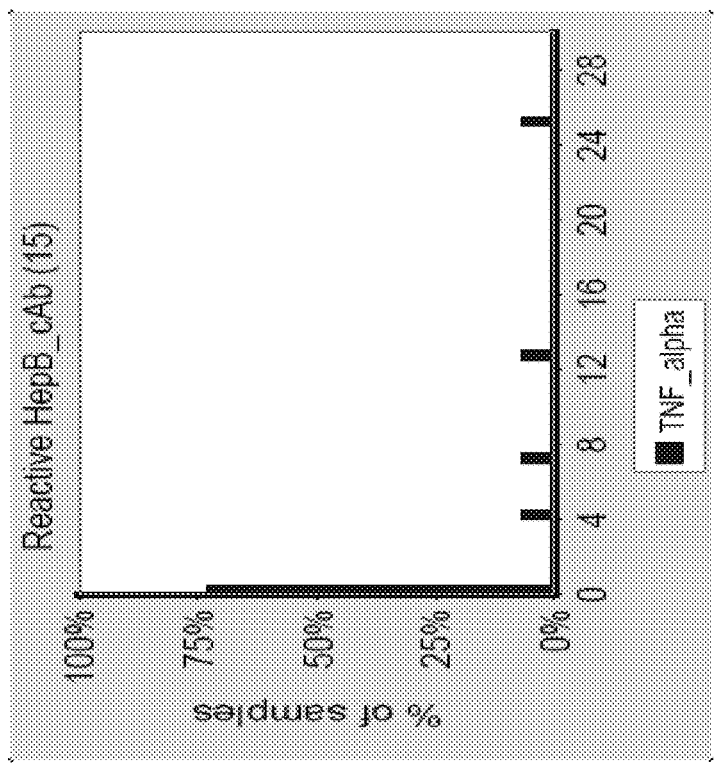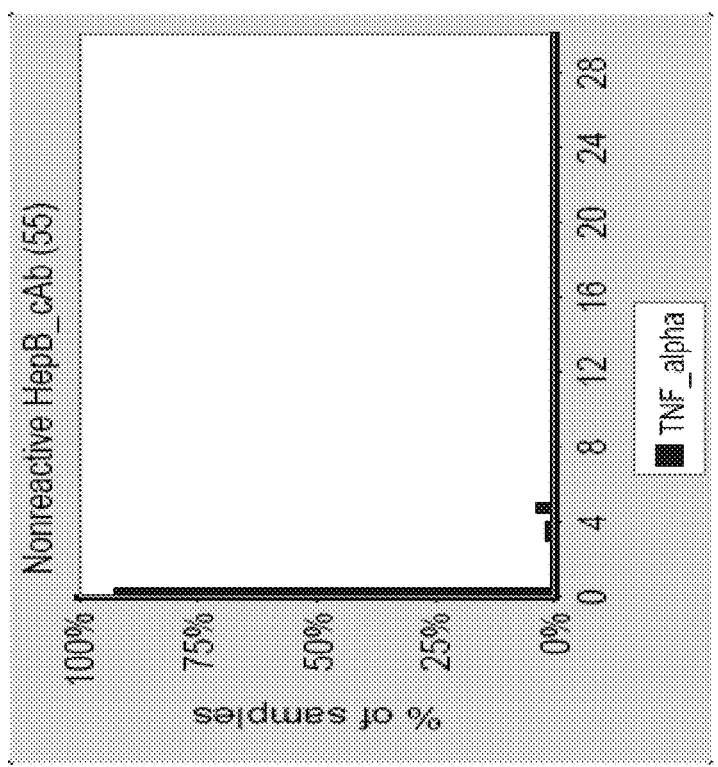
FIG. 21E-3: TNF-α cytokine levels in patients tested for antibody to hepatitis B core antigen.

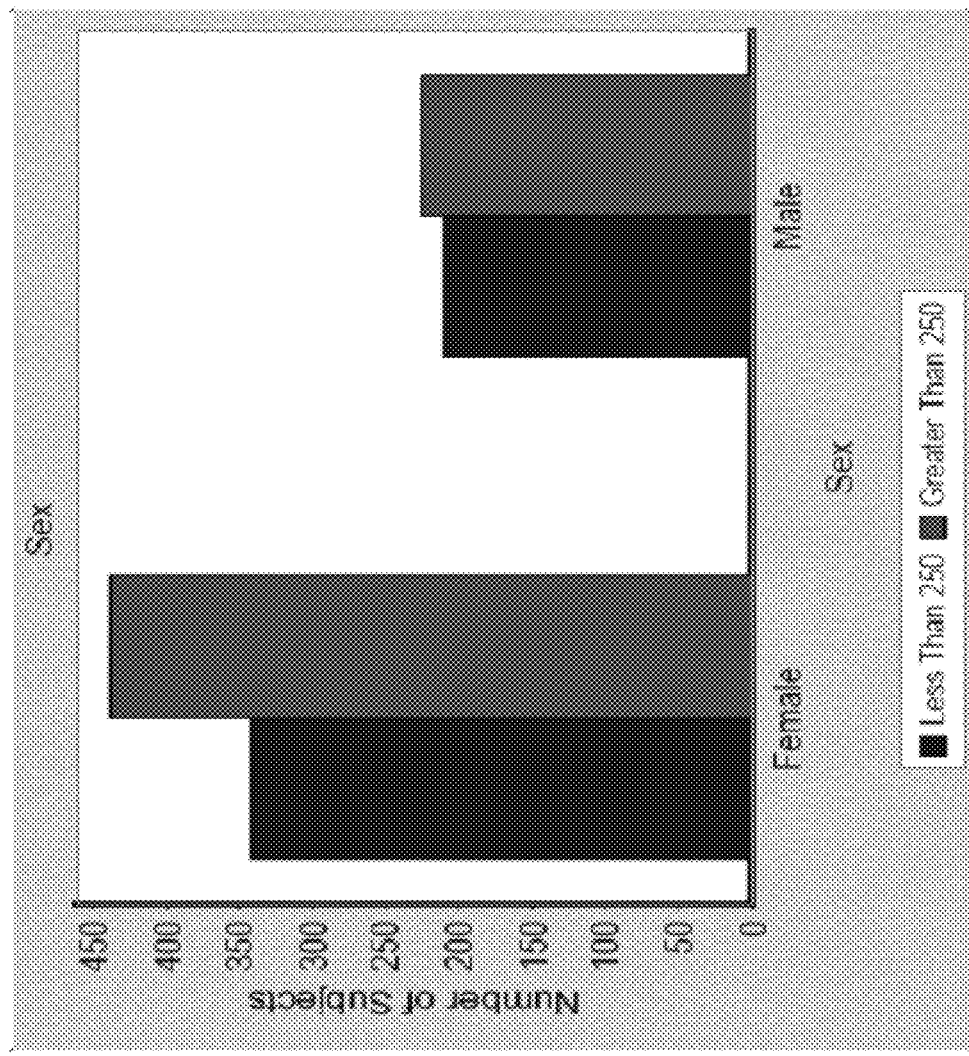
FIG. 21E-4A: Antibody to CMV correlated to gender.

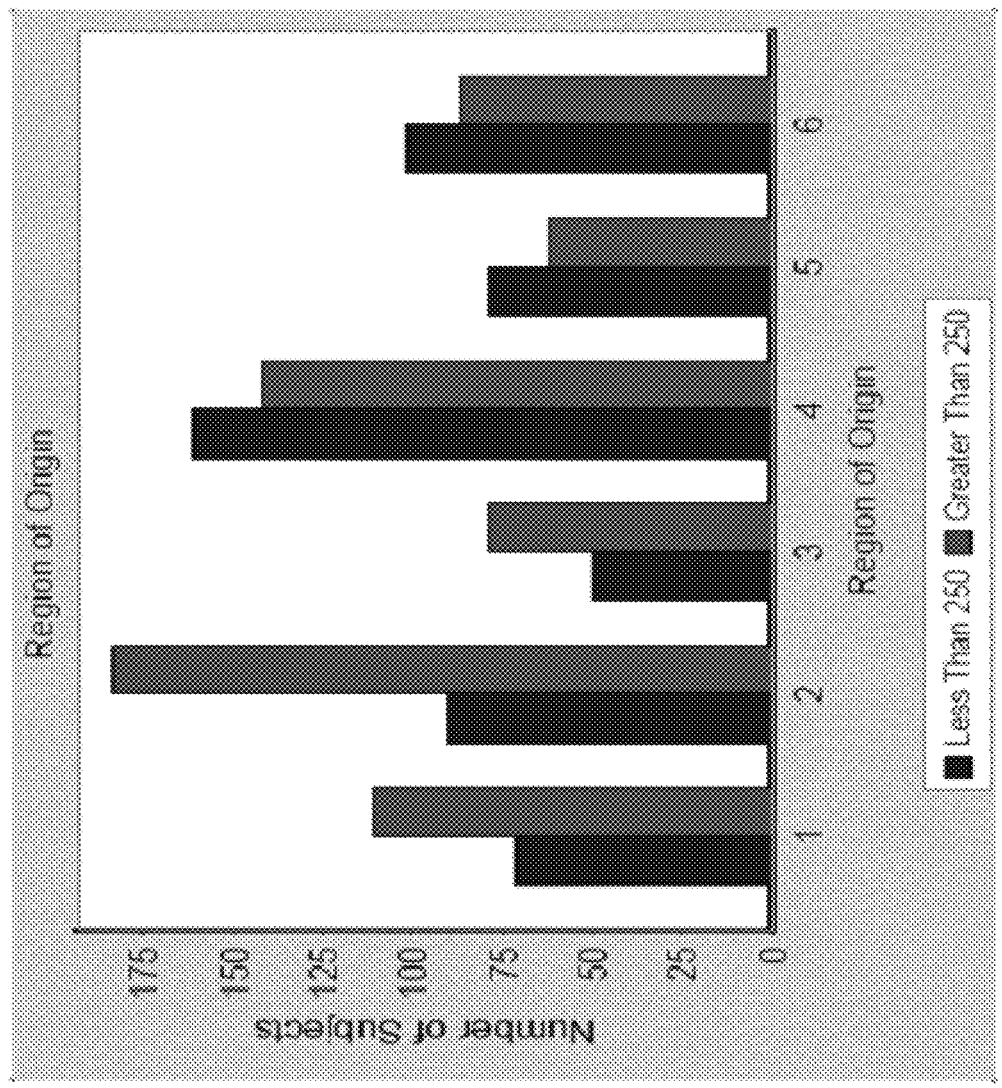
FIG. 21E-4B: Antibody to CMV correlated to region of origin.

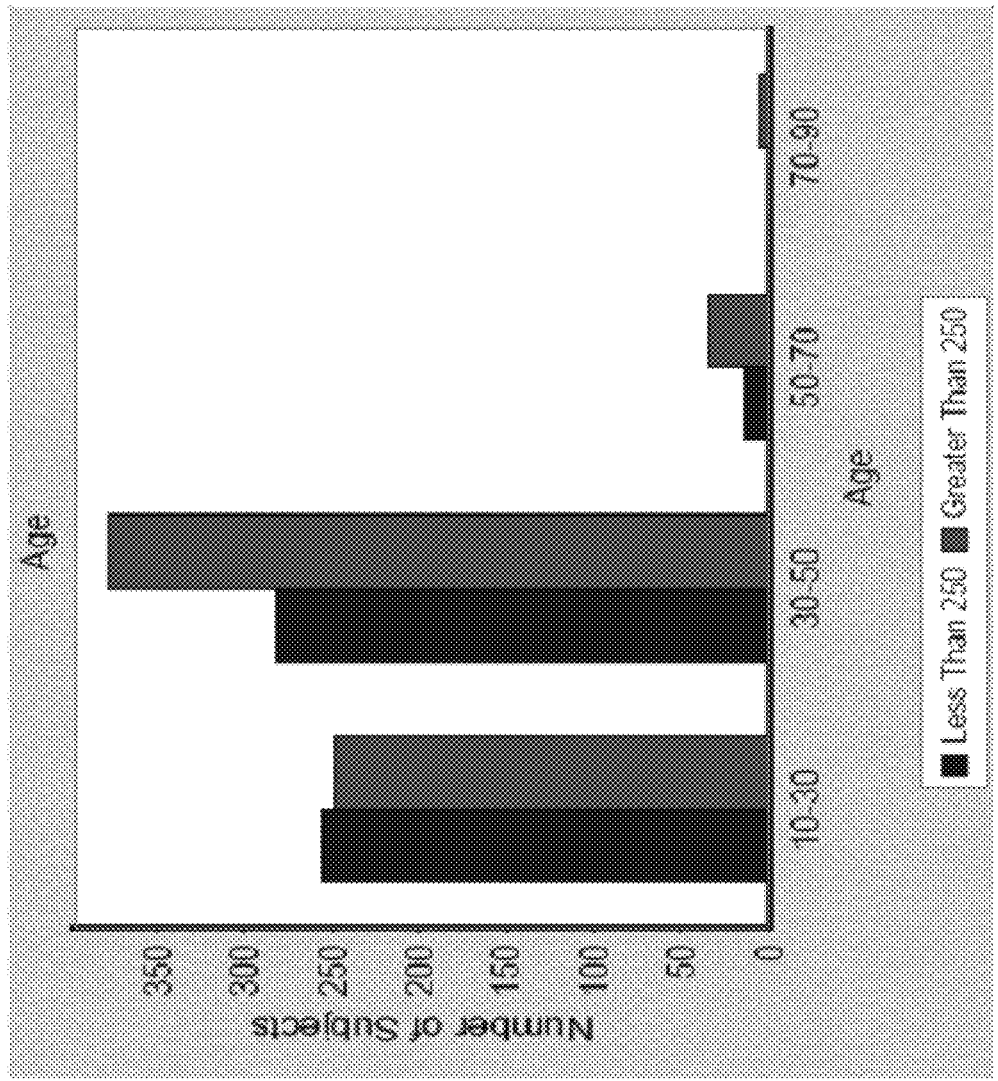
FIG. 21E-4C: Antibody to CMV correlated to age.

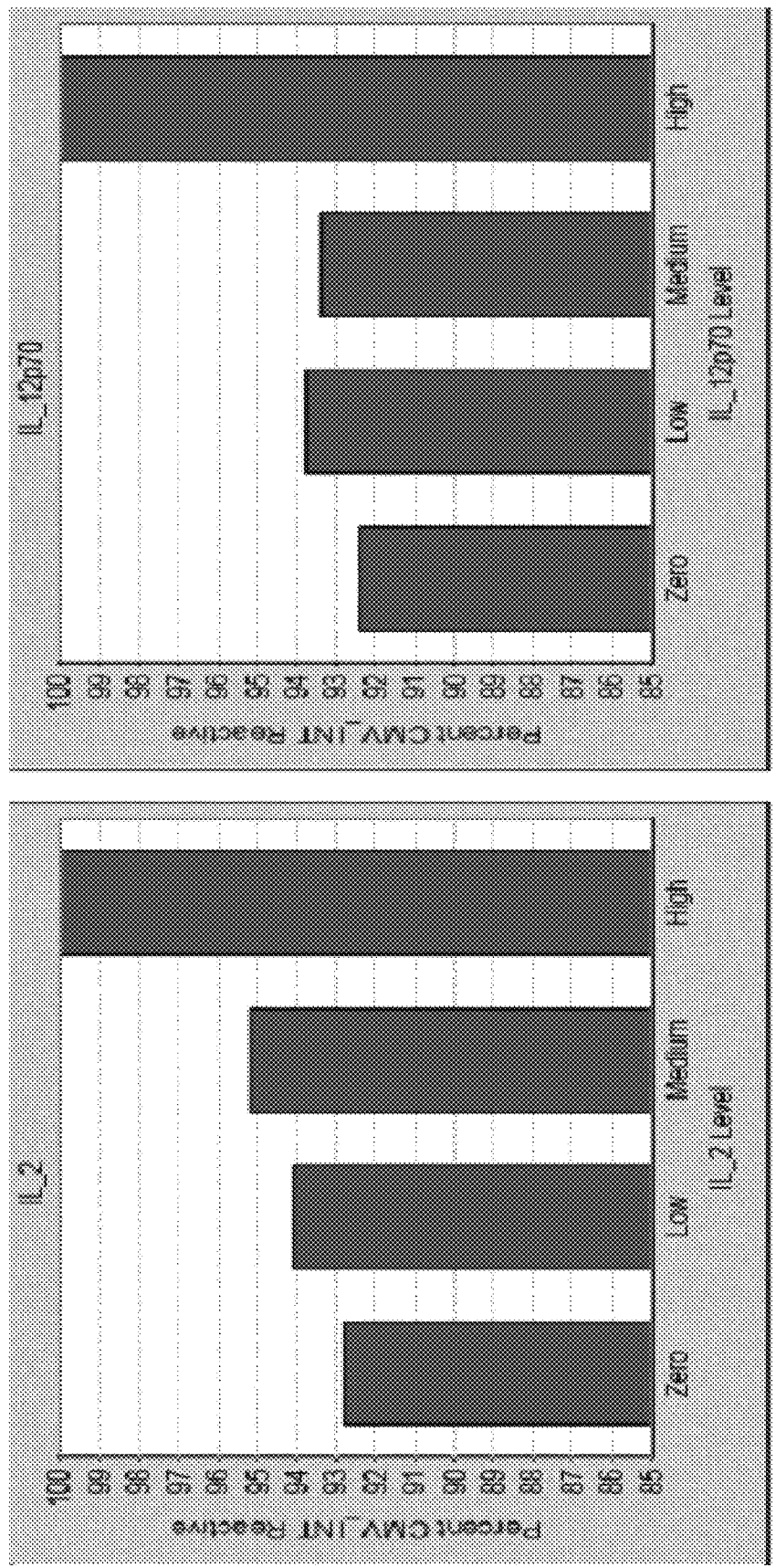
FIG. 21E-5A: Cytokine levels plotted vs. Percent CMV Reactive

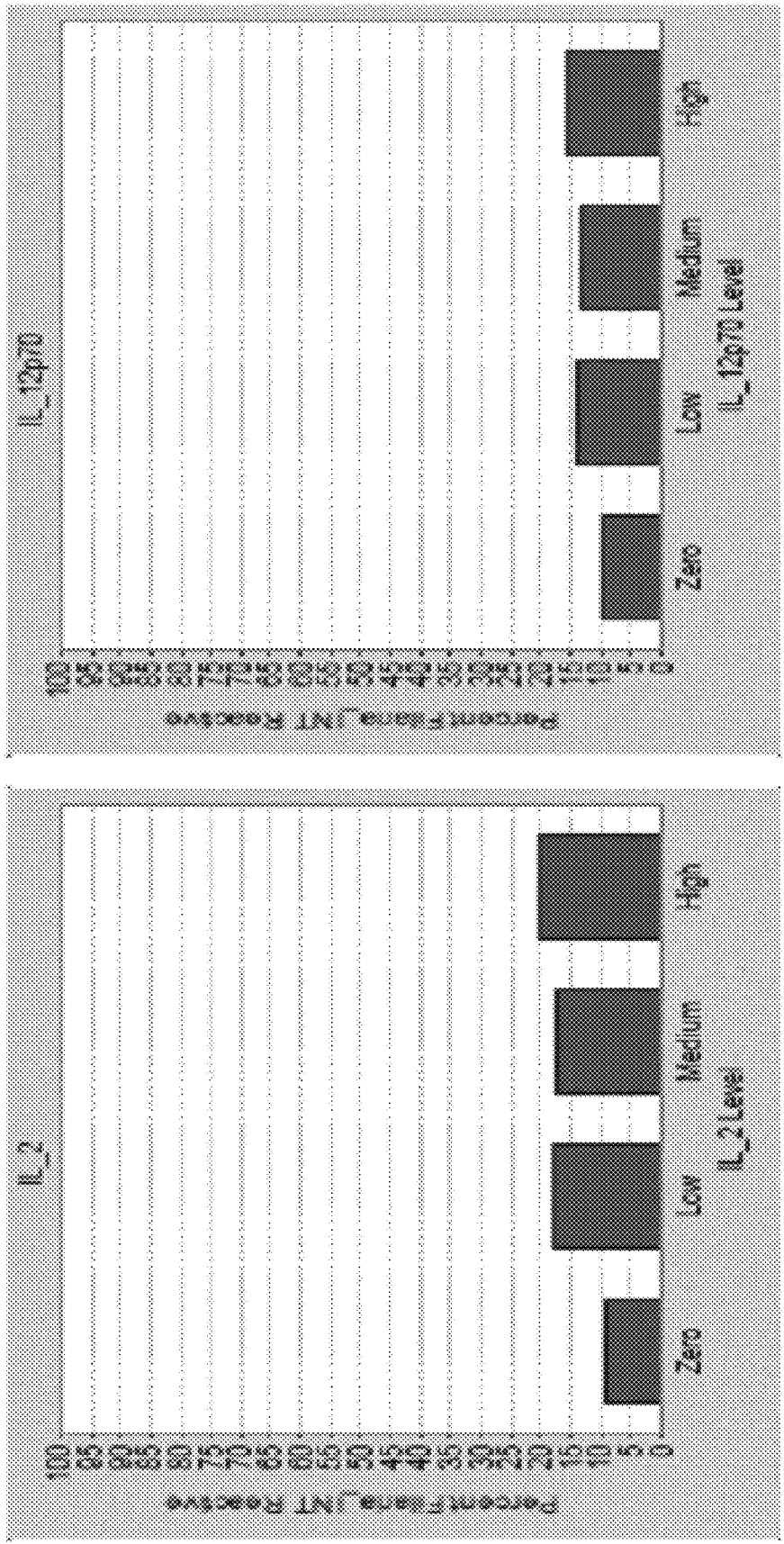
FIG. 21E-6A: Cytokine levels plotted vs. Percent Filaria Reactive

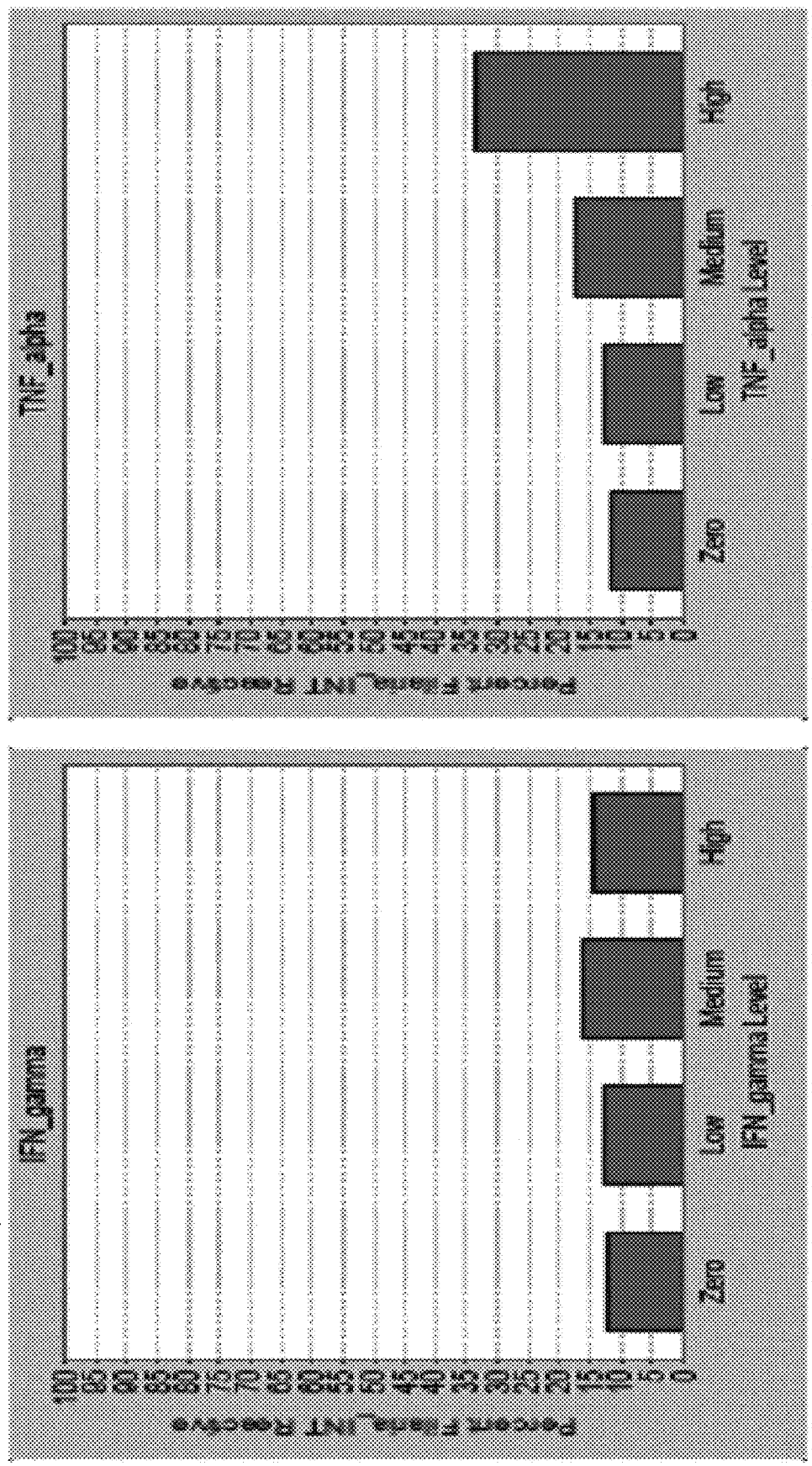
FIG. 21E-6B: Cytokine levels vs. Percent Filaria Reactive

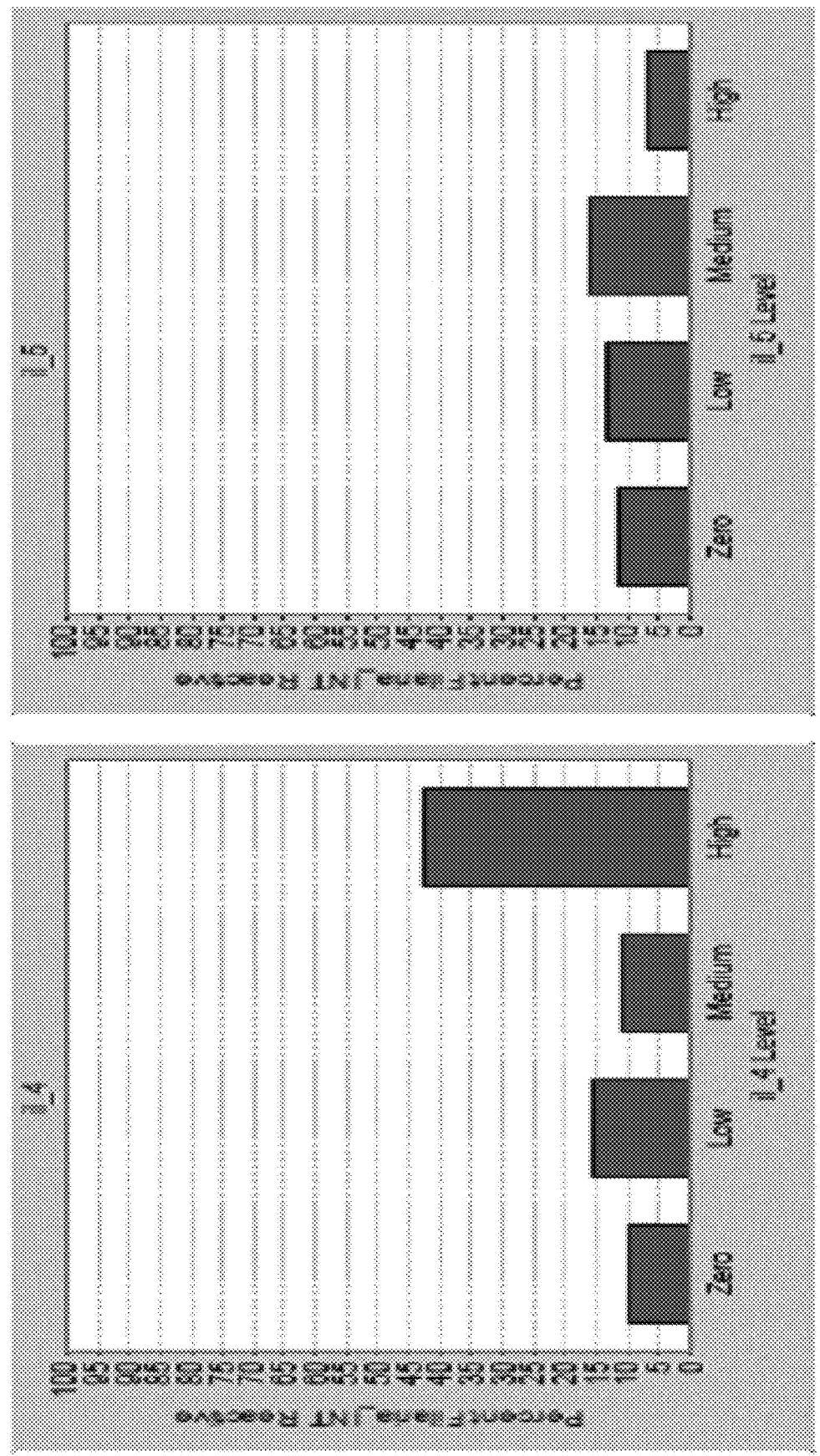
FIG. 21E-6C: Cytokine levels plotted vs. Percent Filaria Reactive

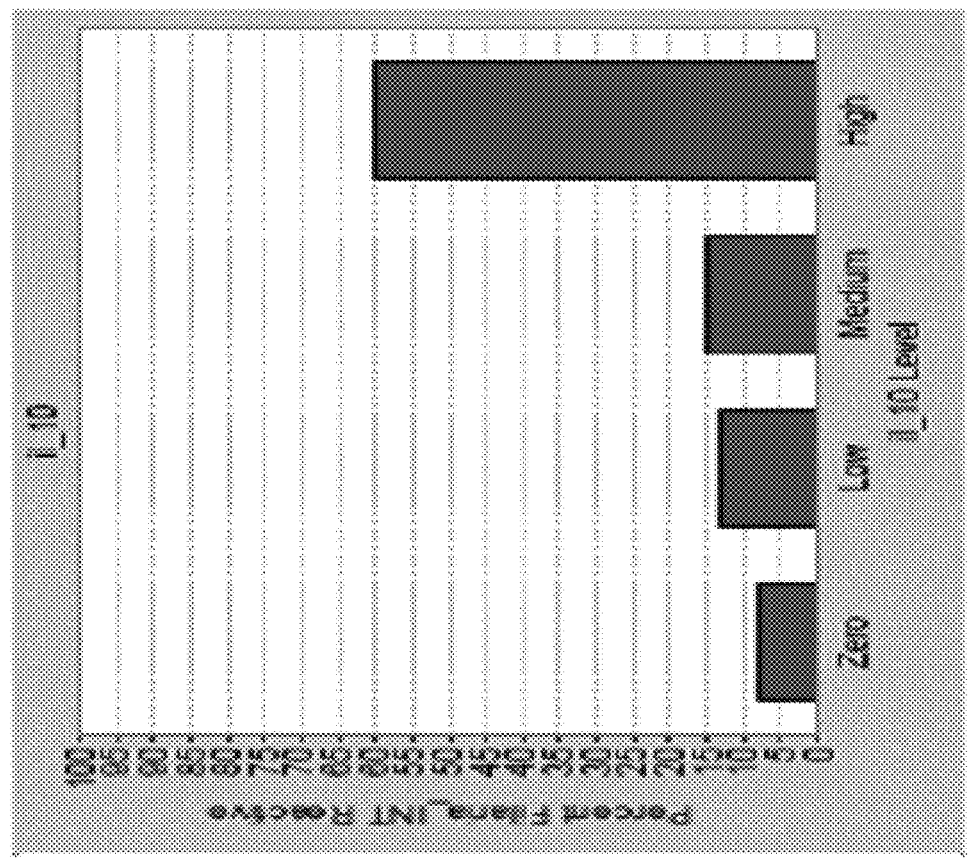
FIG. 21E-6D: Cytokine levels plotted vs. Percent Filaria Reactive

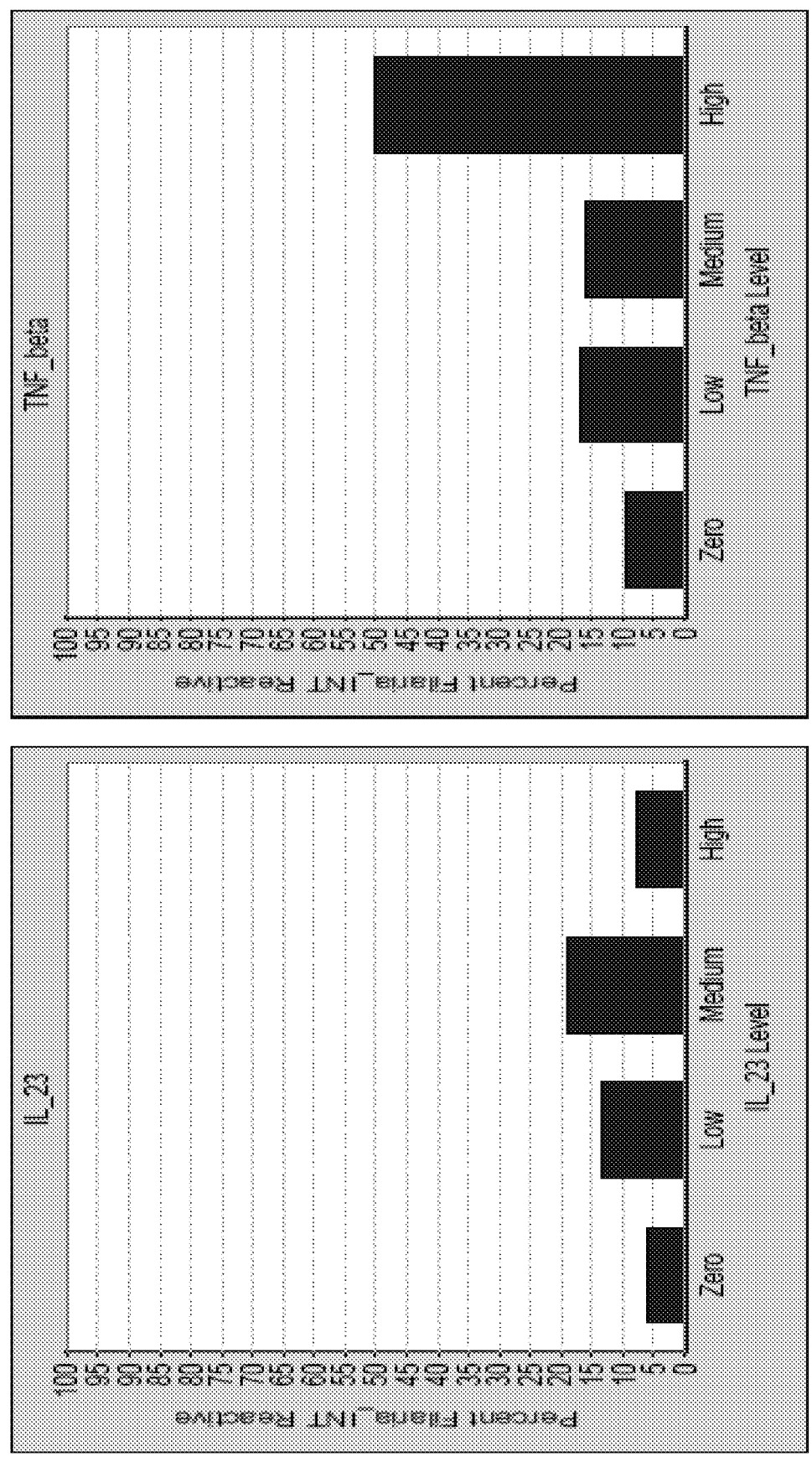
FIG. 21E-6E: Cytokine levels plotted vs. Percent Filaria Reactive

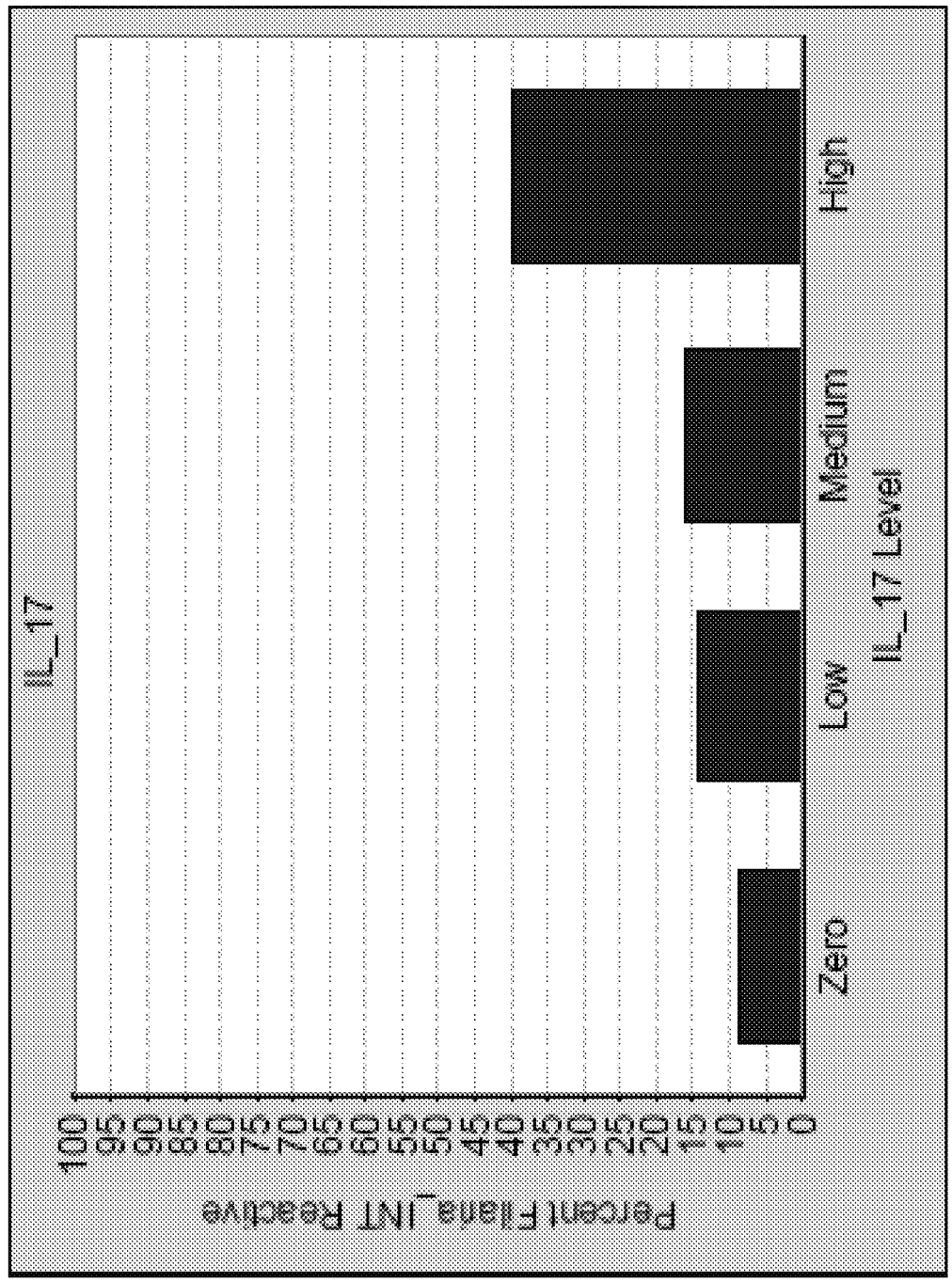
FIG. 21E-6F: Cytokine levels plotted vs. Percent Filaria Reactive

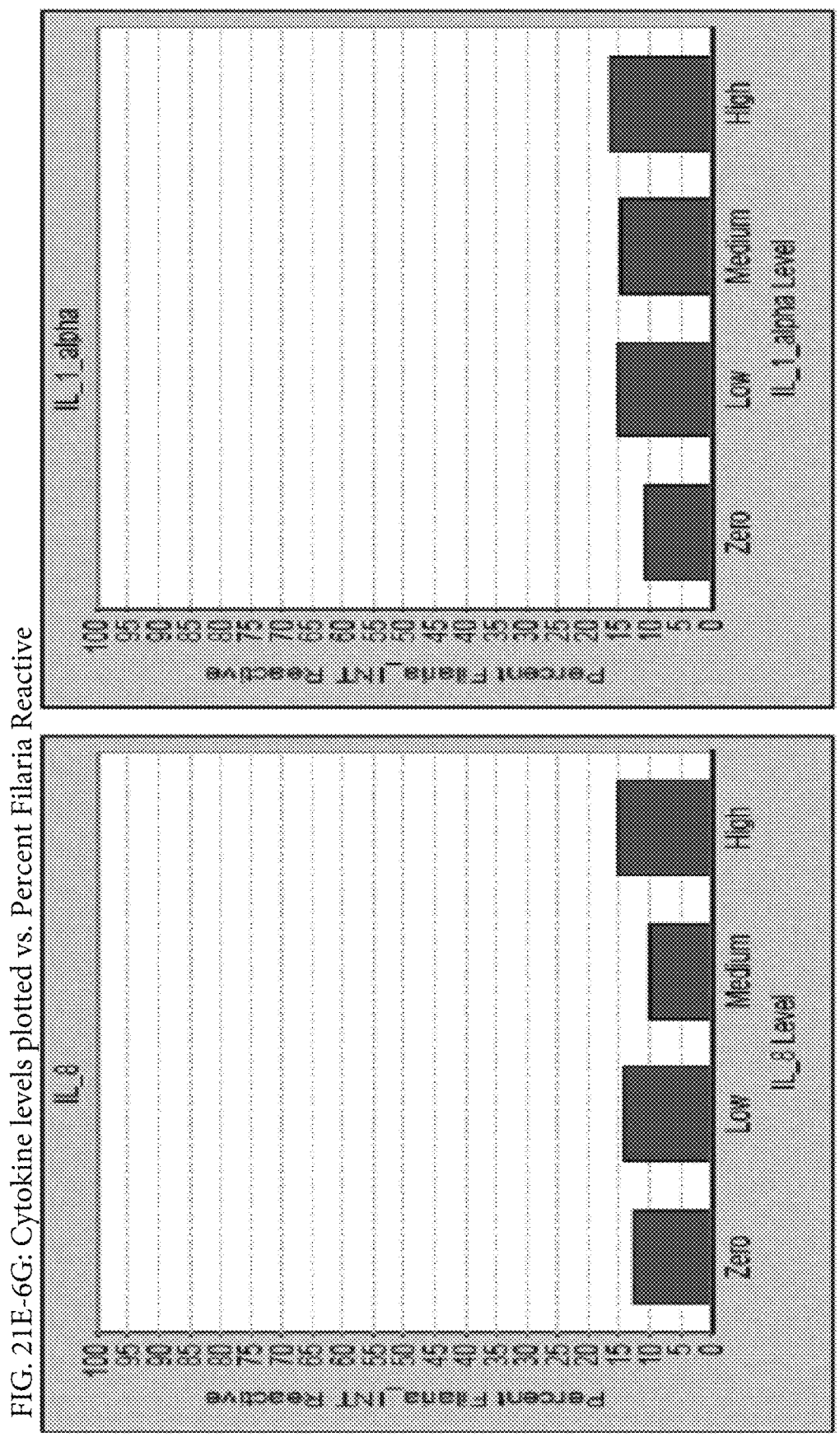
FIG. 21E-6G: Cytokine levels plotted vs. Percent Filaria Reactive

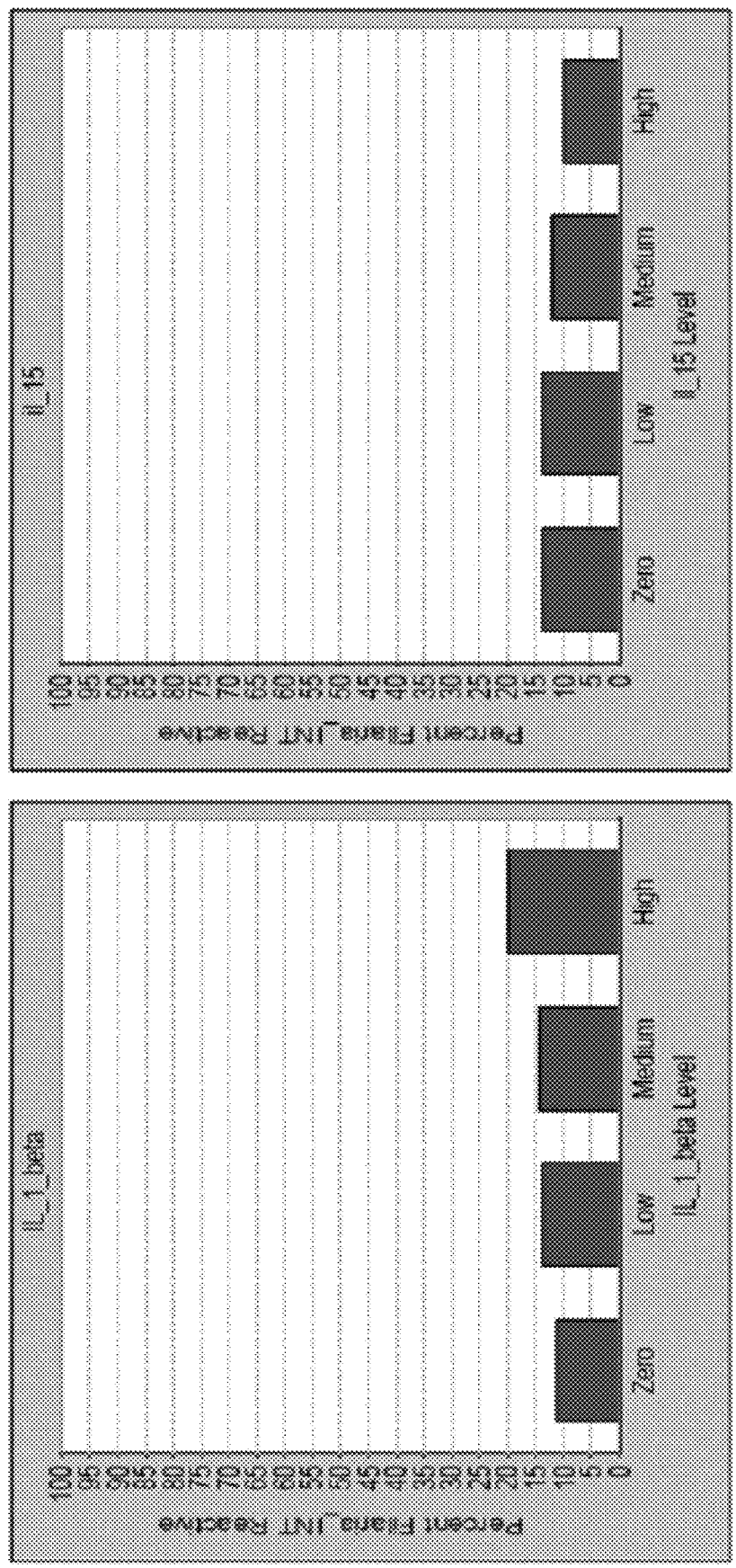
FIG. 21E-6H: Cytokine levels plotted vs. Percent Filaria Reactive

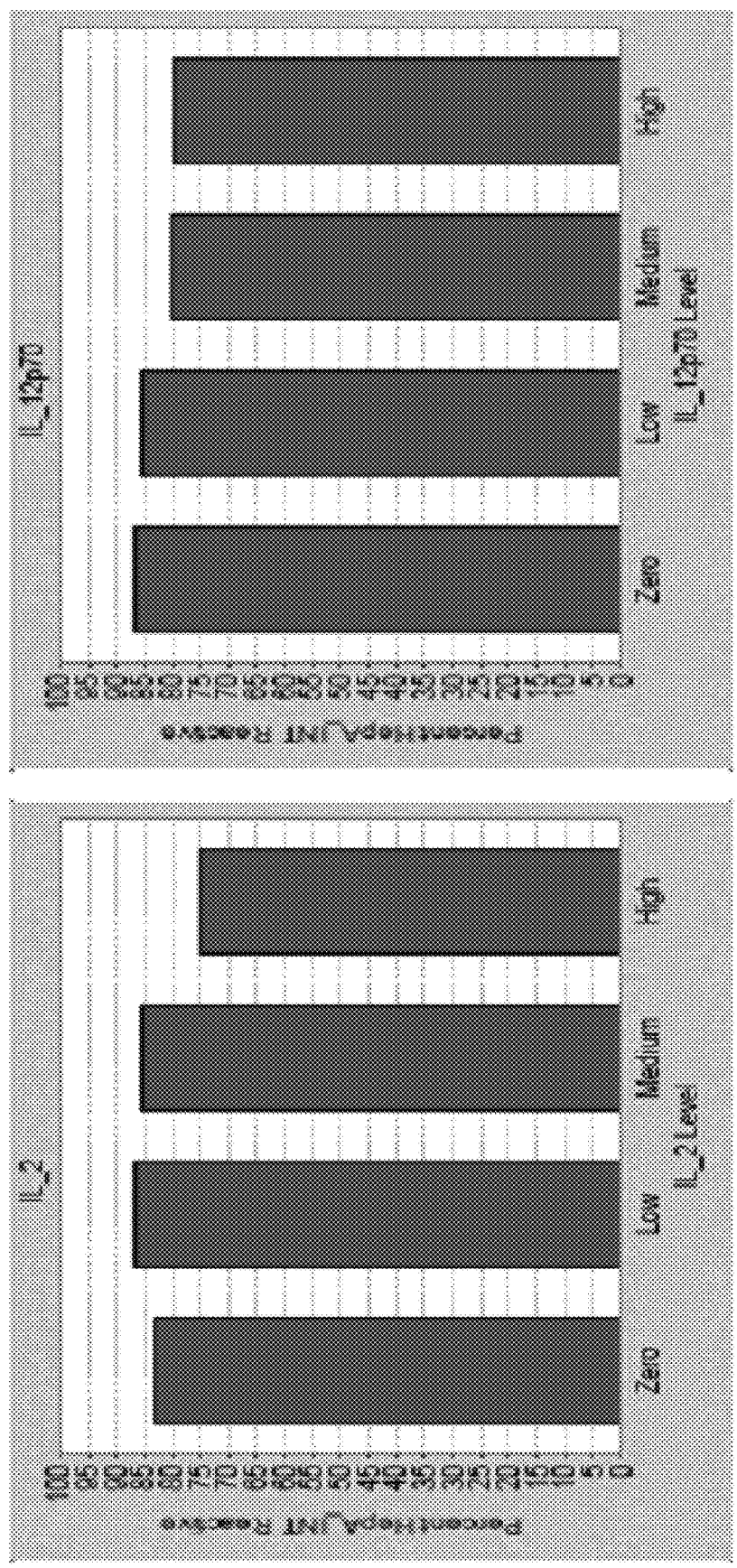
FIG. 21E-7A: Cytokine levels plotted vs. Percent Hepatitis A Reactive

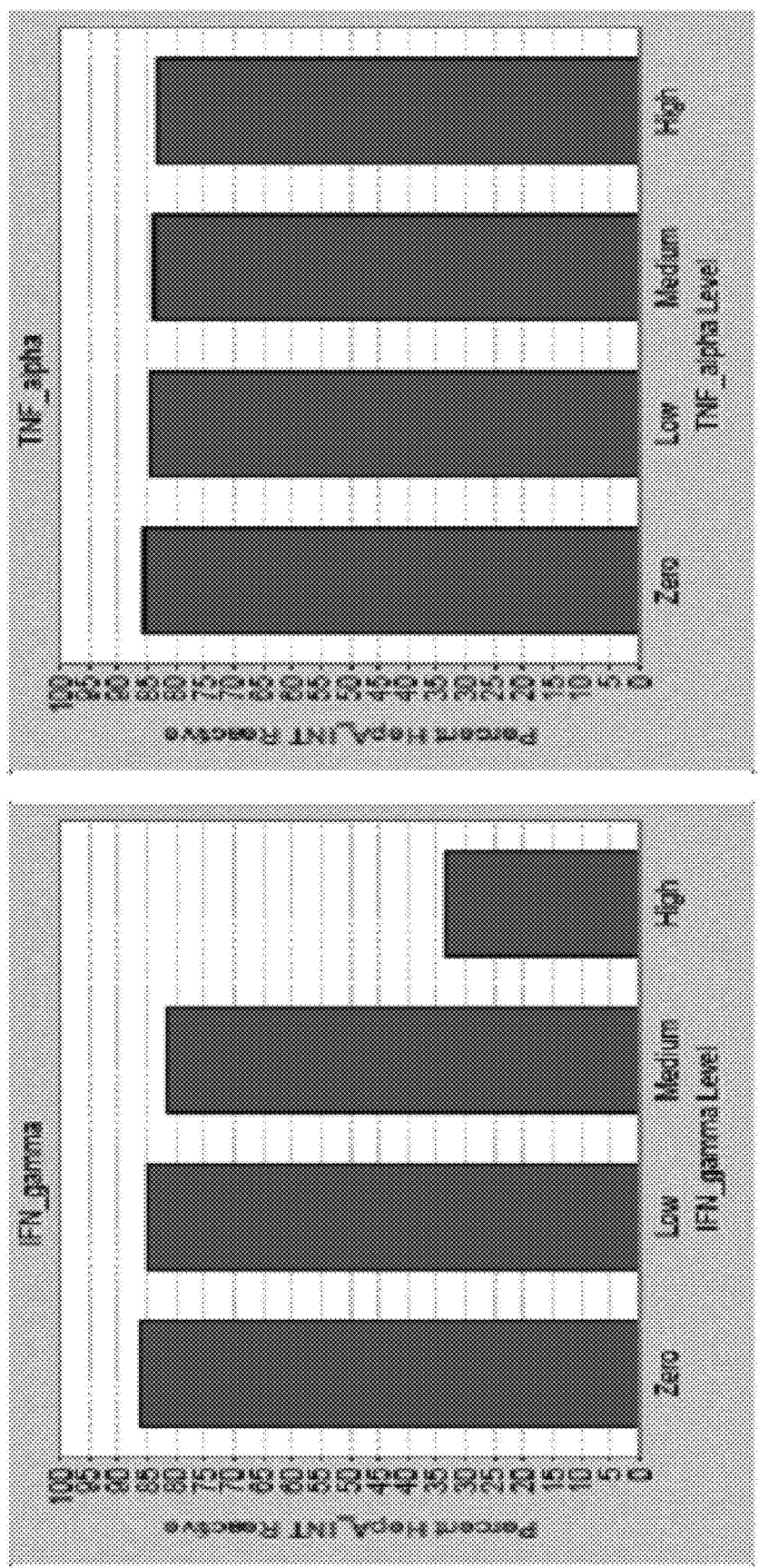
FIG. 21E-7B: Cytokine levels plotted vs. Percent Hepatitis A Reactive

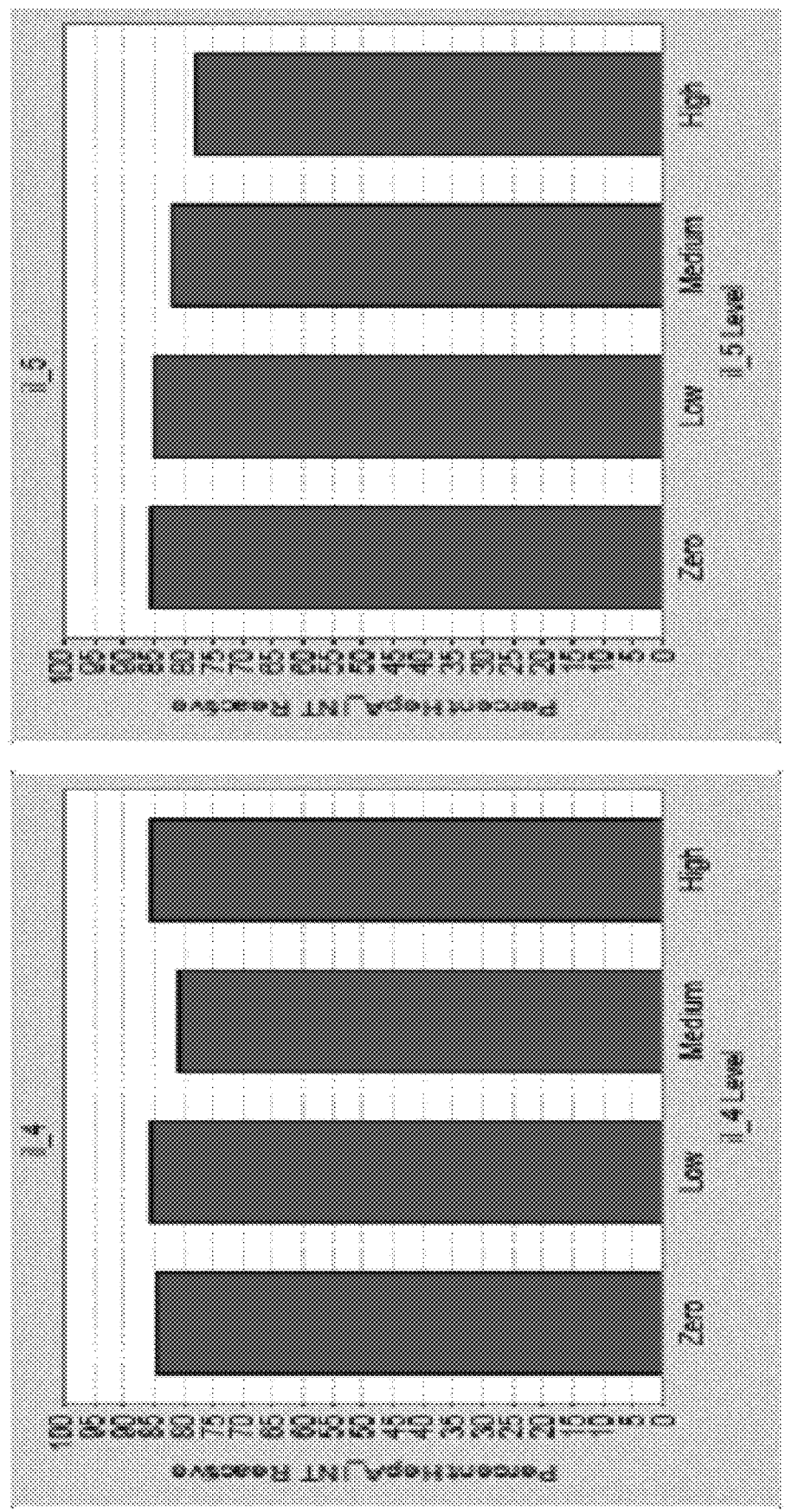
FIG. 21E-7C: Cytokine levels plotted vs. Percent Hepatitis A Reactive

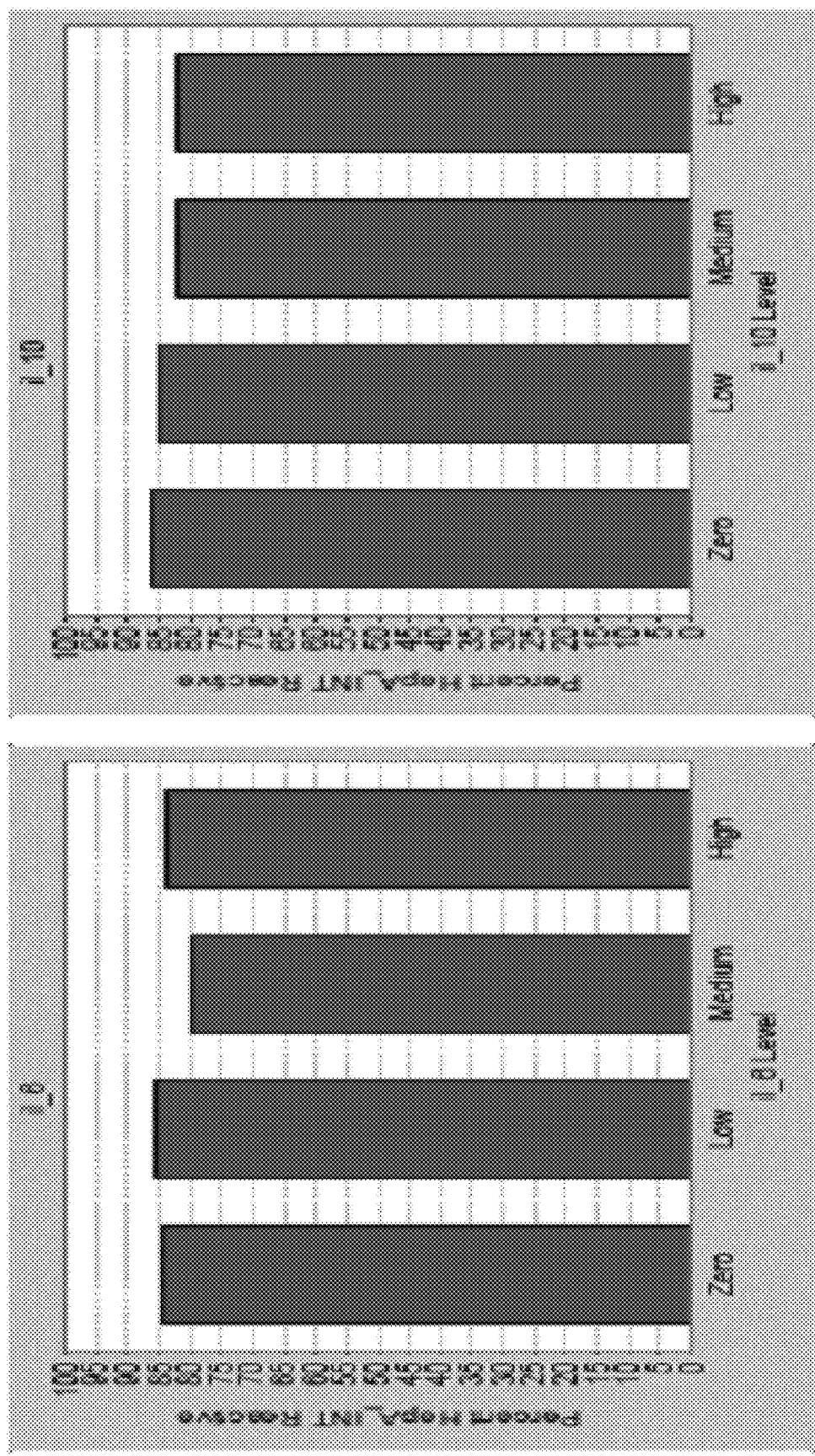
FIG. 21E-7D: Cytokine levels plotted vs. Percent Hepatitis A Reactive

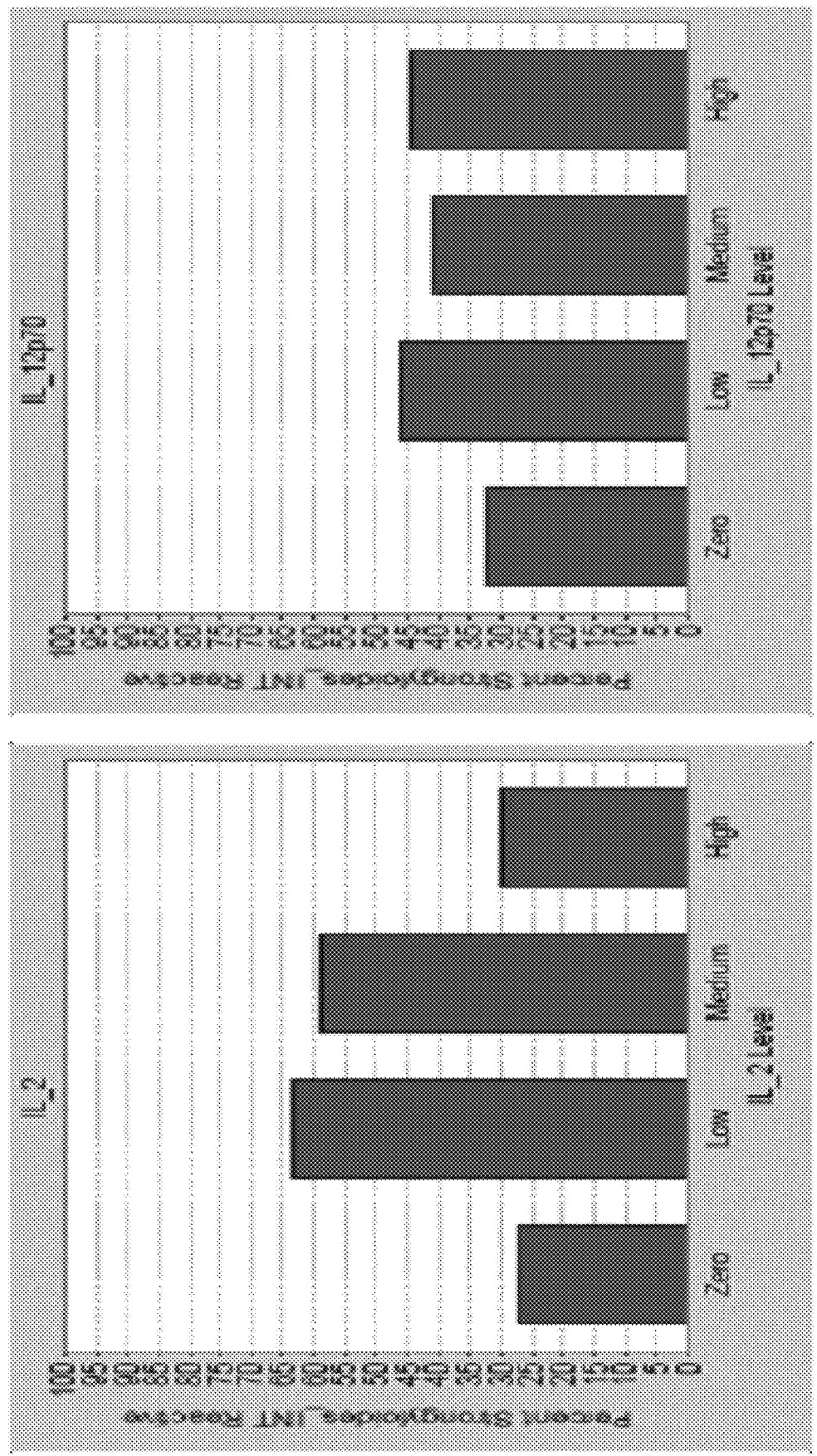
FIG. 21E-8A: Cytokine levels plotted vs. Percent Strongyloides Reactive

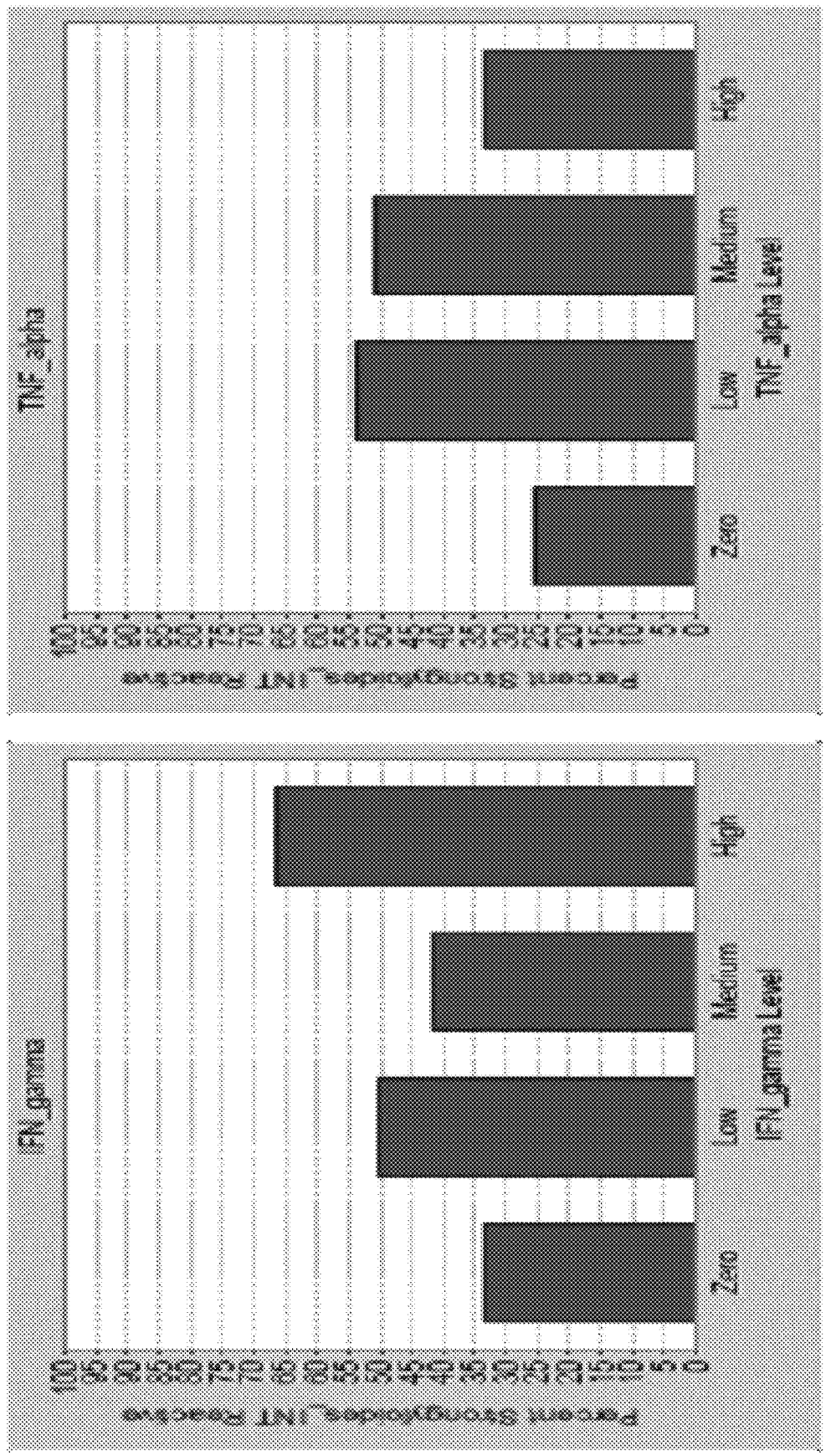
FIG. 21E-8B: Cytokine levels plotted vs. Percent Strongyloides Reactive

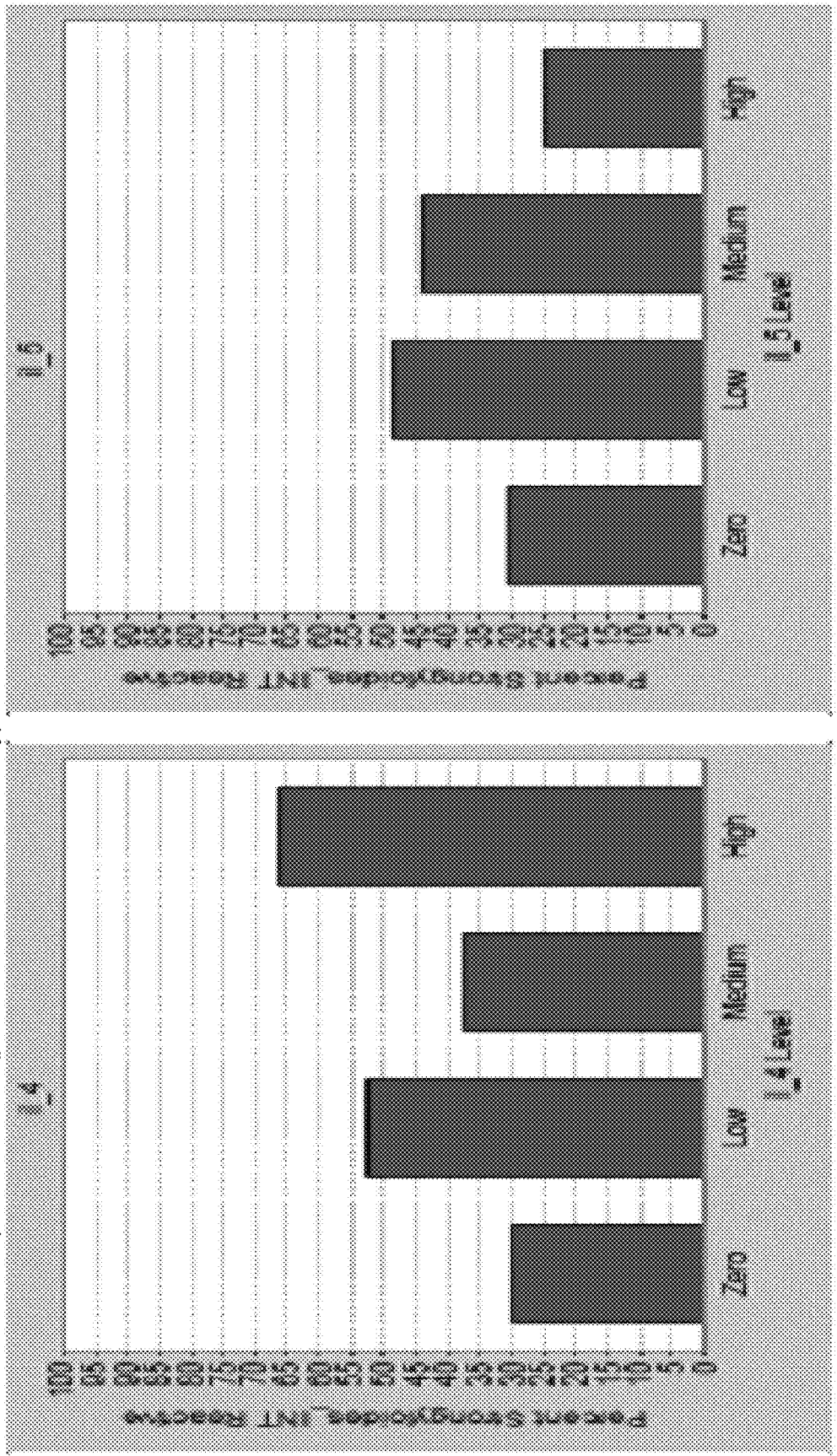
FIG. 21E-8C: Cytokine levels plotted vs. Percent Strongyloides Reactive

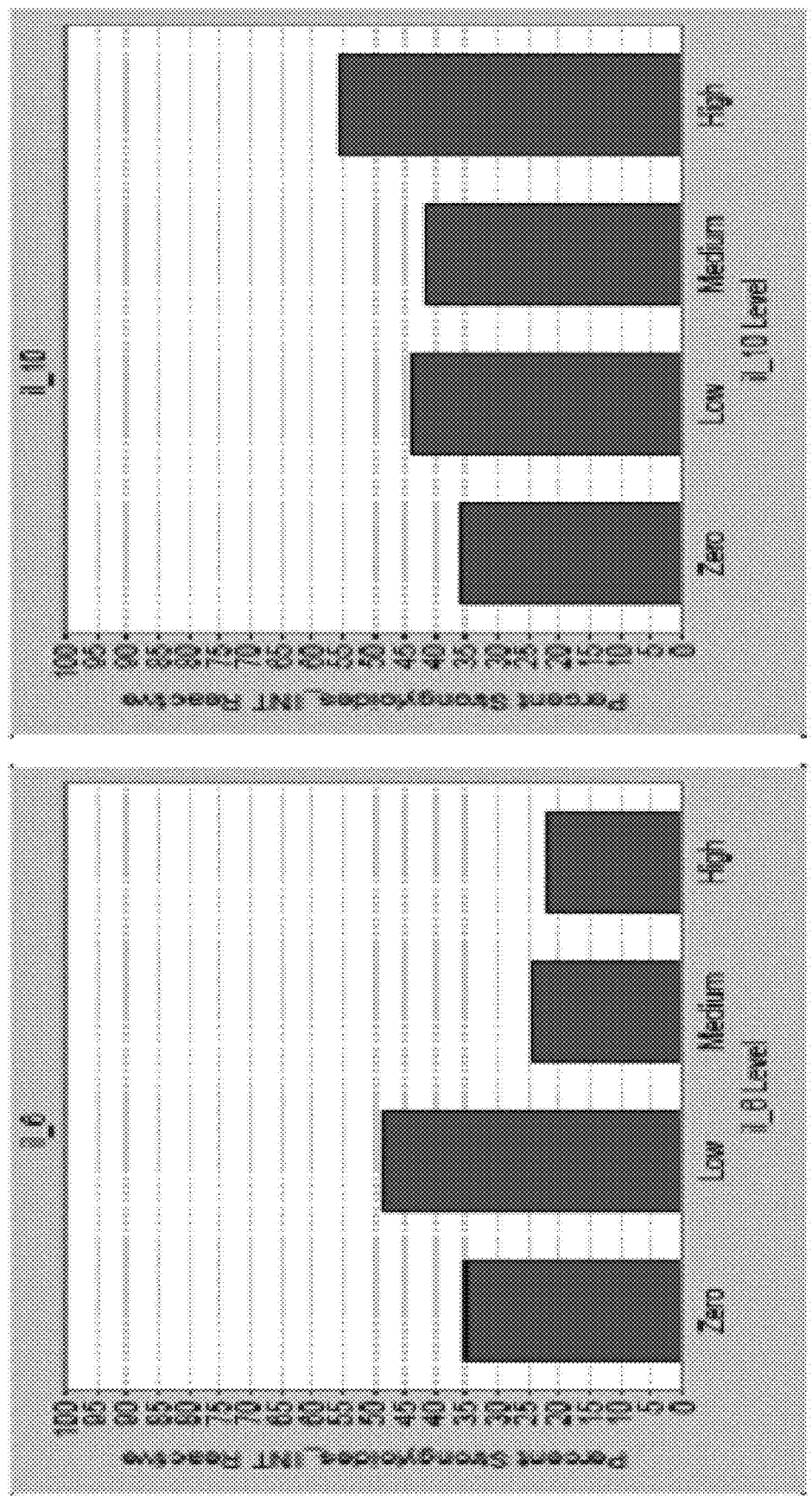
FIG. 21E-8D: Cytokine levels plotted vs. Percent Strongyloides Reactive

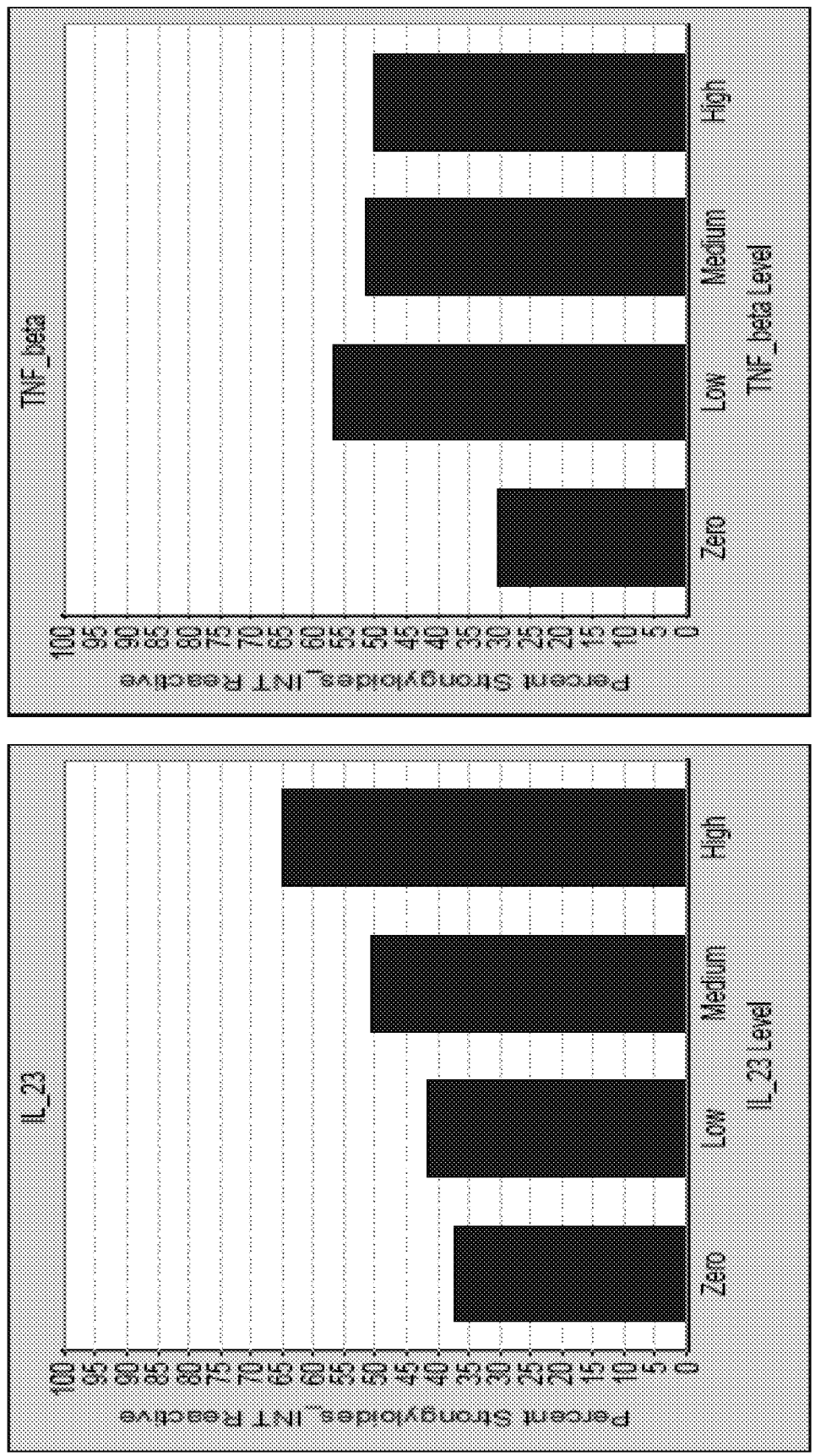
FIG. 21E-8E: Cytokine levels plotted vs. Percent Strongyloides Reactive

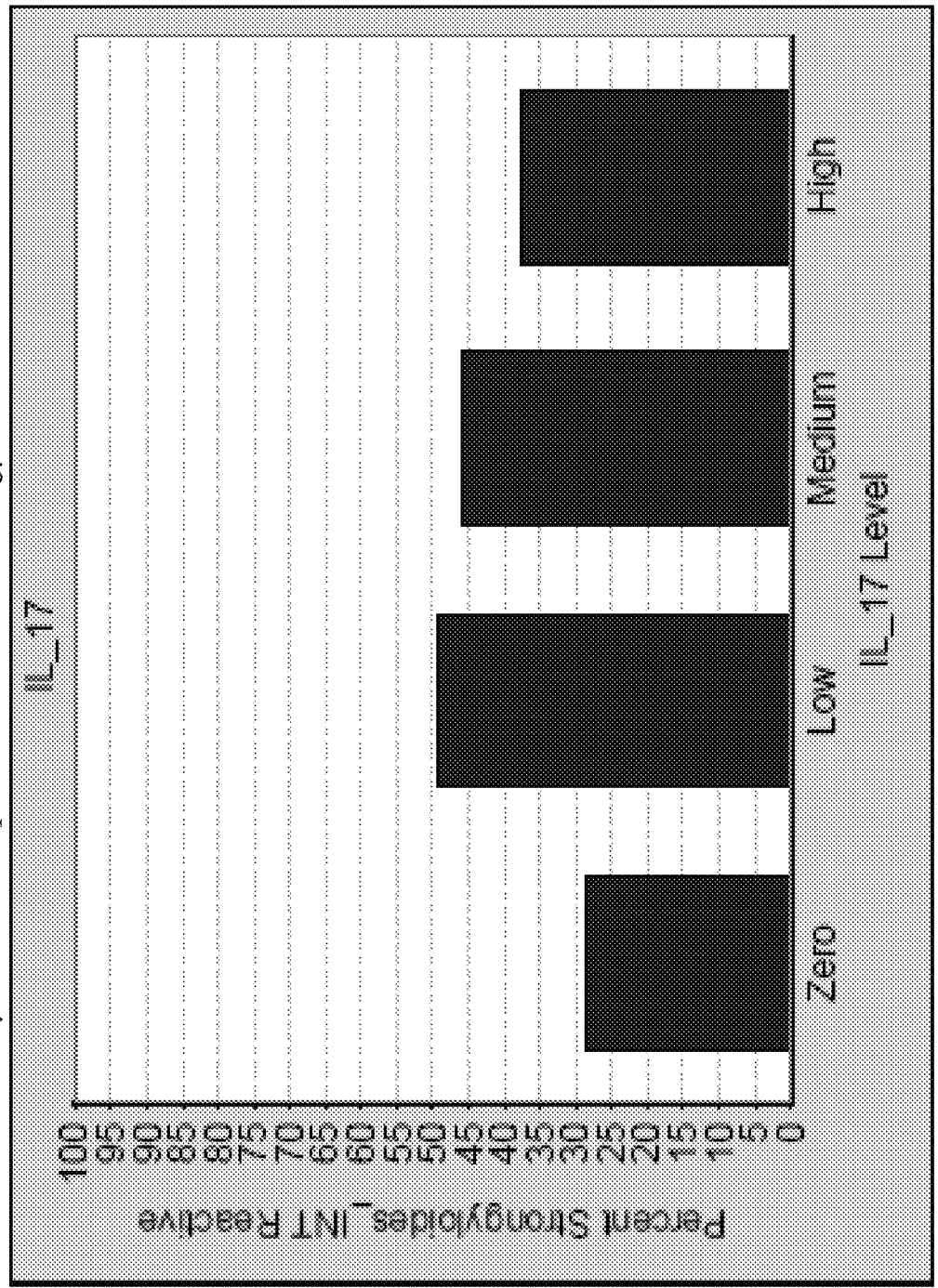
FIG. 21E-8F: Cytokine levels plotted vs. Percent Strongyloides Reactive

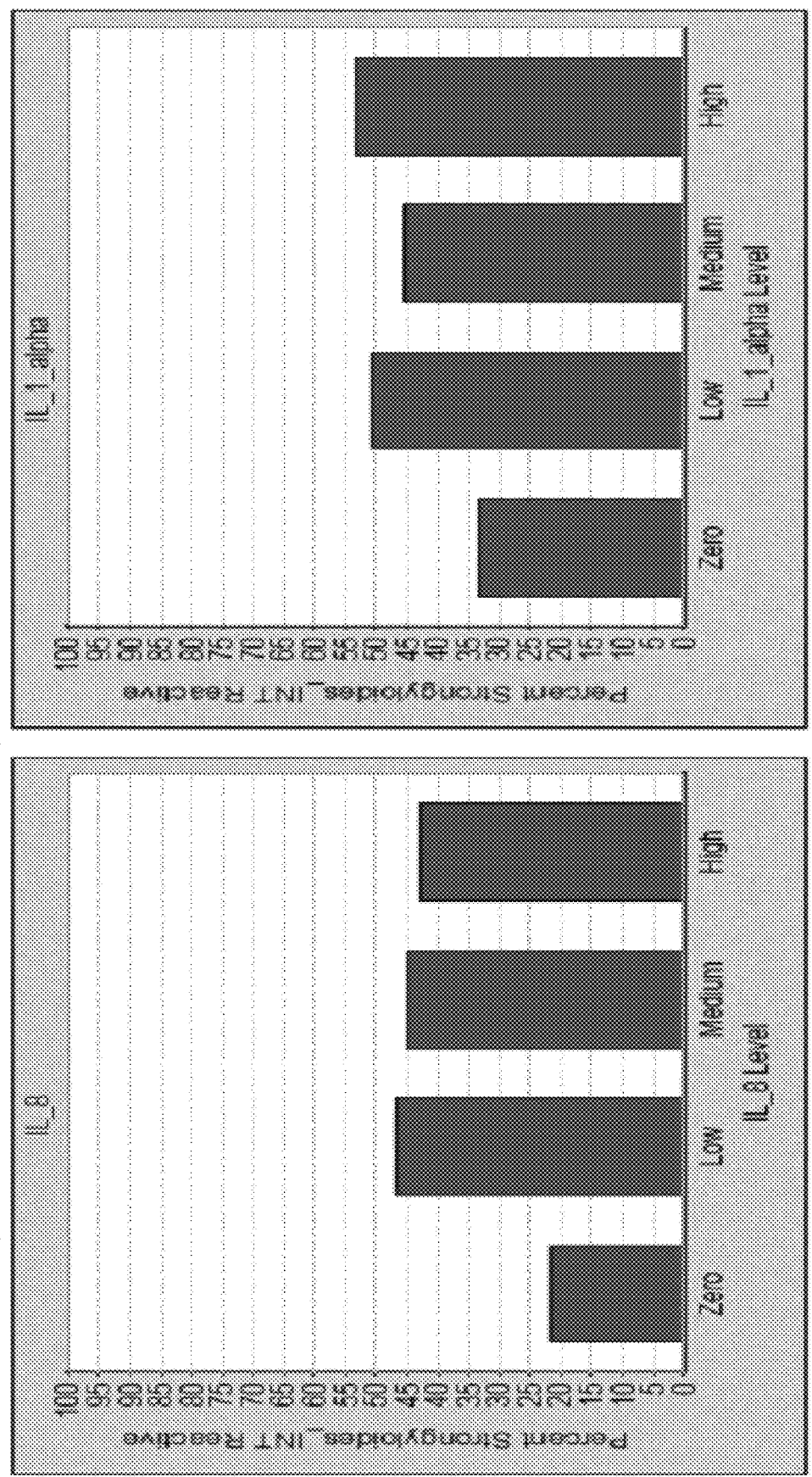
FIG. 21E-8G: Cytokine levels plotted vs. Percent Strongyloides Reactive

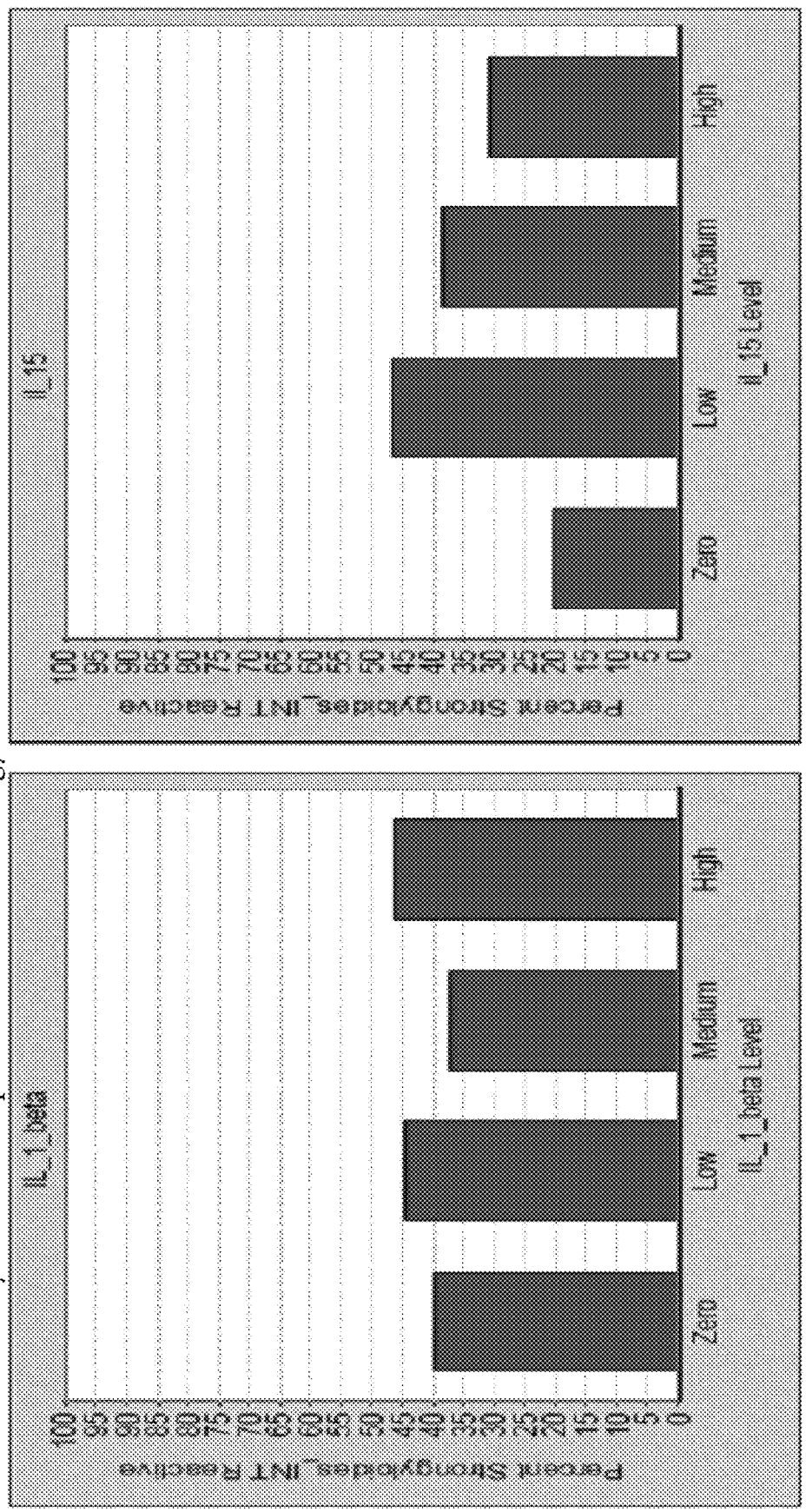
FIG. 21E-8H: Cytokine levels plotted vs. Percent Strongyloides Reactive

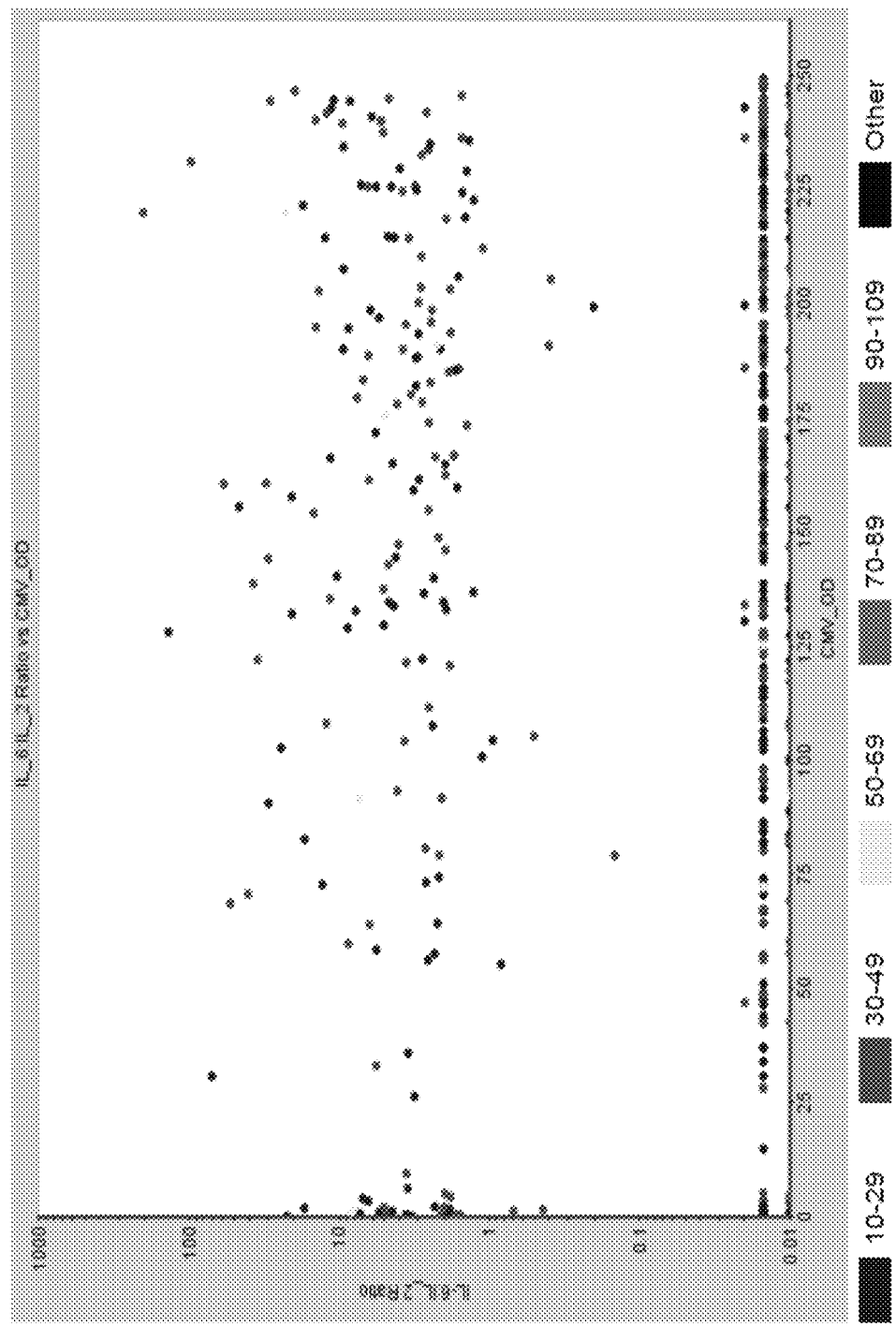
FIG. 21E-9A: Multi-variate Analysis of CIP

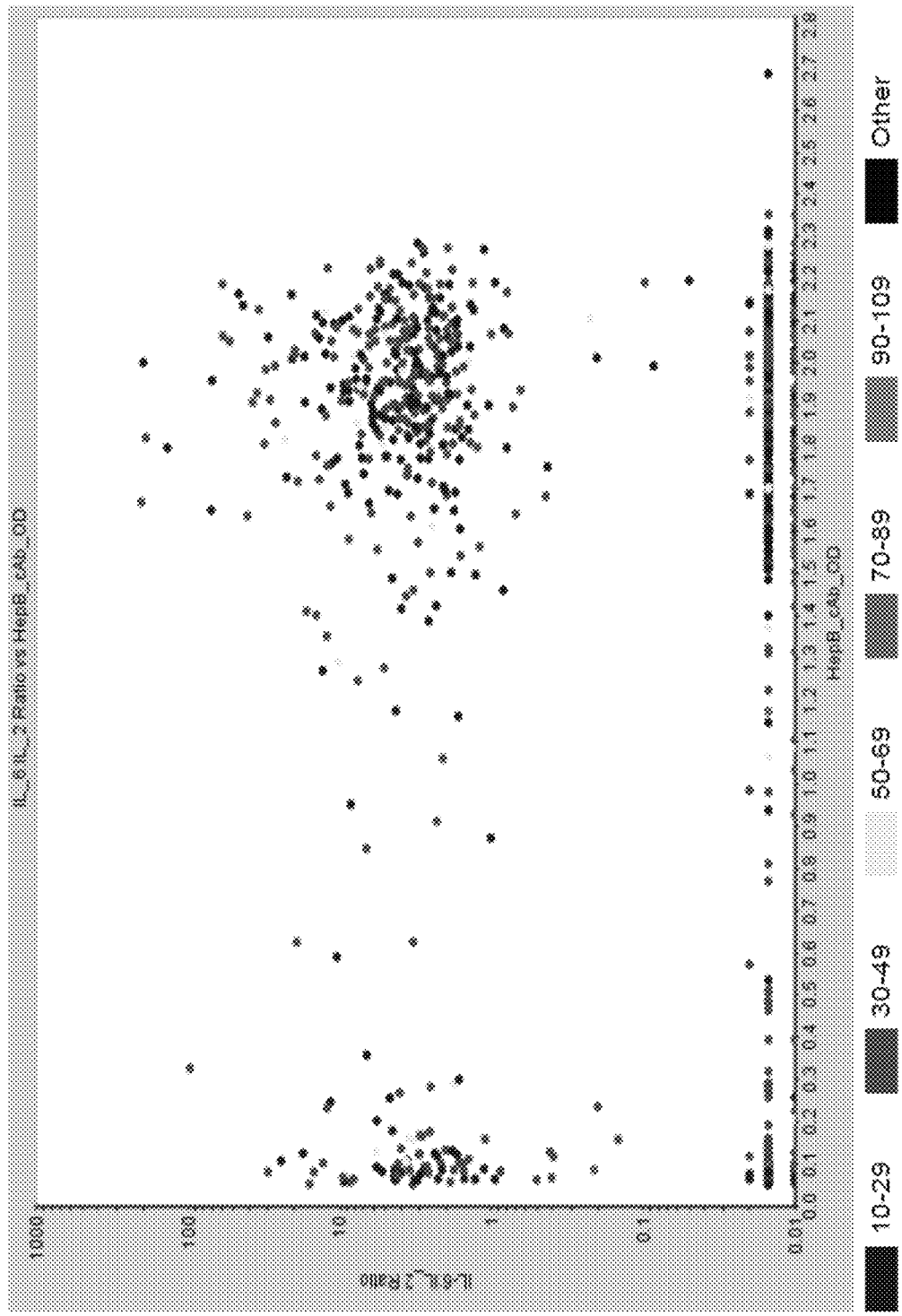
FIG. 21E-9B: Multi-variate Analysis of CIP

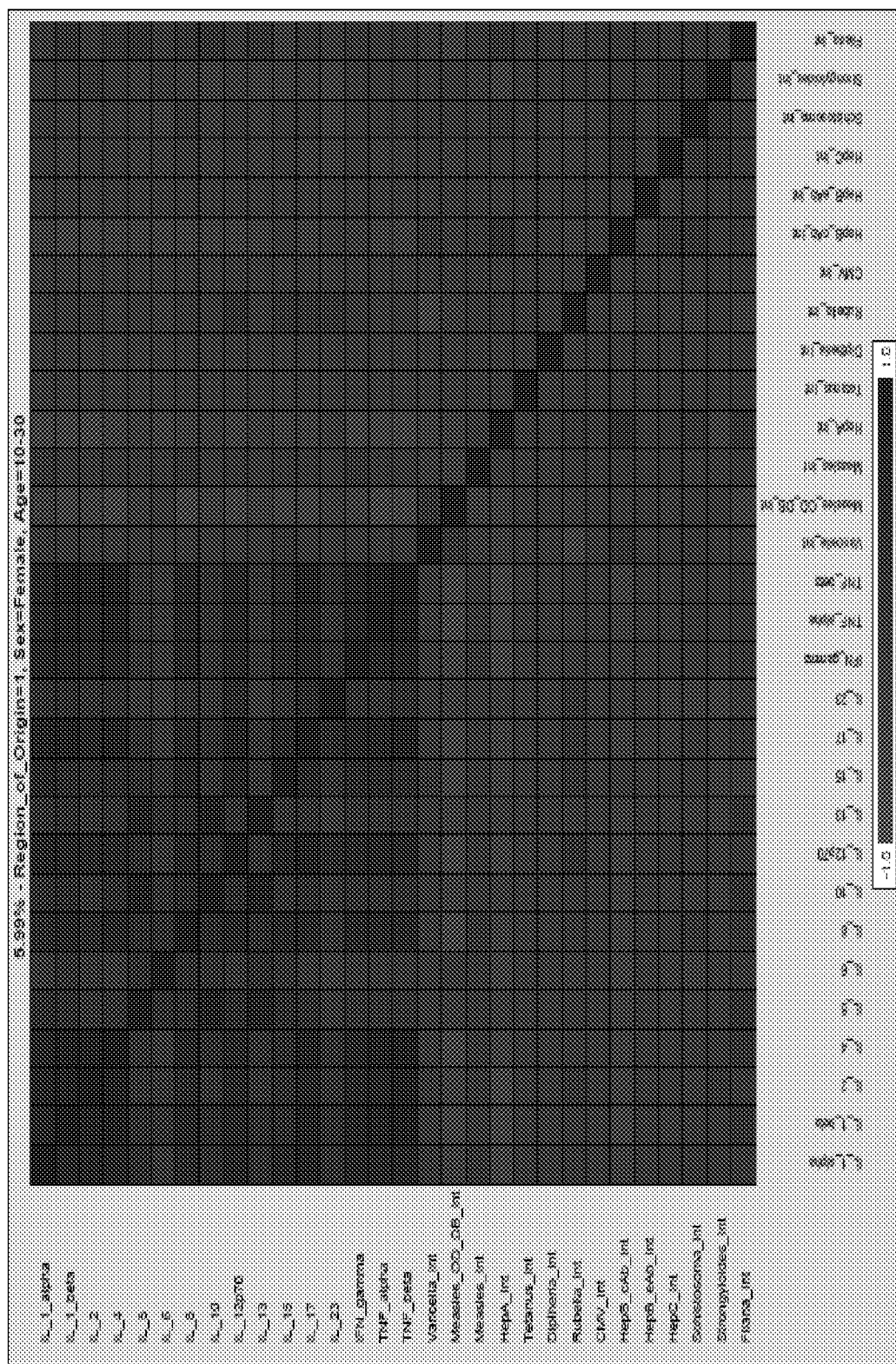
FIG. 21E-10.1A: Heat maps generated from Data Mining Tool. Sub-Saharan Africa, age 10-30. Females

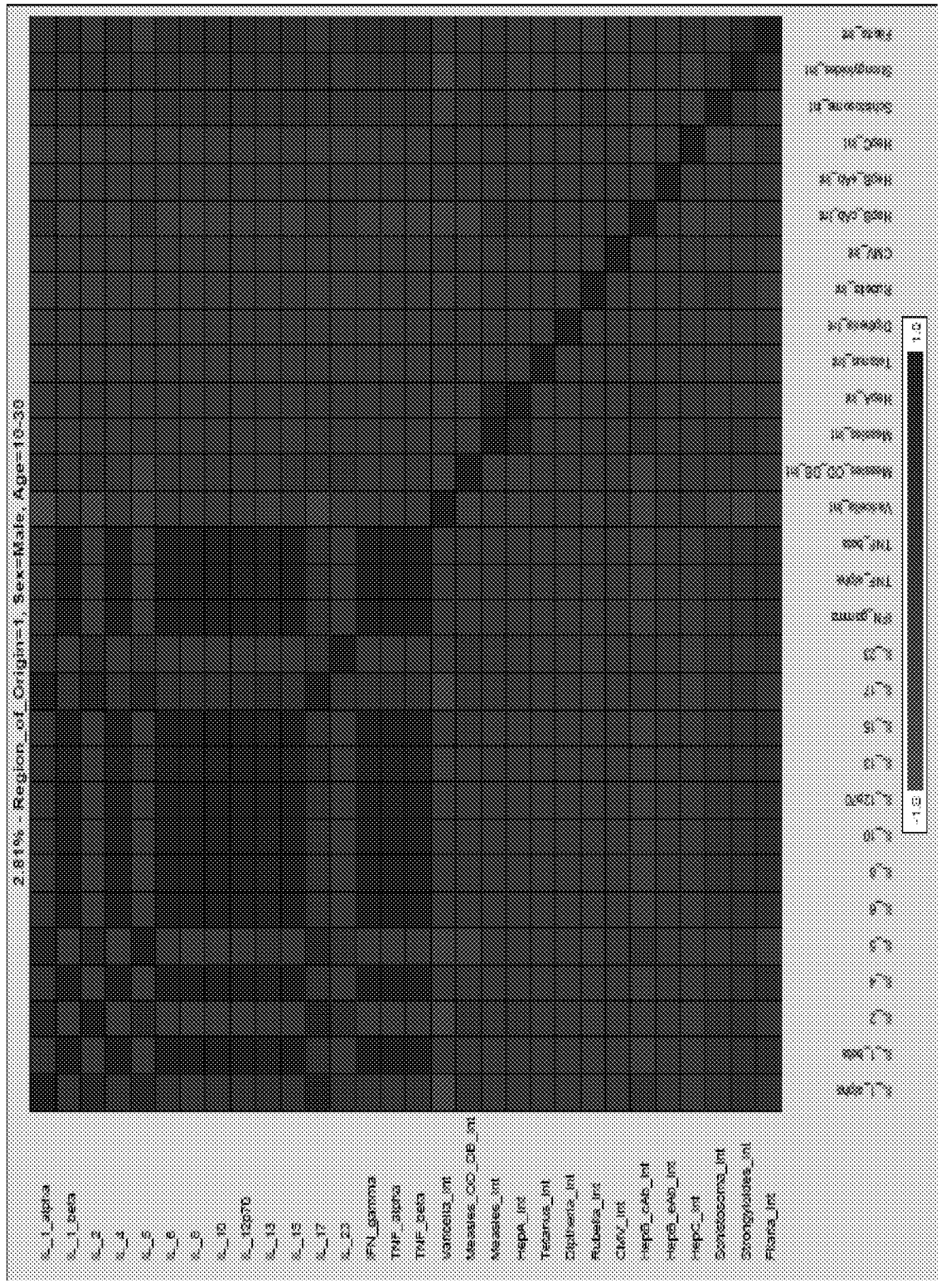
FIG. 21E-10.1B: Heat maps generated from Data Mining Tool. Sub-Saharan Africa, age 10-30. Males

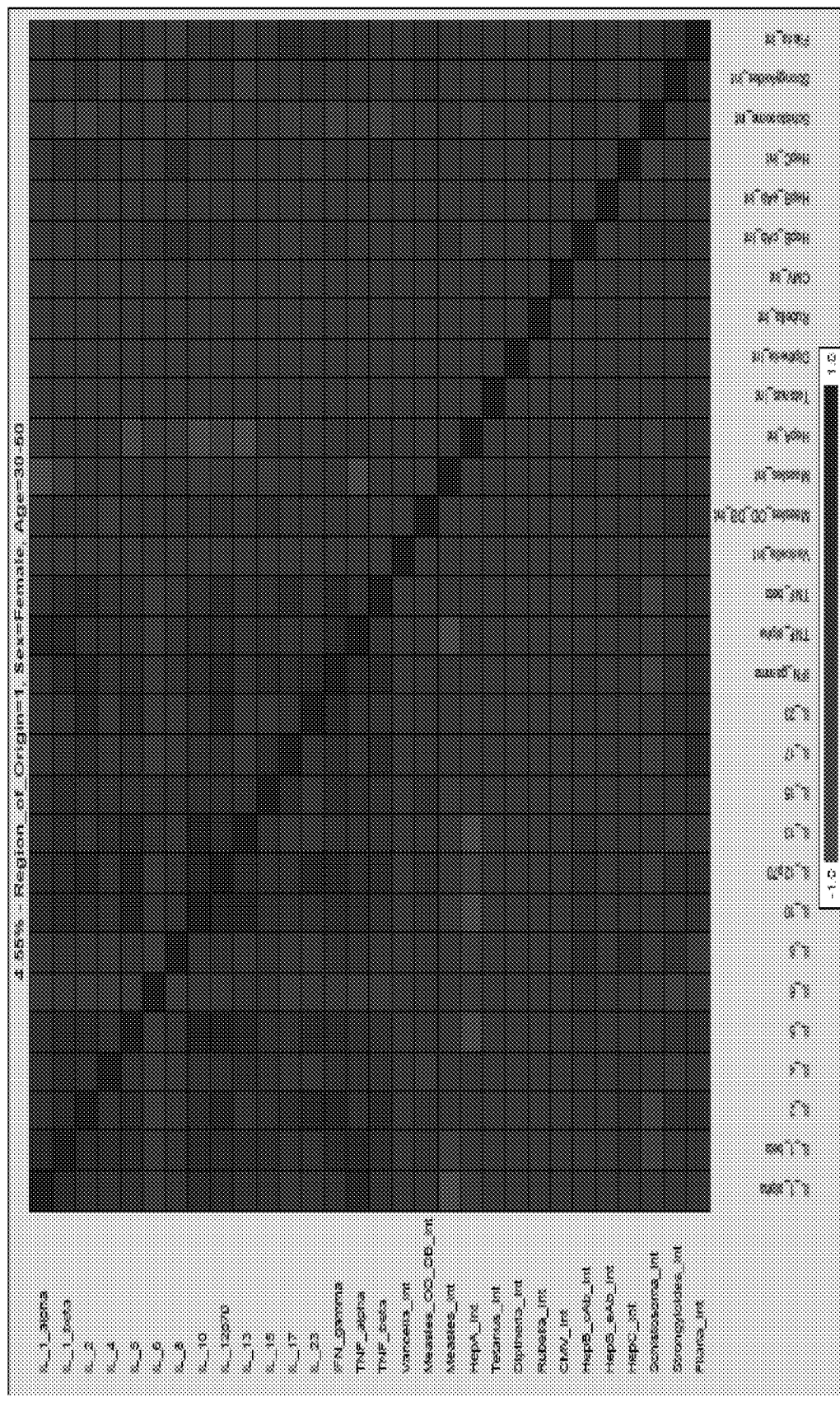
FIG. 21E-10.2A: Heat maps generated from Data Mining Tool. Sub-Saharan Africa, age 30-50. Females

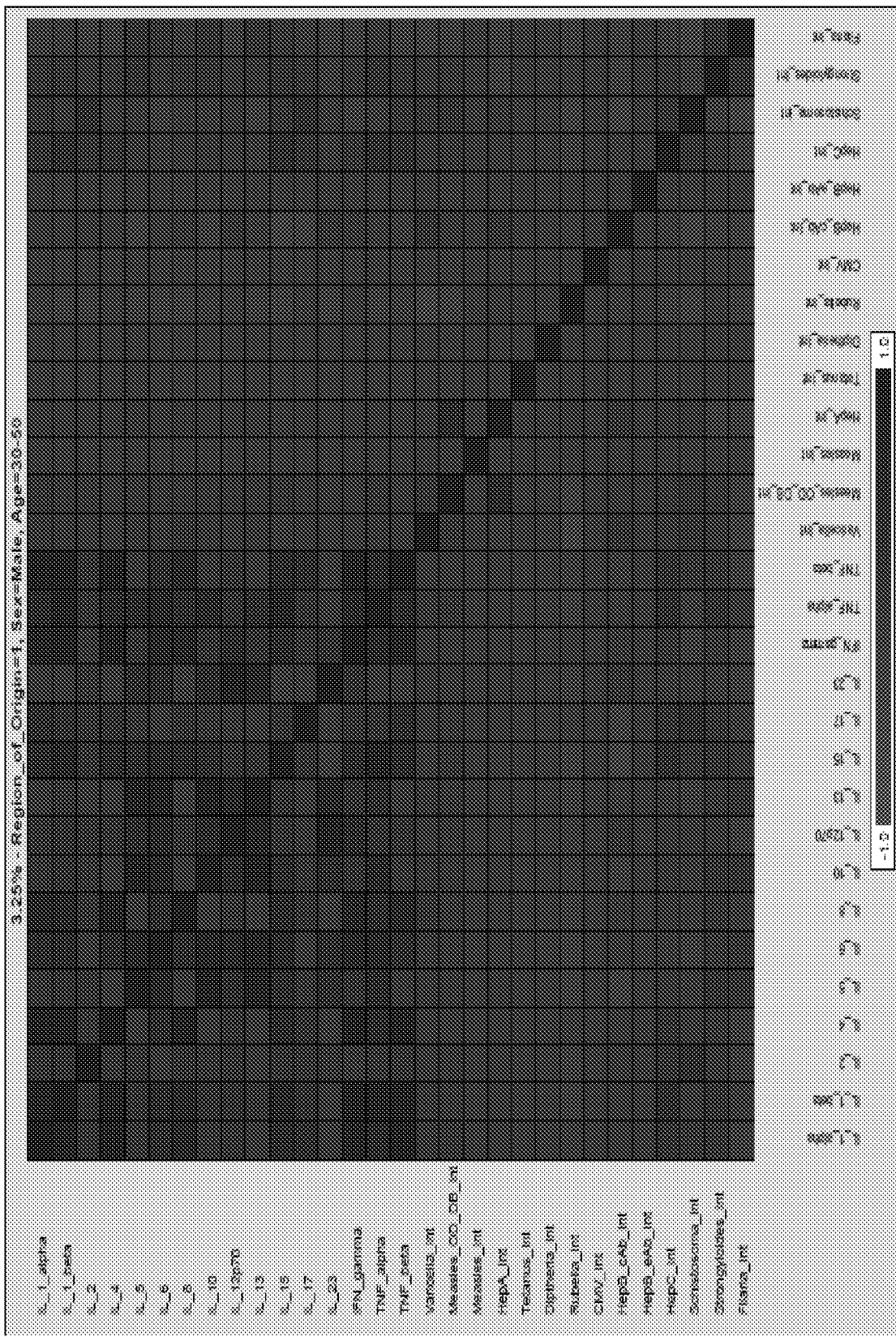
FIG. 21E-10.2B: Heat maps generated from Data Mining Tool. Sub Saharan Africa, age 30-50. Males

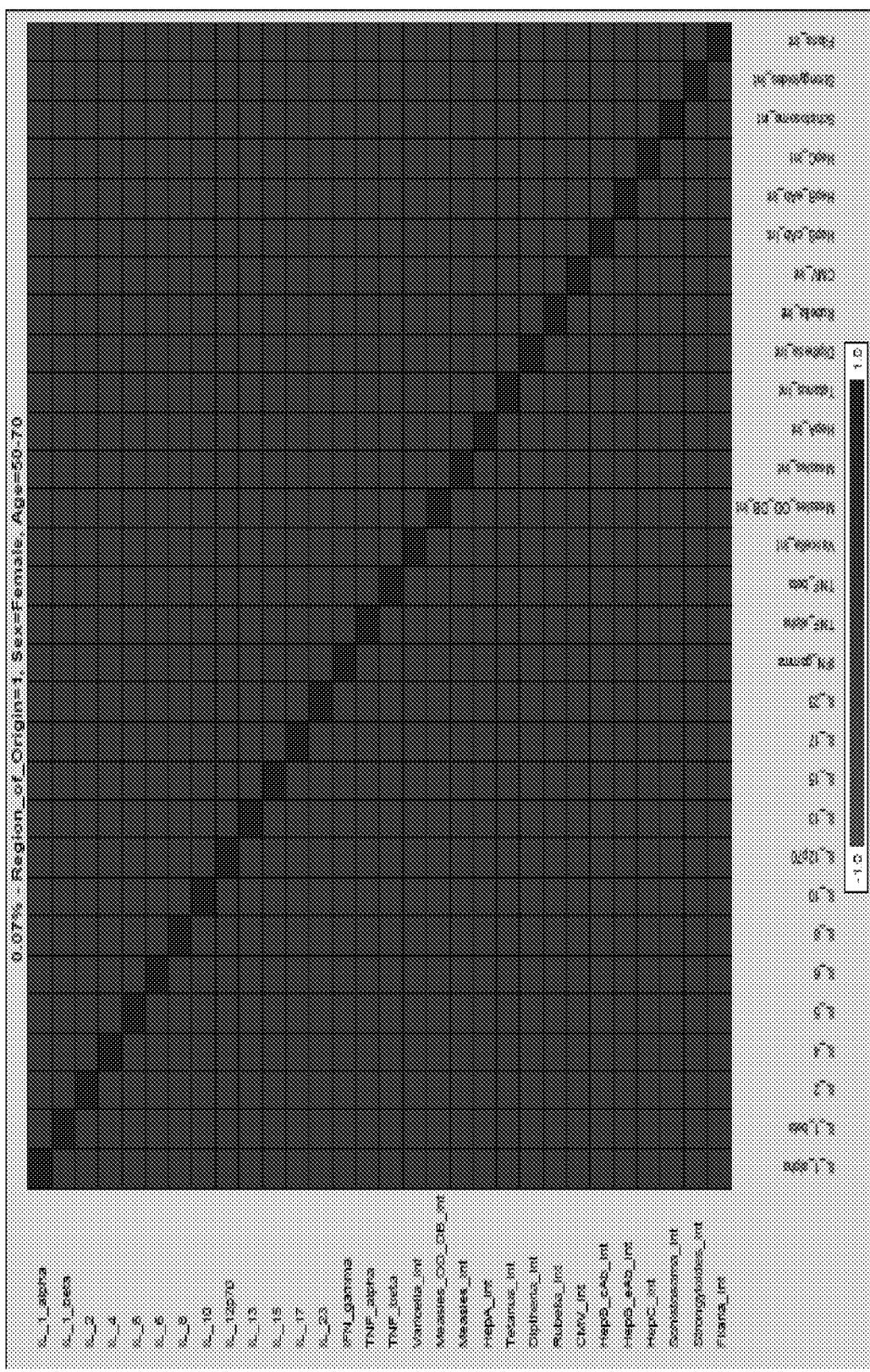
FIG. 21E-10.3A: Heat maps generated from Data Mining Tool. Sub-Saharan Africa, age 50-70. Females

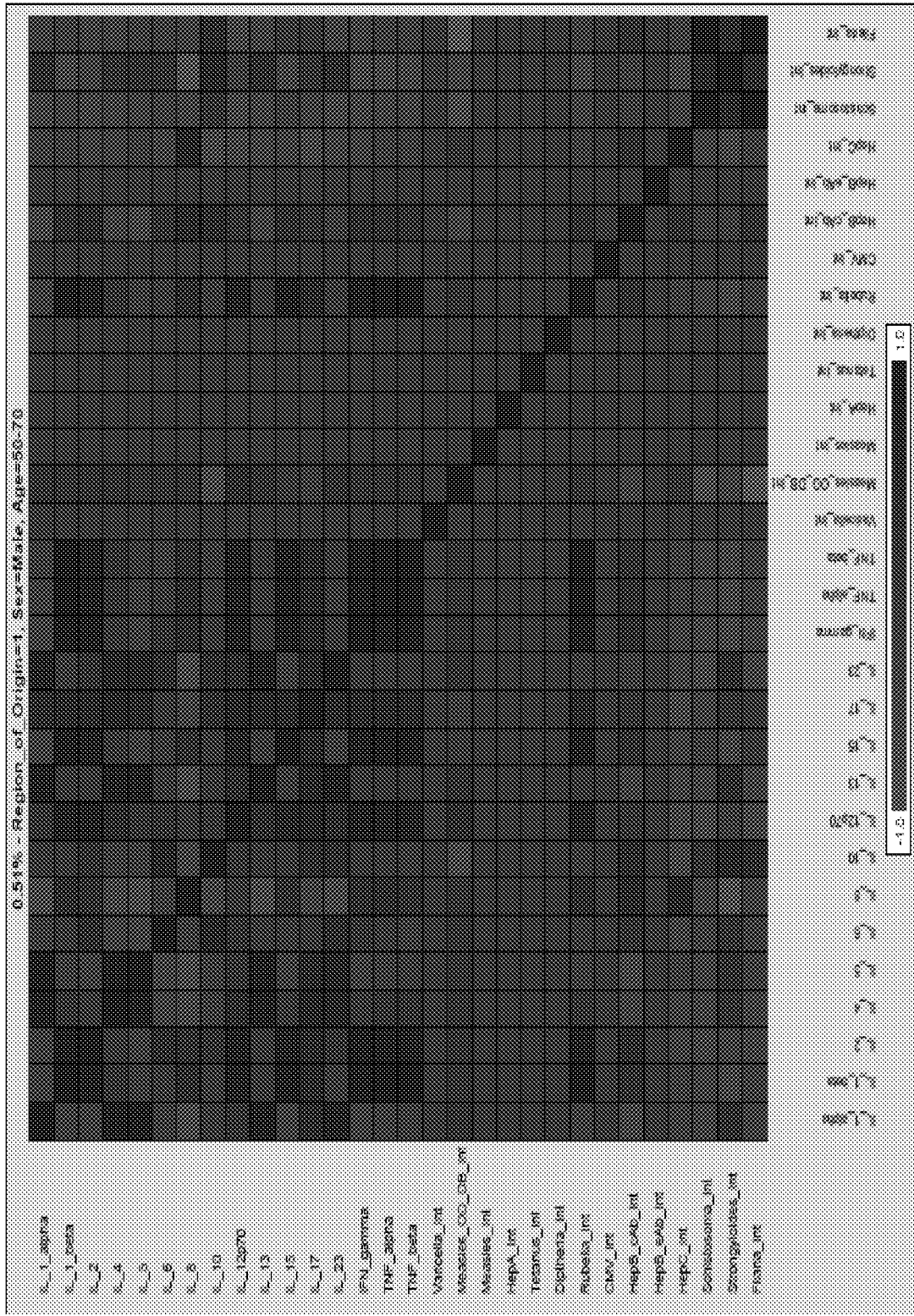
FIG. 21E-10.3B: Heat maps generated from Data Mining Tool. Sub-Saharan Africa, age 50-70. Males

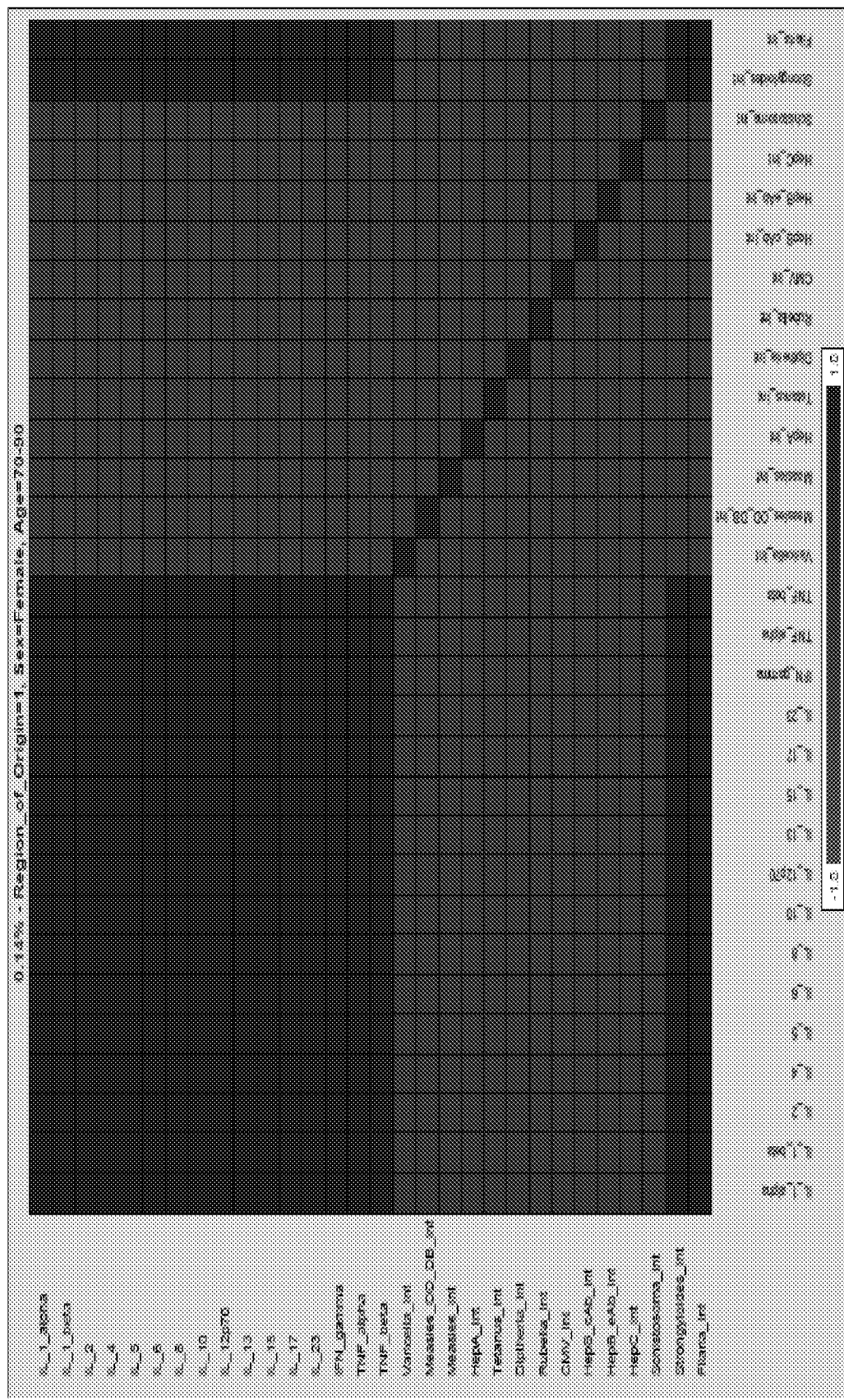
FIG. 21E-10.4A: Heat maps generated from Data Mining Tool. Sub-Saharan Africa, age 70-90. Females

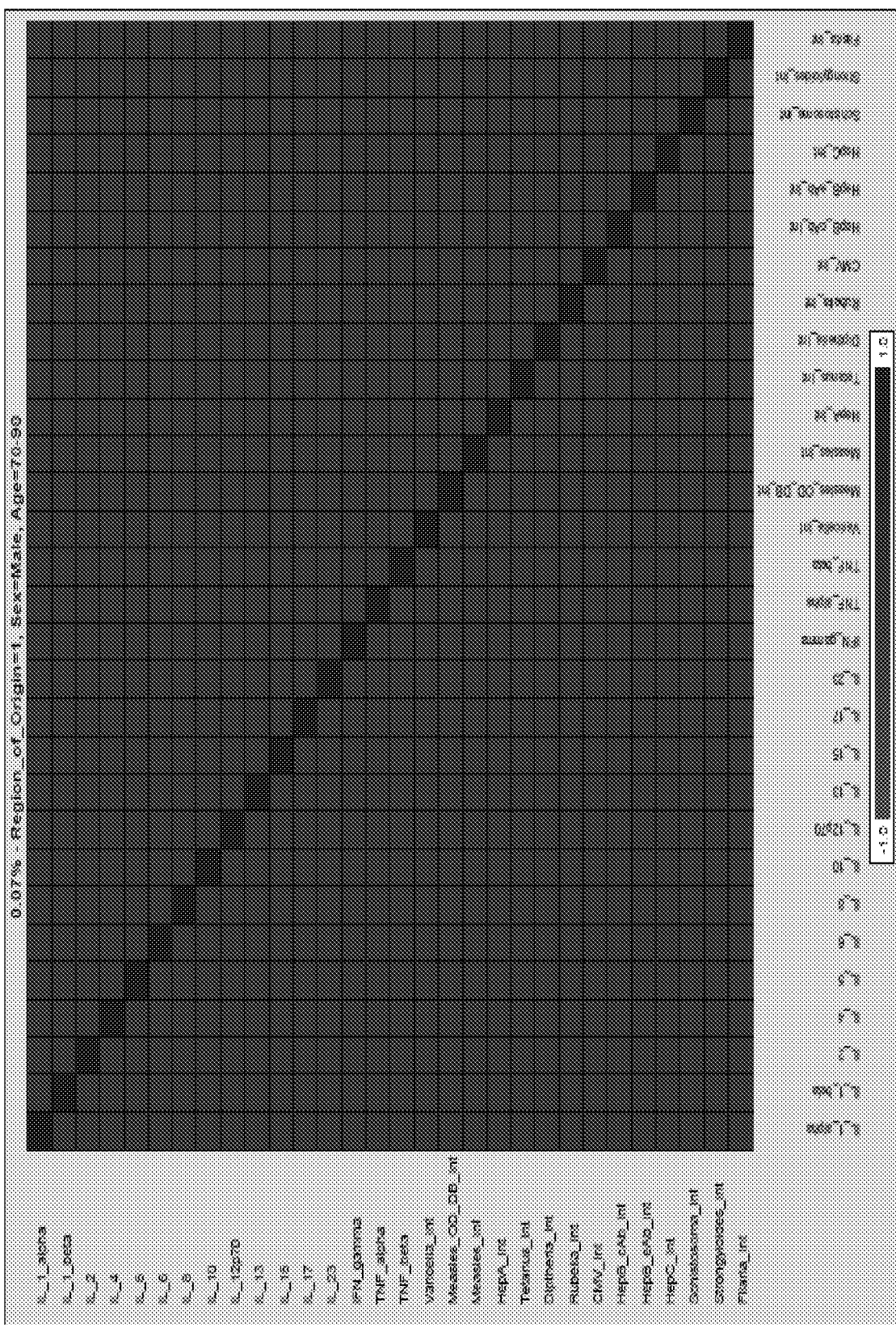
FIG. 21E-10.4B: Heat maps generated from Data Mining Tool. Sub-Saharan Africa, age 70-90. Males

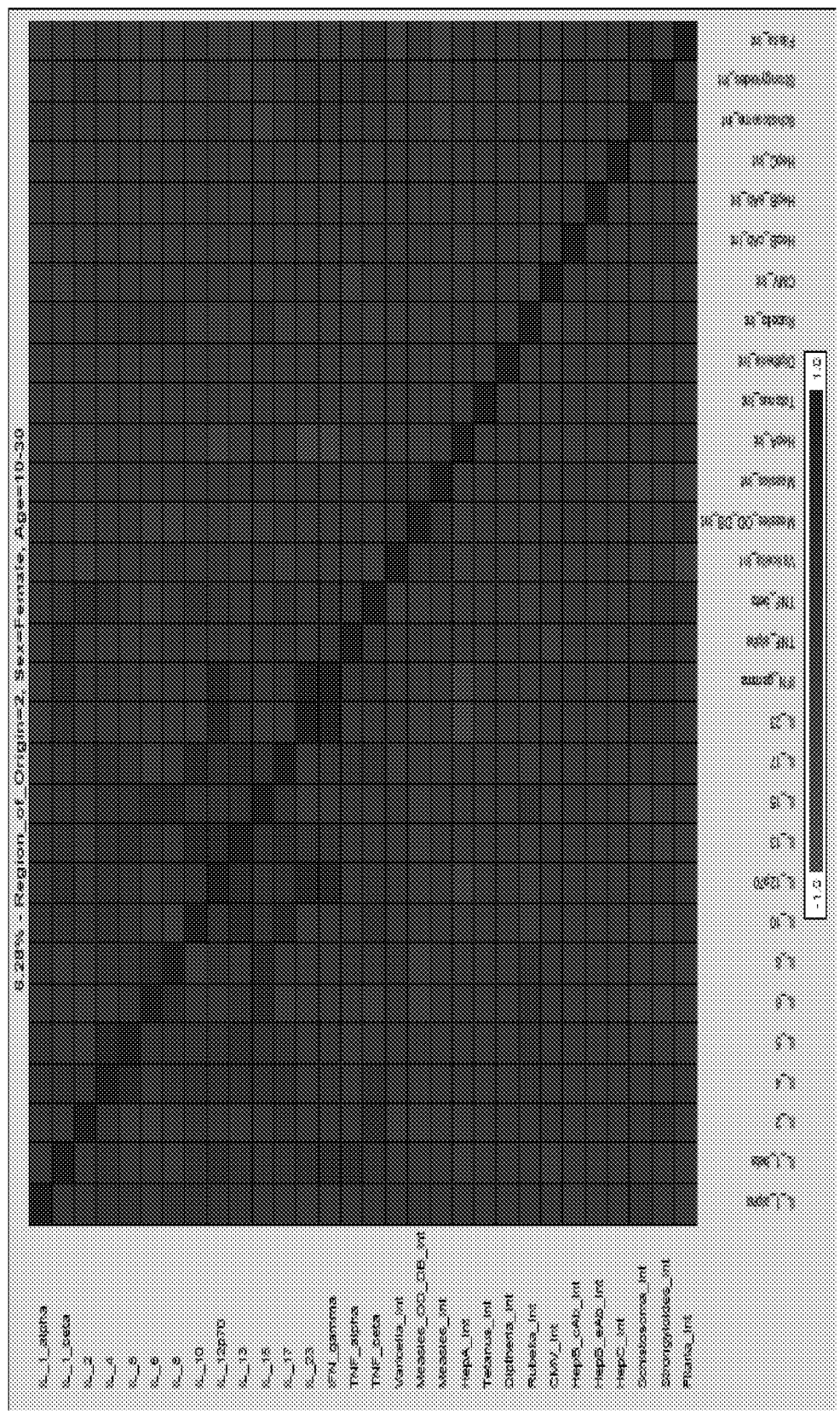
FIG. 21E-10.5A: Heat maps generated from Data Mining Tool. Southern Asia, age 10-30. Females

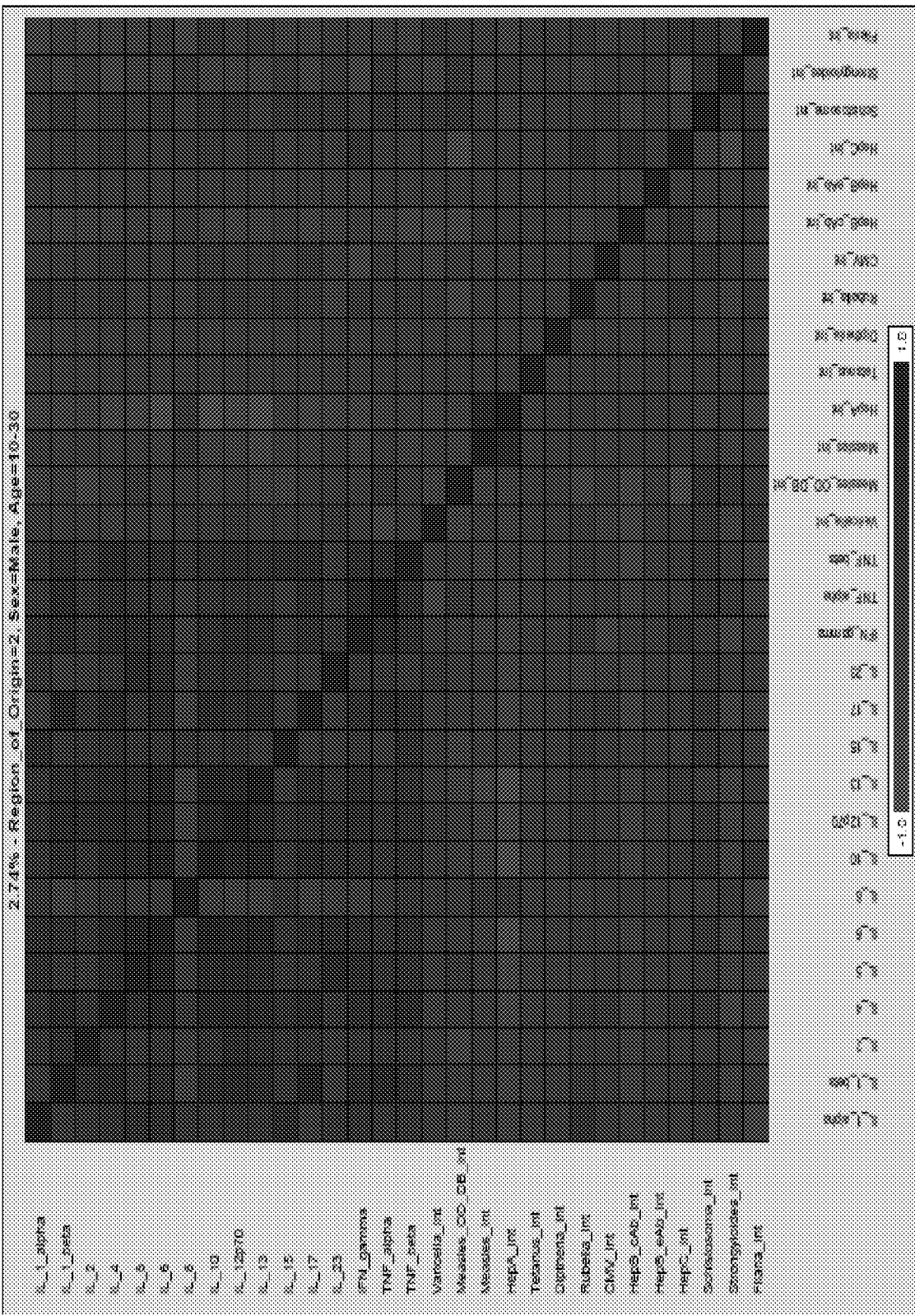
FIG. 21E-10.5B: Heat maps generated from Data Mining Tool. Southern Asia, age 10-30. Males

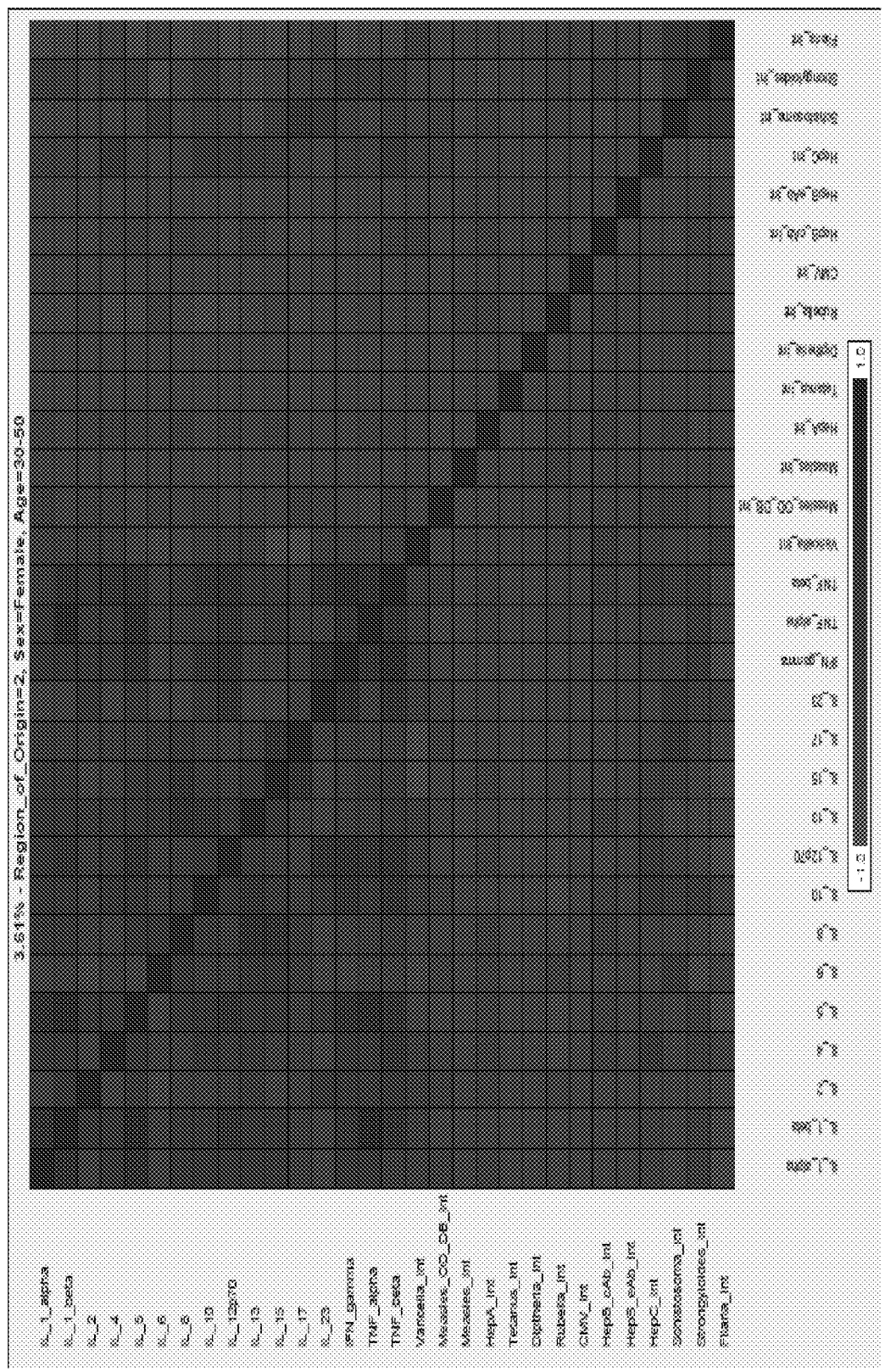
FIG. 21E-10.6A: Heat maps generated from Data Mining Tool. Southern Asia, age 30-50. Females

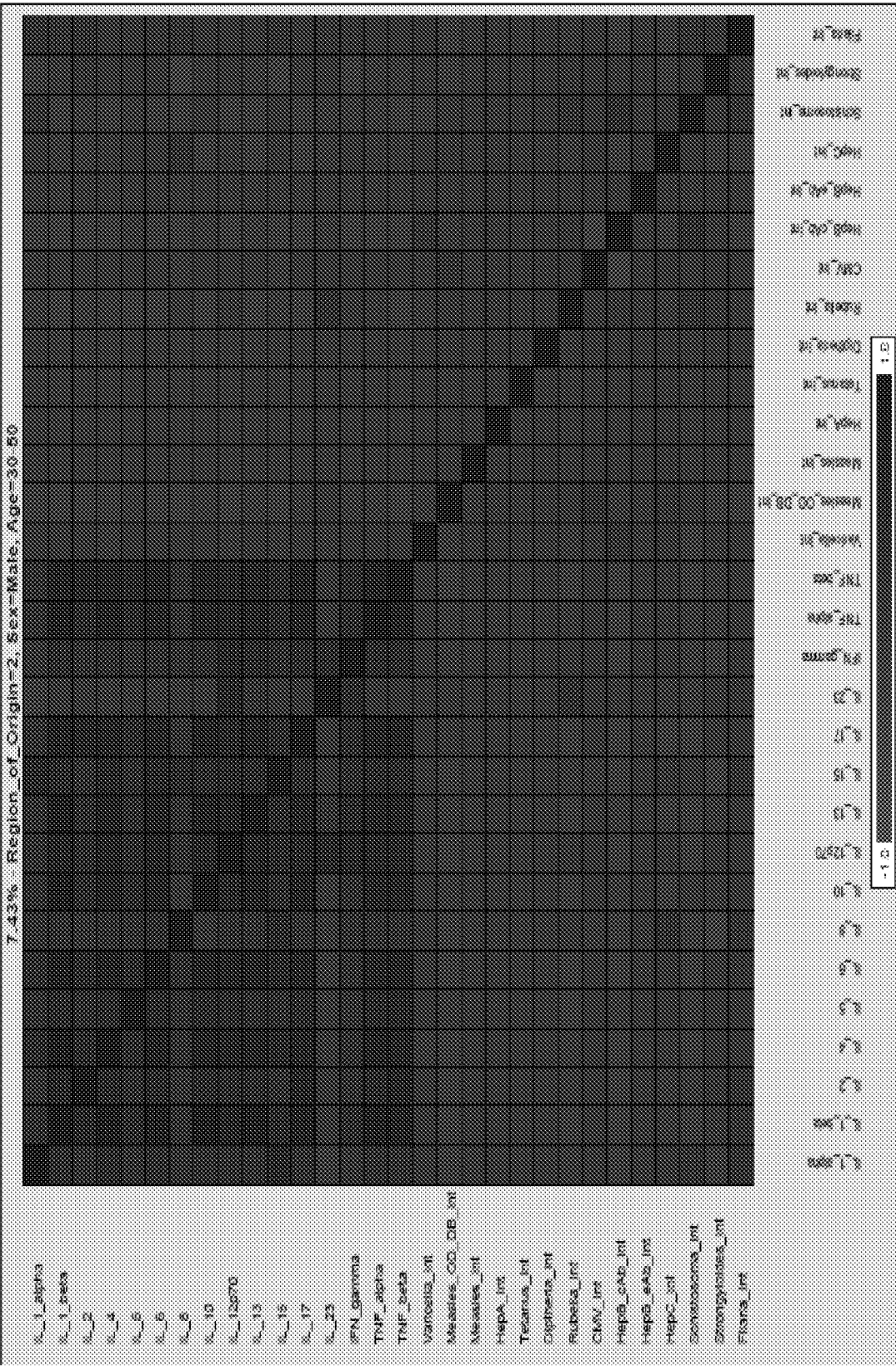
FIG. 21E-10.6B: Heat maps generated from Data Mining Tool. Southern Asia, age 30-50. Males

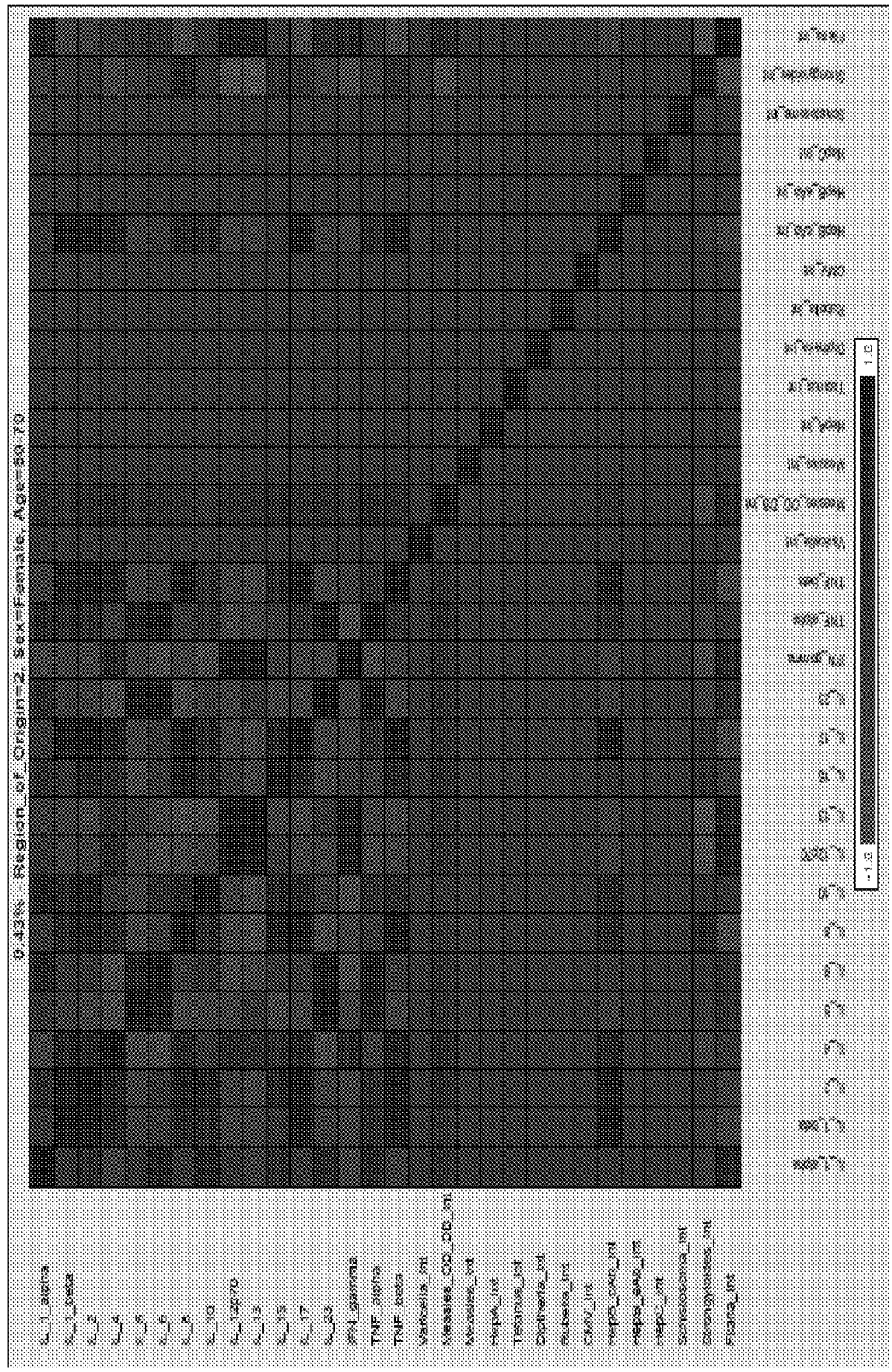
FIG. 21E-10.7A: Heat maps generated from Data Mining Tool. Southern Asia, age 50-70. Females

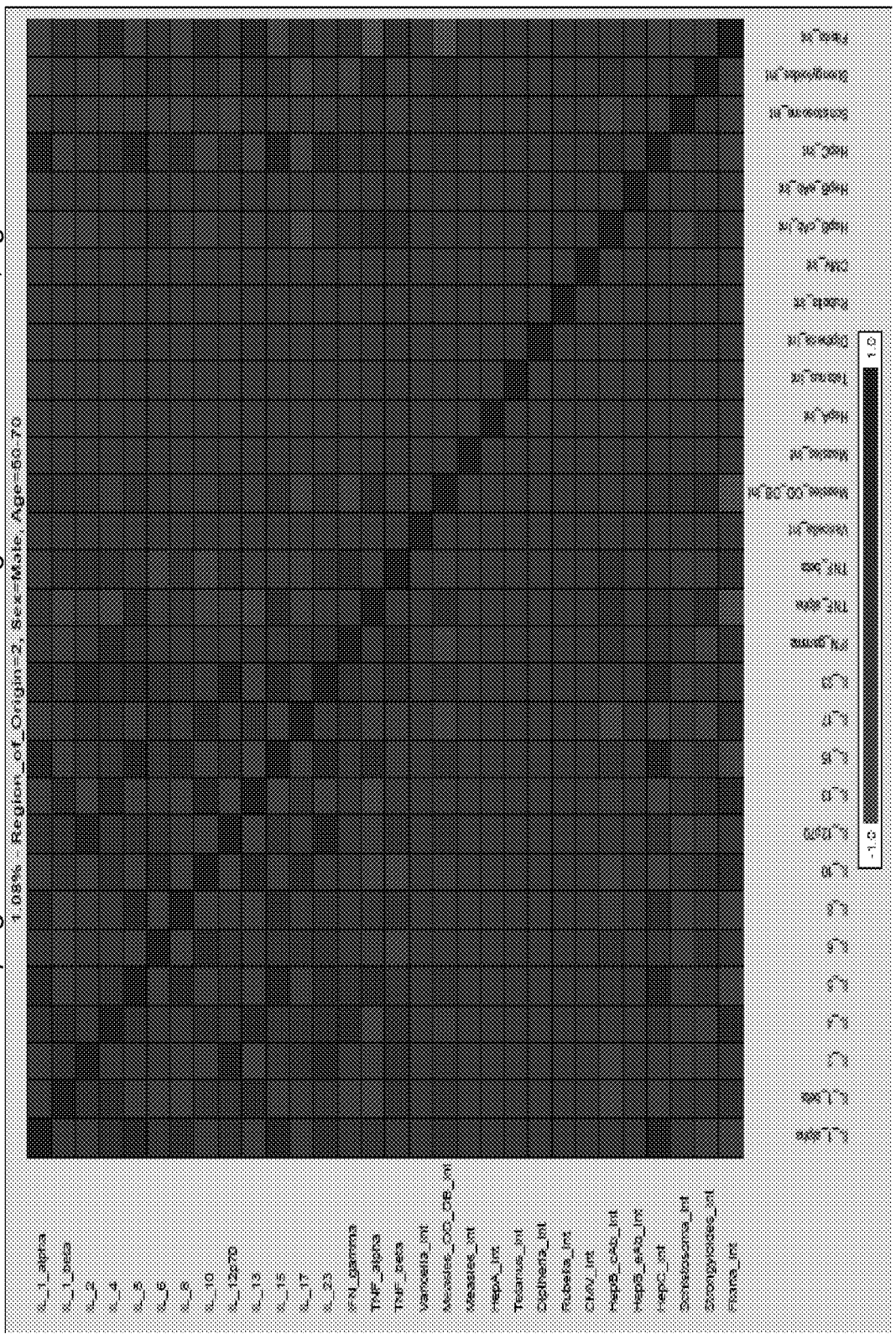
FIG. 21E-10.7B: Heat maps generated from Data Mining Tool. Southern Asia, age 50-70. Males

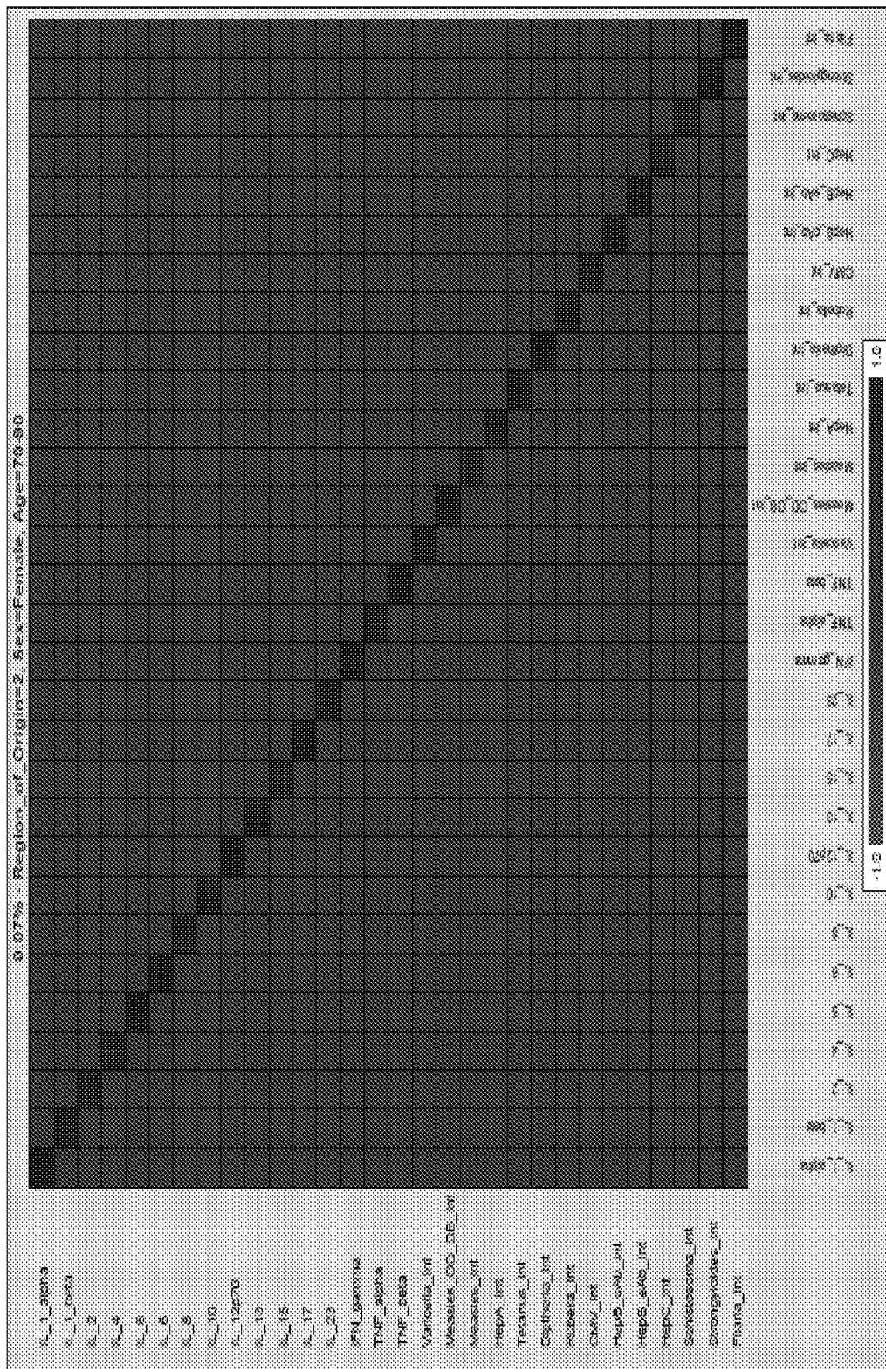
FIG. 21E-10.8: Heat map generated from Data Mining Tool Southern Asia, 70-90. Females.

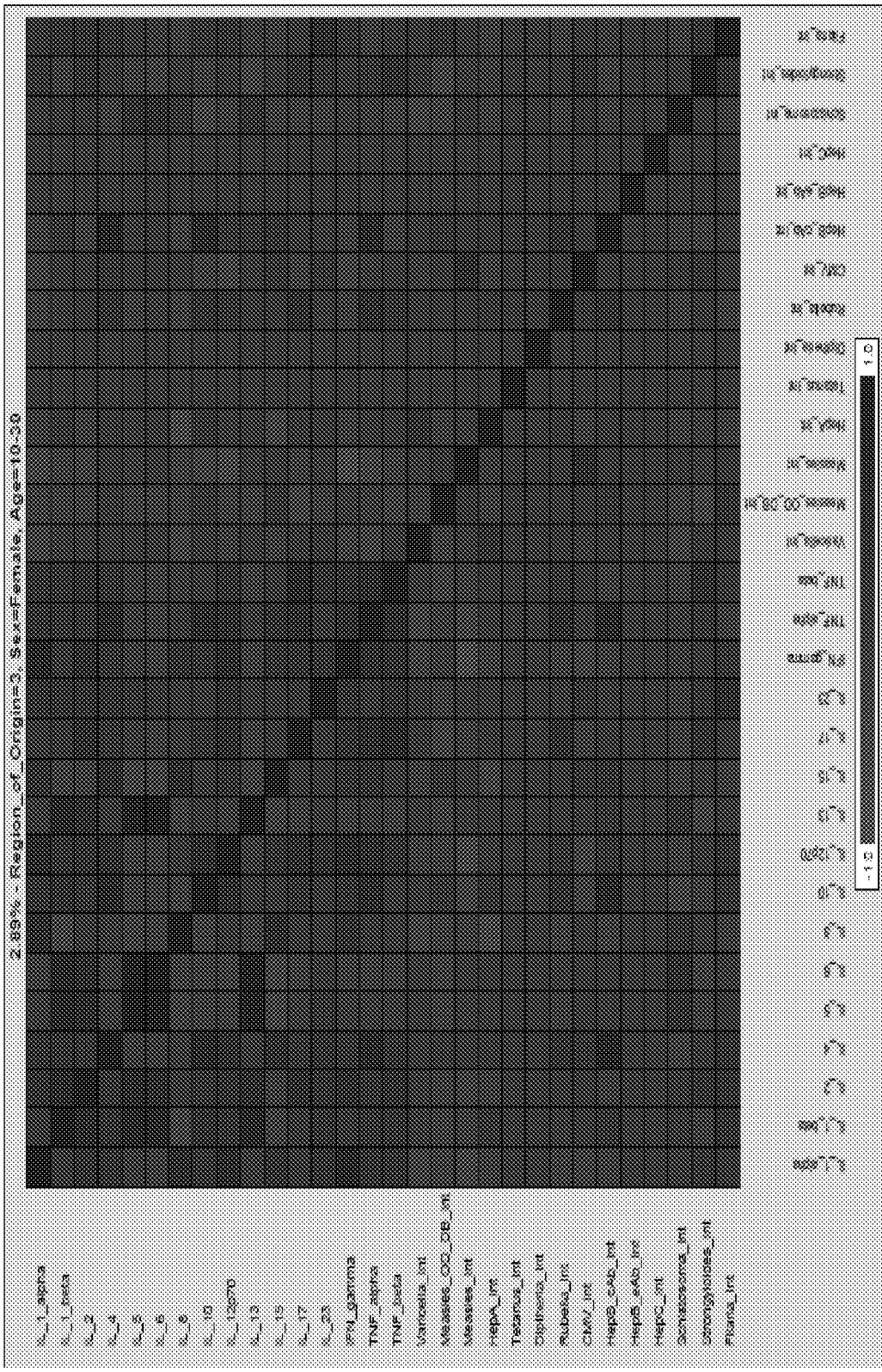
FIG. 21E-10.9A: Heat maps generated from Data Mining Tool. North Africa, age 10-30. Females

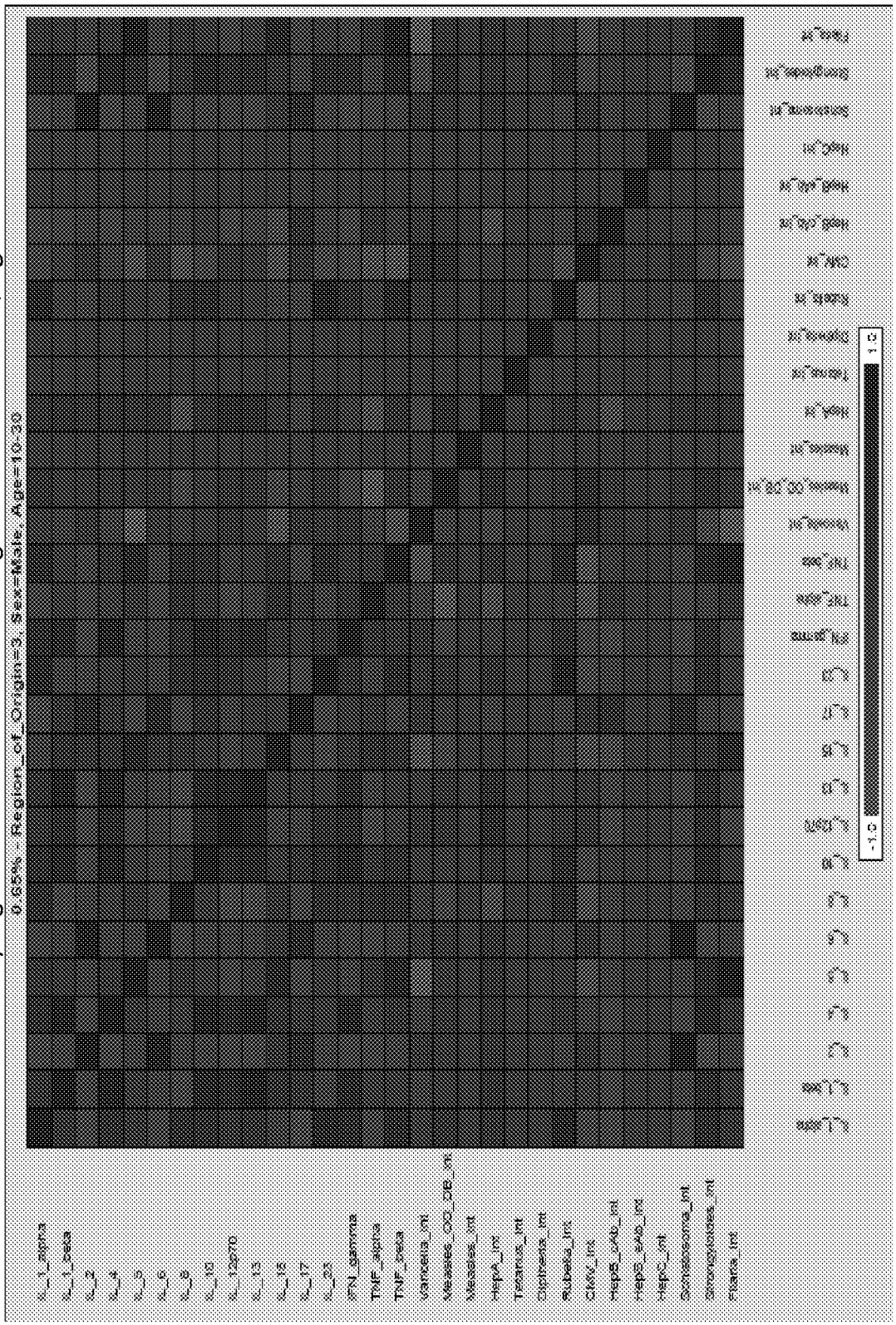
FIG. 21E-10.9B: Heat maps generated from Data Mining Tool. North Africa, age 10-30. Males

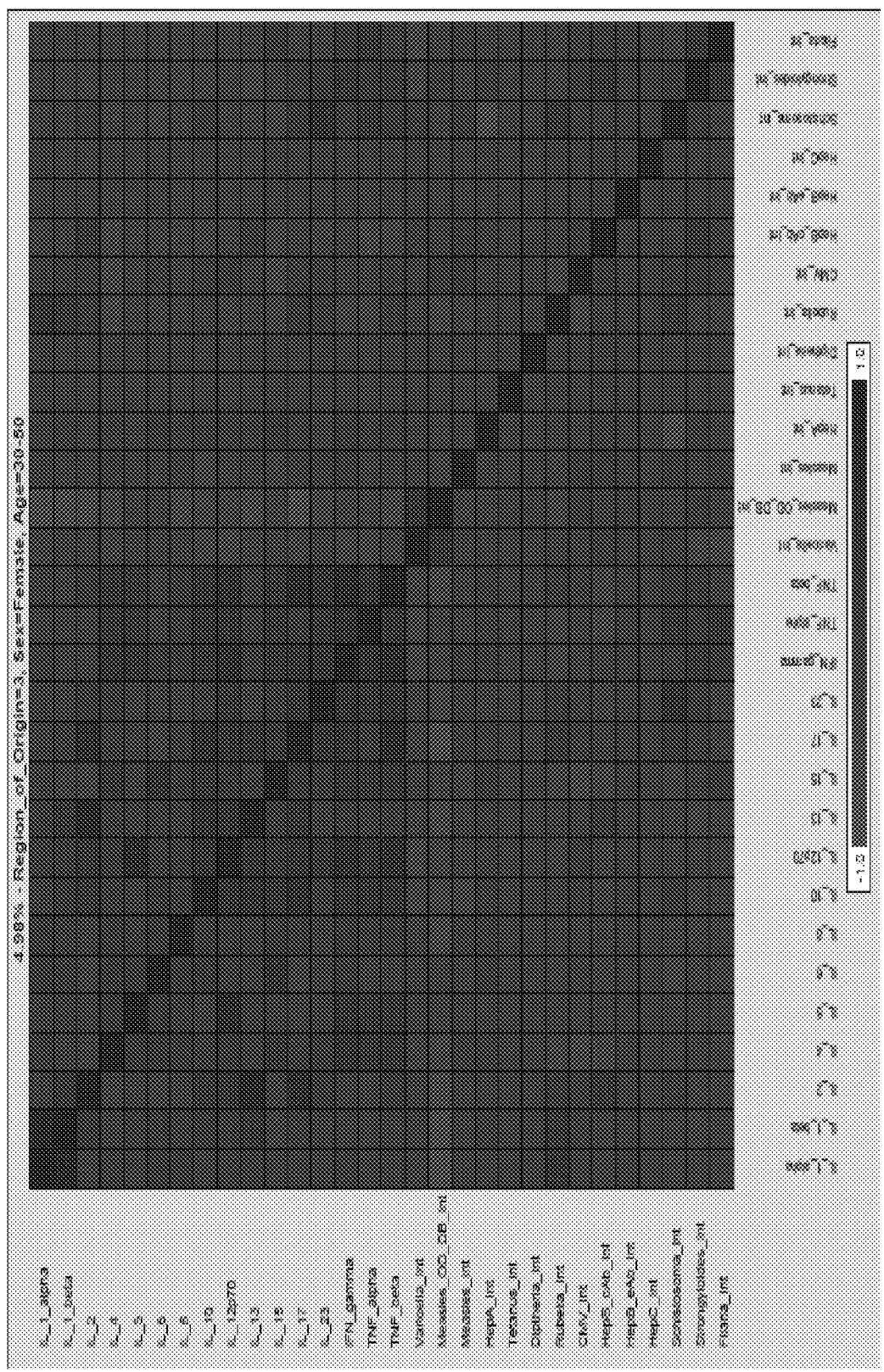
FIG. 21E-10.10A: Heat maps generated from Data Mining Tool. North Africa, age 30-50. Females

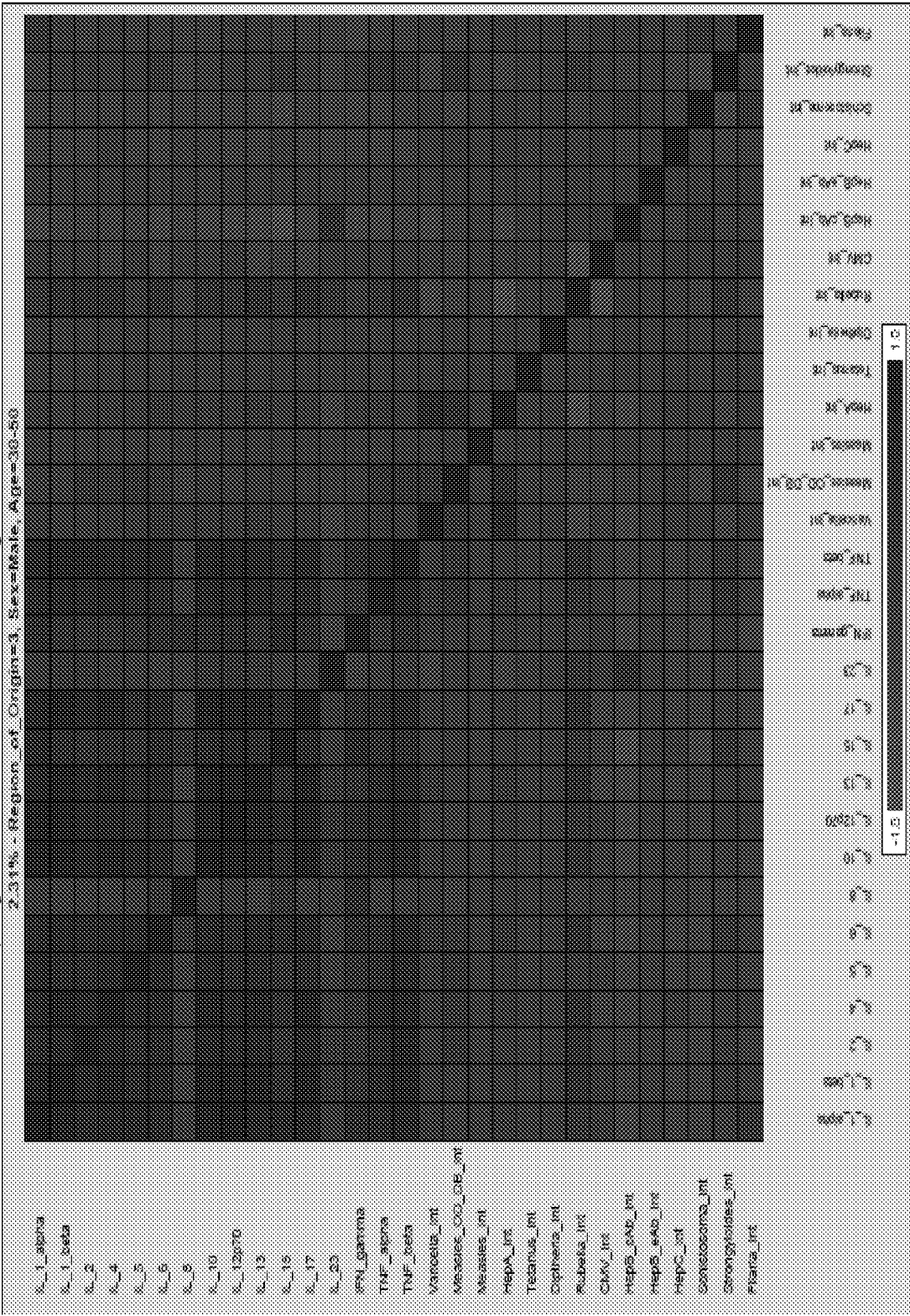
FIG. 21E-10.10B: Heat maps generated from Data Mining Tool. North Africa, 30-50. Males

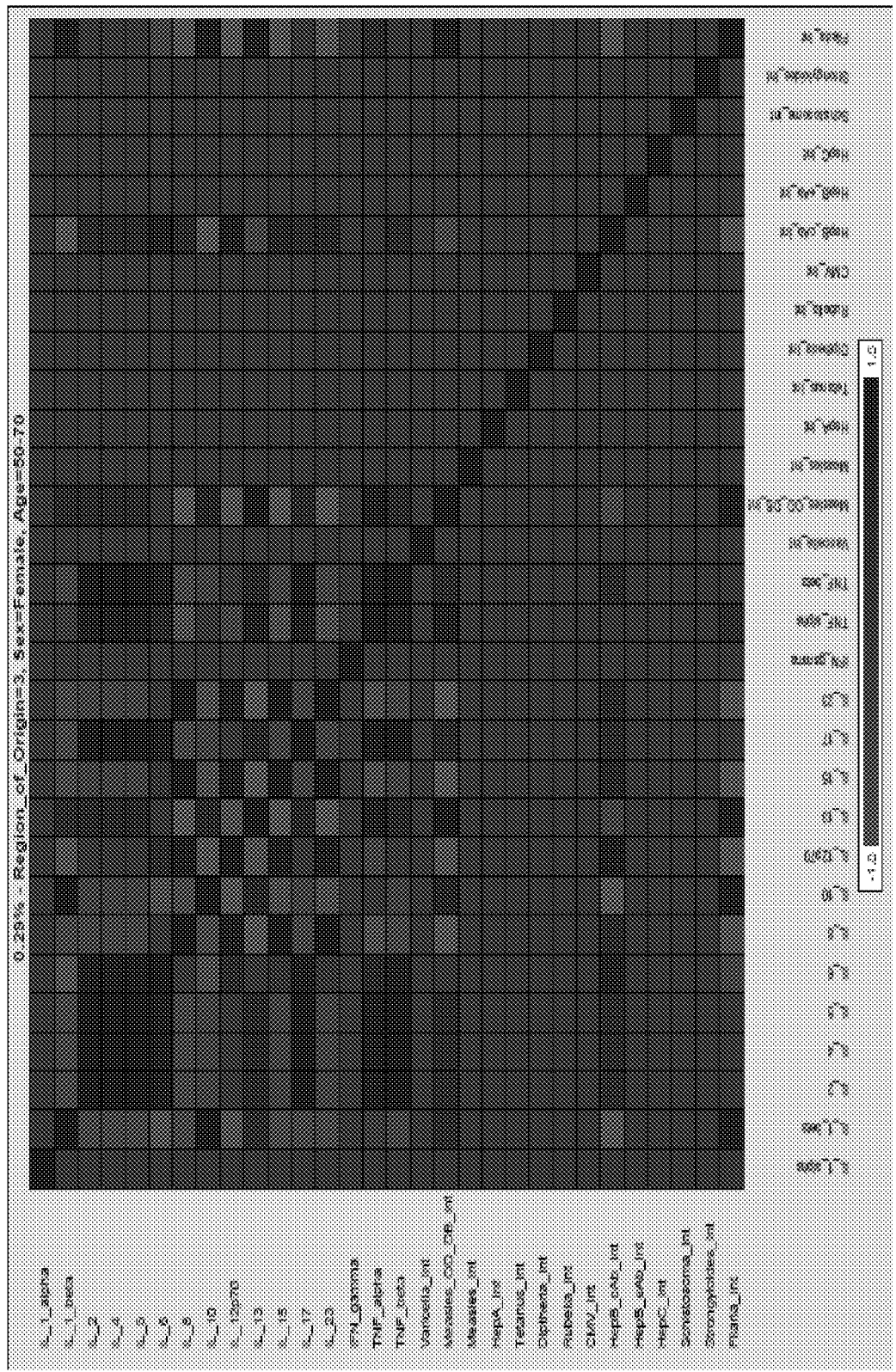
FIG. 21E-10.11A: Heat maps generated from Data Mining Tool. North Africa, age 50-70. Females

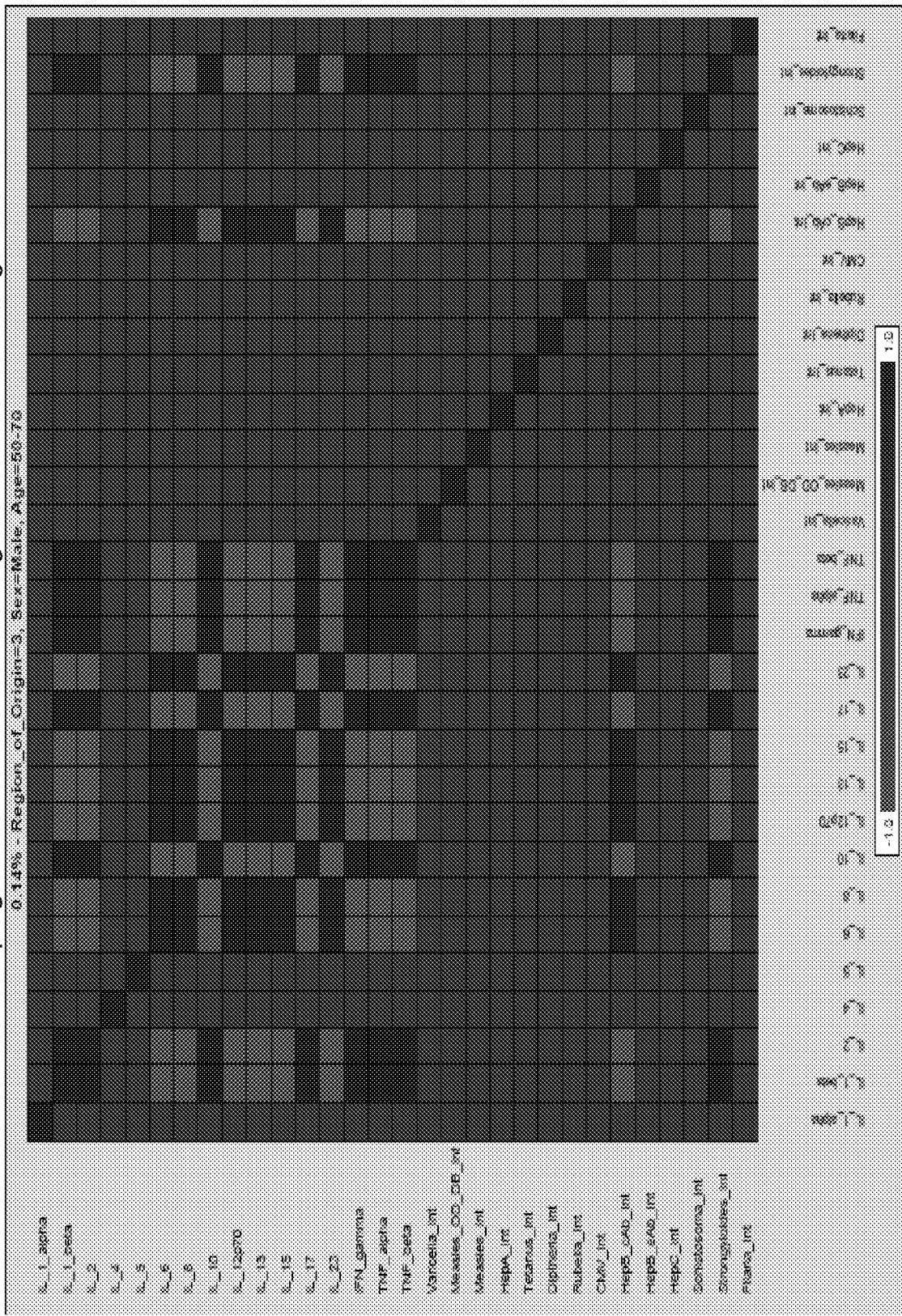
FIG. 21E-10.11B: Heat maps generated from Data Mining Tool. North Africa, age 50-70. Males

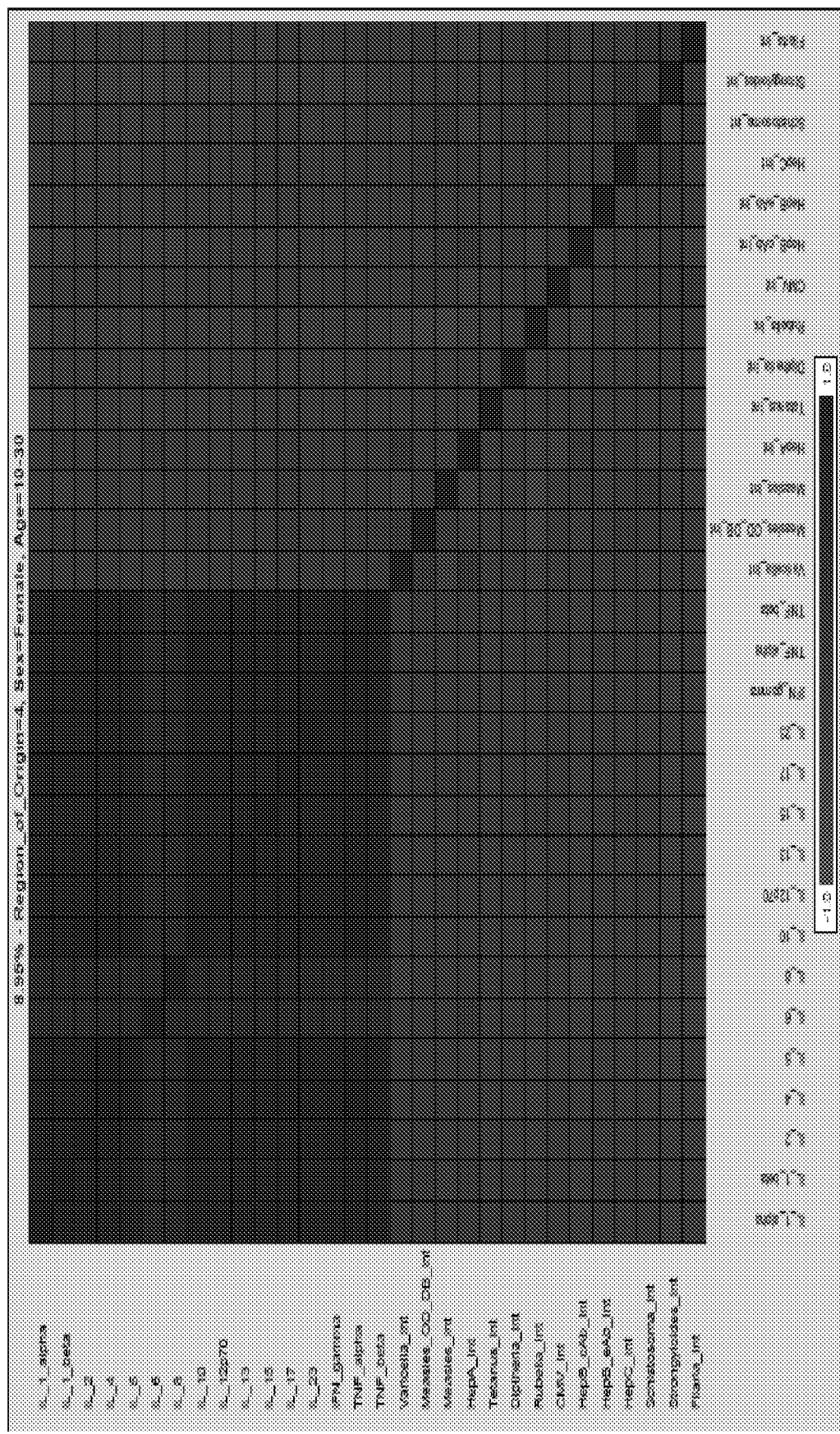
FIG. 21E-10.12A: Heat maps generated from Data Mining Tool. Latin America/Caribbean, age 10-30. Females

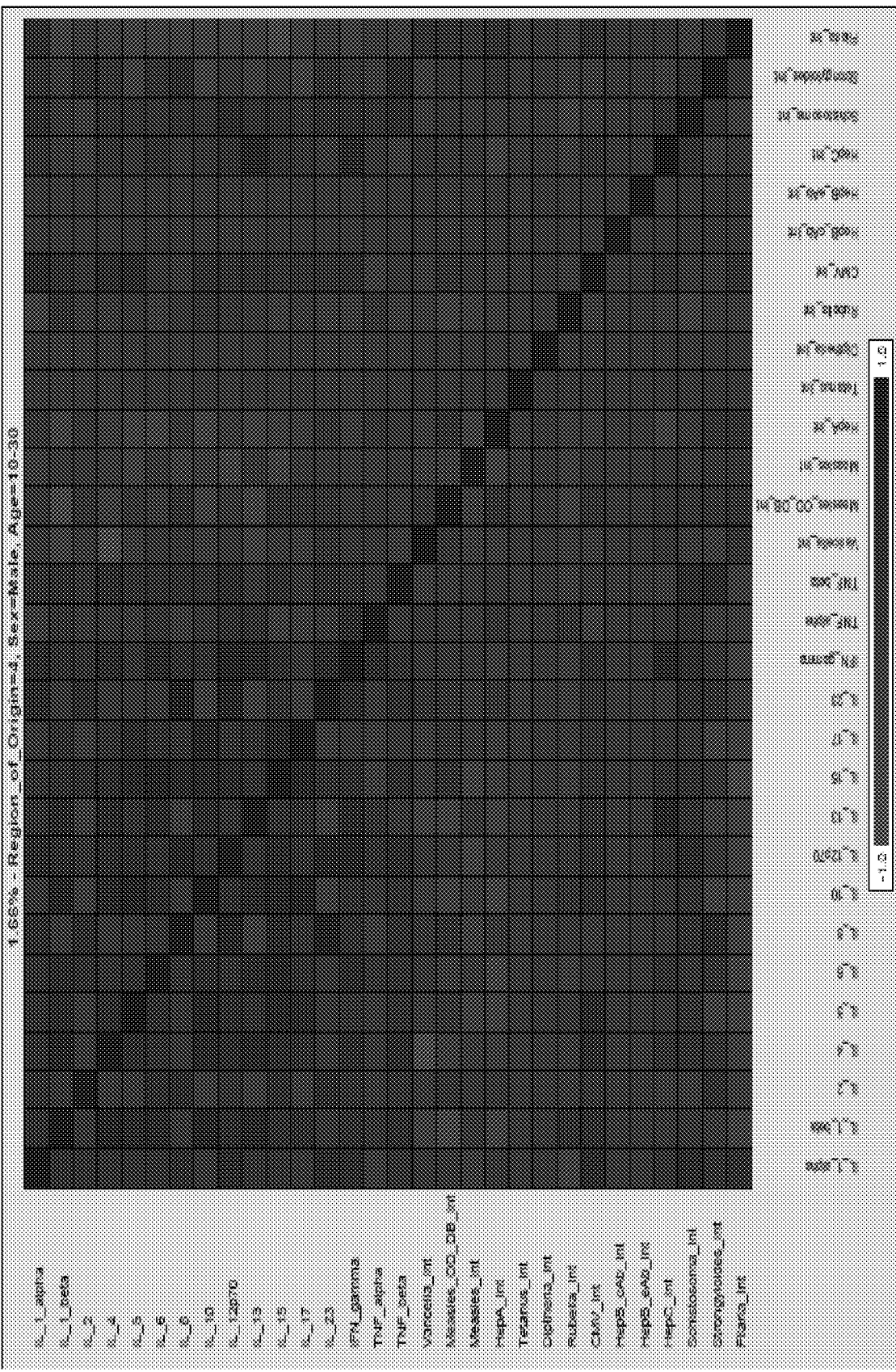
FIG. 21E-10.12B: Heat maps generated from Data Mining Tool. Latin America/Caribbean, age 10-30. Males

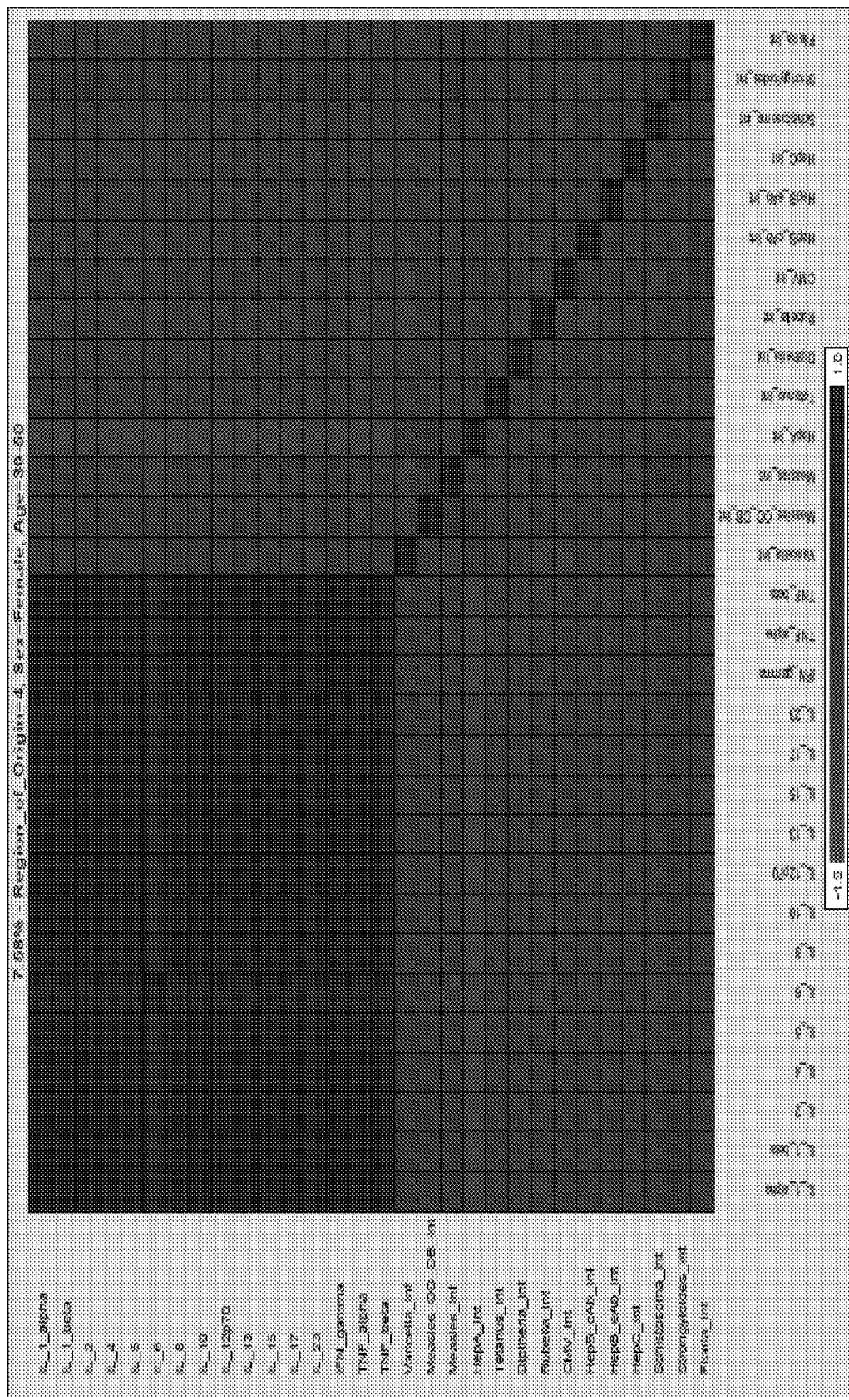
FIG. 21E-10.13A: Heat maps generated from Data Mining Tool. Latin America/Caribbean, age 30-50. Females

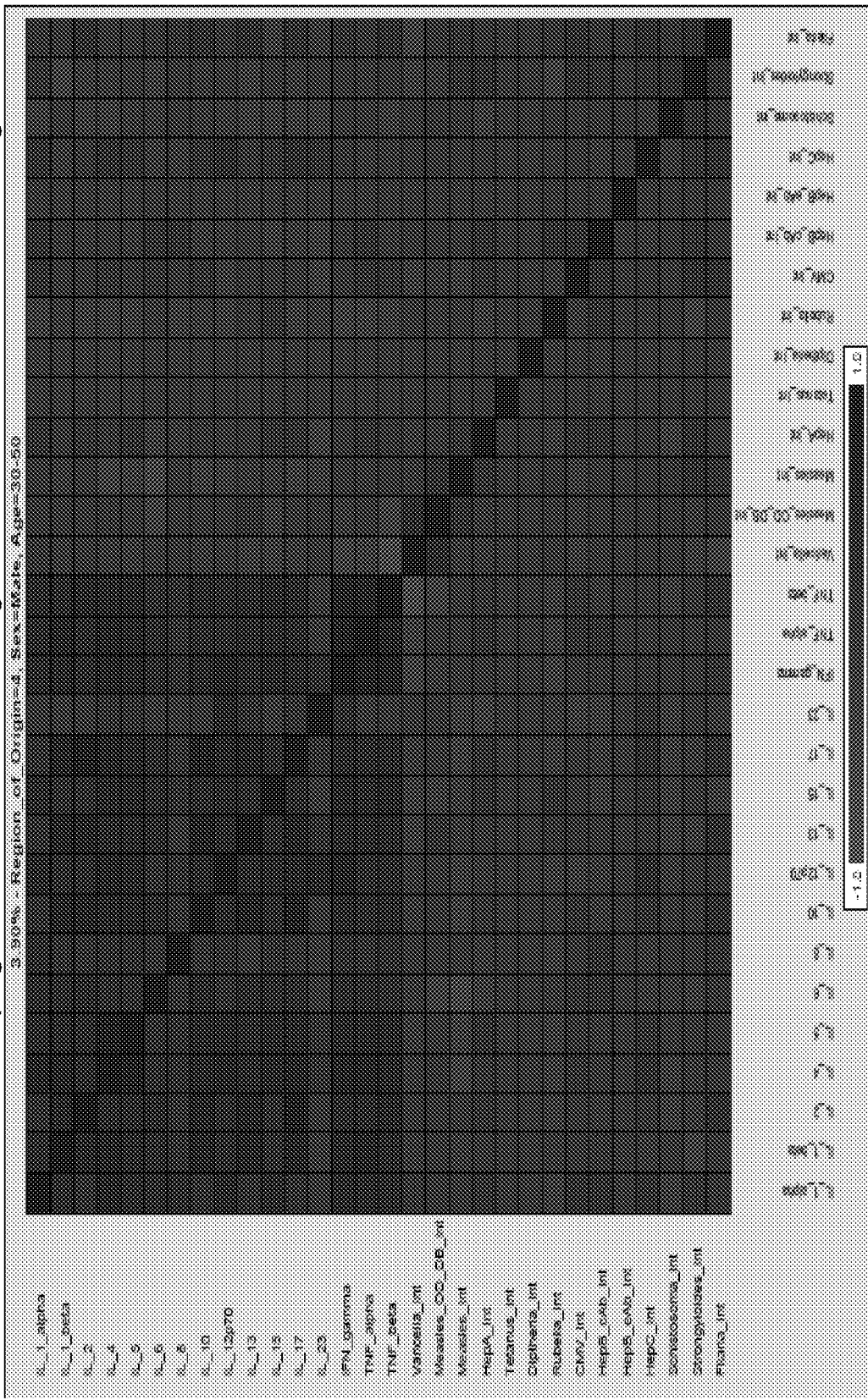
FIG. 21E-10.13B: Heat maps generated from Data Mining Tool. Latin America/Caribbean, age 30-50. Males

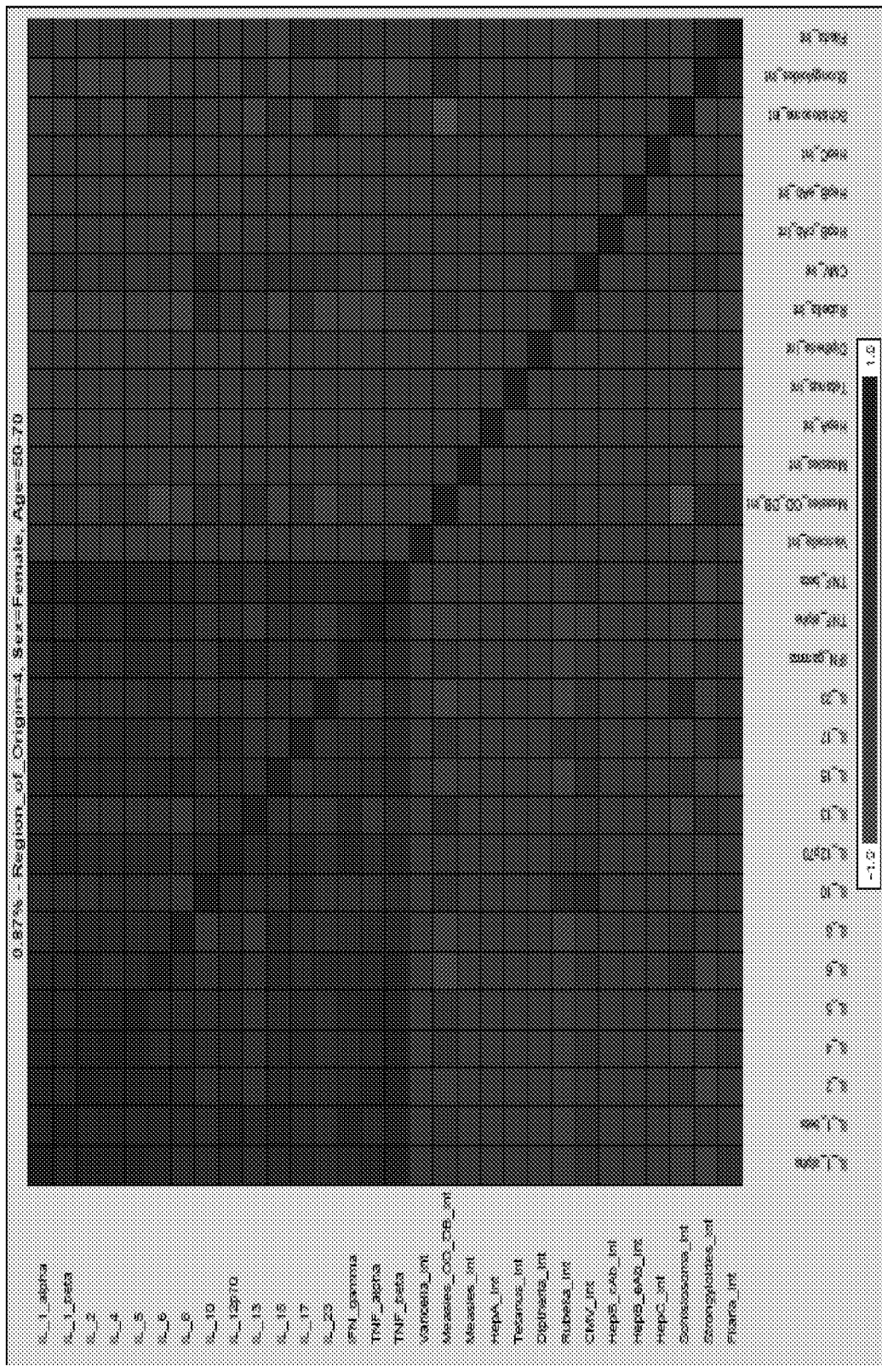
FIG. 21E-10.14A: Heat maps generated from Data Mining Tool. Latin America/Caribbean, age 50-70. Females

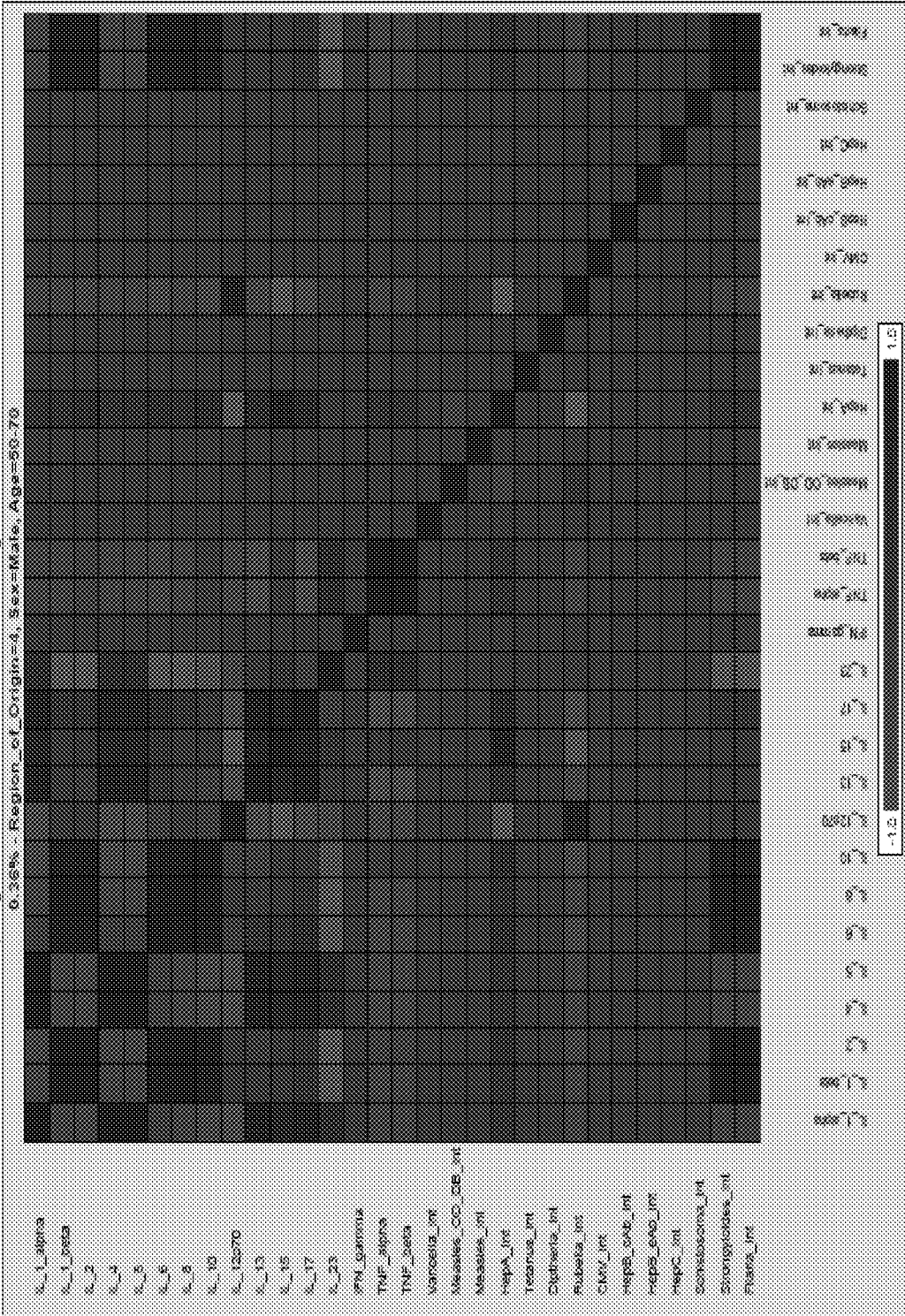
FIG. 21E-10.14B: Heat maps generated from Data Mining Tool. Latin America/Caribbean, 50-70. Males

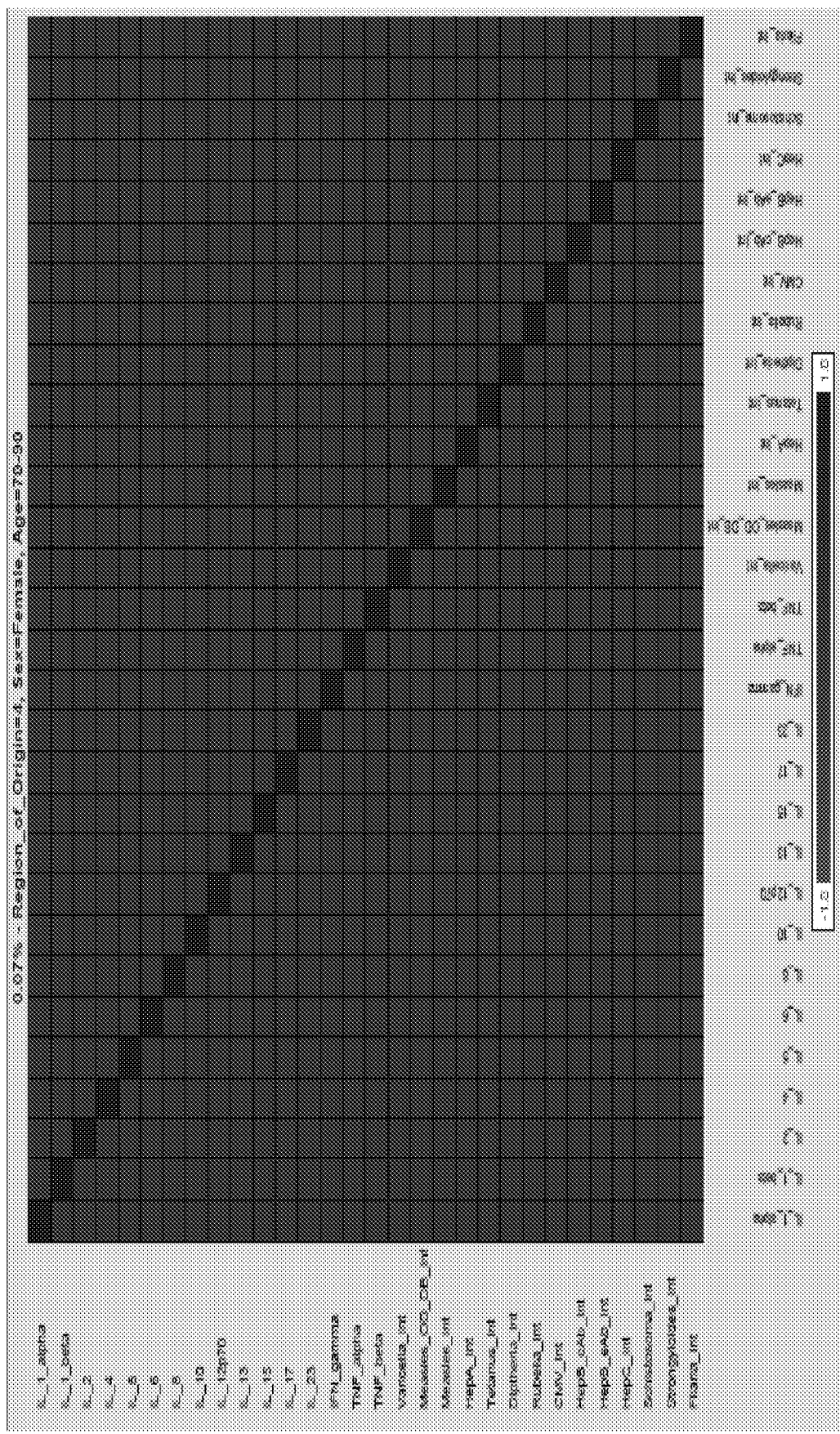
FIG. 21E-10.15A: Heat maps generated from Data Mining Tool. Latin America/Caribbean, age 70-90. Females

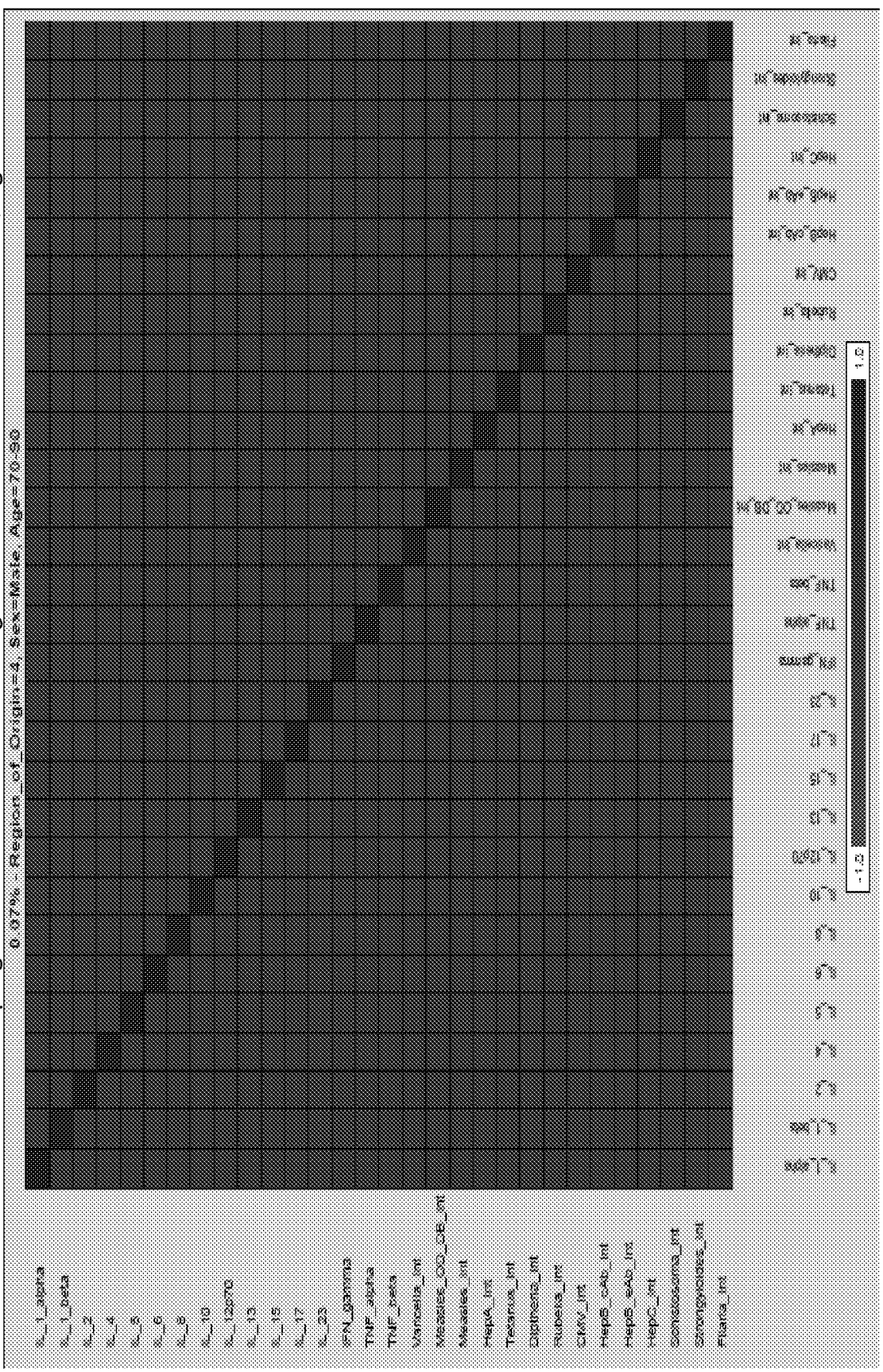
FIG. 21E-10.15B: Heat maps generated from Data Mining Tool. Latin America/Caribbean, age 70-90. Males

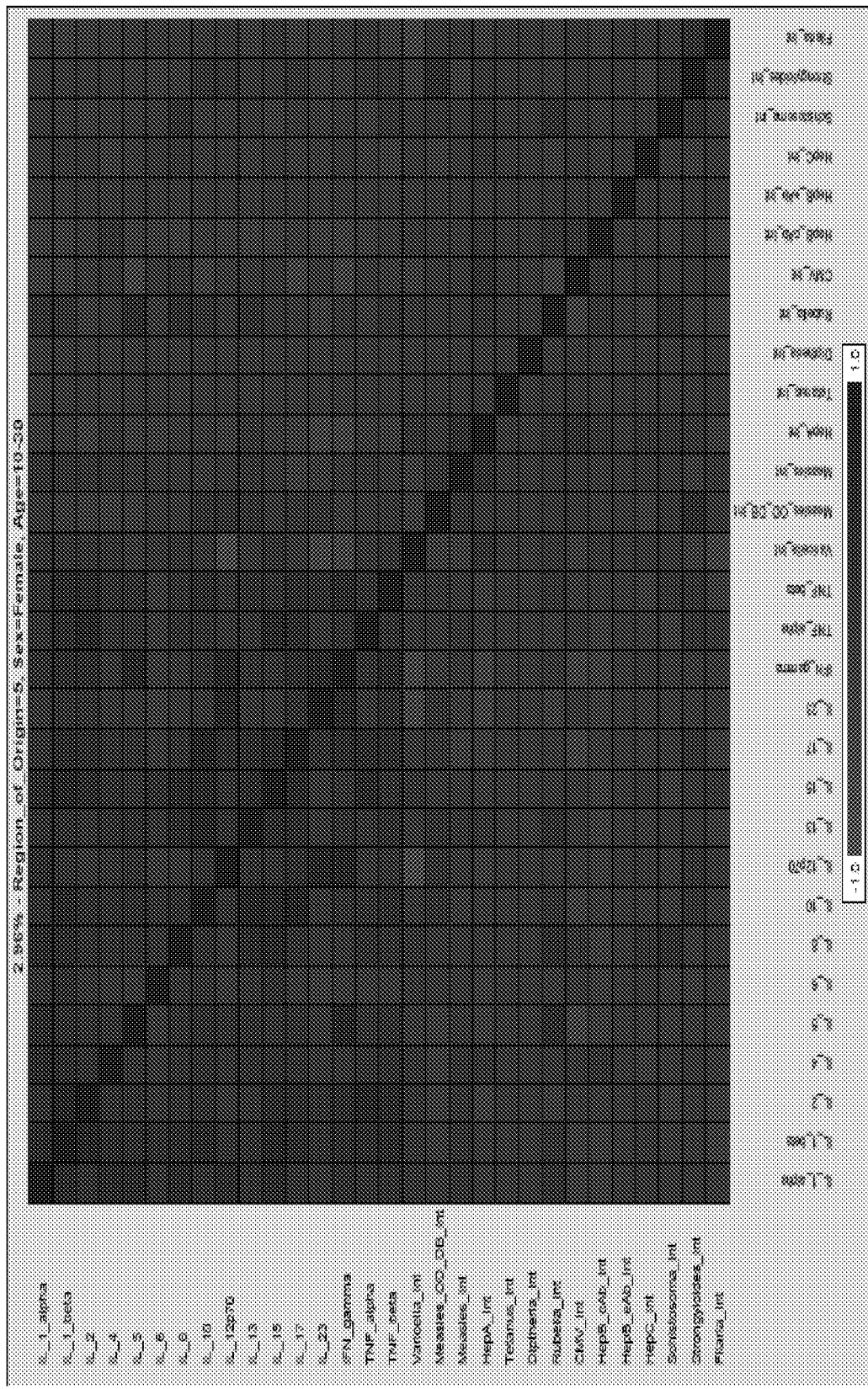
FIG. 21E-10.16A: Heat maps generated from Data Mining Tool. Eastern Europe, age 10-30. Females

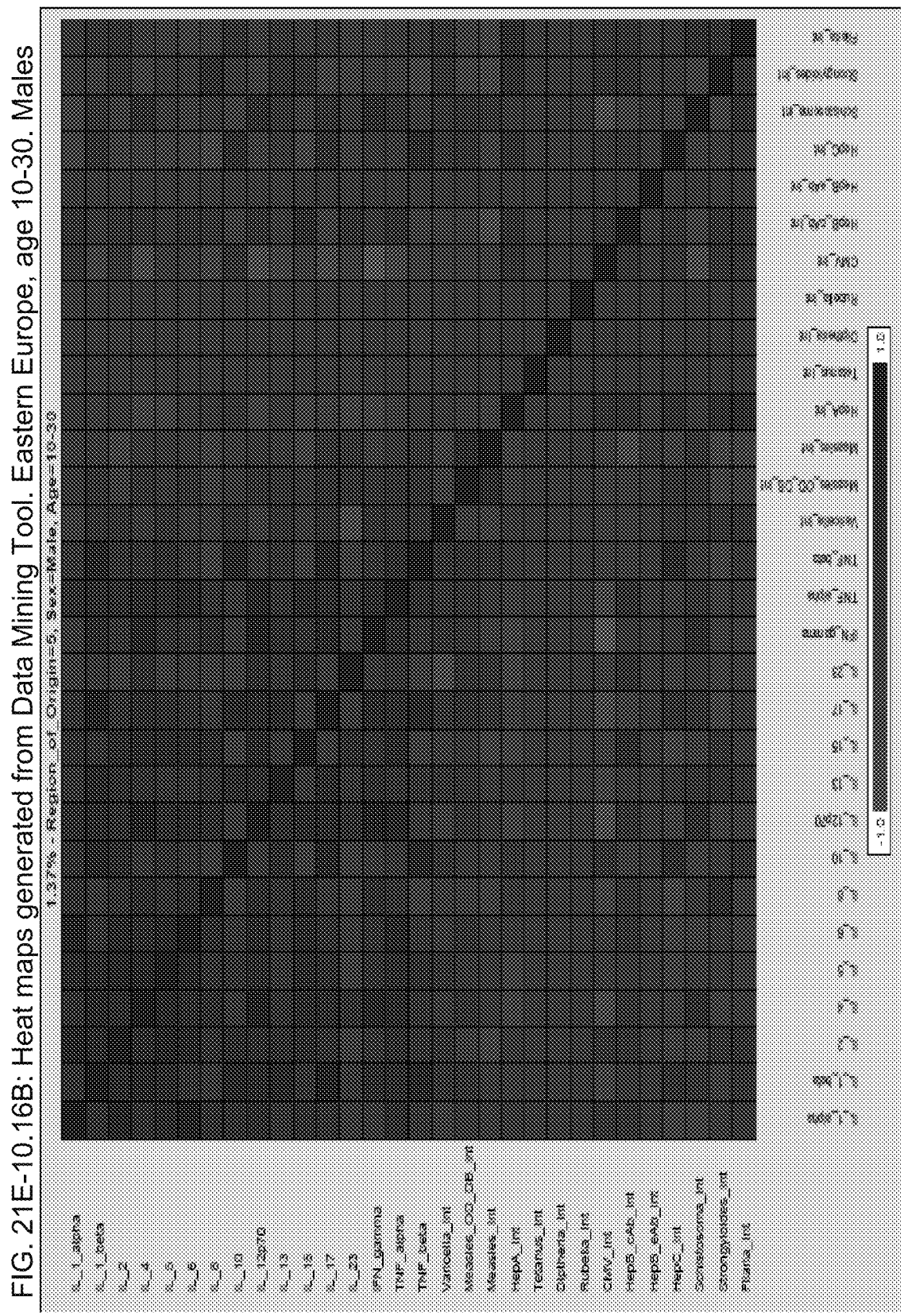
FIG. 21E-10.16B: Heat maps generated from Data Mining Tool. Eastern Europe, age 10-30. Males

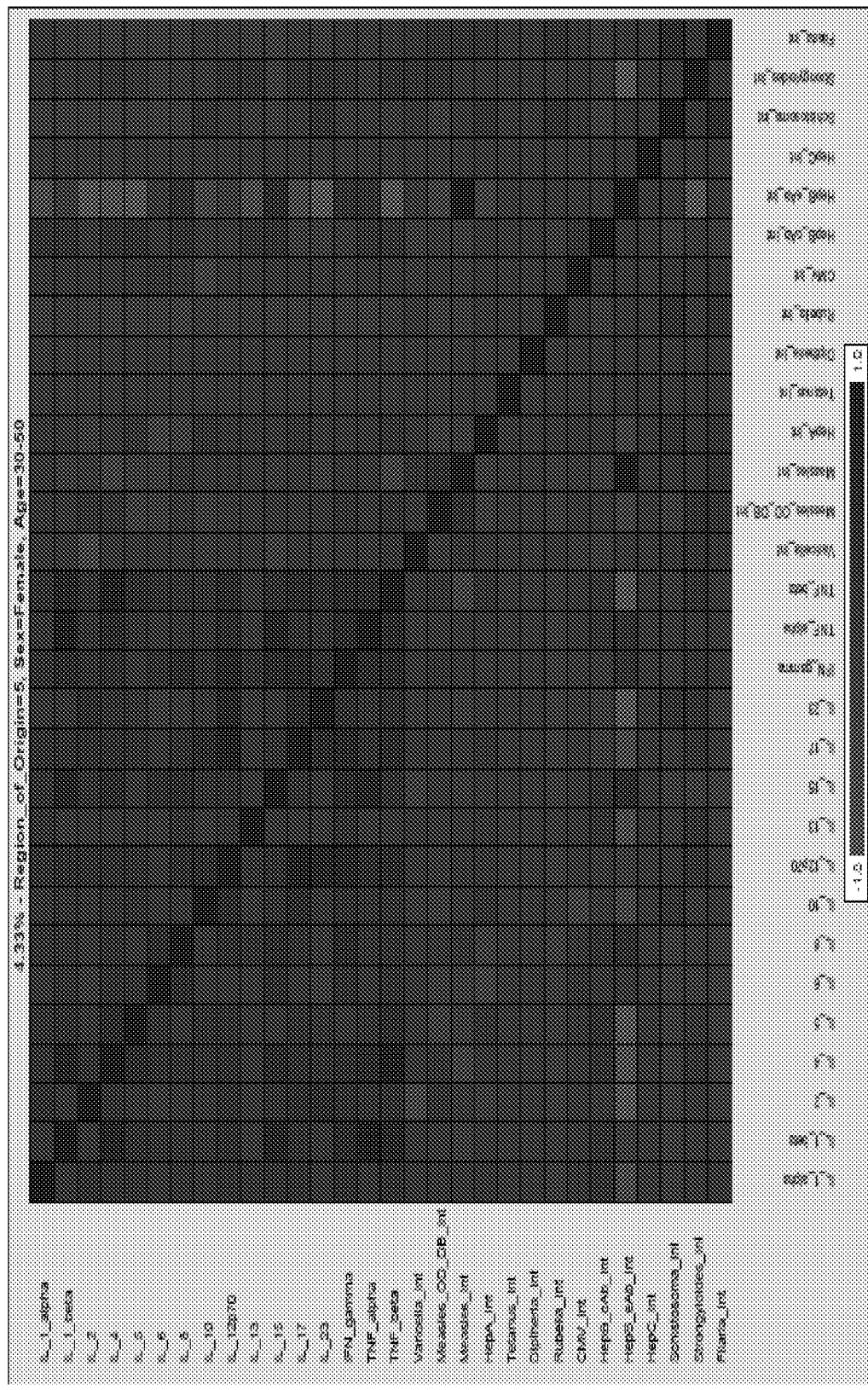
FIG. 21E-10.17A: Heat maps generated from Data Mining Tool. Eastern Europe, age 30-50. Females

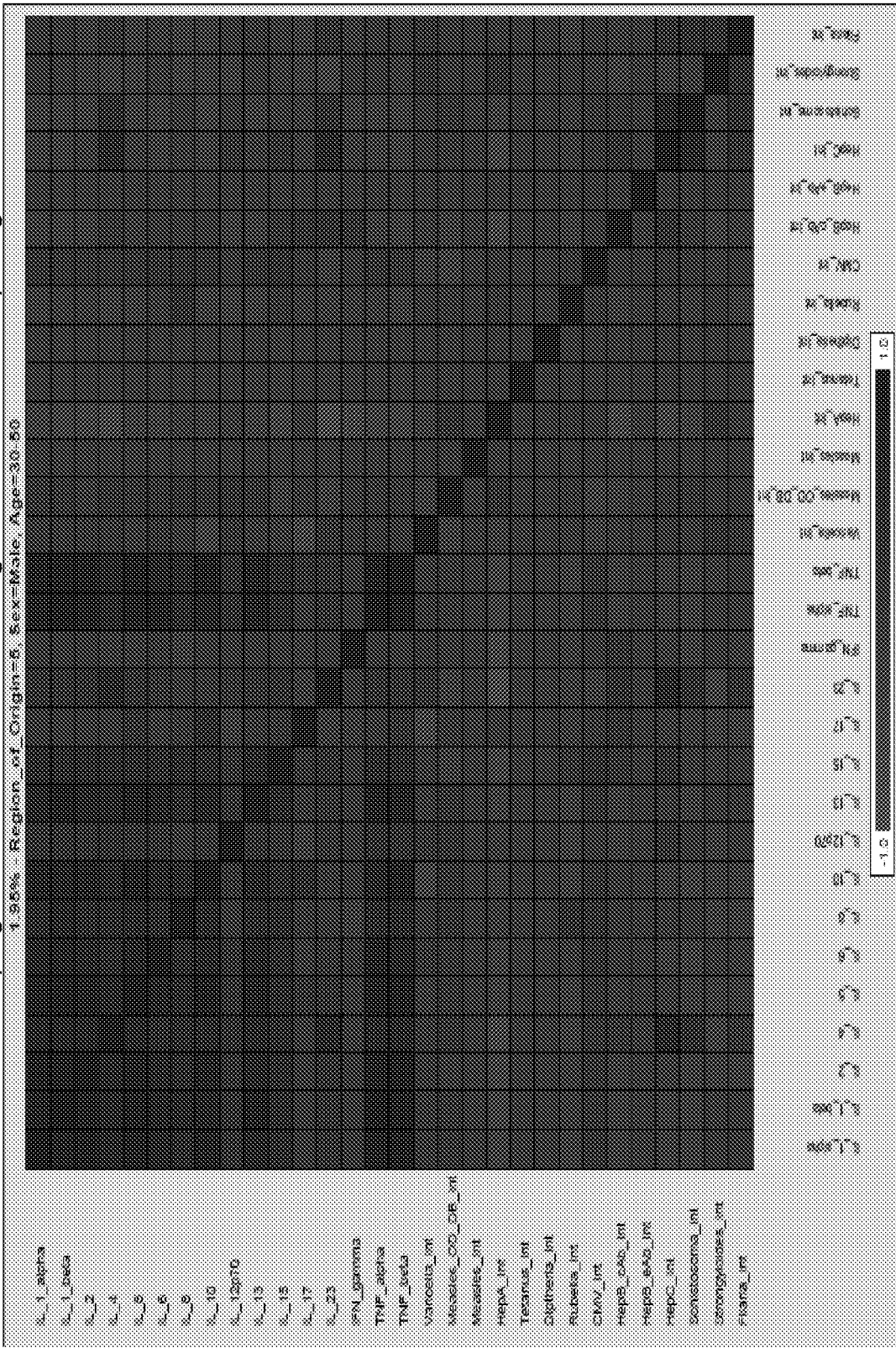
FIG. 21E-10.17B: Heat maps generated from Data Mining Tool. Eastern Europe, age 30-50. Males

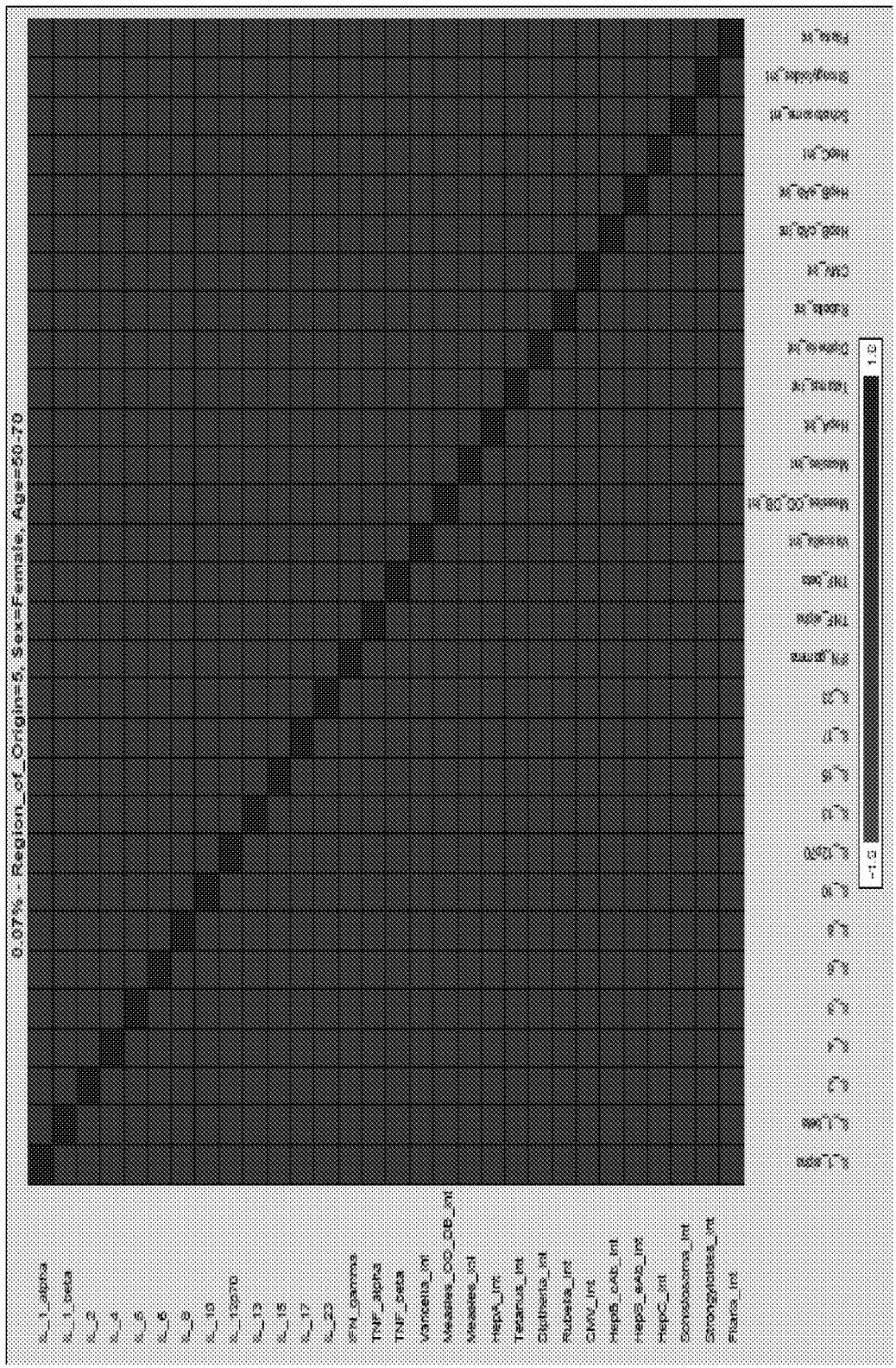
FIG. 21E-10.18: Heat map generated from Data Mining Tool. Eastern Europe, age 50-70. Females.

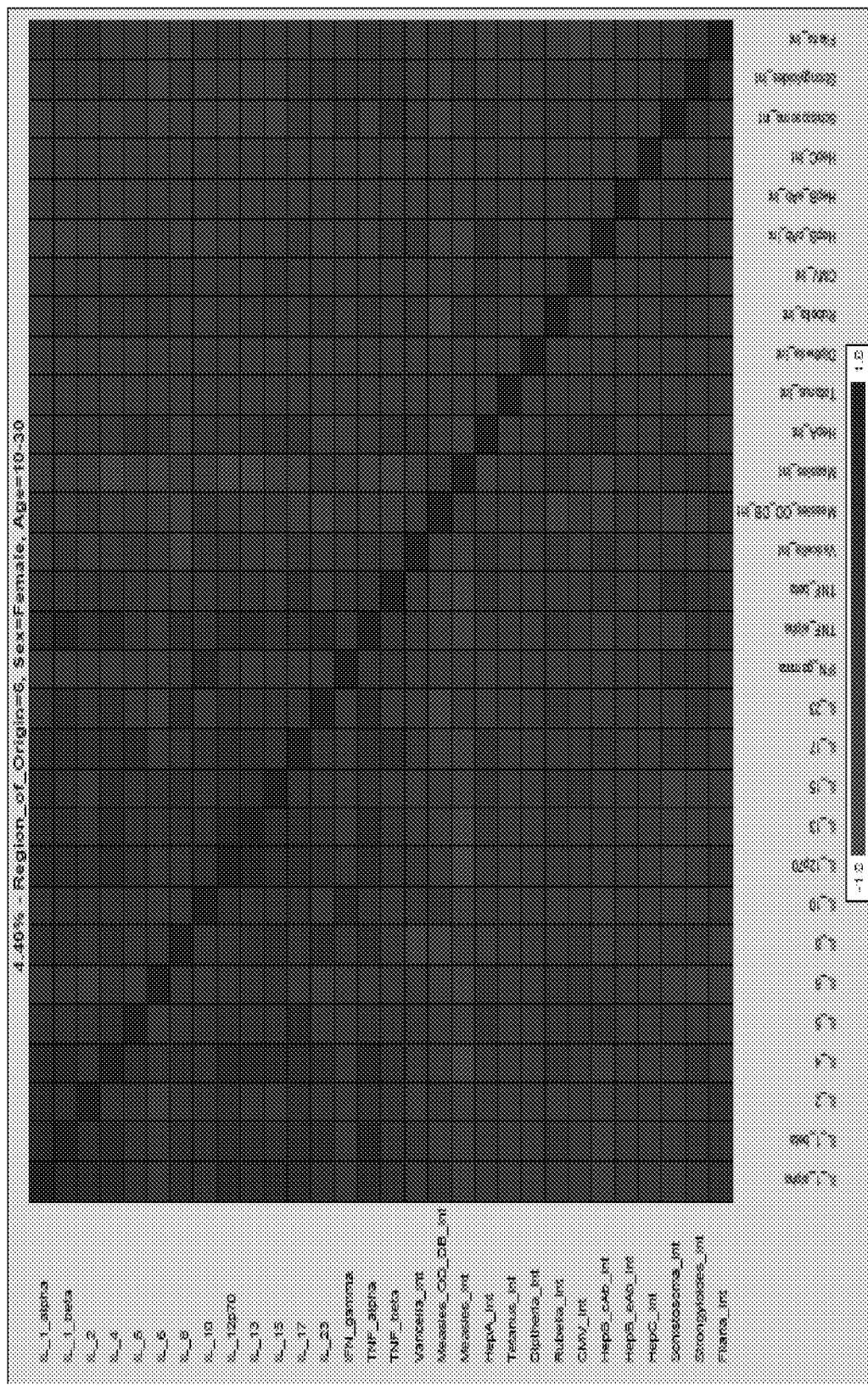
FIG. 21E-10.19A: Heat maps generated from Data Mining Tool. Southeast Asia, age 10-30. Females

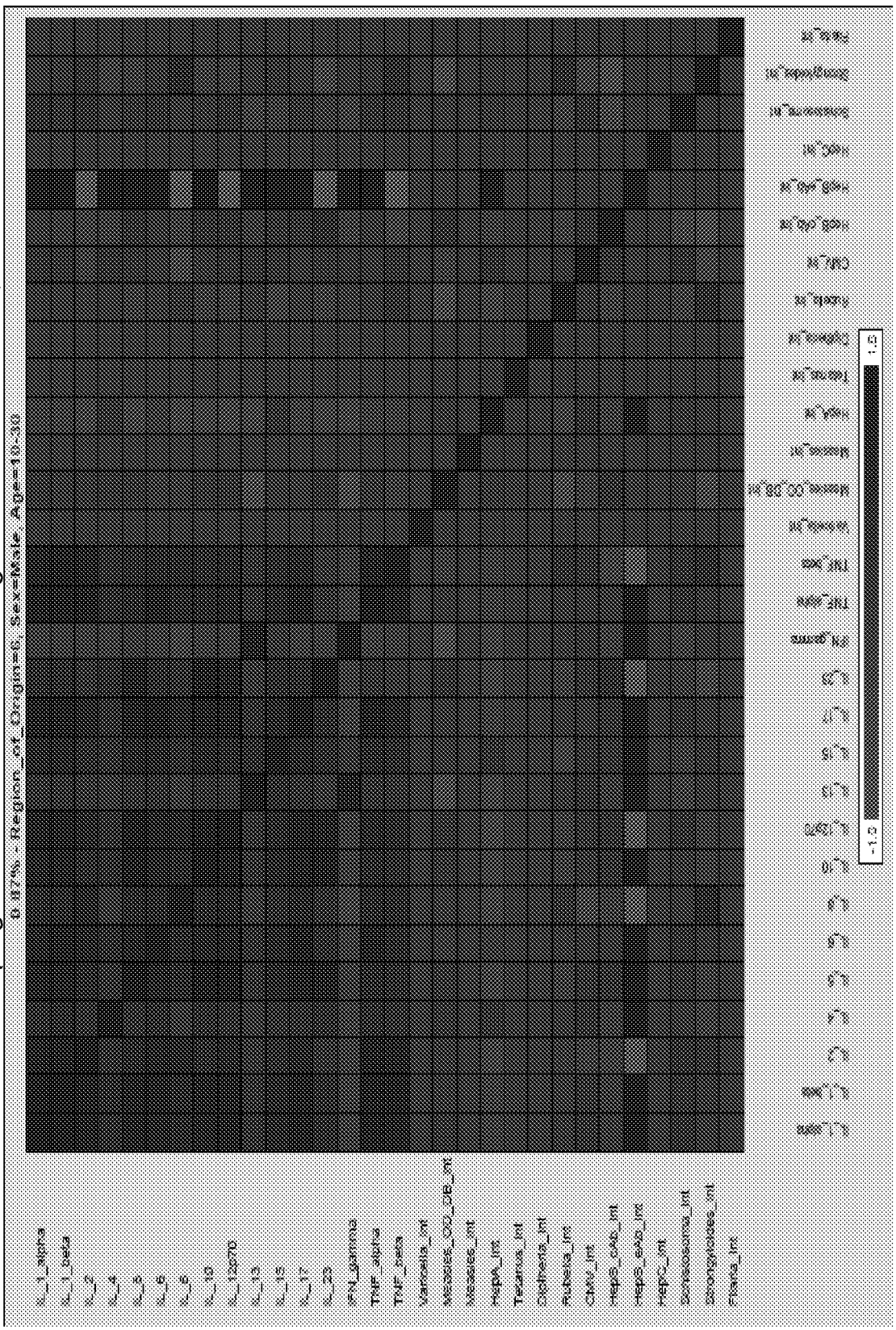
FIG. 21E-10.19B: Heat maps generated from Data Mining Tool. Southeast Asia, 10-30. Males

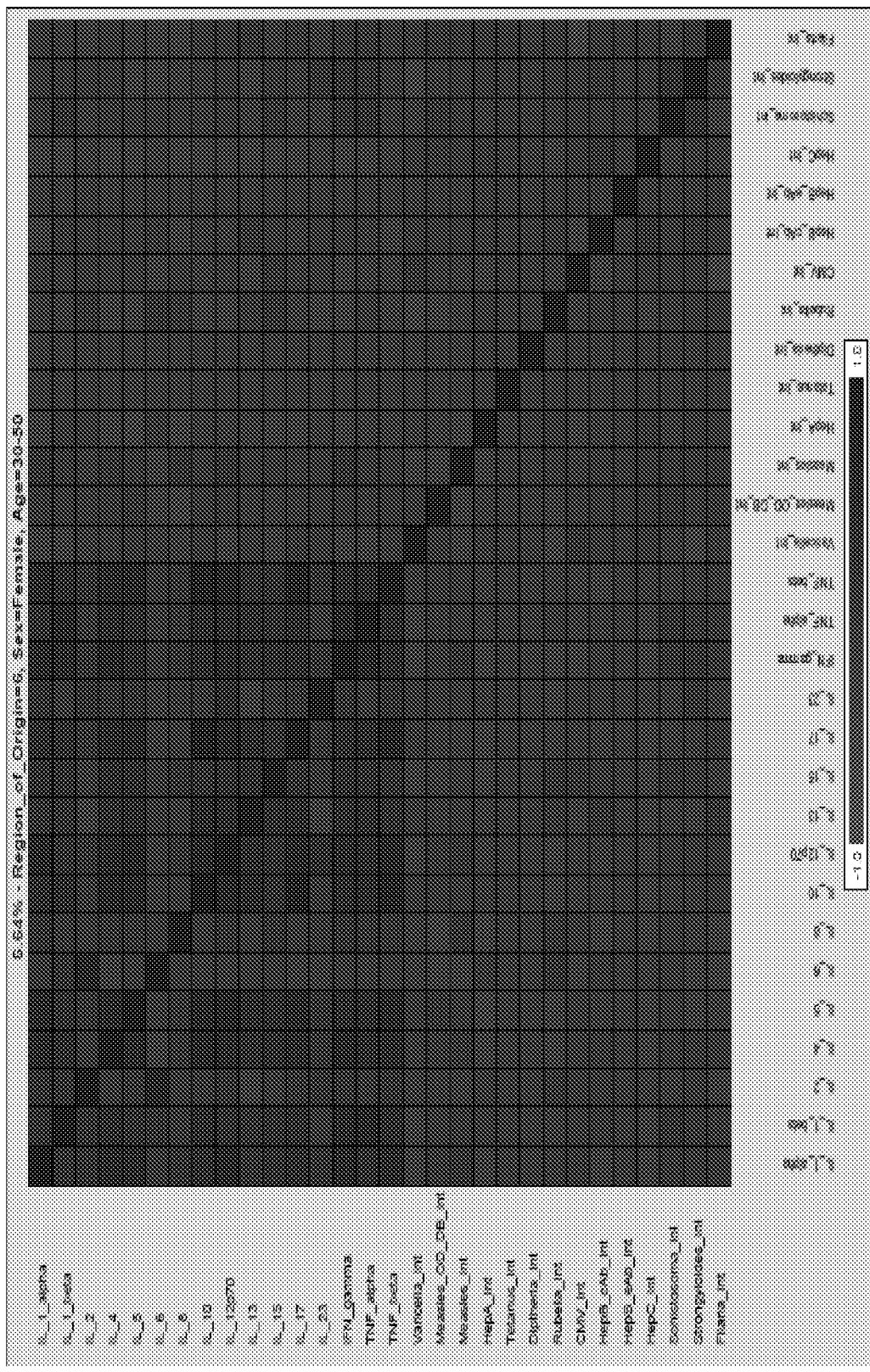
FIG. 21E-10.20A: Heat maps generated from Data Mining Tool. Southeast Asia, age 30-50. Females

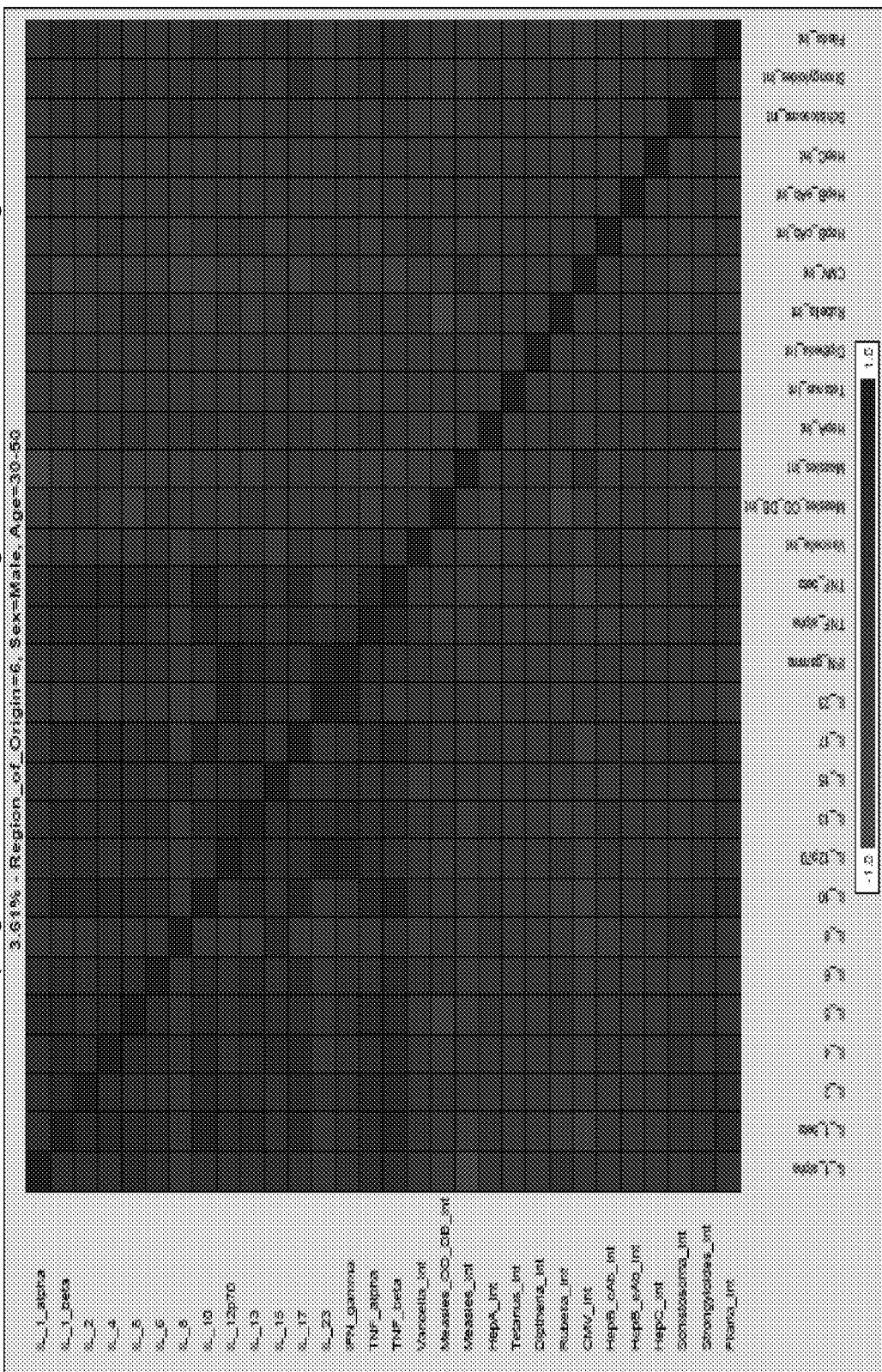
FIG. 21E-10.20B: Heat maps generated from Data Mining Tool. Southeast Asia, age 30-50. Males

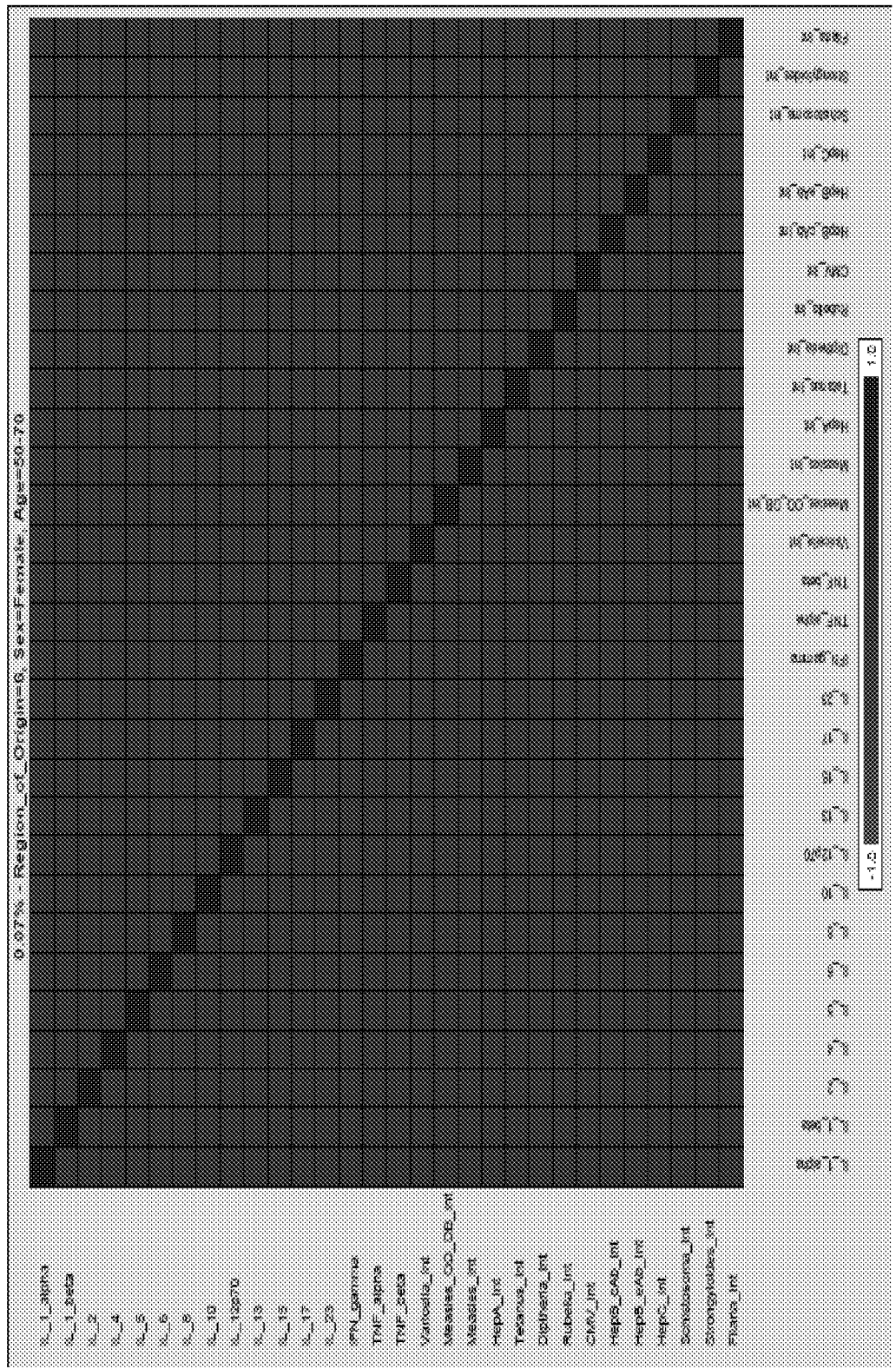
FIG. 21E-10.21: Heat map generated from Data Mining Tool. Southeast Asia, age 50-70. Females.

FIG. 21E-11 - Percent Th1 and Th2 Positive

| Type | TH1 Positive | TH1 # stddevs From Mean | TH2 Positive | TH2 # stddevs From Mean |
|---|---|---|---|---|
| Varicella_Nonreactive (84) | 44.7% | 1.6 | 93.6% | 0.4 |
| CMV_Nonreactive (85) | 46.3% | 1.1 | 88.8% | 2.1 |
| Measles_Nonreactive (84) | 46.4% | 1.1 | 91.7% | 0.5 |
| Strongyloides_Nonreactive (818) | 47.3% | 0.9 | 90.8% | 1.1 |
| HepB_Reactive (289) | 47.4% | 0.8 | 92.8% | 1.6 |
| HepA_Reactive (1030) | 49.3% | 0.3 | 92.4% | 0.2 |
| Rubella_Nonreactive (1069) | 49.6% | 0.2 | 91.8% | 0.5 |
| HepC_Nonreactive (1186) | 49.7% | 0.2 | 92.2% | 0.3 |
| Filaria_Nonreactive (1082) | 49.8% | 0.2 | 92.1% | 0.3 |
| Schistosoma_Reactive (200) | 50.0% | 0.1 | 91.5% | 0.6 |
| Schistosoma_Nonreactive (1018) | 50.0% | 0.1 | 92.4% | 0.2 |
| Entire Population (1218) | 50.0% | 0.1 | 92.3% | 0.2 |
| CMV_Reactive (1133) | 50.3% | 0.0 | 92.5% | 0.1 |
| Measles_Reactive (1134) | 50.3% | 0.0 | 92.3% | 0.2 |
| Varicella_Reactive (1124) | 50.4% | 0.0 | 92.2% | 0.3 |
| HepB_Nonreactive (929) | 50.8% | 0.1 | 91.2% | 0.8 |
| Filaria_Reactive (136) | 51.5% | 0.3 | 94.1% | 0.7 |
| Rubella_Reactive (149) | 53.0% | 0.7 | 96.0% | 1.7 |
| HepA_Nonreactive (188) | 53.7% | 0.9 | 91.5% | 0.6 |
| Strongyloides_Reactive (400) | 55.4% | 1.4 | 95.8% | 1.5 |
| HepC_Reactive (32) | 62.5% | 3.3 | 96.9% | 2.2 |

FIG. 21E-12 - Percent Treg and Th17 Positive

| Type | TReg Positive | TReg # stddevs From Mean | TH17 Positive | TH17 # stddevs From Mean |
|---|---|---|---|---|
| HepC_Reactive (32) | 53.1% | 1.7 | 96.9% | 2.4 |
| Varicella_Nonreactive (84) | 53.3% | 1.7 | 95.3% | 1.3 |
| Strongyloides_Nonreactive (810) | 54.9% | 1.0 | 100.0% | 1.9 |
| Filaria_Nonreactive (1062) | 55.8% | 0.6 | 95.7% | 0.1 |
| HepB_Reactive (289) | 56.1% | 0.5 | 95.2% | 0.3 |
| Schistosoma_Nonreactive (1018) | 56.3% | 0.4 | 96.0% | 0.0 |
| Rubella_Nonreactive (1069) | 56.3% | 0.4 | 95.5% | 0.2 |
| HepA_Reactive (1030) | 56.4% | 0.3 | 95.7% | 0.1 |
| CMV_Reactive (1138) | 56.5% | 0.3 | 96.0% | 0.0 |
| Measles_Reactive (1134) | 56.7% | 0.2 | 95.4% | 0.2 |
| Entire Population (1218) | 56.7% | 0.2 | 95.6% | 0.1 |
| HepC_Nonreactive (1186) | 56.8% | 0.2 | 95.8% | 0.0 |
| HepB_Nonreactive (929) | 56.9% | 0.1 | 95.8% | 0.0 |
| Varicella_Reactive (1124) | 57.0% | 0.1 | 95.4% | 0.2 |
| Measles_Nonreactive (84) | 57.1% | 0.0 | 96.6% | 0.3 |
| HepA_Nonreactive (188) | 58.5% | 0.5 | 95.2% | 0.3 |
| Schistosoma_Reactive (200) | 59.0% | 0.8 | 94.0% | 0.8 |
| Rubella_Reactive (149) | 59.7% | 1.0 | 96.6% | 0.3 |
| CMV_Nonreactive (80) | 60.0% | 1.2 | 91.9% | 2.0 |
| Strongyloides_Reactive (408) | 60.3% | 1.3 | 96.3% | 0.2 |
| Filaria_Reactive (136) | 64.9% | 2.8 | 100.0% | 1.9 |

Model Built Using Worms, Age, Country of Origin, Region of Origin

Training Set Size: 902

Test Set Size: 315

Subjects with Correct Prediction: 0 (0%)

| Worm | Subjects | Total Predicted | Correctly Predicted | False Negative | False Positive |
|---|---|---|---|---|---|
| Strongyloides_Int | 96 | 0 | 0 (0%) | 96 | 0 |
| Schistosoma_int | 45 | 0 | 0 (0%) | 45 | 0 |
| Filaria_Int | 29 | 0 | 0 (0%) | 29 | 0 |

FIG. 21F-1

Model Built Using Viruses Only

Training Set Size: 910

Test Set Size: 307

Subjects with Correct Prediction: 79 (25%)

| Virus | Subjects | Total Predicted | Correctly Predicted | False Negative | False Positive |
|---|---|---|---|---|---|
| Measles_Int | 291 | 276 | 260 (89%) | 31 | 16 |
| Varicella_Int | 290 | 269 | 254 (87%) | 36 | 15 |
| CMV_Int | 291 | 270 | 255 (87%) | 36 | 15 |
| HepA_Int | 265 | 187 | 166 (62%) | 99 | 21 |
| HepB_cAb_Int | 70 | 0 | 0 (0%) | 70 | 0 |
| Rubella_Int | 35 | 0 | 0 (0%) | 35 | 0 |
| HepC_Int | 6 | 0 | 0 (0%) | 6 | 0 |

FIG. 21F-2

Model Built Using Viruses, Worms

Training Set Size: 906

Test Set Size: 311

Subjects with Correct Prediction: 49 (15%)

| Virus | Subjects | Total Predicted | Correctly Predicted | False Negative | False Positive |
|---|---|---|---|---|---|
| Measles_Int | 289 | 291 | 273 (94%) | 16 | 18 |
| Varicella_Int | 285 | 287 | 264 (92%) | 21 | 23 |
| CMV_Int | 289 | 276 | 257 (88%) | 32 | 19 |
| HepA_Int | 266 | 188 | 163 (61%) | 103 | 25 |
| Strongyloides_Int | 98 | 0 | 0 (0%) | 98 | 0 |
| HepB_cAb_Int | 71 | 0 | 0 (0%) | 71 | 0 |
| Schistosoma_int | 47 | 0 | 0 (0%) | 47 | 0 |
| Filaria_Int | 31 | 4 | 0 (0%) | 31 | 4 |
| Rubella_Int | 27 | 0 | 0 (0%) | 27 | 0 |
| HepC_Int | 9 | 0 | 0 (0%) | 9 | 0 |

FIG. 21F-3

Model Built Using Viruses, Worms, Age, Country of Origin, Region of Origin

Training Set Size: 892

Test Set Size: 325

Subjects with Correct Prediction: 27 (8%)

| Virus | Subjects | Total Predicted | Correctly Predicted | False Negative | False Positive |
|---|---|---|---|---|---|
| Varicella_Int | 300 | 297 | 275 (91%) | 25 | 22 |
| Measles_Int | 304 | 277 | 257 (84%) | 47 | 20 |
| CMV_Int | 303 | 267 | 246 (81%) | 57 | 21 |
| HepA_Int | 274 | 158 | 117 (42%) | 157 | 41 |
| Strongyloides_Int | 108 | 2 | 1 (0%) | 107 | 1 |
| HepB_cAb_Int | 84 | 0 | 0 (0%) | 84 | 0 |
| Schistosoma_int | 56 | 0 | 0 (0%) | 56 | 0 |
| Rubella_Int | 54 | 0 | 0 (0%) | 54 | 0 |
| Filaria_Int | 30 | 0 | 0 (0%) | 30 | 0 |
| HepC_Int | 5 | 0 | 0 (0%) | 5 | 0 |

FIG. 21F-4

Model Built Using Viruses, Age, Country of Origin, Region of Origin

Training Set Size: 905

Test Set Size: 312

Subjects with Correct Prediction: 22 (7%)

| Virus | Subjects | Total Predicted | Correctly Predicted | False Negative | False Positive |
|---|---|---|---|---|---|
| CMV_Int | 285 | 264 | 239 (83%) | 46 | 25 |
| Varicella_Int | 287 | 251 | 230 (80%) | 57 | 21 |
| Measles_Int | 287 | 205 | 187 (65%) | 100 | 18 |
| HepA_Int | 269 | 31 | 24 (8%) | 245 | 7 |
| HepB_cAb_Int | 62 | 0 | 0 (0%) | 62 | 0 |
| Rubella_Int | 42 | 0 | 0 (0%) | 42 | 0 |
| HepC_Int | 9 | 1 | 0 (0%) | 9 | 1 |

FIG. 21F-5

Model Built Using Worms Only

Training Set Size: 919

Test Set Size: 298

Subjects with Correct Prediction: 1 (0%)

| Worm | Subjects | Total Predicted | Correctly Predicted | False Negative | False Positive |
|---|---|---|---|---|---|
| Strongyloides_Int | 85 | 2 | 1 (1%) | 84 | 1 |
| Schistosoma_int | 42 | 0 | 0 (0%) | 42 | 0 |
| Filaria_Int | 30 | 0 | 0 (0%) | 30 | 0 |

FIG. 21F-6

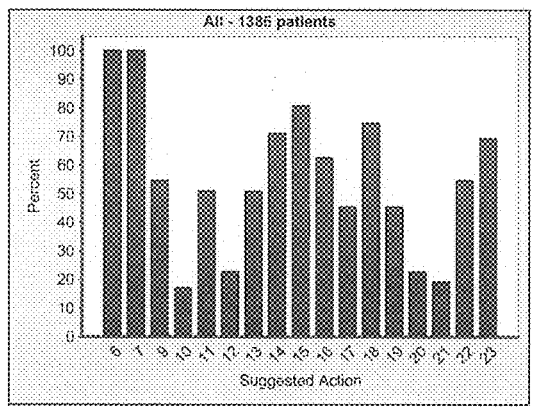

FIG. 21G-1A

Percent Deviation Between Groups

| Rule ID | Suggested Action | StdDev |
|---|---|---|
| 10 | Examine for pregnancy. | 0.00 |
| 11 | Administer ImmunoScore cytokine panel. Rise in pro-inflammatory cytokines (IL-6, IL-12, and/or IL-17) over previous visit would indicate a future autoimmune antibody profile screening to identify possible autoimmune disease manifestation. Rise in regulatory cytokines (IL-10 and TGF-?) could possibly also indicate an autoimmune disease manifestation in regression. Rise in both pro- and regulatory cytokines would trigger subsequent need to attempt to identify autoimmune disease manifestation by ImmunoScore autoimmune disease antibody screening panels.In addition to normal assessment of physical symptoms, elevated levels (>2 SD of mean) of key pro-inflammatory cytokines IL-6, IL-12, and/or IL-17 trigger: a) repeat visit in six weeks to re-measure cytokine values: i) if pro-inflammatory cytokines still elevated, recommend ImmunoScore panel to detect autoimmune antibody profile to identify possible autoimmune disease manifestation. ii) if pro-inflammatory cytokines levels decreased or moderating, recommend ImmunoScore cytokine panel evaluation annually. IL-7 may be particularly important as an initiator of many autoimmune manifestations. Depending on autoimmune disease condition, additional tests ordered can include serum thyroid stimulating hormone (TSH) for Hashimotos or Graves disease, anti-nuclear antibody (ANA) for systemic lupus erythematosus (SLE), neurological examination for multiple sclerosis (MS), and serum rheumatoid factor (RF) for rheumatoid arthritis (RA). Compare on site new ImmunoScore cytokine profile with baseline ImmunoScore cytokine profile. Significant increase (>20%) among grouped cytokines (e.g. Th1, Th2, Th17, and/or Treg) from previous profile values could be indicative of impending autoimmune flare that will likely require disease-specific treatment(s) | 18.25 |
| 12 | Examine for Rheumatoid arthritis. Rheumatoid arthritis (RA) is a chronic disorder for which there is no known cure. The optimal treatment of RA requires a comprehensive program that combines medical, social, and emotional support for the patient. Strategies are all aimed at reducing pain and discomfort, preventing deformities and loss of joint function. Treatment options include reduction of joint stress, physical and occupational therapy, and surgical intervention. Drug treatment prescriptions should be closely tied to ImmunoScore cytokine analyses to monitor RA flares and worsening of disease status. Drug classes to treat rheumatoid arthritis: 1) Non-steroidal anti-inflammatory agents (NSAIDs). NSAIDs reduce acute inflammation, reduce pain and improve function. They do not change the course of disease or prevent joint | 30.65 |

FIG. 21G-1B destruction; 2)Corticosteroids. Corticosteroids have both anti-inflammatory and immunoregulatory activity; 3) Disease modifying anti-rheumatic drugs (DMARDs). DMARD agents have been shown to alter the course of RA and improve radiographic outcomes. There are contra-indications for all of the treatment classes described above. Closely tied ImmunoScore cytokine measurement and courses of treatment will optimize RA treatment for each individual. Anti-inflammatory effect within hours, but reasonable trial period for relief of RA symptoms is 1 month. The most common toxicity is gastrointestinal disturbance which may clinically include burning, belching, or irritation, but which can represent irritation of the lining of the stomach, erosions, and ulcerations that may result in bleeding. Selective COX-2 inhibitors exhibit safer GI profiles than conventional non-selective NSAIDs, but may increase cardiovascular effects on blood pressure and additional effects on vascular beds. The use of NSAIDs medications must take into account their relative risks in an individual patient of gastrointestinal damage versus potential cardiovascular risk factors. Physicians treating RA patients with NSAIDs would periodically monitor serum cytokine levels to track inflammatory cytokines and relate them to symptoms of GI irritation and/or cardiovascular damage. Corticosteroids are useful in early disease as temporary adjunctive therapy while waiting for DMARDs to exert anti-inflammatory effects. This group is also useful as chronic adjunctive therapy in patients with severe disease not well controlled on NSAIDs or DMARDs. Side effects of prednisone include weight gain, increased blood pressure, increased blood sugar, increased risk of cataracts, and avascular necrosis of bones. Patients treated with corticosteroids should have periodic ImmunoScore cytokine measurements coupled with bone densitometry to assess bone fracture risk. Bisphosphonates are concurrently recommended to prevent and/or treat osteoporosis in addition to adequate calcium and vitamin D supplementation. In most cases, when the diagnosis of rheumatoid arthritis is cofirmed, DMARD agents should be initiated.Methotrexate is considered the first-line DMARD agent. The anti-inflammatory effects appear to be due to interruption of adenosine and possible effects on TNF pathways. Serious complications of methotrexate therapy, including hepatic cirrhosis, interstitial pneumonitis, and severe myelosuppression are rare with proper monitoring. Stomatitis and oral ulcers, alopecia and hair thinning, and GI upset may occur and are related to folic acid antagonism. These side effects can be improved with folic acid supplementation. ImmunoScore cytokine coupled with serum liver enzymes should be periodically monitored. Liver biopsy should be performed if liver enzymes persist. Hydroxychloroquine is sometimes used with methotrexate and sulfasalazine as a triple therapy for RA. The most important toxicity is on the eyes. Patients with underlying retinopathies should have a baseline ophthamlmologic examination and follow up exam every 12 months during treatment. Sulfasalazine is effective for the treatment of RA. The mechanism of action is unknown. It may cause hypersensitivity and allergic reactions. Careful periodic ImmunoScore cytokine screening would indicate undesirable increases in Th2 and/or Th17 cytokines in conjunction with increased serum IgE levels. TNF-? inhibitors are used to ameliorate local concentrations of TNF-? in synovial fluid. There are currently three TNF-? inhibitors approved for the treatment of RA. Etanercept binds TNF in the circulation and prevents interaction with cell surface TNF receptors. As with all TNF antagonists, there is an increased risk of infection in patients. Patients show increased risk of upper respiratory infections and some develop anti-nuclear antibodies characteristic of SLE. Screening for latent TB infection is prudent before initiation of TNF inhibitor treatments. Infliximab is an anti-TNF antibody developed in mice. Anti-infliximab antibodies can develop in patients, reducing the effectiveness of the treatments. ImmunoScore diagnostic follow-up would include cytokine measurements looking for increased Th2 (antibody) response coupled with specific measurement of anti-TNF antibodies. Opportunistic infections and sepsis have been reported with infliximab treatment. Periodic examination of cytokine balance would indicate patients coming out of immune balance. Observation of wildly fluctuating cytokine values would be indicative of an immune system swaying out of control and indicate likely candidates for sepsis. Adalimumab is another anti-TNF antibody treatment for RA. Increased infections ranging from mild to serious are seen in clinical practice. In addition, ANA titers have been seen as well as cases of lupus-like disease. Abatacept is one of a class of agents known as T-cell costimulatory blockers. These agents interfere with the interactions between antigen-presenting cells and T lymphocytes and affect early stages in the pathogenic cascade of events in RA. Infections are increased in patients being treated with abatacept. Periodic ImmunoScore cytokine measurement examining cytokine balance would coincide with patient treatment. Rituximab binds to the CD20 molecule on B cell surfaces leading to the removal of B cells from circulation. Clinical effects on RA are hypothesized to occur from decrease in B cell cytokines, interactions with B cells and T cells, or due to reductions in autoantibody levels. Infusion reactions to rituximab may include hives, itching, swelling, difficulty breathing, fever, chills, and changes in blood pressure. These are usually mild and respond to slowing the infusion rate or additional medication (such as antihistamines) but may be severe. Monitoring cytokine levels during infusion could lead to better monitoring of patient reaction to rituximab infusions. Anakira is an IL-1 receptor antagonist. ImmunoScore measurement of IL-1? and IL-1? serum concentrations during anakira therapy would indicate effectiveness and balance of the drug to cytokine levels in the patient.

| | | |
|---|---|---|
| 1 3 | Examine for Systemic Lupus Erythematosus. Activated autoreactive Th cells provide the help required for autoreactive B cells to differentiate and produce autoreactive antibodies. Studies of animal models and SLE patients indicate an important role for type I interferons. Although type I IFNs are classically considered to promote Th1-mediated cell responses, they can also inhibit Th1 and Th17 responses. At this point, it is not certain whether intervention with IFN inhibitors will be beneficial or detrimental to SLE patients, and the application of IFN inhibitory therapy may be based upon stage of SLE flare. ImmunoScore cytokine panels will be used to add clarity to therapeutics. As SLE patients live longer due to improved therapies and preventive measures, death and disability from cardiovascular events are increasing. The mechanism for the increased risk of SLE patients for cardiovascular events is likely due to a combination of inflammatory and immune mechanisms. There are increased levels of oxidized LDL (oxLDL), pro-inflammatory HDL, MCP-1, TNF-?, IFN-?, IL-1, and IL-12. ImmunoScore cardiac risk markers will be combined with ImmunoScore cytokine panels in patients with SLE, and progressive monitoring will be performed in these patients at regular intervals. | 18.43 |
| 1 4 | Examine for cancer. IL-10 is a cytokine with broad anti-inflammatory properties. A penalty of the role of IL-10 to limit immune and inflammatory responses to pathogens and prevent damage to the host is that high or dysregulated levels of IL-10 may result in chronic infection or cancer. There are certainly possible therapeutic roles to II-10 and its antagonists in human disease, all of which would benefit from careful ImmunoScore cytokine monitoring during clinical trials and subsequent evaluations. | 10.73 |
| 1 5 | Examine for Multiple Sclerosis. Upregulated cytokines in MS patients include IL-17, IL-12, IL-23, IL-6, IL-21, TNF-?, and other Th1 cytokines. IL-17-related cytokines are speculated to be related to disease progression. Glatiramer acetate (GA) is believed to induce GA-reactive T cells that secrete anti-inflammatory cytokines at the site of inflammation in MS - presumably increasing anti-inflammatory cytokines IL-10, IL-4, and TGF-?. ImmunoScore to periodically measure patients cytokines and at onset of flare, indicated by increased Th17 and Th1 cytokines, administer treatment. Efficacy of treatment could be monitored with monitoring of Treg cytokines.Interferon-? and atorvastatin have both been used to treat MS. IFN-? increases Th1 cytokines, while atorvastatin increases Th2 cytokines (particularly IL-5). Both may have the same effect of lessening the increase of Th17 cytokines. MS patients have general systemic increases of Th1 cytokines (particularly TNF-?. This is likely related to fatigue and lapses in systemic immunity. This may be a problem in patients treated with natalizumab as systemic rises in TNF-? are correlated with fatigue symptoms. | 7.13 |

FIG. 21G-1E

| 16 | Examine for Inflammatory Bowel Disease. IBD comprises two forms:<br>Ulcerative colitis (UC) increased expression of following:<br>o TNF-?<br>o IL-1?<br>o IL-6<br>o IL-12<br>o IL-23<br>o IL-17<br>o IL-13<br>o IL-5<br>Crohns disease (CD) increased expression of following:<br>o TNF-?<br>o IL-1?<br>o IL-1?<br>o IL-6<br>o IL-18 (in some patients)<br>o IL-10<br>o IL-4 (in some patients)<br>o IL-23<br>o IL-27<br>o IL-17<br>IL-23 appears to be the key mediator of flares of IBD. Mucosal cytokines recently cited (IL-31 and IL-32) as important are members of the IL-17 family. | 14.73 |
|---|---|---|
| 17 | Examine for Diabetes. Diabetes mellitus is characterized by a lack of insulin causing elevated blood glucose, often with associated insulin resistance. Elevated serum levels of TGF-? are associated with diabetic renal disease and will be tracked by the ImmunoScore cytokine diagnostic panel. Studies in animals indicate higher serum TGF-? levels might ameliorate disease. A dysfunctioning endothelium is associated with both initiation and progression of atherosclerotic cardiovascular disease and has been shown to predate the onset of hyperglycemia in the natural history of type 2 diabetes. It is likely that low level inflammation plays an important role in developing this endothelial dysfunction mainly through the action of TNF-? and possibly IL-6. Visceral obesity and inflammation within white adipose tissue may be a crucial step contributing to the emergence of insulin resistance, type 2 diabetes and atherosclerosis. IL-1?, IL-6, IL-8, IL-10 TNF-?, and TGF-? levels all rise under these conditions. IL-27 can promote both anti- and pro-inflammatory responses. IL-27 up-regulates IFN-?, and IL-17 and down-regulates IL-4, TGF-?, and IL-10 secreted by diabetic splenocytes, suggesting a pathogenic role in T cell-mediated autoimmune diabetes. | 21.05 |

FIG. 21G-1F

| 18 | Examine for Breast Cancer. IL-6 is a pleiotropic cytokine with both tumor-promoting and tumor-inhibiting effects. Serum IL-6 levels, however, are a negative prognosticator in breast tumor patients. IL-6, IL-8, and IL-10 levels are higher in women with breast cancer than controls and levels also correlate with the clinical stage of disease. Elevated serum IL-8 levels are related to an accelerated clinical course, a higher tumor load, and the presence of liver or lymph node involvement. On the other hand, elevated IL-8 also has prognostic significance for post-relapse survival. | 9.61 |
|---|---|---|
| 19 | Examine for Cancer. Chronic inflammation has long been associated with the development of cancer. TNF-? is one of the major mediators of inflammation. TNF-? induces other inflammatory mediators and proteases that orchestrate inflammatory responses. TNF-? is also produced by tumors and can act as an endogenous tumor promoter. The role of TNF-? has been linked to all steps involved in tumorigenesis, including cellular transformation, promotion, survival, proliferation, invasion, angiogenesis, and metastasis. ImmunoScore cytokine monitoring of TNF-? levels extremely important in cancer patients. | 0.00 |
| 20 | Examine for Cancer. IL-6 has been proposed as a prognostic factor in several malignancies such as colorectal cancer, breast cancer, gastric cancer, and pancreatic cancer. In addition, elevated serum IL-6 concentrations have been demonstrated in patients with endometrial cancer, non-small cell lung carcinoma, colorectal cancer, renal cell carcinoma, breast and ovarian cancers. | 0.00 |
| 21 | Examine for Atherosclerosis. Atherogenesis is characterized by an intense inflammatory process, involving immune and vascular cells. C-reactive protein (CRP), monocyte/macrophage colony-stimulating factor (M-CSF), and IL-6 promote atherogenesis. They also down-regulate atheroprotective cytokines such as IL-10 and TGF-?. Increased levels of CRP and IL-6 are predictive of a higher cardiovascular event rate in the general population. In coronary artery disease, high levels of M-CSF are additive with those of CRP, suggesting the benefit of a multi-marker approach in assessing risk to coronary artery disease. In addition to the pro-inflammatory cytokines with poor prognostic indications, including TNF-?, IL-6, MCP-1, and IL-1, several adipocytokines are released by fat tissues and are inflammatory in nature. These include leptin, resistin, adiponectin and visfatin. Once possible atherosclerotic complications are revealed in patients, a follow up panel specific for heart patients can be envisioned which contains diagnostic tools for serum adipocytokines. It is not yet clear what function IFN-? has in relationship with atherosclerosis development, but it is likely a key player and should be monitored in cardiac patients. | 7.68 |

FIG. 21G-1G

| | | | |
|---|---|---|---|
| 2 2 | Examine for Allergies. Allergies are the result of aberrant immune reactivity to common innocuous environmental proteins. A pivotal component of allergic pathogenesis is the generation of allergen-specific Th cells with an effector phenotype. Th17 cells may also contribute to the pathogenesis of classically recognized Th2-mediated allergic disorders. This may very by individual patient, and ImmunoScore cytokine profiling would reveal individual differences from patient to patient. Allergic disorders would have a recommendation for treatment plans based upon Th2/Th17 immune balance. | 17.00 | |
| 2 3 | Examine for Asthma. Asthma comprises distinct heterogeneous inflammatory disorders characterized by patients showing different phenotypes with distinct genetic components, environmental causes, and immunopathogenesis. Once considered purely an allergic disorder dominated by Th2 lymphocytes, IgE, mast cells, eosinophils, macrophages, and cytokines, the disease also involves local epithelial, mesenchymal, vascular and neurologic events that are involved in directing the Th2 phenotype to the lung and through aberrant injury-repair mechanisms to remodeling of the airway wall. Responses to asthma medications vary considerably among patients, likely reflecting the differing sensitivities of the various asthma phenotypes. Physicians need to recognize this when making decisions to adjust treatment to improve asthma. IL-4 and IL-13 are considered to be key contributors to cell-mediated and humoral aspects of allergic inflammation. There is controversy surrounding the role of TGF-? in asthma. It is speculated that IL-5 also plays a pivotal role in eosinophila and asthma. Anti-IgE therapy is an approved treatment for adult and childhood asthma. Helminth infections are suggested to minimize asthma symptoms. | 11.44 | |
| 6 | Give a booster dose of tetanus vaccine. Individuals over seven years of age receive the vaccine in combination with diphtheria vaccine (Td). Those children younger than seven years of age can be boosted with a vaccine containing a pertussis component (DTaP). People who had a serious allergic reaction to one dose of tetanus toxoid should not receive another. Persons with a moderate or severe acute illness should postpone receiving the vaccine until they are improved. | 0.00 | |
| 7 | Give a booster dose of diphtheria vaccine. Individuals over seven years of age receive the vaccine in combination with tetanus vaccine (Td). Those children younger than seven can be boosted with a vaccine containing the pertussis component as with the tetanus vaccine described above. People who have had a serious allergic reaction to one dose of DTaP, DT, Td, or Tdap vaccine should not receive another. Persons with a moderate or severe illness should postpone receiving the vaccine until their condition has improved. | 0.00 | |

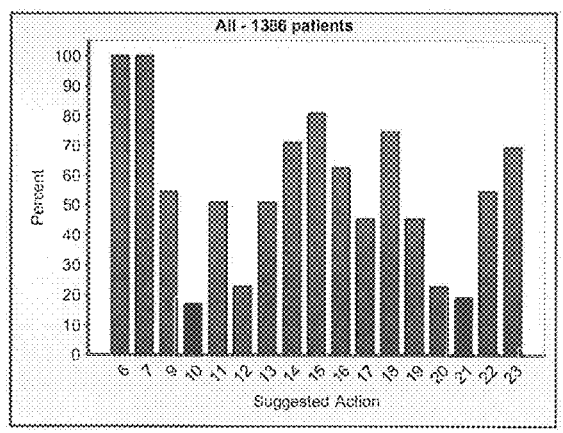

FIG. 21G-2A

Percent Deviation Between Groups

| Rule ID | Suggested Action | StdDev |
|---|---|---|
| 10 | Examine for pregnancy. | 0.00 |
| 11 | Administer ImmunoScore cytokine panel. Rise in pro-inflammatory cytokines (IL-6, IL-12, and/or IL-17) over previous visit would indicate a future autoimmune antibody profile screening to identify possible autoimmune disease manifestation. Rise in regulatory cytokines (IL-10 and TGF-?) could possibly also indicate an autoimmune disease manifestation in regression. Rise in both pro- and regulatory cytokines would trigger subsequent need to attempt to identify autoimmune disease manifestation by ImmunoScore autoimmune disease antibody screening panels. In addition to normal assessment of physical symptoms, elevated levels (>2 SD of mean) of key pro-inflammatory cytokines IL-6, IL-12, and/or IL-17 trigger. a) repeat visit in six weeks to re-measure cytokine values: i) if pro-inflammatory cytokines still elevated, recommend ImmunoScore panel to detect autoimmune antibody profile to identify possible autoimmune disease manifestation. ii) if pro-inflammatory cytokines levels decreased or moderating, recommend ImmunoScore cytokine panel evaluation annually. IL-7 may be particularly important as an initiator of many autoimmune manifestations. Depending on autoimmune disease condition, additional tests ordered can include serum thyroid stimulating hormone (TSH) for Hashimotos or Graves disease, anti-nuclear antibody (ANA) for systemic lupus erythematosus (SLE), neurological examination for multiple sclerosis (MS), and serum rheumatoid factor (RF) for rheumatoid arthritis (RA) Compare on site new ImmunoScore cytokine profile with baseline ImmunoScore cytokine profile. Significant increase (>20%) among grouped cytokines (e.g. Th1, Th2, Th17, and/or Treg) from previous profile values could be indicative of impending autoimmune flare that will likely require disease-specific treatment(s). | 22.42 |
| 12 | Examine for Rheumatoid arthritis. Rheumatoid arthritis (RA) is a chronic disorder for which there is no known cure. The optimal treatment of RA requires a comprehensive program that combines medical, social, and emotional support for the patient. Strategies are all aimed at reducing pain and discomfort, preventing deformities and loss of joint function. Treatment options include reduction of joint stress, physical and occupational therapy, and surgical intervention. Drug treatment prescriptions should be closely tied to ImmunoScore cytokine analyses to monitor RA flares and worsening of disease status. Drug classes to treat rheumatoid arthritis: 1) Non-steroidal anti-inflammatory agents (NSAIDs) NSAIDs reduce acute inflammation, reduce pain and improve function. They do not change the course of disease or prevent joint | 35.08 |

FIG. 21G-2B destruction; 2)Corticosteroids. Corticosteroids have both anti-inflammatory and immunoregulatory activity; 3) Disease modifying anti-rheumatic drugs (DMARDs) DMARD agents have been shown to alter the course of RA and improve radiographic outcomes. There are contra-indications for all of the treatment classes described above. Closely tied ImmunoScore cytokine measurement and courses of treatment will optimize RA treatment for each individual. Anti-inflammatory effect within hours, but reasonable trial period for relief of RA symptoms is 1 month. The most common toxicity is gastrointestinal disturbance which may clinically include burning, belching, or irritation, but which can represent irritation of the lining of the stomach, erosions, and ulcerations that may result in bleeding. Selective COX-2 inhibitors exhibit safer GI profiles than conventional non-selective NSAIDs, but may increase cardiovascular effects on blood pressure and additional effects on vascular beds. The use of NSAIDs medications must take into account their relative risks in an individual patient of gastrointestinal damage versus potential cardiovascular risk factors. Physicians treating RA patients with NSAIDs would periodically monitor serum cytokine levels to track inflammatory cytokines and relate them to symptoms of GI irritation and/or cardiovascular damage. Corticosteroids are useful in early disease as temporary adjunctive therapy while waiting for DMARDs to exert anti-inflammatory effects. This group is also useful as chronic adjunctive therapy in patients with severe disease not well controlled on NSAIDs or DMARDs. Side effects of prednisone include weight gain, increased blood pressure, increased blood sugar, increased risk of cataracts, and avascular necrosis of bones. Patients treated with corticosteroids should have periodic ImmunoScore cytokine measurements coupled with bone densitometry to assess bone fracture risk. Bisphosphonates are concurrently recommended to prevent and/or treat osteoporosis in addition to adequate calcium and vitamin D supplementation. In most cases, when the diagnosis of rheumatoid arthritis is cofirmed, DMARD agents should be initiated.Methotrexate is considered the first-line DMARD agent. The anti-inflammatory effects appear to be due to interruption of adenosine and possible effects on TNF pathways. Serious complications of methotrexate therapy, including hepatic cirrhosis, interstitial pneumonitis, and severe myelosuppression are rare with proper monitoring. Stomatitis and oral ulcers, alopecia and hair thinning, and GI upset may occur and are related to folic acid antagonism. These side effects can be improved with folic acid supplementation. ImmunoScore cytokine coupled with serum liver enzymes should be periodically monitored. Liver biopsy should be performed if liver enzymes persist. Hydroxychloroquine is sometimes used with methotrexate and sulfasalazine as a triple therapy for RA. The most important toxicity is on the eyes. Patients with underlying retinopathies should have a baseline ophthamlmologic examination and follow up

FIG. 21G-2C exam every 12 months during treatment. Sulfasalazine is effective for the treatment of RA. The mechanism of action is unknown. It may cause hypersensitivity and allergic reactions. Careful periodic ImmunoScore cytokine screening would indicate undesirable increases in Th2 and/or Th17 cytokines in conjunction with increased serum IgE levels. TNF-? inhibitors are used to ameliorate local concentrations of TNF-? in synovial fluid. There are currently three TNF-? inhibitors approved for the treatment of RA. Etanercept binds TNF in the circulation and prevents interaction with cell surface TNF receptors. As with all TNF antagonists, there is an increased risk of infection in patients. Patients show increased risk of upper respiratory infections and some develop anti-nuclear antibodies characteristic of SLE. Screening for latent TB infection is prudent before initiation of TNF inhibitor treatments. Infliximab is an anti-TNF antibody developed in mice. Anti-infliximab antibodies can develop in patients, reducing the effectiveness of the treatments. ImmunoScore diagnostic follow-up would include cytokine measurements looking for increased Th2 (antibody) response coupled with specific measurement of anti-TNF antibodies. Opportunistic infections and sepsis have been reported with infliximab treatment. Periodic examination of cytokine balance would indicate patients coming out of immune balance. Observation of wildly fluctuating cytokine values would be indicative of an immune system swaying out of control and indicate likely candidates for sepsis. Adalimumab is another anti-TNF antibody treatment for RA. Increased infections ranging from mild to serious are seen in clinical practice. In addition, ANA titers have been seen as well as cases of lupus-like disease. Abatacept is one of a class of agents known as T-cell costimulatory blockers. These agents interfere with the interactions between antigen-presenting cells and T lymphocytes and affect early stages in the pathogenic cascade of events in RA. Infections are increased in patients being treated with abatacept. Periodic ImmunoScore cytokine measurement examining cytokine balance would coincide with patient treatment. Rituximab binds to the CD20 molecule on B cell surfaces leading to the removal of B cells from circulation. Clinical effects on RA are hypothesized to occur from decrease in B cell cytokines, interactions with B cells and T cells, or due to reductions in autoantibody levels. Infusion reactions to rituximab may include hives, itching, swelling, difficulty breathing, fever, chills, and changes in blood pressure. These are usually mild and respond to slowing the infusion rate or additional medication (such as antihistamines) but may be severe. Monitoring cytokine levels during infusion could lead to better monitoring of patient reaction to rituximab infusions. Anakira is an IL-1 receptor antagonist. ImmunoScore measurement of IL-1? and IL-1? serum concentrations during anakira therapy would indicate effectiveness and balance of the drug to cytokine levels in the patient.

FIG. 21G-2D

| | | |
|---|---|---|
| 1 3 | Examine for Systemic Lupus Erythematosus. Activated autoreactive Th cells provide the help required for autoreactive B cells to differentiate and produce autoreactive antibodies. Studies of animal models and SLE patients indicate an important role for type I interferons. Although type I IFNs are classically considered to promote Th1-mediated cell responses, they can also inhibit Th1 and Th17 responses. At this point, it is not certain whether intervention with IFN inhibitors will be beneficial or detrimental to SLE patients, and the application of IFN inhibitory therapy may be based upon stage of SLE flare. ImmunoScore cytokine panels will be used to add clarity to therapeutics. As SLE patients live longer due to improved therapies and preventive measures, death and disability from cardiovascular events are increasing. The mechanism for the increased risk of SLE patients for cardiovascular events is likely due to a combination of inflammatory and immune mechanisms. There are increased levels of oxidized LDL (oxLDL), pro-inflammatory HDL, MCP-1, TNF-?, IFN-?, IL-1, and IL-12. ImmunoScore cardiac risk markers will be combined with ImmunoScore cytokine panels in patients with SLE, and progressive monitoring will be performed in these patients at regular intervals. | 16.67 |
| 1 4 | Examine for cancer. IL-10 is a cytokine with broad anti-inflammatory properties. A penalty of the role of IL-10 to limit immune and inflammatory responses to pathogens and prevent damage to the host is that high or dysregulated levels of IL-10 may result in chronic infection or cancer. There are certainly possible therapeutic roles to Il-10 and its antagonists in human disease, all of which would benefit from careful ImmunoScore cytokine monitoring during clinical trials and subsequent evaluations. | 9.85 |
| 1 5 | Examine for Multiple Sclerosis. Upregulated cytokines in MS patients include IL-17, IL-12, IL-23, IL-6, IL-21, TNF-?, and other Th1 cytokines. IL-17-related cytokines are speculated to be related to disease progression. Glatiramer acetate (GA) is believed to induce GA-reactive T cells that secrete anti-inflammatory cytokines at the site of inflammation in MS - presumably increasing anti-inflammatory cytokines IL-10, IL-4, and TGF-?. ImmunoScore to periodically measure patients cytokines and at onset of flare, indicated by increased Th17 and Th1 cytokines, administer treatment. Efficacy of treatment could be monitored with monitoring of Treg cytokines.Interferon-? and atorvastatin have both been used to treat MS. IFN-? increases Th1 cytokines, while atorvastatin increases Th2 cytokines (particularly IL-5). Both may have the same effect of lessening the increase of Th17 cytokines. MS patients have general systemic increases of Th1 cytokines (particularly TNF-?. This is likely related to fatigue and lapses in systemic immunity. This may be a problem in patients treated with natalizumab as systemic rises in TNF-? are correlated with fatigue symptoms. | 6.43 |

FIG. 21G-2E

| | | | |
|---|---|---|---|
| 1 6 | Examine for Inflammatory Bowel Disease. IBD comprises two forms:<br>Ulcerative colitis (UC) increased expression of following:<br>○ TNF-?<br>○ IL-1?<br>○ IL-6<br>○ IL-12<br>○ IL-23<br>○ IL-17<br>○ IL-13<br>○ IL-5<br>Crohns disease (CD) increased expression of following:<br>○ TNF-?<br>○ IL-1?<br>○ IL-1?<br>○ IL-6<br>○ IL-18 (in some patients)<br>○ IL-10<br>○ IL-4 (in some patients)<br>○ IL-23<br>○ IL-27<br>○ IL-17<br>IL-23 appears to be the key mediator of flares of IBD. Mucosal cytokines recently cited (IL-31 and IL-32) as important are members of the IL-17 family. | 19.76 | |
| 1 7 | Examine for Diabetes. Diabetes mellitus is characterized by a lack of insulin causing elevated blood glucose, often with associated insulin resistance. Elevated serum levels of TGF-? are associated with diabetic renal disease and will be tracked by the ImmunoScore cytokine diagnostic panel. Studies in animals indicate higher serum TGF-? levels might ameliorate disease. A dysfunctioning endothelium is associated with both initiation and progression of atherosclerotic cardiovascular disease and has been shown to predate the onset of hyperglycemia in the natural history of type 2 diabetes. It is likely that low level inflammation plays an important role in developing this endothelial dysfunction mainly through the action of TNF-? and possibly IL-6. Visceral obesity and inflammation within white adipose tissue may be a crucial step contributing to the emergence of insulin resistance, type 2 diabetes and atherosclerosis. IL-1?, IL-6, IL-8, IL-10 TNF-?, and TGF-? levels all rise under these conditions. IL-27 can promote both anti- and pro-inflammatory responses. IL-27 up-regulates IFN-?, and IL-17 and down-regulates IL-4, TGF-?, and IL-10 secreted by diabetic splenocytes, suggesting a pathogenic role in T cell-mediated autoimmune diabetes. | 25.86 | |

FIG. 21G-2F

| | | |
|---|---|---|
| 18 | Examine for Breast Cancer. IL-6 is a pleiotropic cytokine with both tumor-promoting and tumor-inhibiting effects. Serum IL-6 levels, however, are a negative prognosticator in breast tumor patients.<br>IL-6, IL-8, and IL-10 levels are higher in women with breast cancer than controls and levels also correlate with the clinical stage of disease. Elevated serum IL-8 levels are related to an accelerated clinical course, a higher tumor load, and the presence of liver or lymph node involvement. On the other hand, elevated IL-8 also has prognostic significance for post-relapse survival. | 17.74 |
| 19 | Examine for Cancer. Chronic inflammation has long been associated with the development of cancer. TNF-? is one of the major mediators of inflammation. TNF-? induces other inflammatory mediators and proteases that orchestrate inflammatory responses. TNF-? is also produced by tumors and can act as an endogenous tumor promoter. The role of TNF-? has been linked to all steps involved in tumorigenesis, including cellular transformation, promotion, survival, proliferation, invasion, angiogenesis, and metastasis. ImmunoScore cytokine monitoring of TNF-? levels extremely important in cancer patients. | 26.53 |
| 20 | Examine for Cancer. Il-6 has been proposed as a prognostic factor in several malignancies such as colorectal cancer, breast cancer, gastric cancer, and pancreatic cancer. In addition, elevated serum IL-6 concentrations have been demonstrated in patients with endometrial cancer, non-small cell lung carcinoma, colorectal cancer, renal cell carcinoma, breast and ovarian cancers. | 9.84 |
| 21 | Examine for Atherosclerosis. Atherogenesis is characterized by an intense inflammatory process, involving immune and vascular cells. C-reactive protein (CRP), monocyte/macrophage colony-stimulating factor (M-CSF), and IL-6 promote atherogenesis. They also down-regulate atheroprotective cytokines such as IL-10 and TGF-?. Increased levels of CRP and IL-6 are predictive of a higher cardiovascular event rate in the general population. In coronary artery disease, high levels of M-CSF are additive with those of CRP, suggesting the benefit of a multi-marker approach in assessing risk to coronary artery disease. In addition to the pro-inflammatory cytokines with poor prognostic indications, including TNF-?, IL-6, MCP-1, and IL-1, several adipocytokines are released by fat tissues and are inflammatory in nature. These include leptin, resistin, adiponectin and visfatin. Once possible atherosclerotic complications are revealed in patients, a follow up panel specific for heart patients can be envisioned which contains diagnostic tools for serum adipocytokines. It is not yet clear what function IFN-? has in relationship with atherosclerosis development, but it is likely a key player and should be monitored in cardiac patients. | 8.02 |

FIG. 21G-2G

| | | | |
|---|---|---|---|
| 2 2 | Examine for Allergies. Allergies are the result of aberrant immune reactivity to common innocuous environmental proteins. A pivotal component of allergic pathogenesis is the generation of allergen-specific Th cells with an effector phenotype. Th17 cells may also contribute to the pathogenesis of classically recognized Th2-mediated allergic disorders. This may very by individual patient, and ImmunoScore cytokine profiling would reveal individual differences from patient to patient. Allergic disorders would have a recommendation for treatment plans based upon Th2/Th17 immune balance. | 23.68 | |
| 2 3 | Examine for Asthma. Asthma comprises distinct heterogeneous inflammatory disorders characterized by patients showing different phenotypes with distinct genetic components, environmental causes, and immunopathogenesis. Once considered purely an allergic disorder dominated by Th2 lymphocytes, IgE, mast cells, eosinophils, macrophages, and cytokines, the disease also involves local epithelial, mesenchymal, vascular and neurologic events that are involved in directing the Th2 phenotype to the lung and through aberrant injury-repair mechanisms to remodeling of the airway wall. Responses to asthma medications vary considerably among patients, likely reflecting the differing sensitivities of the various asthma phenotypes. Physicians need to recognize this when making decisions to adjust treatment to improve asthma. IL-4 and IL-13 are considered to be key contributors to cell-mediated and humoral aspects of allergic inflammation. There is controversy surrounding the role of TGF-? in asthma. It is speculated that IL-5 also plays a pivotal role in eosinophila and asthma. Anti-IgE therapy is an approved treatment for adult and childhood asthma. Helminth infections are suggested to minimize asthma symptoms. | 10.29 | |
| 6 | Give a booster dose of tetanus vaccine. Individuals over seven years of age receive the vaccine in combination with diphtheria vaccine (Td). Those children younger than seven years of age can be boosted with a vaccine containing a pertussis component (DTaP). People who had a serious allergic reaction to one dose of tetanus toxoid should not receive another. Persons with a moderate or severe acute illness should postpone receiving the vaccine until they are improved. | 0.00 | |
| 7 | Give a booster dose of diphtheria vaccine. Individuals over seven years of age receive the vaccine in combination with tetanus vaccine (Td). Those children younger than seven can be boosted with a vaccine containing the pertussis component as with the tetanus vaccine described above. People who have had a serious allergic reaction to one dose of DTaP, DT, Td, or Tdap vaccine should not receive another. Persons with a moderate or severe illness should postpone receiving the vaccine until their condition has improved. | 0.00 | |

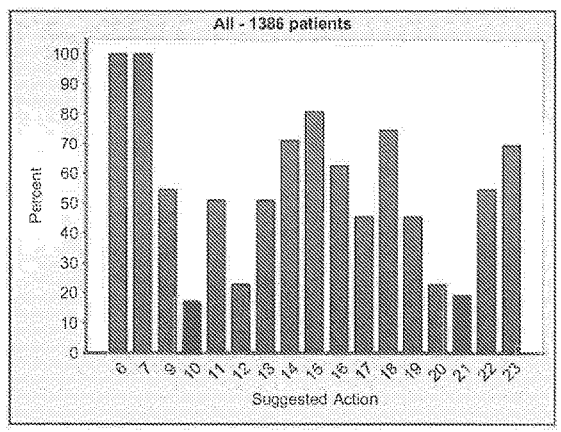

FIG. 21G-3A

Percent Deviation Between Groups

| Rule ID | Suggested Action | StdDev |
|---|---|---|
| 10 | Examine for pregnancy. | 0.00 |
| 11 | Administer ImmunoScore cytokine panel. Rise in pro-inflammatory cytokines (IL-6, IL-12, and/or IL-17) over previous visit would indicate a future autoimmune antibody profile screening to identify possible autoimmune disease manifestation. Rise in regulatory cytokines (IL-10 and TGF-?) could possibly also indicate an autoimmune disease manifestation in regression. Rise in both pro- and regulatory cytokines would trigger subsequent need to attempt to identify autoimmune disease manifestation by ImmunoScore autoimmune disease antibody screening panels. In addition to normal assessment of physical symptoms, elevated levels (>2 SD of mean) of key pro-inflammatory cytokines IL-6, IL-12, and/or IL-17 trigger: a) repeat visit in six weeks to re-measure cytokine values: i) if pro-inflammatory cytokines still elevated, recommend ImmunoScore panel to detect autoimmune antibody profile to identify possible autoimmune disease manifestation. ii) if pro-inflammatory cytokines levels decreased or moderating, recommend ImmunoScore cytokine panel evaluation annually. IL-7 may be particularly important as an initiator of many autoimmune manifestations. Depending on autoimmune disease condition, additional tests ordered can include serum thyroid stimulating hormone (TSH) for Hashimotos or Graves disease, anti-nuclear antibody (ANA) for systemic lupus erythematosus (SLE), neurological examination for multiple sclerosis (MS), and serum rheumatoid factor (RF) for rheumatoid arthritis (RA). Compare on site new ImmunoScore cytokine profile with baseline ImmunoScore cytokine profile. Significant increase (>20%) among grouped cytokines (e.g. Th1, Th2, Th17, and/or Treg) from previous profile values could be indicative of impending autoimmune flare that will likely require disease-specific treatment(s). | 25.62 |
| 12 | Examine for Rheumatoid arthritis. Rheumatoid arthritis (RA) is a chronic disorder for which there is no known cure. The optimal treatment of RA requires a comprehensive program that combines medical, social, and emotional support for the patient. Strategies are all aimed at reducing pain and discomfort, preventing deformities and loss of joint function. Treatment options include reduction of joint stress, physical and occupational therapy, and surgical intervention. Drug treatment prescriptions should be closely tied to ImmunoScore cytokine analyses to monitor RA flares and worsening of disease status. Drug classes to treat rheumatoid arthritis: 1) Non-steroidal anti-inflammatory agents (NSAIDs). NSAIDs reduce acute inflammation, reduce pain and improve function. They do not change the course of disease or prevent joint | 25.16 |

FIG. 21G-3B destruction; 2)Corticosteroids. Corticosteroids have both anti-inflammatory and immunoregulatory activity; 3) Disease modifying anti-rheumatic drugs (DMARDs). DMARD agents have been shown to alter the course of RA and improve radiographic outcomes. There are contra-indications for all of the treatment classes described above. Closely tied ImmunoScore cytokine measurement and courses of treatment will optimize RA treatment for each individual. Anti-inflammatory effect within hours, but reasonable trial period for relief of RA symptoms is 1 month. The most common toxicity is gastrointestinal disturbance which may clinically include burning, belching, or irritation, but which can represent irritation of the lining of the stomach, erosions, and ulcerations that may result in bleeding. Selective COX-2 inhibitors exhibit safer GI profiles than conventional non-selective NSAIDs, but may increase cardiovascular effects on blood pressure and additional effects on vascular beds. The use of NSAIDs medications must take into account their relative risks in an individual patient of gastrointestinal damage versus potential cardiovascular risk factors. Physicians treating RA patients with NSAIDs would periodically monitor serum cytokine levels to track inflammatory cytokines and relate them to symptoms of GI irritation and/or cardiovascular damage. Corticosteroids are useful in early disease as temporary adjunctive therapy while waiting for DMARDs to exert anti-inflammatory effects. This group is also useful as chronic adjunctive therapy in patients with severe disease not well controlled on NSAIDs or DMARDs. Side effects of prednisone include weight gain, increased blood pressure, increased blood sugar, increased risk of cataracts, and avascular necrosis of bones. Patients treated with corticosteroids should have periodic ImmunoScore cytokine measurements coupled with bone densitometry to assess bone fracture risk. Bisphosphonates are concurrently recommended to prevent and/or treat osteoporosis in addition to adequate calcium and vitamin D supplementation. In most cases, when the diagnosis of rheumatoid arthritis is cofirmed, DMARD agents should be initiated.Methotrexate is considered the first-line DMARD agent. The anti-inflammatory effects appear to be due to interruption of adenosine and possible effects on TNF pathways. Serious complications of methotrexate therapy, including hepatic cirrhosis, interstitial pneumonitis, and severe myelosuppression are rare with proper monitoring. Stomatitis and oral ulcers, alopecia and hair thinning, and GI upset may occur and are related to folic acid antagonism. These side effects can be improved with folic acid supplementation. ImmunoScore cytokine coupled with serum liver enzymes should be periodically monitored. Liver biopsy should be performed if liver enzymes persist. Hydroxychloroquine is sometimes used with methotrexate and sulfasalazine as a triple therapy for RA. The most important toxicity is on the eyes. Patients with underlying retinopathies should have a baseline ophthamimologic examination and follow up

FIG. 21G-3 C exam every 12 months during treatment.
Sulfasalazine is effective for the treatment of RA
The mechanism of action is unknown. It may cause
hypersensitivity and allergic reactions. Careful
periodic ImmunoScore cytokine screening would
indicate undesirable increases in Th2 and/or Th17
cytokines in conjunction with increased serum IgE
levels. TNF-? inhibitors are used to ameliorate local
concentrations of TNF-? in synovial fluid. There are
currently three TNF-? inhibitors approved for the
treatment of RA. Etanercept binds TNF in the
circulation and prevents interaction with cell surface
TNF receptors. As with all TNF antagonists, there is
an increased risk of infection in patients. Patients
show increased risk of upper respiratory infections
and some develop anti-nuclear antibodies
characteristic of SLE. Screening for latent TB
infection is prudent before initiation of TNF inhibitor
treatments. Infliximab is an anti-TNF antibody
developed in mice. Anti-infliximab antibodies can
develop in patients, reducing the effectiveness of the
treatments. ImmunoScore diagnostic follow-up
would include cytokine measurements looking for
increased Th2 (antibody) response coupled with
specific measurement of anti-TNF antibodies.
Opportunistic infections and sepsis have been
reported with infliximab treatment. Periodic
examination of cytokine balance would indicate
patients coming out of immune balance. Observation
of wildly fluctuating cytokine values would be
indicative of an immune system swaying out of
control and indicate likely candidates for sepsis.
Adalimumab is another anti-TNF antibody treatment
for RA. Increased infections ranging from mild to
serious are seen in clinical practice. In addition, ANA
titers have been seen as well as cases of lupus-like
disease. Abatacept is one of a class of agents
known as T-cell costimulatory blockers. These
agents interfere with the interactions between
antigen-presenting cells and T lymphocytes and
affect early stages in the pathogenic cascade of
events in RA. Infections are increased in patients
being treated with abatacept. Periodic
ImmunoScore cytokine measurement examining
cytokine balance would coincide with patient
treatment. Rituximab binds to the CD20 molecule on
B cell surfaces leading to the removal of B cells from
circulation. Clinical effects on RA are hypothesized
to occur from decrease in B cell cytokines,
interactions with B cells and T cells, or due to
reductions in autoantibody levels. Infusion reactions
to rituximab may include hives, itching, swelling,
difficulty breathing, fever, chills, and changes in
blood pressure. These are usually mild and respond
to slowing the infusion rate or additional medication
(such as antihistamines) but may be severe.
Monitoring cytokine levels during infusion could lead
to better monitoring of patient reaction to rituximab
infusions. Anakira is an IL-1 receptor antagonist.
ImmunoScore measurement of IL-1? and IL-1?
serum concentrations during anakira therapy would
indicate effectiveness and balance of the drug to
cytokine levels in the patient.

FIG. 21G-3 D

| 1 3 | Examine for Systemic Lupus Erythematosus. Activated autoreactive Th cells provide the help required for autoreactive B cells to differentiate and produce autoreactive antibodies. Studies of animal models and SLE patients indicate an important role for type I interferons. Although type I IFNs are classically considered to promote Th1-mediated cell responses, they can also inhibit Th1 and Th17 responses. At this point, it is not certain whether intervention with IFN inhibitors will be beneficial or detrimental to SLE patients, and the application of IFN inhibitory therapy may be based upon stage of SLE flare. ImmunoScore cytokine panels will be used to add clarity to therapeutics. As SLE patients live longer due to improved therapies and preventive measures, death and disability from cardiovascular events are increasing. The mechanism for the increased risk of SLE patients for cardiovascular events is likely due to a combination of inflammatory and immune mechanisms. There are increased levels of oxidized LDL (oxLDL), pro-inflammatory HDL, MCP-1, TNF-?, IFN-?, IL-1, and IL-12. ImmunoScore cardiac risk markers will be combined with ImmunoScore cytokine panels in patients with SLE, and progressive monitoring will be performed in these patients at regular intervals. | 20.93 |
|---|---|---|
| 1 4 | Examine for cancer. IL-10 is a cytokine with broad anti-inflammatory properties. A penalty of the role of IL-10 to limit immune and inflammatory responses to pathogens and prevent damage to the host is that high or dysregulated levels of IL-10 may result in chronic infection or cancer. There are certainly possible therapeutic roles to Il-10 and its antagonists in human disease, all of which would benefit from careful ImmunoScore cytokine monitoring during clinical trials and subsequent evaluations. | 10.98 |
| 1 5 | Examine for Multiple Sclerosis. Upregulated cytokines in MS patients include IL-17, IL-12, IL-23, IL-6, IL-21, TNF-?, and other Th1 cytokines. IL-17-related cytokines are speculated to be related to disease progression. Glatiramer acetate (GA) is believed to induce GA-reactive T cells that secrete anti-inflammatory cytokines at the site of inflammation in MS - presumably increasing anti-inflammatory cytokines IL-10, IL-4, and TGF-?. ImmunoScore to periodically measure patients cytokines and at onset of flare, indicated by increased Th17 and Th1 cytokines, administer treatment. Efficacy of treatment could be monitored with monitoring of Treg cytokines. Interferon-? and atorvastatin have both been used to treat MS. IFN-? increases Th1 cytokines, while atorvastatin increases Th2 cytokines (particularly IL-5). Both may have the same effect of lessening the increase of Th17 cytokines. MS patients have general systemic increases of Th1 cytokines (particularly TNF-?. This is likely related to fatigue and lapses in systemic immunity. This may be a problem in patients treated with natalizumab as systemic rises in TNF-? are correlated with fatigue symptoms. | 7.03 |

FIG. 21G-3 E

| | | |
|---|---|---|
| 1 6 | Examine for Inflammatory Bowel Disease. IBD comprises two forms:<br>　Ulcerative colitis (UC) increased expression of following:<br>　　o TNF-?<br>　　o IL-1?<br>　　o IL-6<br>　　o IL-12<br>　　o IL-23<br>　　o IL-17<br>　　o IL-13<br>　　o IL-5<br>　Crohns disease (CD) increased expression of following:<br>　　o TNF-?<br>　　o IL-1?<br>　　o IL-1?<br>　　o IL-6<br>　　o IL-18 (in some patients)<br>　　o IL-10<br>　　o IL-4 (in some patients)<br>　　o IL-23<br>　　o IL-27<br>　　o IL-17<br>IL-23 appears to be the key mediator of flares of IBD. Mucosal cytokines recently cited (IL-31 and IL-32) as important are members of the IL-17 family. | 19.45 |
| 1 7 | Examine for Diabetes. Diabetes mellitus is characterized by a lack of insulin causing elevated blood glucose, often with associated insulin resistance. Elevated serum levels of TGF-? are associated with diabetic renal disease and will be tracked by the ImmunoScore cytokine diagnostic panel. Studies in animals indicate higher serum TGF-? levels might ameliorate disease. A dysfunctioning endothelium is associated with both initiation and progression of atherosclerotic cardiovascular disease and has been shown to predate the onset of hyperglycemia in the natural history of type 2 diabetes. It is likely that low level inflammation plays an important role in developing this endothelial dysfunction mainly through the action of TNF-? and possibly IL-6. Visceral obesity and inflammation within white adipose tissue may be a crucial step contributing to the emergence of insulin resistance, type 2 diabetes and atherosclerosis. IL-1?, IL-6, IL-8, IL-10 TNF-?, and TGF-? levels all rise under these conditions. IL-27 can promote both anti- and pro-inflammatory responses. IL-27 up-regulates IFN-?, and IL-17 and down-regulates IL-4, TGF-?, and IL-10 secreted by diabetic splenocytes, suggesting a pathogenic role in T cell-mediated autoimmune diabetes. | 22.48 |

FIG. 21G-3F

| 18 | Examine for Breast Cancer. IL-6 is a pleiotropic cytokine with both tumor-promoting and tumor-inhibiting effects. Serum IL-6 levels, however, are a negative prognosticator in breast tumor patients. IL-6, IL-8, and IL-10 levels are higher in women with breast cancer than controls and levels also correlate with the clinical stage of disease. Elevated serum IL-8 levels are related to an accelerated clinical course, a higher tumor load, and the presence of liver or lymph node involvement. On the other hand, elevated IL-8 also has prognostic significance for post-relapse survival. | 9.67 |
|---|---|---|
| 19 | Examine for Cancer. Chronic inflammation has long been associated with the development of cancer. TNF-? is one of the major mediators of inflammation. TNF-? induces other inflammatory mediators and proteases that orchestrate inflammatory responses. TNF-? is also produced by tumors and can act as an endogenous tumor promoter. The role of TNF-? has been linked to all steps involved in tumorigenesis, including cellular transformation, promotion, survival, proliferation, invasion, angiogenesis, and metastasis. ImmunoScore cytokine monitoring of TNF-? levels extremely important in cancer patients. | 22.48 |
| 20 | Examine for Cancer. IL-6 has been proposed as a prognostic factor in several malignancies such as colorectal cancer, breast cancer, gastric cancer, and pancreatic cancer. In addition, elevated serum IL-6 concentrations have been demonstrated in patients with endometrial cancer, non-small cell lung carcinoma, colorectal cancer, renal cell carcinoma, breast and ovarian cancers. | 0.00 |
| 21 | Examine for Atherosclerosis. Atherogenesis is characterized by an intense inflammatory process, involving immune and vascular cells. C-reactive protein (CRP), monocyte/macrophage colony-stimulating factor (M-CSF), and IL-6 promote atherogenesis. They also down-regulate atheroprotective cytokines such as IL-10 and TGF-?. Increased levels of CRP and IL-6 are predictive of a higher cardiovascular event rate in the general population. In coronary artery disease, high levels of M-CSF are additive with those of CRP, suggesting the benefit of a multi-marker approach in assessing risk to coronary artery disease. In addition to the pro-inflammatory cytokines with poor prognostic indications, including TNF-?, IL-6, MCP-1, and IL-1, several adipocytokines are released by fat tissues and are inflammatory in nature. These include leptin, resistin, adiponectin and visfatin. Once possible atherosclerotic complications are revealed in patients, a follow up panel specific for heart patients can be envisioned which contains diagnostic tools for serum adipocytokines. It is not yet clear what function IFN-? has in relationship with atherosclerosis development, but it is likely a key player and should be monitored in cardiac patients. | 8.87 |

FIG. 21G-3 G

| | | | |
|---|---|---|---|
| 2 2 | Examine for Allergies. Allergies are the result of aberrant immune reactivity to common innocuous environmental proteins. A pivotal component of allergic pathogenesis is the generation of allergen-specific Th cells with an effector phenotype. Th17 cells may also contribute to the pathogenesis of classically recognized Th2-mediated allergic disorders. This may very by individual patient, and ImmunoScore cytokine profiling would reveal individual differences from patient to patient. Allergic disorders would have a recommendation for treatment plans based upon Th2/Th17 immune balance. | 25.40 | |
| 2 3 | Examine for Asthma. Asthma comprises distinct heterogeneous inflammatory disorders characterized by patients showing different phenotypes with distinct genetic components, environmental causes, and immunopathogenesis. Once considered purely an allergic disorder dominated by Th2 lymphocytes, IgE, mast cells, eosinophils, macrophages, and cytokines, the disease also involves local epithelial, mesenchymal, vascular and neurologic events that are involved in directing the Th2 phenotype to the lung and through aberrant injury-repair mechanisms to remodeling of the airway wall. Responses to asthma medications vary considerably among patients, likely reflecting the differing sensitivities of the various asthma phenotypes. Physicians need to recognize this when making decisions to adjust treatment to improve asthma. IL-4 and IL-13 are considered to be key contributors to cell-mediated and humoral aspects of allergic inflammation. There is controversy surrounding the role of TGF-? in asthma. It is speculated that IL-5 also plays a pivotal role in eosinophilia and asthma. Anti-IgE therapy is an approved treatment for adult and childhood asthma. Helminth infections are suggested to minimize asthma symptoms. | 11.23 | |
| 6 | Give a booster dose of tetanus vaccine. Individuals over seven years of age receive the vaccine in combination with diphtheria vaccine (Td). Those children younger than seven years of age can be boosted with a vaccine containing a pertussis component (DTaP). People who had a serious allergic reaction to one dose of tetanus toxoid should not receive another. Persons with a moderate or severe acute illness should postpone receiving the vaccine until they are improved. | 0.00 | |
| 7 | Give a booster dose of diphtheria vaccine. Individuals over seven years of age receive the vaccine in combination with tetanus vaccine (Td). Those children younger than seven can be boosted with a vaccine containing the pertussis component as with the tetanus vaccine described above. People who have had a serious allergic reaction to one dose of DTaP, DT, Td, or Tdap vaccine should not receive another. Persons with a moderate or severe illness should postpone receiving the vaccine until their condition has improved. | 0.00 | |

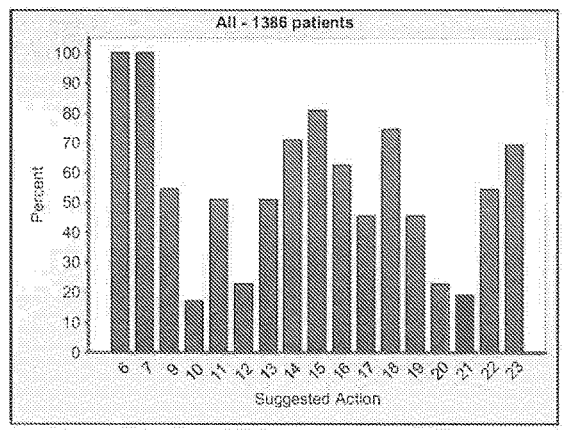

FIG. 21G-4A

Percent Deviation Between Groups

| Rule ID | Suggested Action | StdDev |
|---|---|---|
| 10 | Examine for pregnancy. | 0.00 |
| 11 | Administer ImmunoScore cytokine panel. Rise in pro-inflammatory cytokines (IL-6, IL-12, and/or IL-17) over previous visit would indicate a future autoimmune antibody profile screening to identify possible autoimmune disease manifestation. Rise in regulatory cytokines (IL-10 and TGF-?) could possibly also indicate an autoimmune disease manifestation in regression. Rise in both pro- and regulatory cytokines would trigger subsequent need to attempt to identify autoimmune disease manifestation by ImmunoScore autoimmune disease antibody screening panels. In addition to normal assessment of physical symptoms, elevated levels (>2 SD of mean) of key pro-inflammatory cytokines IL-6, IL-12, and/or IL-17 trigger: a) repeat visit in six weeks to re-measure cytokine values: i) if pro-inflammatory cytokines still elevated, recommend ImmunoScore panel to detect autoimmune antibody profile to identify possible autoimmune disease manifestation. ii) if pro-inflammatory cytokines levels decreased or moderating, recommend ImmunoScore cytokine panel evaluation annually. IL-7 may be particularly important as an initiator of many autoimmune manifestations. Depending on autoimmune disease condition, additional tests ordered can include serum thyroid stimulating hormone (TSH) for Hashimotos or Graves disease, anti-nuclear antibody (ANA) for systemic lupus erythematosus (SLE), neurological examination for multiple sclerosis (MS), and serum rheumatoid factor (RF) for rheumatoid arthritis (RA). Compare on site new ImmunoScore cytokine profile with baseline ImmunoScore cytokine profile. Significant increase (>20%) among grouped cytokines (e.g. Th1, Th2, Th17, and/or Treg) from previous profile values could be indicative of impending autoimmune flare that will likely require disease-specific treatment(s). | 22.36 |
| 12 | Examine for Rheumatoid arthritis. Rheumatoid arthritis (RA) is a chronic disorder for which there is no known cure. The optimal treatment of RA requires a comprehensive program that combines medical, social, and emotional support for the patient. Strategies are all aimed at reducing pain and discomfort, preventing deformities and loss of joint function. Treatment options include reduction of joint stress, physical and occupational therapy, and surgical intervention. Drug treatment prescriptions should be closely tied to ImmunoScore cytokine analyses to monitor RA flares and worsening of disease status. Drug classes to treat rheumatoid arthritis: 1) Non-steroidal anti-inflammatory agents (NSAIDs). NSAIDs reduce acute inflammation, reduce pain and improve function. They do not change the course of disease or prevent joint | 31.39 |

FIG. 21G-4 B destruction; 2)Corticosteroids. Corticosteroids have both anti-inflammatory and immunoregulatory activity; 3) Disease modifying anti-rheumatic drugs (DMARDs). DMARD agents have been shown to alter the course of RA and improve radiographic outcomes. There are contra-indications for all of the treatment classes described above. Closely tied ImmunoScore cytokine measurement and courses of treatment will optimize RA treatment for each individual. Anti-inflammatory effect within hours, but reasonable trial period for relief of RA symptoms is 1 month. The most common toxicity is gastrointestinal disturbance which may clinically include burning, belching, or irritation, but which can represent irritation of the lining of the stomach, erosions, and ulcerations that may result in bleeding. Selective COX-2 inhibitors exhibit safer GI profiles than conventional non-selective NSAIDs, but may increase cardiovascular effects on blood pressure and additional effects on vascular beds. The use of NSAIDs medications must take into account their relative risks in an individual patient of gastrointestinal damage versus potential cardiovascular risk factors. Physicians treating RA patients with NSAIDs would periodically monitor serum cytokine levels to track inflammatory cytokines and relate them to symptoms of GI irritation and/or cardiovascular damage. Corticosteroids are useful in early disease as temporary adjunctive therapy while waiting for DMARDs to exert anti-inflammatory effects. This group is also useful as chronic adjunctive therapy in patients with severe disease not well controlled on NSAIDs or DMARDs. Side effects of prednisone include weight gain, increased blood pressure, increased blood sugar, increased risk of cataracts, and avascular necrosis of bones. Patients treated with corticosteroids should have periodic ImmunoScore cytokine measurements coupled with bone densitometry to assess bone fracture risk. Bisphosphonates are concurrently recommended to prevent and/or treat osteoporosis in addition to adequate calcium and vitamin D supplementation. In most cases, when the diagnosis of rheumatoid arthritis is cofirmed, DMARD agents should be initiated.Methotrexate is considered the first-line DMARD agent. The anti-inflammatory effects appear to be due to interruption of adenosine and possible effects on TNF pathways. Serious complications of methotrexate therapy, including hepatic cirrhosis, interstitial pneumonitis, and severe myelosuppression are rare with proper monitoring. Stomatitis and oral ulcers, alopecia and hair thinning, and GI upset may occur and are related to folic acid antagonism. These side effects can be improved with folic acid supplementation. ImmunoScore cytokine coupled with serum liver enzymes should be periodically monitored. Liver biopsy should be performed if liver enzymes persist. Hydroxychloroquine is sometimes used with methotrexate and sulfasalazine as a triple therapy for RA. The most important toxicity is on the eyes. Patients with underlying retinopathies should have a baseline ophthammologic examination and follow up

FIG. 21G-4 C exam every 12 months during treatment. Sulfasalazine is effective for the treatment of RA. The mechanism of action is unknown. It may cause hypersensitivity and allergic reactions. Careful periodic ImmunoScore cytokine screening would indicate undesirable increases in Th2 and/or Th17 cytokines in conjunction with increased serum IgE levels. TNF-? inhibitors are used to ameliorate local concentrations of TNF-? in synovial fluid. There are currently three TNF-? inhibitors approved for the treatment of RA. Etanercept binds TNF in the circulation and prevents interaction with cell surface TNF receptors. As with all TNF antagonists, there is an increased risk of infection in patients. Patients show increased risk of upper respiratory infections and some develop anti-nuclear antibodies characteristic of SLE. Screening for latent TB infection is prudent before initiation of TNF inhibitor treatments. Infliximab is an anti-TNF antibody developed in mice. Anti-infliximab antibodies can develop in patients, reducing the effectiveness of the treatments. ImmunoScore diagnostic follow-up would include cytokine measurements looking for increased Th2 (antibody) response coupled with specific measurement of anti-TNF antibodies. Opportunistic infections and sepsis have been reported with infliximab treatment. Periodic examination of cytokine balance would indicate patients coming out of immune balance. Observation of wildly fluctuating cytokine values would be indicative of an immune system swaying out of control and indicate likely candidates for sepsis. Adalimumab is another anti-TNF antibody treatment for RA. Increased infections ranging from mild to serious are seen in clinical practice. In addition, ANA titers have been seen as well as cases of lupus-like disease. Abatacept is one of a class of agents known as T-cell costimulatory blockers. These agents interfere with the interactions between antigen-presenting cells and T lymphocytes and affect early stages in the pathogenic cascade of events in RA. Infections are increased in patients being treated with abatacept. Periodic ImmunoScore cytokine measurement examining cytokine balance would coincide with patient treatment. Rituximab binds to the CD20 molecule on B cell surfaces leading to the removal of B cells from circulation. Clinical effects on RA are hypothesized to occur from decrease in B cell cytokines, interactions with B cells and T cells, or due to reductions in autoantibody levels. Infusion reactions to rituximab may include hives, itching, swelling, difficulty breathing, fever, chills, and changes in blood pressure. These are usually mild and respond to slowing the infusion rate or additional medication (such as antihistamines) but may be severe. Monitoring cytokine levels during infusion could lead to better monitoring of patient reaction to rituximab infusions. Anakira is an IL-1 receptor antagonist. ImmunoScore measurement of IL-1? and IL-1? serum concentrations during anakira therapy would indicate effectiveness and balance of the drug to cytokine levels in the patient.

FIG. 21G-4 D

| | | |
|---|---|---|
| 1 3 | Examine for Systemic Lupus Erythematosus. Activated autoreactive Th cells provide the help required for autoreactive B cells to differentiate and produce autoreactive antibodies. Studies of animal models and SLE patients indicate an important role for type I interferons. Although type I IFNs are classically considered to promote Th1-mediated cell responses, they can also inhibit Th1 and Th17 responses. At this point, it is not certain whether intervention with IFN inhibitors will be beneficial or detrimental to SLE patients, and the application of IFN inhibitory therapy may be based upon stage of SLE flare. ImmunoScore cytokine panels will be used to add clarity to therapeutics. As SLE patients live longer due to improved therapies and preventive measures, death and disability from cardiovascular events are increasing. The mechanism for the increased risk of SLE patients for cardiovascular events is likely due to a combination of inflammatory and immune mechanisms. There are increased levels of oxidized LDL (oxLDL), pro-inflammatory HDL, MCP-1, TNF-?, IFN-?, IL-1, and IL-12. ImmunoScore cardiac risk markers will be combined with ImmunoScore cytokine panels in patients with SLE, and progressive monitoring will be performed in these patients at regular intervals. | 22.54 |
| 1 4 | Examine for cancer. IL-10 is a cytokine with broad anti-inflammatory properties. A penalty of the role of IL-10 to limit immune and inflammatory responses to pathogens and prevent damage to the host is that high or dysregulated levels of IL-10 may result in chronic infection or cancer. There are certainly possible therapeutic roles to II-10 and its antagonists in human disease, all of which would benefit from careful ImmunoScore cytokine monitoring during clinical trials and subsequent evaluations. | 10.72 |
| 1 5 | Examine for Multiple Sclerosis. Upregulated cytokines in MS patients include IL-17, IL-12, IL-23, IL-6, IL-21, TNF-?, and other Th1 cytokines. IL-17-related cytokines are speculated to be related to disease progression. Glatiramer acetate (GA) is believed to induce GA-reactive T cells that secrete anti-inflammatory cytokines at the site of inflammation in MS - presumably increasing anti-inflammatory cytokines IL-10, IL-4, and TGF-?. ImmunoScore to periodically measure patients cytokines and at onset of flare, indicated by increased Th17 and Th1 cytokines, administer treatment. Efficacy of treatment could be monitored with monitoring of Treg cytokines.Interferon-? and atorvastatin have both been used to treat MS. IFN-? increases Th1 cytokines, while atorvastatin increases Th2 cytokines (particularly IL-5). Both may have the same effect of lessening the increase of Th17 cytokines. MS patients have general systemic increases of Th1 cytokines (particularly TNF-?. This is likely related to fatigue and lapses in systemic immunity. This may be a problem in patients treated with natalizumab as systemic rises in TNF-? are correlated with fatigue symptoms. | 7.31 |

FIG. 21G-4 E

| 16 | Examine for Inflammatory Bowel Disease. IBD comprises two forms: Ulcerative colitis (UC) increased expression of following: o TNF-? o IL-1? o IL-6 o IL-12 o IL-23 o IL-17 o IL-13 o IL-5 Crohns disease (CD) increased expression of following: o TNF-? o IL-1? o IL-1? o IL-6 o IL-18 (in some patients) o IL-10 o IL-4 (in some patients) o IL-23 o IL-27 o IL-17 IL-23 appears to be the key mediator of flares of IBD. Mucosal cytokines recently cited (IL-31 and IL-32) as important are members of the IL-17 family | 14.91 |
|---|---|---|
| 17 | Examine for Diabetes. Diabetes mellitus is characterized by a lack of insulin causing elevated blood glucose, often with associated insulin resistance. Elevated serum levels of TGF-? are associated with diabetic renal disease and will be tracked by the ImmunoScore cytokine diagnostic panel. Studies in animals indicate higher serum TGF-? levels might ameliorate disease. A dysfunctioning endothelium is associated with both initiation and progression of atherosclerotic cardiovascular disease and has been shown to predate the onset of hyperglycemia in the natural history of type 2 diabetes. It is likely that low level inflammation plays an important role in developing this endothelial dysfunction mainly through the action of TNF-? and possibly IL-6. Visceral obesity and inflammation within white adipose tissue may be a crucial step contributing to the emergence of insulin resistance, type 2 diabetes and atherosclerosis. IL-1?, IL-6, IL-8, IL-10 TNF-?, and TGF-? levels all rise under these conditions. IL-27 can promote both anti- and pro-inflammatory responses. IL-27 up-regulates IFN-?, and IL-17 and down-regulates IL-4, TGF-?, and IL-10 secreted by diabetic splenocytes, suggesting a pathogenic role in T cell-mediated autoimmune diabetes. | 0.00 |

FIG. 21G-4F

| | | |
|---|---|---|
| 18 | Examine for Breast Cancer. IL-6 is a pleiotropic cytokine with both tumor-promoting and tumor-inhibiting effects. Serum IL-6 levels, however, are a negative prognosticator in breast tumor patients. IL-6, IL-8, and IL-10 levels are higher in women with breast cancer than controls and levels also correlate with the clinical stage of disease. Elevated serum IL-8 levels are related to an accelerated clinical course, a higher tumor load, and the presence of liver or lymph node involvement. On the other hand, elevated IL-6 also has prognostic significance for post-relapse survival. | 18.78 |
| 19 | Examine for Cancer. Chronic inflammation has long been associated with the development of cancer. TNF-? is one of the major mediators of inflammation. TNF-? induces other inflammatory mediators and proteases that orchestrate inflammatory responses. TNF-? is also produced by tumors and can act as an endogenous tumor promoter. The role of TNF-? has been linked to all steps involved in tumorigenesis, including cellular transformation, promotion, survival, proliferation, invasion, angiogenesis, and metastasis. ImmunoScore cytokine monitoring of TNF-? levels extremely important in cancer patients. | 13.29 |
| 20 | Examine for Cancer. IL-6 has been proposed as a prognostic factor in several malignancies such as colorectal cancer, breast cancer, gastric cancer, and pancreatic cancer. In addition, elevated serum IL-6 concentrations have been demonstrated in patients with endometrial cancer, non-small cell lung carcinoma, colorectal cancer, renal cell carcinoma, breast and ovarian cancers. | 17.38 |
| 21 | Examine for Atherosclerosis. Atherogenesis is characterized by an intense inflammatory process, involving immune and vascular cells. C-reactive protein (CRP), monocyte/macrophage colony-stimulating factor (M-CSF), and IL-6 promote atherogenesis. They also down-regulate atheroprotective cytokines such as IL-10 and TGF-?. Increased levels of CRP and IL-6 are predictive of a higher cardiovascular event rate in the general population. In coronary artery disease, high levels of M-CSF are additive with those of CRP, suggesting the benefit of a multi-marker approach in assessing risk to coronary artery disease. In addition to the pro-inflammatory cytokines with poor prognostic indications, including TNF-?, IL-6, MCP-1, and IL-1, several adipocytokines are released by fat tissues and are inflammatory in nature. These include leptin, resistin, adiponectin and visfatin. Once possible atherosclerotic complications are revealed in patients, a follow up panel specific for heart patients can be envisioned which contains diagnostic tools for serum adipocytokines. It is not yet clear what function IFN-? has in relationship with atherosclerosis development, but it is likely a key player and should be monitored in cardiac patients. | 0.00 |

FIG. 21G-4 G

| | | | |
|---|---|---|---|
| 2 2 | Examine for Allergies. Allergies are the result of aberrant immune reactivity to common innocuous environmental proteins. A pivotal component of allergic pathogenesis is the generation of allergen-specific Th cells with an effector phenotype. Th17 cells may also contribute to the pathogenesis of classically recognized Th2-mediated allergic disorders. This may very by individual patient, and ImmunoScore cytokine profiling would reveal individual differences from patient to patient. Allergic disorders would have a recommendation for treatment plans based upon Th2/Th17 immune balance. | 17.29 | |
| 2 3 | Examine for Asthma. Asthma comprises distinct heterogeneous inflammatory disorders characterized by patients showing different phenotypes with distinct genetic components, environmental causes, and immunopathogenesis. Once considered purely an allergic disorder dominated by Th2 lymphocytes, IgE, mast cells, eosinophils, macrophages, and cytokines, the disease also involves local epithelial, mesenchymal, vascular and neurologic events that are involved in directing the Th2 phenotype to the lung and through aberrant injury-repair mechanisms to remodeling of the airway wall. Responses to asthma medications vary considerably among patients, likely reflecting the differing sensitivities of the various asthma phenotypes. Physicians need to recognize this when making decisions to adjust treatment to improve asthma. IL-4 and IL-13 are considered to be key contributors to cell-mediated and humoral aspects of allergic inflammation. There is controversy surrounding the role of TGF-? in asthma. It is speculated that IL-5 also plays a pivotal role in eosinophila and asthma. Anti-IgE therapy is an approved treatment for adult and childhood asthma. Helminth infections are suggested to minimize asthma symptoms. | 11.68 | |
| 6 | Give a booster dose of tetanus vaccine. Individuals over seven years of age receive the vaccine in combination with diphtheria vaccine (Td). Those children younger than seven years of age can be boosted with a vaccine containing a pertussis component (DTaP). People who had a serious allergic reaction to one dose of tetanus toxoid should not receive another. Persons with a moderate or severe acute illness should postpone receiving the vaccine until they are improved. | 0.00 | |
| 7 | Give a booster dose of diphtheria vaccine. Individuals over seven years of age receive the vaccine in combination with tetanus vaccine (Td). Those children younger than seven can be boosted with a vaccine containing the pertussis component as with the tetanus vaccine described above. People who have had a serious allergic reaction to one dose of DTaP, DT, Td, or Tdap vaccine should not receive another. Persons with a moderate or severe illness should postpone receiving the vaccine until their condition has improved. | 0.00 | |

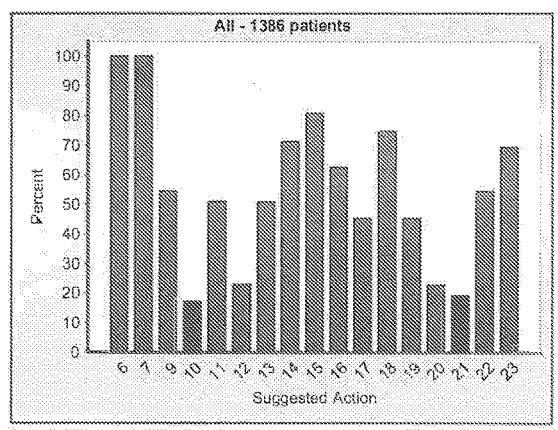

FIG. 21G-5A

Percent Deviation Between Groups

| Rule ID | Suggested Action | StdDev |
|---|---|---|
| 10 | Examine for pregnancy. | 0.00 |
| 11 | Administer ImmunoScore cytokine panel. Rise in pro-inflammatory cytokines (IL-6, IL-12, and/or IL-17) over previous visit would indicate a future autoimmune antibody profile screening to identify possible autoimmune disease manifestation. Rise in regulatory cytokines (IL-10 and TGF-?) could possibly also indicate an autoimmune disease manifestation in regression. Rise in both pro- and regulatory cytokines would trigger subsequent need to attempt to identify autoimmune disease manifestation by ImmunoScore autoimmune disease antibody screening panels. In addition to normal assessment of physical symptoms, elevated levels (>2 SD of mean) of key pro-inflammatory cytokines IL-6, IL-12, and/or IL-17 trigger: a) repeat visit in six weeks to re-measure cytokine values: i) if pro-inflammatory cytokines still elevated, recommend ImmunoScore panel to detect autoimmune antibody profile to identify possible autoimmune disease manifestation. ii) if pro-inflammatory cytokines levels decreased or moderating, recommend ImmunoScore cytokine panel evaluation annually. IL-7 may be particularly important as an initiator of many autoimmune manifestations. Depending on autoimmune disease condition, additional tests ordered can include serum thyroid stimulating hormone (TSH) for Hashimotos or Graves disease, anti-nuclear antibody (ANA) for systemic lupus erythematosus (SLE), neurological examination for multiple sclerosis (MS), and serum rheumatoid factor (RF) for rheumatoid arthritis (RA). Compare on site new ImmunoScore cytokine profile with baseline ImmunoScore cytokine profile. Significant increase (>20%) among grouped cytokines (e.g. Th1, Th2, Th17, and/or Treg) from previous profile values could be indicative of impending autoimmune flare that will likely require disease-specific treatment(s). | 20.25 |
| 12 | Examine for Rheumatoid arthritis. Rheumatoid arthritis (RA) is a chronic disorder for which there is no known cure. The optimal treatment of RA requires a comprehensive program that combines medical, social, and emotional support for the patient. Strategies are all aimed at reducing pain and discomfort, preventing deformities and loss of joint function. Treatment options include reduction of joint stress, physical and occupational therapy, and surgical intervention. Drug treatment prescriptions should be closely tied to ImmunoScore cytokine analyses to monitor RA flares and worsening of disease status. Drug classes to treat rheumatoid arthritis: 1) Non-steroidal anti-inflammatory agents (NSAIDs). NSAIDs reduce acute inflammation, reduce pain and improve function. They do not change the course of disease or prevent joint | 29.19 |

FIG. 21G-5 B destruction; 2)Corticosteroids. Corticosteroids have both anti-inflammatory and immunoregulatory activity; 3) Disease modifying anti-rheumatic drugs (DMARDs). DMARD agents have been shown to alter the course of RA and improve radiographic outcomes. There are contra-indications for all of the treatment classes described above. Closely tied ImmunoScore cytokine measurement and courses of treatment will optimize RA treatment for each individual. Anti-inflammatory effect within hours, but reasonable trial period for relief of RA symptoms is 1 month. The most common toxicity is gastrointestinal disturbance which may clinically include burning, belching, or irritation, but which can represent irritation of the lining of the stomach, erosions, and ulcerations that may result in bleeding. Selective COX-2 inhibitors exhibit safer GI profiles than conventional non-selective NSAIDs, but may increase cardiovascular effects on blood pressure and additional effects on vascular beds. The use of NSAIDs medications must take into account their relative risks in an individual patient of gastrointestinal damage versus potential cardiovascular risk factors. Physicians treating RA patients with NSAIDs would periodically monitor serum cytokine levels to track inflammatory cytokines and relate them to symptoms of GI irritation and/or cardiovascular damage. Corticosteroids are useful in early disease as temporary adjunctive therapy while waiting for DMARDs to exert anti-inflammatory effects. This group is also useful as chronic adjunctive therapy in patients with severe disease not well controlled on NSAIDs or DMARDs. Side effects of prednisone include weight gain, increased blood pressure, increased blood sugar, increased risk of cataracts, and avascular necrosis of bones. Patients treated with corticosteroids should have periodic ImmunoScore cytokine measurements coupled with bone densitometry to assess bone fracture risk. Bisphosphonates are concurrently recommended to prevent and/or treat osteoporosis in addition to adequate calcium and vitamin D supplementation. In most cases, when the diagnosis of rheumatoid arthritis is cofirmed, DMARD agents should be initiated.Methotrexate is considered the first-line DMARD agent. The anti-inflammatory effects appear to be due to interruption of adenosine and possible effects on TNF pathways. Serious complications of methotrexate therapy, including hepatic cirrhosis, interstitial pneumonitis, and severe myelosuppression are rare with proper monitoring. Stomatitis and oral ulcers, alopecia and hair thinning, and GI upset may occur and are related to folic acid antagonism. These side effects can be improved with folic acid supplementation. ImmunoScore cytokine coupled with serum liver enzymes should be periodically monitored. Liver biopsy should be performed if liver enzymes persist. Hydroxychloroquine is sometimes used with methotrexate and sulfasalazine as a triple therapy for RA. The most important toxicity is on the eyes. Patients with underlying retinopathies should have a baseline ophthamimologic examination and follow up

FIG. 21G-5 C exam every 12 months during treatment. Sulfasalazine is effective for the treatment of RA. The mechanism of action is unknown. It may cause hypersensitivity and allergic reactions. Careful periodic ImmunoScore cytokine screening would indicate undesirable increases in Th2 and/or Th17 cytokines in conjunction with increased serum IgE levels. TNF-? inhibitors are used to ameliorate local concentrations of TNF-? in synovial fluid. There are currently three TNF-? inhibitors approved for the treatment of RA. Etanercept binds TNF in the circulation and prevents interaction with cell surface TNF receptors. As with all TNF antagonists, there is an increased risk of infection in patients. Patients show increased risk of upper respiratory infections and some develop anti-nuclear antibodies characteristic of SLE. Screening for latent TB infection is prudent before initiation of TNF inhibitor treatments. Infliximab is an anti-TNF antibody developed in mice. Anti-infliximab antibodies can develop in patients, reducing the effectiveness of the treatments. ImmunoScore diagnostic follow-up would include cytokine measurements looking for increased Th2 (antibody) response coupled with specific measurement of anti-TNF antibodies. Opportunistic infections and sepsis have been reported with infliximab treatment. Periodic examination of cytokine balance would indicate patients coming out of immune balance. Observation of wildly fluctuating cytokine values would be indicative of an immune system swaying out of control and indicate likely candidates for sepsis. Adalimumab is another anti-TNF antibody treatment for RA. Increased infections ranging from mild to serious are seen in clinical practice. In addition, ANA titers have been seen as well as cases of lupus-like disease. Abatacept is one of a class of agents known as T-cell costimulatory blockers. These agents interfere with the interactions between antigen-presenting cells and T lymphocytes and affect early stages in the pathogenic cascade of events in RA. Infections are increased in patients being treated with abatacept. Periodic ImmunoScore cytokine measurement examining cytokine balance would coincide with patient treatment.Rituximab binds to the CD20 molecule on B cell surfaces leading to the removal of B cells from circulation. Clinical effects on RA are hypothesized to occur from decrease in B cell cytokines, interactions with B cells and T cells, or due to reductions in autoantibody levels. Infusion reactions to rituximab may include hives, itching, swelling difficulty breathing, fever, chills, and changes in blood pressure. These are usually mild and respond to slowing the infusion rate or additional medication (such as antihistamines) but may be severe. Monitoring cytokine levels during infusion could lead to better monitoring of patient reaction to rituximab infusions. Anakira is an IL-1 receptor antagonist. ImmunoScore measurement of IL-1? and IL-1? serum concentrations during anakira therapy would indicate effectiveness and balance of the drug to cytokine levels in the patient.

FIG. 21G-5 D

| | | |
|---|---|---|
| 1 3 | Examine for Systemic Lupus Erythematosus. Activated autoreactive Th cells provide the help required for autoreactive B cells to differentiate and produce autoreactive antibodies. Studies of animal models and SLE patients indicate an important role for type I interferons. Although type I IFNs are classically considered to promote Th1-mediated cell responses, they can also inhibit Th1 and Th17 responses. At this point, it is not certain whether intervention with IFN inhibitors will be beneficial or detrimental to SLE patients, and the application of IFN inhibitory therapy may be based upon stage of SLE flare. ImmunoScore cytokine panels will be used to add clarity to therapeutics. As SLE patients live longer due to improved therapies and preventive measures, death and disability from cardiovascular events are increasing. The mechanism for the increased risk of SLE patients for cardiovascular events is likely due to a combination of inflammatory and immune mechanisms. There are increased levels of oxidized LDL (oxLDL), pro-inflammatory HDL, MCP-1, TNF-?, IFN-?, IL-1, and IL-12. ImmunoScore cardiac risk markers will be combined with ImmunoScore cytokine panels in patients with SLE, and progressive monitoring will be performed in these patients at regular intervals. | 20.40 |
| 1 4 | Examine for cancer. IL-10 is a cytokine with broad anti-inflammatory properties. A penalty of the role of IL-10 to limit immune and inflammatory responses to pathogens and prevent damage to the host is that high or dysregulated levels of IL-10 may result in chronic infection or cancer. There are certainly possible therapeutic roles to II-10 and its antagonists in human disease, all of which would benefit from careful ImmunoScore cytokine monitoring during clinical trials and subsequent evaluations. | 13.62 |
| 1 5 | Examine for Multiple Sclerosis. Upregulated cytokines in MS patients include IL-17, IL-12, IL-23, IL-6, IL-21, TNF-?, and other Th1 cytokines. IL-17-related cytokines are speculated to be related to disease progression. Glatiramer acetate (GA) is believed to induce GA-reactive T cells that secrete anti-inflammatory cytokines at the site of inflammation in MS - presumably increasing anti-inflammatory cytokines IL-10, IL-4, and TGF-?. ImmunoScore to periodically measure patients cytokines and at onset of flare, indicated by increased Th17 and Th1 cytokines, administer treatment. Efficacy of treatment could be monitored with monitoring of Treg cytokines.Interferon-? and atorvastatin have both been used to treat MS. IFN-? increases Th1 cytokines, while atorvastatin increases Th2 cytokines (particularly IL-5). Both may have the same effect of lessening the increase of Th17 cytokines. MS patients have general systemic increases of Th1 cytokines (particularly TNF-?. This is likely related to fatigue and lapses in systemic immunity. This may be a problem in patients treated with natalizumab as systemic rises in TNF-? are correlated with fatigue symptoms. | 11.90 |

FIG. 21G-5 E

| | | |
|---|---|---|
| 1 6 | Examine for Inflammatory Bowel Disease. IBD comprises two forms: Ulcerative colitis (UC) increased expression of following: o TNF-? o IL-1? o IL-6 o IL-12 o IL-23 o IL-17 o IL-13 o IL-5 Crohns disease (CD) increased expression of following: o TNF-? o IL-1? o IL-1? o IL-6 o IL-18 (in some patients) o IL-10 o IL-4 (in some patients) o IL-23 o IL-27 o IL-17 IL-23 appears to be the key mediator of flares of IBD. Mucosal cytokines recently cited (IL-31 and IL-32) as important are members of the IL-17 family. | 13.00 |
| 1 7 | Examine for Diabetes. Diabetes mellitus is characterized by a lack of insulin causing elevated blood glucose, often with associated insulin resistance. Elevated serum levels of TGF-? are associated with diabetic renal disease and will be tracked by the ImmunoScore cytokine diagnostic panel. Studies in animals indicate higher serum TGF-? levels might ameliorate disease. A dysfunctioning endothelium is associated with both initiation and progression of atherosclerotic cardiovascular disease and has been shown to predate the onset of hyperglycemia in the natural history of type 2 diabetes. It is likely that low level inflammation plays an important role in developing this endothelial dysfunction mainly through the action of TNF-? and possibly IL-6. Visceral obesity and inflammation within white adipose tissue may be a crucial step contributing to the emergence of insulin resistance, type 2 diabetes and atherosclerosis. IL-1?, IL-6, IL-8, IL-10 TNF-?, and TGF-? levels all rise under these conditions. IL-27 can promote both anti- and pro-inflammatory responses. IL-27 up-regulates IFN-?, and IL-17 and down-regulates IL-4, TGF-?, and IL-10 secreted by diabetic splenocytes, suggesting a pathogenic role in T cell-mediated autoimmune diabetes. | 14.96 |

FIG. 21G-5F

| | | |
|---|---|---|
| 18 | Examine for Breast Cancer. IL-6 is a pleiotropic cytokine with both tumor-promoting and tumor-inhibiting effects. Serum IL-6 levels, however, are a negative prognosticator in breast tumor patients.<br>IL-6, IL-8, and IL-10 levels are higher in women with breast cancer than controls and levels also correlate with the clinical stage of disease. Elevated serum IL-8 levels are related to an accelerated clinical course, a higher tumor load, and the presence of liver or lymph node involvement. On the other hand, elevated IL-8 also has prognostic significance for post-relapse survival. | 12.69 |
| 19 | Examine for Cancer. Chronic inflammation has long been associated with the development of cancer. TNF-? is one of the major mediators of inflammation. TNF-? induces other inflammatory mediators and proteases that orchestrate inflammatory responses. TNF-? is also produced by tumors and can act as an endogenous tumor promoter. The role of TNF-? has been linked to all steps involved in tumorigenesis, including cellular transformation, promotion, survival, proliferation, invasion, angiogenesis, and metastasis. ImmunoScore cytokine monitoring of TNF-? levels extremely important in cancer patients. | 11.25 |
| 20 | Examine for Cancer. IL-6 has been proposed as a prognostic factor in several malignancies such as colorectal cancer, breast cancer, gastric cancer, and pancreatic cancer. In addition, elevated serum IL-6 concentrations have been demonstrated in patients with endometrial cancer, non-small cell lung carcinoma, colorectal cancer, renal cell carcinoma, breast and ovarian cancers. | 6.34 |
| 21 | Examine for Atherosclerosis. Atherogenesis is characterized by an intense inflammatory process, involving immune and vascular cells. C-reactive protein (CRP), monocyte/macrophage colony-stimulating factor (M-CSF), and IL-6 promote atherogenesis. They also down-regulate atheroprotective cytokines such as IL-10 and TGF-?. Increased levels of CRP and IL-6 are predictive of a higher cardiovascular event rate in the general population. In coronary artery disease, high levels of M-CSF are additive with those of CRP, suggesting the benefit of a multi-marker approach in assessing risk to coronary artery disease. In addition to the pro-inflammatory cytokines with poor prognostic indications, including TNF-?, IL-6, MCP-1, and IL-1, several adipocytokines are released by fat tissues and are inflammatory in nature. These include leptin, resistin, adiponectin and visfatin. Once possible atherosclerotic complications are revealed in patients, a follow up panel specific for heart patients can be envisioned which contains diagnostic tools for serum adipocytokines. It is not yet clear what function IFN-? has in relationship with atherosclerosis development, but it is likely a key player and should be monitored in cardiac patients. | 12.82 |

FIG. 21G-5 G

| | | | |
|---|---|---|---|
| 2 2 | Examine for Allergies. Allergies are the result of aberrant immune reactivity to common innocuous environmental proteins. A pivotal component of allergic pathogenesis is the generation of allergen-specific Th cells with an effector phenotype. Th17 cells may also contribute to the pathogenesis of classically recognized Th2-mediated allergic disorders. This may vary by individual patient, and ImmunoScore cytokine profiling would reveal individual differences from patient to patient. Allergic disorders would have a recommendation for treatment plans based upon Th2/Th17 immune balance. | 19.70 | |
| 2 3 | Examine for Asthma. Asthma comprises distinct heterogeneous inflammatory disorders characterized by patients showing different phenotypes with distinct genetic components, environmental causes, and immunopathogenesis. Once considered purely an allergic disorder dominated by Th2 lymphocytes, IgE, mast cells, eosinophils, macrophages, and cytokines, the disease also involves local epithelial, mesenchymal, vascular and neurologic events that are involved in directing the Th2 phenotype to the lung and through aberrant injury-repair mechanisms to remodeling of the airway wall. Responses to asthma medications vary considerably among patients, likely reflecting the differing sensitivities of the various asthma phenotypes. Physicians need to recognize this when making decisions to adjust treatment to improve asthma. IL-4 and IL-13 are considered to be key contributors to cell-mediated and humoral aspects of allergic inflammation. There is controversy surrounding the role of TGF-? in asthma. It is speculated that IL-5 also plays a pivotal role in eosinophila and asthma. Anti-IgE therapy is an approved treatment for adult and childhood asthma. Helminth infections are suggested to minimize asthma symptoms. | 18.55 | |
| 6 | Give a booster dose of tetanus vaccine. Individuals over seven years of age receive the vaccine in combination with diphtheria vaccine (Td). Those children younger than seven years of age can be boosted with a vaccine containing a pertussis component (DTaP). People who had a serious allergic reaction to one dose of tetanus toxoid should not receive another. Persons with a moderate or severe acute illness should postpone receiving the vaccine until they are improved. | 0.00 | |
| 7 | Give a booster dose of diphtheria vaccine. Individuals over seven years of age receive the vaccine in combination with tetanus vaccine (Td). Those children younger than seven can be boosted with a vaccine containing the pertussis component as with the tetanus vaccine described above. People who have had a serious allergic reaction to one dose of DTaP, DT, Td, or Tdap vaccine should not receive another. Persons with a moderate or severe illness should postpone receiving the vaccine until their condition has improved. | 0.00 | |

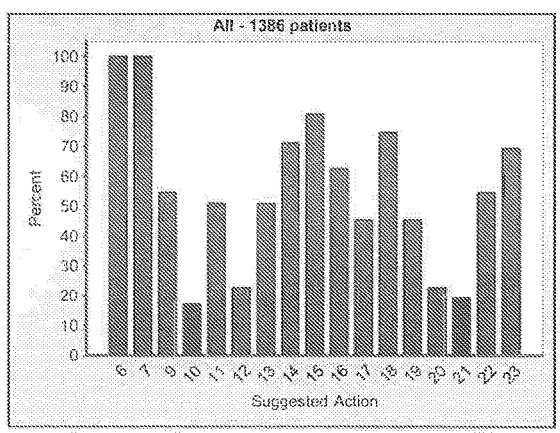

FIG. 21G-6 A

Percent Deviation Between Groups

| Rule ID | Suggested Action | StdDev |
|---|---|---|
| 10 | Examine for pregnancy. | 7.83 |
| 11 | Administer ImmunoScore cytokine panel. Rise in pro-inflammatory cytokines (IL-6, IL-12, and/or IL-17) over previous visit would indicate a future autoimmune antibody profile screening to identify possible autoimmune disease manifestation. Rise in regulatory cytokines (IL-10 and TGF-?) could possibly also indicate an autoimmune disease manifestation in regression. Rise in both pro- and regulatory cytokines would trigger subsequent need to attempt to identify autoimmune disease manifestation by ImmunoScore autoimmune disease antibody screening panels in addition to normal assessment of physical symptoms, elevated levels (>2 SD of mean) of key pro-inflammatory cytokines IL-6, IL-12, and/or IL-17 trigger: a) repeat visit in six weeks to re-measure cytokine values. i) if pro-inflammatory cytokines still elevated, recommend ImmunoScore panel to detect autoimmune antibody profile to identify possible autoimmune disease manifestation. ii) if pro-inflammatory cytokines levels decreased or moderating, recommend ImmunoScore cytokine panel evaluation annually. IL-7 may be particularly important as an initiator of many autoimmune manifestations. Depending on autoimmune disease condition, additional tests ordered can include serum thyroid stimulating hormone (TSH) for Hashimotos or Graves disease, anti-nuclear antibody (ANA) for systemic lupus erythematosus (SLE), neurological examination for multiple sclerosis (MS), and serum rheumatoid factor (RF) for rheumatoid arthritis (RA). Compare on site new ImmunoScore cytokine profile with baseline ImmunoScore cytokine profile. Significant increase (>20%) among grouped cytokines (e.g. Th1, Th2, Th17, and/or Treg) from previous profile values could be indicative of impending autoimmune flare that will likely require disease-specific treatment(s). | 23.27 |
| 12 | Examine for Rheumatoid arthritis. Rheumatoid arthritis (RA) is a chronic disorder for which there is no known cure. The optimal treatment of RA requires a comprehensive program that combines medical, social, and emotional support for the patient. Strategies are all aimed at reducing pain and discomfort, preventing deformities and loss of joint function. Treatment options include reduction of joint stress, physical and occupational therapy, and surgical intervention. Drug treatment prescriptions should be closely tied to ImmunoScore cytokine analyses to monitor RA flares and worsening of disease status. Drug classes to treat rheumatoid arthritis: 1) Non-steroidal anti-inflammatory agents (NSAIDs). NSAIDs reduce acute inflammation, reduce pain and improve function. They do not change the course of disease or prevent joint | 32.59 |

FIG. 21G-6 B destruction; 2)Corticosteroids. Corticosteroids have both anti-inflammatory and immunoregulatory activity; 3) Disease modifying anti-rheumatic drugs (DMARDs). DMARD agents have been shown to alter the course of RA and improve radiographic outcomes. There are contra-indications for all of the treatment classes described above. Closely tied immunoScore cytokine measurement and courses of treatment will optimize RA treatment for each individual. Anti-inflammatory effect within hours, but reasonable trial period for relief of RA symptoms is 1 month. The most common toxicity is gastrointestinal disturbance which may clinically include burning, belching, or irritation, but which can represent irritation of the lining of the stomach, erosions, and ulcerations that may result in bleeding. Selective COX-2 inhibitors exhibit safer GI profiles than conventional non-selective NSAIDs, but may increase cardiovascular effects on blood pressure and additional effects on vascular beds. The use of NSAIDs medications must take into account their relative risks in an individual patient of gastrointestinal damage versus potential cardiovascular risk factors. Physicians treating RA patients with NSAIDs would periodically monitor serum cytokine levels to track inflammatory cytokines and relate them to symptoms of GI irritation and/or cardiovascular damage. Corticosteroids are useful in early disease as temporary adjunctive therapy while waiting for DMARDs to exert anti-inflammatory effects. This group is also useful as chronic adjunctive therapy in patients with severe disease not well controlled on NSAIDs or DMARDs. Side effects of prednisone include weight gain, increased blood pressure, increased blood sugar, increased risk of cataracts, and avascular necrosis of bones. Patients treated with corticosteroids should have periodic immunoScore cytokine measurements coupled with bone densitometry to assess bone fracture risk. Bisphosphonates are concurrently recommended to prevent and/or treat osteoporosis in addition to adequate calcium and vitamin D supplementation. In most cases, when the diagnosis of rheumatoid arthritis is cofirmed, DMARD agents should be initiated.Methotrexate is considered the first-line DMARD agent. The anti-inflammatory effects appear to be due to interruption of adenosine and possible effects on TNF pathways. Serious complications of methotrexate therapy, including hepatic cirrhosis, interstitial pneumonitis, and severe myelosuppression are rare with proper monitoring. Stomatitis and oral ulcers, alopecia and hair thinning, and GI upset may occur and are related to folic acid antagonism. These side effects can be improved with folic acid supplementation. immunoScore cytokine coupled with serum liver enzymes should be periodically monitored. Liver biopsy should be performed if liver enzymes persist. Hydroxychloroquine is sometimes used with methotrexate and sulfasalazine as a triple therapy for RA. The most important toxicity is on the eyes. Patients with underlying retinopathies should have a baseline ophthamimologic examination and follow up

FIG. 21G-6 C exam every 12 months during treatment. Sulfasalazine is effective for the treatment of RA. The mechanism of action is unknown. It may cause hypersensitivity and allergic reactions. Careful periodic ImmunoScore cytokine screening would indicate undesirable increases in Th2 and/or Th17 cytokines in conjunction with increased serum IgE levels. TNF-? inhibitors are used to ameliorate local concentrations of TNF-? in synovial fluid. There are currently three TNF-? inhibitors approved for the treatment of RA. Etanercept binds TNF in the circulation and prevents interaction with cell surface TNF receptors. As with all TNF antagonists, there is an increased risk of infection in patients. Patients show increased risk of upper respiratory infections and some develop anti-nuclear antibodies characteristic of SLE. Screening for latent TB infection is prudent before initiation of TNF inhibitor treatments. Infliximab is an anti-TNF antibody developed in mice. Anti-infliximab antibodies can develop in patients, reducing the effectiveness of the treatments. ImmunoScore diagnostic follow-up would include cytokine measurements looking for increased Th2 (antibody) response coupled with specific measurement of anti-TNF antibodies. Opportunistic infections and sepsis have been reported with infliximab treatment. Periodic examination of cytokine balance would indicate patients coming out of immune balance. Observation of wildly fluctuating cytokine values would be indicative of an immune system swaying out of control and indicate likely candidates for sepsis. Adalimumab is another anti-TNF antibody treatment for RA. Increased infections ranging from mild to serious are seen in clinical practice. In addition, ANA titers have been seen as well as cases of lupus-like disease. Abatacept is one of a class of agents known as T-cell costimulatory blockers. These agents interfere with the interactions between antigen-presenting cells and T lymphocytes and affect early stages in the pathogenic cascade of events in RA. Infections are increased in patients being treated with abatacept. Periodic ImmunoScore cytokine measurement examining cytokine balance would coincide with patient treatment.Rituximab binds to the CD20 molecule on B cell surfaces leading to the removal of B cells from circulation. Clinical effects on RA are hypothesized to occur from decrease in B cell cytokines, interactions with B cells and T cells, or due to reductions in autoantibody levels. Infusion reactions to rituximab may include hives, itching, swelling, difficulty breathing, fever, chills, and changes in blood pressure. These are usually mild and respond to slowing the infusion rate or additional medication (such as antihistamines) but may be severe. Monitoring cytokine levels during infusion could lead to better monitoring of patient reaction to rituximab infusions. Anakira is an IL-1 receptor antagonist. ImmunoScore measurement of IL-1? and IL-1? serum concentrations during anakira therapy would indicate effectiveness and balance of the drug to cytokine levels in the patient.

FIG. 21G-6 D

| | | |
|---|---|---|
| 1 3 | Examine for Systemic Lupus Erythematosus. Activated autoreactive Th cells provide the help required for autoreactive B cells to differentiate and produce autoreactive antibodies. Studies of animal models and SLE patients indicate an important role for type I interferons. Although type I IFNs are classically considered to promote Th1-mediated cell responses, they can also inhibit Th1 and Th17 responses. At this point, it is not certain whether intervention with IFN inhibitors will be beneficial or detrimental to SLE patients, and the application of IFN inhibitory therapy may be based upon stage of SLE flare. ImmunoScore cytokine panels will be used to add clarity to therapeutics. As SLE patients live longer due to improved therapies and preventive measures, death and disability from cardiovascular events are increasing. The mechanism for the increased risk of SLE patients for cardiovascular events is likely due to a combination of inflammatory and immune mechanisms. There are increased levels of oxidized LDL (oxLDL), pro-inflammatory HDL, MCP-1, TNF-?, IFN-?, IL-1, and IL-12. ImmunoScore cardiac risk markers will be combined with ImmunoScore cytokine panels in patients with SLE, and progressive monitoring will be performed in these patients at regular intervals. | 21.26 |
| 1 4 | Examine for cancer. IL-10 is a cytokine with broad anti-inflammatory properties. A penalty of the role of IL-10 to limit immune and inflammatory responses to pathogens and prevent damage to the host is that high or dysregulated levels of IL-10 may result in chronic infection or cancer. There are certainly possible therapeutic roles to Il-10 and its antagonists in human disease, all of which would benefit from careful ImmunoScore cytokine monitoring during clinical trials and subsequent evaluations. | 11.46 |
| 1 5 | Examine for Multiple Sclerosis. Upregulated cytokines in MS patients include IL-17, IL-12, IL-23, IL-6, IL-21, TNF-?, and other Th1 cytokines. IL-17-related cytokines are speculated to be related to disease progression. Glatiramer acetate (GA) is believed to induce GA-reactive T cells that secrete anti-inflammatory cytokines at the site of inflammation in MS presumably increasing anti-inflammatory cytokines IL-10, IL-4, and TGF-?. ImmunoScore to periodically measure patients cytokines and at onset of flare, indicated by increased Th17 and Th1 cytokines, administer treatment. Efficacy of treatment could be monitored with monitoring of Treg cytokines.Interferon-? and atorvastatin have both been used to treat MS. IFN-? increases Th1 cytokines, while atorvastatin increases Th2 cytokines (particularly IL-5). Both may have the same effect of lessening the increase of Th17 cytokines. MS patients have general systemic increases of Th1 cytokines (particularly TNF-?. This is likely related to fatigue and lapses in systemic immunity. This may be a problem in patients treated with natalizumab as systemic rises in TNF-? are correlated with fatigue symptoms. | 14.87 |

FIG. 21G-6E

| | | |
|---|---|---|
| 1 6 | Examine for Inflammatory Bowel Disease. IBD comprises two forms: <br> Ulcerative colitis (UC) increased expression of following: <br> o TNF-? <br> o IL-1? <br> o IL-6 <br> o IL-12 <br> o IL-23 <br> o IL-17 <br> o IL-13 <br> o IL-5 <br> Crohns disease (CD) increased expression of following: <br> o TNF-? <br> o IL-1? <br> o IL-1? <br> o IL-6 <br> o IL-18 (in some patients) <br> o IL-10 <br> o IL-4 (in some patients) <br> o IL-23 <br> o IL-27 <br> o IL-17 <br> IL-23 appears to be the key mediator of flares of IBD. Mucosal cytokines recently cited (IL-31 and IL-32) as important are members of the IL-17 family. | 17.79 |
| 1 7 | Examine for Diabetes. Diabetes mellitus is characterized by a lack of insulin causing elevated blood glucose, often with associated insulin resistance. Elevated serum levels of TGF-? are associated with diabetic renal disease and will be tracked by the ImmunoScore cytokine diagnostic panel. Studies in animals indicate higher serum TGF-? levels might ameliorate disease. A dysfunctioning endothelium is associated with both initiation and progression of atherosclerotic cardiovascular disease and has been shown to predate the onset of hyperglycemia in the natural history of type 2 diabetes. It is likely that low level inflammation plays an important role in developing this endothelial dysfunction mainly through the action of TNF-? and possibly IL-6. Visceral obesity and inflammation within white adipose tissue may be a crucial step contributing to the emergence of insulin resistance, type 2 diabetes and atherosclerosis. IL-1?, IL-6, IL-8, IL-10 TNF-?, and TGF-? levels all rise under these conditions. IL-27 can promote both anti- and pro-inflammatory responses. IL-27 up-regulates IFN-?, and IL-17 and down-regulates IL-4, TGF-?, and IL-10 secreted by diabetic splenocytes, suggesting a pathogenic role in T cell-mediated autoimmune diabetes. | 28.45 |

FIG. 21G-6F

| | | |
|---|---|---|
| 18 | Examine for Breast Cancer. IL-6 is a pleiotropic cytokine with both tumor-promoting and tumor-inhibiting effects. Serum IL-6 levels, however, are a negative prognosticator in breast tumor patients.<br>IL-6, IL-8, and IL-10 levels are higher in women with breast cancer than controls and levels also correlate with the clinical stage of disease. Elevated serum IL-8 levels are related to an accelerated clinical course, a higher tumor load, and the presence of liver or lymph node involvement. On the other hand, elevated IL-8 also has prognostic significance for post-relapse survival. | 9.32 |
| 19 | Examine for Cancer. Chronic inflammation has long been associated with the development of cancer. TNF-? is one of the major mediators of inflammation. TNF-? induces other inflammatory mediators and proteases that orchestrate inflammatory responses. TNF-? is also produced by tumors and can act as an endogenous tumor promoter. The role of TNF-? has been linked to all steps involved in tumorigenesis, including cellular transformation, promotion, survival, proliferation, invasion, angiogenesis, and metastasis. ImmunoScore cytokine monitoring of TNF-? levels extremely important in cancer patients. | 24.64 |
| 20 | Examine for Cancer. Il-6 has been proposed as a prognostic factor in several malignancies such as colorectal cancer, breast cancer, gastric cancer, and pancreatic cancer. In addition, elevated serum IL-6 concentrations have been demonstrated in patients with endometrial cancer, non-small cell lung carcinoma, colorectal cancer, renal cell carcinoma, breast and ovarian cancers. | 0.00 |
| 21 | Examine for Atherosclerosis. Atherogenesis is characterized by an intense inflammatory process, involving immune and vascular cells. C-reactive protein (CRP), monocyte/macrophage colony-stimulating factor (M-CSF), and IL-6 promote atherogenesis. They also down-regulate atheroprotective cytokines such as IL-10 and TGF-?. Increased levels of CRP and IL-6 are predictive of a higher cardiovascular event rate in the general population. In coronary artery disease, high levels of M-CSF are additive with those of CRP, suggesting the benefit of a multi-marker approach in assessing risk to coronary artery disease. In addition to the pro-inflammatory cytokines with poor prognostic indications, including TNF-?, IL-6, MCP-1, and IL-1, several adipocytokines are released by fat tissues and are inflammatory in nature. These include leptin, resistin, adiponectin and visfatin. Once possible atherosclerotic complications are revealed in patients, a follow up panel specific for heart patients can be envisioned which contains diagnostic tools for serum adipocytokines. It is not yet clear what function IFN-? has in relationship with atherosclerosis development, but it is likely a key player and should be monitored in cardiac patients. | 36.92 |

FIG. 21G-6 G

| | | |
|---|---|---|
| 2 2 | Examine for Allergies. Allergies are the result of aberrant immune reactivity to common innocuous environmental proteins. A pivotal component of allergic pathogenesis is the generation of allergen-specific Th cells with an effector phenotype. Th17 cells may also contribute to the pathogenesis of classically recognized Th2-mediated allergic disorders. This may very by individual patient, and ImmunoScore cytokine profiling would reveal individual differences from patient to patient. Allergic disorders would have a recommendation for treatment plans based upon Th2/Th17 immune balance. | 21.11 |
| 2 3 | Examine for Asthma. Asthma comprises distinct heterogeneous inflammatory disorders characterized by patients showing different phenotypes with distinct genetic components, environmental causes, and immunopathogenesis. Once considered purely an allergic disorder dominated by Th2 lymphocytes, IgE, mast cells, eosinophils, macrophages, and cytokines, the disease also involves local epithelial, mesenchymal, vascular and neurologic events that are involved in directing the Th2 phenotype to the lung and through aberrant injury-repair mechanisms to remodeling of the airway wall. Responses to asthma medications vary considerably among patients, likely reflecting the differing sensitivities of the various asthma phenotypes. Physicians need to recognize this when making decisions to adjust treatment to improve asthma. IL-4 and IL-13 are considered to be key contributors to cell-mediated and humoral aspects of allergic inflammation. There is controversy surrounding the role of TGF-? in asthma. It is speculated that IL-5 also plays a pivotal role in eosinophilia and asthma. Anti-IgE therapy is an approved treatment for adult and childhood asthma. Helminth infections are suggested to minimize asthma symptoms. | 9.03 |
| 6 | Give a booster dose of tetanus vaccine. Individuals over seven years of age receive the vaccine in combination with diphtheria vaccine (Td). Those children younger than seven years of age can be boosted with a vaccine containing a pertussis component (DTaP). People who had a serious allergic reaction to one dose of tetanus toxoid should not receive another. Persons with a moderate or severe acute illness should postpone receiving the vaccine until they are improved. | 0.00 |
| 7 | Give a booster dose of diphtheria vaccine. Individuals over seven years of age receive the vaccine in combination with tetanus vaccine (Td). Those children younger than seven can be boosted with a vaccine containing the pertussis component as with the tetanus vaccine described above. People who have had a serious allergic reaction to one dose of DTaP, DT, Td, or Tdap vaccine should not receive another. Persons with a moderate or severe illness should postpone receiving the vaccine until their condition has improved. | 0.00 |

| 9 | Examine for chronic Hepatitis C. Patients with chronic hepatitis C virus have a significantly increased prevalence of type 2 diabetes. Activation of TNF-? has a pivotal role in the inflammatory process of HCV, and TNF-? is known to cause insulin resistance. Patients with chronic HCV need to have periodic ImmunoScore cytokine determinations to help circumvent the onset of type 2 diabetes. Elevated levels of TGF-? also indicate a poor prognosis for diabetes development in HCV patients. | 22.17 |

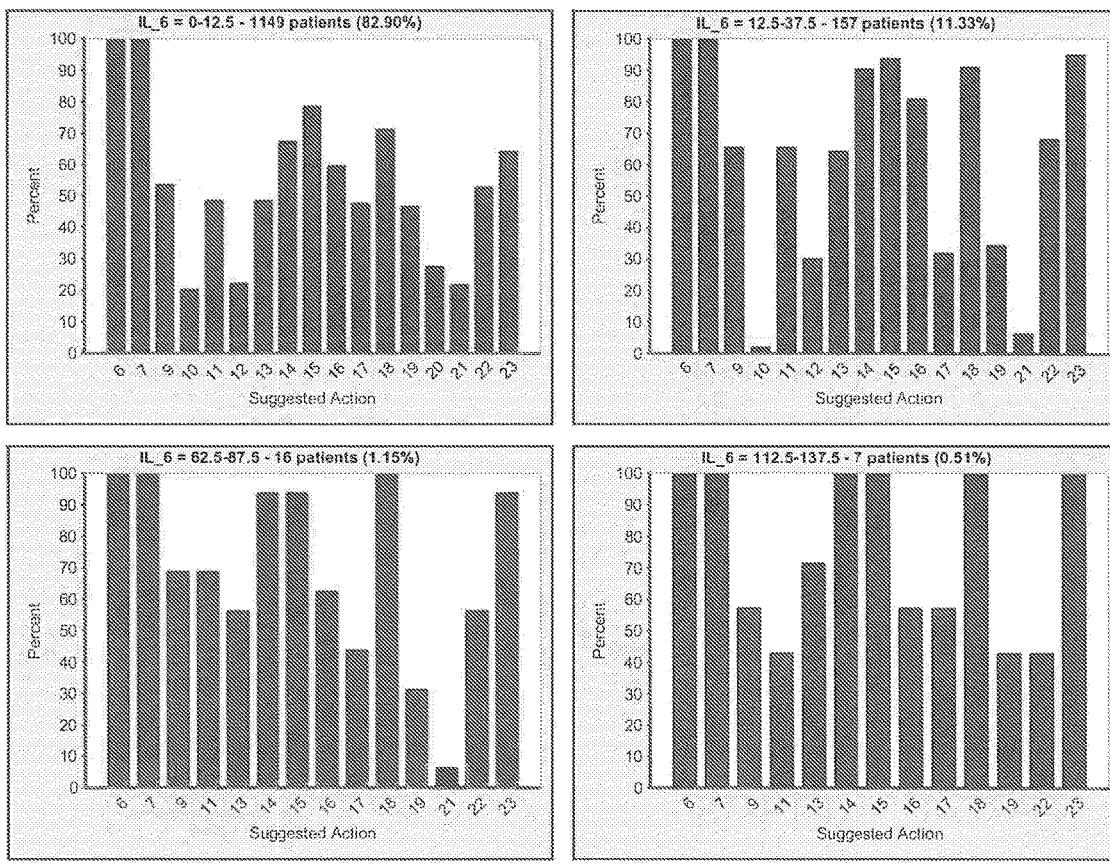

FIG. 21G-6 H

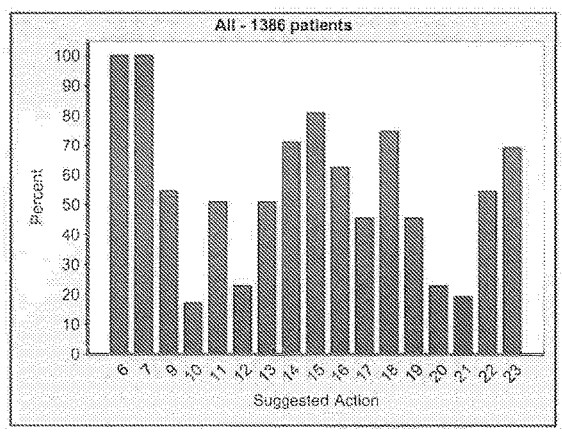

FIG. 21G-7A

Percent Deviation Between Groups

| Rule ID | Suggested Action | StdDev |
|---|---|---|
| 10 | Examine for pregnancy. | 7.09 |
| 11 | Administer ImmunoScore cytokine panel. Rise in pro-inflammatory cytokines (IL-6, IL-12, and/or IL-17) over previous visit would indicate a future autoimmune antibody profile screening to identify possible autoimmune disease manifestation. Rise in regulatory cytokines (IL-10 and TGF-?) could possibly also indicate an autoimmune disease manifestation in regression. Rise in both pro- and regulatory cytokines would trigger subsequent need to attempt to identify autoimmune disease manifestation by ImmunoScore autoimmune disease antibody screening panels. In addition to normal assessment of physical symptoms, elevated levels (>2 SD of mean) of key pro-inflammatory cytokines IL-6, IL-12, and/or IL-17 trigger: a) repeat visit in six weeks to re-measure cytokine values: i) if pro-inflammatory cytokines still elevated, recommend ImmunoScore panel to detect autoimmune antibody profile to identify possible autoimmune disease manifestation. ii) if pro-inflammatory cytokines levels decreased or moderating, recommend ImmunoScore cytokine panel evaluation annually. IL-7 may be particularly important as an initiator of many autoimmune manifestations. Depending on autoimmune disease condition, additional tests ordered can include serum thyroid stimulating hormone (TSH) for Hashimotos or Graves disease, anti-nuclear antibody (ANA) for systemic lupus erythematosus (SLE), neurological examination for multiple sclerosis (MS), and serum rheumatoid factor (RF) for rheumatoid arthritis (RA). Compare on site new ImmunoScore cytokine profile with baseline ImmunoScore cytokine profile. Significant increase (>20%) among grouped cytokines (e.g. Th1, Th2, Th17, and/or Treg) from previous profile values could be indicative of impending autoimmune flare that will likely require disease-specific treatment(s). | 21.46 |
| 12 | Examine for Rheumatoid arthritis. Rheumatoid arthritis (RA) is a chronic disorder for which there is no known cure. The optimal treatment of RA requires a comprehensive program that combines medical, social, and emotional support for the patient. Strategies are all aimed at reducing pain and discomfort, preventing deformities and loss of joint function. Treatment options include reduction of joint stress, physical and occupational therapy, and surgical intervention. Drug treatment prescriptions should be closely tied to ImmunoScore cytokine analyses to monitor RA flares and worsening of disease status. Drug classes to treat rheumatoid arthritis: 1) Non-steroidal anti-inflammatory agents (NSAIDs). NSAIDs reduce acute inflammation, reduce pain and improve function. They do not change the course of disease or prevent joint | 30.64 |

FIG. 21G-7 B destruction; 2)Corticosteroids. Corticosteroids have both anti-inflammatory and immunoregulatory activity; 3) Disease modifying anti-rheumatic drugs (DMARDs). DMARD agents have been shown to alter the course of RA and improve radiographic outcomes. There are contra-indications for all of the treatment classes described above. Closely tied ImmunoScore cytokine measurement and courses of treatment will optimize RA treatment for each individual. Anti-inflammatory effect within hours, but reasonable trial period for relief of RA symptoms is 1 month. The most common toxicity is gastrointestinal disturbance which may clinically include burning, belching, or irritation, but which can represent irritation of the lining of the stomach, erosions, and ulcerations that may result in bleeding. Selective COX-2 inhibitors exhibit safer GI profiles than conventional non-selective NSAIDs, but may increase cardiovascular effects on blood pressure and additional effects on vascular beds. The use of NSAIDs medications must take into account their relative risks in an individual patient of gastrointestinal damage versus potential cardiovascular risk factors. Physicians treating RA patients with NSAIDs would periodically monitor serum cytokine levels to track inflammatory cytokines and relate them to symptoms of GI irritation and/or cardiovascular damage. Corticosteroids are useful in early disease as temporary adjunctive therapy while waiting for DMARDs to exert anti-inflammatory effects. This group is also useful as chronic adjunctive therapy in patients with severe disease not well controlled on NSAIDs or DMARDs. Side effects of prednisone include weight gain, increased blood pressure, increased blood sugar, increased risk of cataracts, and avascular necrosis of bones. Patients treated with corticosteroids should have periodic ImmunoScore cytokine measurements coupled with bone densitometry to assess bone fracture risk. Bisphosphonates are concurrently recommended to prevent and/or treat osteoporosis in addition to adequate calcium and vitamin D supplementation. In most cases, when the diagnosis of rheumatoid arthritis is cofirmed, DMARD agents should be initiated.Methotrexate is considered the first-line DMARD agent. The anti-inflammatory effects appear to be due to interruption of adenosine and possible effects on TNF pathways. Serious complications of methotrexate therapy, including hepatic cirrhosis, interstitial pneumonitis, and severe myelosuppression are rare with proper monitoring. Stomatitis and oral ulcers, alopecia and hair thinning, and GI upset may occur and are related to folic acid antagonism. These side effects can be improved with folic acid supplementation. ImmunoScore cytokine coupled with serum liver enzymes should be periodically monitored. Liver biopsy should be performed if liver enzymes persist. Hydroxychloroquine is sometimes used with methotrexate and sulfasalazine as a triple therapy for RA. The most important toxicity is on the eyes. Patients with underlying retinopathies should have a baseline ophthamimologic examination and follow up

FIG. 21G-7 C exam every 12 months during treatment. Sulfasalazine is effective for the treatment of RA. The mechanism of action is unknown. It may cause hypersensitivity and allergic reactions. Careful periodic ImmunoScore cytokine screening would indicate undesirable increases in Th2 and/or Th17 cytokines in conjunction with increased serum IgE levels. TNF-? inhibitors are used to ameliorate local concentrations of TNF-? in synovial fluid. There are currently three TNF-? inhibitors approved for the treatment of RA. Etanercept binds TNF in the circulation and prevents interaction with cell surface TNF receptors. As with all TNF antagonists, there is an increased risk of infection in patients. Patients show increased risk of upper respiratory infections and some develop anti-nuclear antibodies characteristic of SLE. Screening for latent TB infection is prudent before initiation of TNF inhibitor treatments. Infliximab is an anti-TNF antibody developed in mice. Anti-infliximab antibodies can develop in patients, reducing the effectiveness of the treatments. ImmunoScore diagnostic follow-up would include cytokine measurements looking for increased Th2 (antibody) response coupled with specific measurement of anti-TNF antibodies. Opportunistic infections and sepsis have been reported with infliximab treatment. Periodic examination of cytokine balance would indicate patients coming out of immune balance. Observation of wildly fluctuating cytokine values would be indicative of an immune system swaying out of control and indicate likely candidates for sepsis. Adalimumab is another anti-TNF antibody treatment for RA. Increased infections ranging from mild to serious are seen in clinical practice. In addition, ANA titers have been seen as well as cases of lupus-like disease. Abatacept is one of a class of agents known as T-cell costimulatory blockers. These agents interfere with the interactions between antigen-presenting cells and T lymphocytes and affect early stages in the pathogenic cascade of events in RA. Infections are increased in patients being treated with abatacept. Periodic ImmunoScore cytokine measurement examining cytokine balance would coincide with patient treatment. Rituximab binds to the CD20 molecule on B cell surfaces leading to the removal of B cells from circulation. Clinical effects on RA are hypothesized to occur from decrease in B cell cytokines, interactions with B cells and T cells, or due to reductions in autoantibody levels. Infusion reactions to rituximab may include hives, itching, swelling, difficulty breathing, fever, chills, and changes in blood pressure. These are usually mild and respond to slowing the infusion rate or additional medication (such as antihistamines) but may be severe. Monitoring cytokine levels during infusion could lead to better monitoring of patient reaction to rituximab infusions. Anakira is an IL-1 receptor antagonist. ImmunoScore measurement of IL-1? and IL-1? serum concentrations during anakira therapy would indicate effectiveness and balance of the drug to cytokine levels in the patient.

FIG. 21G-7 D

| | | |
|---|---|---|
| 1 3 | Examine for Systemic Lupus Erythematosus. Activated autoreactive Th cells provide the help required for autoreactive B cells to differentiate and produce autoreactive antibodies. Studies of animal models and SLE patients indicate an important role for type I interferons. Although type I IFNs are classically considered to promote Th1-mediated cell responses, they can also inhibit Th1 and Th17 responses. At this point, it is not certain whether intervention with IFN inhibitors will be beneficial or detrimental to SLE patients, and the application of IFN inhibitory therapy may be based upon stage of SLE flare. ImmunoScore cytokine panels will be used to add clarity to therapeutics. As SLE patients live longer due to improved therapies and preventive measures, death and disability from cardiovascular events are increasing. The mechanism for the increased risk of SLE patients for cardiovascular events is likely due to a combination of inflammatory and immune mechanisms. There are increased levels of oxidized LDL (oxLDL), pro-inflammatory HDL, MCP-1, TNF-?, IFN-?, IL-1, and IL-12. ImmunoScore cardiac risk markers will be combined with ImmunoScore cytokine panels in patients with SLE, and progressive monitoring will be performed in these patients at regular intervals. | 23.38 |
| 1 4 | Examine for cancer. IL-10 is a cytokine with broad anti-inflammatory properties. A penalty of the role of IL-10 to limit immune and inflammatory responses to pathogens and prevent damage to the host is that high or dysregulated levels of IL-10 may result in chronic infection or cancer. There are certainly possible therapeutic roles to Il-10 and its antagonists in human disease, all of which would benefit from careful ImmunoScore cytokine monitoring during clinical trials and subsequent evaluations. | 11.55 |
| 1 5 | Examine for Multiple Sclerosis. Upregulated cytokines in MS patients include IL-17, IL-12, IL-23, IL-6, IL-21, TNF-?, and other Th1 cytokines. IL-17-related cytokines are speculated to be related to disease progression. Glatiramer acetate (GA) is believed to induce GA-reactive T cells that secrete anti-inflammatory cytokines at the site of inflammation in MS - presumably increasing anti-inflammatory cytokines IL-10, IL-4, and TGF-?. ImmunoScore to periodically measure patients cytokines and at onset of flare, indicated by increased Th17 and Th1 cytokines, administer treatment. Efficacy of treatment could be monitored with monitoring of Treg cytokines.Interferon-? and atorvastatin have both been used to treat MS. IFN-? increases Th1 cytokines, while atorvastatin increases Th2 cytokines (particularly IL-5). Both may have the same effect of lessening the increase of Th17 cytokines. MS patients have general systemic increases of Th1 cytokines (particularly TNF-?. This is likely related to fatigue and lapses in systemic immunity. This may be a problem in patients treated with natalizumab as systemic rises in TNF-? are correlated with fatigue symptoms. | 8.99 |

FIG. 21G-7 E

| | | | |
|---|---|---|---|
| 16 | Examine for Inflammatory Bowel Disease. IBD comprises two forms:<br>Ulcerative colitis (UC) increased expression of following:<br>o TNF-?<br>o IL-1?<br>o IL-6<br>o IL-12<br>o IL-23<br>o IL-17<br>o IL-13<br>o IL-5<br>Crohns disease (CD) increased expression of following:<br>o TNF-?<br>o IL-1?<br>o IL-1?<br>o IL-6<br>o IL-18 (in some patients)<br>o IL-10<br>o IL-4 (in some patients)<br>o IL-23<br>o IL-27<br>o IL-17<br>IL-23 appears to be the key mediator of flares of IBD. Mucosal cytokines recently cited (IL-31 and IL-32) as important are members of the IL-17 family. | 18.47 | |
| 17 | Examine for Diabetes. Diabetes mellitus is characterized by a lack of insulin causing elevated blood glucose, often with associated insulin resistance. Elevated serum levels of TGF-? are associated with diabetic renal disease and will be tracked by the ImmunoScore cytokine diagnostic panel. Studies in animals indicate higher serum TGF-? levels might ameliorate disease. A dysfunctioning endothelium is associated with both initiation and progression of atherosclerotic cardiovascular disease and has been shown to predate the onset of hyperglycemia in the natural history of type 2 diabetes. It is likely that low level inflammation plays an important role in developing this endothelial dysfunction mainly through the action of TNF-? and possibly IL-6. Visceral obesity and inflammation within white adipose tissue may be a crucial step contributing to the emergence of insulin resistance, type 2 diabetes and atherosclerosis. IL-1?, IL-6, IL-8, IL-10 TNF-?, and TGF-? levels all rise under these conditions. IL-27 can promote both anti- and pro-inflammatory responses. IL-27 up-regulates IFN-?, and IL-17 and down-regulates IL-4, TGF-?, and IL-10 secreted by diabetic splenocytes, suggesting a pathogenic role in T cell-mediated autoimmune diabetes. | 26.32 | |

FIG. 21G-7F

| | | |
|---|---|---|
| 18 | Examine for Breast Cancer. IL-6 is a pleiotropic cytokine with both tumor-promoting and tumor-inhibiting effects. Serum IL-6 levels, however, are a negative prognosticator in breast tumor patients.<br>IL-6, IL-8, and IL-10 levels are higher in women with breast cancer than controls and levels also correlate with the clinical stage of disease. Elevated serum IL-8 levels are related to an accelerated clinical course, a higher tumor load, and the presence of liver or lymph node involvement. On the other hand, elevated IL-8 also has prognostic significance for post-relapse survival. | 9.05 |
| 19 | Examine for Cancer. Chronic inflammation has long been associated with the development of cancer. TNF-? is one of the major mediators of inflammation. TNF-? induces other inflammatory mediators and proteases that orchestrate inflammatory responses. TNF-? is also produced by tumors and can act as an endogenous tumor promoter. The role of TNF-? has been linked to all steps involved in tumorigenesis, including cellular transformation, promotion, survival, proliferation, invasion, angiogenesis, and metastasis. immunoScore cytokine monitoring of TNF-? levels extremely important in cancer patients. | 24.25 |
| 20 | Examine for Cancer. IL-6 has been proposed as a prognostic factor in several malignancies such as colorectal cancer, breast cancer, gastric cancer, and pancreatic cancer. In addition, elevated serum IL-6 concentrations have been demonstrated in patients with endometrial cancer, non-small cell lung carcinoma, colorectal cancer, renal cell carcinoma, breast and ovarian cancers. | 10.57 |
| 21 | Examine for Atherosclerosis. Atherogenesis is characterized by an intense inflammatory process, involving immune and vascular cells. C-reactive protein (CRP), monocyte/macrophage colony-stimulating factor (M-CSF), and IL-6 promote atherogenesis. They also down-regulate atheroprotective cytokines such as IL-10 and TGF-?. Increased levels of CRP and IL-6 are predictive of a higher cardiovascular event rate in the general population. In coronary artery disease, high levels of M-CSF are additive with those of CRP, suggesting the benefit of a multi-marker approach in assessing risk to coronary artery disease. In addition to the pro-inflammatory cytokines with poor prognostic indications, including TNF-?, IL-6, MCP-1, and IL-1, several adipocytokines are released by fat tissues and are inflammatory in nature. These include leptin, resistin, adiponectin and visfatin. Once possible atherosclerotic complications are revealed in patients, a follow up panel specific for heart patients can be envisioned which contains diagnostic tools for serum adipocytokines. It is not yet clear what function IFN-? has in relationship with atherosclerosis development, but it is likely a key player and should be monitored in cardiac patients. | 7.49 |

FIG. 21G-7 G

| | | |
|---|---|---|
| 2 2 | Examine for Allergies. Allergies are the result of aberrant immune reactivity to common innocuous environmental proteins. A pivotal component of allergic pathogenesis is the generation of allergen-specific Th cells with an effector phenotype. Th17 cells may also contribute to the pathogenesis of classically recognized Th2-mediated allergic disorders. This may very by individual patient, and ImmunoScore cytokine profiling would reveal individual differences from patient to patient. Allergic disorders would have a recommendation for treatment plans based upon Th2/Th17 immune balance. | 20.69 |
| 2 3 | Examine for Asthma. Asthma comprises distinct heterogeneous inflammatory disorders characterized by patients showing different phenotypes with distinct genetic components, environmental causes, and immunopathogenesis. Once considered purely an allergic disorder dominated by Th2 lymphocytes, IgE, mast cells, eosinophils, macrophages, and cytokines, the disease also involves local epithelial, mesenchymal, vascular and neurologic events that are involved in directing the Th2 phenotype to the lung and through aberrant injury-repair mechanisms to remodeling of the airway wall. Responses to asthma medications vary considerably among patients, likely reflecting the differing sensitivities of the various asthma phenotypes. Physicians need to recognize this when making decisions to adjust treatment to improve asthma. IL-4 and IL-13 are considered to be key contributors to cell-mediated and humoral aspects of allergic inflammation. There is controversy surrounding the role of TGF-? in asthma. It is speculated that IL-5 also plays a pivotal role in eosinophila and asthma. Anti-IgE therapy is an approved treatment for adult and childhood asthma. Helminth infections are suggested to minimize asthma symptoms. | 17.57 |
| 6 | Give a booster dose of tetanus vaccine. Individuals over seven years of age receive the vaccine in combination with diphtheria vaccine (Td). Those children younger than seven years of age can be boosted with a vaccine containing a pertussis component (DTaP). People who had a serious allergic reaction to one dose of tetanus toxoid should not receive another. Persons with a moderate or severe acute illness should postpone receiving the vaccine until they are improved. | 0.00 |
| 7 | Give a booster dose of diphtheria vaccine. Individuals over seven years of age receive the vaccine in combination with tetanus vaccine (Td). Those children younger than seven can be boosted with a vaccine containing the pertussis component as with the tetanus vaccine described above. People who have had a serious allergic reaction to one dose of DTaP, DT, Td, or Tdap vaccine should not receive another. Persons with a moderate or severe illness should postpone receiving the vaccine until their condition has improved. | 0.00 |

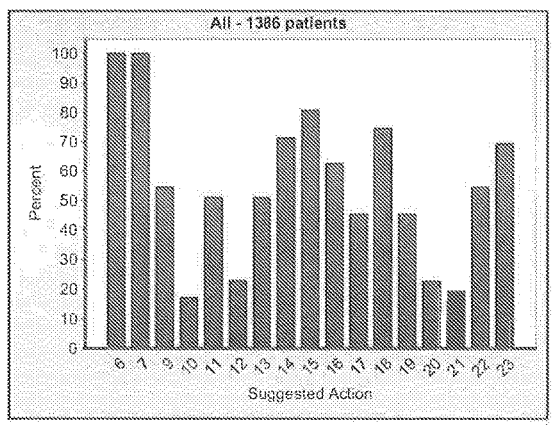

FIG. 21G-8 A

Percent Deviation Between Groups

| Rule ID | Suggested Action | StdDev |
|---|---|---|
| 10 | Examine for pregnancy. | 0.00 |
| 11 | Administer ImmunoScore cytokine panel. Rise in pro-inflammatory cytokines (IL-6, IL-12, and/or IL-17) over previous visit would indicate a future autoimmune antibody profile screening to identify possible autoimmune disease manifestation. Rise in regulatory cytokines (IL-10 and TGF-?) could possibly also indicate an autoimmune disease manifestation in regression. Rise in both pro- and regulatory cytokines would trigger subsequent need to attempt to identify autoimmune disease manifestation by ImmunoScore autoimmune disease antibody screening panels. In addition to normal assessment of physical symptoms, elevated levels (>2 SD of mean) of key pro-inflammatory cytokines IL-6, IL-12, and/or IL-17 trigger: a) repeat visit in six weeks to re-measure cytokine values: i) if pro-inflammatory cytokines still elevated, recommend ImmunoScore panel to detect autoimmune antibody profile to identify possible autoimmune disease manifestation. ii) if pro-inflammatory cytokines levels decreased or moderating, recommend ImmunoScore cytokine panel evaluation annually. IL-7 may be particularly important as an initiator of many autoimmune manifestations. Depending on autoimmune disease condition, additional tests ordered can include serum thyroid stimulating hormone (TSH) for Hashimotos or Graves disease, anti-nuclear antibody (ANA) for systemic lupus erythematosus (SLE), neurological examination for multiple sclerosis (MS), and serum rheumatoid factor (RF) for rheumatoid arthritis (RA). Compare on site new ImmunoScore cytokine profile with baseline ImmunoScore cytokine profile. Significant increase (>20%) among grouped cytokines (e.g. Th1, Th2, Th17, and/or Treg) from previous profile values could be indicative of impending autoimmune flare that will likely require disease-specific treatment(s). | 18.29 |
| 12 | Examine for Rheumatoid arthritis. Rheumatoid arthritis (RA) is a chronic disorder for which there is no known cure. The optimal treatment of RA requires a comprehensive program that combines medical, social, and emotional support for the patient. Strategies are all aimed at reducing pain and discomfort, preventing deformities and loss of joint function. Treatment options include reduction of joint stress, physical and occupational therapy, and surgical intervention. Drug treatment prescriptions should be closely tied to ImmunoScore cytokine analyses to monitor RA flares and worsening of disease status. Drug classes to treat rheumatoid arthritis: 1) Non-steroidal anti-inflammatory agents (NSAIDs). NSAIDs reduce acute inflammation, reduce pain and improve function. They do not change the course of disease or prevent joint | 31.73 |

FIG. 21G-8 B destruction; 2)Corticosteroids. Corticosteroids have both anti-inflammatory and immunoregulatory activity; 3) Disease modifying anti-rheumatic drugs (DMARDs). DMARD agents have been shown to alter the course of RA and improve radiographic outcomes. There are contra-indications for all of the treatment classes described above. Closely tied ImmunoScore cytokine measurement and courses of treatment will optimize RA treatment for each individual. Anti-inflammatory effect within hours, but reasonable trial period for relief of RA symptoms is 1 month. The most common toxicity is gastrointestinal disturbance which may clinically include burning, belching, or irritation, but which can represent irritation of the lining of the stomach, erosions, and ulcerations that may result in bleeding. Selective COX-2 inhibitors exhibit safer GI profiles than conventional non-selective NSAIDs, but may increase cardiovascular effects on blood pressure and additional effects on vascular beds. The use of NSAIDs medications must take into account their relative risks in an individual patient of gastrointestinal damage versus potential cardiovascular risk factors. Physicians treating RA patients with NSAIDs would periodically monitor serum cytokine levels to track inflammatory cytokines and relate them to symptoms of GI irritation and/or cardiovascular damage. Corticosteroids are useful in early disease as temporary adjunctive therapy while waiting for DMARDs to exert anti-inflammatory effects. This group is also useful as chronic adjunctive therapy in patients with severe disease not well controlled on NSAIDs or DMARDs. Side effects of prednisone include weight gain, increased blood pressure, increased blood sugar, increased risk of cataracts, and avascular necrosis of bones. Patients treated with corticosteroids should have periodic ImmunoScore cytokine measurements coupled with bone densitometry to assess bone fracture risk. Bisphosphonates are concurrently recommended to prevent and/or treat osteoporosis in addition to adequate calcium and vitamin D supplementation. In most cases, when the diagnosis of rheumatoid arthritis is cofirmed, DMARD agents should be initiated.Methotrexate is considered the first-line DMARD agent. The anti-inflammatory effects appear to be due to interruption of adenosine and possible effects on TNF pathways. Serious complications of methotrexate therapy, including hepatic cirrhosis, interstitial pneumonitis, and severe myelosuppression are rare with proper monitoring. Stomatitis and oral ulcers, alopecia and hair thinning, and GI upset may occur and are related to folic acid antagonism. These side effects can be improved with folic acid supplementation. ImmunoScore cytokine coupled with serum liver enzymes should be periodically monitored. Liver biopsy should be performed if liver enzymes persist. Hydroxychloroquine is sometimes used with methotrexate and sulfasalazine as a triple therapy for RA. The most important toxicity is on the eyes. Patients with underlying retinopathies should have a baseline ophthamlmologic examination and follow up

FIG. 21G-8 C exam every 12 months during treatment. Sulfasalazine is effective for the treatment of RA. The mechanism of action is unknown. It may cause hypersensitivity and allergic reactions. Careful periodic ImmunoScore cytokine screening would indicate undesirable increases in Th2 and/or Th17 cytokines in conjunction with increased serum IgE levels. TNF-? inhibitors are used to ameliorate local concentrations of TNF-? in synovial fluid. There are currently three TNF-? inhibitors approved for the treatment of RA. Etanercept binds TNF in the circulation and prevents interaction with cell surface TNF receptors. As with all TNF antagonists, there is an increased risk of infection in patients. Patients show increased risk of upper respiratory infections and some develop anti-nuclear antibodies characteristic of SLE. Screening for latent TB infection is prudent before initiation of TNF inhibitor treatments. Infliximab is an anti-TNF antibody developed in mice. Anti-infliximab antibodies can develop in patients, reducing the effectiveness of the treatments. ImmunoScore diagnostic follow-up would include cytokine measurements looking for increased Th2 (antibody) response coupled with specific measurement of anti-TNF antibodies. Opportunistic infections and sepsis have been reported with infliximab treatment. Periodic examination of cytokine balance would indicate patients coming out of immune balance. Observation of wildly fluctuating cytokine values would be indicative of an immune system swaying out of control and indicate likely candidates for sepsis. Adalimumab is another anti-TNF antibody treatment for RA. Increased infections ranging from mild to serious are seen in clinical practice. In addition, ANA titers have been seen as well as cases of lupus-like disease. Abatacept is one of a class of agents known as T-cell costimulatory blockers. These agents interfere with the interactions between antigen-presenting cells and T lymphocytes and affect early stages in the pathogenic cascade of events in RA. Infections are increased in patients being treated with abatacept. Periodic ImmunoScore cytokine measurement examining cytokine balance would coincide with patient treatment. Rituximab binds to the CD20 molecule on B cell surfaces leading to the removal of B cells from circulation. Clinical effects on RA are hypothesized to occur from decrease in B cell cytokines, interactions with B cells and T cells, or due to reductions in autoantibody levels. Infusion reactions to rituximab may include hives, itching, swelling, difficulty breathing, fever, chills, and changes in blood pressure. These are usually mild and respond to slowing the infusion rate or additional medication (such as antihistamines) but may be severe. Monitoring cytokine levels during infusion could lead to better monitoring of patient reaction to rituximab infusions. Anakira is an IL-1 receptor antagonist. ImmunoScore measurement of IL-1? and IL-1? serum concentrations during anakira therapy would indicate effectiveness and balance of the drug to cytokine levels in the patient.

FIG. 21G-8 D

| | | | |
|---|---|---|---|
| 1 3 | Examine for Systemic Lupus Erythematosus. Activated autoreactive Th cells provide the help required for autoreactive B cells to differentiate and produce autoreactive antibodies. Studies of animal models and SLE patients indicate an important role for type I interferons. Although type I IFNs are classically considered to promote Th1-mediated cell responses, they can also inhibit Th1 and Th17 responses. At this point, it is not certain whether intervention with IFN inhibitors will be beneficial or detrimental to SLE patients, and the application of IFN inhibitory therapy may be based upon stage of SLE flare. ImmunoScore cytokine panels will be used to add clarity to therapeutics. As SLE patients live longer due to improved therapies and preventive measures, death and disability from cardiovascular events are increasing. The mechanism for the increased risk of SLE patients for cardiovascular events is likely due to a combination of inflammatory and immune mechanisms. There are increased levels of oxidized LDL (oxLDL), pro-inflammatory HDL, MCP-1, TNF-?, IFN-?, IL-1, and IL-12. ImmunoScore cardiac risk markers will be combined with ImmunoScore cytokine panels in patients with SLE, and progressive monitoring will be performed in these patients at regular intervals. | 17.42 |
| 1 4 | Examine for cancer. IL-10 is a cytokine with broad anti-inflammatory properties. A penalty of the role of IL-10 to limit immune and inflammatory responses to pathogens and prevent damage to the host is that high or dysregulated levels of IL-10 may result in chronic infection or cancer. There are certainly possible therapeutic roles to IL-10 and its antagonists in human disease, all of which would benefit from careful ImmunoScore cytokine monitoring during clinical trials and subsequent evaluations. | 10.40 |
| 1 5 | Examine for Multiple Sclerosis. Upregulated cytokines in MS patients include IL-17, IL-12, IL-23, IL-6, IL-21, TNF-?, and other Th1 cytokines. IL-17-related cytokines are speculated to be related to disease progression. Glatiramer acetate (GA) is believed to induce GA-reactive T cells that secrete anti-inflammatory cytokines at the site of inflammation in MS - presumably increasing anti-inflammatory cytokines IL-10, IL-4, and TGF-?. ImmunoScore to periodically measure patients cytokines and at onset of flare, indicated by increased Th17 and Th1 cytokines, administer treatment. Efficacy of treatment could be monitored with monitoring of Treg cytokines.Interferon-? and atorvastatin have both been used to treat MS. IFN-? increases Th1 cytokines, while atorvastatin increases Th2 cytokines (particularly IL-5). Both may have the same effect of lessening the increase of Th17 cytokines. MS patients have general systemic increases of Th1 cytokines (particularly TNF-?. This is likely related to fatigue and lapses in systemic immunity. This may be a problem in patients treated with natalizumab as systemic rises in TNF-? are correlated with fatigue symptoms. | 7.31 |

FIG. 21G-8 E

| 16 | Examine for Inflammatory Bowel Disease. IBD comprises two forms: Ulcerative colitis (UC) increased expression of following: <br>o TNF-? <br>o IL-1? <br>o IL-6 <br>o IL-12 <br>o IL-23 <br>o IL-17 <br>o IL-13 <br>o IL-5 <br>Crohns disease (CD) increased expression of following: <br>o TNF-? <br>o IL-1? <br>o IL-1? <br>o IL-6 <br>o IL-18 (in some patients) <br>o IL-10 <br>o IL-4 (in some patients) <br>o IL-23 <br>o IL-27 <br>o IL-17 <br>IL-23 appears to be the key mediator of flares of IBD. Mucosal cytokines recently cited (IL-31 and IL-32) as important are members of the IL-17 family. | 14.14 |
|---|---|---|
| 17 | Examine for Diabetes. Diabetes mellitus is characterized by a lack of insulin causing elevated blood glucose, often with associated insulin resistance. Elevated serum levels of TGF-? are associated with diabetic renal disease and will be tracked by the ImmunoScore cytokine diagnostic panel. Studies in animals indicate higher serum TGF-? levels might ameliorate disease. A dysfunctioning endothelium is associated with both initiation and progression of atherosclerotic cardiovascular disease and has been shown to predate the onset of hyperglycemia in the natural history of type 2 diabetes. It is likely that low level inflammation plays an important role in developing this endothelial dysfunction mainly through the action of TNF-? and possibly IL-6. Visceral obesity and inflammation within white adipose tissue may be a crucial step contributing to the emergence of insulin resistance, type 2 diabetes and atherosclerosis. IL-1?, IL-6, IL-8, IL-10 TNF-?, and TGF-? levels all rise under these conditions. IL-27 can promote both anti- and pro-inflammatory responses. IL-27 up-regulates IFN-?, and IL-17 and down-regulates IL-4, TGF-?, and IL-10 secreted by diabetic splenocytes, suggesting a pathogenic role in T cell-mediated autoimmune diabetes. | 10.58 |

FIG. 21G-8F

| 18 | Examine for Breast Cancer. IL-6 is a pleiotropic cytokine with both tumor-promoting and tumor-inhibiting effects. Serum IL-6 levels, however, are a negative prognosticator in breast tumor patients. IL-6, IL-8, and IL-10 levels are higher in women with breast cancer than controls and levels also correlate with the clinical stage of disease. Elevated serum IL-8 levels are related to an accelerated clinical course, a higher tumor load, and the presence of liver or lymph node involvement. On the other hand, elevated IL-8 also has prognostic significance for post-relapse survival. | 9.48 |
|---|---|---|
| 19 | Examine for Cancer. Chronic inflammation has long been associated with the development of cancer. TNF-? is one of the major mediators of inflammation. TNF-? induces other inflammatory mediators and proteases that orchestrate inflammatory responses. TNF-? is also produced by tumors and can act as an endogenous tumor promoter. The role of TNF-? has been linked to all steps involved in tumorigenesis, including cellular transformation, promotion, survival, proliferation, invasion, angiogenesis, and metastasis. ImmunoScore cytokine monitoring of TNF-? levels extremely important in cancer patients. | 16.29 |
| 20 | Examine for Cancer. Il-6 has been proposed as a prognostic factor in several malignancies such as colorectal cancer, breast cancer, gastric cancer, and pancreatic cancer. In addition, elevated serum IL-6 concentrations have been demonstrated in patients with endometrial cancer, non-small cell lung carcinoma, colorectal cancer, renal cell carcinoma, breast and ovarian cancers. | 10.30 |
| 21 | Examine for Atherosclerosis. Atherogenesis is characterized by an intense inflammatory process, involving immune and vascular cells. C-reactive protein (CRP), monocyte/macrophage colony-stimulating factor (M-CSF), and IL-6 promote atherogenesis. They also down-regulate atheroprotective cytokines such as IL-10 and TGF-?. Increased levels of CRP and IL-6 are predictive of a higher cardiovascular event rate in the general population. In coronary artery disease, high levels of M-CSF are additive with those of CRP, suggesting the benefit of a multi-marker approach in assessing risk to coronary artery disease. In addition to the pro-inflammatory cytokines with poor prognostic indications, including TNF-?, IL-6, MCP-1, and IL-1, several adipocytokines are released by fat tissues and are inflammatory in nature. These include leptin, resistin, adiponectin and visfatin. Once possible atherosclerotic complications are revealed in patients, a follow up panel specific for heart patients can be envisioned which contains diagnostic tools for serum adipocytokines. It is not yet clear what function IFN-? has in relationship with atherosclerosis development, but it is likely a key player and should be monitored in cardiac patients. | 40.83 |

FIG. 21G-8 G

| | | | |
|---|---|---|---|
| 2 2 | Examine for Allergies. Allergies are the result of aberrant immune reactivity to common innocuous environmental proteins. A pivotal component of allergic pathogenesis is the generation of allergen specific Th cells with an effector phenotype. Th17 cells may also contribute to the pathogenesis of classically recognized Th2-mediated allergic disorders. This may very by individual patient, and ImmunoScore cytokine profiling would reveal individual differences from patient to patient. Allergic disorders would have a recommendation for treatment plans based upon Th2/Th17 immune balance. | | 17.04 |
| 2 3 | Examine for Asthma. Asthma comprises distinct heterogeneous inflammatory disorders characterized by patients showing different phenotypes with distinct genetic components, environmental causes, and immunopathogenesis. Once considered purely an allergic disorder dominated by Th2 lymphocytes, IgE, mast cells, eosinophils, macrophages, and cytokines, the disease also involves local epithelial, mesenchymal, vascular and neurologic events that are involved in directing the Th2 phenotype to the lung and through aberrant injury-repair mechanisms to remodeling of the airway wall. Responses to asthma medications vary considerably among patients, likely reflecting the differing sensitivities of the various asthma phenotypes. Physicians need to recognize this when making decisions to adjust treatment to improve asthma. IL-4 and IL-13 are considered to be key contributors to cell-mediated and humoral aspects of allergic inflammation. There is controversy surrounding the role of TGF-? in asthma. It is speculated that IL-5 also plays a pivotal role in eosinophila and asthma. Anti-IgE therapy is an approved treatment for adult and childhood asthma. Helminth infections are suggested to minimize asthma symptoms. | | 10.93 |
| 6 | Give a booster dose of tetanus vaccine. Individuals over seven years of age receive the vaccine in combination with diphtheria vaccine (Td). Those children younger than seven years of age can be boosted with a vaccine containing a pertussis component (DTaP). People who had a serious allergic reaction to one dose of tetanus toxoid should not receive another. Persons with a moderate or severe acute illness should postpone receiving the vaccine until they are improved. | | 0.00 |
| 7 | Give a booster dose of diphtheria vaccine. Individuals over seven years of age receive the vaccine in combination with tetanus vaccine (Td). Those children younger than seven can be boosted with a vaccine containing the pertussis component as with the tetanus vaccine described above. People who have had a serious allergic reaction to one dose of DTaP, DT, Td, or Tdap vaccine should not receive another. Persons with a moderate or severe illness should postpone receiving the vaccine until their condition has improved. | | 0.00 |

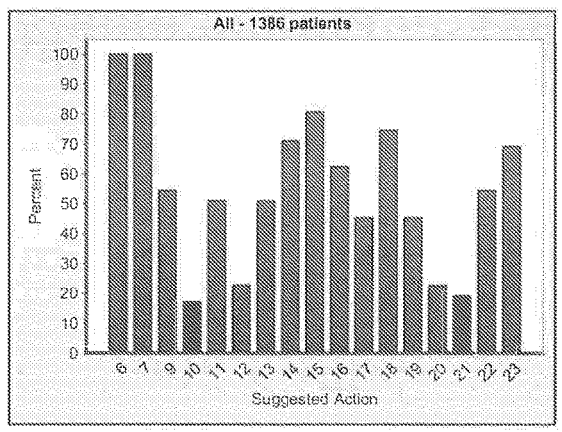

Percent Deviation Between Groups

| Rule ID | Suggested Action | StdDev |
|---|---|---|
| 10 | Examine for pregnancy. | 7.73 |
| 11 | Administer ImmunoScore cytokine panel. Rise in pro-inflammatory cytokines (IL-6, IL-12, and/or IL-17) over previous visit would indicate a future autoimmune antibody profile screening to identify possible autoimmune disease manifestation. Rise in regulatory cytokines (IL-10 and TGF-?) could possibly also indicate an autoimmune disease manifestation in regression. Rise in both pro- and regulatory cytokines would trigger subsequent need to attempt to identify autoimmune disease manifestation by ImmunoScore autoimmune disease antibody screening panels.In addition to normal assessment of physical symptoms, elevated levels (>2 SD of mean) of key pro-inflammatory cytokines IL-6, IL-12, and/or IL-17 trigger: a) repeat visit in six weeks to re-measure cytokine values: i) if pro-inflammatory cytokines still elevated, recommend ImmunoScore panel to detect autoimmune antibody profile to identify possible autoimmune disease manifestation. ii) if pro-inflammatory cytokines levels decreased or moderating, recommend ImmunoScore cytokine panel evaluation annually. IL-7 may be particularly important as an initiator of many autoimmune manifestations. Depending on autoimmune disease condition, additional tests ordered can include serum thyroid stimulating hormone (TSH) for Hashimotos or Graves disease, anti-nuclear antibody (ANA) for systemic lupus erythematosus (SLE), neurological examination for multiple sclerosis (MS), and serum rheumatoid factor (RF) for rheumatoid arthritis (RA). Compare on site new ImmunoScore cytokine profile with baseline ImmunoScore cytokine profile. Significant increase (>20%) among grouped cytokines (e.g. Th1, Th2, Th17, and/or Treg) from previous profile values could be indicative of impending autoimmune flare that will likely require disease-specific treatment(s). | 19.67 |
| 12 | Examine for Rheumatoid arthritis. Rheumatoid arthritis (RA) is a chronic disorder for which there is no known cure. The optimal treatment of RA requires a comprehensive program that combines medical, social, and emotional support for the patient. Strategies are all aimed at reducing pain and discomfort, preventing deformities and loss of joint function. Treatment options include reduction of joint stress, physical and occupational therapy, and surgical intervention. Drug treatment prescriptions should be closely tied to ImmunoScore cytokine analyses to monitor RA flares and worsening of disease status. Drug classes to treat rheumatoid arthritis: 1) Non-steroidal anti-inflammatory agents (NSAIDs). NSAIDs reduce acute inflammation, reduce pain and improve function. They do not change the course of disease or prevent joint | 28.13 |

FIG. 21G-9 B destruction; 2)Corticosteroids. Corticosteroids have both anti-inflammatory and immunoregulatory activity; 3) Disease modifying anti-rheumatic drugs (DMARDs). DMARD agents have been shown to alter the course of RA and improve radiographic outcomes. There are contra-indications for all of the treatment classes described above. Closely tied ImmunoScore cytokine measurement and courses of treatment will optimize RA treatment for each individual. Anti-inflammatory effect within hours, but reasonable trial period for relief of RA symptoms is 1 month. The most common toxicity is gastrointestinal disturbance which may clinically include burning, belching, or irritation, but which can represent irritation of the lining of the stomach, erosions, and ulcerations that may result in bleeding. Selective COX-2 inhibitors exhibit safer GI profiles than conventional non-selective NSAIDs, but may increase cardiovascular effects on blood pressure and additional effects on vascular beds. The use of NSAIDs medications must take into account their relative risks in an individual patient of gastrointestinal damage versus potential cardiovascular risk factors. Physicians treating RA patients with NSAIDs would periodically monitor serum cytokine levels to track inflammatory cytokines and relate them to symptoms of GI irritation and/or cardiovascular damage. Corticosteroids are useful in early disease as temporary adjunctive therapy while waiting for DMARDs to exert anti-inflammatory effects. This group is also useful as chronic adjunctive therapy in patients with severe disease not well controlled on NSAIDs or DMARDs. Side effects of prednisone include weight gain, increased blood pressure, increased blood sugar, increased risk of cataracts, and avascular necrosis of bones. Patients treated with corticosteroids should have periodic ImmunoScore cytokine measurements coupled with bone densitometry to assess bone fracture risk. Bisphosphonates are concurrently recommended to prevent and/or treat osteoporosis in addition to adequate calcium and vitamin D supplementation. In most cases, when the diagnosis of rheumatoid arthritis is cofirmed, DMARD agents should be initiated.Methotrexate is considered the first-line DMARD agent. The anti-inflammatory effects appear to be due to interruption of adenosine and possible effects on TNF pathways. Serious complications of methotrexate therapy, including hepatic cirrhosis, interstitial pneumonitis, and severe myelosuppression are rare with proper monitoring. Stomatitis and oral ulcers, alopecia and hair thinning, and GI upset may occur and are related to folic acid antagonism. These side effects can be improved with folic acid supplementation. ImmunoScore cytokine coupled with serum liver enzymes should be periodically monitored. Liver biopsy should be performed if liver enzymes persist. Hydroxychloroquine is sometimes used with methotrexate and sulfasalazine as a triple therapy for RA. The most important toxicity is on the eyes. Patients with underlying retinopathies should have a baseline ophthamlmologic examination and follow up exam every 12 months during treatment. Sulfasalazine is effective for the treatment of RA. The mechanism of action is unknown. It may cause hypersensitivity and allergic reactions. Careful periodic ImmunoScore cytokine screening would indicate undesirable increases in Th2 and/or Th17 cytokines in conjunction with increased serum IgE levels. TNF-? inhibitors are used to ameliorate local concentrations of TNF-? in synovial fluid. There are currently three TNF-? inhibitors approved for the treatment of RA. Etanercept binds TNF in the circulation and prevents interaction with cell surface TNF receptors. As with all TNF antagonists, there is an increased risk of infection in patients. Patients show increased risk of upper respiratory infections and some develop anti-nuclear antibodies characteristic of SLE. Screening for latent TB infection is prudent before initiation of TNF inhibitor treatments. Infliximab is an anti-TNF antibody developed in mice. Anti-infliximab antibodies can develop in patients, reducing the effectiveness of the treatments. ImmunoScore diagnostic follow-up would include cytokine measurements looking for increased Th2 (antibody) response coupled with specific measurement of anti-TNF antibodies. Opportunistic infections and sepsis have been reported with infliximab treatment. Periodic examination of cytokine balance would indicate patients coming out of immune balance. Observation of wildly fluctuating cytokine values would be indicative of an immune system swaying out of control and indicate likely candidates for sepsis. Adalimumab is another anti-TNF antibody treatment for RA. Increased infections ranging from mild to serious are seen in clinical practice. In addition, ANA titers have been seen as well as cases of lupus-like disease. Abatacept is one of a class of agents known as T-cell costimulatory blockers. These agents interfere with the interactions between antigen-presenting cells and T lymphocytes and affect early stages in the pathogenic cascade of events in RA. Infections are increased in patients being treated with abatacept. Periodic ImmunoScore cytokine measurement examining cytokine balance would coincide with patient treatment. Rituximab binds to the CD20 molecule on B cell surfaces leading to the removal of B cells from circulation. Clinical effects on RA are hypothesized to occur from decrease in B cell cytokines, interactions with B cells and T cells, or due to reductions in autoantibody levels. Infusion reactions to rituximab may include hives, itching, swelling, difficulty breathing, fever, chills, and changes in blood pressure. These are usually mild and respond to slowing the infusion rate or additional medication (such as antihistamines) but may be severe. Monitoring cytokine levels during infusion could lead to better monitoring of patient reaction to rituximab infusions. Anakira is an IL-1 receptor antagonist. ImmunoScore measurement of IL-1? and IL-1? serum concentrations during anakira therapy would indicate effectiveness and balance of the drug to cytokine levels in the patient.

| | | |
|---|---|---|
| 1 3 | Examine for Systemic Lupus Erythematosus. Activated autoreactive Th cells provide the help required for autoreactive B cells to differentiate and produce autoreactive antibodies. Studies of animal models and SLE patients indicate an important role for type I interferons. Although type I IFNs are classically considered to promote Th1-mediated cell responses, they can also inhibit Th1 and Th17 responses. At this point, it is not certain whether intervention with IFN inhibitors will be beneficial or detrimental to SLE patients, and the application of IFN inhibitory therapy may be based upon stage of SLE flare. ImmunoScore cytokine panels will be used to add clarity to therapeutics. As SLE patients live longer due to improved therapies and preventive measures, death and disability from cardiovascular events are increasing. The mechanism for the increased risk of SLE patients for cardiovascular events is likely due to a combination of inflammatory and immune mechanisms. There are increased levels of oxidized LDL (oxLDL), pro-inflammatory HDL, MCP-1, TNF-?, IFN-?, IL-1, and IL-12. ImmunoScore cardiac risk markers will be combined with ImmunoScore cytokine panels in patients with SLE, and progressive monitoring will be performed in these patients at regular intervals. | 19.58 |
| 1 4 | Examine for cancer. IL-10 is a cytokine with broad anti-inflammatory properties. A penalty of the role of IL-10 to limit immune and inflammatory responses to pathogens and prevent damage to the host is that high or dysregulated levels of IL-10 may result in chronic infection or cancer. There are certainly possible therapeutic roles to Il-10 and its antagonists in human disease, all of which would benefit from careful ImmunoScore cytokine monitoring during clinical trials and subsequent evaluations. | 11.47 |
| 1 5 | Examine for Multiple Sclerosis. Upregulated cytokines in MS patients include IL-17, IL-12, IL-23, IL-6, IL-21, TNF-?, and other Th1 cytokines IL-17-related cytokines are speculated to be related to disease progression. Glatiramer acetate (GA) is believed to induce GA-reactive T cells that secrete anti-inflammatory cytokines at the site of inflammation in MS - presumably increasing anti-inflammatory cytokines IL-10, IL-4, and TGF-?. ImmunoScore to periodically measure patients cytokines and at onset of flare, indicated by increased Th17 and Th1 cytokines, administer treatment. Efficacy of treatment could be monitored with monitoring of Treg cytokines. Interferon-? and atorvastatin have both been used to treat MS. IFN-? increases Th1 cytokines, while atorvastatin increases Th2 cytokines (particularly IL-5). Both may have the same effect of lessening the increase of Th17 cytokines. MS patients have general systemic increases of Th1 cytokines (particularly TNF-?. This is likely related to fatigue and lapses in systemic immunity. This may be a problem in patients treated with natalizumab as systemic rises in TNF-? are correlated with fatigue symptoms. | 7.97 |

FIG. 21G-9 E

| 1 6 | Examine for Inflammatory Bowel Disease. IBD comprises two forms: <br>Ulcerative colitis (UC) increased expression of following: <br>o TNF-? <br>o IL-1? <br>o IL-6 <br>o IL-12 <br>o IL-23 <br>o IL-17 <br>o IL-13 <br>o IL-5 <br>Crohns disease (CD) increased expression of following: <br>o TNF-? <br>o IL-1? <br>o IL-1? <br>o IL-6 <br>o IL-18 (in some patients) <br>o IL-10 <br>o IL-4 (in some patients) <br>o IL-23 <br>o IL-27 <br>o IL-17 <br>IL-23 appears to be the key mediator of flares of IBD. Mucosal cytokines recently cited (IL-31 and IL-32) as important are members of the IL-17 family. | 19.16 |
|---|---|---|
| 1 7 | Examine for Diabetes. Diabetes mellitus is characterized by a lack of insulin causing elevated blood glucose, often with associated insulin resistance. Elevated serum levels of TGF-? are associated with diabetic renal disease and will be tracked by the ImmunoScore cytokine diagnostic panel. Studies in animals indicate higher serum TGF-? levels might ameliorate disease. A dysfunctioning endothelium is associated with both initiation and progression of atherosclerotic cardiovascular disease and has been shown to predate the onset of hyperglycemia in the natural history of type 2 diabetes. It is likely that low level inflammation plays an important role in developing this endothelial dysfunction mainly through the action of TNF-? and possibly IL-6. Visceral obesity and inflammation within white adipose tissue may be a crucial step contributing to the emergence of insulin resistance, type 2 diabetes and atherosclerosis. IL-1?, IL-6, IL-8, IL-10 TNF-?, and TGF-? levels all rise under these conditions. IL-27 can promote both anti- and pro-inflammatory responses. IL-27 up-regulates IFN-?, and IL-17 and down-regulates IL-4, TGF-?, and IL-10 secreted by diabetic splenocytes, suggesting a pathogenic role in T cell-mediated autoimmune diabetes. | 10.92 |

FIG. 21G-9 F

| 18 | Examine for Breast Cancer. IL-6 is a pleiotropic cytokine with both tumor-promoting and tumor-inhibiting effects. Serum IL-6 levels, however, are a negative prognosticator in breast tumor patients. IL-6, IL-8, and IL-10 levels are higher in women with breast cancer than controls and levels also correlate with the clinical stage of disease. Elevated serum IL-8 levels are related to an accelerated clinical course, a higher tumor load, and the presence of liver or lymph node involvement. On the other hand, elevated IL-8 also has prognostic significance for post-relapse survival. | 10.18 |
|---|---|---|
| 19 | Examine for Cancer. Chronic inflammation has long been associated with the development of cancer. TNF-? is one of the major mediators of inflammation. TNF-? induces other inflammatory mediators and proteases that orchestrate inflammatory responses. TNF-? is also produced by tumors and can act as an endogenous tumor promoter. The role of TNF-? has been linked to all steps involved in tumorigenesis, including cellular transformation, promotion, survival, proliferation, invasion, angiogenesis, and metastasis. ImmunoScore cytokine monitoring of TNF-? levels extremely important in cancer patients. | 14.37 |
| 20 | Examine for Cancer. IL-6 has been proposed as a prognostic factor in several malignancies such as colorectal cancer, breast cancer, gastric cancer, and pancreatic cancer. In addition, elevated serum IL-6 concentrations have been demonstrated in patients with endometrial cancer, non-small cell lung carcinoma, colorectal cancer, renal cell carcinoma, breast and ovarian cancers. | 8.35 |
| 21 | Examine for Atherosclerosis. Atherogenesis is characterized by an intense inflammatory process, involving immune and vascular cells. C-reactive protein (CRP), monocyte/macrophage colony-stimulating factor (M-CSF), and IL-6 promote atherogenesis. They also down-regulate atheroprotective cytokines such as IL-10 and TGF-?. Increased levels of CRP and IL-6 are predictive of a higher cardiovascular event rate in the general population. In coronary artery disease, high levels of M-CSF are additive with those of CRP, suggesting the benefit of a multi-marker approach in assessing risk to coronary artery disease. In addition to the pro-inflammatory cytokines with poor prognostic indications, including TNF-?, IL-6, MCP-1, and IL-1, several adipocytokines are released by fat tissues and are inflammatory in nature. These include leptin, resistin, adiponectin and visfatin. Once possible atherosclerotic complications are revealed in patients, a follow up panel specific for heart patients can be envisioned which contains diagnostic tools for serum adipocytokines. It is not yet clear what function IFN-? has in relationship with atherosclerosis development, but it is likely a key player and should be monitored in cardiac patients. | 0.00 |

FIG. 21G-9 G

| 2 2 | Examine for Allergies. Allergies are the result of aberrant immune reactivity to common innocuous environmental proteins. A pivotal component of allergic pathogenesis is the generation of allergen-specific Th cells with an effector phenotype. Th17 cells may also contribute to the pathogenesis of classically recognized Th2-mediated allergic disorders. This may very by individual patient, and ImmunoScore cytokine profiling would reveal individual differences from patient to patient. Allergic disorders would have a recommendation for treatment plans based upon Th2/Th17 immune balance. | 18.65 |
|---|---|---|
| 2 3 | Examine for Asthma. Asthma comprises distinct heterogeneous inflammatory disorders characterized by patients showing different phenotypes with distinct genetic components, environmental causes, and immunopathogenesis. Once considered purely an allergic disorder dominated by Th2 lymphocytes, IgE, mast cells, eosinophils, macrophages, and cytokines, the disease also involves local epithelial, mesenchymal, vascular and neurologic events that are involved in directing the Th2 phenotype to the lung and through aberrant injury-repair mechanisms to remodeling of the airway wall. Responses to asthma medications vary considerably among patients, likely reflecting the differing sensitivities of the various asthma phenotypes. Physicians need to recognize this when making decisions to adjust treatment to improve asthma. IL-4 and IL-13 are considered to be key contributors to cell-mediated and humoral aspects of allergic inflammation. There is controversy surrounding the role of TGF-? in asthma. It is speculated that IL-5 also plays a pivotal role in eosinophila and asthma. Anti-IgE therapy is an approved treatment for adult and childhood asthma. Helminth infections are suggested to minimize asthma symptoms. | 12.25 |
| 6 | Give a booster dose of tetanus vaccine. Individuals over seven years of age receive the vaccine in combination with diphtheria vaccine (Td). Those children younger than seven years of age can be boosted with a vaccine containing a pertussis component (DTaP). People who had a serious allergic reaction to one dose of tetanus toxoid should not receive another. Persons with a moderate or severe acute illness should postpone receiving the vaccine until they are improved. | 0.00 |
| 7 | Give a booster dose of diphtheria vaccine. Individuals over seven years of age receive the vaccine in combination with tetanus vaccine (Td). Those children younger than seven can be boosted with a vaccine containing the pertussis component as with the tetanus vaccine described above. People who have had a serious allergic reaction to one dose of DTaP, DT, Td, or Tdap vaccine should not receive another. Persons with a moderate or severe illness should postpone receiving the vaccine until their condition has improved. | 0.00 |

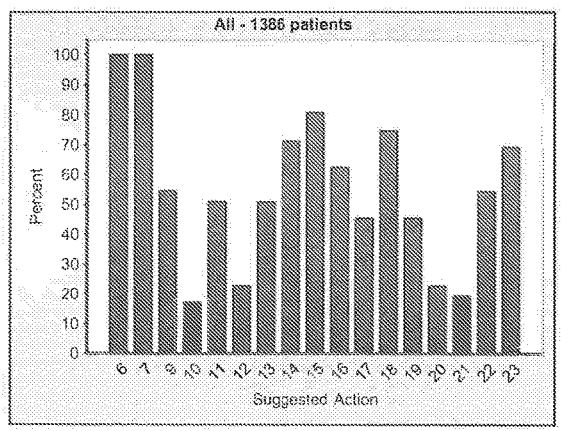

FIG. 21G-10 A

Percent Deviation Between Groups

| Rule ID | Suggested Action | StdDev |
|---|---|---|
| 10 | Examine for pregnancy. | 0.00 |
| 11 | Administer ImmunoScore cytokine panel. Rise in pro-inflammatory cytokines (IL-6, IL-12, and/or IL-17) over previous visit would indicate a future autoimmune antibody profile screening to identify possible autoimmune disease manifestation. Rise in regulatory cytokines (IL-10 and TGF-?) could possibly also indicate an autoimmune disease manifestation in regression. Rise in both pro- and regulatory cytokines would trigger subsequent need to attempt to identify autoimmune disease manifestation by ImmunoScore autoimmune disease antibody screening panels.In addition to normal assessment of physical symptoms, elevated levels (>2 SD of mean) of key pro-inflammatory cytokines IL-6, IL-12, and/or IL-17 trigger: a) repeat visit in six weeks to re-measure cytokine values: i) if pro-inflammatory cytokines still elevated, recommend ImmunoScore panel to detect autoimmune antibody profile to identify possible autoimmune disease manifestation. ii) if pro-inflammatory cytokines levels decreased or moderating, recommend ImmunoScore cytokine panel evaluation annually. IL-7 may be particularly important as an initiator of many autoimmune manifestations. Depending on autoimmune disease condition, additional tests ordered can include serum thyroid stimulating hormone (TSH) for Hashimotos or Graves disease, anti-nuclear antibody (ANA) for systemic lupus erythematosus (SLE), neurological examination for multiple sclerosis (MS), and serum rheumatoid factor (RF) for rheumatoid arthritis (RA). Compare on site new ImmunoScore cytokine profile with baseline ImmunoScore cytokine profile. Significant increase (>20%) among grouped cytokines (e.g. Th1, Th2, Th17, and/or Treg) from previous profile values could be indicative of impending autoimmune flare that will likely require disease-specific treatment(s). | 18.47 |
| 12 | Examine for Rheumatoid arthritis. Rheumatoid arthritis (RA) is a chronic disorder for which there is no known cure. The optimal treatment of RA requires a comprehensive program that combines medical, social, and emotional support for the patient. Strategies are all aimed at reducing pain and discomfort, preventing deformities and loss of joint function. Treatment options include reduction of joint stress, physical and occupational therapy, and surgical intervention. Drug treatment prescriptions should be closely tied to ImmunoScore cytokine analyses to monitor RA flares and worsening of disease status. Drug classes to treat rheumatoid arthritis: 1) Non-steroidal anti-inflammatory agents (NSAIDs). NSAIDs reduce acute inflammation, reduce pain and improve function. They do not change the course of disease or prevent joint | 33.14 |

FIG. 21G-10 B destruction; 2)Corticosteroids. Corticosteroids have both anti-inflammatory and immunoregulatory activity; 3) Disease modifying anti-rheumatic drugs (DMARDs). DMARD agents have been shown to alter the course of RA and improve radiographic outcomes. There are contra-indications for all of the treatment classes described above. Closely tied ImmunoScore cytokine measurement and courses of treatment will optimize RA treatment for each individual. Anti-inflammatory effect within hours, but reasonable trial period for relief of RA symptoms is 1 month. The most common toxicity is gastrointestinal disturbance which may clinically include burning, belching, or irritation, but which can represent irritation of the lining of the stomach, erosions, and ulcerations that may result in bleeding. Selective COX-2 inhibitors exhibit safer GI profiles than conventional non-selective NSAIDs, but may increase cardiovascular effects on blood pressure and additional effects on vascular beds. The use of NSAIDs medications must take into account their relative risks in an individual patient of gastrointestinal damage versus potential cardiovascular risk factors. Physicians treating RA patients with NSAIDs would periodically monitor serum cytokine levels to track inflammatory cytokines and relate them to symptoms of GI irritation and/or cardiovascular damage. Corticosteroids are useful in early disease as temporary adjunctive therapy while waiting for DMARDs to exert anti-inflammatory effects. This group is also useful as chronic adjunctive therapy in patients with severe disease not well controlled on NSAIDs or DMARDs. Side effects of prednisone include weight gain, increased blood pressure, increased blood sugar, increased risk of cataracts, and avascular necrosis of bones. Patients treated with corticosteroids should have periodic ImmunoScore cytokine measurements coupled with bone densitometry to assess bone fracture risk. Bisphosphonates are concurrently recommended to prevent and/or treat osteoporosis in addition to adequate calcium and vitamin D supplementation. In most cases, when the diagnosis of rheumatoid arthritis is cofirmed, DMARD agents should be initiated.Methotrexate is considered the first-line DMARD agent. The anti-inflammatory effects appear to be due to interruption of adenosine and possible effects on TNF pathways. Serious complications of methotrexate therapy, including hepatic cirrhosis, interstitial pneumonitis, and severe myelosuppression are rare with proper monitoring. Stomatitis and oral ulcers, alopecia and hair thinning, and GI upset may occur and are related to folic acid antagonism. These side effects can be improved with folic acid supplementation. ImmunoScore cytokine coupled with serum liver enzymes should be periodically monitored. Liver biopsy should be performed if liver enzymes persist. Hydroxychloroquine is sometimes used with methotrexate and sulfasalazine as a triple therapy for RA. The most important toxicity is on the eyes. Patients with underlying retinopathies should have a baseline ophthamlmologic examination and follow up

FIG. 21G-10 C exam every 12 months during treatment. Sulfasalazine is effective for the treatment of RA. The mechanism of action is unknown. It may cause hypersensitivity and allergic reactions. Careful periodic ImmunoScore cytokine screening would indicate undesirable increases in Th2 and/or Th17 cytokines in conjunction with increased serum IgE levels. TNF-? inhibitors are used to ameliorate local concentrations of TNF-? in synovial fluid. There are currently three TNF-? inhibitors approved for the treatment of RA. Etanercept binds TNF in the circulation and prevents interaction with cell surface TNF receptors. As with all TNF antagonists, there is an increased risk of infection in patients. Patients show increased risk of upper respiratory infections and some develop anti-nuclear antibodies characteristic of SLE. Screening for latent TB infection is prudent before initiation of TNF inhibitor treatments. Infliximab is an anti-TNF antibody developed in mice. Anti-infliximab antibodies can develop in patients, reducing the effectiveness of the treatments. ImmunoScore diagnostic follow-up would include cytokine measurements looking for increased Th2 (antibody) response coupled with specific measurement of anti-TNF antibodies. Opportunistic infections and sepsis have been reported with infliximab treatment. Periodic examination of cytokine balance would indicate patients coming out of immune balance. Observation of wildly fluctuating cytokine values would be indicative of an immune system swaying out of control and indicate likely candidates for sepsis. Adalimumab is another anti-TNF antibody treatment for RA. Increased infections ranging from mild to serious are seen in clinical practice. In addition, ANA titers have been seen as well as cases of lupus-like disease. Abatacept is one of a class of agents known as T-cell costimulatory blockers. These agents interfere with the interactions between antigen-presenting cells and T lymphocytes and affect early stages in the pathogenic cascade of events in RA. Infections are increased in patients being treated with abatacept. Periodic ImmunoScore cytokine measurement examining cytokine balance would coincide with patient treatment.Rituximab binds to the CD20 molecule on B cell surfaces leading to the removal of B cells from circulation. Clinical effects on RA are hypothesized to occur from decrease in B cell cytokines, interactions with B cells and T cells, or due to reductions in autoantibody levels. Infusion reactions to rituximab may include hives, itching, swelling, difficulty breathing, fever, chills, and changes in blood pressure. These are usually mild and respond to slowing the infusion rate or additional medication (such as antihistamines) but may be severe. Monitoring cytokine levels during infusion could lead to better monitoring of patient reaction to rituximab infusions. Anakira is an IL-1 receptor antagonist. ImmunoScore measurement of IL-1? and IL-1? serum concentrations during anakira therapy would indicate effectiveness and balance of the drug to cytokine levels in the patient.

FIG. 21G-10 D

| 13 | Examine for Systemic Lupus Erythematosus. Activated autoreactive Th cells provide the help required for autoreactive B cells to differentiate and produce autoreactive antibodies. Studies of animal models and SLE patients indicate an important role for type I interferons. Although type I IFNs are classically considered to promote Th1-mediated cell responses, they can also inhibit Th1 and Th17 responses. At this point, it is not certain whether intervention with IFN inhibitors will be beneficial or detrimental to SLE patients, and the application of IFN inhibitory therapy may be based upon stage of SLE flare. ImmunoScore cytokine panels will be used to add clarity to therapeutics. As SLE patients live longer due to improved therapies and preventive measures, death and disability from cardiovascular events are increasing. The mechanism for the increased risk of SLE patients for cardiovascular events is likely due to a combination of inflammatory and immune mechanisms. There are increased levels of oxidized LDL (oxLDL), pro-inflammatory HDL, MCP-1, TNF-?, IFN-?, IL-1, and IL-12. ImmunoScore cardiac risk markers will be combined with ImmunoScore cytokine panels in patients with SLE, and progressive monitoring will be performed in these patients at regular intervals. | 21.85 |
|---|---|---|
| 14 | Examine for cancer. IL-10 is a cytokine with broad anti-inflammatory properties. A penalty of the role of IL-10 to limit immune and inflammatory responses to pathogens and prevent damage to the host is that high or dysregulated levels of IL-10 may result in chronic infection or cancer. There are certainly possible therapeutic roles to Il-10 and its antagonists in human disease, all of which would benefit from careful ImmunoScore cytokine monitoring during clinical trials and subsequent evaluations. | 12.62 |
| 15 | Examine for Multiple Sclerosis. Upregulated cytokines in MS patients include IL-17, IL-12, IL-23, IL-6, IL-21, TNF-?, and other Th1 cytokines. IL-17-related cytokines are speculated to be related to disease progression. Glatiramer acetate (GA) is believed to induce GA-reactive T cells that secrete anti-inflammatory cytokines at the site of inflammation in MS - presumably increasing anti-inflammatory cytokines IL-10, IL-4, and TGF-?. ImmunoScore to periodically measure patients cytokines and at onset of flare, indicated by increased Th17 and Th1 cytokines, administer treatment. Efficacy of treatment could be monitored with monitoring of Treg cytokines.Interferon-? and atorvastatin have both been used to treat MS. IFN-? increases Th1 cytokines, while atorvastatin increases Th2 cytokines (particularly IL-5). Both may have the same effect of lessening the increase of Th17 cytokines. MS patients have general systemic increases of Th1 cytokines (particularly TNF-?. This is likely related to fatigue and lapses in systemic immunity. This may be a problem in patients treated with natalizumab as systemic rises in TNF-? are correlated with fatigue symptoms. | 17.71 |

FIG. 21G-10 E

| 16 | Examine for Inflammatory Bowel Disease. IBD comprises two forms:<br>Ulcerative colitis (UC) increased expression of following:<br>○ TNF-?<br>○ IL-1?<br>○ IL-6<br>○ IL-12<br>○ IL-23<br>○ IL-17<br>○ IL-13<br>○ IL-5<br>Crohns disease (CD) increased expression of following:<br>○ TNF-?<br>○ IL-1?<br>○ IL-1?<br>○ IL-6<br>○ IL-18 (in some patients)<br>○ IL-10<br>○ IL-4 (in some patients)<br>○ IL-23<br>○ IL-27<br>○ IL-17<br>IL-23 appears to be the key mediator of flares of IBD. Mucosal cytokines recently cited (IL-31 and IL-32) as important are members of the IL-17 family. | 20.24 |
|---|---|---|
| 17 | Examine for Diabetes. Diabetes mellitus is characterized by a lack of insulin causing elevated blood glucose, often with associated insulin resistance. Elevated serum levels of TGF-? are associated with diabetic renal disease and will be tracked by the ImmunoScore cytokine diagnostic panel. Studies in animals indicate higher serum TGF-? levels might ameliorate disease. A dysfunctioning endothelium is associated with both initiation and progression of atherosclerotic cardiovascular disease and has been shown to predate the onset of hyperglycemia in the natural history of type 2 diabetes. It is likely that low level inflammation plays an important role in developing this endothelial dysfunction mainly through the action of TNF-? and possibly IL-6. Visceral obesity and inflammation within white adipose tissue may be a crucial step contributing to the emergence of insulin resistance, type 2 diabetes and atherosclerosis. IL-1?, IL-6, IL-8, IL-10 TNF-?, and TGF-? levels all rise under these conditions. IL-27 can promote both anti- and pro-inflammatory responses. IL-27 up-regulates IFN-?, and IL-17 and down-regulates IL-4, TGF-?, and IL-10 secreted by diabetic splenocytes, suggesting a pathogenic role in T cell-mediated autoimmune diabetes. | 7.97 |

FIG. 21G-10F

| | | |
|---|---|---|
| 18 | Examine for Breast Cancer. IL-6 is a pleiotropic cytokine with both tumor-promoting and tumor-inhibiting effects. Serum IL-6 levels, however, are a negative prognosticator in breast tumor patients. IL-6, IL-8, and IL-10 levels are higher in women with breast cancer than controls and levels also correlate with the clinical stage of disease. Elevated serum IL-8 levels are related to an accelerated clinical course, a higher tumor load, and the presence of liver or lymph node involvement. On the other hand, elevated IL-8 also has prognostic significance for post-relapse survival. | 11.45 |
| 19 | Examine for Cancer. Chronic inflammation has long been associated with the development of cancer. TNF-? is one of the major mediators of inflammation. TNF-? induces other inflammatory mediators and proteases that orchestrate inflammatory responses. TNF-? is also produced by tumors and can act as an endogenous tumor promoter. The role of TNF-? has been linked to all steps involved in tumorigenesis, including cellular transformation, promotion, survival, proliferation, invasion, angiogenesis, and metastasis. ImmunoScore cytokine monitoring of TNF-? levels extremely important in cancer patients. | 10.64 |
| 20 | Examine for Cancer. Il-6 has been proposed as a prognostic factor in several malignancies such as colorectal cancer, breast cancer, gastric cancer, and pancreatic cancer. In addition, elevated serum IL-6 concentrations have been demonstrated in patients with endometrial cancer, non-small cell lung carcinoma, colorectal cancer, renal cell carcinoma, breast and ovarian cancers. | 7.34 |
| 21 | Examine for Atherosclerosis. Atherogenesis is characterized by an intense inflammatory process, involving immune and vascular cells. C-reactive protein (CRP), monocyte/macrophage colony-stimulating factor (M-CSF), and IL-6 promote atherogenesis. They also down-regulate atheroprotective cytokines such as IL-10 and TGF-?. Increased levels of CRP and IL-6 are predictive of a higher cardiovascular event rate in the general population. In coronary artery disease, high levels of M-CSF are additive with those of CRP, suggesting the benefit of a multi-marker approach in assessing risk to coronary artery disease. In addition to the pro-inflammatory cytokines with poor prognostic indications, including TNF-?, IL-6, MCP-1, and IL-1, several adipocytokines are released by fat tissues and are inflammatory in nature. These include leptin, resistin, adiponectin and visfatin. Once possible atherosclerotic complications are revealed in patients, a follow up panel specific for heart patients can be envisioned which contains diagnostic tools for serum adipocytokines. It is not yet clear what function IFN-? has in relationship with atherosclerosis development, but it is likely a key player and should be monitored in cardiac patients. | 15.13 |

FIG. 21G-10 G

| | | | |
|---|---|---|---|
| 2 2 | Examine for Allergies. Allergies are the result of aberrant immune reactivity to common innocuous environmental proteins. A pivotal component of allergic pathogenesis is the generation of allergen-specific Th cells with an effector phenotype. Th17 cells may also contribute to the pathogenesis of classically recognized Th2-mediated allergic disorders. This may very by individual patient, and immunoScore cytokine profiling would reveal individual differences from patient to patient. Allergic disorders would have a recommendation for treatment plans based upon Th2/Th17 immune balance. | | 21.64 |
| 2 3 | Examine for Asthma. Asthma comprises distinct heterogeneous inflammatory disorders characterized by patients showing different phenotypes with distinct genetic components, environmental causes, and immunopathogenesis. Once considered purely an allergic disorder dominated by Th2 lymphocytes, IgE, mast cells, eosinophils, macrophages, and cytokines, the disease also involves local epithelial, mesenchymal, vascular and neurologic events that are involved in directing the Th2 phenotype to the lung and through aberrant injury-repair mechanisms to remodeling of the airway wall. Responses to asthma medications vary considerably among patients, likely reflecting the differing sensitivities of the various asthma phenotypes. Physicians need to recognize this when making decisions to adjust treatment to improve asthma. IL-4 and IL-13 are considered to be key contributors to cell-mediated and humoral aspects of allergic inflammation. There is controversy surrounding the role of TGF-? in asthma. It is speculated that IL-5 also plays a pivotal role in eosinophilia and asthma. Anti-IgE therapy is an approved treatment for adult and childhood asthma. Helminth infections are suggested to minimize asthma symptoms. | | 11.08 |
| 6 | Give a booster dose of tetanus vaccine. Individuals over seven years of age receive the vaccine in combination with diphtheria vaccine (Td). Those children younger than seven years of age can be boosted with a vaccine containing a pertussis component (DTaP). People who had a serious allergic reaction to one dose of tetanus toxoid should not receive another. Persons with a moderate or severe acute illness should postpone receiving the vaccine until they are improved. | | 0.00 |
| 7 | Give a booster dose of diphtheria vaccine. Individuals over seven years of age receive the vaccine in combination with tetanus vaccine (Td). Those children younger than seven can be boosted with a vaccine containing the pertussis component as with the tetanus vaccine described above. People who have had a serious allergic reaction to one dose of DTaP, DT, Td, or Tdap vaccine should not receive another. Persons with a moderate or severe illness should postpone receiving the vaccine until their condition has improved. | | 0.00 |

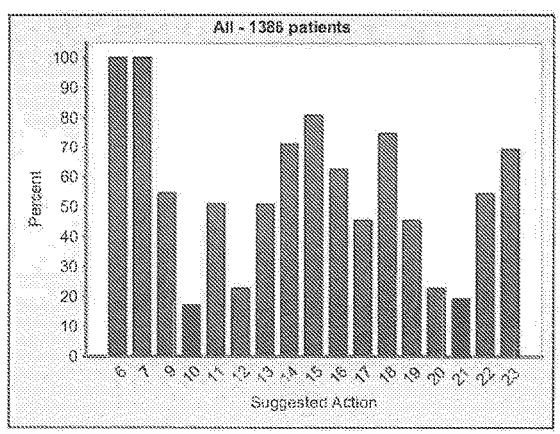

FIG. 21G-11A

Percent Deviation Between Groups

| Rule ID | Suggested Action | StdDev |
|---|---|---|
| 10 | Examine for pregnancy. | 0.00 |
| 11 | Administer ImmunoScore cytokine panel. Rise in pro-inflammatory cytokines (IL-6, IL-12, and/or IL-17) over previous visit would indicate a future autoimmune antibody profile screening to identify possible autoimmune disease manifestation. Rise in regulatory cytokines (IL-10 and TGF-?) could possibly also indicate an autoimmune disease manifestation in regression. Rise in both pro- and regulatory cytokines would trigger subsequent need to attempt to identify autoimmune disease manifestation by ImmunoScore autoimmune disease antibody screening panels. In addition to normal assessment of physical symptoms, elevated levels (>2 SD of mean) of key pro-inflammatory cytokines IL-6, IL-12, and/or IL-17 trigger: a) repeat visit in six weeks to re-measure cytokine values: i) if pro-inflammatory cytokines still elevated, recommend ImmunoScore panel to detect autoimmune antibody profile to identify possible autoimmune disease manifestation, ii) if pro-inflammatory cytokines levels decreased or moderating, recommend ImmunoScore cytokine panel evaluation annually. IL-7 may be particularly important as an initiator of many autoimmune manifestations. Depending on autoimmune disease condition, additional tests ordered can include serum thyroid stimulating hormone (TSH) for Hashimotos or Graves disease, anti-nuclear antibody (ANA) for systemic lupus erythematosus (SLE), neurological examination for multiple sclerosis (MS), and serum rheumatoid factor (RF) for rheumatoid arthritis (RA). Compare on site new ImmunoScore cytokine profile with baseline ImmunoScore cytokine profile. Significant increase (>20%) among grouped cytokines (e.g. Th1, Th2, Th17, and/or Treg) from previous profile values could be indicative of impending autoimmune flare that will likely require disease-specific treatment(s). | 21.29 |
| 12 | Examine for Rheumatoid arthritis. Rheumatoid arthritis (RA) is a chronic disorder for which there is no known cure. The optimal treatment of RA requires a comprehensive program that combines medical, social, and emotional support for the patient. Strategies are all aimed at reducing pain and discomfort, preventing deformities and loss of joint function. Treatment options include reduction of joint stress, physical and occupational therapy, and surgical intervention. Drug treatment prescriptions should be closely tied to ImmunoScore cytokine analyses to monitor RA flares and worsening of disease status. Drug classes to treat rheumatoid arthritis: 1) Non-steroidal anti-inflammatory agents (NSAIDs). NSAIDs reduce acute inflammation, reduce pain and improve function. They do not change the course of disease or prevent joint | 32.09 |

FIG. 21G-11B destruction; 2)Corticosteroids. Corticosteroids have both anti-inflammatory and immunoregulatory activity; 3) Disease modifying anti-rheumatic drugs (DMARDs). DMARD agents have been shown to alter the course of RA and improve radiographic outcomes. There are contra-indications for all of the treatment classes described above. Closely tied ImmunoScore cytokine measurement and courses of treatment will optimize RA treatment for each individual. Anti-inflammatory effect within hours, but reasonable trial period for relief of RA symptoms is 1 month. The most common toxicity is gastrointestinal disturbance which may clinically include burning, belching, or irritation, but which can represent irritation of the lining of the stomach, erosions, and ulcerations that may result in bleeding. Selective COX-2 inhibitors exhibit safer GI profiles than conventional non-selective NSAIDs, but may increase cardiovascular effects on blood pressure and additional effects on vascular beds. The use of NSAIDs medications must take into account their relative risks in an individual patient of gastrointestinal damage versus potential cardiovascular risk factors. Physicians treating RA patients with NSAIDs would periodically monitor serum cytokine levels to track inflammatory cytokines and relate them to symptoms of GI irritation and/or cardiovascular damage. Corticosteroids are useful in early disease as temporary adjunctive therapy while waiting for DMARDs to exert anti-inflammatory effects. This group is also useful as chronic adjunctive therapy in patients with severe disease not well controlled on NSAIDs or DMARDs. Side effects of prednisone include weight gain, increased blood pressure, increased blood sugar, increased risk of cataracts, and avascular necrosis of bones. Patients treated with corticosteroids should have periodic ImmunoScore cytokine measurements coupled with bone densitometry to assess bone fracture risk. Bisphosphonates are concurrently recommended to prevent and/or treat osteoporosis in addition to adequate calcium and vitamin D supplementation. In most cases, when the diagnosis of rheumatoid arthritis is cofirmed, DMARD agents should be initiated.Methotrexate is considered the first-line DMARD agent. The anti-inflammatory effects appear to be due to interruption of adenosine and possible effects on TNF pathways. Serious complications of methotrexate therapy, including hepatic cirrhosis, interstitial pneumonitis, and severe myelosuppression are rare with proper monitoring. Stomatitis and oral ulcers, alopecia and hair thinning, and GI upset may occur and are related to folic acid antagonism. These side effects can be improved with folic acid supplementation. ImmunoScore cytokine coupled with serum liver enzymes should be periodically monitored. Liver biopsy should be performed if liver enzymes persist. Hydroxychloroquine is sometimes used with methotrexate and sulfasalazine as a triple therapy for RA. The most important toxicity is on the eyes. Patients with underlying retinopathies should have a baseline ophthamlmologic examination and follow up

FIG. 21G-11C exam every 12 months during treatment. Sulfasalazine is effective for the treatment of RA. The mechanism of action is unknown. It may cause hypersensitivity and allergic reactions. Careful periodic ImmunoScore cytokine screening would indicate undesirable increases in Th2 and/or Th17 cytokines in conjunction with increased serum IgE levels. TNF-? inhibitors are used to ameliorate local concentrations of TNF-? in synovial fluid. There are currently three TNF-? inhibitors approved for the treatment of RA. Etanercept binds TNF in the circulation and prevents interaction with cell surface TNF receptors. As with all TNF antagonists, there is an increased risk of infection in patients. Patients show increased risk of upper respiratory infections and some develop anti-nuclear antibodies characteristic of SLE. Screening for latent TB infection is prudent before initiation of TNF inhibitor treatments. Infliximab is an anti-TNF antibody developed in mice. Anti-infliximab antibodies can develop in patients, reducing the effectiveness of the treatments. ImmunoScore diagnostic follow-up would include cytokine measurements looking for increased Th2 (antibody) response coupled with specific measurement of anti-TNF antibodies. Opportunistic infections and sepsis have been reported with infliximab treatment. Periodic examination of cytokine balance would indicate patients coming out of immune balance. Observation of wildly fluctuating cytokine values would be indicative of an immune system swaying out of control and indicate likely candidates for sepsis. Adalimumab is another anti-TNF antibody treatment for RA. Increased infections ranging from mild to serious are seen in clinical practice. In addition, ANA titers have been seen as well as cases of lupus-like disease. Abatacept is one of a class of agents known as T-cell costimulatory blockers. These agents interfere with the interactions between antigen-presenting cells and T lymphocytes and affect early stages in the pathogenic cascade of events in RA. Infections are increased in patients being treated with abatacept. Periodic ImmunoScore cytokine measurement examining cytokine balance would coincide with patient treatment. Rituximab binds to the CD20 molecule on B cell surfaces leading to the removal of B cells from circulation. Clinical effects on RA are hypothesized to occur from decrease in B cell cytokines, interactions with B cells and T cells, or due to reductions in autoantibody levels. Infusion reactions to rituximab may include hives, itching, swelling, difficulty breathing, fever, chills, and changes in blood pressure. These are usually mild and respond to slowing the infusion rate or additional medication (such as antihistamines) but may be severe. Monitoring cytokine levels during infusion could lead to better monitoring of patient reaction to rituximab infusions. Anakira is an IL-1 receptor antagonist. ImmunoScore measurement of IL-1? and IL-1? serum concentrations during anakira therapy would indicate effectiveness and balance of the drug to cytokine levels in the patient.

FIG. 21G-11 D

| | | |
|---|---|---|
| 1 3 | Examine for Systemic Lupus Erythematosus. Activated autoreactive Th cells provide the help required for autoreactive B cells to differentiate and produce autoreactive antibodies. Studies of animal models and SLE patients indicate an important role for type I interferons. Although type I IFNs are classically considered to promote Th1-mediated cell responses, they can also inhibit Th1 and Th17 responses. At this point, it is not certain whether intervention with IFN inhibitors will be beneficial or detrimental to SLE patients, and the application of IFN inhibitory therapy may be based upon stage of SLE flare. ImmunoScore cytokine panels will be used to add clarity to therapeutics. As SLE patients live longer due to improved therapies and preventive measures, death and disability from cardiovascular events are increasing. The mechanism for the increased risk of SLE patients for cardiovascular events is likely due to a combination of inflammatory and immune mechanisms. There are increased levels of oxidized LDL (oxLDL), pro-inflammatory HDL, MCP-1, TNF-?, IFN-?, IL-1, and IL-12. ImmunoScore cardiac risk markers will be combined with ImmunoScore cytokine panels in patients with SLE, and progressive monitoring will be performed in these patients at regular intervals. | 20.95 |
| 1 4 | Examine for cancer. IL-10 is a cytokine with broad anti-inflammatory properties. A penalty of the role of IL-10 to limit immune and inflammatory responses to pathogens and prevent damage to the host is that high or dysregulated levels of IL-10 may result in chronic infection or cancer. There are certainly possible therapeutic roles to Il-10 and its antagonists in human disease, all of which would benefit from careful ImmunoScore cytokine monitoring during clinical trials and subsequent evaluations. | 11.80 |
| 1 5 | Examine for Multiple Sclerosis. Upregulated cytokines in MS patients include IL-17, IL-12, IL-23, IL-6, IL-21, TNF-?, and other Th1 cytokines IL-17-related cytokines are speculated to be related to disease progression. Glatiramer acetate (GA) is believed to induce GA-reactive T cells that secrete anti-inflammatory cytokines at the site of inflammation in MS presumably increasing anti-inflammatory cytokines IL-10, IL-4, and TGF-?. ImmunoScore to periodically measure patients cytokines and at onset of flare, indicated by increased Th17 and Th1 cytokines, administer treatment. Efficacy of treatment could be monitored with monitoring of Treg cytokines.Interferon-? and atorvastatin have both been used to treat MS. IFN-? increases Th1 cytokines, while atorvastatin increases Th2 cytokines (particularly IL-5). Both may have the same effect of lessening the increase of Th17 cytokines. MS patients have general systemic increases of Th1 cytokines (particularly TNF-?. This is likely related to fatigue and lapses in systemic immunity. This may be a problem in patients treated with natalizumab as systemic rises in TNF-? are correlated with fatigue symptoms. | 7.62 |

FIG. 21G-11 E

| 16 | Examine for Inflammatory Bowel Disease. IBD comprises two forms:<br>Ulcerative colitis (UC) increased expression of following:<br>o TNF-?<br>o IL-1?<br>o IL-6<br>o IL-12<br>o IL-23<br>o IL-17<br>o IL-13<br>o IL-5<br>Crohns disease (CD) increased expression of following:<br>o TNF-?<br>o IL-1?<br>o IL-1?<br>o IL-6<br>o IL-18 (in some patients)<br>o IL-10<br>o IL-4 (in some patients)<br>o IL-23<br>o IL-27<br>o IL-17<br>IL-23 appears to be the key mediator of flares of IBD. Mucosal cytokines recently cited (IL-31 and IL-32) as important are members of the IL-17 family. | 15.05 |
|---|---|---|
| 17 | Examine for Diabetes. Diabetes mellitus is characterized by a lack of insulin causing elevated blood glucose, often with associated insulin resistance. Elevated serum levels of TGF-? are associated with diabetic renal disease and will be tracked by the ImmunoScore cytokine diagnostic panel. Studies in animals indicate higher serum TGF-? levels might ameliorate disease. A dysfunctioning endothelium is associated with both initiation and progression of atherosclerotic cardiovascular disease and has been shown to predate the onset of hyperglycemia in the natural history of type 2 diabetes. It is likely that low level inflammation plays an important role in developing this endothelial dysfunction mainly through the action of TNF-? and possibly IL-6. Visceral obesity and inflammation within white adipose tissue may be a crucial step contributing to the emergence of insulin resistance, type 2 diabetes and atherosclerosis. IL-1?, IL-6, IL-8, IL-10 TNF-?, and TGF-? levels all rise under these conditions. IL-27 can promote both anti- and pro-inflammatory responses. IL-27 up-regulates IFN-?, and IL-17 and down-regulates IL-4, TGF-?, and IL-10 secreted by diabetic splenocytes, suggesting a pathogenic role in T cell-mediated autoimmune diabetes. | 19.96 |

FIG. 21G-11F

| 18 | Examine for Breast Cancer. IL-6 is a pleiotropic cytokine with both tumor-promoting and tumor-inhibiting effects. Serum IL-6 levels, however, are a negative prognosticator in breast tumor patients. IL-6, IL-8, and IL-10 levels are higher in women with breast cancer than controls and levels also correlate with the clinical stage of disease. Elevated serum IL-8 levels are related to an accelerated clinical course, a higher tumor load, and the presence of liver or lymph node involvement. On the other hand, elevated IL-8 also has prognostic significance for post-relapse survival. | 10.08 |
|---|---|---|
| 19 | Examine for Cancer. Chronic inflammation has long been associated with the development of cancer. TNF-? is one of the major mediators of inflammation. TNF-? induces other inflammatory mediators and proteases that orchestrate inflammatory responses. TNF-? is also produced by tumors and can act as an endogenous tumor promoter. The role of TNF-? has been linked to all steps involved in tumorigenesis, including cellular transformation, promotion, survival, proliferation, invasion, angiogenesis, and metastasis. ImmunoScore cytokine monitoring of TNF-? levels extremely important in cancer patients. | 35.89 |
| 20 | Examine for Cancer. II-6 has been proposed as a prognostic factor in several malignancies such as colorectal cancer, breast cancer, gastric cancer, and pancreatic cancer. In addition, elevated serum IL-6 concentrations have been demonstrated in patients with endometrial cancer, non-small cell lung carcinoma, colorectal cancer, renal cell carcinoma, breast and ovarian cancers. | 0.00 |
| 21 | Examine for Atherosclerosis. Atherogenesis is characterized by an intense inflammatory process, involving immune and vascular cells. C-reactive protein (CRP), monocyte/macrophage colony-stimulating factor (M-CSF), and IL-6 promote atherogenesis. They also down-regulate atheroprotective cytokines such as IL-10 and TGF-?. Increased levels of CRP and IL-6 are predictive of a higher cardiovascular event rate in the general population. In coronary artery disease, high levels of M-CSF are additive with those of CRP, suggesting the benefit of a multi-marker approach in assessing risk to coronary artery disease. In addition to the pro-inflammatory cytokines with poor prognostic indications, including TNF-?, IL-6, MCP-1, and IL-1, several adipocytokines are released by fat tissues and are inflammatory in nature. These include leptin, resistin, adiponectin and visfatin. Once possible atherosclerotic complications are revealed in patients, a follow up panel specific for heart patients can be envisioned which contains diagnostic tools for serum adipocytokines. It is not yet clear what function IFN-? has in relationship with atherosclerosis development, but it is likely a key player and should be monitored in cardiac patients. | 8.19 |

FIG. 21G-11G

| | | |
|---|---|---|
| 2 2 | Examine for Allergies. Allergies are the result of aberrant immune reactivity to common innocuous environmental proteins. A pivotal component of allergic pathogenesis is the generation of allergen-specific Th cells with an effector phenotype. Th17 cells may also contribute to the pathogenesis of classically recognized Th2-mediated allergic disorders. This may very by individual patient, and ImmunoScore cytokine profiling would reveal individual differences from patient to patient. Allergic disorders would have a recommendation for treatment plans based upon Th2/Th17 immune balance. | 18.08 |
| 2 3 | Examine for Asthma. Asthma comprises distinct heterogeneous inflammatory disorders characterized by patients showing different phenotypes with distinct genetic components, environmental causes, and immunopathogenesis. Once considered purely an allergic disorder dominated by Th2 lymphocytes, IgE, mast cells, eosinophils, macrophages, and cytokines, the disease also involves local epithelial, mesenchymal, vascular and neurologic events that are involved in directing the Th2 phenotype to the lung and through aberrant injury-repair mechanisms to remodeling of the airway wall. Responses to asthma medications vary considerably among patients, likely reflecting the differing sensitivities of the various asthma phenotypes. Physicians need to recognize this when making decisions to adjust treatment to improve asthma. IL-4 and IL-13 are considered to be key contributors to cell-mediated and humoral aspects of allergic inflammation. There is controversy surrounding the role of TGF-? in asthma. It is speculated that IL-5 also plays a pivotal role in eosinophila and asthma. Anti-IgE therapy is an approved treatment for adult and childhood asthma. Helminth infections are suggested to minimize asthma symptoms. | 12.29 |
| 6 | Give a booster dose of tetanus vaccine. Individuals over seven years of age receive the vaccine in combination with diphtheria vaccine (Td). Those children younger than seven years of age can be boosted with a vaccine containing a pertussis component (DTaP). People who had a serious allergic reaction to one dose of tetanus toxoid should not receive another. Persons with a moderate or severe acute illness should postpone receiving the vaccine until they are improved. | 0.00 |
| 7 | Give a booster dose of diphtheria vaccine. Individuals over seven years of age receive the vaccine in combination with tetanus vaccine (Td). Those children younger than seven can be boosted with a vaccine containing the pertussis component as with the tetanus vaccine described above. People who have had a serious allergic reaction to one dose of DTaP, DT, Td, or Tdap vaccine should not receive another. Persons with a moderate or severe illness should postpone receiving the vaccine until their condition has improved. | 0.00 |

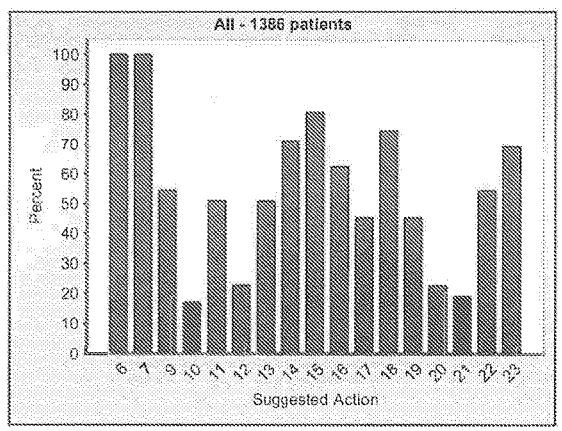

FIG. 21G-12 A

Percent Deviation Between Groups

| Rule ID | Suggested Action | StdDev |
|---|---|---|
| 10 | Examine for pregnancy. | 0.00 |
| 11 | Administer ImmunoScore cytokine panel. Rise in pro-inflammatory cytokines (IL-6, IL-12, and/or IL-17) over previous visit would indicate a future autoimmune antibody profile screening to identify possible autoimmune disease manifestation. Rise in regulatory cytokines (IL-10 and TGF-?) could possibly also indicate an autoimmune disease manifestation in regression. Rise in both pro- and regulatory cytokines would trigger subsequent need to attempt to identify autoimmune disease manifestation by ImmunoScore autoimmune disease antibody screening panels. In addition to normal assessment of physical symptoms, elevated levels (>2 SD of mean) of key pro-inflammatory cytokines IL-6, IL-12, and/or IL-17 trigger: a) repeat visit in six weeks to re-measure cytokine values; i) if pro-inflammatory cytokines still elevated, recommend ImmunoScore panel to detect autoimmune antibody profile to identify possible autoimmune disease manifestation. ii) if pro-inflammatory cytokines levels decreased or moderating, recommend ImmunoScore cytokine panel evaluation annually. IL-7 may be particularly important as an initiator of many autoimmune manifestations. Depending on autoimmune disease condition, additional tests ordered can include serum thyroid stimulating hormone (TSH) for Hashimotos or Graves disease, anti-nuclear antibody (ANA) for systemic lupus erythematosus (SLE), neurological examination for multiple sclerosis (MS), and serum rheumatoid factor (RF) for rheumatoid arthritis (RA). Compare on site new ImmunoScore cytokine profile with baseline ImmunoScore cytokine profile Significant increase (>20%) among grouped cytokines (e.g. Th1, Th2, Th17, and/or Treg) from previous profile values could be indicative of impending autoimmune flare that will likely require disease-specific treatment(s). | 15.09 |
| 12 | Examine for Rheumatoid arthritis. Rheumatoid arthritis (RA) is a chronic disorder for which there is no known cure. The optimal treatment of RA requires a comprehensive program that combines medical, social, and emotional support for the patient. Strategies are all aimed at reducing pain and discomfort, preventing deformities and loss of joint function. Treatment options include reduction of joint stress, physical and occupational therapy, and surgical intervention. Drug treatment prescriptions should be closely tied to ImmunoScore cytokine analyses to monitor RA flares and worsening of disease status. Drug classes to treat rheumatoid arthritis. 1) Non-steroidal anti-inflammatory agents (NSAIDs). NSAIDs reduce acute inflammation, reduce pain and improve function. They do not change the course of disease or prevent joint | 25.88 |

FIG. 21G-12 B destruction; 2)Corticosteroids. Corticosteroids have both anti-inflammatory and immunoregulatory activity; 3) Disease modifying anti-rheumatic drugs (DMARDs). DMARD agents have been shown to alter the course of RA and improve radiographic outcomes. There are contra-indications for all of the treatment classes described above. Closely tied ImmunoScore cytokine measurement and courses of treatment will optimize RA treatment for each individual. Anti-inflammatory effect within hours, but reasonable trial period for relief of RA symptoms is 1 month. The most common toxicity is gastrointestinal disturbance which may clinically include burning, belching, or irritation, but which can represent irritation of the lining of the stomach, erosions, and ulcerations that may result in bleeding. Selective COX-2 inhibitors exhibit safer GI profiles than conventional non-selective NSAIDs, but may increase cardiovascular effects on blood pressure and additional effects on vascular beds. The use of NSAIDs medications must take into account their relative risks in an individual patient of gastrointestinal damage versus potential cardiovascular risk factors. Physicians treating RA patients with NSAIDs would periodically monitor serum cytokine levels to track inflammatory cytokines and relate them to symptoms of GI irritation and/or cardiovascular damage. Corticosteroids are useful in early disease as temporary adjunctive therapy while waiting for DMARDs to exert anti-inflammatory effects. This group is also useful as chronic adjunctive therapy in patients with severe disease not well controlled on NSAIDs or DMARDs. Side effects of prednisone include weight gain, increased blood pressure, increased blood sugar, increased risk of cataracts, and avascular necrosis of bones. Patients treated with corticosteroids should have periodic ImmunoScore cytokine measurements coupled with bone densitometry to assess bone fracture risk. Bisphosphonates are concurrently recommended to prevent and/or treat osteoporosis in addition to adequate calcium and vitamin D supplementation. In most cases, when the diagnosis of rheumatoid arthritis is cofirmed, DMARD agents should be initiated.Methotrexate is considered the first-line DMARD agent. The anti-inflammatory effects appear to be due to interruption of adenosine and possible effects on TNF pathways. Serious complications of methotrexate therapy, including hepatic cirrhosis, interstitial pneumonitis, and severe myelosuppression are rare with proper monitoring. Stomatitis and oral ulcers, alopecia and hair thinning, and GI upset may occur and are related to folic acid antagonism. These side effects can be improved with folic acid supplementation. ImmunoScore cytokine coupled with serum liver enzymes should be periodically monitored. Liver biopsy should be performed if liver enzymes persist.
Hydroxychloroquine is sometimes used with methotrexate and sulfasalazine as a triple therapy for RA. The most important toxicity is on the eyes. Patients with underlying retinopathies should have a baseline ophthamimologic examination and follow up

FIG. 21G-12 C exam every 12 months during treatment.
Sulfasalazine is effective for the treatment of RA.
The mechanism of action is unknown. It may cause
hypersensitivity and allergic reactions. Careful
periodic ImmunoScore cytokine screening would
indicate undesirable increases in Th2 and/or Th17
cytokines in conjunction with increased serum IgE
levels. TNF-? inhibitors are used to ameliorate local
concentrations of TNF-? in synovial fluid. There are
currently three TNF-? inhibitors approved for the
treatment of RA. Etanercept binds TNF in the
circulation and prevents interaction with cell surface
TNF receptors. As with all TNF antagonists, there is
an increased risk of infection in patients. Patients
show increased risk of upper respiratory infections
and some develop anti-nuclear antibodies
characteristic of SLE. Screening for latent TB
infection is prudent before initiation of TNF inhibitor
treatments. Infliximab is an anti-TNF antibody
developed in mice. Anti-infliximab antibodies can
develop in patients, reducing the effectiveness of the
treatments. ImmunoScore diagnostic follow-up
would include cytokine measurements looking for
increased Th2 (antibody) response coupled with
specific measurement of anti-TNF antibodies.
Opportunistic infections and sepsis have been
reported with infliximab treatment. Periodic
examination of cytokine balance would indicate
patients coming out of immune balance. Observation
of wildly fluctuating cytokine values would be
indicative of an immune system swaying out of
control and indicate likely candidates for sepsis.
Adalimumab is another anti-TNF antibody treatment
for RA. Increased infections ranging from mild to
serious are seen in clinical practice. In addition, ANA
titers have been seen as well as cases of lupus-like
disease. Abatacept is one of a class of agents
known as T-cell costimulatory blockers. These
agents interfere with the interactions between
antigen-presenting cells and T lymphocytes and
affect early stages in the pathogenic cascade of
events in RA. Infections are increased in patients
being treated with abatacept. Periodic
ImmunoScore cytokine measurement examining
cytokine balance would coincide with patient
treatment. Rituximab binds to the CD20 molecule on
B cell surfaces leading to the removal of B cells from
circulation. Clinical effects on RA are hypothesized
to occur from decrease in B cell cytokines,
interactions with B cells and T cells, or due to
reductions in autoantibody levels. Infusion reactions
to rituximab may include hives, itching, swelling,
difficulty breathing, fever, chills, and changes in
blood pressure. These are usually mild and respond
to slowing the infusion rate or additional medication
(such as antihistamines) but may be severe.
Monitoring cytokine levels during infusion could lead
to better monitoring of patient reaction to rituximab
infusions. Anakira is an IL-1 receptor antagonist.
ImmunoScore measurement of IL-1? and IL-1?
serum concentrations during anakira therapy would
indicate effectiveness and balance of the drug to
cytokine levels in the patient.

FIG. 21G-12 D

| | | |
|---|---|---|
| 1 3 | Examine for Systemic Lupus Erythematosus. Activated autoreactive Th cells provide the help required for autoreactive B cells to differentiate and produce autoreactive antibodies. Studies of animal models and SLE patients indicate an important role for type I interferons. Although type I IFNs are classically considered to promote Th1-mediated cell responses, they can also inhibit Th1 and Th17 responses. At this point, it is not certain whether intervention with IFN inhibitors will be beneficial or detrimental to SLE patients, and the application of IFN inhibitory therapy may be based upon stage of SLE flare. ImmunoScore cytokine panels will be used to add clarity to therapeutics. As SLE patients live longer due to improved therapies and preventive measures, death and disability from cardiovascular events are increasing. The mechanism for the increased risk of SLE patients for cardiovascular events is likely due to a combination of inflammatory and immune mechanisms. There are increased levels of oxidized LDL (oxLDL), pro-inflammatory HDL, MCP-1, TNF-?, IFN-?, IL-1, and IL-12. ImmunoScore cardiac risk markers will be combined with ImmunoScore cytokine panels in patients with SLE, and progressive monitoring will be performed in these patients at regular intervals. | 14.69 |
| 1 4 | Examine for cancer. IL-10 is a cytokine with broad anti-inflammatory properties. A penalty of the role of IL-10 to limit immune and inflammatory responses to pathogens and prevent damage to the host is that high or dysregulated levels of IL-10 may result in chronic infection or cancer. There are certainly possible therapeutic roles to IL-10 and its antagonists in human disease, all of which would benefit from careful ImmunoScore cytokine monitoring during clinical trials and subsequent evaluations. | 10.65 |
| 1 5 | Examine for Multiple Sclerosis. Upregulated cytokines in MS patients include IL-17, IL-12, IL-23, IL-6, IL-21, TNF-?, and other Th1 cytokines. IL-17-related cytokines are speculated to be related to disease progression. Glatiramer acetate (GA) is believed to induce GA-reactive T cells that secrete anti-inflammatory cytokines at the site of inflammation in MS - presumably increasing anti-inflammatory cytokines IL-10, IL-4, and TGF-?. ImmunoScore to periodically measure patients cytokines and at onset of flare, indicated by increased Th17 and Th1 cytokines, administer treatment. Efficacy of treatment could be monitored with monitoring of Treg cytokines.interferon-? and atorvastatin have both been used to treat MS. IFN-? increases Th1 cytokines, while atorvastatin increases Th2 cytokines (particularly IL-5). Both may have the same effect of lessening the increase of Th17 cytokines. MS patients have general systemic increases of Th1 cytokines (particularly TNF-?. This is likely related to fatigue and lapses in systemic immunity. This may be a problem in patients treated with natalizumab as systemic rises in TNF-? are correlated with fatigue symptoms | 5.78 |

FIG. 21G-12 E

| | | |
|---|---|---|
| 1 6 | Examine for Inflammatory Bowel Disease. IBD comprises two forms:<br>Ulcerative colitis (UC) increased expression of following:<br>o TNF-?<br>o IL-1?<br>o IL-6<br>o IL-12<br>o IL-23<br>o IL-17<br>o IL-13<br>o IL-5<br>Crohns disease (CD) increased expression of following:<br>o TNF-?<br>o IL-1?<br>o IL-1?<br>o IL-6<br>o IL-18 (in some patients)<br>o IL-10<br>o IL-4 (in some patients)<br>o IL-23<br>o IL-27<br>o IL-17<br>IL-23 appears to be the key mediator of flares of IBD. Mucosal cytokines recently cited (IL-31 and IL-32) as important are members of the IL-17 family. | 11.23 |
| 1 7 | Examine for Diabetes. Diabetes mellitus is characterized by a lack of insulin causing elevated blood glucose, often with associated insulin resistance. Elevated serum levels of TGF-? are associated with diabetic renal disease and will be tracked by the ImmunoScore cytokine diagnostic panel. Studies in animals indicate higher serum TGF-? levels might ameliorate disease. A dysfunctioning endothelium is associated with both initiation and progression of atherosclerotic cardiovascular disease and has been shown to predate the onset of hyperglycemia in the natural history of type 2 diabetes. It is likely that low level inflammation plays an important role in developing this endothelial dysfunction mainly through the action of TNF-? and possibly IL-6. Visceral obesity and inflammation within white adipose tissue may be a crucial step contributing to the emergence of insulin resistance, type 2 diabetes and atherosclerosis. IL-1?, IL-6, IL-8, IL-10 TNF-?, and TGF-? levels all rise under these conditions. IL-27 can promote both anti- and pro-inflammatory responses. IL-27 up-regulates IFN-?, and IL-17 and down-regulates IL-4, TGF-?, and IL-10 secreted by diabetic splenocytes, suggesting a pathogenic role in T cell-mediated autoimmune diabetes. | 13.13 |

FIG. 21G-12 F

| 18 | Examine for Breast Cancer. IL-6 is a pleiotropic cytokine with both tumor-promoting and tumor-inhibiting effects. Serum IL-6 levels, however, are a negative prognosticator in breast tumor patients. IL-6, IL-8, and IL-10 levels are higher in women with breast cancer than controls and levels also correlate with the clinical stage of disease. Elevated serum IL-6 levels are related to an accelerated clinical course, a higher tumor load, and the presence of liver or lymph node involvement. On the other hand, elevated IL-6 also has prognostic significance for post-relapse survival. | 9.80 |
|---|---|---|
| 19 | Examine for Cancer. Chronic inflammation has long been associated with the development of cancer. TNF-? is one of the major mediators of inflammation. TNF-? induces other inflammatory mediators and proteases that orchestrate inflammatory responses. TNF-? is also produced by tumors and can act as an endogenous tumor promoter. The role of TNF-? has been linked to all steps involved in tumorigenesis, including cellular transformation, promotion, survival, proliferation, invasion, angiogenesis, and metastasis. ImmunoScore cytokine monitoring of TNF-? levels extremely important in cancer patients. | 14.41 |
| 20 | Examine for Cancer. IL-6 has been proposed as a prognostic factor in several malignancies such as colorectal cancer, breast cancer, gastric cancer, and pancreatic cancer. In addition, elevated serum IL-6 concentrations have been demonstrated in patients with endometrial cancer, non-small cell lung carcinoma, colorectal cancer, renal cell carcinoma, breast and ovarian cancers. | 6.36 |
| 21 | Examine for Atherosclerosis. Atherogenesis is characterized by an intense inflammatory process, involving immune and vascular cells. C-reactive protein (CRP), monocyte/macrophage colony-stimulating factor (M-CSF), and IL-6 promote atherogenesis. They also down-regulate atheroprotective cytokines such as IL-10 and TGF-?. Increased levels of CRP and IL-6 are predictive of a higher cardiovascular event rate in the general population. In coronary artery disease, high levels of M-CSF are additive with those of CRP, suggesting the benefit of a multi-marker approach in assessing risk to coronary artery disease. In addition to the pro-inflammatory cytokines with poor prognostic indications, including TNF-?, IL-6, MCP-1, and IL-1, several adipocytokines are released by fat tissues and are inflammatory in nature. These include leptin, resistin, adiponectin and visfatin. Once possible atherosclerotic complications are revealed in patients, a follow up panel specific for heart patients can be envisioned which contains diagnostic tools for serum adipocytokines. It is not yet clear what function IFN-? has in relationship with atherosclerosis development, but it is likely a key player and should be monitored in cardiac patients. | 0.00 |

| | | |
|---|---|---|
| 2 2 | Examine for Allergies. Allergies are the result of aberrant immune reactivity to common innocuous environmental proteins. A pivotal component of allergic pathogenesis is the generation of allergen-specific Th cells with an effector phenotype. Th17 cells may also contribute to the pathogenesis of classically recognized Th2-mediated allergic disorders This may very by individual patient, and immunoScore cytokine profiling would reveal individual differences from patient to patient. Allergic disorders would have a recommendation for treatment plans based upon Th2/Th17 immune balance. | 15.72 |
| 2 3 | Examine for Asthma. Asthma comprises distinct heterogeneous inflammatory disorders characterized by patients showing different phenotypes with distinct genetic components, environmental causes, and immunopathogenesis. Once considered purely an allergic disorder dominated by Th2 lymphocytes, IgE, mast cells, eosinophils, macrophages, and cytokines, the disease also involves local epithelial, mesenchymal, vascular and neurologic events that are involved in directing the Th2 phenotype to the lung and through aberrant injury-repair mechanisms to remodeling of the airway wall. Responses to asthma medications vary considerably among patients, likely reflecting the differing sensitivities of the various asthma phenotypes. Physicians need to recognize this when making decisions to adjust treatment to improve asthma. IL-4 and IL-13 are considered to be key contributors to cell-mediated and humoral aspects of allergic inflammation. There is controversy surrounding the role of TGF-? in asthma. It is speculated that IL-5 also plays a pivotal role in eosinophila and asthma. Anti-IgE therapy is an approved treatment for adult and childhood asthma. Helminth infections are suggested to minimize asthma symptoms. | 11.12 |
| 6 | Give a booster dose of tetanus vaccine. Individuals over seven years of age receive the vaccine in combination with diphtheria vaccine (Td). Those children younger than seven years of age can be boosted with a vaccine containing a pertussis component (DTaP). People who had a serious allergic reaction to one dose of tetanus toxoid should not receive another. Persons with a moderate or severe acute illness should postpone receiving the vaccine until they are improved. | 0.00 |
| 7 | Give a booster dose of diphtheria vaccine. Individuals over seven years of age receive the vaccine in combination with tetanus vaccine (Td). Those children younger than seven can be boosted with a vaccine containing the pertussis component as with the tetanus vaccine described above. People who have had a serious allergic reaction to one dose of DTaP, DT, Td, or Tdap vaccine should not receive another. Persons with a moderate or severe illness should postpone receiving the vaccine until their condition has improved. | 0.00 |

FIG. 21G-12 G

Patient: 233

Results

| Conditions | Suggested Action | Internal References | External References |
|---|---|---|---|
| Tetanus_Int eq Reactive | Give a booster dose of tetanus vaccine. Individuals over seven years of age receive the vaccine in combination with diphtheria vaccine (Td). Those children younger than seven years of age can be boosted with a vaccine containing a pertussis component (DTaP). People who had a serious allergic reaction to one dose of tetanus toxoid should not receive another. Persons with a moderate or severe acute illness should postpone receiving the vaccine until they are improved. | Hawkes, J.S., et al., Effect of dietary nucleotide supplementation on growth and immune function in term infants: a randomized controlled trial, European J. Clin. Nutrition 60: 254-64 (2006). McQuillan, Geraldine M., et al., Serologic Immunity to diphtheria and Tetanus in the United States, Annals of Internal Medicine 136(9): 660-66 (2002). Pickering, Larry K., et al., Modulation of the Immune System by Human Milk and Infant Formula Containing Nucleotides, Pediatrics 101(2): 242-49 (1998). Vivani, Simonetta, et al., EPI vaccines-induced antibody prevalence in 8-9 year-olds in The Gambia, Trop. Med. & International Health 9(10): 1044-49 (2004). | |
| Diptheria_Int eq Reactive | Give a booster dose of diphtheria vaccine. Individuals over seven years of age receive the vaccine in combination with tetanus vaccine (Td). Those children younger than seven can be boosted with a vaccine containing the pertussis component as with the tetanus vaccine described above. People who have had a serious allergic reaction to one dose of DTaP, DT, Td, or Tdap vaccine should not receive another. Persons with a moderate or severe illness should postpone receiving the vaccine until their condition has improved. | | |

FIG. 21H-1A

| | | | |
|---|---|---|---|
| IL_6_int eq Reactive<br>IL_12_int eq Reactive<br>IL_17_int eq Reactive | Administer ImmunoScore cytokine panel. Rise in pro-inflammatory cytokines (IL-6, IL-12, and/or IL-17) over previous visit would indicate a future autoimmune antibody profile screening to identify possible autoimmune disease manifestation. Rise in regulatory cytokines (IL-10 and TGF-) could possibly also indicate an autoimmune disease manifestation in regression. Rise in both pro- and regulatory cytokines would trigger subsequent need to attempt to identify autoimmune disease manifestation by ImmunoScore autoimmune disease antibody screening panels.In addition to normal assessment of physical symptoms, elevated levels (>2 SD of mean) of key pro-inflammatory cytokines IL-6, IL-12, and/or IL-17 trigger: a) repeat visit in six weeks to re-measure cytokine values: i) if pro-inflammatory cytokines still elevated, recommend ImmunoScore panel to detect autoimmune antibody profile to identify possible autoimmune disease manifestation. ii) if pro-inflammatory cytokines levels decreased or moderating recommend ImmunoScore cytokine panel evaluation annually. IL-7 may be particularly important as an initiator of many autoimmune manifestations. Depending on autoimmune disease condition, additional tests ordered can include serum thyroid stimulating hormone (TSH) for Hashimoto's or Grave's disease, anti-nuclear antibody (ANA) for systemic lupus erythematosus (SLE), neurological examination for multiple sclerosis (MS), and serum rheumatoid factor (RF) for rheumatoid arthritis (RA). Compare on site new ImmunoScore cytokine profile with baseline ImmunoScore cytokine profile. Significant increase (>20%) among grouped cytokines (e.g. Th1, Th2, Th17, and/or Treg) from previous profile values could be indicative of impending autoimmune flare that will likely require disease-specific treatment(s). | | |

FIG. 21H-1B

| | | | |
|---|---|---|---|
| IL_23_int eq Reactive | Examine for Multiple Sclerosis. Upregulated cytokines in MS patients include IL-17, IL-12, IL-23, IL-6, IL-21, TNF-, and other Th1 cytokines. IL-17-related cytokines are speculated to be related to disease progression. Glatiramer acetate (GA) is believed to induce GA-reactive T cells that secrete anti-inflammatory cytokines at the site of inflammation in MS - presumably increasing anti-inflammatory cytokines IL-10, IL-4, and TGF-. ImmunoScore to periodically measure patient's cytokines and at onset of flare, indicated by increased Th17 and Th1 cytokines, administer treatment. Efficacy of treatment could be monitored with monitoring of Treg cytokines.Interferon- and atorvastatin have both been used to treat MS. IFN- increases Th1 cytokines, while atorvastatin increases Th2 cytokines (particularly IL-5). Both may have the same effect of lessening the increase of Th17 cytokines. MS patients have general systemic increases of Th1 cytokines (particularly TNF-. This is likely related to fatigue and lapses in systemic immunity. This may be a problem in patients treated with natalizumab as systemic rises in TNF- are correlated with fatigue symptoms. | Bednáová, J. et al., Relevance of immunological variables in neuroborreliosis and multiple sclerosis, Acta Neurol. Scand. 112. 97-102 (2005) | |
| IL_5_int eq Reactive | Examine for Inflammatory Bowel Disease IBD comprises two forms:<br>• Ulcerative colitis (UC) – increased expression of following:<br>o TNF-<br>o IL-1<br>o IL-6<br>o IL-12<br>o IL-23<br>o IL-17<br>o IL-13<br>o IL-5<br>• Crohn's disease (CD) – increased expression of following:<br>o TNF-<br>o IL-1<br>o IL-1<br>o IL-6<br>o IL-18 (in some patients)<br>o IL-10<br>o IL-4 (in some patients)<br>o IL-23<br>o IL-27<br>o IL-17<br>IL-23 appears to be the key mediator of flares of IBD. Mucosal cytokines recently cited (IL-31 and IL-32) as important are members of the IL-17 family. | | |

FIG. 21H-1C

| | | | |
|---|---|---|---|
| IL_4_int eq Nonreactive | Examine for Diabetes. Diabetes mellitus is characterized by a lack of insulin causing elevated blood glucose, often with associated insulin resistance. Elevated serum levels of TGF- are associated with diabetic renal disease and will be tracked by the ImmunoScore cytokine diagnostic panel. Studies in animals indicate higher serum TGF- levels might ameliorate disease. A dysfunctioning endothelium is associated with both initiation and progression of atherosclerotic cardiovascular disease and has been shown to predate the onset of hyperglycemia in the natural history of type 2 diabetes. It is likely that low level inflammation plays an important role in developing this endothelial dysfunction mainly through the action of TNF- and possibly IL-6. Visceral obesity and inflammation within white adipose tissue may be a crucial step contributing to the emergence of insulin resistance, type 2 diabetes and atherosclerosis. IL-1, IL-6, IL-8, IL-10 TNF-, and TGF- levels all rise under these conditions. IL-27 can promote both anti- and pro-inflammatory responses. IL-27 up-regulates IFN-, and IL-17 and down-regulates IL-4, TGF-, and IL-10 secreted by diabetic splenocytes, suggesting a pathogenic role in T cell-mediated autoimmune diabetes. | Santos, J.L., et al., Associations between HLA-DQB1 high-risk alleges and type I diabetes do not depend on cytomegalovirus antibody status at onset: A case-parent study conducted in Chile, Immunology & Cell Biology 78: 259-63 (2000). | |
| IL_8_int eq Reactive | Examine for Breast Cancer. IL-6 is a pleiotropic cytokine with both tumor-promoting and tumor-inhibiting effects. Serum IL-6 levels, however, are a negative prognosticator in breast tumor patients.<br>IL-6, IL-8, and IL-10 levels are higher in women with breast cancer than controls and levels also correlate with the clinical stage of disease. Elevated serum IL-8 levels are related to an accelerated clinical course, a higher tumor load, and the presence of liver or lymph node involvement. On the other hand, elevated IL-8 also has prognostic significance for post-relapse survival. | | |

FIG. 21H-1D

| | | | |
|---|---|---|---|
| TNF_alpha_inf eq Nonreactive | Examine for Cancer. Chronic inflammation has long been associated with the development of cancer. TNF- is one of the major mediators of inflammation. TNF- induces other inflammatory mediators and proteases that orchestrate inflammatory responses. TNF- is also produced by tumors and can act as an endogenous tumor promoter. The role of TNF- has been linked to all steps involved in tumorigenesis, including cellular transformation, promotion, survival, proliferation, invasion, angiogenesis, and metastasis. ImmunoScore cytokine monitoring of TNF- levels extremely important in cancer patients. | | |
| IL_13_inf eq Reactive | Examine for Asthma. Asthma comprises distinct heterogeneous inflammatory disorders characterized by patients showing different phenotypes with distinct genetic components, environmental causes, and immunopathogenesis. Once considered purely an allergic disorder dominated by Th2 lymphocytes, IgE, mast cells, eosinophils, macrophages, and cytokines, the disease also involves local epithelial, mesenchymal, vascular and neurologic events that are involved in directing the Th2 phenotype to the lung and through aberrant injury-repair mechanisms to remodeling of the airway wall. Responses to asthma medications vary considerably among patients, likely reflecting the differing sensitivities of the various asthma phenotypes. Physicians need to recognize this when making decisions to adjust treatment to improve asthma. IL-4 and IL-13 are considered to be key contributors to cell-mediated and humoral aspects of allergic inflammation. There is controversy surrounding the role of TGF- in asthma. It is speculated that IL-5 also plays a pivotal role in eosinophils and asthma. Anti-IgE therapy is an approved treatment for adult and childhood asthma. Helminth infections are suggested to minimize asthma symptoms. | | |

Patient Data

| Attribute | Value | Percentile Total | Percentile Sex = 0 | Percentile Age = 30-50 | Percentile Region = 4 |
|---|---|---|---|---|---|
| Age | 31 | | | | |
| Chickenpox_Age | | | | | |
| Chickenpox_History | 0 | | | | |

FIG. 21H-1E

| | | | | | |
|---|---|---|---|---|---|
| Citizenship | 4 | | | | |
| CMV_Int | Negative | | | | |
| CMV_OD | 0.6 | 14.71 | 13.07 | 14.27 | 13.54 |
| Country_of_Origin | 8 | | | | |
| Country_of_Origin_name | Mexico | | | | |
| Diptheria_Ab | 0.763 | | | | |
| Diptheria_Age | 21 | | | | |
| Diptheria_history | 2 | | | | |
| Diptheria_Int | Reactive | | | | |
| Diptheria_OD | 0.551 | 74.10 | 64.82 | 73.73 | 77.85 |
| Education | 5 | | | | |
| ELECTRICITY | Y | | | | |
| Filaria_Ab_OD | 0.0685 | 32.32 | 24.48 | 32.13 | 30.77 |
| Filaria_Int | | | | | |
| HepA_Int | Nonreactive | | | | |
| HepA_OD | 1.594 | 87.07 | 89.21 | 90.27 | 93.08 |
| Hepatitis_Age | | | | | |
| Hepatitis_history | 7 | | | | |
| HepB_cAb_Int | Nonreactive | | | | |
| HepB_cAb_OD | 2.076 | 85.35 | 82.78 | 85.70 | 87.23 |
| HepB_eAb_Int | NA (Predicted) | | | | |
| HepB_eAb_ratio | | | | | |
| HepB_eAg_Int | NA (Predicted) | | | | |
| HepB_eAg_ratio | | | | | |
| HepB_SAb_OD | 186.4 | 87.86 | 86.72 | 85.60 | 94.46 |
| HepB_SAg_OD | | 0.00 | 0.00 | 0.00 | 0.00 |
| HepC_Ab_OD | 0.71 | 95.70 | 94.19 | 96.27 | 96.92 |
| HepC_Int | Nonreactive | | | | |
| HepC_LIA | | | | | |
| HepC_PCR | | | | | |
| Hospitalized | 0 | | | | |
| IG | 203 | | | | |
| IFN_gamma | 0 | 0.00 | 0.00 | 0.00 | 0.00 |
| IFN_gamma_int | Nonreactive | | | | |
| IL_10 | 0 | 0.00 | 0.00 | 0.00 | 0.00 |
| IL_10_int | Nonreactive | | | | |
| IL_12_int | Reactive | | | | |
| IL_12p70 | 2.366441909 | 75.40 | 76.76 | 77.29 | 68.92 |
| IL_12p70_int | Reactive | | | | |
| IL_13 | 0.885177752 | 61.62 | 69.09 | 62.67 | 53.85 |
| IL_13_int | Reactive | | | | |
| IL_15 | 5.135628173 | 79.29 | 89.42 | 79.47 | 74.77 |
| IL_15_int | Reactive | | | | |
| IL_17 | 0.265957447 | 45.17 | 42.83 | 46.07 | 36.31 |
| IL_17_int | Reactive | | | | |
| IL_1_alpha | 0 | 0.00 | 0.00 | 0.00 | 0.00 |
| IL_1_alpha_int | Nonreactive | | | | |
| IL_1_beta | 0 | 0.00 | 0.00 | 0.00 | 0.00 |
| IL_1_beta_int | Nonreactive | | | | |
| IL_2 | 0 | 0.00 | 0.00 | 0.00 | 0.00 |
| IL_23 | 17.77728086 | 35.14 | 32.78 | 37.07 | 31.69 |
| IL_23_int | Reactive | | | | |
| IL_2_int | Nonreactive | | | | |
| IL_4 | 0 | 0.00 | 0.00 | 0.00 | 0.00 |
| IL_4_int | Nonreactive | | | | |
| IL_5 | 1.227919603 | 53.32 | 56.85 | 57.07 | 50.46 |

FIG. 21H-1F

| | | | | | |
|---|---|---|---|---|---|
| IL_5_int | Reactive | | | | |
| IL_6 | 0.14370436 | 66.60 | 85.68 | 67.33 | 59.08 |
| IL_6_int | Reactive | | | | |
| IL_8 | 0.388861485 | 27.42 | 21.58 | 26.67 | 22.77 |
| IL_8_int | Reactive | | | | |
| Indoor_toilet | 1 | | | | |
| Indoor_toilet_type | 1 | | | | |
| Interpreter | 0 | | | | |
| Interpreter_Language | | | | | |
| Measles_age | 14 | | | | |
| Measles_history | 1 | | | | |
| Measles_int | Positive | | | | |
| Measles_OD_DB | 0.726 | 72.44 | 65.77 | 70.00 | 80.31 |
| Measles_OD_DB_int | Positive | | | | |
| Measles_OD_Z | | 0.00 | 0.00 | 0.00 | 0.00 |
| Measles_ratio_Z | | | | | |
| Measles_titre_DB | 2600 | 73.52 | 67.84 | 71.60 | 81.54 |
| Medical Problems | 0 | | | | |
| Medications | 0 | | | | |
| Months_CA | 4.3 | | | | |
| Months_pregnant | 91 | | | | |
| Mumps_Age | 8 | | | | |
| Mumps_history | 1 | | | | |
| Mumps_OD_DB | 0.462 | 67.60 | 67.84 | 68.53 | 68.00 |
| Mumps_titre_DB | 950 | 57.14 | 56.85 | 58.67 | 56.62 |
| Outdoor_toilet | 0 | | | | |
| Outdoor_toilet_type | | | | | |
| People_household | 5 | | | | |
| Persons_Rooms | 0.833333333 | | | | |
| Pertussis_Age | 91 | | | | |
| Pertussis_history | 2 | | | | |
| Polio_Age | 91 | | | | |
| Polio_history | 0 | | | | |
| Pregnant | 0 | | | | |
| Refugee_camp | 0 | | | | |
| Region_of_Origin | 4 | | | | |
| Rooms_household | 6 | | | | |
| Rubella_Ab | 0 | | | | |
| Rubella_Age | 91 | | | | |
| Rubella_history | 2 | | | | |
| Rubella_int | 1 | | | | |
| Schistosoma_Ab_OD | 0.243 | 86.32 | 84.65 | 88.03 | 90.77 |
| Schistosoma_int | | | | | |
| School_type | 1 | | | | |
| Sex | 0 | | | | |
| Strongyloides_Ab_OD | 0.136 | 37.23 | 24.48 | 30.89 | 35.09 |
| Strongyloides_int | | | | | |
| Tetanus_Ab | 76.00026021 | | | | |
| Tetanus_Age | 91 | | | | |
| Tetanus_history | 0 | | | | |
| Tetanus_int | Reactive | | | | |
| Tetanus_OD | 7.977 | 99.80 | 99.39 | 99.73 | 99.69 |
| TNF_alpha | 0 | 0.00 | 0.00 | 0.00 | 0.00 |
| TNF_alpha_int | Nonreactive | | | | |
| TNF_beta | 0 | 0.00 | 0.00 | 0.00 | 0.00 |
| TNF_beta_int | Nonreactive | | | | |
| UNIVERSITY | 1 | | | | |

FIG. 21H-1G

| Vaccination-_record | 0 | | | | |
| Varicella_Int | Positive | | | | |
| Varicella_OD_DB | 1.841 | 92.28 | 88.17 | 91.73 | 90.46 |
| Varicella_titre_DB | 1800 | 89.11 | 84.23 | 88.00 | 85.85 |
| Water_supply_type | 1 | | | | |
| Years_Education | 18 | | | | |

FIG. 21H-1H

Patient: 261

Results

| Conditions | Suggested Action | Internal References | External References |
|---|---|---|---|
| Tetanus_Int eq Reactive | Give a booster dose of tetanus vaccine. Individuals over seven years of age receive the vaccine in combination with diphtheria vaccine (Td). Those children younger than seven years of age can be boosted with a vaccine containing a pertussis component (DTaP). People who had a serious allergic reaction to one dose of tetanus toxoid should not receive another. Persons with a moderate or severe acute illness should postpone receiving the vaccine until they are improved. | Hawkes, J.S., et al., Effect of dietary nucleotide supplementation on growth and immune function in term infants: a randomized controlled trial, European J. Clin. Nutrition 60: 254-64 (2006). McQuillan, Geraldine M., et al., Serologic Immunity to diphtheria and Tetanus in the United States, Annals of Internal Medicine 136(9): 660-66 (2002). Pickering, Larry K., et al., Modulation of the Immune System by Human Milk and Infant Formula Containing Nucleotides, Pediatrics 101(2): 242-49 (1998). Vivani, Simonetta, et al., EPI vaccines-induced antibody prevalence in 8-9 year-olds in The Gambia, Trop. Med. & International Health 9(10): 1044-49 (2004). | |
| Diptheria_Int eq Reactive | Give a booster dose of diphtheria vaccine. Individuals over seven years of age receive the vaccine in combination with tetanus vaccine (Td). Those children younger than seven can be boosted with a vaccine containing the pertussis component as with the tetanus vaccine described above. People who have had a serious allergic reaction to one dose of DTaP, DT, Td, or Tdap vaccine should not receive another. Persons with a moderate or severe illness should postpone receiving the vaccine until their condition has improved. | | |

FIG. 21H-2 A

| | | | |
|---|---|---|---|
| IL_6_int eq Reactive<br>IL_12_int eq Reactive<br>IL_17_int eq Reactive | Administer ImmunoScore cytokine panel. Rise in pro-inflammatory cytokines (IL-6, IL-12, and/or IL-17) over previous visit would indicate a future autoimmune antibody profile screening to identify possible autoimmune disease manifestation. Rise in regulatory cytokines (IL-10 and TGF-) could possibly also indicate an autoimmune disease manifestation in regression. Rise in both pro- and regulatory cytokines would trigger subsequent need to attempt to identify autoimmune disease manifestation by ImmunoScore autoimmune disease antibody screening panels.In addition to normal assessment of physical symptoms, elevated levels (>2 SD of mean) of key pro-inflammatory cytokines IL-6, IL-12, and/or IL-17 trigger: a) repeat visit in six weeks to re-measure cytokine values: i) if pro-inflammatory cytokines still elevated, recommend ImmunoScore panel to detect autoimmune antibody profile to identify possible autoimmune disease manifestation. ii) if pro-inflammatory cytokines levels decreased or moderating, recommend ImmunoScore cytokine panel evaluation annually. IL-7 may be particularly important as an initiator of many autoimmune manifestations. Depending on autoimmune disease condition, additional tests ordered can include serum thyroid stimulating hormone (TSH) for Hashimoto's or Grave's disease, anti-nuclear antibody (ANA) for systemic lupus erythematosus (SLE), neurological examination for multiple sclerosis (MS), and serum rheumatoid factor (RF) for rheumatoid arthritis (RA). Compare on site new ImmunoScore cytokine profile with baseline ImmunoScore cytokine profile. Significant increase (>20%) among grouped cytokines (e.g. Th1, Th2, Th17, and/or Treg) from previous profile values could be indicative of impending autoimmune flare that will likely require disease-specific treatment(s). | | |

FIG. 21H-2 B

| | | | |
|---|---|---|---|
| IL_10_int eq Reactive | Examine for cancer. IL-10 is a cytokine with broad anti-inflammatory properties. A penalty of the role of IL-10 to limit immune and inflammatory responses to pathogens and prevent damage to the host is that high or dysregulated levels of IL-10 may result in chronic infection or cancer. There are certainly possible therapeutic roles to Il-10 and its antagonists in human disease, all of which would benefit from careful ImmunoScore cytokine monitoring during clinical trials and subsequent evaluations. | | |
| IL_23_int eq Reactive | Examine for Multiple Sclerosis. Upregulated cytokines in MS patients include IL-17, IL-12, IL-23, IL-6, IL-21, TNF-, and other Th1 cytokines. IL-17-related cytokines are speculated to be related to disease progression. Glatiramer acetate (GA) is believed to induce GA-reactive T cells that secrete anti-inflammatory cytokines at the site of inflammation in MS - presumably increasing anti-inflammatory cytokines IL-10, IL-4, and TGF-. ImmunoScore to periodically measure patient's cytokines and at onset of flare, indicated by increased Th17 and Th1 cytokines, administer treatment. Efficacy of treatment could be monitored with monitoring of Treg cytokines.Interferon- and atorvastatin have both been used to treat MS. IFN- increases Th1 cytokines, while atorvastatin increases Th2 cytokines (particularly IL-5). Both may have the same effect of lessening the increase of Th17 cytokines. MS patients have general systemic increases of Th1 cytokines (particularly TNF-. This is likely related to fatigue and lapses in systemic immunity. This may be a problem in patients treated with natalizumab as systemic rises in TNF- are correlated with fatigue symptoms. | Bednáová, J. et al., Relevance of immunological variables in neuroborreliosis and multiple sclerosis, Acta Neurol. Scand. 112: 97-102 (2005). | |

FIG. 21H-2 C

| | | | |
|---|---|---|---|
| IL_5_int eq Reactive | Examine for Inflammatory Bowel Disease. IBD comprises two forms:<br>• Ulcerative colitis (UC) – increased expression of following:<br>o TNF-<br>o IL-1<br>o IL-6<br>o IL-12<br>o IL-23<br>o IL-17<br>o IL-13<br>o IL-5<br>• Crohn's disease (CD) – increased expression of following:<br>o TNF-<br>o IL-1<br>o IL-1<br>o IL-6<br>o IL-18 (in some patients)<br>o IL-10<br>o IL-4 (in some patients)<br>o IL-23<br>o IL-27<br>o IL-17<br>IL-23 appears to be the key mediator of flares of IBD. Mucosal cytokines recently cited (IL-31 and IL-32) as important are members of the IL-17 family. | | |

FIG. 21H-2 D

| | | | |
|---|---|---|---|
| IL_4_int eq Nonreactive | Examine for Diabetes. Diabetes mellitus is characterized by a lack of insulin causing elevated blood glucose, often with associated insulin resistance. Elevated serum levels of TGF- are associated with diabetic renal disease and will be tracked by the ImmunoScore cytokine diagnostic panel. Studies in animals indicate higher serum TGF- levels might ameliorate disease. A dysfunctioning endothelium is associated with both initiation and progression of atherosclerotic cardiovascular disease and has been shown to predate the onset of hyperglycemia in the natural history of type 2 diabetes. It is likely that low level inflammation plays an important role in developing this endothelial dysfunction mainly through the action of TNF- and possibly IL-6. Visceral obesity and inflammation within white adipose tissue may be a crucial step contributing to the emergence of insulin resistance, type 2 diabetes and atherosclerosis. IL-1, IL-6, IL-8, IL-10 TNF-, and TGF- levels all rise under these conditions. IL-27 can promote both anti- and pro-inflammatory responses. IL-27 up-regulates IFN-, and IL-17 and down-regulates IL-4, TGF-, and IL-10 secreted by diabetic splenocytes, suggesting a pathogenic role in T cell-mediated autoimmune diabetes. | Santos, J.L., et al., Associations between HLA-DQB1 high-risk alleges and type I diabetes do not depend on cytomegalovirus antibody status at onset: A case-parent study conducted in Chile, Immunology & Cell Biology 78: 259-63 (2000). | |
| IL_6_int eq Reactive | Examine for Breast Cancer. IL-6 is a pleiotropic cytokine with both tumor-promoting and tumor-inhibiting effects. Serum IL-6 levels, however, are a negative prognosticator in breast tumor patients. IL-6, IL-8, and IL-10 levels are higher in women with breast cancer than controls and levels also correlate with the clinical stage of disease. Elevated serum IL-8 levels are related to an accelerated clinical course, a higher tumor load, and the presence of liver or lymph node involvement. On the other hand, elevated IL-8 also has prognostic significance for post-relapse survival. | | |

FIG. 21H-2 E

| | | | |
|---|---|---|---|
| TNF_alpha_int eq Nonreactive | Examine for Cancer. Chronic inflammation has long been associated with the development of cancer. TNF- is one of the major mediators of inflammation. TNF- induces other inflammatory mediators and proteases that orchestrate inflammatory responses. TNF- is also produced by tumors and can act as an endogenous tumor promoter. The role of TNF- has been linked to all steps involved in tumorigenesis, including cellular transformation, promotion, survival, proliferation, invasion, angiogenesis, and metastasis. ImmunoScore cytokine monitoring of TNF- levels extremely important in cancer patients. | | |
| IL_13_int eq Reactive | Examine for Asthma. Asthma comprises distinct heterogeneous inflammatory disorders characterized by patients showing different phenotypes with distinct genetic components, environmental causes, and immunopathogenesis. Once considered purely an allergic disorder dominated by Th2 lymphocytes, IgE, mast cells, eosinophils, macrophages, and cytokines, the disease also involves local epithelial, mesenchymal, vascular and neurologic events that are involved in directing the Th2 phenotype to the lung and through aberrant injury-repair mechanisms to remodeling of the airway wall. Responses to asthma medications vary considerably among patients, likely reflecting the differing sensitivities of the various asthma phenotypes. Physicians need to recognize this when making decisions to adjust treatment to improve asthma. IL-4 and IL-13 are considered to be key contributors to cell-mediated and humoral aspects of allergic inflammation. There is controversy surrounding the role of TGF- in asthma. It is speculated that IL-5 also plays a pivotal role in eosinophilia and asthma. Anti-IgE therapy is an approved treatment for adult and childhood asthma. Helminth infections are suggested to minimize asthma symptoms. | | |

Patient Data

| Attribute | Value | Percentile Total | Percentile Sex = 1 | Percentile Age = 30-50 | Percentile Region = 3 |
|---|---|---|---|---|---|
| Age | 33 | | | | |
| Chickenpox_Age | 5 | | | | |
| Chickenpox_history | 1 | | | | |

FIG. 21H-2 F

| Citizenship | 3 | | | | |
|---|---|---|---|---|---|
| CMV_Int | Reactive | | | | |
| CMV_OD | 105.3 | 24.46 | 23.80 | 23.28 | 26.28 |
| Country_of_Origin | 5 | | | | |
| Country_of_Origin_name | Morocco | | | | |
| Dipthena_Ab | 0.19 | | | | |
| Dipthena_Age | 91 | | | | |
| Dipthena_history | 0 | | | | |
| Dipthena_Int | Reactive | | | | |
| Dipthena_OD | 0.344 | 53.54 | 68.07 | 54.13 | 58.33 |
| Education | 3 | | | | |
| ELECTRICITY | 1 | | | | |
| Filaria_Ab_OD | 0.0095 | 12.77 | 14.60 | 12.40 | 17.31 |
| Filaria_Int | | | | | |
| HepA_Int | Reactive | | | | |
| HepA_OD | 0.068 | 76.85 | 67.04 | 73.20 | 77.56 |
| Hepatitis_Age | | | | | |
| Hepatitis_history | 0 | | | | |
| HepB_cAb_Int | Reactive | | | | |
| HepB_cAb_OD | 0.062 | 13.26 | 14.38 | 13.47 | 18.59 |
| HepB_eAb_Int | NA (Predicted) | | | | |
| HepB_eAb_ratio | | | | | |
| HepB_sAg_Int | NA (Predicted) | | | | |
| HepB_eAg_ratio | | | | | |
| HepB_SAb_OD | 1001 | 93.87 | 94.36 | 92.80 | 94.23 |
| HepB_SAg_OD | 1.04 | 95.53 | 96.13 | 95.87 | 94.87 |
| HepC_Ab_OD | 0.33 | 75.61 | 79.20 | 74.53 | 82.69 |
| HepC_Int | Nonreactive | | | | |
| HepC_LIA | | | | | |
| HepC_PCR | | | | | |
| Hospitalized | 0 | | | | |
| ID | 261 | | | | |
| IFN_gamma | 0 | 0.00 | 0.00 | 0.00 | 0.00 |
| IFN_gamma_int | Nonreactive | | | | |
| IL_10 | 3.074942792 | 93.15 | 92.81 | 93.87 | 94.23 |
| IL_10_int | Reactive | | | | |
| IL_12_int | Reactive | | | | |
| IL_12p70 | 7.669588415 | 96.39 | 95.91 | 97.20 | 96.79 |
| IL_12p70_int | Reactive | | | | |
| IL_13 | 21.43017344 | 99.57 | 99.45 | 99.60 | 99.36 |
| IL_13_int | Reactive | | | | |
| IL_15 | 1.85569954 | 26.41 | 25.44 | 28.00 | 35.33 |
| IL_15_int | Reactive | | | | |
| IL_17 | 11.80752841 | 98.05 | 97.99 | 98.13 | 97.44 |
| IL_17_int | Reactive | | | | |
| IL_1_alpha | 0 | 0.00 | 0.00 | 0.00 | 0.00 |
| IL_1_alpha_int | Nonreactive | | | | |
| IL_1_beta | 6.050172964 | 98.85 | 98.67 | 98.67 | 98.08 |
| IL_1_beta_int | Reactive | | | | |
| IL_2 | 70.95564757 | 99.78 | 99.67 | 99.73 | 99.36 |
| IL_23 | 42.32673267 | 54.49 | 53.87 | 57.20 | 58.59 |
| IL_23_int | Reactive | | | | |
| IL_2_int | Reactive | | | | |
| IL_4 | 0 | 0.00 | 0.00 | 0.00 | 0.00 |
| IL_4_int | Nonreactive | | | | |
| IL_5 | 9.691948399 | 93.58 | 92.81 | 95.20 | 93.59 |

FIG. 21H-2 G

| | | | | | |
|---|---|---|---|---|---|
| IL_5_int | Reactive | | | | |
| IL_6 | 1.557831267 | 35.71 | 29.76 | 36.67 | 36.54 |
| IL_6_int | Reactive | | | | |
| IL_8 | 4.064980084 | 55.92 | 57.41 | 55.47 | 62.16 |
| IL_8_int | Reactive | | | | |
| Indoor_toilet | | | | | |
| Indoor_toilet_type | | | | | |
| Interpreter | 0 | | | | |
| Interpreter_Language | | | | | |
| Measles_age | 4 | | | | |
| Measles_history | 1 | | | | |
| Measles_Int | Positive | | | | |
| Measles_OD_DB | | 0.00 | 0.00 | 0.00 | 0.00 |
| Measles_OD_DB_int | Equivocal | | | | |
| Measles_OD_Z | 0.89 | 63.92 | 67.28 | 62.27 | 58.33 |
| Measles_rate_Z | 2.39 | | | | |
| Measles_titre_DB | | 0.00 | 0.00 | 0.00 | 0.00 |
| Medical_Problems | 0 | | | | |
| Medications | 0 | | | | |
| Months_CA | 2.3 | | | | |
| Months_pregnant | 91 | | | | |
| Mumps_Age | | | | | |
| Mumps_history | 0 | | | | |
| Mumps_OD_DB | 0.102 | 10.89 | 10.95 | 10.07 | 7.05 |
| Mumps_titre_DB | <230 | 0.00 | 0.00 | 0.00 | 0.00 |
| Outdoor_toilet | 0 | | | | |
| Outdoor_toilet_type | | | | | |
| People_household | 0 | | | | |
| Persons_Rooms | 0.857142857 | | | | |
| Pertussis_Age | 91 | | | | |
| Pertussis_history | 0 | | | | |
| Polio_Age | 91 | | | | |
| Polio_history | 0 | | | | |
| Pregnant | 0 | | | | |
| Refugee_camp | 0 | | | | |
| Region_of_Origin | 3 | | | | |
| Rooms_household | 7 | | | | |
| Rubella_Ab | 27.1 | | | | |
| Rubella_Age | 91 | | | | |
| Rubella_history | 2 | | | | |
| Rubella_Int | 0 | | | | |
| Schistosoma_Ab_OD | 0.032 | 32.97 | 38.05 | 32.87 | 36.46 |
| Schistosoma_int | | | | | |
| School_type | 2 | | | | |
| Sex | 1 | | | | |
| Strongyloides_Ab_OD | 0.0745 | 70.46 | 25.11 | 19.73 | 31.41 |
| Strongyloides_int | | | | | |
| Tetanus_Ab | 1.824 | | | | |
| Tetanus_Age | 91 | | | | |
| Tetanus_history | 0 | | | | |
| Tetanus_Int | Reactive | | | | |
| Tetanus_OD | 1.442 | 79.98 | 79.96 | 81.33 | 78.25 |
| TNF_alpha | 0 | 0.00 | 0.00 | 0.00 | 0.00 |
| TNF_alpha_int | Nonreactive | | | | |
| TNF_beta | 0 | 0.00 | 0.00 | 0.00 | 0.00 |
| TNF_beta_int | Nonreactive | | | | |
| UNIVERSITY | 0 | | | | |

FIG. 21H-2 H

| Vaccination-_record | 0 | | | | |
| Varicella_Int | Positive | | | | |
| Varicella_OD_DB | 0.457 | 17.82 | 18.58 | 15.73 | 16.67 |
| Varicella_titre_DB | 200 | 17.97 | 19.14 | 16.80 | 16.03 |
| Water_supply_type | 1 | | | | |
| Years_Education | 11 | | | | |

FIG. 21H-2I

Patient: 339

Results

| Conditions | Suggested Action | Internal References | External References |
|---|---|---|---|
| Tetanus_int eq Reactive | Give a booster dose of tetanus vaccine. Individuals over seven years of age receive the vaccine in combination with diphtheria vaccine (Td). Those children younger than seven years of age can be boosted with a vaccine containing a pertussis component (DTaP). People who had a serious allergic reaction to one dose of tetanus toxoid should not receive another. Persons with a moderate or severe acute illness should postpone receiving the vaccine until they are improved. | Hawkes, J.S., et al., Effect of dietary nucleotide supplementation on growth and immune function in term infants: a randomized controlled trial, European J. Clin. Nutrition 60: 254-64 (2006). McQuillan, Geraldine M., et al., Serologic Immunity to diphtheria and Tetanus in the United States, Annals of Internal Medicine 136(9): 660-66 (2002). Pickering, Larry K., et al., Modulation of the Immune System by Human Milk and Infant Formula Containing Nucleotides, Pediatrics 101(2), 242-49 (1998). Vivani, Simonetta, et al., EPI vaccines-induced antibody prevalence in 8-9 year-olds in The Gambia, Trop. Med. & International Health 9(10): 1044-49 (2004). | |
| Diptheria_int eq Reactive | Give a booster dose of diphtheria vaccine. Individuals over seven years of age receive the vaccine in combination with tetanus vaccine (Td). Those children younger than seven can be boosted with a vaccine containing the pertussis component as with the tetanus vaccine described above. People who have had a serious allergic reaction to one dose of DTaP, DT, Td, or Tdap vaccine should not receive another. Persons with a moderate or severe illness should postpone receiving the vaccine until their condition has improved. | | |
| IL_10_int eq Reactive | Examine for cancer. IL-10 is a cytokine with broad anti-inflammatory properties. A penalty of the role of IL-10 to limit immune and inflammatory responses to pathogens and prevent damage to the host is that high or dysregulated levels of IL-10 may result in chronic infection or cancer. There are certainly possible therapeutic roles to Il-10 and its antagonists in human disease, all of which would benefit from careful ImmunoScore cytokine monitoring during clinical trials and subsequent evaluations. | | |

FIG. 21H-3A

| IL_23_int eq Reactive | Examine for Multiple Sclerosis. Upregulated cytokines in MS patients include IL-17, IL-12, IL-23, IL-6, IL-21, TNF-, and other Th1 cytokines. IL-17-related cytokines are speculated to be related to disease progression. Glatiramer acetate (GA) is believed to induce GA-reactive T cells that secrete anti-inflammatory cytokines at the site of inflammation in MS - presumably increasing anti-inflammatory cytokines IL-10, IL-4, and TGF-. ImmunoScore to periodically measure patient's cytokines and at onset of flare, indicated by increased Th17 and Th1 cytokines, administer treatment  Efficacy of treatment could be monitored with monitoring of Treg cytokines.Interferon- and atorvastatin have both been used to treat MS. IFN- increases Th1 cytokines, while atorvastatin increases Th2 cytokines (particularly IL-5). Both may have the same effect of lessening the increase of Th17 cytokines. MS patients have general systemic increases of Th1 cytokines (particularly TNF-. This is likely related to fatigue and lapses in systemic immunity. This may be a problem in patients treated with natalizumab as systemic rises in TNF- are correlated with fatigue symptoms. | Bednářová, J. et al., Relevance of immunological variables in neuroborreliosis and multiple sclerosis, Acta Neurol. Scand. 112: 97-102 (2005). | |
|---|---|---|---|

FIG. 21H-3 B

| | | | |
|---|---|---|---|
| IL_4_int eq Nonreactive | Examine for Diabetes. Diabetes mellitus is characterized by a lack of insulin causing elevated blood glucose, often with associated insulin resistance. Elevated serum levels of TGF- are associated with diabetic renal disease and will be tracked by the ImmunoScore cytokine diagnostic panel. Studies in animals indicate higher serum TGF- levels might ameliorate disease. A dysfunctioning endothelium is associated with both initiation and progression of atherosclerotic cardiovascular disease and has been shown to predate the onset of hyperglycemia in the natural history of type 2 diabetes. It is likely that low level inflammation plays an important role in developing this endothelial dysfunction mainly through the action of TNF- and possibly IL-6. Visceral obesity and inflammation within white adipose tissue may be a crucial step contributing to the emergence of insulin resistance, type 2 diabetes and atherosclerosis. IL-1, IL-6, IL-8, IL-10 TNF-, and TGF- levels all rise under these conditions. IL-27 can promote both anti- and pro-inflammatory responses. IL-27 up-regulates IFN-, and IL-17 and down-regulates IL-4, TGF-, and IL-10 secreted by diabetic splenocytes, suggesting a pathogenic role in T cell-mediated autoimmune diabetes. | Santos, J.L., et al., Associations between HLA-DQB1 high-risk alleges and type I diabetes do not depend on cytomegalovirus antibody status at onset: A case-parent study conducted in Chile. Immunology & Cell Biology 78: 259-63 (2000). | |
| IL_8_int eq Reactive | Examine for Breast Cancer. IL-6 is a pleiotropic cytokine with both tumor-promoting and tumor-inhibiting effects. Serum IL-6 levels, however, are a negative prognosticator in breast tumor patients IL-6, IL-8, and IL-10 levels are higher in women with breast cancer than controls and levels also correlate with the clinical stage of disease Elevated serum IL-8 levels are related to an accelerated clinical course, a higher tumor load, and the presence of liver or lymph node involvement. On the other hand, elevated IL-8 also has prognostic significance for post-relapse survival. | | |

FIG. 21H-3 C

| | | | |
|---|---|---|---|
| TNF_alpha_int eq Nonreactive | Examine for Cancer. Chronic inflammation has long been associated with the development of cancer. TNF- is one of the major mediators of inflammation. TNF- induces other inflammatory mediators and proteases that orchestrate inflammatory responses. TNF- is also produced by tumors and can act as an endogenous tumor promoter. The role of TNF- has been linked to all steps involved in tumorigenesis, including cellular transformation, promotion, survival, proliferation, invasion, angiogenesis, and metastasis. ImmunoScore cytokine monitoring of TNF- levels extremely important in cancer patients. | | |

Patient Data

| Attribute | Value | Percentile Total | Percentile Sex = 1 | Percentile Age = 30-50 | Percentile Region = 4 |
|---|---|---|---|---|---|
| Age | 43 | | | | |
| Chickenpox_Age | 6 | | | | |
| Chickenpox_history | 1 | | | | |
| Citizenship | 1 | | | | |
| CMV_int | Reactive | | | | |
| CMV_OD | 235.7 | 47.55 | 46.79 | 44.40 | 53.23 |
| Country_of_Origin | 5 | | | | |
| Country_of_Origin_na me | Mexico | | | | |
| Diptheria_Ab | 0.194 | | | | |
| Diptheria_Age | 91 | | | | |
| Diptheria_history | 2 | | | | |
| Diptheria_Int | Reactive | | | | |
| Diptheria_OD | 0.34 | 52.81 | 53.40 | 53.20 | 55.89 |
| Education | 5 | | | | |
| ELECTRICITY | 1 | | | | |
| Filaria_Ab_OD | 0.0315 | 19.05 | 21.90 | 19.33 | 13.23 |
| Filaria_Int | | | | | |
| HepA_Int | Reactive | | | | |
| HepA_OD | 0.086 | 53.46 | 49.12 | 54.27 | 53.85 |
| Hepatitis_Age | | | | | |
| Hepatitis_history | 2 | | | | |
| HepB_cAb_Int | Nonreactive | | | | |
| HepB_cAb_OD | 2.173 | 95.24 | 95.91 | 95.07 | 93.85 |
| HepB_eAb_Int | NA (Predicted) | | | | |
| HepB_eAb_ratio | | | | | |
| HepB_eAg_Int | NA (Predicted) | | | | |
| HepB_eAg_ratio | | | | | |
| HepB_SAb_OD | 0.1 | 67.89 | 69.14 | 64.67 | 81.23 |
| HepB_SAg_OD | | 0.00 | 0.00 | 0.00 | 0.00 |
| HepC_Ab_OD | 0.19 | 20.13 | 24.34 | 19.07 | 19.08 |
| HepC_Int | Nonreactive | | | | |
| HepC_LIA | | | | | |
| HepC_PCR | | | | | |
| Hospitalized | 1 | | | | |

FIG. 21H-3 D

| ID | 339 | | | | |
|---|---|---|---|---|---|
| IFN_gamma | 0 | 0.00 | 0.00 | 0.00 | 0.00 |
| IFN_gamma_int | Nonreactive | | | | |
| IL_10 | 0.718998263 | 35.71 | 35.40 | 37.07 | 25.85 |
| IL_10_int | Reactive | | | | |
| IL_12_int | Nonreactive | | | | |
| IL_12p70 | 0 | 0.00 | 0.00 | 0.00 | 0.00 |
| IL_12p70_int | Nonreactive | | | | |
| IL_13 | 0 | 0.00 | 0.00 | 0.00 | 0.00 |
| IL_13_int | Nonreactive | | | | |
| IL_15 | 2.547791648 | 36.09 | 35.41 | 36.00 | 35.77 |
| IL_15_int | Reactive | | | | |
| IL_17 | 0 | 0.00 | 0.00 | 0.00 | 0.00 |
| IL_17_int | Nonreactive | | | | |
| IL_1_alpha | 0 | 0.00 | 0.00 | 0.00 | 0.00 |
| IL_1_alpha_int | Nonreactive | | | | |
| IL_1_beta | 0 | 0.00 | 0.00 | 0.00 | 0.00 |
| IL_1_beta_int | Nonreactive | | | | |
| IL_2 | 0 | 0.00 | 0.00 | 0.00 | 0.00 |
| IL_23 | 74.68638063 | 41.85 | 47.81 | 44.13 | 39.38 |
| IL_23_int | Reactive | | | | |
| IL_2_int | Nonreactive | | | | |
| IL_4 | 0 | 0.00 | 0.00 | 0.00 | 0.00 |
| IL_4_int | Nonreactive | | | | |
| IL_5 | 0 | 0.00 | 0.00 | 0.00 | 0.00 |
| IL_5_int | Nonreactive | | | | |
| IL_6 | 0.760775761 | 27.34 | 24.12 | 26.07 | 21.23 |
| IL_6_int | Reactive | | | | |
| IL_8 | 5.167603646 | 63.46 | 65.04 | 65.20 | 65.31 |
| IL_8_int | Reactive | | | | |
| Indoor_toilet | 1 | | | | |
| Indoor_toilet_type | 1 | | | | |
| Interpreter | 0 | | | | |
| Interpreter_Language | | | | | |
| Measles_Age | 8 | | | | |
| Measles_history | 1 | | | | |
| Measles_Int | Positive | | | | |
| Measles_OD_DB | | 0.00 | 0.00 | 0.00 | 0.00 |
| Measles_OD_DB_int | Positive | | | | |
| Measles_OD_Z | 0.37 | 58.59 | 58.08 | 58.53 | 55.69 |
| Measles_ratio_Z | 1.57 | | | | |
| Measles_titre_DB | | 0.00 | 0.00 | 0.00 | 0.00 |
| Medical Problems | 1 | | | | |
| Medications | 1 | | | | |
| Months_CA | 25.4 | | | | |
| Months_pregnant | 91 | | | | |
| Mumps_Age | | | | | |
| Mumps_history | 0 | | | | |
| Mumps_OD_DB | 0.272 | 38.46 | 38.94 | 38.67 | 38.15 |
| Mumps_titre_DB | 520 | 32.68 | 33.41 | 32.27 | 32.00 |
| Outdoor_toilet | 0 | | | | |
| Outdoor_toilet_type | | | | | |
| People_household | 8 | | | | |
| Persons_Rooms | 1.6 | | | | |
| Pertussis_Age | 91 | | | | |
| Pertussis_history | 2 | | | | |
| Polio_Age | 91 | | | | |

FIG. 21H-3 E

| | | | | | |
|---|---|---|---|---|---|
| Polio_history | 0 | | | | |
| Pregnant | 0 | | | | |
| Refugee_camp | 0 | | | | |
| Region_of_Origin | 4 | | | | |
| Rooms_household | 5 | | | | |
| Rubella_Ab | 11.4 | | | | |
| Rubella_Age | 91 | | | | |
| Rubella_history | 2 | | | | |
| Rubella_int | 0 | | | | |
| Schistosoma_Ab_OD | 0.008 | 15.51 | 18.14 | 14.93 | 11.08 |
| Schistosoma_int | -- | | | | |
| School_type | 2 | | | | |
| Sex | 1 | | | | |
| Strongyloides_Ab_OD | 0.084 | 23.02 | 27.99 | 22.27 | 17.85 |
| Strongyloides_int | -- | | | | |
| Tetanus_Ab | 25.521 | | | | |
| Tetanus_Age | 91 | | | | |
| Tetanus_history | 0 | | | | |
| Tetanus_Int | Reactive | | | | |
| Tetanus_OD | 2.868 | 99.42 | 99.45 | 99.33 | 98.46 |
| TNF_alpha | 0 | 0.00 | 0.00 | 0.00 | 0.00 |
| TNF_alpha_int | Nonreactive | | | | |
| TNF_beta | 0 | 0.00 | 0.00 | 0.00 | 0.00 |
| TNF_beta_int | Nonreactive | | | | |
| UNIVERSITY | 1 | | | | |
| Vaccination_record | 0 | | | | |
| Varicella_int | Positive | | | | |
| Varicella_OD_DB | 1.43 | 86.08 | 89.16 | 84.80 | 84.00 |
| Varicella_titre_DB | 1400 | 83.41 | 87.50 | 81.20 | 77.85 |
| Water_supply_type | 4 | | | | |
| Years_Education | 18 | | | | |

FIG. 21H-3F

Patient: 437

Results

| Conditions | Suggested Action | Internal References | External References |
|---|---|---|---|
| Tetanus_Int eq Reactive | Give a booster dose of tetanus vaccine. Individuals over seven years of age receive the vaccine in combination with diphtheria vaccine (Td). Those children younger than seven years of age can be boosted with a vaccine containing a pertussis component (DTaP). People who had a serious allergic reaction to one dose of tetanus toxoid should not receive another. Persons with a moderate or severe acute illness should postpone receiving the vaccine until they are improved | Hawkes, J.S., et al., Effect of dietary nucleotide supplementation on growth and immune function in term infants: a randomized controlled trial, European J. Clin. Nutrition 60: 254-64 (2006). McQuillan, Geraldine M., et al., Serologic immunity to diphtheria and Tetanus in the United States, Annals of Internal Medicine 136(9): 660-66 (2002). Pickering, Larry K., et al., Modulation of the Immune System by Human Milk and Infant Formula Containing Nucleotides, Pediatrics 101(2): 242-49 (1998). Vivani, Simonetta, et al., EPI vaccines-induced antibody prevalence in 8-9 year-olds in The Gambia, Trop. Med. & International Health 9(10): 1044-49 (2004) | |
| Diptheria_Int eq Reactive | Give a booster dose of diphtheria vaccine. Individuals over seven years of age receive the vaccine in combination with tetanus vaccine (Td). Those children younger than seven can be boosted with a vaccine containing the pertussis component as with the tetanus vaccine described above. People who have had a serious allergic reaction to one dose of DTaP, DT, Td, or Tdap vaccine should not receive another. Persons with a moderate or severe illness should postpone receiving the vaccine until their condition has improved. | | |

FIG. 21H-4 A

| | | | |
|---|---|---|---|
| IL_6_int eq Reactive<br>IL_12_int eq Reactive<br>IL_17_int eq Reactive | Administer ImmunoScore cytokine panel. Rise in pro-inflammatory cytokines (IL-6, IL-12, and/or IL-17) over previous visit would indicate a future autoimmune antibody profile screening to identify possible autoimmune disease manifestation. Rise in regulatory cytokines (IL-10 and TGF-) could possibly also indicate an autoimmune disease manifestation in regression. Rise in both pro- and regulatory cytokines would trigger subsequent need to attempt to identify autoimmune disease manifestation by ImmunoScore autoimmune disease antibody screening panels.In addition to normal assessment of physical symptoms, elevated levels (>2 SD of mean) of key pro-inflammatory cytokines IL-6, IL-12, and/or IL-17 trigger: a) repeat visit in six weeks to re-measure cytokine values: i) if pro-inflammatory cytokines still elevated, recommend ImmunoScore panel to detect autoimmune antibody profile to identify possible autoimmune disease manifestation. ii) If pro-inflammatory cytokines levels decreased or moderating, recommend ImmunoScore cytokine panel evaluation annually. IL-7 may be particularly important as an initiator of many autoimmune manifestations. Depending on autoimmune disease condition, additional tests ordered can include serum thyroid stimulating hormone (TSH) for Hashimoto's or Grave's disease, anti-nuclear antibody (ANA) for systemic lupus erythematosus (SLE), neurological examination for multiple sclerosis (MS), and serum rheumatoid factor (RF) for rheumatoid arthritis (RA). Compare on site new ImmunoScore cytokine profile with baseline ImmunoScore cytokine profile. Significant increase (>20%) among grouped cytokines (e.g. Th1, Th2, Th17, and/or Treg) from previous profile values could be indicative of impending autoimmune flare that will likely require disease-specific treatment(s). | | |

FIG. 21H-4 B

| | | | |
|---|---|---|---|
| IFN_gamma_int eq Reactive | Examine for Systemic Lupus Erythematosus. Activated autoreactive Th cells provide the help required for autoreactive B cells to differentiate and produce autoreactive antibodies. Studies of animal models and SLE patients indicate an important role for type I interferons. Although type I IFNs are classically considered to promote Th1-mediated cell responses, they can also inhibit Th1 and Th17 responses. At this point, it is not certain whether intervention with IFN inhibitors will be beneficial or detrimental to SLE patients, and the application of IFN inhibitory therapy may be based upon stage of SLE flare. ImmunoScore cytokine panels will be used to add clarity to therapeutics. As SLE patients live longer due to improved therapies and preventive measures, death and disability from cardiovascular events are increasing. The mechanism for the increased risk of SLE patients for cardiovascular events is likely due to a combination of inflammatory and immune mechanisms. There are increased levels of oxidized LDL (oxLDL), pro-inflammatory HDL, MCP-1, TNF-, IFN-, IL-1, and IL-12. ImmunoScore cardiac risk markers will be combined with ImmunoScore cytokine panels in patients with SLE, and progressive monitoring will be performed in these patients at regular intervals. | | |
| IL_10_int eq Reactive | Examine for cancer. IL-10 is a cytokine with broad anti-inflammatory properties. A penalty of the role of IL-10 to limit immune and inflammatory responses to pathogens and prevent damage to the host is that high or dysregulated levels of IL-10 may result in chronic infection or cancer. There are certainly possible therapeutic roles to IL-10 and its antagonists in human disease, all of which would benefit from careful ImmunoScore cytokine monitoring during clinical trials and subsequent evaluations | | |

FIG. 21H-4 C

| | | | |
|---|---|---|---|
| IL_23_int eq Reactive | Examine for Multiple Sclerosis. Upregulated cytokines in MS patients include IL-17, IL-12, IL-23, IL-6, IL-21, TNF-, and other Th1 cytokines. IL-17-related cytokines are speculated to be related to disease progression. Glatiramer acetate (GA) is believed to induce GA-reactive T cells that secrete anti-inflammatory cytokines at the site of inflammation in MS - presumably increasing anti-inflammatory cytokines IL-10, IL-4, and TGF-. ImmunoScore to periodically measure patient's cytokines and at onset of flare, indicated by increased Th17 and Th1 cytokines, administer treatment. Efficacy of treatment could be monitored with monitoring of Treg cytokines.Interferon- and atorvastatin have both been used to treat MS. IFN- increases Th1 cytokines, while atorvastatin increases Th2 cytokines (particularly IL-5). Both may have the same effect of lessening the increase of Th17 cytokines. MS patients have general systemic increases of Th1 cytokines (particularly TNF-. This is likely related to fatigue and lapses in systemic immunity. This may be a problem in patients treated with natalizumab as systemic rises in TNF- are correlated with fatigue symptoms. | Bednaová, J. et al., Relevance of immunological variables in neuroborreliosis and multiple sclerosis, Acta Neurol. Scand. 112: 97-102 (2005). | |
| IL_5_int eq Reactive | Examine for Inflammatory Bowel Disease. IBD comprises two forms: <br> • Ulcerative colitis (UC) – increased expression of following: <br> o TNF- <br> o IL-1 <br> o IL-6 <br> o IL-12 <br> o IL-23 <br> o IL-17 <br> o IL-13 <br> o IL-5 <br> • Crohn's disease (CD) – increased expression of following: <br> o TNF- <br> o IL-1 <br> o IL-1 <br> o IL-6 <br> o IL-18 (in some patients) <br> o IL-10 <br> o IL-4 (in some patients) <br> o IL-23 <br> o IL-27 <br> o IL-17 <br> IL-23 appears to be the key mediator of flares of IBD. Mucosal cytokines recently cited (IL-31 and IL-32) as important are members of the IL-17 family. | | |

FIG. 21H-4 D

| | | | |
|---|---|---|---|
| IL_6_int eq Reactive | Examine for Breast Cancer. IL-6 is a pleiotropic cytokine with both tumor-promoting and tumor-inhibiting effects. Serum IL-6 levels, however, are a negative prognosticator in breast tumor patients.<br>IL-6, IL-8, and IL-10 levels are higher in women with breast cancer than controls and levels also correlate with the clinical stage of disease. Elevated serum IL-8 levels are related to an accelerated clinical course, a higher tumor load, and the presence of liver or lymph node involvement. On the other hand, elevated IL-8 also has prognostic significance for post-relapse survival. | | |
| TNF_alpha_int eq Nonreactive | Examine for Cancer. Chronic inflammation has long been associated with the development of cancer. TNF- is one of the major mediators of inflammation. TNF- induces other inflammatory mediators and proteases that orchestrate inflammatory responses. TNF- is also produced by tumors and can act as an endogenous tumor promoter. The role of TNF- has been linked to all steps involved in tumorigenesis, including cellular transformation, promotion, survival, proliferation, invasion, angiogenesis, and metastasis. ImmunoScore cytokine monitoring of TNF- levels extremely important in cancer patients. | | |
| IL_4_int eq Reactive | Examine for Allergies. Allergies are the result of aberrant immune reactivity to common innocuous environmental proteins. A pivotal component of allergic pathogenesis is the generation of allergen-specific Th cells with an effector phenotype. Th17 cells may also contribute to the pathogenesis of classically recognized Th2-mediated allergic disorders. This may very by individual patient, and ImmunoScore cytokine profiling would reveal individual differences from patient to patient. Allergic disorders would have a recommendation for treatment plans based upon Th2/Th17 immune balance. | | |

FIG. 21H-4 E

| | | | | | |
|---|---|---|---|---|---|
| IL_13_int eq Reactive | Examine for Asthma. Asthma comprises distinct heterogeneous inflammatory disorders characterized by patients showing different phenotypes with distinct genetic components, environmental causes, and immunopathogenesis. Once considered purely an allergic disorder dominated by Th2 lymphocytes, IgE, mast cells, eosinophils, macrophages, and cytokines, the disease also involves local epithelial, mesenchymal, vascular and neurologic events that are involved in directing the Th2 phenotype to the lung and through aberrant injury-repair mechanisms to remodeling of the airway wall. Responses to asthma medications vary considerably among patients, likely reflecting the differing sensitivities of the various asthma phenotypes. Physicians need to recognize this when making decisions to adjust treatment to improve asthma. IL-4 and IL-13 are considered to be key contributors to cell-mediated and humoral aspects of allergic inflammation. There is controversy surrounding the role of TGF- in asthma. It is speculated that IL-5 also plays a pivotal role in eosinophilia and asthma. Anti-IgE therapy is an approved treatment for adult and childhood asthma. Helminth infections are suggested to minimize asthma symptoms. | | | | |

Patient Data

| Attribute | Value | Percentile Total | Percentile Sex = 1 | Percentile Age = 10-30 | Percentile Region = 6 |
|---|---|---|---|---|---|
| Age | 20 | | | | |
| Chickenpox_Age | 5 | | | | |
| Chickenpox_history | 1 | | | | |
| Citizenship | 3 | | | | |
| CMV_int | Reactive | | | | |
| CMV_OD | 103.5 | 24.03 | 23.34 | 26.22 | 24.07 |
| Country_of_Origin | 8 | | | | |
| Country_of_Origin_name | China | | | | |
| Diphena_Ab | 0.072 | | | | |
| Diphena_Age | 91 | | | | |
| Diphena_history | 0 | | | | |
| Diphena_int | Reactive | | | | |
| Diphena_OD | 0.3 | 46.02 | 51.66 | 47.22 | 67.96 |
| Education | 5 | | | | |
| ELECTRICITY | 1 | | | | |
| Filaria_Ab_OD | 0.0876 | 47.26 | 51.99 | 50.52 | 55.00 |
| Filaria_int | | | | | |
| HepA_int | Nonreactive | | | | |
| HepA_OD | 7.07 | 99.49 | 99.45 | 99.31 | 96.61 |

FIG. 21H-4 F

| Hepatitis_Age | | | | | |
|---|---|---|---|---|---|
| Hepatitis_history | 0 | | | | |
| HepB_cAb_int | Nonreactive | | | | |
| HepB_cAb_OD | 1.901 | 61.33 | 52.94 | 59.55 | 75.00 |
| HepB_sAb_int | NA (Predicted) | | | | |
| HepB_sAb_ratio | | | | | |
| HepB_sAg_int | NA (Predicted) | | | | |
| HepB_sAg_ratio | | | | | |
| HepB_SAB_OD | 0 | 0.00 | 0.00 | 0.00 | 0.00 |
| HepB_SAg_OD | | 0.00 | 0.00 | 0.00 | 0.00 |
| HepC_Ab_OD | 0.24 | 47.47 | 46.76 | 47.46 | 50.00 |
| HepC_int | Nonreactive | | | | |
| HepC_LIA | | | | | |
| HepC_PCR | | | | | |
| Hospitalized | 0 | | | | |
| ID | 437 | | | | |
| IFN_gamma | 0.137645208 | 51.30 | 52.21 | 49.83 | 49.07 |
| IFN_gamma_int | Reactive | | | | |
| IL_10 | 1.148617861 | 70.55 | 68.92 | 66.15 | 66.98 |
| IL_10_int | Reactive | | | | |
| IL_12_int | Reactive | | | | |
| IL_12p70 | 2.14568862 | 72.29 | 71.35 | 69.97 | 69.91 |
| IL_12p70_int | Reactive | | | | |
| IL_13 | 0.65524835 | 53.87 | 50.55 | 51.39 | 49.70 |
| IL_13_int | Reactive | | | | |
| IL_15 | 5.81743789 | 77.97 | 72.01 | 75.69 | 73.15 |
| IL_15_int | Reactive | | | | |
| IL_17 | 0.130697615 | 42.06 | 43.58 | 40.45 | 44.91 |
| IL_17_int | Reactive | | | | |
| IL_1_alpha | 0.815874295 | 62.19 | 61.73 | 59.55 | 60.65 |
| IL_1_alpha_int | Reactive | | | | |
| IL_1_beta | 0.502315334 | 70.95 | 66.36 | 65.45 | 70.37 |
| IL_1_beta_int | Reactive | | | | |
| IL_2 | 0 | 0.00 | 0.00 | 0.00 | 0.00 |
| IL_23 | 114.6982755 | 78.28 | 77.86 | 75.52 | 74.07 |
| IL_23_int | Reactive | | | | |
| IL_2_int | Nonreactive | | | | |
| IL_4 | 0.815055249 | 61.40 | 60.64 | 58.66 | 58.94 |
| IL_4_int | Reactive | | | | |
| IL_5 | 1.43442623 | 56.49 | 54.42 | 51.39 | 53.24 |
| IL_5_int | Reactive | | | | |
| IL_6 | 6.699961239 | 71.93 | 61.94 | 66.06 | 62.04 |
| IL_6_int | Reactive | | | | |
| IL_8 | 1.622395933 | 35.21 | 38.06 | 35.42 | 38.89 |
| IL_8_int | Reactive | | | | |
| Indoor_toilet | 1 | | | | |
| Indoor_toilet_type | 1 | | | | |
| Interpreter | 0 | | | | |
| Interpreter_Language | | | | | |
| Measles_age | 91 | | | | |
| Measles_history | 0 | | | | |
| Measles_Int | Positive | | | | |
| Measles_OD_DB | | 0.00 | 0.00 | 0.00 | 0.00 |
| Measles_OD_DB_int | Positive | | | | |
| Measles_OD_7 | 0.4 | 59.90 | 57.74 | 58.90 | 60.19 |
| Measles_ratio_7 | 1.4 | | | | |
| Measles_tim_DB | | 0.00 | 0.00 | 0.00 | 0.00 |

FIG. 21H-4 G

| | | | | | |
|---|---|---|---|---|---|
| Medical Problems | 0 | | | | |
| Medications | 0 | | | | |
| Months_CA | 12.3 | | | | |
| Months_pregnant | 91 | | | | |
| Mumps_Age | | | | | |
| Mumps_history | 0 | | | | |
| Mumps_OD_DB | 0.43 | 63.20 | 63.05 | 62.85 | 75.00 |
| Mumps_titre_DB | 760 | 47.33 | 48.23 | 46.26 | 54.63 |
| Outdoor_toilet | 0 | | | | |
| Outdoor_toilet_type | | | | | |
| People_household | 3 | | | | |
| Persons_Rooms | 0.5 | | | | |
| Pertussis_Age | 91 | | | | |
| Pertussis_history | 0 | | | | |
| Polio_Age | 91 | | | | |
| Polio_history | 0 | | | | |
| Pregnant | 0 | | | | |
| Refugee_camp | 0 | | | | |
| Region_of_Origin | 6 | | | | |
| Rooms_household | 8 | | | | |
| Rubella_Ab | 0 | | | | |
| Rubella_Age | 91 | | | | |
| Rubella_history | 0 | | | | |
| Rubella_Int | 1 | | | | |
| Schistosoma_Ab_OD | 0.054 | 46.61 | 51.22 | 46.70 | 48.61 |
| Schistosoma_Int | - | | | | |
| School_type | 2 | | | | |
| Sex | 1 | | | | |
| Strongyloides_Ab_OD | 0.094 | 25.76 | 31.42 | 28.13 | 31.48 |
| Strongyloides_Int | - | | | | |
| Tetanus_Ab | 0.049 | | | | |
| Tetanus_Age | 91 | | | | |
| Tetanus_history | 0 | | | | |
| Tetanus_Int | Reactive | | | | |
| Tetanus_OD | 0.116 | 8.95 | 9.40 | 6.42 | 25.00 |
| TNF_alpha | 0 | 0.00 | 0.00 | 0.00 | 0.00 |
| TNF_alpha_int | Non-reactive | | | | |
| TNF_beta | 0.333213256 | 69.34 | 69.91 | 68.06 | 71.30 |
| TNF_beta_int | Reactive | | | | |
| UNIVERSITY | 1 | | | | |
| Vaccination-_record | 0 | | | | |
| Varicella_Int | Positive | | | | |
| Varicella_OD_DB | 0.958 | 58.23 | 62.94 | 65.84 | 63.89 |
| Varicella_titre_DB | 660 | 53.54 | 58.30 | 59.90 | 59.72 |
| Water_supply_type | 1 | | | | |
| Years_Education | 16 | | | | |

FIG. 21H-4H

Patient: 596

Results

| Conditions | Suggested Action | Internal References | External References |
|---|---|---|---|
| Tetanus_Int eq Reactive | Give a booster dose of tetanus vaccine. Individuals over seven years of age receive the vaccine in combination with diphtheria vaccine (Td). Those children younger than seven years of age can be boosted with a vaccine containing a pertussis component (DTaP). People who had a serious allergic reaction to one dose of tetanus toxoid should not receive another. Persons with a moderate or severe acute illness should postpone receiving the vaccine until they are improved. | Hawkes, J.S., et al., Effect of dietary nucleotide supplementation on growth and immune function in term infants: a randomized controlled trial, European J. Clin. Nutrition 60: 254-64 (2006). McQuillan, Geraldine M., et al., Serologic immunity to diphtheria and Tetanus in the United States, Annals of Internal Medicine 136(9): 660-66 (2002). Pickering, Larry K., et al., Modulation of the Immune System by Human Milk and Infant Formula Containing Nucleotides, Pediatrics 101(2): 242-49 (1998). Vivani, Simonetta, et al., EPI vaccines-induced antibody prevalence in 8-9 year-olds in The Gambia, Trop. Med. & International Health 9(10): 1044-49 (2004). | |
| Diptheria_Int eq Reactive | Give a booster dose of diphtheria vaccine. Individuals over seven years of age receive the vaccine in combination with tetanus vaccine (Td). Those children younger than seven can be boosted with a vaccine containing the pertussis component as with the tetanus vaccine described above. People who have had a serious allergic reaction to one dose of DTaP, DT, Td, or Tdap vaccine should not receive another. Persons with a moderate or severe illness should postpone receiving the vaccine until their condition has improved. | | |
| TNF_alpha_inf eq Reactive | Examine for chronic Hepatitis C. Patients with chronic hepatitis C virus have a significantly increased prevalence of type 2 diabetes. Activation of TNF- has a pivotal role in the inflammatory process of HCV, and TNF- is known to cause insulin resistance. Patients with chronic HCV need to have periodic ImmunoScore cytokine determinations to help circumvent the onset of type 2 diabetes. Elevated levels of TGF- also indicate a poor prognosis for diabetes development in HCV patients. | | |

FIG. 21H-5A

| | | | |
|---|---|---|---|
| IL_6_int eq Reactive<br>IL_12_int eq Reactive<br>IL_17_int eq Reactive | Administer ImmunoScore cytokine panel. Rise in pro-inflammatory cytokines (IL-6, IL-12, and/or IL-17) over previous visit would indicate a future autoimmune antibody profile screening to identify possible autoimmune disease manifestation. Rise in regulatory cytokines (IL-10 and TGF-) could possibly also indicate an autoimmune disease manifestation in regression. Rise in both pro- and regulatory cytokines would trigger subsequent need to attempt to identify autoimmune disease manifestation by ImmunoScore autoimmune disease antibody screening panels. In addition to normal assessment of physical symptoms, elevated levels (>2 SD of mean) of key pro-inflammatory cytokines IL-6, IL-12, and/or IL-17 trigger: a) repeat visit in six weeks to re-measure cytokine values: i) if pro-inflammatory cytokines still elevated, recommend ImmunoScore panel to detect autoimmune antibody profile to identify possible autoimmune disease manifestation. ii) if pro-inflammatory cytokines levels decreased or moderating, recommend ImmunoScore cytokine panel evaluation annually. IL-7 may be particularly important as an initiator of many autoimmune manifestations. Depending on autoimmune disease condition, additional tests ordered can include serum thyroid stimulating hormone (TSH) for Hashimoto's or Grave's disease, anti-nuclear antibody (ANA) for systemic lupus erythematosus (SLE), neurological examination for multiple sclerosis (MS), and serum rheumatoid factor (RF) for rheumatoid arthritis (RA). Compare on site new ImmunoScore cytokine profile with baseline ImmunoScore cytokine profile. Significant increase (>20%) among grouped cytokines (e.g. Th1, Th2, Th17, and/or Treg) from previous profile values could be indicative of impending autoimmune flare that will likely require disease-specific treatment(s). | | |

FIG. 21H-5 B

| | | | |
|---|---|---|---|
| IL_10_int eq Reactive | Examine for cancer. IL-10 is a cytokine with broad anti-inflammatory properties. A penalty of the role of IL-10 to limit immune and inflammatory responses to pathogens and prevent damage to the host is that high or dysregulated levels of IL-10 may result in chronic infection or cancer. There are certainly possible therapeutic roles to Il-10 and its antagonists in human disease, all of which would benefit from careful ImmunoScore cytokine monitoring during clinical trials and subsequent evaluations. | | |
| IL_23_int eq Reactive | Examine for Multiple Sclerosis. Upregulated cytokines in MS patients include IL-17, IL-12, IL-23, IL-6, IL-21, TNF-, and other Th1 cytokines. IL-17-related cytokines are speculated to be related to disease progression. Glatiramer acetate (GA) is believed to induce GA-reactive T cells that secrete anti-inflammatory cytokines at the site of inflammation in MS - presumably increasing anti-inflammatory cytokines IL-10, IL-4, and TGF-. ImmunoScore to periodically measure patient's cytokines and at onset of flare, indicated by increased Th17 and Th1 cytokines, administer treatment. Efficacy of treatment could be monitored with monitoring of Treg cytokines interferon- and atorvastatin have both been used to treat MS. IFN- increases Th1 cytokines, while atorvastatin increases Th2 cytokines (particularly IL-5). Both may have the same effect of lessening the increase of Th17 cytokines. MS patients have general systemic increases of Th1 cytokines (particularly TNF-. This is likely related to fatigue and lapses in systemic immunity. This may be a problem in patients treated with natalizumab as systemic rises in TNF- are correlated with fatigue symptoms. | Bednáová, J. et al., Relevance of immunological variables in neuroborreliosis and multiple sclerosis, Acta Neurol. Scand. 112: 97-102 (2005). | |

FIG. 21H-5 C

| | | | |
|---|---|---|---|
| IL_5_int eq Reactive | Examine for Inflammatory Bowel Disease. IBD comprises two forms:<br>• Ulcerative colitis (UC) – increased expression of following:<br>o TNF-<br>o IL-1<br>o IL-6<br>o IL-12<br>o IL-23<br>o IL-17<br>o IL-13<br>o IL-5<br>• Crohn's disease (CD) – increased expression of following:<br>o TNF-<br>o IL-1<br>o IL-1<br>o IL-6<br>o IL-18 (in some patients)<br>o IL-10<br>o IL-4 (in some patients)<br>o IL-23<br>o IL-27<br>o IL-17<br>IL-23 appears to be the key mediator of flares of IBD. Mucosal cytokines recently cited (IL-31 and IL-32) as important are members of the IL-17 family. | | |

FIG. 21H-5 D

| | | | |
|---|---|---|---|
| IL_4_int eq Nonreactive | Examine for Diabetes. Diabetes mellitus is characterized by a lack of insulin causing elevated blood glucose, often with associated insulin resistance. Elevated serum levels of TGF- are associated with diabetic renal disease and will be tracked by the ImmunoScore cytokine diagnostic panel. Studies in animals indicate higher serum TGF- levels might ameliorate disease. A dysfunctioning endothelium is associated with both initiation and progression of atherosclerotic cardiovascular disease and has been shown to predate the onset of hyperglycemia in the natural history of type 2 diabetes. It is likely that low level inflammation plays an important role in developing this endothelial dysfunction mainly through the action of TNF- and possibly IL-6. Visceral obesity and inflammation within white adipose tissue may be a crucial step contributing to the emergence of insulin resistance, type 2 diabetes and atherosclerosis. IL-1, IL-6, IL-8, IL-10 TNF-, and TGF- levels all rise under these conditions. IL-27 can promote both anti- and pro-inflammatory responses. IL-27 up-regulates IFN-, and IL-17 and down-regulates IL-4, TGF-, and IL-10 secreted by diabetic splenocytes, suggesting a pathogenic role in T cell-mediated autoimmune diabetes. | Santos, J.L., et al., Associations between HLA-DQB1 high-risk alleges and type I diabetes do not depend on cytomegalovirus antibody status at onset: A case-parent study conducted in Chile, Immunology & Cell Biology 78: 259-63 (2000). | |
| IL_8_int eq Reactive | Examine for Breast Cancer. IL-6 is a pleiotropic cytokine with both tumor-promoting and tumor-inhibiting effects. Serum IL-6 levels, however, are a negative prognosticator in breast tumor patients. IL-6, IL-8, and IL-10 levels are higher in women with breast cancer than controls and levels also correlate with the clinical stage of disease. Elevated serum IL-8 levels are related to an accelerated clinical course, a higher tumor load, and the presence of liver or lymph node involvement. On the other hand, elevated IL-8 also has prognostic significance for post-relapse survival. | | |

FIG. 21H-5 E

| | | | | | |
|---|---|---|---|---|---|
| IL_13_Int eq Reactive | Examine for Asthma. Asthma comprises distinct heterogeneous inflammatory disorders characterized by patients showing different phenotypes with distinct genetic components, environmental causes and various pathogenesis. Once considered purely an allergic disorder dominated by Th2 lymphocytes, IgE, mast cells, eosinophils, macrophages, and cytokines, the disease also involves local epithelial, mesenchymal, vascular and neurologic events that are involved in directing the Th2 phenotype to the lung and through aberrant injury-repair mechanisms to remodeling of the airway wall. Responses to asthma medications vary considerably among patients, likely reflecting the differing sensitivities of the various asthma phenotypes. Physicians need to recognize this when making decisions to adjust treatment to improve asthma. IL-4 and IL-13 are considered to be key contributors to cell-mediated and humoral aspects of allergic inflammation. There is controversy surrounding the role of TGF- in asthma. It is speculated that IL-6 also plays a pivotal role in eosinophilia and asthma. Anti-IgE therapy is an approved treatment for adult and childhood asthma. Helminth infections are suggested to minimize asthma symptoms. | | | | |

Patient Data

| Attribute | Value | Percentile Total | Percentile Sex = 1 | Percentile Age = 10-30 | Percentile Region = 4 |
|---|---|---|---|---|---|
| Age | 20 | | | | |
| Chickenpox_Age | | | | | |
| Chickenpox_History | 0 | | | | |
| Citizenship | 3 | | | | |
| CMV_Int | Reactive | | | | |
| CMV_OD | 1.157 | 26.47 | 24.60 | 27.60 | 26.62 |
| Country_of_Origin | 6 | | | | |
| Country_of_Origin_name | Peru | | | | |
| Diptheria_Ab | 0.197 | | | | |
| Diptheria_Age | 91 | | | | |
| Diptheria_history | 0 | | | | |
| Diptheria_Int | Reactive | | | | |
| Diptheria_OD | 0.367 | 57.00 | 53.60 | 57.12 | 60.97 |
| Education | 3 | | | | |
| ELECTRICITY | 1 | | | | |
| Filaria_Ab_OD | 0.266 | 88.61 | 91.26 | 70.53 | 88.92 |
| Filaria_Int | 4 | | | | |
| HepA_Int | Reactive | | | | |
| HepA_OD | 0.069 | 7.07 | 1.44 | 1.90 | 2.36 |

FIG. 21H-5 F

| | | | | | |
|---|---|---|---|---|---|
| Hepatitis_Age | | | | | |
| Hepatitis_history | 0 | | | | |
| HepB_cAb_int | Nonreactive | | | | |
| HepB_cAb_OD | 1.855 | 46.98 | 46.36 | 37.85 | 20.31 |
| HepB_sAb_int | NA (Predicted) | | | | |
| HepB_sAb_ratio | | | | | |
| HepB_sAg_int | NA (Predicted) | | | | |
| HepB_sAg_ratio | | | | | |
| HepB_SAb_OD | 2.7 | 73.81 | 74.66 | 76.13 | 86.76 |
| HepB_SAg_OD | | 0.00 | 0.00 | 0.00 | 0.00 |
| HepC_Ab_OD | 0.31 | 42.42 | 48.76 | 47.46 | 45.23 |
| HepC_Int | Nonreactive | | | | |
| HepC_LIA | | | | | |
| HepC_PCR | | | | | |
| Hospitalized | 0 | | | | |
| ID | 596 | | | | |
| IFN_gamma | 0 | 0.00 | 0.00 | 0.00 | 0.00 |
| IFN_gamma_int | Nonreactive | | | | |
| IL_10 | 0.786648738 | 58.95 | 56.64 | 55.90 | 48.82 |
| IL_10_int | Reactive | | | | |
| IL_12_int | Reactive | | | | |
| IL_12p70 | 0.614606613 | 49.64 | 46.34 | 44.10 | 41.85 |
| IL_12p70_int | Reactive | | | | |
| IL_13 | 0.176639435 | 35.90 | 33.53 | 33.68 | 27.08 |
| IL_13_int | Reactive | | | | |
| IL_15 | 4.494439901 | 70.27 | 64.93 | 65.84 | 64.92 |
| IL_15_int | Reactive | | | | |
| IL_17 | 0.550793307 | 50.94 | 52.43 | 49.31 | 42.15 |
| IL_17_int | Reactive | | | | |
| IL_1_alpha | 0.426577042 | 57.00 | 55.57 | 53.90 | 52.82 |
| IL_1_alpha_int | Reactive | | | | |
| IL_1_beta | 0.393608443 | 61.33 | 57.52 | 54.66 | 49.85 |
| IL_1_beta_int | Reactive | | | | |
| IL_2 | 0 | 0.00 | 0.00 | 0.00 | 0.00 |
| IL_23 | 2.013963488 | 37.37 | 36.63 | 34.72 | 33.54 |
| IL_23_int | Reactive | | | | |
| IL_2_int | Nonreactive | | | | |
| IL_4 | 0 | 0.00 | 0.00 | 0.00 | 0.00 |
| IL_4_int | Nonreactive | | | | |
| IL_5 | 3.752281022 | 78.79 | 75.33 | 74.31 | 75.06 |
| IL_5_int | Reactive | | | | |
| IL_6 | 6.195950774 | 70.35 | 59.96 | 58.87 | 64.31 |
| IL_6_int | Reactive | | | | |
| IL_8 | 3.080865915 | 47.87 | 46.89 | 46.65 | 42.15 |
| IL_8_int | Reactive | | | | |
| Indoor_toilet | 1 | | | | |
| Indoor_toilet_type | 1 | | | | |
| Interpreter | 0 | | | | |
| Interpreter_Language | | | | | |
| Measles_age | 6 | | | | |
| Measles_history | 1 | | | | |
| Measles_int | Negative | | | | |
| Measles_OD_DB | | 0.00 | 0.00 | 0.00 | 0.00 |
| Measles_OD_DB_int | Positive | | | | |
| Measles_OD_2 | 0.24 | 56.93 | 54.09 | 55.77 | 53.23 |
| Measles_ratio_2 | 0.83 | | | | |
| Measles_titre_DB | | 0.00 | 0.00 | 0.00 | 0.00 |

FIG. 21H-5 G

| | | | | | |
|---|---|---|---|---|---|
| Medical Problems | 0 | | | | |
| Medications | 0 | | | | |
| Months_CA | 45.5 | | | | |
| Months_pregnant | 91 | | | | |
| Mumps_Age | | | | | |
| Mumps_history | 0 | | | | |
| Mumps_OD_DB | 0.238 | 31.39 | 32.19 | 32.64 | 31.69 |
| Mumps_titre_DB | 663 | 43.22 | 43.81 | 44.97 | 44.00 |
| Outdoor_toilet | 0 | | | | |
| Outdoor_toilet_type | | | | | |
| People_household | 5 | | | | |
| Persons_Rooms | 1.25 | | | | |
| Pertussis_Age | 91 | | | | |
| Pertussis_history | 0 | | | | |
| Polio_Age | 91 | | | | |
| Polio_history | 0 | | | | |
| Pregnant | 0 | | | | |
| Refugee_camp | 0 | | | | |
| Region_of_Origin | 4 | | | | |
| Rooms_household | 4 | | | | |
| Rubella_Ab | 19.2 | | | | |
| Rubella_Age | 91 | | | | |
| Rubella_history | 0 | | | | |
| Rubella_Int | 0 | | | | |
| Schistosoma_Ab_OD | 0.016 | 21.79 | 25.66 | 23.09 | 21.23 |
| Schistosoma_int | - | | | | |
| School_type | 2 | | | | |
| Sex | 1 | | | | |
| Strongyloides_Ab_OD | 2.1485 | 98.99 | 98.78 | 98.96 | 99.38 |
| Strongyloides_int | + | | | | |
| Tetanus_Ab | 5.719 | | | | |
| Tetanus_Age | 91 | | | | |
| Tetanus_history | 0 | | | | |
| Tetanus_Int | Reactive | | | | |
| Tetanus_OD | 2.095 | 93.58 | 93.69 | 92.01 | 90.15 |
| TNF_alpha | 1.499000666 | 67.53 | 66.92 | 64.06 | 60.92 |
| TNF_alpha_int | Reactive | | | | |
| TNF_beta | 0.382653061 | 70.56 | 71.02 | 69.27 | 65.23 |
| TNF_beta_int | Reactive | | | | |
| UNIVERSITY | 0 | | | | |
| Vaccination-_record | 0 | | | | |
| Varicella_Int | Positive | | | | |
| Varicella_OD_DB | 0.553 | 24.31 | 26.44 | 29.34 | 24.31 |
| Varicella_titre_DB | 468 | 37.95 | 40.93 | 43.92 | 35.69 |
| Water_supply_type | 1 | | | | |
| Years_Education | 9 | | | | |

FIG. 21H-5H

Patient: 614
Results

| Conditions | Suggested Action | Internal References | External References |
|---|---|---|---|
| Tetanus_int eq Reactive | Give a booster dose of tetanus vaccine. Individuals over seven years of age receive the vaccine in combination with diphtheria vaccine (Td). Those children younger than seven years of age can be boosted with a vaccine containing a pertussis component (DTaP). People who had a serious allergic reaction to one dose of tetanus toxoid should not receive another. Persons with a moderate or severe acute illness should postpone receiving the vaccine until they are improved. | Hawkes, J.S., et al., Effect of dietary nucleotide supplementation on growth and immune function in term infants: a randomized controlled trial, European J. Clin. Nutrition 60: 254-64 (2006). McQuillan, Geraldine M., et al., Serologic Immunity to diphtheria and Tetanus in the United States, Annals of Internal Medicine 136(9): 660-66 (2002). Pickering, Larry K., et al., Modulation of the Immune System by Human Milk and Infant Formula Containing Nucleotides, Pediatrics 101(2): 242-49 (1998). Vivani, Simonetta, et al., EPI vaccines-induced antibody prevalence in 8-9 year-olds in The Gambia, Trop. Med. & International Health 9(10): 1044-49 (2004). | |
| Diptheria_int eq Reactive | Give a booster dose of diphtheria vaccine. Individuals over seven years of age receive the vaccine in combination with tetanus vaccine (Td). Those children younger than seven can be boosted with a vaccine containing the pertussis component as with the tetanus vaccine described above. People who have had a serious allergic reaction to one dose of DTaP, DT, Td, or Tdap vaccine should not receive another. Persons with a moderate or severe illness should postpone receiving the vaccine until their condition has improved. | | |
| TNF_alpha_int eq Reactive | Examine for chronic Hepatitis C. Patients with chronic hepatitis C virus have a significantly increased prevalence of type 2 diabetes. Activation of TNF- has a pivotal role in the inflammatory process of HCV, and TNF- is known to cause insulin resistance. Patients with chronic HCV need to have periodic immunoScore cytokine determinations to help circumvent the onset of type 2 diabetes. Elevated levels of TGF- also indicate a poor prognosis for diabetes development in HCV patients. | | |

FIG. 21H-6A

| | | | |
|---|---|---|---|
| IL_6_int eq Reactive<br>IL_12_int eq Reactive<br>IL_17_int eq Reactive | Administer ImmunoScore cytokine panel. Rise in pro-inflammatory cytokines (IL-6, IL-12, and/or IL-17) over previous visit would indicate a future autoimmune antibody profile screening to identify possible autoimmune disease manifestation. Rise in regulatory cytokines (IL-10 and TGF-) could possibly also indicate an autoimmune disease manifestation in regression. Rise in both pro- and regulatory cytokines would trigger subsequent need to attempt to identify autoimmune disease manifestation by ImmunoScore autoimmune disease antibody screening panels. In addition to normal assessment of physical symptoms, elevated levels (>2 SD of mean) of key pro-inflammatory cytokines IL-6, IL-12, and/or IL-17 trigger: a) repeat visit in six weeks to re-measure cytokine values: i) if pro-inflammatory cytokines still elevated, recommend ImmunoScore panel to detect autoimmune antibody profile to identify possible autoimmune disease manifestation. ii) if pro-inflammatory cytokines levels decreased or moderating, recommend ImmunoScore cytokine panel evaluation annually. IL-7 may be particularly important as an initiator of many autoimmune manifestations. Depending on autoimmune disease condition, additional tests ordered can include serum thyroid stimulating hormone (TSH) for Hashimoto's or Grave's disease, anti-nuclear antibody (ANA) for systemic lupus erythematosus (SLE), neurological examination for multiple sclerosis (MS), and serum rheumatoid factor (RF) for rheumatoid arthritis (RA). Compare on site new ImmunoScore cytokine profile with baseline ImmunoScore cytokine profile. Significant increase (>20%) among grouped cytokines (e.g. Th1, Th2, Th17, and/or Treg) from previous profile values could be indicative of impending autoimmune flare that will likely require disease-specific treatment(s). | | |

FIG. 21H-6B

| | | | |
|---|---|---|---|
| IFN_gamma_int eq Reactive | Examine for Systemic Lupus Erythematosus. Activated autoreactive Th cells provide the help required for autoreactive B cells to differentiate and produce autoreactive antibodies. Studies of animal models and SLE patients indicate an important role for type I interferons. Although type I IFNs are classically considered to promote Th1-mediated cell responses, they can also inhibit Th1 and Th17 responses. At this point, it is not certain whether intervention with IFN inhibitors will be beneficial or detrimental to SLE patients, and the application of IFN inhibitory therapy may be based upon stage of SLE flare. ImmunoScore cytokine panels will be used to add clarity to therapeutics. As SLE patients live longer due to improved therapies and preventive measures, death and disability from cardiovascular events are increasing. The mechanism for the increased risk of SLE patients for cardiovascular events is likely due to a combination of inflammatory and immune mechanisms. There are increased levels of oxidized LDL (oxLDL), pro-inflammatory HDL, MCP-1, TNF-, IFN-, IL-1, and IL-12. ImmunoScore cardiac risk markers will be combined with ImmunoScore cytokine panels in patients with SLE, and progressive monitoring will be performed in these patients at regular intervals. | | |

FIG. 21H-6 C

| | | | |
|---|---|---|---|
| IL_23_int eq Reactive | Examine for Multiple Sclerosis. Upregulated cytokines in MS patients include IL-17, IL-12, IL-23, IL-6, IL-21, TNF-, and other Th1 cytokines. IL-17-related cytokines are speculated to be related to disease progression. Glatiramer acetate (GA) is believed to induce GA-reactive T cells that secrete anti-inflammatory cytokines at the site of inflammation in MS - presumably increasing anti-inflammatory cytokines IL-10, IL-4, and TGF-. ImmunoScore to periodically measure patient's cytokines and at onset of flare, indicated by increased Th17 and Th1 cytokines, administer treatment. Efficacy of treatment could be monitored with monitoring of Treg cytokines. Interferon- and atorvastatin have both been used to treat MS. IFN- increases Th1 cytokines, while atorvastatin increases Th2 cytokines (particularly IL-5). Both may have the same effect of lessening the increase of Th17 cytokines. MS patients have general systemic increases of Th1 cytokines (particularly TNF-. This is likely related to fatigue and lapses in systemic immunity. This may be a problem in patients treated with natalizumab as systemic rises in TNF- are correlated with fatigue symptoms. | Bednářová, J. et al. Relevance of immunological variables in neuroborreliosis and multiple sclerosis. Acta Neurol. Scand. 112: 97-102 (2005). | |
| IL_5_int eq Reactive | Examine for Inflammatory Bowel Disease. IBD comprises two forms.<br>• Ulcerative colitis (UC) - increased expression of following:<br>o TNF-<br>o IL-1<br>o IL-6<br>o IL-12<br>o IL-23<br>o IL-17<br>o IL-13<br>o IL-5<br>• Crohn's disease (CD) -- increased expression of following:<br>o TNF<br>o IL-1<br>o IL-1<br>o IL-6<br>o IL-18 (in some patients)<br>o IL-10<br>o IL-4 (in some patients)<br>o IL-23<br>o IL-27<br>o IL-17<br>IL-23 appears to be the key mediator of flares of IBD. Mucosal cytokines recently cited (IL-31 and IL-32) as important are members of the IL-17 family. | | |

FIG. 21H-6 D

| | | | |
|---|---|---|---|
| IL_4_int eq Nonreactive | Examine for Diabetes. Diabetes mellitus is characterized by a lack of insulin causing elevated blood glucose, often with associated insulin resistance. Elevated serum levels of TGF- are associated with diabetic renal disease and will be tracked by the ImmunoScore cytokine diagnostic panel. Studies in animals indicate higher serum TGF- levels might ameliorate disease. A dysfunctioning endothelium is associated with both initiation and progression of atherosclerotic cardiovascular disease and has been shown to predate the onset of hyperglycemia in the natural history of type 2 diabetes. It is likely that low level inflammation plays an important role in developing this endothelial dysfunction mainly through the action of TNF- and possibly IL-6. Visceral obesity and inflammation within white adipose tissue may be a crucial step contributing to the emergence of insulin resistance, type 2 diabetes and atherosclerosis. IL-1, IL-6, IL-8, IL-10 TNF-, and TGF- levels all rise under these conditions. IL-27 can promote both anti- and pro-inflammatory responses. IL-27 up-regulates IFN-, and IL-17 and down-regulates IL-4, TGF-, and IL-10 secreted by diabetic splenocytes, suggesting a pathogenic role in T cell-mediated autoimmune diabetes. | Santos, J.L., et al., Associations between HLA-DQB1 high-risk alleges and type I diabetes do not depend on cytomegalovirus antibody status at onset. A case-parent study conducted in Chile, Immunology & Cell Biology 78: 259-63 (2000). | |
| IL_8_int eq Reactive | Examine for Breast Cancer. IL-6 is a pleiotropic cytokine with both tumor-promoting and tumor-inhibiting effects. Serum IL-6 levels, however, are a negative prognosticator in breast tumor patients. IL-6, IL-8, and IL-10 levels are higher in women with breast cancer than controls and levels also correlate with the clinical stage of disease. Elevated serum IL-8 levels are related to an accelerated clinical course, a higher tumor load, and the presence of liver or lymph node involvement. On the other hand, elevated IL-8 also has prognostic significance for post-relapse survival. | | |

FIG. 21H-6 E

| | | | | | |
|---|---|---|---|---|---|
| IL_13_int eq Reactive | Examine for Asthma. Asthma comprises distinct heterogeneous inflammatory disorders characterized by patients showing different phenotypes with distinct genetic components, environmental causes, and immunological diatheses. Once considered purely an allergic disorder dominated by Th2 lymphocytes, IgE, mast cells, eosinophils, macrophages, and cytokines, the disease also involves local epithelial, mesenchymal, vascular and neurologic events that are involved in directing the Th2 phenotype to the lung and through aberrant injury-repair mechanisms to remodeling of the airway wall. Responses to asthma medications vary considerably among patients, likely reflecting the differing sensitivities of the various asthma phenotypes. Physicians need to recognize this when making decisions to adjust treatment to improve asthma. IL-4 and IL-13 are considered to be key contributors to cell-mediated and humoral aspects of allergic inflammation. There is controversy surrounding the role of TGF- in asthma. It is speculated that IL-5 also plays a pivotal role in eosinophils and asthma. Anti IgE therapy is an approved treatment for adult and childhood asthma. Helminth infections are suggested to minimize asthma symptoms. | | | | |

Patient Data

| Attribute | Value | Percentile Total | Percentile Sex = 0 | Percentile Age = 30-50 | Percentile Region = 3 |
|---|---|---|---|---|---|
| Age | 30 | | | | |
| Chickenpox_Age | | | | | |
| Chickenpox_history | 0 | | | | |
| Citizenship | 0 | | | | |
| CMV_Int | Reactive | | | | |
| CMV_OD | >250.00 | 0.00 | 0.00 | 0.00 | 0.00 |
| Country_of_Origin | 0 | | | | |
| Country_of_Origin_name | Morocco | | | | |
| Diptheria_Ab | 0.246 | | | | |
| Diptheria_Age | 91 | | | | |
| Diptheria_history | 0 | | | | |
| Diptheria_Int | Reactive | | | | |
| Diptheria_OD | 0.400 | 64.79 | 54.15 | 65.47 | 66.85 |
| Education | 5 | | | | |
| ELECTRICITY | 1 | | | | |
| Filaria_Ab_OD | 0.186 | 75.85 | 70.33 | 76.27 | 87.82 |
| Filaria_Int | | | | | |
| HepA_Int | Reactive | | | | |
| HepA_OD | 0.071 | 21.28 | 27.59 | 21.73 | 17.85 |

FIG. 21H-6F

| Hepatitis_Age | | | | | |
|---|---|---|---|---|---|
| Hepatitis_history | 0 | | | | |
| HepB_cAb_int | Nonreactive | | | | |
| HepB_cAb_OD | 2.166 | 96.03 | 94.81 | 95.73 | 94.87 |
| HepB_eAb_int | NA (Predicted) | | | | |
| HepB_eAb_ratio | | | | | |
| HepB_eAg_int | NA (Predicted) | | | | |
| HepB_eAg_ratio | | | | | |
| HepB_sAb_OD | 0 | 0.00 | 0.00 | 0.00 | 0.00 |
| HepB_sAg_OD | | 0.00 | 0.00 | 0.00 | 0.00 |
| HepC_Ab_OD | 0.23 | 38.80 | 48.96 | 56.07 | 67.95 |
| HepC_int | Nonreactive | | | | |
| HepC_RIA | | | | | |
| HepC_PCR | | | | | |
| Hospitalized | 0 | | | | |
| ID | 614 | | | | |
| IFN_gamma | 0.078938168 | 61.28 | 66.58 | 62.27 | 68.59 |
| IFN_gamma_int | Reactive | | | | |
| IL_10 | 0 | 0.00 | 0.00 | 0.00 | 0.00 |
| IL_10_int | Nonreactive | | | | |
| IL_12_int | Reactive | | | | |
| IL_12p70 | 1.413918712 | 66.68 | 61.29 | 62.93 | 74.36 |
| IL_12p70_int | Reactive | | | | |
| IL_13 | 0.079652174 | 33.04 | 37.76 | 34.40 | 38.46 |
| IL_13_int | Reactive | | | | |
| IL_15 | 2.748037214 | 40.84 | 46.06 | 43.60 | 48.08 |
| IL_15_int | Reactive | | | | |
| IL_17 | 0.388500655 | 51.37 | 48.13 | 52.67 | 56.03 |
| IL_17_int | Reactive | | | | |
| IL_1_alpha | 0.155118025 | 52.80 | 54.36 | 54.53 | 57.87 |
| IL_1_alpha_int | Reactive | | | | |
| IL_1_beta | 0 | 0.00 | 0.00 | 0.00 | 0.00 |
| IL_1_beta_int | Nonreactive | | | | |
| IL_2 | 0 | 0.00 | 0.00 | 0.00 | 0.00 |
| IL_23 | 9.302325581 | 27.63 | 25.52 | 29.20 | 41.67 |
| IL_23_int | Reactive | | | | |
| IL_2_int | Nonreactive | | | | |
| IL_4 | 0 | 0.00 | 0.00 | 0.00 | 0.00 |
| IL_4_int | Nonreactive | | | | |
| IL_5 | 0.798357664 | 47.76 | 49.38 | 56.67 | 64.10 |
| IL_5_int | Reactive | | | | |
| IL_6 | 0.060403226 | 27.86 | 26.97 | 24.13 | 26.26 |
| IL_6_int | Reactive | | | | |
| IL_8 | 4.46943662 | 58.44 | 56.64 | 58.13 | 64.74 |
| IL_8_int | Reactive | | | | |
| Indoor_toilet | 1 | | | | |
| Indoor_toilet_type | 2 | | | | |
| Interpreter | 0 | | | | |
| Interpreter_Language | | | | | |
| Measles_age | 91 | | | | |
| Measles_history | 0 | | | | |
| Measles_int | Positive | | | | |
| Measles_OD_OB | | 0.00 | 0.00 | 0.00 | 0.00 |
| Measles_OD_OB_int | Positive | | | | |
| Measles_OD_Z | 1.23 | 79.44 | 76.25 | 78.46 | 76.26 |
| Measles_ratio_Z | 6.25 | | | | |
| Measles_titre_OB | | 0.00 | 0.00 | 0.00 | 0.00 |

FIG. 21H-6 G

| | | | | | |
|---|---|---|---|---|---|
| Medical Problems | 0 | | | | |
| Medications | 0 | | | | |
| Months_CA | 4.3 | | | | |
| Months_pregnant | 91 | | | | |
| Mumps_Age | | | | | |
| Mumps_history | 0 | | | | |
| Mumps_OD_DB | 0.278 | 39.83 | 38.38 | 40.13 | 35.26 |
| Mumps_titre_DB | 520 | 32.68 | 31.33 | 32.27 | 30.13 |
| Outdoor_toilet | 0 | | | | |
| Outdoor_toilet_type | | | | | |
| People_household | 11 | | | | |
| Persons_Rooms | 0.916666667 | | | | |
| Pertussis_Age | 91 | | | | |
| Pertussis_history | 0 | | | | |
| Polio_Age | 91 | | | | |
| Polio_history | 0 | | | | |
| Pregnant | 0 | | | | |
| Refugee_camp | 0 | | | | |
| Region_of_Origin | 3 | | | | |
| Rooms_household | 12 | | | | |
| Rubella_Ab | 14.4 | | | | |
| Rubella_Age | 91 | | | | |
| Rubella_history | 2 | | | | |
| Rubella_int | 0 | | | | |
| Schistosoma_Ab_OD | 0.04 | 37.66 | 27.80 | 37.87 | 43.59 |
| Schistosoma_int | - | | | | |
| School_type | 2 | | | | |
| Sex | 0 | | | | |
| Strongyloides_Ab_OD | 0.5735 | 87.81 | 85.48 | 86.67 | 90.38 |
| Strongyloides_Int | + | | | | |
| Tetanus_Ab | 0.106 | | | | |
| Tetanus_Age | 91 | | | | |
| Tetanus_history | 0 | | | | |
| Tetanus_Int | Reactive | | | | |
| Tetanus_OD | 0.183 | 25.40 | 26.76 | 26.80 | 28.21 |
| TNF_alpha | 2.023650899 | 73.52 | 75.73 | 74.80 | 80.77 |
| TNF_alpha_int | Reactive | | | | |
| TNF_beta | 0.255102041 | 66.88 | 65.15 | 68.00 | 77.56 |
| TNF_beta_int | Reactive | | | | |
| UNIVERSITY | 1 | | | | |
| Vaccination-_record | 0 | | | | |
| Varicella_Int | Positive | | | | |
| Varicella_OD_DB | 0.761 | 41.99 | 33.40 | 38.40 | 47.44 |
| Varicella_titre_DB | 804 | 62.12 | 53.73 | 58.27 | 70.51 |
| Water_supply_type | 1 | | | | |
| Years_Education | 17 | | | | |

FIG. 21H-6H

Patient: 715

Results

| Conditions | Suggested Action | Internal References | External References |
|---|---|---|---|
| Tetanus_int eq Reactive | Give a booster dose of tetanus vaccine. Individuals over seven years of age receive the vaccine in combination with diphtheria vaccine (Td). Those children younger than seven years of age can be boosted with a vaccine containing a pertussis component (DTaP). People who had a serious allergic reaction to one dose of tetanus toxoid should not receive another. Persons with a moderate or severe acute illness should postpone receiving the vaccine until they are improved. | Hawkes, J.S., et al., Effect of dietary nucleotide supplementation on growth and immune function in term infants: a randomized controlled trial, European J. Clin. Nutrition 60: 254-64 (2006). McQuillan, Geraldine M., et al., Serologic Immunity to diphtheria and Tetanus in the United States, Annals of Internal Medicine 136(9): 660-66 (2002). Pickering, Larry K., et al., Modulation of the Immune System by Human Milk and Infant Formula Containing Nucleotides, Pediatrics 101(2): 242-49 (1998). Vivani, Simonetta, et al., EPI vaccines-induced antibody prevalence in 6-9 year-olds in The Gambia, Trop. Med. & International Health 9(10): 1044-49 (2004). | |
| Diptheria_int eq Reactive | Give a booster dose of diphtheria vaccine. Individuals over seven years of age receive the vaccine in combination with tetanus vaccine (Td). Those children younger than seven can be boosted with a vaccine containing the pertussis component as with the tetanus vaccine described above. People who have had a serious allergic reaction to one dose of DTaP, DT, Td, or Tdap vaccine should not receive another. Persons with a moderate or severe illness should postpone receiving the vaccine until their condition has improved. | | |
| TNF_alpha_int eq Reactive | Examine for chronic Hepatitis C. Patients with chronic hepatitis C virus have a significantly increased prevalence of type 2 diabetes. Activation of TNF- has a pivotal role in the inflammatory process of HCV, and TNF- is known to cause insulin resistance. Patients with chronic HCV need to have periodic ImmunoScore cytokine determinations to help circumvent the onset of type 2 diabetes. Elevated levels of TGF- also indicate a poor prognosis for diabetes development in HCV patients. | | |

FIG. 21H-7A

| | | | |
|---|---|---|---|
| IL_6_int eq Reactive<br>IL_12_int eq Reactive<br>IL_17_int eq Reactive | Administer ImmunoScore cytokine panel. Rise in pro-inflammatory cytokines (IL-6, IL-12, and/or IL-17) over previous visit would indicate a future autoimmune antibody profile screening to identify possible autoimmune disease manifestation. Rise in regulatory cytokines (IL-10 and TGF-) could possibly also indicate an autoimmune disease manifestation in regression. Rise in both pro- and regulatory cytokines would trigger subsequent need to attempt to identify autoimmune disease manifestation by ImmunoScore autoimmune disease antibody screening panels. In addition to normal assessment of physical symptoms, elevated levels (>2 SD of mean) of key pro-inflammatory cytokines IL-6, IL-12, and/or IL-17 trigger: a) repeat visit in six weeks to re-measure cytokine values. i) if pro-inflammatory cytokines still elevated, recommend ImmunoScore panel to detect autoimmune antibody profile to identify possible autoimmune disease manifestation. ii) if pro-inflammatory cytokines levels decreased or moderating, recommend ImmunoScore cytokine panel evaluation annually. IL-7 may be particularly important as an initiator of many autoimmune manifestations. Depending on autoimmune disease condition, additional tests ordered can include serum thyroid stimulating hormone (TSH) for Hashimoto's or Grave's disease, anti-nuclear antibody (ANA) for systemic lupus erythematosus (SLE), neurological examination for multiple sclerosis (MS), and serum rheumatoid factor (RF) for rheumatoid arthritis (RA). Compare on site new ImmunoScore cytokine profile with baseline ImmunoScore cytokine profile. Significant increase (>20%) among grouped cytokines (e.g., Th1, Th2, Th17, and/or Treg) from previous profile values could be indicative of impending autoimmune flare that will likely require disease-specific treatment(s). | | |
| IL_7_int eq Reactive<br>IL_1_alpha_int eq Reactive<br>IL_1_beta_int eq Reactive | Examine for Rheumatoid arthritis. Rheumatoid arthritis (RA) is a chronic disorder for which there is no known cure. The optimal treatment of RA requires a comprehensive program that combines medical, social, and emotional support for the patient. Strategies are all aimed at reducing pain and discomfort, preventing | | |

FIG. 21H-7 B deformities, and loss of joint function. Treatment options include reduction of joint stress, physical and occupational therapy, and surgical intervention. Drug treatment prescriptions should be closely tied to ImmunoScore cytokine analyses to monitor RA flares and worsening of disease status. Drug classes to treat rheumatoid arthritis. 1) Non-steroidal anti-inflammatory agents (NSAIDs). NSAIDs reduce acute inflammation, reduce pain and improve function. They do not change the course of disease or prevent joint destruction; 2)Corticosteroids. Corticosteroids have both anti-inflammatory and immunoregulatory activity; 3) Disease modifying anti-rheumatic drugs (DMARDs). DMARD agents have been shown to alter the course of RA and improve radiographic outcomes. There are contra-indications for all of the treatment classes described above. Closely tied ImmunoScore cytokine measurement and courses of treatment will optimize RA treatment for each individual. Anti-inflammatory effect within hours, but reasonable trial period for relief of RA symptoms is 1 month. The most common toxicity is gastrointestinal disturbance which may clinically include burning, belching, or irritation, but which can represent irritation of the lining of the stomach, erosions, and ulcerations that may result in bleeding. Selective COX-2 inhibitors exhibit safer GI profiles than conventional non-selective NSAIDs, but may increase cardiovascular effects on blood pressure and additional effects on vascular beds. The use of NSAIDs medications must take into account their relative risks in an individual patient of gastrointestinal damage versus potential cardiovascular risk factors. Physicians treating RA patients with NSAIDs would periodically monitor serum cytokine levels to track inflammatory cytokines and relate them to symptoms of GI irritation and/or cardiovascular damage. Corticosteroids are useful in early disease as temporary adjunctive therapy while waiting for DMARDs to exert anti-inflammatory effects. This group is also useful as chronic adjunctive therapy in patients with severe disease not well controlled on NSAIDs or DMARDs. Side effects of prednisone include weight

FIG. 21H-7 C

FIG. 21H-7D and some develop anti-nuclear antibodies characteristic of SLE. Screening for latent TB infection is prudent before initiation of TNF inhibitor treatments. Infliximab is an anti-TNF antibody developed in mice. Anti-infliximab antibodies can develop in patients, reducing the effectiveness of the treatments. ImmunoScore diagnostic follow-up would include cytokine measurements looking for increased Th2 (antibody) response coupled with specific measurement of anti-TNF antibodies. Opportunistic infections and sepsis have been reported with infliximab treatment. Periodic examination of cytokine balance would indicate patients coming out of immune balance. Observation of wildly fluctuating cytokine values would be indicative of an immune system swaying out of control and indicate likely candidates for sepsis. Adalimumab is another anti-TNF antibody treatment for RA. Increased infections ranging from mild to serious are seen in clinical practice. In addition, ANA titers have been seen as well as cases of lupus-like disease. Abatacept is one of a class of agents known as T-cell costimulatory blockers. These agents interfere with the interactions between antigen-presenting cells and T lymphocytes and affect early stages in the pathogenic cascade of events in RA. Infections are increased in patients being treated with abatacept. Periodic ImmunoScore cytokine measurement examining cytokine balance would coincide with patient treatment. Rituximab binds to the CD20 molecule on B cell surfaces leading to the removal of B cells from circulation. Clinical effects on RA are hypothesized to occur from decrease in B cell cytokines, interactions with B cells and T cells, or due to reductions in autoantibody levels. Infusion reactions to rituximab may include hives, itching, swelling, difficulty breathing, fever, chills, and changes in blood pressure. These are usually mild and respond to slowing the infusion rate or additional medication (such as antihistamines) but may be severe. Monitoring cytokine levels during infusion could lead to better monitoring of patient reaction to rituximab infusions. Anakinra is an IL-1 receptor antagonist. ImmunoScore measurement of IL-1

FIG. 21H-7 E

| | | | |
|---|---|---|---|
| | and IL-1 serum concentrations during anakinra therapy would indicate effectiveness and balance of the drug to cytokine levels in the patient. | | |
| IFN_gamma_int eq Reactive | Examine for Systemic Lupus Erythematosus. Activated autoreactive Th cells provide the help required for autoreactive B cells to differentiate and produce autoreactive antibodies. Studies of animal models and SLE patients indicate an important role for type I interferons. Although type I IFNs are classically considered to promote Th1-mediated cell responses, they can also inhibit Th1 and Th17 responses. At this point, it is not certain whether intervention with IFN inhibitors will be beneficial or detrimental to SLE patients, and the application of IFN inhibitory therapy may be based upon stage of SLE flare. ImmunoScore cytokine panels will be used to add clarity to therapeutics. As SLE patients live longer due to improved therapies and preventive measures, death and disability from cardiovascular events are increasing. The mechanism for the increased risk of SLE patients for cardiovascular events is likely due to a combination of inflammatory and immune mechanisms. There are increased levels of oxidized LDL (oxLDL), pro-inflammatory HDL, MCP-1, TNF-, IFN-, IL-1, and IL-12. ImmunoScore cardiac risk markers will be combined with ImmunoScore cytokine panels in patients with SLE, and progressive monitoring will be performed in these patients at regular intervals. | | |
| IL_10_int eq Reactive | Examine for cancer. IL-10 is a cytokine with broad anti-inflammatory properties. A penalty of the role of IL-10 to limit immune and inflammatory responses to pathogens and prevent damage to the host is that high or dysregulated levels of IL-10 may result in chronic infection or cancer. There are certainly possible therapeutic roles for IL-10 and its antagonists in human disease, all of which would benefit from careful ImmunoScore cytokine monitoring during clinical trials and subsequent evaluations. | | |

FIG. 21H-7 F

| | | | |
|---|---|---|---|
| IL_23_int eq Reactive | Examine for Multiple Sclerosis. Upregulated cytokines in MS patients include IL-17, IL-12, IL-23, IL-6, IL-21, TNF-, and other Th1 cytokines. IL-17 related cytokines are speculated to be related to disease progression. Glatiramer acetate (GA) is believed to induce GA-reactive T cells that secrete anti-inflammatory cytokines at the site of inflammation in MS - presumably increasing anti-inflammatory cytokines IL-10, IL-4, and TGF-. ImmunoScore to periodically measure patient's cytokines and at onset of flare, indicated by increased Th17 and Th1 cytokines, administer treatment. Efficacy of treatment could be monitored with monitoring of Treg cytokines Interferon- and atorvastatin have both been used to treat MS. IFN increases Th1 cytokines, while atorvastatin increases Th2 cytokines (particularly IL-5). Both may have the same effect of lessening the increase of Th17 cytokines. MS patients have general systemic increases of Th1 cytokines (particularly TNF-. This is likely related to fatigue and lapses in systemic immunity. This may be a problem in patients treated with natalizumab as systemic rises in TNF- are correlated with fatigue symptoms. | Bednářová, J. et al., Relevance of immunological variables in neuroborreliosis and multiple sclerosis. Acta Neurol. Scand. 112: 97-102 (2005). | |
| IL_5_int eq Reactive | Examine for Inflammatory Bowel Disease. IBD comprises two forms:<br>• Ulcerative colitis (UC) – increased expression of following:<br>o TNF-<br>o IL-1<br>o IL-6<br>o IL-12<br>o IL-23<br>o IL-17<br>o IL-13<br>o IL-5<br>• Crohn's disease (CD) – increased expression of following:<br>o TNF-<br>o IL-1<br>o IL-1<br>o IL-6<br>o IL-18 (in some patients)<br>o IL-10<br>o IL-4 (in some patients)<br>o IL-23<br>o IL-27<br>o IL-17<br>IL-23 appears to be the key mediator of flares of IBD. Mucosal cytokines recently cited (IL-31 and IL-32) as important are members of the IL-17 family. | | |

FIG. 21H-7 G

| | | | |
|---|---|---|---|
| IL_6_int eq Reactive | Examine for Breast Cancer. IL-6 is a pleiotropic cytokine with both tumor-promoting and tumor-inhibiting effects. Serum IL-6 levels, however, are a negative prognosticator in breast tumor patients.<br>IL-6, IL-8, and IL-10 levels are higher in women with breast cancer than controls and levels also correlate with the clinical stage of disease. Elevated serum IL-8 levels are related to an accelerated clinical course, a higher tumor load, and the presence of liver or lymph node involvement. On the other hand, elevated IL-8 also has prognostic significance for post-relapse survival. | | |
| IL_4_int eq Reactive | Examine for Allergies. Allergies are the result of aberrant immune reactivity to common innocuous environmental proteins. A pivotal component of allergic pathogenesis is the generation of allergen-specific Th cells with an effector phenotype. Th17 cells may also contribute to the pathogenesis of classically recognized Th2-mediated allergic disorders. This may vary by individual patient, and immunoScore cytokine profiling would reveal individual differences from patient to patient. Allergic disorders would have a recommendation for treatment plans based upon Th2/Th17 immune balance | | |

FIG. 21H-7 H

| | | | | | |
|---|---|---|---|---|---|
| IL_13_Int eq Reactive | Examine for Asthma. Asthma comprises distinct heterogeneous inflammatory disorders characterized by patients showing different phenotypes with distinct genetic components, environmental causes, and immunopathogenesis. Once considered purely an allergic disorder dominated by Th2 lymphocytes, IgE, mast cells, eosinophils, macrophages, and cytokines, the disease also involves local epithelial, mesenchymal, vascular and neurologic events that are involved in directing the Th2 phenotype to the lung and through aberrant injury-repair mechanisms to remodeling of the airway wall. Responses to asthma medications vary considerably among patients, likely reflecting the differing sensitivities of the various asthma phenotypes. Physicians need to recognize this when making decisions to adjust treatment to improve asthma. IL-4 and IL-13 are considered to be key contributors to cell-mediated and humoral aspects of allergic inflammation. There is controversy surrounding the role of TGF- in asthma. It is speculated that IL-6 also plays a pivotal role in eosinophils and asthma. Anti-IgE therapy is an approved treatment for adult and childhood asthma. Helminth infections are suggested to minimize asthma symptoms. | | | | |

Patient Data

| Attribute | Value | Percentile Total | Percentile Sex = 0 | Percentile Age = 10-30 | Percentile Region = 5 |
|---|---|---|---|---|---|
| Age | 27 | | | | |
| Chickenpox_Age | | | | | |
| Chickenpox_history | 0 | | | | |
| Citizenship | 0 | | | | |
| CMV_Int | Reactive | | | | |
| CMV_OD | 196.2 | 37.73 | 38.59 | 42.88 | 47.57 |
| Country_of_Origin | 8 | | | | |
| Country_of_Origin_name | Bulgaria | | | | |
| Diptheria_Ab | 0.932 | | | | |
| Diptheria_Age | 91 | | | | |
| Diptheria_history | 0 | | | | |
| Diptheria_Int | Reactive | | | | |
| Diptheria_OD | 1.037 | 88.25 | 88.31 | 88.37 | 92.57 |
| Education | 3 | | | | |
| ELECTRICITY | 1 | | | | |
| Filaria_Ab_OD | 0.3425 | 91.70 | 89.21 | 91.87 | 95.62 |
| Filaria_Int | + | | | | |
| HepA_Int | Reactive | | | | |
| HepA_OD | 0.889 | 59.31 | 66.80 | 55.56 | 32.43 |

FIG. 21H-71

| | | | | | |
|---|---|---|---|---|---|
| Hepatitis_Age | | | | | |
| Hepatitis_history | 0 | | | | |
| HepB_cAb_int | Reactive | | | | |
| HepB_cAb_OD | 0.086 | 71.43 | 18.66 | 22.22 | 19.59 |
| HepB_eAb_int | NA (Predicted) | | | | |
| HepB_eAb_ratio | | | | | |
| HepB_eAg_int | Reactive (Predicted) | | | | |
| HepB_eAg_ratio | | | | | |
| HepB_sAb_OD | 266.8 | 89.83 | 88.88 | 91.32 | 88.88 |
| HepB_sAg_OD | 0.71 | 88.65 | 77.58 | 82.78 | 77.63 |
| HepC_Ab_OD | 0.2 | 23.45 | 11.11 | 27.66 | 16.99 |
| HepC_Int | Nonreactive | | | | |
| HepC_TIA | | | | | |
| HepC_PCR | | | | | |
| Hospitalized | 0 | | | | |
| ID | 715 | | | | |
| IFN_gamma | 0.843382353 | 60.61 | 59.75 | 58.85 | 62.84 |
| IFN_gamma_int | Reactive | | | | |
| IL_10 | 0.861587783 | 61.11 | 64.73 | 57.12 | 56.76 |
| IL_10_int | Reactive | | | | |
| IL_17_int | Reactive | | | | |
| IL_12p70 | 2.163305385 | 71.57 | 73.24 | 68.98 | 66.22 |
| IL_12p70_int | Reactive | | | | |
| IL_13 | 1.26953125 | 70.13 | 77.59 | 67.61 | 74.32 |
| IL_13_int | Reactive | | | | |
| IL_15 | 3.284699879 | 56.27 | 56.64 | 46.18 | 58.11 |
| IL_15_int | Reactive | | | | |
| IL_17 | 0.065275899 | 40.69 | 37.34 | 38.83 | 36.49 |
| IL_17_int | Reactive | | | | |
| IL_1_alpha | 7.461129944 | 78.50 | 78.64 | 76.91 | 81.76 |
| IL_1_alpha_int | Reactive | | | | |
| IL_1_beta | 0.448462415 | 63.78 | 70.95 | 58.16 | 66.89 |
| IL_1_beta_int | Reactive | | | | |
| IL_2 | 2.221445687 | 89.54 | 87.76 | 89.76 | 89.86 |
| IL_23 | 84.39717326 | 73.74 | 74.07 | 71.35 | 70.27 |
| IL_23_int | Reactive | | | | |
| IL_2_int | Reactive | | | | |
| IL_4 | 0.104746663 | 46.32 | 44.81 | 44.62 | 48.65 |
| IL_4_int | Reactive | | | | |
| IL_5 | 0.830896700 | 48.12 | 49.79 | 43.23 | 51.35 |
| IL_5_int | Reactive | | | | |
| IL_6 | 1.851696552 | 39.90 | 52.70 | 37.33 | 42.57 |
| IL_6_int | Reactive | | | | |
| IL_8 | 5.05733945 | 62.84 | 61.00 | 66.24 | 60.14 |
| IL_8_int | Reactive | | | | |
| Indoor_toilet | 1 | | | | |
| Indoor_toilet_type | 1 | | | | |
| Interpreter | 1 | | | | |
| Interpreter_Language | Russian | | | | |
| Measles_age | 91 | | | | |
| Measles_history | 0 | | | | |
| Measles_Int | Negative | | | | |
| Measles_OD_08 | | 0.00 | 0.00 | 0.00 | 0.00 |
| Measles_OD_08_int | Equivocal | | | | |
| Measles_OD_Z | 0.02 | 53.88 | 60.17 | 51.74 | 47.38 |
| Measles_ratio_Z | 0.08 | | | | |
| Measles_tare_08 | | 0.00 | 0.00 | 0.00 | 0.00 |

FIG. 21H-7J

| | | | | | |
|---|---|---|---|---|---|
| Medical Problems | 0 | | | | |
| Medications | 0 | | | | |
| Months_CA | 6 | | | | |
| Months_pregnant | 91 | | | | |
| Mumps_Age | | | | | |
| Mumps_history | 0 | | | | |
| Mumps_OD_DB | 0.143 | 16.81 | 15.77 | 18.58 | 18.92 |
| Mumps_titre_DB | 250 | 15.01 | 13.90 | 16.15 | 15.54 |
| Outdoor_toilet | 1 | | | | |
| Outdoor_toilet_type | 3 | | | | |
| People_household | 3 | | | | |
| Persons_Rooms | 1 | | | | |
| Pertussis_Age | 91 | | | | |
| Pertussis_history | 0 | | | | |
| Polio_Age | 91 | | | | |
| Polio_history | 0 | | | | |
| Pregnant | 0 | | | | |
| Refugee_camp | 0 | | | | |
| Region_of_Origin | 5 | | | | |
| Rooms_household | 3 | | | | |
| Rubella_Ab | 155.2 | | | | |
| Rubella_Age | 91 | | | | |
| Rubella_history | 2 | | | | |
| Rubella_Int | 0 | | | | |
| Schistosoma_Ab_OD | 0.047 | 41.99 | 34.02 | 43.23 | 44.59 |
| Schistosoma_Int | - | | | | |
| School_type | 2 | | | | |
| Sex | 0 | | | | |
| Strongyloides_Ab_OD | 0.3825 | 77.56 | 70.33 | 79.17 | 85.81 |
| Strongyloides_Int | + | | | | |
| Tetanus_Ab | 0.915 | | | | |
| Tetanus_Age | 91 | | | | |
| Tetanus_history | 0 | | | | |
| Tetanus_Int | Reactive | | | | |
| Tetanus_OD | 0.867 | 59.74 | 60.58 | 53.47 | 38.51 |
| TNF_alpha | 3.119584055 | 82.11 | 84.02 | 80.03 | 79.73 |
| TNF_alpha_int | Reactive | | | | |
| TNF_beta | 0.128424658 | 63.20 | 61.62 | 61.11 | 70.27 |
| TNF_beta_int | Reactive | | | | |
| UNIVERSITY | 0 | | | | |
| Vaccination-_record | 0 | | | | |
| Varicella_Int | Positive | | | | |
| Varicella_OD_DB | 0.773 | 43.07 | 34.65 | 50.00 | 42.57 |
| Varicella_titre_DB | 460 | 37.37 | 31.54 | 43.06 | 45.27 |
| Water_supply_type | 1 | | | | |
| Years_Education | 10 | | | | |

FIG. 21H-7 K

Patient: 738

Results

| Conditions | Suggested Action | Internal References | External References |
|---|---|---|---|
| Tetanus_int eq Reactive | Give a booster dose of tetanus vaccine. Individuals over seven years of age receive the vaccine in combination with diphtheria vaccine (Td). Those children younger than seven years of age can be boosted with a vaccine containing a pertussis component (DTaP). People who had a serious allergic reaction to one dose of tetanus toxoid should not receive another. Persons with a moderate or severe acute illness should postpone receiving the vaccine until they are improved. | Hawkes, J.S., et al., Effect of dietary nucleotide supplementation on growth and immune function in term infants: a randomized controlled trial, European J. Clin. Nutrition 60: 254-64 (2006). McQuillan, Geraldine M., et al., Serologic Immunity to diphtheria and Tetanus in the United States, Annals of Internal Medicine 136(9): 660-66 (2002). Pickering, Larry K., et al., Modulation of the Immune System by Human Milk and Infant Formula Containing Nucleotides, Pediatrics 101(2): 242-49 (1998). Vivani, Simonetta, et al., EPI vaccines-induced antibody prevalence in 8-9 year-olds in The Gambia, Trop. Med. & International Health 9(10): 1044-49 (2004). | |
| Diptheria_int eq Reactive | Give a booster dose of diphtheria vaccine. Individuals over seven years of age receive the vaccine in combination with tetanus vaccine (Td). Those children younger than seven can be boosted with a vaccine containing the pertussis component as with the tetanus vaccine described above. People who have had a serious allergic reaction to one dose of DTaP, DT, Td, or Tdap vaccine should not receive another. Persons with a moderate or severe illness should postpone receiving the vaccine until their condition has improved. | | |
| TNF_alpha_int eq Reactive | Examine for chronic Hepatitis C. Patients with chronic hepatitis C virus have a significantly increased prevalence of type 2 diabetes. Activation of TNF- has a pivotal role in the inflammatory process of HCV, and TNF- is known to cause insulin resistance. Patients with chronic HCV need to have periodic ImmunoScore cytokine determinations to help circumvent the onset of type 2 diabetes. Elevated levels of TGF- also indicate a poor prognosis for diabetes development in HCV patients. | | |

FIG. 21H-8A

| | | | |
|---|---|---|---|
| IL_6_int eq Reactive<br>IL_12_int eq Reactive<br>IL_17_int eq Reactive | Administer ImmunoScore cytokine panel. Rise in pro-inflammatory cytokines (IL-6, IL-12, and/or IL-17) over previous visit would indicate a future autoimmune antibody profile screening to identify possible autoimmune disease manifestation. Rise in regulatory cytokines (IL-10 and TGF-) could possibly also indicate an autoimmune disease manifestation in regression. Rise in both pro- and regulatory cytokines would trigger subsequent need to attempt to identify autoimmune disease manifestation by ImmunoScore autoimmune disease antibody screening panels. In addition to normal assessment of physical symptoms, elevated levels (>2 SD of mean) of key pro-inflammatory cytokines IL-6, IL-12, and/or IL-17 trigger: a) repeat visit in six weeks to re-measure cytokine values: i) if pro-inflammatory cytokines still elevated, recommend ImmunoScore panel to detect autoimmune antibody profile to identify possible autoimmune disease manifestation. ii) if pro-inflammatory cytokines levels decreased or moderating, recommend ImmunoScore cytokine panel evaluation annually. IL-7 may be particularly important as an initiator of many autoimmune manifestations. Depending on autoimmune disease condition, additional tests ordered can include serum thyroid stimulating hormone (TSH) for Hashimoto's or Grave's disease, anti-nuclear antibody (ANA) for systemic lupus erythematosus (SLE), neurological examination for multiple sclerosis (MS), and serum rheumatoid factor (RF) for rheumatoid arthritis (RA). Compare on site new ImmunoScore cytokine profile with baseline ImmunoScore cytokine profile. Significant increase (>20%) among grouped cytokines (e.g. Th1, Th2, Th17, and/or Treg) from previous profile values could be indicative of impending autoimmune flare that will likely require disease-specific treatment(s) | | |

FIG. 21H-8 B

| | | | |
|---|---|---|---|
| IFN_gamma_inf eq Reactive | Examine for Systemic Lupus Erythematosus. Activated autoreactive Th cells provide the help required for autoreactive B cells to differentiate and produce autoreactive antibodies. Studies of animal models and SLE patients indicate an important role for type I interferons. Although type I IFNs are classically considered to promote Th1-mediated cell responses, they can also inhibit Th1 and Th17 responses. At this point, it is not certain whether intervention with IFN inhibitors will be beneficial or detrimental to SLE patients, and the application of IFN inhibitory therapy may be based upon stage of SLE flare. ImmunoScore cytokine panels will be used to add clarity to therapeutics. As SLE patients live longer due to improved therapies and preventive measures, death and disability from cardiovascular events are increasing. The mechanism for the increased risk of SLE patients for cardiovascular events is likely due to a combination of inflammatory and immune mechanisms. There are increased levels of oxidized LDL (oxLDL), pro-inflammatory HDL, MCP-1, TNF-, IFN-, IL-1, and IL-12. ImmunoScore cardiac risk markers will be combined with ImmunoScore cytokine panels in patients with SLE, and progressive monitoring will be performed in these patients at regular intervals. | | |
| IL_10_inf eq Reactive | Examine for cancer. IL-10 is a cytokine with broad anti-inflammatory properties. A penalty of the role of IL-10 to limit immune and inflammatory responses to pathogens and prevent damage to the host is that high or dysregulated levels of IL-10 may result in chronic infection or cancer. There are certainty possible therapeutic roles to IL-10 and its antagonists in human disease, all of which would benefit from careful ImmunoScore cytokine monitoring during clinical trials and subsequent evaluations. | | |

FIG. 21H-8 C

| | | | |
|---|---|---|---|
| IL_23, et eq Reactive | Examine for Multiple Sclerosis. Upregulated cytokines in MS patients include IL-17, IL-12, IL-23, IL-6, IL-21, TNF-, and other Th1 cytokines. IL-17-related cytokines are speculated to be related to disease progression. Glatiramer acetate (GA) is believed to induce GA-reactive T cells that secrete anti-inflammatory cytokines at the site of inflammation in MS, presumably increasing anti-inflammatory cytokines IL-10, IL-4, and TGF-. ImmunoScore to periodically measure patient's cytokines, and at onset of flare indicated by increased Th17 and Th1 cytokines, administer treatment. Efficacy of treatment could be monitored with monitoring of Treg cytokines. Interferon- and atorvastatin have both been used to treat MS. IFN- increases Th1 cytokines, while atorvastatin increases Th2 cytokines (particularly IL-5). Both may have the same effect of lessening the increase of Th17 cytokines. MS patients have general systemic increases of Th1 cytokines (particularly TNF-). This is likely related to fatigue and lapses in systemic immunity. This may be a problem in patients treated with natalizumab as systemic rises in TNF- are correlated with fatigue symptoms. | Bednářová, J. et al., Relevance of immunological variables in neuroborreliosis and multiple sclerosis, Acta Neurol. Scand. 112: 97-102 (2005). | |
| IL_3, et eq Reactive | Examine for Inflammatory Bowel Disease. IBD comprises two forms:<br>• Ulcerative colitis (UC) – increased expression of following.<br>  o TNF-<br>  o IL-1<br>  o IL-6<br>  o IL-12<br>  o IL-23<br>  o IL-17<br>  o IL-13<br>  o IL-5<br>• Crohn's disease (CD) – increased expression of following.<br>  o TNF-<br>  o IL-1<br>  o IL-1<br>  o IL-6<br>  o IL-18 (in some patients)<br>  o IL-10<br>  o IL-4 (in some patients)<br>  o IL-23<br>  o IL-27<br>  o IL-17<br>IL-21 appears to be the key mediator of flares of IBD. Mucosal cytokines recently cited (IL-31 and IL-32) as important are members of the IL-17 family | | |

FIG. 21H-8D

| | | | |
|---|---|---|---|
| IL_6_int eq Reactive | Examine for Breast Cancer. IL-6 is a pleiotropic cytokine with both tumor-promoting and tumor-inhibiting effects. Serum IL-6 levels, however, are a negative prognosticator in breast tumor patients.<br>IL-6, IL-8, and IL-10 levels are higher in women with breast cancer than controls and levels also correlate with the clinical stage of disease. Elevated serum IL-8 levels are related to an accelerated clinical course, a higher tumor load, and the presence of liver or lymph node involvement. On the other hand, elevated IL-8 also has prognostic significance for post-relapse survival. | | |
| IL_4_int eq Reactive | Examine for Allergies. Allergies are the result of aberrant immune reactivity to common innocuous environmental proteins. A pivotal component of allergic pathogenesis is the generation of allergen-specific Th cells with an effector phenotype. Th17 cells may also contribute to the pathogenesis of classically recognized Th2-mediated allergic disorders. This may very by individual patient, and ImmunoScore cytokine profiling would reveal individual differences from patient to patient. Allergic disorders would have a recommendation for treatment plans based upon Th2/Th17 immune balance. | | |

FIG. 21H-8 E

| IL_13_int eq Reactive | Examine for Asthma. Asthma comprises distinct heterogeneous inflammatory disorders characterized by patients showing different phenotypes with distinct genetic components, environmental causes, and immunopathogenesis. Once considered solely an allergic disorder dominated by Th2 lymphocytes, IgE, mast cells, eosinophils, macrophages, and cytokines, the disease also involves local epithelial, mesenchymal, vascular and neurologic events that are involved in directing the Th2 phenotype to the lung and through aberrant injury-repair mechanisms to remodeling of the airway wall. Responses to asthma medications vary considerably among patients, likely reflecting the differing sensitivities of the various asthma phenotypes. Physicians need to recognize this when making decisions to adjust treatment to improve asthma. IL-4 and IL-13 are considered to be key contributors to cell-mediated and humoral aspects of allergic inflammation. There is controversy surrounding the role of TGF- in asthma. It is speculated that IL-5 also plays a pivotal role in eosinophils and asthma. Anti-IgE therapy is an approved treatment for adult and childhood asthma. Helminth infections are suggested to minimize asthma symptoms. | | | |

Patient Data

| Attribute | Value | Percentile Total | Percentile Sex = 0 | Percentile Age = 30-50 | Percentile Region = 3 |
|---|---|---|---|---|---|
| Age | 37 | | | | |
| Chickenpox_Age | | | | | |
| Chickenpox_history | 2 | | | | |
| Citizenship | 0 | | | | |
| CMV_Int | Reactive | | | | |
| CMV_OD | >250.00 | 0.00 | 0.00 | 0.00 | 0.00 |
| Country_of_Origin | 8 | | | | |
| Country_of_Origin_name | Lebanon | | | | |
| Diptheria_Ab | 0.255 | | | | |
| Diptheria_Age | 51 | | | | |
| Diptheria_history | 2 | | | | |
| Diptheria_Int | Reactive | | | | |
| Diptheria_OD | 0.385 | 55.56 | 47.72 | 66.83 | 64.16 |
| Education | 4 | | | | |
| ELECTRICITY | 1 | | | | |
| Filaria_Ab_OD | 0.185 | 77.50 | 72.20 | 77.50 | 88.46 |
| Filaria_Int | eq | | | | |
| HepA_Int | Reactive | | | | |
| HepA_OD | 0.081 | 44.56 | 53.53 | 44.67 | 41.93 |

FIG. 21H-8 F

| | | | | | |
|---|---|---|---|---|---|
| Hepatitis_Age | | | | | |
| Hepatitis_history | 2 | | | | |
| HepB_cAb_int | Nonreactive | | | | |
| HepB_cAb_OD | 1.312 | 33.55 | 35.06 | 35.60 | 39.13 |
| HepB_eAg_int | NA (Predicted) | | | | |
| HepB_eAg_ratio | | | | | |
| HepB_eAg_int | NA (Predicted) | | | | |
| HepB_eAg_ratio | | | | | |
| HepB_SAb_OD | 0 | 0.00 | 0.00 | 0.00 | 0.00 |
| HepB_SAg_OD | | 0.00 | 0.00 | 0.00 | 0.00 |
| HepC_Ab_OD | 0.28 | 58.90 | 88.96 | 58.67 | 87.95 |
| HepC_int | Nonreactive | | | | |
| HepC_UA | | | | | |
| HepC_PCR | | | | | |
| Hospitalized | 0 | | | | |
| ID | 736 | | | | |
| IFN_gamma | 0.338013874 | 55.34 | 54.77 | 54.93 | 63.46 |
| IFN_gamma_int | Reactive | | | | |
| IL_10 | 1.815618592 | 83.12 | 85.89 | 85.47 | 86.54 |
| IL_10_int | Reactive | | | | |
| IL_12_int | Reactive | | | | |
| IL_12p70 | 2.14771879 | 72.58 | 74.27 | 73.73 | 82.05 |
| IL_12p70_int | Reactive | | | | |
| IL_13 | 2.065272901 | 83.12 | 88.80 | 86.13 | 86.54 |
| IL_13_int | Reactive | | | | |
| IL_15 | 3.041284843 | 46.10 | 52.70 | 49.33 | 53.21 |
| IL_15_int | Reactive | | | | |
| IL_17 | 2.397986243 | 80.69 | 80.71 | 83.07 | 87.16 |
| IL_17_int | Reactive | | | | |
| IL_1_alpha | 2.399451554 | 78.43 | 78.83 | 78.53 | 83.33 |
| IL_1_alpha_int | Reactive | | | | |
| IL_1_beta | 0.767857143 | 74.31 | 81.12 | 76.67 | 76.28 |
| IL_1_beta_int | Reactive | | | | |
| IL_2 | 0 | 0.00 | 0.00 | 0.00 | 0.00 |
| IL_23 | 29.06534954 | 45.82 | 43.78 | 47.47 | 60.26 |
| IL_23_int | Reactive | | | | |
| IL_2_int | Nonreactive | | | | |
| IL_4 | 1.15921327 | 68.45 | 68.26 | 67.73 | 76.28 |
| IL_4_int | Reactive | | | | |
| IL_5 | 1.901423611 | 62.91 | 67.84 | 66.13 | 73.08 |
| IL_5_int | Reactive | | | | |
| IL_6 | 1.700165663 | 38.74 | 56.83 | 40.00 | 41.03 |
| IL_6_int | Reactive | | | | |
| IL_8 | 0.441919192 | 27.71 | 21.99 | 27.07 | 37.18 |
| IL_8_int | Reactive | | | | |
| indoor_toilet | 1 | | | | |
| indoor_toilet_type | 1 | | | | |
| Interpreter | 0 | | | | |
| Interpreter_Language | | | | | |
| Measles_age | 91 | | | | |
| Measles_history | 2 | | | | |
| Measles_int | Positive | | | | |
| Measles_OD_08 | | 0.00 | 0.00 | 0.00 | 0.00 |
| Measles_OD_08_int | Positive | | | | |
| Measles_OD_Z | 1.39 | 83.76 | 82.57 | 82.53 | 79.49 |
| Measles_ratio_Z | 8.07 | | | | |
| Measles_titre_08 | | 0.00 | 0.00 | 0.00 | 0.00 |

FIG. 21H-8 G

| | | | | | |
|---|---|---|---|---|---|
| Medical Problems | 0 | | | | |
| Medications | 0 | | | | |
| Months_CA | 30.4 | | | | |
| Months_pregnant | 91 | | | | |
| Mumps_Age | | | | | |
| Mumps_history | 2 | | | | |
| Mumps_OD_DB | 0.354 | 52.96 | 52.49 | 54.40 | 48.08 |
| Mumps_titre_DB | 1143 | 64.43 | 64.32 | 65.87 | 63.46 |
| Outdoor_toilet | 0 | | | | |
| Outdoor_toilet_type | | | | | |
| People_household | 9 | | | | |
| Persons_Rooms | 1.5 | | | | |
| Pertussis_Age | 91 | | | | |
| Pertussis_history | 2 | | | | |
| Polio_Age | 91 | | | | |
| Polio_history | 0 | | | | |
| Pregnant | 0 | | | | |
| Refugee_camp | 0 | | | | |
| Region_of_Origin | 3 | | | | |
| Rooms_household | 6 | | | | |
| Rubella_Ab | 333.4 | | | | |
| Rubella_Age | 91 | | | | |
| Rubella_history | 2 | | | | |
| Rubella_int | 0 | | | | |
| Schistosoma_Ab_OD | 0.038 | 36.94 | 26.56 | 36.93 | 41.67 |
| Schistosoma_int | - | | | | |
| School_type | 1 | | | | |
| Sex | 0 | | | | |
| Strongyloides_Ab_OD | 0.211 | 53.75 | 40.46 | 52.00 | 58.97 |
| Strongyloides_Int | EQ | | | | |
| Tetanus_Ab | 0.056 | | | | |
| Tetanus_Age | 91 | | | | |
| Tetanus_history | 0 | | | | |
| Tetanus_int | Reactive | | | | |
| Tetanus_OD | 0.126 | 12.91 | 12.45 | 15.33 | 14.74 |
| TNF_alpha | 3.345658397 | 82.90 | 84.85 | 84.00 | 86.46 |
| TNF_alpha_int | Reactive | | | | |
| TNF_beta | 0.122149837 | 62.91 | 61.00 | 64.40 | 72.44 |
| TNF_beta_int | Reactive | | | | |
| UNIVERSITY | 0 | | | | |
| Vaccination_record | 0 | | | | |
| Varicella_int | Positive | | | | |
| Varicella_OD_DB | 1.248 | 78.14 | 69.92 | 75.07 | 83.97 |
| Varicella_titre_DB | 2048 | 91.63 | 86.51 | 90.93 | 92.31 |
| Water_supply_type | 1 | | | | |
| Years_Education | 17 | | | | |

FIG. 21H-8H

Patient: 1107

Results

| Conditions | Suggested Action | Internal References | External References |
|---|---|---|---|
| Tetanus_int eq Reactive | Give a booster dose of tetanus vaccine. Individuals over seven years of age receive the vaccine in combination with diphtheria vaccine (Td). Those children younger than seven years of age can be boosted with a vaccine containing a pertussis component (DTaP). People who had a serious allergic reaction to one dose of tetanus toxoid should not receive another. Persons with a moderate or severe acute illness should postpone receiving the vaccine until they are improved. | Hawkes, J.S., et al., Effect of dietary nucleotide supplementation on growth and immune function in term infants: a randomized controlled trial, European J. Clin. Nutrition 60: 254-64 (2006). McQuillan, Geraldine M., et al., Serologic Immunity to diphtheria and Tetanus in the United States, Annals of Internal Medicine 136(9): 660-66 (2002). Pickering, Larry K., et al., Modulation of the Immune System by Human Milk and Infant Formula Containing Nucleotides, Pediatrics 101(2): 242-49 (1998). Vivani, Simonetta, et al., EPI vaccines-induced antibody prevalence in 8-9 year-olds in The Gambia, Trop. Med. & International Health 9(10): 1044-49 (2004). | |
| Diptheria_int eq Reactive | Give a booster dose of diphtheria vaccine. Individuals over seven years of age receive the vaccine in combination with tetanus vaccine (Td). Those children younger than seven can be boosted with a vaccine containing the pertussis component as with the tetanus vaccine described above. People who have had a serious allergic reaction to one dose of DTaP, DT, Td, or Tdap vaccine should not receive another. Persons with a moderate or severe illness should postpone receiving the vaccine until their condition has improved. | | |
| TNF_alpha_int eq Reactive | Examine for chronic Hepatitis C. Patients with chronic hepatitis C virus have a significantly increased prevalence of type 2 diabetes. Activation of TNF- has a pivotal role in the inflammatory process of HCV, and TNF- is known to cause insulin resistance. Patients with chronic HCV need to have periodic immunoScore cytokine determinations to help circumvent the onset of type 2 diabetes. Elevated levels of TGF- also indicate a poor prognosis for diabetes development in HCV patients. | | |

FIG. 21H-9 A

| | | | |
|---|---|---|---|
| IL_10_int eq Reactive | Examine for cancer. IL-10 is a cytokine with broad anti-inflammatory properties. A penalty of the role of IL-10 to limit immune and inflammatory responses to pathogens and prevent damage to the host is that high or dysregulated levels of IL-10 may result in chronic infection or cancer. There are certainly possible therapeutic roles to IL-10 and its antagonists in human disease, all of which would benefit from careful ImmunoScore cytokine monitoring during clinical trials and subsequent evaluations. | | |
| IL_23_int eq Reactive | Examine for Multiple Sclerosis. Upregulated cytokines in MS patients include IL-17, IL-12, IL-23, IL-6, IL-21, TNF-, and other Th1 cytokines. IL-17-related cytokines are speculated to be related to disease progression. Glatiramer acetate (GA) is believed to induce GA-reactive T cells that secrete anti-inflammatory cytokines at the site of inflammation in MS - presumably increasing anti-inflammatory cytokines IL-10, IL-4, and TGF-. ImmunoScore to periodically measure patient's cytokines and at onset of flare, indicated by increased Th17 and Th1 cytokines, administer treatment. Efficacy of treatment could be monitored with monitoring of Treg cytokines.interferon- and atorvastatin have both been used to treat MS. IFN- increases Th1 cytokines, while atorvastatin increases Th2 cytokines (particularly IL-5). Both may have the same effect of lessening the increase of Th17 cytokines. MS patients have general systemic increases of Th1 cytokines (particularly TNF-. This is likely related to fatigue and lapses in systemic immunity. This may be a problem in patients treated with natalizumab as systemic rises in TNF- are correlated with fatigue symptoms. | Bednářová, J. et al., Relevance of immunological variables in neuroborreliosis and multiple sclerosis, Acta Neurol. Scand. 112: 97-102 (2005). | |

FIG. 21H-9 B

| | | | |
|---|---|---|---|
| IL_4_int eq Nonreactive | Examine for Diabetes. Diabetes mellitus is characterized by a lack of insulin causing elevated blood glucose, often with associated insulin resistance. Elevated serum levels of TGF- are associated with diabetic renal disease and will be tracked by the ImmunoScore cytokine diagnostic panel. Studies in animals indicate higher serum TGF- levels might ameliorate disease. A dysfunctioning endothelium is associated with both initiation and progression of atherosclerotic cardiovascular disease and has been shown to predate the onset of hyperglycemia in the natural history of type 2 diabetes. It is likely that low level inflammation plays an important role in developing this endothelial dysfunction mainly through the action of TNF- and possibly IL-6. Visceral obesity and inflammation within white adipose tissue may be a crucial step contributing to the emergence of insulin resistance, type 2 diabetes and atherosclerosis. IL-1, IL-6, IL-8, IL-10 TNF-, and TGF- levels all rise under these conditions. IL-27 can promote both anti- and pro-inflammatory responses. IL-27 up-regulates IFN-, and IL-17 and down-regulates IL-4, TGF-, and IL-10 secreted by diabetic splenocytes, suggesting a pathogenic role in T cell-mediated autoimmune diabetes | Santos, J.L., et al., Associations between HLA-DQB1 high-risk alleges and type I diabetes do not depend on cytomegalovirus antibody status at onset: A case-parent study conducted in Chile, Immunology & Cell Biology 78: 259-63 (2000). | |
| IL_8_int eq Reactive | Examine for Breast Cancer. IL-6 is a pleiotropic cytokine with both tumor-promoting and tumor-inhibiting effects. Serum IL-6 levels, however, are a negative prognosticator in breast tumor patients. IL-6, IL-8, and IL-10 levels are higher in women with breast cancer than controls and levels also correlate with the clinical stage of disease. Elevated serum IL-8 levels are related to an accelerated clinical course, a higher tumor load, and the presence of liver or lymph node involvement. On the other hand, elevated IL-8 also has prognostic significance for post-relapse survival. | | |

FIG. 21H-9 C

| | |
|---|---|
| IL_13_int eq Reactive | Excerpt for Asthma: Asthma comprises distinct heterogeneous inflammatory disorders characterized by patients showing different phenotypes with distinct genetic components, environmental causes, and immunopathogenesis. Once considered purely an allergic disorder dominated by Th2 lymphocytes, IgE, mast cells, eosinophils, macrophages and cytokines, the disease also involves local epithelial, mesenchymal, vascular and neurologic events that are involved in directing the Th2 phenotype to the lung and through aberrant injury-repair mechanisms to remodeling of the airway wall. Responses to asthma medications vary considerably among patients, likely reflecting the differing sensitivities of the various asthma phenotypes. Physicians need to recognize this when making decisions to adjust treatment to improve asthma. IL-4 and IL-13 are considered to be key contributors to cell-mediated and humoral aspects of allergic inflammation. There is controversy surrounding the role of TGF- in asthma. It is speculated that IL-5 also plays a pivotal role in eosinophilia and asthma. Anti-IgE therapy is an approved treatment for adult and childhood asthma. Helminth infections are suggested to minimize asthma symptoms. |

Patient Data

| Attribute | Value | Percentile Total | Percentile Sex = 1 | Percentile Age = 10-30 | Percentile Region = 3 |
|---|---|---|---|---|---|
| Age | 25 | | | | |
| Chickenpox_Age | 10 | | | | |
| Chickenpox_History | 1 | | | | |
| Citizenship | 4 | | | | |
| CMV_Int | Reactive | | | | |
| CMV_OD | >250.00 | 0.00 | 0.00 | 0.00 | 0.00 |
| Country_of_Origin | 8 | | | | |
| Country_of_Origin_name | Iran | | | | |
| Diptheria_Ab | 0.616 | | | | |
| Diptheria_Age | 01 | | | | |
| Diptheria_history | 2 | | | | |
| Diptheria_int | Reactive | | | | |
| Diptheria_OD | 0.758 | 83.04 | 85.96 | 83.16 | 83.97 |
| Education | 3 | | | | |
| ELECTRICITY | 1 | | | | |
| Filaria_Ab_OD | 0.039 | 21.68 | 25.33 | 22.49 | 33.33 |
| Filaria_Int | | | | | |
| HepA_Int | Reactive | | | | |
| HepA_OD | 0.073 | 25.97 | 21.68 | 25.35 | 23.08 |

FIG. 21H-9 D

| | | | | | |
|---|---|---|---|---|---|
| Hepatitis_Age | 2 | | | | |
| Hepatitis_history | 1 | | | | |
| HepE_eAb_int | Nonreactive | | | | |
| HepE_eAb_OD | 1.962 | 69.70 | 71.50 | 68.58 | 80.80 |
| HepE_eAg_int | NA (Predicted) | | | | |
| HepE_eAg_int2 | | | | | |
| HepE_eAg_int | NA (Predicted) | | | | |
| HepE_eAg_ratio | | | | | |
| HepE_SAb_OD | 0.3 | 70.06 | 71.13 | 74.85 | 81.41 |
| HepE_SAg_OD | | 0.00 | 0.00 | 0.00 | 0.00 |
| HepC_Ab_OD | 0.34 | 78.07 | 81.52 | 82.47 | 63.97 |
| HepC_int | Nonreactive | | | | |
| HepC_IIA | | | | | |
| HepC_PCR | | | | | |
| Hospitalized | 0 | | | | |
| ID | 1197 | | | | |
| IFN_gamma | 0 | 0.00 | 0.00 | 0.00 | 0.00 |
| IFN_gamma_int | Nonreactive | | | | |
| IL_10 | 0.431345287 | 43.00 | 43.14 | 40.63 | 57.05 |
| IL_10_int | Reactive | | | | |
| IL_17_int | Nonreactive | | | | |
| IL_12p70 | 0 | 0.00 | 0.00 | 0.00 | 0.00 |
| IL_12p70_int | Nonreactive | | | | |
| IL_13 | 0.165756301 | 33.98 | 31.31 | 31.77 | 29.74 |
| IL_13_int | Reactive | | | | |
| IL_15 | 2.778458213 | 37.18 | 36.09 | 28.17 | 27.10 |
| IL_15_int | Reactive | | | | |
| IL_17 | 0.268404906 | 45.24 | 46.97 | 43.58 | 62.18 |
| IL_17_int | Reactive | | | | |
| IL_1_alpha | 0 | 0.00 | 0.00 | 0.00 | 0.00 |
| IL_1_alpha_int | Nonreactive | | | | |
| IL_1_beta | 0 | 0.00 | 0.00 | 0.00 | 0.00 |
| IL_1_beta_int | Nonreactive | | | | |
| IL_2 | 0.606060606 | 71.21 | 73.01 | 59.27 | 79.49 |
| IL_23 | 42.73343373 | 54.59 | 54.09 | 59.59 | 66.23 |
| IL_23_int | Reactive | | | | |
| IL_2_int | Reactive | | | | |
| IL_4 | 0 | 0.00 | 0.00 | 0.00 | 0.00 |
| IL_4_int | Nonreactive | | | | |
| IL_5 | 0 | 0.00 | 0.00 | 0.00 | 0.00 |
| IL_5_int | Nonreactive | | | | |
| IL_6 | 2.881533531 | 50.65 | 41.81 | 45.49 | 59.90 |
| IL_6_int | Reactive | | | | |
| IL_8 | 3.828554802 | 51.90 | 54.31 | 55.30 | 59.52 |
| IL_8_int | Reactive | | | | |
| Indoor_toilet | 1 | | | | |
| Indoor_toilet_type | 1 | | | | |
| Interpreter | 1 | | | | |
| Interpreter_Language | Persian | | | | |
| Measles_age | 81 | | | | |
| Measles_history | 2 | | | | |
| Measles_int | Positive | | | | |
| Measles_OD_DB | 1.587 | 91.37 | 92.04 | 87.18 | 90.38 |
| Measles_OD_DB_int | Positive | | | | |
| Measles_OD_Z | | 0.00 | 0.00 | 0.00 | 0.00 |
| Measles_ratio_Z | | | | | |
| Measles_titre_DB | 0.726.37 | 91.00 | 92.04 | 92.18 | 86.46 |

FIG. 21H-9 E

| | | | | | |
|---|---|---|---|---|---|
| Medical Problems | 0 | | | | |
| Medications | 0 | | | | |
| Months_CA | 4.3 | | | | |
| Months_pregnant | 91 | | | | |
| Mumps_Age | | | | | |
| Mumps_history | 0 | | | | |
| Mumps_OD_DB | 0.215 | 27.56 | 28.10 | 29.34 | 21.15 |
| Mumps_titre_DB | 504.57 | 31.96 | 32.63 | 33.51 | 28.21 |
| Outdoor_toilet | 0 | | | | |
| Outdoor_toilet_type | | | | | |
| People_household | 10 | | | | |
| Persons_Rooms | 1.25 | | | | |
| Pertussis_Age | 91 | | | | |
| Pertussis_history | 0 | | | | |
| Polio_Age | 91 | | | | |
| Polio_history | 0 | | | | |
| Pregnant | 0 | | | | |
| Refugee_camp | 0 | | | | |
| Region_of_Origin | 3 | | | | |
| Rooms_household | 8 | | | | |
| Rubella_Ab | 0 | | | | |
| Rubella_Age | 91 | | | | |
| Rubella_history | 2 | | | | |
| Rubella_Int | 1 | | | | |
| Schistosoma_Ab_OD | 0.151 | 79.58 | 83.19 | 79.17 | 87.18 |
| Schistosoma_int | - | | | | |
| School_type | 2 | | | | |
| Sex | 1 | | | | |
| Strongyloides_Ab_OD | 0.41 | 79.94 | 83.41 | 82.12 | 80.13 |
| Strongyloides_Int | - | | | | |
| Tetanus_Ab | 2.55 | | | | |
| Tetanus_Age | 91 | | | | |
| Tetanus_history | 2 | | | | |
| Tetanus_Int | Reactive | | | | |
| Tetanus_OD | 1.347 | 76.26 | 76.66 | 73.09 | 73.08 |
| TNF_alpha | 0.03158338 | 45.96 | 46.90 | 43.92 | 61.54 |
| TNF_alpha_int | Reactive | | | | |
| TNF_beta | 0 | 0.00 | 0.00 | 0.00 | 0.00 |
| TNF_beta_int | Nonreactive | | | | |
| UNIVERSITY | 0 | | | | |
| Vaccination-_record | 0 | | | | |
| Varicella_Int | Positive | | | | |
| Varicella_OD_DB | 0.84 | 49.28 | 53.98 | 57.47 | 57.69 |
| Varicella_titre_DB | 521.88 | 49.86 | 54.09 | 56.42 | 59.62 |
| Water_supply_type | 1 | | | | |
| Years_Education | 12 | | | | |

FIG. 21H-9F

Results                                     Patient: 1237

| Conditions | Suggested Action | Internal References | External References |
|---|---|---|---|
| Tetanus_Int eq Reactive | Give a booster dose of tetanus vaccine. Individuals over seven years of age receive the vaccine in combination with diphtheria vaccine (Td). Those children younger than seven years of age can be boosted with a vaccine containing a pertussis component (DTaP). People who had a serious allergic reaction to one dose of tetanus toxoid should not receive another. Persons with a moderate or severe acute illness should postpone receiving the vaccine until they are improved. | Hawkes, J.S., et al., Effect of dietary nucleotide supplementation on growth and immune function in term infants: a randomized controlled trial, European J. Clin. Nutrition 60: 254-64 (2006). McQuillan, Geraldine M., et al., Serologic Immunity to diphtheria and Tetanus in the United States, Annals of Internal Medicine 136(9): 660-66 (2002). Pickering, Larry K., et al., Modulation of the Immune System by Human Milk and Infant Formula Containing Nucleotides, Pediatrics 101(2): 242-49 (1998). Vivani, Simonetta, et al., EPI vaccines-induced antibody prevalence in 8-9 year-olds in The Gambia, Trop. Med. & International Health 9(10): 1044-49 (2004). | |
| Diptheria_Int eq Reactive | Give a booster dose of diphtheria vaccine. Individuals over seven years of age receive the vaccine in combination with tetanus vaccine (Td). Those children younger than seven can be boosted with a vaccine containing the pertussis component as with the tetanus vaccine described above. People who have had a serious allergic reaction to one dose of DTaP, DT, Td, or Tdap vaccine should not receive another. Persons with a moderate or severe illness should postpone receiving the vaccine until their condition has improved. | | |
| TNF_alpha_int eq Reactive | Examine for chronic Hepatitis C. Patients with chronic hepatitis C virus have a significantly increased prevalence of type 2 diabetes. Activation of TNF- has a pivotal role in the inflammatory process of HCV, and TNF- is known to cause insulin resistance. Patients with chronic HCV need to have periodic ImmunoScore cytokine determinations to help circumvent the onset of type 2 diabetes. Elevated levels of TGF- also indicate a poor prognosis for diabetes development in HCV patients. | | |

FIG. 21H-10 A

| | | | |
|---|---|---|---|
| IL_6_int eq Reactive<br>IL_12_int eq Reactive<br>IL_17_int eq Reactive | Administer ImmunoScore cytokine panel. Rise in pro-inflammatory cytokines (IL-6, IL-12, and/or IL-17) over previous visit would indicate a future autoimmune antibody profile screening to identify possible autoimmune disease manifestation. Rise in regulatory cytokines (IL-10 and TGF-) could possibly also indicate an autoimmune disease manifestation in regression. Rise in both pro- and regulatory cytokines would trigger subsequent need to attempt to identify autoimmune disease manifestation by ImmunoScore autoimmune disease antibody screening panels. In addition to normal assessment of physical symptoms, elevated levels (>2 SD of mean) of key pro-inflammatory cytokines IL-6, IL-12, and/or IL-17 trigger: a) repeat visit in six weeks to re-measure cytokine values; I) if pro-inflammatory cytokines still elevated, recommend ImmunoScore panel to detect autoimmune antibody profile to identify possible autoimmune disease manifestation. Ii) If pro-inflammatory cytokines levels decreased or moderating, recommend ImmunoScore cytokine panel evaluation annually. IL-7 may be particularly important as an initiator of many autoimmune manifestations. Depending on autoimmune disease condition, additional tests ordered can include serum thyroid stimulating hormone (TSH) for Hashimoto's or Grave's disease, anti-nuclear antibody (ANA) for systemic lupus erythematosus (SLE), neurological examination for multiple sclerosis (MS), and serum rheumatoid factor (RF) for rheumatoid arthritis (RA). Compare on site new ImmunoScore cytokine profile with baseline ImmunoScore cytokine profile. Significant increase (>20%) among grouped cytokines (e.g. Th1, Th2, Th17, and/or Treg) from previous profile values could be indicative of impending autoimmune flare that will likely require disease-specific treatment(s). | | |
| IL_2_int eq Reactive<br>IL_1_alpha_int eq Reactive<br>IL_1_beta_int eq Reactive | Examine for Rheumatoid arthritis. Rheumatoid arthritis (RA) is a chronic disorder for which there is no known cure. The optimal treatment of RA requires a comprehensive program that combines medical, social, and emotional support for the patient. Strategies are all aimed at reducing pain and discomfort, preventing | | |

FIG. 21H-10 B deformities and loss of joint function. Treatment options include reduction of joint stress, physical and occupational therapy, and surgical intervention. Drug treatment prescriptions should be closely tied to ImmunoScore cytokine analyses to monitor RA flares and worsening of disease status. Drug classes to treat rheumatoid arthritis: 1) Non-steroidal anti-inflammatory agents (NSAIDs). NSAIDs reduce acute inflammation, reduce pain and improve function. They do not change the course of disease or prevent joint destruction; 2)Corticosteroids. Corticosteroids have both anti-inflammatory and immunoregulatory activity; 3) Disease modifying anti-rheumatic drugs (DMARDs). DMARD agents have been shown to alter the course of RA and improve radiographic outcomes. There are contra-indications for all of the treatment classes described above. Closely tied ImmunoScore cytokine measurement and courses of treatment will optimize RA treatment for each individual. Anti-inflammatory effect within hours, but reasonable trial period for relief of RA symptoms is 1 month. The most common toxicity is gastrointestinal disturbance which may clinically include burning, belching, or irritation, but which can represent irritation of the lining of the stomach, erosions, and ulcerations that may result in bleeding. Selective COX-2 inhibitors exhibit safer GI profiles than conventional non-selective NSAIDs, but may increase cardiovascular effects on blood pressure and additional effects on vascular beds. The use of NSAIDs medications must take into account their relative risks in an individual patient of gastrointestinal damage versus potential cardiovascular risk factors. Physicians treating RA patients with NSAIDs would periodically monitor serum cytokine levels to track inflammatory cytokines and relate them to symptoms of GI irritation and/or cardiovascular damage. Corticosteroids are useful in early disease as temporary adjunctive therapy while waiting for DMARDs to exert anti-inflammatory effects. This group is also useful as chronic adjunctive therapy in patients with severe disease not well controlled on NSAIDs or DMARDs. Side effects of prednisone include weight

FIG. 21H-10 C gain, increased blood pressure, increased blood sugar, increased risk of cataracts, and avascular necrosis of bones. Patients treated with corticosteroids should have periodic ImmunoScore cytokine measurements coupled with bone densitometry to assess bone fracture risk. Bisphosphonates are concurrently recommended to prevent and/or treat osteoporosis in addition to adequate calcium and vitamin D supplementation. In most cases, when the diagnosis of rheumatoid arthritis is confirmed, DMARD agents should be initiated. Methotrexate is considered the first-line DMARD agent. The anti-inflammatory effects appear to be due to interruption of adenosine and possible effects on TNF pathways. Serious complications of methotrexate therapy, including hepatic cirrhosis, interstitial pneumonitis, and severe myelosuppression are rare with proper monitoring. Stomatitis and oral ulcers, alopecia and hair thinning, and GI upset may occur and are related to folic acid antagonism. These side effects can be improved with folic acid supplementation. ImmunoScore cytokine coupled with serum liver enzymes should be periodically monitored. Liver biopsy should be performed if liver enzymes persist. Hydroxychloroquine is sometimes used with methotrexate and sulfasalazine as a triple therapy for RA. The most important toxicity is on the eyes. Patients with underlying retinopathies should have a baseline ophthalmologic examination and follow up exam every 12 months during treatment. Sulfasalazine is effective for the treatment of RA. The mechanism of action is unknown. It may cause hypersensitivity and allergic reactions. Careful periodic ImmunoScore cytokine screening would indicate undesirable increases in Th2 and/or Th17 cytokines in conjunction with increased serum IgE levels. TNF-inhibitors are used to ameliorate local concentrations of TNF- in synovial fluid. There are currently three TNF- inhibitors approved for the treatment of RA. Etanercept binds TNF in the circulation and prevents interaction with cell surface TNF receptors. As with all TNF antagonists, there is an increased risk of infection in patients. Patients show increased risk of upper respiratory infections

FIG. 21H-10 D and some develop anti-nuclear antibodies characteristic of SLE. Screening for latent TB infection is prudent before initiation of TNF inhibitor treatments. Infliximab is an anti-TNF antibody developed in mice. Anti-infliximab antibodies can develop in patients, reducing the effectiveness of the treatments. ImmunoScore diagnostic follow-up would include cytokine measurements looking for increased Th2 (antibody) response coupled with specific measurement of anti-TNF antibodies. Opportunistic infections and sepsis have been reported with infliximab treatment. Periodic examination of cytokine balance would indicate patients coming out of immune balance. Observation of wildly fluctuating cytokine values would be indicative of an immune system swaying out of control and indicate likely candidates for sepsis. Adalimumab is another anti-TNF antibody treatment for RA. Increased infections ranging from mild to serious are seen in clinical practice. In addition, ANA titers have been seen as well as cases of lupus-like disease. Abatacept is one of a class of agents known as T-cell costimulatory blockers. These agents interfere with the interactions between antigen-presenting cells and T lymphocytes and affect early stages in the pathogenic cascade of events in RA. Infections are increased in patients being treated with abatacept. Periodic ImmunoScore cytokine measurement examining cytokine balance would coincide with patient treatment. Rituximab binds to the CD20 molecule on B cell surfaces leading to the removal of B cells from circulation. Clinical effects on RA are hypothesized to occur from decrease in B cell cytokines, interactions with B cells and T cells, or due to reductions in autoantibody levels. Infusion reactions to rituximab may include hives, itching, swelling, difficulty breathing, fever, chills, and changes in blood pressure. These are usually mild and respond to slowing the infusion rate or additional medication (such as antihistamines) but may be severe. Monitoring cytokine levels during infusion could lead to better monitoring of patient reaction to rituximab infusions. Anakinra is an IL-1 receptor antagonist. ImmunoScore measurement of IL-1

FIG. 21H-10 E

| | | | |
|---|---|---|---|
| | and IL-1 serum concentrations during anakira therapy would indicate effectiveness and balance of the drug to cytokine levels in the patient. | | |
| IFN_gamma_int eq Reactive | Examine for Systemic Lupus Erythematosus. Activated autoreactive Th cells provide the help required for autoreactive B cells to differentiate and produce autoreactive antibodies. Studies of animal models and SLE patients indicate an important role for type I interferons. Although type I IFNs are classically considered to promote Th1-mediated cell responses, they can also inhibit Th1 and Th17 responses. At this point, it is not certain whether intervention with IFN inhibitors will be beneficial or detrimental to SLE patients, and the application of IFN inhibitory therapy may be based upon stage of SLE flare. ImmunoScore cytokine panels will be used to add clarity to therapeutics. As SLE patients live longer due to improved therapies and preventive measures, death and disability from cardiovascular events are increasing. The mechanism for the increased risk of SLE patients for cardiovascular events is likely due to a combination of inflammatory and immune mechanisms. There are increased levels of oxidized LDL (oxLDL), pro-inflammatory HDL, MCP-1, TNF-, IFN-, IL-1, and IL-12. ImmunoScore cardiac risk markers will be combined with ImmunoScore cytokine panels in patients with SLE, and progressive monitoring will be performed in these patients at regular intervals. | | |
| IL_10_int eq Reactive | Examine for cancer. IL-10 is a cytokine with broad anti-inflammatory properties. A penalty of the role of IL-10 to limit immune and inflammatory responses to pathogens and prevent damage to the host is that high or dysregulated levels of IL-10 may result in chronic infection or cancer. There are certainly possible therapeutic roles to Il-10 and its antagonists in human disease, all of which would benefit from careful ImmunoScore cytokine monitoring during clinical trials and subsequent evaluations. | | |

FIG. 21H-10 F

| | | | |
|---|---|---|---|
| IL_5_int eq Reactive | Examine for Inflammatory Bowel Disease. IBD comprises two forms:<br>• Ulcerative colitis (UC) – increased expression of following:<br>o TNF-<br>o IL-1<br>o IL-6<br>o IL-12<br>o IL-23<br>o IL-17<br>o IL-13<br>o IL-5<br>• Crohn's disease (CD) – increased expression of following:<br>o TNF-<br>o IL-1<br>o IL-1<br>o IL-6<br>o IL-18 (in some patients)<br>o IL-10<br>o IL-4 (in some patients)<br>o IL-23<br>o IL-27<br>o IL-17<br>IL-23 appears to be the key mediator of flares of IBD. Mucosal cytokines recently cited (IL-31 and IL-32) as important are members of the IL-17 family. | | |
| IL_8_int eq Reactive | Examine for Breast Cancer. IL-6 is a pleiotropic cytokine with both tumor-promoting and tumor-inhibiting effects. Serum IL-6 levels, however, are a negative prognosticator in breast tumor patients.<br>IL-6, IL-8, and IL-10 levels are higher in women with breast cancer than controls and levels also correlate with the clinical stage of disease. Elevated serum IL-8 levels are related to an accelerated clinical course, a higher tumor load, and the presence of liver or lymph node involvement. On the other hand, elevated IL-8 also has prognostic significance for post-relapse survival. | | |

FIG. 21H-10 G

| | | | |
|---|---|---|---|
| IL_23_int eq Nonreactive | Examine for Atherosclerosis. Atherogenesis is characterized by an intense inflammatory process, involving immune and vascular cells. C-reactive protein (CRP), monocyte/macrophage colony-stimulating factor (M-CSF), and IL-6 promote atherogenesis. They also down-regulate atheroprotective cytokines such as IL-10 and TGF-. Increased levels of CRP and IL-6 are predictive of a higher cardiovascular event rate in the general population. In coronary artery disease, high levels of M-CSF are additive with those of CRP, suggesting the benefit of a multi-marker approach in assessing risk to coronary artery disease. In addition to the pro-inflammatory cytokines with poor prognostic indications, including TNF-, IL-6, MCP-1, and IL-1, several adipocytokines are released by fat tissues and are inflammatory in nature. These include leptin, resistin, adiponectin and visfatin. Once possible atherosclerotic complications are revealed in patients, a follow up panel specific for heart patients can be envisioned which contains diagnostic tools for serum adipocytokines. It is not yet clear what function IFN- has in relationship with atherosclerosis development, but it is likely a key player and should be monitored in cardiac patients. | | |
| IL_4_int eq Reactive | Examine for Allergies. Allergies are the result of aberrant immune reactivity to common innocuous environmental proteins. A pivotal component of allergic pathogenesis is the generation of allergen-specific Th cells with an effector phenotype. Th17 cells may also contribute to the pathogenesis of classically recognized Th2-mediated allergic disorders. This may very by individual patient, and ImmunoScore cytokine profiling would reveal individual differences from patient to patient. Allergic disorders would have a recommendation for treatment plans based upon Th2/Th17 immune balance. | | |

FIG. 21H-10 H

| | | | | | |
|---|---|---|---|---|---|
| IL_13_int eq Reactive | Examine for Asthma. Asthma comprises distinct heterogeneous inflammatory disorders characterized by patients showing different phenotypes with distinct genetic components, environmental causes, and immunopathogenesis. Once considered purely an allergic disorder dominated by Th2 lymphocytes, IgE, mast cells, eosinophils, macrophages, and cytokines, the disease also involves local epithelial, mesenchymal, vascular and neurologic events that are involved in directing the Th2 phenotype to the lung and through aberrant injury-repair mechanisms to remodeling of the airway wall. Responses to asthma medications vary considerably among patients, likely reflecting the differing sensitivities of the various asthma phenotypes. Physicians need to recognize this when making decisions to adjust treatment to improve asthma. IL-4 and IL-13 are considered to be key contributors to cell-mediated and humoral aspects of allergic inflammation. There is controversy surrounding the role of TGF- in asthma. It is speculated that IL-5 also plays a pivotal role in eosinophilia and asthma. Anti-IgE therapy is an approved treatment for adult and childhood asthma. Helminth infections are suggested to minimize asthma symptoms. | | | | |

Patient Data

| Attribute | Value | Percentile Total | Percentile Sex = 0 | Percentile Age = 30-50 | Percentile Region = 5 |
|---|---|---|---|---|---|
| Age | 44 | | | | |
| Chickenpox_Age | 3 | | | | |
| Chickenpox_history | 1 | | | | |
| Citizenship | 3 | | | | |
| CMV_int | Reactive | | | | |
| CMV_OD | >250.00 | 0.00 | 0.00 | 0.00 | 0.00 |
| Country_of_Origin | 8 | | | | |
| Country_of_Origin_name | Afghans | | | | |
| Diptheria_Ab | 0.815 | | | | |
| Diptheria_Age | 30 | | | | |
| Diptheria_history | 2 | | | | |
| Diptheria_int | Reactive | | | | |
| Diptheria_OD | 0.755 | 82.97 | 77.39 | 82.30 | 83.33 |
| Education | 3 | | | | |
| ELECTRICITY | 1 | | | | |
| Filaria_Ab_OD | 0.142 | 66.81 | 58.51 | 66.27 | 78.21 |
| Filaria_int | - | | | | |
| HepA_int | Reactive | | | | |
| HepA_OD | 0.684 | 49.78 | 57.89 | 56.89 | 48.06 |

FIG. 21H-10 I

| | | | | | |
|---|---|---|---|---|---|
| Hepatitis_Age | 20 | | | | |
| Hepatitis_history | 1 | | | | |
| HepB_cAb_Int | Nonreactive | | | | |
| HepB_cAb_OD | 1.875 | 57.50 | 55.19 | 58.07 | 51.23 |
| HepB_sAb_Int | NA (Predicted) | | | | |
| HepB_sAb_ratio | | | | | |
| HepB_eAg_Int | NA (Predicted) | | | | |
| HepB_eAg_ratio | | | | | |
| HepB_SAb_OD | 0 | 0.00 | 0.00 | 0.00 | 0.00 |
| HepB_SAg_OD | | 0.00 | 0.00 | 0.00 | 0.00 |
| HepC_Ab_OD | 0.55 | 79.67 | 73.86 | 78.13 | 85.90 |
| HepC_Int | Nonreactive | | | | |
| HepC_LIA | | | | | |
| HepC_PCR | | | | | |
| Hospitalized | 0 | | | | |
| ID | 1237 | | | | |
| IFN_gamma | 2.442354369 | 84.20 | 82.37 | 84.87 | 87.18 |
| IFN_gamma_int | Reactive | | | | |
| IL_10 | 0.65400364 | 53.10 | 55.39 | 55.20 | 63.46 |
| IL_10_int | Reactive | | | | |
| IL_12_int | Reactive | | | | |
| IL_12p70 | 0.133167614 | 33.46 | 39.29 | 36.00 | 46.68 |
| IL_12p70_int | Reactive | | | | |
| IL_13 | 0.249690158 | 38.74 | 44.19 | 39.73 | 44.87 |
| IL_13_int | Reactive | | | | |
| IL_15 | 5.734674881 | 84.20 | 93.57 | 83.47 | 82.69 |
| IL_15_int | Reactive | | | | |
| IL_17 | 1.040946278 | 61.11 | 68.30 | 62.80 | 75.90 |
| IL_17_int | Reactive | | | | |
| IL_1_alpha | 0.680180287 | 60.25 | 61.63 | 61.07 | 67.95 |
| IL_1_alpha_int | Reactive | | | | |
| IL_1_beta | 0.069637883 | 44.88 | 46.35 | 47.33 | 49.36 |
| IL_1_beta_int | Reactive | | | | |
| IL_2 | 0.525484439 | 69.84 | 66.18 | 71.60 | 78.85 |
| IL_23 | 0 | 0.00 | 0.00 | 0.00 | 0.00 |
| IL_23_int | Nonreactive | | | | |
| IL_2_int | Reactive | | | | |
| IL_4 | 0.412735649 | 52.09 | 51.66 | 53.20 | 64.10 |
| IL_4_int | Reactive | | | | |
| IL_5 | 2.039184915 | 64.29 | 69.29 | 67.33 | 74.36 |
| IL_5_int | Reactive | | | | |
| IL_6 | 8.689376448 | 75.40 | 92.53 | 76.13 | 71.79 |
| IL_6_int | Reactive | | | | |
| IL_8 | 3.936653083 | 54.55 | 51.24 | 53.67 | 60.60 |
| IL_8_int | Reactive | | | | |
| Indoor_toilet | 1 | | | | |
| Indoor_toilet_type | 1 | | | | |
| Interpreter | 1 | | | | |
| Interpreter_Language | Dari | | | | |
| Measles_age | 91 | | | | |
| Measles_history | 2 | | | | |
| Measles_Int | Positive | | | | |
| Measles_OD_DB | 1.519 | 89.83 | 87.95 | 89.73 | 87.18 |
| Measles_OD_DB_Int | Positive | | | | |
| Measles_OD_Z | | 0.00 | 0.00 | 0.00 | 0.00 |
| Measles_ratio_Z | | | | | |
| Measles_titre_DB | 5925.11 | 89.11 | 88.17 | 86.53 | 83.97 |

FIG. 21H-10 J

| | | | | | |
|---|---|---|---|---|---|
| Medical Problems | 0 | | | | |
| Medications | 0 | | | | |
| Months_CA | 28.9 | | | | |
| Months_pregnant | 91 | | | | |
| Mumps_Age | | | | | |
| Mumps_history | 0 | | | | |
| Mumps_OD_DB | 0.693 | 87.09 | 87.34 | 86.53 | 87.82 |
| Mumps_titre_DB | 1904.11 | 84.99 | 86.51 | 85.33 | 85.90 |
| Outdoor_toilet | 1 | | | | |
| Outdoor_toilet_type | 1 | | | | |
| People_household | 4 | | | | |
| Persons_Rooms | 0.666666667 | | | | |
| Pertussis_Age | 91 | | | | |
| Pertussis_history | 2 | | | | |
| Polio_Age | 91 | | | | |
| Polio_history | 0 | | | | |
| Pregnant | 0 | | | | |
| Refugee_camp | 0 | | | | |
| Region_of_Origin | 3 | | | | |
| Rooms_household | 6 | | | | |
| Rubella_Ab | 71.6 | | | | |
| Rubella_Age | 91 | | | | |
| Rubella_history | 2 | | | | |
| Rubella_Int | 0 | | | | |
| Schistosoma_Ab_OD | 0.024 | 27.34 | 18.88 | 27.07 | 32.05 |
| Schistosoma_int | - | | | | |
| School_type | 2 | | | | |
| Sex | 0 | | | | |
| Strongyloides_Ab_OD | 0.4 | 79.08 | 72.41 | 77.73 | 78.85 |
| Strongyloides_Int | + | | | | |
| Tetanus_Ab | 0.094 | | | | |
| Tetanus_Age | 91 | | | | |
| Tetanus_history | 0 | | | | |
| Tetanus_Int | Reactive | | | | |
| Tetanus_OD | 0.156 | 21.00 | 21.16 | 23.87 | 22.44 |
| TNF_alpha | 1.206341912 | 63.35 | 65.15 | 65.07 | 75.00 |
| TNF_alpha_int | Reactive | | | | |
| TNF_beta | 0.307539683 | 68.25 | 66.39 | 69.20 | 78.85 |
| TNF_beta_int | Reactive | | | | |
| UNIVERSITY | 0 | | | | |
| Vaccination-_record | 0 | | | | |
| Varicella_Int | Positive | | | | |
| Varicella_OD_DB | 0.666 | 34.20 | 28.01 | 30.53 | 39.10 |
| Varicella_titre_DB | 356.27 | 29.80 | 24.90 | 28.13 | 33.97 |
| Water_supply_type | 1 | | | | |
| Years_Education | 7 | | | | |

FIG. 21H-10 K

Group By: Region_of_Origin, Sex, IFN_gamma
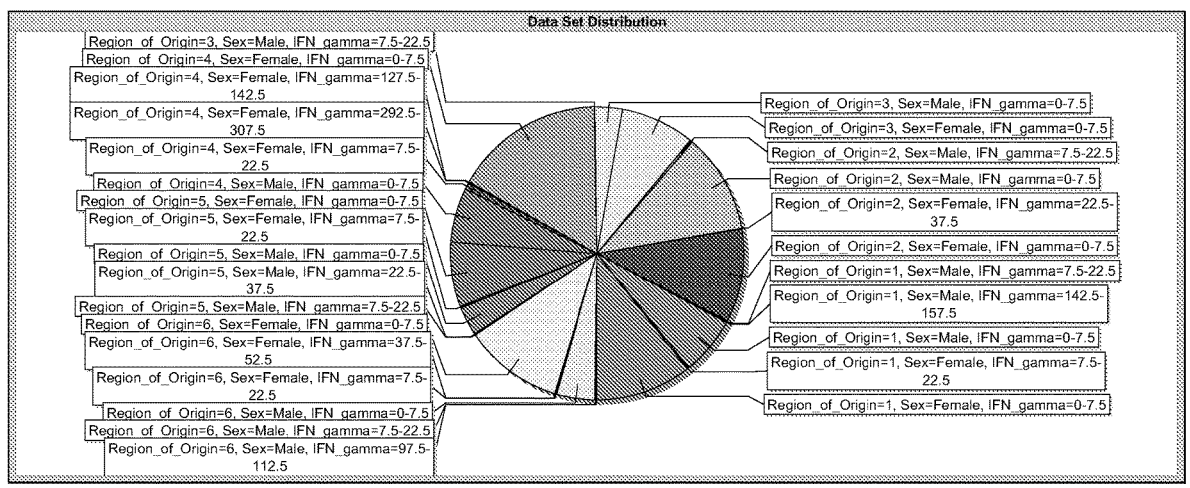
FIG. 21I1

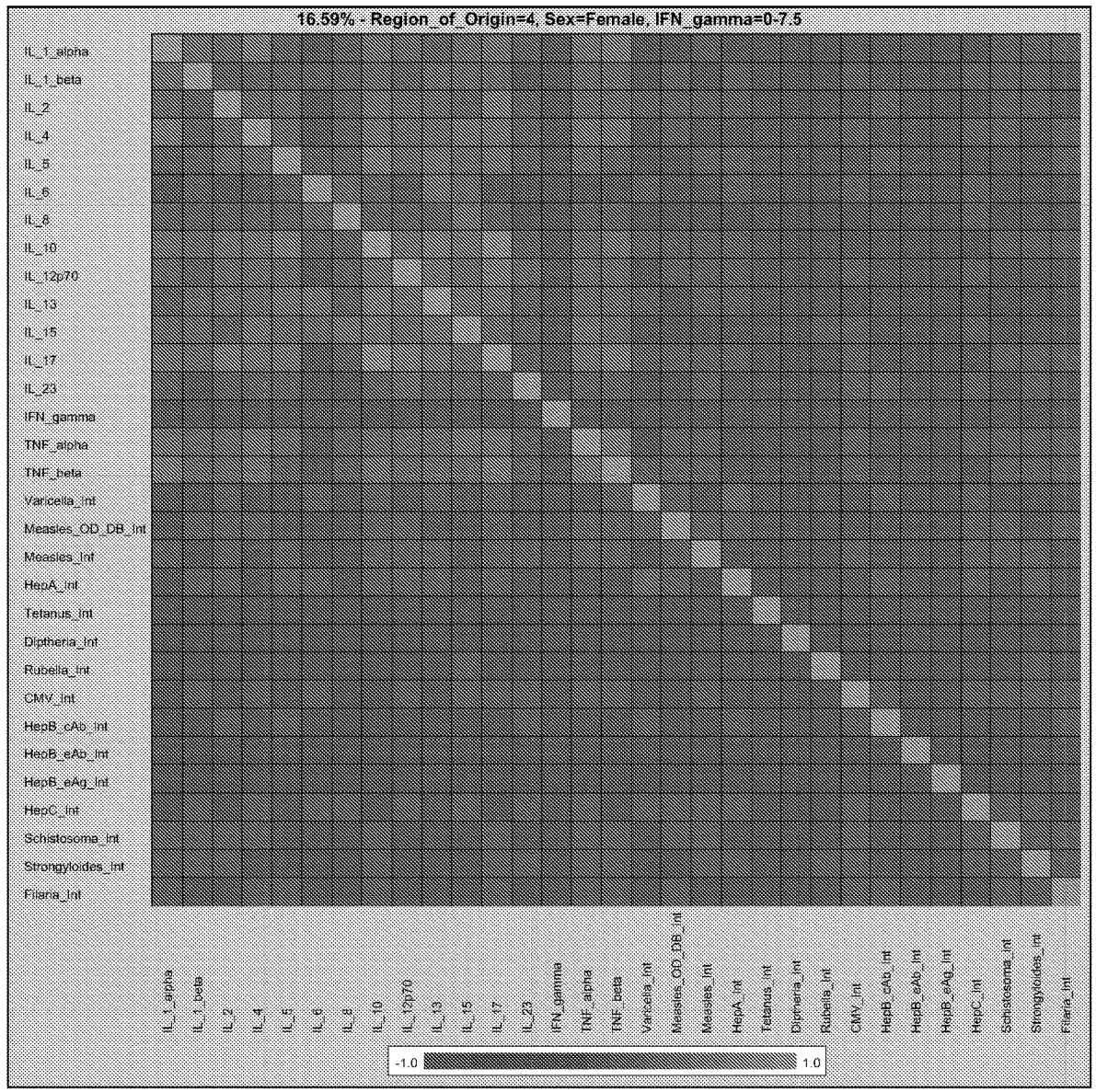
FIG. 21I2-AA

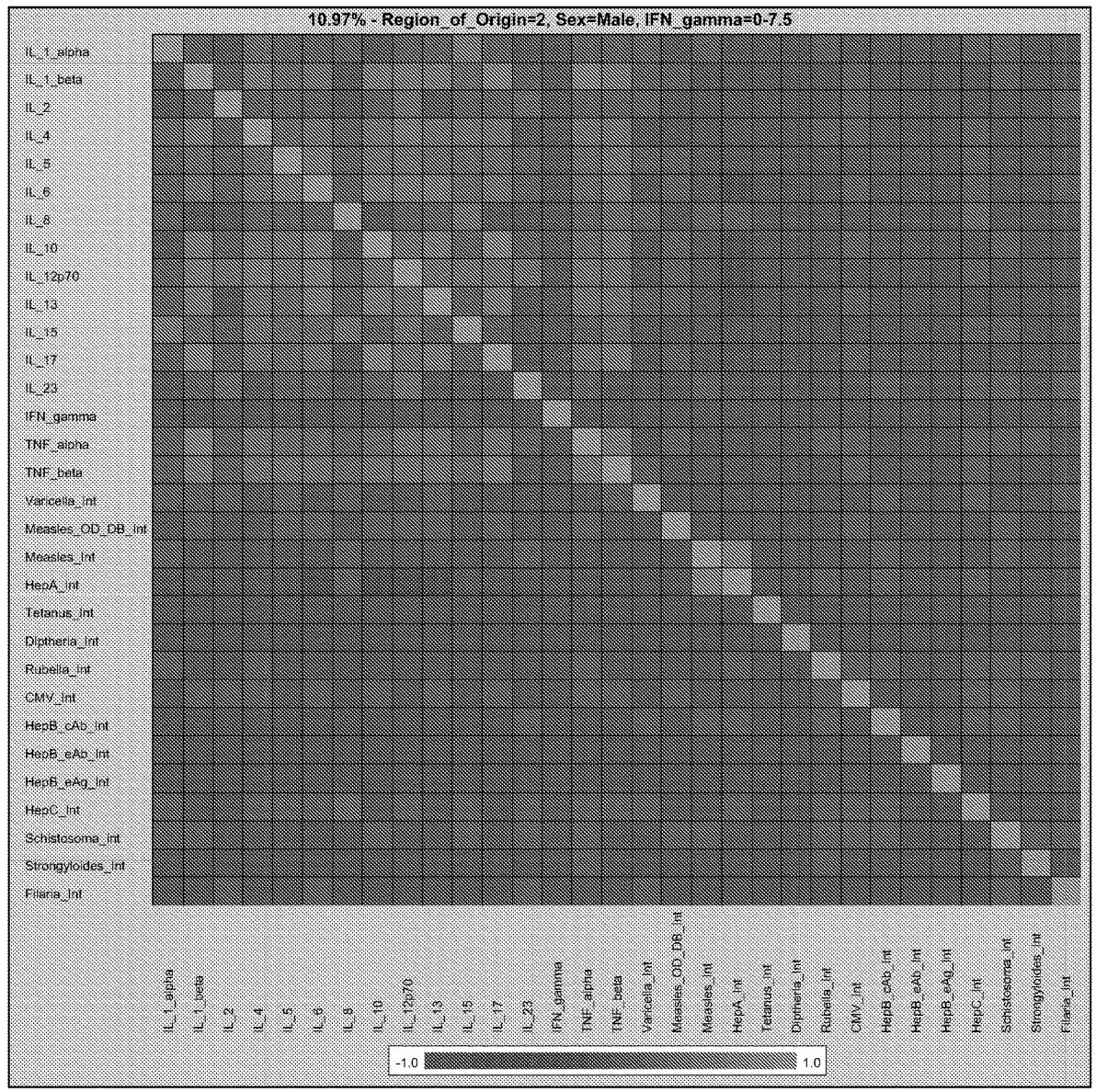
FIG. 21I2-AB

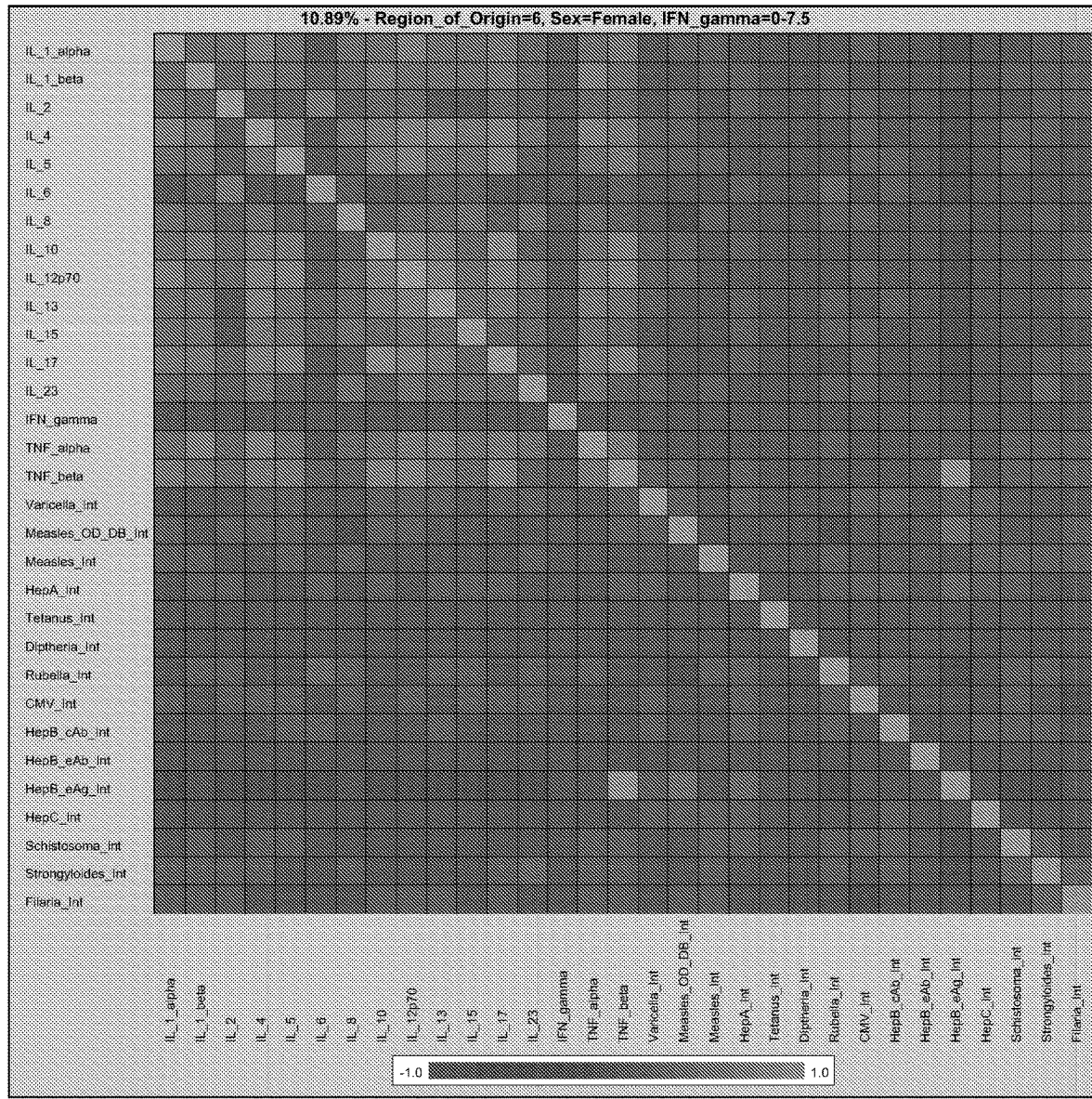
FIG. 21I2-AC

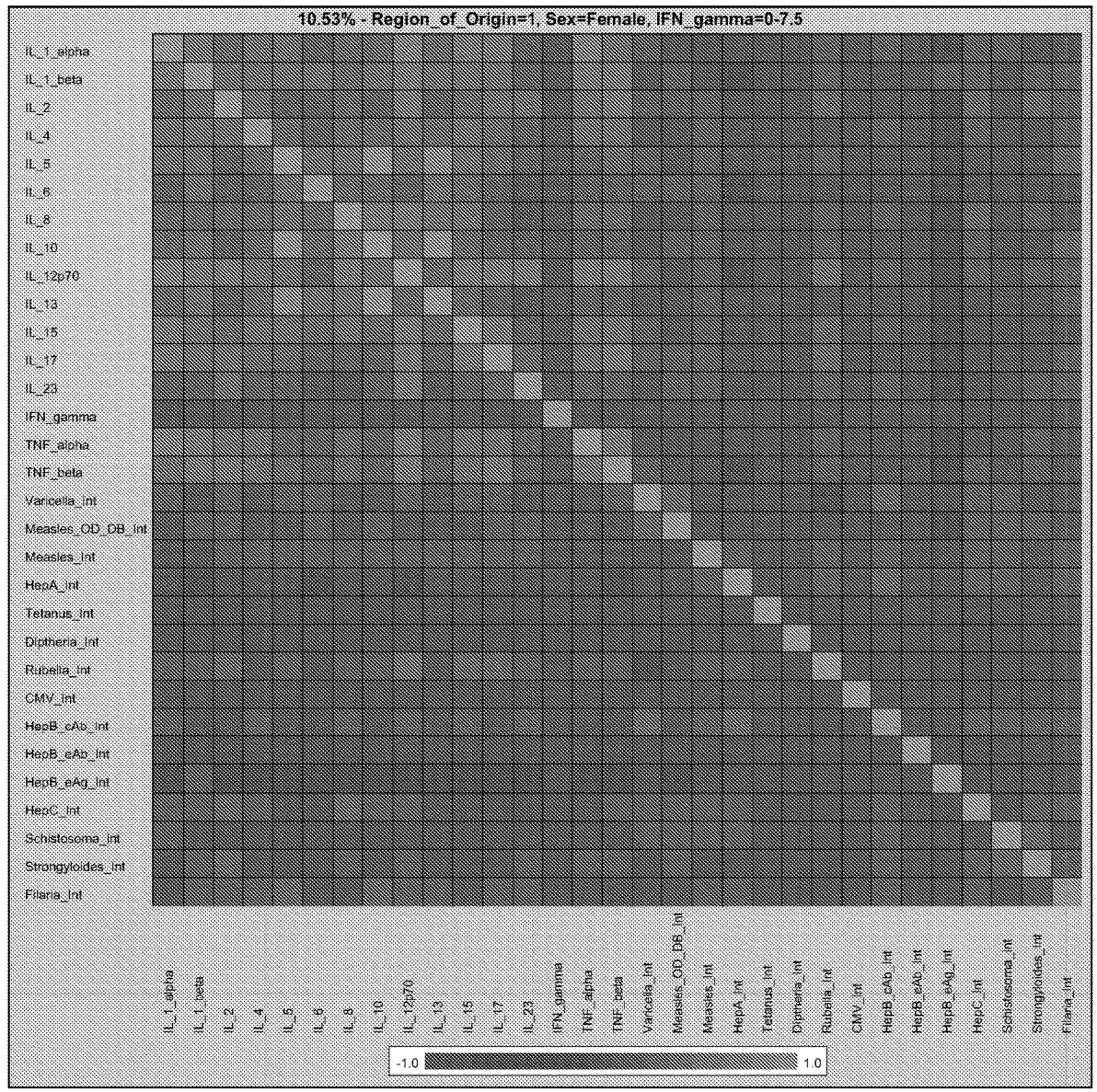
FIG. 21I2-AD

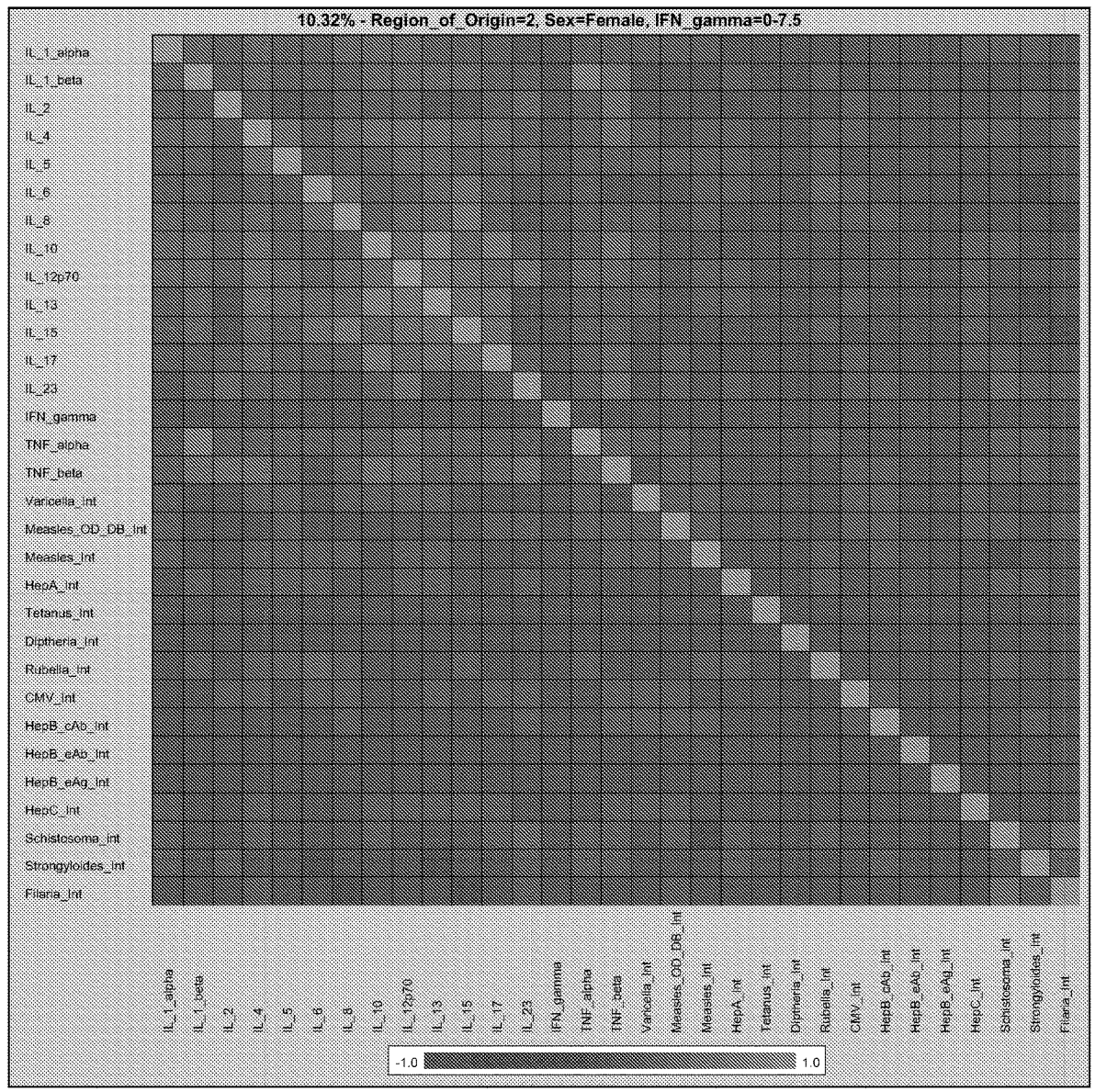
FIG. 21I2-AE

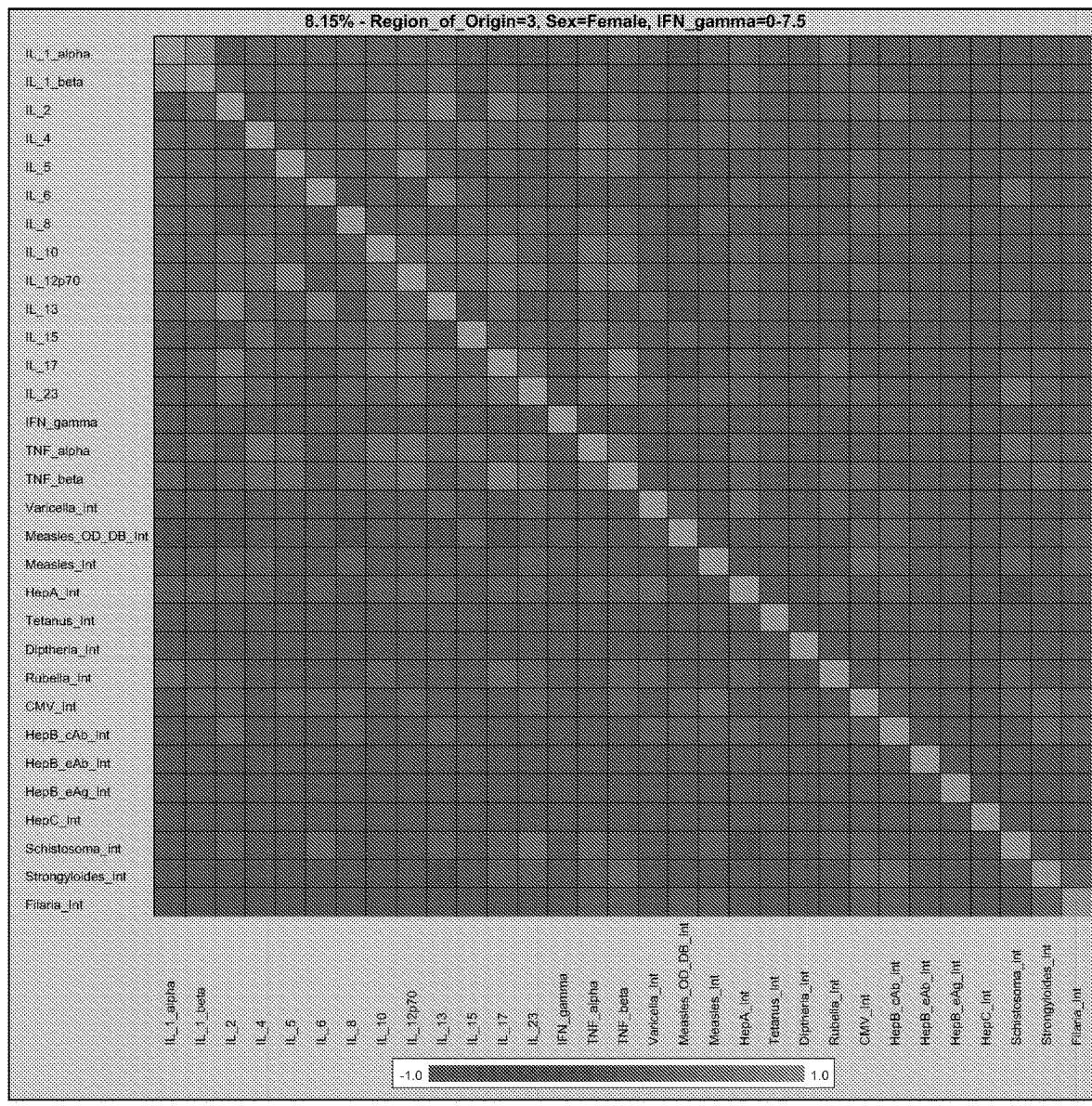
FIG. 21I2-AF

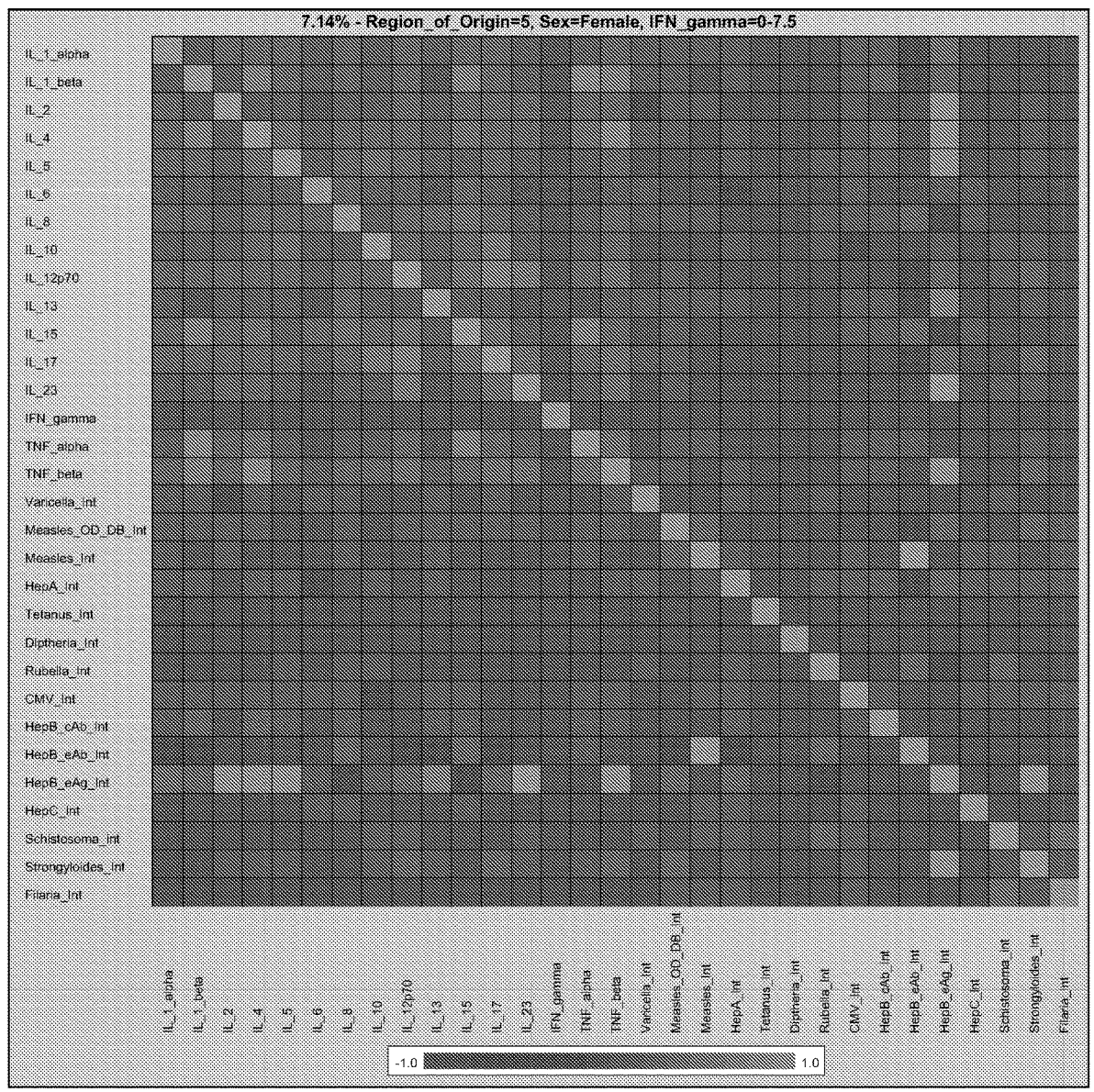
FIG. 21I2-AG

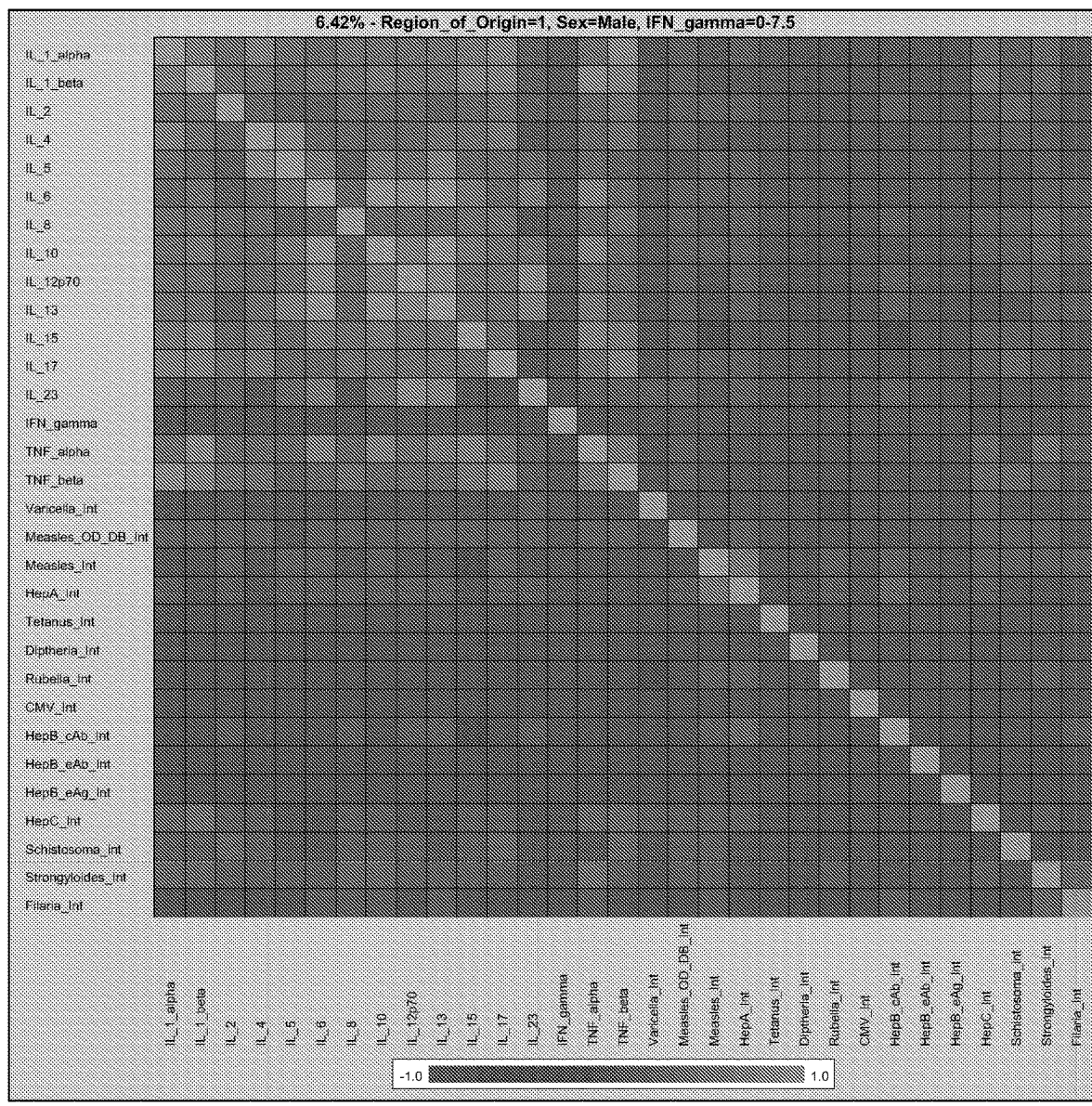
FIG. 21I2-AH

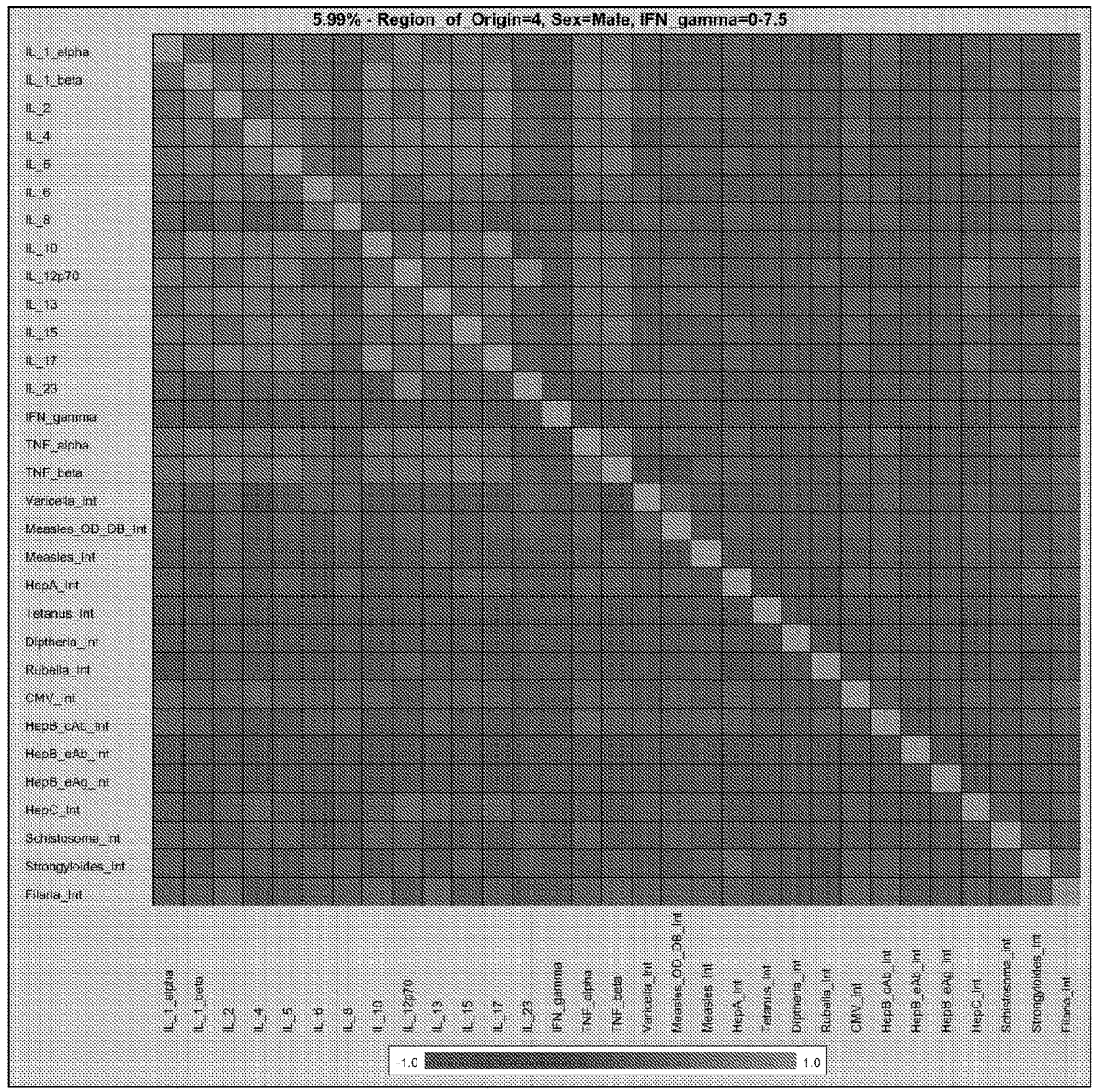
FIG. 21I2-AI

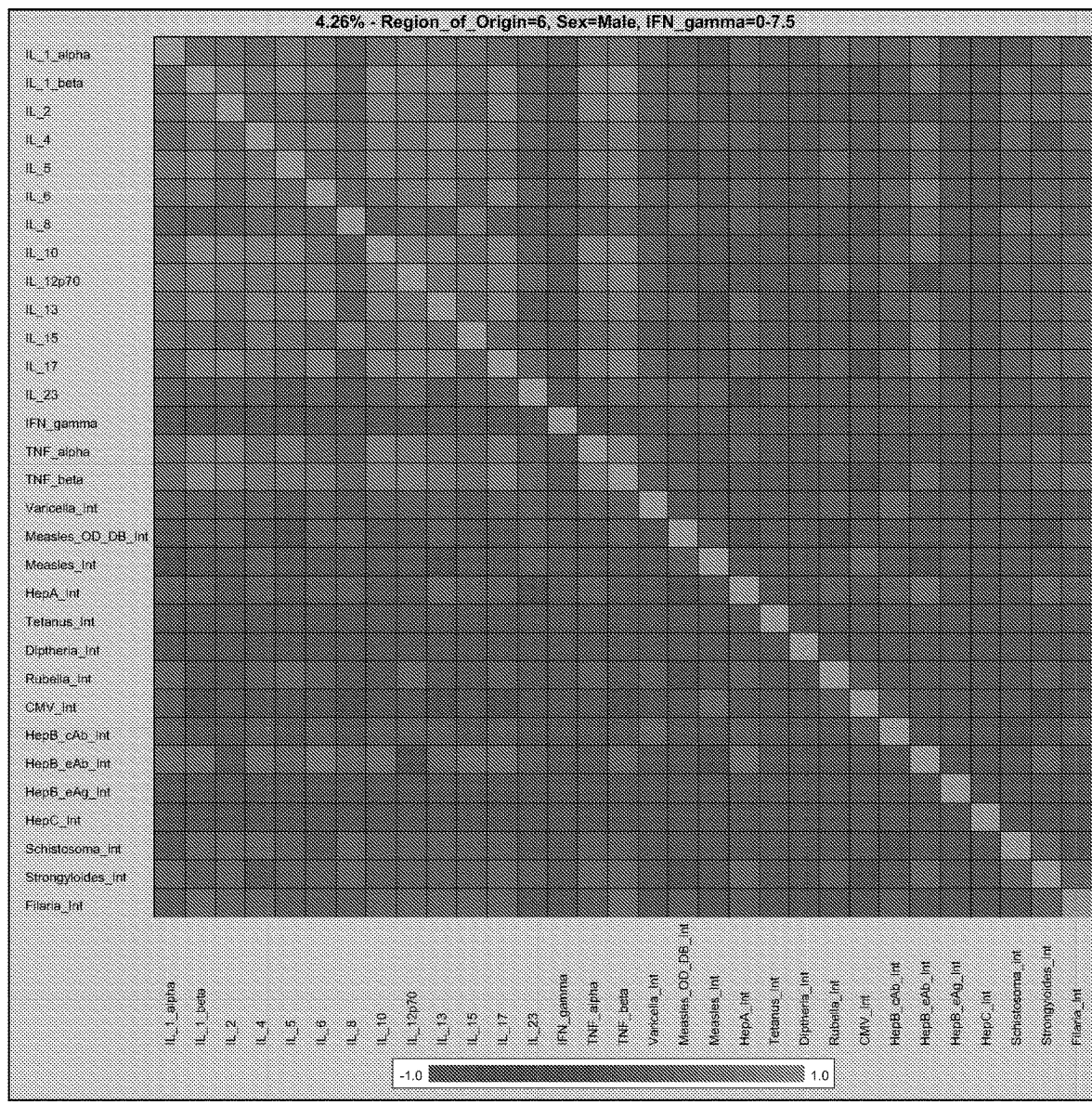
FIG. 21I2-AJ

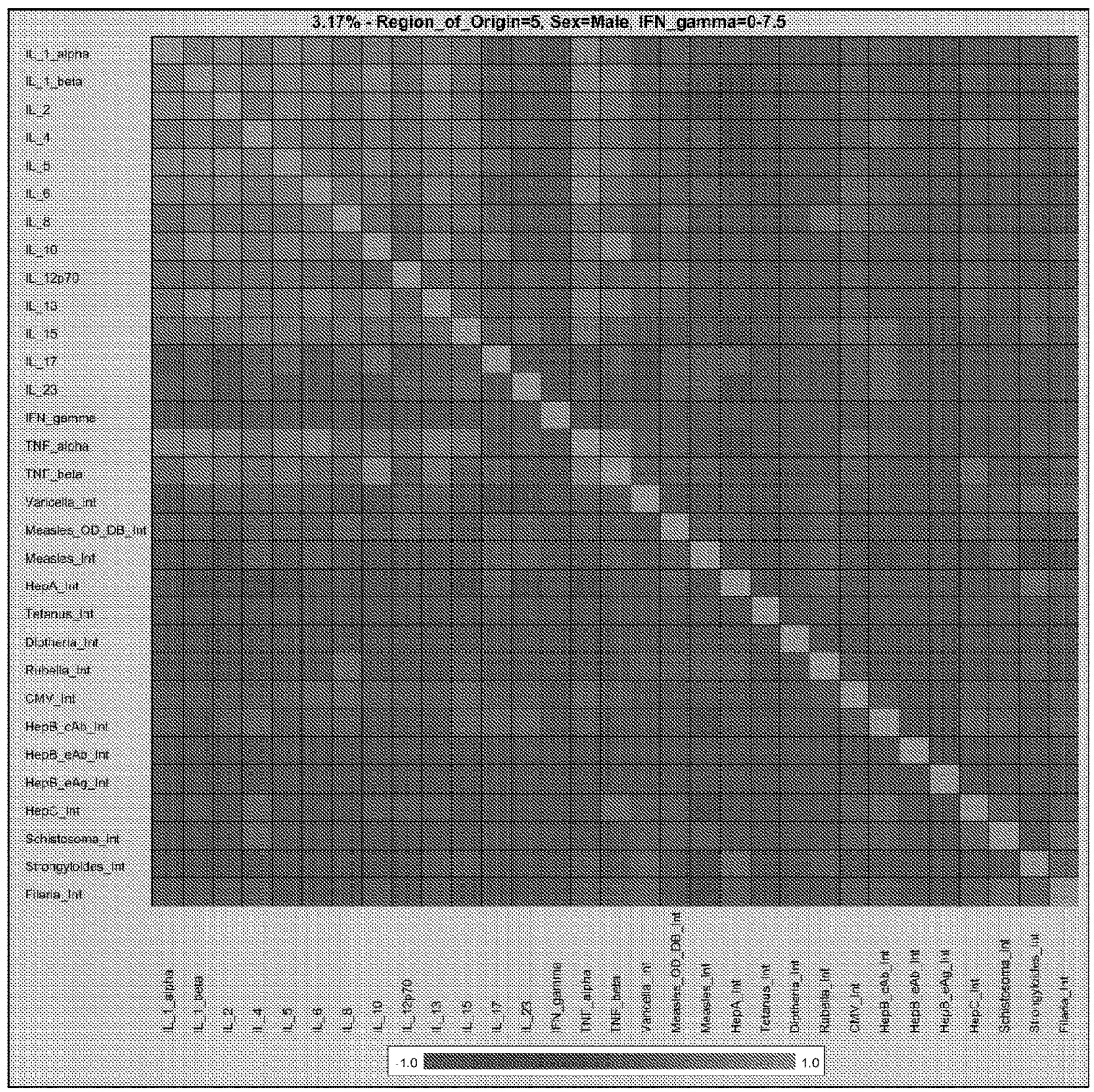
FIG. 21I2-AK

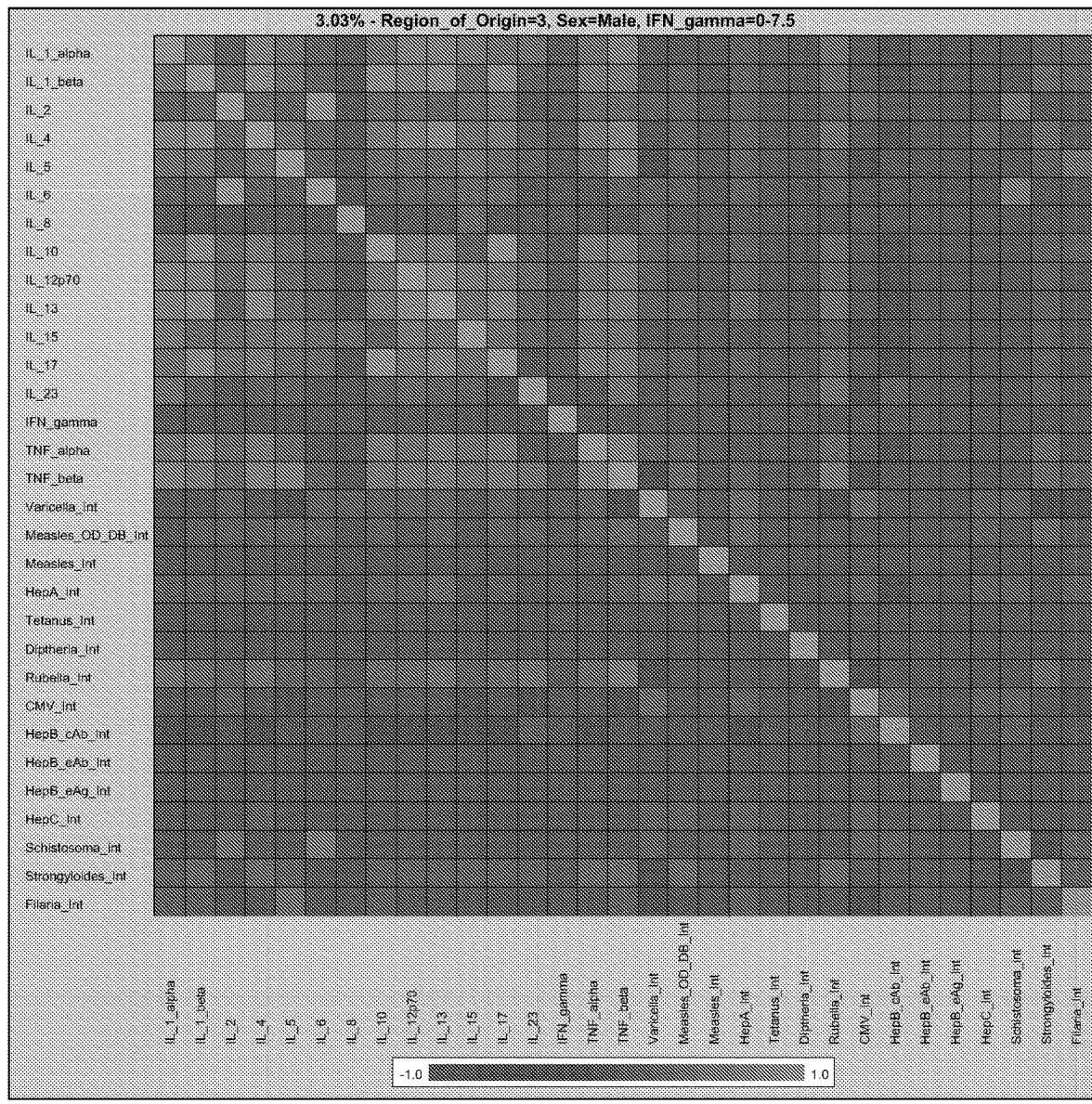
FIG. 21I2-AL

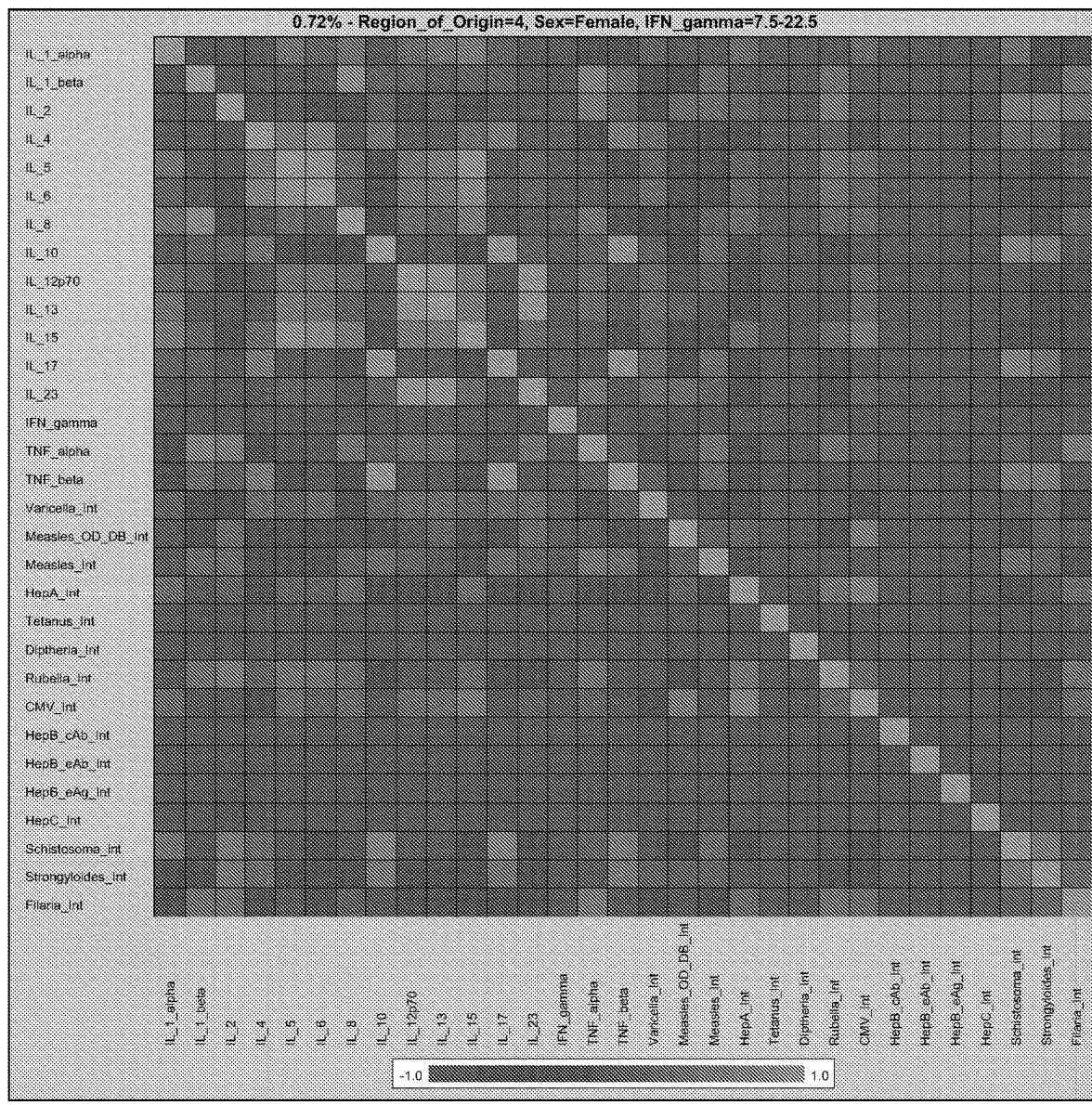
FIG. 21I2-AM

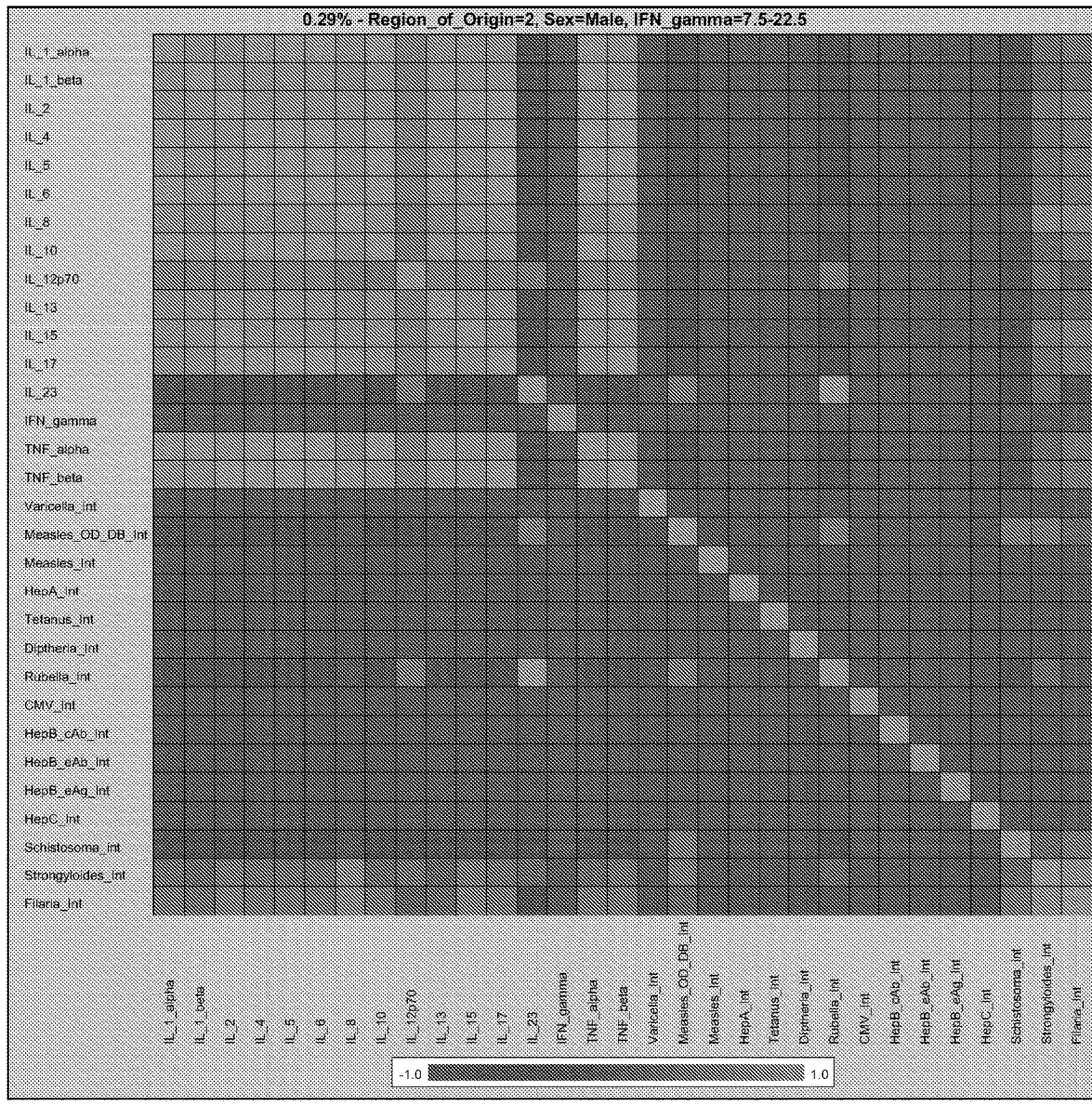
FIG. 21I2-AN

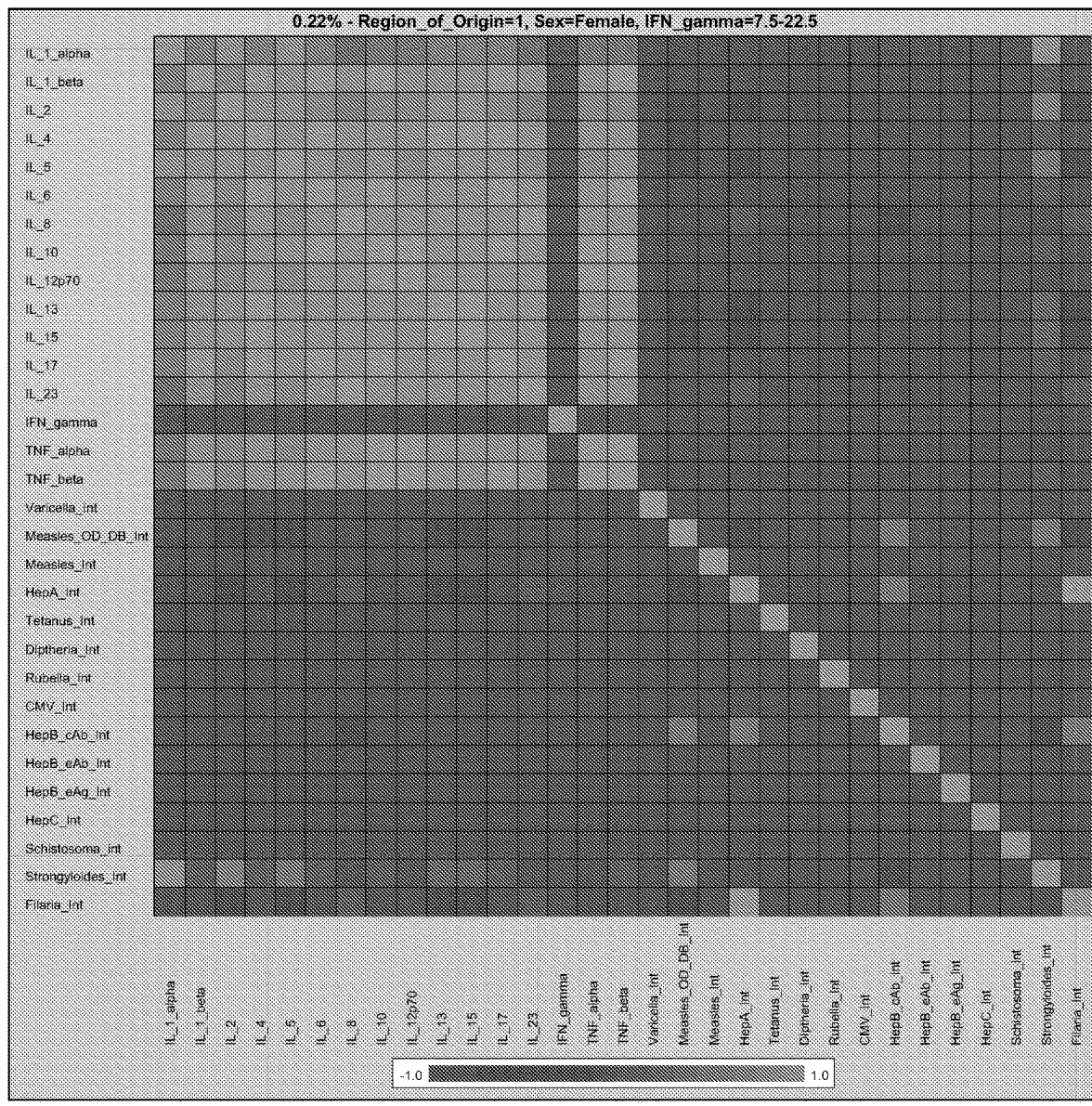
FIG. 21I2-AO

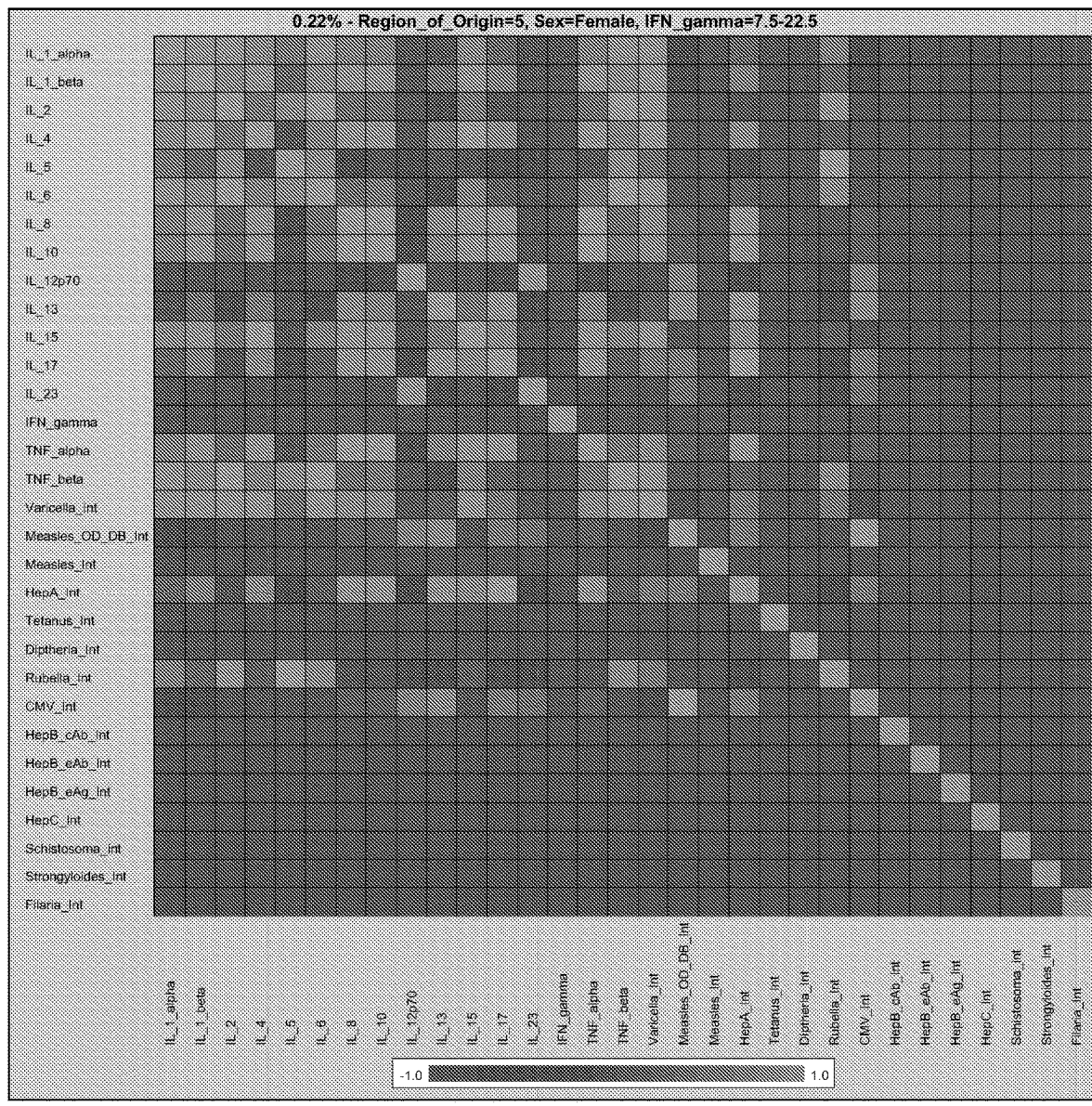
FIG. 2112-AP

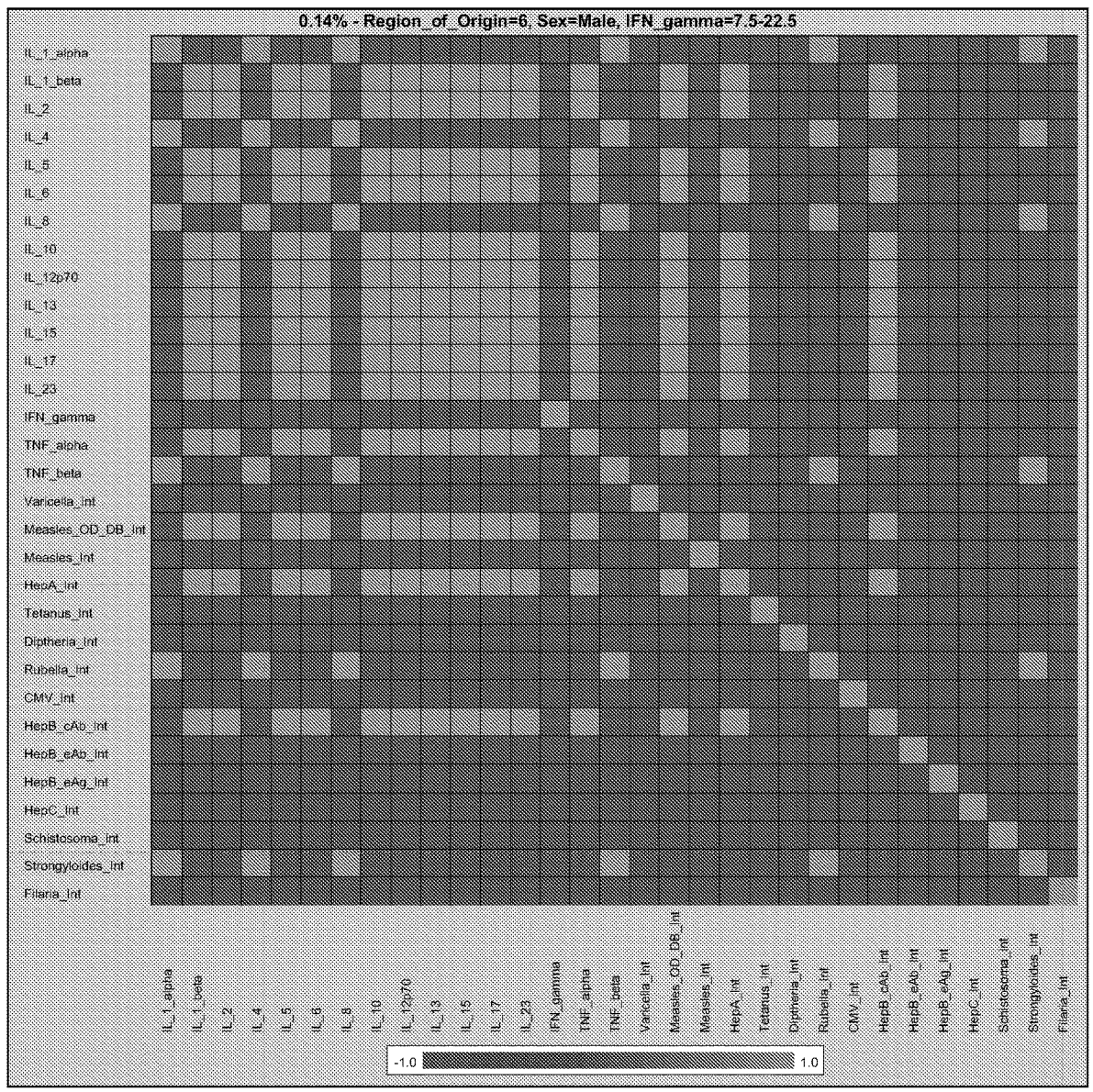
FIG. 21I2-AQ

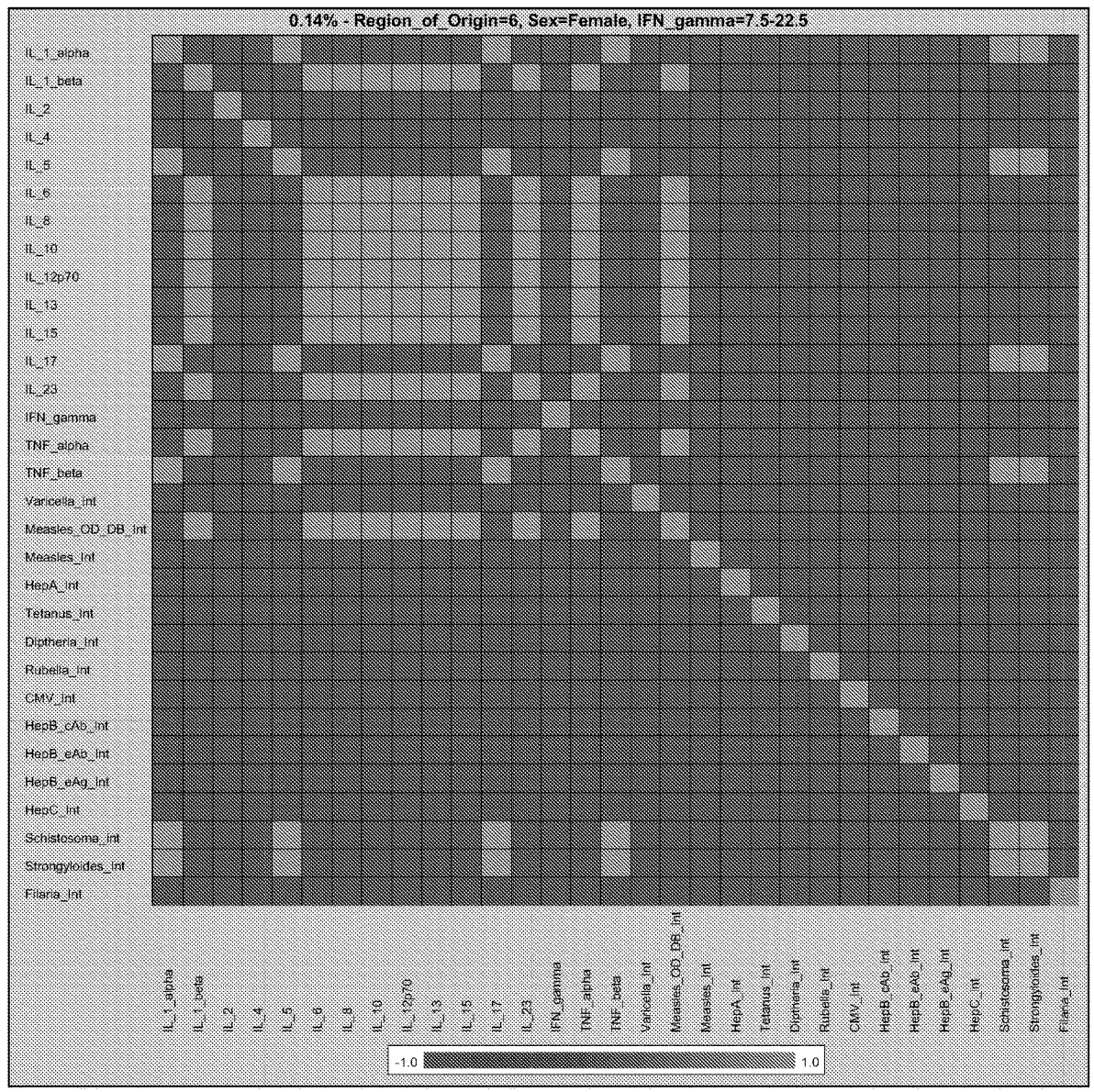
FIG. 21I2-AR

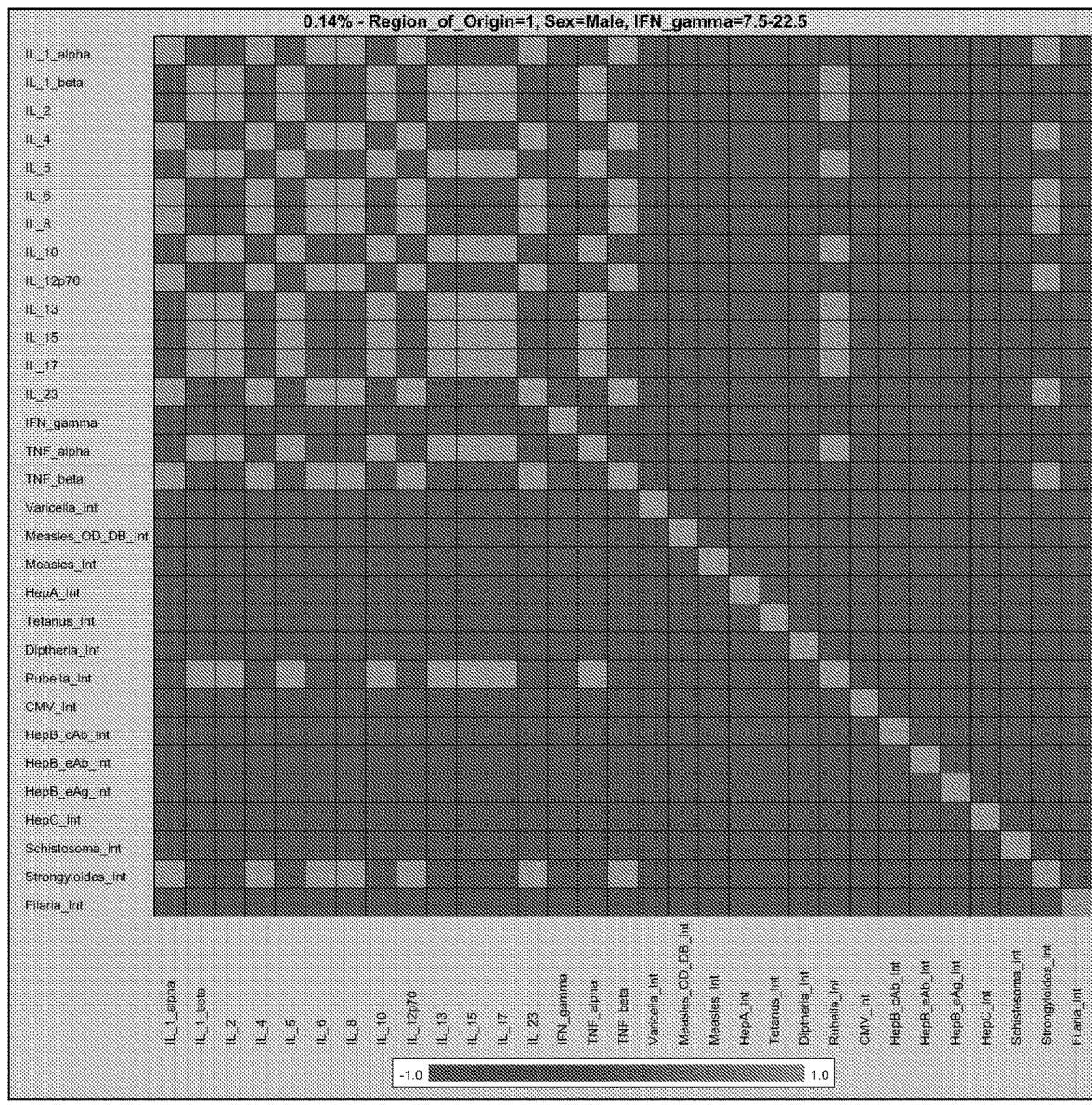
FIG. 21I2-AS

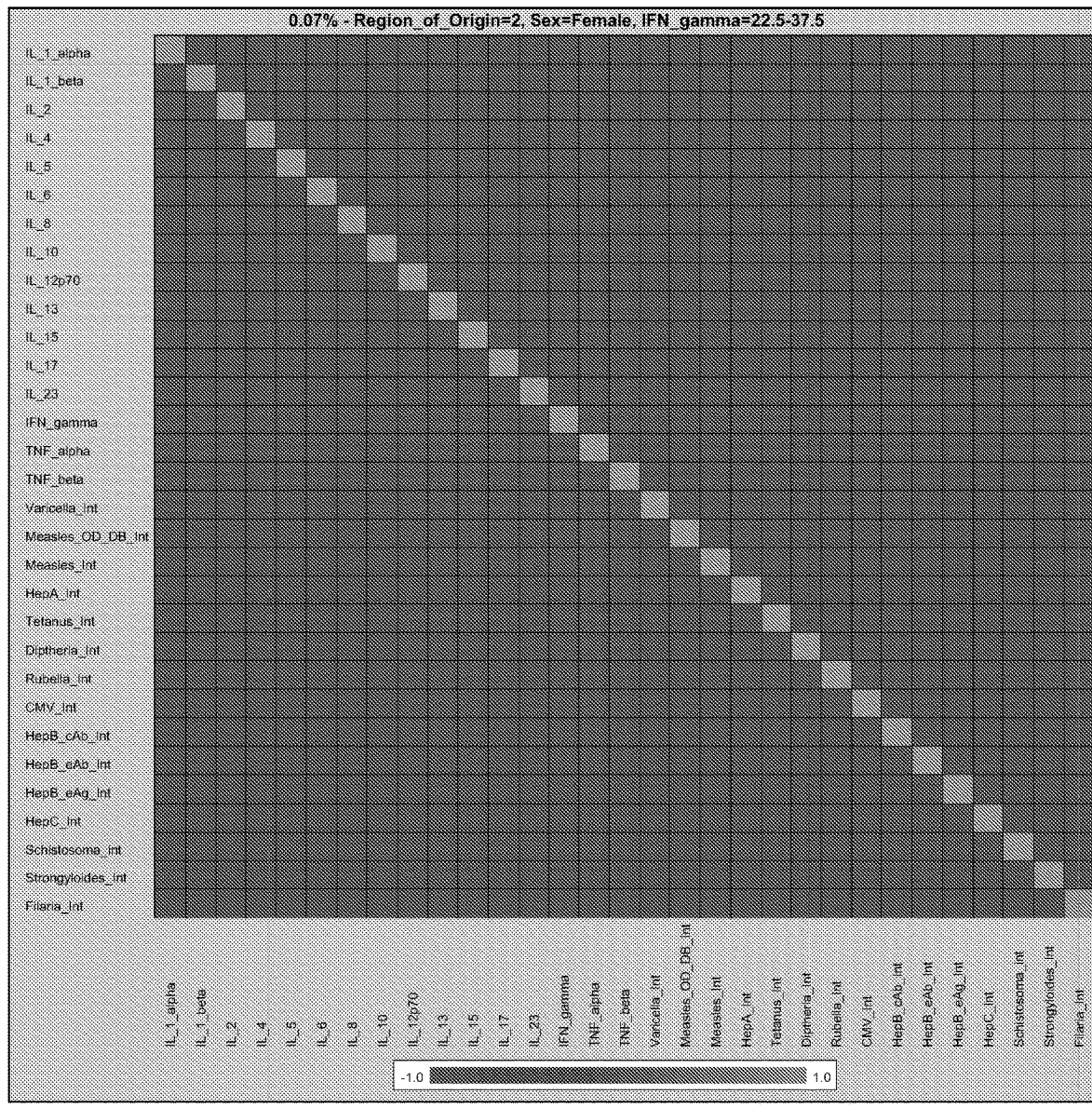
FIG. 21I2-AT

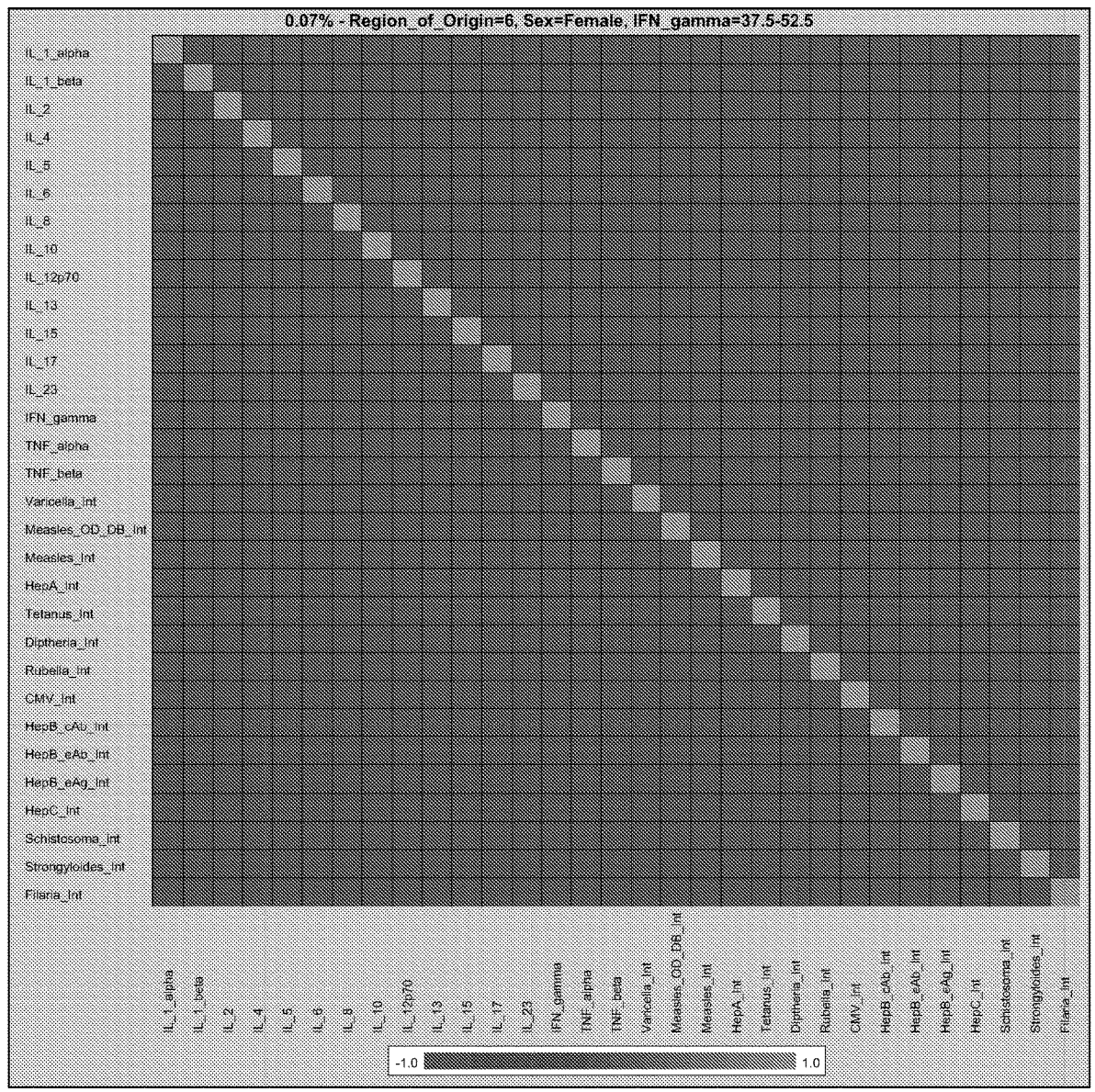
FIG. 21I2-AU

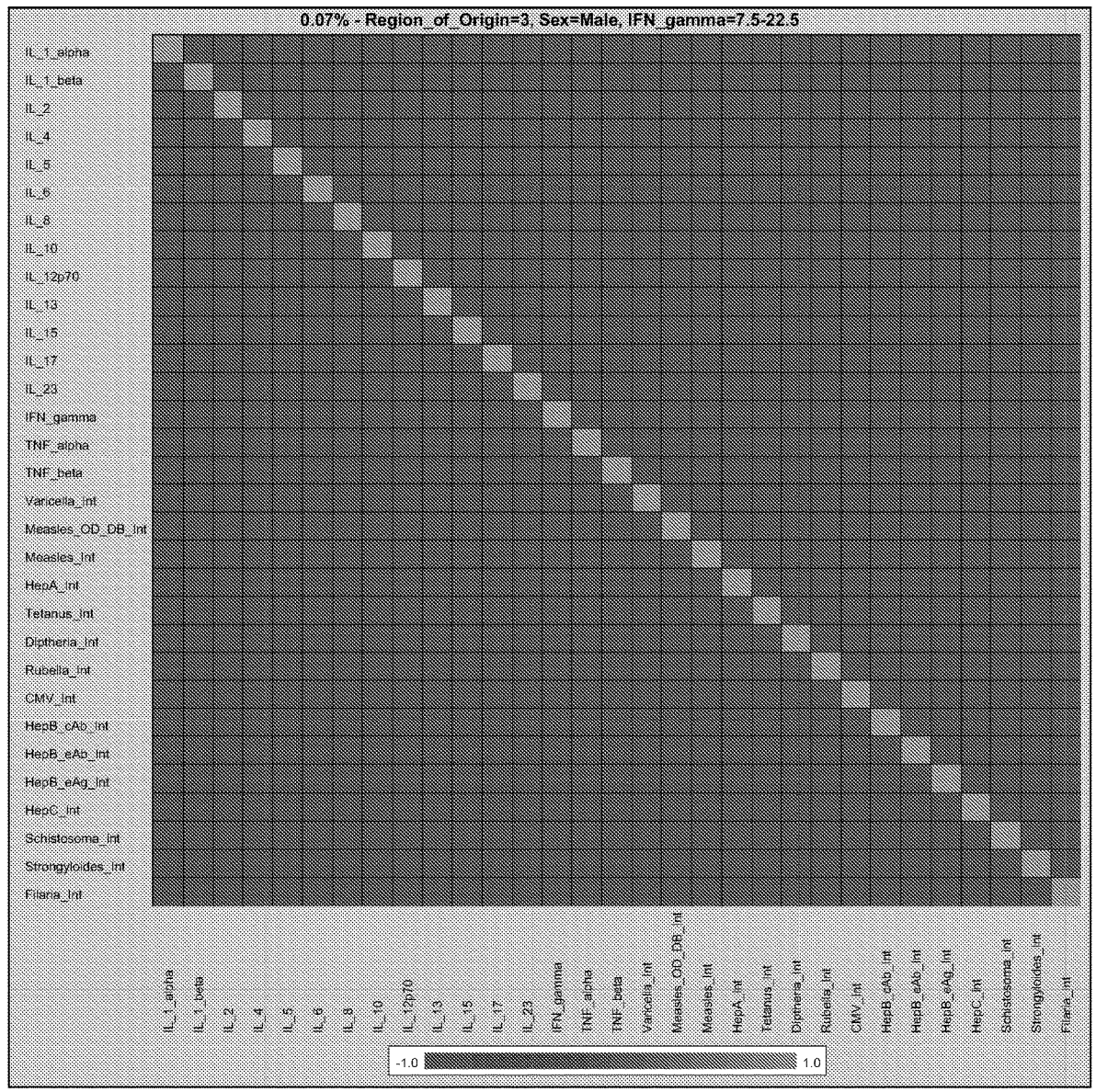
FIG. 21I2-AV

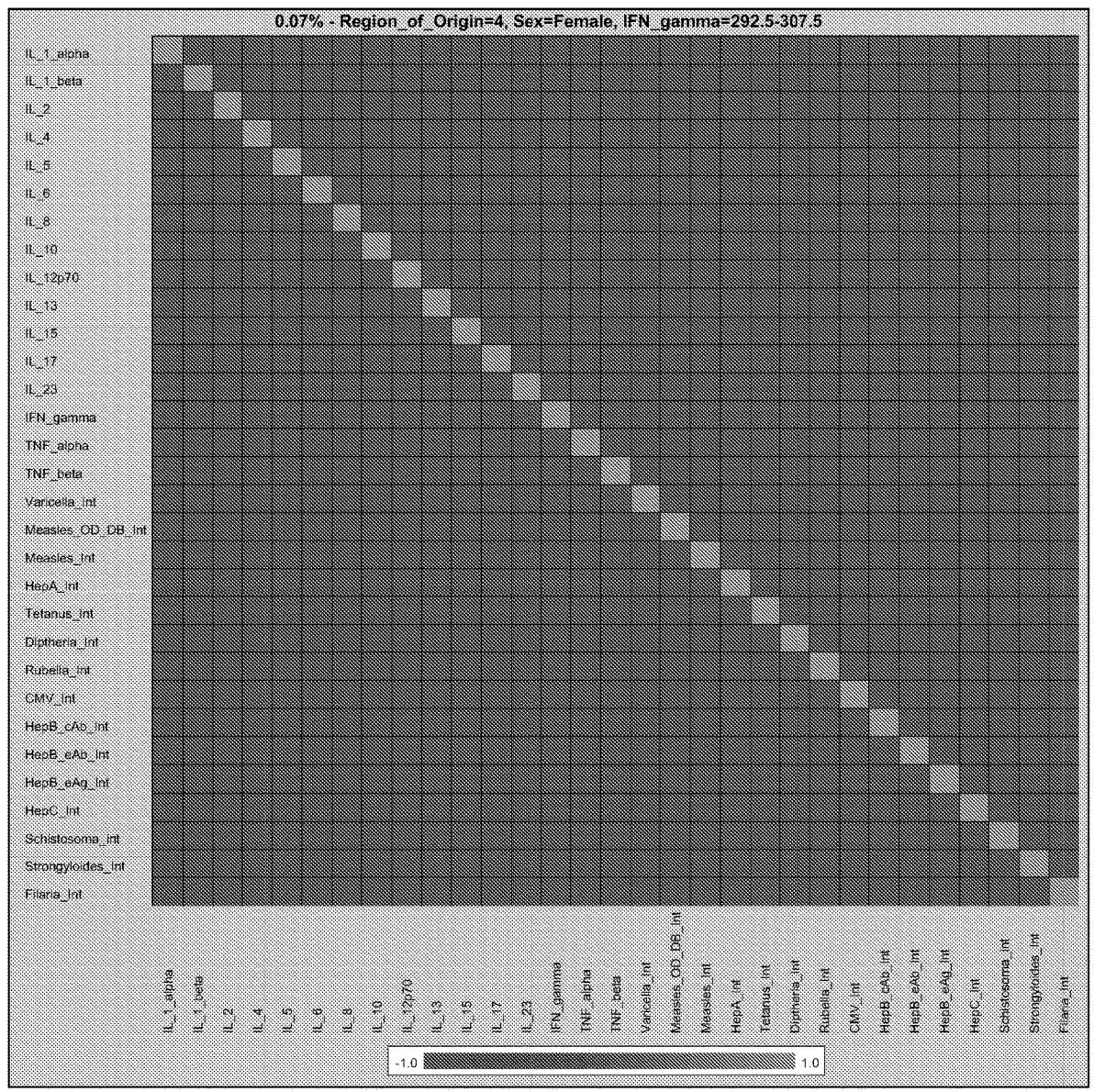
FIG. 21I2-AW

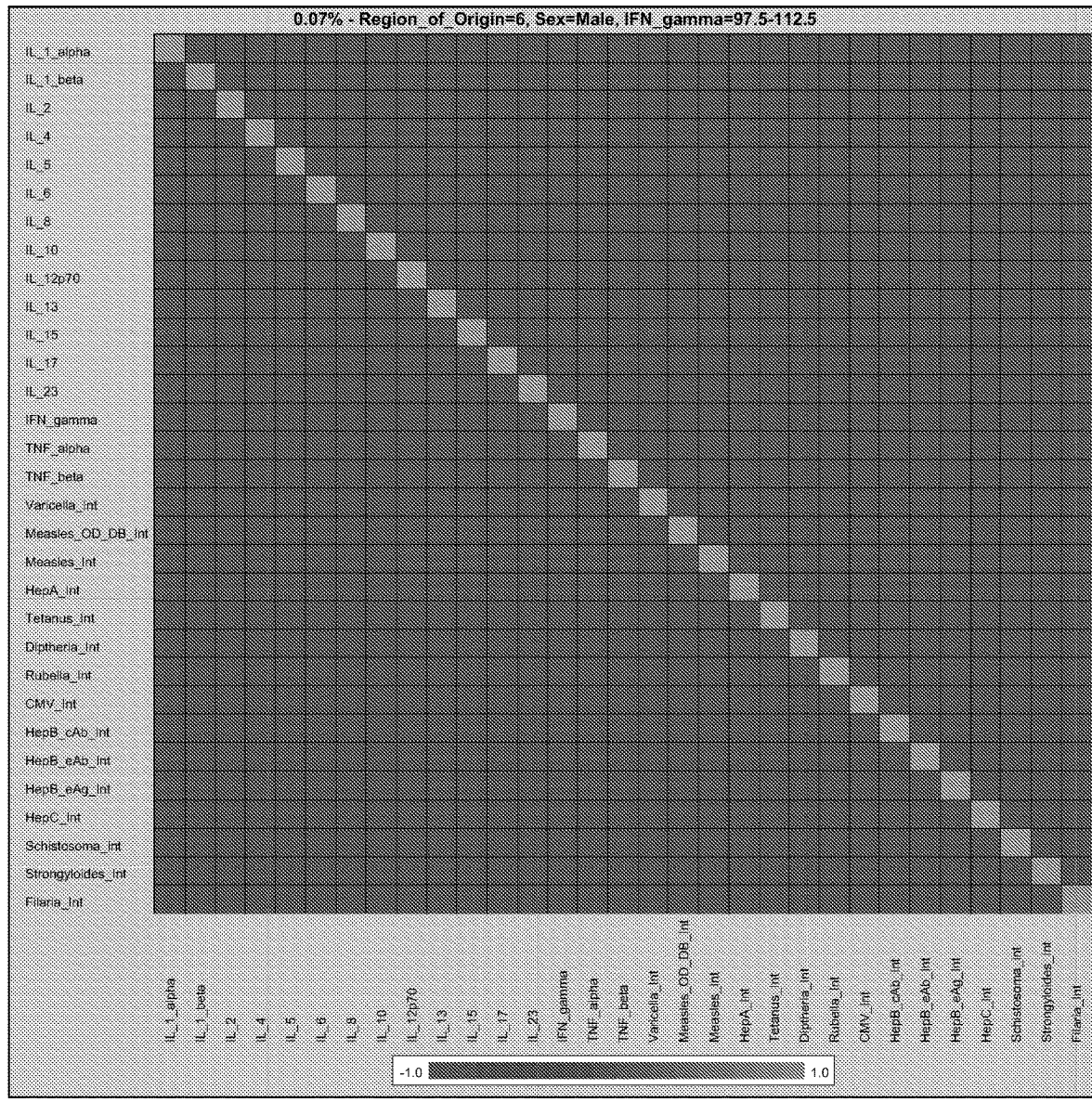
FIG. 21I2-AX

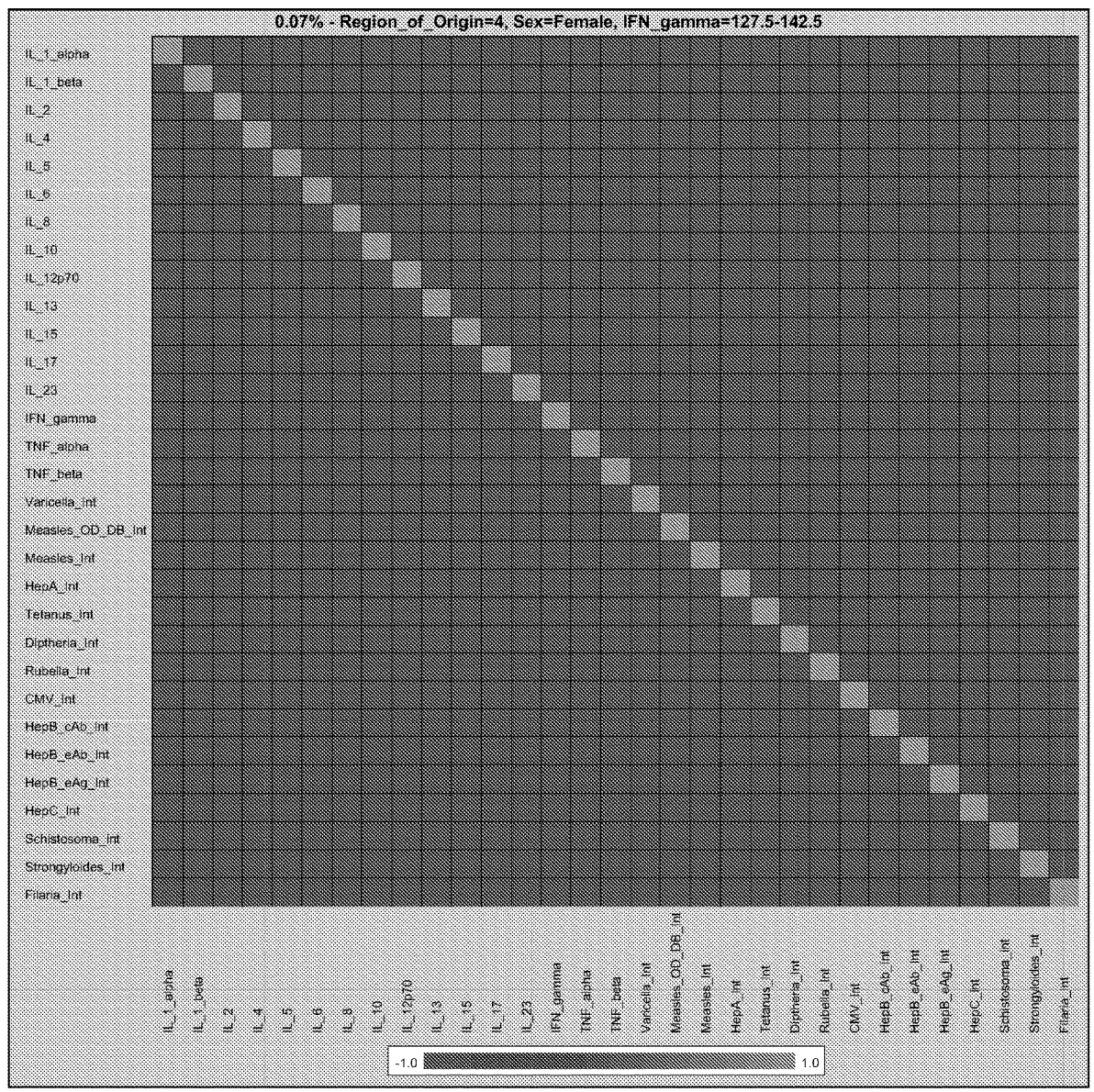
FIG. 21I2-AY

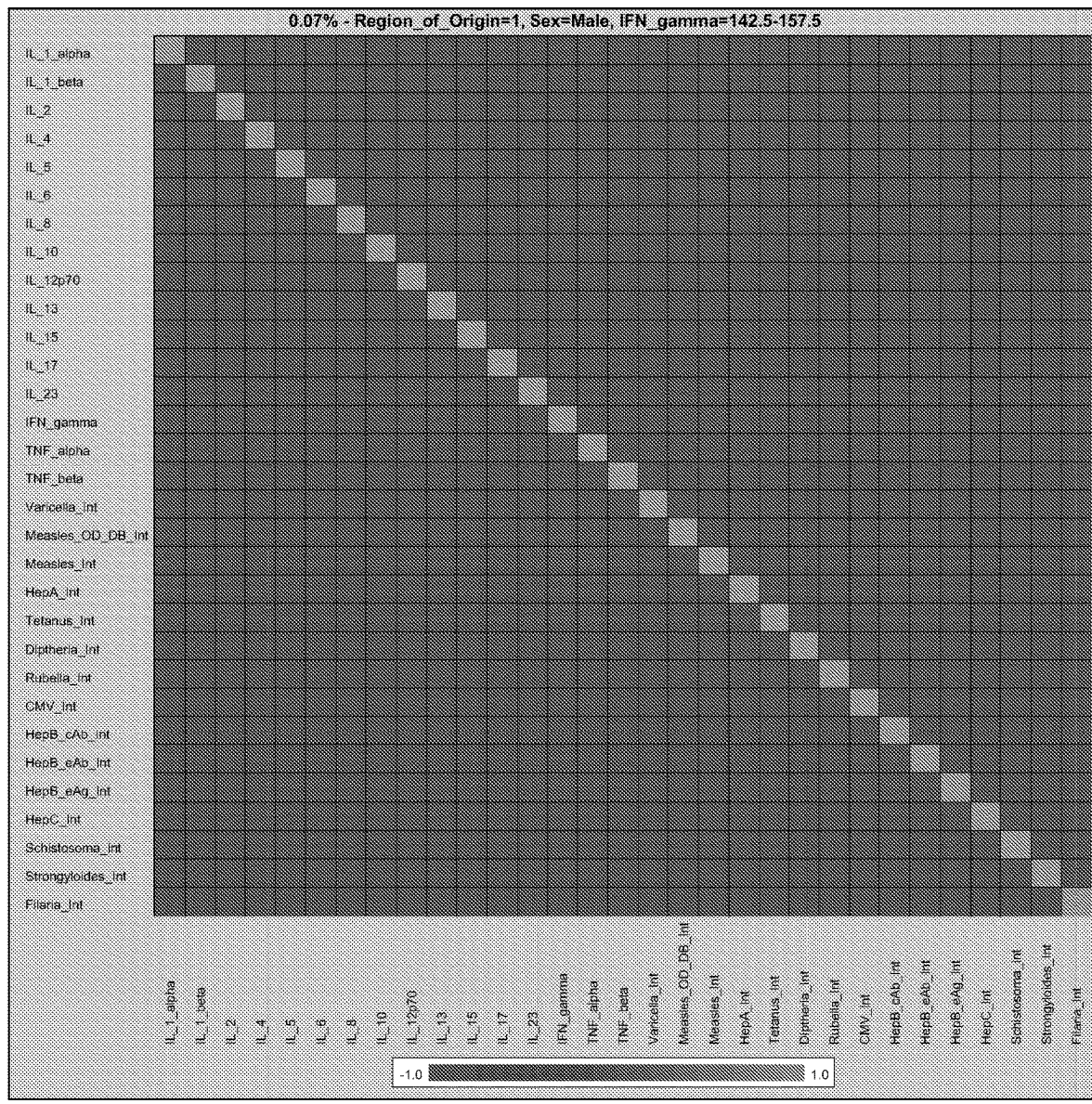
FIG. 21I2-AZ

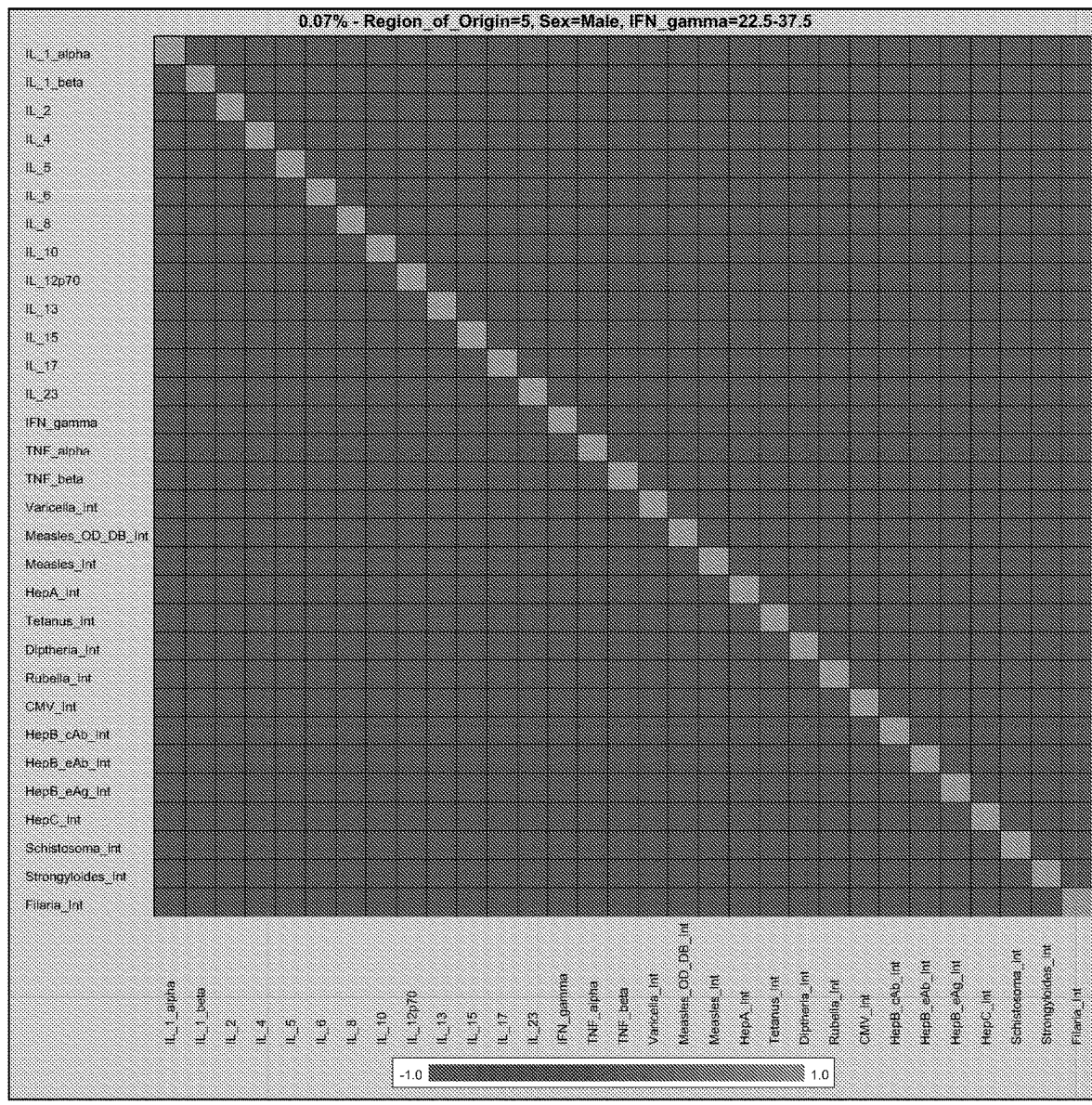
FIG. 21I2-BA

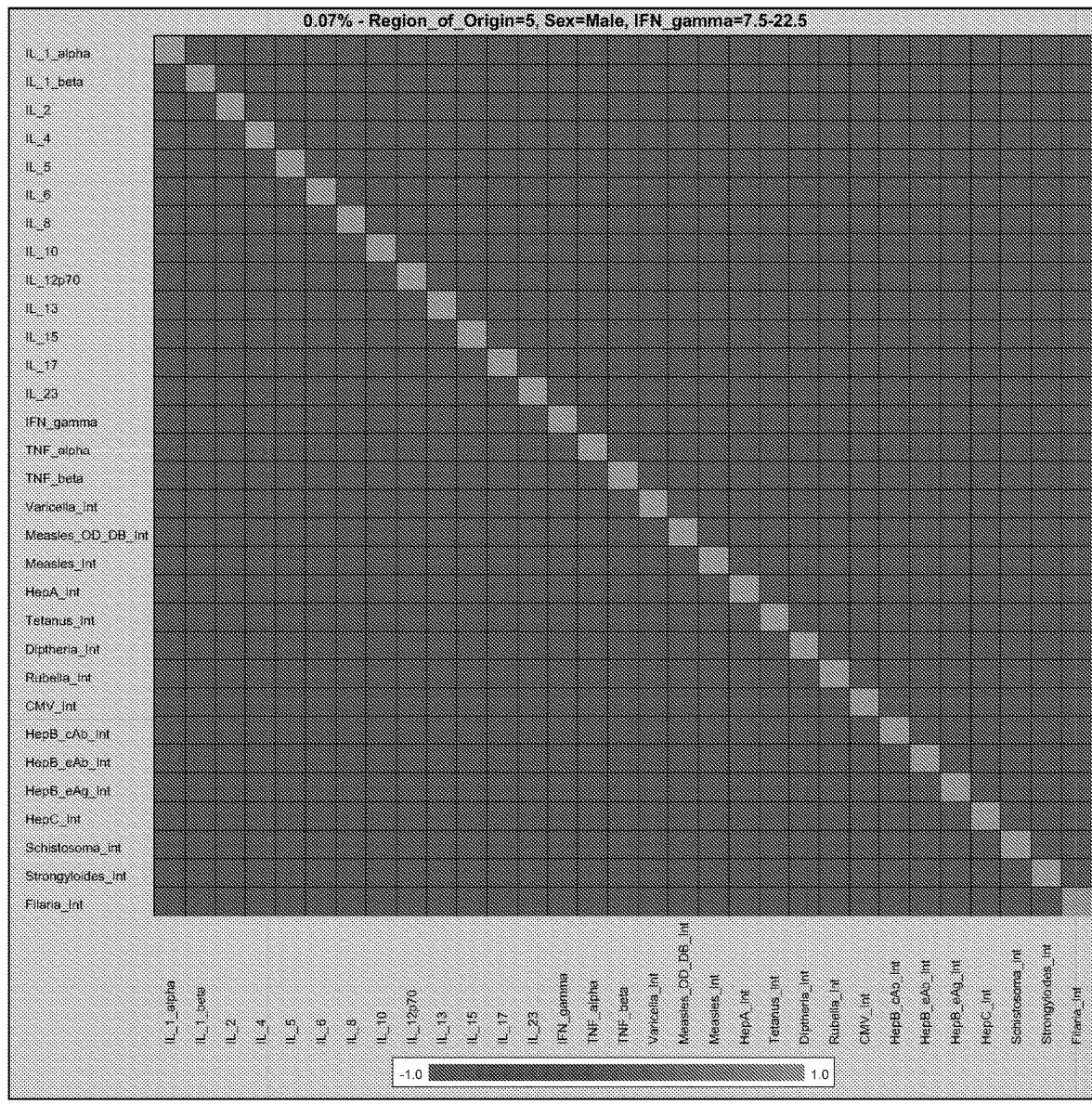
FIG. 21I2-BB

| 16.59% - Region_of_Origin=4, Sex=Female, IFN_gamma=0-7.5 | | |
|---|---|---|
| Property 1 | Property 2 | Corr. Coefficient |
| IL_1_alpha | IL_1_alpha | 1.000 |
| IL_1_alpha | IL_1_beta | 0.335 |
| IL_1_alpha | IL_2 | 0.303 |
| IL_1_alpha | IL_4 | 0.492 |
| IL_1_alpha | IL_5 | 0.189 |
| IL_1_alpha | IL_6 | -0.071 |
| IL_1_alpha | IL_8 | 0.191 |
| IL_1_alpha | IL_10 | 0.344 |

| 10.97% - Region_of_Origin=2, Sex=Male, IFN_gamma=0-7.5 | | |
|---|---|---|
| Property 1 | Property 2 | Corr. Coefficient |
| IL_1_alpha | IL_1_alpha | 1.000 |
| IL_1_alpha | IL_1_beta | 0.086 |
| IL_1_alpha | IL_2 | -0.019 |
| IL_1_alpha | IL_4 | 0.227 |
| IL_1_alpha | IL_5 | 0.190 |
| IL_1_alpha | IL_6 | 0.177 |
| IL_1_alpha | IL_8 | 0.138 |
| IL_1_alpha | IL_10 | 0.018 |

FIG. 21I3-A

| | | | | | | |
|---|---|---|---|---|---|---|
| IL_1_alpha | IL_12p70 | 0.290 | | IL_1_alpha | IL_12p70 | 0.184 |
| IL_1_alpha | IL_13 | 0.191 | | IL_1_alpha | IL_13 | 0.064 |
| IL_1_alpha | IL_15 | 0.253 | | IL_1_alpha | IL_15 | 0.509 |
| IL_1_alpha | IL_17 | 0.451 | | IL_1_alpha | IL_17 | 0.067 |
| IL_1_alpha | IL_23 | 0.025 | | IL_1_alpha | IL_23 | -0.036 |
| IL_1_alpha | IFN_gamma | 0.000 | | IL_1_alpha | IFN_gamma | 0.000 |
| IL_1_alpha | TNF_alpha | 0.371 | | IL_1_alpha | TNF_alpha | 0.098 |
| IL_1_alpha | TNF_beta | 0.511 | | IL_1_alpha | TNF_beta | 0.099 |
| IL_1_alpha | Varicella_Int | -0.056 | | IL_1_alpha | Varicella_Int | 0.034 |
| IL_1_alpha | Measles_OD_DB_Int | 0.024 | | IL_1_alpha | Measles_OD_DB_Int | -0.052 |
| IL_1_alpha | Measles_Int | 0.066 | | IL_1_alpha | Measles_Int | 0.037 |
| IL_1_alpha | HepA_Int | -0.054 | | IL_1_alpha | HepA_Int | -0.035 |
| IL_1_alpha | Tetanus_Int | 0.000 | | IL_1_alpha | Tetanus_Int | 0.000 |
| IL_1_alpha | Diptheria_Int | 0.000 | | IL_1_alpha | Diptheria_Int | 0.000 |
| IL_1_alpha | Rubella_Int | -0.062 | | IL_1_alpha | Rubella_Int | 0.050 |
| IL_1_alpha | CMV_Int | 0.009 | | IL_1_alpha | CMV_Int | -0.004 |
| IL_1_alpha | HepB_cAb_Int | -0.082 | | IL_1_alpha | HepB_cAb_Int | -0.083 |
| IL_1_alpha | HepB_eAb_Int | 0.000 | | IL_1_alpha | HepB_eAb_Int | 0.000 |
| IL_1_alpha | HepB_eAg_Int | 0.000 | | IL_1_alpha | HepB_eAg_Int | 0.000 |
| IL_1_alpha | HepC_Int | -0.012 | | IL_1_alpha | HepC_Int | 0.085 |
| IL_1_alpha | Schistosoma_int | 0.041 | | IL_1_alpha | Schistosoma_int | 0.146 |
| IL_1_alpha | Strongyloides_Int | 0.066 | | IL_1_alpha | Strongyloides_Int | -0.117 |
| IL_1_alpha | Filaria_Int | 0.036 | | IL_1_alpha | Filaria_Int | 0.024 |
| IL_1_beta | IL_1_alpha | 0.335 | | IL_1_beta | IL_1_alpha | 0.086 |
| IL_1_beta | IL_1_beta | 1.000 | | IL_1_beta | IL_1_beta | 1.000 |
| IL_1_beta | IL_2 | 0.160 | | IL_1_beta | IL_2 | 0.128 |
| IL_1_beta | IL_4 | 0.186 | | IL_1_beta | IL_4 | 0.524 |
| IL_1_beta | IL_5 | 0.127 | | IL_1_beta | IL_5 | 0.290 |
| IL_1_beta | IL_6 | 0.067 | | IL_1_beta | IL_6 | 0.416 |
| IL_1_beta | IL_8 | 0.088 | | IL_1_beta | IL_8 | 0.007 |
| IL_1_beta | IL_10 | 0.216 | | IL_1_beta | IL_10 | 0.605 |
| IL_1_beta | IL_12p70 | 0.112 | | IL_1_beta | IL_12p70 | 0.495 |
| IL_1_beta | IL_13 | 0.201 | | IL_1_beta | IL_13 | 0.571 |
| IL_1_beta | IL_15 | 0.198 | | IL_1_beta | IL_15 | 0.207 |
| IL_1_beta | IL_17 | 0.222 | | IL_1_beta | IL_17 | 0.689 |
| IL_1_beta | IL_23 | -0.010 | | IL_1_beta | IL_23 | 0.031 |
| IL_1_beta | IFN_gamma | 0.000 | | IL_1_beta | IFN_gamma | 0.000 |
| IL_1_beta | TNF_alpha | 0.234 | | IL_1_beta | TNF_alpha | 0.618 |
| IL_1_beta | TNF_beta | 0.246 | | IL_1_beta | TNF_beta | 0.534 |
| IL_1_beta | Varicella_Int | 0.019 | | IL_1_beta | Varicella_Int | 0.031 |
| IL_1_beta | Measles_OD_DB_Int | 0.090 | | IL_1_beta | Measles_OD_DB_Int | 0.072 |
| IL_1_beta | Measles_Int | -0.131 | | IL_1_beta | Measles_Int | -0.049 |
| IL_1_beta | HepA_Int | 0.048 | | IL_1_beta | HepA_Int | -0.188 |
| IL_1_beta | Tetanus_Int | 0.000 | | IL_1_beta | Tetanus_Int | 0.000 |
| IL_1_beta | Diptheria_Int | 0.000 | | IL_1_beta | Diptheria_Int | 0.000 |
| IL_1_beta | Rubella_Int | -0.024 | | IL_1_beta | Rubella_Int | -0.008 |
| IL_1_beta | CMV_Int | 0.046 | | IL_1_beta | CMV_Int | 0.063 |
| IL_1_beta | HepB_cAb_Int | -0.049 | | IL_1_beta | HepB_cAb_Int | -0.191 |
| IL_1_beta | HepB_eAb_Int | 0.000 | | IL_1_beta | HepB_eAb_Int | 0.000 |
| IL_1_beta | HepB_eAg_Int | 0.000 | | IL_1_beta | HepB_eAg_Int | 0.000 |
| IL_1_beta | HepC_Int | 0.108 | | IL_1_beta | HepC_Int | 0.000 |
| IL_1_beta | Schistosoma_int | 0.027 | | IL_1_beta | Schistosoma_int | 0.035 |
| IL_1_beta | Strongyloides_Int | 0.069 | | IL_1_beta | Strongyloides_Int | -0.091 |
| IL_1_beta | Filaria_Int | -0.018 | | IL_1_beta | Filaria_Int | -0.017 |
| IL_2 | IL_1_alpha | 0.303 | | IL_2 | IL_1_alpha | -0.019 |
| IL_2 | IL_1_beta | 0.160 | | IL_2 | IL_1_beta | 0.128 |
| IL_2 | IL_2 | 1.000 | | IL_2 | IL_2 | 1.000 |

FIG. 2II3-B

| | | | | | | |
|---|---|---|---|---|---|---|
| IL_2 | IL_4 | 0.253 | | IL_2 | IL_4 | 0.049 |
| IL_2 | IL_5 | 0.240 | | IL_2 | IL_5 | 0.080 |
| IL_2 | IL_6 | -0.102 | | IL_2 | IL_6 | 0.124 |
| IL_2 | IL_8 | 0.075 | | IL_2 | IL_8 | 0.008 |
| IL_2 | IL_10 | 0.375 | | IL_2 | IL_10 | 0.030 |
| IL_2 | IL_12p70 | 0.263 | | IL_2 | IL_12p70 | 0.375 |
| IL_2 | IL_13 | 0.333 | | IL_2 | IL_13 | 0.017 |
| IL_2 | IL_15 | 0.073 | | IL_2 | IL_15 | 0.082 |
| IL_2 | IL_17 | 0.509 | | IL_2 | IL_17 | 0.146 |
| IL_2 | IL_23 | 0.112 | | IL_2 | IL_23 | 0.255 |
| IL_2 | IFN_gamma | 0.000 | | IL_2 | IFN_gamma | 0.000 |
| IL_2 | TNF_alpha | 0.255 | | IL_2 | TNF_alpha | 0.055 |
| IL_2 | TNF_beta | 0.328 | | IL_2 | TNF_beta | 0.192 |
| IL_2 | Varicella_Int | 0.033 | | IL_2 | Varicella_Int | 0.027 |
| IL_2 | Measles_OD_DB_Int | 0.028 | | IL_2 | Measles_OD_DB_Int | 0.023 |
| IL_2 | Measles_Int | 0.079 | | IL_2 | Measles_Int | 0.016 |
| IL_2 | HepA_Int | 0.072 | | IL_2 | HepA_Int | -0.010 |
| IL_2 | Tetanus_Int | 0.000 | | IL_2 | Tetanus_Int | 0.000 |
| IL_2 | Diptheria_Int | 0.000 | | IL_2 | Diptheria_Int | 0.000 |
| IL_2 | Rubella_Int | -0.033 | | IL_2 | Rubella_Int | -0.029 |
| IL_2 | CMV_Int | 0.001 | | IL_2 | CMV_Int | 0.028 |
| IL_2 | HepB_cAb_Int | 0.078 | | IL_2 | HepB_cAb_Int | -0.070 |
| IL_2 | HepB_eAb_Int | 0.000 | | IL_2 | HepB_eAb_Int | 0.000 |
| IL_2 | HepB_eAg_Int | 0.000 | | IL_2 | HepB_eAg_Int | 0.000 |
| IL_2 | HepC_Int | -0.026 | | IL_2 | HepC_Int | -0.014 |
| IL_2 | Schistosoma_int | 0.059 | | IL_2 | Schistosoma_int | -0.042 |
| IL_2 | Strongyloides_Int | 0.188 | | IL_2 | Strongyloides_Int | -0.025 |
| IL_2 | Filaria_Int | 0.019 | | IL_2 | Filaria_Int | 0.048 |
| IL_4 | IL_1_alpha | 0.492 | | IL_4 | IL_1_alpha | 0.227 |
| IL_4 | IL_1_beta | 0.186 | | IL_4 | IL_1_beta | 0.524 |
| IL_4 | IL_2 | 0.253 | | IL_4 | IL_2 | 0.049 |
| IL_4 | IL_4 | 1.000 | | IL_4 | IL_4 | 1.000 |
| IL_4 | IL_5 | 0.211 | | IL_4 | IL_5 | 0.307 |
| IL_4 | IL_6 | -0.016 | | IL_4 | IL_6 | 0.419 |
| IL_4 | IL_8 | 0.157 | | IL_4 | IL_8 | 0.163 |
| IL_4 | IL_10 | 0.365 | | IL_4 | IL_10 | 0.381 |
| IL_4 | IL_12p70 | 0.308 | | IL_4 | IL_12p70 | 0.510 |
| IL_4 | IL_13 | 0.262 | | IL_4 | IL_13 | 0.449 |
| IL_4 | IL_15 | 0.358 | | IL_4 | IL_15 | 0.338 |
| IL_4 | IL_17 | 0.391 | | IL_4 | IL_17 | 0.406 |
| IL_4 | IL_23 | 0.047 | | IL_4 | IL_23 | -0.000 |
| IL_4 | IFN_gamma | 0.000 | | IL_4 | IFN_gamma | 0.000 |
| IL_4 | TNF_alpha | 0.404 | | IL_4 | TNF_alpha | 0.448 |
| IL_4 | TNF_beta | 0.427 | | IL_4 | TNF_beta | 0.439 |
| IL_4 | Varicella_Int | -0.042 | | IL_4 | Varicella_Int | -0.120 |
| IL_4 | Measles_OD_DB_Int | 0.086 | | IL_4 | Measles_OD_DB_Int | -0.017 |
| IL_4 | Measles_Int | 0.008 | | IL_4 | Measles_Int | -0.019 |
| IL_4 | HepA_Int | -0.001 | | IL_4 | HepA_Int | -0.165 |
| IL_4 | Tetanus_Int | 0.000 | | IL_4 | Tetanus_Int | 0.000 |
| IL_4 | Diptheria_Int | 0.000 | | IL_4 | Diptheria_Int | 0.000 |
| IL_4 | Rubella_Int | -0.078 | | IL_4 | Rubella_Int | 0.062 |
| IL_4 | CMV_Int | 0.032 | | IL_4 | CMV_Int | 0.072 |
| IL_4 | HepB_cAb_Int | -0.010 | | IL_4 | HepB_cAb_Int | -0.168 |
| IL_4 | HepB_eAb_Int | 0.000 | | IL_4 | HepB_eAb_Int | 0.000 |
| IL_4 | HepB_eAg_Int | 0.000 | | IL_4 | HepB_eAg_Int | 0.000 |
| IL_4 | HepC_Int | 0.039 | | IL_4 | HepC_Int | 0.092 |
| IL_4 | Schistosoma_int | 0.042 | | IL_4 | Schistosoma_int | -0.030 |

FIG. 21I3-C

| IL_4 | Strongyloides_Int | -0.002 |
|---|---|---|
| IL_4 | Filaria_Int | 0.064 |
| IL_5 | IL_1_alpha | 0.189 |
| IL_5 | IL_1_beta | 0.127 |
| IL_5 | IL_2 | 0.240 |
| IL_5 | IL_4 | 0.211 |
| IL_5 | IL_5 | 1.000 |
| IL_5 | IL_6 | 0.069 |
| IL_5 | IL_8 | 0.041 |
| IL_5 | IL_10 | 0.560 |
| IL_5 | IL_12p70 | 0.292 |
| IL_5 | IL_13 | 0.396 |
| IL_5 | IL_15 | 0.217 |
| IL_5 | IL_17 | 0.378 |
| IL_5 | IL_23 | 0.129 |
| IL_5 | IFN_gamma | 0.000 |
| IL_5 | TNF_alpha | 0.200 |
| IL_5 | TNF_beta | 0.166 |
| IL_5 | Varicella_Int | -0.086 |
| IL_5 | Measles_OD_DB_Int | -0.042 |
| IL_5 | Measles_Int | 0.065 |
| IL_5 | HepA_Int | 0.029 |
| IL_5 | Tetanus_Int | 0.000 |
| IL_5 | Diptheria_Int | 0.000 |
| IL_5 | Rubella_Int | 0.021 |
| IL_5 | CMV_Int | -0.134 |
| IL_5 | HepB_cAb_Int | 0.073 |
| IL_5 | HepB_eAb_Int | 0.000 |
| IL_5 | HepB_eAg_Int | 0.000 |
| IL_5 | HepC_Int | -0.051 |
| IL_5 | Schistosoma_int | -0.071 |
| IL_5 | Strongyloides_Int | -0.006 |
| IL_5 | Filaria_Int | 0.068 |
| IL_6 | IL_1_alpha | -0.071 |
| IL_6 | IL_1_beta | 0.067 |
| IL_6 | IL_2 | -0.102 |
| IL_6 | IL_4 | -0.016 |
| IL_6 | IL_5 | 0.069 |
| IL_6 | IL_6 | 1.000 |
| IL_6 | IL_8 | 0.294 |
| IL_6 | IL_10 | 0.083 |
| IL_6 | IL_12p70 | 0.021 |
| IL_6 | IL_13 | 0.335 |
| IL_6 | IL_15 | 0.329 |
| IL_6 | IL_17 | -0.069 |
| IL_6 | IL_23 | -0.036 |
| IL_6 | IFN_gamma | 0.000 |
| IL_6 | TNF_alpha | -0.066 |
| IL_6 | TNF_beta | -0.079 |
| IL_6 | Varicella_Int | 0.031 |
| IL_6 | Measles_OD_DB_Int | -0.054 |
| IL_6 | Measles_Int | -0.094 |
| IL_6 | HepA_Int | 0.044 |
| IL_6 | Tetanus_Int | 0.000 |
| IL_6 | Diptheria_Int | 0.000 |
| IL_6 | Rubella_Int | -0.025 |
| IL_6 | CMV_Int | 0.067 |

| IL_4 | Strongyloides_Int | -0.084 |
|---|---|---|
| IL_4 | Filaria_Int | -0.133 |
| IL_5 | IL_1_alpha | 0.190 |
| IL_5 | IL_1_beta | 0.290 |
| IL_5 | IL_2 | 0.080 |
| IL_5 | IL_4 | 0.307 |
| IL_5 | IL_5 | 1.000 |
| IL_5 | IL_6 | 0.489 |
| IL_5 | IL_8 | 0.180 |
| IL_5 | IL_10 | 0.357 |
| IL_5 | IL_12p70 | 0.444 |
| IL_5 | IL_13 | 0.273 |
| IL_5 | IL_15 | 0.273 |
| IL_5 | IL_17 | 0.291 |
| IL_5 | IL_23 | 0.145 |
| IL_5 | IFN_gamma | 0.000 |
| IL_5 | TNF_alpha | 0.328 |
| IL_5 | TNF_beta | 0.440 |
| IL_5 | Varicella_Int | 0.061 |
| IL_5 | Measles_OD_DB_Int | 0.061 |
| IL_5 | Measles_Int | -0.020 |
| IL_5 | HepA_Int | -0.160 |
| IL_5 | Tetanus_Int | 0.000 |
| IL_5 | Diptheria_Int | 0.000 |
| IL_5 | Rubella_Int | -0.062 |
| IL_5 | CMV_Int | 0.022 |
| IL_5 | HepB_cAb_Int | -0.029 |
| IL_5 | HepB_eAb_Int | 0.000 |
| IL_5 | HepB_eAg_Int | 0.000 |
| IL_5 | HepC_Int | 0.119 |
| IL_5 | Schistosoma_int | -0.022 |
| IL_5 | Strongyloides_Int | -0.015 |
| IL_5 | Filaria_Int | -0.087 |
| IL_6 | IL_1_alpha | 0.177 |
| IL_6 | IL_1_beta | 0.416 |
| IL_6 | IL_2 | 0.124 |
| IL_6 | IL_4 | 0.419 |
| IL_6 | IL_5 | 0.489 |
| IL_6 | IL_6 | 1.000 |
| IL_6 | IL_8 | 0.160 |
| IL_6 | IL_10 | 0.530 |
| IL_6 | IL_12p70 | 0.569 |
| IL_6 | IL_13 | 0.539 |
| IL_6 | IL_15 | 0.311 |
| IL_6 | IL_17 | 0.413 |
| IL_6 | IL_23 | 0.160 |
| IL_6 | IFN_gamma | 0.000 |
| IL_6 | TNF_alpha | 0.313 |
| IL_6 | TNF_beta | 0.431 |
| IL_6 | Varicella_Int | 0.016 |
| IL_6 | Measles_OD_DB_Int | 0.062 |
| IL_6 | Measles_Int | -0.046 |
| IL_6 | HepA_Int | -0.365 |
| IL_6 | Tetanus_Int | 0.000 |
| IL_6 | Diptheria_Int | 0.000 |
| IL_6 | Rubella_Int | -0.019 |
| IL_6 | CMV_Int | 0.032 |

FIG. 21I3-D

| | | | | | | |
|---|---|---|---|---|---|---|
| IL_6 | HepB_cAb_Int | -0.060 | | IL_6 | HepB_cAb_Int | -0.052 |
| IL_6 | HepB_eAb_Int | 0.000 | | IL_6 | HepB_eAb_Int | 0.000 |
| IL_6 | HepB_eAg_Int | 0.000 | | IL_6 | HepB_eAg_Int | 0.000 |
| IL_6 | HepC_Int | 0.040 | | IL_6 | HepC_Int | 0.077 |
| IL_6 | Schistosoma_int | -0.014 | | IL_6 | Schistosoma_int | -0.026 |
| IL_6 | Strongyloides_Int | -0.106 | | IL_6 | Strongyloides_Int | -0.006 |
| IL_6 | Filaria_Int | -0.079 | | IL_6 | Filaria_Int | 0.029 |
| IL_8 | IL_1_alpha | 0.191 | | IL_8 | IL_1_alpha | 0.138 |
| IL_8 | IL_1_beta | 0.088 | | IL_8 | IL_1_beta | 0.007 |
| IL_8 | IL_2 | 0.075 | | IL_8 | IL_2 | 0.008 |
| IL_8 | IL_4 | 0.157 | | IL_8 | IL_4 | 0.163 |
| IL_8 | IL_5 | 0.041 | | IL_8 | IL_5 | 0.180 |
| IL_8 | IL_6 | 0.294 | | IL_8 | IL_6 | 0.160 |
| IL_8 | IL_8 | 1.000 | | IL_8 | IL_8 | 1.000 |
| IL_8 | IL_10 | 0.108 | | IL_8 | IL_10 | -0.070 |
| IL_8 | IL_12p70 | 0.106 | | IL_8 | IL_12p70 | 0.093 |
| IL_8 | IL_13 | 0.119 | | IL_8 | IL_13 | 0.039 |
| IL_8 | IL_15 | 0.453 | | IL_8 | IL_15 | 0.391 |
| IL_8 | IL_17 | 0.092 | | IL_8 | IL_17 | 0.018 |
| IL_8 | IL_23 | -0.012 | | IL_8 | IL_23 | 0.006 |
| IL_8 | IFN_gamma | 0.000 | | IL_8 | IFN_gamma | 0.000 |
| IL_8 | TNF_alpha | 0.177 | | IL_8 | TNF_alpha | 0.081 |
| IL_8 | TNF_beta | 0.186 | | IL_8 | TNF_beta | 0.208 |
| IL_8 | Varicella_Int | -0.114 | | IL_8 | Varicella_Int | 0.079 |
| IL_8 | Measles_OD_DB_Int | 0.020 | | IL_8 | Measles_OD_DB_Int | -0.046 |
| IL_8 | Measles_Int | 0.023 | | IL_8 | Measles_Int | 0.097 |
| IL_8 | HepA_Int | -0.021 | | IL_8 | HepA_Int | 0.067 |
| IL_8 | Tetanus_Int | 0.000 | | IL_8 | Tetanus_Int | 0.000 |
| IL_8 | Diptheria_Int | 0.000 | | IL_8 | Diptheria_Int | 0.000 |
| IL_8 | Rubella_Int | -0.029 | | IL_8 | Rubella_Int | 0.008 |
| IL_8 | CMV_Int | -0.068 | | IL_8 | CMV_Int | -0.012 |
| IL_8 | HepB_cAb_Int | -0.080 | | IL_8 | HepB_cAb_Int | -0.089 |
| IL_8 | HepB_eAb_Int | 0.000 | | IL_8 | HepB_eAb_Int | 0.000 |
| IL_8 | HepB_eAg_Int | 0.000 | | IL_8 | HepB_eAg_Int | 0.000 |
| IL_8 | HepC_Int | 0.039 | | IL_8 | HepC_Int | 0.199 |
| IL_8 | Schistosoma_int | -0.011 | | IL_8 | Schistosoma_int | -0.103 |
| IL_8 | Strongyloides_Int | 0.009 | | IL_8 | Strongyloides_Int | -0.148 |
| IL_8 | Filaria_Int | -0.105 | | IL_8 | Filaria_Int | -0.055 |
| IL_10 | IL_1_alpha | 0.344 | | IL_10 | IL_1_alpha | 0.018 |
| IL_10 | IL_1_beta | 0.216 | | IL_10 | IL_1_beta | 0.605 |
| IL_10 | IL_2 | 0.375 | | IL_10 | IL_2 | 0.030 |
| IL_10 | IL_4 | 0.365 | | IL_10 | IL_4 | 0.381 |
| IL_10 | IL_5 | 0.560 | | IL_10 | IL_5 | 0.357 |
| IL_10 | IL_6 | 0.083 | | IL_10 | IL_6 | 0.530 |
| IL_10 | IL_8 | 0.108 | | IL_10 | IL_8 | -0.070 |
| IL_10 | IL_10 | 1.000 | | IL_10 | IL_10 | 1.000 |
| IL_10 | IL_12p70 | 0.408 | | IL_10 | IL_12p70 | 0.412 |
| IL_10 | IL_13 | 0.479 | | IL_10 | IL_13 | 0.588 |
| IL_10 | IL_15 | 0.337 | | IL_10 | IL_15 | 0.088 |
| IL_10 | IL_17 | 0.760 | | IL_10 | IL_17 | 0.610 |
| IL_10 | IL_23 | 0.108 | | IL_10 | IL_23 | 0.086 |
| IL_10 | IFN_gamma | 0.000 | | IL_10 | IFN_gamma | 0.000 |
| IL_10 | TNF_alpha | 0.330 | | IL_10 | TNF_alpha | 0.295 |
| IL_10 | TNF_beta | 0.342 | | IL_10 | TNF_beta | 0.403 |
| IL_10 | Varicella_Int | 0.057 | | IL_10 | Varicella_Int | 0.005 |
| IL_10 | Measles_OD_DB_Int | 0.161 | | IL_10 | Measles_OD_DB_Int | 0.081 |
| IL_10 | Measles_Int | 0.108 | | IL_10 | Measles_Int | -0.122 |

FIG. 21I3-E

| | | | | | | |
|---|---|---|---|---|---|---|
| IL_10 | HepA_Int | 0.108 | | IL_10 | HepA_Int | -0.405 |
| IL_10 | Tetanus_Int | 0.000 | | IL_10 | Tetanus_Int | 0.000 |
| IL_10 | Diptheria_Int | 0.000 | | IL_10 | Diptheria_Int | 0.000 |
| IL_10 | Rubella_Int | 0.008 | | IL_10 | Rubella_Int | -0.000 |
| IL_10 | CMV_Int | 0.001 | | IL_10 | CMV_Int | 0.081 |
| IL_10 | HepB_cAb_Int | -0.002 | | IL_10 | HepB_cAb_Int | -0.125 |
| IL_10 | HepB_eAb_Int | 0.000 | | IL_10 | HepB_eAb_Int | 0.000 |
| IL_10 | HepB_eAg_Int | 0.000 | | IL_10 | HepB_eAg_Int | 0.000 |
| IL_10 | HepC_Int | -0.037 | | IL_10 | HepC_Int | -0.023 |
| IL_10 | Schistosoma_int | 0.113 | | IL_10 | Schistosoma_int | 0.128 |
| IL_10 | Strongyloides_Int | 0.036 | | IL_10 | Strongyloides_Int | -0.080 |
| IL_10 | Filaria_Int | 0.169 | | IL_10 | Filaria_Int | -0.017 |
| IL_12p70 | IL_1_alpha | 0.290 | | IL_12p70 | IL_1_alpha | 0.184 |
| IL_12p70 | IL_1_beta | 0.112 | | IL_12p70 | IL_1_beta | 0.495 |
| IL_12p70 | IL_2 | 0.263 | | IL_12p70 | IL_2 | 0.375 |
| IL_12p70 | IL_4 | 0.308 | | IL_12p70 | IL_4 | 0.510 |
| IL_12p70 | IL_5 | 0.292 | | IL_12p70 | IL_5 | 0.444 |
| IL_12p70 | IL_6 | 0.021 | | IL_12p70 | IL_6 | 0.569 |
| IL_12p70 | IL_8 | 0.106 | | IL_12p70 | IL_8 | 0.093 |
| IL_12p70 | IL_10 | 0.408 | | IL_12p70 | IL_10 | 0.412 |
| IL_12p70 | IL_12p70 | 1.000 | | IL_12p70 | IL_12p70 | 1.000 |
| IL_12p70 | IL_13 | 0.348 | | IL_12p70 | IL_13 | 0.443 |
| IL_12p70 | IL_15 | 0.304 | | IL_12p70 | IL_15 | 0.395 |
| IL_12p70 | IL_17 | 0.485 | | IL_12p70 | IL_17 | 0.367 |
| IL_12p70 | IL_23 | 0.293 | | IL_12p70 | IL_23 | 0.473 |
| IL_12p70 | IFN_gamma | 0.000 | | IL_12p70 | IFN_gamma | 0.000 |
| IL_12p70 | TNF_alpha | 0.269 | | IL_12p70 | TNF_alpha | 0.347 |
| IL_12p70 | TNF_beta | 0.215 | | IL_12p70 | TNF_beta | 0.413 |
| IL_12p70 | Varicella_Int | -0.002 | | IL_12p70 | Varicella_Int | -0.011 |
| IL_12p70 | Measles_OD_DB_Int | 0.061 | | IL_12p70 | Measles_OD_DB_Int | 0.036 |
| IL_12p70 | Measles_Int | 0.125 | | IL_12p70 | Measles_Int | -0.073 |
| IL_12p70 | HepA_Int | 0.055 | | IL_12p70 | HepA_Int | -0.244 |
| IL_12p70 | Tetanus_Int | 0.000 | | IL_12p70 | Tetanus_Int | 0.000 |
| IL_12p70 | Diptheria_Int | 0.000 | | IL_12p70 | Diptheria_Int | 0.000 |
| IL_12p70 | Rubella_Int | -0.019 | | IL_12p70 | Rubella_Int | -0.039 |
| IL_12p70 | CMV_Int | 0.093 | | IL_12p70 | CMV_Int | -0.026 |
| IL_12p70 | HepB_cAb_Int | -0.017 | | IL_12p70 | HepB_cAb_Int | -0.108 |
| IL_12p70 | HepB_eAb_Int | 0.000 | | IL_12p70 | HepB_eAb_Int | 0.000 |
| IL_12p70 | HepB_eAg_Int | 0.000 | | IL_12p70 | HepB_eAg_Int | 0.000 |
| IL_12p70 | HepC_Int | 0.028 | | IL_12p70 | HepC_Int | 0.079 |
| IL_12p70 | Schistosoma_int | -0.006 | | IL_12p70 | Schistosoma_int | -0.011 |
| IL_12p70 | Strongyloides_Int | -0.036 | | IL_12p70 | Strongyloides_Int | -0.052 |
| IL_12p70 | Filaria_Int | 0.013 | | IL_12p70 | Filaria_Int | -0.052 |
| IL_13 | IL_1_alpha | 0.191 | | IL_13 | IL_1_alpha | 0.064 |
| IL_13 | IL_1_beta | 0.201 | | IL_13 | IL_1_beta | 0.571 |
| IL_13 | IL_2 | 0.333 | | IL_13 | IL_2 | 0.017 |
| IL_13 | IL_4 | 0.262 | | IL_13 | IL_4 | 0.449 |
| IL_13 | IL_5 | 0.396 | | IL_13 | IL_5 | 0.273 |
| IL_13 | IL_6 | 0.335 | | IL_13 | IL_6 | 0.539 |
| IL_13 | IL_8 | 0.119 | | IL_13 | IL_8 | 0.039 |
| IL_13 | IL_10 | 0.479 | | IL_13 | IL_10 | 0.588 |
| IL_13 | IL_12p70 | 0.348 | | IL_13 | IL_12p70 | 0.443 |
| IL_13 | IL_13 | 1.000 | | IL_13 | IL_13 | 1.000 |
| IL_13 | IL_15 | 0.369 | | IL_13 | IL_15 | 0.120 |
| IL_13 | IL_17 | 0.409 | | IL_13 | IL_17 | 0.499 |
| IL_13 | IL_23 | 0.077 | | IL_13 | IL_23 | 0.017 |
| IL_13 | IFN_gamma | 0.000 | | IL_13 | IFN_gamma | 0.000 |

FIG. 21I3-F

| IL_13 | TNF_alpha | 0.207 | IL_13 | TNF_alpha | 0.350 |
|---|---|---|---|---|---|
| IL_13 | TNF_beta | 0.207 | IL_13 | TNF_beta | 0.385 |
| IL_13 | Varicella_Int | 0.029 | IL_13 | Varicella_Int | 0.042 |
| IL_13 | Measles_OD_DB_Int | 0.001 | IL_13 | Measles_OD_DB_Int | 0.094 |
| IL_13 | Measles_Int | 0.107 | IL_13 | Measles_Int | -0.186 |
| IL_13 | HepA_Int | 0.051 | IL_13 | HepA_Int | -0.332 |
| IL_13 | Tetanus_Int | 0.000 | IL_13 | Tetanus_Int | 0.000 |
| IL_13 | Diptheria_Int | 0.000 | IL_13 | Diptheria_Int | 0.000 |
| IL_13 | Rubella_Int | -0.028 | IL_13 | Rubella_Int | -0.052 |
| IL_13 | CMV_Int | -0.039 | IL_13 | CMV_Int | 0.058 |
| IL_13 | HepB_cAb_Int | -0.015 | IL_13 | HepB_cAb_Int | -0.061 |
| IL_13 | HepB_eAb_Int | 0.000 | IL_13 | HepB_eAb_Int | 0.000 |
| IL_13 | HepB_eAg_Int | 0.000 | IL_13 | HepB_eAg_Int | 0.000 |
| IL_13 | HepC_Int | -0.025 | IL_13 | HepC_Int | -0.023 |
| IL_13 | Schistosoma_int | -0.010 | IL_13 | Schistosoma_int | -0.063 |
| IL_13 | Strongyloides_Int | -0.114 | IL_13 | Strongyloides_Int | -0.152 |
| IL_13 | Filaria_Int | -0.061 | IL_13 | Filaria_Int | -0.030 |
| IL_15 | IL_1_alpha | 0.253 | IL_15 | IL_1_alpha | 0.509 |
| IL_15 | IL_1_beta | 0.198 | IL_15 | IL_1_beta | 0.207 |
| IL_15 | IL_2 | 0.073 | IL_15 | IL_2 | 0.082 |
| IL_15 | IL_4 | 0.358 | IL_15 | IL_4 | 0.338 |
| IL_15 | IL_5 | 0.217 | IL_15 | IL_5 | 0.273 |
| IL_15 | IL_6 | 0.329 | IL_15 | IL_6 | 0.311 |
| IL_15 | IL_8 | 0.453 | IL_15 | IL_8 | 0.391 |
| IL_15 | IL_10 | 0.337 | IL_15 | IL_10 | 0.088 |
| IL_15 | IL_12p70 | 0.304 | IL_15 | IL_12p70 | 0.395 |
| IL_15 | IL_13 | 0.369 | IL_15 | IL_13 | 0.120 |
| IL_15 | IL_15 | 1.000 | IL_15 | IL_15 | 1.000 |
| IL_15 | IL_17 | 0.319 | IL_15 | IL_17 | 0.118 |
| IL_15 | IL_23 | 0.039 | IL_15 | IL_23 | 0.019 |
| IL_15 | IFN_gamma | 0.000 | IL_15 | IFN_gamma | 0.000 |
| IL_15 | TNF_alpha | 0.366 | IL_15 | TNF_alpha | 0.149 |
| IL_15 | TNF_beta | 0.266 | IL_15 | TNF_beta | 0.221 |
| IL_15 | Varicella_Int | -0.095 | IL_15 | Varicella_Int | 0.023 |
| IL_15 | Measles_OD_DB_Int | 0.020 | IL_15 | Measles_OD_DB_Int | -0.064 |
| IL_15 | Measles_Int | -0.020 | IL_15 | Measles_Int | -0.011 |
| IL_15 | HepA_Int | -0.101 | IL_15 | HepA_Int | -0.042 |
| IL_15 | Tetanus_Int | 0.000 | IL_15 | Tetanus_Int | 0.000 |
| IL_15 | Diptheria_Int | 0.000 | IL_15 | Diptheria_Int | 0.000 |
| IL_15 | Rubella_Int | 0.119 | IL_15 | Rubella_Int | -0.010 |
| IL_15 | CMV_Int | 0.092 | IL_15 | CMV_Int | -0.036 |
| IL_15 | HepB_cAb_Int | 0.012 | IL_15 | HepB_cAb_Int | -0.025 |
| IL_15 | HepB_eAb_Int | 0.000 | IL_15 | HepB_eAb_Int | 0.000 |
| IL_15 | HepB_eAg_Int | 0.000 | IL_15 | HepB_eAg_Int | 0.000 |
| IL_15 | HepC_Int | 0.176 | IL_15 | HepC_Int | 0.161 |
| IL_15 | Schistosoma_int | 0.001 | IL_15 | Schistosoma_int | 0.127 |
| IL_15 | Strongyloides_Int | -0.104 | IL_15 | Strongyloides_Int | -0.178 |
| IL_15 | Filaria_Int | -0.091 | IL_15 | Filaria_Int | -0.003 |
| IL_17 | IL_1_alpha | 0.451 | IL_17 | IL_1_alpha | 0.067 |
| IL_17 | IL_1_beta | 0.222 | IL_17 | IL_1_beta | 0.689 |
| IL_17 | IL_2 | 0.509 | IL_17 | IL_2 | 0.146 |
| IL_17 | IL_4 | 0.391 | IL_17 | IL_4 | 0.406 |
| IL_17 | IL_5 | 0.378 | IL_17 | IL_5 | 0.291 |
| IL_17 | IL_6 | -0.069 | IL_17 | IL_6 | 0.413 |
| IL_17 | IL_8 | 0.092 | IL_17 | IL_8 | 0.018 |
| IL_17 | IL_10 | 0.760 | IL_17 | IL_10 | 0.610 |
| IL_17 | IL_12p70 | 0.485 | IL_17 | IL_12p70 | 0.367 |

FIG. 21I3-G

| | | | | | | |
|---|---|---|---|---|---|---|
| IL_17 | IL_13 | 0.409 | | IL_17 | IL_13 | 0.499 |
| IL_17 | IL_15 | 0.319 | | IL_17 | IL_15 | 0.118 |
| IL_17 | IL_17 | 1.000 | | IL_17 | IL_17 | 1.000 |
| IL_17 | IL_23 | 0.158 | | IL_17 | IL_23 | -0.003 |
| IL_17 | IFN_gamma | 0.000 | | IL_17 | IFN_gamma | 0.000 |
| IL_17 | TNF_alpha | 0.399 | | IL_17 | TNF_alpha | 0.458 |
| IL_17 | TNF_beta | 0.521 | | IL_17 | TNF_beta | 0.575 |
| IL_17 | Varicella_Int | 0.094 | | IL_17 | Varicella_Int | 0.006 |
| IL_17 | Measles_OD_DB_Int | 0.139 | | IL_17 | Measles_OD_DB_Int | 0.077 |
| IL_17 | Measles_Int | 0.152 | | IL_17 | Measles_Int | -0.038 |
| IL_17 | HepA_Int | 0.100 | | IL_17 | HepA_Int | -0.135 |
| IL_17 | Tetanus_Int | 0.000 | | IL_17 | Tetanus_Int | 0.000 |
| IL_17 | Diptheria_Int | 0.000 | | IL_17 | Diptheria_Int | 0.000 |
| IL_17 | Rubella_Int | 0.001 | | IL_17 | Rubella_Int | -0.031 |
| IL_17 | CMV_Int | 0.116 | | IL_17 | CMV_Int | 0.096 |
| IL_17 | HepB_cAb_Int | -0.012 | | IL_17 | HepB_cAb_Int | -0.176 |
| IL_17 | HepB_eAb_Int | 0.000 | | IL_17 | HepB_eAb_Int | 0.000 |
| IL_17 | HepB_eAg_Int | 0.000 | | IL_17 | HepB_eAg_Int | 0.000 |
| IL_17 | HepC_Int | -0.037 | | IL_17 | HepC_Int | -0.043 |
| IL_17 | Schistosoma_int | 0.156 | | IL_17 | Schistosoma_int | -0.021 |
| IL_17 | Strongyloides_Int | 0.078 | | IL_17 | Strongyloides_Int | -0.041 |
| IL_17 | Filaria_Int | 0.152 | | IL_17 | Filaria_Int | -0.106 |
| IL_23 | IL_1_alpha | 0.025 | | IL_23 | IL_1_alpha | -0.036 |
| IL_23 | IL_1_beta | -0.010 | | IL_23 | IL_1_beta | 0.031 |
| IL_23 | IL_2 | 0.112 | | IL_23 | IL_2 | 0.255 |
| IL_23 | IL_4 | 0.047 | | IL_23 | IL_4 | -0.000 |
| IL_23 | IL_5 | 0.129 | | IL_23 | IL_5 | 0.145 |
| IL_23 | IL_6 | -0.036 | | IL_23 | IL_6 | 0.160 |
| IL_23 | IL_8 | -0.012 | | IL_23 | IL_8 | 0.006 |
| IL_23 | IL_10 | 0.108 | | IL_23 | IL_10 | 0.086 |
| IL_23 | IL_12p70 | 0.293 | | IL_23 | IL_12p70 | 0.473 |
| IL_23 | IL_13 | 0.077 | | IL_23 | IL_13 | 0.017 |
| IL_23 | IL_15 | 0.039 | | IL_23 | IL_15 | 0.019 |
| IL_23 | IL_17 | 0.158 | | IL_23 | IL_17 | -0.003 |
| IL_23 | IL_23 | 1.000 | | IL_23 | IL_23 | 1.000 |
| IL_23 | IFN_gamma | 0.000 | | IL_23 | IFN_gamma | 0.000 |
| IL_23 | TNF_alpha | 0.057 | | IL_23 | TNF_alpha | 0.039 |
| IL_23 | TNF_beta | 0.089 | | IL_23 | TNF_beta | -0.011 |
| IL_23 | Varicella_Int | -0.036 | | IL_23 | Varicella_Int | -0.039 |
| IL_23 | Measles_OD_DB_Int | -0.026 | | IL_23 | Measles_OD_DB_Int | -0.087 |
| IL_23 | Measles_Int | 0.083 | | IL_23 | Measles_Int | 0.027 |
| IL_23 | HepA_Int | -0.034 | | IL_23 | HepA_Int | -0.054 |
| IL_23 | Tetanus_Int | 0.000 | | IL_23 | Tetanus_Int | 0.000 |
| IL_23 | Diptheria_Int | 0.000 | | IL_23 | Diptheria_Int | 0.000 |
| IL_23 | Rubella_Int | -0.034 | | IL_23 | Rubella_Int | -0.046 |
| IL_23 | CMV_Int | 0.063 | | IL_23 | CMV_Int | 0.014 |
| IL_23 | HepB_cAb_Int | 0.034 | | IL_23 | HepB_cAb_Int | 0.079 |
| IL_23 | HepB_eAb_Int | 0.000 | | IL_23 | HepB_eAb_Int | 0.000 |
| IL_23 | HepB_eAg_Int | 0.000 | | IL_23 | HepB_eAg_Int | 0.000 |
| IL_23 | HepC_Int | 0.034 | | IL_23 | HepC_Int | 0.049 |
| IL_23 | Schistosoma_int | 0.012 | | IL_23 | Schistosoma_int | 0.026 |
| IL_23 | Strongyloides_Int | 0.087 | | IL_23 | Strongyloides_Int | -0.026 |
| IL_23 | Filaria_Int | -0.040 | | IL_23 | Filaria_Int | 0.099 |
| IFN_gamma | IL_1_alpha | 0.000 | | IFN_gamma | IL_1_alpha | 0.000 |
| IFN_gamma | IL_1_beta | 0.000 | | IFN_gamma | IL_1_beta | 0.000 |
| IFN_gamma | IL_2 | 0.000 | | IFN_gamma | IL_2 | 0.000 |
| IFN_gamma | IL_4 | 0.000 | | IFN_gamma | IL_4 | 0.000 |

FIG. 21I3-H

| | | | | | | |
|---|---|---|---|---|---|---|
| IFN_gamma | IL_5 | 0.000 | | IFN_gamma | IL_5 | 0.000 |
| IFN_gamma | IL_6 | 0.000 | | IFN_gamma | IL_6 | 0.000 |
| IFN_gamma | IL_8 | 0.000 | | IFN_gamma | IL_8 | 0.000 |
| IFN_gamma | IL_10 | 0.000 | | IFN_gamma | IL_10 | 0.000 |
| IFN_gamma | IL_12p70 | 0.000 | | IFN_gamma | IL_12p70 | 0.000 |
| IFN_gamma | IL_13 | 0.000 | | IFN_gamma | IL_13 | 0.000 |
| IFN_gamma | IL_15 | 0.000 | | IFN_gamma | IL_15 | 0.000 |
| IFN_gamma | IL_17 | 0.000 | | IFN_gamma | IL_17 | 0.000 |
| IFN_gamma | IL_23 | 0.000 | | IFN_gamma | IL_23 | 0.000 |
| IFN_gamma | IFN_gamma | 1.000 | | IFN_gamma | IFN_gamma | 1.000 |
| IFN_gamma | TNF_alpha | 0.000 | | IFN_gamma | TNF_alpha | 0.000 |
| IFN_gamma | TNF_beta | 0.000 | | IFN_gamma | TNF_beta | 0.000 |
| IFN_gamma | Varicella_Int | 0.000 | | IFN_gamma | Varicella_Int | 0.000 |
| IFN_gamma | Measles_OD_DB_Int | 0.000 | | IFN_gamma | Measles_OD_DB_Int | 0.000 |
| IFN_gamma | Measles_Int | 0.000 | | IFN_gamma | Measles_Int | 0.000 |
| IFN_gamma | HepA_Int | 0.000 | | IFN_gamma | HepA_Int | 0.000 |
| IFN_gamma | Tetanus_Int | 0.000 | | IFN_gamma | Tetanus_Int | 0.000 |
| IFN_gamma | Diptheria_Int | 0.000 | | IFN_gamma | Diptheria_Int | 0.000 |
| IFN_gamma | Rubella_Int | 0.000 | | IFN_gamma | Rubella_Int | 0.000 |
| IFN_gamma | CMV_Int | 0.000 | | IFN_gamma | CMV_Int | 0.000 |
| IFN_gamma | HepB_cAb_Int | 0.000 | | IFN_gamma | HepB_cAb_Int | 0.000 |
| IFN_gamma | HepB_eAb_Int | 0.000 | | IFN_gamma | HepB_eAb_Int | 0.000 |
| IFN_gamma | HepB_eAg_Int | 0.000 | | IFN_gamma | HepB_eAg_Int | 0.000 |
| IFN_gamma | HepC_Int | 0.000 | | IFN_gamma | HepC_Int | 0.000 |
| IFN_gamma | Schistosoma_int | 0.000 | | IFN_gamma | Schistosoma_int | 0.000 |
| IFN_gamma | Strongyloides_Int | 0.000 | | IFN_gamma | Strongyloides_Int | 0.000 |
| IFN_gamma | Filaria_Int | 0.000 | | IFN_gamma | Filaria_Int | 0.000 |
| TNF_alpha | IL_1_alpha | 0.371 | | TNF_alpha | IL_1_alpha | 0.098 |
| TNF_alpha | IL_1_beta | 0.234 | | TNF_alpha | IL_1_beta | 0.618 |
| TNF_alpha | IL_2 | 0.255 | | TNF_alpha | IL_2 | 0.055 |
| TNF_alpha | IL_4 | 0.404 | | TNF_alpha | IL_4 | 0.448 |
| TNF_alpha | IL_5 | 0.200 | | TNF_alpha | IL_5 | 0.328 |
| TNF_alpha | IL_6 | -0.066 | | TNF_alpha | IL_6 | 0.313 |
| TNF_alpha | IL_8 | 0.177 | | TNF_alpha | IL_8 | 0.081 |
| TNF_alpha | IL_10 | 0.330 | | TNF_alpha | IL_10 | 0.295 |
| TNF_alpha | IL_12p70 | 0.269 | | TNF_alpha | IL_12p70 | 0.347 |
| TNF_alpha | IL_13 | 0.207 | | TNF_alpha | IL_13 | 0.350 |
| TNF_alpha | IL_15 | 0.366 | | TNF_alpha | IL_15 | 0.149 |
| TNF_alpha | IL_17 | 0.399 | | TNF_alpha | IL_17 | 0.458 |
| TNF_alpha | IL_23 | 0.057 | | TNF_alpha | IL_23 | 0.039 |
| TNF_alpha | IFN_gamma | 0.000 | | TNF_alpha | IFN_gamma | 0.000 |
| TNF_alpha | TNF_alpha | 1.000 | | TNF_alpha | TNF_alpha | 1.000 |
| TNF_alpha | TNF_beta | 0.525 | | TNF_alpha | TNF_beta | 0.498 |
| TNF_alpha | Varicella_Int | 0.006 | | TNF_alpha | Varicella_Int | -0.094 |
| TNF_alpha | Measles_OD_DB_Int | 0.109 | | TNF_alpha | Measles_OD_DB_Int | 0.149 |
| TNF_alpha | Measles_Int | 0.130 | | TNF_alpha | Measles_Int | -0.050 |
| TNF_alpha | HepA_Int | -0.068 | | TNF_alpha | HepA_Int | -0.104 |
| TNF_alpha | Tetanus_Int | 0.000 | | TNF_alpha | Tetanus_Int | 0.000 |
| TNF_alpha | Diptheria_Int | 0.000 | | TNF_alpha | Diptheria_Int | 0.000 |
| TNF_alpha | Rubella_Int | -0.040 | | TNF_alpha | Rubella_Int | 0.035 |
| TNF_alpha | CMV_Int | 0.096 | | TNF_alpha | CMV_Int | 0.073 |
| TNF_alpha | HepB_cAb_Int | -0.013 | | TNF_alpha | HepB_cAb_Int | -0.086 |
| TNF_alpha | HepB_eAb_Int | 0.000 | | TNF_alpha | HepB_eAb_Int | 0.000 |
| TNF_alpha | HepB_eAg_Int | 0.000 | | TNF_alpha | HepB_eAg_Int | 0.000 |
| TNF_alpha | HepC_Int | 0.176 | | TNF_alpha | HepC_Int | 0.025 |
| TNF_alpha | Schistosoma_int | 0.093 | | TNF_alpha | Schistosoma_int | 0.096 |
| TNF_alpha | Strongyloides_Int | 0.094 | | TNF_alpha | Strongyloides_Int | 0.033 |

FIG. 21I3-I

| | | | | | | |
|---|---|---|---|---|---|---|
| TNF_alpha | Filaria_Int | 0.127 | | TNF_alpha | Filaria_Int | -0.144 |
| TNF_beta | IL_1_alpha | 0.511 | | TNF_beta | IL_1_alpha | 0.099 |
| TNF_beta | IL_1_beta | 0.246 | | TNF_beta | IL_1_beta | 0.534 |
| TNF_beta | IL_2 | 0.328 | | TNF_beta | IL_2 | 0.192 |
| TNF_beta | IL_4 | 0.427 | | TNF_beta | IL_4 | 0.439 |
| TNF_beta | IL_5 | 0.166 | | TNF_beta | IL_5 | 0.440 |
| TNF_beta | IL_6 | -0.079 | | TNF_beta | IL_6 | 0.431 |
| TNF_beta | IL_8 | 0.186 | | TNF_beta | IL_8 | 0.208 |
| TNF_beta | IL_10 | 0.342 | | TNF_beta | IL_10 | 0.403 |
| TNF_beta | IL_12p70 | 0.215 | | TNF_beta | IL_12p70 | 0.413 |
| TNF_beta | IL_13 | 0.207 | | TNF_beta | IL_13 | 0.385 |
| TNF_beta | IL_15 | 0.266 | | TNF_beta | IL_15 | 0.221 |
| TNF_beta | IL_17 | 0.521 | | TNF_beta | IL_17 | 0.575 |
| TNF_beta | IL_23 | 0.089 | | TNF_beta | IL_23 | -0.011 |
| TNF_beta | IFN_gamma | 0.000 | | TNF_beta | IFN_gamma | 0.000 |
| TNF_beta | TNF_alpha | 0.525 | | TNF_beta | TNF_alpha | 0.498 |
| TNF_beta | TNF_beta | 1.000 | | TNF_beta | TNF_beta | 1.000 |
| TNF_beta | Varicella_Int | 0.030 | | TNF_beta | Varicella_Int | 0.047 |
| TNF_beta | Measles_OD_DB_Int | 0.089 | | TNF_beta | Measles_OD_DB_Int | -0.000 |
| TNF_beta | Measles_Int | 0.112 | | TNF_beta | Measles_Int | -0.079 |
| TNF_beta | HepA_Int | -0.034 | | TNF_beta | HepA_Int | -0.059 |
| TNF_beta | Tetanus_Int | 0.000 | | TNF_beta | Tetanus_Int | 0.000 |
| TNF_beta | Diptheria_Int | 0.000 | | TNF_beta | Diptheria_Int | 0.000 |
| TNF_beta | Rubella_Int | -0.142 | | TNF_beta | Rubella_Int | -0.037 |
| TNF_beta | CMV_Int | 0.106 | | TNF_beta | CMV_Int | 0.036 |
| TNF_beta | HepB_cAb_Int | -0.043 | | TNF_beta | HepB_cAb_Int | -0.144 |
| TNF_beta | HepB_eAb_Int | 0.000 | | TNF_beta | HepB_eAb_Int | 0.000 |
| TNF_beta | HepB_eAg_Int | 0.000 | | TNF_beta | HepB_eAg_Int | 0.000 |
| TNF_beta | HepC_Int | -0.028 | | TNF_beta | HepC_int | 0.038 |
| TNF_beta | Schistosoma_int | 0.114 | | TNF_beta | Schistosoma_int | -0.058 |
| TNF_beta | Strongyloides_Int | 0.065 | | TNF_beta | Strongyloides_Int | -0.085 |
| TNF_beta | Filaria_Int | 0.113 | | TNF_beta | Filaria_Int | -0.089 |
| Varicella_Int | IL_1_alpha | -0.056 | | Varicella_Int | IL_1_alpha | 0.034 |
| Varicella_Int | IL_1_beta | 0.019 | | Varicella_Int | IL_1_beta | 0.031 |
| Varicella_Int | IL_2 | 0.033 | | Varicella_Int | IL_2 | 0.027 |
| Varicella_Int | IL_4 | -0.042 | | Varicella_Int | IL_4 | -0.120 |
| Varicella_Int | IL_5 | -0.086 | | Varicella_Int | IL_5 | 0.061 |
| Varicella_Int | IL_6 | 0.031 | | Varicella_Int | IL_6 | 0.016 |
| Varicella_Int | IL_8 | -0.114 | | Varicella_Int | IL_8 | 0.079 |
| Varicella_Int | IL_10 | 0.057 | | Varicella_Int | IL_10 | 0.005 |
| Varicella_Int | IL_12p70 | -0.002 | | Varicella_Int | IL_12p70 | -0.011 |
| Varicella_Int | IL_13 | 0.029 | | Varicella_Int | IL_13 | 0.042 |
| Varicella_Int | IL_15 | -0.095 | | Varicella_Int | IL_15 | 0.023 |
| Varicella_Int | IL_17 | 0.094 | | Varicella_Int | IL_17 | 0.006 |
| Varicella_Int | IL_23 | -0.036 | | Varicella_Int | IL_23 | -0.039 |
| Varicella_Int | IFN_gamma | 0.000 | | Varicella_Int | IFN_gamma | 0.000 |
| Varicella_Int | TNF_alpha | 0.006 | | Varicella_Int | TNF_alpha | -0.094 |
| Varicella_Int | TNF_beta | 0.030 | | Varicella_Int | TNF_beta | 0.047 |
| Varicella_Int | Varicella_Int | 1.000 | | Varicella_Int | Varicella_Int | 1.000 |
| Varicella_Int | Measles_OD_DB_Int | 0.082 | | Varicella_Int | Measles_OD_DB_Int | -0.077 |
| Varicella_Int | Measles_Int | -0.079 | | Varicella_Int | Measles_Int | -0.025 |
| Varicella_Int | HepA_Int | 0.312 | | Varicella_Int | HepA_Int | -0.036 |
| Varicella_Int | Tetanus_Int | 0.000 | | Varicella_Int | Tetanus_Int | 0.000 |
| Varicella_Int | Diptheria_Int | 0.000 | | Varicella_Int | Diptheria_Int | 0.000 |
| Varicella_Int | Rubella_Int | -0.033 | | Varicella_Int | Rubella_Int | -0.005 |
| Varicella_Int | CMV_Int | -0.028 | | Varicella_Int | CMV_Int | -0.044 |
| Varicella_Int | HepB_cAb_Int | 0.065 | | Varicella_Int | HepB_cAb_Int | 0.058 |

FIG. 2113-J

| Varicella_Int | HepB_eAb_Int | 0.000 | Varicella_Int | HepB_eAb_Int | 0.000 |
|---|---|---|---|---|---|
| Varicella_Int | HepB_eAg_Int | 0.000 | Varicella_Int | HepB_eAg_Int | 0.000 |
| Varicella_Int | HepC_Int | 0.027 | Varicella_Int | HepC_Int | 0.068 |
| Varicella_Int | Schistosoma_int | -0.013 | Varicella_Int | Schistosoma_int | -0.042 |
| Varicella_Int | Strongyloides_Int | 0.008 | Varicella_Int | Strongyloides_Int | -0.083 |
| Varicella_Int | Filaria_Int | 0.015 | Varicella_Int | Filaria_Int | 0.063 |
| Measles_OD_DB_Int | IL_1_alpha | 0.024 | Measles_OD_DB_Int | IL_1_alpha | -0.052 |
| Measles_OD_DB_Int | IL_1_beta | 0.090 | Measles_OD_DB_Int | IL_1_beta | 0.072 |
| Measles_OD_DB_Int | IL_2 | 0.028 | Measles_OD_DB_Int | IL_2 | 0.023 |
| Measles_OD_DB_Int | IL_4 | 0.086 | Measles_OD_DB_Int | IL_4 | -0.017 |
| Measles_OD_DB_Int | IL_5 | -0.042 | Measles_OD_DB_Int | IL_5 | 0.061 |
| Measles_OD_DB_Int | IL_6 | -0.054 | Measles_OD_DB_Int | IL_6 | 0.062 |
| Measles_OD_DB_Int | IL_8 | 0.020 | Measles_OD_DB_Int | IL_8 | -0.046 |
| Measles_OD_DB_Int | IL_10 | 0.161 | Measles_OD_DB_Int | IL_10 | 0.081 |
| Measles_OD_DB_Int | IL_12p70 | 0.061 | Measles_OD_DB_Int | IL_12p70 | 0.036 |
| Measles_OD_DB_Int | IL_13 | 0.001 | Measles_OD_DB_Int | IL_13 | 0.094 |
| Measles_OD_DB_Int | IL_15 | 0.020 | Measles_OD_DB_Int | IL_15 | -0.064 |
| Measles_OD_DB_Int | IL_17 | 0.139 | Measles_OD_DB_Int | IL_17 | 0.077 |
| Measles_OD_DB_Int | IL_23 | -0.026 | Measles_OD_DB_Int | IL_23 | -0.087 |
| Measles_OD_DB_Int | IFN_gamma | 0.000 | Measles_OD_DB_Int | IFN_gamma | 0.000 |
| Measles_OD_DB_Int | TNF_alpha | 0.109 | Measles_OD_DB_Int | TNF_alpha | 0.149 |
| Measles_OD_DB_Int | TNF_beta | 0.089 | Measles_OD_DB_Int | TNF_beta | -0.000 |
| Measles_OD_DB_Int | Varicella_Int | 0.082 | Measles_OD_DB_Int | Varicella_Int | -0.077 |
| Measles_OD_DB_Int | Measles_OD_DB_Int | 1.000 | Measles_OD_DB_Int | Measles_OD_DB_Int | 1.000 |
| Measles_OD_DB_Int | Measles_Int | 0.089 | Measles_OD_DB_Int | Measles_Int | -0.053 |
| Measles_OD_DB_Int | HepA_Int | 0.056 | Measles_OD_DB_Int | HepA_Int | -0.076 |
| Measles_OD_DB_Int | Tetanus_Int | 0.000 | Measles_OD_DB_Int | Tetanus_Int | 0.000 |
| Measles_OD_DB_Int | Diptheria_Int | 0.000 | Measles_OD_DB_Int | Diptheria_Int | 0.000 |
| Measles_OD_DB_Int | Rubella_Int | -0.047 | Measles_OD_DB_Int | Rubella_Int | -0.019 |
| Measles_OD_DB_Int | CMV_Int | 0.018 | Measles_OD_DB_Int | CMV_Int | 0.095 |
| Measles_OD_DB_Int | HepB_cAb_Int | 0.009 | Measles_OD_DB_Int | HepB_cAb_Int | -0.082 |
| Measles_OD_DB_Int | HepB_eAb_Int | 0.000 | Measles_OD_DB_Int | HepB_eAb_Int | 0.000 |
| Measles_OD_DB_Int | HepB_eAg_Int | 0.000 | Measles_OD_DB_Int | HepB_eAg_Int | 0.000 |
| Measles_OD_DB_Int | HepC_Int | 0.055 | Measles_OD_DB_Int | HepC_Int | -0.018 |
| Measles_OD_DB_Int | Schistosoma_int | 0.056 | Measles_OD_DB_Int | Schistosoma_int | 0.076 |
| Measles_OD_DB_Int | Strongyloides_Int | 0.006 | Measles_OD_DB_Int | Strongyloides_Int | -0.041 |
| Measles_OD_DB_Int | Filaria_Int | 0.088 | Measles_OD_DB_Int | Filaria_Int | -0.145 |
| Measles_Int | IL_1_alpha | 0.066 | Measles_Int | IL_1_alpha | 0.037 |
| Measles_Int | IL_1_beta | -0.131 | Measles_Int | IL_1_beta | -0.049 |
| Measles_Int | IL_2 | 0.079 | Measles_Int | IL_2 | 0.016 |
| Measles_Int | IL_4 | 0.008 | Measles_Int | IL_4 | -0.019 |
| Measles_Int | IL_5 | 0.065 | Measles_Int | IL_5 | -0.020 |
| Measles_Int | IL_6 | -0.094 | Measles_Int | IL_6 | -0.046 |
| Measles_Int | IL_8 | 0.023 | Measles_Int | IL_8 | 0.097 |
| Measles_Int | IL_10 | 0.108 | Measles_Int | IL_10 | -0.122 |
| Measles_Int | IL_12p70 | 0.125 | Measles_Int | IL_12p70 | -0.073 |
| Measles_Int | IL_13 | 0.107 | Measles_Int | IL_13 | -0.186 |
| Measles_Int | IL_15 | -0.020 | Measles_Int | IL_15 | -0.011 |
| Measles_Int | IL_17 | 0.152 | Measles_Int | IL_17 | -0.038 |
| Measles_Int | IL_23 | 0.083 | Measles_Int | IL_23 | 0.027 |
| Measles_Int | IFN_gamma | 0.000 | Measles_Int | IFN_gamma | 0.000 |
| Measles_Int | TNF_alpha | 0.130 | Measles_Int | TNF_alpha | -0.050 |
| Measles_Int | TNF_beta | 0.112 | Measles_Int | TNF_beta | -0.079 |
| Measles_Int | Varicella_Int | -0.079 | Measles_Int | Varicella_Int | -0.025 |
| Measles_Int | Measles_OD_DB_Int | 0.089 | Measles_Int | Measles_OD_DB_Int | -0.053 |
| Measles_Int | Measles_Int | 1.000 | Measles_Int | Measles_Int | 1.000 |
| Measles_Int | HepA_Int | 0.014 | Measles_Int | HepA_Int | 0.705 |

FIG. 21I3-K

| | | | | | | |
|---|---|---|---|---|---|---|
| Measles_Int | Tetanus_Int | 0.000 | | Measles_Int | Tetanus_Int | 0.000 |
| Measles_Int | Diptheria_Int | 0.000 | | Measles_Int | Diptheria_Int | 0.000 |
| Measles_Int | Rubella_Int | -0.089 | | Measles_Int | Rubella_Int | 0.023 |
| Measles_Int | CMV_Int | 0.027 | | Measles_Int | CMV_Int | -0.012 |
| Measles_Int | HepB_cAb_Int | 0.021 | | Measles_Int | HepB_cAb_Int | 0.037 |
| Measles_Int | HepB_eAb_Int | 0.000 | | Measles_Int | HepB_eAb_Int | 0.000 |
| Measles_Int | HepB_eAg_Int | 0.000 | | Measles_Int | HepB_eAg_Int | 0.000 |
| Measles_Int | HepC_Int | 0.038 | | Measles_Int | HepC_Int | 0.019 |
| Measles_Int | Schistosoma_int | 0.122 | | Measles_Int | Schistosoma_int | 0.050 |
| Measles_Int | Strongyloides_Int | 0.096 | | Measles_Int | Strongyloides_Int | -0.070 |
| Measles_Int | Filaria_Int | -0.005 | | Measles_Int | Filaria_Int | -0.039 |
| HepA_Int | IL_1_alpha | -0.054 | | HepA_Int | IL_1_alpha | -0.035 |
| HepA_Int | IL_1_beta | 0.048 | | HepA_Int | IL_1_beta | -0.188 |
| HepA_Int | IL_2 | 0.072 | | HepA_Int | IL_2 | -0.010 |
| HepA_Int | IL_4 | -0.001 | | HepA_Int | IL_4 | -0.165 |
| HepA_Int | IL_5 | 0.029 | | HepA_Int | IL_5 | -0.160 |
| HepA_Int | IL_6 | 0.044 | | HepA_Int | IL_6 | -0.365 |
| HepA_Int | IL_8 | -0.021 | | HepA_Int | IL_8 | 0.067 |
| HepA_Int | IL_10 | 0.108 | | HepA_Int | IL_10 | -0.405 |
| HepA_Int | IL_12p70 | 0.055 | | HepA_Int | IL_12p70 | -0.244 |
| HepA_Int | IL_13 | 0.051 | | HepA_Int | IL_13 | -0.332 |
| HepA_Int | IL_15 | -0.101 | | HepA_Int | IL_15 | -0.042 |
| HepA_Int | IL_17 | 0.100 | | HepA_Int | IL_17 | -0.135 |
| HepA_Int | IL_23 | -0.034 | | HepA_Int | IL_23 | -0.054 |
| HepA_Int | IFN_gamma | 0.000 | | HepA_Int | IFN_gamma | 0.000 |
| HepA_Int | TNF_alpha | -0.068 | | HepA_Int | TNF_alpha | -0.104 |
| HepA_Int | TNF_beta | -0.034 | | HepA_Int | TNF_beta | -0.059 |
| HepA_Int | Varicella_Int | 0.312 | | HepA_Int | Varicella_Int | -0.036 |
| HepA_Int | Measles_OD_DB_Int | 0.056 | | HepA_Int | Measles_OD_DB_Int | -0.076 |
| HepA_Int | Measles_Int | 0.014 | | HepA_Int | Measles_Int | 0.705 |
| HepA_Int | HepA_Int | 1.000 | | HepA_Int | HepA_Int | 1.000 |
| HepA_Int | Tetanus_Int | 0.000 | | HepA_Int | Tetanus_Int | 0.000 |
| HepA_Int | Diptheria_Int | 0.000 | | HepA_Int | Diptheria_Int | 0.000 |
| HepA_Int | Rubella_Int | -0.107 | | HepA_Int | Rubella_Int | 0.032 |
| HepA_Int | CMV_Int | -0.059 | | HepA_Int | CMV_Int | -0.018 |
| HepA_Int | HepB_cAb_Int | 0.102 | | HepA_Int | HepB_cAb_Int | 0.053 |
| HepA_Int | HepB_eAb_Int | 0.000 | | HepA_Int | HepB_eAb_Int | 0.000 |
| HepA_Int | HepB_eAg_Int | 0.000 | | HepA_Int | HepB_eAg_Int | 0.000 |
| HepA_Int | HepC_Int | 0.043 | | HepA_Int | HepC_Int | 0.027 |
| HepA_Int | Schistosoma_int | -0.042 | | HepA_Int | Schistosoma_int | -0.067 |
| HepA_Int | Strongyloides_Int | 0.049 | | HepA_Int | Strongyloides_Int | -0.019 |
| HepA_Int | Filaria_Int | -0.029 | | HepA_Int | Filaria_Int | -0.130 |
| Tetanus_Int | IL_1_alpha | 0.000 | | Tetanus_Int | IL_1_alpha | 0.000 |
| Tetanus_Int | IL_1_beta | 0.000 | | Tetanus_Int | IL_1_beta | 0.000 |
| Tetanus_Int | IL_2 | 0.000 | | Tetanus_Int | IL_2 | 0.000 |
| Tetanus_Int | IL_4 | 0.000 | | Tetanus_Int | IL_4 | 0.000 |
| Tetanus_Int | IL_5 | 0.000 | | Tetanus_Int | IL_5 | 0.000 |
| Tetanus_Int | IL_6 | 0.000 | | Tetanus_Int | IL_6 | 0.000 |
| Tetanus_Int | IL_8 | 0.000 | | Tetanus_Int | IL_8 | 0.000 |
| Tetanus_Int | IL_10 | 0.000 | | Tetanus_Int | IL_10 | 0.000 |
| Tetanus_Int | IL_12p70 | 0.000 | | Tetanus_Int | IL_12p70 | 0.000 |
| Tetanus_Int | IL_13 | 0.000 | | Tetanus_Int | IL_13 | 0.000 |
| Tetanus_Int | IL_15 | 0.000 | | Tetanus_Int | IL_15 | 0.000 |
| Tetanus_Int | IL_17 | 0.000 | | Tetanus_Int | IL_17 | 0.000 |
| Tetanus_Int | IL_23 | 0.000 | | Tetanus_Int | IL_23 | 0.000 |
| Tetanus_Int | IFN_gamma | 0.000 | | Tetanus_Int | IFN_gamma | 0.000 |
| Tetanus_Int | TNF_alpha | 0.000 | | Tetanus_Int | TNF_alpha | 0.000 |

FIG. 21I3-L

| Tetanus_Int | TNF_beta | 0.000 | Tetanus_Int | TNF_beta | 0.000 |
|---|---|---|---|---|---|
| Tetanus_Int | Varicella_Int | 0.000 | Tetanus_Int | Varicella_Int | 0.000 |
| Tetanus_Int | Measles_OD_DB_Int | 0.000 | Tetanus_Int | Measles_OD_DB_Int | 0.000 |
| Tetanus_Int | Measles_Int | 0.000 | Tetanus_Int | Measles_Int | 0.000 |
| Tetanus_Int | HepA_Int | 0.000 | Tetanus_Int | HepA_Int | 0.000 |
| Tetanus_Int | Tetanus_Int | 1.000 | Tetanus_Int | Tetanus_Int | 1.000 |
| Tetanus_Int | Diptheria_Int | 0.000 | Tetanus_Int | Diptheria_Int | 0.000 |
| Tetanus_Int | Rubella_Int | 0.000 | Tetanus_Int | Rubella_Int | 0.000 |
| Tetanus_Int | CMV_Int | 0.000 | Tetanus_Int | CMV_Int | 0.000 |
| Tetanus_Int | HepB_cAb_Int | 0.000 | Tetanus_Int | HepB_cAb_Int | 0.000 |
| Tetanus_Int | HepB_eAb_Int | 0.000 | Tetanus_Int | HepB_eAb_Int | 0.000 |
| Tetanus_Int | HepB_eAg_Int | 0.000 | Tetanus_Int | HepB_eAg_Int | 0.000 |
| Tetanus_Int | HepC_Int | 0.000 | Tetanus_Int | HepC_Int | 0.000 |
| Tetanus_Int | Schistosoma_int | 0.000 | Tetanus_Int | Schistosoma_int | 0.000 |
| Tetanus_Int | Strongyloides_Int | 0.000 | Tetanus_Int | Strongyloides_Int | 0.000 |
| Tetanus_Int | Filaria_Int | 0.000 | Tetanus_Int | Filaria_Int | 0.000 |
| Diptheria_Int | IL_1_alpha | 0.000 | Diptheria_Int | IL_1_alpha | 0.000 |
| Diptheria_Int | IL_1_beta | 0.000 | Diptheria_Int | IL_1_beta | 0.000 |
| Diptheria_Int | IL_2 | 0.000 | Diptheria_Int | IL_2 | 0.000 |
| Diptheria_Int | IL_4 | 0.000 | Diptheria_Int | IL_4 | 0.000 |
| Diptheria_Int | IL_5 | 0.000 | Diptheria_Int | IL_5 | 0.000 |
| Diptheria_Int | IL_6 | 0.000 | Diptheria_Int | IL_6 | 0.000 |
| Diptheria_Int | IL_8 | 0.000 | Diptheria_Int | IL_8 | 0.000 |
| Diptheria_Int | IL_10 | 0.000 | Diptheria_Int | IL_10 | 0.000 |
| Diptheria_Int | IL_12p70 | 0.000 | Diptheria_Int | IL_12p70 | 0.000 |
| Diptheria_Int | IL_13 | 0.000 | Diptheria_Int | IL_13 | 0.000 |
| Diptheria_Int | IL_15 | 0.000 | Diptheria_Int | IL_15 | 0.000 |
| Diptheria_Int | IL_17 | 0.000 | Diptheria_Int | IL_17 | 0.000 |
| Diptheria_Int | IL_23 | 0.000 | Diptheria_Int | IL_23 | 0.000 |
| Diptheria_Int | IFN_gamma | 0.000 | Diptheria_Int | IFN_gamma | 0.000 |
| Diptheria_Int | TNF_alpha | 0.000 | Diptheria_Int | TNF_alpha | 0.000 |
| Diptheria_Int | TNF_beta | 0.000 | Diptheria_Int | TNF_beta | 0.000 |
| Diptheria_Int | Varicella_Int | 0.000 | Diptheria_Int | Varicella_Int | 0.000 |
| Diptheria_Int | Measles_OD_DB_Int | 0.000 | Diptheria_Int | Measles_OD_DB_Int | 0.000 |
| Diptheria_Int | Measles_Int | 0.000 | Diptheria_Int | Measles_Int | 0.000 |
| Diptheria_Int | HepA_Int | 0.000 | Diptheria_Int | HepA_Int | 0.000 |
| Diptheria_Int | Tetanus_Int | 0.000 | Diptheria_Int | Tetanus_Int | 0.000 |
| Diptheria_Int | Diptheria_Int | 1.000 | Diptheria_Int | Diptheria_Int | 1.000 |
| Diptheria_Int | Rubella_Int | 0.000 | Diptheria_Int | Rubella_Int | 0.000 |
| Diptheria_Int | CMV_Int | 0.000 | Diptheria_Int | CMV_Int | 0.000 |
| Diptheria_Int | HepB_cAb_Int | 0.000 | Diptheria_Int | HepB_cAb_Int | 0.000 |
| Diptheria_Int | HepB_eAb_Int | 0.000 | Diptheria_Int | HepB_eAb_Int | 0.000 |
| Diptheria_Int | HepB_eAg_Int | 0.000 | Diptheria_Int | HepB_eAg_Int | 0.000 |
| Diptheria_Int | HepC_Int | 0.000 | Diptheria_Int | HepC_Int | 0.000 |
| Diptheria_Int | Schistosoma_int | 0.000 | Diptheria_Int | Schistosoma_int | 0.000 |
| Diptheria_Int | Strongyloides_Int | 0.000 | Diptheria_Int | Strongyloides_Int | 0.000 |
| Diptheria_Int | Filaria_Int | 0.000 | Diptheria_Int | Filaria_Int | 0.000 |
| Rubella_Int | IL_1_alpha | -0.062 | Rubella_Int | IL_1_alpha | 0.050 |
| Rubella_Int | IL_1_beta | -0.024 | Rubella_Int | IL_1_beta | -0.008 |
| Rubella_Int | IL_2 | -0.033 | Rubella_Int | IL_2 | -0.029 |
| Rubella_Int | IL_4 | -0.078 | Rubella_Int | IL_4 | 0.062 |
| Rubella_Int | IL_5 | 0.021 | Rubella_Int | IL_5 | -0.062 |
| Rubella_Int | IL_6 | -0.025 | Rubella_Int | IL_6 | -0.019 |
| Rubella_Int | IL_8 | -0.029 | Rubella_Int | IL_8 | 0.008 |
| Rubella_Int | IL_10 | 0.008 | Rubella_Int | IL_10 | -0.000 |
| Rubella_Int | IL_12p70 | -0.019 | Rubella_Int | IL_12p70 | -0.039 |
| Rubella_Int | IL_13 | -0.028 | Rubella_Int | IL_13 | -0.052 |

FIG. 21I3-M

| | | | | | | |
|---|---|---|---|---|---|---|
| Rubella_Int | IL_15 | 0.119 | | Rubella_Int | IL_15 | -0.010 |
| Rubella_Int | IL_17 | 0.001 | | Rubella_Int | IL_17 | -0.031 |
| Rubella_Int | IL_23 | -0.034 | | Rubella_Int | IL_23 | -0.046 |
| Rubella_Int | IFN_gamma | 0.000 | | Rubella_Int | IFN_gamma | 0.000 |
| Rubella_Int | TNF_alpha | -0.040 | | Rubella_Int | TNF_alpha | 0.035 |
| Rubella_Int | TNF_beta | -0.142 | | Rubella_Int | TNF_beta | -0.037 |
| Rubella_Int | Varicella_Int | -0.033 | | Rubella_Int | Varicella_Int | -0.005 |
| Rubella_Int | Measles_OD_DB_Int | -0.047 | | Rubella_Int | Measles_OD_DB_Int | -0.019 |
| Rubella_Int | Measles_Int | -0.089 | | Rubella_Int | Measles_Int | 0.023 |
| Rubella_Int | HepA_Int | -0.107 | | Rubella_Int | HepA_Int | 0.032 |
| Rubella_Int | Tetanus_Int | 0.000 | | Rubella_Int | Tetanus_Int | 0.000 |
| Rubella_Int | Diptheria_Int | 0.000 | | Rubella_Int | Diptheria_Int | 0.000 |
| Rubella_Int | Rubella_Int | 1.000 | | Rubella_Int | Rubella_Int | 1.000 |
| Rubella_Int | CMV_Int | -0.026 | | Rubella_Int | CMV_Int | 0.041 |
| Rubella_Int | HepB_cAb_Int | -0.086 | | Rubella_Int | HepB_cAb_Int | 0.028 |
| Rubella_Int | HepB_eAb_Int | 0.000 | | Rubella_Int | HepB_eAb_Int | 0.000 |
| Rubella_Int | HepB_eAg_Int | 0.000 | | Rubella_Int | HepB_eAg_Int | 0.000 |
| Rubella_Int | HepC_Int | -0.034 | | Rubella_Int | HepC_Int | 0.064 |
| Rubella_Int | Schistosoma_int | -0.065 | | Rubella_Int | Schistosoma_int | 0.154 |
| Rubella_Int | Strongyloides_Int | 0.068 | | Rubella_Int | Strongyloides_Int | 0.043 |
| Rubella_Int | Filaria_Int | -0.018 | | Rubella_Int | Filaria_Int | -0.009 |
| CMV_Int | IL_1_alpha | 0.009 | | CMV_Int | IL_1_alpha | -0.004 |
| CMV_Int | IL_1_beta | 0.046 | | CMV_Int | IL_1_beta | 0.063 |
| CMV_Int | IL_2 | 0.001 | | CMV_Int | IL_2 | 0.028 |
| CMV_Int | IL_4 | 0.032 | | CMV_Int | IL_4 | 0.072 |
| CMV_Int | IL_5 | -0.134 | | CMV_Int | IL_5 | 0.022 |
| CMV_Int | IL_6 | 0.067 | | CMV_Int | IL_6 | 0.032 |
| CMV_Int | IL_8 | -0.068 | | CMV_Int | IL_8 | -0.012 |
| CMV_Int | IL_10 | 0.001 | | CMV_Int | IL_10 | 0.081 |
| CMV_Int | IL_12p70 | 0.093 | | CMV_Int | IL_12p70 | -0.026 |
| CMV_Int | IL_13 | -0.039 | | CMV_Int | IL_13 | 0.058 |
| CMV_Int | IL_15 | 0.092 | | CMV_Int | IL_15 | -0.036 |
| CMV_Int | IL_17 | 0.116 | | CMV_Int | IL_17 | 0.096 |
| CMV_Int | IL_23 | 0.063 | | CMV_Int | IL_23 | 0.014 |
| CMV_Int | IFN_gamma | 0.000 | | CMV_Int | IFN_gamma | 0.000 |
| CMV_Int | TNF_alpha | 0.096 | | CMV_Int | TNF_alpha | 0.073 |
| CMV_Int | TNF_beta | 0.106 | | CMV_Int | TNF_beta | 0.036 |
| CMV_Int | Varicella_Int | -0.028 | | CMV_Int | Varicella_Int | -0.044 |
| CMV_Int | Measles_OD_DB_Int | 0.018 | | CMV_Int | Measles_OD_DB_Int | 0.095 |
| CMV_Int | Measles_Int | 0.027 | | CMV_Int | Measles_Int | -0.012 |
| CMV_Int | HepA_Int | -0.059 | | CMV_Int | HepA_Int | -0.018 |
| CMV_Int | Tetanus_Int | 0.000 | | CMV_Int | Tetanus_Int | 0.000 |
| CMV_Int | Diptheria_Int | 0.000 | | CMV_Int | Diptheria_Int | 0.000 |
| CMV_Int | Rubella_Int | -0.026 | | CMV_Int | Rubella_Int | 0.041 |
| CMV_Int | CMV_Int | 1.000 | | CMV_Int | CMV_Int | 1.000 |
| CMV_Int | HepB_cAb_Int | 0.078 | | CMV_Int | HepB_cAb_Int | -0.068 |
| CMV_Int | HepB_eAb_Int | 0.000 | | CMV_Int | HepB_eAb_Int | 0.000 |
| CMV_Int | HepB_eAg_Int | 0.000 | | CMV_Int | HepB_eAg_Int | 0.000 |
| CMV_Int | HepC_Int | 0.033 | | CMV_Int | HepC_Int | 0.034 |
| CMV_Int | Schistosoma_int | 0.050 | | CMV_Int | Schistosoma_int | 0.087 |
| CMV_Int | Strongyloides_Int | 0.074 | | CMV_Int | Strongyloides_Int | 0.010 |
| CMV_Int | Filaria_Int | 0.137 | | CMV_Int | Filaria_Int | -0.008 |
| HepB_cAb_Int | IL_1_alpha | -0.082 | | HepB_cAb_Int | IL_1_alpha | -0.083 |
| HepB_cAb_Int | IL_1_beta | -0.049 | | HepB_cAb_Int | IL_1_beta | -0.191 |
| HepB_cAb_Int | IL_2 | 0.078 | | HepB_cAb_Int | IL_2 | -0.070 |
| HepB_cAb_Int | IL_4 | -0.010 | | HepB_cAb_Int | IL_4 | -0.168 |
| HepB_cAb_Int | IL_5 | 0.073 | | HepB_cAb_Int | IL_5 | -0.029 |

FIG. 21I3-N

| | | | | | | |
|---|---|---|---|---|---|---|
| HepB_cAb_Int | IL_6 | -0.060 | | HepB_cAb_Int | IL_6 | -0.052 |
| HepB_cAb_Int | IL_8 | -0.080 | | HepB_cAb_Int | IL_8 | -0.089 |
| HepB_cAb_Int | IL_10 | -0.002 | | HepB_cAb_Int | IL_10 | -0.125 |
| HepB_cAb_Int | IL_12p70 | -0.017 | | HepB_cAb_Int | IL_12p70 | -0.108 |
| HepB_cAb_Int | IL_13 | -0.015 | | HepB_cAb_Int | IL_13 | -0.061 |
| HepB_cAb_Int | IL_15 | 0.012 | | HepB_cAb_Int | IL_15 | -0.025 |
| HepB_cAb_Int | IL_17 | -0.012 | | HepB_cAb_Int | IL_17 | -0.176 |
| HepB_cAb_Int | IL_23 | 0.034 | | HepB_cAb_Int | IL_23 | 0.079 |
| HepB_cAb_Int | IFN_gamma | 0.000 | | HepB_cAb_Int | IFN_gamma | 0.000 |
| HepB_cAb_Int | TNF_alpha | -0.013 | | HepB_cAb_Int | TNF_alpha | -0.086 |
| HepB_cAb_Int | TNF_beta | -0.043 | | HepB_cAb_Int | TNF_beta | -0.144 |
| HepB_cAb_Int | Varicella_Int | 0.065 | | HepB_cAb_Int | Varicella_Int | 0.058 |
| HepB_cAb_Int | Measles_OD_DB_Int | 0.009 | | HepB_cAb_Int | Measles_OD_DB_Int | -0.082 |
| HepB_cAb_Int | Measles_Int | 0.021 | | HepB_cAb_Int | Measles_Int | 0.037 |
| HepB_cAb_Int | HepA_Int | 0.102 | | HepB_cAb_Int | HepA_Int | 0.053 |
| HepB_cAb_Int | Tetanus_Int | 0.000 | | HepB_cAb_Int | Tetanus_Int | 0.000 |
| HepB_cAb_Int | Diptheria_Int | 0.000 | | HepB_cAb_Int | Diptheria_Int | 0.000 |
| HepB_cAb_Int | Rubella_Int | -0.086 | | HepB_cAb_Int | Rubella_Int | 0.028 |
| HepB_cAb_Int | CMV_Int | 0.078 | | HepB_cAb_Int | CMV_Int | -0.068 |
| HepB_cAb_Int | HepB_cAb_Int | 1.000 | | HepB_cAb_Int | HepB_cAb_Int | 1.000 |
| HepB_cAb_Int | HepB_eAb_Int | 0.000 | | HepB_cAb_Int | HepB_eAb_Int | 0.000 |
| HepB_cAb_Int | HepB_eAg_Int | 0.000 | | HepB_cAb_Int | HepB_eAg_Int | 0.000 |
| HepB_cAb_Int | HepC_Int | -0.023 | | HepB_cAb_Int | HepC_Int | 0.076 |
| HepB_cAb_Int | Schistosoma_int | 0.007 | | HepB_cAb_Int | Schistosoma_int | 0.180 |
| HepB_cAb_Int | Strongyloides_Int | -0.030 | | HepB_cAb_Int | Strongyloides_Int | 0.003 |
| HepB_cAb_Int | Filaria_Int | 0.066 | | HepB_cAb_Int | Filaria_Int | -0.033 |
| HepB_eAb_Int | IL_1_alpha | 0.000 | | HepB_eAb_Int | IL_1_alpha | 0.000 |
| HepB_eAb_Int | IL_1_beta | 0.000 | | HepB_eAb_Int | IL_1_beta | 0.000 |
| HepB_eAb_Int | IL_2 | 0.000 | | HepB_eAb_Int | IL_2 | 0.000 |
| HepB_eAb_Int | IL_4 | 0.000 | | HepB_eAb_Int | IL_4 | 0.000 |
| HepB_eAb_Int | IL_5 | 0.000 | | HepB_eAb_Int | IL_5 | 0.000 |
| HepB_eAb_Int | IL_6 | 0.000 | | HepB_eAb_Int | IL_6 | 0.000 |
| HepB_eAb_Int | IL_8 | 0.000 | | HepB_eAb_Int | IL_8 | 0.000 |
| HepB_eAb_Int | IL_10 | 0.000 | | HepB_eAb_Int | IL_10 | 0.000 |
| HepB_eAb_Int | IL_12p70 | 0.000 | | HepB_eAb_Int | IL_12p70 | 0.000 |
| HepB_eAb_Int | IL_13 | 0.000 | | HepB_eAb_Int | IL_13 | 0.000 |
| HepB_eAb_Int | IL_15 | 0.000 | | HepB_eAb_Int | IL_15 | 0.000 |
| HepB_eAb_Int | IL_17 | 0.000 | | HepB_eAb_Int | IL_17 | 0.000 |
| HepB_eAb_Int | IL_23 | 0.000 | | HepB_eAb_Int | IL_23 | 0.000 |
| HepB_eAb_Int | IFN_gamma | 0.000 | | HepB_eAb_Int | IFN_gamma | 0.000 |
| HepB_eAb_Int | TNF_alpha | 0.000 | | HepB_eAb_Int | TNF_alpha | 0.000 |
| HepB_eAb_Int | TNF_beta | 0.000 | | HepB_eAb_Int | TNF_beta | 0.000 |
| HepB_eAb_Int | Varicella_Int | 0.000 | | HepB_eAb_Int | Varicella_Int | 0.000 |
| HepB_eAb_Int | Measles_OD_DB_Int | 0.000 | | HepB_eAb_Int | Measles_OD_DB_Int | 0.000 |
| HepB_eAb_Int | Measles_Int | 0.000 | | HepB_eAb_Int | Measles_Int | 0.000 |
| HepB_eAb_Int | HepA_Int | 0.000 | | HepB_eAb_Int | HepA_Int | 0.000 |
| HepB_eAb_Int | Tetanus_Int | 0.000 | | HepB_eAb_Int | Tetanus_Int | 0.000 |
| HepB_eAb_Int | Diptheria_Int | 0.000 | | HepB_eAb_Int | Diptheria_Int | 0.000 |
| HepB_eAb_Int | Rubella_Int | 0.000 | | HepB_eAb_Int | Rubella_Int | 0.000 |
| HepB_eAb_Int | CMV_Int | 0.000 | | HepB_eAb_Int | CMV_Int | 0.000 |
| HepB_eAb_Int | HepB_cAb_Int | 0.000 | | HepB_eAb_Int | HepB_cAb_Int | 0.000 |
| HepB_eAb_Int | HepB_eAb_Int | 1.000 | | HepB_eAb_Int | HepB_eAb_Int | 1.000 |
| HepB_eAb_Int | HepB_eAg_Int | 0.000 | | HepB_eAb_Int | HepB_eAg_Int | 0.000 |
| HepB_eAb_Int | HepC_Int | 0.000 | | HepB_eAb_Int | HepC_Int | 0.000 |
| HepB_eAb_Int | Schistosoma_int | 0.000 | | HepB_eAb_Int | Schistosoma_int | 0.000 |
| HepB_eAb_Int | Strongyloides_Int | 0.000 | | HepB_eAb_Int | Strongyloides_Int | 0.000 |
| HepB_eAb_Int | Filaria_Int | 0.000 | | HepB_eAb_Int | Filaria_Int | 0.000 |

FIG. 21I3-O

| HepB_eAg_Int | IL_1_alpha | 0.000 | HepB_eAg_Int | IL_1_alpha | 0.000 |
|---|---|---|---|---|---|
| HepB_eAg_Int | IL_1_beta | 0.000 | HepB_eAg_Int | IL_1_beta | 0.000 |
| HepB_eAg_Int | IL_2 | 0.000 | HepB_eAg_Int | IL_2 | 0.000 |
| HepB_eAg_Int | IL_4 | 0.000 | HepB_eAg_Int | IL_4 | 0.000 |
| HepB_eAg_Int | IL_5 | 0.000 | HepB_eAg_Int | IL_5 | 0.000 |
| HepB_eAg_Int | IL_6 | 0.000 | HepB_eAg_Int | IL_6 | 0.000 |
| HepB_eAg_Int | IL_8 | 0.000 | HepB_eAg_Int | IL_8 | 0.000 |
| HepB_eAg_Int | IL_10 | 0.000 | HepB_eAg_Int | IL_10 | 0.000 |
| HepB_eAg_Int | IL_12p70 | 0.000 | HepB_eAg_Int | IL_12p70 | 0.000 |
| HepB_eAg_Int | IL_13 | 0.000 | HepB_eAg_Int | IL_13 | 0.000 |
| HepB_eAg_Int | IL_15 | 0.000 | HepB_eAg_Int | IL_15 | 0.000 |
| HepB_eAg_Int | IL_17 | 0.000 | HepB_eAg_Int | IL_17 | 0.000 |
| HepB_eAg_Int | IL_23 | 0.000 | HepB_eAg_Int | IL_23 | 0.000 |
| HepB_eAg_Int | IFN_gamma | 0.000 | HepB_eAg_Int | IFN_gamma | 0.000 |
| HepB_eAg_Int | TNF_alpha | 0.000 | HepB_eAg_Int | TNF_alpha | 0.000 |
| HepB_eAg_Int | TNF_beta | 0.000 | HepB_eAg_Int | TNF_beta | 0.000 |
| HepB_eAg_Int | Varicella_Int | 0.000 | HepB_eAg_Int | Varicella_Int | 0.000 |
| HepB_eAg_Int | Measles_OD_DB_Int | 0.000 | HepB_eAg_Int | Measles_OD_DB_Int | 0.000 |
| HepB_eAg_Int | Measles_Int | 0.000 | HepB_eAg_Int | Measles_Int | 0.000 |
| HepB_eAg_Int | HepA_Int | 0.000 | HepB_eAg_Int | HepA_Int | 0.000 |
| HepB_eAg_Int | Tetanus_Int | 0.000 | HepB_eAg_Int | Tetanus_Int | 0.000 |
| HepB_eAg_Int | Diptheria_Int | 0.000 | HepB_eAg_Int | Diptheria_Int | 0.000 |
| HepB_eAg_Int | Rubella_Int | 0.000 | HepB_eAg_Int | Rubella_Int | 0.000 |
| HepB_eAg_Int | CMV_Int | 0.000 | HepB_eAg_Int | CMV_Int | 0.000 |
| HepB_eAg_Int | HepB_cAb_Int | 0.000 | HepB_eAg_Int | HepB_cAb_Int | 0.000 |
| HepB_eAg_Int | HepB_eAb_Int | 0.000 | HepB_eAg_Int | HepB_eAb_Int | 0.000 |
| HepB_eAg_Int | HepB_eAg_Int | 1.000 | HepB_eAg_Int | HepB_eAg_Int | 1.000 |
| HepB_eAg_Int | HepC_Int | 0.000 | HepB_eAg_Int | HepC_Int | 0.000 |
| HepB_eAg_Int | Schistosoma_int | 0.000 | HepB_eAg_Int | Schistosoma_int | 0.000 |
| HepB_eAg_Int | Strongyloides_Int | 0.000 | HepB_eAg_Int | Strongyloides_Int | 0.000 |
| HepB_eAg_Int | Filaria_Int | 0.000 | HepB_eAg_Int | Filaria_Int | 0.000 |
| HepC_Int | IL_1_alpha | -0.012 | HepC_Int | IL_1_alpha | 0.085 |
| HepC_Int | IL_1_beta | 0.108 | HepC_Int | IL_1_beta | 0.000 |
| HepC_Int | IL_2 | -0.026 | HepC_Int | IL_2 | -0.014 |
| HepC_Int | IL_4 | 0.039 | HepC_Int | IL_4 | 0.092 |
| HepC_Int | IL_5 | -0.051 | HepC_Int | IL_5 | 0.119 |
| HepC_Int | IL_6 | 0.040 | HepC_Int | IL_6 | 0.077 |
| HepC_Int | IL_8 | 0.039 | HepC_Int | IL_8 | 0.199 |
| HepC_Int | IL_10 | -0.037 | HepC_Int | IL_10 | -0.023 |
| HepC_Int | IL_12p70 | 0.028 | HepC_Int | IL_12p70 | 0.079 |
| HepC_Int | IL_13 | -0.025 | HepC_Int | IL_13 | -0.023 |
| HepC_Int | IL_15 | 0.176 | HepC_Int | IL_15 | 0.161 |
| HepC_Int | IL_17 | -0.037 | HepC_Int | IL_17 | -0.043 |
| HepC_Int | IL_23 | 0.034 | HepC_Int | IL_23 | 0.049 |
| HepC_Int | IFN_gamma | 0.000 | HepC_Int | IFN_gamma | 0.000 |
| HepC_Int | TNF_alpha | 0.176 | HepC_Int | TNF_alpha | 0.025 |
| HepC_Int | TNF_beta | -0.028 | HepC_Int | TNF_beta | 0.038 |
| HepC_Int | Varicella_Int | 0.027 | HepC_Int | Varicella_Int | 0.068 |
| HepC_Int | Measles_OD_DB_Int | 0.055 | HepC_Int | Measles_OD_DB_Int | -0.018 |
| HepC_Int | Measles_Int | 0.038 | HepC_Int | Measles_Int | 0.019 |
| HepC_Int | HepA_Int | 0.043 | HepC_Int | HepA_Int | 0.027 |
| HepC_Int | Tetanus_Int | 0.000 | HepC_Int | Tetanus_Int | 0.000 |
| HepC_Int | Diptheria_Int | 0.000 | HepC_Int | Diptheria_Int | 0.000 |
| HepC_Int | Rubella_Int | -0.034 | HepC_Int | Rubella_Int | 0.064 |
| HepC_Int | CMV_Int | 0.033 | HepC_Int | CMV_Int | 0.034 |
| HepC_Int | HepB_cAb_Int | -0.023 | HepC_Int | HepB_cAb_Int | 0.076 |
| HepC_Int | HepB_eAb_Int | 0.000 | HepC_Int | HepB_eAb_Int | 0.000 |

FIG. 21I3-P

| | | | | | | |
|---|---|---|---|---|---|---|
| HepC_Int | HepB_eAg_Int | 0.000 | | HepC_Int | HepB_eAg_Int | 0.000 |
| HepC_Int | HepC_Int | 1.000 | | HepC_Int | HepC_Int | 1.000 |
| HepC_Int | Schistosoma_int | 0.140 | | HepC_Int | Schistosoma_int | -0.044 |
| HepC_Int | Strongyloides_Int | 0.149 | | HepC_Int | Strongyloides_Int | -0.157 |
| HepC_Int | Filaria_Int | -0.047 | | HepC_Int | Filaria_Int | -0.033 |
| Schistosoma_int | IL_1_alpha | 0.041 | | Schistosoma_int | IL_1_alpha | 0.146 |
| Schistosoma_int | IL_1_beta | 0.027 | | Schistosoma_int | IL_1_beta | 0.035 |
| Schistosoma_int | IL_2 | 0.059 | | Schistosoma_int | IL_2 | -0.042 |
| Schistosoma_int | IL_4 | 0.042 | | Schistosoma_int | IL_4 | -0.030 |
| Schistosoma_int | IL_5 | -0.071 | | Schistosoma_int | IL_5 | -0.022 |
| Schistosoma_int | IL_6 | -0.014 | | Schistosoma_int | IL_6 | -0.026 |
| Schistosoma_int | IL_8 | -0.011 | | Schistosoma_int | IL_8 | -0.103 |
| Schistosoma_int | IL_10 | 0.113 | | Schistosoma_int | IL_10 | 0.128 |
| Schistosoma_int | IL_12p70 | -0.006 | | Schistosoma_int | IL_12p70 | -0.011 |
| Schistosoma_int | IL_13 | -0.010 | | Schistosoma_int | IL_13 | -0.063 |
| Schistosoma_int | IL_15 | 0.001 | | Schistosoma_int | IL_15 | 0.127 |
| Schistosoma_int | IL_17 | 0.156 | | Schistosoma_int | IL_17 | -0.021 |
| Schistosoma_int | IL_23 | 0.012 | | Schistosoma_int | IL_23 | 0.026 |
| Schistosoma_int | IFN_gamma | 0.000 | | Schistosoma_int | IFN_gamma | 0.000 |
| Schistosoma_int | TNF_alpha | 0.093 | | Schistosoma_int | TNF_alpha | 0.096 |
| Schistosoma_int | TNF_beta | 0.114 | | Schistosoma_int | TNF_beta | -0.058 |
| Schistosoma_int | Varicella_Int | -0.013 | | Schistosoma_int | Varicella_Int | -0.042 |
| Schistosoma_int | Measles_OD_DB_Int | 0.056 | | Schistosoma_int | Measles_OD_DB_Int | 0.076 |
| Schistosoma_int | Measles_Int | 0.122 | | Schistosoma_int | Measles_Int | 0.050 |
| Schistosoma_int | HepA_Int | -0.042 | | Schistosoma_int | HepA_int | -0.067 |
| Schistosoma_int | Tetanus_Int | 0.000 | | Schistosoma_int | Tetanus_Int | 0.000 |
| Schistosoma_int | Diptheria_Int | 0.000 | | Schistosoma_int | Diptheria_Int | 0.000 |
| Schistosoma_int | Rubella_Int | -0.065 | | Schistosoma_int | Rubella_Int | 0.154 |
| Schistosoma_int | CMV_Int | 0.050 | | Schistosoma_int | CMV_Int | 0.087 |
| Schistosoma_int | HepB_cAb_Int | 0.007 | | Schistosoma_int | HepB_cAb_Int | 0.180 |
| Schistosoma_int | HepB_eAb_Int | 0.000 | | Schistosoma_int | HepB_eAb_Int | 0.000 |
| Schistosoma_int | HepB_eAg_Int | 0.000 | | Schistosoma_int | HepB_eAg_Int | 0.000 |
| Schistosoma_int | HepC_Int | 0.140 | | Schistosoma_int | HepC_int | -0.044 |
| Schistosoma_int | Schistosoma_int | 1.000 | | Schistosoma_int | Schistosoma_int | 1.000 |
| Schistosoma_int | Strongyloides_Int | 0.048 | | Schistosoma_int | Strongyloides_Int | 0.047 |
| Schistosoma_int | Filaria_Int | 0.080 | | Schistosoma_int | Filaria_Int | 0.091 |
| Strongyloides_Int | IL_1_alpha | 0.066 | | Strongyloides_Int | IL_1_alpha | -0.117 |
| Strongyloides_Int | IL_1_beta | 0.069 | | Strongyloides_Int | IL_1_beta | -0.091 |
| Strongyloides_Int | IL_2 | 0.188 | | Strongyloides_Int | IL_2 | -0.025 |
| Strongyloides_Int | IL_4 | -0.002 | | Strongyloides_Int | IL_4 | -0.084 |
| Strongyloides_Int | IL_5 | -0.006 | | Strongyloides_Int | IL_5 | -0.015 |
| Strongyloides_Int | IL_6 | -0.106 | | Strongyloides_Int | IL_6 | -0.006 |
| Strongyloides_Int | IL_8 | 0.009 | | Strongyloides_Int | IL_8 | -0.148 |
| Strongyloides_Int | IL_10 | 0.036 | | Strongyloides_Int | IL_10 | -0.080 |
| Strongyloides_Int | IL_12p70 | -0.036 | | Strongyloides_Int | IL_12p70 | -0.052 |
| Strongyloides_Int | IL_13 | -0.114 | | Strongyloides_Int | IL_13 | -0.152 |
| Strongyloides_Int | IL_15 | -0.104 | | Strongyloides_Int | IL_15 | -0.178 |
| Strongyloides_Int | IL_17 | 0.078 | | Strongyloides_Int | IL_17 | -0.041 |
| Strongyloides_Int | IL_23 | 0.087 | | Strongyloides_Int | IL_23 | -0.026 |
| Strongyloides_Int | IFN_gamma | 0.000 | | Strongyloides_Int | IFN_gamma | 0.000 |
| Strongyloides_Int | TNF_alpha | 0.094 | | Strongyloides_Int | TNF_alpha | 0.033 |
| Strongyloides_Int | TNF_beta | 0.065 | | Strongyloides_Int | TNF_beta | -0.085 |
| Strongyloides_Int | Varicella_Int | 0.008 | | Strongyloides_Int | Varicella_Int | -0.083 |
| Strongyloides_Int | Measles_OD_DB_Int | 0.006 | | Strongyloides_Int | Measles_OD_DB_Int | -0.041 |
| Strongyloides_Int | Measles_Int | 0.096 | | Strongyloides_Int | Measles_Int | -0.070 |
| Strongyloides_Int | HepA_Int | 0.049 | | Strongyloides_Int | HepA_int | -0.019 |
| Strongyloides_Int | Tetanus_Int | 0.000 | | Strongyloides_Int | Tetanus_Int | 0.000 |

FIG. 21I3-Q

| | | |
|---|---|---|
| Strongyloides_Int | Diptheria_Int | 0.000 |
| Strongyloides_Int | Rubella_Int | 0.068 |
| Strongyloides_Int | CMV_Int | 0.074 |
| Strongyloides_Int | HepB_cAb_Int | -0.030 |
| Strongyloides_Int | HepB_eAb_Int | 0.000 |
| Strongyloides_Int | HepB_eAg_Int | 0.000 |
| Strongyloides_Int | HepC_Int | 0.149 |
| Strongyloides_Int | Schistosoma_int | 0.048 |
| Strongyloides_Int | Strongyloides_Int | 1.000 |
| Strongyloides_Int | Filaria_Int | 0.180 |
| Filaria_Int | IL_1_alpha | 0.036 |
| Filaria_Int | IL_1_beta | -0.018 |
| Filaria_Int | IL_2 | 0.019 |
| Filaria_Int | IL_4 | 0.064 |
| Filaria_Int | IL_5 | 0.068 |
| Filaria_Int | IL_6 | -0.079 |
| Filaria_Int | IL_8 | -0.105 |
| Filaria_Int | IL_10 | 0.169 |
| Filaria_Int | IL_12p70 | 0.013 |
| Filaria_Int | IL_13 | -0.061 |
| Filaria_Int | IL_15 | -0.091 |
| Filaria_Int | IL_17 | 0.152 |
| Filaria_Int | IL_23 | -0.040 |
| Filaria_Int | IFN_gamma | 0.000 |
| Filaria_Int | TNF_alpha | 0.127 |
| Filaria_Int | TNF_beta | 0.113 |
| Filaria_Int | Varicella_Int | 0.015 |
| Filaria_Int | Measles_OD_DB_Int | 0.088 |
| Filaria_Int | Measles_Int | -0.005 |
| Filaria_Int | HepA_Int | -0.029 |
| Filaria_Int | Tetanus_Int | 0.000 |
| Filaria_Int | Diptheria_Int | 0.000 |
| Filaria_Int | Rubella_Int | -0.018 |
| Filaria_Int | CMV_Int | 0.137 |
| Filaria_Int | HepB_cAb_Int | 0.066 |
| Filaria_Int | HepB_eAb_Int | 0.000 |
| Filaria_Int | HepB_eAg_Int | 0.000 |
| Filaria_Int | HepC_Int | -0.047 |
| Filaria_Int | Schistosoma_int | 0.080 |
| Filaria_Int | Strongyloides_Int | 0.180 |
| Filaria_Int | Filaria_Int | 1.000 |

| | | |
|---|---|---|
| Strongyloides_Int | Diptheria_Int | 0.000 |
| Strongyloides_Int | Rubella_Int | 0.043 |
| Strongyloides_Int | CMV_Int | 0.010 |
| Strongyloides_Int | HepB_cAb_Int | 0.003 |
| Strongyloides_Int | HepB_eAb_Int | 0.000 |
| Strongyloides_Int | HepB_eAg_Int | 0.000 |
| Strongyloides_Int | HepC_Int | -0.157 |
| Strongyloides_Int | Schistosoma_int | 0.047 |
| Strongyloides_Int | Strongyloides_Int | 1.000 |
| Strongyloides_Int | Filaria_Int | 0.001 |
| Filaria_Int | IL_1_alpha | 0.024 |
| Filaria_Int | IL_1_beta | -0.017 |
| Filaria_Int | IL_2 | 0.048 |
| Filaria_Int | IL_4 | -0.133 |
| Filaria_Int | IL_5 | -0.087 |
| Filaria_Int | IL_6 | 0.029 |
| Filaria_Int | IL_8 | -0.055 |
| Filaria_Int | IL_10 | -0.017 |
| Filaria_Int | IL_12p70 | -0.052 |
| Filaria_Int | IL_13 | -0.030 |
| Filaria_Int | IL_15 | -0.003 |
| Filaria_Int | IL_17 | -0.106 |
| Filaria_Int | IL_23 | 0.099 |
| Filaria_Int | IFN_gamma | 0.000 |
| Filaria_Int | TNF_alpha | -0.144 |
| Filaria_Int | TNF_beta | -0.089 |
| Filaria_Int | Varicella_Int | 0.063 |
| Filaria_Int | Measles_OD_DB_Int | -0.145 |
| Filaria_Int | Measles_Int | -0.039 |
| Filaria_Int | HepA_Int | -0.130 |
| Filaria_Int | Tetanus_Int | 0.000 |
| Filaria_Int | Diptheria_Int | 0.000 |
| Filaria_Int | Rubella_Int | -0.009 |
| Filaria_Int | CMV_Int | -0.008 |
| Filaria_Int | HepB_cAb_Int | -0.033 |
| Filaria_Int | HepB_eAb_Int | 0.000 |
| Filaria_Int | HepB_eAg_Int | 0.000 |
| Filaria_Int | HepC_Int | -0.033 |
| Filaria_Int | Schistosoma_int | 0.091 |
| Filaria_Int | Strongyloides_Int | 0.001 |
| Filaria_Int | Filaria_Int | 1.000 |

FIG. 21I3-R

| 10.89% - Region_of_Origin=6, Sex=Female, IFN_gamma=0-7.5 |||
|---|---|---|
| Property 1 | Property 2 | Corr. Coefficient |
| IL_1_alpha | IL_1_alpha | 1.000 |
| IL_1_alpha | IL_1_beta | 0.389 |
| IL_1_alpha | IL_2 | 0.386 |
| IL_1_alpha | IL_4 | 0.628 |
| IL_1_alpha | IL_5 | 0.474 |
| IL_1_alpha | IL_6 | 0.008 |
| IL_1_alpha | IL_8 | 0.351 |
| IL_1_alpha | IL_10 | 0.472 |
| IL_1_alpha | IL_12p70 | 0.694 |
| IL_1_alpha | IL_13 | 0.375 |
| IL_1_alpha | IL_15 | 0.458 |
| IL_1_alpha | IL_17 | 0.526 |

| 10.53% - Region_of_Origin=1, Sex=Female, IFN_gamma=0-7.5 |||
|---|---|---|
| Property 1 | Property 2 | Corr. Coefficient |
| IL_1_alpha | IL_1_alpha | 1.000 |
| IL_1_alpha | IL_1_beta | 0.542 |
| IL_1_alpha | IL_2 | 0.318 |
| IL_1_alpha | IL_4 | 0.388 |
| IL_1_alpha | IL_5 | 0.398 |
| IL_1_alpha | IL_6 | 0.090 |
| IL_1_alpha | IL_8 | 0.325 |
| IL_1_alpha | IL_10 | 0.278 |
| IL_1_alpha | IL_12p70 | 0.657 |
| IL_1_alpha | IL_13 | 0.272 |
| IL_1_alpha | IL_15 | 0.540 |
| IL_1_alpha | IL_17 | 0.478 |

FIG. 21I4-A

| | | | | | | |
|---|---|---|---|---|---|---|
| IL_1_alpha | IL_23 | 0.287 | | IL_1_alpha | IL_23 | 0.143 |
| IL_1_alpha | IFN_gamma | 0.000 | | IL_1_alpha | IFN_gamma | 0.000 |
| IL_1_alpha | TNF_alpha | 0.456 | | IL_1_alpha | TNF_alpha | 0.608 |
| IL_1_alpha | TNF_beta | 0.578 | | IL_1_alpha | TNF_beta | 0.407 |
| IL_1_alpha | Varicella_Int | -0.049 | | IL_1_alpha | Varicella_Int | 0.103 |
| IL_1_alpha | Measles_OD_DB_Int | 0.139 | | IL_1_alpha | Measles_OD_DB_Int | -0.056 |
| IL_1_alpha | Measles_Int | 0.083 | | IL_1_alpha | Measles_Int | -0.147 |
| IL_1_alpha | HepA_Int | -0.040 | | IL_1_alpha | HepA_Int | -0.157 |
| IL_1_alpha | Tetanus_Int | 0.000 | | IL_1_alpha | Tetanus_Int | 0.000 |
| IL_1_alpha | Diptheria_Int | 0.000 | | IL_1_alpha | Diptheria_Int | 0.000 |
| IL_1_alpha | Rubella_Int | -0.033 | | IL_1_alpha | Rubella_Int | 0.176 |
| IL_1_alpha | CMV_Int | 0.065 | | IL_1_alpha | CMV_Int | 0.000 |
| IL_1_alpha | HepB_cAb_Int | -0.165 | | IL_1_alpha | HepB_cAb_Int | 0.059 |
| IL_1_alpha | HepB_eAb_Int | 0.000 | | IL_1_alpha | HepB_eAb_Int | 0.000 |
| IL_1_alpha | HepB_eAg_Int | -0.208 | | IL_1_alpha | HepB_eAg_Int | -0.252 |
| IL_1_alpha | HepC_Int | -0.078 | | IL_1_alpha | HepC_Int | 0.073 |
| IL_1_alpha | Schistosoma_int | 0.010 | | IL_1_alpha | Schistosoma_int | 0.079 |
| IL_1_alpha | Strongyloides_Int | 0.083 | | IL_1_alpha | Strongyloides_Int | 0.006 |
| IL_1_alpha | Filaria_Int | 0.116 | | IL_1_alpha | Filaria_Int | -0.038 |
| IL_1_beta | IL_1_alpha | 0.389 | | IL_1_beta | IL_1_alpha | 0.542 |
| IL_1_beta | IL_1_beta | 1.000 | | IL_1_beta | IL_1_beta | 1.000 |
| IL_1_beta | IL_2 | 0.328 | | IL_1_beta | IL_2 | 0.415 |
| IL_1_beta | IL_4 | 0.560 | | IL_1_beta | IL_4 | 0.471 |
| IL_1_beta | IL_5 | 0.367 | | IL_1_beta | IL_5 | 0.421 |
| IL_1_beta | IL_6 | 0.189 | | IL_1_beta | IL_6 | 0.397 |
| IL_1_beta | IL_8 | 0.245 | | IL_1_beta | IL_8 | 0.319 |
| IL_1_beta | IL_10 | 0.495 | | IL_1_beta | IL_10 | 0.394 |
| IL_1_beta | IL_12p70 | 0.435 | | IL_1_beta | IL_12p70 | 0.531 |
| IL_1_beta | IL_13 | 0.384 | | IL_1_beta | IL_13 | 0.390 |
| IL_1_beta | IL_15 | 0.347 | | IL_1_beta | IL_15 | 0.417 |
| IL_1_beta | IL_17 | 0.481 | | IL_1_beta | IL_17 | 0.437 |
| IL_1_beta | IL_23 | 0.278 | | IL_1_beta | IL_23 | 0.139 |
| IL_1_beta | IFN_gamma | 0.000 | | IL_1_beta | IFN_gamma | 0.000 |
| IL_1_beta | TNF_alpha | 0.725 | | IL_1_beta | TNF_alpha | 0.525 |
| IL_1_beta | TNF_beta | 0.454 | | IL_1_beta | TNF_beta | 0.506 |
| IL_1_beta | Varicella_Int | 0.005 | | IL_1_beta | Varicella_Int | -0.056 |
| IL_1_beta | Measles_OD_DB_Int | 0.016 | | IL_1_beta | Measles_OD_DB_Int | 0.110 |
| IL_1_beta | Measles_Int | 0.058 | | IL_1_beta | Measles_Int | -0.037 |
| IL_1_beta | HepA_Int | 0.033 | | IL_1_beta | HepA_Int | -0.255 |
| IL_1_beta | Tetanus_Int | 0.000 | | IL_1_beta | Tetanus_Int | 0.000 |
| IL_1_beta | Diptheria_Int | 0.000 | | IL_1_beta | Diptheria_Int | 0.000 |
| IL_1_beta | Rubella_Int | 0.025 | | IL_1_beta | Rubella_Int | 0.165 |
| IL_1_beta | CMV_Int | 0.021 | | IL_1_beta | CMV_Int | 0.000 |
| IL_1_beta | HepB_cAb_Int | -0.025 | | IL_1_beta | HepB_cAb_Int | -0.152 |
| IL_1_beta | HepB_eAb_Int | 0.000 | | IL_1_beta | HepB_eAb_Int | 0.000 |
| IL_1_beta | HepB_eAg_Int | -0.090 | | IL_1_beta | HepB_eAg_Int | 0.159 |
| IL_1_beta | HepC_Int | -0.084 | | IL_1_beta | HepC_Int | 0.072 |
| IL_1_beta | Schistosoma_int | 0.183 | | IL_1_beta | Schistosoma_int | -0.122 |
| IL_1_beta | Strongyloides_Int | 0.129 | | IL_1_beta | Strongyloides_Int | 0.027 |
| IL_1_beta | Filaria_Int | 0.072 | | IL_1_beta | Filaria_Int | 0.067 |
| IL_2 | IL_1_alpha | 0.386 | | IL_2 | IL_1_alpha | 0.318 |
| IL_2 | IL_1_beta | 0.328 | | IL_2 | IL_1_beta | 0.415 |
| IL_2 | IL_2 | 1.000 | | IL_2 | IL_2 | 1.000 |
| IL_2 | IL_4 | 0.166 | | IL_2 | IL_4 | 0.355 |
| IL_2 | IL_5 | 0.173 | | IL_2 | IL_5 | 0.120 |
| IL_2 | IL_6 | 0.568 | | IL_2 | IL_6 | 0.151 |
| IL_2 | IL_8 | 0.117 | | IL_2 | IL_8 | 0.255 |

FIG. 2114-B

| | | | | | | |
|---|---|---|---|---|---|---|
| IL_2 | IL_10 | 0.222 | | IL_2 | IL_10 | 0.077 |
| IL_2 | IL_12p70 | 0.271 | | IL_2 | IL_12p70 | 0.567 |
| IL_2 | IL_13 | 0.012 | | IL_2 | IL_13 | 0.045 |
| IL_2 | IL_15 | 0.019 | | IL_2 | IL_15 | 0.248 |
| IL_2 | IL_17 | 0.255 | | IL_2 | IL_17 | 0.379 |
| IL_2 | IL_23 | 0.167 | | IL_2 | IL_23 | 0.432 |
| IL_2 | IFN_gamma | 0.000 | | IL_2 | IFN_gamma | 0.000 |
| IL_2 | TNF_alpha | 0.203 | | IL_2 | TNF_alpha | 0.398 |
| IL_2 | TNF_beta | 0.289 | | IL_2 | TNF_beta | 0.547 |
| IL_2 | Varicella_Int | -0.043 | | IL_2 | Varicella_Int | 0.116 |
| IL_2 | Measles_OD_DB_Int | 0.036 | | IL_2 | Measles_OD_DB_Int | 0.067 |
| IL_2 | Measles_Int | -0.070 | | IL_2 | Measles_Int | 0.130 |
| IL_2 | HepA_Int | 0.054 | | IL_2 | HepA_Int | -0.194 |
| IL_2 | Tetanus_Int | 0.000 | | IL_2 | Tetanus_Int | 0.000 |
| IL_2 | Diptheria_Int | 0.000 | | IL_2 | Diptheria_Int | 0.000 |
| IL_2 | Rubella_Int | 0.077 | | IL_2 | Rubella_Int | 0.257 |
| IL_2 | CMV_Int | 0.055 | | IL_2 | CMV_Int | 0.000 |
| IL_2 | HepB_cAb_Int | 0.019 | | IL_2 | HepB_cAb_Int | -0.035 |
| IL_2 | HepB_eAb_Int | 0.000 | | IL_2 | HepB_eAb_Int | 0.000 |
| IL_2 | HepB_eAg_Int | -0.258 | | IL_2 | HepB_eAg_Int | -0.250 |
| IL_2 | HepC_Int | -0.049 | | IL_2 | HepC_Int | 0.197 |
| IL_2 | Schistosoma_int | -0.026 | | IL_2 | Schistosoma_int | -0.141 |
| IL_2 | Strongyloides_Int | 0.066 | | IL_2 | Strongyloides_Int | 0.224 |
| IL_2 | Filaria_Int | 0.070 | | IL_2 | Filaria_Int | 0.074 |
| IL_4 | IL_1_alpha | 0.628 | | IL_4 | IL_1_alpha | 0.388 |
| IL_4 | IL_1_beta | 0.560 | | IL_4 | IL_1_beta | 0.471 |
| IL_4 | IL_2 | 0.166 | | IL_4 | IL_2 | 0.355 |
| IL_4 | IL_4 | 1.000 | | IL_4 | IL_4 | 1.000 |
| IL_4 | IL_5 | 0.544 | | IL_4 | IL_5 | 0.287 |
| IL_4 | IL_6 | -0.019 | | IL_4 | IL_6 | 0.101 |
| IL_4 | IL_8 | 0.360 | | IL_4 | IL_8 | 0.282 |
| IL_4 | IL_10 | 0.544 | | IL_4 | IL_10 | 0.253 |
| IL_4 | IL_12p70 | 0.649 | | IL_4 | IL_12p70 | 0.443 |
| IL_4 | IL_13 | 0.628 | | IL_4 | IL_13 | 0.262 |
| IL_4 | IL_15 | 0.504 | | IL_4 | IL_15 | 0.383 |
| IL_4 | IL_17 | 0.615 | | IL_4 | IL_17 | 0.325 |
| IL_4 | IL_23 | 0.405 | | IL_4 | IL_23 | 0.058 |
| IL_4 | IFN_gamma | 0.000 | | IL_4 | IFN_gamma | 0.000 |
| IL_4 | TNF_alpha | 0.607 | | IL_4 | TNF_alpha | 0.452 |
| IL_4 | TNF_beta | 0.546 | | IL_4 | TNF_beta | 0.452 |
| IL_4 | Varicella_Int | 0.050 | | IL_4 | Varicella_Int | -0.151 |
| IL_4 | Measles_OD_DB_Int | 0.047 | | IL_4 | Measles_OD_DB_Int | -0.158 |
| IL_4 | Measles_Int | -0.061 | | IL_4 | Measles_Int | 0.099 |
| IL_4 | HepA_Int | -0.016 | | IL_4 | HepA_Int | -0.109 |
| IL_4 | Tetanus_Int | 0.000 | | IL_4 | Tetanus_Int | 0.000 |
| IL_4 | Diptheria_Int | 0.000 | | IL_4 | Diptheria_Int | 0.000 |
| IL_4 | Rubella_Int | 0.007 | | IL_4 | Rubella_Int | 0.015 |
| IL_4 | CMV_Int | 0.064 | | IL_4 | CMV_Int | 0.000 |
| IL_4 | HepB_cAb_Int | 0.012 | | IL_4 | HepB_cAb_Int | 0.046 |
| IL_4 | HepB_eAb_Int | 0.000 | | IL_4 | HepB_eAb_Int | 0.000 |
| IL_4 | HepB_eAg_Int | -0.272 | | IL_4 | HepB_eAg_Int | -0.339 |
| IL_4 | HepC_Int | -0.064 | | IL_4 | HepC_Int | 0.088 |
| IL_4 | Schistosoma_int | 0.044 | | IL_4 | Schistosoma_int | 0.001 |
| IL_4 | Strongyloides_Int | 0.152 | | IL_4 | Strongyloides_Int | -0.045 |
| IL_4 | Filaria_Int | 0.020 | | IL_4 | Filaria_Int | 0.071 |
| IL_5 | IL_1_alpha | 0.474 | | IL_5 | IL_1_alpha | 0.398 |
| IL_5 | IL_1_beta | 0.367 | | IL_5 | IL_1_beta | 0.421 |

FIG. 2114-C

| | | | | | | |
|---|---|---|---|---|---|---|
| IL_5 | IL_2 | 0.173 | | IL_5 | IL_2 | 0.120 |
| IL_5 | IL_4 | 0.544 | | IL_5 | IL_4 | 0.287 |
| IL_5 | IL_5 | 1.000 | | IL_5 | IL_5 | 1.000 |
| IL_5 | IL_6 | -0.011 | | IL_5 | IL_6 | 0.342 |
| IL_5 | IL_8 | 0.156 | | IL_5 | IL_8 | 0.384 |
| IL_5 | IL_10 | 0.557 | | IL_5 | IL_10 | 0.865 |
| IL_5 | IL_12p70 | 0.628 | | IL_5 | IL_12p70 | 0.464 |
| IL_5 | IL_13 | 0.458 | | IL_5 | IL_13 | 0.833 |
| IL_5 | IL_15 | 0.366 | | IL_5 | IL_15 | 0.396 |
| IL_5 | IL_17 | 0.691 | | IL_5 | IL_17 | 0.289 |
| IL_5 | IL_23 | 0.139 | | IL_5 | IL_23 | 0.128 |
| IL_5 | IFN_gamma | 0.000 | | IL_5 | IFN_gamma | 0.000 |
| IL_5 | TNF_alpha | 0.387 | | IL_5 | TNF_alpha | 0.171 |
| IL_5 | TNF_beta | 0.592 | | IL_5 | TNF_beta | 0.214 |
| IL_5 | Varicella_Int | 0.066 | | IL_5 | Varicella_Int | 0.039 |
| IL_5 | Measles_OD_DB_Int | 0.115 | | IL_5 | Measles_OD_DB_Int | 0.011 |
| IL_5 | Measles_Int | 0.045 | | IL_5 | Measles_Int | 0.069 |
| IL_5 | HepA_Int | -0.000 | | IL_5 | HepA_Int | -0.062 |
| IL_5 | Tetanus_Int | 0.000 | | IL_5 | Tetanus_Int | 0.000 |
| IL_5 | Diptheria_Int | 0.000 | | IL_5 | Diptheria_Int | 0.000 |
| IL_5 | Rubella_Int | -0.058 | | IL_5 | Rubella_Int | 0.089 |
| IL_5 | CMV_Int | 0.091 | | IL_5 | CMV_Int | 0.000 |
| IL_5 | HepB_cAb_Int | 0.068 | | IL_5 | HepB_cAb_Int | -0.019 |
| IL_5 | HepB_eAb_Int | 0.000 | | IL_5 | HepB_eAb_Int | 0.000 |
| IL_5 | HepB_eAg_Int | -0.316 | | IL_5 | HepB_eAg_Int | -0.292 |
| IL_5 | HepC_Int | -0.078 | | IL_5 | HepC_Int | -0.029 |
| IL_5 | Schistosoma_int | 0.037 | | IL_5 | Schistosoma_int | -0.008 |
| IL_5 | Strongyloides_Int | -0.016 | | IL_5 | Strongyloides_Int | -0.033 |
| IL_5 | Filaria_Int | -0.038 | | IL_5 | Filaria_Int | 0.287 |
| IL_6 | IL_1_alpha | 0.008 | | IL_6 | IL_1_alpha | 0.090 |
| IL_6 | IL_1_beta | 0.189 | | IL_6 | IL_1_beta | 0.397 |
| IL_6 | IL_2 | 0.568 | | IL_6 | IL_2 | 0.151 |
| IL_6 | IL_4 | -0.019 | | IL_6 | IL_4 | 0.101 |
| IL_6 | IL_5 | -0.011 | | IL_6 | IL_5 | 0.342 |
| IL_6 | IL_6 | 1.000 | | IL_6 | IL_6 | 1.000 |
| IL_6 | IL_8 | 0.037 | | IL_6 | IL_8 | 0.277 |
| IL_6 | IL_10 | 0.024 | | IL_6 | IL_10 | 0.315 |
| IL_6 | IL_12p70 | 0.010 | | IL_6 | IL_12p70 | 0.112 |
| IL_6 | IL_13 | 0.053 | | IL_6 | IL_13 | 0.385 |
| IL_6 | IL_15 | 0.064 | | IL_6 | IL_15 | 0.284 |
| IL_6 | IL_17 | -0.029 | | IL_6 | IL_17 | 0.052 |
| IL_6 | IL_23 | -0.063 | | IL_6 | IL_23 | -0.055 |
| IL_6 | IFN_gamma | 0.000 | | IL_6 | IFN_gamma | 0.000 |
| IL_6 | TNF_alpha | 0.012 | | IL_6 | TNF_alpha | 0.049 |
| IL_6 | TNF_beta | 0.025 | | IL_6 | TNF_beta | 0.104 |
| IL_6 | Varicella_Int | -0.019 | | IL_6 | Varicella_Int | 0.028 |
| IL_6 | Measles_OD_DB_Int | -0.107 | | IL_6 | Measles_OD_DB_Int | 0.098 |
| IL_6 | Measles_Int | -0.130 | | IL_6 | Measles_Int | 0.066 |
| IL_6 | HepA_Int | 0.106 | | IL_6 | HepA_Int | -0.222 |
| IL_6 | Tetanus_Int | 0.000 | | IL_6 | Tetanus_Int | 0.000 |
| IL_6 | Diptheria_Int | 0.000 | | IL_6 | Diptheria_Int | 0.000 |
| IL_6 | Rubella_Int | 0.207 | | IL_6 | Rubella_Int | -0.025 |
| IL_6 | CMV_Int | -0.036 | | IL_6 | CMV_Int | 0.000 |
| IL_6 | HepB_cAb_Int | 0.115 | | IL_6 | HepB_cAb_Int | -0.094 |
| IL_6 | HepB_eAb_Int | 0.000 | | IL_6 | HepB_eAb_Int | 0.000 |
| IL_6 | HepB_eAg_Int | -0.350 | | IL_6 | HepB_eAg_Int | -0.292 |
| IL_6 | HepC_Int | -0.044 | | IL_6 | HepC_Int | -0.060 |

FIG. 2114-D

| | | | | | | |
|---|---|---|---|---|---|---|
| IL_6 | Schistosoma_int | -0.024 | | IL_6 | Schistosoma_int | -0.108 |
| IL_6 | Strongyloides_Int | -0.159 | | IL_6 | Strongyloides_Int | -0.087 |
| IL_6 | Filaria_Int | -0.095 | | IL_6 | Filaria_Int | -0.040 |
| IL_8 | IL_1_alpha | 0.351 | | IL_8 | IL_1_alpha | 0.325 |
| IL_8 | IL_1_beta | 0.245 | | IL_8 | IL_1_beta | 0.319 |
| IL_8 | IL_2 | 0.117 | | IL_8 | IL_2 | 0.255 |
| IL_8 | IL_4 | 0.360 | | IL_8 | IL_4 | 0.282 |
| IL_8 | IL_5 | 0.156 | | IL_8 | IL_5 | 0.384 |
| IL_8 | IL_6 | 0.037 | | IL_8 | IL_6 | 0.277 |
| IL_8 | IL_8 | 1.000 | | IL_8 | IL_8 | 1.000 |
| IL_8 | IL_10 | 0.116 | | IL_8 | IL_10 | 0.483 |
| IL_8 | IL_12p70 | 0.240 | | IL_8 | IL_12p70 | 0.478 |
| IL_8 | IL_13 | 0.247 | | IL_8 | IL_13 | 0.335 |
| IL_8 | IL_15 | 0.386 | | IL_8 | IL_15 | 0.388 |
| IL_8 | IL_17 | 0.189 | | IL_8 | IL_17 | 0.181 |
| IL_8 | IL_23 | 0.419 | | IL_8 | IL_23 | -0.013 |
| IL_8 | IFN_gamma | 0.000 | | IL_8 | IFN_gamma | 0.000 |
| IL_8 | TNF_alpha | 0.295 | | IL_8 | TNF_alpha | 0.240 |
| IL_8 | TNF_beta | 0.177 | | IL_8 | TNF_beta | 0.239 |
| IL_8 | Varicella_Int | -0.174 | | IL_8 | Varicella_Int | -0.020 |
| IL_8 | Measles_OD_DB_Int | -0.257 | | IL_8 | Measles_OD_DB_Int | -0.045 |
| IL_8 | Measles_Int | 0.098 | | IL_8 | Measles_Int | 0.127 |
| IL_8 | HepA_Int | -0.156 | | IL_8 | HepA_Int | -0.127 |
| IL_8 | Tetanus_Int | 0.000 | | IL_8 | Tetanus_Int | 0.000 |
| IL_8 | Diptheria_Int | 0.000 | | IL_8 | Diptheria_Int | 0.000 |
| IL_8 | Rubella_Int | 0.101 | | IL_8 | Rubella_Int | 0.123 |
| IL_8 | CMV_Int | 0.101 | | IL_8 | CMV_Int | 0.000 |
| IL_8 | HepB_cAb_Int | -0.134 | | IL_8 | HepB_cAb_Int | 0.122 |
| IL_8 | HepB_eAb_Int | 0.000 | | IL_8 | HepB_eAb_Int | 0.000 |
| IL_8 | HepB_eAg_Int | -0.183 | | IL_8 | HepB_eAg_Int | -0.227 |
| IL_8 | HepC_Int | -0.063 | | IL_8 | HepC_Int | 0.298 |
| IL_8 | Schistosoma_int | -0.004 | | IL_8 | Schistosoma_int | 0.019 |
| IL_8 | Strongyloides_Int | 0.031 | | IL_8 | Strongyloides_Int | 0.162 |
| IL_8 | Filaria_Int | -0.099 | | IL_8 | Filaria_Int | 0.010 |
| IL_10 | IL_1_alpha | 0.472 | | IL_10 | IL_1_alpha | 0.278 |
| IL_10 | IL_1_beta | 0.495 | | IL_10 | IL_1_beta | 0.394 |
| IL_10 | IL_2 | 0.222 | | IL_10 | IL_2 | 0.077 |
| IL_10 | IL_4 | 0.544 | | IL_10 | IL_4 | 0.253 |
| IL_10 | IL_5 | 0.557 | | IL_10 | IL_5 | 0.865 |
| IL_10 | IL_6 | 0.024 | | IL_10 | IL_6 | 0.315 |
| IL_10 | IL_8 | 0.116 | | IL_10 | IL_8 | 0.483 |
| IL_10 | IL_10 | 1.000 | | IL_10 | IL_10 | 1.000 |
| IL_10 | IL_12p70 | 0.612 | | IL_10 | IL_12p70 | 0.383 |
| IL_10 | IL_13 | 0.545 | | IL_10 | IL_13 | 0.888 |
| IL_10 | IL_15 | 0.295 | | IL_10 | IL_15 | 0.211 |
| IL_10 | IL_17 | 0.750 | | IL_10 | IL_17 | 0.182 |
| IL_10 | IL_23 | 0.103 | | IL_10 | IL_23 | 0.059 |
| IL_10 | IFN_gamma | 0.000 | | IL_10 | IFN_gamma | 0.000 |
| IL_10 | TNF_alpha | 0.412 | | IL_10 | TNF_alpha | 0.091 |
| IL_10 | TNF_beta | 0.654 | | IL_10 | TNF_beta | 0.172 |
| IL_10 | Varicella_Int | 0.083 | | IL_10 | Varicella_Int | 0.022 |
| IL_10 | Measles_OD_DB_Int | 0.137 | | IL_10 | Measles_OD_DB_Int | 0.062 |
| IL_10 | Measles_Int | -0.037 | | IL_10 | Measles_Int | 0.028 |
| IL_10 | HepA_Int | 0.077 | | IL_10 | HepA_Int | -0.048 |
| IL_10 | Tetanus_Int | 0.000 | | IL_10 | Tetanus_Int | 0.000 |
| IL_10 | Diptheria_Int | 0.000 | | IL_10 | Diptheria_Int | 0.000 |
| IL_10 | Rubella_Int | -0.089 | | IL_10 | Rubella_Int | 0.041 |

FIG. 2114-E

| | | | | | | |
|---|---|---|---|---|---|---|
| IL_10 | CMV_Int | -0.003 | | IL_10 | CMV_Int | 0.000 |
| IL_10 | HepB_cAb_Int | -0.093 | | IL_10 | HepB_cAb_Int | -0.047 |
| IL_10 | HepB_eAb_Int | 0.000 | | IL_10 | HepB_eAb_Int | 0.000 |
| IL_10 | HepB_eAg_Int | -0.366 | | IL_10 | HepB_eAg_Int | -0.200 |
| IL_10 | HepC_Int | -0.095 | | IL_10 | HepC_int | 0.086 |
| IL_10 | Schistosoma_int | -0.031 | | IL_10 | Schistosoma_int | -0.080 |
| IL_10 | Strongyloides_Int | -0.042 | | IL_10 | Strongyloides_Int | -0.079 |
| IL_10 | Filaria_Int | 0.104 | | IL_10 | Filaria_Int | 0.288 |
| IL_12p70 | IL_1_alpha | 0.694 | | IL_12p70 | IL_1_alpha | 0.657 |
| IL_12p70 | IL_1_beta | 0.435 | | IL_12p70 | IL_1_beta | 0.531 |
| IL_12p70 | IL_2 | 0.271 | | IL_12p70 | IL_2 | 0.567 |
| IL_12p70 | IL_4 | 0.649 | | IL_12p70 | IL_4 | 0.443 |
| IL_12p70 | IL_5 | 0.628 | | IL_12p70 | IL_5 | 0.464 |
| IL_12p70 | IL_6 | 0.010 | | IL_12p70 | IL_6 | 0.112 |
| IL_12p70 | IL_8 | 0.240 | | IL_12p70 | IL_8 | 0.478 |
| IL_12p70 | IL_10 | 0.612 | | IL_12p70 | IL_10 | 0.383 |
| IL_12p70 | IL_12p70 | 1.000 | | IL_12p70 | IL_12p70 | 1.000 |
| IL_12p70 | IL_13 | 0.629 | | IL_12p70 | IL_13 | 0.299 |
| IL_12p70 | IL_15 | 0.401 | | IL_12p70 | IL_15 | 0.598 |
| IL_12p70 | IL_17 | 0.626 | | IL_12p70 | IL_17 | 0.590 |
| IL_12p70 | IL_23 | 0.374 | | IL_12p70 | IL_23 | 0.488 |
| IL_12p70 | IFN_gamma | 0.000 | | IL_12p70 | IFN_gamma | 0.000 |
| IL_12p70 | TNF_alpha | 0.504 | | IL_12p70 | TNF_alpha | 0.491 |
| IL_12p70 | TNF_beta | 0.662 | | IL_12p70 | TNF_beta | 0.528 |
| IL_12p70 | Varicella_Int | 0.041 | | IL_12p70 | Varicella_Int | 0.028 |
| IL_12p70 | Measles_OD_DB_Int | 0.075 | | IL_12p70 | Measles_OD_DB_Int | -0.043 |
| IL_12p70 | Measles_Int | -0.019 | | IL_12p70 | Measles_Int | 0.060 |
| IL_12p70 | HepA_Int | -0.023 | | IL_12p70 | HepA_Int | -0.235 |
| IL_12p70 | Tetanus_Int | 0.000 | | IL_12p70 | Tetanus_Int | 0.000 |
| IL_12p70 | Diptheria_Int | 0.000 | | IL_12p70 | Diptheria_Int | 0.000 |
| IL_12p70 | Rubella_Int | -0.061 | | IL_12p70 | Rubella_Int | 0.371 |
| IL_12p70 | CMV_Int | 0.031 | | IL_12p70 | CMV_Int | 0.000 |
| IL_12p70 | HepB_cAb_Int | -0.058 | | IL_12p70 | HepB_cAb_Int | 0.062 |
| IL_12p70 | HepB_eAb_Int | 0.000 | | IL_12p70 | HepB_eAb_Int | 0.000 |
| IL_12p70 | HepB_eAg_Int | -0.504 | | IL_12p70 | HepB_eAg_Int | -0.320 |
| IL_12p70 | HepC_Int | -0.101 | | IL_12p70 | HepC_int | 0.106 |
| IL_12p70 | Schistosoma_int | -0.021 | | IL_12p70 | Schistosoma_int | -0.030 |
| IL_12p70 | Strongyloides_Int | 0.020 | | IL_12p70 | Strongyloides_Int | 0.066 |
| IL_12p70 | Filaria_Int | 0.103 | | IL_12p70 | Filaria_Int | 0.099 |
| IL_13 | IL_1_alpha | 0.375 | | IL_13 | IL_1_alpha | 0.272 |
| IL_13 | IL_1_beta | 0.384 | | IL_13 | IL_1_beta | 0.390 |
| IL_13 | IL_2 | 0.012 | | IL_13 | IL_2 | 0.045 |
| IL_13 | IL_4 | 0.628 | | IL_13 | IL_4 | 0.262 |
| IL_13 | IL_5 | 0.458 | | IL_13 | IL_5 | 0.833 |
| IL_13 | IL_6 | 0.053 | | IL_13 | IL_6 | 0.385 |
| IL_13 | IL_8 | 0.247 | | IL_13 | IL_8 | 0.335 |
| IL_13 | IL_10 | 0.545 | | IL_13 | IL_10 | 0.888 |
| IL_13 | IL_12p70 | 0.629 | | IL_13 | IL_12p70 | 0.299 |
| IL_13 | IL_13 | 1.000 | | IL_13 | IL_13 | 1.000 |
| IL_13 | IL_15 | 0.454 | | IL_13 | IL_15 | 0.199 |
| IL_13 | IL_17 | 0.545 | | IL_13 | IL_17 | 0.181 |
| IL_13 | IL_23 | 0.226 | | IL_13 | IL_23 | -0.002 |
| IL_13 | IFN_gamma | 0.000 | | IL_13 | IFN_gamma | 0.000 |
| IL_13 | TNF_alpha | 0.499 | | IL_13 | TNF_alpha | 0.143 |
| IL_13 | TNF_beta | 0.429 | | IL_13 | TNF_beta | 0.162 |
| IL_13 | Varicella_Int | 0.059 | | IL_13 | Varicella_Int | 0.014 |
| IL_13 | Measles_OD_DB_Int | -0.024 | | IL_13 | Measles_OD_DB_Int | 0.005 |

FIG. 21I4-F

| | | | | | | |
|---|---|---|---|---|---|---|
| IL_13 | Measles_Int | -0.124 | | IL_13 | Measles_Int | 0.043 |
| IL_13 | HepA_Int | 0.027 | | IL_13 | HepA_Int | -0.098 |
| IL_13 | Tetanus_Int | 0.000 | | IL_13 | Tetanus_Int | 0.000 |
| IL_13 | Diptheria_Int | 0.000 | | IL_13 | Diptheria_Int | 0.000 |
| IL_13 | Rubella_Int | 0.118 | | IL_13 | Rubella_Int | 0.017 |
| IL_13 | CMV_Int | -0.017 | | IL_13 | CMV_Int | 0.000 |
| IL_13 | HepB_cAb_Int | 0.092 | | IL_13 | HepB_cAb_Int | -0.041 |
| IL_13 | HepB_eAb_Int | 0.000 | | IL_13 | HepB_eAb_Int | 0.000 |
| IL_13 | HepB_eAg_Int | -0.357 | | IL_13 | HepB_eAg_Int | -0.235 |
| IL_13 | HepC_Int | -0.106 | | IL_13 | HepC_Int | -0.037 |
| IL_13 | Schistosoma_int | -0.061 | | IL_13 | Schistosoma_int | -0.072 |
| IL_13 | Strongyloides_Int | -0.050 | | IL_13 | Strongyloides_Int | -0.149 |
| IL_13 | Filaria_Int | 0.125 | | IL_13 | Filaria_Int | 0.185 |
| IL_15 | IL_1_alpha | 0.458 | | IL_15 | IL_1_alpha | 0.540 |
| IL_15 | IL_1_beta | 0.347 | | IL_15 | IL_1_beta | 0.417 |
| IL_15 | IL_2 | 0.019 | | IL_15 | IL_2 | 0.248 |
| IL_15 | IL_4 | 0.504 | | IL_15 | IL_4 | 0.383 |
| IL_15 | IL_5 | 0.366 | | IL_15 | IL_5 | 0.396 |
| IL_15 | IL_6 | 0.064 | | IL_15 | IL_6 | 0.284 |
| IL_15 | IL_8 | 0.386 | | IL_15 | IL_8 | 0.388 |
| IL_15 | IL_10 | 0.295 | | IL_15 | IL_10 | 0.211 |
| IL_15 | IL_12p70 | 0.401 | | IL_15 | IL_12p70 | 0.598 |
| IL_15 | IL_13 | 0.454 | | IL_15 | IL_13 | 0.199 |
| IL_15 | IL_15 | 1.000 | | IL_15 | IL_15 | 1.000 |
| IL_15 | IL_17 | 0.334 | | IL_15 | IL_17 | 0.543 |
| IL_15 | IL_23 | 0.217 | | IL_15 | IL_23 | 0.104 |
| IL_15 | IFN_gamma | 0.000 | | IL_15 | IFN_gamma | 0.000 |
| IL_15 | TNF_alpha | 0.349 | | IL_15 | TNF_alpha | 0.444 |
| IL_15 | TNF_beta | 0.293 | | IL_15 | TNF_beta | 0.365 |
| IL_15 | Varicella_Int | -0.112 | | IL_15 | Varicella_Int | 0.096 |
| IL_15 | Measles_OD_DB_Int | -0.037 | | IL_15 | Measles_OD_DB_Int | -0.021 |
| IL_15 | Measles_Int | -0.054 | | IL_15 | Measles_Int | 0.035 |
| IL_15 | HepA_Int | 0.083 | | IL_15 | HepA_Int | -0.095 |
| IL_15 | Tetanus_Int | 0.000 | | IL_15 | Tetanus_Int | 0.000 |
| IL_15 | Diptheria_Int | 0.000 | | IL_15 | Diptheria_Int | 0.000 |
| IL_15 | Rubella_Int | 0.155 | | IL_15 | Rubella_Int | 0.239 |
| IL_15 | CMV_Int | 0.189 | | IL_15 | CMV_Int | 0.000 |
| IL_15 | HepB_cAb_Int | 0.015 | | IL_15 | HepB_cAb_Int | 0.085 |
| IL_15 | HepB_eAb_Int | 0.000 | | IL_15 | HepB_eAb_Int | 0.000 |
| IL_15 | HepB_eAg_Int | -0.262 | | IL_15 | HepB_eAg_Int | -0.347 |
| IL_15 | HepC_Int | -0.108 | | IL_15 | HepC_Int | -0.049 |
| IL_15 | Schistosoma_int | -0.041 | | IL_15 | Schistosoma_int | 0.021 |
| IL_15 | Strongyloides_Int | 0.003 | | IL_15 | Strongyloides_Int | -0.041 |
| IL_15 | Filaria_Int | -0.069 | | IL_15 | Filaria_Int | -0.079 |
| IL_17 | IL_1_alpha | 0.526 | | IL_17 | IL_1_alpha | 0.478 |
| IL_17 | IL_1_beta | 0.481 | | IL_17 | IL_1_beta | 0.437 |
| IL_17 | IL_2 | 0.255 | | IL_17 | IL_2 | 0.379 |
| IL_17 | IL_4 | 0.615 | | IL_17 | IL_4 | 0.325 |
| IL_17 | IL_5 | 0.691 | | IL_17 | IL_5 | 0.289 |
| IL_17 | IL_6 | -0.029 | | IL_17 | IL_6 | 0.052 |
| IL_17 | IL_8 | 0.189 | | IL_17 | IL_8 | 0.181 |
| IL_17 | IL_10 | 0.750 | | IL_17 | IL_10 | 0.182 |
| IL_17 | IL_12p70 | 0.626 | | IL_17 | IL_12p70 | 0.590 |
| IL_17 | IL_13 | 0.545 | | IL_17 | IL_13 | 0.181 |
| IL_17 | IL_15 | 0.334 | | IL_17 | IL_15 | 0.543 |
| IL_17 | IL_17 | 1.000 | | IL_17 | IL_17 | 1.000 |
| IL_17 | IL_23 | 0.236 | | IL_17 | IL_23 | 0.247 |

FIG. 2114-G

| | | | | | | |
|---|---|---|---|---|---|---|
| IL_17 | IFN_gamma | 0.000 | | IL_17 | IFN_gamma | 0.000 |
| IL_17 | TNF_alpha | 0.487 | | IL_17 | TNF_alpha | 0.362 |
| IL_17 | TNF_beta | 0.657 | | IL_17 | TNF_beta | 0.499 |
| IL_17 | Varicella_Int | 0.122 | | IL_17 | Varicella_Int | 0.039 |
| IL_17 | Measles_OD_DB_Int | 0.007 | | IL_17 | Measles_OD_DB_Int | 0.032 |
| IL_17 | Measles_Int | -0.069 | | IL_17 | Measles_Int | 0.074 |
| IL_17 | HepA_Int | 0.044 | | IL_17 | HepA_Int | -0.086 |
| IL_17 | Tetanus_Int | 0.000 | | IL_17 | Tetanus_Int | 0.000 |
| IL_17 | Diptheria_Int | 0.000 | | IL_17 | Diptheria_Int | 0.000 |
| IL_17 | Rubella_Int | -0.043 | | IL_17 | Rubella_Int | 0.264 |
| IL_17 | CMV_Int | 0.025 | | IL_17 | CMV_Int | 0.000 |
| IL_17 | HepB_cAb_Int | -0.017 | | IL_17 | HepB_cAb_Int | 0.022 |
| IL_17 | HepB_eAb_Int | 0.000 | | IL_17 | HepB_eAb_Int | 0.000 |
| IL_17 | HepB_eAg_Int | -0.394 | | IL_17 | HepB_eAg_Int | -0.313 |
| IL_17 | HepC_Int | -0.083 | | IL_17 | HepC_Int | -0.025 |
| IL_17 | Schistosoma_int | -0.012 | | IL_17 | Schistosoma_int | -0.012 |
| IL_17 | Strongyloides_Int | 0.053 | | IL_17 | Strongyloides_Int | -0.019 |
| IL_17 | Filaria_Int | 0.107 | | IL_17 | Filaria_Int | 0.167 |
| IL_23 | IL_1_alpha | 0.287 | | IL_23 | IL_1_alpha | 0.143 |
| IL_23 | IL_1_beta | 0.278 | | IL_23 | IL_1_beta | 0.139 |
| IL_23 | IL_2 | 0.167 | | IL_23 | IL_2 | 0.432 |
| IL_23 | IL_4 | 0.405 | | IL_23 | IL_4 | 0.058 |
| IL_23 | IL_5 | 0.139 | | IL_23 | IL_5 | 0.128 |
| IL_23 | IL_6 | -0.063 | | IL_23 | IL_6 | -0.055 |
| IL_23 | IL_8 | 0.419 | | IL_23 | IL_8 | -0.013 |
| IL_23 | IL_10 | 0.103 | | IL_23 | IL_10 | 0.059 |
| IL_23 | IL_12p70 | 0.374 | | IL_23 | IL_12p70 | 0.488 |
| IL_23 | IL_13 | 0.226 | | IL_23 | IL_13 | -0.002 |
| IL_23 | IL_15 | 0.217 | | IL_23 | IL_15 | 0.104 |
| IL_23 | IL_17 | 0.236 | | IL_23 | IL_17 | 0.247 |
| IL_23 | IL_23 | 1.000 | | IL_23 | IL_23 | 1.000 |
| IL_23 | IFN_gamma | 0.000 | | IL_23 | IFN_gamma | 0.000 |
| IL_23 | TNF_alpha | 0.376 | | IL_23 | TNF_alpha | 0.142 |
| IL_23 | TNF_beta | 0.178 | | IL_23 | TNF_beta | 0.134 |
| IL_23 | Varicella_Int | 0.051 | | IL_23 | Varicella_Int | 0.018 |
| IL_23 | Measles_OD_DB_Int | -0.172 | | IL_23 | Measles_OD_DB_Int | 0.094 |
| IL_23 | Measles_Int | 0.050 | | IL_23 | Measles_Int | 0.042 |
| IL_23 | HepA_Int | -0.112 | | IL_23 | HepA_Int | 0.010 |
| IL_23 | Tetanus_Int | 0.000 | | IL_23 | Tetanus_Int | 0.000 |
| IL_23 | Diptheria_Int | 0.000 | | IL_23 | Diptheria_Int | 0.000 |
| IL_23 | Rubella_Int | 0.068 | | IL_23 | Rubella_Int | 0.091 |
| IL_23 | CMV_Int | 0.045 | | IL_23 | CMV_Int | 0.000 |
| IL_23 | HepB_cAb_Int | -0.015 | | IL_23 | HepB_cAb_Int | 0.077 |
| IL_23 | HepB_eAb_Int | 0.000 | | IL_23 | HepB_eAb_Int | 0.000 |
| IL_23 | HepB_eAg_Int | -0.320 | | IL_23 | HepB_eAg_Int | -0.343 |
| IL_23 | HepC_Int | -0.034 | | IL_23 | HepC_Int | -0.054 |
| IL_23 | Schistosoma_int | -0.025 | | IL_23 | Schistosoma_int | -0.054 |
| IL_23 | Strongyloides_Int | 0.224 | | IL_23 | Strongyloides_Int | 0.036 |
| IL_23 | Filaria_Int | 0.005 | | IL_23 | Filaria_Int | 0.141 |
| IFN_gamma | IL_1_alpha | 0.000 | | IFN_gamma | IL_1_alpha | 0.000 |
| IFN_gamma | IL_1_beta | 0.000 | | IFN_gamma | IL_1_beta | 0.000 |
| IFN_gamma | IL_2 | 0.000 | | IFN_gamma | IL_2 | 0.000 |
| IFN_gamma | IL_4 | 0.000 | | IFN_gamma | IL_4 | 0.000 |
| IFN_gamma | IL_5 | 0.000 | | IFN_gamma | IL_5 | 0.000 |
| IFN_gamma | IL_6 | 0.000 | | IFN_gamma | IL_6 | 0.000 |
| IFN_gamma | IL_8 | 0.000 | | IFN_gamma | IL_8 | 0.000 |
| IFN_gamma | IL_10 | 0.000 | | IFN_gamma | IL_10 | 0.000 |

FIG. 21I4-H

| | | | | | | |
|---|---|---|---|---|---|---|
| IFN_gamma | IL_12p70 | 0.000 | | IFN_gamma | IL_12p70 | 0.000 |
| IFN_gamma | IL_13 | 0.000 | | IFN_gamma | IL_13 | 0.000 |
| IFN_gamma | IL_15 | 0.000 | | IFN_gamma | IL_15 | 0.000 |
| IFN_gamma | IL_17 | 0.000 | | IFN_gamma | IL_17 | 0.000 |
| IFN_gamma | IL_23 | 0.000 | | IFN_gamma | IL_23 | 0.000 |
| IFN_gamma | IFN_gamma | 1.000 | | IFN_gamma | IFN_gamma | 1.000 |
| IFN_gamma | TNF_alpha | 0.000 | | IFN_gamma | TNF_alpha | 0.000 |
| IFN_gamma | TNF_beta | 0.000 | | IFN_gamma | TNF_beta | 0.000 |
| IFN_gamma | Varicella_Int | 0.000 | | IFN_gamma | Varicella_Int | 0.000 |
| IFN_gamma | Measles_OD_DB_Int | 0.000 | | IFN_gamma | Measles_OD_DB_Int | 0.000 |
| IFN_gamma | Measles_Int | 0.000 | | IFN_gamma | Measles_Int | 0.000 |
| IFN_gamma | HepA_Int | 0.000 | | IFN_gamma | HepA_Int | 0.000 |
| IFN_gamma | Tetanus_Int | 0.000 | | IFN_gamma | Tetanus_Int | 0.000 |
| IFN_gamma | Diptheria_Int | 0.000 | | IFN_gamma | Diptheria_Int | 0.000 |
| IFN_gamma | Rubella_Int | 0.000 | | IFN_gamma | Rubella_Int | 0.000 |
| IFN_gamma | CMV_Int | 0.000 | | IFN_gamma | CMV_Int | 0.000 |
| IFN_gamma | HepB_cAb_Int | 0.000 | | IFN_gamma | HepB_cAb_Int | 0.000 |
| IFN_gamma | HepB_eAb_Int | 0.000 | | IFN_gamma | HepB_eAb_Int | 0.000 |
| IFN_gamma | HepB_eAg_Int | 0.000 | | IFN_gamma | HepB_eAg_Int | 0.000 |
| IFN_gamma | HepC_Int | 0.000 | | IFN_gamma | HepC_Int | 0.000 |
| IFN_gamma | Schistosoma_int | 0.000 | | IFN_gamma | Schistosoma_int | 0.000 |
| IFN_gamma | Strongyloides_Int | 0.000 | | IFN_gamma | Strongyloides_Int | 0.000 |
| IFN_gamma | Filaria_Int | 0.000 | | IFN_gamma | Filaria_Int | 0.000 |
| TNF_alpha | IL_1_alpha | 0.456 | | TNF_alpha | IL_1_alpha | 0.608 |
| TNF_alpha | IL_1_beta | 0.725 | | TNF_alpha | IL_1_beta | 0.525 |
| TNF_alpha | IL_2 | 0.203 | | TNF_alpha | IL_2 | 0.398 |
| TNF_alpha | IL_4 | 0.607 | | TNF_alpha | IL_4 | 0.452 |
| TNF_alpha | IL_5 | 0.387 | | TNF_alpha | IL_5 | 0.171 |
| TNF_alpha | IL_6 | 0.012 | | TNF_alpha | IL_6 | 0.049 |
| TNF_alpha | IL_8 | 0.295 | | TNF_alpha | IL_8 | 0.240 |
| TNF_alpha | IL_10 | 0.412 | | TNF_alpha | IL_10 | 0.091 |
| TNF_alpha | IL_12p70 | 0.504 | | TNF_alpha | IL_12p70 | 0.491 |
| TNF_alpha | IL_13 | 0.499 | | TNF_alpha | IL_13 | 0.143 |
| TNF_alpha | IL_15 | 0.349 | | TNF_alpha | IL_15 | 0.444 |
| TNF_alpha | IL_17 | 0.487 | | TNF_alpha | IL_17 | 0.362 |
| TNF_alpha | IL_23 | 0.376 | | TNF_alpha | IL_23 | 0.142 |
| TNF_alpha | IFN_gamma | 0.000 | | TNF_alpha | IFN_gamma | 0.000 |
| TNF_alpha | TNF_alpha | 1.000 | | TNF_alpha | TNF_alpha | 1.000 |
| TNF_alpha | TNF_beta | 0.526 | | TNF_alpha | TNF_beta | 0.576 |
| TNF_alpha | Varicella_Int | -0.024 | | TNF_alpha | Varicella_Int | -0.056 |
| TNF_alpha | Measles_OD_DB_Int | -0.028 | | TNF_alpha | Measles_OD_DB_Int | -0.077 |
| TNF_alpha | Measles_Int | -0.034 | | TNF_alpha | Measles_Int | -0.158 |
| TNF_alpha | HepA_Int | -0.023 | | TNF_alpha | HepA_Int | -0.144 |
| TNF_alpha | Tetanus_Int | 0.000 | | TNF_alpha | Tetanus_Int | 0.000 |
| TNF_alpha | Diptheria_Int | 0.000 | | TNF_alpha | Diptheria_Int | 0.000 |
| TNF_alpha | Rubella_Int | 0.110 | | TNF_alpha | Rubella_Int | 0.030 |
| TNF_alpha | CMV_Int | -0.010 | | TNF_alpha | CMV_Int | 0.000 |
| TNF_alpha | HepB_cAb_Int | -0.062 | | TNF_alpha | HepB_cAb_Int | -0.012 |
| TNF_alpha | HepB_eAb_Int | 0.000 | | TNF_alpha | HepB_eAb_Int | 0.000 |
| TNF_alpha | HepB_eAg_Int | -0.090 | | TNF_alpha | HepB_eAg_Int | -0.250 |
| TNF_alpha | HepC_Int | -0.078 | | TNF_alpha | HepC_Int | -0.032 |
| TNF_alpha | Schistosoma_int | 0.133 | | TNF_alpha | Schistosoma_int | -0.001 |
| TNF_alpha | Strongyloides_Int | 0.180 | | TNF_alpha | Strongyloides_Int | 0.071 |
| TNF_alpha | Filaria_Int | 0.133 | | TNF_alpha | Filaria_Int | -0.030 |
| TNF_beta | IL_1_alpha | 0.578 | | TNF_beta | IL_1_alpha | 0.407 |
| TNF_beta | IL_1_beta | 0.454 | | TNF_beta | IL_1_beta | 0.506 |
| TNF_beta | IL_2 | 0.289 | | TNF_beta | IL_2 | 0.547 |

FIG. 2114-I

| | | | | | | |
|---|---|---|---|---|---|---|
| TNF_beta | IL_4 | 0.546 | | TNF_beta | IL_4 | 0.452 |
| TNF_beta | IL_5 | 0.592 | | TNF_beta | IL_5 | 0.214 |
| TNF_beta | IL_6 | 0.025 | | TNF_beta | IL_6 | 0.104 |
| TNF_beta | IL_8 | 0.177 | | TNF_beta | IL_8 | 0.239 |
| TNF_beta | IL_10 | 0.654 | | TNF_beta | IL_10 | 0.172 |
| TNF_beta | IL_12p70 | 0.662 | | TNF_beta | IL_12p70 | 0.528 |
| TNF_beta | IL_13 | 0.429 | | TNF_beta | IL_13 | 0.162 |
| TNF_beta | IL_15 | 0.293 | | TNF_beta | IL_15 | 0.365 |
| TNF_beta | IL_17 | 0.657 | | TNF_beta | IL_17 | 0.499 |
| TNF_beta | IL_23 | 0.178 | | TNF_beta | IL_23 | 0.134 |
| TNF_beta | IFN_gamma | 0.000 | | TNF_beta | IFN_gamma | 0.000 |
| TNF_beta | TNF_alpha | 0.526 | | TNF_beta | TNF_alpha | 0.576 |
| TNF_beta | TNF_beta | 1.000 | | TNF_beta | TNF_beta | 1.000 |
| TNF_beta | Varicella_Int | 0.044 | | TNF_beta | Varicella_Int | 0.063 |
| TNF_beta | Measles_OD_DB_Int | 0.079 | | TNF_beta | Measles_OD_DB_Int | -0.046 |
| TNF_beta | Measles_Int | -0.051 | | TNF_beta | Measles_Int | 0.025 |
| TNF_beta | HepA_Int | 0.029 | | TNF_beta | HepA_Int | -0.299 |
| TNF_beta | Tetanus_Int | 0.000 | | TNF_beta | Tetanus_Int | 0.000 |
| TNF_beta | Diptheria_Int | 0.000 | | TNF_beta | Diptheria_Int | 0.000 |
| TNF_beta | Rubella_Int | -0.010 | | TNF_beta | Rubella_Int | 0.191 |
| TNF_beta | CMV_Int | -0.027 | | TNF_beta | CMV_Int | 0.000 |
| TNF_beta | HepB_cAb_Int | -0.081 | | TNF_beta | HepB_cAb_Int | -0.065 |
| TNF_beta | HepB_eAb_Int | 0.000 | | TNF_beta | HepB_eAb_Int | 0.000 |
| TNF_beta | HepB_eAg_Int | 0.948 | | TNF_beta | HepB_eAg_Int | -0.250 |
| TNF_beta | HepC_Int | -0.057 | | TNF_beta | HepC_Int | 0.078 |
| TNF_beta | Schistosoma_int | 0.032 | | TNF_beta | Schistosoma_int | -0.057 |
| TNF_beta | Strongyloides_Int | 0.056 | | TNF_beta | Strongyloides_Int | 0.167 |
| TNF_beta | Filaria_Int | 0.060 | | TNF_beta | Filaria_Int | -0.001 |
| Varicella_Int | IL_1_alpha | -0.049 | | Varicella_Int | IL_1_alpha | 0.103 |
| Varicella_Int | IL_1_beta | 0.005 | | Varicella_Int | IL_1_beta | -0.056 |
| Varicella_Int | IL_2 | -0.043 | | Varicella_Int | IL_2 | 0.116 |
| Varicella_Int | IL_4 | 0.050 | | Varicella_Int | IL_4 | -0.151 |
| Varicella_Int | IL_5 | 0.066 | | Varicella_Int | IL_5 | 0.039 |
| Varicella_Int | IL_6 | -0.019 | | Varicella_Int | IL_6 | 0.028 |
| Varicella_Int | IL_8 | -0.174 | | Varicella_Int | IL_8 | -0.020 |
| Varicella_Int | IL_10 | 0.083 | | Varicella_Int | IL_10 | 0.022 |
| Varicella_Int | IL_12p70 | 0.041 | | Varicella_Int | IL_12p70 | 0.028 |
| Varicella_Int | IL_13 | 0.059 | | Varicella_Int | IL_13 | 0.014 |
| Varicella_Int | IL_15 | -0.112 | | Varicella_Int | IL_15 | 0.096 |
| Varicella_Int | IL_17 | 0.122 | | Varicella_Int | IL_17 | 0.039 |
| Varicella_Int | IL_23 | 0.051 | | Varicella_Int | IL_23 | 0.018 |
| Varicella_Int | IFN_gamma | 0.000 | | Varicella_Int | IFN_gamma | 0.000 |
| Varicella_Int | TNF_alpha | -0.024 | | Varicella_Int | TNF_alpha | -0.056 |
| Varicella_Int | TNF_beta | 0.044 | | Varicella_Int | TNF_beta | 0.063 |
| Varicella_Int | Varicella_Int | 1.000 | | Varicella_Int | Varicella_Int | 1.000 |
| Varicella_Int | Measles_OD_DB_Int | 0.043 | | Varicella_Int | Measles_OD_DB_Int | 0.205 |
| Varicella_Int | Measles_Int | -0.090 | | Varicella_Int | Measles_Int | -0.042 |
| Varicella_Int | HepA_Int | 0.114 | | Varicella_Int | HepA_Int | -0.048 |
| Varicella_Int | Tetanus_Int | 0.000 | | Varicella_Int | Tetanus_Int | 0.000 |
| Varicella_Int | Diptheria_Int | 0.000 | | Varicella_Int | Diptheria_Int | 0.000 |
| Varicella_Int | Rubella_Int | -0.024 | | Varicella_Int | Rubella_Int | -0.316 |
| Varicella_Int | CMV_Int | 0.041 | | Varicella_Int | CMV_Int | 0.000 |
| Varicella_Int | HepB_cAb_Int | 0.123 | | Varicella_Int | HepB_cAb_Int | 0.213 |
| Varicella_Int | HepB_eAb_Int | 0.000 | | Varicella_Int | HepB_eAb_Int | 0.000 |
| Varicella_Int | HepB_eAg_Int | 0.167 | | Varicella_Int | HepB_eAg_Int | 0.000 |
| Varicella_Int | HepC_Int | 0.034 | | Varicella_Int | HepC_Int | 0.055 |
| Varicella_Int | Schistosoma_int | 0.012 | | Varicella_Int | Schistosoma_int | 0.109 |

FIG. 2114-J

| | | | | | | |
|---|---|---|---|---|---|---|
| Varicella_Int | Strongyloides_Int | -0.139 | | Varicella_Int | Strongyloides_Int | 0.015 |
| Varicella_Int | Filaria_Int | -0.026 | | Varicella_Int | Filaria_Int | -0.057 |
| Measles_OD_DB_Int | IL_1_alpha | 0.139 | | Measles_OD_DB_Int | IL_1_alpha | -0.056 |
| Measles_OD_DB_Int | IL_1_beta | 0.016 | | Measles_OD_DB_Int | IL_1_beta | 0.110 |
| Measles_OD_DB_Int | IL_2 | 0.036 | | Measles_OD_DB_Int | IL_2 | 0.067 |
| Measles_OD_DB_Int | IL_4 | 0.047 | | Measles_OD_DB_Int | IL_4 | -0.158 |
| Measles_OD_DB_Int | IL_5 | 0.115 | | Measles_OD_DB_Int | IL_5 | 0.011 |
| Measles_OD_DB_Int | IL_6 | -0.107 | | Measles_OD_DB_Int | IL_6 | 0.098 |
| Measles_OD_DB_Int | IL_8 | -0.257 | | Measles_OD_DB_Int | IL_8 | -0.045 |
| Measles_OD_DB_Int | IL_10 | 0.137 | | Measles_OD_DB_Int | IL_10 | 0.062 |
| Measles_OD_DB_Int | IL_12p70 | 0.075 | | Measles_OD_DB_Int | IL_12p70 | -0.043 |
| Measles_OD_DB_Int | IL_13 | -0.024 | | Measles_OD_DB_Int | IL_13 | 0.005 |
| Measles_OD_DB_Int | IL_15 | -0.037 | | Measles_OD_DB_Int | IL_15 | -0.021 |
| Measles_OD_DB_Int | IL_17 | 0.007 | | Measles_OD_DB_Int | IL_17 | 0.032 |
| Measles_OD_DB_Int | IL_23 | -0.172 | | Measles_OD_DB_Int | IL_23 | 0.094 |
| Measles_OD_DB_Int | IFN_gamma | 0.000 | | Measles_OD_DB_Int | IFN_gamma | 0.000 |
| Measles_OD_DB_Int | TNF_alpha | -0.028 | | Measles_OD_DB_Int | TNF_alpha | -0.077 |
| Measles_OD_DB_Int | TNF_beta | 0.079 | | Measles_OD_DB_Int | TNF_beta | -0.046 |
| Measles_OD_DB_Int | Varicella_Int | 0.043 | | Measles_OD_DB_Int | Varicella_Int | 0.205 |
| Measles_OD_DB_Int | Measles_OD_DB_Int | 1.000 | | Measles_OD_DB_Int | Measles_OD_DB_Int | 1.000 |
| Measles_OD_DB_Int | Measles_Int | -0.002 | | Measles_OD_DB_Int | Measles_Int | -0.081 |
| Measles_OD_DB_Int | HepA_Int | -0.036 | | Measles_OD_DB_Int | HepA_Int | -0.093 |
| Measles_OD_DB_Int | Tetanus_Int | 0.000 | | Measles_OD_DB_Int | Tetanus_Int | 0.000 |
| Measles_OD_DB_Int | Diptheria_Int | 0.000 | | Measles_OD_DB_Int | Diptheria_Int | 0.000 |
| Measles_OD_DB_Int | Rubella_Int | -0.234 | | Measles_OD_DB_Int | Rubella_Int | -0.089 |
| Measles_OD_DB_Int | CMV_Int | -0.013 | | Measles_OD_DB_Int | CMV_Int | 0.000 |
| Measles_OD_DB_Int | HepB_cAb_Int | -0.021 | | Measles_OD_DB_Int | HepB_cAb_Int | -0.034 |
| Measles_OD_DB_Int | HepB_eAb_Int | 0.000 | | Measles_OD_DB_Int | HepB_eAb_Int | 0.000 |
| Measles_OD_DB_Int | HepB_eAg_Int | 0.420 | | Measles_OD_DB_Int | HepB_eAg_Int | -0.408 |
| Measles_OD_DB_Int | HepC_Int | 0.078 | | Measles_OD_DB_Int | HepC_Int | 0.040 |
| Measles_OD_DB_Int | Schistosoma_int | 0.018 | | Measles_OD_DB_Int | Schistosoma_int | 0.027 |
| Measles_OD_DB_Int | Strongyloides_Int | -0.012 | | Measles_OD_DB_Int | Strongyloides_Int | 0.101 |
| Measles_OD_DB_Int | Filaria_Int | 0.143 | | Measles_OD_DB_Int | Filaria_Int | 0.008 |
| Measles_Int | IL_1_alpha | 0.083 | | Measles_Int | IL_1_alpha | -0.147 |
| Measles_Int | IL_1_beta | 0.058 | | Measles_Int | IL_1_beta | -0.037 |
| Measles_Int | IL_2 | -0.070 | | Measles_Int | IL_2 | 0.130 |
| Measles_Int | IL_4 | -0.061 | | Measles_Int | IL_4 | 0.099 |
| Measles_Int | IL_5 | 0.045 | | Measles_Int | IL_5 | 0.069 |
| Measles_Int | IL_6 | -0.130 | | Measles_Int | IL_6 | 0.066 |
| Measles_Int | IL_8 | 0.098 | | Measles_Int | IL_8 | 0.127 |
| Measles_Int | IL_10 | -0.037 | | Measles_Int | IL_10 | 0.028 |
| Measles_Int | IL_12p70 | -0.019 | | Measles_Int | IL_12p70 | 0.060 |
| Measles_Int | IL_13 | -0.124 | | Measles_Int | IL_13 | 0.043 |
| Measles_Int | IL_15 | -0.054 | | Measles_Int | IL_15 | 0.035 |
| Measles_Int | IL_17 | -0.069 | | Measles_Int | IL_17 | 0.074 |
| Measles_Int | IL_23 | 0.050 | | Measles_Int | IL_23 | 0.042 |
| Measles_Int | IFN_gamma | 0.000 | | Measles_Int | IFN_gamma | 0.000 |
| Measles_Int | TNF_alpha | -0.034 | | Measles_Int | TNF_alpha | -0.158 |
| Measles_Int | TNF_beta | -0.051 | | Measles_Int | TNF_beta | 0.025 |
| Measles_Int | Varicella_Int | -0.090 | | Measles_Int | Varicella_Int | -0.042 |
| Measles_Int | Measles_OD_DB_Int | -0.002 | | Measles_Int | Measles_OD_DB_Int | -0.081 |
| Measles_Int | Measles_Int | 1.000 | | Measles_Int | Measles_Int | 1.000 |
| Measles_Int | HepA_Int | -0.160 | | Measles_Int | HepA_Int | 0.070 |
| Measles_Int | Tetanus_Int | 0.000 | | Measles_Int | Tetanus_Int | 0.000 |
| Measles_Int | Diptheria_Int | 0.000 | | Measles_Int | Diptheria_Int | 0.000 |
| Measles_Int | Rubella_Int | 0.057 | | Measles_Int | Rubella_Int | 0.044 |
| Measles_Int | CMV_Int | -0.064 | | Measles_Int | CMV_Int | 0.000 |

FIG. 2I4-K

| | | | | | | |
|---|---|---|---|---|---|---|
| Measles_Int | HepB_cAb_Int | -0.050 | | Measles_Int | HepB_cAb_Int | 0.144 |
| Measles_Int | HepB_eAb_Int | 0.000 | | Measles_Int | HepB_eAb_Int | 0.000 |
| Measles_Int | HepB_eAg_Int | 0.000 | | Measles_Int | HepB_eAg_Int | 0.000 |
| Measles_Int | HepC_Int | 0.040 | | Measles_Int | HepC_Int | 0.067 |
| Measles_Int | Schistosoma_int | 0.087 | | Measles_Int | Schistosoma_int | 0.064 |
| Measles_Int | Strongyloides_Int | 0.112 | | Measles_Int | Strongyloides_Int | -0.029 |
| Measles_Int | Filaria_Int | 0.098 | | Measles_Int | Filaria_Int | 0.070 |
| HepA_Int | IL_1_alpha | -0.040 | | HepA_Int | IL_1_alpha | -0.157 |
| HepA_Int | IL_1_beta | 0.033 | | HepA_Int | IL_1_beta | -0.255 |
| HepA_Int | IL_2 | 0.054 | | HepA_Int | IL_2 | -0.194 |
| HepA_Int | IL_4 | -0.016 | | HepA_Int | IL_4 | -0.109 |
| HepA_Int | IL_5 | -0.000 | | HepA_Int | IL_5 | -0.062 |
| HepA_Int | IL_6 | 0.106 | | HepA_Int | IL_6 | -0.222 |
| HepA_Int | IL_8 | -0.156 | | HepA_Int | IL_8 | -0.127 |
| HepA_Int | IL_10 | 0.077 | | HepA_Int | IL_10 | -0.048 |
| HepA_Int | IL_12p70 | -0.023 | | HepA_Int | IL_12p70 | -0.235 |
| HepA_Int | IL_13 | 0.027 | | HepA_Int | IL_13 | -0.098 |
| HepA_Int | IL_15 | 0.083 | | HepA_Int | IL_15 | -0.095 |
| HepA_Int | IL_17 | 0.044 | | HepA_Int | IL_17 | -0.086 |
| HepA_Int | IL_23 | -0.112 | | HepA_Int | IL_23 | 0.010 |
| HepA_Int | IFN_gamma | 0.000 | | HepA_Int | IFN_gamma | 0.000 |
| HepA_Int | TNF_alpha | -0.023 | | HepA_Int | TNF_alpha | -0.144 |
| HepA_Int | TNF_beta | 0.029 | | HepA_Int | TNF_beta | -0.299 |
| HepA_Int | Varicella_Int | 0.114 | | HepA_Int | Varicella_Int | -0.048 |
| HepA_Int | Measles_OD_DB_Int | -0.036 | | HepA_Int | Measles_OD_DB_Int | -0.093 |
| HepA_Int | Measles_Int | -0.160 | | HepA_Int | Measles_Int | 0.070 |
| HepA_Int | HepA_Int | 1.000 | | HepA_Int | HepA_Int | 1.000 |
| HepA_Int | Tetanus_Int | 0.000 | | HepA_Int | Tetanus_Int | 0.000 |
| HepA_Int | Diptheria_Int | 0.000 | | HepA_Int | Diptheria_Int | 0.000 |
| HepA_Int | Rubella_Int | 0.066 | | HepA_Int | Rubella_Int | 0.050 |
| HepA_Int | CMV_Int | 0.137 | | HepA_Int | CMV_Int | 0.000 |
| HepA_Int | HepB_cAb_Int | 0.140 | | HepA_Int | HepB_cAb_Int | 0.224 |
| HepA_Int | HepB_eAb_Int | 0.000 | | HepA_Int | HepB_eAb_Int | 0.000 |
| HepA_Int | HepB_eAg_Int | 0.258 | | HepA_Int | HepB_eAg_Int | 0.000 |
| HepA_Int | HepC_Int | 0.079 | | HepA_Int | HepC_Int | 0.078 |
| HepA_Int | Schistosoma_int | 0.057 | | HepA_Int | Schistosoma_int | 0.062 |
| HepA_Int | Strongyloides_Int | 0.007 | | HepA_Int | Strongyloides_Int | -0.081 |
| HepA_Int | Filaria_Int | -0.044 | | HepA_Int | Filaria_Int | 0.164 |
| Tetanus_Int | IL_1_alpha | 0.000 | | Tetanus_Int | IL_1_alpha | 0.000 |
| Tetanus_Int | IL_1_beta | 0.000 | | Tetanus_Int | IL_1_beta | 0.000 |
| Tetanus_Int | IL_2 | 0.000 | | Tetanus_Int | IL_2 | 0.000 |
| Tetanus_Int | IL_4 | 0.000 | | Tetanus_Int | IL_4 | 0.000 |
| Tetanus_Int | IL_5 | 0.000 | | Tetanus_Int | IL_5 | 0.000 |
| Tetanus_Int | IL_6 | 0.000 | | Tetanus_Int | IL_6 | 0.000 |
| Tetanus_Int | IL_8 | 0.000 | | Tetanus_Int | IL_8 | 0.000 |
| Tetanus_Int | IL_10 | 0.000 | | Tetanus_Int | IL_10 | 0.000 |
| Tetanus_Int | IL_12p70 | 0.000 | | Tetanus_Int | IL_12p70 | 0.000 |
| Tetanus_Int | IL_13 | 0.000 | | Tetanus_Int | IL_13 | 0.000 |
| Tetanus_Int | IL_15 | 0.000 | | Tetanus_Int | IL_15 | 0.000 |
| Tetanus_Int | IL_17 | 0.000 | | Tetanus_Int | IL_17 | 0.000 |
| Tetanus_Int | IL_23 | 0.000 | | Tetanus_Int | IL_23 | 0.000 |
| Tetanus_Int | IFN_gamma | 0.000 | | Tetanus_Int | IFN_gamma | 0.000 |
| Tetanus_Int | TNF_alpha | 0.000 | | Tetanus_Int | TNF_alpha | 0.000 |
| Tetanus_Int | TNF_beta | 0.000 | | Tetanus_Int | TNF_beta | 0.000 |
| Tetanus_Int | Varicella_Int | 0.000 | | Tetanus_Int | Varicella_Int | 0.000 |
| Tetanus_Int | Measles_OD_DB_Int | 0.000 | | Tetanus_Int | Measles_OD_DB_Int | 0.000 |
| Tetanus_Int | Measles_Int | 0.000 | | Tetanus_Int | Measles_Int | 0.000 |

FIG. 21I4-L

| | | | | | | |
|---|---|---|---|---|---|---|
| Tetanus_Int | HepA_Int | 0.000 | | Tetanus_Int | HepA_Int | 0.000 |
| Tetanus_Int | Tetanus_Int | 1.000 | | Tetanus_Int | Tetanus_Int | 1.000 |
| Tetanus_Int | Diptheria_Int | 0.000 | | Tetanus_Int | Diptheria_Int | 0.000 |
| Tetanus_Int | Rubella_Int | 0.000 | | Tetanus_Int | Rubella_Int | 0.000 |
| Tetanus_Int | CMV_Int | 0.000 | | Tetanus_Int | CMV_Int | 0.000 |
| Tetanus_Int | HepB_cAb_Int | 0.000 | | Tetanus_Int | HepB_cAb_Int | 0.000 |
| Tetanus_Int | HepB_eAb_Int | 0.000 | | Tetanus_Int | HepB_eAb_Int | 0.000 |
| Tetanus_Int | HepB_eAg_Int | 0.000 | | Tetanus_Int | HepB_eAg_Int | 0.000 |
| Tetanus_Int | HepC_Int | 0.000 | | Tetanus_Int | HepC_Int | 0.000 |
| Tetanus_Int | Schistosoma_int | 0.000 | | Tetanus_Int | Schistosoma_int | 0.000 |
| Tetanus_Int | Strongyloides_Int | 0.000 | | Tetanus_Int | Strongyloides_Int | 0.000 |
| Tetanus_Int | Filaria_Int | 0.000 | | Tetanus_Int | Filaria_Int | 0.000 |
| Diptheria_Int | IL_1_alpha | 0.000 | | Diptheria_Int | IL_1_alpha | 0.000 |
| Diptheria_Int | IL_1_beta | 0.000 | | Diptheria_Int | IL_1_beta | 0.000 |
| Diptheria_Int | IL_2 | 0.000 | | Diptheria_Int | IL_2 | 0.000 |
| Diptheria_Int | IL_4 | 0.000 | | Diptheria_Int | IL_4 | 0.000 |
| Diptheria_Int | IL_5 | 0.000 | | Diptheria_Int | IL_5 | 0.000 |
| Diptheria_Int | IL_6 | 0.000 | | Diptheria_Int | IL_6 | 0.000 |
| Diptheria_Int | IL_8 | 0.000 | | Diptheria_Int | IL_8 | 0.000 |
| Diptheria_Int | IL_10 | 0.000 | | Diptheria_Int | IL_10 | 0.000 |
| Diptheria_Int | IL_12p70 | 0.000 | | Diptheria_Int | IL_12p70 | 0.000 |
| Diptheria_Int | IL_13 | 0.000 | | Diptheria_Int | IL_13 | 0.000 |
| Diptheria_Int | IL_15 | 0.000 | | Diptheria_Int | IL_15 | 0.000 |
| Diptheria_Int | IL_17 | 0.000 | | Diptheria_Int | IL_17 | 0.000 |
| Diptheria_Int | IL_23 | 0.000 | | Diptheria_Int | IL_23 | 0.000 |
| Diptheria_Int | IFN_gamma | 0.000 | | Diptheria_Int | IFN_gamma | 0.000 |
| Diptheria_Int | TNF_alpha | 0.000 | | Diptheria_Int | TNF_alpha | 0.000 |
| Diptheria_Int | TNF_beta | 0.000 | | Diptheria_Int | TNF_beta | 0.000 |
| Diptheria_Int | Varicella_Int | 0.000 | | Diptheria_Int | Varicella_Int | 0.000 |
| Diptheria_Int | Measles_OD_DB_Int | 0.000 | | Diptheria_Int | Measles_OD_DB_Int | 0.000 |
| Diptheria_Int | Measles_Int | 0.000 | | Diptheria_Int | Measles_Int | 0.000 |
| Diptheria_Int | HepA_Int | 0.000 | | Diptheria_Int | HepA_Int | 0.000 |
| Diptheria_Int | Tetanus_Int | 0.000 | | Diptheria_Int | Tetanus_Int | 0.000 |
| Diptheria_Int | Diptheria_Int | 1.000 | | Diptheria_Int | Diptheria_Int | 1.000 |
| Diptheria_Int | Rubella_Int | 0.000 | | Diptheria_Int | Rubella_Int | 0.000 |
| Diptheria_Int | CMV_Int | 0.000 | | Diptheria_Int | CMV_Int | 0.000 |
| Diptheria_Int | HepB_cAb_Int | 0.000 | | Diptheria_Int | HepB_cAb_Int | 0.000 |
| Diptheria_Int | HepB_eAb_Int | 0.000 | | Diptheria_Int | HepB_eAb_Int | 0.000 |
| Diptheria_Int | HepB_eAg_Int | 0.000 | | Diptheria_Int | HepB_eAg_Int | 0.000 |
| Diptheria_Int | HepC_Int | 0.000 | | Diptheria_Int | HepC_Int | 0.000 |
| Diptheria_Int | Schistosoma_int | 0.000 | | Diptheria_Int | Schistosoma_int | 0.000 |
| Diptheria_Int | Strongyloides_Int | 0.000 | | Diptheria_Int | Strongyloides_Int | 0.000 |
| Diptheria_Int | Filaria_Int | 0.000 | | Diptheria_Int | Filaria_Int | 0.000 |
| Rubella_Int | IL_1_alpha | -0.033 | | Rubella_Int | IL_1_alpha | 0.176 |
| Rubella_Int | IL_1_beta | 0.025 | | Rubella_Int | IL_1_beta | 0.165 |
| Rubella_Int | IL_2 | 0.077 | | Rubella_Int | IL_2 | 0.257 |
| Rubella_Int | IL_4 | 0.007 | | Rubella_Int | IL_4 | 0.015 |
| Rubella_Int | IL_5 | -0.058 | | Rubella_Int | IL_5 | 0.089 |
| Rubella_Int | IL_6 | 0.207 | | Rubella_Int | IL_6 | -0.025 |
| Rubella_Int | IL_8 | 0.101 | | Rubella_Int | IL_8 | 0.123 |
| Rubella_Int | IL_10 | -0.089 | | Rubella_Int | IL_10 | 0.041 |
| Rubella_Int | IL_12p70 | -0.061 | | Rubella_Int | IL_12p70 | 0.371 |
| Rubella_Int | IL_13 | 0.118 | | Rubella_Int | IL_13 | 0.017 |
| Rubella_Int | IL_15 | 0.155 | | Rubella_Int | IL_15 | 0.239 |
| Rubella_Int | IL_17 | -0.043 | | Rubella_Int | IL_17 | 0.264 |
| Rubella_Int | IL_23 | 0.068 | | Rubella_Int | IL_23 | 0.091 |
| Rubella_Int | IFN_gamma | 0.000 | | Rubella_Int | IFN_gamma | 0.000 |

FIG. 21I4-M

| | | | | | | |
|---|---|---|---|---|---|---|
| Rubella_Int | TNF_alpha | 0.110 | | Rubella_Int | TNF_alpha | 0.030 |
| Rubella_Int | TNF_beta | -0.010 | | Rubella_Int | TNF_beta | 0.191 |
| Rubella_Int | Varicella_Int | -0.024 | | Rubella_Int | Varicella_Int | -0.316 |
| Rubella_Int | Measles_OD_DB_Int | -0.234 | | Rubella_Int | Measles_OD_DB_Int | -0.089 |
| Rubella_Int | Measles_Int | 0.057 | | Rubella_Int | Measles_Int | 0.044 |
| Rubella_Int | HepA_Int | 0.066 | | Rubella_Int | HepA_Int | 0.050 |
| Rubella_Int | Tetanus_Int | 0.000 | | Rubella_Int | Tetanus_Int | 0.000 |
| Rubella_Int | Diptheria_Int | 0.000 | | Rubella_Int | Diptheria_Int | 0.000 |
| Rubella_Int | Rubella_Int | 1.000 | | Rubella_Int | Rubella_Int | 1.000 |
| Rubella_Int | CMV_Int | 0.050 | | Rubella_Int | CMV_Int | 0.000 |
| Rubella_Int | HepB_cAb_Int | 0.039 | | Rubella_Int | HepB_cAb_Int | -0.078 |
| Rubella_Int | HepB_eAb_Int | 0.000 | | Rubella_Int | HepB_eAb_Int | 0.000 |
| Rubella_Int | HepB_eAg_Int | -0.354 | | Rubella_Int | HepB_eAg_Int | 0.000 |
| Rubella_Int | HepC_Int | -0.085 | | Rubella_Int | HepC_Int | -0.050 |
| Rubella_Int | Schistosoma_int | 0.055 | | Rubella_Int | Schistosoma_int | -0.099 |
| Rubella_Int | Strongyloides_Int | 0.068 | | Rubella_Int | Strongyloides_Int | 0.022 |
| Rubella_Int | Filaria_Int | -0.042 | | Rubella_Int | Filaria_Int | -0.114 |
| CMV_Int | IL_1_alpha | 0.065 | | CMV_Int | IL_1_alpha | 0.000 |
| CMV_Int | IL_1_beta | 0.021 | | CMV_Int | IL_1_beta | 0.000 |
| CMV_Int | IL_2 | 0.055 | | CMV_Int | IL_2 | 0.000 |
| CMV_Int | IL_4 | 0.064 | | CMV_Int | IL_4 | 0.000 |
| CMV_Int | IL_5 | 0.091 | | CMV_Int | IL_5 | 0.000 |
| CMV_Int | IL_6 | -0.036 | | CMV_Int | IL_6 | 0.000 |
| CMV_Int | IL_8 | 0.101 | | CMV_Int | IL_8 | 0.000 |
| CMV_Int | IL_10 | -0.003 | | CMV_Int | IL_10 | 0.000 |
| CMV_Int | IL_12p70 | 0.031 | | CMV_Int | IL_12p70 | 0.000 |
| CMV_Int | IL_13 | -0.017 | | CMV_Int | IL_13 | 0.000 |
| CMV_Int | IL_15 | 0.189 | | CMV_Int | IL_15 | 0.000 |
| CMV_Int | IL_17 | 0.025 | | CMV_Int | IL_17 | 0.000 |
| CMV_Int | IL_23 | 0.045 | | CMV_Int | IL_23 | 0.000 |
| CMV_Int | IFN_gamma | 0.000 | | CMV_Int | IFN_gamma | 0.000 |
| CMV_Int | TNF_alpha | -0.010 | | CMV_Int | TNF_alpha | 0.000 |
| CMV_Int | TNF_beta | -0.027 | | CMV_Int | TNF_beta | 0.000 |
| CMV_Int | Varicella_Int | 0.041 | | CMV_Int | Varicella_Int | 0.000 |
| CMV_Int | Measles_OD_DB_Int | -0.013 | | CMV_Int | Measles_OD_DB_Int | 0.000 |
| CMV_Int | Measles_Int | -0.064 | | CMV_Int | Measles_Int | 0.000 |
| CMV_Int | HepA_Int | 0.137 | | CMV_Int | HepA_Int | 0.000 |
| CMV_Int | Tetanus_Int | 0.000 | | CMV_Int | Tetanus_Int | 0.000 |
| CMV_Int | Diptheria_Int | 0.000 | | CMV_Int | Diptheria_Int | 0.000 |
| CMV_Int | Rubella_Int | 0.050 | | CMV_Int | Rubella_Int | 0.000 |
| CMV_Int | CMV_Int | 1.000 | | CMV_Int | CMV_Int | 1.000 |
| CMV_Int | HepB_cAb_Int | -0.071 | | CMV_Int | HepB_cAb_Int | 0.000 |
| CMV_Int | HepB_eAb_Int | 0.000 | | CMV_Int | HepB_eAb_Int | 0.000 |
| CMV_Int | HepB_eAg_Int | 0.000 | | CMV_Int | HepB_eAg_Int | 0.000 |
| CMV_Int | HepC_Int | 0.025 | | CMV_Int | HepC_Int | 0.000 |
| CMV_Int | Schistosoma_int | 0.059 | | CMV_Int | Schistosoma_int | 0.000 |
| CMV_Int | Strongyloides_Int | 0.019 | | CMV_Int | Strongyloides_Int | 0.000 |
| CMV_Int | Filaria_Int | -0.283 | | CMV_Int | Filaria_Int | 0.000 |
| HepB_cAb_Int | IL_1_alpha | -0.165 | | HepB_cAb_Int | IL_1_alpha | 0.059 |
| HepB_cAb_Int | IL_1_beta | -0.025 | | HepB_cAb_Int | IL_1_beta | -0.152 |
| HepB_cAb_Int | IL_2 | 0.019 | | HepB_cAb_Int | IL_2 | -0.035 |
| HepB_cAb_Int | IL_4 | 0.012 | | HepB_cAb_Int | IL_4 | 0.046 |
| HepB_cAb_Int | IL_5 | 0.068 | | HepB_cAb_Int | IL_5 | -0.019 |
| HepB_cAb_Int | IL_6 | 0.115 | | HepB_cAb_Int | IL_6 | -0.094 |
| HepB_cAb_Int | IL_8 | -0.134 | | HepB_cAb_Int | IL_8 | 0.122 |
| HepB_cAb_Int | IL_10 | -0.093 | | HepB_cAb_Int | IL_10 | -0.047 |
| HepB_cAb_Int | IL_12p70 | -0.058 | | HepB_cAb_Int | IL_12p70 | 0.062 |

FIG. 2I4-N

| | | | | | | |
|---|---|---|---|---|---|---|
| HepB_cAb_Int | IL_13 | 0.092 | | HepB_cAb_Int | IL_13 | -0.041 |
| HepB_cAb_Int | IL_15 | 0.015 | | HepB_cAb_Int | IL_15 | 0.085 |
| HepB_cAb_Int | IL_17 | -0.017 | | HepB_cAb_Int | IL_17 | 0.022 |
| HepB_cAb_Int | IL_23 | -0.015 | | HepB_cAb_Int | IL_23 | 0.077 |
| HepB_cAb_Int | IFN_gamma | 0.000 | | HepB_cAb_Int | IFN_gamma | 0.000 |
| HepB_cAb_Int | TNF_alpha | -0.062 | | HepB_cAb_Int | TNF_alpha | -0.012 |
| HepB_cAb_Int | TNF_beta | -0.081 | | HepB_cAb_Int | TNF_beta | -0.065 |
| HepB_cAb_Int | Varicella_Int | 0.123 | | HepB_cAb_Int | Varicella_Int | 0.213 |
| HepB_cAb_Int | Measles_OD_DB_Int | -0.021 | | HepB_cAb_Int | Measles_OD_DB_Int | -0.034 |
| HepB_cAb_Int | Measles_Int | -0.050 | | HepB_cAb_Int | Measles_Int | 0.144 |
| HepB_cAb_Int | HepA_Int | 0.140 | | HepB_cAb_Int | HepA_Int | 0.224 |
| HepB_cAb_Int | Tetanus_Int | 0.000 | | HepB_cAb_Int | Tetanus_Int | 0.000 |
| HepB_cAb_Int | Diptheria_Int | 0.000 | | HepB_cAb_Int | Diptheria_Int | 0.000 |
| HepB_cAb_Int | Rubella_Int | 0.039 | | HepB_cAb_Int | Rubella_Int | -0.078 |
| HepB_cAb_Int | CMV_Int | -0.071 | | HepB_cAb_Int | CMV_Int | 0.000 |
| HepB_cAb_Int | HepB_cAb_Int | 1.000 | | HepB_cAb_Int | HepB_cAb_Int | 1.000 |
| HepB_cAb_Int | HepB_eAb_Int | 0.000 | | HepB_cAb_Int | HepB_eAb_Int | 0.000 |
| HepB_cAb_Int | HepB_eAg_Int | 0.000 | | HepB_cAb_Int | HepB_eAg_Int | 0.000 |
| HepB_cAb_Int | HepC_Int | 0.144 | | HepB_cAb_Int | HepC_Int | 0.184 |
| HepB_cAb_Int | Schistosoma_int | 0.051 | | HepB_cAb_Int | Schistosoma_int | 0.190 |
| HepB_cAb_Int | Strongyloides_Int | 0.061 | | HepB_cAb_Int | Strongyloides_Int | 0.156 |
| HepB_cAb_Int | Filaria_Int | -0.012 | | HepB_cAb_Int | Filaria_Int | 0.120 |
| HepB_eAb_Int | IL_1_alpha | 0.000 | | HepB_eAb_Int | IL_1_alpha | 0.000 |
| HepB_eAb_Int | IL_1_beta | 0.000 | | HepB_eAb_Int | IL_1_beta | 0.000 |
| HepB_eAb_Int | IL_2 | 0.000 | | HepB_eAb_Int | IL_2 | 0.000 |
| HepB_eAb_Int | IL_4 | 0.000 | | HepB_eAb_Int | IL_4 | 0.000 |
| HepB_eAb_Int | IL_5 | 0.000 | | HepB_eAb_Int | IL_5 | 0.000 |
| HepB_eAb_Int | IL_6 | 0.000 | | HepB_eAb_Int | IL_6 | 0.000 |
| HepB_eAb_Int | IL_8 | 0.000 | | HepB_eAb_Int | IL_8 | 0.000 |
| HepB_eAb_Int | IL_10 | 0.000 | | HepB_eAb_Int | IL_10 | 0.000 |
| HepB_eAb_Int | IL_12p70 | 0.000 | | HepB_eAb_Int | IL_12p70 | 0.000 |
| HepB_eAb_Int | IL_13 | 0.000 | | HepB_eAb_Int | IL_13 | 0.000 |
| HepB_eAb_Int | IL_15 | 0.000 | | HepB_eAb_Int | IL_15 | 0.000 |
| HepB_eAb_Int | IL_17 | 0.000 | | HepB_eAb_Int | IL_17 | 0.000 |
| HepB_eAb_Int | IL_23 | 0.000 | | HepB_eAb_Int | IL_23 | 0.000 |
| HepB_eAb_Int | IFN_gamma | 0.000 | | HepB_eAb_Int | IFN_gamma | 0.000 |
| HepB_eAb_Int | TNF_alpha | 0.000 | | HepB_eAb_Int | TNF_alpha | 0.000 |
| HepB_eAb_Int | TNF_beta | 0.000 | | HepB_eAb_Int | TNF_beta | 0.000 |
| HepB_eAb_Int | Varicella_Int | 0.000 | | HepB_eAb_Int | Varicella_Int | 0.000 |
| HepB_eAb_Int | Measles_OD_DB_Int | 0.000 | | HepB_eAb_Int | Measles_OD_DB_Int | 0.000 |
| HepB_eAb_Int | Measles_int | 0.000 | | HepB_eAb_Int | Measles_Int | 0.000 |
| HepB_eAb_Int | HepA_Int | 0.000 | | HepB_eAb_Int | HepA_Int | 0.000 |
| HepB_eAb_Int | Tetanus_Int | 0.000 | | HepB_eAb_Int | Tetanus_Int | 0.000 |
| HepB_eAb_Int | Diptheria_Int | 0.000 | | HepB_eAb_Int | Diptheria_Int | 0.000 |
| HepB_eAb_Int | Rubella_Int | 0.000 | | HepB_eAb_Int | Rubella_Int | 0.000 |
| HepB_eAb_Int | CMV_Int | 0.000 | | HepB_eAb_Int | CMV_Int | 0.000 |
| HepB_eAb_Int | HepB_cAb_Int | 0.000 | | HepB_eAb_Int | HepB_cAb_Int | 0.000 |
| HepB_eAb_Int | HepB_eAb_Int | 1.000 | | HepB_eAb_Int | HepB_eAb_Int | 1.000 |
| HepB_eAb_Int | HepB_eAg_Int | 0.000 | | HepB_eAb_Int | HepB_eAg_Int | 0.000 |
| HepB_eAb_Int | HepC_Int | 0.000 | | HepB_eAb_Int | HepC_Int | 0.000 |
| HepB_eAb_Int | Schistosoma_int | 0.000 | | HepB_eAb_Int | Schistosoma_int | 0.000 |
| HepB_eAb_Int | Strongyloides_Int | 0.000 | | HepB_eAb_Int | Strongyloides_Int | 0.000 |
| HepB_eAb_Int | Filaria_Int | 0.000 | | HepB_eAb_Int | Filaria_Int | 0.000 |
| HepB_eAg_Int | IL_1_alpha | -0.208 | | HepB_eAg_Int | IL_1_alpha | -0.252 |
| HepB_eAg_Int | IL_1_beta | -0.090 | | HepB_eAg_Int | IL_1_beta | 0.159 |
| HepB_eAg_Int | IL_2 | -0.258 | | HepB_eAg_Int | IL_2 | -0.250 |
| HepB_eAg_Int | IL_4 | -0.272 | | HepB_eAg_Int | IL_4 | -0.339 |

FIG. 2114-O

| | | | | | | |
|---|---|---|---|---|---|---|
| HepB_eAg_Int | IL_5 | -0.316 | | HepB_eAg_Int | IL_5 | -0.292 |
| HepB_eAg_Int | IL_6 | -0.350 | | HepB_eAg_Int | IL_6 | -0.292 |
| HepB_eAg_Int | IL_8 | -0.183 | | HepB_eAg_Int | IL_8 | -0.227 |
| HepB_eAg_Int | IL_10 | -0.366 | | HepB_eAg_Int | IL_10 | -0.200 |
| HepB_eAg_Int | IL_12p70 | -0.504 | | HepB_eAg_Int | IL_12p70 | -0.320 |
| HepB_eAg_Int | IL_13 | -0.357 | | HepB_eAg_Int | IL_13 | -0.235 |
| HepB_eAg_Int | IL_15 | -0.262 | | HepB_eAg_Int | IL_15 | -0.347 |
| HepB_eAg_Int | IL_17 | -0.394 | | HepB_eAg_Int | IL_17 | -0.313 |
| HepB_eAg_Int | IL_23 | -0.320 | | HepB_eAg_Int | IL_23 | -0.343 |
| HepB_eAg_Int | IFN_gamma | 0.000 | | HepB_eAg_Int | IFN_gamma | 0.000 |
| HepB_eAg_Int | TNF_alpha | -0.090 | | HepB_eAg_Int | TNF_alpha | -0.250 |
| HepB_eAg_Int | TNF_beta | 0.948 | | HepB_eAg_Int | TNF_beta | -0.250 |
| HepB_eAg_Int | Varicella_Int | 0.167 | | HepB_eAg_Int | Varicella_Int | 0.000 |
| HepB_eAg_Int | Measles_OD_DB_Int | 0.420 | | HepB_eAg_Int | Measles_OD_DB_Int | -0.408 |
| HepB_eAg_Int | Measles_Int | 0.000 | | HepB_eAg_Int | Measles_Int | 0.000 |
| HepB_eAg_Int | HepA_Int | 0.258 | | HepB_eAg_Int | HepA_Int | 0.000 |
| HepB_eAg_Int | Tetanus_Int | 0.000 | | HepB_eAg_Int | Tetanus_Int | 0.000 |
| HepB_eAg_Int | Diptheria_Int | 0.000 | | HepB_eAg_Int | Diptheria_Int | 0.000 |
| HepB_eAg_Int | Rubella_Int | -0.354 | | HepB_eAg_Int | Rubella_Int | 0.000 |
| HepB_eAg_Int | CMV_Int | 0.000 | | HepB_eAg_Int | CMV_Int | 0.000 |
| HepB_eAg_Int | HepB_cAb_Int | 0.000 | | HepB_eAg_Int | HepB_cAb_Int | 0.000 |
| HepB_eAg_Int | HepB_eAb_Int | 0.000 | | HepB_eAg_Int | HepB_eAb_Int | 0.000 |
| HepB_eAg_Int | HepB_eAg_Int | 1.000 | | HepB_eAg_Int | HepB_eAg_Int | 1.000 |
| HepB_eAg_Int | HepC_Int | 0.000 | | HepB_eAg_Int | HepC_Int | 0.000 |
| HepB_eAg_Int | Schistosoma_int | -0.200 | | HepB_eAg_Int | Schistosoma_int | 0.000 |
| HepB_eAg_Int | Strongyloides_Int | -0.415 | | HepB_eAg_Int | Strongyloides_Int | 0.000 |
| HepB_eAg_Int | Filaria_Int | 0.000 | | HepB_eAg_Int | Filaria_Int | 0.000 |
| HepC_Int | IL_1_alpha | -0.078 | | HepC_Int | IL_1_alpha | 0.073 |
| HepC_Int | IL_1_beta | -0.084 | | HepC_Int | IL_1_beta | 0.072 |
| HepC_Int | IL_2 | -0.049 | | HepC_Int | IL_2 | 0.197 |
| HepC_Int | IL_4 | -0.064 | | HepC_Int | IL_4 | 0.088 |
| HepC_Int | IL_5 | -0.078 | | HepC_Int | IL_5 | -0.029 |
| HepC_Int | IL_6 | -0.044 | | HepC_Int | IL_6 | -0.060 |
| HepC_Int | IL_8 | -0.063 | | HepC_Int | IL_8 | 0.298 |
| HepC_Int | IL_10 | -0.095 | | HepC_Int | IL_10 | 0.086 |
| HepC_Int | IL_12p70 | -0.101 | | HepC_Int | IL_12p70 | 0.106 |
| HepC_Int | IL_13 | -0.106 | | HepC_Int | IL_13 | -0.037 |
| HepC_Int | IL_15 | -0.108 | | HepC_Int | IL_15 | -0.049 |
| HepC_Int | IL_17 | -0.083 | | HepC_Int | IL_17 | -0.025 |
| HepC_Int | IL_23 | -0.034 | | HepC_Int | IL_23 | -0.054 |
| HepC_Int | IFN_gamma | 0.000 | | HepC_Int | IFN_gamma | 0.000 |
| HepC_Int | TNF_alpha | -0.078 | | HepC_Int | TNF_alpha | -0.032 |
| HepC_Int | TNF_beta | -0.057 | | HepC_Int | TNF_beta | 0.078 |
| HepC_Int | Varicella_Int | 0.034 | | HepC_Int | Varicella_Int | 0.055 |
| HepC_Int | Measles_OD_DB_Int | 0.078 | | HepC_Int | Measles_OD_DB_Int | 0.040 |
| HepC_Int | Measles_Int | 0.040 | | HepC_Int | Measles_Int | 0.067 |
| HepC_Int | HepA_Int | 0.079 | | HepC_Int | HepA_Int | 0.078 |
| HepC_Int | Tetanus_Int | 0.000 | | HepC_Int | Tetanus_Int | 0.000 |
| HepC_Int | Diptheria_Int | 0.000 | | HepC_Int | Diptheria_Int | 0.000 |
| HepC_Int | Rubella_Int | -0.085 | | HepC_Int | Rubella_Int | -0.050 |
| HepC_Int | CMV_Int | 0.025 | | HepC_Int | CMV_Int | 0.000 |
| HepC_Int | HepB_cAb_Int | 0.144 | | HepC_Int | HepB_cAb_Int | 0.184 |
| HepC_Int | HepB_eAb_Int | 0.000 | | HepC_Int | HepB_eAb_Int | 0.000 |
| HepC_Int | HepB_eAg_Int | 0.000 | | HepC_Int | HepB_eAg_Int | 0.000 |
| HepC_Int | HepC_Int | 1.000 | | HepC_Int | HepC_int | 1.000 |
| HepC_Int | Schistosoma_int | -0.037 | | HepC_Int | Schistosoma_int | -0.062 |
| HepC_Int | Strongyloides_Int | -0.026 | | HepC_Int | Strongyloides_Int | 0.081 |

FIG. 21I4-P

| | | | | | | |
|---|---|---|---|---|---|---|
| HepC_Int | Filaria_Int | -0.043 | | HepC_Int | Filaria_Int | 0.043 |
| Schistosoma_int | IL_1_alpha | 0.010 | | Schistosoma_int | IL_1_alpha | 0.079 |
| Schistosoma_int | IL_1_beta | 0.183 | | Schistosoma_int | IL_1_beta | -0.122 |
| Schistosoma_int | IL_2 | -0.026 | | Schistosoma_int | IL_2 | -0.141 |
| Schistosoma_int | IL_4 | 0.044 | | Schistosoma_int | IL_4 | 0.001 |
| Schistosoma_int | IL_5 | 0.037 | | Schistosoma_int | IL_5 | -0.008 |
| Schistosoma_int | IL_6 | -0.024 | | Schistosoma_int | IL_6 | -0.108 |
| Schistosoma_int | IL_8 | -0.004 | | Schistosoma_int | IL_8 | 0.019 |
| Schistosoma_int | IL_10 | -0.031 | | Schistosoma_int | IL_10 | -0.080 |
| Schistosoma_int | IL_12p70 | -0.021 | | Schistosoma_int | IL_12p70 | -0.030 |
| Schistosoma_int | IL_13 | -0.061 | | Schistosoma_int | IL_13 | -0.072 |
| Schistosoma_int | IL_15 | -0.041 | | Schistosoma_int | IL_15 | 0.021 |
| Schistosoma_int | IL_17 | -0.012 | | Schistosoma_int | IL_17 | -0.012 |
| Schistosoma_int | IL_23 | -0.025 | | Schistosoma_int | IL_23 | -0.054 |
| Schistosoma_int | IFN_gamma | 0.000 | | Schistosoma_int | IFN_gamma | 0.000 |
| Schistosoma_int | TNF_alpha | 0.133 | | Schistosoma_int | TNF_alpha | -0.001 |
| Schistosoma_int | TNF_beta | 0.032 | | Schistosoma_int | TNF_beta | -0.057 |
| Schistosoma_int | Varicella_Int | 0.012 | | Schistosoma_int | Varicella_Int | 0.109 |
| Schistosoma_int | Measles_OD_DB_Int | 0.018 | | Schistosoma_int | Measles_OD_DB_Int | 0.027 |
| Schistosoma_int | Measles_Int | 0.087 | | Schistosoma_int | Measles_Int | 0.064 |
| Schistosoma_int | HepA_Int | 0.057 | | Schistosoma_int | HepA_Int | 0.062 |
| Schistosoma_int | Tetanus_Int | 0.000 | | Schistosoma_int | Tetanus_Int | 0.000 |
| Schistosoma_int | Diptheria_Int | 0.000 | | Schistosoma_int | Diptheria_Int | 0.000 |
| Schistosoma_int | Rubella_Int | 0.055 | | Schistosoma_int | Rubella_Int | -0.099 |
| Schistosoma_int | CMV_Int | 0.059 | | Schistosoma_int | CMV_Int | 0.000 |
| Schistosoma_int | HepB_cAb_Int | 0.051 | | Schistosoma_int | HepB_cAb_Int | 0.190 |
| Schistosoma_int | HepB_eAb_Int | 0.000 | | Schistosoma_int | HepB_eAb_Int | 0.000 |
| Schistosoma_int | HepB_eAg_Int | -0.200 | | Schistosoma_int | HepB_eAg_Int | 0.000 |
| Schistosoma_int | HepC_Int | -0.037 | | Schistosoma_int | HepC_Int | -0.062 |
| Schistosoma_int | Schistosoma_int | 1.000 | | Schistosoma_int | Schistosoma_int | 1.000 |
| Schistosoma_int | Strongyloides_Int | 0.299 | | Schistosoma_int | Strongyloides_Int | 0.240 |
| Schistosoma_int | Filaria_Int | -0.037 | | Schistosoma_int | Filaria_Int | -0.034 |
| Strongyloides_Int | IL_1_alpha | 0.083 | | Strongyloides_Int | IL_1_alpha | 0.006 |
| Strongyloides_Int | IL_1_beta | 0.129 | | Strongyloides_Int | IL_1_beta | 0.027 |
| Strongyloides_Int | IL_2 | 0.066 | | Strongyloides_Int | IL_2 | 0.224 |
| Strongyloides_Int | IL_4 | 0.152 | | Strongyloides_Int | IL_4 | -0.045 |
| Strongyloides_Int | IL_5 | -0.016 | | Strongyloides_Int | IL_5 | -0.033 |
| Strongyloides_Int | IL_6 | -0.159 | | Strongyloides_Int | IL_6 | -0.087 |
| Strongyloides_Int | IL_8 | 0.031 | | Strongyloides_Int | IL_8 | 0.162 |
| Strongyloides_Int | IL_10 | -0.042 | | Strongyloides_Int | IL_10 | -0.079 |
| Strongyloides_Int | IL_12p70 | 0.020 | | Strongyloides_Int | IL_12p70 | 0.066 |
| Strongyloides_Int | IL_13 | -0.050 | | Strongyloides_Int | IL_13 | -0.149 |
| Strongyloides_Int | IL_15 | 0.003 | | Strongyloides_Int | IL_15 | -0.041 |
| Strongyloides_Int | IL_17 | 0.053 | | Strongyloides_Int | IL_17 | -0.019 |
| Strongyloides_Int | IL_23 | 0.224 | | Strongyloides_Int | IL_23 | 0.036 |
| Strongyloides_Int | IFN_gamma | 0.000 | | Strongyloides_Int | IFN_gamma | 0.000 |
| Strongyloides_Int | TNF_alpha | 0.180 | | Strongyloides_Int | TNF_alpha | 0.071 |
| Strongyloides_Int | TNF_beta | 0.056 | | Strongyloides_Int | TNF_beta | 0.167 |
| Strongyloides_Int | Varicella_Int | -0.139 | | Strongyloides_Int | Varicella_Int | 0.015 |
| Strongyloides_Int | Measles_OD_DB_Int | -0.012 | | Strongyloides_Int | Measles_OD_DB_Int | 0.101 |
| Strongyloides_Int | Measles_Int | 0.112 | | Strongyloides_Int | Measles_Int | -0.029 |
| Strongyloides_Int | HepA_Int | 0.007 | | Strongyloides_Int | HepA_Int | -0.081 |
| Strongyloides_Int | Tetanus_Int | 0.000 | | Strongyloides_Int | Tetanus_Int | 0.000 |
| Strongyloides_Int | Diptheria_Int | 0.000 | | Strongyloides_Int | Diptheria_Int | 0.000 |
| Strongyloides_Int | Rubella_Int | 0.068 | | Strongyloides_Int | Rubella_Int | 0.022 |
| Strongyloides_Int | CMV_Int | 0.019 | | Strongyloides_Int | CMV_Int | 0.000 |
| Strongyloides_Int | HepB_cAb_Int | 0.061 | | Strongyloides_Int | HepB_cAb_Int | 0.156 |

FIG. 21I4-Q

| | | | | | | |
|---|---|---|---|---|---|---|
| Strongyloides_Int | HepB_eAb_Int | 0.000 | | Strongyloides_Int | HepB_eAb_Int | 0.000 |
| Strongyloides_Int | HepB_eAg_Int | -0.415 | | Strongyloides_Int | HepB_eAg_Int | 0.000 |
| Strongyloides_Int | HepC_Int | -0.026 | | Strongyloides_Int | HepC_Int | 0.081 |
| Strongyloides_Int | Schistosoma_int | 0.299 | | Strongyloides_Int | Schistosoma_int | 0.240 |
| Strongyloides_Int | Strongyloides_Int | 1.000 | | Strongyloides_Int | Strongyloides_Int | 1.000 |
| Strongyloides_Int | Filaria_Int | 0.223 | | Strongyloides_Int | Filaria_Int | 0.169 |
| Filaria_Int | IL_1_alpha | 0.116 | | Filaria_Int | IL_1_alpha | -0.038 |
| Filaria_Int | IL_1_beta | 0.072 | | Filaria_Int | IL_1_beta | 0.067 |
| Filaria_Int | IL_2 | 0.070 | | Filaria_Int | IL_2 | 0.074 |
| Filaria_Int | IL_4 | 0.020 | | Filaria_Int | IL_4 | 0.071 |
| Filaria_Int | IL_5 | -0.038 | | Filaria_Int | IL_5 | 0.287 |
| Filaria_Int | IL_6 | -0.095 | | Filaria_Int | IL_6 | -0.040 |
| Filaria_Int | IL_8 | -0.099 | | Filaria_Int | IL_8 | 0.010 |
| Filaria_Int | IL_10 | 0.104 | | Filaria_Int | IL_10 | 0.288 |
| Filaria_Int | IL_12p70 | 0.103 | | Filaria_Int | IL_12p70 | 0.099 |
| Filaria_Int | IL_13 | 0.125 | | Filaria_Int | IL_13 | 0.185 |
| Filaria_Int | IL_15 | -0.069 | | Filaria_Int | IL_15 | -0.079 |
| Filaria_Int | IL_17 | 0.107 | | Filaria_Int | IL_17 | 0.167 |
| Filaria_Int | IL_23 | 0.005 | | Filaria_Int | IL_23 | 0.141 |
| Filaria_Int | IFN_gamma | 0.000 | | Filaria_Int | IFN_gamma | 0.000 |
| Filaria_Int | TNF_alpha | 0.133 | | Filaria_Int | TNF_alpha | -0.030 |
| Filaria_Int | TNF_beta | 0.060 | | Filaria_Int | TNF_beta | -0.001 |
| Filaria_Int | Varicella_Int | -0.026 | | Filaria_Int | Varicella_Int | -0.057 |
| Filaria_Int | Measles_OD_DB_Int | 0.143 | | Filaria_Int | Measles_OD_DB_Int | 0.008 |
| Filaria_Int | Measles_Int | 0.098 | | Filaria_Int | Measles_Int | 0.070 |
| Filaria_Int | HepA_Int | -0.044 | | Filaria_Int | HepA_Int | 0.164 |
| Filaria_Int | Tetanus_Int | 0.000 | | Filaria_Int | Tetanus_Int | 0.000 |
| Filaria_Int | Diptheria_Int | 0.000 | | Filaria_Int | Diptheria_Int | 0.000 |
| Filaria_Int | Rubella_Int | -0.042 | | Filaria_Int | Rubella_Int | -0.114 |
| Filaria_Int | CMV_Int | -0.283 | | Filaria_Int | CMV_Int | 0.000 |
| Filaria_Int | HepB_cAb_Int | -0.012 | | Filaria_Int | HepB_cAb_Int | 0.120 |
| Filaria_Int | HepB_eAb_Int | 0.000 | | Filaria_Int | HepB_eAb_Int | 0.000 |
| Filaria_Int | HepB_eAg_Int | 0.000 | | Filaria_Int | HepB_eAg_Int | 0.000 |
| Filaria_Int | HepC_Int | -0.043 | | Filaria_Int | HepC_Int | 0.043 |
| Filaria_Int | Schistosoma_int | -0.037 | | Filaria_Int | Schistosoma_int | -0.034 |
| Filaria_Int | Strongyloides_Int | 0.223 | | Filaria_Int | Strongyloides_Int | 0.169 |
| Filaria_Int | Filaria_Int | 1.000 | | Filaria_Int | Filaria_Int | 1.000 |

FIG. 21I4-R

| 10.32% - Region_of_Origin=2, Sex=Female, IFN_gamma=0-7.5 | | |
|---|---|---|
| Property 1 | Property 2 | Corr. Coefficient |
| IL_1_alpha | IL_1_alpha | 1.000 |
| IL_1_alpha | IL_1_beta | 0.301 |
| IL_1_alpha | IL_2 | 0.064 |
| IL_1_alpha | IL_4 | 0.222 |
| IL_1_alpha | IL_5 | 0.158 |
| IL_1_alpha | IL_6 | 0.041 |
| IL_1_alpha | IL_8 | 0.208 |
| IL_1_alpha | IL_10 | 0.248 |
| IL_1_alpha | IL_12p70 | 0.284 |
| IL_1_alpha | IL_13 | 0.195 |
| IL_1_alpha | IL_15 | 0.149 |
| IL_1_alpha | IL_17 | 0.128 |
| IL_1_alpha | IL_23 | -0.037 |
| IL_1_alpha | IFN_gamma | 0.000 |
| IL_1_alpha | TNF_alpha | 0.175 |
| IL_1_alpha | TNF_beta | 0.147 |

| 8.15% - Region_of_Origin=3, Sex=Female, IFN_gamma=0-7.5 | | |
|---|---|---|
| Property 1 | Property 2 | Corr. Coefficient |
| IL_1_alpha | IL_1_alpha | 1.000 |
| IL_1_alpha | IL_1_beta | 0.792 |
| IL_1_alpha | IL_2 | -0.022 |
| IL_1_alpha | IL_4 | 0.079 |
| IL_1_alpha | IL_5 | 0.049 |
| IL_1_alpha | IL_6 | 0.066 |
| IL_1_alpha | IL_8 | 0.147 |
| IL_1_alpha | IL_10 | 0.051 |
| IL_1_alpha | IL_12p70 | 0.081 |
| IL_1_alpha | IL_13 | 0.046 |
| IL_1_alpha | IL_15 | 0.013 |
| IL_1_alpha | IL_17 | 0.008 |
| IL_1_alpha | IL_23 | 0.020 |
| IL_1_alpha | IFN_gamma | 0.000 |
| IL_1_alpha | TNF_alpha | 0.020 |
| IL_1_alpha | TNF_beta | 0.040 |

FIG. 21I5-A

| | | | | | | |
|---|---|---|---|---|---|---|
| IL_1_alpha | Varicella_Int | 0.077 | | IL_1_alpha | Varicella_Int | -0.057 |
| IL_1_alpha | Measles_OD_DB_Int | 0.099 | | IL_1_alpha | Measles_OD_DB_Int | -0.382 |
| IL_1_alpha | Measles_Int | 0.039 | | IL_1_alpha | Measles_Int | -0.027 |
| IL_1_alpha | HepA_Int | 0.017 | | IL_1_alpha | HepA_Int | 0.028 |
| IL_1_alpha | Tetanus_Int | 0.000 | | IL_1_alpha | Tetanus_Int | 0.000 |
| IL_1_alpha | Diptheria_Int | 0.000 | | IL_1_alpha | Diptheria_Int | 0.000 |
| IL_1_alpha | Rubella_Int | -0.012 | | IL_1_alpha | Rubella_Int | 0.249 |
| IL_1_alpha | CMV_Int | -0.021 | | IL_1_alpha | CMV_Int | 0.006 |
| IL_1_alpha | HepB_cAb_Int | -0.070 | | IL_1_alpha | HepB_cAb_Int | -0.094 |
| IL_1_alpha | HepB_eAb_Int | 0.000 | | IL_1_alpha | HepB_eAb_Int | 0.000 |
| IL_1_alpha | HepB_eAg_Int | 0.000 | | IL_1_alpha | HepB_eAg_Int | 0.000 |
| IL_1_alpha | HepC_Int | 0.051 | | IL_1_alpha | HepC_Int | 0.000 |
| IL_1_alpha | Schistosoma_int | 0.032 | | IL_1_alpha | Schistosoma_int | -0.056 |
| IL_1_alpha | Strongyloides_Int | 0.054 | | IL_1_alpha | Strongyloides_Int | -0.072 |
| IL_1_alpha | Filaria_Int | -0.167 | | IL_1_alpha | Filaria_Int | -0.044 |
| IL_1_beta | IL_1_alpha | 0.301 | | IL_1_beta | IL_1_alpha | 0.792 |
| IL_1_beta | IL_1_beta | 1.000 | | IL_1_beta | IL_1_beta | 1.000 |
| IL_1_beta | IL_2 | 0.175 | | IL_1_beta | IL_2 | 0.221 |
| IL_1_beta | IL_4 | 0.270 | | IL_1_beta | IL_4 | 0.034 |
| IL_1_beta | IL_5 | 0.086 | | IL_1_beta | IL_5 | 0.094 |
| IL_1_beta | IL_6 | 0.074 | | IL_1_beta | IL_6 | 0.127 |
| IL_1_beta | IL_8 | 0.073 | | IL_1_beta | IL_8 | 0.056 |
| IL_1_beta | IL_10 | 0.308 | | IL_1_beta | IL_10 | 0.156 |
| IL_1_beta | IL_12p70 | 0.306 | | IL_1_beta | IL_12p70 | 0.143 |
| IL_1_beta | IL_13 | 0.216 | | IL_1_beta | IL_13 | 0.287 |
| IL_1_beta | IL_15 | 0.210 | | IL_1_beta | IL_15 | -0.074 |
| IL_1_beta | IL_17 | 0.189 | | IL_1_beta | IL_17 | 0.075 |
| IL_1_beta | IL_23 | 0.025 | | IL_1_beta | IL_23 | 0.023 |
| IL_1_beta | IFN_gamma | 0.000 | | IL_1_beta | IFN_gamma | 0.000 |
| IL_1_beta | TNF_alpha | 0.639 | | IL_1_beta | TNF_alpha | 0.060 |
| IL_1_beta | TNF_beta | 0.339 | | IL_1_beta | TNF_beta | 0.009 |
| IL_1_beta | Varicella_Int | 0.017 | | IL_1_beta | Varicella_Int | -0.003 |
| IL_1_beta | Measles_OD_DB_Int | 0.010 | | IL_1_beta | Measles_OD_DB_Int | -0.296 |
| IL_1_beta | Measles_Int | 0.006 | | IL_1_beta | Measles_Int | 0.007 |
| IL_1_beta | HepA_Int | 0.027 | | IL_1_beta | HepA_Int | 0.068 |
| IL_1_beta | Tetanus_Int | 0.000 | | IL_1_beta | Tetanus_Int | 0.000 |
| IL_1_beta | Diptheria_Int | 0.000 | | IL_1_beta | Diptheria_Int | 0.000 |
| IL_1_beta | Rubella_Int | 0.037 | | IL_1_beta | Rubella_Int | 0.189 |
| IL_1_beta | CMV_Int | -0.173 | | IL_1_beta | CMV_Int | 0.051 |
| IL_1_beta | HepB_cAb_Int | -0.076 | | IL_1_beta | HepB_cAb_Int | -0.036 |
| IL_1_beta | HepB_eAb_Int | 0.000 | | IL_1_beta | HepB_eAb_Int | 0.000 |
| IL_1_beta | HepB_eAg_Int | 0.000 | | IL_1_beta | HepB_eAg_Int | 0.000 |
| IL_1_beta | HepC_Int | 0.020 | | IL_1_beta | HepC_Int | 0.000 |
| IL_1_beta | Schistosoma_int | -0.025 | | IL_1_beta | Schistosoma_int | -0.044 |
| IL_1_beta | Strongyloides_Int | -0.009 | | IL_1_beta | Strongyloides_Int | -0.134 |
| IL_1_beta | Filaria_Int | -0.098 | | IL_1_beta | Filaria_Int | -0.026 |
| IL_2 | IL_1_alpha | 0.064 | | IL_2 | IL_1_alpha | -0.022 |
| IL_2 | IL_1_beta | 0.175 | | IL_2 | IL_1_beta | 0.221 |
| IL_2 | IL_2 | 1.000 | | IL_2 | IL_2 | 1.000 |
| IL_2 | IL_4 | 0.125 | | IL_2 | IL_4 | -0.028 |
| IL_2 | IL_5 | -0.029 | | IL_2 | IL_5 | 0.054 |
| IL_2 | IL_6 | -0.130 | | IL_2 | IL_6 | -0.023 |
| IL_2 | IL_8 | 0.043 | | IL_2 | IL_8 | 0.013 |
| IL_2 | IL_10 | 0.102 | | IL_2 | IL_10 | 0.239 |
| IL_2 | IL_12p70 | 0.147 | | IL_2 | IL_12p70 | 0.312 |
| IL_2 | IL_13 | 0.014 | | IL_2 | IL_13 | 0.693 |
| IL_2 | IL_15 | 0.007 | | IL_2 | IL_15 | -0.052 |

FIG. 2115-B

| | | | | | | |
|---|---|---|---|---|---|---|
| IL_2 | IL_17 | 0.132 | | IL_2 | IL_17 | 0.557 |
| IL_2 | IL_23 | 0.223 | | IL_2 | IL_23 | 0.195 |
| IL_2 | IFN_gamma | 0.000 | | IL_2 | IFN_gamma | 0.000 |
| IL_2 | TNF_alpha | 0.120 | | IL_2 | TNF_alpha | 0.012 |
| IL_2 | TNF_beta | 0.364 | | IL_2 | TNF_beta | 0.164 |
| IL_2 | Varicella_Int | -0.015 | | IL_2 | Varicella_Int | 0.007 |
| IL_2 | Measles_OD_DB_Int | -0.014 | | IL_2 | Measles_OD_DB_Int | -0.260 |
| IL_2 | Measles_Int | -0.039 | | IL_2 | Measles_Int | 0.027 |
| IL_2 | HepA_Int | -0.025 | | IL_2 | HepA_Int | 0.029 |
| IL_2 | Tetanus_Int | 0.000 | | IL_2 | Tetanus_Int | 0.000 |
| IL_2 | Diptheria_Int | 0.000 | | IL_2 | Diptheria_Int | 0.000 |
| IL_2 | Rubella_Int | 0.015 | | IL_2 | Rubella_Int | 0.072 |
| IL_2 | CMV_Int | 0.057 | | IL_2 | CMV_Int | 0.041 |
| IL_2 | HepB_cAb_Int | 0.010 | | IL_2 | HepB_cAb_Int | 0.224 |
| IL_2 | HepB_eAb_Int | 0.000 | | IL_2 | HepB_eAb_Int | 0.000 |
| IL_2 | HepB_eAg_Int | 0.000 | | IL_2 | HepB_eAg_Int | 0.000 |
| IL_2 | HepC_Int | -0.054 | | IL_2 | HepC_Int | 0.000 |
| IL_2 | Schistosoma_int | 0.021 | | IL_2 | Schistosoma_int | 0.080 |
| IL_2 | Strongyloides_Int | 0.110 | | IL_2 | Strongyloides_Int | -0.085 |
| IL_2 | Filaria_Int | -0.084 | | IL_2 | Filaria_Int | -0.035 |
| IL_4 | IL_1_alpha | 0.222 | | IL_4 | IL_1_alpha | 0.079 |
| IL_4 | IL_1_beta | 0.270 | | IL_4 | IL_1_beta | 0.034 |
| IL_4 | IL_2 | 0.125 | | IL_4 | IL_2 | -0.028 |
| IL_4 | IL_4 | 1.000 | | IL_4 | IL_4 | 1.000 |
| IL_4 | IL_5 | 0.438 | | IL_4 | IL_5 | 0.146 |
| IL_4 | IL_6 | 0.087 | | IL_4 | IL_6 | 0.068 |
| IL_4 | IL_8 | 0.212 | | IL_4 | IL_8 | 0.125 |
| IL_4 | IL_10 | 0.393 | | IL_4 | IL_10 | 0.198 |
| IL_4 | IL_12p70 | 0.408 | | IL_4 | IL_12p70 | 0.210 |
| IL_4 | IL_13 | 0.367 | | IL_4 | IL_13 | 0.073 |
| IL_4 | IL_15 | 0.280 | | IL_4 | IL_15 | 0.327 |
| IL_4 | IL_17 | 0.275 | | IL_4 | IL_17 | 0.087 |
| IL_4 | IL_23 | 0.059 | | IL_4 | IL_23 | 0.157 |
| IL_4 | IFN_gamma | 0.000 | | IL_4 | IFN_gamma | 0.000 |
| IL_4 | TNF_alpha | 0.085 | | IL_4 | TNF_alpha | 0.377 |
| IL_4 | TNF_beta | 0.383 | | IL_4 | TNF_beta | 0.252 |
| IL_4 | Varicella_Int | 0.054 | | IL_4 | Varicella_Int | -0.034 |
| IL_4 | Measles_OD_DB_Int | -0.006 | | IL_4 | Measles_OD_DB_Int | -0.112 |
| IL_4 | Measles_Int | 0.043 | | IL_4 | Measles_Int | 0.051 |
| IL_4 | HepA_Int | 0.077 | | IL_4 | HepA_Int | 0.087 |
| IL_4 | Tetanus_Int | 0.000 | | IL_4 | Tetanus_Int | 0.000 |
| IL_4 | Diptheria_Int | 0.000 | | IL_4 | Diptheria_Int | 0.000 |
| IL_4 | Rubella_Int | 0.086 | | IL_4 | Rubella_Int | -0.026 |
| IL_4 | CMV_Int | 0.033 | | IL_4 | CMV_Int | -0.128 |
| IL_4 | HepB_cAb_Int | -0.023 | | IL_4 | HepB_cAb_Int | -0.070 |
| IL_4 | HepB_eAb_Int | 0.000 | | IL_4 | HepB_eAb_Int | 0.000 |
| IL_4 | HepB_eAg_Int | 0.000 | | IL_4 | HepB_eAg_Int | 0.000 |
| IL_4 | HepC_Int | 0.149 | | IL_4 | HepC_Int | 0.000 |
| IL_4 | Schistosoma_int | 0.055 | | IL_4 | Schistosoma_int | -0.097 |
| IL_4 | Strongyloides_Int | 0.004 | | IL_4 | Strongyloides_Int | 0.003 |
| IL_4 | Filaria_Int | 0.039 | | IL_4 | Filaria_Int | -0.001 |
| IL_5 | IL_1_alpha | 0.158 | | IL_5 | IL_1_alpha | 0.049 |
| IL_5 | IL_1_beta | 0.086 | | IL_5 | IL_1_beta | 0.094 |
| IL_5 | IL_2 | -0.029 | | IL_5 | IL_2 | 0.054 |
| IL_5 | IL_4 | 0.438 | | IL_5 | IL_4 | 0.146 |
| IL_5 | IL_5 | 1.000 | | IL_5 | IL_5 | 1.000 |
| IL_5 | IL_6 | 0.081 | | IL_5 | IL_6 | 0.220 |

FIG. 21I5-C

| | | | | | | |
|---|---|---|---|---|---|---|
| IL_5 | IL_8 | 0.126 | | IL_5 | IL_8 | 0.063 |
| IL_5 | IL_10 | 0.124 | | IL_5 | IL_10 | 0.036 |
| IL_5 | IL_12p70 | 0.264 | | IL_5 | IL_12p70 | 0.683 |
| IL_5 | IL_13 | 0.306 | | IL_5 | IL_13 | 0.145 |
| IL_5 | IL_15 | 0.170 | | IL_5 | IL_15 | 0.021 |
| IL_5 | IL_17 | 0.095 | | IL_5 | IL_17 | 0.038 |
| IL_5 | IL_23 | 0.033 | | IL_5 | IL_23 | 0.008 |
| IL_5 | IFN_gamma | 0.000 | | IL_5 | IFN_gamma | 0.000 |
| IL_5 | TNF_alpha | 0.071 | | IL_5 | TNF_alpha | 0.274 |
| IL_5 | TNF_beta | 0.039 | | IL_5 | TNF_beta | 0.195 |
| IL_5 | Varicella_Int | 0.065 | | IL_5 | Varicella_Int | 0.023 |
| IL_5 | Measles_OD_DB_Int | 0.095 | | IL_5 | Measles_OD_DB_Int | 0.023 |
| IL_5 | Measles_Int | 0.025 | | IL_5 | Measles_Int | 0.020 |
| IL_5 | HepA_Int | 0.036 | | IL_5 | HepA_Int | 0.022 |
| IL_5 | Tetanus_Int | 0.000 | | IL_5 | Tetanus_Int | 0.000 |
| IL_5 | Diptheria_Int | 0.000 | | IL_5 | Diptheria_Int | 0.000 |
| IL_5 | Rubella_Int | 0.109 | | IL_5 | Rubella_Int | -0.055 |
| IL_5 | CMV_Int | 0.025 | | IL_5 | CMV_Int | 0.028 |
| IL_5 | HepB_cAb_Int | -0.034 | | IL_5 | HepB_cAb_Int | -0.053 |
| IL_5 | HepB_eAb_Int | 0.000 | | IL_5 | HepB_eAb_Int | 0.000 |
| IL_5 | HepB_eAg_Int | 0.000 | | IL_5 | HepB_eAg_Int | 0.000 |
| IL_5 | HepC_Int | -0.007 | | IL_5 | HepC_Int | 0.000 |
| IL_5 | Schistosoma_int | -0.046 | | IL_5 | Schistosoma_int | 0.008 |
| IL_5 | Strongyloides_Int | -0.033 | | IL_5 | Strongyloides_Int | -0.080 |
| IL_5 | Filaria_Int | -0.049 | | IL_5 | Filaria_Int | -0.039 |
| IL_6 | IL_1_alpha | 0.041 | | IL_6 | IL_1_alpha | 0.066 |
| IL_6 | IL_1_beta | 0.074 | | IL_6 | IL_1_beta | 0.127 |
| IL_6 | IL_2 | -0.130 | | IL_6 | IL_2 | -0.023 |
| IL_6 | IL_4 | 0.087 | | IL_6 | IL_4 | 0.068 |
| IL_6 | IL_5 | 0.081 | | IL_6 | IL_5 | 0.220 |
| IL_6 | IL_6 | 1.000 | | IL_6 | IL_6 | 1.000 |
| IL_6 | IL_8 | 0.417 | | IL_6 | IL_8 | 0.022 |
| IL_6 | IL_10 | 0.081 | | IL_6 | IL_10 | 0.043 |
| IL_6 | IL_12p70 | 0.140 | | IL_6 | IL_12p70 | -0.002 |
| IL_6 | IL_13 | 0.262 | | IL_6 | IL_13 | 0.548 |
| IL_6 | IL_15 | 0.458 | | IL_6 | IL_15 | 0.041 |
| IL_6 | IL_17 | 0.069 | | IL_6 | IL_17 | -0.061 |
| IL_6 | IL_23 | -0.076 | | IL_6 | IL_23 | 0.004 |
| IL_6 | IFN_gamma | 0.000 | | IL_6 | IFN_gamma | 0.000 |
| IL_6 | TNF_alpha | 0.027 | | IL_6 | TNF_alpha | -0.007 |
| IL_6 | TNF_beta | -0.015 | | IL_6 | TNF_beta | -0.069 |
| IL_6 | Varicella_Int | -0.010 | | IL_6 | Varicella_Int | -0.000 |
| IL_6 | Measles_OD_DB_Int | -0.122 | | IL_6 | Measles_OD_DB_Int | -0.103 |
| IL_6 | Measles_Int | 0.038 | | IL_6 | Measles_Int | 0.010 |
| IL_6 | HepA_Int | 0.026 | | IL_6 | HepA_Int | 0.072 |
| IL_6 | Tetanus_Int | 0.000 | | IL_6 | Tetanus_Int | 0.000 |
| IL_6 | Diptheria_Int | 0.000 | | IL_6 | Diptheria_Int | 0.000 |
| IL_6 | Rubella_Int | 0.252 | | IL_6 | Rubella_Int | -0.059 |
| IL_6 | CMV_Int | 0.040 | | IL_6 | CMV_Int | 0.039 |
| IL_6 | HepB_cAb_Int | -0.071 | | IL_6 | HepB_cAb_Int | -0.056 |
| IL_6 | HepB_eAb_Int | 0.000 | | IL_6 | HepB_eAb_Int | 0.000 |
| IL_6 | HepB_eAg_Int | 0.000 | | IL_6 | HepB_eAg_Int | 0.000 |
| IL_6 | HepC_Int | -0.006 | | IL_6 | HepC_Int | 0.000 |
| IL_6 | Schistosoma_int | -0.007 | | IL_6 | Schistosoma_int | 0.203 |
| IL_6 | Strongyloides_Int | -0.215 | | IL_6 | Strongyloides_Int | -0.180 |
| IL_6 | Filaria_Int | -0.120 | | IL_6 | Filaria_Int | -0.092 |
| IL_8 | IL_1_alpha | 0.208 | | IL_8 | IL_1_alpha | 0.147 |

FIG. 2115-D

| IL_8 | IL_1_beta | 0.073 | IL_8 | IL_1_beta | 0.056 |
|---|---|---|---|---|---|
| IL_8 | IL_2 | 0.043 | IL_8 | IL_2 | 0.013 |
| IL_8 | IL_4 | 0.212 | IL_8 | IL_4 | 0.125 |
| IL_8 | IL_5 | 0.126 | IL_8 | IL_5 | 0.063 |
| IL_8 | IL_6 | 0.417 | IL_8 | IL_6 | 0.022 |
| IL_8 | IL_8 | 1.000 | IL_8 | IL_8 | 1.000 |
| IL_8 | IL_10 | 0.035 | IL_8 | IL_10 | 0.100 |
| IL_8 | IL_12p70 | 0.218 | IL_8 | IL_12p70 | 0.122 |
| IL_8 | IL_13 | 0.240 | IL_8 | IL_13 | 0.016 |
| IL_8 | IL_15 | 0.552 | IL_8 | IL_15 | 0.169 |
| IL_8 | IL_17 | 0.160 | IL_8 | IL_17 | 0.071 |
| IL_8 | IL_23 | -0.062 | IL_8 | IL_23 | 0.054 |
| IL_8 | IFN_gamma | 0.000 | IL_8 | IFN_gamma | 0.000 |
| IL_8 | TNF_alpha | 0.126 | IL_8 | TNF_alpha | 0.111 |
| IL_8 | TNF_beta | 0.161 | IL_8 | TNF_beta | 0.117 |
| IL_8 | Varicella_Int | 0.074 | IL_8 | Varicella_Int | -0.010 |
| IL_8 | Measles_OD_DB_Int | -0.130 | IL_8 | Measles_OD_DB_Int | -0.236 |
| IL_8 | Measles_Int | 0.046 | IL_8 | Measles_Int | 0.031 |
| IL_8 | HepA_Int | 0.015 | IL_8 | HepA_Int | 0.002 |
| IL_8 | Tetanus_Int | 0.000 | IL_8 | Tetanus_Int | 0.000 |
| IL_8 | Diptheria_Int | 0.000 | IL_8 | Diptheria_Int | 0.000 |
| IL_8 | Rubella_Int | 0.146 | IL_8 | Rubella_Int | -0.068 |
| IL_8 | CMV_Int | 0.025 | IL_8 | CMV_Int | 0.026 |
| IL_8 | HepB_cAb_Int | 0.065 | IL_8 | HepB_cAb_Int | 0.039 |
| IL_8 | HepB_eAb_Int | 0.000 | IL_8 | HepB_eAb_Int | 0.000 |
| IL_8 | HepB_eAg_Int | 0.000 | IL_8 | HepB_eAg_Int | 0.000 |
| IL_8 | HepC_Int | 0.003 | IL_8 | HepC_Int | 0.000 |
| IL_8 | Schistosoma_int | -0.040 | IL_8 | Schistosoma_int | -0.044 |
| IL_8 | Strongyloides_Int | -0.060 | IL_8 | Strongyloides_Int | -0.057 |
| IL_8 | Filaria_Int | -0.225 | IL_8 | Filaria_Int | -0.093 |
| IL_10 | IL_1_alpha | 0.248 | IL_10 | IL_1_alpha | 0.051 |
| IL_10 | IL_1_beta | 0.308 | IL_10 | IL_1_beta | 0.156 |
| IL_10 | IL_2 | 0.102 | IL_10 | IL_2 | 0.239 |
| IL_10 | IL_4 | 0.393 | IL_10 | IL_4 | 0.198 |
| IL_10 | IL_5 | 0.124 | IL_10 | IL_5 | 0.036 |
| IL_10 | IL_6 | 0.081 | IL_10 | IL_6 | 0.043 |
| IL_10 | IL_8 | 0.035 | IL_10 | IL_8 | 0.100 |
| IL_10 | IL_10 | 1.000 | IL_10 | IL_10 | 1.000 |
| IL_10 | IL_12p70 | 0.466 | IL_10 | IL_12p70 | 0.389 |
| IL_10 | IL_13 | 0.633 | IL_10 | IL_13 | 0.356 |
| IL_10 | IL_15 | 0.282 | IL_10 | IL_15 | 0.285 |
| IL_10 | IL_17 | 0.476 | IL_10 | IL_17 | 0.451 |
| IL_10 | IL_23 | 0.168 | IL_10 | IL_23 | 0.083 |
| IL_10 | IFN_gamma | 0.000 | IL_10 | IFN_gamma | 0.000 |
| IL_10 | TNF_alpha | 0.169 | IL_10 | TNF_alpha | 0.403 |
| IL_10 | TNF_beta | 0.382 | IL_10 | TNF_beta | 0.274 |
| IL_10 | Varicella_Int | 0.047 | IL_10 | Varicella_Int | -0.040 |
| IL_10 | Measles_OD_DB_Int | 0.017 | IL_10 | Measles_OD_DB_Int | -0.069 |
| IL_10 | Measles_Int | 0.019 | IL_10 | Measles_Int | -0.173 |
| IL_10 | HepA_Int | -0.082 | IL_10 | HepA_Int | 0.131 |
| IL_10 | Tetanus_Int | 0.000 | IL_10 | Tetanus_Int | 0.000 |
| IL_10 | Diptheria_Int | 0.000 | IL_10 | Diptheria_Int | 0.000 |
| IL_10 | Rubella_Int | -0.118 | IL_10 | Rubella_Int | 0.098 |
| IL_10 | CMV_Int | 0.020 | IL_10 | CMV_Int | 0.005 |
| IL_10 | HepB_cAb_Int | -0.036 | IL_10 | HepB_cAb_Int | 0.008 |
| IL_10 | HepB_eAb_Int | 0.000 | IL_10 | HepB_eAb_Int | 0.000 |
| IL_10 | HepB_eAg_Int | 0.000 | IL_10 | HepB_eAg_Int | 0.000 |

FIG. 21I5-E

| | | | | | | |
|---|---|---|---|---|---|---|
| IL_10 | HepC_Int | 0.135 | | IL_10 | HepC_Int | 0.000 |
| IL_10 | Schistosoma_int | 0.032 | | IL_10 | Schistosoma_int | -0.011 |
| IL_10 | Strongyloides_Int | -0.008 | | IL_10 | Strongyloides_Int | -0.110 |
| IL_10 | Filaria_Int | -0.025 | | IL_10 | Filaria_Int | -0.013 |
| IL_12p70 | IL_1_alpha | 0.284 | | IL_12p70 | IL_1_alpha | 0.081 |
| IL_12p70 | IL_1_beta | 0.306 | | IL_12p70 | IL_1_beta | 0.143 |
| IL_12p70 | IL_2 | 0.147 | | IL_12p70 | IL_2 | 0.312 |
| IL_12p70 | IL_4 | 0.408 | | IL_12p70 | IL_4 | 0.210 |
| IL_12p70 | IL_5 | 0.264 | | IL_12p70 | IL_5 | 0.683 |
| IL_12p70 | IL_6 | 0.140 | | IL_12p70 | IL_6 | -0.002 |
| IL_12p70 | IL_8 | 0.218 | | IL_12p70 | IL_8 | 0.122 |
| IL_12p70 | IL_10 | 0.466 | | IL_12p70 | IL_10 | 0.389 |
| IL_12p70 | IL_12p70 | 1.000 | | IL_12p70 | IL_12p70 | 1.000 |
| IL_12p70 | IL_13 | 0.565 | | IL_12p70 | IL_13 | 0.278 |
| IL_12p70 | IL_15 | 0.401 | | IL_12p70 | IL_15 | 0.228 |
| IL_12p70 | IL_17 | 0.322 | | IL_12p70 | IL_17 | 0.411 |
| IL_12p70 | IL_23 | 0.337 | | IL_12p70 | IL_23 | 0.290 |
| IL_12p70 | IFN_gamma | 0.000 | | IL_12p70 | IFN_gamma | 0.000 |
| IL_12p70 | TNF_alpha | 0.251 | | IL_12p70 | TNF_alpha | 0.379 |
| IL_12p70 | TNF_beta | 0.296 | | IL_12p70 | TNF_beta | 0.433 |
| IL_12p70 | Varicella_Int | 0.100 | | IL_12p70 | Varicella_Int | -0.119 |
| IL_12p70 | Measles_OD_DB_Int | -0.015 | | IL_12p70 | Measles_OD_DB_Int | -0.090 |
| IL_12p70 | Measles_Int | 0.034 | | IL_12p70 | Measles_Int | -0.073 |
| IL_12p70 | HepA_Int | 0.048 | | IL_12p70 | HepA_Int | 0.057 |
| IL_12p70 | Tetanus_Int | 0.000 | | IL_12p70 | Tetanus_Int | 0.000 |
| IL_12p70 | Diptheria_Int | 0.000 | | IL_12p70 | Diptheria_Int | 0.000 |
| IL_12p70 | Rubella_Int | -0.077 | | IL_12p70 | Rubella_Int | -0.059 |
| IL_12p70 | CMV_Int | 0.002 | | IL_12p70 | CMV_Int | 0.055 |
| IL_12p70 | HepB_cAb_Int | -0.093 | | IL_12p70 | HepB_cAb_Int | -0.033 |
| IL_12p70 | HepB_eAb_Int | 0.000 | | IL_12p70 | HepB_eAb_Int | 0.000 |
| IL_12p70 | HepB_eAg_Int | 0.000 | | IL_12p70 | HepB_eAg_Int | 0.000 |
| IL_12p70 | HepC_Int | 0.150 | | IL_12p70 | HepC_Int | 0.000 |
| IL_12p70 | Schistosoma_int | -0.028 | | IL_12p70 | Schistosoma_int | -0.008 |
| IL_12p70 | Strongyloides_Int | -0.088 | | IL_12p70 | Strongyloides_Int | 0.006 |
| IL_12p70 | Filaria_Int | -0.189 | | IL_12p70 | Filaria_Int | -0.034 |
| IL_13 | IL_1_alpha | 0.195 | | IL_13 | IL_1_alpha | 0.046 |
| IL_13 | IL_1_beta | 0.216 | | IL_13 | IL_1_beta | 0.287 |
| IL_13 | IL_2 | 0.014 | | IL_13 | IL_2 | 0.693 |
| IL_13 | IL_4 | 0.367 | | IL_13 | IL_4 | 0.073 |
| IL_13 | IL_5 | 0.306 | | IL_13 | IL_5 | 0.145 |
| IL_13 | IL_6 | 0.262 | | IL_13 | IL_6 | 0.548 |
| IL_13 | IL_8 | 0.240 | | IL_13 | IL_8 | 0.016 |
| IL_13 | IL_10 | 0.633 | | IL_13 | IL_10 | 0.356 |
| IL_13 | IL_12p70 | 0.565 | | IL_13 | IL_12p70 | 0.278 |
| IL_13 | IL_13 | 1.000 | | IL_13 | IL_13 | 1.000 |
| IL_13 | IL_15 | 0.352 | | IL_13 | IL_15 | 0.012 |
| IL_13 | IL_17 | 0.343 | | IL_13 | IL_17 | 0.279 |
| IL_13 | IL_23 | 0.001 | | IL_13 | IL_23 | 0.016 |
| IL_13 | IFN_gamma | 0.000 | | IL_13 | IFN_gamma | 0.000 |
| IL_13 | TNF_alpha | 0.134 | | IL_13 | TNF_alpha | 0.069 |
| IL_13 | TNF_beta | 0.153 | | IL_13 | TNF_beta | 0.000 |
| IL_13 | Varicella_Int | 0.077 | | IL_13 | Varicella_Int | 0.025 |
| IL_13 | Measles_OD_DB_Int | -0.045 | | IL_13 | Measles_OD_DB_Int | -0.227 |
| IL_13 | Measles_Int | 0.074 | | IL_13 | Measles_Int | -0.027 |
| IL_13 | HepA_Int | 0.038 | | IL_13 | HepA_Int | 0.057 |
| IL_13 | Tetanus_Int | 0.000 | | IL_13 | Tetanus_Int | 0.000 |
| IL_13 | Diptheria_Int | 0.000 | | IL_13 | Diptheria_Int | 0.000 |

FIG. 2115-F

| | | | | | | |
|---|---|---|---|---|---|---|
| IL_13 | Rubella_Int | -0.033 | | IL_13 | Rubella_Int | 0.003 |
| IL_13 | CMV_Int | 0.042 | | IL_13 | CMV_Int | 0.013 |
| IL_13 | HepB_cAb_Int | -0.025 | | IL_13 | HepB_cAb_Int | 0.168 |
| IL_13 | HepB_eAb_Int | 0.000 | | IL_13 | HepB_eAb_Int | 0.000 |
| IL_13 | HepB_eAg_Int | 0.000 | | IL_13 | HepB_eAg_Int | 0.000 |
| IL_13 | HepC_Int | 0.073 | | IL_13 | HepC_Int | 0.000 |
| IL_13 | Schistosoma_int | -0.098 | | IL_13 | Schistosoma_int | 0.104 |
| IL_13 | Strongyloides_Int | -0.231 | | IL_13 | Strongyloides_Int | -0.204 |
| IL_13 | Filaria_Int | -0.125 | | IL_13 | Filaria_Int | -0.076 |
| IL_15 | IL_1_alpha | 0.149 | | IL_15 | IL_1_alpha | 0.013 |
| IL_15 | IL_1_beta | 0.210 | | IL_15 | IL_1_beta | -0.074 |
| IL_15 | IL_2 | 0.007 | | IL_15 | IL_2 | -0.052 |
| IL_15 | IL_4 | 0.280 | | IL_15 | IL_4 | 0.327 |
| IL_15 | IL_5 | 0.170 | | IL_15 | IL_5 | 0.021 |
| IL_15 | IL_6 | 0.458 | | IL_15 | IL_6 | 0.041 |
| IL_15 | IL_8 | 0.552 | | IL_15 | IL_8 | 0.169 |
| IL_15 | IL_10 | 0.282 | | IL_15 | IL_10 | 0.285 |
| IL_15 | IL_12p70 | 0.401 | | IL_15 | IL_12p70 | 0.228 |
| IL_15 | IL_13 | 0.352 | | IL_15 | IL_13 | 0.012 |
| IL_15 | IL_15 | 1.000 | | IL_15 | IL_15 | 1.000 |
| IL_15 | IL_17 | 0.404 | | IL_15 | IL_17 | 0.191 |
| IL_15 | IL_23 | 0.002 | | IL_15 | IL_23 | 0.126 |
| IL_15 | IFN_gamma | 0.000 | | IL_15 | IFN_gamma | 0.000 |
| IL_15 | TNF_alpha | 0.187 | | IL_15 | TNF_alpha | 0.291 |
| IL_15 | TNF_beta | 0.136 | | IL_15 | TNF_beta | 0.141 |
| IL_15 | Varicella_Int | -0.032 | | IL_15 | Varicella_Int | -0.030 |
| IL_15 | Measles_OD_DB_Int | -0.104 | | IL_15 | Measles_OD_DB_Int | 0.037 |
| IL_15 | Measles_Int | 0.017 | | IL_15 | Measles_Int | -0.071 |
| IL_15 | HepA_Int | -0.029 | | IL_15 | HepA_Int | -0.030 |
| IL_15 | Tetanus_Int | 0.000 | | IL_15 | Tetanus_Int | 0.000 |
| IL_15 | Diptheria_Int | 0.000 | | IL_15 | Diptheria_Int | 0.000 |
| IL_15 | Rubella_Int | 0.155 | | IL_15 | Rubella_Int | -0.074 |
| IL_15 | CMV_Int | -0.056 | | IL_15 | CMV_Int | -0.147 |
| IL_15 | HepB_cAb_Int | -0.027 | | IL_15 | HepB_cAb_Int | -0.087 |
| IL_15 | HepB_eAb_Int | 0.000 | | IL_15 | HepB_eAb_Int | 0.000 |
| IL_15 | HepB_eAg_Int | 0.000 | | IL_15 | HepB_eAg_Int | 0.000 |
| IL_15 | HepC_Int | 0.082 | | IL_15 | HepC_Int | 0.000 |
| IL_15 | Schistosoma_int | -0.086 | | IL_15 | Schistosoma_int | -0.124 |
| IL_15 | Strongyloides_Int | -0.085 | | IL_15 | Strongyloides_Int | -0.046 |
| IL_15 | Filaria_Int | -0.227 | | IL_15 | Filaria_Int | -0.003 |
| IL_17 | IL_1_alpha | 0.128 | | IL_17 | IL_1_alpha | 0.008 |
| IL_17 | IL_1_beta | 0.189 | | IL_17 | IL_1_beta | 0.075 |
| IL_17 | IL_2 | 0.132 | | IL_17 | IL_2 | 0.557 |
| IL_17 | IL_4 | 0.275 | | IL_17 | IL_4 | 0.087 |
| IL_17 | IL_5 | 0.095 | | IL_17 | IL_5 | 0.038 |
| IL_17 | IL_6 | 0.069 | | IL_17 | IL_6 | -0.061 |
| IL_17 | IL_8 | 0.160 | | IL_17 | IL_8 | 0.071 |
| IL_17 | IL_10 | 0.476 | | IL_17 | IL_10 | 0.451 |
| IL_17 | IL_12p70 | 0.322 | | IL_17 | IL_12p70 | 0.411 |
| IL_17 | IL_13 | 0.343 | | IL_17 | IL_13 | 0.279 |
| IL_17 | IL_15 | 0.404 | | IL_17 | IL_15 | 0.191 |
| IL_17 | IL_17 | 1.000 | | IL_17 | IL_17 | 1.000 |
| IL_17 | IL_23 | 0.109 | | IL_17 | IL_23 | 0.352 |
| IL_17 | IFN_gamma | 0.000 | | IL_17 | IFN_gamma | 0.000 |
| IL_17 | TNF_alpha | 0.130 | | IL_17 | TNF_alpha | 0.189 |
| IL_17 | TNF_beta | 0.247 | | IL_17 | TNF_beta | 0.641 |
| IL_17 | Varicella_Int | -0.175 | | IL_17 | Varicella_Int | -0.007 |

FIG. 21I5-G

| | | | | | | |
|---|---|---|---|---|---|---|
| IL_17 | Measles_OD_DB_Int | 0.069 | | IL_17 | Measles_OD_DB_Int | -0.376 |
| IL_17 | Measles_Int | -0.020 | | IL_17 | Measles_Int | 0.008 |
| IL_17 | HepA_Int | 0.016 | | IL_17 | HepA_Int | 0.062 |
| IL_17 | Tetanus_Int | 0.000 | | IL_17 | Tetanus_Int | 0.000 |
| IL_17 | Diptheria_Int | 0.000 | | IL_17 | Diptheria_Int | 0.000 |
| IL_17 | Rubella_Int | -0.096 | | IL_17 | Rubella_Int | 0.276 |
| IL_17 | CMV_Int | 0.038 | | IL_17 | CMV_Int | 0.013 |
| IL_17 | HepB_cAb_Int | -0.052 | | IL_17 | HepB_cAb_Int | -0.003 |
| IL_17 | HepB_eAb_Int | 0.000 | | IL_17 | HepB_eAb_Int | 0.000 |
| IL_17 | HepB_eAg_Int | 0.000 | | IL_17 | HepB_eAg_Int | 0.000 |
| IL_17 | HepC_Int | 0.042 | | IL_17 | HepC_Int | 0.000 |
| IL_17 | Schistosoma_int | 0.171 | | IL_17 | Schistosoma_int | 0.114 |
| IL_17 | Strongyloides_Int | 0.011 | | IL_17 | Strongyloides_Int | 0.091 |
| IL_17 | Filaria_Int | -0.061 | | IL_17 | Filaria_Int | -0.033 |
| IL_23 | IL_1_alpha | -0.037 | | IL_23 | IL_1_alpha | 0.020 |
| IL_23 | IL_1_beta | 0.025 | | IL_23 | IL_1_beta | 0.023 |
| IL_23 | IL_2 | 0.223 | | IL_23 | IL_2 | 0.195 |
| IL_23 | IL_4 | 0.059 | | IL_23 | IL_4 | 0.157 |
| IL_23 | IL_5 | 0.033 | | IL_23 | IL_5 | 0.008 |
| IL_23 | IL_6 | -0.076 | | IL_23 | IL_6 | 0.004 |
| IL_23 | IL_8 | -0.062 | | IL_23 | IL_8 | 0.054 |
| IL_23 | IL_10 | 0.168 | | IL_23 | IL_10 | 0.083 |
| IL_23 | IL_12p70 | 0.337 | | IL_23 | IL_12p70 | 0.290 |
| IL_23 | IL_13 | 0.001 | | IL_23 | IL_13 | 0.016 |
| IL_23 | IL_15 | 0.002 | | IL_23 | IL_15 | 0.126 |
| IL_23 | IL_17 | 0.109 | | IL_23 | IL_17 | 0.352 |
| IL_23 | IL_23 | 1.000 | | IL_23 | IL_23 | 1.000 |
| IL_23 | IFN_gamma | 0.000 | | IL_23 | IFN_gamma | 0.000 |
| IL_23 | TNF_alpha | 0.122 | | IL_23 | TNF_alpha | 0.262 |
| IL_23 | TNF_beta | 0.387 | | IL_23 | TNF_beta | 0.337 |
| IL_23 | Varicella_Int | -0.021 | | IL_23 | Varicella_Int | 0.034 |
| IL_23 | Measles_OD_DB_Int | 0.079 | | IL_23 | Measles_OD_DB_Int | -0.099 |
| IL_23 | Measles_Int | -0.027 | | IL_23 | Measles_Int | 0.043 |
| IL_23 | HepA_Int | 0.046 | | IL_23 | HepA_Int | 0.044 |
| IL_23 | Tetanus_Int | 0.000 | | IL_23 | Tetanus_Int | 0.000 |
| IL_23 | Diptheria_Int | 0.000 | | IL_23 | Diptheria_Int | 0.000 |
| IL_23 | Rubella_Int | -0.082 | | IL_23 | Rubella_Int | 0.087 |
| IL_23 | CMV_Int | 0.051 | | IL_23 | CMV_Int | 0.056 |
| IL_23 | HepB_cAb_Int | 0.033 | | IL_23 | HepB_cAb_Int | -0.048 |
| IL_23 | HepB_eAb_Int | 0.000 | | IL_23 | HepB_eAb_Int | 0.000 |
| IL_23 | HepB_eAg_Int | 0.000 | | IL_23 | HepB_eAg_Int | 0.000 |
| IL_23 | HepC_Int | -0.025 | | IL_23 | HepC_Int | 0.000 |
| IL_23 | Schistosoma_int | 0.232 | | IL_23 | Schistosoma_int | 0.363 |
| IL_23 | Strongyloides_Int | 0.143 | | IL_23 | Strongyloides_Int | 0.128 |
| IL_23 | Filaria_Int | 0.087 | | IL_23 | Filaria_Int | -0.028 |
| IFN_gamma | IL_1_alpha | 0.000 | | IFN_gamma | IL_1_alpha | 0.000 |
| IFN_gamma | IL_1_beta | 0.000 | | IFN_gamma | IL_1_beta | 0.000 |
| IFN_gamma | IL_2 | 0.000 | | IFN_gamma | IL_2 | 0.000 |
| IFN_gamma | IL_4 | 0.000 | | IFN_gamma | IL_4 | 0.000 |
| IFN_gamma | IL_5 | 0.000 | | IFN_gamma | IL_5 | 0.000 |
| IFN_gamma | IL_6 | 0.000 | | IFN_gamma | IL_6 | 0.000 |
| IFN_gamma | IL_8 | 0.000 | | IFN_gamma | IL_8 | 0.000 |
| IFN_gamma | IL_10 | 0.000 | | IFN_gamma | IL_10 | 0.000 |
| IFN_gamma | IL_12p70 | 0.000 | | IFN_gamma | IL_12p70 | 0.000 |
| IFN_gamma | IL_13 | 0.000 | | IFN_gamma | IL_13 | 0.000 |
| IFN_gamma | IL_15 | 0.000 | | IFN_gamma | IL_15 | 0.000 |
| IFN_gamma | IL_17 | 0.000 | | IFN_gamma | IL_17 | 0.000 |

FIG. 2115-H

| | | | | | | |
|---|---|---|---|---|---|---|
| IFN_gamma | IL_23 | 0.000 | | IFN_gamma | IL_23 | 0.000 |
| IFN_gamma | IFN_gamma | 1.000 | | IFN_gamma | IFN_gamma | 1.000 |
| IFN_gamma | TNF_alpha | 0.000 | | IFN_gamma | TNF_alpha | 0.000 |
| IFN_gamma | TNF_beta | 0.000 | | IFN_gamma | TNF_beta | 0.000 |
| IFN_gamma | Varicella_Int | 0.000 | | IFN_gamma | Varicella_Int | 0.000 |
| IFN_gamma | Measles_OD_DB_Int | 0.000 | | IFN_gamma | Measles_OD_DB_Int | 0.000 |
| IFN_gamma | Measles_Int | 0.000 | | IFN_gamma | Measles_Int | 0.000 |
| IFN_gamma | HepA_Int | 0.000 | | IFN_gamma | HepA_Int | 0.000 |
| IFN_gamma | Tetanus_Int | 0.000 | | IFN_gamma | Tetanus_Int | 0.000 |
| IFN_gamma | Diptheria_Int | 0.000 | | IFN_gamma | Diptheria_Int | 0.000 |
| IFN_gamma | Rubella_Int | 0.000 | | IFN_gamma | Rubella_Int | 0.000 |
| IFN_gamma | CMV_Int | 0.000 | | IFN_gamma | CMV_Int | 0.000 |
| IFN_gamma | HepB_cAb_Int | 0.000 | | IFN_gamma | HepB_cAb_Int | 0.000 |
| IFN_gamma | HepB_eAb_Int | 0.000 | | IFN_gamma | HepB_eAb_Int | 0.000 |
| IFN_gamma | HepB_eAg_Int | 0.000 | | IFN_gamma | HepB_eAg_Int | 0.000 |
| IFN_gamma | HepC_Int | 0.000 | | IFN_gamma | HepC_Int | 0.000 |
| IFN_gamma | Schistosoma_int | 0.000 | | IFN_gamma | Schistosoma_int | 0.000 |
| IFN_gamma | Strongyloides_Int | 0.000 | | IFN_gamma | Strongyloides_Int | 0.000 |
| IFN_gamma | Filaria_Int | 0.000 | | IFN_gamma | Filaria_Int | 0.000 |
| TNF_alpha | IL_1_alpha | 0.175 | | TNF_alpha | IL_1_alpha | 0.020 |
| TNF_alpha | IL_1_beta | 0.639 | | TNF_alpha | IL_1_beta | 0.060 |
| TNF_alpha | IL_2 | 0.120 | | TNF_alpha | IL_2 | 0.012 |
| TNF_alpha | IL_4 | 0.085 | | TNF_alpha | IL_4 | 0.377 |
| TNF_alpha | IL_5 | 0.071 | | TNF_alpha | IL_5 | 0.274 |
| TNF_alpha | IL_6 | 0.027 | | TNF_alpha | IL_6 | -0.007 |
| TNF_alpha | IL_8 | 0.126 | | TNF_alpha | IL_8 | 0.111 |
| TNF_alpha | IL_10 | 0.169 | | TNF_alpha | IL_10 | 0.403 |
| TNF_alpha | IL_12p70 | 0.251 | | TNF_alpha | IL_12p70 | 0.379 |
| TNF_alpha | IL_13 | 0.134 | | TNF_alpha | IL_13 | 0.069 |
| TNF_alpha | IL_15 | 0.187 | | TNF_alpha | IL_15 | 0.291 |
| TNF_alpha | IL_17 | 0.130 | | TNF_alpha | IL_17 | 0.189 |
| TNF_alpha | IL_23 | 0.122 | | TNF_alpha | IL_23 | 0.262 |
| TNF_alpha | IFN_gamma | 0.000 | | TNF_alpha | IFN_gamma | 0.000 |
| TNF_alpha | TNF_alpha | 1.000 | | TNF_alpha | TNF_alpha | 1.000 |
| TNF_alpha | TNF_beta | 0.324 | | TNF_alpha | TNF_beta | 0.356 |
| TNF_alpha | Varicella_Int | 0.065 | | TNF_alpha | Varicella_Int | -0.126 |
| TNF_alpha | Measles_OD_DB_Int | 0.026 | | TNF_alpha | Measles_OD_DB_Int | -0.025 |
| TNF_alpha | Measles_Int | 0.017 | | TNF_alpha | Measles_Int | -0.058 |
| TNF_alpha | HepA_Int | 0.021 | | TNF_alpha | HepA_Int | 0.060 |
| TNF_alpha | Tetanus_Int | 0.000 | | TNF_alpha | Tetanus_Int | 0.000 |
| TNF_alpha | Diptheria_Int | 0.000 | | TNF_alpha | Diptheria_Int | 0.000 |
| TNF_alpha | Rubella_Int | 0.062 | | TNF_alpha | Rubella_Int | -0.009 |
| TNF_alpha | CMV_Int | -0.169 | | TNF_alpha | CMV_Int | 0.004 |
| TNF_alpha | HepB_cAb_Int | -0.057 | | TNF_alpha | HepB_cAb_Int | -0.088 |
| TNF_alpha | HepB_eAb_Int | 0.000 | | TNF_alpha | HepB_eAb_Int | 0.000 |
| TNF_alpha | HepB_eAg_Int | 0.000 | | TNF_alpha | HepB_eAg_Int | 0.000 |
| TNF_alpha | HepC_Int | 0.023 | | TNF_alpha | HepC_Int | 0.000 |
| TNF_alpha | Schistosoma_int | 0.046 | | TNF_alpha | Schistosoma_int | 0.201 |
| TNF_alpha | Strongyloides_Int | 0.179 | | TNF_alpha | Strongyloides_Int | 0.119 |
| TNF_alpha | Filaria_Int | -0.109 | | TNF_alpha | Filaria_Int | 0.155 |
| TNF_beta | IL_1_alpha | 0.147 | | TNF_beta | IL_1_alpha | 0.040 |
| TNF_beta | IL_1_beta | 0.339 | | TNF_beta | IL_1_beta | 0.009 |
| TNF_beta | IL_2 | 0.364 | | TNF_beta | IL_2 | 0.164 |
| TNF_beta | IL_4 | 0.383 | | TNF_beta | IL_4 | 0.252 |
| TNF_beta | IL_5 | 0.039 | | TNF_beta | IL_5 | 0.195 |
| TNF_beta | IL_6 | -0.015 | | TNF_beta | IL_6 | -0.069 |
| TNF_beta | IL_8 | 0.161 | | TNF_beta | IL_8 | 0.117 |

FIG. 2115-I

| | | | | | | |
|---|---|---|---|---|---|---|
| TNF_beta | IL_10 | 0.382 | | TNF_beta | IL_10 | 0.274 |
| TNF_beta | IL_12p70 | 0.296 | | TNF_beta | IL_12p70 | 0.433 |
| TNF_beta | IL_13 | 0.153 | | TNF_beta | IL_13 | 0.000 |
| TNF_beta | IL_15 | 0.136 | | TNF_beta | IL_15 | 0.141 |
| TNF_beta | IL_17 | 0.247 | | TNF_beta | IL_17 | 0.641 |
| TNF_beta | IL_23 | 0.387 | | TNF_beta | IL_23 | 0.337 |
| TNF_beta | IFN_gamma | 0.000 | | TNF_beta | IFN_gamma | 0.000 |
| TNF_beta | TNF_alpha | 0.324 | | TNF_beta | TNF_alpha | 0.356 |
| TNF_beta | TNF_beta | 1.000 | | TNF_beta | TNF_beta | 1.000 |
| TNF_beta | Varicella_Int | -0.016 | | TNF_beta | Varicella_Int | -0.036 |
| TNF_beta | Measles_OD_DB_Int | 0.027 | | TNF_beta | Measles_OD_DB_Int | -0.188 |
| TNF_beta | Measles_Int | 0.037 | | TNF_beta | Measles_Int | -0.006 |
| TNF_beta | HepA_Int | 0.015 | | TNF_beta | HepA_Int | 0.047 |
| TNF_beta | Tetanus_Int | 0.000 | | TNF_beta | Tetanus_Int | 0.000 |
| TNF_beta | Diptheria_Int | 0.000 | | TNF_beta | Diptheria_Int | 0.000 |
| TNF_beta | Rubella_Int | -0.064 | | TNF_beta | Rubella_Int | 0.096 |
| TNF_beta | CMV_Int | 0.028 | | TNF_beta | CMV_Int | 0.074 |
| TNF_beta | HepB_cAb_Int | 0.071 | | TNF_beta | HepB_cAb_Int | -0.002 |
| TNF_beta | HepB_eAb_Int | 0.000 | | TNF_beta | HepB_eAb_Int | 0.000 |
| TNF_beta | HepB_eAg_Int | 0.000 | | TNF_beta | HepB_eAg_Int | 0.000 |
| TNF_beta | HepC_Int | 0.184 | | TNF_beta | HepC_Int | 0.000 |
| TNF_beta | Schistosoma_int | 0.135 | | TNF_beta | Schistosoma_int | 0.037 |
| TNF_beta | Strongyloides_Int | 0.185 | | TNF_beta | Strongyloides_Int | 0.283 |
| TNF_beta | Filaria_Int | 0.022 | | TNF_beta | Filaria_Int | 0.089 |
| Varicella_Int | IL_1_alpha | 0.077 | | Varicella_Int | IL_1_alpha | -0.057 |
| Varicella_Int | IL_1_beta | 0.017 | | Varicella_Int | IL_1_beta | -0.003 |
| Varicella_Int | IL_2 | -0.015 | | Varicella_Int | IL_2 | 0.007 |
| Varicella_Int | IL_4 | 0.054 | | Varicella_Int | IL_4 | -0.034 |
| Varicella_Int | IL_5 | 0.065 | | Varicella_Int | IL_5 | 0.023 |
| Varicella_Int | IL_6 | -0.010 | | Varicella_Int | IL_6 | -0.000 |
| Varicella_Int | IL_8 | 0.074 | | Varicella_Int | IL_8 | -0.010 |
| Varicella_Int | IL_10 | 0.047 | | Varicella_Int | IL_10 | -0.040 |
| Varicella_Int | IL_12p70 | 0.100 | | Varicella_Int | IL_12p70 | -0.119 |
| Varicella_Int | IL_13 | 0.077 | | Varicella_Int | IL_13 | 0.025 |
| Varicella_Int | IL_15 | -0.032 | | Varicella_Int | IL_15 | -0.030 |
| Varicella_Int | IL_17 | -0.175 | | Varicella_Int | IL_17 | -0.007 |
| Varicella_Int | IL_23 | -0.021 | | Varicella_Int | IL_23 | 0.034 |
| Varicella_Int | IFN_gamma | 0.000 | | Varicella_Int | IFN_gamma | 0.000 |
| Varicella_Int | TNF_alpha | 0.065 | | Varicella_Int | TNF_alpha | -0.126 |
| Varicella_Int | TNF_beta | -0.016 | | Varicella_Int | TNF_beta | -0.036 |
| Varicella_Int | Varicella_Int | 1.000 | | Varicella_Int | Varicella_Int | 1.000 |
| Varicella_Int | Measles_OD_DB_Int | 0.088 | | Varicella_Int | Measles_OD_DB_Int | 0.131 |
| Varicella_Int | Measles_Int | 0.174 | | Varicella_Int | Measles_Int | -0.039 |
| Varicella_Int | HepA_Int | -0.078 | | Varicella_Int | HepA_Int | 0.266 |
| Varicella_Int | Tetanus_Int | 0.000 | | Varicella_Int | Tetanus_Int | 0.000 |
| Varicella_Int | Diptheria_Int | 0.000 | | Varicella_Int | Diptheria_Int | 0.000 |
| Varicella_Int | Rubella_Int | -0.081 | | Varicella_Int | Rubella_Int | 0.055 |
| Varicella_Int | CMV_Int | 0.088 | | Varicella_Int | CMV_Int | -0.044 |
| Varicella_Int | HepB_cAb_Int | 0.048 | | Varicella_Int | HepB_cAb_Int | 0.074 |
| Varicella_Int | HepB_eAb_Int | 0.000 | | Varicella_Int | HepB_eAb_Int | 0.000 |
| Varicella_Int | HepB_eAg_Int | 0.000 | | Varicella_Int | HepB_eAg_Int | 0.000 |
| Varicella_Int | HepC_Int | 0.035 | | Varicella_Int | HepC_Int | 0.000 |
| Varicella_Int | Schistosoma_int | -0.116 | | Varicella_Int | Schistosoma_int | -0.120 |
| Varicella_Int | Strongyloides_Int | -0.010 | | Varicella_Int | Strongyloides_Int | -0.053 |
| Varicella_Int | Filaria_Int | -0.120 | | Varicella_Int | Filaria_Int | -0.055 |
| Measles_OD_DB_Int | IL_1_alpha | 0.099 | | Measles_OD_DB_Int | IL_1_alpha | -0.382 |
| Measles_OD_DB_Int | IL_1_beta | 0.010 | | Measles_OD_DB_Int | IL_1_beta | -0.296 |

FIG. 2115-J

| | | | | | | |
|---|---|---|---|---|---|---|
| Measles_OD_DB_Int | IL_2 | -0.014 | | Measles_OD_DB_Int | IL_2 | -0.260 |
| Measles_OD_DB_Int | IL_4 | -0.006 | | Measles_OD_DB_Int | IL_4 | -0.112 |
| Measles_OD_DB_Int | IL_5 | 0.095 | | Measles_OD_DB_Int | IL_5 | 0.023 |
| Measles_OD_DB_Int | IL_6 | -0.122 | | Measles_OD_DB_Int | IL_6 | -0.103 |
| Measles_OD_DB_Int | IL_8 | -0.130 | | Measles_OD_DB_Int | IL_8 | -0.236 |
| Measles_OD_DB_Int | IL_10 | 0.017 | | Measles_OD_DB_Int | IL_10 | -0.069 |
| Measles_OD_DB_Int | IL_12p70 | -0.015 | | Measles_OD_DB_Int | IL_12p70 | -0.090 |
| Measles_OD_DB_Int | IL_13 | -0.045 | | Measles_OD_DB_Int | IL_13 | -0.227 |
| Measles_OD_DB_Int | IL_15 | -0.104 | | Measles_OD_DB_Int | IL_15 | 0.037 |
| Measles_OD_DB_Int | IL_17 | 0.069 | | Measles_OD_DB_Int | IL_17 | -0.376 |
| Measles_OD_DB_Int | IL_23 | 0.079 | | Measles_OD_DB_Int | IL_23 | -0.099 |
| Measles_OD_DB_Int | IFN_gamma | 0.000 | | Measles_OD_DB_Int | IFN_gamma | 0.000 |
| Measles_OD_DB_Int | TNF_alpha | 0.026 | | Measles_OD_DB_Int | TNF_alpha | -0.025 |
| Measles_OD_DB_Int | TNF_beta | 0.027 | | Measles_OD_DB_Int | TNF_beta | -0.188 |
| Measles_OD_DB_Int | Varicella_Int | 0.088 | | Measles_OD_DB_Int | Varicella_Int | 0.131 |
| Measles_OD_DB_Int | Measles_OD_DB_Int | 1.000 | | Measles_OD_DB_Int | Measles_OD_DB_Int | 1.000 |
| Measles_OD_DB_Int | Measles_Int | 0.134 | | Measles_OD_DB_Int | Measles_Int | -0.033 |
| Measles_OD_DB_Int | HepA_Int | -0.123 | | Measles_OD_DB_Int | HepA_Int | -0.086 |
| Measles_OD_DB_Int | Tetanus_Int | 0.000 | | Measles_OD_DB_Int | Tetanus_Int | 0.000 |
| Measles_OD_DB_Int | Diptheria_Int | 0.000 | | Measles_OD_DB_Int | Diptheria_Int | 0.000 |
| Measles_OD_DB_Int | Rubella_Int | -0.059 | | Measles_OD_DB_Int | Rubella_Int | -0.131 |
| Measles_OD_DB_Int | CMV_Int | 0.042 | | Measles_OD_DB_Int | CMV_Int | 0.142 |
| Measles_OD_DB_Int | HepB_cAb_Int | 0.093 | | Measles_OD_DB_Int | HepB_cAb_Int | 0.030 |
| Measles_OD_DB_Int | HepB_eAb_Int | 0.000 | | Measles_OD_DB_Int | HepB_eAb_Int | 0.000 |
| Measles_OD_DB_Int | HepB_eAg_Int | 0.000 | | Measles_OD_DB_Int | HepB_eAg_Int | 0.000 |
| Measles_OD_DB_Int | HepC_Int | 0.056 | | Measles_OD_DB_Int | HepC_Int | 0.000 |
| Measles_OD_DB_Int | Schistosoma_int | 0.125 | | Measles_OD_DB_Int | Schistosoma_int | -0.118 |
| Measles_OD_DB_Int | Strongyloides_Int | 0.002 | | Measles_OD_DB_Int | Strongyloides_Int | -0.053 |
| Measles_OD_DB_Int | Filaria_Int | 0.127 | | Measles_OD_DB_Int | Filaria_Int | 0.092 |
| Measles_Int | IL_1_alpha | 0.039 | | Measles_Int | IL_1_alpha | -0.027 |
| Measles_Int | IL_1_beta | 0.006 | | Measles_Int | IL_1_beta | 0.007 |
| Measles_Int | IL_2 | -0.039 | | Measles_Int | IL_2 | 0.027 |
| Measles_Int | IL_4 | 0.043 | | Measles_Int | IL_4 | 0.051 |
| Measles_Int | IL_5 | 0.025 | | Measles_Int | IL_5 | 0.020 |
| Measles_Int | IL_6 | 0.038 | | Measles_Int | IL_6 | 0.010 |
| Measles_Int | IL_8 | 0.046 | | Measles_Int | IL_8 | 0.031 |
| Measles_Int | IL_10 | 0.019 | | Measles_Int | IL_10 | -0.173 |
| Measles_Int | IL_12p70 | 0.034 | | Measles_Int | IL_12p70 | -0.073 |
| Measles_Int | IL_13 | 0.074 | | Measles_Int | IL_13 | -0.027 |
| Measles_Int | IL_15 | 0.017 | | Measles_Int | IL_15 | -0.071 |
| Measles_Int | IL_17 | -0.020 | | Measles_Int | IL_17 | 0.008 |
| Measles_Int | IL_23 | -0.027 | | Measles_Int | IL_23 | 0.043 |
| Measles_Int | IFN_gamma | 0.000 | | Measles_Int | IFN_gamma | 0.000 |
| Measles_Int | TNF_alpha | 0.017 | | Measles_Int | TNF_alpha | -0.058 |
| Measles_Int | TNF_beta | 0.037 | | Measles_Int | TNF_beta | -0.006 |
| Measles_Int | Varicella_Int | 0.174 | | Measles_Int | Varicella_Int | -0.039 |
| Measles_Int | Measles_OD_DB_Int | 0.134 | | Measles_Int | Measles_OD_DB_Int | -0.033 |
| Measles_Int | Measles_Int | 1.000 | | Measles_Int | Measles_Int | 1.000 |
| Measles_Int | HepA_Int | -0.021 | | Measles_Int | HepA_Int | -0.046 |
| Measles_Int | Tetanus_Int | 0.000 | | Measles_Int | Tetanus_Int | 0.000 |
| Measles_Int | Diptheria_Int | 0.000 | | Measles_Int | Diptheria_Int | 0.000 |
| Measles_Int | Rubella_Int | 0.044 | | Measles_Int | Rubella_Int | -0.055 |
| Measles_Int | CMV_Int | -0.013 | | Measles_Int | CMV_Int | 0.325 |
| Measles_Int | HepB_cAb_Int | 0.027 | | Measles_Int | HepB_cAb_Int | 0.107 |
| Measles_Int | HepB_eAb_Int | 0.000 | | Measles_Int | HepB_eAb_Int | 0.000 |
| Measles_Int | HepB_eAg_Int | 0.000 | | Measles_Int | HepB_eAg_Int | 0.000 |
| Measles_Int | HepC_Int | 0.008 | | Measles_Int | HepC_Int | 0.000 |

FIG. 21I5-K

| | | | | | | |
|---|---|---|---|---|---|---|
| Measles_Int | Schistosoma_int | -0.195 | | Measles_Int | Schistosoma_int | 0.100 |
| Measles_Int | Strongyloides_Int | -0.105 | | Measles_Int | Strongyloides_Int | 0.023 |
| Measles_Int | Filaria_Int | -0.165 | | Measles_Int | Filaria_Int | 0.090 |
| HepA_Int | IL_1_alpha | 0.017 | | HepA_Int | IL_1_alpha | 0.028 |
| HepA_Int | IL_1_beta | 0.027 | | HepA_Int | IL_1_beta | 0.068 |
| HepA_Int | IL_2 | -0.025 | | HepA_Int | IL_2 | 0.029 |
| HepA_Int | IL_4 | 0.077 | | HepA_Int | IL_4 | 0.087 |
| HepA_Int | IL_5 | 0.036 | | HepA_Int | IL_5 | 0.022 |
| HepA_Int | IL_6 | 0.026 | | HepA_Int | IL_6 | 0.072 |
| HepA_Int | IL_8 | 0.015 | | HepA_Int | IL_8 | 0.002 |
| HepA_Int | IL_10 | -0.082 | | HepA_Int | IL_10 | 0.131 |
| HepA_Int | IL_12p70 | 0.048 | | HepA_Int | IL_12p70 | 0.057 |
| HepA_Int | IL_13 | 0.038 | | HepA_Int | IL_13 | 0.057 |
| HepA_Int | IL_15 | -0.029 | | HepA_Int | IL_15 | -0.030 |
| HepA_Int | IL_17 | 0.016 | | HepA_Int | IL_17 | 0.062 |
| HepA_Int | IL_23 | 0.046 | | HepA_Int | IL_23 | 0.044 |
| HepA_Int | IFN_gamma | 0.000 | | HepA_Int | IFN_gamma | 0.000 |
| HepA_Int | TNF_alpha | 0.021 | | HepA_Int | TNF_alpha | 0.060 |
| HepA_Int | TNF_beta | 0.015 | | HepA_Int | TNF_beta | 0.047 |
| HepA_Int | Varicella_Int | -0.078 | | HepA_Int | Varicella_Int | 0.266 |
| HepA_Int | Measles_OD_DB_Int | -0.123 | | HepA_Int | Measles_OD_DB_Int | -0.086 |
| HepA_Int | Measles_Int | -0.021 | | HepA_Int | Measles_Int | -0.046 |
| HepA_Int | HepA_Int | 1.000 | | HepA_Int | HepA_Int | 1.000 |
| HepA_Int | Tetanus_Int | 0.000 | | HepA_Int | Tetanus_Int | 0.000 |
| HepA_Int | Diptheria_Int | 0.000 | | HepA_Int | Diptheria_Int | 0.000 |
| HepA_Int | Rubella_Int | 0.075 | | HepA_Int | Rubella_Int | 0.064 |
| HepA_Int | CMV_Int | -0.030 | | HepA_Int | CMV_Int | -0.051 |
| HepA_Int | HepB_cAb_Int | -0.076 | | HepA_Int | HepB_cAb_Int | 0.086 |
| HepA_Int | HepB_eAb_Int | 0.000 | | HepA_Int | HepB_eAb_Int | 0.000 |
| HepA_Int | HepB_eAg_Int | 0.000 | | HepA_Int | HepB_eAg_Int | 0.000 |
| HepA_Int | HepC_Int | 0.017 | | HepA_Int | HepC_Int | 0.000 |
| HepA_Int | Schistosoma_int | 0.080 | | HepA_Int | Schistosoma_int | -0.249 |
| HepA_Int | Strongyloides_Int | 0.034 | | HepA_Int | Strongyloides_Int | -0.001 |
| HepA_Int | Filaria_Int | 0.011 | | HepA_Int | Filaria_Int | -0.029 |
| Tetanus_Int | IL_1_alpha | 0.000 | | Tetanus_Int | IL_1_alpha | 0.000 |
| Tetanus_Int | IL_1_beta | 0.000 | | Tetanus_Int | IL_1_beta | 0.000 |
| Tetanus_Int | IL_2 | 0.000 | | Tetanus_Int | IL_2 | 0.000 |
| Tetanus_Int | IL_4 | 0.000 | | Tetanus_Int | IL_4 | 0.000 |
| Tetanus_Int | IL_5 | 0.000 | | Tetanus_Int | IL_5 | 0.000 |
| Tetanus_Int | IL_6 | 0.000 | | Tetanus_Int | IL_6 | 0.000 |
| Tetanus_Int | IL_8 | 0.000 | | Tetanus_Int | IL_8 | 0.000 |
| Tetanus_Int | IL_10 | 0.000 | | Tetanus_Int | IL_10 | 0.000 |
| Tetanus_Int | IL_12p70 | 0.000 | | Tetanus_Int | IL_12p70 | 0.000 |
| Tetanus_Int | IL_13 | 0.000 | | Tetanus_Int | IL_13 | 0.000 |
| Tetanus_Int | IL_15 | 0.000 | | Tetanus_Int | IL_15 | 0.000 |
| Tetanus_Int | IL_17 | 0.000 | | Tetanus_Int | IL_17 | 0.000 |
| Tetanus_Int | IL_23 | 0.000 | | Tetanus_Int | IL_23 | 0.000 |
| Tetanus_Int | IFN_gamma | 0.000 | | Tetanus_Int | IFN_gamma | 0.000 |
| Tetanus_Int | TNF_alpha | 0.000 | | Tetanus_Int | TNF_alpha | 0.000 |
| Tetanus_Int | TNF_beta | 0.000 | | Tetanus_Int | TNF_beta | 0.000 |
| Tetanus_Int | Varicella_Int | 0.000 | | Tetanus_Int | Varicella_Int | 0.000 |
| Tetanus_Int | Measles_OD_DB_Int | 0.000 | | Tetanus_Int | Measles_OD_DB_Int | 0.000 |
| Tetanus_Int | Measles_Int | 0.000 | | Tetanus_Int | Measles_Int | 0.000 |
| Tetanus_Int | HepA_Int | 0.000 | | Tetanus_Int | HepA_Int | 0.000 |
| Tetanus_Int | Tetanus_Int | 1.000 | | Tetanus_Int | Tetanus_Int | 1.000 |
| Tetanus_Int | Diptheria_Int | 0.000 | | Tetanus_Int | Diptheria_Int | 0.000 |
| Tetanus_Int | Rubella_Int | 0.000 | | Tetanus_Int | Rubella_Int | 0.000 |

FIG. 2115-L

| | | | | | | |
|---|---|---|---|---|---|---|
| Tetanus_Int | CMV_Int | 0.000 | | Tetanus_Int | CMV_Int | 0.000 |
| Tetanus_Int | HepB_cAb_Int | 0.000 | | Tetanus_Int | HepB_cAb_Int | 0.000 |
| Tetanus_Int | HepB_eAb_Int | 0.000 | | Tetanus_Int | HepB_eAb_Int | 0.000 |
| Tetanus_Int | HepB_eAg_Int | 0.000 | | Tetanus_Int | HepB_eAg_Int | 0.000 |
| Tetanus_Int | HepC_Int | 0.000 | | Tetanus_Int | HepC_Int | 0.000 |
| Tetanus_Int | Schistosoma_int | 0.000 | | Tetanus_Int | Schistosoma_int | 0.000 |
| Tetanus_Int | Strongyloides_Int | 0.000 | | Tetanus_Int | Strongyloides_Int | 0.000 |
| Tetanus_Int | Filaria_Int | 0.000 | | Tetanus_Int | Filaria_Int | 0.000 |
| Diptheria_Int | IL_1_alpha | 0.000 | | Diptheria_Int | IL_1_alpha | 0.000 |
| Diptheria_Int | IL_1_beta | 0.000 | | Diptheria_Int | IL_1_beta | 0.000 |
| Diptheria_Int | IL_2 | 0.000 | | Diptheria_Int | IL_2 | 0.000 |
| Diptheria_Int | IL_4 | 0.000 | | Diptheria_Int | IL_4 | 0.000 |
| Diptheria_Int | IL_5 | 0.000 | | Diptheria_Int | IL_5 | 0.000 |
| Diptheria_Int | IL_6 | 0.000 | | Diptheria_Int | IL_6 | 0.000 |
| Diptheria_Int | IL_8 | 0.000 | | Diptheria_Int | IL_8 | 0.000 |
| Diptheria_Int | IL_10 | 0.000 | | Diptheria_Int | IL_10 | 0.000 |
| Diptheria_Int | IL_12p70 | 0.000 | | Diptheria_Int | IL_12p70 | 0.000 |
| Diptheria_Int | IL_13 | 0.000 | | Diptheria_Int | IL_13 | 0.000 |
| Diptheria_Int | IL_15 | 0.000 | | Diptheria_Int | IL_15 | 0.000 |
| Diptheria_Int | IL_17 | 0.000 | | Diptheria_Int | IL_17 | 0.000 |
| Diptheria_Int | IL_23 | 0.000 | | Diptheria_Int | IL_23 | 0.000 |
| Diptheria_Int | IFN_gamma | 0.000 | | Diptheria_Int | IFN_gamma | 0.000 |
| Diptheria_Int | TNF_alpha | 0.000 | | Diptheria_Int | TNF_alpha | 0.000 |
| Diptheria_Int | TNF_beta | 0.000 | | Diptheria_Int | TNF_beta | 0.000 |
| Diptheria_Int | Varicella_Int | 0.000 | | Diptheria_Int | Varicella_Int | 0.000 |
| Diptheria_Int | Measles_OD_DB_Int | 0.000 | | Diptheria_Int | Measles_OD_DB_Int | 0.000 |
| Diptheria_Int | Measles_Int | 0.000 | | Diptheria_Int | Measles_Int | 0.000 |
| Diptheria_Int | HepA_Int | 0.000 | | Diptheria_Int | HepA_Int | 0.000 |
| Diptheria_Int | Tetanus_Int | 0.000 | | Diptheria_Int | Tetanus_Int | 0.000 |
| Diptheria_Int | Diptheria_Int | 1.000 | | Diptheria_Int | Diptheria_Int | 1.000 |
| Diptheria_Int | Rubella_Int | 0.000 | | Diptheria_Int | Rubella_Int | 0.000 |
| Diptheria_Int | CMV_Int | 0.000 | | Diptheria_Int | CMV_Int | 0.000 |
| Diptheria_Int | HepB_cAb_Int | 0.000 | | Diptheria_Int | HepB_cAb_Int | 0.000 |
| Diptheria_Int | HepB_eAb_Int | 0.000 | | Diptheria_Int | HepB_eAb_Int | 0.000 |
| Diptheria_Int | HepB_eAg_Int | 0.000 | | Diptheria_Int | HepB_eAg_Int | 0.000 |
| Diptheria_Int | HepC_Int | 0.000 | | Diptheria_Int | HepC_Int | 0.000 |
| Diptheria_Int | Schistosoma_int | 0.000 | | Diptheria_Int | Schistosoma_int | 0.000 |
| Diptheria_Int | Strongyloides_Int | 0.000 | | Diptheria_Int | Strongyloides_Int | 0.000 |
| Diptheria_Int | Filaria_Int | 0.000 | | Diptheria_Int | Filaria_Int | 0.000 |
| Rubella_Int | IL_1_alpha | -0.012 | | Rubella_Int | IL_1_alpha | 0.249 |
| Rubella_Int | IL_1_beta | 0.037 | | Rubella_Int | IL_1_beta | 0.189 |
| Rubella_Int | IL_2 | 0.015 | | Rubella_Int | IL_2 | 0.072 |
| Rubella_Int | IL_4 | 0.086 | | Rubella_Int | IL_4 | -0.026 |
| Rubella_Int | IL_5 | 0.109 | | Rubella_Int | IL_5 | -0.055 |
| Rubella_Int | IL_6 | 0.252 | | Rubella_Int | IL_6 | -0.059 |
| Rubella_Int | IL_8 | 0.146 | | Rubella_Int | IL_8 | -0.068 |
| Rubella_Int | IL_10 | -0.118 | | Rubella_Int | IL_10 | 0.098 |
| Rubella_Int | IL_12p70 | -0.077 | | Rubella_Int | IL_12p70 | -0.059 |
| Rubella_Int | IL_13 | -0.033 | | Rubella_Int | IL_13 | 0.003 |
| Rubella_Int | IL_15 | 0.155 | | Rubella_Int | IL_15 | -0.074 |
| Rubella_Int | IL_17 | -0.096 | | Rubella_Int | IL_17 | 0.276 |
| Rubella_Int | IL_23 | -0.082 | | Rubella_Int | IL_23 | 0.087 |
| Rubella_Int | IFN_gamma | 0.000 | | Rubella_Int | IFN_gamma | 0.000 |
| Rubella_Int | TNF_alpha | 0.062 | | Rubella_Int | TNF_alpha | -0.009 |
| Rubella_Int | TNF_beta | -0.064 | | Rubella_Int | TNF_beta | 0.096 |
| Rubella_Int | Varicella_Int | -0.081 | | Rubella_Int | Varicella_Int | 0.055 |
| Rubella_Int | Measles_OD_DB_Int | -0.059 | | Rubella_Int | Measles_OD_DB_Int | -0.131 |

FIG. 21I5-M

| | | | | | | |
|---|---|---|---|---|---|---|
| Rubella_Int | Measles_Int | 0.044 | | Rubella_Int | Measles_Int | -0.055 |
| Rubella_Int | HepA_Int | 0.075 | | Rubella_Int | HepA_Int | 0.064 |
| Rubella_Int | Tetanus_Int | 0.000 | | Rubella_Int | Tetanus_Int | 0.000 |
| Rubella_Int | Diptheria_Int | 0.000 | | Rubella_Int | Diptheria_Int | 0.000 |
| Rubella_Int | Rubella_Int | 1.000 | | Rubella_Int | Rubella_Int | 1.000 |
| Rubella_Int | CMV_Int | -0.083 | | Rubella_Int | CMV_Int | -0.050 |
| Rubella_Int | HepB_cAb_Int | -0.054 | | Rubella_Int | HepB_cAb_Int | 0.060 |
| Rubella_Int | HepB_eAb_Int | 0.000 | | Rubella_Int | HepB_eAb_Int | 0.000 |
| Rubella_Int | HepB_eAg_Int | 0.000 | | Rubella_Int | HepB_eAg_Int | 0.000 |
| Rubella_Int | HepC_Int | -0.036 | | Rubella_Int | HepC_Int | 0.000 |
| Rubella_Int | Schistosoma_int | 0.046 | | Rubella_Int | Schistosoma_int | 0.085 |
| Rubella_Int | Strongyloides_Int | 0.011 | | Rubella_Int | Strongyloides_Int | -0.053 |
| Rubella_Int | Filaria_Int | 0.005 | | Rubella_Int | Filaria_Int | -0.117 |
| CMV_Int | IL_1_alpha | -0.021 | | CMV_Int | IL_1_alpha | 0.006 |
| CMV_Int | IL_1_beta | -0.173 | | CMV_Int | IL_1_beta | 0.051 |
| CMV_Int | IL_2 | 0.057 | | CMV_Int | IL_2 | 0.041 |
| CMV_Int | IL_4 | 0.033 | | CMV_Int | IL_4 | -0.128 |
| CMV_Int | IL_5 | 0.025 | | CMV_Int | IL_5 | 0.028 |
| CMV_Int | IL_6 | 0.040 | | CMV_Int | IL_6 | 0.039 |
| CMV_Int | IL_8 | 0.025 | | CMV_Int | IL_8 | 0.026 |
| CMV_Int | IL_10 | 0.020 | | CMV_Int | IL_10 | 0.005 |
| CMV_Int | IL_12p70 | 0.002 | | CMV_Int | IL_12p70 | 0.055 |
| CMV_Int | IL_13 | 0.042 | | CMV_Int | IL_13 | 0.013 |
| CMV_Int | IL_15 | -0.056 | | CMV_Int | IL_15 | -0.147 |
| CMV_Int | IL_17 | 0.038 | | CMV_Int | IL_17 | 0.013 |
| CMV_Int | IL_23 | 0.051 | | CMV_Int | IL_23 | 0.056 |
| CMV_Int | IFN_gamma | 0.000 | | CMV_Int | IFN_gamma | 0.000 |
| CMV_Int | TNF_alpha | -0.169 | | CMV_Int | TNF_alpha | 0.004 |
| CMV_Int | TNF_beta | 0.028 | | CMV_Int | TNF_beta | 0.074 |
| CMV_Int | Varicella_Int | 0.088 | | CMV_Int | Varicella_Int | -0.044 |
| CMV_Int | Measles_OD_DB_Int | 0.042 | | CMV_Int | Measles_OD_DB_Int | 0.142 |
| CMV_Int | Measles_Int | -0.013 | | CMV_Int | Measles_Int | 0.325 |
| CMV_Int | HepA_Int | -0.030 | | CMV_Int | HepA_Int | -0.051 |
| CMV_Int | Tetanus_Int | 0.000 | | CMV_Int | Tetanus_Int | 0.000 |
| CMV_Int | Diptheria_Int | 0.000 | | CMV_Int | Diptheria_Int | 0.000 |
| CMV_Int | Rubella_Int | -0.083 | | CMV_Int | Rubella_Int | -0.050 |
| CMV_Int | CMV_Int | 1.000 | | CMV_Int | CMV_Int | 1.000 |
| CMV_Int | HepB_cAb_Int | 0.048 | | CMV_Int | HepB_cAb_Int | 0.106 |
| CMV_Int | HepB_eAb_Int | 0.000 | | CMV_Int | HepB_eAb_Int | 0.000 |
| CMV_Int | HepB_eAg_Int | 0.000 | | CMV_Int | HepB_eAg_Int | 0.000 |
| CMV_Int | HepC_Int | 0.013 | | CMV_Int | HepC_Int | 0.000 |
| CMV_Int | Schistosoma_int | -0.067 | | CMV_Int | Schistosoma_int | 0.089 |
| CMV_Int | Strongyloides_Int | -0.127 | | CMV_Int | Strongyloides_Int | 0.197 |
| CMV_Int | Filaria_Int | -0.024 | | CMV_Int | Filaria_Int | 0.081 |
| HepB_cAb_Int | IL_1_alpha | -0.070 | | HepB_cAb_Int | IL_1_alpha | -0.094 |
| HepB_cAb_Int | IL_1_beta | -0.076 | | HepB_cAb_Int | IL_1_beta | -0.036 |
| HepB_cAb_Int | IL_2 | 0.010 | | HepB_cAb_Int | IL_2 | 0.224 |
| HepB_cAb_Int | IL_4 | -0.023 | | HepB_cAb_Int | IL_4 | -0.070 |
| HepB_cAb_Int | IL_5 | -0.034 | | HepB_cAb_Int | IL_5 | -0.053 |
| HepB_cAb_Int | IL_6 | -0.071 | | HepB_cAb_Int | IL_6 | -0.056 |
| HepB_cAb_Int | IL_8 | 0.065 | | HepB_cAb_Int | IL_8 | 0.039 |
| HepB_cAb_Int | IL_10 | -0.036 | | HepB_cAb_Int | IL_10 | 0.008 |
| HepB_cAb_Int | IL_12p70 | -0.093 | | HepB_cAb_Int | IL_12p70 | -0.033 |
| HepB_cAb_Int | IL_13 | -0.025 | | HepB_cAb_Int | IL_13 | 0.168 |
| HepB_cAb_Int | IL_15 | -0.027 | | HepB_cAb_Int | IL_15 | -0.087 |
| HepB_cAb_Int | IL_17 | -0.052 | | HepB_cAb_Int | IL_17 | -0.003 |
| HepB_cAb_Int | IL_23 | 0.033 | | HepB_cAb_Int | IL_23 | -0.048 |

FIG. 2I15-N

| HepB_cAb_Int | IFN_gamma | 0.000 | HepB_cAb_Int | IFN_gamma | 0.000 |
|---|---|---|---|---|---|
| HepB_cAb_Int | TNF_alpha | -0.057 | HepB_cAb_Int | TNF_alpha | -0.088 |
| HepB_cAb_Int | TNF_beta | 0.071 | HepB_cAb_Int | TNF_beta | -0.002 |
| HepB_cAb_Int | Varicella_Int | 0.048 | HepB_cAb_Int | Varicella_Int | 0.074 |
| HepB_cAb_Int | Measles_OD_DB_Int | 0.093 | HepB_cAb_Int | Measles_OD_DB_Int | 0.030 |
| HepB_cAb_Int | Measles_Int | 0.027 | HepB_cAb_Int | Measles_Int | 0.107 |
| HepB_cAb_Int | HepA_Int | -0.076 | HepB_cAb_Int | HepA_int | 0.086 |
| HepB_cAb_Int | Tetanus_Int | 0.000 | HepB_cAb_Int | Tetanus_Int | 0.000 |
| HepB_cAb_Int | Diptheria_Int | 0.000 | HepB_cAb_Int | Diptheria_Int | 0.000 |
| HepB_cAb_Int | Rubella_Int | -0.054 | HepB_cAb_Int | Rubella_Int | 0.060 |
| HepB_cAb_Int | CMV_Int | 0.048 | HepB_cAb_Int | CMV_Int | 0.106 |
| HepB_cAb_Int | HepB_cAb_Int | 1.000 | HepB_cAb_Int | HepB_cAb_Int | 1.000 |
| HepB_cAb_Int | HepB_eAb_Int | 0.000 | HepB_cAb_Int | HepB_eAb_Int | 0.000 |
| HepB_cAb_Int | HepB_eAg_Int | 0.000 | HepB_cAb_Int | HepB_eAg_Int | 0.000 |
| HepB_cAb_Int | HepC_Int | -0.028 | HepB_cAb_Int | HepC_Int | 0.000 |
| HepB_cAb_Int | Schistosoma_int | -0.064 | HepB_cAb_Int | Schistosoma_int | -0.045 |
| HepB_cAb_Int | Strongyloides_Int | 0.149 | HepB_cAb_Int | Strongyloides_Int | 0.223 |
| HepB_cAb_Int | Filaria_Int | -0.018 | HepB_cAb_Int | Filaria_Int | 0.055 |
| HepB_eAb_Int | IL_1_alpha | 0.000 | HepB_eAb_Int | IL_1_alpha | 0.000 |
| HepB_eAb_Int | IL_1_beta | 0.000 | HepB_eAb_Int | IL_1_beta | 0.000 |
| HepB_eAb_Int | IL_2 | 0.000 | HepB_eAb_Int | IL_2 | 0.000 |
| HepB_eAb_Int | IL_4 | 0.000 | HepB_eAb_Int | IL_4 | 0.000 |
| HepB_eAb_Int | IL_5 | 0.000 | HepB_eAb_Int | IL_5 | 0.000 |
| HepB_eAb_Int | IL_6 | 0.000 | HepB_eAb_Int | IL_6 | 0.000 |
| HepB_eAb_Int | IL_8 | 0.000 | HepB_eAb_Int | IL_8 | 0.000 |
| HepB_eAb_Int | IL_10 | 0.000 | HepB_eAb_Int | IL_10 | 0.000 |
| HepB_eAb_Int | IL_12p70 | 0.000 | HepB_eAb_Int | IL_12p70 | 0.000 |
| HepB_eAb_Int | IL_13 | 0.000 | HepB_eAb_Int | IL_13 | 0.000 |
| HepB_eAb_Int | IL_15 | 0.000 | HepB_eAb_Int | IL_15 | 0.000 |
| HepB_eAb_Int | IL_17 | 0.000 | HepB_eAb_Int | IL_17 | 0.000 |
| HepB_eAb_Int | IL_23 | 0.000 | HepB_eAb_Int | IL_23 | 0.000 |
| HepB_eAb_Int | IFN_gamma | 0.000 | HepB_eAb_Int | IFN_gamma | 0.000 |
| HepB_eAb_Int | TNF_alpha | 0.000 | HepB_eAb_Int | TNF_alpha | 0.000 |
| HepB_eAb_Int | TNF_beta | 0.000 | HepB_eAb_Int | TNF_beta | 0.000 |
| HepB_eAb_Int | Varicella_Int | 0.000 | HepB_eAb_Int | Varicella_Int | 0.000 |
| HepB_eAb_Int | Measles_OD_DB_Int | 0.000 | HepB_eAb_Int | Measles_OD_DB_Int | 0.000 |
| HepB_eAb_Int | Measles_Int | 0.000 | HepB_eAb_Int | Measles_Int | 0.000 |
| HepB_eAb_Int | HepA_Int | 0.000 | HepB_eAb_Int | HepA_int | 0.000 |
| HepB_eAb_Int | Tetanus_Int | 0.000 | HepB_eAb_Int | Tetanus_Int | 0.000 |
| HepB_eAb_Int | Diptheria_Int | 0.000 | HepB_eAb_Int | Diptheria_Int | 0.000 |
| HepB_eAb_Int | Rubella_Int | 0.000 | HepB_eAb_Int | Rubella_Int | 0.000 |
| HepB_eAb_Int | CMV_Int | 0.000 | HepB_eAb_Int | CMV_Int | 0.000 |
| HepB_eAb_Int | HepB_cAb_Int | 0.000 | HepB_eAb_Int | HepB_cAb_Int | 0.000 |
| HepB_eAb_Int | HepB_eAb_Int | 1.000 | HepB_eAb_Int | HepB_eAb_Int | 1.000 |
| HepB_eAb_Int | HepB_eAg_Int | 0.000 | HepB_eAb_Int | HepB_eAg_Int | 0.000 |
| HepB_eAb_Int | HepC_Int | 0.000 | HepB_eAb_Int | HepC_Int | 0.000 |
| HepB_eAb_Int | Schistosoma_int | 0.000 | HepB_eAb_Int | Schistosoma_int | 0.000 |
| HepB_eAb_Int | Strongyloides_Int | 0.000 | HepB_eAb_Int | Strongyloides_Int | 0.000 |
| HepB_eAb_Int | Filaria_Int | 0.000 | HepB_eAb_Int | Filaria_Int | 0.000 |
| HepB_eAg_Int | IL_1_alpha | 0.000 | HepB_eAg_Int | IL_1_alpha | 0.000 |
| HepB_eAg_Int | IL_1_beta | 0.000 | HepB_eAg_Int | IL_1_beta | 0.000 |
| HepB_eAg_Int | IL_2 | 0.000 | HepB_eAg_Int | IL_2 | 0.000 |
| HepB_eAg_Int | IL_4 | 0.000 | HepB_eAg_Int | IL_4 | 0.000 |
| HepB_eAg_Int | IL_5 | 0.000 | HepB_eAg_Int | IL_5 | 0.000 |
| HepB_eAg_Int | IL_6 | 0.000 | HepB_eAg_Int | IL_6 | 0.000 |
| HepB_eAg_Int | IL_8 | 0.000 | HepB_eAg_Int | IL_8 | 0.000 |
| HepB_eAg_Int | IL_10 | 0.000 | HepB_eAg_Int | IL_10 | 0.000 |

FIG. 2115-O

| | | | | | | |
|---|---|---|---|---|---|---|
| HepB_eAg_Int | IL_12p70 | 0.000 | | HepB_eAg_Int | IL_12p70 | 0.000 |
| HepB_eAg_Int | IL_13 | 0.000 | | HepB_eAg_Int | IL_13 | 0.000 |
| HepB_eAg_Int | IL_15 | 0.000 | | HepB_eAg_Int | IL_15 | 0.000 |
| HepB_eAg_Int | IL_17 | 0.000 | | HepB_eAg_Int | IL_17 | 0.000 |
| HepB_eAg_Int | IL_23 | 0.000 | | HepB_eAg_Int | IL_23 | 0.000 |
| HepB_eAg_Int | IFN_gamma | 0.000 | | HepB_eAg_Int | IFN_gamma | 0.000 |
| HepB_eAg_Int | TNF_alpha | 0.000 | | HepB_eAg_Int | TNF_alpha | 0.000 |
| HepB_eAg_Int | TNF_beta | 0.000 | | HepB_eAg_Int | TNF_beta | 0.000 |
| HepB_eAg_Int | Varicella_Int | 0.000 | | HepB_eAg_Int | Varicella_Int | 0.000 |
| HepB_eAg_Int | Measles_OD_DB_Int | 0.000 | | HepB_eAg_Int | Measles_OD_DB_Int | 0.000 |
| HepB_eAg_Int | Measles_Int | 0.000 | | HepB_eAg_Int | Measles_Int | 0.000 |
| HepB_eAg_Int | HepA_Int | 0.000 | | HepB_eAg_Int | HepA_Int | 0.000 |
| HepB_eAg_Int | Tetanus_Int | 0.000 | | HepB_eAg_Int | Tetanus_Int | 0.000 |
| HepB_eAg_Int | Diptheria_Int | 0.000 | | HepB_eAg_Int | Diptheria_Int | 0.000 |
| HepB_eAg_Int | Rubella_Int | 0.000 | | HepB_eAg_Int | Rubella_Int | 0.000 |
| HepB_eAg_Int | CMV_Int | 0.000 | | HepB_eAg_Int | CMV_Int | 0.000 |
| HepB_eAg_Int | HepB_cAb_Int | 0.000 | | HepB_eAg_Int | HepB_cAb_Int | 0.000 |
| HepB_eAg_Int | HepB_eAb_Int | 0.000 | | HepB_eAg_Int | HepB_eAb_Int | 0.000 |
| HepB_eAg_Int | HepB_eAg_Int | 1.000 | | HepB_eAg_Int | HepB_eAg_Int | 1.000 |
| HepB_eAg_Int | HepC_Int | 0.000 | | HepB_eAg_Int | HepC_Int | 0.000 |
| HepB_eAg_Int | Schistosoma_int | 0.000 | | HepB_eAg_Int | Schistosoma_int | 0.000 |
| HepB_eAg_Int | Strongyloides_Int | 0.000 | | HepB_eAg_Int | Strongyloides_Int | 0.000 |
| HepB_eAg_Int | Filaria_Int | 0.000 | | HepB_eAg_Int | Filaria_Int | 0.000 |
| HepC_Int | IL_1_alpha | 0.051 | | HepC_Int | IL_1_alpha | 0.000 |
| HepC_Int | IL_1_beta | 0.020 | | HepC_Int | IL_1_beta | 0.000 |
| HepC_Int | IL_2 | -0.054 | | HepC_Int | IL_2 | 0.000 |
| HepC_Int | IL_4 | 0.149 | | HepC_Int | IL_4 | 0.000 |
| HepC_Int | IL_5 | -0.007 | | HepC_Int | IL_5 | 0.000 |
| HepC_Int | IL_6 | -0.006 | | HepC_Int | IL_6 | 0.000 |
| HepC_Int | IL_8 | 0.003 | | HepC_Int | IL_8 | 0.000 |
| HepC_Int | IL_10 | 0.135 | | HepC_Int | IL_10 | 0.000 |
| HepC_Int | IL_12p70 | 0.150 | | HepC_Int | IL_12p70 | 0.000 |
| HepC_Int | IL_13 | 0.073 | | HepC_Int | IL_13 | 0.000 |
| HepC_Int | IL_15 | 0.082 | | HepC_Int | IL_15 | 0.000 |
| HepC_Int | IL_17 | 0.042 | | HepC_Int | IL_17 | 0.000 |
| HepC_Int | IL_23 | -0.025 | | HepC_Int | IL_23 | 0.000 |
| HepC_Int | IFN_gamma | 0.000 | | HepC_Int | IFN_gamma | 0.000 |
| HepC_Int | TNF_alpha | 0.023 | | HepC_Int | TNF_alpha | 0.000 |
| HepC_Int | TNF_beta | 0.184 | | HepC_Int | TNF_beta | 0.000 |
| HepC_Int | Varicella_Int | 0.035 | | HepC_Int | Varicella_Int | 0.000 |
| HepC_Int | Measles_OD_DB_Int | 0.056 | | HepC_Int | Measles_OD_DB_Int | 0.000 |
| HepC_Int | Measles_Int | 0.008 | | HepC_Int | Measles_Int | 0.000 |
| HepC_Int | HepA_Int | 0.017 | | HepC_Int | HepA_Int | 0.000 |
| HepC_Int | Tetanus_Int | 0.000 | | HepC_Int | Tetanus_Int | 0.000 |
| HepC_Int | Diptheria_Int | 0.000 | | HepC_Int | Diptheria_Int | 0.000 |
| HepC_Int | Rubella_Int | -0.036 | | HepC_Int | Rubella_Int | 0.000 |
| HepC_Int | CMV_Int | 0.013 | | HepC_Int | CMV_Int | 0.000 |
| HepC_Int | HepB_cAb_Int | -0.028 | | HepC_Int | HepB_cAb_Int | 0.000 |
| HepC_Int | HepB_eAb_Int | 0.000 | | HepC_Int | HepB_eAb_Int | 0.000 |
| HepC_Int | HepB_eAg_Int | 0.000 | | HepC_Int | HepB_eAg_Int | 0.000 |
| HepC_Int | HepC_Int | 1.000 | | HepC_Int | HepC_Int | 1.000 |
| HepC_Int | Schistosoma_int | -0.040 | | HepC_Int | Schistosoma_int | 0.000 |
| HepC_Int | Strongyloides_Int | -0.090 | | HepC_Int | Strongyloides_Int | 0.000 |
| HepC_Int | Filaria_Int | -0.062 | | HepC_Int | Filaria_Int | 0.000 |
| Schistosoma_int | IL_1_alpha | 0.032 | | Schistosoma_int | IL_1_alpha | -0.056 |
| Schistosoma_int | IL_1_beta | -0.025 | | Schistosoma_int | IL_1_beta | -0.044 |
| Schistosoma_int | IL_2 | 0.021 | | Schistosoma_int | IL_2 | 0.080 |

FIG. 2I15-P

| | | | | | | |
|---|---|---|---|---|---|---|
| Schistosoma_int | IL_4 | 0.055 | | Schistosoma_int | IL_4 | -0.097 |
| Schistosoma_int | IL_5 | -0.046 | | Schistosoma_int | IL_5 | 0.008 |
| Schistosoma_int | IL_6 | -0.007 | | Schistosoma_int | IL_6 | 0.203 |
| Schistosoma_int | IL_8 | -0.040 | | Schistosoma_int | IL_8 | -0.044 |
| Schistosoma_int | IL_10 | 0.032 | | Schistosoma_int | IL_10 | -0.011 |
| Schistosoma_int | IL_12p70 | -0.028 | | Schistosoma_int | IL_12p70 | -0.008 |
| Schistosoma_int | IL_13 | -0.098 | | Schistosoma_int | IL_13 | 0.104 |
| Schistosoma_int | IL_15 | -0.086 | | Schistosoma_int | IL_15 | -0.124 |
| Schistosoma_int | IL_17 | 0.171 | | Schistosoma_int | IL_17 | 0.114 |
| Schistosoma_int | IL_23 | 0.232 | | Schistosoma_int | IL_23 | 0.363 |
| Schistosoma_int | IFN_gamma | 0.000 | | Schistosoma_int | IFN_gamma | 0.000 |
| Schistosoma_int | TNF_alpha | 0.046 | | Schistosoma_int | TNF_alpha | 0.201 |
| Schistosoma_int | TNF_beta | 0.135 | | Schistosoma_int | TNF_beta | 0.037 |
| Schistosoma_int | Varicella_Int | -0.116 | | Schistosoma_int | Varicella_Int | -0.120 |
| Schistosoma_int | Measles_OD_DB_Int | 0.125 | | Schistosoma_int | Measles_OD_DB_Int | -0.118 |
| Schistosoma_int | Measles_Int | -0.195 | | Schistosoma_int | Measles_Int | 0.100 |
| Schistosoma_int | HepA_Int | 0.080 | | Schistosoma_int | HepA_Int | -0.249 |
| Schistosoma_int | Tetanus_Int | 0.000 | | Schistosoma_int | Tetanus_Int | 0.000 |
| Schistosoma_int | Diptheria_Int | 0.000 | | Schistosoma_int | Diptheria_Int | 0.000 |
| Schistosoma_int | Rubella_Int | 0.046 | | Schistosoma_int | Rubella_Int | 0.085 |
| Schistosoma_int | CMV_Int | -0.067 | | Schistosoma_int | CMV_Int | 0.089 |
| Schistosoma_int | HepB_cAb_Int | -0.064 | | Schistosoma_int | HepB_cAb_Int | -0.045 |
| Schistosoma_int | HepB_eAb_Int | 0.000 | | Schistosoma_int | HepB_eAb_Int | 0.000 |
| Schistosoma_int | HepB_eAg_Int | 0.000 | | Schistosoma_int | HepB_eAg_Int | 0.000 |
| Schistosoma_int | HepC_Int | -0.040 | | Schistosoma_int | HepC_Int | 0.000 |
| Schistosoma_int | Schistosoma_int | 1.000 | | Schistosoma_int | Schistosoma_int | 1.000 |
| Schistosoma_int | Strongyloides_Int | 0.153 | | Schistosoma_int | Strongyloides_Int | 0.071 |
| Schistosoma_int | Filaria_Int | 0.366 | | Schistosoma_int | Filaria_Int | -0.124 |
| Strongyloides_Int | IL_1_alpha | 0.054 | | Strongyloides_Int | IL_1_alpha | -0.072 |
| Strongyloides_Int | IL_1_beta | -0.009 | | Strongyloides_Int | IL_1_beta | -0.134 |
| Strongyloides_Int | IL_2 | 0.110 | | Strongyloides_Int | IL_2 | -0.085 |
| Strongyloides_Int | IL_4 | 0.004 | | Strongyloides_Int | IL_4 | 0.003 |
| Strongyloides_Int | IL_5 | -0.033 | | Strongyloides_Int | IL_5 | -0.080 |
| Strongyloides_Int | IL_6 | -0.215 | | Strongyloides_Int | IL_6 | -0.180 |
| Strongyloides_Int | IL_8 | -0.060 | | Strongyloides_Int | IL_8 | -0.057 |
| Strongyloides_Int | IL_10 | -0.008 | | Strongyloides_Int | IL_10 | -0.110 |
| Strongyloides_Int | IL_12p70 | -0.088 | | Strongyloides_Int | IL_12p70 | 0.006 |
| Strongyloides_Int | IL_13 | -0.231 | | Strongyloides_Int | IL_13 | -0.204 |
| Strongyloides_Int | IL_15 | -0.085 | | Strongyloides_Int | IL_15 | -0.046 |
| Strongyloides_Int | IL_17 | 0.011 | | Strongyloides_Int | IL_17 | 0.091 |
| Strongyloides_Int | IL_23 | 0.143 | | Strongyloides_Int | IL_23 | 0.128 |
| Strongyloides_Int | IFN_gamma | 0.000 | | Strongyloides_Int | IFN_gamma | 0.000 |
| Strongyloides_Int | TNF_alpha | 0.179 | | Strongyloides_Int | TNF_alpha | 0.119 |
| Strongyloides_Int | TNF_beta | 0.185 | | Strongyloides_Int | TNF_beta | 0.283 |
| Strongyloides_Int | Varicella_Int | -0.010 | | Strongyloides_Int | Varicella_Int | -0.053 |
| Strongyloides_Int | Measles_OD_DB_Int | 0.002 | | Strongyloides_Int | Measles_OD_DB_Int | -0.053 |
| Strongyloides_Int | Measles_Int | -0.105 | | Strongyloides_Int | Measles_Int | 0.023 |
| Strongyloides_Int | HepA_Int | 0.034 | | Strongyloides_Int | HepA_Int | -0.001 |
| Strongyloides_Int | Tetanus_Int | 0.000 | | Strongyloides_Int | Tetanus_Int | 0.000 |
| Strongyloides_Int | Diptheria_Int | 0.000 | | Strongyloides_Int | Diptheria_Int | 0.000 |
| Strongyloides_Int | Rubella_Int | 0.011 | | Strongyloides_Int | Rubella_Int | -0.053 |
| Strongyloides_Int | CMV_Int | -0.127 | | Strongyloides_Int | CMV_Int | 0.197 |
| Strongyloides_Int | HepB_cAb_Int | 0.149 | | Strongyloides_Int | HepB_cAb_Int | 0.223 |
| Strongyloides_Int | HepB_eAb_Int | 0.000 | | Strongyloides_Int | HepB_eAb_Int | 0.000 |
| Strongyloides_Int | HepB_eAg_Int | 0.000 | | Strongyloides_Int | HepB_eAg_Int | 0.000 |
| Strongyloides_Int | HepC_Int | -0.090 | | Strongyloides_Int | HepC_Int | 0.000 |
| Strongyloides_Int | Schistosoma_int | 0.153 | | Strongyloides_Int | Schistosoma_int | 0.071 |

FIG. 2115-Q

| | | | | | | |
|---|---|---|---|---|---|---|
| Strongyloides_Int | Strongyloides_Int | 1.000 | | Strongyloides_Int | Strongyloides_Int | 1.000 |
| Strongyloides_Int | Filaria_Int | 0.153 | | Strongyloides_Int | Filaria_Int | 0.330 |
| Filaria_Int | IL_1_alpha | -0.167 | | Filaria_Int | IL_1_alpha | -0.044 |
| Filaria_Int | IL_1_beta | -0.098 | | Filaria_Int | IL_1_beta | -0.026 |
| Filaria_Int | IL_2 | -0.084 | | Filaria_Int | IL_2 | -0.035 |
| Filaria_Int | IL_4 | 0.039 | | Filaria_Int | IL_4 | -0.001 |
| Filaria_Int | IL_5 | -0.049 | | Filaria_Int | IL_5 | -0.039 |
| Filaria_Int | IL_6 | -0.120 | | Filaria_Int | IL_6 | -0.092 |
| Filaria_Int | IL_8 | -0.225 | | Filaria_Int | IL_8 | -0.093 |
| Filaria_Int | IL_10 | -0.025 | | Filaria_Int | IL_10 | -0.013 |
| Filaria_Int | IL_12p70 | -0.189 | | Filaria_Int | IL_12p70 | -0.034 |
| Filaria_Int | IL_13 | -0.125 | | Filaria_Int | IL_13 | -0.076 |
| Filaria_Int | IL_15 | -0.227 | | Filaria_Int | IL_15 | -0.003 |
| Filaria_Int | IL_17 | -0.061 | | Filaria_Int | IL_17 | -0.033 |
| Filaria_Int | IL_23 | 0.087 | | Filaria_Int | IL_23 | -0.028 |
| Filaria_Int | IFN_gamma | 0.000 | | Filaria_Int | IFN_gamma | 0.000 |
| Filaria_Int | TNF_alpha | -0.109 | | Filaria_Int | TNF_alpha | 0.155 |
| Filaria_Int | TNF_beta | 0.022 | | Filaria_Int | TNF_beta | 0.089 |
| Filaria_Int | Varicella_Int | -0.120 | | Filaria_Int | Varicella_Int | -0.055 |
| Filaria_Int | Measles_OD_DB_Int | 0.127 | | Filaria_Int | Measles_OD_DB_Int | 0.092 |
| Filaria_Int | Measles_Int | -0.165 | | Filaria_Int | Measles_Int | 0.090 |
| Filaria_Int | HepA_Int | 0.011 | | Filaria_Int | HepA_Int | -0.029 |
| Filaria_Int | Tetanus_Int | 0.000 | | Filaria_Int | Tetanus_Int | 0.000 |
| Filaria_Int | Diptheria_Int | 0.000 | | Filaria_Int | Diptheria_Int | 0.000 |
| Filaria_Int | Rubella_Int | 0.005 | | Filaria_Int | Rubella_Int | -0.117 |
| Filaria_Int | CMV_Int | -0.024 | | Filaria_Int | CMV_Int | 0.081 |
| Filaria_Int | HepB_cAb_Int | -0.018 | | Filaria_Int | HepB_cAb_Int | 0.055 |
| Filaria_Int | HepB_eAb_Int | 0.000 | | Filaria_Int | HepB_eAb_Int | 0.000 |
| Filaria_Int | HepB_eAg_Int | 0.000 | | Filaria_Int | HepB_eAg_Int | 0.000 |
| Filaria_Int | HepC_Int | -0.062 | | Filaria_Int | HepC_Int | 0.000 |
| Filaria_Int | Schistosoma_int | 0.366 | | Filaria_Int | Schistosoma_int | -0.124 |
| Filaria_Int | Strongyloides_Int | 0.153 | | Filaria_Int | Strongyloides_Int | 0.330 |
| Filaria_Int | Filaria_Int | 1.000 | | Filaria_Int | Filaria_Int | 1.000 |

FIG. 2I5-R

| 7.14% - Region_of_Origin=5, Sex=Female, IFN_gamma=0-7.5 |||
| --- | --- | --- |
| Property 1 | Property 2 | Corr. Coefficient |
| IL_1_alpha | IL_1_alpha | 1.000 |
| IL_1_alpha | IL_1_beta | 0.153 |
| IL_1_alpha | IL_2 | 0.314 |
| IL_1_alpha | IL_4 | 0.244 |
| IL_1_alpha | IL_5 | 0.228 |
| IL_1_alpha | IL_6 | 0.080 |
| IL_1_alpha | IL_8 | 0.209 |
| IL_1_alpha | IL_10 | 0.119 |
| IL_1_alpha | IL_12p70 | 0.300 |
| IL_1_alpha | IL_13 | 0.150 |
| IL_1_alpha | IL_15 | 0.239 |
| IL_1_alpha | IL_17 | 0.200 |
| IL_1_alpha | IL_23 | 0.067 |
| IL_1_alpha | IFN_gamma | 0.000 |
| IL_1_alpha | TNF_alpha | 0.107 |
| IL_1_alpha | TNF_beta | 0.217 |
| IL_1_alpha | Varicella_Int | 0.063 |
| IL_1_alpha | Measles_OD_DB_Int | 0.135 |
| IL_1_alpha | Measles_Int | 0.089 |
| IL_1_alpha | HepA_Int | 0.087 |

| 6.42% - Region_of_Origin=1, Sex=Male, IFN_gamma=0-7.5 |||
| --- | --- | --- |
| Property 1 | Property 2 | Corr. Coefficient |
| IL_1_alpha | IL_1_alpha | 1.000 |
| IL_1_alpha | IL_1_beta | 0.683 |
| IL_1_alpha | IL_2 | 0.347 |
| IL_1_alpha | IL_4 | 0.637 |
| IL_1_alpha | IL_5 | 0.390 |
| IL_1_alpha | IL_6 | 0.324 |
| IL_1_alpha | IL_8 | 0.441 |
| IL_1_alpha | IL_10 | 0.384 |
| IL_1_alpha | IL_12p70 | 0.421 |
| IL_1_alpha | IL_13 | 0.359 |
| IL_1_alpha | IL_15 | 0.489 |
| IL_1_alpha | IL_17 | 0.689 |
| IL_1_alpha | IL_23 | 0.042 |
| IL_1_alpha | IFN_gamma | 0.000 |
| IL_1_alpha | TNF_alpha | 0.428 |
| IL_1_alpha | TNF_beta | 0.764 |
| IL_1_alpha | Varicella_Int | -0.187 |
| IL_1_alpha | Measles_OD_DB_Int | 0.128 |
| IL_1_alpha | Measles_Int | -0.012 |
| IL_1_alpha | HepA_Int | 0.035 |

FIG. 2116-A

| | | | | | | |
|---|---|---|---|---|---|---|
| IL_1_alpha | Tetanus_Int | 0.000 | | IL_1_alpha | Tetanus_Int | 0.000 |
| IL_1_alpha | Diptheria_Int | 0.000 | | IL_1_alpha | Diptheria_Int | 0.000 |
| IL_1_alpha | Rubella_Int | -0.035 | | IL_1_alpha | Rubella_Int | -0.052 |
| IL_1_alpha | CMV_Int | 0.086 | | IL_1_alpha | CMV_Int | 0.000 |
| IL_1_alpha | HepB_cAb_Int | 0.187 | | IL_1_alpha | HepB_cAb_Int | 0.020 |
| IL_1_alpha | HepB_eAb_Int | -0.446 | | IL_1_alpha | HepB_eAb_Int | 0.000 |
| IL_1_alpha | HepB_eAg_Int | 0.446 | | IL_1_alpha | HepB_eAg_Int | 0.000 |
| IL_1_alpha | HepC_Int | 0.024 | | IL_1_alpha | HepC_Int | 0.200 |
| IL_1_alpha | Schistosoma_int | -0.079 | | IL_1_alpha | Schistosoma_int | 0.185 |
| IL_1_alpha | Strongyloides_Int | 0.014 | | IL_1_alpha | Strongyloides_Int | 0.287 |
| IL_1_alpha | Filaria_Int | 0.017 | | IL_1_alpha | Filaria_Int | 0.021 |
| IL_1_beta | IL_1_alpha | 0.153 | | IL_1_beta | IL_1_alpha | 0.683 |
| IL_1_beta | IL_1_beta | 1.000 | | IL_1_beta | IL_1_beta | 1.000 |
| IL_1_beta | IL_2 | 0.151 | | IL_1_beta | IL_2 | 0.408 |
| IL_1_beta | IL_4 | 0.716 | | IL_1_beta | IL_4 | 0.451 |
| IL_1_beta | IL_5 | 0.264 | | IL_1_beta | IL_5 | 0.267 |
| IL_1_beta | IL_6 | 0.182 | | IL_1_beta | IL_6 | 0.465 |
| IL_1_beta | IL_8 | 0.206 | | IL_1_beta | IL_8 | 0.407 |
| IL_1_beta | IL_10 | 0.168 | | IL_1_beta | IL_10 | 0.520 |
| IL_1_beta | IL_12p70 | 0.279 | | IL_1_beta | IL_12p70 | 0.467 |
| IL_1_beta | IL_13 | 0.013 | | IL_1_beta | IL_13 | 0.388 |
| IL_1_beta | IL_15 | 0.669 | | IL_1_beta | IL_15 | 0.680 |
| IL_1_beta | IL_17 | 0.224 | | IL_1_beta | IL_17 | 0.610 |
| IL_1_beta | IL_23 | 0.137 | | IL_1_beta | IL_23 | 0.123 |
| IL_1_beta | IFN_gamma | 0.000 | | IL_1_beta | IFN_gamma | 0.000 |
| IL_1_beta | TNF_alpha | 0.839 | | IL_1_beta | TNF_alpha | 0.765 |
| IL_1_beta | TNF_beta | 0.610 | | IL_1_beta | TNF_beta | 0.730 |
| IL_1_beta | Varicella_Int | 0.050 | | IL_1_beta | Varicella_Int | -0.089 |
| IL_1_beta | Measles_OD_DB_Int | 0.068 | | IL_1_beta | Measles_OD_DB_Int | 0.112 |
| IL_1_beta | Measles_Int | -0.051 | | IL_1_beta | Measles_Int | -0.145 |
| IL_1_beta | HepA_Int | 0.062 | | IL_1_beta | HepA_Int | -0.021 |
| IL_1_beta | Tetanus_Int | 0.000 | | IL_1_beta | Tetanus_Int | 0.000 |
| IL_1_beta | Diptheria_Int | 0.000 | | IL_1_beta | Diptheria_Int | 0.000 |
| IL_1_beta | Rubella_Int | -0.029 | | IL_1_beta | Rubella_Int | -0.070 |
| IL_1_beta | CMV_Int | 0.062 | | IL_1_beta | CMV_Int | 0.000 |
| IL_1_beta | HepB_cAb_Int | 0.202 | | IL_1_beta | HepB_cAb_Int | -0.039 |
| IL_1_beta | HepB_eAb_Int | -0.269 | | IL_1_beta | HepB_eAb_Int | 0.000 |
| IL_1_beta | HepB_eAg_Int | 0.269 | | IL_1_beta | HepB_eAg_Int | 0.000 |
| IL_1_beta | HepC_Int | 0.024 | | IL_1_beta | HepC_Int | 0.385 |
| IL_1_beta | Schistosoma_int | -0.054 | | IL_1_beta | Schistosoma_int | 0.106 |
| IL_1_beta | Strongyloides_Int | -0.002 | | IL_1_beta | Strongyloides_Int | 0.276 |
| IL_1_beta | Filaria_Int | -0.045 | | IL_1_beta | Filaria_Int | -0.014 |
| IL_2 | IL_1_alpha | 0.314 | | IL_2 | IL_1_alpha | 0.347 |
| IL_2 | IL_1_beta | 0.151 | | IL_2 | IL_1_beta | 0.408 |
| IL_2 | IL_2 | 1.000 | | IL_2 | IL_2 | 1.000 |
| IL_2 | IL_4 | 0.179 | | IL_2 | IL_4 | 0.232 |
| IL_2 | IL_5 | 0.080 | | IL_2 | IL_5 | 0.144 |
| IL_2 | IL_6 | -0.014 | | IL_2 | IL_6 | 0.181 |
| IL_2 | IL_8 | 0.088 | | IL_2 | IL_8 | 0.324 |
| IL_2 | IL_10 | 0.121 | | IL_2 | IL_10 | 0.256 |
| IL_2 | IL_12p70 | 0.250 | | IL_2 | IL_12p70 | 0.321 |
| IL_2 | IL_13 | 0.027 | | IL_2 | IL_13 | 0.170 |
| IL_2 | IL_15 | 0.201 | | IL_2 | IL_15 | 0.313 |
| IL_2 | IL_17 | 0.295 | | IL_2 | IL_17 | 0.343 |
| IL_2 | IL_23 | 0.327 | | IL_2 | IL_23 | 0.142 |
| IL_2 | IFN_gamma | 0.000 | | IL_2 | IFN_gamma | 0.000 |
| IL_2 | TNF_alpha | 0.212 | | IL_2 | TNF_alpha | 0.258 |

FIG. 21I6-B

| | | | | | | |
|---|---|---|---|---|---|---|
| IL_2 | TNF_beta | 0.269 | | IL_2 | TNF_beta | 0.397 |
| IL_2 | Varicella_Int | -0.367 | | IL_2 | Varicella_Int | -0.076 |
| IL_2 | Measles_OD_DB_Int | 0.128 | | IL_2 | Measles_OD_DB_Int | 0.148 |
| IL_2 | Measles_Int | 0.027 | | IL_2 | Measles_Int | 0.044 |
| IL_2 | HepA_Int | -0.098 | | IL_2 | HepA_Int | 0.077 |
| IL_2 | Tetanus_Int | 0.000 | | IL_2 | Tetanus_Int | 0.000 |
| IL_2 | Diptheria_Int | 0.000 | | IL_2 | Diptheria_Int | 0.000 |
| IL_2 | Rubella_Int | -0.124 | | IL_2 | Rubella_Int | -0.064 |
| IL_2 | CMV_Int | 0.088 | | IL_2 | CMV_Int | 0.000 |
| IL_2 | HepB_cAb_Int | -0.004 | | IL_2 | HepB_cAb_Int | 0.034 |
| IL_2 | HepB_eAb_Int | -0.966 | | IL_2 | HepB_eAb_Int | 0.000 |
| IL_2 | HepB_eAg_Int | 0.966 | | IL_2 | HepB_eAg_Int | 0.000 |
| IL_2 | HepC_Int | 0.011 | | IL_2 | HepC_Int | 0.088 |
| IL_2 | Schistosoma_int | -0.097 | | IL_2 | Schistosoma_int | 0.271 |
| IL_2 | Strongyloides_Int | 0.047 | | IL_2 | Strongyloides_Int | 0.140 |
| IL_2 | Filaria_Int | -0.076 | | IL_2 | Filaria_Int | -0.037 |
| IL_4 | IL_1_alpha | 0.244 | | IL_4 | IL_1_alpha | 0.637 |
| IL_4 | IL_1_beta | 0.716 | | IL_4 | IL_1_beta | 0.451 |
| IL_4 | IL_2 | 0.179 | | IL_4 | IL_2 | 0.232 |
| IL_4 | IL_4 | 1.000 | | IL_4 | IL_4 | 1.000 |
| IL_4 | IL_5 | 0.406 | | IL_4 | IL_5 | 0.784 |
| IL_4 | IL_6 | 0.117 | | IL_4 | IL_6 | 0.208 |
| IL_4 | IL_8 | 0.221 | | IL_4 | IL_8 | 0.258 |
| IL_4 | IL_10 | 0.198 | | IL_4 | IL_10 | 0.262 |
| IL_4 | IL_12p70 | 0.295 | | IL_4 | IL_12p70 | 0.292 |
| IL_4 | IL_13 | 0.078 | | IL_4 | IL_13 | 0.380 |
| IL_4 | IL_15 | 0.392 | | IL_4 | IL_15 | 0.364 |
| IL_4 | IL_17 | 0.276 | | IL_4 | IL_17 | 0.544 |
| IL_4 | IL_23 | 0.206 | | IL_4 | IL_23 | -0.007 |
| IL_4 | IFN_gamma | 0.000 | | IL_4 | IFN_gamma | 0.000 |
| IL_4 | TNF_alpha | 0.460 | | IL_4 | TNF_alpha | 0.236 |
| IL_4 | TNF_beta | 0.765 | | IL_4 | TNF_beta | 0.474 |
| IL_4 | Varicella_Int | 0.036 | | IL_4 | Varicella_Int | -0.161 |
| IL_4 | Measles_OD_DB_Int | 0.061 | | IL_4 | Measles_OD_DB_Int | 0.099 |
| IL_4 | Measles_Int | -0.138 | | IL_4 | Measles_Int | -0.060 |
| IL_4 | HepA_Int | 0.098 | | IL_4 | HepA_Int | 0.013 |
| IL_4 | Tetanus_Int | 0.000 | | IL_4 | Tetanus_Int | 0.000 |
| IL_4 | Diptheria_Int | 0.000 | | IL_4 | Diptheria_Int | 0.000 |
| IL_4 | Rubella_Int | -0.049 | | IL_4 | Rubella_Int | -0.036 |
| IL_4 | CMV_Int | 0.083 | | IL_4 | CMV_Int | 0.000 |
| IL_4 | HepB_cAb_Int | 0.262 | | IL_4 | HepB_cAb_Int | -0.093 |
| IL_4 | HepB_eAb_Int | -0.860 | | IL_4 | HepB_eAb_Int | 0.000 |
| IL_4 | HepB_eAg_Int | 0.860 | | IL_4 | HepB_eAg_Int | 0.000 |
| IL_4 | HepC_Int | -0.041 | | IL_4 | HepC_Int | 0.078 |
| IL_4 | Schistosoma_int | -0.090 | | IL_4 | Schistosoma_int | 0.056 |
| IL_4 | Strongyloides_Int | 0.103 | | IL_4 | Strongyloides_Int | 0.156 |
| IL_4 | Filaria_Int | -0.071 | | IL_4 | Filaria_Int | -0.083 |
| IL_5 | IL_1_alpha | 0.228 | | IL_5 | IL_1_alpha | 0.390 |
| IL_5 | IL_1_beta | 0.264 | | IL_5 | IL_1_beta | 0.267 |
| IL_5 | IL_2 | 0.080 | | IL_5 | IL_2 | 0.144 |
| IL_5 | IL_4 | 0.406 | | IL_5 | IL_4 | 0.784 |
| IL_5 | IL_5 | 1.000 | | IL_5 | IL_5 | 1.000 |
| IL_5 | IL_6 | 0.094 | | IL_5 | IL_6 | 0.501 |
| IL_5 | IL_8 | 0.224 | | IL_5 | IL_8 | 0.091 |
| IL_5 | IL_10 | 0.348 | | IL_5 | IL_10 | 0.505 |
| IL_5 | IL_12p70 | 0.287 | | IL_5 | IL_12p70 | 0.432 |
| IL_5 | IL_13 | 0.114 | | IL_5 | IL_13 | 0.642 |

FIG. 2116-C

| IL_5 | IL_15 | 0.191 | IL_5 | IL_15 | 0.328 |
|---|---|---|---|---|---|
| IL_5 | IL_17 | 0.309 | IL_5 | IL_17 | 0.297 |
| IL_5 | IL_23 | 0.134 | IL_5 | IL_23 | 0.206 |
| IL_5 | IFN_gamma | 0.000 | IL_5 | IFN_gamma | 0.000 |
| IL_5 | TNF_alpha | 0.187 | IL_5 | TNF_alpha | 0.307 |
| IL_5 | TNF_beta | 0.320 | IL_5 | TNF_beta | 0.193 |
| IL_5 | Varicella_Int | 0.023 | IL_5 | Varicella_Int | -0.046 |
| IL_5 | Measles_OD_DB_Int | -0.033 | IL_5 | Measles_OD_DB_Int | 0.021 |
| IL_5 | Measles_Int | -0.035 | IL_5 | Measles_Int | 0.046 |
| IL_5 | HepA_Int | 0.099 | IL_5 | HepA_Int | 0.060 |
| IL_5 | Tetanus_Int | 0.000 | IL_5 | Tetanus_Int | 0.000 |
| IL_5 | Diptheria_Int | 0.000 | IL_5 | Diptheria_Int | 0.000 |
| IL_5 | Rubella_Int | 0.104 | IL_5 | Rubella_Int | -0.094 |
| IL_5 | CMV_Int | 0.044 | IL_5 | CMV_Int | 0.000 |
| IL_5 | HepB_cAb_Int | 0.143 | IL_5 | HepB_cAb_Int | -0.121 |
| IL_5 | HepB_eAb_Int | -0.954 | IL_5 | HepB_eAb_Int | 0.000 |
| IL_5 | HepB_eAg_Int | 0.954 | IL_5 | HepB_eAg_Int | 0.000 |
| IL_5 | HepC_Int | -0.033 | IL_5 | HepC_Int | -0.030 |
| IL_5 | Schistosoma_int | -0.098 | IL_5 | Schistosoma_int | -0.067 |
| IL_5 | Strongyloides_Int | 0.089 | IL_5 | Strongyloides_Int | 0.134 |
| IL_5 | Filaria_Int | -0.067 | IL_5 | Filaria_Int | -0.008 |
| IL_6 | IL_1_alpha | 0.080 | IL_6 | IL_1_alpha | 0.324 |
| IL_6 | IL_1_beta | 0.182 | IL_6 | IL_1_beta | 0.465 |
| IL_6 | IL_2 | -0.014 | IL_6 | IL_2 | 0.181 |
| IL_6 | IL_4 | 0.117 | IL_6 | IL_4 | 0.208 |
| IL_6 | IL_5 | 0.094 | IL_6 | IL_5 | 0.501 |
| IL_6 | IL_6 | 1.000 | IL_6 | IL_6 | 1.000 |
| IL_6 | IL_8 | 0.239 | IL_6 | IL_8 | 0.200 |
| IL_6 | IL_10 | 0.139 | IL_6 | IL_10 | 0.937 |
| IL_6 | IL_12p70 | 0.034 | IL_6 | IL_12p70 | 0.747 |
| IL_6 | IL_13 | 0.010 | IL_6 | IL_13 | 0.913 |
| IL_6 | IL_15 | 0.302 | IL_6 | IL_15 | 0.513 |
| IL_6 | IL_17 | 0.039 | IL_6 | IL_17 | 0.284 |
| IL_6 | IL_23 | -0.070 | IL_6 | IL_23 | 0.569 |
| IL_6 | IFN_gamma | 0.000 | IL_6 | IFN_gamma | 0.000 |
| IL_6 | TNF_alpha | 0.018 | IL_6 | TNF_alpha | 0.634 |
| IL_6 | TNF_beta | 0.073 | IL_6 | TNF_beta | 0.215 |
| IL_6 | Varicella_Int | 0.043 | IL_6 | Varicella_Int | -0.074 |
| IL_6 | Measles_OD_DB_Int | -0.000 | IL_6 | Measles_OD_DB_Int | 0.091 |
| IL_6 | Measles_Int | -0.018 | IL_6 | Measles_Int | 0.025 |
| IL_6 | HepA_Int | -0.221 | IL_6 | HepA_Int | 0.067 |
| IL_6 | Tetanus_Int | 0.000 | IL_6 | Tetanus_Int | 0.000 |
| IL_6 | Diptheria_Int | 0.000 | IL_6 | Diptheria_Int | 0.000 |
| IL_6 | Rubella_Int | -0.064 | IL_6 | Rubella_Int | -0.076 |
| IL_6 | CMV_Int | 0.077 | IL_6 | CMV_Int | 0.000 |
| IL_6 | HepB_cAb_Int | -0.043 | IL_6 | HepB_cAb_Int | -0.014 |
| IL_6 | HepB_eAb_Int | -0.146 | IL_6 | HepB_eAb_Int | 0.000 |
| IL_6 | HepB_eAg_Int | 0.146 | IL_6 | HepB_eAg_Int | 0.000 |
| IL_6 | HepC_Int | 0.045 | IL_6 | HepC_Int | 0.006 |
| IL_6 | Schistosoma_int | -0.112 | IL_6 | Schistosoma_int | -0.019 |
| IL_6 | Strongyloides_Int | -0.132 | IL_6 | Strongyloides_Int | 0.170 |
| IL_6 | Filaria_Int | -0.101 | IL_6 | Filaria_Int | 0.104 |
| IL_8 | IL_1_alpha | 0.209 | IL_8 | IL_1_alpha | 0.441 |
| IL_8 | IL_1_beta | 0.206 | IL_8 | IL_1_beta | 0.407 |
| IL_8 | IL_2 | 0.088 | IL_8 | IL_2 | 0.324 |
| IL_8 | IL_4 | 0.221 | IL_8 | IL_4 | 0.258 |
| IL_8 | IL_5 | 0.224 | IL_8 | IL_5 | 0.091 |

FIG. 21I6-D

| | | | | | | |
|---|---|---|---|---|---|---|
| IL_8 | IL_6 | 0.239 | | IL_8 | IL_6 | 0.200 |
| IL_8 | IL_8 | 1.000 | | IL_8 | IL_8 | 1.000 |
| IL_8 | IL_10 | 0.145 | | IL_8 | IL_10 | 0.209 |
| IL_8 | IL_12p70 | 0.259 | | IL_8 | IL_12p70 | 0.246 |
| IL_8 | IL_13 | 0.218 | | IL_8 | IL_13 | 0.198 |
| IL_8 | IL_15 | 0.445 | | IL_8 | IL_15 | 0.449 |
| IL_8 | IL_17 | 0.219 | | IL_8 | IL_17 | 0.421 |
| IL_8 | IL_23 | 0.087 | | IL_8 | IL_23 | -0.001 |
| IL_8 | IFN_gamma | 0.000 | | IL_8 | IFN_gamma | 0.000 |
| IL_8 | TNF_alpha | 0.165 | | IL_8 | TNF_alpha | 0.234 |
| IL_8 | TNF_beta | 0.221 | | IL_8 | TNF_beta | 0.358 |
| IL_8 | Varicella_Int | 0.078 | | IL_8 | Varicella_Int | -0.168 |
| IL_8 | Measles_OD_DB_Int | 0.050 | | IL_8 | Measles_OD_DB_Int | 0.146 |
| IL_8 | Measles_Int | 0.098 | | IL_8 | Measles_Int | 0.022 |
| IL_8 | HepA_Int | -0.160 | | IL_8 | HepA_Int | 0.063 |
| IL_8 | Tetanus_Int | 0.000 | | IL_8 | Tetanus_Int | 0.000 |
| IL_8 | Diptheria_Int | 0.000 | | IL_8 | Diptheria_Int | 0.000 |
| IL_8 | Rubella_Int | 0.144 | | IL_8 | Rubella_Int | -0.114 |
| IL_8 | CMV_Int | 0.125 | | IL_8 | CMV_Int | 0.000 |
| IL_8 | HepB_cAb_Int | 0.101 | | IL_8 | HepB_cAb_Int | 0.028 |
| IL_8 | HepB_eAb_Int | 0.198 | | IL_8 | HepB_eAb_Int | 0.000 |
| IL_8 | HepB_eAg_Int | -0.198 | | IL_8 | HepB_eAg_Int | 0.000 |
| IL_8 | HepC_Int | 0.098 | | IL_8 | HepC_Int | 0.154 |
| IL_8 | Schistosoma_int | -0.035 | | IL_8 | Schistosoma_int | 0.163 |
| IL_8 | Strongyloides_Int | -0.056 | | IL_8 | Strongyloides_Int | 0.300 |
| IL_8 | Filaria_Int | -0.067 | | IL_8 | Filaria_Int | 0.033 |
| IL_10 | IL_1_alpha | 0.119 | | IL_10 | IL_1_alpha | 0.384 |
| IL_10 | IL_1_beta | 0.168 | | IL_10 | IL_1_beta | 0.520 |
| IL_10 | IL_2 | 0.121 | | IL_10 | IL_2 | 0.256 |
| IL_10 | IL_4 | 0.198 | | IL_10 | IL_4 | 0.262 |
| IL_10 | IL_5 | 0.348 | | IL_10 | IL_5 | 0.505 |
| IL_10 | IL_6 | 0.139 | | IL_10 | IL_6 | 0.937 |
| IL_10 | IL_8 | 0.145 | | IL_10 | IL_8 | 0.209 |
| IL_10 | IL_10 | 1.000 | | IL_10 | IL_10 | 1.000 |
| IL_10 | IL_12p70 | 0.329 | | IL_10 | IL_12p70 | 0.667 |
| IL_10 | IL_13 | 0.051 | | IL_10 | IL_13 | 0.895 |
| IL_10 | IL_15 | 0.291 | | IL_10 | IL_15 | 0.535 |
| IL_10 | IL_17 | 0.550 | | IL_10 | IL_17 | 0.383 |
| IL_10 | IL_23 | 0.150 | | IL_10 | IL_23 | 0.459 |
| IL_10 | IFN_gamma | 0.000 | | IL_10 | IFN_gamma | 0.000 |
| IL_10 | TNF_alpha | 0.151 | | IL_10 | TNF_alpha | 0.698 |
| IL_10 | TNF_beta | 0.244 | | IL_10 | TNF_beta | 0.311 |
| IL_10 | Varicella_Int | -0.021 | | IL_10 | Varicella_Int | -0.066 |
| IL_10 | Measles_OD_DB_Int | 0.005 | | IL_10 | Measles_OD_DB_Int | 0.103 |
| IL_10 | Measles_int | -0.005 | | IL_10 | Measles_Int | 0.063 |
| IL_10 | HepA_Int | 0.078 | | IL_10 | HepA_Int | 0.036 |
| IL_10 | Tetanus_Int | 0.000 | | IL_10 | Tetanus_Int | 0.000 |
| IL_10 | Diptheria_Int | 0.000 | | IL_10 | Diptheria_Int | 0.000 |
| IL_10 | Rubella_Int | 0.056 | | IL_10 | Rubella_Int | -0.035 |
| IL_10 | CMV_Int | -0.269 | | IL_10 | CMV_Int | 0.000 |
| IL_10 | HepB_cAb_Int | -0.033 | | IL_10 | HepB_cAb_Int | -0.027 |
| IL_10 | HepB_eAb_Int | -0.180 | | IL_10 | HepB_eAb_Int | 0.000 |
| IL_10 | HepB_eAg_Int | 0.180 | | IL_10 | HepB_eAg_Int | 0.000 |
| IL_10 | HepC_Int | -0.010 | | IL_10 | HepC_Int | 0.053 |
| IL_10 | Schistosoma_int | 0.086 | | IL_10 | Schistosoma_int | 0.034 |
| IL_10 | Strongyloides_Int | 0.065 | | IL_10 | Strongyloides_Int | 0.233 |
| IL_10 | Filaria_Int | -0.025 | | IL_10 | Filaria_Int | 0.174 |

FIG. 21I6-E

| | | | | | | |
|---|---|---|---|---|---|---|
| IL_12p70 | IL_1_alpha | 0.300 | | IL_12p70 | IL_1_alpha | 0.421 |
| IL_12p70 | IL_1_beta | 0.279 | | IL_12p70 | IL_1_beta | 0.467 |
| IL_12p70 | IL_2 | 0.250 | | IL_12p70 | IL_2 | 0.321 |
| IL_12p70 | IL_4 | 0.295 | | IL_12p70 | IL_4 | 0.292 |
| IL_12p70 | IL_5 | 0.287 | | IL_12p70 | IL_5 | 0.432 |
| IL_12p70 | IL_6 | 0.034 | | IL_12p70 | IL_6 | 0.747 |
| IL_12p70 | IL_8 | 0.259 | | IL_12p70 | IL_8 | 0.246 |
| IL_12p70 | IL_10 | 0.329 | | IL_12p70 | IL_10 | 0.667 |
| IL_12p70 | IL_12p70 | 1.000 | | IL_12p70 | IL_12p70 | 1.000 |
| IL_12p70 | IL_13 | 0.134 | | IL_12p70 | IL_13 | 0.802 |
| IL_12p70 | IL_15 | 0.341 | | IL_12p70 | IL_15 | 0.337 |
| IL_12p70 | IL_17 | 0.617 | | IL_12p70 | IL_17 | 0.363 |
| IL_12p70 | IL_23 | 0.519 | | IL_12p70 | IL_23 | 0.847 |
| IL_12p70 | IFN_gamma | 0.000 | | IL_12p70 | IFN_gamma | 0.000 |
| IL_12p70 | TNF_alpha | 0.326 | | IL_12p70 | TNF_alpha | 0.340 |
| IL_12p70 | TNF_beta | 0.376 | | IL_12p70 | TNF_beta | 0.327 |
| IL_12p70 | Varicella_Int | 0.012 | | IL_12p70 | Varicella_Int | -0.102 |
| IL_12p70 | Measles_OD_DB_Int | 0.082 | | IL_12p70 | Measles_OD_DB_Int | 0.071 |
| IL_12p70 | Measles_Int | -0.004 | | IL_12p70 | Measles_Int | -0.042 |
| IL_12p70 | HepA_Int | -0.000 | | IL_12p70 | HepA_Int | 0.033 |
| IL_12p70 | Tetanus_Int | 0.000 | | IL_12p70 | Tetanus_Int | 0.000 |
| IL_12p70 | Diptheria_Int | 0.000 | | IL_12p70 | Diptheria_Int | 0.000 |
| IL_12p70 | Rubella_Int | -0.042 | | IL_12p70 | Rubella_Int | -0.058 |
| IL_12p70 | CMV_Int | -0.008 | | IL_12p70 | CMV_Int | 0.000 |
| IL_12p70 | HepB_cAb_Int | -0.055 | | IL_12p70 | HepB_cAb_Int | 0.142 |
| IL_12p70 | HepB_eAb_Int | -0.213 | | IL_12p70 | HepB_eAb_Int | 0.000 |
| IL_12p70 | HepB_eAg_Int | 0.213 | | IL_12p70 | HepB_eAg_Int | 0.000 |
| IL_12p70 | HepC_Int | 0.022 | | IL_12p70 | HepC_int | 0.011 |
| IL_12p70 | Schistosoma_int | 0.042 | | IL_12p70 | Schistosoma_int | 0.025 |
| IL_12p70 | Strongyloides_Int | 0.278 | | IL_12p70 | Strongyloides_Int | 0.110 |
| IL_12p70 | Filaria_Int | -0.024 | | IL_12p70 | Filaria_Int | -0.066 |
| IL_13 | IL_1_alpha | 0.150 | | IL_13 | IL_1_alpha | 0.359 |
| IL_13 | IL_1_beta | 0.013 | | IL_13 | IL_1_beta | 0.388 |
| IL_13 | IL_2 | 0.027 | | IL_13 | IL_2 | 0.170 |
| IL_13 | IL_4 | 0.078 | | IL_13 | IL_4 | 0.380 |
| IL_13 | IL_5 | 0.114 | | IL_13 | IL_5 | 0.642 |
| IL_13 | IL_6 | 0.010 | | IL_13 | IL_6 | 0.913 |
| IL_13 | IL_8 | 0.218 | | IL_13 | IL_8 | 0.198 |
| IL_13 | IL_10 | 0.051 | | IL_13 | IL_10 | 0.895 |
| IL_13 | IL_12p70 | 0.134 | | IL_13 | IL_12p70 | 0.802 |
| IL_13 | IL_13 | 1.000 | | IL_13 | IL_13 | 1.000 |
| IL_13 | IL_15 | 0.100 | | IL_13 | IL_15 | 0.383 |
| IL_13 | IL_17 | 0.062 | | IL_13 | IL_17 | 0.366 |
| IL_13 | IL_23 | 0.008 | | IL_13 | IL_23 | 0.606 |
| IL_13 | IFN_gamma | 0.000 | | IL_13 | IFN_gamma | 0.000 |
| IL_13 | TNF_alpha | 0.005 | | IL_13 | TNF_alpha | 0.485 |
| IL_13 | TNF_beta | 0.070 | | IL_13 | TNF_beta | 0.196 |
| IL_13 | Varicella_Int | 0.029 | | IL_13 | Varicella_Int | -0.119 |
| IL_13 | Measles_OD_DB_Int | 0.069 | | IL_13 | Measles_OD_DB_Int | 0.087 |
| IL_13 | Measles_int | 0.044 | | IL_13 | Measles_Int | 0.011 |
| IL_13 | HepA_Int | 0.102 | | IL_13 | HepA_Int | 0.041 |
| IL_13 | Tetanus_Int | 0.000 | | IL_13 | Tetanus_Int | 0.000 |
| IL_13 | Diptheria_Int | 0.000 | | IL_13 | Diptheria_Int | 0.000 |
| IL_13 | Rubella_Int | 0.014 | | IL_13 | Rubella_Int | -0.067 |
| IL_13 | CMV_Int | 0.041 | | IL_13 | CMV_Int | 0.000 |
| IL_13 | HepB_cAb_Int | 0.154 | | IL_13 | HepB_cAb_Int | 0.041 |
| IL_13 | HepB_eAb_Int | -0.659 | | IL_13 | HepB_eAb_Int | 0.000 |

FIG. 2I6-F

| | | | | | | |
|---|---|---|---|---|---|---|
| IL_13 | HepB_eAg_Int | 0.659 | | IL_13 | HepB_eAg_Int | 0.000 |
| IL_13 | HepC_Int | -0.012 | | IL_13 | HepC_Int | -0.033 |
| IL_13 | Schistosoma_int | -0.047 | | IL_13 | Schistosoma_int | -0.053 |
| IL_13 | Strongyloides_Int | 0.166 | | IL_13 | Strongyloides_Int | 0.132 |
| IL_13 | Filaria_Int | -0.069 | | IL_13 | Filaria_Int | 0.115 |
| IL_15 | IL_1_alpha | 0.239 | | IL_15 | IL_1_alpha | 0.489 |
| IL_15 | IL_1_beta | 0.669 | | IL_15 | IL_1_beta | 0.680 |
| IL_15 | IL_2 | 0.201 | | IL_15 | IL_2 | 0.313 |
| IL_15 | IL_4 | 0.392 | | IL_15 | IL_4 | 0.364 |
| IL_15 | IL_5 | 0.191 | | IL_15 | IL_5 | 0.328 |
| IL_15 | IL_6 | 0.302 | | IL_15 | IL_6 | 0.513 |
| IL_15 | IL_8 | 0.445 | | IL_15 | IL_8 | 0.449 |
| IL_15 | IL_10 | 0.291 | | IL_15 | IL_10 | 0.535 |
| IL_15 | IL_12p70 | 0.341 | | IL_15 | IL_12p70 | 0.337 |
| IL_15 | IL_13 | 0.100 | | IL_15 | IL_13 | 0.383 |
| IL_15 | IL_15 | 1.000 | | IL_15 | IL_15 | 1.000 |
| IL_15 | IL_17 | 0.344 | | IL_15 | IL_17 | 0.448 |
| IL_15 | IL_23 | 0.111 | | IL_15 | IL_23 | 0.001 |
| IL_15 | IFN_gamma | 0.000 | | IL_15 | IFN_gamma | 0.000 |
| IL_15 | TNF_alpha | 0.699 | | IL_15 | TNF_alpha | 0.616 |
| IL_15 | TNF_beta | 0.327 | | IL_15 | TNF_beta | 0.531 |
| IL_15 | Varicella_Int | -0.127 | | IL_15 | Varicella_Int | -0.158 |
| IL_15 | Measles_OD_DB_Int | 0.043 | | IL_15 | Measles_OD_DB_Int | 0.144 |
| IL_15 | Measles_Int | -0.024 | | IL_15 | Measles_Int | -0.317 |
| IL_15 | HepA_Int | -0.072 | | IL_15 | HepA_Int | -0.191 |
| IL_15 | Tetanus_Int | 0.000 | | IL_15 | Tetanus_Int | 0.000 |
| IL_15 | Diptheria_Int | 0.000 | | IL_15 | Diptheria_Int | 0.000 |
| IL_15 | Rubella_Int | -0.030 | | IL_15 | Rubella_Int | -0.138 |
| IL_15 | CMV_Int | 0.064 | | IL_15 | CMV_Int | 0.000 |
| IL_15 | HepB_cAb_Int | 0.110 | | IL_15 | HepB_cAb_Int | -0.199 |
| IL_15 | HepB_eAb_Int | 0.298 | | IL_15 | HepB_eAb_Int | 0.000 |
| IL_15 | HepB_eAg_Int | -0.298 | | IL_15 | HepB_eAg_Int | 0.000 |
| IL_15 | HepC_Int | 0.055 | | IL_15 | HepC_Int | 0.159 |
| IL_15 | Schistosoma_int | -0.118 | | IL_15 | Schistosoma_int | 0.145 |
| IL_15 | Strongyloides_Int | -0.116 | | IL_15 | Strongyloides_Int | 0.187 |
| IL_15 | Filaria_Int | -0.148 | | IL_15 | Filaria_Int | -0.019 |
| IL_17 | IL_1_alpha | 0.200 | | IL_17 | IL_1_alpha | 0.689 |
| IL_17 | IL_1_beta | 0.224 | | IL_17 | IL_1_beta | 0.610 |
| IL_17 | IL_2 | 0.295 | | IL_17 | IL_2 | 0.343 |
| IL_17 | IL_4 | 0.276 | | IL_17 | IL_4 | 0.544 |
| IL_17 | IL_5 | 0.309 | | IL_17 | IL_5 | 0.297 |
| IL_17 | IL_6 | 0.039 | | IL_17 | IL_6 | 0.284 |
| IL_17 | IL_8 | 0.219 | | IL_17 | IL_8 | 0.421 |
| IL_17 | IL_10 | 0.550 | | IL_17 | IL_10 | 0.383 |
| IL_17 | IL_12p70 | 0.617 | | IL_17 | IL_12p70 | 0.363 |
| IL_17 | IL_13 | 0.062 | | IL_17 | IL_13 | 0.366 |
| IL_17 | IL_15 | 0.344 | | IL_17 | IL_15 | 0.448 |
| IL_17 | IL_17 | 1.000 | | IL_17 | IL_17 | 1.000 |
| IL_17 | IL_23 | 0.425 | | IL_17 | IL_23 | 0.015 |
| IL_17 | IFN_gamma | 0.000 | | IL_17 | IFN_gamma | 0.000 |
| IL_17 | TNF_alpha | 0.296 | | IL_17 | TNF_alpha | 0.355 |
| IL_17 | TNF_beta | 0.443 | | IL_17 | TNF_beta | 0.703 |
| IL_17 | Varicella_Int | 0.063 | | IL_17 | Varicella_Int | -0.190 |
| IL_17 | Measles_OD_DB_Int | 0.087 | | IL_17 | Measles_OD_DB_Int | 0.117 |
| IL_17 | Measles_Int | -0.117 | | IL_17 | Measles_Int | 0.063 |
| IL_17 | HepA_Int | -0.020 | | IL_17 | HepA_Int | 0.074 |
| IL_17 | Tetanus_Int | 0.000 | | IL_17 | Tetanus_Int | 0.000 |

FIG. 2I6-G

| | | | | | | |
|---|---|---|---|---|---|---|
| IL_17 | Diptheria_Int | 0.000 | | IL_17 | Diptheria_Int | 0.000 |
| IL_17 | Rubella_Int | -0.040 | | IL_17 | Rubella_Int | -0.022 |
| IL_17 | CMV_Int | -0.173 | | IL_17 | CMV_Int | 0.000 |
| IL_17 | HepB_cAb_Int | -0.104 | | IL_17 | HepB_cAb_Int | -0.064 |
| IL_17 | HepB_eAb_Int | -0.212 | | IL_17 | HepB_eAb_Int | 0.000 |
| IL_17 | HepB_eAg_Int | 0.212 | | IL_17 | HepB_eAg_Int | 0.000 |
| IL_17 | HepC_Int | -0.034 | | IL_17 | HepC_Int | 0.071 |
| IL_17 | Schistosoma_int | -0.024 | | IL_17 | Schistosoma_int | 0.238 |
| IL_17 | Strongyloides_Int | 0.216 | | IL_17 | Strongyloides_Int | 0.191 |
| IL_17 | Filaria_Int | -0.043 | | IL_17 | Filaria_Int | -0.052 |
| IL_23 | IL_1_alpha | 0.067 | | IL_23 | IL_1_alpha | 0.042 |
| IL_23 | IL_1_beta | 0.137 | | IL_23 | IL_1_beta | 0.123 |
| IL_23 | IL_2 | 0.327 | | IL_23 | IL_2 | 0.142 |
| IL_23 | IL_4 | 0.206 | | IL_23 | IL_4 | -0.007 |
| IL_23 | IL_5 | 0.134 | | IL_23 | IL_5 | 0.206 |
| IL_23 | IL_6 | -0.070 | | IL_23 | IL_6 | 0.569 |
| IL_23 | IL_8 | 0.087 | | IL_23 | IL_8 | -0.001 |
| IL_23 | IL_10 | 0.150 | | IL_23 | IL_10 | 0.459 |
| IL_23 | IL_12p70 | 0.519 | | IL_23 | IL_12p70 | 0.847 |
| IL_23 | IL_13 | 0.008 | | IL_23 | IL_13 | 0.606 |
| IL_23 | IL_15 | 0.111 | | IL_23 | IL_15 | 0.001 |
| IL_23 | IL_17 | 0.425 | | IL_23 | IL_17 | 0.015 |
| IL_23 | IL_23 | 1.000 | | IL_23 | IL_23 | 1.000 |
| IL_23 | IFN_gamma | 0.000 | | IL_23 | IFN_gamma | 0.000 |
| IL_23 | TNF_alpha | 0.136 | | IL_23 | TNF_alpha | 0.087 |
| IL_23 | TNF_beta | 0.442 | | IL_23 | TNF_beta | 0.032 |
| IL_23 | Varicella_Int | -0.008 | | IL_23 | Varicella_Int | 0.043 |
| IL_23 | Measles_OD_DB_Int | 0.095 | | IL_23 | Measles_OD_DB_Int | 0.066 |
| IL_23 | Measles_Int | -0.103 | | IL_23 | Measles_Int | 0.020 |
| IL_23 | HepA_Int | -0.146 | | IL_23 | HepA_Int | 0.035 |
| IL_23 | Tetanus_Int | 0.000 | | IL_23 | Tetanus_Int | 0.000 |
| IL_23 | Diptheria_Int | 0.000 | | IL_23 | Diptheria_Int | 0.000 |
| IL_23 | Rubella_Int | -0.123 | | IL_23 | Rubella_Int | -0.050 |
| IL_23 | CMV_Int | -0.037 | | IL_23 | CMV_Int | 0.000 |
| IL_23 | HepB_cAb_Int | -0.133 | | IL_23 | HepB_cAb_Int | 0.110 |
| IL_23 | HepB_eAb_Int | -0.999 | | IL_23 | HepB_eAb_Int | 0.000 |
| IL_23 | HepB_eAg_Int | 0.999 | | IL_23 | HepB_eAg_Int | 0.000 |
| IL_23 | HepC_Int | -0.030 | | IL_23 | HepC_int | -0.016 |
| IL_23 | Schistosoma_int | 0.140 | | IL_23 | Schistosoma_int | -0.039 |
| IL_23 | Strongyloides_Int | 0.158 | | IL_23 | Strongyloides_Int | 0.007 |
| IL_23 | Filaria_Int | -0.109 | | IL_23 | Filaria_Int | -0.079 |
| IFN_gamma | IL_1_alpha | 0.000 | | IFN_gamma | IL_1_alpha | 0.000 |
| IFN_gamma | IL_1_beta | 0.000 | | IFN_gamma | IL_1_beta | 0.000 |
| IFN_gamma | IL_2 | 0.000 | | IFN_gamma | IL_2 | 0.000 |
| IFN_gamma | IL_4 | 0.000 | | IFN_gamma | IL_4 | 0.000 |
| IFN_gamma | IL_5 | 0.000 | | IFN_gamma | IL_5 | 0.000 |
| IFN_gamma | IL_6 | 0.000 | | IFN_gamma | IL_6 | 0.000 |
| IFN_gamma | IL_8 | 0.000 | | IFN_gamma | IL_8 | 0.000 |
| IFN_gamma | IL_10 | 0.000 | | IFN_gamma | IL_10 | 0.000 |
| IFN_gamma | IL_12p70 | 0.000 | | IFN_gamma | IL_12p70 | 0.000 |
| IFN_gamma | IL_13 | 0.000 | | IFN_gamma | IL_13 | 0.000 |
| IFN_gamma | IL_15 | 0.000 | | IFN_gamma | IL_15 | 0.000 |
| IFN_gamma | IL_17 | 0.000 | | IFN_gamma | IL_17 | 0.000 |
| IFN_gamma | IL_23 | 0.000 | | IFN_gamma | IL_23 | 0.000 |
| IFN_gamma | IFN_gamma | 1.000 | | IFN_gamma | IFN_gamma | 1.000 |
| IFN_gamma | TNF_alpha | 0.000 | | IFN_gamma | TNF_alpha | 0.000 |
| IFN_gamma | TNF_beta | 0.000 | | IFN_gamma | TNF_beta | 0.000 |

FIG. 2I6-H

| IFN_gamma | Varicella_Int | 0.000 | IFN_gamma | Varicella_Int | 0.000 |
|---|---|---|---|---|---|
| IFN_gamma | Measles_OD_DB_Int | 0.000 | IFN_gamma | Measles_OD_DB_Int | 0.000 |
| IFN_gamma | Measles_Int | 0.000 | IFN_gamma | Measles_Int | 0.000 |
| IFN_gamma | HepA_Int | 0.000 | IFN_gamma | HepA_Int | 0.000 |
| IFN_gamma | Tetanus_Int | 0.000 | IFN_gamma | Tetanus_Int | 0.000 |
| IFN_gamma | Diptheria_Int | 0.000 | IFN_gamma | Diptheria_Int | 0.000 |
| IFN_gamma | Rubella_Int | 0.000 | IFN_gamma | Rubella_Int | 0.000 |
| IFN_gamma | CMV_Int | 0.000 | IFN_gamma | CMV_Int | 0.000 |
| IFN_gamma | HepB_cAb_Int | 0.000 | IFN_gamma | HepB_cAb_Int | 0.000 |
| IFN_gamma | HepB_eAb_Int | 0.000 | IFN_gamma | HepB_eAb_Int | 0.000 |
| IFN_gamma | HepB_eAg_Int | 0.000 | IFN_gamma | HepB_eAg_Int | 0.000 |
| IFN_gamma | HepC_Int | 0.000 | IFN_gamma | HepC_Int | 0.000 |
| IFN_gamma | Schistosoma_int | 0.000 | IFN_gamma | Schistosoma_int | 0.000 |
| IFN_gamma | Strongyloides_Int | 0.000 | IFN_gamma | Strongyloides_Int | 0.000 |
| IFN_gamma | Filaria_Int | 0.000 | IFN_gamma | Filaria_Int | 0.000 |
| TNF_alpha | IL_1_alpha | 0.107 | TNF_alpha | IL_1_alpha | 0.428 |
| TNF_alpha | IL_1_beta | 0.839 | TNF_alpha | IL_1_beta | 0.765 |
| TNF_alpha | IL_2 | 0.212 | TNF_alpha | IL_2 | 0.258 |
| TNF_alpha | IL_4 | 0.460 | TNF_alpha | IL_4 | 0.236 |
| TNF_alpha | IL_5 | 0.187 | TNF_alpha | IL_5 | 0.307 |
| TNF_alpha | IL_6 | 0.018 | TNF_alpha | IL_6 | 0.634 |
| TNF_alpha | IL_8 | 0.165 | TNF_alpha | IL_8 | 0.234 |
| TNF_alpha | IL_10 | 0.151 | TNF_alpha | IL_10 | 0.698 |
| TNF_alpha | IL_12p70 | 0.326 | TNF_alpha | IL_12p70 | 0.340 |
| TNF_alpha | IL_13 | 0.005 | TNF_alpha | IL_13 | 0.485 |
| TNF_alpha | IL_15 | 0.699 | TNF_alpha | IL_15 | 0.616 |
| TNF_alpha | IL_17 | 0.296 | TNF_alpha | IL_17 | 0.355 |
| TNF_alpha | IL_23 | 0.136 | TNF_alpha | IL_23 | 0.087 |
| TNF_alpha | IFN_gamma | 0.000 | TNF_alpha | IFN_gamma | 0.000 |
| TNF_alpha | TNF_alpha | 1.000 | TNF_alpha | TNF_alpha | 1.000 |
| TNF_alpha | TNF_beta | 0.412 | TNF_alpha | TNF_beta | 0.504 |
| TNF_alpha | Varicella_Int | 0.000 | TNF_alpha | Varicella_Int | 0.022 |
| TNF_alpha | Measles_OD_DB_Int | 0.073 | TNF_alpha | Measles_OD_DB_Int | 0.057 |
| TNF_alpha | Measles_Int | 0.054 | TNF_alpha | Measles_Int | -0.029 |
| TNF_alpha | HepA_Int | 0.021 | TNF_alpha | HepA_Int | -0.003 |
| TNF_alpha | Tetanus_Int | 0.000 | TNF_alpha | Tetanus_Int | 0.000 |
| TNF_alpha | Diptheria_Int | 0.000 | TNF_alpha | Diptheria_Int | 0.000 |
| TNF_alpha | Rubella_Int | -0.063 | TNF_alpha | Rubella_Int | -0.081 |
| TNF_alpha | CMV_Int | 0.060 | TNF_alpha | CMV_Int | 0.000 |
| TNF_alpha | HepB_cAb_Int | 0.115 | TNF_alpha | HepB_cAb_Int | -0.041 |
| TNF_alpha | HepB_eAb_Int | 0.102 | TNF_alpha | HepB_eAb_Int | 0.000 |
| TNF_alpha | HepB_eAg_Int | -0.102 | TNF_alpha | HepB_eAg_Int | 0.000 |
| TNF_alpha | HepC_Int | -0.014 | TNF_alpha | HepC_Int | 0.320 |
| TNF_alpha | Schistosoma_int | -0.024 | TNF_alpha | Schistosoma_int | 0.005 |
| TNF_alpha | Strongyloides_Int | 0.026 | TNF_alpha | Strongyloides_Int | 0.341 |
| TNF_alpha | Filaria_Int | -0.024 | TNF_alpha | Filaria_Int | 0.143 |
| TNF_beta | IL_1_alpha | 0.217 | TNF_beta | IL_1_alpha | 0.764 |
| TNF_beta | IL_1_beta | 0.610 | TNF_beta | IL_1_beta | 0.730 |
| TNF_beta | IL_2 | 0.269 | TNF_beta | IL_2 | 0.397 |
| TNF_beta | IL_4 | 0.765 | TNF_beta | IL_4 | 0.474 |
| TNF_beta | IL_5 | 0.320 | TNF_beta | IL_5 | 0.193 |
| TNF_beta | IL_6 | 0.073 | TNF_beta | IL_6 | 0.215 |
| TNF_beta | IL_8 | 0.221 | TNF_beta | IL_8 | 0.358 |
| TNF_beta | IL_10 | 0.244 | TNF_beta | IL_10 | 0.311 |
| TNF_beta | IL_12p70 | 0.376 | TNF_beta | IL_12p70 | 0.327 |
| TNF_beta | IL_13 | 0.070 | TNF_beta | IL_13 | 0.196 |
| TNF_beta | IL_15 | 0.327 | TNF_beta | IL_15 | 0.531 |

FIG. 21I6-I

| | | | | | | |
|---|---|---|---|---|---|---|
| TNF_beta | IL_17 | 0.443 | | TNF_beta | IL_17 | 0.703 |
| TNF_beta | IL_23 | 0.442 | | TNF_beta | IL_23 | 0.032 |
| TNF_beta | IFN_gamma | 0.000 | | TNF_beta | IFN_gamma | 0.000 |
| TNF_beta | TNF_alpha | 0.412 | | TNF_beta | TNF_alpha | 0.504 |
| TNF_beta | TNF_beta | 1.000 | | TNF_beta | TNF_beta | 1.000 |
| TNF_beta | Varicella_Int | 0.088 | | TNF_beta | Varicella_Int | -0.115 |
| TNF_beta | Measles_OD_DB_Int | 0.166 | | TNF_beta | Measles_OD_DB_Int | 0.106 |
| TNF_beta | Measles_Int | -0.175 | | TNF_beta | Measles_Int | -0.049 |
| TNF_beta | HepA_Int | 0.062 | | TNF_beta | HepA_Int | -0.013 |
| TNF_beta | Tetanus_Int | 0.000 | | TNF_beta | Tetanus_Int | 0.000 |
| TNF_beta | Diptheria_Int | 0.000 | | TNF_beta | Diptheria_Int | 0.000 |
| TNF_beta | Rubella_Int | 0.017 | | TNF_beta | Rubella_Int | -0.054 |
| TNF_beta | CMV_Int | 0.084 | | TNF_beta | CMV_Int | 0.000 |
| TNF_beta | HepB_cAb_Int | 0.105 | | TNF_beta | HepB_cAb_Int | -0.141 |
| TNF_beta | HepB_eAb_Int | -0.898 | | TNF_beta | HepB_eAb_Int | 0.000 |
| TNF_beta | HepB_eAg_Int | 0.898 | | TNF_beta | HepB_eAg_Int | 0.000 |
| TNF_beta | HepC_Int | -0.043 | | TNF_beta | HepC_Int | 0.302 |
| TNF_beta | Schistosoma_int | -0.011 | | TNF_beta | Schistosoma_int | 0.242 |
| TNF_beta | Strongyloides_Int | 0.227 | | TNF_beta | Strongyloides_Int | 0.173 |
| TNF_beta | Filaria_Int | -0.035 | | TNF_beta | Filaria_Int | -0.081 |
| Varicella_Int | IL_1_alpha | 0.063 | | Varicella_Int | IL_1_alpha | -0.187 |
| Varicella_Int | IL_1_beta | 0.050 | | Varicella_Int | IL_1_beta | -0.089 |
| Varicella_Int | IL_2 | -0.367 | | Varicella_Int | IL_2 | -0.076 |
| Varicella_Int | IL_4 | 0.036 | | Varicella_Int | IL_4 | -0.161 |
| Varicella_Int | IL_5 | 0.023 | | Varicella_Int | IL_5 | -0.046 |
| Varicella_Int | IL_6 | 0.043 | | Varicella_Int | IL_6 | -0.074 |
| Varicella_Int | IL_8 | 0.078 | | Varicella_Int | IL_8 | -0.168 |
| Varicella_Int | IL_10 | -0.021 | | Varicella_Int | IL_10 | -0.066 |
| Varicella_Int | IL_12p70 | 0.012 | | Varicella_Int | IL_12p70 | -0.102 |
| Varicella_Int | IL_13 | 0.029 | | Varicella_Int | IL_13 | -0.119 |
| Varicella_Int | IL_15 | -0.127 | | Varicella_Int | IL_15 | -0.158 |
| Varicella_Int | IL_17 | 0.063 | | Varicella_Int | IL_17 | -0.190 |
| Varicella_Int | IL_23 | -0.008 | | Varicella_Int | IL_23 | 0.043 |
| Varicella_Int | IFN_gamma | 0.000 | | Varicella_Int | IFN_gamma | 0.000 |
| Varicella_Int | TNF_alpha | 0.000 | | Varicella_Int | TNF_alpha | 0.022 |
| Varicella_Int | TNF_beta | 0.088 | | Varicella_Int | TNF_beta | -0.115 |
| Varicella_Int | Varicella_Int | 1.000 | | Varicella_Int | Varicella_Int | 1.000 |
| Varicella_Int | Measles_OD_DB_Int | -0.067 | | Varicella_Int | Measles_OD_DB_Int | 0.009 |
| Varicella_Int | Measles_Int | 0.017 | | Varicella_Int | Measles_Int | -0.031 |
| Varicella_Int | HepA_Int | 0.081 | | Varicella_Int | HepA_Int | -0.054 |
| Varicella_Int | Tetanus_Int | 0.000 | | Varicella_Int | Tetanus_Int | 0.000 |
| Varicella_Int | Diptheria_Int | 0.000 | | Varicella_Int | Diptheria_Int | 0.000 |
| Varicella_Int | Rubella_Int | 0.067 | | Varicella_Int | Rubella_Int | -0.244 |
| Varicella_Int | CMV_Int | -0.052 | | Varicella_Int | CMV_Int | 0.000 |
| Varicella_Int | HepB_cAb_Int | -0.077 | | Varicella_Int | HepB_cAb_Int | -0.040 |
| Varicella_Int | HepB_eAb_Int | 0.000 | | Varicella_Int | HepB_eAb_Int | 0.000 |
| Varicella_Int | HepB_eAg_Int | 0.000 | | Varicella_Int | HepB_eAg_Int | 0.000 |
| Varicella_Int | HepC_Int | 0.021 | | Varicella_Int | HepC_Int | 0.094 |
| Varicella_Int | Schistosoma_int | 0.070 | | Varicella_Int | Schistosoma_int | -0.049 |
| Varicella_Int | Strongyloides_Int | 0.016 | | Varicella_Int | Strongyloides_Int | -0.169 |
| Varicella_Int | Filaria_Int | -0.047 | | Varicella_Int | Filaria_Int | -0.159 |
| Measles_OD_DB_Int | IL_1_alpha | 0.135 | | Measles_OD_DB_Int | IL_1_alpha | 0.128 |
| Measles_OD_DB_Int | IL_1_beta | 0.068 | | Measles_OD_DB_Int | IL_1_beta | 0.112 |
| Measles_OD_DB_Int | IL_2 | 0.128 | | Measles_OD_DB_Int | IL_2 | 0.148 |
| Measles_OD_DB_Int | IL_4 | 0.061 | | Measles_OD_DB_Int | IL_4 | 0.099 |
| Measles_OD_DB_Int | IL_5 | -0.033 | | Measles_OD_DB_Int | IL_5 | 0.021 |
| Measles_OD_DB_Int | IL_6 | -0.000 | | Measles_OD_DB_Int | IL_6 | 0.091 |

FIG. 2116-J

| | | | | | | |
|---|---|---|---|---|---|---|
| Measles_OD_DB_Int | IL_8 | 0.050 | | Measles_OD_DB_Int | IL_8 | 0.146 |
| Measles_OD_DB_Int | IL_10 | 0.005 | | Measles_OD_DB_Int | IL_10 | 0.103 |
| Measles_OD_DB_Int | IL_12p70 | 0.082 | | Measles_OD_DB_Int | IL_12p70 | 0.071 |
| Measles_OD_DB_Int | IL_13 | 0.069 | | Measles_OD_DB_Int | IL_13 | 0.087 |
| Measles_OD_DB_Int | IL_15 | 0.043 | | Measles_OD_DB_Int | IL_15 | 0.144 |
| Measles_OD_DB_Int | IL_17 | 0.087 | | Measles_OD_DB_Int | IL_17 | 0.117 |
| Measles_OD_DB_Int | IL_23 | 0.095 | | Measles_OD_DB_Int | IL_23 | 0.066 |
| Measles_OD_DB_Int | IFN_gamma | 0.000 | | Measles_OD_DB_Int | IFN_gamma | 0.000 |
| Measles_OD_DB_Int | TNF_alpha | 0.073 | | Measles_OD_DB_Int | TNF_alpha | 0.057 |
| Measles_OD_DB_Int | TNF_beta | 0.166 | | Measles_OD_DB_Int | TNF_beta | 0.106 |
| Measles_OD_DB_Int | Varicella_Int | -0.067 | | Measles_OD_DB_Int | Varicella_Int | 0.009 |
| Measles_OD_DB_Int | Measles_OD_DB_Int | 1.000 | | Measles_OD_DB_Int | Measles_OD_DB_Int | 1.000 |
| Measles_OD_DB_Int | Measles_Int | 0.289 | | Measles_OD_DB_Int | Measles_Int | -0.043 |
| Measles_OD_DB_Int | HepA_Int | -0.078 | | Measles_OD_DB_Int | HepA_Int | 0.160 |
| Measles_OD_DB_Int | Tetanus_Int | 0.000 | | Measles_OD_DB_Int | Tetanus_Int | 0.000 |
| Measles_OD_DB_Int | Diptheria_Int | 0.000 | | Measles_OD_DB_Int | Diptheria_Int | 0.000 |
| Measles_OD_DB_Int | Rubella_Int | -0.019 | | Measles_OD_DB_Int | Rubella_Int | -0.119 |
| Measles_OD_DB_Int | CMV_Int | -0.075 | | Measles_OD_DB_Int | CMV_Int | 0.000 |
| Measles_OD_DB_Int | HepB_cAb_Int | -0.005 | | Measles_OD_DB_Int | HepB_cAb_Int | -0.115 |
| Measles_OD_DB_Int | HepB_eAb_Int | -0.200 | | Measles_OD_DB_Int | HepB_eAb_Int | 0.000 |
| Measles_OD_DB_Int | HepB_eAg_Int | 0.200 | | Measles_OD_DB_Int | HepB_eAg_Int | 0.000 |
| Measles_OD_DB_Int | HepC_Int | -0.102 | | Measles_OD_DB_Int | HepC_Int | 0.050 |
| Measles_OD_DB_Int | Schistosoma_int | -0.075 | | Measles_OD_DB_Int | Schistosoma_int | 0.054 |
| Measles_OD_DB_Int | Strongyloides_Int | 0.317 | | Measles_OD_DB_Int | Strongyloides_Int | 0.043 |
| Measles_OD_DB_Int | Filaria_Int | 0.148 | | Measles_OD_DB_Int | Filaria_Int | -0.095 |
| Measles_Int | IL_1_alpha | 0.089 | | Measles_Int | IL_1_alpha | -0.012 |
| Measles_Int | IL_1_beta | -0.051 | | Measles_Int | IL_1_beta | -0.145 |
| Measles_Int | IL_2 | 0.027 | | Measles_Int | IL_2 | 0.044 |
| Measles_Int | IL_4 | -0.138 | | Measles_Int | IL_4 | -0.060 |
| Measles_Int | IL_5 | -0.035 | | Measles_Int | IL_5 | 0.046 |
| Measles_Int | IL_6 | -0.018 | | Measles_Int | IL_6 | 0.025 |
| Measles_Int | IL_8 | 0.098 | | Measles_Int | IL_8 | 0.022 |
| Measles_Int | IL_10 | -0.005 | | Measles_Int | IL_10 | 0.063 |
| Measles_Int | IL_12p70 | -0.004 | | Measles_Int | IL_12p70 | -0.042 |
| Measles_Int | IL_13 | 0.044 | | Measles_Int | IL_13 | 0.011 |
| Measles_Int | IL_15 | -0.024 | | Measles_Int | IL_15 | -0.317 |
| Measles_Int | IL_17 | -0.117 | | Measles_Int | IL_17 | 0.063 |
| Measles_Int | IL_23 | -0.103 | | Measles_Int | IL_23 | 0.020 |
| Measles_Int | IFN_gamma | 0.000 | | Measles_Int | IFN_gamma | 0.000 |
| Measles_Int | TNF_alpha | 0.054 | | Measles_Int | TNF_alpha | -0.029 |
| Measles_Int | TNF_beta | -0.175 | | Measles_Int | TNF_beta | -0.049 |
| Measles_Int | Varicella_Int | 0.017 | | Measles_Int | Varicella_Int | -0.031 |
| Measles_Int | Measles_OD_DB_Int | 0.289 | | Measles_Int | Measles_OD_DB_Int | -0.043 |
| Measles_Int | Measles_Int | 1.000 | | Measles_Int | Measles_Int | 1.000 |
| Measles_Int | HepA_Int | 0.183 | | Measles_Int | HepA_Int | 0.571 |
| Measles_Int | Tetanus_Int | 0.000 | | Measles_Int | Tetanus_Int | 0.000 |
| Measles_Int | Diptheria_Int | 0.000 | | Measles_Int | Diptheria_Int | 0.000 |
| Measles_Int | Rubella_Int | -0.037 | | Measles_Int | Rubella_Int | 0.031 |
| Measles_Int | CMV_Int | 0.049 | | Measles_Int | CMV_Int | 0.000 |
| Measles_Int | HepB_cAb_Int | -0.021 | | Measles_Int | HepB_cAb_Int | 0.134 |
| Measles_Int | HepB_eAb_Int | 1.000 | | Measles_Int | HepB_eAb_Int | 0.000 |
| Measles_Int | HepB_eAg_Int | -1.000 | | Measles_Int | HepB_eAg_Int | 0.000 |
| Measles_Int | HepC_int | 0.038 | | Measles_Int | HepC_int | 0.038 |
| Measles_Int | Schistosoma_int | 0.069 | | Measles_Int | Schistosoma_int | 0.088 |
| Measles_Int | Strongyloides_Int | -0.053 | | Measles_Int | Strongyloides_Int | 0.146 |
| Measles_Int | Filaria_Int | 0.138 | | Measles_Int | Filaria_Int | 0.066 |
| HepA_Int | IL_1_alpha | 0.087 | | HepA_Int | IL_1_alpha | 0.035 |

FIG. 21I6-K

| | | | | | | |
|---|---|---|---|---|---|---|
| HepA_Int | IL_1_beta | 0.062 | | HepA_Int | IL_1_beta | -0.021 |
| HepA_Int | IL_2 | -0.098 | | HepA_Int | IL_2 | 0.077 |
| HepA_Int | IL_4 | 0.098 | | HepA_Int | IL_4 | 0.013 |
| HepA_Int | IL_5 | 0.099 | | HepA_Int | IL_5 | 0.060 |
| HepA_Int | IL_6 | -0.221 | | HepA_Int | IL_6 | 0.067 |
| HepA_Int | IL_8 | -0.160 | | HepA_Int | IL_8 | 0.063 |
| HepA_Int | IL_10 | 0.078 | | HepA_Int | IL_10 | 0.036 |
| HepA_Int | IL_12p70 | -0.000 | | HepA_Int | IL_12p70 | 0.033 |
| HepA_Int | IL_13 | 0.102 | | HepA_Int | IL_13 | 0.041 |
| HepA_Int | IL_15 | -0.072 | | HepA_Int | IL_15 | -0.191 |
| HepA_Int | IL_17 | -0.020 | | HepA_Int | IL_17 | 0.074 |
| HepA_Int | IL_23 | -0.146 | | HepA_Int | IL_23 | 0.035 |
| HepA_Int | IFN_gamma | 0.000 | | HepA_Int | IFN_gamma | 0.000 |
| HepA_Int | TNF_alpha | 0.021 | | HepA_Int | TNF_alpha | -0.003 |
| HepA_Int | TNF_beta | 0.062 | | HepA_Int | TNF_beta | -0.013 |
| HepA_Int | Varicella_Int | 0.081 | | HepA_Int | Varicella_Int | -0.054 |
| HepA_Int | Measles_OD_DB_Int | -0.078 | | HepA_Int | Measles_OD_DB_Int | 0.160 |
| HepA_Int | Measles_Int | 0.183 | | HepA_Int | Measles_Int | 0.571 |
| HepA_Int | HepA_Int | 1.000 | | HepA_Int | HepA_Int | 1.000 |
| HepA_Int | Tetanus_Int | 0.000 | | HepA_Int | Tetanus_Int | 0.000 |
| HepA_Int | Diptheria_Int | 0.000 | | HepA_Int | Diptheria_Int | 0.000 |
| HepA_Int | Rubella_Int | 0.051 | | HepA_Int | Rubella_Int | 0.055 |
| HepA_Int | CMV_Int | 0.156 | | HepA_Int | CMV_Int | 0.000 |
| HepA_Int | HepB_cAb_Int | 0.116 | | HepA_Int | HepB_cAb_Int | 0.235 |
| HepA_Int | HepB_eAb_Int | -0.200 | | HepA_Int | HepB_eAb_Int | 0.000 |
| HepA_Int | HepB_eAg_Int | 0.200 | | HepA_Int | HepB_eAg_Int | 0.000 |
| HepA_Int | HepC_Int | 0.081 | | HepA_Int | HepC_Int | 0.066 |
| HepA_Int | Schistosoma_int | 0.191 | | HepA_Int | Schistosoma_int | 0.010 |
| HepA_Int | Strongyloides_Int | 0.044 | | HepA_Int | Strongyloides_Int | -0.077 |
| HepA_Int | Filaria_Int | 0.103 | | HepA_Int | Filaria_Int | -0.090 |
| Tetanus_Int | IL_1_alpha | 0.000 | | Tetanus_Int | IL_1_alpha | 0.000 |
| Tetanus_Int | IL_1_beta | 0.000 | | Tetanus_Int | IL_1_beta | 0.000 |
| Tetanus_Int | IL_2 | 0.000 | | Tetanus_Int | IL_2 | 0.000 |
| Tetanus_Int | IL_4 | 0.000 | | Tetanus_Int | IL_4 | 0.000 |
| Tetanus_Int | IL_5 | 0.000 | | Tetanus_Int | IL_5 | 0.000 |
| Tetanus_Int | IL_6 | 0.000 | | Tetanus_Int | IL_6 | 0.000 |
| Tetanus_Int | IL_8 | 0.000 | | Tetanus_Int | IL_8 | 0.000 |
| Tetanus_Int | IL_10 | 0.000 | | Tetanus_Int | IL_10 | 0.000 |
| Tetanus_Int | IL_12p70 | 0.000 | | Tetanus_Int | IL_12p70 | 0.000 |
| Tetanus_Int | IL_13 | 0.000 | | Tetanus_Int | IL_13 | 0.000 |
| Tetanus_Int | IL_15 | 0.000 | | Tetanus_Int | IL_15 | 0.000 |
| Tetanus_Int | IL_17 | 0.000 | | Tetanus_Int | IL_17 | 0.000 |
| Tetanus_Int | IL_23 | 0.000 | | Tetanus_Int | IL_23 | 0.000 |
| Tetanus_Int | IFN_gamma | 0.000 | | Tetanus_Int | IFN_gamma | 0.000 |
| Tetanus_Int | TNF_alpha | 0.000 | | Tetanus_Int | TNF_alpha | 0.000 |
| Tetanus_Int | TNF_beta | 0.000 | | Tetanus_Int | TNF_beta | 0.000 |
| Tetanus_Int | Varicella_Int | 0.000 | | Tetanus_Int | Varicella_Int | 0.000 |
| Tetanus_Int | Measles_OD_DB_Int | 0.000 | | Tetanus_Int | Measles_OD_DB_Int | 0.000 |
| Tetanus_Int | Measles_Int | 0.000 | | Tetanus_Int | Measles_Int | 0.000 |
| Tetanus_Int | HepA_Int | 0.000 | | Tetanus_Int | HepA_Int | 0.000 |
| Tetanus_Int | Tetanus_Int | 1.000 | | Tetanus_Int | Tetanus_Int | 1.000 |
| Tetanus_Int | Diptheria_Int | 0.000 | | Tetanus_Int | Diptheria_Int | 0.000 |
| Tetanus_Int | Rubella_Int | 0.000 | | Tetanus_Int | Rubella_Int | 0.000 |
| Tetanus_Int | CMV_Int | 0.000 | | Tetanus_Int | CMV_Int | 0.000 |
| Tetanus_Int | HepB_cAb_Int | 0.000 | | Tetanus_Int | HepB_cAb_Int | 0.000 |
| Tetanus_Int | HepB_eAb_Int | 0.000 | | Tetanus_Int | HepB_eAb_Int | 0.000 |
| Tetanus_Int | HepB_eAg_Int | 0.000 | | Tetanus_Int | HepB_eAg_Int | 0.000 |

FIG. 21I6-L

| | | | | | | |
|---|---|---|---|---|---|---|
| Tetanus_Int | HepC_Int | 0.000 | | Tetanus_Int | HepC_Int | 0.000 |
| Tetanus_Int | Schistosoma_int | 0.000 | | Tetanus_Int | Schistosoma_int | 0.000 |
| Tetanus_Int | Strongyloides_Int | 0.000 | | Tetanus_Int | Strongyloides_Int | 0.000 |
| Tetanus_Int | Filaria_Int | 0.000 | | Tetanus_Int | Filaria_Int | 0.000 |
| Diptheria_Int | IL_1_alpha | 0.000 | | Diptheria_Int | IL_1_alpha | 0.000 |
| Diptheria_Int | IL_1_beta | 0.000 | | Diptheria_Int | IL_1_beta | 0.000 |
| Diptheria_Int | IL_2 | 0.000 | | Diptheria_Int | IL_2 | 0.000 |
| Diptheria_Int | IL_4 | 0.000 | | Diptheria_Int | IL_4 | 0.000 |
| Diptheria_Int | IL_5 | 0.000 | | Diptheria_Int | IL_5 | 0.000 |
| Diptheria_Int | IL_6 | 0.000 | | Diptheria_Int | IL_6 | 0.000 |
| Diptheria_Int | IL_8 | 0.000 | | Diptheria_Int | IL_8 | 0.000 |
| Diptheria_Int | IL_10 | 0.000 | | Diptheria_Int | IL_10 | 0.000 |
| Diptheria_Int | IL_12p70 | 0.000 | | Diptheria_Int | IL_12p70 | 0.000 |
| Diptheria_Int | IL_13 | 0.000 | | Diptheria_Int | IL_13 | 0.000 |
| Diptheria_Int | IL_15 | 0.000 | | Diptheria_Int | IL_15 | 0.000 |
| Diptheria_Int | IL_17 | 0.000 | | Diptheria_Int | IL_17 | 0.000 |
| Diptheria_Int | IL_23 | 0.000 | | Diptheria_Int | IL_23 | 0.000 |
| Diptheria_Int | IFN_gamma | 0.000 | | Diptheria_Int | IFN_gamma | 0.000 |
| Diptheria_Int | TNF_alpha | 0.000 | | Diptheria_Int | TNF_alpha | 0.000 |
| Diptheria_Int | TNF_beta | 0.000 | | Diptheria_Int | TNF_beta | 0.000 |
| Diptheria_Int | Varicella_Int | 0.000 | | Diptheria_Int | Varicella_Int | 0.000 |
| Diptheria_Int | Measles_OD_DB_Int | 0.000 | | Diptheria_Int | Measles_OD_DB_Int | 0.000 |
| Diptheria_Int | Measles_Int | 0.000 | | Diptheria_Int | Measles_Int | 0.000 |
| Diptheria_Int | HepA_Int | 0.000 | | Diptheria_Int | HepA_Int | 0.000 |
| Diptheria_Int | Tetanus_Int | 0.000 | | Diptheria_Int | Tetanus_Int | 0.000 |
| Diptheria_Int | Diptheria_Int | 1.000 | | Diptheria_Int | Diptheria_Int | 1.000 |
| Diptheria_Int | Rubella_Int | 0.000 | | Diptheria_Int | Rubella_Int | 0.000 |
| Diptheria_Int | CMV_Int | 0.000 | | Diptheria_Int | CMV_Int | 0.000 |
| Diptheria_Int | HepB_cAb_Int | 0.000 | | Diptheria_Int | HepB_cAb_Int | 0.000 |
| Diptheria_Int | HepB_eAb_Int | 0.000 | | Diptheria_Int | HepB_eAb_Int | 0.000 |
| Diptheria_Int | HepB_eAg_Int | 0.000 | | Diptheria_Int | HepB_eAg_Int | 0.000 |
| Diptheria_Int | HepC_Int | 0.000 | | Diptheria_Int | HepC_Int | 0.000 |
| Diptheria_Int | Schistosoma_int | 0.000 | | Diptheria_Int | Schistosoma_int | 0.000 |
| Diptheria_Int | Strongyloides_Int | 0.000 | | Diptheria_Int | Strongyloides_Int | 0.000 |
| Diptheria_Int | Filaria_Int | 0.000 | | Diptheria_Int | Filaria_Int | 0.000 |
| Rubella_Int | IL_1_alpha | -0.035 | | Rubella_Int | IL_1_alpha | -0.052 |
| Rubella_Int | IL_1_beta | -0.029 | | Rubella_Int | IL_1_beta | -0.070 |
| Rubella_Int | IL_2 | -0.124 | | Rubella_Int | IL_2 | -0.064 |
| Rubella_Int | IL_4 | -0.049 | | Rubella_Int | IL_4 | -0.036 |
| Rubella_Int | IL_5 | 0.104 | | Rubella_Int | IL_5 | -0.094 |
| Rubella_Int | IL_6 | -0.064 | | Rubella_Int | IL_6 | -0.076 |
| Rubella_Int | IL_8 | 0.144 | | Rubella_Int | IL_8 | -0.114 |
| Rubella_Int | IL_10 | 0.056 | | Rubella_Int | IL_10 | -0.035 |
| Rubella_Int | IL_12p70 | -0.042 | | Rubella_Int | IL_12p70 | -0.058 |
| Rubella_Int | IL_13 | 0.014 | | Rubella_Int | IL_13 | -0.067 |
| Rubella_Int | IL_15 | -0.030 | | Rubella_Int | IL_15 | -0.138 |
| Rubella_Int | IL_17 | -0.040 | | Rubella_Int | IL_17 | -0.022 |
| Rubella_Int | IL_23 | -0.123 | | Rubella_Int | IL_23 | -0.050 |
| Rubella_Int | IFN_gamma | 0.000 | | Rubella_Int | IFN_gamma | 0.000 |
| Rubella_Int | TNF_alpha | -0.063 | | Rubella_Int | TNF_alpha | -0.081 |
| Rubella_Int | TNF_beta | 0.017 | | Rubella_Int | TNF_beta | -0.054 |
| Rubella_Int | Varicella_Int | 0.067 | | Rubella_Int | Varicella_Int | -0.244 |
| Rubella_Int | Measles_OD_DB_Int | -0.019 | | Rubella_Int | Measles_OD_DB_Int | -0.119 |
| Rubella_Int | Measles_Int | -0.037 | | Rubella_Int | Measles_Int | 0.031 |
| Rubella_Int | HepA_Int | 0.051 | | Rubella_Int | HepA_Int | 0.055 |
| Rubella_Int | Tetanus_Int | 0.000 | | Rubella_Int | Tetanus_Int | 0.000 |
| Rubella_Int | Diptheria_Int | 0.000 | | Rubella_Int | Diptheria_Int | 0.000 |

FIG. 2I6-M

| | | | | | | |
|---|---|---|---|---|---|---|
| Rubella_Int | Rubella_Int | 1.000 | | Rubella_Int | Rubella_Int | 1.000 |
| Rubella_Int | CMV_Int | -0.053 | | Rubella_Int | CMV_Int | 0.000 |
| Rubella_Int | HepB_cAb_Int | -0.047 | | Rubella_Int | HepB_cAb_Int | -0.041 |
| Rubella_Int | HepB_eAb_Int | 0.200 | | Rubella_Int | HepB_eAb_Int | 0.000 |
| Rubella_Int | HepB_eAg_Int | -0.200 | | Rubella_Int | HepB_eAg_Int | 0.000 |
| Rubella_Int | HepC_Int | -0.035 | | Rubella_Int | HepC_Int | -0.096 |
| Rubella_Int | Schistosoma_int | 0.218 | | Rubella_Int | Schistosoma_int | -0.014 |
| Rubella_Int | Strongyloides_Int | -0.015 | | Rubella_Int | Strongyloides_Int | 0.050 |
| Rubella_Int | Filaria_Int | 0.014 | | Rubella_Int | Filaria_Int | -0.167 |
| CMV_Int | IL_1_alpha | 0.086 | | CMV_Int | IL_1_alpha | 0.000 |
| CMV_Int | IL_1_beta | 0.062 | | CMV_Int | IL_1_beta | 0.000 |
| CMV_Int | IL_2 | 0.088 | | CMV_Int | IL_2 | 0.000 |
| CMV_Int | IL_4 | 0.083 | | CMV_Int | IL_4 | 0.000 |
| CMV_Int | IL_5 | 0.044 | | CMV_Int | IL_5 | 0.000 |
| CMV_Int | IL_6 | 0.077 | | CMV_Int | IL_6 | 0.000 |
| CMV_Int | IL_8 | 0.125 | | CMV_Int | IL_8 | 0.000 |
| CMV_Int | IL_10 | -0.269 | | CMV_Int | IL_10 | 0.000 |
| CMV_Int | IL_12p70 | -0.008 | | CMV_Int | IL_12p70 | 0.000 |
| CMV_Int | IL_13 | 0.041 | | CMV_Int | IL_13 | 0.000 |
| CMV_Int | IL_15 | 0.064 | | CMV_Int | IL_15 | 0.000 |
| CMV_Int | IL_17 | -0.173 | | CMV_Int | IL_17 | 0.000 |
| CMV_Int | IL_23 | -0.037 | | CMV_Int | IL_23 | 0.000 |
| CMV_Int | IFN_gamma | 0.000 | | CMV_Int | IFN_gamma | 0.000 |
| CMV_Int | TNF_alpha | 0.060 | | CMV_Int | TNF_alpha | 0.000 |
| CMV_Int | TNF_beta | 0.084 | | CMV_Int | TNF_beta | 0.000 |
| CMV_Int | Varicella_Int | -0.052 | | CMV_Int | Varicella_Int | 0.000 |
| CMV_Int | Measles_OD_DB_Int | -0.075 | | CMV_Int | Measles_OD_DB_Int | 0.000 |
| CMV_Int | Measles_Int | 0.049 | | CMV_Int | Measles_Int | 0.000 |
| CMV_Int | HepA_Int | 0.156 | | CMV_Int | HepA_Int | 0.000 |
| CMV_Int | Tetanus_Int | 0.000 | | CMV_Int | Tetanus_Int | 0.000 |
| CMV_Int | Diptheria_Int | 0.000 | | CMV_Int | Diptheria_Int | 0.000 |
| CMV_Int | Rubella_Int | -0.053 | | CMV_Int | Rubella_Int | 0.000 |
| CMV_Int | CMV_Int | 1.000 | | CMV_Int | CMV_Int | 1.000 |
| CMV_Int | HepB_cAb_Int | 0.153 | | CMV_Int | HepB_cAb_Int | 0.000 |
| CMV_Int | HepB_eAb_Int | 0.000 | | CMV_Int | HepB_eAb_Int | 0.000 |
| CMV_Int | HepB_eAg_Int | 0.000 | | CMV_Int | HepB_eAg_Int | 0.000 |
| CMV_Int | HepC_Int | 0.027 | | CMV_Int | HepC_int | 0.000 |
| CMV_Int | Schistosoma_int | 0.089 | | CMV_Int | Schistosoma_int | 0.000 |
| CMV_Int | Strongyloides_Int | 0.042 | | CMV_Int | Strongyloides_Int | 0.000 |
| CMV_Int | Filaria_Int | 0.093 | | CMV_Int | Filaria_Int | 0.000 |
| HepB_cAb_Int | IL_1_alpha | 0.187 | | HepB_cAb_Int | IL_1_alpha | 0.020 |
| HepB_cAb_Int | IL_1_beta | 0.202 | | HepB_cAb_Int | IL_1_beta | -0.039 |
| HepB_cAb_Int | IL_2 | -0.004 | | HepB_cAb_Int | IL_2 | 0.034 |
| HepB_cAb_Int | IL_4 | 0.262 | | HepB_cAb_Int | IL_4 | -0.093 |
| HepB_cAb_Int | IL_5 | 0.143 | | HepB_cAb_Int | IL_5 | -0.121 |
| HepB_cAb_Int | IL_6 | -0.043 | | HepB_cAb_Int | IL_6 | -0.014 |
| HepB_cAb_Int | IL_8 | 0.101 | | HepB_cAb_Int | IL_8 | 0.028 |
| HepB_cAb_Int | IL_10 | -0.033 | | HepB_cAb_Int | IL_10 | -0.027 |
| HepB_cAb_Int | IL_12p70 | -0.055 | | HepB_cAb_Int | IL_12p70 | 0.142 |
| HepB_cAb_Int | IL_13 | 0.154 | | HepB_cAb_Int | IL_13 | 0.041 |
| HepB_cAb_Int | IL_15 | 0.110 | | HepB_cAb_Int | IL_15 | -0.199 |
| HepB_cAb_Int | IL_17 | -0.104 | | HepB_cAb_Int | IL_17 | -0.064 |
| HepB_cAb_Int | IL_23 | -0.133 | | HepB_cAb_Int | IL_23 | 0.110 |
| HepB_cAb_Int | IFN_gamma | 0.000 | | HepB_cAb_Int | IFN_gamma | 0.000 |
| HepB_cAb_Int | TNF_alpha | 0.115 | | HepB_cAb_Int | TNF_alpha | -0.041 |
| HepB_cAb_Int | TNF_beta | 0.105 | | HepB_cAb_Int | TNF_beta | -0.141 |
| HepB_cAb_Int | Varicella_Int | -0.077 | | HepB_cAb_Int | Varicella_Int | -0.040 |

FIG. 2I6-N

| | | | | | | |
|---|---|---|---|---|---|---|
| HepB_cAb_Int | Measles_OD_DB_Int | -0.005 | | HepB_cAb_Int | Measles_OD_DB_Int | -0.115 |
| HepB_cAb_Int | Measles_Int | -0.021 | | HepB_cAb_Int | Measles_Int | 0.134 |
| HepB_cAb_Int | HepA_Int | 0.116 | | HepB_cAb_Int | HepA_Int | 0.235 |
| HepB_cAb_Int | Tetanus_Int | 0.000 | | HepB_cAb_Int | Tetanus_Int | 0.000 |
| HepB_cAb_Int | Diptheria_Int | 0.000 | | HepB_cAb_Int | Diptheria_Int | 0.000 |
| HepB_cAb_Int | Rubella_Int | -0.047 | | HepB_cAb_Int | Rubella_Int | -0.041 |
| HepB_cAb_Int | CMV_Int | 0.153 | | HepB_cAb_Int | CMV_Int | 0.000 |
| HepB_cAb_Int | HepB_cAb_Int | 1.000 | | HepB_cAb_Int | HepB_cAb_Int | 1.000 |
| HepB_cAb_Int | HepB_eAb_Int | 0.000 | | HepB_cAb_Int | HepB_eAb_Int | 0.000 |
| HepB_cAb_Int | HepB_eAg_Int | 0.000 | | HepB_cAb_Int | HepB_eAg_Int | 0.000 |
| HepB_cAb_Int | HepC_Int | -0.062 | | HepB_cAb_Int | HepC_Int | -0.091 |
| HepB_cAb_Int | Schistosoma_int | -0.120 | | HepB_cAb_Int | Schistosoma_int | -0.150 |
| HepB_cAb_Int | Strongyloides_Int | -0.037 | | HepB_cAb_Int | Strongyloides_Int | -0.037 |
| HepB_cAb_Int | Filaria_Int | -0.071 | | HepB_cAb_Int | Filaria_Int | 0.026 |
| HepB_eAb_Int | IL_1_alpha | -0.446 | | HepB_eAb_Int | IL_1_alpha | 0.000 |
| HepB_eAb_Int | IL_1_beta | -0.269 | | HepB_eAb_Int | IL_1_beta | 0.000 |
| HepB_eAb_Int | IL_2 | -0.966 | | HepB_eAb_Int | IL_2 | 0.000 |
| HepB_eAb_Int | IL_4 | -0.860 | | HepB_eAb_Int | IL_4 | 0.000 |
| HepB_eAb_Int | IL_5 | -0.954 | | HepB_eAb_Int | IL_5 | 0.000 |
| HepB_eAb_Int | IL_6 | -0.146 | | HepB_eAb_Int | IL_6 | 0.000 |
| HepB_eAb_Int | IL_8 | 0.198 | | HepB_eAb_Int | IL_8 | 0.000 |
| HepB_eAb_Int | IL_10 | -0.180 | | HepB_eAb_Int | IL_10 | 0.000 |
| HepB_eAb_Int | IL_12p70 | -0.213 | | HepB_eAb_Int | IL_12p70 | 0.000 |
| HepB_eAb_Int | IL_13 | -0.659 | | HepB_eAb_Int | IL_13 | 0.000 |
| HepB_eAb_Int | IL_15 | 0.298 | | HepB_eAb_Int | IL_15 | 0.000 |
| HepB_eAb_Int | IL_17 | -0.212 | | HepB_eAb_Int | IL_17 | 0.000 |
| HepB_eAb_Int | IL_23 | -0.999 | | HepB_eAb_Int | IL_23 | 0.000 |
| HepB_eAb_Int | IFN_gamma | 0.000 | | HepB_eAb_Int | IFN_gamma | 0.000 |
| HepB_eAb_Int | TNF_alpha | 0.102 | | HepB_eAb_Int | TNF_alpha | 0.000 |
| HepB_eAb_Int | TNF_beta | -0.898 | | HepB_eAb_Int | TNF_beta | 0.000 |
| HepB_eAb_Int | Varicella_Int | 0.000 | | HepB_eAb_Int | Varicella_Int | 0.000 |
| HepB_eAb_Int | Measles_OD_DB_Int | -0.200 | | HepB_eAb_Int | Measles_OD_DB_Int | 0.000 |
| HepB_eAb_Int | Measles_Int | 1.000 | | HepB_eAb_Int | Measles_Int | 0.000 |
| HepB_eAb_Int | HepA_Int | -0.200 | | HepB_eAb_Int | HepA_Int | 0.000 |
| HepB_eAb_Int | Tetanus_Int | 0.000 | | HepB_eAb_Int | Tetanus_Int | 0.000 |
| HepB_eAb_Int | Diptheria_Int | 0.000 | | HepB_eAb_Int | Diptheria_Int | 0.000 |
| HepB_eAb_Int | Rubella_Int | 0.200 | | HepB_eAb_Int | Rubella_Int | 0.000 |
| HepB_eAb_Int | CMV_Int | 0.000 | | HepB_eAb_Int | CMV_Int | 0.000 |
| HepB_eAb_Int | HepB_cAb_Int | 0.000 | | HepB_eAb_Int | HepB_cAb_Int | 0.000 |
| HepB_eAb_Int | HepB_eAb_Int | 1.000 | | HepB_eAb_Int | HepB_eAb_Int | 1.000 |
| HepB_eAb_Int | HepB_eAg_Int | -1.000 | | HepB_eAb_Int | HepB_eAg_Int | 0.000 |
| HepB_eAb_Int | HepC_Int | 0.000 | | HepB_eAb_Int | HepC_Int | 0.000 |
| HepB_eAb_Int | Schistosoma_int | 0.000 | | HepB_eAb_Int | Schistosoma_int | 0.000 |
| HepB_eAb_Int | Strongyloides_Int | -0.878 | | HepB_eAb_Int | Strongyloides_Int | 0.000 |
| HepB_eAb_Int | Filaria_Int | 0.000 | | HepB_eAb_Int | Filaria_Int | 0.000 |
| HepB_eAg_Int | IL_1_alpha | 0.446 | | HepB_eAg_Int | IL_1_alpha | 0.000 |
| HepB_eAg_Int | IL_1_beta | 0.269 | | HepB_eAg_Int | IL_1_beta | 0.000 |
| HepB_eAg_Int | IL_2 | 0.966 | | HepB_eAg_Int | IL_2 | 0.000 |
| HepB_eAg_Int | IL_4 | 0.860 | | HepB_eAg_Int | IL_4 | 0.000 |
| HepB_eAg_Int | IL_5 | 0.954 | | HepB_eAg_Int | IL_5 | 0.000 |
| HepB_eAg_Int | IL_6 | 0.146 | | HepB_eAg_Int | IL_6 | 0.000 |
| HepB_eAg_Int | IL_8 | -0.198 | | HepB_eAg_Int | IL_8 | 0.000 |
| HepB_eAg_Int | IL_10 | 0.180 | | HepB_eAg_Int | IL_10 | 0.000 |
| HepB_eAg_Int | IL_12p70 | 0.213 | | HepB_eAg_Int | IL_12p70 | 0.000 |
| HepB_eAg_Int | IL_13 | 0.659 | | HepB_eAg_Int | IL_13 | 0.000 |
| HepB_eAg_Int | IL_15 | -0.298 | | HepB_eAg_Int | IL_15 | 0.000 |
| HepB_eAg_Int | IL_17 | 0.212 | | HepB_eAg_Int | IL_17 | 0.000 |

FIG. 21I6-O

| | | | | | | |
|---|---|---|---|---|---|---|
| HepB_eAg_Int | IL_23 | 0.999 | | HepB_eAg_Int | IL_23 | 0.000 |
| HepB_eAg_Int | IFN_gamma | 0.000 | | HepB_eAg_Int | IFN_gamma | 0.000 |
| HepB_eAg_Int | TNF_alpha | -0.102 | | HepB_eAg_Int | TNF_alpha | 0.000 |
| HepB_eAg_Int | TNF_beta | 0.898 | | HepB_eAg_Int | TNF_beta | 0.000 |
| HepB_eAg_Int | Varicella_Int | 0.000 | | HepB_eAg_Int | Varicella_Int | 0.000 |
| HepB_eAg_Int | Measles_OD_DB_Int | 0.200 | | HepB_eAg_Int | Measles_OD_DB_Int | 0.000 |
| HepB_eAg_Int | Measles_Int | -1.000 | | HepB_eAg_Int | Measles_Int | 0.000 |
| HepB_eAg_Int | HepA_Int | 0.200 | | HepB_eAg_Int | HepA_Int | 0.000 |
| HepB_eAg_Int | Tetanus_Int | 0.000 | | HepB_eAg_Int | Tetanus_Int | 0.000 |
| HepB_eAg_Int | Diptheria_Int | 0.000 | | HepB_eAg_Int | Diptheria_Int | 0.000 |
| HepB_eAg_Int | Rubella_Int | -0.200 | | HepB_eAg_Int | Rubella_Int | 0.000 |
| HepB_eAg_Int | CMV_Int | 0.000 | | HepB_eAg_Int | CMV_Int | 0.000 |
| HepB_eAg_Int | HepB_cAb_Int | 0.000 | | HepB_eAg_Int | HepB_cAb_Int | 0.000 |
| HepB_eAg_Int | HepB_eAb_Int | -1.000 | | HepB_eAg_Int | HepB_eAb_Int | 0.000 |
| HepB_eAg_Int | HepB_eAg_Int | 1.000 | | HepB_eAg_Int | HepB_eAg_Int | 1.000 |
| HepB_eAg_Int | HepC_Int | 0.000 | | HepB_eAg_Int | HepC_Int | 0.000 |
| HepB_eAg_Int | Schistosoma_int | 0.000 | | HepB_eAg_Int | Schistosoma_int | 0.000 |
| HepB_eAg_Int | Strongyloides_Int | 0.878 | | HepB_eAg_Int | Strongyloides_Int | 0.000 |
| HepB_eAg_Int | Filaria_Int | 0.000 | | HepB_eAg_Int | Filaria_Int | 0.000 |
| HepC_Int | IL_1_alpha | 0.024 | | HepC_Int | IL_1_alpha | 0.200 |
| HepC_Int | IL_1_beta | 0.024 | | HepC_Int | IL_1_beta | 0.385 |
| HepC_Int | IL_2 | 0.011 | | HepC_Int | IL_2 | 0.088 |
| HepC_Int | IL_4 | -0.041 | | HepC_Int | IL_4 | 0.078 |
| HepC_Int | IL_5 | -0.033 | | HepC_Int | IL_5 | -0.030 |
| HepC_Int | IL_6 | 0.045 | | HepC_Int | IL_6 | 0.006 |
| HepC_Int | IL_8 | 0.098 | | HepC_Int | IL_8 | 0.154 |
| HepC_Int | IL_10 | -0.010 | | HepC_Int | IL_10 | 0.053 |
| HepC_Int | IL_12p70 | 0.022 | | HepC_Int | IL_12p70 | 0.011 |
| HepC_Int | IL_13 | -0.012 | | HepC_Int | IL_13 | -0.033 |
| HepC_Int | IL_15 | 0.055 | | HepC_Int | IL_15 | 0.159 |
| HepC_Int | IL_17 | -0.034 | | HepC_Int | IL_17 | 0.071 |
| HepC_Int | IL_23 | -0.030 | | HepC_Int | IL_23 | -0.016 |
| HepC_Int | IFN_gamma | 0.000 | | HepC_Int | IFN_gamma | 0.000 |
| HepC_Int | TNF_alpha | -0.014 | | HepC_Int | TNF_alpha | 0.320 |
| HepC_Int | TNF_beta | -0.043 | | HepC_Int | TNF_beta | 0.302 |
| HepC_Int | Varicella_Int | 0.021 | | HepC_Int | Varicella_Int | 0.094 |
| HepC_Int | Measles_OD_DB_Int | -0.102 | | HepC_Int | Measles_OD_DB_Int | 0.050 |
| HepC_Int | Measles_Int | 0.038 | | HepC_Int | Measles_Int | 0.038 |
| HepC_Int | HepA_Int | 0.081 | | HepC_Int | HepA_Int | 0.066 |
| HepC_Int | Tetanus_Int | 0.000 | | HepC_Int | Tetanus_Int | 0.000 |
| HepC_Int | Diptheria_Int | 0.000 | | HepC_Int | Diptheria_Int | 0.000 |
| HepC_Int | Rubella_Int | -0.035 | | HepC_Int | Rubella_Int | -0.096 |
| HepC_Int | CMV_Int | 0.027 | | HepC_Int | CMV_Int | 0.000 |
| HepC_Int | HepB_cAb_Int | -0.062 | | HepC_Int | HepB_cAb_Int | -0.091 |
| HepC_Int | HepB_eAb_Int | 0.000 | | HepC_Int | HepB_eAb_Int | 0.000 |
| HepC_Int | HepB_eAg_Int | 0.000 | | HepC_Int | HepB_eAg_Int | 0.000 |
| HepC_Int | HepC_Int | 1.000 | | HepC_Int | HepC_Int | 1.000 |
| HepC_Int | Schistosoma_int | -0.036 | | HepC_Int | Schistosoma_int | -0.048 |
| HepC_Int | Strongyloides_Int | -0.078 | | HepC_Int | Strongyloides_Int | 0.045 |
| HepC_Int | Filaria_Int | -0.041 | | HepC_Int | Filaria_Int | -0.113 |
| Schistosoma_int | IL_1_alpha | -0.079 | | Schistosoma_int | IL_1_alpha | 0.185 |
| Schistosoma_int | IL_1_beta | -0.054 | | Schistosoma_int | IL_1_beta | 0.106 |
| Schistosoma_int | IL_2 | -0.097 | | Schistosoma_int | IL_2 | 0.271 |
| Schistosoma_int | IL_4 | -0.090 | | Schistosoma_int | IL_4 | 0.056 |
| Schistosoma_int | IL_5 | -0.098 | | Schistosoma_int | IL_5 | -0.067 |
| Schistosoma_int | IL_6 | -0.112 | | Schistosoma_int | IL_6 | -0.019 |
| Schistosoma_int | IL_8 | -0.035 | | Schistosoma_int | IL_8 | 0.163 |

FIG. 2I6-P

| | | | | | | |
|---|---|---|---|---|---|---|
| Schistosoma_int | IL_10 | 0.086 | | Schistosoma_int | IL_10 | 0.034 |
| Schistosoma_int | IL_12p70 | 0.042 | | Schistosoma_int | IL_12p70 | 0.025 |
| Schistosoma_int | IL_13 | -0.047 | | Schistosoma_int | IL_13 | -0.053 |
| Schistosoma_int | IL_15 | -0.118 | | Schistosoma_int | IL_15 | 0.145 |
| Schistosoma_int | IL_17 | -0.024 | | Schistosoma_int | IL_17 | 0.238 |
| Schistosoma_int | IL_23 | 0.140 | | Schistosoma_int | IL_23 | -0.039 |
| Schistosoma_int | IFN_gamma | 0.000 | | Schistosoma_int | IFN_gamma | 0.000 |
| Schistosoma_int | TNF_alpha | -0.024 | | Schistosoma_int | TNF_alpha | 0.005 |
| Schistosoma_int | TNF_beta | -0.011 | | Schistosoma_int | TNF_beta | 0.242 |
| Schistosoma_int | Varicella_Int | 0.070 | | Schistosoma_int | Varicella_Int | -0.049 |
| Schistosoma_int | Measles_OD_DB_Int | -0.075 | | Schistosoma_int | Measles_OD_DB_Int | 0.054 |
| Schistosoma_int | Measles_Int | 0.069 | | Schistosoma_int | Measles_Int | 0.088 |
| Schistosoma_int | HepA_Int | 0.191 | | Schistosoma_int | HepA_Int | 0.010 |
| Schistosoma_int | Tetanus_Int | 0.000 | | Schistosoma_int | Tetanus_Int | 0.000 |
| Schistosoma_int | Diptheria_Int | 0.000 | | Schistosoma_int | Diptheria_Int | 0.000 |
| Schistosoma_int | Rubella_Int | 0.218 | | Schistosoma_int | Rubella_Int | -0.014 |
| Schistosoma_int | CMV_Int | 0.089 | | Schistosoma_int | CMV_Int | 0.000 |
| Schistosoma_int | HepB_cAb_Int | -0.120 | | Schistosoma_int | HepB_cAb_Int | -0.150 |
| Schistosoma_int | HepB_eAb_Int | 0.000 | | Schistosoma_int | HepB_eAb_Int | 0.000 |
| Schistosoma_int | HepB_eAg_Int | 0.000 | | Schistosoma_int | HepB_eAg_Int | 0.000 |
| Schistosoma_int | HepC_Int | -0.036 | | Schistosoma_int | HepC_Int | -0.048 |
| Schistosoma_int | Schistosoma_int | 1.000 | | Schistosoma_int | Schistosoma_int | 1.000 |
| Schistosoma_int | Strongyloides_Int | 0.105 | | Schistosoma_int | Strongyloides_Int | 0.010 |
| Schistosoma_int | Filaria_Int | 0.389 | | Schistosoma_int | Filaria_Int | -0.103 |
| Strongyloides_Int | IL_1_alpha | 0.014 | | Strongyloides_Int | IL_1_alpha | 0.287 |
| Strongyloides_Int | IL_1_beta | -0.002 | | Strongyloides_Int | IL_1_beta | 0.276 |
| Strongyloides_Int | IL_2 | 0.047 | | Strongyloides_Int | IL_2 | 0.140 |
| Strongyloides_Int | IL_4 | 0.103 | | Strongyloides_Int | IL_4 | 0.156 |
| Strongyloides_Int | IL_5 | 0.089 | | Strongyloides_Int | IL_5 | 0.134 |
| Strongyloides_Int | IL_6 | -0.132 | | Strongyloides_Int | IL_6 | 0.170 |
| Strongyloides_Int | IL_8 | -0.056 | | Strongyloides_Int | IL_8 | 0.300 |
| Strongyloides_Int | IL_10 | 0.065 | | Strongyloides_Int | IL_10 | 0.233 |
| Strongyloides_Int | IL_12p70 | 0.278 | | Strongyloides_Int | IL_12p70 | 0.110 |
| Strongyloides_Int | IL_13 | 0.166 | | Strongyloides_Int | IL_13 | 0.132 |
| Strongyloides_Int | IL_15 | -0.116 | | Strongyloides_Int | IL_15 | 0.187 |
| Strongyloides_Int | IL_17 | 0.216 | | Strongyloides_Int | IL_17 | 0.191 |
| Strongyloides_Int | IL_23 | 0.158 | | Strongyloides_Int | IL_23 | 0.007 |
| Strongyloides_Int | IFN_gamma | 0.000 | | Strongyloides_Int | IFN_gamma | 0.000 |
| Strongyloides_Int | TNF_alpha | 0.026 | | Strongyloides_Int | TNF_alpha | 0.341 |
| Strongyloides_Int | TNF_beta | 0.227 | | Strongyloides_Int | TNF_beta | 0.173 |
| Strongyloides_Int | Varicella_Int | 0.016 | | Strongyloides_Int | Varicella_Int | -0.169 |
| Strongyloides_Int | Measles_OD_DB_Int | 0.317 | | Strongyloides_Int | Measles_OD_DB_Int | 0.043 |
| Strongyloides_Int | Measles_Int | -0.053 | | Strongyloides_Int | Measles_Int | 0.146 |
| Strongyloides_Int | HepA_Int | 0.044 | | Strongyloides_Int | HepA_Int | -0.077 |
| Strongyloides_Int | Tetanus_Int | 0.000 | | Strongyloides_Int | Tetanus_Int | 0.000 |
| Strongyloides_Int | Diptheria_Int | 0.000 | | Strongyloides_Int | Diptheria_Int | 0.000 |
| Strongyloides_Int | Rubella_Int | -0.015 | | Strongyloides_Int | Rubella_Int | 0.050 |
| Strongyloides_Int | CMV_Int | 0.042 | | Strongyloides_Int | CMV_Int | 0.000 |
| Strongyloides_Int | HepB_cAb_Int | -0.037 | | Strongyloides_Int | HepB_cAb_Int | -0.037 |
| Strongyloides_Int | HepB_eAb_Int | -0.878 | | Strongyloides_Int | HepB_eAb_Int | 0.000 |
| Strongyloides_Int | HepB_eAg_Int | 0.878 | | Strongyloides_Int | HepB_eAg_Int | 0.000 |
| Strongyloides_Int | HepC_Int | -0.078 | | Strongyloides_Int | HepC_Int | 0.045 |
| Strongyloides_Int | Schistosoma_int | 0.105 | | Strongyloides_Int | Schistosoma_int | 0.010 |
| Strongyloides_Int | Strongyloides_Int | 1.000 | | Strongyloides_Int | Strongyloides_Int | 1.000 |
| Strongyloides_Int | Filaria_Int | 0.120 | | Strongyloides_Int | Filaria_Int | 0.302 |
| Filaria_Int | IL_1_alpha | 0.017 | | Filaria_Int | IL_1_alpha | 0.021 |
| Filaria_Int | IL_1_beta | -0.045 | | Filaria_Int | IL_1_beta | -0.014 |

FIG. 2I6-Q

| | | | | | | |
|---|---|---|---|---|---|---|
| Filaria_Int | IL_2 | -0.076 | | Filaria_Int | IL_2 | -0.037 |
| Filaria_Int | IL_4 | -0.071 | | Filaria_Int | IL_4 | -0.083 |
| Filaria_Int | IL_5 | -0.067 | | Filaria_Int | IL_5 | -0.008 |
| Filaria_Int | IL_6 | -0.101 | | Filaria_Int | IL_6 | 0.104 |
| Filaria_Int | IL_8 | -0.067 | | Filaria_Int | IL_8 | 0.033 |
| Filaria_Int | IL_10 | -0.025 | | Filaria_Int | IL_10 | 0.174 |
| Filaria_Int | IL_12p70 | -0.024 | | Filaria_Int | IL_12p70 | -0.066 |
| Filaria_Int | IL_13 | -0.069 | | Filaria_Int | IL_13 | 0.115 |
| Filaria_Int | IL_15 | -0.148 | | Filaria_Int | IL_15 | -0.019 |
| Filaria_Int | IL_17 | -0.043 | | Filaria_Int | IL_17 | -0.052 |
| Filaria_Int | IL_23 | -0.109 | | Filaria_Int | IL_23 | -0.079 |
| Filaria_Int | IFN_gamma | 0.000 | | Filaria_Int | IFN_gamma | 0.000 |
| Filaria_Int | TNF_alpha | -0.024 | | Filaria_Int | TNF_alpha | 0.143 |
| Filaria_Int | TNF_beta | -0.035 | | Filaria_Int | TNF_beta | -0.081 |
| Filaria_Int | Varicella_Int | -0.047 | | Filaria_Int | Varicella_Int | -0.159 |
| Filaria_Int | Measles_OD_DB_Int | 0.148 | | Filaria_Int | Measles_OD_DB_Int | -0.095 |
| Filaria_Int | Measles_Int | 0.138 | | Filaria_Int | Measles_Int | 0.066 |
| Filaria_Int | HepA_Int | 0.103 | | Filaria_Int | HepA_Int | -0.090 |
| Filaria_Int | Tetanus_Int | 0.000 | | Filaria_Int | Tetanus_Int | 0.000 |
| Filaria_Int | Diptheria_Int | 0.000 | | Filaria_Int | Diptheria_Int | 0.000 |
| Filaria_Int | Rubella_Int | 0.014 | | Filaria_Int | Rubella_Int | -0.167 |
| Filaria_Int | CMV_Int | 0.093 | | Filaria_Int | CMV_Int | 0.000 |
| Filaria_Int | HepB_cAb_Int | -0.071 | | Filaria_Int | HepB_cAb_Int | 0.026 |
| Filaria_Int | HepB_eAb_Int | 0.000 | | Filaria_Int | HepB_eAb_Int | 0.000 |
| Filaria_Int | HepB_eAg_Int | 0.000 | | Filaria_Int | HepB_eAg_Int | 0.000 |
| Filaria_Int | HepC_Int | -0.041 | | Filaria_Int | HepC_Int | -0.113 |
| Filaria_Int | Schistosoma_int | 0.389 | | Filaria_Int | Schistosoma_int | -0.103 |
| Filaria_Int | Strongyloides_Int | 0.120 | | Filaria_Int | Strongyloides_Int | 0.302 |
| Filaria_Int | Filaria_Int | 1.000 | | Filaria_Int | Filaria_Int | 1.000 |

FIG. 2I6-R

| 5.99% - Region_of_Origin=4, Sex=Male, IFN_gamma=0-7.5 ||| 4.26% - Region_of_Origin=6, Sex=Male, IFN_gamma=0-7.5 |||
|---|---|---|---|---|---|
| Property 1 | Property 2 | Corr. Coefficient | Property 1 | Property 2 | Corr. Coefficient |
| IL_1_alpha | IL_1_alpha | 1.000 | IL_1_alpha | IL_1_alpha | 1.000 |
| IL_1_alpha | IL_1_beta | 0.380 | IL_1_alpha | IL_1_beta | 0.383 |
| IL_1_alpha | IL_2 | 0.273 | IL_1_alpha | IL_2 | 0.414 |
| IL_1_alpha | IL_4 | 0.458 | IL_1_alpha | IL_4 | 0.313 |
| IL_1_alpha | IL_5 | 0.388 | IL_1_alpha | IL_5 | 0.582 |
| IL_1_alpha | IL_6 | 0.242 | IL_1_alpha | IL_6 | 0.387 |
| IL_1_alpha | IL_8 | 0.049 | IL_1_alpha | IL_8 | 0.121 |
| IL_1_alpha | IL_10 | 0.232 | IL_1_alpha | IL_10 | 0.378 |
| IL_1_alpha | IL_12p70 | 0.511 | IL_1_alpha | IL_12p70 | 0.553 |
| IL_1_alpha | IL_13 | 0.250 | IL_1_alpha | IL_13 | 0.433 |
| IL_1_alpha | IL_15 | 0.410 | IL_1_alpha | IL_15 | 0.372 |
| IL_1_alpha | IL_17 | 0.199 | IL_1_alpha | IL_17 | 0.301 |
| IL_1_alpha | IL_23 | 0.182 | IL_1_alpha | IL_23 | 0.106 |
| IL_1_alpha | IFN_gamma | 0.000 | IL_1_alpha | IFN_gamma | 0.000 |
| IL_1_alpha | TNF_alpha | 0.425 | IL_1_alpha | TNF_alpha | 0.471 |
| IL_1_alpha | TNF_beta | 0.470 | IL_1_alpha | TNF_beta | 0.456 |
| IL_1_alpha | Varicella_Int | 0.047 | IL_1_alpha | Varicella_Int | 0.028 |
| IL_1_alpha | Measles_OD_DB_Int | 0.036 | IL_1_alpha | Measles_OD_DB_Int | -0.091 |
| IL_1_alpha | Measles_Int | -0.015 | IL_1_alpha | Measles_Int | -0.545 |
| IL_1_alpha | HepA_Int | 0.151 | IL_1_alpha | HepA_Int | 0.036 |
| IL_1_alpha | Tetanus_Int | 0.000 | IL_1_alpha | Tetanus_Int | 0.000 |
| IL_1_alpha | Diptheria_Int | 0.000 | IL_1_alpha | Diptheria_Int | 0.000 |
| IL_1_alpha | Rubella_Int | -0.204 | IL_1_alpha | Rubella_Int | 0.210 |
| IL_1_alpha | CMV_Int | 0.238 | IL_1_alpha | CMV_Int | 0.052 |

FIG. 21I7-A

| | | | | | | |
|---|---|---|---|---|---|---|
| IL_1_alpha | HepB_cAb_Int | 0.217 | | IL_1_alpha | HepB_cAb_Int | 0.042 |
| IL_1_alpha | HepB_eAb_Int | 0.000 | | IL_1_alpha | HepB_eAb_Int | 0.340 |
| IL_1_alpha | HepB_eAg_Int | 0.000 | | IL_1_alpha | HepB_eAg_Int | 0.000 |
| IL_1_alpha | HepC_Int | 0.193 | | IL_1_alpha | HepC_Int | 0.000 |
| IL_1_alpha | Schistosoma_int | 0.033 | | IL_1_alpha | Schistosoma_int | 0.012 |
| IL_1_alpha | Strongyloides_Int | 0.170 | | IL_1_alpha | Strongyloides_Int | 0.233 |
| IL_1_alpha | Filaria_Int | 0.166 | | IL_1_alpha | Filaria_Int | 0.031 |
| IL_1_beta | IL_1_alpha | 0.380 | | IL_1_beta | IL_1_alpha | 0.383 |
| IL_1_beta | IL_1_beta | 1.000 | | IL_1_beta | IL_1_beta | 1.000 |
| IL_1_beta | IL_2 | 0.524 | | IL_1_beta | IL_2 | 0.634 |
| IL_1_beta | IL_4 | 0.558 | | IL_1_beta | IL_4 | 0.603 |
| IL_1_beta | IL_5 | 0.478 | | IL_1_beta | IL_5 | 0.610 |
| IL_1_beta | IL_6 | 0.292 | | IL_1_beta | IL_6 | 0.535 |
| IL_1_beta | IL_8 | 0.016 | | IL_1_beta | IL_8 | 0.193 |
| IL_1_beta | IL_10 | 0.669 | | IL_1_beta | IL_10 | 0.831 |
| IL_1_beta | IL_12p70 | 0.379 | | IL_1_beta | IL_12p70 | 0.705 |
| IL_1_beta | IL_13 | 0.603 | | IL_1_beta | IL_13 | 0.724 |
| IL_1_beta | IL_15 | 0.339 | | IL_1_beta | IL_15 | 0.387 |
| IL_1_beta | IL_17 | 0.542 | | IL_1_beta | IL_17 | 0.659 |
| IL_1_beta | IL_23 | 0.017 | | IL_1_beta | IL_23 | 0.048 |
| IL_1_beta | IFN_gamma | 0.000 | | IL_1_beta | IFN_gamma | 0.000 |
| IL_1_beta | TNF_alpha | 0.595 | | IL_1_beta | TNF_alpha | 0.665 |
| IL_1_beta | TNF_beta | 0.523 | | IL_1_beta | TNF_beta | 0.806 |
| IL_1_beta | Varicella_Int | -0.085 | | IL_1_beta | Varicella_Int | 0.123 |
| IL_1_beta | Measles_OD_DB_Int | -0.095 | | IL_1_beta | Measles_OD_DB_Int | 0.052 |
| IL_1_beta | Measles_Int | -0.011 | | IL_1_beta | Measles_Int | -0.152 |
| IL_1_beta | HepA_Int | -0.080 | | IL_1_beta | HepA_Int | 0.029 |
| IL_1_beta | Tetanus_Int | 0.000 | | IL_1_beta | Tetanus_Int | 0.000 |
| IL_1_beta | Diptheria_Int | 0.000 | | IL_1_beta | Diptheria_Int | 0.000 |
| IL_1_beta | Rubella_Int | 0.024 | | IL_1_beta | Rubella_Int | -0.102 |
| IL_1_beta | CMV_Int | 0.116 | | IL_1_beta | CMV_Int | -0.216 |
| IL_1_beta | HepB_cAb_Int | 0.135 | | IL_1_beta | HepB_cAb_Int | 0.014 |
| IL_1_beta | HepB_eAb_Int | 0.000 | | IL_1_beta | HepB_eAb_Int | 0.372 |
| IL_1_beta | HepB_eAg_Int | 0.000 | | IL_1_beta | HepB_eAg_Int | 0.000 |
| IL_1_beta | HepC_Int | -0.029 | | IL_1_beta | HepC_Int | 0.000 |
| IL_1_beta | Schistosoma_int | 0.034 | | IL_1_beta | Schistosoma_int | 0.212 |
| IL_1_beta | Strongyloides_Int | -0.131 | | IL_1_beta | Strongyloides_Int | 0.143 |
| IL_1_beta | Filaria_Int | 0.061 | | IL_1_beta | Filaria_Int | 0.392 |
| IL_2 | IL_1_alpha | 0.273 | | IL_2 | IL_1_alpha | 0.414 |
| IL_2 | IL_1_beta | 0.524 | | IL_2 | IL_1_beta | 0.634 |
| IL_2 | IL_2 | 1.000 | | IL_2 | IL_2 | 1.000 |
| IL_2 | IL_4 | 0.272 | | IL_2 | IL_4 | 0.443 |
| IL_2 | IL_5 | 0.366 | | IL_2 | IL_5 | 0.400 |
| IL_2 | IL_6 | 0.440 | | IL_2 | IL_6 | 0.318 |
| IL_2 | IL_8 | 0.174 | | IL_2 | IL_8 | 0.181 |
| IL_2 | IL_10 | 0.584 | | IL_2 | IL_10 | 0.635 |
| IL_2 | IL_12p70 | 0.330 | | IL_2 | IL_12p70 | 0.586 |
| IL_2 | IL_13 | 0.558 | | IL_2 | IL_13 | 0.426 |
| IL_2 | IL_15 | 0.316 | | IL_2 | IL_15 | 0.259 |
| IL_2 | IL_17 | 0.692 | | IL_2 | IL_17 | 0.613 |
| IL_2 | IL_23 | 0.060 | | IL_2 | IL_23 | 0.150 |
| IL_2 | IFN_gamma | 0.000 | | IL_2 | IFN_gamma | 0.000 |
| IL_2 | TNF_alpha | 0.387 | | IL_2 | TNF_alpha | 0.687 |
| IL_2 | TNF_beta | 0.524 | | IL_2 | TNF_beta | 0.719 |
| IL_2 | Varicella_Int | 0.026 | | IL_2 | Varicella_Int | 0.099 |
| IL_2 | Measles_OD_DB_Int | 0.066 | | IL_2 | Measles_OD_DB_Int | 0.129 |
| IL_2 | Measles_Int | 0.053 | | IL_2 | Measles_Int | 0.013 |

FIG. 2I7-B

| | | | | | | |
|---|---|---|---|---|---|---|
| IL_2 | HepA_Int | 0.149 | | IL_2 | HepA_Int | -0.087 |
| IL_2 | Tetanus_Int | 0.000 | | IL_2 | Tetanus_Int | 0.000 |
| IL_2 | Diptheria_Int | 0.000 | | IL_2 | Diptheria_Int | 0.000 |
| IL_2 | Rubella_Int | -0.093 | | IL_2 | Rubella_Int | -0.102 |
| IL_2 | CMV_Int | 0.077 | | IL_2 | CMV_Int | -0.105 |
| IL_2 | HepB_cAb_Int | 0.006 | | IL_2 | HepB_cAb_Int | -0.125 |
| IL_2 | HepB_eAb_Int | 0.000 | | IL_2 | HepB_eAb_Int | -1.000 |
| IL_2 | HepB_eAg_Int | 0.000 | | IL_2 | HepB_eAg_Int | 0.000 |
| IL_2 | HepC_Int | 0.042 | | IL_2 | HepC_Int | 0.000 |
| IL_2 | Schistosoma_int | -0.086 | | IL_2 | Schistosoma_int | 0.214 |
| IL_2 | Strongyloides_Int | 0.027 | | IL_2 | Strongyloides_Int | 0.254 |
| IL_2 | Filaria_Int | 0.286 | | IL_2 | Filaria_Int | 0.317 |
| IL_4 | IL_1_alpha | 0.458 | | IL_4 | IL_1_alpha | 0.313 |
| IL_4 | IL_1_beta | 0.558 | | IL_4 | IL_1_beta | 0.603 |
| IL_4 | IL_2 | 0.272 | | IL_4 | IL_2 | 0.443 |
| IL_4 | IL_4 | 1.000 | | IL_4 | IL_4 | 1.000 |
| IL_4 | IL_5 | 0.633 | | IL_4 | IL_5 | 0.495 |
| IL_4 | IL_6 | 0.201 | | IL_4 | IL_6 | 0.509 |
| IL_4 | IL_8 | -0.015 | | IL_4 | IL_8 | 0.220 |
| IL_4 | IL_10 | 0.508 | | IL_4 | IL_10 | 0.613 |
| IL_4 | IL_12p70 | 0.521 | | IL_4 | IL_12p70 | 0.491 |
| IL_4 | IL_13 | 0.518 | | IL_4 | IL_13 | 0.607 |
| IL_4 | IL_15 | 0.485 | | IL_4 | IL_15 | 0.540 |
| IL_4 | IL_17 | 0.479 | | IL_4 | IL_17 | 0.593 |
| IL_4 | IL_23 | 0.140 | | IL_4 | IL_23 | 0.095 |
| IL_4 | IFN_gamma | 0.000 | | IL_4 | IFN_gamma | 0.000 |
| IL_4 | TNF_alpha | 0.381 | | IL_4 | TNF_alpha | 0.389 |
| IL_4 | TNF_beta | 0.445 | | IL_4 | TNF_beta | 0.570 |
| IL_4 | Varicella_Int | -0.440 | | IL_4 | Varicella_Int | 0.097 |
| IL_4 | Measles_OD_DB_Int | -0.053 | | IL_4 | Measles_OD_DB_Int | -0.020 |
| IL_4 | Measles_Int | -0.151 | | IL_4 | Measles_Int | 0.042 |
| IL_4 | HepA_Int | -0.017 | | IL_4 | HepA_Int | 0.122 |
| IL_4 | Tetanus_Int | 0.000 | | IL_4 | Tetanus_Int | 0.000 |
| IL_4 | Diptheria_Int | 0.000 | | IL_4 | Diptheria_Int | 0.000 |
| IL_4 | Rubella_Int | -0.091 | | IL_4 | Rubella_Int | 0.089 |
| IL_4 | CMV_Int | 0.217 | | IL_4 | CMV_Int | -0.029 |
| IL_4 | HepB_cAb_Int | 0.021 | | IL_4 | HepB_cAb_Int | 0.094 |
| IL_4 | HepB_eAb_Int | 0.000 | | IL_4 | HepB_eAb_Int | 0.402 |
| IL_4 | HepB_eAg_Int | 0.000 | | IL_4 | HepB_eAg_Int | 0.000 |
| IL_4 | HepC_Int | 0.256 | | IL_4 | HepC_Int | 0.000 |
| IL_4 | Schistosoma_int | 0.095 | | IL_4 | Schistosoma_int | 0.223 |
| IL_4 | Strongyloides_Int | 0.036 | | IL_4 | Strongyloides_Int | -0.025 |
| IL_4 | Filaria_Int | -0.087 | | IL_4 | Filaria_Int | 0.250 |
| IL_5 | IL_1_alpha | 0.388 | | IL_5 | IL_1_alpha | 0.582 |
| IL_5 | IL_1_beta | 0.478 | | IL_5 | IL_1_beta | 0.610 |
| IL_5 | IL_2 | 0.366 | | IL_5 | IL_2 | 0.400 |
| IL_5 | IL_4 | 0.633 | | IL_5 | IL_4 | 0.495 |
| IL_5 | IL_5 | 1.000 | | IL_5 | IL_5 | 1.000 |
| IL_5 | IL_6 | 0.206 | | IL_5 | IL_6 | 0.449 |
| IL_5 | IL_8 | 0.016 | | IL_5 | IL_8 | 0.203 |
| IL_5 | IL_10 | 0.579 | | IL_5 | IL_10 | 0.708 |
| IL_5 | IL_12p70 | 0.527 | | IL_5 | IL_12p70 | 0.599 |
| IL_5 | IL_13 | 0.443 | | IL_5 | IL_13 | 0.526 |
| IL_5 | IL_15 | 0.556 | | IL_5 | IL_15 | 0.417 |
| IL_5 | IL_17 | 0.576 | | IL_5 | IL_17 | 0.466 |
| IL_5 | IL_23 | 0.147 | | IL_5 | IL_23 | 0.022 |
| IL_5 | IFN_gamma | 0.000 | | IL_5 | IFN_gamma | 0.000 |

FIG. 2117-C

| IL_5 | TNF_alpha | 0.420 | IL_5 | TNF_alpha | 0.562 |
|---|---|---|---|---|---|
| IL_5 | TNF_beta | 0.477 | IL_5 | TNF_beta | 0.547 |
| IL_5 | Varicella_Int | -0.104 | IL_5 | Varicella_Int | 0.001 |
| IL_5 | Measles_OD_DB_Int | 0.049 | IL_5 | Measles_OD_DB_Int | -0.211 |
| IL_5 | Measles_Int | -0.184 | IL_5 | Measles_Int | -0.108 |
| IL_5 | HepA_Int | 0.055 | IL_5 | HepA_Int | -0.048 |
| IL_5 | Tetanus_Int | 0.000 | IL_5 | Tetanus_Int | 0.000 |
| IL_5 | Diptheria_Int | 0.000 | IL_5 | Diptheria_Int | 0.000 |
| IL_5 | Rubella_Int | -0.049 | IL_5 | Rubella_Int | 0.206 |
| IL_5 | CMV_Int | 0.153 | IL_5 | CMV_Int | -0.036 |
| IL_5 | HepB_cAb_Int | -0.036 | IL_5 | HepB_cAb_Int | 0.012 |
| IL_5 | HepB_eAb_Int | 0.000 | IL_5 | HepB_eAb_Int | 0.206 |
| IL_5 | HepB_eAg_Int | 0.000 | IL_5 | HepB_eAg_Int | 0.000 |
| IL_5 | HepC_Int | 0.145 | IL_5 | HepC_Int | 0.000 |
| IL_5 | Schistosoma_int | 0.053 | IL_5 | Schistosoma_int | 0.178 |
| IL_5 | Strongyloides_Int | -0.045 | IL_5 | Strongyloides_Int | 0.108 |
| IL_5 | Filaria_Int | -0.050 | IL_5 | Filaria_Int | 0.029 |
| IL_6 | IL_1_alpha | 0.242 | IL_6 | IL_1_alpha | 0.387 |
| IL_6 | IL_1_beta | 0.292 | IL_6 | IL_1_beta | 0.535 |
| IL_6 | IL_2 | 0.440 | IL_6 | IL_2 | 0.318 |
| IL_6 | IL_4 | 0.201 | IL_6 | IL_4 | 0.509 |
| IL_6 | IL_5 | 0.206 | IL_6 | IL_5 | 0.449 |
| IL_6 | IL_6 | 1.000 | IL_6 | IL_6 | 1.000 |
| IL_6 | IL_8 | 0.603 | IL_6 | IL_8 | 0.213 |
| IL_6 | IL_10 | 0.375 | IL_6 | IL_10 | 0.464 |
| IL_6 | IL_12p70 | 0.177 | IL_6 | IL_12p70 | 0.513 |
| IL_6 | IL_13 | 0.377 | IL_6 | IL_13 | 0.677 |
| IL_6 | IL_15 | 0.333 | IL_6 | IL_15 | 0.304 |
| IL_6 | IL_17 | 0.268 | IL_6 | IL_17 | 0.623 |
| IL_6 | IL_23 | -0.024 | IL_6 | IL_23 | 0.035 |
| IL_6 | IFN_gamma | 0.000 | IL_6 | IFN_gamma | 0.000 |
| IL_6 | TNF_alpha | 0.229 | IL_6 | TNF_alpha | 0.320 |
| IL_6 | TNF_beta | 0.250 | IL_6 | TNF_beta | 0.542 |
| IL_6 | Varicella_Int | 0.044 | IL_6 | Varicella_Int | 0.107 |
| IL_6 | Measles_OD_DB_Int | -0.125 | IL_6 | Measles_OD_DB_Int | 0.099 |
| IL_6 | Measles_Int | -0.122 | IL_6 | Measles_Int | -0.093 |
| IL_6 | HepA_Int | -0.069 | IL_6 | HepA_Int | 0.035 |
| IL_6 | Tetanus_Int | 0.000 | IL_6 | Tetanus_Int | 0.000 |
| IL_6 | Diptheria_Int | 0.000 | IL_6 | Diptheria_Int | 0.000 |
| IL_6 | Rubella_Int | -0.101 | IL_6 | Rubella_Int | 0.167 |
| IL_6 | CMV_Int | 0.130 | IL_6 | CMV_Int | -0.078 |
| IL_6 | HepB_cAb_Int | 0.124 | IL_6 | HepB_cAb_Int | 0.043 |
| IL_6 | HepB_eAb_Int | 0.000 | IL_6 | HepB_eAb_Int | 0.488 |
| IL_6 | HepB_eAg_Int | 0.000 | IL_6 | HepB_eAg_Int | 0.000 |
| IL_6 | HepC_Int | 0.015 | IL_6 | HepC_Int | 0.000 |
| IL_6 | Schistosoma_int | -0.060 | IL_6 | Schistosoma_int | 0.014 |
| IL_6 | Strongyloides_Int | 0.055 | IL_6 | Strongyloides_Int | 0.123 |
| IL_6 | Filaria_Int | 0.095 | IL_6 | Filaria_Int | 0.101 |
| IL_8 | IL_1_alpha | 0.049 | IL_8 | IL_1_alpha | 0.121 |
| IL_8 | IL_1_beta | 0.016 | IL_8 | IL_1_beta | 0.193 |
| IL_8 | IL_2 | 0.174 | IL_8 | IL_2 | 0.181 |
| IL_8 | IL_4 | -0.015 | IL_8 | IL_4 | 0.220 |
| IL_8 | IL_5 | 0.016 | IL_8 | IL_5 | 0.203 |
| IL_8 | IL_6 | 0.603 | IL_8 | IL_6 | 0.213 |
| IL_8 | IL_8 | 1.000 | IL_8 | IL_8 | 1.000 |
| IL_8 | IL_10 | 0.043 | IL_8 | IL_10 | 0.157 |
| IL_8 | IL_12p70 | 0.069 | IL_8 | IL_12p70 | 0.234 |

FIG. 2117-D

| | | | | | | |
|---|---|---|---|---|---|---|
| IL_8 | IL_13 | 0.010 | | IL_8 | IL_13 | 0.154 |
| IL_8 | IL_15 | 0.062 | | IL_8 | IL_15 | 0.491 |
| IL_8 | IL_17 | 0.016 | | IL_8 | IL_17 | 0.052 |
| IL_8 | IL_23 | 0.009 | | IL_8 | IL_23 | -0.051 |
| IL_8 | IFN_gamma | 0.000 | | IL_8 | IFN_gamma | 0.000 |
| IL_8 | TNF_alpha | -0.017 | | IL_8 | TNF_alpha | 0.143 |
| IL_8 | TNF_beta | 0.040 | | IL_8 | TNF_beta | 0.229 |
| IL_8 | Varicella_Int | 0.056 | | IL_8 | Varicella_Int | -0.160 |
| IL_8 | Measles_OD_DB_Int | 0.078 | | IL_8 | Measles_OD_DB_Int | 0.091 |
| IL_8 | Measles_Int | 0.020 | | IL_8 | Measles_Int | -0.159 |
| IL_8 | HepA_Int | 0.062 | | IL_8 | HepA_Int | 0.124 |
| IL_8 | Tetanus_Int | 0.000 | | IL_8 | Tetanus_Int | 0.000 |
| IL_8 | Diptheria_Int | 0.000 | | IL_8 | Diptheria_Int | 0.000 |
| IL_8 | Rubella_Int | -0.075 | | IL_8 | Rubella_Int | -0.047 |
| IL_8 | CMV_Int | 0.077 | | IL_8 | CMV_Int | -0.361 |
| IL_8 | HepB_cAb_Int | 0.045 | | IL_8 | HepB_cAb_Int | -0.159 |
| IL_8 | HepB_eAb_Int | 0.000 | | IL_8 | HepB_eAb_Int | 0.239 |
| IL_8 | HepB_eAg_Int | 0.000 | | IL_8 | HepB_eAg_Int | 0.000 |
| IL_8 | HepC_Int | -0.037 | | IL_8 | HepC_Int | 0.000 |
| IL_8 | Schistosoma_int | -0.032 | | IL_8 | Schistosoma_int | 0.226 |
| IL_8 | Strongyloides_Int | 0.167 | | IL_8 | Strongyloides_Int | 0.198 |
| IL_8 | Filaria_Int | 0.115 | | IL_8 | Filaria_Int | 0.087 |
| IL_10 | IL_1_alpha | 0.232 | | IL_10 | IL_1_alpha | 0.378 |
| IL_10 | IL_1_beta | 0.669 | | IL_10 | IL_1_beta | 0.831 |
| IL_10 | IL_2 | 0.584 | | IL_10 | IL_2 | 0.635 |
| IL_10 | IL_4 | 0.508 | | IL_10 | IL_4 | 0.613 |
| IL_10 | IL_5 | 0.579 | | IL_10 | IL_5 | 0.708 |
| IL_10 | IL_6 | 0.375 | | IL_10 | IL_6 | 0.464 |
| IL_10 | IL_8 | 0.043 | | IL_10 | IL_8 | 0.157 |
| IL_10 | IL_10 | 1.000 | | IL_10 | IL_10 | 1.000 |
| IL_10 | IL_12p70 | 0.435 | | IL_10 | IL_12p70 | 0.709 |
| IL_10 | IL_13 | 0.689 | | IL_10 | IL_13 | 0.625 |
| IL_10 | IL_15 | 0.412 | | IL_10 | IL_15 | 0.393 |
| IL_10 | IL_17 | 0.763 | | IL_10 | IL_17 | 0.727 |
| IL_10 | IL_23 | -0.010 | | IL_10 | IL_23 | 0.119 |
| IL_10 | IFN_gamma | 0.000 | | IL_10 | IFN_gamma | 0.000 |
| IL_10 | TNF_alpha | 0.343 | | IL_10 | TNF_alpha | 0.655 |
| IL_10 | TNF_beta | 0.432 | | IL_10 | TNF_beta | 0.726 |
| IL_10 | Varicella_Int | -0.078 | | IL_10 | Varicella_Int | 0.160 |
| IL_10 | Measles_OD_DB_Int | -0.080 | | IL_10 | Measles_OD_DB_Int | 0.024 |
| IL_10 | Measles_Int | -0.138 | | IL_10 | Measles_Int | -0.030 |
| IL_10 | HepA_Int | -0.034 | | IL_10 | HepA_Int | -0.037 |
| IL_10 | Tetanus_Int | 0.000 | | IL_10 | Tetanus_Int | 0.000 |
| IL_10 | Diptheria_Int | 0.000 | | IL_10 | Diptheria_Int | 0.000 |
| IL_10 | Rubella_Int | 0.002 | | IL_10 | Rubella_Int | -0.100 |
| IL_10 | CMV_Int | 0.173 | | IL_10 | CMV_Int | -0.140 |
| IL_10 | HepB_cAb_Int | -0.038 | | IL_10 | HepB_cAb_Int | 0.067 |
| IL_10 | HepB_eAb_Int | 0.000 | | IL_10 | HepB_eAb_Int | 0.440 |
| IL_10 | HepB_eAg_Int | 0.000 | | IL_10 | HepB_eAg_Int | 0.000 |
| IL_10 | HepC_Int | 0.157 | | IL_10 | HepC_Int | 0.000 |
| IL_10 | Schistosoma_int | 0.041 | | IL_10 | Schistosoma_int | 0.194 |
| IL_10 | Strongyloides_Int | -0.062 | | IL_10 | Strongyloides_Int | 0.150 |
| IL_10 | Filaria_Int | 0.196 | | IL_10 | Filaria_Int | 0.260 |
| IL_12p70 | IL_1_alpha | 0.511 | | IL_12p70 | IL_1_alpha | 0.553 |
| IL_12p70 | IL_1_beta | 0.379 | | IL_12p70 | IL_1_beta | 0.705 |
| IL_12p70 | IL_2 | 0.330 | | IL_12p70 | IL_2 | 0.586 |
| IL_12p70 | IL_4 | 0.521 | | IL_12p70 | IL_4 | 0.491 |

FIG. 2117-E

| IL_12p70 | IL_5 | 0.527 | IL_12p70 | IL_5 | 0.599 |
|---|---|---|---|---|---|
| IL_12p70 | IL_6 | 0.177 | IL_12p70 | IL_6 | 0.513 |
| IL_12p70 | IL_8 | 0.069 | IL_12p70 | IL_8 | 0.234 |
| IL_12p70 | IL_10 | 0.435 | IL_12p70 | IL_10 | 0.709 |
| IL_12p70 | IL_12p70 | 1.000 | IL_12p70 | IL_12p70 | 1.000 |
| IL_12p70 | IL_13 | 0.433 | IL_12p70 | IL_13 | 0.570 |
| IL_12p70 | IL_15 | 0.413 | IL_12p70 | IL_15 | 0.487 |
| IL_12p70 | IL_17 | 0.442 | IL_12p70 | IL_17 | 0.648 |
| IL_12p70 | IL_23 | 0.611 | IL_12p70 | IL_23 | 0.249 |
| IL_12p70 | IFN_gamma | 0.000 | IL_12p70 | IFN_gamma | 0.000 |
| IL_12p70 | TNF_alpha | 0.356 | IL_12p70 | TNF_alpha | 0.584 |
| IL_12p70 | TNF_beta | 0.416 | IL_12p70 | TNF_beta | 0.655 |
| IL_12p70 | Varicella_Int | 0.009 | IL_12p70 | Varicella_Int | 0.102 |
| IL_12p70 | Measles_OD_DB_Int | 0.049 | IL_12p70 | Measles_OD_DB_Int | -0.118 |
| IL_12p70 | Measles_Int | -0.183 | IL_12p70 | Measles_Int | -0.123 |
| IL_12p70 | HepA_Int | -0.069 | IL_12p70 | HepA_Int | -0.079 |
| IL_12p70 | Tetanus_Int | 0.000 | IL_12p70 | Tetanus_Int | 0.000 |
| IL_12p70 | Diptheria_Int | 0.000 | IL_12p70 | Diptheria_Int | 0.000 |
| IL_12p70 | Rubella_Int | 0.030 | IL_12p70 | Rubella_Int | 0.238 |
| IL_12p70 | CMV_Int | -0.015 | IL_12p70 | CMV_Int | -0.097 |
| IL_12p70 | HepB_cAb_Int | -0.027 | IL_12p70 | HepB_cAb_Int | 0.062 |
| IL_12p70 | HepB_eAb_Int | 0.000 | IL_12p70 | HepB_eAb_Int | -0.273 |
| IL_12p70 | HepB_eAg_Int | 0.000 | IL_12p70 | HepB_eAg_Int | 0.000 |
| IL_12p70 | HepC_Int | 0.341 | IL_12p70 | HepC_Int | 0.000 |
| IL_12p70 | Schistosoma_int | 0.155 | IL_12p70 | Schistosoma_int | 0.117 |
| IL_12p70 | Strongyloides_Int | 0.063 | IL_12p70 | Strongyloides_Int | 0.173 |
| IL_12p70 | Filaria_Int | 0.004 | IL_12p70 | Filaria_Int | 0.272 |
| IL_13 | IL_1_alpha | 0.250 | IL_13 | IL_1_alpha | 0.433 |
| IL_13 | IL_1_beta | 0.603 | IL_13 | IL_1_beta | 0.724 |
| IL_13 | IL_2 | 0.558 | IL_13 | IL_2 | 0.426 |
| IL_13 | IL_4 | 0.518 | IL_13 | IL_4 | 0.607 |
| IL_13 | IL_5 | 0.443 | IL_13 | IL_5 | 0.526 |
| IL_13 | IL_6 | 0.377 | IL_13 | IL_6 | 0.677 |
| IL_13 | IL_8 | 0.010 | IL_13 | IL_8 | 0.154 |
| IL_13 | IL_10 | 0.689 | IL_13 | IL_10 | 0.625 |
| IL_13 | IL_12p70 | 0.433 | IL_13 | IL_12p70 | 0.570 |
| IL_13 | IL_13 | 1.000 | IL_13 | IL_13 | 1.000 |
| IL_13 | IL_15 | 0.364 | IL_13 | IL_15 | 0.443 |
| IL_13 | IL_17 | 0.548 | IL_13 | IL_17 | 0.688 |
| IL_13 | IL_23 | 0.049 | IL_13 | IL_23 | -0.015 |
| IL_13 | IFN_gamma | 0.000 | IL_13 | IFN_gamma | 0.000 |
| IL_13 | TNF_alpha | 0.441 | IL_13 | TNF_alpha | 0.362 |
| IL_13 | TNF_beta | 0.447 | IL_13 | TNF_beta | 0.604 |
| IL_13 | Varicella_Int | -0.119 | IL_13 | Varicella_Int | 0.138 |
| IL_13 | Measles_OD_DB_Int | 0.035 | IL_13 | Measles_OD_DB_Int | 0.097 |
| IL_13 | Measles_Int | 0.057 | IL_13 | Measles_Int | -0.222 |
| IL_13 | HepA_Int | -0.026 | IL_13 | HepA_Int | 0.238 |
| IL_13 | Tetanus_Int | 0.000 | IL_13 | Tetanus_Int | 0.000 |
| IL_13 | Diptheria_Int | 0.000 | IL_13 | Diptheria_Int | 0.000 |
| IL_13 | Rubella_Int | 0.019 | IL_13 | Rubella_Int | -0.055 |
| IL_13 | CMV_Int | 0.140 | IL_13 | CMV_Int | -0.200 |
| IL_13 | HepB_cAb_Int | 0.073 | IL_13 | HepB_cAb_Int | 0.162 |
| IL_13 | HepB_eAb_Int | 0.000 | IL_13 | HepB_eAb_Int | 0.286 |
| IL_13 | HepB_eAg_Int | 0.000 | IL_13 | HepB_eAg_Int | 0.000 |
| IL_13 | HepC_Int | 0.293 | IL_13 | HepC_Int | 0.000 |
| IL_13 | Schistosoma_int | -0.032 | IL_13 | Schistosoma_int | 0.047 |
| IL_13 | Strongyloides_Int | -0.132 | IL_13 | Strongyloides_Int | 0.122 |

FIG. 2117-F

| | | | | | | |
|---|---|---|---|---|---|---|
| IL_13 | Filaria_Int | 0.237 | | IL_13 | Filaria_Int | 0.297 |
| IL_15 | IL_1_alpha | 0.410 | | IL_15 | IL_1_alpha | 0.372 |
| IL_15 | IL_1_beta | 0.339 | | IL_15 | IL_1_beta | 0.387 |
| IL_15 | IL_2 | 0.316 | | IL_15 | IL_2 | 0.259 |
| IL_15 | IL_4 | 0.485 | | IL_15 | IL_4 | 0.540 |
| IL_15 | IL_5 | 0.556 | | IL_15 | IL_5 | 0.417 |
| IL_15 | IL_6 | 0.333 | | IL_15 | IL_6 | 0.304 |
| IL_15 | IL_8 | 0.062 | | IL_15 | IL_8 | 0.491 |
| IL_15 | IL_10 | 0.412 | | IL_15 | IL_10 | 0.393 |
| IL_15 | IL_12p70 | 0.413 | | IL_15 | IL_12p70 | 0.487 |
| IL_15 | IL_13 | 0.364 | | IL_15 | IL_13 | 0.443 |
| IL_15 | IL_15 | 1.000 | | IL_15 | IL_15 | 1.000 |
| IL_15 | IL_17 | 0.444 | | IL_15 | IL_17 | 0.284 |
| IL_15 | IL_23 | 0.063 | | IL_15 | IL_23 | 0.115 |
| IL_15 | IFN_gamma | 0.000 | | IL_15 | IFN_gamma | 0.000 |
| IL_15 | TNF_alpha | 0.338 | | IL_15 | TNF_alpha | 0.316 |
| IL_15 | TNF_beta | 0.497 | | IL_15 | TNF_beta | 0.392 |
| IL_15 | Varicella_Int | -0.061 | | IL_15 | Varicella_Int | -0.163 |
| IL_15 | Measles_OD_DB_Int | -0.044 | | IL_15 | Measles_OD_DB_Int | 0.006 |
| IL_15 | Measles_Int | -0.132 | | IL_15 | Measles_Int | 0.024 |
| IL_15 | HepA_Int | 0.111 | | IL_15 | HepA_Int | 0.050 |
| IL_15 | Tetanus_Int | 0.000 | | IL_15 | Tetanus_Int | 0.000 |
| IL_15 | Diptheria_Int | 0.000 | | IL_15 | Diptheria_Int | 0.000 |
| IL_15 | Rubella_Int | -0.026 | | IL_15 | Rubella_Int | -0.022 |
| IL_15 | CMV_Int | 0.054 | | IL_15 | CMV_Int | -0.072 |
| IL_15 | HepB_cAb_Int | -0.078 | | IL_15 | HepB_cAb_Int | -0.133 |
| IL_15 | HepB_eAb_Int | 0.000 | | IL_15 | HepB_eAb_Int | 0.352 |
| IL_15 | HepB_eAg_Int | 0.000 | | IL_15 | HepB_eAg_Int | 0.000 |
| IL_15 | HepC_Int | 0.148 | | IL_15 | HepC_Int | 0.000 |
| IL_15 | Schistosoma_int | -0.022 | | IL_15 | Schistosoma_int | 0.036 |
| IL_15 | Strongyloides_Int | 0.035 | | IL_15 | Strongyloides_Int | 0.036 |
| IL_15 | Filaria_Int | -0.173 | | IL_15 | Filaria_Int | 0.308 |
| IL_17 | IL_1_alpha | 0.199 | | IL_17 | IL_1_alpha | 0.301 |
| IL_17 | IL_1_beta | 0.542 | | IL_17 | IL_1_beta | 0.659 |
| IL_17 | IL_2 | 0.692 | | IL_17 | IL_2 | 0.613 |
| IL_17 | IL_4 | 0.479 | | IL_17 | IL_4 | 0.593 |
| IL_17 | IL_5 | 0.576 | | IL_17 | IL_5 | 0.466 |
| IL_17 | IL_6 | 0.268 | | IL_17 | IL_6 | 0.623 |
| IL_17 | IL_8 | 0.016 | | IL_17 | IL_8 | 0.052 |
| IL_17 | IL_10 | 0.763 | | IL_17 | IL_10 | 0.727 |
| IL_17 | IL_12p70 | 0.442 | | IL_17 | IL_12p70 | 0.648 |
| IL_17 | IL_13 | 0.548 | | IL_17 | IL_13 | 0.688 |
| IL_17 | IL_15 | 0.444 | | IL_17 | IL_15 | 0.284 |
| IL_17 | IL_17 | 1.000 | | IL_17 | IL_17 | 1.000 |
| IL_17 | IL_23 | 0.037 | | IL_17 | IL_23 | 0.234 |
| IL_17 | IFN_gamma | 0.000 | | IL_17 | IFN_gamma | 0.000 |
| IL_17 | TNF_alpha | 0.291 | | IL_17 | TNF_alpha | 0.574 |
| IL_17 | TNF_beta | 0.418 | | IL_17 | TNF_beta | 0.680 |
| IL_17 | Varicella_Int | -0.088 | | IL_17 | Varicella_Int | 0.158 |
| IL_17 | Measles_OD_DB_Int | 0.041 | | IL_17 | Measles_OD_DB_Int | 0.024 |
| IL_17 | Measles_Int | -0.102 | | IL_17 | Measles_Int | -0.035 |
| IL_17 | HepA_Int | 0.083 | | IL_17 | HepA_Int | 0.068 |
| IL_17 | Tetanus_Int | 0.000 | | IL_17 | Tetanus_Int | 0.000 |
| IL_17 | Diptheria_Int | 0.000 | | IL_17 | Diptheria_Int | 0.000 |
| IL_17 | Rubella_Int | -0.084 | | IL_17 | Rubella_Int | 0.175 |
| IL_17 | CMV_Int | 0.073 | | IL_17 | CMV_Int | -0.202 |
| IL_17 | HepB_cAb_Int | -0.047 | | IL_17 | HepB_cAb_Int | 0.067 |

FIG. 21I7-G

| | | | | | | |
|---|---|---|---|---|---|---|
| IL_17 | HepB_eAb_Int | 0.000 | | IL_17 | HepB_eAb_Int | 0.434 |
| IL_17 | HepB_eAg_Int | 0.000 | | IL_17 | HepB_eAg_Int | 0.000 |
| IL_17 | HepC_Int | 0.255 | | IL_17 | HepC_Int | 0.000 |
| IL_17 | Schistosoma_int | -0.003 | | IL_17 | Schistosoma_int | 0.165 |
| IL_17 | Strongyloides_Int | -0.124 | | IL_17 | Strongyloides_Int | 0.333 |
| IL_17 | Filaria_Int | 0.142 | | IL_17 | Filaria_Int | 0.272 |
| IL_23 | IL_1_alpha | 0.182 | | IL_23 | IL_1_alpha | 0.106 |
| IL_23 | IL_1_beta | 0.017 | | IL_23 | IL_1_beta | 0.048 |
| IL_23 | IL_2 | 0.060 | | IL_23 | IL_2 | 0.150 |
| IL_23 | IL_4 | 0.140 | | IL_23 | IL_4 | 0.095 |
| IL_23 | IL_5 | 0.147 | | IL_23 | IL_5 | 0.022 |
| IL_23 | IL_6 | -0.024 | | IL_23 | IL_6 | 0.035 |
| IL_23 | IL_8 | 0.009 | | IL_23 | IL_8 | -0.051 |
| IL_23 | IL_10 | -0.010 | | IL_23 | IL_10 | 0.119 |
| IL_23 | IL_12p70 | 0.611 | | IL_23 | IL_12p70 | 0.249 |
| IL_23 | IL_13 | 0.049 | | IL_23 | IL_13 | -0.015 |
| IL_23 | IL_15 | 0.063 | | IL_23 | IL_15 | 0.115 |
| IL_23 | IL_17 | 0.037 | | IL_23 | IL_17 | 0.234 |
| IL_23 | IL_23 | 1.000 | | IL_23 | IL_23 | 1.000 |
| IL_23 | IFN_gamma | 0.000 | | IL_23 | IFN_gamma | 0.000 |
| IL_23 | TNF_alpha | -0.010 | | IL_23 | TNF_alpha | 0.046 |
| IL_23 | TNF_beta | 0.071 | | IL_23 | TNF_beta | 0.225 |
| IL_23 | Varicella_Int | 0.053 | | IL_23 | Varicella_Int | 0.063 |
| IL_23 | Measles_OD_DB_Int | 0.103 | | IL_23 | Measles_OD_DB_Int | 0.068 |
| IL_23 | Measles_Int | -0.051 | | IL_23 | Measles_Int | 0.032 |
| IL_23 | HepA_Int | -0.060 | | IL_23 | HepA_Int | -0.289 |
| IL_23 | Tetanus_Int | 0.000 | | IL_23 | Tetanus_Int | 0.000 |
| IL_23 | Diptheria_Int | 0.000 | | IL_23 | Diptheria_Int | 0.000 |
| IL_23 | Rubella_Int | -0.077 | | IL_23 | Rubella_Int | -0.051 |
| IL_23 | CMV_Int | -0.032 | | IL_23 | CMV_Int | 0.023 |
| IL_23 | HepB_cAb_Int | -0.064 | | IL_23 | HepB_cAb_Int | -0.097 |
| IL_23 | HepB_eAb_Int | 0.000 | | IL_23 | HepB_eAb_Int | 0.128 |
| IL_23 | HepB_eAg_Int | 0.000 | | IL_23 | HepB_eAg_Int | 0.000 |
| IL_23 | HepC_Int | 0.092 | | IL_23 | HepC_Int | 0.000 |
| IL_23 | Schistosoma_int | 0.125 | | IL_23 | Schistosoma_int | -0.063 |
| IL_23 | Strongyloides_Int | 0.120 | | IL_23 | Strongyloides_Int | 0.148 |
| IL_23 | Filaria_Int | -0.087 | | IL_23 | Filaria_Int | -0.057 |
| IFN_gamma | IL_1_alpha | 0.000 | | IFN_gamma | IL_1_alpha | 0.000 |
| IFN_gamma | IL_1_beta | 0.000 | | IFN_gamma | IL_1_beta | 0.000 |
| IFN_gamma | IL_2 | 0.000 | | IFN_gamma | IL_2 | 0.000 |
| IFN_gamma | IL_4 | 0.000 | | IFN_gamma | IL_4 | 0.000 |
| IFN_gamma | IL_5 | 0.000 | | IFN_gamma | IL_5 | 0.000 |
| IFN_gamma | IL_6 | 0.000 | | IFN_gamma | IL_6 | 0.000 |
| IFN_gamma | IL_8 | 0.000 | | IFN_gamma | IL_8 | 0.000 |
| IFN_gamma | IL_10 | 0.000 | | IFN_gamma | IL_10 | 0.000 |
| IFN_gamma | IL_12p70 | 0.000 | | IFN_gamma | IL_12p70 | 0.000 |
| IFN_gamma | IL_13 | 0.000 | | IFN_gamma | IL_13 | 0.000 |
| IFN_gamma | IL_15 | 0.000 | | IFN_gamma | IL_15 | 0.000 |
| IFN_gamma | IL_17 | 0.000 | | IFN_gamma | IL_17 | 0.000 |
| IFN_gamma | IL_23 | 0.000 | | IFN_gamma | IL_23 | 0.000 |
| IFN_gamma | IFN_gamma | 1.000 | | IFN_gamma | IFN_gamma | 1.000 |
| IFN_gamma | TNF_alpha | 0.000 | | IFN_gamma | TNF_alpha | 0.000 |
| IFN_gamma | TNF_beta | 0.000 | | IFN_gamma | TNF_beta | 0.000 |
| IFN_gamma | Varicella_Int | 0.000 | | IFN_gamma | Varicella_Int | 0.000 |
| IFN_gamma | Measles_OD_DB_Int | 0.000 | | IFN_gamma | Measles_OD_DB_Int | 0.000 |
| IFN_gamma | Measles_Int | 0.000 | | IFN_gamma | Measles_Int | 0.000 |
| IFN_gamma | HepA_Int | 0.000 | | IFN_gamma | HepA_Int | 0.000 |

FIG. 2117-H

| | | | | | | |
|---|---|---|---|---|---|---|
| IFN_gamma | Tetanus_Int | 0.000 | | IFN_gamma | Tetanus_Int | 0.000 |
| IFN_gamma | Diptheria_Int | 0.000 | | IFN_gamma | Diptheria_Int | 0.000 |
| IFN_gamma | Rubella_Int | 0.000 | | IFN_gamma | Rubella_Int | 0.000 |
| IFN_gamma | CMV_Int | 0.000 | | IFN_gamma | CMV_Int | 0.000 |
| IFN_gamma | HepB_cAb_Int | 0.000 | | IFN_gamma | HepB_cAb_Int | 0.000 |
| IFN_gamma | HepB_eAb_Int | 0.000 | | IFN_gamma | HepB_eAb_Int | 0.000 |
| IFN_gamma | HepB_eAg_Int | 0.000 | | IFN_gamma | HepB_eAg_Int | 0.000 |
| IFN_gamma | HepC_Int | 0.000 | | IFN_gamma | HepC_Int | 0.000 |
| IFN_gamma | Schistosoma_int | 0.000 | | IFN_gamma | Schistosoma_int | 0.000 |
| IFN_gamma | Strongyloides_Int | 0.000 | | IFN_gamma | Strongyloides_Int | 0.000 |
| IFN_gamma | Filaria_Int | 0.000 | | IFN_gamma | Filaria_Int | 0.000 |
| TNF_alpha | IL_1_alpha | 0.425 | | TNF_alpha | IL_1_alpha | 0.471 |
| TNF_alpha | IL_1_beta | 0.595 | | TNF_alpha | IL_1_beta | 0.665 |
| TNF_alpha | IL_2 | 0.387 | | TNF_alpha | IL_2 | 0.687 |
| TNF_alpha | IL_4 | 0.381 | | TNF_alpha | IL_4 | 0.389 |
| TNF_alpha | IL_5 | 0.420 | | TNF_alpha | IL_5 | 0.562 |
| TNF_alpha | IL_6 | 0.229 | | TNF_alpha | IL_6 | 0.320 |
| TNF_alpha | IL_8 | -0.017 | | TNF_alpha | IL_8 | 0.143 |
| TNF_alpha | IL_10 | 0.343 | | TNF_alpha | IL_10 | 0.655 |
| TNF_alpha | IL_12p70 | 0.356 | | TNF_alpha | IL_12p70 | 0.584 |
| TNF_alpha | IL_13 | 0.441 | | TNF_alpha | IL_13 | 0.362 |
| TNF_alpha | IL_15 | 0.338 | | TNF_alpha | IL_15 | 0.316 |
| TNF_alpha | IL_17 | 0.291 | | TNF_alpha | IL_17 | 0.574 |
| TNF_alpha | IL_23 | -0.010 | | TNF_alpha | IL_23 | 0.046 |
| TNF_alpha | IFN_gamma | 0.000 | | TNF_alpha | IFN_gamma | 0.000 |
| TNF_alpha | TNF_alpha | 1.000 | | TNF_alpha | TNF_alpha | 1.000 |
| TNF_alpha | TNF_beta | 0.569 | | TNF_alpha | TNF_beta | 0.688 |
| TNF_alpha | Varicella_Int | -0.030 | | TNF_alpha | Varicella_Int | 0.156 |
| TNF_alpha | Measles_OD_DB_Int | 0.036 | | TNF_alpha | Measles_OD_DB_Int | -0.084 |
| TNF_alpha | Measles_int | 0.020 | | TNF_alpha | Measles_Int | -0.093 |
| TNF_alpha | HepA_Int | 0.177 | | TNF_alpha | HepA_Int | 0.033 |
| TNF_alpha | Tetanus_Int | 0.000 | | TNF_alpha | Tetanus_Int | 0.000 |
| TNF_alpha | Diptheria_Int | 0.000 | | TNF_alpha | Diptheria_Int | 0.000 |
| TNF_alpha | Rubella_Int | -0.101 | | TNF_alpha | Rubella_Int | 0.141 |
| TNF_alpha | CMV_Int | 0.061 | | TNF_alpha | CMV_Int | -0.053 |
| TNF_alpha | HepB_cAb_Int | 0.253 | | TNF_alpha | HepB_cAb_Int | -0.146 |
| TNF_alpha | HepB_eAb_Int | 0.000 | | TNF_alpha | HepB_eAb_Int | 0.024 |
| TNF_alpha | HepB_eAg_Int | 0.000 | | TNF_alpha | HepB_eAg_Int | 0.000 |
| TNF_alpha | HepC_Int | 0.006 | | TNF_alpha | HepC_Int | 0.000 |
| TNF_alpha | Schistosoma_int | 0.093 | | TNF_alpha | Schistosoma_int | 0.143 |
| TNF_alpha | Strongyloides_Int | 0.003 | | TNF_alpha | Strongyloides_Int | 0.244 |
| TNF_alpha | Filaria_Int | 0.082 | | TNF_alpha | Filaria_Int | 0.189 |
| TNF_beta | IL_1_alpha | 0.470 | | TNF_beta | IL_1_alpha | 0.456 |
| TNF_beta | IL_1_beta | 0.523 | | TNF_beta | IL_1_beta | 0.806 |
| TNF_beta | IL_2 | 0.524 | | TNF_beta | IL_2 | 0.719 |
| TNF_beta | IL_4 | 0.445 | | TNF_beta | IL_4 | 0.570 |
| TNF_beta | IL_5 | 0.477 | | TNF_beta | IL_5 | 0.547 |
| TNF_beta | IL_6 | 0.250 | | TNF_beta | IL_6 | 0.542 |
| TNF_beta | IL_8 | 0.040 | | TNF_beta | IL_8 | 0.229 |
| TNF_beta | IL_10 | 0.432 | | TNF_beta | IL_10 | 0.726 |
| TNF_beta | IL_12p70 | 0.416 | | TNF_beta | IL_12p70 | 0.655 |
| TNF_beta | IL_13 | 0.447 | | TNF_beta | IL_13 | 0.604 |
| TNF_beta | IL_15 | 0.497 | | TNF_beta | IL_15 | 0.392 |
| TNF_beta | IL_17 | 0.418 | | TNF_beta | IL_17 | 0.680 |
| TNF_beta | IL_23 | 0.071 | | TNF_beta | IL_23 | 0.225 |
| TNF_beta | IFN_gamma | 0.000 | | TNF_beta | IFN_gamma | 0.000 |
| TNF_beta | TNF_alpha | 0.569 | | TNF_beta | TNF_alpha | 0.688 |

FIG. 2117-I

| | | | | | | |
|---|---|---|---|---|---|---|
| TNF_beta | TNF_beta | 1.000 | | TNF_beta | TNF_beta | 1.000 |
| TNF_beta | Varicella_Int | -0.247 | | TNF_beta | Varicella_Int | 0.133 |
| TNF_beta | Measles_OD_DB_Int | -0.205 | | TNF_beta | Measles_OD_DB_Int | 0.051 |
| TNF_beta | Measles_Int | 0.029 | | TNF_beta | Measles_Int | -0.180 |
| TNF_beta | HepA_Int | 0.098 | | TNF_beta | HepA_Int | -0.022 |
| TNF_beta | Tetanus_Int | 0.000 | | TNF_beta | Tetanus_Int | 0.000 |
| TNF_beta | Diptheria_Int | 0.000 | | TNF_beta | Diptheria_Int | 0.000 |
| TNF_beta | Rubella_Int | -0.147 | | TNF_beta | Rubella_Int | -0.007 |
| TNF_beta | CMV_Int | 0.122 | | TNF_beta | CMV_Int | -0.242 |
| TNF_beta | HepB_cAb_Int | 0.032 | | TNF_beta | HepB_cAb_Int | -0.004 |
| TNF_beta | HepB_eAb_Int | 0.000 | | TNF_beta | HepB_eAb_Int | 0.294 |
| TNF_beta | HepB_eAg_Int | 0.000 | | TNF_beta | HepB_eAg_Int | 0.000 |
| TNF_beta | HepC_Int | -0.051 | | TNF_beta | HepC_Int | 0.000 |
| TNF_beta | Schistosoma_int | 0.010 | | TNF_beta | Schistosoma_int | 0.190 |
| TNF_beta | Strongyloides_Int | 0.133 | | TNF_beta | Strongyloides_Int | 0.207 |
| TNF_beta | Filaria_Int | 0.208 | | TNF_beta | Filaria_Int | 0.350 |
| Varicella_Int | IL_1_alpha | 0.047 | | Varicella_Int | IL_1_alpha | 0.028 |
| Varicella_Int | IL_1_beta | -0.085 | | Varicella_Int | IL_1_beta | 0.123 |
| Varicella_Int | IL_2 | 0.026 | | Varicella_Int | IL_2 | 0.099 |
| Varicella_Int | IL_4 | -0.440 | | Varicella_Int | IL_4 | 0.097 |
| Varicella_Int | IL_5 | -0.104 | | Varicella_Int | IL_5 | 0.001 |
| Varicella_Int | IL_6 | 0.044 | | Varicella_Int | IL_6 | 0.107 |
| Varicella_Int | IL_8 | 0.056 | | Varicella_Int | IL_8 | -0.160 |
| Varicella_Int | IL_10 | -0.078 | | Varicella_Int | IL_10 | 0.160 |
| Varicella_Int | IL_12p70 | 0.009 | | Varicella_Int | IL_12p70 | 0.102 |
| Varicella_Int | IL_13 | -0.119 | | Varicella_Int | IL_13 | 0.138 |
| Varicella_Int | IL_15 | -0.061 | | Varicella_Int | IL_15 | -0.163 |
| Varicella_Int | IL_17 | -0.088 | | Varicella_Int | IL_17 | 0.158 |
| Varicella_Int | IL_23 | 0.053 | | Varicella_Int | IL_23 | 0.063 |
| Varicella_Int | IFN_gamma | 0.000 | | Varicella_Int | IFN_gamma | 0.000 |
| Varicella_Int | TNF_alpha | -0.030 | | Varicella_Int | TNF_alpha | 0.156 |
| Varicella_Int | TNF_beta | -0.247 | | Varicella_Int | TNF_beta | 0.133 |
| Varicella_Int | Varicella_Int | 1.000 | | Varicella_Int | Varicella_Int | 1.000 |
| Varicella_Int | Measles_OD_DB_Int | 0.211 | | Varicella_Int | Measles_OD_DB_Int | 0.023 |
| Varicella_Int | Measles_int | -0.060 | | Varicella_Int | Measles_Int | -0.077 |
| Varicella_Int | HepA_Int | -0.024 | | Varicella_Int | HepA_Int | -0.150 |
| Varicella_Int | Tetanus_Int | 0.000 | | Varicella_Int | Tetanus_Int | 0.000 |
| Varicella_Int | Diptheria_Int | 0.000 | | Varicella_Int | Diptheria_Int | 0.000 |
| Varicella_Int | Rubella_Int | -0.089 | | Varicella_Int | Rubella_Int | 0.073 |
| Varicella_Int | CMV_Int | -0.037 | | Varicella_Int | CMV_Int | -0.083 |
| Varicella_Int | HepB_cAb_Int | 0.067 | | Varicella_Int | HepB_cAb_Int | 0.257 |
| Varicella_Int | HepB_eAb_Int | 0.000 | | Varicella_Int | HepB_eAb_Int | 0.000 |
| Varicella_Int | HepB_eAg_Int | 0.000 | | Varicella_Int | HepB_eAg_Int | 0.000 |
| Varicella_Int | HepC_Int | 0.041 | | Varicella_Int | HepC_Int | 0.000 |
| Varicella_Int | Schistosoma_int | -0.097 | | Varicella_Int | Schistosoma_int | -0.061 |
| Varicella_Int | Strongyloides_Int | -0.138 | | Varicella_Int | Strongyloides_Int | -0.025 |
| Varicella_Int | Filaria_Int | 0.026 | | Varicella_Int | Filaria_Int | -0.012 |
| Measles_OD_DB_Int | IL_1_alpha | 0.036 | | Measles_OD_DB_Int | IL_1_alpha | -0.091 |
| Measles_OD_DB_Int | IL_1_beta | -0.095 | | Measles_OD_DB_Int | IL_1_beta | 0.052 |
| Measles_OD_DB_Int | IL_2 | 0.066 | | Measles_OD_DB_Int | IL_2 | 0.129 |
| Measles_OD_DB_Int | IL_4 | -0.053 | | Measles_OD_DB_Int | IL_4 | -0.020 |
| Measles_OD_DB_Int | IL_5 | 0.049 | | Measles_OD_DB_Int | IL_5 | -0.211 |
| Measles_OD_DB_Int | IL_6 | -0.125 | | Measles_OD_DB_Int | IL_6 | 0.099 |
| Measles_OD_DB_Int | IL_8 | 0.078 | | Measles_OD_DB_Int | IL_8 | 0.091 |
| Measles_OD_DB_Int | IL_10 | -0.080 | | Measles_OD_DB_Int | IL_10 | 0.024 |
| Measles_OD_DB_Int | IL_12p70 | 0.049 | | Measles_OD_DB_Int | IL_12p70 | -0.118 |
| Measles_OD_DB_Int | IL_13 | 0.035 | | Measles_OD_DB_Int | IL_13 | 0.097 |

FIG. 2117-J

| | | | | | | |
|---|---|---|---|---|---|---|
| Measles_OD_DB_Int | IL_15 | -0.044 | | Measles_OD_DB_Int | IL_15 | 0.006 |
| Measles_OD_DB_Int | IL_17 | 0.041 | | Measles_OD_DB_Int | IL_17 | 0.024 |
| Measles_OD_DB_Int | IL_23 | 0.103 | | Measles_OD_DB_Int | IL_23 | 0.068 |
| Measles_OD_DB_Int | IFN_gamma | 0.000 | | Measles_OD_DB_Int | IFN_gamma | 0.000 |
| Measles_OD_DB_Int | TNF_alpha | 0.036 | | Measles_OD_DB_Int | TNF_alpha | -0.084 |
| Measles_OD_DB_Int | TNF_beta | -0.205 | | Measles_OD_DB_Int | TNF_beta | 0.051 |
| Measles_OD_DB_Int | Varicella_Int | 0.211 | | Measles_OD_DB_Int | Varicella_Int | 0.023 |
| Measles_OD_DB_Int | Measles_OD_DB_Int | 1.000 | | Measles_OD_DB_Int | Measles_OD_DB_Int | 1.000 |
| Measles_OD_DB_Int | Measles_Int | -0.001 | | Measles_OD_DB_Int | Measles_Int | 0.068 |
| Measles_OD_DB_Int | HepA_Int | 0.102 | | Measles_OD_DB_Int | HepA_Int | -0.208 |
| Measles_OD_DB_Int | Tetanus_Int | 0.000 | | Measles_OD_DB_Int | Tetanus_Int | 0.000 |
| Measles_OD_DB_Int | Diptheria_Int | 0.000 | | Measles_OD_DB_Int | Diptheria_Int | 0.000 |
| Measles_OD_DB_Int | Rubella_Int | -0.113 | | Measles_OD_DB_Int | Rubella_Int | -0.394 |
| Measles_OD_DB_Int | CMV_Int | 0.044 | | Measles_OD_DB_Int | CMV_Int | -0.108 |
| Measles_OD_DB_Int | HepB_cAb_Int | 0.037 | | Measles_OD_DB_Int | HepB_cAb_Int | -0.009 |
| Measles_OD_DB_Int | HepB_eAb_Int | 0.000 | | Measles_OD_DB_Int | HepB_eAb_Int | 0.000 |
| Measles_OD_DB_Int | HepB_eAg_Int | 0.000 | | Measles_OD_DB_Int | HepB_eAg_Int | 0.000 |
| Measles_OD_DB_Int | HepC_Int | 0.075 | | Measles_OD_DB_Int | HepC_Int | 0.000 |
| Measles_OD_DB_Int | Schistosoma_int | 0.073 | | Measles_OD_DB_Int | Schistosoma_int | -0.191 |
| Measles_OD_DB_Int | Strongyloides_Int | -0.023 | | Measles_OD_DB_Int | Strongyloides_Int | -0.222 |
| Measles_OD_DB_Int | Filaria_Int | 0.078 | | Measles_OD_DB_Int | Filaria_Int | 0.029 |
| Measles_Int | IL_1_alpha | -0.015 | | Measles_Int | IL_1_alpha | -0.545 |
| Measles_Int | IL_1_beta | -0.011 | | Measles_Int | IL_1_beta | -0.152 |
| Measles_Int | IL_2 | 0.053 | | Measles_Int | IL_2 | 0.013 |
| Measles_Int | IL_4 | -0.151 | | Measles_Int | IL_4 | 0.042 |
| Measles_Int | IL_5 | -0.184 | | Measles_Int | IL_5 | -0.108 |
| Measles_Int | IL_6 | -0.122 | | Measles_Int | IL_6 | -0.093 |
| Measles_Int | IL_8 | 0.020 | | Measles_Int | IL_8 | -0.159 |
| Measles_Int | IL_10 | -0.138 | | Measles_Int | IL_10 | -0.030 |
| Measles_Int | IL_12p70 | -0.183 | | Measles_Int | IL_12p70 | -0.123 |
| Measles_Int | IL_13 | 0.057 | | Measles_Int | IL_13 | -0.222 |
| Measles_Int | IL_15 | -0.132 | | Measles_Int | IL_15 | 0.024 |
| Measles_Int | IL_17 | -0.102 | | Measles_Int | IL_17 | -0.035 |
| Measles_Int | IL_23 | -0.051 | | Measles_Int | IL_23 | 0.032 |
| Measles_Int | IFN_gamma | 0.000 | | Measles_Int | IFN_gamma | 0.000 |
| Measles_Int | TNF_alpha | 0.020 | | Measles_Int | TNF_alpha | -0.093 |
| Measles_Int | TNF_beta | 0.029 | | Measles_Int | TNF_beta | -0.180 |
| Measles_Int | Varicella_Int | -0.060 | | Measles_Int | Varicella_Int | -0.077 |
| Measles_Int | Measles_OD_DB_Int | -0.001 | | Measles_Int | Measles_OD_DB_Int | 0.068 |
| Measles_Int | Measles_Int | 1.000 | | Measles_Int | Measles_Int | 1.000 |
| Measles_Int | HepA_Int | -0.055 | | Measles_Int | HepA_Int | -0.048 |
| Measles_Int | Tetanus_Int | 0.000 | | Measles_Int | Tetanus_Int | 0.000 |
| Measles_Int | Diptheria_Int | 0.000 | | Measles_Int | Diptheria_Int | 0.000 |
| Measles_Int | Rubella_Int | -0.153 | | Measles_Int | Rubella_Int | -0.113 |
| Measles_Int | CMV_Int | 0.013 | | Measles_Int | CMV_Int | 0.296 |
| Measles_Int | HepB_cAb_Int | 0.063 | | Measles_Int | HepB_cAb_Int | -0.139 |
| Measles_Int | HepB_eAb_Int | 0.000 | | Measles_Int | HepB_eAb_Int | -0.200 |
| Measles_Int | HepB_eAg_Int | 0.000 | | Measles_Int | HepB_eAg_Int | 0.000 |
| Measles_Int | HepC_Int | 0.039 | | Measles_Int | HepC_Int | 0.000 |
| Measles_Int | Schistosoma_int | -0.026 | | Measles_Int | Schistosoma_int | 0.003 |
| Measles_Int | Strongyloides_Int | 0.091 | | Measles_Int | Strongyloides_Int | -0.186 |
| Measles_Int | Filaria_Int | 0.152 | | Measles_Int | Filaria_Int | -0.057 |
| HepA_Int | IL_1_alpha | 0.151 | | HepA_Int | IL_1_alpha | 0.036 |
| HepA_Int | IL_1_beta | -0.080 | | HepA_Int | IL_1_beta | 0.029 |
| HepA_Int | IL_2 | 0.149 | | HepA_Int | IL_2 | -0.087 |
| HepA_Int | IL_4 | -0.017 | | HepA_Int | IL_4 | 0.122 |
| HepA_Int | IL_5 | 0.055 | | HepA_Int | IL_5 | -0.048 |

FIG. 2117-K

| | | | | | | |
|---|---|---|---|---|---|---|
| HepA_Int | IL_6 | -0.069 | | HepA_Int | IL_6 | 0.035 |
| HepA_Int | IL_8 | 0.062 | | HepA_Int | IL_8 | 0.124 |
| HepA_Int | IL_10 | -0.034 | | HepA_Int | IL_10 | -0.037 |
| HepA_Int | IL_12p70 | -0.069 | | HepA_Int | IL_12p70 | -0.079 |
| HepA_Int | IL_13 | -0.026 | | HepA_Int | IL_13 | 0.238 |
| HepA_Int | IL_15 | 0.111 | | HepA_Int | IL_15 | 0.050 |
| HepA_Int | IL_17 | 0.083 | | HepA_Int | IL_17 | 0.068 |
| HepA_Int | IL_23 | -0.060 | | HepA_Int | IL_23 | -0.289 |
| HepA_Int | IFN_gamma | 0.000 | | HepA_Int | IFN_gamma | 0.000 |
| HepA_Int | TNF_alpha | 0.177 | | HepA_Int | TNF_alpha | 0.033 |
| HepA_Int | TNF_beta | 0.098 | | HepA_Int | TNF_beta | -0.022 |
| HepA_Int | Varicella_Int | -0.024 | | HepA_Int | Varicella_Int | -0.150 |
| HepA_Int | Measles_OD_DB_Int | 0.102 | | HepA_Int | Measles_OD_DB_Int | -0.208 |
| HepA_Int | Measles_Int | -0.055 | | HepA_Int | Measles_Int | -0.048 |
| HepA_Int | HepA_Int | 1.000 | | HepA_Int | HepA_Int | 1.000 |
| HepA_Int | Tetanus_Int | 0.000 | | HepA_Int | Tetanus_Int | 0.000 |
| HepA_Int | Diptheria_Int | 0.000 | | HepA_Int | Diptheria_Int | 0.000 |
| HepA_Int | Rubella_Int | -0.198 | | HepA_Int | Rubella_Int | 0.150 |
| HepA_Int | CMV_Int | 0.049 | | HepA_Int | CMV_Int | 0.013 |
| HepA_Int | HepB_cAb_Int | 0.149 | | HepA_Int | HepB_cAb_Int | 0.028 |
| HepA_Int | HepB_eAb_Int | 0.000 | | HepA_Int | HepB_eAb_Int | 0.447 |
| HepA_Int | HepB_eAg_Int | 0.000 | | HepA_Int | HepB_eAg_Int | 0.000 |
| HepA_Int | HepC_Int | -0.092 | | HepA_Int | HepC_Int | 0.000 |
| HepA_Int | Schistosoma_int | -0.149 | | HepA_Int | Schistosoma_int | 0.005 |
| HepA_Int | Strongyloides_Int | 0.198 | | HepA_Int | Strongyloides_Int | 0.208 |
| HepA_Int | Filaria_Int | 0.133 | | HepA_Int | Filaria_Int | 0.057 |
| Tetanus_Int | IL_1_alpha | 0.000 | | Tetanus_Int | IL_1_alpha | 0.000 |
| Tetanus_Int | IL_1_beta | 0.000 | | Tetanus_Int | IL_1_beta | 0.000 |
| Tetanus_Int | IL_2 | 0.000 | | Tetanus_Int | IL_2 | 0.000 |
| Tetanus_Int | IL_4 | 0.000 | | Tetanus_Int | IL_4 | 0.000 |
| Tetanus_Int | IL_5 | 0.000 | | Tetanus_Int | IL_5 | 0.000 |
| Tetanus_Int | IL_6 | 0.000 | | Tetanus_Int | IL_6 | 0.000 |
| Tetanus_Int | IL_8 | 0.000 | | Tetanus_Int | IL_8 | 0.000 |
| Tetanus_Int | IL_10 | 0.000 | | Tetanus_Int | IL_10 | 0.000 |
| Tetanus_Int | IL_12p70 | 0.000 | | Tetanus_Int | IL_12p70 | 0.000 |
| Tetanus_Int | IL_13 | 0.000 | | Tetanus_Int | IL_13 | 0.000 |
| Tetanus_Int | IL_15 | 0.000 | | Tetanus_Int | IL_15 | 0.000 |
| Tetanus_Int | IL_17 | 0.000 | | Tetanus_Int | IL_17 | 0.000 |
| Tetanus_Int | IL_23 | 0.000 | | Tetanus_Int | IL_23 | 0.000 |
| Tetanus_Int | IFN_gamma | 0.000 | | Tetanus_Int | IFN_gamma | 0.000 |
| Tetanus_Int | TNF_alpha | 0.000 | | Tetanus_Int | TNF_alpha | 0.000 |
| Tetanus_Int | TNF_beta | 0.000 | | Tetanus_Int | TNF_beta | 0.000 |
| Tetanus_Int | Varicella_Int | 0.000 | | Tetanus_Int | Varicella_Int | 0.000 |
| Tetanus_Int | Measles_OD_DB_Int | 0.000 | | Tetanus_Int | Measles_OD_DB_Int | 0.000 |
| Tetanus_Int | Measles_Int | 0.000 | | Tetanus_Int | Measles_Int | 0.000 |
| Tetanus_Int | HepA_Int | 0.000 | | Tetanus_Int | HepA_Int | 0.000 |
| Tetanus_Int | Tetanus_Int | 1.000 | | Tetanus_Int | Tetanus_Int | 1.000 |
| Tetanus_Int | Diptheria_Int | 0.000 | | Tetanus_Int | Diptheria_Int | 0.000 |
| Tetanus_Int | Rubella_Int | 0.000 | | Tetanus_Int | Rubella_Int | 0.000 |
| Tetanus_Int | CMV_Int | 0.000 | | Tetanus_Int | CMV_Int | 0.000 |
| Tetanus_Int | HepB_cAb_Int | 0.000 | | Tetanus_Int | HepB_cAb_Int | 0.000 |
| Tetanus_Int | HepB_eAb_Int | 0.000 | | Tetanus_Int | HepB_eAb_Int | 0.000 |
| Tetanus_Int | HepB_eAg_Int | 0.000 | | Tetanus_Int | HepB_eAg_Int | 0.000 |
| Tetanus_Int | HepC_Int | 0.000 | | Tetanus_Int | HepC_Int | 0.000 |
| Tetanus_Int | Schistosoma_int | 0.000 | | Tetanus_Int | Schistosoma_int | 0.000 |
| Tetanus_Int | Strongyloides_Int | 0.000 | | Tetanus_Int | Strongyloides_Int | 0.000 |
| Tetanus_Int | Filaria_Int | 0.000 | | Tetanus_Int | Filaria_Int | 0.000 |

FIG. 2117-L

| | | | | | | |
|---|---|---|---|---|---|---|
| Diptheria_Int | IL_1_alpha | 0.000 | | Diptheria_Int | IL_1_alpha | 0.000 |
| Diptheria_Int | IL_1_beta | 0.000 | | Diptheria_Int | IL_1_beta | 0.000 |
| Diptheria_Int | IL_2 | 0.000 | | Diptheria_Int | IL_2 | 0.000 |
| Diptheria_Int | IL_4 | 0.000 | | Diptheria_Int | IL_4 | 0.000 |
| Diptheria_Int | IL_5 | 0.000 | | Diptheria_Int | IL_5 | 0.000 |
| Diptheria_Int | IL_6 | 0.000 | | Diptheria_Int | IL_6 | 0.000 |
| Diptheria_Int | IL_8 | 0.000 | | Diptheria_Int | IL_8 | 0.000 |
| Diptheria_Int | IL_10 | 0.000 | | Diptheria_Int | IL_10 | 0.000 |
| Diptheria_Int | IL_12p70 | 0.000 | | Diptheria_Int | IL_12p70 | 0.000 |
| Diptheria_Int | IL_13 | 0.000 | | Diptheria_Int | IL_13 | 0.000 |
| Diptheria_Int | IL_15 | 0.000 | | Diptheria_Int | IL_15 | 0.000 |
| Diptheria_Int | IL_17 | 0.000 | | Diptheria_Int | IL_17 | 0.000 |
| Diptheria_Int | IL_23 | 0.000 | | Diptheria_Int | IL_23 | 0.000 |
| Diptheria_Int | IFN_gamma | 0.000 | | Diptheria_Int | IFN_gamma | 0.000 |
| Diptheria_Int | TNF_alpha | 0.000 | | Diptheria_Int | TNF_alpha | 0.000 |
| Diptheria_Int | TNF_beta | 0.000 | | Diptheria_Int | TNF_beta | 0.000 |
| Diptheria_Int | Varicella_Int | 0.000 | | Diptheria_Int | Varicella_Int | 0.000 |
| Diptheria_Int | Measles_OD_DB_Int | 0.000 | | Diptheria_Int | Measles_OD_DB_Int | 0.000 |
| Diptheria_Int | Measles_Int | 0.000 | | Diptheria_Int | Measles_Int | 0.000 |
| Diptheria_Int | HepA_Int | 0.000 | | Diptheria_Int | HepA_Int | 0.000 |
| Diptheria_Int | Tetanus_Int | 0.000 | | Diptheria_Int | Tetanus_Int | 0.000 |
| Diptheria_Int | Diptheria_Int | 1.000 | | Diptheria_Int | Diptheria_Int | 1.000 |
| Diptheria_Int | Rubella_Int | 0.000 | | Diptheria_Int | Rubella_Int | 0.000 |
| Diptheria_Int | CMV_Int | 0.000 | | Diptheria_Int | CMV_Int | 0.000 |
| Diptheria_Int | HepB_cAb_Int | 0.000 | | Diptheria_Int | HepB_cAb_Int | 0.000 |
| Diptheria_Int | HepB_eAb_Int | 0.000 | | Diptheria_Int | HepB_eAb_Int | 0.000 |
| Diptheria_Int | HepB_eAg_Int | 0.000 | | Diptheria_Int | HepB_eAg_Int | 0.000 |
| Diptheria_Int | HepC_Int | 0.000 | | Diptheria_Int | HepC_Int | 0.000 |
| Diptheria_Int | Schistosoma_int | 0.000 | | Diptheria_Int | Schistosoma_int | 0.000 |
| Diptheria_Int | Strongyloides_Int | 0.000 | | Diptheria_Int | Strongyloides_Int | 0.000 |
| Diptheria_Int | Filaria_Int | 0.000 | | Diptheria_Int | Filaria_Int | 0.000 |
| Rubella_Int | IL_1_alpha | -0.204 | | Rubella_Int | IL_1_alpha | 0.210 |
| Rubella_Int | IL_1_beta | 0.024 | | Rubella_Int | IL_1_beta | -0.102 |
| Rubella_Int | IL_2 | -0.093 | | Rubella_Int | IL_2 | -0.102 |
| Rubella_Int | IL_4 | -0.091 | | Rubella_Int | IL_4 | 0.089 |
| Rubella_Int | IL_5 | -0.049 | | Rubella_Int | IL_5 | 0.206 |
| Rubella_Int | IL_6 | -0.101 | | Rubella_Int | IL_6 | 0.167 |
| Rubella_Int | IL_8 | -0.075 | | Rubella_Int | IL_8 | -0.047 |
| Rubella_Int | IL_10 | 0.002 | | Rubella_Int | IL_10 | -0.100 |
| Rubella_Int | IL_12p70 | 0.030 | | Rubella_Int | IL_12p70 | 0.238 |
| Rubella_Int | IL_13 | 0.019 | | Rubella_Int | IL_13 | -0.055 |
| Rubella_Int | IL_15 | -0.026 | | Rubella_Int | IL_15 | -0.022 |
| Rubella_Int | IL_17 | -0.084 | | Rubella_Int | IL_17 | 0.175 |
| Rubella_Int | IL_23 | -0.077 | | Rubella_Int | IL_23 | -0.051 |
| Rubella_Int | IFN_gamma | 0.000 | | Rubella_Int | IFN_gamma | 0.000 |
| Rubella_Int | TNF_alpha | -0.101 | | Rubella_Int | TNF_alpha | 0.141 |
| Rubella_Int | TNF_beta | -0.147 | | Rubella_Int | TNF_beta | -0.007 |
| Rubella_Int | Varicella_Int | -0.089 | | Rubella_Int | Varicella_Int | 0.073 |
| Rubella_Int | Measles_OD_DB_Int | -0.113 | | Rubella_Int | Measles_OD_DB_Int | -0.394 |
| Rubella_Int | Measles_Int | -0.153 | | Rubella_Int | Measles_Int | -0.113 |
| Rubella_Int | HepA_Int | -0.198 | | Rubella_Int | HepA_Int | 0.150 |
| Rubella_Int | Tetanus_Int | 0.000 | | Rubella_Int | Tetanus_Int | 0.000 |
| Rubella_Int | Diptheria_Int | 0.000 | | Rubella_Int | Diptheria_Int | 0.000 |
| Rubella_Int | Rubella_Int | 1.000 | | Rubella_Int | Rubella_Int | 1.000 |
| Rubella_Int | CMV_Int | -0.085 | | Rubella_Int | CMV_Int | 0.058 |
| Rubella_Int | HepB_cAb_Int | 0.086 | | Rubella_Int | HepB_cAb_Int | 0.023 |
| Rubella_Int | HepB_eAb_Int | 0.000 | | Rubella_Int | HepB_eAb_Int | 0.000 |

FIG. 21I7-M

| | | | | | | |
|---|---|---|---|---|---|---|
| Rubella_Int | HepB_eAg_Int | 0.000 | | Rubella_Int | HepB_eAg_Int | 0.000 |
| Rubella_Int | HepC_Int | -0.053 | | Rubella_Int | HepC_Int | 0.000 |
| Rubella_Int | Schistosoma_int | -0.091 | | Rubella_Int | Schistosoma_int | -0.111 |
| Rubella_Int | Strongyloides_Int | -0.242 | | Rubella_Int | Strongyloides_Int | 0.113 |
| Rubella_Int | Filaria_Int | -0.099 | | Rubella_Int | Filaria_Int | -0.097 |
| CMV_Int | IL_1_alpha | 0.238 | | CMV_Int | IL_1_alpha | 0.052 |
| CMV_Int | IL_1_beta | 0.116 | | CMV_Int | IL_1_beta | -0.216 |
| CMV_Int | IL_2 | 0.077 | | CMV_Int | IL_2 | -0.105 |
| CMV_Int | IL_4 | 0.217 | | CMV_Int | IL_4 | -0.029 |
| CMV_Int | IL_5 | 0.153 | | CMV_Int | IL_5 | -0.036 |
| CMV_Int | IL_6 | 0.130 | | CMV_Int | IL_6 | -0.078 |
| CMV_Int | IL_8 | 0.077 | | CMV_Int | IL_8 | -0.361 |
| CMV_Int | IL_10 | 0.173 | | CMV_Int | IL_10 | -0.140 |
| CMV_Int | IL_12p70 | -0.015 | | CMV_Int | IL_12p70 | -0.097 |
| CMV_Int | IL_13 | 0.140 | | CMV_Int | IL_13 | -0.200 |
| CMV_Int | IL_15 | 0.054 | | CMV_Int | IL_15 | -0.072 |
| CMV_Int | IL_17 | 0.073 | | CMV_Int | IL_17 | -0.202 |
| CMV_Int | IL_23 | -0.032 | | CMV_Int | IL_23 | 0.023 |
| CMV_Int | IFN_gamma | 0.000 | | CMV_Int | IFN_gamma | 0.000 |
| CMV_Int | TNF_alpha | 0.061 | | CMV_Int | TNF_alpha | -0.053 |
| CMV_Int | TNF_beta | 0.122 | | CMV_Int | TNF_beta | -0.242 |
| CMV_Int | Varicella_Int | -0.037 | | CMV_Int | Varicella_Int | -0.083 |
| CMV_Int | Measles_OD_DB_Int | 0.044 | | CMV_Int | Measles_OD_DB_Int | -0.108 |
| CMV_Int | Measles_Int | 0.013 | | CMV_Int | Measles_Int | 0.296 |
| CMV_Int | HepA_Int | 0.049 | | CMV_Int | HepA_Int | 0.013 |
| CMV_Int | Tetanus_Int | 0.000 | | CMV_Int | Tetanus_Int | 0.000 |
| CMV_Int | Diptheria_Int | 0.000 | | CMV_Int | Diptheria_Int | 0.000 |
| CMV_Int | Rubella_Int | -0.085 | | CMV_Int | Rubella_Int | 0.058 |
| CMV_Int | CMV_Int | 1.000 | | CMV_Int | CMV_Int | 1.000 |
| CMV_Int | HepB_cAb_Int | 0.154 | | CMV_Int | HepB_cAb_Int | 0.112 |
| CMV_Int | HepB_eAb_Int | 0.000 | | CMV_Int | HepB_eAb_Int | 0.000 |
| CMV_Int | HepB_eAg_Int | 0.000 | | CMV_Int | HepB_eAg_Int | 0.000 |
| CMV_Int | HepC_Int | 0.096 | | CMV_Int | HepC_Int | 0.000 |
| CMV_Int | Schistosoma_int | -0.064 | | CMV_Int | Schistosoma_int | -0.059 |
| CMV_Int | Strongyloides_Int | 0.099 | | CMV_Int | Strongyloides_Int | -0.196 |
| CMV_Int | Filaria_Int | 0.224 | | CMV_Int | Filaria_Int | -0.135 |
| HepB_cAb_Int | IL_1_alpha | 0.217 | | HepB_cAb_Int | IL_1_alpha | 0.042 |
| HepB_cAb_Int | IL_1_beta | 0.135 | | HepB_cAb_Int | IL_1_beta | 0.014 |
| HepB_cAb_Int | IL_2 | 0.006 | | HepB_cAb_Int | IL_2 | -0.125 |
| HepB_cAb_Int | IL_4 | 0.021 | | HepB_cAb_Int | IL_4 | 0.094 |
| HepB_cAb_Int | IL_5 | -0.036 | | HepB_cAb_Int | IL_5 | 0.012 |
| HepB_cAb_Int | IL_6 | 0.124 | | HepB_cAb_Int | IL_6 | 0.043 |
| HepB_cAb_Int | IL_8 | 0.045 | | HepB_cAb_Int | IL_8 | -0.159 |
| HepB_cAb_Int | IL_10 | -0.038 | | HepB_cAb_Int | IL_10 | 0.067 |
| HepB_cAb_Int | IL_12p70 | -0.027 | | HepB_cAb_Int | IL_12p70 | 0.062 |
| HepB_cAb_Int | IL_13 | 0.073 | | HepB_cAb_Int | IL_13 | 0.162 |
| HepB_cAb_Int | IL_15 | -0.078 | | HepB_cAb_Int | IL_15 | -0.133 |
| HepB_cAb_Int | IL_17 | -0.047 | | HepB_cAb_Int | IL_17 | 0.067 |
| HepB_cAb_Int | IL_23 | -0.064 | | HepB_cAb_Int | IL_23 | -0.097 |
| HepB_cAb_Int | IFN_gamma | 0.000 | | HepB_cAb_Int | IFN_gamma | 0.000 |
| HepB_cAb_Int | TNF_alpha | 0.253 | | HepB_cAb_Int | TNF_alpha | -0.146 |
| HepB_cAb_Int | TNF_beta | 0.032 | | HepB_cAb_Int | TNF_beta | -0.004 |
| HepB_cAb_Int | Varicella_Int | 0.067 | | HepB_cAb_Int | Varicella_Int | 0.257 |
| HepB_cAb_Int | Measles_OD_DB_Int | 0.037 | | HepB_cAb_Int | Measles_OD_DB_Int | -0.009 |
| HepB_cAb_Int | Measles_Int | 0.063 | | HepB_cAb_Int | Measles_Int | -0.139 |
| HepB_cAb_Int | HepA_Int | 0.149 | | HepB_cAb_Int | HepA_Int | 0.028 |
| HepB_cAb_Int | Tetanus_Int | 0.000 | | HepB_cAb_Int | Tetanus_Int | 0.000 |

FIG. 2117-N

| | | | | | | |
|---|---|---|---|---|---|---|
| HepB_cAb_Int | Diptheria_Int | 0.000 | | HepB_cAb_Int | Diptheria_Int | 0.000 |
| HepB_cAb_Int | Rubella_Int | 0.086 | | HepB_cAb_Int | Rubella_Int | 0.023 |
| HepB_cAb_Int | CMV_Int | 0.154 | | HepB_cAb_Int | CMV_Int | 0.112 |
| HepB_cAb_Int | HepB_cAb_Int | 1.000 | | HepB_cAb_Int | HepB_cAb_Int | 1.000 |
| HepB_cAb_Int | HepB_eAb_Int | 0.000 | | HepB_cAb_Int | HepB_eAb_Int | 0.000 |
| HepB_cAb_Int | HepB_eAg_Int | 0.000 | | HepB_cAb_Int | HepB_eAg_Int | 0.000 |
| HepB_cAb_Int | HepC_Int | -0.041 | | HepB_cAb_Int | HepC_Int | 0.000 |
| HepB_cAb_Int | Schistosoma_int | 0.005 | | HepB_cAb_Int | Schistosoma_int | -0.203 |
| HepB_cAb_Int | Strongyloides_Int | 0.138 | | HepB_cAb_Int | Strongyloides_Int | -0.171 |
| HepB_cAb_Int | Filaria_Int | 0.111 | | HepB_cAb_Int | Filaria_Int | 0.114 |
| HepB_eAb_Int | IL_1_alpha | 0.000 | | HepB_eAb_Int | IL_1_alpha | 0.340 |
| HepB_eAb_Int | IL_1_beta | 0.000 | | HepB_eAb_Int | IL_1_beta | 0.372 |
| HepB_eAb_Int | IL_2 | 0.000 | | HepB_eAb_Int | IL_2 | -1.000 |
| HepB_eAb_Int | IL_4 | 0.000 | | HepB_eAb_Int | IL_4 | 0.402 |
| HepB_eAb_Int | IL_5 | 0.000 | | HepB_eAb_Int | IL_5 | 0.206 |
| HepB_eAb_Int | IL_6 | 0.000 | | HepB_eAb_Int | IL_6 | 0.488 |
| HepB_eAb_Int | IL_8 | 0.000 | | HepB_eAb_Int | IL_8 | 0.239 |
| HepB_eAb_Int | IL_10 | 0.000 | | HepB_eAb_Int | IL_10 | 0.440 |
| HepB_eAb_Int | IL_12p70 | 0.000 | | HepB_eAb_Int | IL_12p70 | -0.273 |
| HepB_eAb_Int | IL_13 | 0.000 | | HepB_eAb_Int | IL_13 | 0.286 |
| HepB_eAb_Int | IL_15 | 0.000 | | HepB_eAb_Int | IL_15 | 0.352 |
| HepB_eAb_Int | IL_17 | 0.000 | | HepB_eAb_Int | IL_17 | 0.434 |
| HepB_eAb_Int | IL_23 | 0.000 | | HepB_eAb_Int | IL_23 | 0.128 |
| HepB_eAb_Int | IFN_gamma | 0.000 | | HepB_eAb_Int | IFN_gamma | 0.000 |
| HepB_eAb_Int | TNF_alpha | 0.000 | | HepB_eAb_Int | TNF_alpha | 0.024 |
| HepB_eAb_Int | TNF_beta | 0.000 | | HepB_eAb_Int | TNF_beta | 0.294 |
| HepB_eAb_Int | Varicella_Int | 0.000 | | HepB_eAb_Int | Varicella_Int | 0.000 |
| HepB_eAb_Int | Measles_OD_DB_Int | 0.000 | | HepB_eAb_Int | Measles_OD_DB_Int | 0.000 |
| HepB_eAb_Int | Measles_Int | 0.000 | | HepB_eAb_Int | Measles_Int | -0.200 |
| HepB_eAb_Int | HepA_Int | 0.000 | | HepB_eAb_Int | HepA_Int | 0.447 |
| HepB_eAb_Int | Tetanus_Int | 0.000 | | HepB_eAb_Int | Tetanus_Int | 0.000 |
| HepB_eAb_Int | Diptheria_Int | 0.000 | | HepB_eAb_Int | Diptheria_Int | 0.000 |
| HepB_eAb_Int | Rubella_Int | 0.000 | | HepB_eAb_Int | Rubella_Int | 0.000 |
| HepB_eAb_Int | CMV_Int | 0.000 | | HepB_eAb_Int | CMV_Int | 0.000 |
| HepB_eAb_Int | HepB_cAb_Int | 0.000 | | HepB_eAb_Int | HepB_cAb_Int | 0.000 |
| HepB_eAb_Int | HepB_eAb_Int | 1.000 | | HepB_eAb_Int | HepB_eAb_Int | 1.000 |
| HepB_eAb_Int | HepB_eAg_Int | 0.000 | | HepB_eAb_Int | HepB_eAg_Int | 0.000 |
| HepB_eAb_Int | HepC_Int | 0.000 | | HepB_eAb_Int | HepC_Int | 0.000 |
| HepB_eAb_Int | Schistosoma_int | 0.000 | | HepB_eAb_Int | Schistosoma_int | 0.000 |
| HepB_eAb_Int | Strongyloides_Int | 0.000 | | HepB_eAb_Int | Strongyloides_Int | 0.200 |
| HepB_eAb_Int | Filaria_Int | 0.000 | | HepB_eAb_Int | Filaria_Int | 0.000 |
| HepB_eAg_Int | IL_1_alpha | 0.000 | | HepB_eAg_Int | IL_1_alpha | 0.000 |
| HepB_eAg_Int | IL_1_beta | 0.000 | | HepB_eAg_Int | IL_1_beta | 0.000 |
| HepB_eAg_Int | IL_2 | 0.000 | | HepB_eAg_Int | IL_2 | 0.000 |
| HepB_eAg_Int | IL_4 | 0.000 | | HepB_eAg_Int | IL_4 | 0.000 |
| HepB_eAg_Int | IL_5 | 0.000 | | HepB_eAg_Int | IL_5 | 0.000 |
| HepB_eAg_Int | IL_6 | 0.000 | | HepB_eAg_Int | IL_6 | 0.000 |
| HepB_eAg_Int | IL_8 | 0.000 | | HepB_eAg_Int | IL_8 | 0.000 |
| HepB_eAg_Int | IL_10 | 0.000 | | HepB_eAg_Int | IL_10 | 0.000 |
| HepB_eAg_Int | IL_12p70 | 0.000 | | HepB_eAg_Int | IL_12p70 | 0.000 |
| HepB_eAg_Int | IL_13 | 0.000 | | HepB_eAg_Int | IL_13 | 0.000 |
| HepB_eAg_Int | IL_15 | 0.000 | | HepB_eAg_Int | IL_15 | 0.000 |
| HepB_eAg_Int | IL_17 | 0.000 | | HepB_eAg_Int | IL_17 | 0.000 |
| HepB_eAg_Int | IL_23 | 0.000 | | HepB_eAg_Int | IL_23 | 0.000 |
| HepB_eAg_Int | IFN_gamma | 0.000 | | HepB_eAg_Int | IFN_gamma | 0.000 |
| HepB_eAg_Int | TNF_alpha | 0.000 | | HepB_eAg_Int | TNF_alpha | 0.000 |
| HepB_eAg_Int | TNF_beta | 0.000 | | HepB_eAg_Int | TNF_beta | 0.000 |

FIG. 21I7-O

| | | | | | | |
|---|---|---|---|---|---|---|
| HepB_eAg_Int | Varicella_Int | 0.000 | | HepB_eAg_Int | Varicella_Int | 0.000 |
| HepB_eAg_Int | Measles_OD_DB_Int | 0.000 | | HepB_eAg_Int | Measles_OD_DB_Int | 0.000 |
| HepB_eAg_Int | Measles_Int | 0.000 | | HepB_eAg_Int | Measles_Int | 0.000 |
| HepB_eAg_Int | HepA_Int | 0.000 | | HepB_eAg_Int | HepA_Int | 0.000 |
| HepB_eAg_Int | Tetanus_Int | 0.000 | | HepB_eAg_Int | Tetanus_Int | 0.000 |
| HepB_eAg_Int | Diptheria_Int | 0.000 | | HepB_eAg_Int | Diptheria_Int | 0.000 |
| HepB_eAg_Int | Rubella_Int | 0.000 | | HepB_eAg_Int | Rubella_Int | 0.000 |
| HepB_eAg_Int | CMV_Int | 0.000 | | HepB_eAg_Int | CMV_Int | 0.000 |
| HepB_eAg_Int | HepB_cAb_Int | 0.000 | | HepB_eAg_Int | HepB_cAb_Int | 0.000 |
| HepB_eAg_Int | HepB_eAb_Int | 0.000 | | HepB_eAg_Int | HepB_eAb_Int | 0.000 |
| HepB_eAg_Int | HepB_eAg_Int | 1.000 | | HepB_eAg_Int | HepB_eAg_Int | 1.000 |
| HepB_eAg_Int | HepC_Int | 0.000 | | HepB_eAg_Int | HepC_Int | 0.000 |
| HepB_eAg_Int | Schistosoma_int | 0.000 | | HepB_eAg_Int | Schistosoma_int | 0.000 |
| HepB_eAg_Int | Strongyloides_Int | 0.000 | | HepB_eAg_Int | Strongyloides_Int | 0.000 |
| HepB_eAg_Int | Filaria_Int | 0.000 | | HepB_eAg_Int | Filaria_Int | 0.000 |
| HepC_Int | IL_1_alpha | 0.193 | | HepC_Int | IL_1_alpha | 0.000 |
| HepC_Int | IL_1_beta | -0.029 | | HepC_Int | IL_1_beta | 0.000 |
| HepC_Int | IL_2 | 0.042 | | HepC_Int | IL_2 | 0.000 |
| HepC_Int | IL_4 | 0.256 | | HepC_Int | IL_4 | 0.000 |
| HepC_Int | IL_5 | 0.145 | | HepC_Int | IL_5 | 0.000 |
| HepC_Int | IL_6 | 0.015 | | HepC_Int | IL_6 | 0.000 |
| HepC_Int | IL_8 | -0.037 | | HepC_Int | IL_8 | 0.000 |
| HepC_Int | IL_10 | 0.157 | | HepC_Int | IL_10 | 0.000 |
| HepC_Int | IL_12p70 | 0.341 | | HepC_Int | IL_12p70 | 0.000 |
| HepC_Int | IL_13 | 0.293 | | HepC_Int | IL_13 | 0.000 |
| HepC_Int | IL_15 | 0.148 | | HepC_Int | IL_15 | 0.000 |
| HepC_Int | IL_17 | 0.255 | | HepC_Int | IL_17 | 0.000 |
| HepC_Int | IL_23 | 0.092 | | HepC_Int | IL_23 | 0.000 |
| HepC_Int | IFN_gamma | 0.000 | | HepC_Int | IFN_gamma | 0.000 |
| HepC_Int | TNF_alpha | 0.006 | | HepC_Int | TNF_alpha | 0.000 |
| HepC_Int | TNF_beta | -0.051 | | HepC_Int | TNF_beta | 0.000 |
| HepC_Int | Varicella_Int | 0.041 | | HepC_Int | Varicella_Int | 0.000 |
| HepC_Int | Measles_OD_DB_Int | 0.075 | | HepC_Int | Measles_OD_DB_Int | 0.000 |
| HepC_Int | Measles_Int | 0.039 | | HepC_Int | Measles_Int | 0.000 |
| HepC_Int | HepA_Int | -0.092 | | HepC_Int | HepA_Int | 0.000 |
| HepC_Int | Tetanus_Int | 0.000 | | HepC_Int | Tetanus_Int | 0.000 |
| HepC_Int | Diptheria_Int | 0.000 | | HepC_Int | Diptheria_Int | 0.000 |
| HepC_Int | Rubella_Int | -0.053 | | HepC_Int | Rubella_Int | 0.000 |
| HepC_Int | CMV_Int | 0.096 | | HepC_Int | CMV_Int | 0.000 |
| HepC_Int | HepB_cAb_Int | -0.041 | | HepC_Int | HepB_cAb_Int | 0.000 |
| HepC_Int | HepB_eAb_Int | 0.000 | | HepC_Int | HepB_eAb_Int | 0.000 |
| HepC_Int | HepB_eAg_Int | 0.000 | | HepC_Int | HepB_eAg_Int | 0.000 |
| HepC_Int | HepC_Int | 1.000 | | HepC_Int | HepC_Int | 1.000 |
| HepC_Int | Schistosoma_int | 0.098 | | HepC_Int | Schistosoma_int | 0.000 |
| HepC_Int | Strongyloides_Int | 0.015 | | HepC_Int | Strongyloides_Int | 0.000 |
| HepC_Int | Filaria_Int | 0.111 | | HepC_Int | Filaria_Int | 0.000 |
| Schistosoma_int | IL_1_alpha | 0.033 | | Schistosoma_int | IL_1_alpha | 0.012 |
| Schistosoma_int | IL_1_beta | 0.034 | | Schistosoma_int | IL_1_beta | 0.212 |
| Schistosoma_int | IL_2 | -0.086 | | Schistosoma_int | IL_2 | 0.214 |
| Schistosoma_int | IL_4 | 0.095 | | Schistosoma_int | IL_4 | 0.223 |
| Schistosoma_int | IL_5 | 0.053 | | Schistosoma_int | IL_5 | 0.178 |
| Schistosoma_int | IL_6 | -0.060 | | Schistosoma_int | IL_6 | 0.014 |
| Schistosoma_int | IL_8 | -0.032 | | Schistosoma_int | IL_8 | 0.226 |
| Schistosoma_int | IL_10 | 0.041 | | Schistosoma_int | IL_10 | 0.194 |
| Schistosoma_int | IL_12p70 | 0.155 | | Schistosoma_int | IL_12p70 | 0.117 |
| Schistosoma_int | IL_13 | -0.032 | | Schistosoma_int | IL_13 | 0.047 |
| Schistosoma_int | IL_15 | -0.022 | | Schistosoma_int | IL_15 | 0.036 |

FIG. 2117-P

| | | | | | | |
|---|---|---|---|---|---|---|
| Schistosoma_int | IL_17 | -0.003 | | Schistosoma_int | IL_17 | 0.165 |
| Schistosoma_int | IL_23 | 0.125 | | Schistosoma_int | IL_23 | -0.063 |
| Schistosoma_int | IFN_gamma | 0.000 | | Schistosoma_int | IFN_gamma | 0.000 |
| Schistosoma_int | TNF_alpha | 0.093 | | Schistosoma_int | TNF_alpha | 0.143 |
| Schistosoma_int | TNF_beta | 0.010 | | Schistosoma_int | TNF_beta | 0.190 |
| Schistosoma_int | Varicella_Int | -0.097 | | Schistosoma_int | Varicella_Int | -0.061 |
| Schistosoma_int | Measles_OD_DB_Int | 0.073 | | Schistosoma_int | Measles_OD_DB_Int | -0.191 |
| Schistosoma_int | Measles_Int | -0.026 | | Schistosoma_int | Measles_Int | 0.003 |
| Schistosoma_int | HepA_Int | -0.149 | | Schistosoma_int | HepA_Int | 0.005 |
| Schistosoma_int | Tetanus_Int | 0.000 | | Schistosoma_int | Tetanus_Int | 0.000 |
| Schistosoma_int | Diptheria_Int | 0.000 | | Schistosoma_int | Diptheria_Int | 0.000 |
| Schistosoma_int | Rubella_Int | -0.091 | | Schistosoma_int | Rubella_Int | -0.111 |
| Schistosoma_int | CMV_Int | -0.064 | | Schistosoma_int | CMV_Int | -0.059 |
| Schistosoma_int | HepB_cAb_Int | 0.005 | | Schistosoma_int | HepB_cAb_Int | -0.203 |
| Schistosoma_int | HepB_eAb_Int | 0.000 | | Schistosoma_int | HepB_eAb_Int | 0.000 |
| Schistosoma_int | HepB_eAg_Int | 0.000 | | Schistosoma_int | HepB_eAg_Int | 0.000 |
| Schistosoma_int | HepC_Int | 0.098 | | Schistosoma_int | HepC_Int | 0.000 |
| Schistosoma_int | Schistosoma_int | 1.000 | | Schistosoma_int | Schistosoma_int | 1.000 |
| Schistosoma_int | Strongyloides_Int | 0.193 | | Schistosoma_int | Strongyloides_Int | 0.210 |
| Schistosoma_int | Filaria_Int | -0.005 | | Schistosoma_int | Filaria_Int | -0.003 |
| Strongyloides_Int | IL_1_alpha | 0.170 | | Strongyloides_Int | IL_1_alpha | 0.233 |
| Strongyloides_Int | IL_1_beta | -0.131 | | Strongyloides_Int | IL_1_beta | 0.143 |
| Strongyloides_Int | IL_2 | 0.027 | | Strongyloides_Int | IL_2 | 0.254 |
| Strongyloides_Int | IL_4 | 0.036 | | Strongyloides_Int | IL_4 | -0.025 |
| Strongyloides_Int | IL_5 | -0.045 | | Strongyloides_Int | IL_5 | 0.108 |
| Strongyloides_Int | IL_6 | 0.055 | | Strongyloides_Int | IL_6 | 0.123 |
| Strongyloides_Int | IL_8 | 0.167 | | Strongyloides_Int | IL_8 | 0.198 |
| Strongyloides_Int | IL_10 | -0.062 | | Strongyloides_Int | IL_10 | 0.150 |
| Strongyloides_Int | IL_12p70 | 0.063 | | Strongyloides_Int | IL_12p70 | 0.173 |
| Strongyloides_Int | IL_13 | -0.132 | | Strongyloides_Int | IL_13 | 0.122 |
| Strongyloides_Int | IL_15 | 0.035 | | Strongyloides_Int | IL_15 | 0.036 |
| Strongyloides_Int | IL_17 | -0.124 | | Strongyloides_Int | IL_17 | 0.333 |
| Strongyloides_Int | IL_23 | 0.120 | | Strongyloides_Int | IL_23 | 0.148 |
| Strongyloides_Int | IFN_gamma | 0.000 | | Strongyloides_Int | IFN_gamma | 0.000 |
| Strongyloides_Int | TNF_alpha | 0.003 | | Strongyloides_Int | TNF_alpha | 0.244 |
| Strongyloides_Int | TNF_beta | 0.133 | | Strongyloides_Int | TNF_beta | 0.207 |
| Strongyloides_Int | Varicella_Int | -0.138 | | Strongyloides_Int | Varicella_Int | -0.025 |
| Strongyloides_Int | Measles_OD_DB_Int | -0.023 | | Strongyloides_Int | Measles_OD_DB_Int | -0.222 |
| Strongyloides_Int | Measles_Int | 0.091 | | Strongyloides_Int | Measles_Int | -0.186 |
| Strongyloides_Int | HepA_Int | 0.198 | | Strongyloides_Int | HepA_Int | 0.208 |
| Strongyloides_Int | Tetanus_Int | 0.000 | | Strongyloides_Int | Tetanus_Int | 0.000 |
| Strongyloides_Int | Diptheria_Int | 0.000 | | Strongyloides_Int | Diptheria_Int | 0.000 |
| Strongyloides_Int | Rubella_Int | -0.242 | | Strongyloides_Int | Rubella_Int | 0.113 |
| Strongyloides_Int | CMV_Int | 0.099 | | Strongyloides_Int | CMV_Int | -0.196 |
| Strongyloides_Int | HepB_cAb_Int | 0.138 | | Strongyloides_Int | HepB_cAb_Int | -0.171 |
| Strongyloides_Int | HepB_eAb_Int | 0.000 | | Strongyloides_Int | HepB_eAb_Int | 0.200 |
| Strongyloides_Int | HepB_eAg_Int | 0.000 | | Strongyloides_Int | HepB_eAg_Int | 0.000 |
| Strongyloides_Int | HepC_Int | 0.015 | | Strongyloides_Int | HepC_Int | 0.000 |
| Strongyloides_Int | Schistosoma_int | 0.193 | | Strongyloides_Int | Schistosoma_int | 0.210 |
| Strongyloides_Int | Strongyloides_Int | 1.000 | | Strongyloides_Int | Strongyloides_Int | 1.000 |
| Strongyloides_Int | Filaria_Int | 0.259 | | Strongyloides_Int | Filaria_Int | 0.258 |
| Filaria_Int | IL_1_alpha | 0.166 | | Filaria_Int | IL_1_alpha | 0.031 |
| Filaria_Int | IL_1_beta | 0.061 | | Filaria_Int | IL_1_beta | 0.392 |
| Filaria_Int | IL_2 | 0.286 | | Filaria_Int | IL_2 | 0.317 |
| Filaria_Int | IL_4 | -0.087 | | Filaria_Int | IL_4 | 0.250 |
| Filaria_Int | IL_5 | -0.050 | | Filaria_Int | IL_5 | 0.029 |
| Filaria_Int | IL_6 | 0.095 | | Filaria_Int | IL_6 | 0.101 |

FIG. 21I7-Q

| Filaria_Int | IL_8 | 0.115 |
|---|---|---|
| Filaria_Int | IL_10 | 0.196 |
| Filaria_Int | IL_12p70 | 0.004 |
| Filaria_Int | IL_13 | 0.237 |
| Filaria_Int | IL_15 | -0.173 |
| Filaria_Int | IL_17 | 0.142 |
| Filaria_Int | IL_23 | -0.087 |
| Filaria_Int | IFN_gamma | 0.000 |
| Filaria_Int | TNF_alpha | 0.082 |
| Filaria_Int | TNF_beta | 0.208 |
| Filaria_Int | Varicella_Int | 0.026 |
| Filaria_Int | Measles_OD_DB_Int | 0.078 |
| Filaria_Int | Measles_Int | 0.152 |
| Filaria_Int | HepA_Int | 0.133 |
| Filaria_Int | Tetanus_Int | 0.000 |
| Filaria_Int | Diptheria_Int | 0.000 |
| Filaria_Int | Rubella_Int | -0.099 |
| Filaria_Int | CMV_Int | 0.224 |
| Filaria_Int | HepB_cAb_Int | 0.111 |
| Filaria_Int | HepB_eAb_Int | 0.000 |
| Filaria_Int | HepB_eAg_Int | 0.000 |
| Filaria_Int | HepC_Int | 0.111 |
| Filaria_Int | Schistosoma_int | -0.005 |
| Filaria_Int | Strongyloides_Int | 0.259 |
| Filaria_Int | Filaria_Int | 1.000 |

| Filaria_Int | IL_8 | 0.087 |
|---|---|---|
| Filaria_Int | IL_10 | 0.260 |
| Filaria_Int | IL_12p70 | 0.272 |
| Filaria_Int | IL_13 | 0.297 |
| Filaria_Int | IL_15 | 0.308 |
| Filaria_Int | IL_17 | 0.272 |
| Filaria_Int | IL_23 | -0.057 |
| Filaria_Int | IFN_gamma | 0.000 |
| Filaria_Int | TNF_alpha | 0.189 |
| Filaria_Int | TNF_beta | 0.350 |
| Filaria_Int | Varicella_Int | -0.012 |
| Filaria_Int | Measles_OD_DB_Int | 0.029 |
| Filaria_Int | Measles_Int | -0.057 |
| Filaria_Int | HepA_Int | 0.057 |
| Filaria_Int | Tetanus_Int | 0.000 |
| Filaria_Int | Diptheria_Int | 0.000 |
| Filaria_Int | Rubella_Int | -0.097 |
| Filaria_Int | CMV_Int | -0.135 |
| Filaria_Int | HepB_cAb_Int | 0.114 |
| Filaria_Int | HepB_eAb_Int | 0.000 |
| Filaria_Int | HepB_eAg_Int | 0.000 |
| Filaria_Int | HepC_Int | 0.000 |
| Filaria_Int | Schistosoma_int | -0.003 |
| Filaria_Int | Strongyloides_Int | 0.258 |
| Filaria_Int | Filaria_Int | 1.000 |

FIG. 21I7-R

| 3.17% - Region_of_Origin=5, Sex=Male, IFN_gamma=0-7.5 | | |
|---|---|---|
| Property 1 | Property 2 | Corr. Coefficient |
| IL_1_alpha | IL_1_alpha | 1.000 |
| IL_1_alpha | IL_1_beta | 0.649 |
| IL_1_alpha | IL_2 | 0.841 |
| IL_1_alpha | IL_4 | 0.512 |
| IL_1_alpha | IL_5 | 0.740 |
| IL_1_alpha | IL_6 | 0.729 |
| IL_1_alpha | IL_8 | 0.409 |
| IL_1_alpha | IL_10 | 0.598 |
| IL_1_alpha | IL_12p70 | 0.354 |
| IL_1_alpha | IL_13 | 0.539 |
| IL_1_alpha | IL_15 | 0.439 |
| IL_1_alpha | IL_17 | -0.007 |
| IL_1_alpha | IL_23 | 0.030 |
| IL_1_alpha | IFN_gamma | 0.000 |
| IL_1_alpha | TNF_alpha | 0.741 |
| IL_1_alpha | TNF_beta | 0.471 |
| IL_1_alpha | Varicella_Int | -0.016 |
| IL_1_alpha | Measles_OD_DB_Int | 0.128 |
| IL_1_alpha | Measles_Int | -0.078 |
| IL_1_alpha | HepA_Int | -0.160 |
| IL_1_alpha | Tetanus_Int | 0.000 |
| IL_1_alpha | Diptheria_Int | 0.000 |
| IL_1_alpha | Rubella_Int | -0.092 |
| IL_1_alpha | CMV_Int | 0.192 |
| IL_1_alpha | HepB_cAb_Int | 0.043 |
| IL_1_alpha | HepB_eAb_Int | 0.000 |
| IL_1_alpha | HepB_eAg_Int | 0.000 |
| IL_1_alpha | HepC_Int | -0.164 |

| 3.03% - Region_of_Origin=3, Sex=Male, IFN_gamma=0-7.5 | | |
|---|---|---|
| Property 1 | Property 2 | Corr. Coefficient |
| IL_1_alpha | IL_1_alpha | 1.000 |
| IL_1_alpha | IL_1_beta | 0.581 |
| IL_1_alpha | IL_2 | 0.165 |
| IL_1_alpha | IL_4 | 0.646 |
| IL_1_alpha | IL_5 | 0.409 |
| IL_1_alpha | IL_6 | 0.046 |
| IL_1_alpha | IL_8 | 0.009 |
| IL_1_alpha | IL_10 | 0.473 |
| IL_1_alpha | IL_12p70 | 0.723 |
| IL_1_alpha | IL_13 | 0.616 |
| IL_1_alpha | IL_15 | 0.486 |
| IL_1_alpha | IL_17 | 0.458 |
| IL_1_alpha | IL_23 | 0.358 |
| IL_1_alpha | IFN_gamma | 0.000 |
| IL_1_alpha | TNF_alpha | 0.346 |
| IL_1_alpha | TNF_beta | 0.674 |
| IL_1_alpha | Varicella_Int | 0.024 |
| IL_1_alpha | Measles_OD_DB_Int | 0.010 |
| IL_1_alpha | Measles_Int | 0.000 |
| IL_1_alpha | HepA_Int | 0.062 |
| IL_1_alpha | Tetanus_Int | 0.000 |
| IL_1_alpha | Diptheria_Int | 0.000 |
| IL_1_alpha | Rubella_Int | 0.364 |
| IL_1_alpha | CMV_Int | -0.175 |
| IL_1_alpha | HepB_cAb_Int | -0.331 |
| IL_1_alpha | HepB_eAb_Int | 0.000 |
| IL_1_alpha | HepB_eAg_Int | 0.000 |
| IL_1_alpha | HepC_Int | -0.078 |

FIG. 21I8-A

| | | | | | | |
|---|---|---|---|---|---|---|
| IL_1_alpha | Schistosoma_int | -0.164 | | IL_1_alpha | Schistosoma_int | -0.178 |
| IL_1_alpha | Strongyloides_Int | -0.035 | | IL_1_alpha | Strongyloides_Int | 0.045 |
| IL_1_alpha | Filaria_Int | 0.039 | | IL_1_alpha | Filaria_Int | 0.124 |
| IL_1_beta | IL_1_alpha | 0.649 | | IL_1_beta | IL_1_alpha | 0.581 |
| IL_1_beta | IL_1_beta | 1.000 | | IL_1_beta | IL_1_beta | 1.000 |
| IL_1_beta | IL_2 | 0.755 | | IL_1_beta | IL_2 | 0.225 |
| IL_1_beta | IL_4 | 0.626 | | IL_1_beta | IL_4 | 0.793 |
| IL_1_beta | IL_5 | 0.777 | | IL_1_beta | IL_5 | 0.343 |
| IL_1_beta | IL_6 | 0.700 | | IL_1_beta | IL_6 | 0.101 |
| IL_1_beta | IL_8 | 0.543 | | IL_1_beta | IL_8 | -0.084 |
| IL_1_beta | IL_10 | 0.763 | | IL_1_beta | IL_10 | 0.814 |
| IL_1_beta | IL_12p70 | 0.342 | | IL_1_beta | IL_12p70 | 0.733 |
| IL_1_beta | IL_13 | 0.801 | | IL_1_beta | IL_13 | 0.826 |
| IL_1_beta | IL_15 | 0.442 | | IL_1_beta | IL_15 | 0.326 |
| IL_1_beta | IL_17 | 0.036 | | IL_1_beta | IL_17 | 0.785 |
| IL_1_beta | IL_23 | 0.058 | | IL_1_beta | IL_23 | 0.032 |
| IL_1_beta | IFN_gamma | 0.000 | | IL_1_beta | IFN_gamma | 0.000 |
| IL_1_beta | TNF_alpha | 0.808 | | IL_1_beta | TNF_alpha | 0.508 |
| IL_1_beta | TNF_beta | 0.707 | | IL_1_beta | TNF_beta | 0.597 |
| IL_1_beta | Varicella_Int | 0.123 | | IL_1_beta | Varicella_Int | -0.025 |
| IL_1_beta | Measles_OD_DB_Int | 0.155 | | IL_1_beta | Measles_OD_DB_Int | 0.037 |
| IL_1_beta | Measles_Int | -0.044 | | IL_1_beta | Measles_Int | 0.000 |
| IL_1_beta | HepA_Int | -0.205 | | IL_1_beta | HepA_Int | 0.112 |
| IL_1_beta | Tetanus_Int | 0.000 | | IL_1_beta | Tetanus_Int | 0.000 |
| IL_1_beta | Diptheria_Int | 0.000 | | IL_1_beta | Diptheria_Int | 0.000 |
| IL_1_beta | Rubella_Int | -0.073 | | IL_1_beta | Rubella_Int | 0.233 |
| IL_1_beta | CMV_Int | 0.145 | | IL_1_beta | CMV_Int | -0.014 |
| IL_1_beta | HepB_cAb_Int | -0.077 | | IL_1_beta | HepB_cAb_Int | -0.246 |
| IL_1_beta | HepB_eAb_Int | 0.000 | | IL_1_beta | HepB_eAb_Int | 0.000 |
| IL_1_beta | HepB_eAg_Int | 0.000 | | IL_1_beta | HepB_eAg_Int | 0.000 |
| IL_1_beta | HepC_Int | 0.084 | | IL_1_beta | HepC_Int | -0.097 |
| IL_1_beta | Schistosoma_int | -0.102 | | IL_1_beta | Schistosoma_int | -0.151 |
| IL_1_beta | Strongyloides_Int | -0.002 | | IL_1_beta | Strongyloides_Int | 0.253 |
| IL_1_beta | Filaria_Int | 0.092 | | IL_1_beta | Filaria_Int | 0.078 |
| IL_2 | IL_1_alpha | 0.841 | | IL_2 | IL_1_alpha | 0.165 |
| IL_2 | IL_1_beta | 0.755 | | IL_2 | IL_1_beta | 0.225 |
| IL_2 | IL_2 | 1.000 | | IL_2 | IL_2 | 1.000 |
| IL_2 | IL_4 | 0.575 | | IL_2 | IL_4 | 0.208 |
| IL_2 | IL_5 | 0.794 | | IL_2 | IL_5 | 0.118 |
| IL_2 | IL_6 | 0.608 | | IL_2 | IL_6 | 0.888 |
| IL_2 | IL_8 | 0.450 | | IL_2 | IL_8 | -0.031 |
| IL_2 | IL_10 | 0.662 | | IL_2 | IL_10 | 0.199 |
| IL_2 | IL_12p70 | 0.352 | | IL_2 | IL_12p70 | 0.269 |
| IL_2 | IL_13 | 0.613 | | IL_2 | IL_13 | 0.151 |
| IL_2 | IL_15 | 0.473 | | IL_2 | IL_15 | 0.292 |
| IL_2 | IL_17 | 0.018 | | IL_2 | IL_17 | 0.461 |
| IL_2 | IL_23 | 0.010 | | IL_2 | IL_23 | -0.012 |
| IL_2 | IFN_gamma | 0.000 | | IL_2 | IFN_gamma | 0.000 |
| IL_2 | TNF_alpha | 0.733 | | IL_2 | TNF_alpha | 0.217 |
| IL_2 | TNF_beta | 0.523 | | IL_2 | TNF_beta | 0.321 |
| IL_2 | Varicella_Int | 0.170 | | IL_2 | Varicella_Int | 0.070 |
| IL_2 | Measles_OD_DB_Int | -0.035 | | IL_2 | Measles_OD_DB_Int | 0.160 |
| IL_2 | Measles_Int | -0.231 | | IL_2 | Measles_Int | 0.000 |
| IL_2 | HepA_Int | -0.265 | | IL_2 | HepA_Int | 0.051 |
| IL_2 | Tetanus_Int | 0.000 | | IL_2 | Tetanus_Int | 0.000 |
| IL_2 | Diptheria_Int | 0.000 | | IL_2 | Diptheria_Int | 0.000 |
| IL_2 | Rubella_Int | -0.076 | | IL_2 | Rubella_Int | 0.134 |

FIG. 21I8-B

| | | | | | | |
|---|---|---|---|---|---|---|
| IL_2 | CMV_Int | 0.158 | | IL_2 | CMV_Int | 0.073 |
| IL_2 | HepB_cAb_Int | 0.067 | | IL_2 | HepB_cAb_Int | -0.159 |
| IL_2 | HepB_eAb_Int | 0.000 | | IL_2 | HepB_eAb_Int | 0.000 |
| IL_2 | HepB_eAg_Int | 0.000 | | IL_2 | HepB_eAg_Int | 0.000 |
| IL_2 | HepC_Int | -0.107 | | IL_2 | HepC_Int | -0.058 |
| IL_2 | Schistosoma_int | -0.072 | | IL_2 | Schistosoma_int | 0.432 |
| IL_2 | Strongyloides_Int | -0.006 | | IL_2 | Strongyloides_Int | -0.110 |
| IL_2 | Filaria_Int | 0.098 | | IL_2 | Filaria_Int | -0.145 |
| IL_4 | IL_1_alpha | 0.512 | | IL_4 | IL_1_alpha | 0.646 |
| IL_4 | IL_1_beta | 0.626 | | IL_4 | IL_1_beta | 0.793 |
| IL_4 | IL_2 | 0.575 | | IL_4 | IL_2 | 0.208 |
| IL_4 | IL_4 | 1.000 | | IL_4 | IL_4 | 1.000 |
| IL_4 | IL_5 | 0.649 | | IL_4 | IL_5 | 0.442 |
| IL_4 | IL_6 | 0.511 | | IL_4 | IL_6 | 0.085 |
| IL_4 | IL_8 | 0.440 | | IL_4 | IL_8 | -0.029 |
| IL_4 | IL_10 | 0.495 | | IL_4 | IL_10 | 0.524 |
| IL_4 | IL_12p70 | 0.396 | | IL_4 | IL_12p70 | 0.698 |
| IL_4 | IL_13 | 0.532 | | IL_4 | IL_13 | 0.835 |
| IL_4 | IL_15 | 0.509 | | IL_4 | IL_15 | 0.470 |
| IL_4 | IL_17 | 0.074 | | IL_4 | IL_17 | 0.547 |
| IL_4 | IL_23 | 0.133 | | IL_4 | IL_23 | 0.121 |
| IL_4 | IFN_gamma | 0.000 | | IL_4 | IFN_gamma | 0.000 |
| IL_4 | TNF_alpha | 0.499 | | IL_4 | TNF_alpha | 0.532 |
| IL_4 | TNF_beta | 0.350 | | IL_4 | TNF_beta | 0.660 |
| IL_4 | Varicella_Int | 0.065 | | IL_4 | Varicella_Int | -0.011 |
| IL_4 | Measles_OD_DB_Int | 0.191 | | IL_4 | Measles_OD_DB_Int | 0.183 |
| IL_4 | Measles_Int | 0.034 | | IL_4 | Measles_Int | 0.000 |
| IL_4 | HepA_Int | -0.368 | | IL_4 | HepA_Int | 0.101 |
| IL_4 | Tetanus_Int | 0.000 | | IL_4 | Tetanus_Int | 0.000 |
| IL_4 | Diptheria_Int | 0.000 | | IL_4 | Diptheria_Int | 0.000 |
| IL_4 | Rubella_Int | -0.081 | | IL_4 | Rubella_Int | 0.343 |
| IL_4 | CMV_Int | 0.120 | | IL_4 | CMV_Int | -0.156 |
| IL_4 | HepB_cAb_Int | 0.201 | | IL_4 | HepB_cAb_Int | -0.263 |
| IL_4 | HepB_eAb_Int | 0.000 | | IL_4 | HepB_eAb_Int | 0.000 |
| IL_4 | HepB_eAg_Int | 0.000 | | IL_4 | HepB_eAg_Int | 0.000 |
| IL_4 | HepC_Int | 0.312 | | IL_4 | HepC_Int | 0.073 |
| IL_4 | Schistosoma_int | 0.323 | | IL_4 | Schistosoma_int | -0.153 |
| IL_4 | Strongyloides_Int | -0.192 | | IL_4 | Strongyloides_Int | 0.259 |
| IL_4 | Filaria_Int | 0.088 | | IL_4 | Filaria_Int | -0.001 |
| IL_5 | IL_1_alpha | 0.740 | | IL_5 | IL_1_alpha | 0.409 |
| IL_5 | IL_1_beta | 0.777 | | IL_5 | IL_1_beta | 0.343 |
| IL_5 | IL_2 | 0.794 | | IL_5 | IL_2 | 0.118 |
| IL_5 | IL_4 | 0.649 | | IL_5 | IL_4 | 0.442 |
| IL_5 | IL_5 | 1.000 | | IL_5 | IL_5 | 1.000 |
| IL_5 | IL_6 | 0.721 | | IL_5 | IL_6 | 0.047 |
| IL_5 | IL_8 | 0.463 | | IL_5 | IL_8 | -0.019 |
| IL_5 | IL_10 | 0.687 | | IL_5 | IL_10 | 0.258 |
| IL_5 | IL_12p70 | 0.337 | | IL_5 | IL_12p70 | 0.217 |
| IL_5 | IL_13 | 0.602 | | IL_5 | IL_13 | 0.284 |
| IL_5 | IL_15 | 0.547 | | IL_5 | IL_15 | 0.424 |
| IL_5 | IL_17 | 0.214 | | IL_5 | IL_17 | 0.205 |
| IL_5 | IL_23 | -0.028 | | IL_5 | IL_23 | 0.052 |
| IL_5 | IFN_gamma | 0.000 | | IL_5 | IFN_gamma | 0.000 |
| IL_5 | TNF_alpha | 0.725 | | IL_5 | TNF_alpha | 0.315 |
| IL_5 | TNF_beta | 0.578 | | IL_5 | TNF_beta | 0.669 |
| IL_5 | Varicella_Int | 0.108 | | IL_5 | Varicella_Int | -0.497 |
| IL_5 | Measles_OD_DB_Int | 0.137 | | IL_5 | Measles_OD_DB_Int | 0.174 |

FIG. 21I8-C

| | | | | | | |
|---|---|---|---|---|---|---|
| IL_5 | Measles_Int | 0.004 | | IL_5 | Measles_Int | 0.000 |
| IL_5 | HepA_Int | -0.254 | | IL_5 | HepA_Int | 0.115 |
| IL_5 | Tetanus_Int | 0.000 | | IL_5 | Tetanus_Int | 0.000 |
| IL_5 | Diptheria_Int | 0.000 | | IL_5 | Diptheria_Int | 0.000 |
| IL_5 | Rubella_Int | -0.093 | | IL_5 | Rubella_Int | 0.087 |
| IL_5 | CMV_Int | 0.130 | | IL_5 | CMV_Int | -0.382 |
| IL_5 | HepB_cAb_Int | -0.016 | | IL_5 | HepB_cAb_Int | -0.185 |
| IL_5 | HepB_eAb_Int | 0.000 | | IL_5 | HepB_eAb_Int | 0.000 |
| IL_5 | HepB_eAg_Int | 0.000 | | IL_5 | HepB_eAg_Int | 0.000 |
| IL_5 | HepC_Int | -0.116 | | IL_5 | HepC_Int | -0.073 |
| IL_5 | Schistosoma_int | -0.118 | | IL_5 | Schistosoma_int | -0.129 |
| IL_5 | Strongyloides_Int | -0.100 | | IL_5 | Strongyloides_Int | 0.182 |
| IL_5 | Filaria_Int | -0.104 | | IL_5 | Filaria_Int | 0.365 |
| IL_6 | IL_1_alpha | 0.729 | | IL_6 | IL_1_alpha | 0.046 |
| IL_6 | IL_1_beta | 0.700 | | IL_6 | IL_1_beta | 0.101 |
| IL_6 | IL_2 | 0.608 | | IL_6 | IL_2 | 0.888 |
| IL_6 | IL_4 | 0.511 | | IL_6 | IL_4 | 0.085 |
| IL_6 | IL_5 | 0.721 | | IL_6 | IL_5 | 0.047 |
| IL_6 | IL_6 | 1.000 | | IL_6 | IL_6 | 1.000 |
| IL_6 | IL_8 | 0.506 | | IL_6 | IL_8 | 0.012 |
| IL_6 | IL_10 | 0.537 | | IL_6 | IL_10 | 0.065 |
| IL_6 | IL_12p70 | 0.311 | | IL_6 | IL_12p70 | 0.131 |
| IL_6 | IL_13 | 0.623 | | IL_6 | IL_13 | 0.049 |
| IL_6 | IL_15 | 0.454 | | IL_6 | IL_15 | 0.273 |
| IL_6 | IL_17 | -0.006 | | IL_6 | IL_17 | 0.305 |
| IL_6 | IL_23 | 0.011 | | IL_6 | IL_23 | -0.022 |
| IL_6 | IFN_gamma | 0.000 | | IL_6 | IFN_gamma | 0.000 |
| IL_6 | TNF_alpha | 0.783 | | IL_6 | TNF_alpha | -0.003 |
| IL_6 | TNF_beta | 0.408 | | IL_6 | TNF_beta | 0.102 |
| IL_6 | Varicella_Int | 0.074 | | IL_6 | Varicella_Int | 0.044 |
| IL_6 | Measles_OD_DB_Int | 0.179 | | IL_6 | Measles_OD_DB_Int | 0.114 |
| IL_6 | Measles_Int | 0.025 | | IL_6 | Measles_Int | 0.000 |
| IL_6 | HepA_Int | -0.122 | | IL_6 | HepA_Int | 0.109 |
| IL_6 | Tetanus_Int | 0.000 | | IL_6 | Tetanus_Int | 0.000 |
| IL_6 | Diptheria_Int | 0.000 | | IL_6 | Diptheria_Int | 0.000 |
| IL_6 | Rubella_Int | -0.005 | | IL_6 | Rubella_Int | 0.049 |
| IL_6 | CMV_Int | 0.223 | | IL_6 | CMV_Int | -0.003 |
| IL_6 | HepB_cAb_Int | 0.137 | | IL_6 | HepB_cAb_Int | -0.162 |
| IL_6 | HepB_eAb_Int | 0.000 | | IL_6 | HepB_eAb_Int | 0.000 |
| IL_6 | HepB_eAg_Int | 0.000 | | IL_6 | HepB_eAg_Int | 0.000 |
| IL_6 | HepC_Int | -0.136 | | IL_6 | HepC_int | -0.065 |
| IL_6 | Schistosoma_int | -0.189 | | IL_6 | Schistosoma_int | 0.512 |
| IL_6 | Strongyloides_Int | -0.018 | | IL_6 | Strongyloides_Int | -0.115 |
| IL_6 | Filaria_Int | -0.097 | | IL_6 | Filaria_Int | -0.066 |
| IL_8 | IL_1_alpha | 0.409 | | IL_8 | IL_1_alpha | 0.009 |
| IL_8 | IL_1_beta | 0.543 | | IL_8 | IL_1_beta | -0.084 |
| IL_8 | IL_2 | 0.450 | | IL_8 | IL_2 | -0.031 |
| IL_8 | IL_4 | 0.440 | | IL_8 | IL_4 | -0.029 |
| IL_8 | IL_5 | 0.463 | | IL_8 | IL_5 | -0.019 |
| IL_8 | IL_6 | 0.506 | | IL_8 | IL_6 | 0.012 |
| IL_8 | IL_8 | 1.000 | | IL_8 | IL_8 | 1.000 |
| IL_8 | IL_10 | 0.421 | | IL_8 | IL_10 | 0.004 |
| IL_8 | IL_12p70 | 0.059 | | IL_8 | IL_12p70 | 0.006 |
| IL_8 | IL_13 | 0.432 | | IL_8 | IL_13 | -0.091 |
| IL_8 | IL_15 | 0.466 | | IL_8 | IL_15 | 0.216 |
| IL_8 | IL_17 | 0.110 | | IL_8 | IL_17 | -0.067 |
| IL_8 | IL_23 | -0.047 | | IL_8 | IL_23 | -0.002 |

FIG. 21I8-D

| IL_8 | IFN_gamma | 0.000 | IL_8 | IFN_gamma | 0.000 |
|---|---|---|---|---|---|
| IL_8 | TNF_alpha | 0.393 | IL_8 | TNF_alpha | -0.030 |
| IL_8 | TNF_beta | 0.197 | IL_8 | TNF_beta | 0.013 |
| IL_8 | Varicella_Int | -0.006 | IL_8 | Varicella_Int | 0.049 |
| IL_8 | Measles_OD_DB_Int | 0.217 | IL_8 | Measles_OD_DB_Int | -0.138 |
| IL_8 | Measles_Int | -0.072 | IL_8 | Measles_Int | 0.000 |
| IL_8 | HepA_Int | -0.023 | IL_8 | HepA_Int | 0.009 |
| IL_8 | Tetanus_Int | 0.000 | IL_8 | Tetanus_Int | 0.000 |
| IL_8 | Diptheria_Int | 0.000 | IL_8 | Diptheria_Int | 0.000 |
| IL_8 | Rubella_Int | 0.339 | IL_8 | Rubella_Int | 0.004 |
| IL_8 | CMV_Int | 0.232 | IL_8 | CMV_Int | -0.043 |
| IL_8 | HepB_cAb_Int | 0.123 | IL_8 | HepB_cAb_Int | -0.167 |
| IL_8 | HepB_eAb_Int | 0.000 | IL_8 | HepB_eAb_Int | 0.000 |
| IL_8 | HepB_eAg_Int | 0.000 | IL_8 | HepB_eAg_Int | 0.000 |
| IL_8 | HepC_Int | -0.138 | IL_8 | HepC_Int | -0.052 |
| IL_8 | Schistosoma_int | -0.032 | IL_8 | Schistosoma_int | -0.104 |
| IL_8 | Strongyloides_Int | -0.009 | IL_8 | Strongyloides_Int | -0.153 |
| IL_8 | Filaria_Int | -0.110 | IL_8 | Filaria_Int | -0.110 |
| IL_10 | IL_1_alpha | 0.598 | IL_10 | IL_1_alpha | 0.473 |
| IL_10 | IL_1_beta | 0.763 | IL_10 | IL_1_beta | 0.814 |
| IL_10 | IL_2 | 0.662 | IL_10 | IL_2 | 0.199 |
| IL_10 | IL_4 | 0.495 | IL_10 | IL_4 | 0.524 |
| IL_10 | IL_5 | 0.687 | IL_10 | IL_5 | 0.258 |
| IL_10 | IL_6 | 0.537 | IL_10 | IL_6 | 0.065 |
| IL_10 | IL_8 | 0.421 | IL_10 | IL_8 | 0.004 |
| IL_10 | IL_10 | 1.000 | IL_10 | IL_10 | 1.000 |
| IL_10 | IL_12p70 | 0.167 | IL_10 | IL_12p70 | 0.525 |
| IL_10 | IL_13 | 0.712 | IL_10 | IL_13 | 0.543 |
| IL_10 | IL_15 | 0.259 | IL_10 | IL_15 | 0.194 |
| IL_10 | IL_17 | 0.375 | IL_10 | IL_17 | 0.867 |
| IL_10 | IL_23 | -0.066 | IL_10 | IL_23 | 0.115 |
| IL_10 | IFN_gamma | 0.000 | IL_10 | IFN_gamma | 0.000 |
| IL_10 | TNF_alpha | 0.554 | IL_10 | TNF_alpha | 0.501 |
| IL_10 | TNF_beta | 0.737 | IL_10 | TNF_beta | 0.547 |
| IL_10 | Varicella_Int | -0.030 | IL_10 | Varicella_Int | 0.082 |
| IL_10 | Measles_OD_DB_Int | 0.164 | IL_10 | Measles_OD_DB_Int | 0.062 |
| IL_10 | Measles_Int | 0.014 | IL_10 | Measles_Int | 0.000 |
| IL_10 | HepA_Int | -0.034 | IL_10 | HepA_Int | 0.121 |
| IL_10 | Tetanus_Int | 0.000 | IL_10 | Tetanus_Int | 0.000 |
| IL_10 | Diptheria_Int | 0.000 | IL_10 | Diptheria_Int | 0.000 |
| IL_10 | Rubella_Int | -0.084 | IL_10 | Rubella_Int | 0.238 |
| IL_10 | CMV_Int | 0.137 | IL_10 | CMV_Int | -0.013 |
| IL_10 | HepB_cAb_Int | -0.023 | IL_10 | HepB_cAb_Int | -0.207 |
| IL_10 | HepB_eAb_Int | 0.000 | IL_10 | HepB_eAb_Int | 0.000 |
| IL_10 | HepB_eAg_Int | 0.000 | IL_10 | HepB_eAg_Int | 0.000 |
| IL_10 | HepC_Int | 0.119 | IL_10 | HepC_Int | -0.069 |
| IL_10 | Schistosoma_int | -0.178 | IL_10 | Schistosoma_int | -0.157 |
| IL_10 | Strongyloides_Int | -0.117 | IL_10 | Strongyloides_Int | 0.147 |
| IL_10 | Filaria_Int | 0.038 | IL_10 | Filaria_Int | 0.095 |
| IL_12p70 | IL_1_alpha | 0.354 | IL_12p70 | IL_1_alpha | 0.723 |
| IL_12p70 | IL_1_beta | 0.342 | IL_12p70 | IL_1_beta | 0.733 |
| IL_12p70 | IL_2 | 0.352 | IL_12p70 | IL_2 | 0.269 |
| IL_12p70 | IL_4 | 0.396 | IL_12p70 | IL_4 | 0.698 |
| IL_12p70 | IL_5 | 0.337 | IL_12p70 | IL_5 | 0.217 |
| IL_12p70 | IL_6 | 0.311 | IL_12p70 | IL_6 | 0.131 |
| IL_12p70 | IL_8 | 0.059 | IL_12p70 | IL_8 | 0.006 |
| IL_12p70 | IL_10 | 0.167 | IL_12p70 | IL_10 | 0.525 |

FIG. 21I8-E

| | | | | | | |
|---|---|---|---|---|---|---|
| IL_12p70 | IL_12p70 | 1.000 | | IL_12p70 | IL_12p70 | 1.000 |
| IL_12p70 | IL_13 | 0.271 | | IL_12p70 | IL_13 | 0.789 |
| IL_12p70 | IL_15 | 0.263 | | IL_12p70 | IL_15 | 0.522 |
| IL_12p70 | IL_17 | -0.065 | | IL_12p70 | IL_17 | 0.594 |
| IL_12p70 | IL_23 | 0.146 | | IL_12p70 | IL_23 | 0.313 |
| IL_12p70 | IFN_gamma | 0.000 | | IL_12p70 | IFN_gamma | 0.000 |
| IL_12p70 | TNF_alpha | 0.365 | | IL_12p70 | TNF_alpha | 0.466 |
| IL_12p70 | TNF_beta | 0.158 | | IL_12p70 | TNF_beta | 0.579 |
| IL_12p70 | Varicella_Int | 0.044 | | IL_12p70 | Varicella_Int | 0.096 |
| IL_12p70 | Measles_OD_DB_Int | 0.231 | | IL_12p70 | Measles_OD_DB_Int | -0.005 |
| IL_12p70 | Measles_Int | -0.001 | | IL_12p70 | Measles_Int | 0.000 |
| IL_12p70 | HepA_Int | -0.056 | | IL_12p70 | HepA_Int | 0.105 |
| IL_12p70 | Tetanus_Int | 0.000 | | IL_12p70 | Tetanus_Int | 0.000 |
| IL_12p70 | Diptheria_Int | 0.000 | | IL_12p70 | Diptheria_Int | 0.000 |
| IL_12p70 | Rubella_Int | -0.106 | | IL_12p70 | Rubella_Int | 0.274 |
| IL_12p70 | CMV_Int | 0.053 | | IL_12p70 | CMV_Int | -0.009 |
| IL_12p70 | HepB_cAb_Int | -0.010 | | IL_12p70 | HepB_cAb_Int | -0.297 |
| IL_12p70 | HepB_eAb_Int | 0.000 | | IL_12p70 | HepB_eAb_Int | 0.000 |
| IL_12p70 | HepB_eAg_Int | 0.000 | | IL_12p70 | HepB_eAg_Int | 0.000 |
| IL_12p70 | HepC_Int | 0.043 | | IL_12p70 | HepC_Int | -0.110 |
| IL_12p70 | Schistosoma_int | 0.015 | | IL_12p70 | Schistosoma_int | -0.136 |
| IL_12p70 | Strongyloides_Int | -0.135 | | IL_12p70 | Strongyloides_Int | 0.061 |
| IL_12p70 | Filaria_Int | 0.010 | | IL_12p70 | Filaria_Int | -0.073 |
| IL_13 | IL_1_alpha | 0.539 | | IL_13 | IL_1_alpha | 0.616 |
| IL_13 | IL_1_beta | 0.801 | | IL_13 | IL_1_beta | 0.826 |
| IL_13 | IL_2 | 0.613 | | IL_13 | IL_2 | 0.151 |
| IL_13 | IL_4 | 0.532 | | IL_13 | IL_4 | 0.835 |
| IL_13 | IL_5 | 0.602 | | IL_13 | IL_5 | 0.284 |
| IL_13 | IL_6 | 0.623 | | IL_13 | IL_6 | 0.049 |
| IL_13 | IL_8 | 0.432 | | IL_13 | IL_8 | -0.091 |
| IL_13 | IL_10 | 0.712 | | IL_13 | IL_10 | 0.543 |
| IL_13 | IL_12p70 | 0.271 | | IL_13 | IL_12p70 | 0.789 |
| IL_13 | IL_13 | 1.000 | | IL_13 | IL_13 | 1.000 |
| IL_13 | IL_15 | 0.451 | | IL_13 | IL_15 | 0.406 |
| IL_13 | IL_17 | 0.109 | | IL_13 | IL_17 | 0.624 |
| IL_13 | IL_23 | 0.069 | | IL_13 | IL_23 | 0.107 |
| IL_13 | IFN_gamma | 0.000 | | IL_13 | IFN_gamma | 0.000 |
| IL_13 | TNF_alpha | 0.611 | | IL_13 | TNF_alpha | 0.481 |
| IL_13 | TNF_beta | 0.479 | | IL_13 | TNF_beta | 0.542 |
| IL_13 | Varicella_Int | 0.102 | | IL_13 | Varicella_Int | 0.073 |
| IL_13 | Measles_OD_DB_Int | 0.175 | | IL_13 | Measles_OD_DB_Int | 0.080 |
| IL_13 | Measles_Int | -0.030 | | IL_13 | Measles_Int | 0.000 |
| IL_13 | HepA_Int | -0.064 | | IL_13 | HepA_Int | 0.206 |
| IL_13 | Tetanus_Int | 0.000 | | IL_13 | Tetanus_Int | 0.000 |
| IL_13 | Diptheria_Int | 0.000 | | IL_13 | Diptheria_Int | 0.000 |
| IL_13 | Rubella_Int | -0.111 | | IL_13 | Rubella_Int | 0.357 |
| IL_13 | CMV_Int | 0.160 | | IL_13 | CMV_Int | -0.085 |
| IL_13 | HepB_cAb_Int | -0.059 | | IL_13 | HepB_cAb_Int | -0.284 |
| IL_13 | HepB_eAb_Int | 0.000 | | IL_13 | HepB_eAb_Int | 0.000 |
| IL_13 | HepB_eAg_Int | 0.000 | | IL_13 | HepB_eAg_Int | 0.000 |
| IL_13 | HepC_Int | 0.040 | | IL_13 | HepC_Int | -0.111 |
| IL_13 | Schistosoma_int | -0.108 | | IL_13 | Schistosoma_int | -0.141 |
| IL_13 | Strongyloides_Int | 0.181 | | IL_13 | Strongyloides_Int | 0.146 |
| IL_13 | Filaria_Int | 0.138 | | IL_13 | Filaria_Int | -0.067 |
| IL_15 | IL_1_alpha | 0.439 | | IL_15 | IL_1_alpha | 0.486 |
| IL_15 | IL_1_beta | 0.442 | | IL_15 | IL_1_beta | 0.326 |
| IL_15 | IL_2 | 0.473 | | IL_15 | IL_2 | 0.292 |

FIG. 2118-F

| IL_15 | IL_4 | 0.509 | | IL_15 | IL_4 | 0.470 |
|---|---|---|---|---|---|---|
| IL_15 | IL_5 | 0.547 | | IL_15 | IL_5 | 0.424 |
| IL_15 | IL_6 | 0.454 | | IL_15 | IL_6 | 0.273 |
| IL_15 | IL_8 | 0.466 | | IL_15 | IL_8 | 0.216 |
| IL_15 | IL_10 | 0.259 | | IL_15 | IL_10 | 0.194 |
| IL_15 | IL_12p70 | 0.263 | | IL_15 | IL_12p70 | 0.522 |
| IL_15 | IL_13 | 0.451 | | IL_15 | IL_13 | 0.406 |
| IL_15 | IL_15 | 1.000 | | IL_15 | IL_15 | 1.000 |
| IL_15 | IL_17 | 0.114 | | IL_15 | IL_17 | 0.354 |
| IL_15 | IL_23 | 0.235 | | IL_15 | IL_23 | 0.072 |
| IL_15 | IFN_gamma | 0.000 | | IL_15 | IFN_gamma | 0.000 |
| IL_15 | TNF_alpha | 0.551 | | IL_15 | TNF_alpha | 0.348 |
| IL_15 | TNF_beta | 0.180 | | IL_15 | TNF_beta | 0.387 |
| IL_15 | Varicella_Int | -0.039 | | IL_15 | Varicella_Int | -0.187 |
| IL_15 | Measles_OD_DB_Int | -0.080 | | IL_15 | Measles_OD_DB_Int | -0.008 |
| IL_15 | Measles_Int | -0.165 | | IL_15 | Measles_Int | 0.000 |
| IL_15 | HepA_Int | -0.284 | | IL_15 | HepA_Int | -0.080 |
| IL_15 | Tetanus_Int | 0.000 | | IL_15 | Tetanus_Int | 0.000 |
| IL_15 | Diptheria_Int | 0.000 | | IL_15 | Diptheria_Int | 0.000 |
| IL_15 | Rubella_Int | 0.130 | | IL_15 | Rubella_Int | 0.172 |
| IL_15 | CMV_Int | 0.288 | | IL_15 | CMV_Int | -0.371 |
| IL_15 | HepB_cAb_Int | 0.313 | | IL_15 | HepB_cAb_Int | -0.501 |
| IL_15 | HepB_eAb_Int | 0.000 | | IL_15 | HepB_eAb_Int | 0.000 |
| IL_15 | HepB_eAg_Int | 0.000 | | IL_15 | HepB_eAg_Int | 0.000 |
| IL_15 | HepC_Int | -0.021 | | IL_15 | HepC_Int | -0.027 |
| IL_15 | Schistosoma_int | -0.084 | | IL_15 | Schistosoma_int | -0.152 |
| IL_15 | Strongyloides_Int | 0.049 | | IL_15 | Strongyloides_Int | 0.102 |
| IL_15 | Filaria_Int | -0.025 | | IL_15 | Filaria_Int | -0.015 |
| IL_17 | IL_1_alpha | -0.007 | | IL_17 | IL_1_alpha | 0.458 |
| IL_17 | IL_1_beta | 0.036 | | IL_17 | IL_1_beta | 0.785 |
| IL_17 | IL_2 | 0.018 | | IL_17 | IL_2 | 0.461 |
| IL_17 | IL_4 | 0.074 | | IL_17 | IL_4 | 0.547 |
| IL_17 | IL_5 | 0.214 | | IL_17 | IL_5 | 0.205 |
| IL_17 | IL_6 | -0.006 | | IL_17 | IL_6 | 0.305 |
| IL_17 | IL_8 | 0.110 | | IL_17 | IL_8 | -0.067 |
| IL_17 | IL_10 | 0.375 | | IL_17 | IL_10 | 0.867 |
| IL_17 | IL_12p70 | -0.065 | | IL_17 | IL_12p70 | 0.594 |
| IL_17 | IL_13 | 0.109 | | IL_17 | IL_13 | 0.624 |
| IL_17 | IL_15 | 0.114 | | IL_17 | IL_15 | 0.354 |
| IL_17 | IL_17 | 1.000 | | IL_17 | IL_17 | 1.000 |
| IL_17 | IL_23 | -0.039 | | IL_17 | IL_23 | -0.017 |
| IL_17 | IFN_gamma | 0.000 | | IL_17 | IFN_gamma | 0.000 |
| IL_17 | TNF_alpha | -0.011 | | IL_17 | TNF_alpha | 0.534 |
| IL_17 | TNF_beta | 0.140 | | IL_17 | TNF_beta | 0.542 |
| IL_17 | Varicella_Int | -0.217 | | IL_17 | Varicella_Int | 0.106 |
| IL_17 | Measles_OD_DB_Int | 0.099 | | IL_17 | Measles_OD_DB_Int | 0.027 |
| IL_17 | Measles_Int | 0.061 | | IL_17 | Measles_Int | 0.000 |
| IL_17 | HepA_Int | 0.069 | | IL_17 | HepA_Int | 0.028 |
| IL_17 | Tetanus_Int | 0.000 | | IL_17 | Tetanus_Int | 0.000 |
| IL_17 | Diptheria_Int | 0.000 | | IL_17 | Diptheria_Int | 0.000 |
| IL_17 | Rubella_Int | -0.037 | | IL_17 | Rubella_Int | 0.323 |
| IL_17 | CMV_Int | 0.051 | | IL_17 | CMV_Int | -0.043 |
| IL_17 | HepB_cAb_Int | 0.234 | | IL_17 | HepB_cAb_Int | -0.228 |
| IL_17 | HepB_eAb_Int | 0.000 | | IL_17 | HepB_eAb_Int | 0.000 |
| IL_17 | HepB_eAg_Int | 0.000 | | IL_17 | HepB_eAg_Int | 0.000 |
| IL_17 | HepC_Int | -0.027 | | IL_17 | HepC_Int | -0.098 |
| IL_17 | Schistosoma_int | -0.056 | | IL_17 | Schistosoma_int | -0.014 |

FIG. 2I18-G

| | | | | | | |
|---|---|---|---|---|---|---|
| IL_17 | Strongyloides_Int | -0.145 | | IL_17 | Strongyloides_Int | 0.094 |
| IL_17 | Filaria_Int | -0.082 | | IL_17 | Filaria_Int | -0.048 |
| IL_23 | IL_1_alpha | 0.030 | | IL_23 | IL_1_alpha | 0.358 |
| IL_23 | IL_1_beta | 0.058 | | IL_23 | IL_1_beta | 0.032 |
| IL_23 | IL_2 | 0.010 | | IL_23 | IL_2 | -0.012 |
| IL_23 | IL_4 | 0.133 | | IL_23 | IL_4 | 0.121 |
| IL_23 | IL_5 | -0.028 | | IL_23 | IL_5 | 0.052 |
| IL_23 | IL_6 | 0.011 | | IL_23 | IL_6 | -0.022 |
| IL_23 | IL_8 | -0.047 | | IL_23 | IL_8 | -0.002 |
| IL_23 | IL_10 | -0.066 | | IL_23 | IL_10 | 0.115 |
| IL_23 | IL_12p70 | 0.146 | | IL_23 | IL_12p70 | 0.313 |
| IL_23 | IL_13 | 0.069 | | IL_23 | IL_13 | 0.107 |
| IL_23 | IL_15 | 0.235 | | IL_23 | IL_15 | 0.072 |
| IL_23 | IL_17 | -0.039 | | IL_23 | IL_17 | -0.017 |
| IL_23 | IL_23 | 1.000 | | IL_23 | IL_23 | 1.000 |
| IL_23 | IFN_gamma | 0.000 | | IL_23 | IFN_gamma | 0.000 |
| IL_23 | TNF_alpha | 0.146 | | IL_23 | TNF_alpha | -0.049 |
| IL_23 | TNF_beta | -0.055 | | IL_23 | TNF_beta | 0.344 |
| IL_23 | Varicella_Int | -0.485 | | IL_23 | Varicella_Int | -0.059 |
| IL_23 | Measles_OD_DB_Int | 0.088 | | IL_23 | Measles_OD_DB_Int | 0.075 |
| IL_23 | Measles_Int | 0.049 | | IL_23 | Measles_Int | 0.000 |
| IL_23 | HepA_Int | -0.314 | | IL_23 | HepA_Int | 0.007 |
| IL_23 | Tetanus_Int | 0.000 | | IL_23 | Tetanus_Int | 0.000 |
| IL_23 | Diptheria_Int | 0.000 | | IL_23 | Diptheria_Int | 0.000 |
| IL_23 | Rubella_Int | -0.035 | | IL_23 | Rubella_Int | 0.459 |
| IL_23 | CMV_Int | 0.052 | | IL_23 | CMV_Int | -0.317 |
| IL_23 | HepB_cAb_Int | 0.268 | | IL_23 | HepB_cAb_Int | 0.119 |
| IL_23 | HepB_eAb_Int | 0.000 | | IL_23 | HepB_eAb_Int | 0.000 |
| IL_23 | HepB_eAg_Int | 0.000 | | IL_23 | HepB_eAg_Int | 0.000 |
| IL_23 | HepC_Int | -0.015 | | IL_23 | HepC_Int | -0.076 |
| IL_23 | Schistosoma_int | 0.004 | | IL_23 | Schistosoma_int | -0.122 |
| IL_23 | Strongyloides_Int | -0.146 | | IL_23 | Strongyloides_Int | 0.129 |
| IL_23 | Filaria_Int | -0.056 | | IL_23 | Filaria_Int | -0.128 |
| IFN_gamma | IL_1_alpha | 0.000 | | IFN_gamma | IL_1_alpha | 0.000 |
| IFN_gamma | IL_1_beta | 0.000 | | IFN_gamma | IL_1_beta | 0.000 |
| IFN_gamma | IL_2 | 0.000 | | IFN_gamma | IL_2 | 0.000 |
| IFN_gamma | IL_4 | 0.000 | | IFN_gamma | IL_4 | 0.000 |
| IFN_gamma | IL_5 | 0.000 | | IFN_gamma | IL_5 | 0.000 |
| IFN_gamma | IL_6 | 0.000 | | IFN_gamma | IL_6 | 0.000 |
| IFN_gamma | IL_8 | 0.000 | | IFN_gamma | IL_8 | 0.000 |
| IFN_gamma | IL_10 | 0.000 | | IFN_gamma | IL_10 | 0.000 |
| IFN_gamma | IL_12p70 | 0.000 | | IFN_gamma | IL_12p70 | 0.000 |
| IFN_gamma | IL_13 | 0.000 | | IFN_gamma | IL_13 | 0.000 |
| IFN_gamma | IL_15 | 0.000 | | IFN_gamma | IL_15 | 0.000 |
| IFN_gamma | IL_17 | 0.000 | | IFN_gamma | IL_17 | 0.000 |
| IFN_gamma | IL_23 | 0.000 | | IFN_gamma | IL_23 | 0.000 |
| IFN_gamma | IFN_gamma | 1.000 | | IFN_gamma | IFN_gamma | 1.000 |
| IFN_gamma | TNF_alpha | 0.000 | | IFN_gamma | TNF_alpha | 0.000 |
| IFN_gamma | TNF_beta | 0.000 | | IFN_gamma | TNF_beta | 0.000 |
| IFN_gamma | Varicella_Int | 0.000 | | IFN_gamma | Varicella_Int | 0.000 |
| IFN_gamma | Measles_OD_DB_Int | 0.000 | | IFN_gamma | Measles_OD_DB_Int | 0.000 |
| IFN_gamma | Measles_Int | 0.000 | | IFN_gamma | Measles_Int | 0.000 |
| IFN_gamma | HepA_Int | 0.000 | | IFN_gamma | HepA_Int | 0.000 |
| IFN_gamma | Tetanus_Int | 0.000 | | IFN_gamma | Tetanus_Int | 0.000 |
| IFN_gamma | Diptheria_Int | 0.000 | | IFN_gamma | Diptheria_Int | 0.000 |
| IFN_gamma | Rubella_Int | 0.000 | | IFN_gamma | Rubella_Int | 0.000 |
| IFN_gamma | CMV_Int | 0.000 | | IFN_gamma | CMV_Int | 0.000 |

FIG. 21I8-H

| | | | | | | |
|---|---|---|---|---|---|---|
| IFN_gamma | HepB_cAb_Int | 0.000 | | IFN_gamma | HepB_cAb_Int | 0.000 |
| IFN_gamma | HepB_eAb_Int | 0.000 | | IFN_gamma | HepB_eAb_Int | 0.000 |
| IFN_gamma | HepB_eAg_Int | 0.000 | | IFN_gamma | HepB_eAg_Int | 0.000 |
| IFN_gamma | HepC_Int | 0.000 | | IFN_gamma | HepC_Int | 0.000 |
| IFN_gamma | Schistosoma_int | 0.000 | | IFN_gamma | Schistosoma_int | 0.000 |
| IFN_gamma | Strongyloides_Int | 0.000 | | IFN_gamma | Strongyloides_Int | 0.000 |
| IFN_gamma | Filaria_Int | 0.000 | | IFN_gamma | Filaria_Int | 0.000 |
| TNF_alpha | IL_1_alpha | 0.741 | | TNF_alpha | IL_1_alpha | 0.346 |
| TNF_alpha | IL_1_beta | 0.808 | | TNF_alpha | IL_1_beta | 0.508 |
| TNF_alpha | IL_2 | 0.733 | | TNF_alpha | IL_2 | 0.217 |
| TNF_alpha | IL_4 | 0.499 | | TNF_alpha | IL_4 | 0.532 |
| TNF_alpha | IL_5 | 0.725 | | TNF_alpha | IL_5 | 0.315 |
| TNF_alpha | IL_6 | 0.783 | | TNF_alpha | IL_6 | -0.003 |
| TNF_alpha | IL_8 | 0.393 | | TNF_alpha | IL_8 | -0.030 |
| TNF_alpha | IL_10 | 0.554 | | TNF_alpha | IL_10 | 0.501 |
| TNF_alpha | IL_12p70 | 0.365 | | TNF_alpha | IL_12p70 | 0.466 |
| TNF_alpha | IL_13 | 0.611 | | TNF_alpha | IL_13 | 0.481 |
| TNF_alpha | IL_15 | 0.551 | | TNF_alpha | IL_15 | 0.348 |
| TNF_alpha | IL_17 | -0.011 | | TNF_alpha | IL_17 | 0.534 |
| TNF_alpha | IL_23 | 0.146 | | TNF_alpha | IL_23 | -0.049 |
| TNF_alpha | IFN_gamma | 0.000 | | TNF_alpha | IFN_gamma | 0.000 |
| TNF_alpha | TNF_alpha | 1.000 | | TNF_alpha | TNF_alpha | 1.000 |
| TNF_alpha | TNF_beta | 0.617 | | TNF_alpha | TNF_beta | 0.606 |
| TNF_alpha | Varicella_Int | 0.099 | | TNF_alpha | Varicella_Int | 0.063 |
| TNF_alpha | Measles_OD_DB_Int | 0.136 | | TNF_alpha | Measles_OD_DB_Int | 0.182 |
| TNF_alpha | Measles_Int | -0.078 | | TNF_alpha | Measles_Int | 0.000 |
| TNF_alpha | HepA_Int | -0.224 | | TNF_alpha | HepA_Int | -0.006 |
| TNF_alpha | Tetanus_Int | 0.000 | | TNF_alpha | Tetanus_Int | 0.000 |
| TNF_alpha | Diptheria_Int | 0.000 | | TNF_alpha | Diptheria_Int | 0.000 |
| TNF_alpha | Rubella_Int | -0.071 | | TNF_alpha | Rubella_Int | 0.237 |
| TNF_alpha | CMV_Int | 0.196 | | TNF_alpha | CMV_Int | -0.079 |
| TNF_alpha | HepB_cAb_Int | 0.106 | | TNF_alpha | HepB_cAb_Int | -0.198 |
| TNF_alpha | HepB_eAb_Int | 0.000 | | TNF_alpha | HepB_eAb_Int | 0.000 |
| TNF_alpha | HepB_eAg_Int | 0.000 | | TNF_alpha | HepB_eAg_Int | 0.000 |
| TNF_alpha | HepC_Int | -0.015 | | TNF_alpha | HepC_Int | -0.105 |
| TNF_alpha | Schistosoma_int | -0.167 | | TNF_alpha | Schistosoma_int | -0.121 |
| TNF_alpha | Strongyloides_Int | 0.036 | | TNF_alpha | Strongyloides_Int | 0.297 |
| TNF_alpha | Filaria_Int | 0.057 | | TNF_alpha | Filaria_Int | 0.001 |
| TNF_beta | IL_1_alpha | 0.471 | | TNF_beta | IL_1_alpha | 0.674 |
| TNF_beta | IL_1_beta | 0.707 | | TNF_beta | IL_1_beta | 0.597 |
| TNF_beta | IL_2 | 0.523 | | TNF_beta | IL_2 | 0.321 |
| TNF_beta | IL_4 | 0.350 | | TNF_beta | IL_4 | 0.660 |
| TNF_beta | IL_5 | 0.578 | | TNF_beta | IL_5 | 0.669 |
| TNF_beta | IL_6 | 0.408 | | TNF_beta | IL_6 | 0.102 |
| TNF_beta | IL_8 | 0.197 | | TNF_beta | IL_8 | 0.013 |
| TNF_beta | IL_10 | 0.737 | | TNF_beta | IL_10 | 0.547 |
| TNF_beta | IL_12p70 | 0.158 | | TNF_beta | IL_12p70 | 0.579 |
| TNF_beta | IL_13 | 0.479 | | TNF_beta | IL_13 | 0.542 |
| TNF_beta | IL_15 | 0.180 | | TNF_beta | IL_15 | 0.387 |
| TNF_beta | IL_17 | 0.140 | | TNF_beta | IL_17 | 0.542 |
| TNF_beta | IL_23 | -0.055 | | TNF_beta | IL_23 | 0.344 |
| TNF_beta | IFN_gamma | 0.000 | | TNF_beta | IFN_gamma | 0.000 |
| TNF_beta | TNF_alpha | 0.617 | | TNF_beta | TNF_alpha | 0.606 |
| TNF_beta | TNF_beta | 1.000 | | TNF_beta | TNF_beta | 1.000 |
| TNF_beta | Varicella_Int | 0.130 | | TNF_beta | Varicella_Int | -0.205 |
| TNF_beta | Measles_OD_DB_Int | 0.180 | | TNF_beta | Measles_OD_DB_Int | 0.201 |
| TNF_beta | Measles_Int | 0.066 | | TNF_beta | Measles_Int | 0.000 |

FIG. 21I8-I

| | | | | | | |
|---|---|---|---|---|---|---|
| TNF_beta | HepA_Int | -0.122 | | TNF_beta | HepA_Int | 0.097 |
| TNF_beta | Tetanus_Int | 0.000 | | TNF_beta | Tetanus_Int | 0.000 |
| TNF_beta | Diptheria_Int | 0.000 | | TNF_beta | Diptheria_Int | 0.000 |
| TNF_beta | Rubella_Int | -0.075 | | TNF_beta | Rubella_Int | 0.515 |
| TNF_beta | CMV_Int | 0.155 | | TNF_beta | CMV_Int | -0.317 |
| TNF_beta | HepB_cAb_Int | -0.100 | | TNF_beta | HepB_cAb_Int | -0.193 |
| TNF_beta | HepB_eAb_Int | 0.000 | | TNF_beta | HepB_eAb_Int | 0.000 |
| TNF_beta | HepB_eAg_Int | 0.000 | | TNF_beta | HepB_eAg_Int | 0.000 |
| TNF_beta | HepC_Int | 0.367 | | TNF_beta | HepC_Int | -0.068 |
| TNF_beta | Schistosoma_int | -0.131 | | TNF_beta | Schistosoma_int | -0.069 |
| TNF_beta | Strongyloides_Int | -0.168 | | TNF_beta | Strongyloides_Int | 0.285 |
| TNF_beta | Filaria_Int | 0.074 | | TNF_beta | Filaria_Int | 0.140 |
| Varicella_Int | IL_1_alpha | -0.016 | | Varicella_Int | IL_1_alpha | 0.024 |
| Varicella_Int | IL_1_beta | 0.123 | | Varicella_Int | IL_1_beta | -0.025 |
| Varicella_Int | IL_2 | 0.170 | | Varicella_Int | IL_2 | 0.070 |
| Varicella_Int | IL_4 | 0.065 | | Varicella_Int | IL_4 | -0.011 |
| Varicella_Int | IL_5 | 0.108 | | Varicella_Int | IL_5 | -0.497 |
| Varicella_Int | IL_6 | 0.074 | | Varicella_Int | IL_6 | 0.044 |
| Varicella_Int | IL_8 | -0.006 | | Varicella_Int | IL_8 | 0.049 |
| Varicella_Int | IL_10 | -0.030 | | Varicella_Int | IL_10 | 0.082 |
| Varicella_Int | IL_12p70 | 0.044 | | Varicella_Int | IL_12p70 | 0.096 |
| Varicella_Int | IL_13 | 0.102 | | Varicella_Int | IL_13 | 0.073 |
| Varicella_Int | IL_15 | -0.039 | | Varicella_Int | IL_15 | -0.187 |
| Varicella_Int | IL_17 | -0.217 | | Varicella_Int | IL_17 | 0.106 |
| Varicella_Int | IL_23 | -0.485 | | Varicella_Int | IL_23 | -0.059 |
| Varicella_Int | IFN_gamma | 0.000 | | Varicella_Int | IFN_gamma | 0.000 |
| Varicella_Int | TNF_alpha | 0.099 | | Varicella_Int | TNF_alpha | 0.063 |
| Varicella_Int | TNF_beta | 0.130 | | Varicella_Int | TNF_beta | -0.205 |
| Varicella_Int | Varicella_Int | 1.000 | | Varicella_Int | Varicella_Int | 1.000 |
| Varicella_Int | Measles_OD_DB_Int | -0.126 | | Varicella_Int | Measles_OD_DB_Int | 0.156 |
| Varicella_Int | Measles_Int | -0.108 | | Varicella_Int | Measles_Int | 0.000 |
| Varicella_Int | HepA_Int | -0.017 | | Varicella_Int | HepA_Int | 0.225 |
| Varicella_Int | Tetanus_Int | 0.000 | | Varicella_Int | Tetanus_Int | 0.000 |
| Varicella_Int | Diptheria_Int | 0.000 | | Varicella_Int | Diptheria_Int | 0.000 |
| Varicella_Int | Rubella_Int | 0.052 | | Varicella_Int | Rubella_Int | -0.225 |
| Varicella_Int | CMV_Int | -0.116 | | Varicella_Int | CMV_Int | 0.302 |
| Varicella_Int | HepB_cAb_Int | -0.064 | | Varicella_Int | HepB_cAb_Int | -0.143 |
| Varicella_Int | HepB_eAb_Int | 0.000 | | Varicella_Int | HepB_eAb_Int | 0.000 |
| Varicella_Int | HepB_eAg_Int | 0.000 | | Varicella_Int | HepB_eAg_Int | 0.000 |
| Varicella_Int | HepC_Int | 0.100 | | Varicella_Int | HepC_Int | 0.040 |
| Varicella_Int | Schistosoma_int | 0.100 | | Varicella_Int | Schistosoma_int | 0.071 |
| Varicella_Int | Strongyloides_Int | 0.213 | | Varicella_Int | Strongyloides_Int | -0.288 |
| Varicella_Int | Filaria_Int | 0.199 | | Varicella_Int | Filaria_Int | -0.333 |
| Measles_OD_DB_Int | IL_1_alpha | 0.128 | | Measles_OD_DB_Int | IL_1_alpha | 0.010 |
| Measles_OD_DB_Int | IL_1_beta | 0.155 | | Measles_OD_DB_Int | IL_1_beta | 0.037 |
| Measles_OD_DB_Int | IL_2 | -0.035 | | Measles_OD_DB_Int | IL_2 | 0.160 |
| Measles_OD_DB_Int | IL_4 | 0.191 | | Measles_OD_DB_Int | IL_4 | 0.183 |
| Measles_OD_DB_Int | IL_5 | 0.137 | | Measles_OD_DB_Int | IL_5 | 0.174 |
| Measles_OD_DB_Int | IL_6 | 0.179 | | Measles_OD_DB_Int | IL_6 | 0.114 |
| Measles_OD_DB_Int | IL_8 | 0.217 | | Measles_OD_DB_Int | IL_8 | -0.138 |
| Measles_OD_DB_Int | IL_10 | 0.164 | | Measles_OD_DB_Int | IL_10 | 0.062 |
| Measles_OD_DB_Int | IL_12p70 | 0.231 | | Measles_OD_DB_Int | IL_12p70 | -0.005 |
| Measles_OD_DB_Int | IL_13 | 0.175 | | Measles_OD_DB_Int | IL_13 | 0.080 |
| Measles_OD_DB_Int | IL_15 | -0.080 | | Measles_OD_DB_Int | IL_15 | -0.008 |
| Measles_OD_DB_Int | IL_17 | 0.099 | | Measles_OD_DB_Int | IL_17 | 0.027 |
| Measles_OD_DB_Int | IL_23 | 0.088 | | Measles_OD_DB_Int | IL_23 | 0.075 |
| Measles_OD_DB_Int | IFN_gamma | 0.000 | | Measles_OD_DB_Int | IFN_gamma | 0.000 |

FIG. 21I8-J

| | | | | | | |
|---|---|---|---|---|---|---|
| Measles_OD_DB_Int | TNF_alpha | 0.136 | | Measles_OD_DB_Int | TNF_alpha | 0.182 |
| Measles_OD_DB_Int | TNF_beta | 0.180 | | Measles_OD_DB_Int | TNF_beta | 0.201 |
| Measles_OD_DB_Int | Varicella_Int | -0.126 | | Measles_OD_DB_Int | Varicella_Int | 0.156 |
| Measles_OD_DB_Int | Measles_OD_DB_Int | 1.000 | | Measles_OD_DB_Int | Measles_OD_DB_Int | 1.000 |
| Measles_OD_DB_Int | Measles_Int | 0.190 | | Measles_OD_DB_Int | Measles_Int | 0.000 |
| Measles_OD_DB_Int | HepA_Int | 0.130 | | Measles_OD_DB_Int | HepA_Int | 0.225 |
| Measles_OD_DB_Int | Tetanus_Int | 0.000 | | Measles_OD_DB_Int | Tetanus_Int | 0.000 |
| Measles_OD_DB_Int | Diptheria_Int | 0.000 | | Measles_OD_DB_Int | Diptheria_Int | 0.000 |
| Measles_OD_DB_Int | Rubella_Int | 0.086 | | Measles_OD_DB_Int | Rubella_Int | -0.097 |
| Measles_OD_DB_Int | CMV_Int | -0.184 | | Measles_OD_DB_Int | CMV_Int | -0.039 |
| Measles_OD_DB_Int | HepB_cAb_Int | -0.132 | | Measles_OD_DB_Int | HepB_cAb_Int | -0.103 |
| Measles_OD_DB_Int | HepB_eAb_Int | 0.000 | | Measles_OD_DB_Int | HepB_eAb_Int | 0.000 |
| Measles_OD_DB_Int | HepB_eAg_Int | 0.000 | | Measles_OD_DB_Int | HepB_eAg_Int | 0.000 |
| Measles_OD_DB_Int | HepC_Int | 0.157 | | Measles_OD_DB_Int | HepC_Int | 0.082 |
| Measles_OD_DB_Int | Schistosoma_int | 0.157 | | Measles_OD_DB_Int | Schistosoma_int | -0.154 |
| Measles_OD_DB_Int | Strongyloides_Int | -0.065 | | Measles_OD_DB_Int | Strongyloides_Int | 0.320 |
| Measles_OD_DB_Int | Filaria_Int | -0.054 | | Measles_OD_DB_Int | Filaria_Int | -0.000 |
| Measles_Int | IL_1_alpha | -0.078 | | Measles_Int | IL_1_alpha | 0.000 |
| Measles_Int | IL_1_beta | -0.044 | | Measles_Int | IL_1_beta | 0.000 |
| Measles_Int | IL_2 | -0.231 | | Measles_Int | IL_2 | 0.000 |
| Measles_Int | IL_4 | 0.034 | | Measles_Int | IL_4 | 0.000 |
| Measles_Int | IL_5 | 0.004 | | Measles_Int | IL_5 | 0.000 |
| Measles_Int | IL_6 | 0.025 | | Measles_Int | IL_6 | 0.000 |
| Measles_Int | IL_8 | -0.072 | | Measles_Int | IL_8 | 0.000 |
| Measles_Int | IL_10 | 0.014 | | Measles_Int | IL_10 | 0.000 |
| Measles_Int | IL_12p70 | -0.001 | | Measles_Int | IL_12p70 | 0.000 |
| Measles_Int | IL_13 | -0.030 | | Measles_Int | IL_13 | 0.000 |
| Measles_Int | IL_15 | -0.165 | | Measles_Int | IL_15 | 0.000 |
| Measles_Int | IL_17 | 0.061 | | Measles_Int | IL_17 | 0.000 |
| Measles_Int | IL_23 | 0.049 | | Measles_Int | IL_23 | 0.000 |
| Measles_Int | IFN_gamma | 0.000 | | Measles_Int | IFN_gamma | 0.000 |
| Measles_Int | TNF_alpha | -0.078 | | Measles_Int | TNF_alpha | 0.000 |
| Measles_Int | TNF_beta | 0.066 | | Measles_Int | TNF_beta | 0.000 |
| Measles_Int | Varicella_Int | -0.108 | | Measles_Int | Varicella_Int | 0.000 |
| Measles_Int | Measles_OD_DB_Int | 0.190 | | Measles_Int | Measles_OD_DB_Int | 0.000 |
| Measles_Int | Measles_Int | 1.000 | | Measles_Int | Measles_Int | 1.000 |
| Measles_Int | HepA_Int | -0.016 | | Measles_Int | HepA_Int | 0.000 |
| Measles_Int | Tetanus_Int | 0.000 | | Measles_Int | Tetanus_Int | 0.000 |
| Measles_Int | Diptheria_Int | 0.000 | | Measles_Int | Diptheria_Int | 0.000 |
| Measles_Int | Rubella_Int | 0.048 | | Measles_Int | Rubella_Int | 0.000 |
| Measles_Int | CMV_Int | -0.108 | | Measles_Int | CMV_Int | 0.000 |
| Measles_Int | HepB_cAb_Int | -0.330 | | Measles_Int | HepB_cAb_Int | 0.000 |
| Measles_Int | HepB_eAb_Int | 0.000 | | Measles_Int | HepB_eAb_Int | 0.000 |
| Measles_Int | HepB_eAg_Int | 0.000 | | Measles_Int | HepB_eAg_Int | 0.000 |
| Measles_Int | HepC_Int | -0.223 | | Measles_Int | HepC_int | 0.000 |
| Measles_Int | Schistosoma_int | 0.092 | | Measles_Int | Schistosoma_int | 0.000 |
| Measles_Int | Strongyloides_Int | -0.239 | | Measles_Int | Strongyloides_Int | 0.000 |
| Measles_Int | Filaria_Int | -0.220 | | Measles_Int | Filaria_Int | 0.000 |
| HepA_Int | IL_1_alpha | -0.160 | | HepA_Int | IL_1_alpha | 0.062 |
| HepA_Int | IL_1_beta | -0.205 | | HepA_Int | IL_1_beta | 0.112 |
| HepA_Int | IL_2 | -0.265 | | HepA_Int | IL_2 | 0.051 |
| HepA_Int | IL_4 | -0.368 | | HepA_Int | IL_4 | 0.101 |
| HepA_Int | IL_5 | -0.254 | | HepA_Int | IL_5 | 0.115 |
| HepA_Int | IL_6 | -0.122 | | HepA_Int | IL_6 | 0.109 |
| HepA_Int | IL_8 | -0.023 | | HepA_Int | IL_8 | 0.009 |
| HepA_Int | IL_10 | -0.034 | | HepA_Int | IL_10 | 0.121 |
| HepA_Int | IL_12p70 | -0.056 | | HepA_Int | IL_12p70 | 0.105 |

FIG. 21I8-K

| | | | | | | |
|---|---|---|---|---|---|---|
| HepA_Int | IL_13 | -0.064 | | HepA_Int | IL_13 | 0.206 |
| HepA_Int | IL_15 | -0.284 | | HepA_Int | IL_15 | -0.080 |
| HepA_Int | IL_17 | 0.069 | | HepA_Int | IL_17 | 0.028 |
| HepA_Int | IL_23 | -0.314 | | HepA_Int | IL_23 | 0.007 |
| HepA_Int | IFN_gamma | 0.000 | | HepA_Int | IFN_gamma | 0.000 |
| HepA_Int | TNF_alpha | -0.224 | | HepA_Int | TNF_alpha | -0.006 |
| HepA_Int | TNF_beta | -0.122 | | HepA_Int | TNF_beta | 0.097 |
| HepA_Int | Varicella_Int | -0.017 | | HepA_Int | Varicella_Int | 0.225 |
| HepA_Int | Measles_OD_DB_Int | 0.130 | | HepA_Int | Measles_OD_DB_Int | 0.225 |
| HepA_Int | Measles_Int | -0.016 | | HepA_Int | Measles_Int | 0.000 |
| HepA_Int | HepA_Int | 1.000 | | HepA_Int | HepA_Int | 1.000 |
| HepA_Int | Tetanus_Int | 0.000 | | HepA_Int | Tetanus_Int | 0.000 |
| HepA_Int | Diptheria_Int | 0.000 | | HepA_Int | Diptheria_Int | 0.000 |
| HepA_Int | Rubella_Int | 0.093 | | HepA_Int | Rubella_Int | -0.171 |
| HepA_Int | CMV_Int | -0.031 | | HepA_Int | CMV_Int | 0.159 |
| HepA_Int | HepB_cAb_Int | -0.057 | | HepA_Int | HepB_cAb_Int | -0.208 |
| HepA_Int | HepB_eAb_Int | 0.000 | | HepA_Int | HepB_eAb_Int | 0.000 |
| HepA_Int | HepB_eAg_Int | 0.000 | | HepA_Int | HepB_eAg_Int | 0.000 |
| HepA_Int | HepC_Int | -0.025 | | HepA_Int | HepC_Int | 0.058 |
| HepA_Int | Schistosoma_int | -0.025 | | HepA_Int | Schistosoma_int | 0.103 |
| HepA_Int | Strongyloides_Int | 0.354 | | HepA_Int | Strongyloides_Int | -0.011 |
| HepA_Int | Filaria_Int | 0.185 | | HepA_Int | Filaria_Int | 0.162 |
| Tetanus_Int | IL_1_alpha | 0.000 | | Tetanus_Int | IL_1_alpha | 0.000 |
| Tetanus_Int | IL_1_beta | 0.000 | | Tetanus_Int | IL_1_beta | 0.000 |
| Tetanus_Int | IL_2 | 0.000 | | Tetanus_Int | IL_2 | 0.000 |
| Tetanus_Int | IL_4 | 0.000 | | Tetanus_Int | IL_4 | 0.000 |
| Tetanus_Int | IL_5 | 0.000 | | Tetanus_Int | IL_5 | 0.000 |
| Tetanus_Int | IL_6 | 0.000 | | Tetanus_Int | IL_6 | 0.000 |
| Tetanus_Int | IL_8 | 0.000 | | Tetanus_Int | IL_8 | 0.000 |
| Tetanus_Int | IL_10 | 0.000 | | Tetanus_Int | IL_10 | 0.000 |
| Tetanus_Int | IL_12p70 | 0.000 | | Tetanus_Int | IL_12p70 | 0.000 |
| Tetanus_Int | IL_13 | 0.000 | | Tetanus_Int | IL_13 | 0.000 |
| Tetanus_Int | IL_15 | 0.000 | | Tetanus_Int | IL_15 | 0.000 |
| Tetanus_Int | IL_17 | 0.000 | | Tetanus_Int | IL_17 | 0.000 |
| Tetanus_Int | IL_23 | 0.000 | | Tetanus_Int | IL_23 | 0.000 |
| Tetanus_Int | IFN_gamma | 0.000 | | Tetanus_Int | IFN_gamma | 0.000 |
| Tetanus_Int | TNF_alpha | 0.000 | | Tetanus_Int | TNF_alpha | 0.000 |
| Tetanus_Int | TNF_beta | 0.000 | | Tetanus_Int | TNF_beta | 0.000 |
| Tetanus_Int | Varicella_Int | 0.000 | | Tetanus_Int | Varicella_Int | 0.000 |
| Tetanus_Int | Measles_OD_DB_Int | 0.000 | | Tetanus_Int | Measles_OD_DB_Int | 0.000 |
| Tetanus_Int | Measles_Int | 0.000 | | Tetanus_Int | Measles_Int | 0.000 |
| Tetanus_Int | HepA_Int | 0.000 | | Tetanus_Int | HepA_Int | 0.000 |
| Tetanus_Int | Tetanus_Int | 1.000 | | Tetanus_Int | Tetanus_Int | 1.000 |
| Tetanus_Int | Diptheria_Int | 0.000 | | Tetanus_Int | Diptheria_Int | 0.000 |
| Tetanus_Int | Rubella_Int | 0.000 | | Tetanus_Int | Rubella_Int | 0.000 |
| Tetanus_Int | CMV_Int | 0.000 | | Tetanus_Int | CMV_Int | 0.000 |
| Tetanus_Int | HepB_cAb_Int | 0.000 | | Tetanus_Int | HepB_cAb_Int | 0.000 |
| Tetanus_Int | HepB_eAb_Int | 0.000 | | Tetanus_Int | HepB_eAb_Int | 0.000 |
| Tetanus_Int | HepB_eAg_Int | 0.000 | | Tetanus_Int | HepB_eAg_Int | 0.000 |
| Tetanus_Int | HepC_Int | 0.000 | | Tetanus_Int | HepC_Int | 0.000 |
| Tetanus_Int | Schistosoma_int | 0.000 | | Tetanus_Int | Schistosoma_int | 0.000 |
| Tetanus_Int | Strongyloides_Int | 0.000 | | Tetanus_Int | Strongyloides_Int | 0.000 |
| Tetanus_Int | Filaria_Int | 0.000 | | Tetanus_Int | Filaria_Int | 0.000 |
| Diptheria_Int | IL_1_alpha | 0.000 | | Diptheria_Int | IL_1_alpha | 0.000 |
| Diptheria_Int | IL_1_beta | 0.000 | | Diptheria_Int | IL_1_beta | 0.000 |
| Diptheria_Int | IL_2 | 0.000 | | Diptheria_Int | IL_2 | 0.000 |
| Diptheria_Int | IL_4 | 0.000 | | Diptheria_Int | IL_4 | 0.000 |

FIG. 21I8-L

| | | | | | | |
|---|---|---|---|---|---|---|
| Diptheria_Int | IL_5 | 0.000 | | Diptheria_Int | IL_5 | 0.000 |
| Diptheria_Int | IL_6 | 0.000 | | Diptheria_Int | IL_6 | 0.000 |
| Diptheria_Int | IL_8 | 0.000 | | Diptheria_Int | IL_8 | 0.000 |
| Diptheria_Int | IL_10 | 0.000 | | Diptheria_Int | IL_10 | 0.000 |
| Diptheria_Int | IL_12p70 | 0.000 | | Diptheria_Int | IL_12p70 | 0.000 |
| Diptheria_Int | IL_13 | 0.000 | | Diptheria_Int | IL_13 | 0.000 |
| Diptheria_Int | IL_15 | 0.000 | | Diptheria_Int | IL_15 | 0.000 |
| Diptheria_Int | IL_17 | 0.000 | | Diptheria_Int | IL_17 | 0.000 |
| Diptheria_Int | IL_23 | 0.000 | | Diptheria_Int | IL_23 | 0.000 |
| Diptheria_Int | IFN_gamma | 0.000 | | Diptheria_Int | IFN_gamma | 0.000 |
| Diptheria_Int | TNF_alpha | 0.000 | | Diptheria_Int | TNF_alpha | 0.000 |
| Diptheria_Int | TNF_beta | 0.000 | | Diptheria_Int | TNF_beta | 0.000 |
| Diptheria_Int | Varicella_Int | 0.000 | | Diptheria_Int | Varicella_Int | 0.000 |
| Diptheria_Int | Measles_OD_DB_Int | 0.000 | | Diptheria_Int | Measles_OD_DB_Int | 0.000 |
| Diptheria_Int | Measles_Int | 0.000 | | Diptheria_Int | Measles_Int | 0.000 |
| Diptheria_Int | HepA_Int | 0.000 | | Diptheria_Int | HepA_Int | 0.000 |
| Diptheria_Int | Tetanus_Int | 0.000 | | Diptheria_Int | Tetanus_Int | 0.000 |
| Diptheria_Int | Diptheria_Int | 1.000 | | Diptheria_Int | Diptheria_Int | 1.000 |
| Diptheria_Int | Rubella_Int | 0.000 | | Diptheria_Int | Rubella_Int | 0.000 |
| Diptheria_Int | CMV_Int | 0.000 | | Diptheria_Int | CMV_Int | 0.000 |
| Diptheria_Int | HepB_cAb_Int | 0.000 | | Diptheria_Int | HepB_cAb_Int | 0.000 |
| Diptheria_Int | HepB_eAb_Int | 0.000 | | Diptheria_Int | HepB_eAb_Int | 0.000 |
| Diptheria_Int | HepB_eAg_Int | 0.000 | | Diptheria_Int | HepB_eAg_Int | 0.000 |
| Diptheria_Int | HepC_Int | 0.000 | | Diptheria_Int | HepC_Int | 0.000 |
| Diptheria_Int | Schistosoma_int | 0.000 | | Diptheria_Int | Schistosoma_int | 0.000 |
| Diptheria_Int | Strongyloides_Int | 0.000 | | Diptheria_Int | Strongyloides_Int | 0.000 |
| Diptheria_Int | Filaria_Int | 0.000 | | Diptheria_Int | Filaria_Int | 0.000 |
| Rubella_Int | IL_1_alpha | -0.092 | | Rubella_Int | IL_1_alpha | 0.364 |
| Rubella_Int | IL_1_beta | -0.073 | | Rubella_Int | IL_1_beta | 0.233 |
| Rubella_Int | IL_2 | -0.076 | | Rubella_Int | IL_2 | 0.134 |
| Rubella_Int | IL_4 | -0.081 | | Rubella_Int | IL_4 | 0.343 |
| Rubella_Int | IL_5 | -0.093 | | Rubella_Int | IL_5 | 0.087 |
| Rubella_Int | IL_6 | -0.005 | | Rubella_Int | IL_6 | 0.049 |
| Rubella_Int | IL_8 | 0.339 | | Rubella_Int | IL_8 | 0.004 |
| Rubella_Int | IL_10 | -0.084 | | Rubella_Int | IL_10 | 0.238 |
| Rubella_Int | IL_12p70 | -0.106 | | Rubella_Int | IL_12p70 | 0.274 |
| Rubella_Int | IL_13 | -0.111 | | Rubella_Int | IL_13 | 0.357 |
| Rubella_Int | IL_15 | 0.130 | | Rubella_Int | IL_15 | 0.172 |
| Rubella_Int | IL_17 | -0.037 | | Rubella_Int | IL_17 | 0.323 |
| Rubella_Int | IL_23 | -0.035 | | Rubella_Int | IL_23 | 0.459 |
| Rubella_Int | IFN_gamma | 0.000 | | Rubella_Int | IFN_gamma | 0.000 |
| Rubella_Int | TNF_alpha | -0.071 | | Rubella_Int | TNF_alpha | 0.237 |
| Rubella_Int | TNF_beta | -0.075 | | Rubella_Int | TNF_beta | 0.515 |
| Rubella_Int | Varicella_Int | 0.052 | | Rubella_Int | Varicella_Int | -0.225 |
| Rubella_Int | Measles_OD_DB_Int | 0.086 | | Rubella_Int | Measles_OD_DB_Int | -0.097 |
| Rubella_Int | Measles_Int | 0.048 | | Rubella_Int | Measles_Int | 0.000 |
| Rubella_Int | HepA_Int | 0.093 | | Rubella_Int | HepA_Int | -0.171 |
| Rubella_Int | Tetanus_Int | 0.000 | | Rubella_Int | Tetanus_Int | 0.000 |
| Rubella_Int | Diptheria_Int | 0.000 | | Rubella_Int | Diptheria_Int | 0.000 |
| Rubella_Int | Rubella_Int | 1.000 | | Rubella_Int | Rubella_Int | 1.000 |
| Rubella_Int | CMV_Int | 0.052 | | Rubella_Int | CMV_Int | -0.439 |
| Rubella_Int | HepB_cAb_Int | -0.102 | | Rubella_Int | HepB_cAb_Int | 0.005 |
| Rubella_Int | HepB_eAb_Int | 0.000 | | Rubella_Int | HepB_eAb_Int | 0.000 |
| Rubella_Int | HepB_eAg_Int | 0.000 | | Rubella_Int | HepB_eAg_Int | 0.000 |
| Rubella_Int | HepC_Int | -0.044 | | Rubella_Int | HepC_Int | -0.058 |
| Rubella_Int | Schistosoma_int | -0.044 | | Rubella_Int | Schistosoma_int | -0.103 |
| Rubella_Int | Strongyloides_Int | 0.068 | | Rubella_Int | Strongyloides_Int | 0.317 |

FIG. 2I8-M

| Rubella_Int | Filaria_Int | -0.089 | | Rubella_Int | Filaria_Int | -0.138 |
|---|---|---|---|---|---|---|
| CMV_Int | IL_1_alpha | 0.192 | | CMV_Int | IL_1_alpha | -0.175 |
| CMV_Int | IL_1_beta | 0.145 | | CMV_Int | IL_1_beta | -0.014 |
| CMV_Int | IL_2 | 0.158 | | CMV_Int | IL_2 | 0.073 |
| CMV_Int | IL_4 | 0.120 | | CMV_Int | IL_4 | -0.156 |
| CMV_Int | IL_5 | 0.130 | | CMV_Int | IL_5 | -0.382 |
| CMV_Int | IL_6 | 0.223 | | CMV_Int | IL_6 | -0.003 |
| CMV_Int | IL_8 | 0.232 | | CMV_Int | IL_8 | -0.043 |
| CMV_Int | IL_10 | 0.137 | | CMV_Int | IL_10 | -0.013 |
| CMV_Int | IL_12p70 | 0.053 | | CMV_Int | IL_12p70 | -0.009 |
| CMV_Int | IL_13 | 0.160 | | CMV_Int | IL_13 | -0.085 |
| CMV_Int | IL_15 | 0.288 | | CMV_Int | IL_15 | -0.371 |
| CMV_Int | IL_17 | 0.051 | | CMV_Int | IL_17 | -0.043 |
| CMV_Int | IL_23 | 0.052 | | CMV_Int | IL_23 | -0.317 |
| CMV_Int | IFN_gamma | 0.000 | | CMV_Int | IFN_gamma | 0.000 |
| CMV_Int | TNF_alpha | 0.196 | | CMV_Int | TNF_alpha | -0.079 |
| CMV_Int | TNF_beta | 0.155 | | CMV_Int | TNF_beta | -0.317 |
| CMV_Int | Varicella_Int | -0.116 | | CMV_Int | Varicella_Int | 0.302 |
| CMV_Int | Measles_OD_DB_Int | -0.184 | | CMV_Int | Measles_OD_DB_Int | -0.039 |
| CMV_Int | Measles_Int | -0.108 | | CMV_Int | Measles_Int | 0.000 |
| CMV_Int | HepA_Int | -0.031 | | CMV_Int | HepA_Int | 0.159 |
| CMV_Int | Tetanus_Int | 0.000 | | CMV_Int | Tetanus_Int | 0.000 |
| CMV_Int | Diptheria_Int | 0.000 | | CMV_Int | Diptheria_Int | 0.000 |
| CMV_Int | Rubella_Int | 0.052 | | CMV_Int | Rubella_Int | -0.439 |
| CMV_Int | CMV_Int | 1.000 | | CMV_Int | CMV_Int | 1.000 |
| CMV_Int | HepB_cAb_Int | 0.031 | | CMV_Int | HepB_cAb_Int | 0.197 |
| CMV_Int | HepB_eAb_Int | 0.000 | | CMV_Int | HepB_eAb_Int | 0.000 |
| CMV_Int | HepB_eAg_Int | 0.000 | | CMV_Int | HepB_eAg_Int | 0.000 |
| CMV_Int | HepC_Int | 0.092 | | CMV_Int | HepC_Int | 0.058 |
| CMV_Int | Schistosoma_int | 0.092 | | CMV_Int | Schistosoma_int | 0.103 |
| CMV_Int | Strongyloides_Int | -0.045 | | CMV_Int | Strongyloides_Int | -0.113 |
| CMV_Int | Filaria_Int | 0.049 | | CMV_Int | Filaria_Int | -0.230 |
| HepB_cAb_Int | IL_1_alpha | 0.043 | | HepB_cAb_Int | IL_1_alpha | -0.331 |
| HepB_cAb_Int | IL_1_beta | -0.077 | | HepB_cAb_Int | IL_1_beta | -0.246 |
| HepB_cAb_Int | IL_2 | 0.067 | | HepB_cAb_Int | IL_2 | -0.159 |
| HepB_cAb_Int | IL_4 | 0.201 | | HepB_cAb_Int | IL_4 | -0.263 |
| HepB_cAb_Int | IL_5 | -0.016 | | HepB_cAb_Int | IL_5 | -0.185 |
| HepB_cAb_Int | IL_6 | 0.137 | | HepB_cAb_Int | IL_6 | -0.162 |
| HepB_cAb_Int | IL_8 | 0.123 | | HepB_cAb_Int | IL_8 | -0.167 |
| HepB_cAb_Int | IL_10 | -0.023 | | HepB_cAb_Int | IL_10 | -0.207 |
| HepB_cAb_Int | IL_12p70 | -0.010 | | HepB_cAb_Int | IL_12p70 | -0.297 |
| HepB_cAb_Int | IL_13 | -0.059 | | HepB_cAb_Int | IL_13 | -0.284 |
| HepB_cAb_Int | IL_15 | 0.313 | | HepB_cAb_Int | IL_15 | -0.501 |
| HepB_cAb_Int | IL_17 | 0.234 | | HepB_cAb_Int | IL_17 | -0.228 |
| HepB_cAb_Int | IL_23 | 0.268 | | HepB_cAb_Int | IL_23 | 0.119 |
| HepB_cAb_Int | IFN_gamma | 0.000 | | HepB_cAb_Int | IFN_gamma | 0.000 |
| HepB_cAb_Int | TNF_alpha | 0.106 | | HepB_cAb_Int | TNF_alpha | -0.198 |
| HepB_cAb_Int | TNF_beta | -0.100 | | HepB_cAb_Int | TNF_beta | -0.193 |
| HepB_cAb_Int | Varicella_Int | -0.064 | | HepB_cAb_Int | Varicella_Int | -0.143 |
| HepB_cAb_Int | Measles_OD_DB_Int | -0.132 | | HepB_cAb_Int | Measles_OD_DB_Int | -0.103 |
| HepB_cAb_Int | Measles_Int | -0.330 | | HepB_cAb_Int | Measles_Int | 0.000 |
| HepB_cAb_Int | HepA_Int | -0.057 | | HepB_cAb_Int | HepA_Int | -0.208 |
| HepB_cAb_Int | Tetanus_Int | 0.000 | | HepB_cAb_Int | Tetanus_Int | 0.000 |
| HepB_cAb_Int | Diptheria_Int | 0.000 | | HepB_cAb_Int | Diptheria_Int | 0.000 |
| HepB_cAb_Int | Rubella_Int | -0.102 | | HepB_cAb_Int | Rubella_Int | 0.005 |
| HepB_cAb_Int | CMV_Int | 0.031 | | HepB_cAb_Int | CMV_Int | 0.197 |
| HepB_cAb_Int | HepB_cAb_Int | 1.000 | | HepB_cAb_Int | HepB_cAb_Int | 1.000 |

FIG. 2I18-N

| | | | | | | |
|---|---|---|---|---|---|---|
| HepB_cAb_Int | HepB_eAb_Int | 0.000 | | HepB_cAb_Int | HepB_eAb_Int | 0.000 |
| HepB_cAb_Int | HepB_eAg_Int | 0.000 | | HepB_cAb_Int | HepB_eAg_Int | 0.000 |
| HepB_cAb_Int | HepC_Int | 0.231 | | HepB_cAb_Int | HepC_Int | -0.094 |
| HepB_cAb_Int | Schistosoma_int | 0.025 | | HepB_cAb_Int | Schistosoma_int | 0.062 |
| HepB_cAb_Int | Strongyloides_Int | -0.039 | | HepB_cAb_Int | Strongyloides_Int | -0.130 |
| HepB_cAb_Int | Filaria_Int | 0.079 | | HepB_cAb_Int | Filaria_Int | -0.029 |
| HepB_eAb_Int | IL_1_alpha | 0.000 | | HepB_eAb_Int | IL_1_alpha | 0.000 |
| HepB_eAb_Int | IL_1_beta | 0.000 | | HepB_eAb_Int | IL_1_beta | 0.000 |
| HepB_eAb_Int | IL_2 | 0.000 | | HepB_eAb_Int | IL_2 | 0.000 |
| HepB_eAb_Int | IL_4 | 0.000 | | HepB_eAb_Int | IL_4 | 0.000 |
| HepB_eAb_Int | IL_5 | 0.000 | | HepB_eAb_Int | IL_5 | 0.000 |
| HepB_eAb_Int | IL_6 | 0.000 | | HepB_eAb_Int | IL_6 | 0.000 |
| HepB_eAb_Int | IL_8 | 0.000 | | HepB_eAb_Int | IL_8 | 0.000 |
| HepB_eAb_Int | IL_10 | 0.000 | | HepB_eAb_Int | IL_10 | 0.000 |
| HepB_eAb_Int | IL_12p70 | 0.000 | | HepB_eAb_Int | IL_12p70 | 0.000 |
| HepB_eAb_Int | IL_13 | 0.000 | | HepB_eAb_Int | IL_13 | 0.000 |
| HepB_eAb_Int | IL_15 | 0.000 | | HepB_eAb_Int | IL_15 | 0.000 |
| HepB_eAb_Int | IL_17 | 0.000 | | HepB_eAb_Int | IL_17 | 0.000 |
| HepB_eAb_Int | IL_23 | 0.000 | | HepB_eAb_Int | IL_23 | 0.000 |
| HepB_eAb_Int | IFN_gamma | 0.000 | | HepB_eAb_Int | IFN_gamma | 0.000 |
| HepB_eAb_Int | TNF_alpha | 0.000 | | HepB_eAb_Int | TNF_alpha | 0.000 |
| HepB_eAb_Int | TNF_beta | 0.000 | | HepB_eAb_Int | TNF_beta | 0.000 |
| HepB_eAb_Int | Varicella_Int | 0.000 | | HepB_eAb_Int | Varicella_Int | 0.000 |
| HepB_eAb_Int | Measles_OD_DB_Int | 0.000 | | HepB_eAb_Int | Measles_OD_DB_Int | 0.000 |
| HepB_eAb_Int | Measles_Int | 0.000 | | HepB_eAb_Int | Measles_Int | 0.000 |
| HepB_eAb_Int | HepA_Int | 0.000 | | HepB_eAb_Int | HepA_Int | 0.000 |
| HepB_eAb_Int | Tetanus_Int | 0.000 | | HepB_eAb_Int | Tetanus_Int | 0.000 |
| HepB_eAb_Int | Diptheria_Int | 0.000 | | HepB_eAb_Int | Diptheria_Int | 0.000 |
| HepB_eAb_Int | Rubella_Int | 0.000 | | HepB_eAb_Int | Rubella_Int | 0.000 |
| HepB_eAb_Int | CMV_Int | 0.000 | | HepB_eAb_Int | CMV_Int | 0.000 |
| HepB_eAb_Int | HepB_cAb_Int | 0.000 | | HepB_eAb_Int | HepB_cAb_Int | 0.000 |
| HepB_eAb_Int | HepB_eAb_Int | 1.000 | | HepB_eAb_Int | HepB_eAb_Int | 1.000 |
| HepB_eAb_Int | HepB_eAg_Int | 0.000 | | HepB_eAb_Int | HepB_eAg_Int | 0.000 |
| HepB_eAb_Int | HepC_Int | 0.000 | | HepB_eAb_Int | HepC_Int | 0.000 |
| HepB_eAb_Int | Schistosoma_int | 0.000 | | HepB_eAb_Int | Schistosoma_int | 0.000 |
| HepB_eAb_Int | Strongyloides_Int | 0.000 | | HepB_eAb_Int | Strongyloides_Int | 0.000 |
| HepB_eAb_Int | Filaria_Int | 0.000 | | HepB_eAb_Int | Filaria_Int | 0.000 |
| HepB_eAg_Int | IL_1_alpha | 0.000 | | HepB_eAg_Int | IL_1_alpha | 0.000 |
| HepB_eAg_Int | IL_1_beta | 0.000 | | HepB_eAg_Int | IL_1_beta | 0.000 |
| HepB_eAg_Int | IL_2 | 0.000 | | HepB_eAg_Int | IL_2 | 0.000 |
| HepB_eAg_Int | IL_4 | 0.000 | | HepB_eAg_Int | IL_4 | 0.000 |
| HepB_eAg_Int | IL_5 | 0.000 | | HepB_eAg_Int | IL_5 | 0.000 |
| HepB_eAg_Int | IL_6 | 0.000 | | HepB_eAg_Int | IL_6 | 0.000 |
| HepB_eAg_Int | IL_8 | 0.000 | | HepB_eAg_Int | IL_8 | 0.000 |
| HepB_eAg_Int | IL_10 | 0.000 | | HepB_eAg_Int | IL_10 | 0.000 |
| HepB_eAg_Int | IL_12p70 | 0.000 | | HepB_eAg_Int | IL_12p70 | 0.000 |
| HepB_eAg_Int | IL_13 | 0.000 | | HepB_eAg_Int | IL_13 | 0.000 |
| HepB_eAg_Int | IL_15 | 0.000 | | HepB_eAg_Int | IL_15 | 0.000 |
| HepB_eAg_Int | IL_17 | 0.000 | | HepB_eAg_Int | IL_17 | 0.000 |
| HepB_eAg_Int | IL_23 | 0.000 | | HepB_eAg_Int | IL_23 | 0.000 |
| HepB_eAg_Int | IFN_gamma | 0.000 | | HepB_eAg_Int | IFN_gamma | 0.000 |
| HepB_eAg_Int | TNF_alpha | 0.000 | | HepB_eAg_Int | TNF_alpha | 0.000 |
| HepB_eAg_Int | TNF_beta | 0.000 | | HepB_eAg_Int | TNF_beta | 0.000 |
| HepB_eAg_Int | Varicella_Int | 0.000 | | HepB_eAg_Int | Varicella_Int | 0.000 |
| HepB_eAg_Int | Measles_OD_DB_Int | 0.000 | | HepB_eAg_Int | Measles_OD_DB_Int | 0.000 |
| HepB_eAg_Int | Measles_Int | 0.000 | | HepB_eAg_Int | Measles_Int | 0.000 |
| HepB_eAg_Int | HepA_Int | 0.000 | | HepB_eAg_Int | HepA_Int | 0.000 |

FIG. 21I8-O

| | | | | | | |
|---|---|---|---|---|---|---|
| HepB_eAg_Int | Tetanus_Int | 0.000 | | HepB_eAg_Int | Tetanus_Int | 0.000 |
| HepB_eAg_Int | Diptheria_Int | 0.000 | | HepB_eAg_Int | Diptheria_Int | 0.000 |
| HepB_eAg_Int | Rubella_Int | 0.000 | | HepB_eAg_Int | Rubella_Int | 0.000 |
| HepB_eAg_Int | CMV_Int | 0.000 | | HepB_eAg_Int | CMV_Int | 0.000 |
| HepB_eAg_Int | HepB_cAb_Int | 0.000 | | HepB_eAg_Int | HepB_cAb_Int | 0.000 |
| HepB_eAg_Int | HepB_eAb_Int | 0.000 | | HepB_eAg_Int | HepB_eAb_Int | 0.000 |
| HepB_eAg_Int | HepB_eAg_Int | 1.000 | | HepB_eAg_Int | HepB_eAg_Int | 1.000 |
| HepB_eAg_Int | HepC_Int | 0.000 | | HepB_eAg_Int | HepC_Int | 0.000 |
| HepB_eAg_Int | Schistosoma_int | 0.000 | | HepB_eAg_Int | Schistosoma_int | 0.000 |
| HepB_eAg_Int | Strongyloides_Int | 0.000 | | HepB_eAg_Int | Strongyloides_Int | 0.000 |
| HepB_eAg_Int | Filaria_Int | 0.000 | | HepB_eAg_Int | Filaria_Int | 0.000 |
| HepC_Int | IL_1_alpha | -0.164 | | HepC_Int | IL_1_alpha | -0.078 |
| HepC_Int | IL_1_beta | 0.084 | | HepC_Int | IL_1_beta | -0.097 |
| HepC_Int | IL_2 | -0.107 | | HepC_Int | IL_2 | -0.058 |
| HepC_Int | IL_4 | 0.312 | | HepC_Int | IL_4 | 0.073 |
| HepC_Int | IL_5 | -0.116 | | HepC_Int | IL_5 | -0.073 |
| HepC_Int | IL_6 | -0.136 | | HepC_Int | IL_6 | -0.065 |
| HepC_Int | IL_8 | -0.138 | | HepC_Int | IL_8 | -0.052 |
| HepC_Int | IL_10 | 0.119 | | HepC_Int | IL_10 | -0.069 |
| HepC_Int | IL_12p70 | 0.043 | | HepC_Int | IL_12p70 | -0.110 |
| HepC_Int | IL_13 | 0.040 | | HepC_Int | IL_13 | -0.111 |
| HepC_Int | IL_15 | -0.021 | | HepC_Int | IL_15 | -0.027 |
| HepC_Int | IL_17 | -0.027 | | HepC_Int | IL_17 | -0.098 |
| HepC_Int | IL_23 | -0.015 | | HepC_Int | IL_23 | -0.076 |
| HepC_Int | IFN_gamma | 0.000 | | HepC_Int | IFN_gamma | 0.000 |
| HepC_Int | TNF_alpha | -0.015 | | HepC_Int | TNF_alpha | -0.105 |
| HepC_Int | TNF_beta | 0.367 | | HepC_Int | TNF_beta | -0.068 |
| HepC_Int | Varicella_Int | 0.100 | | HepC_Int | Varicella_Int | 0.040 |
| HepC_Int | Measles_OD_DB_Int | 0.157 | | HepC_Int | Measles_OD_DB_Int | 0.082 |
| HepC_Int | Measles_Int | -0.223 | | HepC_Int | Measles_Int | 0.000 |
| HepC_Int | HepA_Int | -0.025 | | HepC_Int | HepA_Int | 0.058 |
| HepC_Int | Tetanus_Int | 0.000 | | HepC_Int | Tetanus_Int | 0.000 |
| HepC_Int | Diptheria_Int | 0.000 | | HepC_Int | Diptheria_Int | 0.000 |
| HepC_Int | Rubella_Int | -0.044 | | HepC_Int | Rubella_Int | -0.058 |
| HepC_Int | CMV_Int | 0.092 | | HepC_Int | CMV_Int | 0.058 |
| HepC_Int | HepB_cAb_Int | 0.231 | | HepC_Int | HepB_cAb_Int | -0.094 |
| HepC_Int | HepB_eAb_Int | 0.000 | | HepC_Int | HepB_eAb_Int | 0.000 |
| HepC_Int | HepB_eAg_Int | 0.000 | | HepC_Int | HepB_eAg_Int | 0.000 |
| HepC_Int | HepC_Int | 1.000 | | HepC_Int | HepC_Int | 1.000 |
| HepC_Int | Schistosoma_int | 0.281 | | HepC_Int | Schistosoma_int | -0.050 |
| HepC_Int | Strongyloides_Int | -0.100 | | HepC_Int | Strongyloides_Int | -0.190 |
| HepC_Int | Filaria_Int | 0.150 | | HepC_Int | Filaria_Int | -0.077 |
| Schistosoma_int | IL_1_alpha | -0.164 | | Schistosoma_int | IL_1_alpha | -0.178 |
| Schistosoma_int | IL_1_beta | -0.102 | | Schistosoma_int | IL_1_beta | -0.151 |
| Schistosoma_int | IL_2 | -0.072 | | Schistosoma_int | IL_2 | 0.432 |
| Schistosoma_int | IL_4 | 0.323 | | Schistosoma_int | IL_4 | -0.153 |
| Schistosoma_int | IL_5 | -0.118 | | Schistosoma_int | IL_5 | -0.129 |
| Schistosoma_int | IL_6 | -0.189 | | Schistosoma_int | IL_6 | 0.512 |
| Schistosoma_int | IL_8 | -0.032 | | Schistosoma_int | IL_8 | -0.104 |
| Schistosoma_int | IL_10 | -0.178 | | Schistosoma_int | IL_10 | -0.157 |
| Schistosoma_int | IL_12p70 | 0.015 | | Schistosoma_int | IL_12p70 | -0.136 |
| Schistosoma_int | IL_13 | -0.108 | | Schistosoma_int | IL_13 | -0.141 |
| Schistosoma_int | IL_15 | -0.084 | | Schistosoma_int | IL_15 | -0.152 |
| Schistosoma_int | IL_17 | -0.056 | | Schistosoma_int | IL_17 | -0.014 |
| Schistosoma_int | IL_23 | 0.004 | | Schistosoma_int | IL_23 | -0.122 |
| Schistosoma_int | IFN_gamma | 0.000 | | Schistosoma_int | IFN_gamma | 0.000 |
| Schistosoma_int | TNF_alpha | -0.167 | | Schistosoma_int | TNF_alpha | -0.121 |

FIG. 21I8-P

| | | | | | | |
|---|---|---|---|---|---|---|
| Schistosoma_int | TNF_beta | -0.131 | | Schistosoma_int | TNF_beta | -0.069 |
| Schistosoma_int | Varicella_Int | 0.100 | | Schistosoma_int | Varicella_Int | 0.071 |
| Schistosoma_int | Measles_OD_DB_Int | 0.157 | | Schistosoma_int | Measles_OD_DB_Int | -0.154 |
| Schistosoma_int | Measles_Int | 0.092 | | Schistosoma_int | Measles_Int | 0.000 |
| Schistosoma_int | HepA_Int | -0.025 | | Schistosoma_int | HepA_Int | 0.103 |
| Schistosoma_int | Tetanus_Int | 0.000 | | Schistosoma_int | Tetanus_Int | 0.000 |
| Schistosoma_int | Diptheria_Int | 0.000 | | Schistosoma_int | Diptheria_Int | 0.000 |
| Schistosoma_int | Rubella_Int | -0.044 | | Schistosoma_int | Rubella_Int | -0.103 |
| Schistosoma_int | CMV_Int | 0.092 | | Schistosoma_int | CMV_Int | 0.103 |
| Schistosoma_int | HepB_cAb_Int | 0.025 | | Schistosoma_int | HepB_cAb_Int | 0.062 |
| Schistosoma_int | HepB_eAb_Int | 0.000 | | Schistosoma_int | HepB_eAb_Int | 0.000 |
| Schistosoma_int | HepB_eAg_Int | 0.000 | | Schistosoma_int | HepB_eAg_Int | 0.000 |
| Schistosoma_int | HepC_Int | 0.281 | | Schistosoma_int | HepC_Int | -0.050 |
| Schistosoma_int | Schistosoma_int | 1.000 | | Schistosoma_int | Schistosoma_int | 1.000 |
| Schistosoma_int | Strongyloides_Int | -0.100 | | Schistosoma_int | Strongyloides_Int | -0.338 |
| Schistosoma_int | Filaria_Int | 0.457 | | Schistosoma_int | Filaria_Int | 0.046 |
| Strongyloides_Int | IL_1_alpha | -0.035 | | Strongyloides_Int | IL_1_alpha | 0.045 |
| Strongyloides_Int | IL_1_beta | -0.002 | | Strongyloides_Int | IL_1_beta | 0.253 |
| Strongyloides_Int | IL_2 | -0.006 | | Strongyloides_Int | IL_2 | -0.110 |
| Strongyloides_Int | IL_4 | -0.192 | | Strongyloides_Int | IL_4 | 0.259 |
| Strongyloides_Int | IL_5 | -0.100 | | Strongyloides_Int | IL_5 | 0.182 |
| Strongyloides_Int | IL_6 | -0.018 | | Strongyloides_Int | IL_6 | -0.115 |
| Strongyloides_Int | IL_8 | -0.009 | | Strongyloides_Int | IL_8 | -0.153 |
| Strongyloides_Int | IL_10 | -0.117 | | Strongyloides_Int | IL_10 | 0.147 |
| Strongyloides_Int | IL_12p70 | -0.135 | | Strongyloides_Int | IL_12p70 | 0.061 |
| Strongyloides_Int | IL_13 | 0.181 | | Strongyloides_Int | IL_13 | 0.146 |
| Strongyloides_Int | IL_15 | 0.049 | | Strongyloides_Int | IL_15 | 0.102 |
| Strongyloides_Int | IL_17 | -0.145 | | Strongyloides_Int | IL_17 | 0.094 |
| Strongyloides_Int | IL_23 | -0.146 | | Strongyloides_Int | IL_23 | 0.129 |
| Strongyloides_Int | IFN_gamma | 0.000 | | Strongyloides_Int | IFN_gamma | 0.000 |
| Strongyloides_Int | TNF_alpha | 0.036 | | Strongyloides_Int | TNF_alpha | 0.297 |
| Strongyloides_Int | TNF_beta | -0.168 | | Strongyloides_Int | TNF_beta | 0.285 |
| Strongyloides_Int | Varicella_Int | 0.213 | | Strongyloides_Int | Varicella_Int | -0.288 |
| Strongyloides_Int | Measles_OD_DB_Int | -0.065 | | Strongyloides_Int | Measles_OD_DB_Int | 0.320 |
| Strongyloides_Int | Measles_Int | -0.239 | | Strongyloides_Int | Measles_Int | 0.000 |
| Strongyloides_Int | HepA_Int | 0.354 | | Strongyloides_Int | HepA_Int | -0.011 |
| Strongyloides_Int | Tetanus_Int | 0.000 | | Strongyloides_Int | Tetanus_Int | 0.000 |
| Strongyloides_Int | Diptheria_Int | 0.000 | | Strongyloides_Int | Diptheria_Int | 0.000 |
| Strongyloides_Int | Rubella_Int | 0.068 | | Strongyloides_Int | Rubella_Int | 0.317 |
| Strongyloides_Int | CMV_Int | -0.045 | | Strongyloides_Int | CMV_Int | -0.113 |
| Strongyloides_Int | HepB_cAb_Int | -0.039 | | Strongyloides_Int | HepB_cAb_Int | -0.130 |
| Strongyloides_Int | HepB_eAb_Int | 0.000 | | Strongyloides_Int | HepB_eAb_Int | 0.000 |
| Strongyloides_Int | HepB_eAg_Int | 0.000 | | Strongyloides_Int | HepB_eAg_Int | 0.000 |
| Strongyloides_Int | HepC_Int | -0.100 | | Strongyloides_Int | HepC_Int | -0.190 |
| Strongyloides_Int | Schistosoma_int | -0.100 | | Strongyloides_Int | Schistosoma_int | -0.338 |
| Strongyloides_Int | Strongyloides_Int | 1.000 | | Strongyloides_Int | Strongyloides_Int | 1.000 |
| Strongyloides_Int | Filaria_Int | 0.289 | | Strongyloides_Int | Filaria_Int | 0.150 |
| Filaria_Int | IL_1_alpha | 0.039 | | Filaria_Int | IL_1_alpha | 0.124 |
| Filaria_Int | IL_1_beta | 0.092 | | Filaria_Int | IL_1_beta | 0.078 |
| Filaria_Int | IL_2 | 0.098 | | Filaria_Int | IL_2 | -0.145 |
| Filaria_Int | IL_4 | 0.088 | | Filaria_Int | IL_4 | -0.001 |
| Filaria_Int | IL_5 | -0.104 | | Filaria_Int | IL_5 | 0.365 |
| Filaria_Int | IL_6 | -0.097 | | Filaria_Int | IL_6 | -0.066 |
| Filaria_Int | IL_8 | -0.110 | | Filaria_Int | IL_8 | -0.110 |
| Filaria_Int | IL_10 | 0.038 | | Filaria_Int | IL_10 | 0.095 |
| Filaria_Int | IL_12p70 | 0.010 | | Filaria_Int | IL_12p70 | -0.073 |
| Filaria_Int | IL_13 | 0.138 | | Filaria_Int | IL_13 | -0.067 |

FIG. 21I8-Q

| Filaria_Int | IL_15 | -0.025 |
|---|---|---|
| Filaria_Int | IL_17 | -0.082 |
| Filaria_Int | IL_23 | -0.056 |
| Filaria_Int | IFN_gamma | 0.000 |
| Filaria_Int | TNF_alpha | 0.057 |
| Filaria_Int | TNF_beta | 0.074 |
| Filaria_Int | Varicella_Int | 0.199 |
| Filaria_Int | Measles_OD_DB_Int | -0.054 |
| Filaria_Int | Measles_Int | -0.220 |
| Filaria_Int | HepA_Int | 0.185 |
| Filaria_Int | Tetanus_Int | 0.000 |
| Filaria_Int | Diptheria_Int | 0.000 |
| Filaria_Int | Rubella_Int | -0.089 |
| Filaria_Int | CMV_Int | 0.049 |
| Filaria_Int | HepB_cAb_Int | 0.079 |
| Filaria_Int | HepB_eAb_Int | 0.000 |
| Filaria_Int | HepB_eAg_Int | 0.000 |
| Filaria_Int | HepC_Int | 0.150 |
| Filaria_Int | Schistosoma_int | 0.457 |
| Filaria_Int | Strongyloides_Int | 0.289 |
| Filaria_Int | Filaria_Int | 1.000 |

| Filaria_Int | IL_15 | -0.015 |
|---|---|---|
| Filaria_Int | IL_17 | -0.048 |
| Filaria_Int | IL_23 | -0.128 |
| Filaria_Int | IFN_gamma | 0.000 |
| Filaria_Int | TNF_alpha | 0.001 |
| Filaria_Int | TNF_beta | 0.140 |
| Filaria_Int | Varicella_Int | -0.333 |
| Filaria_Int | Measles_OD_DB_Int | -0.000 |
| Filaria_Int | Measles_Int | 0.000 |
| Filaria_Int | HepA_Int | 0.162 |
| Filaria_Int | Tetanus_Int | 0.000 |
| Filaria_Int | Diptheria_Int | 0.000 |
| Filaria_Int | Rubella_Int | -0.138 |
| Filaria_Int | CMV_Int | -0.230 |
| Filaria_Int | HepB_cAb_Int | -0.029 |
| Filaria_Int | HepB_eAb_Int | 0.000 |
| Filaria_Int | HepB_eAg_Int | 0.000 |
| Filaria_Int | HepC_int | -0.077 |
| Filaria_Int | Schistosoma_int | 0.046 |
| Filaria_Int | Strongyloides_Int | 0.150 |
| Filaria_Int | Filaria_Int | 1.000 |

FIG. 21I8-R

| 0.72% - Region_of_Origin=4, Sex=Female, IFN_gamma=7.5-22.5 | | |
|---|---|---|
| Property 1 | Property 2 | Corr. Coefficient |
| IL_1_alpha | IL_1_alpha | 1.000 |
| IL_1_alpha | IL_1_beta | -0.122 |
| IL_1_alpha | IL_2 | -0.077 |
| IL_1_alpha | IL_4 | -0.027 |
| IL_1_alpha | IL_5 | 0.392 |
| IL_1_alpha | IL_6 | 0.186 |
| IL_1_alpha | IL_8 | 0.359 |
| IL_1_alpha | IL_10 | -0.024 |
| IL_1_alpha | IL_12p70 | 0.316 |
| IL_1_alpha | IL_13 | 0.335 |
| IL_1_alpha | IL_15 | 0.551 |
| IL_1_alpha | IL_17 | 0.159 |
| IL_1_alpha | IL_23 | -0.031 |
| IL_1_alpha | IFN_gamma | 0.000 |
| IL_1_alpha | TNF_alpha | -0.287 |
| IL_1_alpha | TNF_beta | -0.244 |
| IL_1_alpha | Varicella_Int | 0.181 |
| IL_1_alpha | Measles_OD_DB_Int | -0.104 |
| IL_1_alpha | Measles_Int | -0.011 |
| IL_1_alpha | HepA_Int | 0.217 |
| IL_1_alpha | Tetanus_Int | 0.000 |
| IL_1_alpha | Diptheria_Int | 0.000 |
| IL_1_alpha | Rubella_Int | -0.055 |
| IL_1_alpha | CMV_Int | 0.246 |
| IL_1_alpha | HepB_cAb_Int | 0.000 |
| IL_1_alpha | HepB_eAb_Int | 0.000 |
| IL_1_alpha | HepB_eAg_Int | 0.000 |
| IL_1_alpha | HepC_Int | 0.000 |
| IL_1_alpha | Schistosoma_int | 0.420 |
| IL_1_alpha | Strongyloides_Int | -0.422 |
| IL_1_alpha | Filaria_Int | -0.295 |
| IL_1_beta | IL_1_alpha | -0.122 |

| 0.29% - Region_of_Origin=2, Sex=Male, IFN_gamma=7.5-22.5 | | |
|---|---|---|
| Property 1 | Property 2 | Corr. Coefficient |
| IL_1_alpha | IL_1_alpha | 1.000 |
| IL_1_alpha | IL_1_beta | 0.994 |
| IL_1_alpha | IL_2 | 0.985 |
| IL_1_alpha | IL_4 | 0.998 |
| IL_1_alpha | IL_5 | 0.998 |
| IL_1_alpha | IL_6 | 0.999 |
| IL_1_alpha | IL_8 | 0.872 |
| IL_1_alpha | IL_10 | 1.000 |
| IL_1_alpha | IL_12p70 | 0.618 |
| IL_1_alpha | IL_13 | 0.964 |
| IL_1_alpha | IL_15 | 0.983 |
| IL_1_alpha | IL_17 | 0.994 |
| IL_1_alpha | IL_23 | -0.364 |
| IL_1_alpha | IFN_gamma | 0.000 |
| IL_1_alpha | TNF_alpha | 0.997 |
| IL_1_alpha | TNF_beta | 0.993 |
| IL_1_alpha | Varicella_Int | 0.000 |
| IL_1_alpha | Measles_OD_DB_Int | -0.569 |
| IL_1_alpha | Measles_Int | 0.000 |
| IL_1_alpha | HepA_Int | 0.000 |
| IL_1_alpha | Tetanus_Int | 0.000 |
| IL_1_alpha | Diptheria_Int | 0.000 |
| IL_1_alpha | Rubella_Int | -0.343 |
| IL_1_alpha | CMV_Int | 0.000 |
| IL_1_alpha | HepB_cAb_Int | 0.000 |
| IL_1_alpha | HepB_eAb_Int | 0.000 |
| IL_1_alpha | HepB_eAg_Int | 0.000 |
| IL_1_alpha | HepC_Int | 0.000 |
| IL_1_alpha | Schistosoma_int | -0.314 |
| IL_1_alpha | Strongyloides_Int | 0.343 |
| IL_1_alpha | Filaria_Int | 0.537 |
| IL_1_beta | IL_1_alpha | 0.994 |

FIG. 2119-A

| IL_1_beta | IL_1_beta | 1.000 | IL_1_beta | IL_1_beta | 1.000 |
|---|---|---|---|---|---|
| IL_1_beta | IL_2 | -0.132 | IL_1_beta | IL_2 | 0.964 |
| IL_1_beta | IL_4 | -0.091 | IL_1_beta | IL_4 | 0.992 |
| IL_1_beta | IL_5 | -0.073 | IL_1_beta | IL_5 | 0.989 |
| IL_1_beta | IL_6 | -0.173 | IL_1_beta | IL_6 | 0.990 |
| IL_1_beta | IL_8 | 0.760 | IL_1_beta | IL_8 | 0.816 |
| IL_1_beta | IL_10 | 0.067 | IL_1_beta | IL_10 | 0.995 |
| IL_1_beta | IL_12p70 | 0.033 | IL_1_beta | IL_12p70 | 0.636 |
| IL_1_beta | IL_13 | -0.084 | IL_1_beta | IL_13 | 0.985 |
| IL_1_beta | IL_15 | 0.065 | IL_1_beta | IL_15 | 0.961 |
| IL_1_beta | IL_17 | 0.075 | IL_1_beta | IL_17 | 0.983 |
| IL_1_beta | IL_23 | -0.071 | IL_1_beta | IL_23 | -0.361 |
| IL_1_beta | IFN_gamma | 0.000 | IL_1_beta | IFN_gamma | 0.000 |
| IL_1_beta | TNF_alpha | 0.612 | IL_1_beta | TNF_alpha | 0.998 |
| IL_1_beta | TNF_beta | 0.208 | IL_1_beta | TNF_beta | 0.983 |
| IL_1_beta | Varicella_Int | -0.520 | IL_1_beta | Varicella_Int | 0.000 |
| IL_1_beta | Measles_OD_DB_Int | -0.585 | IL_1_beta | Measles_OD_DB_Int | -0.647 |
| IL_1_beta | Measles_Int | 0.312 | IL_1_beta | Measles_Int | 0.000 |
| IL_1_beta | HepA_Int | -0.022 | IL_1_beta | HepA_Int | 0.000 |
| IL_1_beta | Tetanus_Int | 0.000 | IL_1_beta | Tetanus_Int | 0.000 |
| IL_1_beta | Diptheria_Int | 0.000 | IL_1_beta | Diptheria_Int | 0.000 |
| IL_1_beta | Rubella_Int | 0.376 | IL_1_beta | Rubella_Int | -0.345 |
| IL_1_beta | CMV_Int | -0.108 | IL_1_beta | CMV_Int | 0.000 |
| IL_1_beta | HepB_cAb_Int | 0.000 | IL_1_beta | HepB_cAb_Int | 0.000 |
| IL_1_beta | HepB_eAb_Int | 0.000 | IL_1_beta | HepB_eAb_Int | 0.000 |
| IL_1_beta | HepB_eAg_Int | 0.000 | IL_1_beta | HepB_eAg_Int | 0.000 |
| IL_1_beta | HepC_Int | 0.000 | IL_1_beta | HepC_Int | 0.000 |
| IL_1_beta | Schistosoma_int | -0.025 | IL_1_beta | Schistosoma_int | -0.403 |
| IL_1_beta | Strongyloides_Int | -0.312 | IL_1_beta | Strongyloides_Int | 0.248 |
| IL_1_beta | Filaria_Int | 0.340 | IL_1_beta | Filaria_Int | 0.439 |
| IL_2 | IL_1_alpha | -0.077 | IL_2 | IL_1_alpha | 0.985 |
| IL_2 | IL_1_beta | -0.132 | IL_2 | IL_1_beta | 0.964 |
| IL_2 | IL_2 | 1.000 | IL_2 | IL_2 | 1.000 |
| IL_2 | IL_4 | -0.016 | IL_2 | IL_4 | 0.990 |
| IL_2 | IL_5 | -0.074 | IL_2 | IL_5 | 0.993 |
| IL_2 | IL_6 | -0.209 | IL_2 | IL_6 | 0.990 |
| IL_2 | IL_8 | -0.280 | IL_2 | IL_8 | 0.939 |
| IL_2 | IL_10 | 0.109 | IL_2 | IL_10 | 0.980 |
| IL_2 | IL_12p70 | -0.249 | IL_2 | IL_12p70 | 0.671 |
| IL_2 | IL_13 | -0.111 | IL_2 | IL_13 | 0.931 |
| IL_2 | IL_15 | -0.303 | IL_2 | IL_15 | 1.000 |
| IL_2 | IL_17 | 0.001 | IL_2 | IL_17 | 0.996 |
| IL_2 | IL_23 | -0.164 | IL_2 | IL_23 | -0.253 |
| IL_2 | IFN_gamma | 0.000 | IL_2 | IFN_gamma | 0.000 |
| IL_2 | TNF_alpha | 0.476 | IL_2 | TNF_alpha | 0.980 |
| IL_2 | TNF_beta | 0.149 | IL_2 | TNF_beta | 0.995 |
| IL_2 | Varicella_Int | -0.621 | IL_2 | Varicella_Int | 0.000 |
| IL_2 | Measles_OD_DB_Int | 0.252 | IL_2 | Measles_OD_DB_Int | -0.423 |
| IL_2 | Measles_Int | 0.240 | IL_2 | Measles_Int | 0.000 |
| IL_2 | HepA_Int | 0.132 | IL_2 | HepA_Int | 0.000 |
| IL_2 | Tetanus_Int | 0.000 | IL_2 | Tetanus_Int | 0.000 |
| IL_2 | Diptheria_Int | 0.000 | IL_2 | Diptheria_Int | 0.000 |
| IL_2 | Rubella_Int | 0.482 | IL_2 | Rubella_Int | -0.226 |
| IL_2 | CMV_Int | 0.016 | IL_2 | CMV_Int | 0.000 |
| IL_2 | HepB_cAb_Int | 0.000 | IL_2 | HepB_cAb_Int | 0.000 |
| IL_2 | HepB_eAb_Int | 0.000 | IL_2 | HepB_eAb_Int | 0.000 |
| IL_2 | HepB_eAg_Int | 0.000 | IL_2 | HepB_eAg_Int | 0.000 |

FIG. 2119-B

| IL_2 | HepC_Int | 0.000 | IL_2 | HepC_Int | 0.000 |
|---|---|---|---|---|---|
| IL_2 | Schistosoma_int | 0.520 | IL_2 | Schistosoma_int | -0.262 |
| IL_2 | Strongyloides_Int | 0.559 | IL_2 | Strongyloides_Int | 0.496 |
| IL_2 | Filaria_Int | 0.450 | IL_2 | Filaria_Int | 0.636 |
| IL_4 | IL_1_alpha | -0.027 | IL_4 | IL_1_alpha | 0.998 |
| IL_4 | IL_1_beta | -0.091 | IL_4 | IL_1_beta | 0.992 |
| IL_4 | IL_2 | -0.016 | IL_4 | IL_2 | 0.990 |
| IL_4 | IL_4 | 1.000 | IL_4 | IL_4 | 1.000 |
| IL_4 | IL_5 | 0.556 | IL_4 | IL_5 | 1.000 |
| IL_4 | IL_6 | 0.637 | IL_4 | IL_6 | 0.999 |
| IL_4 | IL_8 | -0.192 | IL_4 | IL_8 | 0.880 |
| IL_4 | IL_10 | 0.442 | IL_4 | IL_10 | 0.996 |
| IL_4 | IL_12p70 | -0.099 | IL_4 | IL_12p70 | 0.668 |
| IL_4 | IL_13 | 0.007 | IL_4 | IL_13 | 0.971 |
| IL_4 | IL_15 | 0.218 | IL_4 | IL_15 | 0.988 |
| IL_4 | IL_17 | 0.522 | IL_4 | IL_17 | 0.998 |
| IL_4 | IL_23 | -0.191 | IL_4 | IL_23 | -0.301 |
| IL_4 | IFN_gamma | 0.000 | IL_4 | IFN_gamma | 0.000 |
| IL_4 | TNF_alpha | -0.200 | IL_4 | TNF_alpha | 0.998 |
| IL_4 | TNF_beta | 0.584 | IL_4 | TNF_beta | 0.998 |
| IL_4 | Varicella_Int | 0.266 | IL_4 | Varicella_Int | 0.000 |
| IL_4 | Measles_OD_DB_Int | -0.697 | IL_4 | Measles_OD_DB_Int | -0.546 |
| IL_4 | Measles_Int | -0.400 | IL_4 | Measles_Int | 0.000 |
| IL_4 | HepA_Int | -0.315 | IL_4 | HepA_Int | 0.000 |
| IL_4 | Tetanus_Int | 0.000 | IL_4 | Tetanus_Int | 0.000 |
| IL_4 | Diptheria_Int | 0.000 | IL_4 | Diptheria_Int | 0.000 |
| IL_4 | Rubella_Int | 0.190 | IL_4 | Rubella_Int | -0.280 |
| IL_4 | CMV_Int | -0.603 | IL_4 | CMV_Int | 0.000 |
| IL_4 | HepB_cAb_Int | 0.000 | IL_4 | HepB_cAb_Int | 0.000 |
| IL_4 | HepB_eAb_Int | 0.000 | IL_4 | HepB_eAb_Int | 0.000 |
| IL_4 | HepB_eAg_Int | 0.000 | IL_4 | HepB_eAg_Int | 0.000 |
| IL_4 | HepC_Int | 0.000 | IL_4 | HepC_Int | 0.000 |
| IL_4 | Schistosoma_int | 0.249 | IL_4 | Schistosoma_int | -0.351 |
| IL_4 | Strongyloides_Int | 0.222 | IL_4 | Strongyloides_Int | 0.368 |
| IL_4 | Filaria_Int | -0.266 | IL_4 | Filaria_Int | 0.530 |
| IL_5 | IL_1_alpha | 0.392 | IL_5 | IL_1_alpha | 0.998 |
| IL_5 | IL_1_beta | -0.073 | IL_5 | IL_1_beta | 0.989 |
| IL_5 | IL_2 | -0.074 | IL_5 | IL_2 | 0.993 |
| IL_5 | IL_4 | 0.556 | IL_5 | IL_4 | 1.000 |
| IL_5 | IL_5 | 1.000 | IL_5 | IL_5 | 1.000 |
| IL_5 | IL_6 | 0.940 | IL_5 | IL_6 | 0.999 |
| IL_5 | IL_8 | 0.254 | IL_5 | IL_8 | 0.893 |
| IL_5 | IL_10 | -0.260 | IL_5 | IL_10 | 0.996 |
| IL_5 | IL_12p70 | 0.472 | IL_5 | IL_12p70 | 0.661 |
| IL_5 | IL_13 | 0.563 | IL_5 | IL_13 | 0.963 |
| IL_5 | IL_15 | 0.888 | IL_5 | IL_15 | 0.992 |
| IL_5 | IL_17 | -0.139 | IL_5 | IL_17 | 0.999 |
| IL_5 | IL_23 | 0.190 | IL_5 | IL_23 | -0.304 |
| IL_5 | IFN_gamma | 0.000 | IL_5 | IFN_gamma | 0.000 |
| IL_5 | TNF_alpha | 0.002 | IL_5 | TNF_alpha | 0.997 |
| IL_5 | TNF_beta | -0.203 | IL_5 | TNF_beta | 0.999 |
| IL_5 | Varicella_Int | 0.127 | IL_5 | Varicella_Int | 0.000 |
| IL_5 | Measles_OD_DB_Int | -0.437 | IL_5 | Measles_OD_DB_Int | -0.526 |
| IL_5 | Measles_Int | -0.493 | IL_5 | Measles_Int | 0.000 |
| IL_5 | HepA_Int | 0.043 | IL_5 | HepA_Int | 0.000 |
| IL_5 | Tetanus_Int | 0.000 | IL_5 | Tetanus_Int | 0.000 |
| IL_5 | Diptheria_Int | 0.000 | IL_5 | Diptheria_Int | 0.000 |

FIG. 21I9-C

| IL_5 | Rubella_Int | 0.432 | | IL_5 | Rubella_Int | -0.282 |
|---|---|---|---|---|---|---|
| IL_5 | CMV_Int | 0.243 | | IL_5 | CMV_Int | 0.000 |
| IL_5 | HepB_cAb_Int | 0.000 | | IL_5 | HepB_cAb_Int | 0.000 |
| IL_5 | HepB_eAb_Int | 0.000 | | IL_5 | HepB_eAb_Int | 0.000 |
| IL_5 | HepB_eAg_Int | 0.000 | | IL_5 | HepB_eAg_Int | 0.000 |
| IL_5 | HepC_Int | 0.000 | | IL_5 | HepC_Int | 0.000 |
| IL_5 | Schistosoma_int | -0.106 | | IL_5 | Schistosoma_int | -0.326 |
| IL_5 | Strongyloides_Int | -0.466 | | IL_5 | Strongyloides_Int | 0.390 |
| IL_5 | Filaria_Int | -0.186 | | IL_5 | Filaria_Int | 0.555 |
| IL_6 | IL_1_alpha | 0.186 | | IL_6 | IL_1_alpha | 0.999 |
| IL_6 | IL_1_beta | -0.173 | | IL_6 | IL_1_beta | 0.990 |
| IL_6 | IL_2 | -0.209 | | IL_6 | IL_2 | 0.990 |
| IL_6 | IL_4 | 0.637 | | IL_6 | IL_4 | 0.999 |
| IL_6 | IL_5 | 0.940 | | IL_6 | IL_5 | 0.999 |
| IL_6 | IL_6 | 1.000 | | IL_6 | IL_6 | 1.000 |
| IL_6 | IL_8 | 0.100 | | IL_6 | IL_8 | 0.887 |
| IL_6 | IL_10 | -0.280 | | IL_6 | IL_10 | 0.998 |
| IL_6 | IL_12p70 | 0.337 | | IL_6 | IL_12p70 | 0.630 |
| IL_6 | IL_13 | 0.442 | | IL_6 | IL_13 | 0.960 |
| IL_6 | IL_15 | 0.810 | | IL_6 | IL_15 | 0.988 |
| IL_6 | IL_17 | -0.179 | | IL_6 | IL_17 | 0.996 |
| IL_6 | IL_23 | 0.116 | | IL_6 | IL_23 | -0.343 |
| IL_6 | IFN_gamma | 0.000 | | IL_6 | IFN_gamma | 0.000 |
| IL_6 | TNF_alpha | -0.174 | | IL_6 | TNF_alpha | 0.996 |
| IL_6 | TNF_beta | -0.189 | | IL_6 | TNF_beta | 0.996 |
| IL_6 | Varicella_Int | 0.265 | | IL_6 | Varicella_Int | 0.000 |
| IL_6 | Measles_OD_DB_Int | -0.416 | | IL_6 | Measles_OD_DB_Int | -0.543 |
| IL_6 | Measles_Int | -0.593 | | IL_6 | Measles_Int | 0.000 |
| IL_6 | HepA_Int | 0.044 | | IL_6 | HepA_Int | 0.000 |
| IL_6 | Tetanus_Int | 0.000 | | IL_6 | Tetanus_Int | 0.000 |
| IL_6 | Diptheria_Int | 0.000 | | IL_6 | Diptheria_Int | 0.000 |
| IL_6 | Rubella_Int | 0.341 | | IL_6 | Rubella_Int | -0.321 |
| IL_6 | CMV_Int | 0.174 | | IL_6 | CMV_Int | 0.000 |
| IL_6 | HepB_cAb_Int | 0.000 | | IL_6 | HepB_cAb_Int | 0.000 |
| IL_6 | HepB_eAb_Int | 0.000 | | IL_6 | HepB_eAb_Int | 0.000 |
| IL_6 | HepB_eAg_Int | 0.000 | | IL_6 | HepB_eAg_Int | 0.000 |
| IL_6 | HepC_Int | 0.000 | | IL_6 | HepC_Int | 0.000 |
| IL_6 | Schistosoma_int | -0.275 | | IL_6 | Schistosoma_int | -0.305 |
| IL_6 | Strongyloides_Int | -0.389 | | IL_6 | Strongyloides_Int | 0.372 |
| IL_6 | Filaria_Int | -0.275 | | IL_6 | Filaria_Int | 0.557 |
| IL_8 | IL_1_alpha | 0.359 | | IL_8 | IL_1_alpha | 0.872 |
| IL_8 | IL_1_beta | 0.760 | | IL_8 | IL_1_beta | 0.816 |
| IL_8 | IL_2 | -0.280 | | IL_8 | IL_2 | 0.939 |
| IL_8 | IL_4 | -0.192 | | IL_8 | IL_4 | 0.880 |
| IL_8 | IL_5 | 0.254 | | IL_8 | IL_5 | 0.893 |
| IL_8 | IL_6 | 0.100 | | IL_8 | IL_6 | 0.887 |
| IL_8 | IL_8 | 1.000 | | IL_8 | IL_8 | 1.000 |
| IL_8 | IL_10 | -0.304 | | IL_8 | IL_10 | 0.861 |
| IL_8 | IL_12p70 | 0.265 | | IL_8 | IL_12p70 | 0.590 |
| IL_8 | IL_13 | 0.151 | | IL_8 | IL_13 | 0.751 |
| IL_8 | IL_15 | 0.529 | | IL_8 | IL_15 | 0.942 |
| IL_8 | IL_17 | -0.196 | | IL_8 | IL_17 | 0.904 |
| IL_8 | IL_23 | -0.048 | | IL_8 | IL_23 | -0.150 |
| IL_8 | IFN_gamma | 0.000 | | IL_8 | IFN_gamma | 0.000 |
| IL_8 | TNF_alpha | 0.360 | | IL_8 | TNF_alpha | 0.852 |
| IL_8 | TNF_beta | -0.244 | | IL_8 | TNF_beta | 0.902 |
| IL_8 | Varicella_Int | -0.243 | | IL_8 | Varicella_Int | 0.000 |

FIG. 21I9-D

| IL_8 | Measles_OD_DB_Int | -0.504 | IL_8 | Measles_OD_DB_Int | -0.096 |
|---|---|---|---|---|---|
| IL_8 | Measles_Int | 0.182 | IL_8 | Measles_Int | 0.000 |
| IL_8 | HepA_Int | 0.284 | IL_8 | HepA_Int | 0.000 |
| IL_8 | Tetanus_Int | 0.000 | IL_8 | Tetanus_Int | 0.000 |
| IL_8 | Diptheria_Int | 0.000 | IL_8 | Diptheria_Int | 0.000 |
| IL_8 | Rubella_Int | 0.271 | IL_8 | Rubella_Int | -0.114 |
| IL_8 | CMV_Int | 0.315 | IL_8 | CMV_Int | 0.000 |
| IL_8 | HepB_cAb_Int | 0.000 | IL_8 | HepB_cAb_Int | 0.000 |
| IL_8 | HepB_eAb_Int | 0.000 | IL_8 | HepB_eAb_Int | 0.000 |
| IL_8 | HepB_eAg_Int | 0.000 | IL_8 | HepB_eAg_Int | 0.000 |
| IL_8 | HepC_Int | 0.000 | IL_8 | HepC_Int | 0.000 |
| IL_8 | Schistosoma_int | -0.063 | IL_8 | Schistosoma_int | 0.002 |
| IL_8 | Strongyloides_Int | -0.598 | IL_8 | Strongyloides_Int | 0.755 |
| IL_8 | Filaria_Int | 0.165 | IL_8 | Filaria_Int | 0.848 |
| IL_10 | IL_1_alpha | -0.024 | IL_10 | IL_1_alpha | 1.000 |
| IL_10 | IL_1_beta | 0.067 | IL_10 | IL_1_beta | 0.995 |
| IL_10 | IL_2 | 0.109 | IL_10 | IL_2 | 0.980 |
| IL_10 | IL_4 | 0.442 | IL_10 | IL_4 | 0.996 |
| IL_10 | IL_5 | -0.260 | IL_10 | IL_5 | 0.996 |
| IL_10 | IL_6 | -0.280 | IL_10 | IL_6 | 0.998 |
| IL_10 | IL_8 | -0.304 | IL_10 | IL_8 | 0.861 |
| IL_10 | IL_10 | 1.000 | IL_10 | IL_10 | 1.000 |
| IL_10 | IL_12p70 | -0.051 | IL_10 | IL_12p70 | 0.604 |
| IL_10 | IL_13 | -0.027 | IL_10 | IL_13 | 0.965 |
| IL_10 | IL_15 | -0.474 | IL_10 | IL_15 | 0.977 |
| IL_10 | IL_17 | 0.963 | IL_10 | IL_17 | 0.990 |
| IL_10 | IL_23 | 0.038 | IL_10 | IL_23 | -0.385 |
| IL_10 | IFN_gamma | 0.000 | IL_10 | IFN_gamma | 0.000 |
| IL_10 | TNF_alpha | 0.026 | IL_10 | TNF_alpha | 0.997 |
| IL_10 | TNF_beta | 0.935 | IL_10 | TNF_beta | 0.990 |
| IL_10 | Varicella_Int | 0.184 | IL_10 | Varicella_Int | 0.000 |
| IL_10 | Measles_OD_DB_Int | -0.343 | IL_10 | Measles_OD_DB_Int | -0.588 |
| IL_10 | Measles_Int | 0.278 | IL_10 | Measles_Int | 0.000 |
| IL_10 | HepA_Int | -0.729 | IL_10 | HepA_Int | 0.000 |
| IL_10 | Tetanus_Int | 0.000 | IL_10 | Tetanus_Int | 0.000 |
| IL_10 | Diptheria_Int | 0.000 | IL_10 | Diptheria_Int | 0.000 |
| IL_10 | Rubella_Int | -0.335 | IL_10 | Rubella_Int | -0.364 |
| IL_10 | CMV_Int | -0.925 | IL_10 | CMV_Int | 0.000 |
| IL_10 | HepB_cAb_Int | 0.000 | IL_10 | HepB_cAb_Int | 0.000 |
| IL_10 | HepB_eAb_Int | 0.000 | IL_10 | HepB_eAb_Int | 0.000 |
| IL_10 | HepB_eAg_Int | 0.000 | IL_10 | HepB_eAg_Int | 0.000 |
| IL_10 | HepC_Int | 0.000 | IL_10 | HepC_int | 0.000 |
| IL_10 | Schistosoma_int | 0.702 | IL_10 | Schistosoma_int | -0.315 |
| IL_10 | Strongyloides_Int | 0.522 | IL_10 | Strongyloides_Int | 0.320 |
| IL_10 | Filaria_Int | -0.185 | IL_10 | Filaria_Int | 0.525 |
| IL_12p70 | IL_1_alpha | 0.316 | IL_12p70 | IL_1_alpha | 0.618 |
| IL_12p70 | IL_1_beta | 0.033 | IL_12p70 | IL_1_beta | 0.636 |
| IL_12p70 | IL_2 | -0.249 | IL_12p70 | IL_2 | 0.671 |
| IL_12p70 | IL_4 | -0.099 | IL_12p70 | IL_4 | 0.668 |
| IL_12p70 | IL_5 | 0.472 | IL_12p70 | IL_5 | 0.661 |
| IL_12p70 | IL_6 | 0.337 | IL_12p70 | IL_6 | 0.630 |
| IL_12p70 | IL_8 | 0.265 | IL_12p70 | IL_8 | 0.590 |
| IL_12p70 | IL_10 | -0.051 | IL_12p70 | IL_10 | 0.604 |
| IL_12p70 | IL_12p70 | 1.000 | IL_12p70 | IL_12p70 | 1.000 |
| IL_12p70 | IL_13 | 0.970 | IL_12p70 | IL_13 | 0.725 |
| IL_12p70 | IL_15 | 0.556 | IL_12p70 | IL_15 | 0.677 |
| IL_12p70 | IL_17 | -0.058 | IL_12p70 | IL_17 | 0.687 |

FIG. 2119-E

| | | | | | | |
|---|---|---|---|---|---|---|
| IL_12p70 | IL_23 | 0.895 | | IL_12p70 | IL_23 | 0.485 |
| IL_12p70 | IFN_gamma | 0.000 | | IL_12p70 | IFN_gamma | 0.000 |
| IL_12p70 | TNF_alpha | 0.309 | | IL_12p70 | TNF_alpha | 0.661 |
| IL_12p70 | TNF_beta | -0.188 | | IL_12p70 | TNF_beta | 0.692 |
| IL_12p70 | Varicella_Int | 0.261 | | IL_12p70 | Varicella_Int | 0.000 |
| IL_12p70 | Measles_OD_DB_Int | 0.014 | | IL_12p70 | Measles_OD_DB_Int | -0.201 |
| IL_12p70 | Measles_Int | 0.050 | | IL_12p70 | Measles_Int | 0.000 |
| IL_12p70 | HepA_Int | -0.483 | | IL_12p70 | HepA_Int | 0.000 |
| IL_12p70 | Tetanus_Int | 0.000 | | IL_12p70 | Tetanus_Int | 0.000 |
| IL_12p70 | Diptheria_Int | 0.000 | | IL_12p70 | Diptheria_Int | 0.000 |
| IL_12p70 | Rubella_Int | -0.173 | | IL_12p70 | Rubella_Int | 0.497 |
| IL_12p70 | CMV_Int | 0.245 | | IL_12p70 | CMV_Int | 0.000 |
| IL_12p70 | HepB_cAb_Int | 0.000 | | IL_12p70 | HepB_cAb_Int | 0.000 |
| IL_12p70 | HepB_eAb_Int | 0.000 | | IL_12p70 | HepB_eAb_Int | 0.000 |
| IL_12p70 | HepB_eAg_Int | 0.000 | | IL_12p70 | HepB_eAg_Int | 0.000 |
| IL_12p70 | HepC_Int | 0.000 | | IL_12p70 | HepC_Int | 0.000 |
| IL_12p70 | Schistosoma_int | -0.116 | | IL_12p70 | Schistosoma_int | -0.730 |
| IL_12p70 | Strongyloides_Int | -0.529 | | IL_12p70 | Strongyloides_Int | 0.397 |
| IL_12p70 | Filaria_Int | -0.220 | | IL_12p70 | Filaria_Int | 0.155 |
| IL_13 | IL_1_alpha | 0.335 | | IL_13 | IL_1_alpha | 0.964 |
| IL_13 | IL_1_beta | -0.084 | | IL_13 | IL_1_beta | 0.985 |
| IL_13 | IL_2 | -0.111 | | IL_13 | IL_2 | 0.931 |
| IL_13 | IL_4 | 0.007 | | IL_13 | IL_4 | 0.971 |
| IL_13 | IL_5 | 0.563 | | IL_13 | IL_5 | 0.963 |
| IL_13 | IL_6 | 0.442 | | IL_13 | IL_6 | 0.960 |
| IL_13 | IL_8 | 0.151 | | IL_13 | IL_8 | 0.751 |
| IL_13 | IL_10 | -0.027 | | IL_13 | IL_10 | 0.965 |
| IL_13 | IL_12p70 | 0.970 | | IL_13 | IL_12p70 | 0.725 |
| IL_13 | IL_13 | 1.000 | | IL_13 | IL_13 | 1.000 |
| IL_13 | IL_15 | 0.586 | | IL_13 | IL_15 | 0.928 |
| IL_13 | IL_17 | -0.044 | | IL_13 | IL_17 | 0.960 |
| IL_13 | IL_23 | 0.858 | | IL_13 | IL_23 | -0.250 |
| IL_13 | IFN_gamma | 0.000 | | IL_13 | IFN_gamma | 0.000 |
| IL_13 | TNF_alpha | 0.284 | | IL_13 | TNF_alpha | 0.980 |
| IL_13 | TNF_beta | -0.167 | | IL_13 | TNF_beta | 0.962 |
| IL_13 | Varicella_Int | 0.239 | | IL_13 | Varicella_Int | 0.000 |
| IL_13 | Measles_OD_DB_Int | 0.034 | | IL_13 | Measles_OD_DB_Int | -0.684 |
| IL_13 | Measles_Int | 0.011 | | IL_13 | Measles_Int | 0.000 |
| IL_13 | HepA_Int | -0.464 | | IL_13 | HepA_Int | 0.000 |
| IL_13 | Tetanus_Int | 0.000 | | IL_13 | Tetanus_Int | 0.000 |
| IL_13 | Diptheria_Int | 0.000 | | IL_13 | Diptheria_Int | 0.000 |
| IL_13 | Rubella_Int | -0.091 | | IL_13 | Rubella_Int | -0.238 |
| IL_13 | CMV_Int | 0.235 | | IL_13 | CMV_Int | 0.000 |
| IL_13 | HepB_cAb_Int | 0.000 | | IL_13 | HepB_cAb_Int | 0.000 |
| IL_13 | HepB_eAb_Int | 0.000 | | IL_13 | HepB_eAb_Int | 0.000 |
| IL_13 | HepB_eAg_Int | 0.000 | | IL_13 | HepB_eAg_Int | 0.000 |
| IL_13 | HepC_Int | 0.000 | | IL_13 | HepC_Int | 0.000 |
| IL_13 | Schistosoma_int | -0.039 | | IL_13 | Schistosoma_int | -0.552 |
| IL_13 | Strongyloides_Int | -0.446 | | IL_13 | Strongyloides_Int | 0.180 |
| IL_13 | Filaria_Int | -0.246 | | IL_13 | Filaria_Int | 0.312 |
| IL_15 | IL_1_alpha | 0.551 | | IL_15 | IL_1_alpha | 0.983 |
| IL_15 | IL_1_beta | 0.065 | | IL_15 | IL_1_beta | 0.961 |
| IL_15 | IL_2 | -0.303 | | IL_15 | IL_2 | 1.000 |
| IL_15 | IL_4 | 0.218 | | IL_15 | IL_4 | 0.988 |
| IL_15 | IL_5 | 0.888 | | IL_15 | IL_5 | 0.992 |
| IL_15 | IL_6 | 0.810 | | IL_15 | IL_6 | 0.988 |
| IL_15 | IL_8 | 0.529 | | IL_15 | IL_8 | 0.942 |

FIG. 2I19-F

| | | | | | | |
|---|---|---|---|---|---|---|
| IL_15 | IL_10 | -0.474 | | IL_15 | IL_10 | 0.977 |
| IL_15 | IL_12p70 | 0.556 | | IL_15 | IL_12p70 | 0.677 |
| IL_15 | IL_13 | 0.586 | | IL_15 | IL_13 | 0.928 |
| IL_15 | IL_15 | 1.000 | | IL_15 | IL_15 | 1.000 |
| IL_15 | IL_17 | -0.319 | | IL_15 | IL_17 | 0.995 |
| IL_15 | IL_23 | 0.217 | | IL_15 | IL_23 | -0.241 |
| IL_15 | IFN_gamma | 0.000 | | IL_15 | IFN_gamma | 0.000 |
| IL_15 | TNF_alpha | -0.048 | | IL_15 | TNF_alpha | 0.978 |
| IL_15 | TNF_beta | -0.475 | | IL_15 | TNF_beta | 0.995 |
| IL_15 | Varicella_Int | 0.123 | | IL_15 | Varicella_Int | 0.000 |
| IL_15 | Measles_OD_DB_Int | -0.333 | | IL_15 | Measles_OD_DB_Int | -0.412 |
| IL_15 | Measles_Int | -0.318 | | IL_15 | Measles_Int | 0.000 |
| IL_15 | HepA_Int | 0.214 | | IL_15 | HepA_Int | 0.000 |
| IL_15 | Tetanus_Int | 0.000 | | IL_15 | Tetanus_Int | 0.000 |
| IL_15 | Diptheria_Int | 0.000 | | IL_15 | Diptheria_Int | 0.000 |
| IL_15 | Rubella_Int | 0.334 | | IL_15 | Rubella_Int | -0.214 |
| IL_15 | CMV_Int | 0.490 | | IL_15 | CMV_Int | 0.000 |
| IL_15 | HepB_cAb_Int | 0.000 | | IL_15 | HepB_cAb_Int | 0.000 |
| IL_15 | HepB_eAb_Int | 0.000 | | IL_15 | HepB_eAb_Int | 0.000 |
| IL_15 | HepB_eAg_Int | 0.000 | | IL_15 | HepB_eAg_Int | 0.000 |
| IL_15 | HepC_Int | 0.000 | | IL_15 | HepC_Int | 0.000 |
| IL_15 | Schistosoma_int | -0.261 | | IL_15 | Schistosoma_int | -0.261 |
| IL_15 | Strongyloides_Int | -0.763 | | IL_15 | Strongyloides_Int | 0.506 |
| IL_15 | Filaria_Int | -0.279 | | IL_15 | Filaria_Int | 0.640 |
| IL_17 | IL_1_alpha | 0.159 | | IL_17 | IL_1_alpha | 0.994 |
| IL_17 | IL_1_beta | 0.075 | | IL_17 | IL_1_beta | 0.983 |
| IL_17 | IL_2 | 0.001 | | IL_17 | IL_2 | 0.996 |
| IL_17 | IL_4 | 0.522 | | IL_17 | IL_4 | 0.998 |
| IL_17 | IL_5 | -0.139 | | IL_17 | IL_5 | 0.999 |
| IL_17 | IL_6 | -0.179 | | IL_17 | IL_6 | 0.996 |
| IL_17 | IL_8 | -0.196 | | IL_17 | IL_8 | 0.904 |
| IL_17 | IL_10 | 0.963 | | IL_17 | IL_10 | 0.990 |
| IL_17 | IL_12p70 | -0.058 | | IL_17 | IL_12p70 | 0.687 |
| IL_17 | IL_13 | -0.044 | | IL_17 | IL_13 | 0.960 |
| IL_17 | IL_15 | -0.319 | | IL_17 | IL_15 | 0.995 |
| IL_17 | IL_17 | 1.000 | | IL_17 | IL_17 | 1.000 |
| IL_17 | IL_23 | -0.048 | | IL_17 | IL_23 | -0.264 |
| IL_17 | IFN_gamma | 0.000 | | IL_17 | IFN_gamma | 0.000 |
| IL_17 | TNF_alpha | -0.108 | | IL_17 | TNF_alpha | 0.993 |
| IL_17 | TNF_beta | 0.897 | | IL_17 | TNF_beta | 1.000 |
| IL_17 | Varicella_Int | 0.240 | | IL_17 | Varicella_Int | 0.000 |
| IL_17 | Measles_OD_DB_Int | -0.459 | | IL_17 | Measles_OD_DB_Int | -0.497 |
| IL_17 | Measles_Int | 0.232 | | IL_17 | Measles_Int | 0.000 |
| IL_17 | HepA_Int | -0.649 | | IL_17 | HepA_Int | 0.000 |
| IL_17 | Tetanus_Int | 0.000 | | IL_17 | Tetanus_Int | 0.000 |
| IL_17 | Diptheria_Int | 0.000 | | IL_17 | Diptheria_Int | 0.000 |
| IL_17 | Rubella_Int | -0.307 | | IL_17 | Rubella_Int | -0.241 |
| IL_17 | CMV_Int | -0.907 | | IL_17 | CMV_Int | 0.000 |
| IL_17 | HepB_cAb_Int | 0.000 | | IL_17 | HepB_cAb_Int | 0.000 |
| IL_17 | HepB_eAb_Int | 0.000 | | IL_17 | HepB_eAb_Int | 0.000 |
| IL_17 | HepB_eAg_Int | 0.000 | | IL_17 | HepB_eAg_Int | 0.000 |
| IL_17 | HepC_Int | 0.000 | | IL_17 | HepC_Int | 0.000 |
| IL_17 | Schistosoma_int | 0.713 | | IL_17 | Schistosoma_int | -0.333 |
| IL_17 | Strongyloides_Int | 0.385 | | IL_17 | Strongyloides_Int | 0.420 |
| IL_17 | Filaria_Int | -0.317 | | IL_17 | Filaria_Int | 0.565 |
| IL_23 | IL_1_alpha | -0.031 | | IL_23 | IL_1_alpha | -0.364 |
| IL_23 | IL_1_beta | -0.071 | | IL_23 | IL_1_beta | -0.361 |

FIG. 21I9-G

| IL_23 | IL_2 | -0.164 | IL_23 | IL_2 | -0.253 |
|---|---|---|---|---|---|
| IL_23 | IL_4 | -0.191 | IL_23 | IL_4 | -0.301 |
| IL_23 | IL_5 | 0.190 | IL_23 | IL_5 | -0.304 |
| IL_23 | IL_6 | 0.116 | IL_23 | IL_6 | -0.343 |
| IL_23 | IL_8 | -0.048 | IL_23 | IL_8 | -0.150 |
| IL_23 | IL_10 | 0.038 | IL_23 | IL_10 | -0.385 |
| IL_23 | IL_12p70 | 0.895 | IL_23 | IL_12p70 | 0.485 |
| IL_23 | IL_13 | 0.858 | IL_23 | IL_13 | -0.250 |
| IL_23 | IL_15 | 0.217 | IL_23 | IL_15 | -0.241 |
| IL_23 | IL_17 | -0.048 | IL_23 | IL_17 | -0.264 |
| IL_23 | IL_23 | 1.000 | IL_23 | IL_23 | 1.000 |
| IL_23 | IFN_gamma | 0.000 | IL_23 | IFN_gamma | 0.000 |
| IL_23 | TNF_alpha | 0.359 | IL_23 | TNF_alpha | -0.322 |
| IL_23 | TNF_beta | -0.075 | IL_23 | TNF_beta | -0.259 |
| IL_23 | Varicella_Int | 0.213 | IL_23 | Varicella_Int | 0.000 |
| IL_23 | Measles_OD_DB_Int | 0.257 | IL_23 | Measles_OD_DB_Int | 0.560 |
| IL_23 | Measles_Int | 0.171 | IL_23 | Measles_Int | 0.000 |
| IL_23 | HepA_Int | -0.658 | IL_23 | HepA_Int | 0.000 |
| IL_23 | Tetanus_Int | 0.000 | IL_23 | Tetanus_Int | 0.000 |
| IL_23 | Diptheria_Int | 0.000 | IL_23 | Diptheria_Int | 0.000 |
| IL_23 | Rubella_Int | -0.267 | IL_23 | Rubella_Int | 0.999 |
| IL_23 | CMV_Int | 0.122 | IL_23 | CMV_Int | 0.000 |
| IL_23 | HepB_cAb_Int | 0.000 | IL_23 | HepB_cAb_Int | 0.000 |
| IL_23 | HepB_eAb_Int | 0.000 | IL_23 | HepB_eAb_Int | 0.000 |
| IL_23 | HepB_eAg_Int | 0.000 | IL_23 | HepB_eAg_Int | 0.000 |
| IL_23 | HepC_Int | 0.000 | IL_23 | HepC_Int | 0.000 |
| IL_23 | Schistosoma_int | -0.220 | IL_23 | Schistosoma_int | -0.352 |
| IL_23 | Strongyloides_Int | -0.313 | IL_23 | Strongyloides_Int | 0.293 |
| IL_23 | Filaria_Int | -0.219 | IL_23 | Filaria_Int | -0.216 |
| IFN_gamma | IL_1_alpha | 0.000 | IFN_gamma | IL_1_alpha | 0.000 |
| IFN_gamma | IL_1_beta | 0.000 | IFN_gamma | IL_1_beta | 0.000 |
| IFN_gamma | IL_2 | 0.000 | IFN_gamma | IL_2 | 0.000 |
| IFN_gamma | IL_4 | 0.000 | IFN_gamma | IL_4 | 0.000 |
| IFN_gamma | IL_5 | 0.000 | IFN_gamma | IL_5 | 0.000 |
| IFN_gamma | IL_6 | 0.000 | IFN_gamma | IL_6 | 0.000 |
| IFN_gamma | IL_8 | 0.000 | IFN_gamma | IL_8 | 0.000 |
| IFN_gamma | IL_10 | 0.000 | IFN_gamma | IL_10 | 0.000 |
| IFN_gamma | IL_12p70 | 0.000 | IFN_gamma | IL_12p70 | 0.000 |
| IFN_gamma | IL_13 | 0.000 | IFN_gamma | IL_13 | 0.000 |
| IFN_gamma | IL_15 | 0.000 | IFN_gamma | IL_15 | 0.000 |
| IFN_gamma | IL_17 | 0.000 | IFN_gamma | IL_17 | 0.000 |
| IFN_gamma | IL_23 | 0.000 | IFN_gamma | IL_23 | 0.000 |
| IFN_gamma | IFN_gamma | 1.000 | IFN_gamma | IFN_gamma | 1.000 |
| IFN_gamma | TNF_alpha | 0.000 | IFN_gamma | TNF_alpha | 0.000 |
| IFN_gamma | TNF_beta | 0.000 | IFN_gamma | TNF_beta | 0.000 |
| IFN_gamma | Varicella_Int | 0.000 | IFN_gamma | Varicella_Int | 0.000 |
| IFN_gamma | Measles_OD_DB_Int | 0.000 | IFN_gamma | Measles_OD_DB_Int | 0.000 |
| IFN_gamma | Measles_Int | 0.000 | IFN_gamma | Measles_Int | 0.000 |
| IFN_gamma | HepA_Int | 0.000 | IFN_gamma | HepA_Int | 0.000 |
| IFN_gamma | Tetanus_Int | 0.000 | IFN_gamma | Tetanus_Int | 0.000 |
| IFN_gamma | Diptheria_Int | 0.000 | IFN_gamma | Diptheria_Int | 0.000 |
| IFN_gamma | Rubella_Int | 0.000 | IFN_gamma | Rubella_Int | 0.000 |
| IFN_gamma | CMV_Int | 0.000 | IFN_gamma | CMV_Int | 0.000 |
| IFN_gamma | HepB_cAb_Int | 0.000 | IFN_gamma | HepB_cAb_Int | 0.000 |
| IFN_gamma | HepB_eAb_Int | 0.000 | IFN_gamma | HepB_eAb_Int | 0.000 |
| IFN_gamma | HepB_eAg_Int | 0.000 | IFN_gamma | HepB_eAg_Int | 0.000 |
| IFN_gamma | HepC_Int | 0.000 | IFN_gamma | HepC_Int | 0.000 |

FIG. 21I9-H

| | | | | | | |
|---|---|---|---|---|---|---|
| IFN_gamma | Schistosoma_int | 0.000 | | IFN_gamma | Schistosoma_int | 0.000 |
| IFN_gamma | Strongyloides_Int | 0.000 | | IFN_gamma | Strongyloides_Int | 0.000 |
| IFN_gamma | Filaria_Int | 0.000 | | IFN_gamma | Filaria_Int | 0.000 |
| TNF_alpha | IL_1_alpha | -0.287 | | TNF_alpha | IL_1_alpha | 0.997 |
| TNF_alpha | IL_1_beta | 0.612 | | TNF_alpha | IL_1_beta | 0.998 |
| TNF_alpha | IL_2 | 0.476 | | TNF_alpha | IL_2 | 0.980 |
| TNF_alpha | IL_4 | -0.200 | | TNF_alpha | IL_4 | 0.998 |
| TNF_alpha | IL_5 | 0.002 | | TNF_alpha | IL_5 | 0.997 |
| TNF_alpha | IL_6 | -0.174 | | TNF_alpha | IL_6 | 0.996 |
| TNF_alpha | IL_8 | 0.360 | | TNF_alpha | IL_8 | 0.852 |
| TNF_alpha | IL_10 | 0.026 | | TNF_alpha | IL_10 | 0.997 |
| TNF_alpha | IL_12p70 | 0.309 | | TNF_alpha | IL_12p70 | 0.661 |
| TNF_alpha | IL_13 | 0.284 | | TNF_alpha | IL_13 | 0.980 |
| TNF_alpha | IL_15 | -0.048 | | TNF_alpha | IL_15 | 0.978 |
| TNF_alpha | IL_17 | -0.108 | | TNF_alpha | IL_17 | 0.993 |
| TNF_alpha | IL_23 | 0.359 | | TNF_alpha | IL_23 | -0.322 |
| TNF_alpha | IFN_gamma | 0.000 | | TNF_alpha | IFN_gamma | 0.000 |
| TNF_alpha | TNF_alpha | 1.000 | | TNF_alpha | TNF_alpha | 1.000 |
| TNF_alpha | TNF_beta | 0.141 | | TNF_alpha | TNF_beta | 0.994 |
| TNF_alpha | Varicella_Int | -0.675 | | TNF_alpha | Varicella_Int | 0.000 |
| TNF_alpha | Measles_OD_DB_Int | -0.110 | | TNF_alpha | Measles_OD_DB_Int | -0.593 |
| TNF_alpha | Measles_Int | 0.396 | | TNF_alpha | Measles_Int | 0.000 |
| TNF_alpha | HepA_Int | -0.217 | | TNF_alpha | HepA_Int | 0.000 |
| TNF_alpha | Tetanus_Int | 0.000 | | TNF_alpha | Tetanus_Int | 0.000 |
| TNF_alpha | Diptheria_Int | 0.000 | | TNF_alpha | Diptheria_Int | 0.000 |
| TNF_alpha | Rubella_Int | 0.470 | | TNF_alpha | Rubella_Int | -0.303 |
| TNF_alpha | CMV_Int | 0.067 | | TNF_alpha | CMV_Int | 0.000 |
| TNF_alpha | HepB_cAb_Int | 0.000 | | TNF_alpha | HepB_cAb_Int | 0.000 |
| TNF_alpha | HepB_eAb_Int | 0.000 | | TNF_alpha | HepB_eAb_Int | 0.000 |
| TNF_alpha | HepB_eAg_Int | 0.000 | | TNF_alpha | HepB_eAg_Int | 0.000 |
| TNF_alpha | HepC_Int | 0.000 | | TNF_alpha | HepC_Int | 0.000 |
| TNF_alpha | Schistosoma_int | 0.097 | | TNF_alpha | Schistosoma_int | -0.381 |
| TNF_alpha | Strongyloides_Int | 0.012 | | TNF_alpha | Strongyloides_Int | 0.314 |
| TNF_alpha | Filaria_Int | 0.553 | | TNF_alpha | Filaria_Int | 0.487 |
| TNF_beta | IL_1_alpha | -0.244 | | TNF_beta | IL_1_alpha | 0.993 |
| TNF_beta | IL_1_beta | 0.208 | | TNF_beta | IL_1_beta | 0.983 |
| TNF_beta | IL_2 | 0.149 | | TNF_beta | IL_2 | 0.995 |
| TNF_beta | IL_4 | 0.584 | | TNF_beta | IL_4 | 0.998 |
| TNF_beta | IL_5 | -0.203 | | TNF_beta | IL_5 | 0.999 |
| TNF_beta | IL_6 | -0.189 | | TNF_beta | IL_6 | 0.996 |
| TNF_beta | IL_8 | -0.244 | | TNF_beta | IL_8 | 0.902 |
| TNF_beta | IL_10 | 0.935 | | TNF_beta | IL_10 | 0.990 |
| TNF_beta | IL_12p70 | -0.188 | | TNF_beta | IL_12p70 | 0.692 |
| TNF_beta | IL_13 | -0.167 | | TNF_beta | IL_13 | 0.962 |
| TNF_beta | IL_15 | -0.475 | | TNF_beta | IL_15 | 0.995 |
| TNF_beta | IL_17 | 0.897 | | TNF_beta | IL_17 | 1.000 |
| TNF_beta | IL_23 | -0.075 | | TNF_beta | IL_23 | -0.259 |
| TNF_beta | IFN_gamma | 0.000 | | TNF_beta | IFN_gamma | 0.000 |
| TNF_beta | TNF_alpha | 0.141 | | TNF_beta | TNF_alpha | 0.994 |
| TNF_beta | TNF_beta | 1.000 | | TNF_beta | TNF_beta | 1.000 |
| TNF_beta | Varicella_Int | 0.053 | | TNF_beta | Varicella_Int | 0.000 |
| TNF_beta | Measles_OD_DB_Int | -0.506 | | TNF_beta | Measles_OD_DB_Int | -0.498 |
| TNF_beta | Measles_Int | 0.245 | | TNF_beta | Measles_Int | 0.000 |
| TNF_beta | HepA_Int | -0.681 | | TNF_beta | HepA_Int | 0.000 |
| TNF_beta | Tetanus_Int | 0.000 | | TNF_beta | Tetanus_Int | 0.000 |
| TNF_beta | Diptheria_Int | 0.000 | | TNF_beta | Diptheria_Int | 0.000 |
| TNF_beta | Rubella_Int | -0.134 | | TNF_beta | Rubella_Int | -0.236 |

FIG. 2I9-I

| TNF_beta | CMV_Int | -0.973 | TNF_beta | CMV_Int | 0.000 |
|---|---|---|---|---|---|
| TNF_beta | HepB_cAb_Int | 0.000 | TNF_beta | HepB_cAb_Int | 0.000 |
| TNF_beta | HepB_eAb_Int | 0.000 | TNF_beta | HepB_eAb_Int | 0.000 |
| TNF_beta | HepB_eAg_Int | 0.000 | TNF_beta | HepB_eAg_Int | 0.000 |
| TNF_beta | HepC_Int | 0.000 | TNF_beta | HepC_Int | 0.000 |
| TNF_beta | Schistosoma_int | 0.593 | TNF_beta | Schistosoma_int | -0.340 |
| TNF_beta | Strongyloides_Int | 0.573 | TNF_beta | Strongyloides_Int | 0.418 |
| TNF_beta | Filaria_Int | -0.097 | TNF_beta | Filaria_Int | 0.560 |
| Varicella_Int | IL_1_alpha | 0.181 | Varicella_Int | IL_1_alpha | 0.000 |
| Varicella_Int | IL_1_beta | -0.520 | Varicella_Int | IL_1_beta | 0.000 |
| Varicella_Int | IL_2 | -0.621 | Varicella_Int | IL_2 | 0.000 |
| Varicella_Int | IL_4 | 0.266 | Varicella_Int | IL_4 | 0.000 |
| Varicella_Int | IL_5 | 0.127 | Varicella_Int | IL_5 | 0.000 |
| Varicella_Int | IL_6 | 0.265 | Varicella_Int | IL_6 | 0.000 |
| Varicella_Int | IL_8 | -0.243 | Varicella_Int | IL_8 | 0.000 |
| Varicella_Int | IL_10 | 0.184 | Varicella_Int | IL_10 | 0.000 |
| Varicella_Int | IL_12p70 | 0.261 | Varicella_Int | IL_12p70 | 0.000 |
| Varicella_Int | IL_13 | 0.239 | Varicella_Int | IL_13 | 0.000 |
| Varicella_Int | IL_15 | 0.123 | Varicella_Int | IL_15 | 0.000 |
| Varicella_Int | IL_17 | 0.240 | Varicella_Int | IL_17 | 0.000 |
| Varicella_Int | IL_23 | 0.213 | Varicella_Int | IL_23 | 0.000 |
| Varicella_Int | IFN_gamma | 0.000 | Varicella_Int | IFN_gamma | 0.000 |
| Varicella_Int | TNF_alpha | -0.675 | Varicella_Int | TNF_alpha | 0.000 |
| Varicella_Int | TNF_beta | 0.053 | Varicella_Int | TNF_beta | 0.000 |
| Varicella_Int | Varicella_Int | 1.000 | Varicella_Int | Varicella_Int | 1.000 |
| Varicella_Int | Measles_OD_DB_Int | -0.024 | Varicella_Int | Measles_OD_DB_Int | 0.000 |
| Varicella_Int | Measles_Int | -0.327 | Varicella_Int | Measles_Int | 0.000 |
| Varicella_Int | HepA_Int | -0.327 | Varicella_Int | HepA_Int | 0.000 |
| Varicella_Int | Tetanus_Int | 0.000 | Varicella_Int | Tetanus_Int | 0.000 |
| Varicella_Int | Diptheria_Int | 0.000 | Varicella_Int | Diptheria_Int | 0.000 |
| Varicella_Int | Rubella_Int | -0.802 | Varicella_Int | Rubella_Int | 0.000 |
| Varicella_Int | CMV_Int | -0.218 | Varicella_Int | CMV_Int | 0.000 |
| Varicella_Int | HepB_cAb_Int | 0.000 | Varicella_Int | HepB_cAb_Int | 0.000 |
| Varicella_Int | HepB_eAb_Int | 0.000 | Varicella_Int | HepB_eAb_Int | 0.000 |
| Varicella_Int | HepB_eAg_Int | 0.000 | Varicella_Int | HepB_eAg_Int | 0.000 |
| Varicella_Int | HepC_Int | 0.000 | Varicella_Int | HepC_Int | 0.000 |
| Varicella_Int | Schistosoma_int | -0.048 | Varicella_Int | Schistosoma_int | 0.000 |
| Varicella_Int | Strongyloides_Int | 0.028 | Varicella_Int | Strongyloides_Int | 0.000 |
| Varicella_Int | Filaria_Int | -0.524 | Varicella_Int | Filaria_Int | 0.000 |
| Measles_OD_DB_Int | IL_1_alpha | -0.104 | Measles_OD_DB_Int | IL_1_alpha | -0.569 |
| Measles_OD_DB_Int | IL_1_beta | -0.585 | Measles_OD_DB_Int | IL_1_beta | -0.647 |
| Measles_OD_DB_Int | IL_2 | 0.252 | Measles_OD_DB_Int | IL_2 | -0.423 |
| Measles_OD_DB_Int | IL_4 | -0.697 | Measles_OD_DB_Int | IL_4 | -0.546 |
| Measles_OD_DB_Int | IL_5 | -0.437 | Measles_OD_DB_Int | IL_5 | -0.526 |
| Measles_OD_DB_Int | IL_6 | -0.416 | Measles_OD_DB_Int | IL_6 | -0.543 |
| Measles_OD_DB_Int | IL_8 | -0.504 | Measles_OD_DB_Int | IL_8 | -0.096 |
| Measles_OD_DB_Int | IL_10 | -0.343 | Measles_OD_DB_Int | IL_10 | -0.588 |
| Measles_OD_DB_Int | IL_12p70 | 0.014 | Measles_OD_DB_Int | IL_12p70 | -0.201 |
| Measles_OD_DB_Int | IL_13 | 0.034 | Measles_OD_DB_Int | IL_13 | -0.684 |
| Measles_OD_DB_Int | IL_15 | -0.333 | Measles_OD_DB_Int | IL_15 | -0.412 |
| Measles_OD_DB_Int | IL_17 | -0.459 | Measles_OD_DB_Int | IL_17 | -0.497 |
| Measles_OD_DB_Int | IL_23 | 0.257 | Measles_OD_DB_Int | IL_23 | 0.560 |
| Measles_OD_DB_Int | IFN_gamma | 0.000 | Measles_OD_DB_Int | IFN_gamma | 0.000 |
| Measles_OD_DB_Int | TNF_alpha | -0.110 | Measles_OD_DB_Int | TNF_alpha | -0.593 |
| Measles_OD_DB_Int | TNF_beta | -0.506 | Measles_OD_DB_Int | TNF_beta | -0.498 |
| Measles_OD_DB_Int | Varicella_Int | -0.024 | Measles_OD_DB_Int | Varicella_Int | 0.000 |
| Measles_OD_DB_Int | Measles_OD_DB_Int | 1.000 | Measles_OD_DB_Int | Measles_OD_DB_Int | 1.000 |

FIG. 21I9-J

| | | | | | | |
|---|---|---|---|---|---|---|
| Measles_OD_DB_Int | Measles_Int | 0.167 | | Measles_OD_DB_Int | Measles_Int | 0.000 |
| Measles_OD_DB_Int | HepA_Int | 0.167 | | Measles_OD_DB_Int | HepA_Int | 0.000 |
| Measles_OD_DB_Int | Tetanus_Int | 0.000 | | Measles_OD_DB_Int | Tetanus_Int | 0.000 |
| Measles_OD_DB_Int | Diptheria_Int | 0.000 | | Measles_OD_DB_Int | Diptheria_Int | 0.000 |
| Measles_OD_DB_Int | Rubella_Int | -0.272 | | Measles_OD_DB_Int | Rubella_Int | 0.577 |
| Measles_OD_DB_Int | CMV_Int | 0.481 | | Measles_OD_DB_Int | CMV_Int | 0.000 |
| Measles_OD_DB_Int | HepB_cAb_Int | 0.000 | | Measles_OD_DB_Int | HepB_cAb_Int | 0.000 |
| Measles_OD_DB_Int | HepB_eAb_Int | 0.000 | | Measles_OD_DB_Int | HepB_eAb_Int | 0.000 |
| Measles_OD_DB_Int | HepB_eAg_Int | 0.000 | | Measles_OD_DB_Int | HepB_eAg_Int | 0.000 |
| Measles_OD_DB_Int | HepC_Int | 0.000 | | Measles_OD_DB_Int | HepC_Int | 0.000 |
| Measles_OD_DB_Int | Schistosoma_int | -0.218 | | Measles_OD_DB_Int | Schistosoma_int | 0.577 |
| Measles_OD_DB_Int | Strongyloides_Int | 0.128 | | Measles_OD_DB_Int | Strongyloides_Int | 0.577 |
| Measles_OD_DB_Int | Filaria_Int | 0.024 | | Measles_OD_DB_Int | Filaria_Int | 0.302 |
| Measles_Int | IL_1_alpha | -0.011 | | Measles_Int | IL_1_alpha | 0.000 |
| Measles_Int | IL_1_beta | 0.312 | | Measles_Int | IL_1_beta | 0.000 |
| Measles_Int | IL_2 | 0.240 | | Measles_Int | IL_2 | 0.000 |
| Measles_Int | IL_4 | -0.400 | | Measles_Int | IL_4 | 0.000 |
| Measles_Int | IL_5 | -0.493 | | Measles_Int | IL_5 | 0.000 |
| Measles_Int | IL_6 | -0.593 | | Measles_Int | IL_6 | 0.000 |
| Measles_Int | IL_8 | 0.182 | | Measles_Int | IL_8 | 0.000 |
| Measles_Int | IL_10 | 0.278 | | Measles_Int | IL_10 | 0.000 |
| Measles_Int | IL_12p70 | 0.050 | | Measles_Int | IL_12p70 | 0.000 |
| Measles_Int | IL_13 | 0.011 | | Measles_Int | IL_13 | 0.000 |
| Measles_Int | IL_15 | -0.318 | | Measles_Int | IL_15 | 0.000 |
| Measles_Int | IL_17 | 0.232 | | Measles_Int | IL_17 | 0.000 |
| Measles_Int | IL_23 | 0.171 | | Measles_Int | IL_23 | 0.000 |
| Measles_Int | IFN_gamma | 0.000 | | Measles_Int | IFN_gamma | 0.000 |
| Measles_Int | TNF_alpha | 0.396 | | Measles_Int | TNF_alpha | 0.000 |
| Measles_Int | TNF_beta | 0.245 | | Measles_Int | TNF_beta | 0.000 |
| Measles_Int | Varicella_Int | -0.327 | | Measles_Int | Varicella_Int | 0.000 |
| Measles_Int | Measles_OD_DB_Int | 0.167 | | Measles_Int | Measles_OD_DB_Int | 0.000 |
| Measles_Int | Measles_Int | 1.000 | | Measles_Int | Measles_Int | 1.000 |
| Measles_Int | HepA_Int | -0.250 | | Measles_Int | HepA_Int | 0.000 |
| Measles_Int | Tetanus_Int | 0.000 | | Measles_Int | Tetanus_Int | 0.000 |
| Measles_Int | Diptheria_Int | 0.000 | | Measles_Int | Diptheria_Int | 0.000 |
| Measles_Int | Rubella_Int | -0.102 | | Measles_Int | Rubella_Int | 0.000 |
| Measles_Int | CMV_Int | -0.167 | | Measles_Int | CMV_Int | 0.000 |
| Measles_Int | HepB_cAb_Int | 0.000 | | Measles_Int | HepB_cAb_Int | 0.000 |
| Measles_Int | HepB_eAb_Int | 0.000 | | Measles_Int | HepB_eAb_Int | 0.000 |
| Measles_Int | HepB_eAg_Int | 0.000 | | Measles_Int | HepB_eAg_Int | 0.000 |
| Measles_Int | HepC_Int | 0.000 | | Measles_Int | HepC_int | 0.000 |
| Measles_Int | Schistosoma_int | 0.327 | | Measles_Int | Schistosoma_int | 0.000 |
| Measles_Int | Strongyloides_Int | 0.128 | | Measles_Int | Strongyloides_Int | 0.000 |
| Measles_Int | Filaria_Int | -0.218 | | Measles_Int | Filaria_Int | 0.000 |
| HepA_Int | IL_1_alpha | 0.217 | | HepA_Int | IL_1_alpha | 0.000 |
| HepA_Int | IL_1_beta | -0.022 | | HepA_Int | IL_1_beta | 0.000 |
| HepA_Int | IL_2 | 0.132 | | HepA_Int | IL_2 | 0.000 |
| HepA_Int | IL_4 | -0.315 | | HepA_Int | IL_4 | 0.000 |
| HepA_Int | IL_5 | 0.043 | | HepA_Int | IL_5 | 0.000 |
| HepA_Int | IL_6 | 0.044 | | HepA_Int | IL_6 | 0.000 |
| HepA_Int | IL_8 | 0.284 | | HepA_Int | IL_8 | 0.000 |
| HepA_Int | IL_10 | -0.729 | | HepA_Int | IL_10 | 0.000 |
| HepA_Int | IL_12p70 | -0.483 | | HepA_Int | IL_12p70 | 0.000 |
| HepA_Int | IL_13 | -0.464 | | HepA_Int | IL_13 | 0.000 |
| HepA_Int | IL_15 | 0.214 | | HepA_Int | IL_15 | 0.000 |
| HepA_Int | IL_17 | -0.649 | | HepA_Int | IL_17 | 0.000 |
| HepA_Int | IL_23 | -0.658 | | HepA_Int | IL_23 | 0.000 |

FIG. 21I9-K

| | | | | | | |
|---|---|---|---|---|---|---|
| HepA_Int | IFN_gamma | 0.000 | | HepA_Int | IFN_gamma | 0.000 |
| HepA_Int | TNF_alpha | -0.217 | | HepA_Int | TNF_alpha | 0.000 |
| HepA_Int | TNF_beta | -0.681 | | HepA_Int | TNF_beta | 0.000 |
| HepA_Int | Varicella_Int | -0.327 | | HepA_Int | Varicella_Int | 0.000 |
| HepA_Int | Measles_OD_DB_Int | 0.167 | | HepA_Int | Measles_OD_DB_Int | 0.000 |
| HepA_Int | Measles_Int | -0.250 | | HepA_Int | Measles_Int | 0.000 |
| HepA_Int | HepA_Int | 1.000 | | HepA_Int | HepA_Int | 1.000 |
| HepA_Int | Tetanus_Int | 0.000 | | HepA_Int | Tetanus_Int | 0.000 |
| HepA_Int | Diptheria_Int | 0.000 | | HepA_Int | Diptheria_Int | 0.000 |
| HepA_Int | Rubella_Int | 0.408 | | HepA_Int | Rubella_Int | 0.000 |
| HepA_Int | CMV_Int | 0.667 | | HepA_Int | CMV_Int | 0.000 |
| HepA_Int | HepB_cAb_Int | 0.000 | | HepA_Int | HepB_cAb_Int | 0.000 |
| HepA_Int | HepB_eAb_Int | 0.000 | | HepA_Int | HepB_eAb_Int | 0.000 |
| HepA_Int | HepB_eAg_Int | 0.000 | | HepA_Int | HepB_eAg_Int | 0.000 |
| HepA_Int | HepC_Int | 0.000 | | HepA_Int | HepC_Int | 0.000 |
| HepA_Int | Schistosoma_int | -0.218 | | HepA_Int | Schistosoma_int | 0.000 |
| HepA_Int | Strongyloides_Int | -0.192 | | HepA_Int | Strongyloides_Int | 0.000 |
| HepA_Int | Filaria_Int | 0.327 | | HepA_Int | Filaria_Int | 0.000 |
| Tetanus_Int | IL_1_alpha | 0.000 | | Tetanus_Int | IL_1_alpha | 0.000 |
| Tetanus_Int | IL_1_beta | 0.000 | | Tetanus_Int | IL_1_beta | 0.000 |
| Tetanus_Int | IL_2 | 0.000 | | Tetanus_Int | IL_2 | 0.000 |
| Tetanus_Int | IL_4 | 0.000 | | Tetanus_Int | IL_4 | 0.000 |
| Tetanus_Int | IL_5 | 0.000 | | Tetanus_Int | IL_5 | 0.000 |
| Tetanus_Int | IL_6 | 0.000 | | Tetanus_Int | IL_6 | 0.000 |
| Tetanus_Int | IL_8 | 0.000 | | Tetanus_Int | IL_8 | 0.000 |
| Tetanus_Int | IL_10 | 0.000 | | Tetanus_Int | IL_10 | 0.000 |
| Tetanus_Int | IL_12p70 | 0.000 | | Tetanus_Int | IL_12p70 | 0.000 |
| Tetanus_Int | IL_13 | 0.000 | | Tetanus_Int | IL_13 | 0.000 |
| Tetanus_Int | IL_15 | 0.000 | | Tetanus_Int | IL_15 | 0.000 |
| Tetanus_Int | IL_17 | 0.000 | | Tetanus_Int | IL_17 | 0.000 |
| Tetanus_Int | IL_23 | 0.000 | | Tetanus_Int | IL_23 | 0.000 |
| Tetanus_Int | IFN_gamma | 0.000 | | Tetanus_Int | IFN_gamma | 0.000 |
| Tetanus_Int | TNF_alpha | 0.000 | | Tetanus_Int | TNF_alpha | 0.000 |
| Tetanus_Int | TNF_beta | 0.000 | | Tetanus_Int | TNF_beta | 0.000 |
| Tetanus_Int | Varicella_Int | 0.000 | | Tetanus_Int | Varicella_Int | 0.000 |
| Tetanus_Int | Measles_OD_DB_Int | 0.000 | | Tetanus_Int | Measles_OD_DB_Int | 0.000 |
| Tetanus_Int | Measles_Int | 0.000 | | Tetanus_Int | Measles_Int | 0.000 |
| Tetanus_Int | HepA_Int | 0.000 | | Tetanus_Int | HepA_Int | 0.000 |
| Tetanus_Int | Tetanus_Int | 1.000 | | Tetanus_Int | Tetanus_Int | 1.000 |
| Tetanus_Int | Diptheria_Int | 0.000 | | Tetanus_Int | Diptheria_Int | 0.000 |
| Tetanus_Int | Rubella_Int | 0.000 | | Tetanus_Int | Rubella_Int | 0.000 |
| Tetanus_Int | CMV_Int | 0.000 | | Tetanus_Int | CMV_Int | 0.000 |
| Tetanus_Int | HepB_cAb_Int | 0.000 | | Tetanus_Int | HepB_cAb_Int | 0.000 |
| Tetanus_Int | HepB_eAb_Int | 0.000 | | Tetanus_Int | HepB_eAb_Int | 0.000 |
| Tetanus_Int | HepB_eAg_Int | 0.000 | | Tetanus_Int | HepB_eAg_Int | 0.000 |
| Tetanus_Int | HepC_Int | 0.000 | | Tetanus_Int | HepC_Int | 0.000 |
| Tetanus_Int | Schistosoma_int | 0.000 | | Tetanus_Int | Schistosoma_int | 0.000 |
| Tetanus_Int | Strongyloides_Int | 0.000 | | Tetanus_Int | Strongyloides_Int | 0.000 |
| Tetanus_Int | Filaria_Int | 0.000 | | Tetanus_Int | Filaria_Int | 0.000 |
| Diptheria_Int | IL_1_alpha | 0.000 | | Diptheria_Int | IL_1_alpha | 0.000 |
| Diptheria_Int | IL_1_beta | 0.000 | | Diptheria_Int | IL_1_beta | 0.000 |
| Diptheria_Int | IL_2 | 0.000 | | Diptheria_Int | IL_2 | 0.000 |
| Diptheria_Int | IL_4 | 0.000 | | Diptheria_Int | IL_4 | 0.000 |
| Diptheria_Int | IL_5 | 0.000 | | Diptheria_Int | IL_5 | 0.000 |
| Diptheria_Int | IL_6 | 0.000 | | Diptheria_Int | IL_6 | 0.000 |
| Diptheria_Int | IL_8 | 0.000 | | Diptheria_Int | IL_8 | 0.000 |
| Diptheria_Int | IL_10 | 0.000 | | Diptheria_Int | IL_10 | 0.000 |

FIG. 21I9-L

| | | | | | | |
|---|---|---|---|---|---|---|
| Diptheria_Int | IL_12p70 | 0.000 | | Diptheria_Int | IL_12p70 | 0.000 |
| Diptheria_Int | IL_13 | 0.000 | | Diptheria_Int | IL_13 | 0.000 |
| Diptheria_Int | IL_15 | 0.000 | | Diptheria_Int | IL_15 | 0.000 |
| Diptheria_Int | IL_17 | 0.000 | | Diptheria_Int | IL_17 | 0.000 |
| Diptheria_Int | IL_23 | 0.000 | | Diptheria_Int | IL_23 | 0.000 |
| Diptheria_Int | IFN_gamma | 0.000 | | Diptheria_Int | IFN_gamma | 0.000 |
| Diptheria_Int | TNF_alpha | 0.000 | | Diptheria_Int | TNF_alpha | 0.000 |
| Diptheria_Int | TNF_beta | 0.000 | | Diptheria_Int | TNF_beta | 0.000 |
| Diptheria_Int | Varicella_Int | 0.000 | | Diptheria_Int | Varicella_Int | 0.000 |
| Diptheria_Int | Measles_OD_DB_Int | 0.000 | | Diptheria_Int | Measles_OD_DB_Int | 0.000 |
| Diptheria_Int | Measles_Int | 0.000 | | Diptheria_Int | Measles_Int | 0.000 |
| Diptheria_Int | HepA_Int | 0.000 | | Diptheria_Int | HepA_Int | 0.000 |
| Diptheria_Int | Tetanus_Int | 0.000 | | Diptheria_Int | Tetanus_Int | 0.000 |
| Diptheria_Int | Diptheria_Int | 1.000 | | Diptheria_Int | Diptheria_Int | 1.000 |
| Diptheria_Int | Rubella_Int | 0.000 | | Diptheria_Int | Rubella_Int | 0.000 |
| Diptheria_Int | CMV_Int | 0.000 | | Diptheria_Int | CMV_Int | 0.000 |
| Diptheria_Int | HepB_cAb_Int | 0.000 | | Diptheria_Int | HepB_cAb_Int | 0.000 |
| Diptheria_Int | HepB_eAb_Int | 0.000 | | Diptheria_Int | HepB_eAb_Int | 0.000 |
| Diptheria_Int | HepB_eAg_Int | 0.000 | | Diptheria_Int | HepB_eAg_Int | 0.000 |
| Diptheria_Int | HepC_Int | 0.000 | | Diptheria_Int | HepC_Int | 0.000 |
| Diptheria_Int | Schistosoma_int | 0.000 | | Diptheria_Int | Schistosoma_int | 0.000 |
| Diptheria_Int | Strongyloides_Int | 0.000 | | Diptheria_Int | Strongyloides_Int | 0.000 |
| Diptheria_Int | Filaria_Int | 0.000 | | Diptheria_Int | Filaria_Int | 0.000 |
| Rubella_Int | IL_1_alpha | -0.055 | | Rubella_Int | IL_1_alpha | -0.343 |
| Rubella_Int | IL_1_beta | 0.376 | | Rubella_Int | IL_1_beta | -0.345 |
| Rubella_Int | IL_2 | 0.482 | | Rubella_Int | IL_2 | -0.226 |
| Rubella_Int | IL_4 | 0.190 | | Rubella_Int | IL_4 | -0.280 |
| Rubella_Int | IL_5 | 0.432 | | Rubella_Int | IL_5 | -0.282 |
| Rubella_Int | IL_6 | 0.341 | | Rubella_Int | IL_6 | -0.321 |
| Rubella_Int | IL_8 | 0.271 | | Rubella_Int | IL_8 | -0.114 |
| Rubella_Int | IL_10 | -0.335 | | Rubella_Int | IL_10 | -0.364 |
| Rubella_Int | IL_12p70 | -0.173 | | Rubella_Int | IL_12p70 | 0.497 |
| Rubella_Int | IL_13 | -0.091 | | Rubella_Int | IL_13 | -0.238 |
| Rubella_Int | IL_15 | 0.334 | | Rubella_Int | IL_15 | -0.214 |
| Rubella_Int | IL_17 | -0.307 | | Rubella_Int | IL_17 | -0.241 |
| Rubella_Int | IL_23 | -0.267 | | Rubella_Int | IL_23 | 0.999 |
| Rubella_Int | IFN_gamma | 0.000 | | Rubella_Int | IFN_gamma | 0.000 |
| Rubella_Int | TNF_alpha | 0.470 | | Rubella_Int | TNF_alpha | -0.303 |
| Rubella_Int | TNF_beta | -0.134 | | Rubella_Int | TNF_beta | -0.236 |
| Rubella_Int | Varicella_Int | -0.802 | | Rubella_Int | Varicella_Int | 0.000 |
| Rubella_Int | Measles_OD_DB_Int | -0.272 | | Rubella_Int | Measles_OD_DB_Int | 0.577 |
| Rubella_Int | Measles_Int | -0.102 | | Rubella_Int | Measles_Int | 0.000 |
| Rubella_Int | HepA_Int | 0.408 | | Rubella_Int | HepA_Int | 0.000 |
| Rubella_Int | Tetanus_Int | 0.000 | | Rubella_Int | Tetanus_Int | 0.000 |
| Rubella_Int | Diptheria_Int | 0.000 | | Rubella_Int | Diptheria_Int | 0.000 |
| Rubella_Int | Rubella_Int | 1.000 | | Rubella_Int | Rubella_Int | 1.000 |
| Rubella_Int | CMV_Int | 0.272 | | Rubella_Int | CMV_Int | 0.000 |
| Rubella_Int | HepB_cAb_Int | 0.000 | | Rubella_Int | HepB_cAb_Int | 0.000 |
| Rubella_Int | HepB_eAb_Int | 0.000 | | Rubella_Int | HepB_eAb_Int | 0.000 |
| Rubella_Int | HepB_eAg_Int | 0.000 | | Rubella_Int | HepB_eAg_Int | 0.000 |
| Rubella_Int | HepC_Int | 0.000 | | Rubella_Int | HepC_Int | 0.000 |
| Rubella_Int | Schistosoma_int | -0.089 | | Rubella_Int | Schistosoma_int | -0.333 |
| Rubella_Int | Strongyloides_Int | -0.209 | | Rubella_Int | Strongyloides_Int | 0.333 |
| Rubella_Int | Filaria_Int | 0.356 | | Rubella_Int | Filaria_Int | -0.174 |
| CMV_Int | IL_1_alpha | 0.246 | | CMV_Int | IL_1_alpha | 0.000 |
| CMV_Int | IL_1_beta | -0.108 | | CMV_Int | IL_1_beta | 0.000 |
| CMV_Int | IL_2 | 0.016 | | CMV_Int | IL_2 | 0.000 |

FIG. 21I9-M

| | | | | | | |
|---|---|---|---|---|---|---|
| CMV_Int | IL_4 | -0.603 | | CMV_Int | IL_4 | 0.000 |
| CMV_Int | IL_5 | 0.243 | | CMV_Int | IL_5 | 0.000 |
| CMV_Int | IL_6 | 0.174 | | CMV_Int | IL_6 | 0.000 |
| CMV_Int | IL_8 | 0.315 | | CMV_Int | IL_8 | 0.000 |
| CMV_Int | IL_10 | -0.925 | | CMV_Int | IL_10 | 0.000 |
| CMV_Int | IL_12p70 | 0.245 | | CMV_Int | IL_12p70 | 0.000 |
| CMV_Int | IL_13 | 0.235 | | CMV_Int | IL_13 | 0.000 |
| CMV_Int | IL_15 | 0.490 | | CMV_Int | IL_15 | 0.000 |
| CMV_Int | IL_17 | -0.907 | | CMV_Int | IL_17 | 0.000 |
| CMV_Int | IL_23 | 0.122 | | CMV_Int | IL_23 | 0.000 |
| CMV_Int | IFN_gamma | 0.000 | | CMV_Int | IFN_gamma | 0.000 |
| CMV_Int | TNF_alpha | 0.067 | | CMV_Int | TNF_alpha | 0.000 |
| CMV_Int | TNF_beta | -0.973 | | CMV_Int | TNF_beta | 0.000 |
| CMV_Int | Varicella_Int | -0.218 | | CMV_Int | Varicella_Int | 0.000 |
| CMV_Int | Measles_OD_DB_Int | 0.481 | | CMV_Int | Measles_OD_DB_Int | 0.000 |
| CMV_Int | Measles_Int | -0.167 | | CMV_Int | Measles_Int | 0.000 |
| CMV_Int | HepA_Int | 0.667 | | CMV_Int | HepA_Int | 0.000 |
| CMV_Int | Tetanus_Int | 0.000 | | CMV_Int | Tetanus_Int | 0.000 |
| CMV_Int | Diptheria_Int | 0.000 | | CMV_Int | Diptheria_Int | 0.000 |
| CMV_Int | Rubella_Int | 0.272 | | CMV_Int | Rubella_Int | 0.000 |
| CMV_Int | CMV_Int | 1.000 | | CMV_Int | CMV_Int | 1.000 |
| CMV_Int | HepB_cAb_Int | 0.000 | | CMV_Int | HepB_cAb_Int | 0.000 |
| CMV_Int | HepB_eAb_Int | 0.000 | | CMV_Int | HepB_eAb_Int | 0.000 |
| CMV_Int | HepB_eAg_Int | 0.000 | | CMV_Int | HepB_eAg_Int | 0.000 |
| CMV_Int | HepC_Int | 0.000 | | CMV_Int | HepC_int | 0.000 |
| CMV_Int | Schistosoma_int | -0.509 | | CMV_Int | Schistosoma_int | 0.000 |
| CMV_Int | Strongyloides_Int | -0.555 | | CMV_Int | Strongyloides_Int | 0.000 |
| CMV_Int | Filaria_Int | 0.218 | | CMV_Int | Filaria_Int | 0.000 |
| HepB_cAb_Int | IL_1_alpha | 0.000 | | HepB_cAb_Int | IL_1_alpha | 0.000 |
| HepB_cAb_Int | IL_1_beta | 0.000 | | HepB_cAb_Int | IL_1_beta | 0.000 |
| HepB_cAb_Int | IL_2 | 0.000 | | HepB_cAb_Int | IL_2 | 0.000 |
| HepB_cAb_Int | IL_4 | 0.000 | | HepB_cAb_Int | IL_4 | 0.000 |
| HepB_cAb_Int | IL_5 | 0.000 | | HepB_cAb_Int | IL_5 | 0.000 |
| HepB_cAb_Int | IL_6 | 0.000 | | HepB_cAb_Int | IL_6 | 0.000 |
| HepB_cAb_Int | IL_8 | 0.000 | | HepB_cAb_Int | IL_8 | 0.000 |
| HepB_cAb_Int | IL_10 | 0.000 | | HepB_cAb_Int | IL_10 | 0.000 |
| HepB_cAb_Int | IL_12p70 | 0.000 | | HepB_cAb_Int | IL_12p70 | 0.000 |
| HepB_cAb_Int | IL_13 | 0.000 | | HepB_cAb_Int | IL_13 | 0.000 |
| HepB_cAb_Int | IL_15 | 0.000 | | HepB_cAb_Int | IL_15 | 0.000 |
| HepB_cAb_Int | IL_17 | 0.000 | | HepB_cAb_Int | IL_17 | 0.000 |
| HepB_cAb_Int | IL_23 | 0.000 | | HepB_cAb_Int | IL_23 | 0.000 |
| HepB_cAb_Int | IFN_gamma | 0.000 | | HepB_cAb_Int | IFN_gamma | 0.000 |
| HepB_cAb_Int | TNF_alpha | 0.000 | | HepB_cAb_Int | TNF_alpha | 0.000 |
| HepB_cAb_Int | TNF_beta | 0.000 | | HepB_cAb_Int | TNF_beta | 0.000 |
| HepB_cAb_Int | Varicella_Int | 0.000 | | HepB_cAb_Int | Varicella_Int | 0.000 |
| HepB_cAb_Int | Measles_OD_DB_Int | 0.000 | | HepB_cAb_Int | Measles_OD_DB_Int | 0.000 |
| HepB_cAb_Int | Measles_Int | 0.000 | | HepB_cAb_Int | Measles_Int | 0.000 |
| HepB_cAb_Int | HepA_Int | 0.000 | | HepB_cAb_Int | HepA_Int | 0.000 |
| HepB_cAb_Int | Tetanus_Int | 0.000 | | HepB_cAb_Int | Tetanus_Int | 0.000 |
| HepB_cAb_Int | Diptheria_Int | 0.000 | | HepB_cAb_Int | Diptheria_Int | 0.000 |
| HepB_cAb_Int | Rubella_Int | 0.000 | | HepB_cAb_Int | Rubella_Int | 0.000 |
| HepB_cAb_Int | CMV_Int | 0.000 | | HepB_cAb_Int | CMV_Int | 0.000 |
| HepB_cAb_Int | HepB_cAb_Int | 1.000 | | HepB_cAb_Int | HepB_cAb_Int | 1.000 |
| HepB_cAb_Int | HepB_eAb_Int | 0.000 | | HepB_cAb_Int | HepB_eAb_Int | 0.000 |
| HepB_cAb_Int | HepB_eAg_Int | 0.000 | | HepB_cAb_Int | HepB_eAg_Int | 0.000 |
| HepB_cAb_Int | HepC_Int | 0.000 | | HepB_cAb_Int | HepC_int | 0.000 |
| HepB_cAb_Int | Schistosoma_int | 0.000 | | HepB_cAb_Int | Schistosoma_int | 0.000 |

FIG. 2119-N

| | | | | | | |
|---|---|---|---|---|---|---|
| HepB_cAb_Int | Strongyloides_Int | 0.000 | | HepB_cAb_Int | Strongyloides_Int | 0.000 |
| HepB_cAb_Int | Filaria_Int | 0.000 | | HepB_cAb_Int | Filaria_Int | 0.000 |
| HepB_eAb_Int | IL_1_alpha | 0.000 | | HepB_eAb_Int | IL_1_alpha | 0.000 |
| HepB_eAb_Int | IL_1_beta | 0.000 | | HepB_eAb_Int | IL_1_beta | 0.000 |
| HepB_eAb_Int | IL_2 | 0.000 | | HepB_eAb_Int | IL_2 | 0.000 |
| HepB_eAb_Int | IL_4 | 0.000 | | HepB_eAb_Int | IL_4 | 0.000 |
| HepB_eAb_Int | IL_5 | 0.000 | | HepB_eAb_Int | IL_5 | 0.000 |
| HepB_eAb_Int | IL_6 | 0.000 | | HepB_eAb_Int | IL_6 | 0.000 |
| HepB_eAb_Int | IL_8 | 0.000 | | HepB_eAb_Int | IL_8 | 0.000 |
| HepB_eAb_Int | IL_10 | 0.000 | | HepB_eAb_Int | IL_10 | 0.000 |
| HepB_eAb_Int | IL_12p70 | 0.000 | | HepB_eAb_Int | IL_12p70 | 0.000 |
| HepB_eAb_Int | IL_13 | 0.000 | | HepB_eAb_Int | IL_13 | 0.000 |
| HepB_eAb_Int | IL_15 | 0.000 | | HepB_eAb_Int | IL_15 | 0.000 |
| HepB_eAb_Int | IL_17 | 0.000 | | HepB_eAb_Int | IL_17 | 0.000 |
| HepB_eAb_Int | IL_23 | 0.000 | | HepB_eAb_Int | IL_23 | 0.000 |
| HepB_eAb_Int | IFN_gamma | 0.000 | | HepB_eAb_Int | IFN_gamma | 0.000 |
| HepB_eAb_Int | TNF_alpha | 0.000 | | HepB_eAb_Int | TNF_alpha | 0.000 |
| HepB_eAb_Int | TNF_beta | 0.000 | | HepB_eAb_Int | TNF_beta | 0.000 |
| HepB_eAb_Int | Varicella_Int | 0.000 | | HepB_eAb_Int | Varicella_Int | 0.000 |
| HepB_eAb_Int | Measles_OD_DB_Int | 0.000 | | HepB_eAb_Int | Measles_OD_DB_Int | 0.000 |
| HepB_eAb_Int | Measles_Int | 0.000 | | HepB_eAb_Int | Measles_Int | 0.000 |
| HepB_eAb_Int | HepA_Int | 0.000 | | HepB_eAb_Int | HepA_Int | 0.000 |
| HepB_eAb_Int | Tetanus_Int | 0.000 | | HepB_eAb_Int | Tetanus_Int | 0.000 |
| HepB_eAb_Int | Diptheria_Int | 0.000 | | HepB_eAb_Int | Diptheria_Int | 0.000 |
| HepB_eAb_Int | Rubella_Int | 0.000 | | HepB_eAb_Int | Rubella_Int | 0.000 |
| HepB_eAb_Int | CMV_Int | 0.000 | | HepB_eAb_Int | CMV_Int | 0.000 |
| HepB_eAb_Int | HepB_cAb_Int | 0.000 | | HepB_eAb_Int | HepB_cAb_Int | 0.000 |
| HepB_eAb_Int | HepB_eAb_Int | 1.000 | | HepB_eAb_Int | HepB_eAb_Int | 1.000 |
| HepB_eAb_Int | HepB_eAg_Int | 0.000 | | HepB_eAb_Int | HepB_eAg_Int | 0.000 |
| HepB_eAb_Int | HepC_Int | 0.000 | | HepB_eAb_Int | HepC_Int | 0.000 |
| HepB_eAb_Int | Schistosoma_int | 0.000 | | HepB_eAb_Int | Schistosoma_int | 0.000 |
| HepB_eAb_Int | Strongyloides_Int | 0.000 | | HepB_eAb_Int | Strongyloides_Int | 0.000 |
| HepB_eAb_Int | Filaria_Int | 0.000 | | HepB_eAb_Int | Filaria_Int | 0.000 |
| HepB_eAg_Int | IL_1_alpha | 0.000 | | HepB_eAg_Int | IL_1_alpha | 0.000 |
| HepB_eAg_Int | IL_1_beta | 0.000 | | HepB_eAg_Int | IL_1_beta | 0.000 |
| HepB_eAg_Int | IL_2 | 0.000 | | HepB_eAg_Int | IL_2 | 0.000 |
| HepB_eAg_Int | IL_4 | 0.000 | | HepB_eAg_Int | IL_4 | 0.000 |
| HepB_eAg_Int | IL_5 | 0.000 | | HepB_eAg_Int | IL_5 | 0.000 |
| HepB_eAg_Int | IL_6 | 0.000 | | HepB_eAg_Int | IL_6 | 0.000 |
| HepB_eAg_Int | IL_8 | 0.000 | | HepB_eAg_Int | IL_8 | 0.000 |
| HepB_eAg_Int | IL_10 | 0.000 | | HepB_eAg_Int | IL_10 | 0.000 |
| HepB_eAg_Int | IL_12p70 | 0.000 | | HepB_eAg_Int | IL_12p70 | 0.000 |
| HepB_eAg_Int | IL_13 | 0.000 | | HepB_eAg_Int | IL_13 | 0.000 |
| HepB_eAg_Int | IL_15 | 0.000 | | HepB_eAg_Int | IL_15 | 0.000 |
| HepB_eAg_Int | IL_17 | 0.000 | | HepB_eAg_Int | IL_17 | 0.000 |
| HepB_eAg_Int | IL_23 | 0.000 | | HepB_eAg_Int | IL_23 | 0.000 |
| HepB_eAg_Int | IFN_gamma | 0.000 | | HepB_eAg_Int | IFN_gamma | 0.000 |
| HepB_eAg_Int | TNF_alpha | 0.000 | | HepB_eAg_Int | TNF_alpha | 0.000 |
| HepB_eAg_Int | TNF_beta | 0.000 | | HepB_eAg_Int | TNF_beta | 0.000 |
| HepB_eAg_Int | Varicella_Int | 0.000 | | HepB_eAg_Int | Varicella_Int | 0.000 |
| HepB_eAg_Int | Measles_OD_DB_Int | 0.000 | | HepB_eAg_Int | Measles_OD_DB_Int | 0.000 |
| HepB_eAg_Int | Measles_Int | 0.000 | | HepB_eAg_Int | Measles_Int | 0.000 |
| HepB_eAg_Int | HepA_Int | 0.000 | | HepB_eAg_Int | HepA_Int | 0.000 |
| HepB_eAg_Int | Tetanus_Int | 0.000 | | HepB_eAg_Int | Tetanus_Int | 0.000 |
| HepB_eAg_Int | Diptheria_Int | 0.000 | | HepB_eAg_Int | Diptheria_Int | 0.000 |
| HepB_eAg_Int | Rubella_Int | 0.000 | | HepB_eAg_Int | Rubella_Int | 0.000 |
| HepB_eAg_Int | CMV_Int | 0.000 | | HepB_eAg_Int | CMV_Int | 0.000 |

FIG. 2I9-O

| | | | | | | |
|---|---|---|---|---|---|---|
| HepB_eAg_Int | HepB_cAb_Int | 0.000 | | HepB_eAg_Int | HepB_cAb_Int | 0.000 |
| HepB_eAg_Int | HepB_eAb_Int | 0.000 | | HepB_eAg_Int | HepB_eAb_Int | 0.000 |
| HepB_eAg_Int | HepB_eAg_Int | 1.000 | | HepB_eAg_Int | HepB_eAg_Int | 1.000 |
| HepB_eAg_Int | HepC_Int | 0.000 | | HepB_eAg_Int | HepC_Int | 0.000 |
| HepB_eAg_Int | Schistosoma_int | 0.000 | | HepB_eAg_Int | Schistosoma_int | 0.000 |
| HepB_eAg_Int | Strongyloides_Int | 0.000 | | HepB_eAg_Int | Strongyloides_Int | 0.000 |
| HepB_eAg_Int | Filaria_Int | 0.000 | | HepB_eAg_Int | Filaria_Int | 0.000 |
| HepC_Int | IL_1_alpha | 0.000 | | HepC_Int | IL_1_alpha | 0.000 |
| HepC_Int | IL_1_beta | 0.000 | | HepC_Int | IL_1_beta | 0.000 |
| HepC_Int | IL_2 | 0.000 | | HepC_Int | IL_2 | 0.000 |
| HepC_Int | IL_4 | 0.000 | | HepC_Int | IL_4 | 0.000 |
| HepC_Int | IL_5 | 0.000 | | HepC_Int | IL_5 | 0.000 |
| HepC_Int | IL_6 | 0.000 | | HepC_Int | IL_6 | 0.000 |
| HepC_Int | IL_8 | 0.000 | | HepC_Int | IL_8 | 0.000 |
| HepC_Int | IL_10 | 0.000 | | HepC_Int | IL_10 | 0.000 |
| HepC_Int | IL_12p70 | 0.000 | | HepC_Int | IL_12p70 | 0.000 |
| HepC_Int | IL_13 | 0.000 | | HepC_Int | IL_13 | 0.000 |
| HepC_Int | IL_15 | 0.000 | | HepC_Int | IL_15 | 0.000 |
| HepC_Int | IL_17 | 0.000 | | HepC_Int | IL_17 | 0.000 |
| HepC_Int | IL_23 | 0.000 | | HepC_Int | IL_23 | 0.000 |
| HepC_Int | IFN_gamma | 0.000 | | HepC_Int | IFN_gamma | 0.000 |
| HepC_Int | TNF_alpha | 0.000 | | HepC_Int | TNF_alpha | 0.000 |
| HepC_Int | TNF_beta | 0.000 | | HepC_Int | TNF_beta | 0.000 |
| HepC_Int | Varicella_Int | 0.000 | | HepC_Int | Varicella_Int | 0.000 |
| HepC_Int | Measles_OD_DB_Int | 0.000 | | HepC_Int | Measles_OD_DB_Int | 0.000 |
| HepC_Int | Measles_Int | 0.000 | | HepC_Int | Measles_Int | 0.000 |
| HepC_Int | HepA_Int | 0.000 | | HepC_Int | HepA_int | 0.000 |
| HepC_Int | Tetanus_Int | 0.000 | | HepC_Int | Tetanus_Int | 0.000 |
| HepC_Int | Diptheria_Int | 0.000 | | HepC_Int | Diptheria_Int | 0.000 |
| HepC_Int | Rubella_Int | 0.000 | | HepC_Int | Rubella_Int | 0.000 |
| HepC_Int | CMV_Int | 0.000 | | HepC_Int | CMV_Int | 0.000 |
| HepC_Int | HepB_cAb_Int | 0.000 | | HepC_Int | HepB_cAb_Int | 0.000 |
| HepC_Int | HepB_eAb_Int | 0.000 | | HepC_Int | HepB_eAb_Int | 0.000 |
| HepC_Int | HepB_eAg_Int | 0.000 | | HepC_Int | HepB_eAg_Int | 0.000 |
| HepC_Int | HepC_Int | 1.000 | | HepC_Int | HepC_Int | 1.000 |
| HepC_Int | Schistosoma_int | 0.000 | | HepC_Int | Schistosoma_int | 0.000 |
| HepC_Int | Strongyloides_Int | 0.000 | | HepC_Int | Strongyloides_Int | 0.000 |
| HepC_Int | Filaria_Int | 0.000 | | HepC_Int | Filaria_Int | 0.000 |
| Schistosoma_int | IL_1_alpha | 0.420 | | Schistosoma_int | IL_1_alpha | -0.314 |
| Schistosoma_int | IL_1_beta | -0.025 | | Schistosoma_int | IL_1_beta | -0.403 |
| Schistosoma_int | IL_2 | 0.520 | | Schistosoma_int | IL_2 | -0.262 |
| Schistosoma_int | IL_4 | 0.249 | | Schistosoma_int | IL_4 | -0.351 |
| Schistosoma_int | IL_5 | -0.106 | | Schistosoma_int | IL_5 | -0.326 |
| Schistosoma_int | IL_6 | -0.275 | | Schistosoma_int | IL_6 | -0.305 |
| Schistosoma_int | IL_8 | -0.063 | | Schistosoma_int | IL_8 | 0.002 |
| Schistosoma_int | IL_10 | 0.702 | | Schistosoma_int | IL_10 | -0.315 |
| Schistosoma_int | IL_12p70 | -0.116 | | Schistosoma_int | IL_12p70 | -0.730 |
| Schistosoma_int | IL_13 | -0.039 | | Schistosoma_int | IL_13 | -0.552 |
| Schistosoma_int | IL_15 | -0.261 | | Schistosoma_int | IL_15 | -0.261 |
| Schistosoma_int | IL_17 | 0.713 | | Schistosoma_int | IL_17 | -0.333 |
| Schistosoma_int | IL_23 | -0.220 | | Schistosoma_int | IL_23 | -0.352 |
| Schistosoma_int | IFN_gamma | 0.000 | | Schistosoma_int | IFN_gamma | 0.000 |
| Schistosoma_int | TNF_alpha | 0.097 | | Schistosoma_int | TNF_alpha | -0.381 |
| Schistosoma_int | TNF_beta | 0.593 | | Schistosoma_int | TNF_beta | -0.340 |
| Schistosoma_int | Varicella_Int | -0.048 | | Schistosoma_int | Varicella_Int | 0.000 |
| Schistosoma_int | Measles_OD_DB_Int | -0.218 | | Schistosoma_int | Measles_OD_DB_Int | 0.577 |
| Schistosoma_int | Measles_Int | 0.327 | | Schistosoma_int | Measles_Int | 0.000 |

FIG. 21I9-P

| | | | | | | |
|---|---|---|---|---|---|---|
| Schistosoma_int | HepA_Int | -0.218 | | Schistosoma_int | HepA_Int | 0.000 |
| Schistosoma_int | Tetanus_Int | 0.000 | | Schistosoma_int | Tetanus_Int | 0.000 |
| Schistosoma_int | Diptheria_Int | 0.000 | | Schistosoma_int | Diptheria_Int | 0.000 |
| Schistosoma_int | Rubella_Int | -0.089 | | Schistosoma_int | Rubella_Int | -0.333 |
| Schistosoma_int | CMV_Int | -0.509 | | Schistosoma_int | CMV_Int | 0.000 |
| Schistosoma_int | HepB_cAb_Int | 0.000 | | Schistosoma_int | HepB_cAb_Int | 0.000 |
| Schistosoma_int | HepB_eAb_Int | 0.000 | | Schistosoma_int | HepB_eAb_Int | 0.000 |
| Schistosoma_int | HepB_eAg_Int | 0.000 | | Schistosoma_int | HepB_eAg_Int | 0.000 |
| Schistosoma_int | HepC_Int | 0.000 | | Schistosoma_int | HepC_Int | 0.000 |
| Schistosoma_int | Schistosoma_int | 1.000 | | Schistosoma_int | Schistosoma_int | 1.000 |
| Schistosoma_int | Strongyloides_Int | 0.531 | | Schistosoma_int | Strongyloides_Int | 0.333 |
| Schistosoma_int | Filaria_Int | 0.048 | | Schistosoma_int | Filaria_Int | 0.522 |
| Strongyloides_Int | IL_1_alpha | -0.422 | | Strongyloides_Int | IL_1_alpha | 0.343 |
| Strongyloides_Int | IL_1_beta | -0.312 | | Strongyloides_Int | IL_1_beta | 0.248 |
| Strongyloides_Int | IL_2 | 0.559 | | Strongyloides_Int | IL_2 | 0.496 |
| Strongyloides_Int | IL_4 | 0.222 | | Strongyloides_Int | IL_4 | 0.368 |
| Strongyloides_Int | IL_5 | -0.466 | | Strongyloides_Int | IL_5 | 0.390 |
| Strongyloides_Int | IL_6 | -0.389 | | Strongyloides_Int | IL_6 | 0.372 |
| Strongyloides_Int | IL_8 | -0.598 | | Strongyloides_Int | IL_8 | 0.755 |
| Strongyloides_Int | IL_10 | 0.522 | | Strongyloides_Int | IL_10 | 0.320 |
| Strongyloides_Int | IL_12p70 | -0.529 | | Strongyloides_Int | IL_12p70 | 0.397 |
| Strongyloides_Int | IL_13 | -0.446 | | Strongyloides_Int | IL_13 | 0.180 |
| Strongyloides_Int | IL_15 | -0.763 | | Strongyloides_Int | IL_15 | 0.506 |
| Strongyloides_Int | IL_17 | 0.385 | | Strongyloides_Int | IL_17 | 0.420 |
| Strongyloides_Int | IL_23 | -0.313 | | Strongyloides_Int | IL_23 | 0.293 |
| Strongyloides_Int | IFN_gamma | 0.000 | | Strongyloides_Int | IFN_gamma | 0.000 |
| Strongyloides_Int | TNF_alpha | 0.012 | | Strongyloides_Int | TNF_alpha | 0.314 |
| Strongyloides_Int | TNF_beta | 0.573 | | Strongyloides_Int | TNF_beta | 0.418 |
| Strongyloides_Int | Varicella_Int | 0.028 | | Strongyloides_Int | Varicella_Int | 0.000 |
| Strongyloides_Int | Measles_OD_DB_Int | 0.128 | | Strongyloides_Int | Measles_OD_DB_Int | 0.577 |
| Strongyloides_Int | Measles_Int | 0.128 | | Strongyloides_Int | Measles_Int | 0.000 |
| Strongyloides_Int | HepA_Int | -0.192 | | Strongyloides_Int | HepA_Int | 0.000 |
| Strongyloides_Int | Tetanus_Int | 0.000 | | Strongyloides_Int | Tetanus_Int | 0.000 |
| Strongyloides_Int | Diptheria_Int | 0.000 | | Strongyloides_Int | Diptheria_Int | 0.000 |
| Strongyloides_Int | Rubella_Int | -0.209 | | Strongyloides_Int | Rubella_Int | 0.333 |
| Strongyloides_Int | CMV_Int | -0.555 | | Strongyloides_Int | CMV_Int | 0.000 |
| Strongyloides_Int | HepB_cAb_Int | 0.000 | | Strongyloides_Int | HepB_cAb_Int | 0.000 |
| Strongyloides_Int | HepB_eAb_Int | 0.000 | | Strongyloides_Int | HepB_eAb_Int | 0.000 |
| Strongyloides_Int | HepB_eAg_Int | 0.000 | | Strongyloides_Int | HepB_eAg_Int | 0.000 |
| Strongyloides_Int | HepC_Int | 0.000 | | Strongyloides_Int | HepC_Int | 0.000 |
| Strongyloides_Int | Schistosoma_int | 0.531 | | Strongyloides_Int | Schistosoma_int | 0.333 |
| Strongyloides_Int | Strongyloides_Int | 1.000 | | Strongyloides_Int | Strongyloides_Int | 1.000 |
| Strongyloides_Int | Filaria_Int | 0.251 | | Strongyloides_Int | Filaria_Int | 0.870 |
| Filaria_Int | IL_1_alpha | -0.295 | | Filaria_Int | IL_1_alpha | 0.537 |
| Filaria_Int | IL_1_beta | 0.340 | | Filaria_Int | IL_1_beta | 0.439 |
| Filaria_Int | IL_2 | 0.450 | | Filaria_Int | IL_2 | 0.636 |
| Filaria_Int | IL_4 | -0.266 | | Filaria_Int | IL_4 | 0.530 |
| Filaria_Int | IL_5 | -0.186 | | Filaria_Int | IL_5 | 0.555 |
| Filaria_Int | IL_6 | -0.275 | | Filaria_Int | IL_6 | 0.557 |
| Filaria_Int | IL_8 | 0.165 | | Filaria_Int | IL_8 | 0.848 |
| Filaria_Int | IL_10 | -0.185 | | Filaria_Int | IL_10 | 0.525 |
| Filaria_Int | IL_12p70 | -0.220 | | Filaria_Int | IL_12p70 | 0.155 |
| Filaria_Int | IL_13 | -0.246 | | Filaria_Int | IL_13 | 0.312 |
| Filaria_Int | IL_15 | -0.279 | | Filaria_Int | IL_15 | 0.640 |
| Filaria_Int | IL_17 | -0.317 | | Filaria_Int | IL_17 | 0.565 |
| Filaria_Int | IL_23 | -0.219 | | Filaria_Int | IL_23 | -0.216 |
| Filaria_Int | IFN_gamma | 0.000 | | Filaria_Int | IFN_gamma | 0.000 |

FIG. 21I9-Q

| Filaria_Int | TNF_alpha | 0.553 |
| --- | --- | --- |
| Filaria_Int | TNF_beta | -0.097 |
| Filaria_Int | Varicella_Int | -0.524 |
| Filaria_Int | Measles_OD_DB_Int | 0.024 |
| Filaria_Int | Measles_Int | -0.218 |
| Filaria_Int | HepA_Int | 0.327 |
| Filaria_Int | Tetanus_Int | 0.000 |
| Filaria_Int | Diptheria_Int | 0.000 |
| Filaria_Int | Rubella_Int | 0.356 |
| Filaria_Int | CMV_Int | 0.218 |
| Filaria_Int | HepB_cAb_Int | 0.000 |
| Filaria_Int | HepB_eAb_Int | 0.000 |
| Filaria_Int | HepB_eAg_Int | 0.000 |
| Filaria_Int | HepC_Int | 0.000 |
| Filaria_Int | Schistosoma_int | 0.048 |
| Filaria_Int | Strongyloides_Int | 0.251 |
| Filaria_Int | Filaria_Int | 1.000 |

| Filaria_Int | TNF_alpha | 0.487 |
| --- | --- | --- |
| Filaria_Int | TNF_beta | 0.560 |
| Filaria_Int | Varicella_Int | 0.000 |
| Filaria_Int | Measles_OD_DB_Int | 0.302 |
| Filaria_Int | Measles_Int | 0.000 |
| Filaria_Int | HepA_Int | 0.000 |
| Filaria_Int | Tetanus_Int | 0.000 |
| Filaria_Int | Diptheria_Int | 0.000 |
| Filaria_Int | Rubella_Int | -0.174 |
| Filaria_Int | CMV_Int | 0.000 |
| Filaria_Int | HepB_cAb_Int | 0.000 |
| Filaria_Int | HepB_eAb_Int | 0.000 |
| Filaria_Int | HepB_eAg_Int | 0.000 |
| Filaria_Int | HepC_Int | 0.000 |
| Filaria_Int | Schistosoma_int | 0.522 |
| Filaria_Int | Strongyloides_Int | 0.870 |
| Filaria_Int | Filaria_Int | 1.000 |

FIG. 21I9-R

| 0.22% - Region_of_Origin=1, Sex=Female, IFN_gamma=7.5-22.5 ||| 0.22% - Region_of_Origin=5, Sex=Female, IFN_gamma=7.5-22.5 |||
|---|---|---|---|---|---|
| Property 1 | Property 2 | Corr. Coefficient | Property 1 | Property 2 | Corr. Coefficient |
| IL_1_alpha | IL_1_alpha | 1.000 | IL_1_alpha | IL_1_alpha | 1.000 |
| IL_1_alpha | IL_1_beta | 0.606 | IL_1_alpha | IL_1_beta | 0.919 |
| IL_1_alpha | IL_2 | 0.949 | IL_1_alpha | IL_2 | 0.945 |
| IL_1_alpha | IL_4 | 0.669 | IL_1_alpha | IL_4 | 0.799 |
| IL_1_alpha | IL_5 | 0.887 | IL_1_alpha | IL_5 | 0.591 |
| IL_1_alpha | IL_6 | 0.610 | IL_1_alpha | IL_6 | 0.962 |
| IL_1_alpha | IL_8 | 0.363 | IL_1_alpha | IL_8 | 0.646 |
| IL_1_alpha | IL_10 | 0.533 | IL_1_alpha | IL_10 | 0.704 |
| IL_1_alpha | IL_12p70 | 0.516 | IL_1_alpha | IL_12p70 | -0.998 |
| IL_1_alpha | IL_13 | 0.698 | IL_1_alpha | IL_13 | -0.024 |
| IL_1_alpha | IL_15 | 0.700 | IL_1_alpha | IL_15 | 0.805 |
| IL_1_alpha | IL_17 | 0.613 | IL_1_alpha | IL_17 | 0.311 |
| IL_1_alpha | IL_23 | 0.399 | IL_1_alpha | IL_23 | -0.975 |
| IL_1_alpha | IFN_gamma | 0.000 | IL_1_alpha | IFN_gamma | 0.000 |
| IL_1_alpha | TNF_alpha | 0.501 | IL_1_alpha | TNF_alpha | 0.702 |
| IL_1_alpha | TNF_beta | 0.533 | IL_1_alpha | TNF_beta | 0.967 |
| IL_1_alpha | Varicella_Int | 0.000 | IL_1_alpha | Varicella_Int | 0.982 |
| IL_1_alpha | Measles_OD_DB_Int | -0.014 | IL_1_alpha | Measles_OD_DB_Int | -0.655 |
| IL_1_alpha | Measles_Int | 0.000 | IL_1_alpha | Measles_Int | 0.000 |
| IL_1_alpha | HepA_Int | -0.859 | IL_1_alpha | HepA_Int | 0.327 |
| IL_1_alpha | Tetanus_Int | 0.000 | IL_1_alpha | Tetanus_Int | 0.000 |
| IL_1_alpha | Diptheria_Int | 0.000 | IL_1_alpha | Diptheria_Int | 0.000 |
| IL_1_alpha | Rubella_Int | 0.000 | IL_1_alpha | Rubella_Int | 0.655 |
| IL_1_alpha | CMV_Int | 0.000 | IL_1_alpha | CMV_Int | -0.655 |
| IL_1_alpha | HepB_cAb_Int | -0.873 | IL_1_alpha | HepB_cAb_Int | 0.000 |
| IL_1_alpha | HepB_eAb_Int | 0.000 | IL_1_alpha | HepB_eAb_Int | 0.000 |
| IL_1_alpha | HepB_eAg_Int | 0.000 | IL_1_alpha | HepB_eAg_Int | 0.000 |
| IL_1_alpha | HepC_Int | 0.000 | IL_1_alpha | HepC_Int | 0.000 |
| IL_1_alpha | Schistosoma_int | 0.000 | IL_1_alpha | Schistosoma_int | 0.000 |
| IL_1_alpha | Strongyloides_Int | 0.859 | IL_1_alpha | Strongyloides_Int | 0.000 |
| IL_1_alpha | Filaria_Int | -0.859 | IL_1_alpha | Filaria_Int | 0.000 |
| IL_1_beta | IL_1_alpha | 0.606 | IL_1_beta | IL_1_alpha | 0.919 |
| IL_1_beta | IL_1_beta | 1.000 | IL_1_beta | IL_1_beta | 1.000 |
| IL_1_beta | IL_2 | 0.827 | IL_1_beta | IL_2 | 0.739 |
| IL_1_beta | IL_4 | 0.997 | IL_1_beta | IL_4 | 0.972 |
| IL_1_beta | IL_5 | 0.905 | IL_1_beta | IL_5 | 0.224 |

FIG. 21I10-A

| | | | | | | |
|---|---|---|---|---|---|---|
| IL_1_beta | IL_6 | 1.000 | | IL_1_beta | IL_6 | 0.777 |
| IL_1_beta | IL_8 | 0.961 | | IL_1_beta | IL_8 | 0.895 |
| IL_1_beta | IL_10 | 0.996 | | IL_1_beta | IL_10 | 0.927 |
| IL_1_beta | IL_12p70 | 0.994 | | IL_1_beta | IL_12p70 | -0.941 |
| IL_1_beta | IL_13 | 0.993 | | IL_1_beta | IL_13 | 0.373 |
| IL_1_beta | IL_15 | 0.992 | | IL_1_beta | IL_15 | 0.974 |
| IL_1_beta | IL_17 | 1.000 | | IL_1_beta | IL_17 | 0.661 |
| IL_1_beta | IL_23 | 0.971 | | IL_1_beta | IL_23 | -0.983 |
| IL_1_beta | IFN_gamma | 0.000 | | IL_1_beta | IFN_gamma | 0.000 |
| IL_1_beta | TNF_alpha | 0.992 | | IL_1_beta | TNF_alpha | 0.926 |
| IL_1_beta | TNF_beta | 0.996 | | IL_1_beta | TNF_beta | 0.788 |
| IL_1_beta | Varicella_Int | 0.000 | | IL_1_beta | Varicella_Int | 0.977 |
| IL_1_beta | Measles_OD_DB_Int | -0.804 | | IL_1_beta | Measles_OD_DB_Int | -0.302 |
| IL_1_beta | Measles_Int | 0.000 | | IL_1_beta | Measles_Int | 0.000 |
| IL_1_beta | HepA_Int | -0.114 | | IL_1_beta | HepA_Int | 0.674 |
| IL_1_beta | Tetanus_Int | 0.000 | | IL_1_beta | Tetanus_Int | 0.000 |
| IL_1_beta | Diptheria_Int | 0.000 | | IL_1_beta | Diptheria_Int | 0.000 |
| IL_1_beta | Rubella_Int | 0.000 | | IL_1_beta | Rubella_Int | 0.302 |
| IL_1_beta | CMV_Int | 0.000 | | IL_1_beta | CMV_Int | -0.302 |
| IL_1_beta | HepB_cAb_Int | -0.917 | | IL_1_beta | HepB_cAb_Int | 0.000 |
| IL_1_beta | HepB_eAb_Int | 0.000 | | IL_1_beta | HepB_eAb_Int | 0.000 |
| IL_1_beta | HepB_eAg_Int | 0.000 | | IL_1_beta | HepB_eAg_Int | 0.000 |
| IL_1_beta | HepC_Int | 0.000 | | IL_1_beta | HepC_Int | 0.000 |
| IL_1_beta | Schistosoma_int | 0.000 | | IL_1_beta | Schistosoma_int | 0.000 |
| IL_1_beta | Strongyloides_Int | 0.114 | | IL_1_beta | Strongyloides_Int | 0.000 |
| IL_1_beta | Filaria_Int | -0.114 | | IL_1_beta | Filaria_Int | 0.000 |
| IL_2 | IL_1_alpha | 0.949 | | IL_2 | IL_1_alpha | 0.945 |
| IL_2 | IL_1_beta | 0.827 | | IL_2 | IL_1_beta | 0.739 |
| IL_2 | IL_2 | 1.000 | | IL_2 | IL_2 | 1.000 |
| IL_2 | IL_4 | 0.870 | | IL_2 | IL_4 | 0.558 |
| IL_2 | IL_5 | 0.988 | | IL_2 | IL_5 | 0.822 |
| IL_2 | IL_6 | 0.829 | | IL_2 | IL_6 | 0.998 |
| IL_2 | IL_8 | 0.639 | | IL_2 | IL_8 | 0.361 |
| IL_2 | IL_10 | 0.774 | | IL_2 | IL_10 | 0.432 |
| IL_2 | IL_12p70 | 0.760 | | IL_2 | IL_12p70 | -0.924 |
| IL_2 | IL_13 | 0.889 | | IL_2 | IL_13 | -0.350 |
| IL_2 | IL_15 | 0.890 | | IL_2 | IL_15 | 0.567 |
| IL_2 | IL_17 | 0.832 | | IL_2 | IL_17 | -0.018 |
| IL_2 | IL_23 | 0.669 | | IL_2 | IL_23 | -0.850 |
| IL_2 | IFN_gamma | 0.000 | | IL_2 | IFN_gamma | 0.000 |
| IL_2 | TNF_alpha | 0.749 | | IL_2 | TNF_alpha | 0.430 |
| IL_2 | TNF_beta | 0.774 | | IL_2 | TNF_beta | 0.997 |
| IL_2 | Varicella_Int | 0.000 | | IL_2 | Varicella_Int | 0.866 |
| IL_2 | Measles_OD_DB_Int | -0.329 | | IL_2 | Measles_OD_DB_Int | -0.866 |
| IL_2 | Measles_Int | 0.000 | | IL_2 | Measles_Int | 0.000 |
| IL_2 | HepA_Int | -0.653 | | IL_2 | HepA_Int | -0.000 |
| IL_2 | Tetanus_Int | 0.000 | | IL_2 | Tetanus_Int | 0.000 |
| IL_2 | Diptheria_Int | 0.000 | | IL_2 | Diptheria_Int | 0.000 |
| IL_2 | Rubella_Int | 0.000 | | IL_2 | Rubella_Int | 0.866 |
| IL_2 | CMV_Int | 0.000 | | IL_2 | CMV_Int | -0.866 |
| IL_2 | HepB_cAb_Int | -0.982 | | IL_2 | HepB_cAb_Int | 0.000 |
| IL_2 | HepB_eAb_Int | 0.000 | | IL_2 | HepB_eAb_Int | 0.000 |
| IL_2 | HepB_eAg_Int | 0.000 | | IL_2 | HepB_eAg_Int | 0.000 |
| IL_2 | HepC_Int | 0.000 | | IL_2 | HepC_Int | 0.000 |
| IL_2 | Schistosoma_int | 0.000 | | IL_2 | Schistosoma_int | 0.000 |
| IL_2 | Strongyloides_Int | 0.653 | | IL_2 | Strongyloides_Int | 0.000 |
| IL_2 | Filaria_Int | -0.653 | | IL_2 | Filaria_Int | 0.000 |

FIG. 21I10-B

| | | | | | | |
|---|---|---|---|---|---|---|
| IL_4 | IL_1_alpha | 0.669 | | IL_4 | IL_1_alpha | 0.799 |
| IL_4 | IL_1_beta | 0.997 | | IL_4 | IL_1_beta | 0.972 |
| IL_4 | IL_2 | 0.870 | | IL_4 | IL_2 | 0.558 |
| IL_4 | IL_4 | 1.000 | | IL_4 | IL_4 | 1.000 |
| IL_4 | IL_5 | 0.936 | | IL_4 | IL_5 | -0.013 |
| IL_4 | IL_6 | 0.997 | | IL_4 | IL_6 | 0.605 |
| IL_4 | IL_8 | 0.936 | | IL_4 | IL_8 | 0.975 |
| IL_4 | IL_10 | 0.986 | | IL_4 | IL_10 | 0.990 |
| IL_4 | IL_12p70 | 0.982 | | IL_4 | IL_12p70 | -0.833 |
| IL_4 | IL_13 | 0.999 | | IL_4 | IL_13 | 0.582 |
| IL_4 | IL_15 | 0.999 | | IL_4 | IL_15 | 1.000 |
| IL_4 | IL_17 | 0.997 | | IL_4 | IL_17 | 0.820 |
| IL_4 | IL_23 | 0.949 | | IL_4 | IL_23 | -0.912 |
| IL_4 | IFN_gamma | 0.000 | | IL_4 | IFN_gamma | 0.000 |
| IL_4 | TNF_alpha | 0.979 | | IL_4 | TNF_alpha | 0.989 |
| IL_4 | TNF_beta | 0.986 | | IL_4 | TNF_beta | 0.619 |
| IL_4 | Varicella_Int | 0.000 | | IL_4 | Varicella_Int | 0.898 |
| IL_4 | Measles_OD_DB_Int | -0.753 | | IL_4 | Measles_OD_DB_Int | -0.068 |
| IL_4 | Measles_Int | 0.000 | | IL_4 | Measles_Int | 0.000 |
| IL_4 | HepA_Int | -0.194 | | IL_4 | HepA_Int | 0.830 |
| IL_4 | Tetanus_Int | 0.000 | | IL_4 | Tetanus_Int | 0.000 |
| IL_4 | Diptheria_Int | 0.000 | | IL_4 | Diptheria_Int | 0.000 |
| IL_4 | Rubella_Int | 0.000 | | IL_4 | Rubella_Int | 0.068 |
| IL_4 | CMV_Int | 0.000 | | IL_4 | CMV_Int | -0.068 |
| IL_4 | HepB_cAb_Int | -0.947 | | IL_4 | HepB_cAb_Int | 0.000 |
| IL_4 | HepB_eAb_Int | 0.000 | | IL_4 | HepB_eAb_Int | 0.000 |
| IL_4 | HepB_eAg_Int | 0.000 | | IL_4 | HepB_eAg_Int | 0.000 |
| IL_4 | HepC_Int | 0.000 | | IL_4 | HepC_Int | 0.000 |
| IL_4 | Schistosoma_int | 0.000 | | IL_4 | Schistosoma_int | 0.000 |
| IL_4 | Strongyloides_Int | 0.194 | | IL_4 | Strongyloides_Int | 0.000 |
| IL_4 | Filaria_Int | -0.194 | | IL_4 | Filaria_Int | 0.000 |
| IL_5 | IL_1_alpha | 0.887 | | IL_5 | IL_1_alpha | 0.591 |
| IL_5 | IL_1_beta | 0.905 | | IL_5 | IL_1_beta | 0.224 |
| IL_5 | IL_2 | 0.988 | | IL_5 | IL_2 | 0.822 |
| IL_5 | IL_4 | 0.936 | | IL_5 | IL_4 | -0.013 |
| IL_5 | IL_5 | 1.000 | | IL_5 | IL_5 | 1.000 |
| IL_5 | IL_6 | 0.907 | | IL_5 | IL_6 | 0.788 |
| IL_5 | IL_8 | 0.752 | | IL_5 | IL_8 | -0.234 |
| IL_5 | IL_10 | 0.864 | | IL_5 | IL_10 | -0.157 |
| IL_5 | IL_12p70 | 0.853 | | IL_5 | IL_12p70 | -0.542 |
| IL_5 | IL_13 | 0.950 | | IL_5 | IL_13 | -0.821 |
| IL_5 | IL_15 | 0.951 | | IL_5 | IL_15 | -0.003 |
| IL_5 | IL_17 | 0.909 | | IL_5 | IL_17 | -0.583 |
| IL_5 | IL_23 | 0.777 | | IL_5 | IL_23 | -0.399 |
| IL_5 | IFN_gamma | 0.000 | | IL_5 | IFN_gamma | 0.000 |
| IL_5 | TNF_alpha | 0.844 | | IL_5 | TNF_alpha | -0.160 |
| IL_5 | TNF_beta | 0.864 | | IL_5 | TNF_beta | 0.777 |
| IL_5 | Varicella_Int | 0.000 | | IL_5 | Varicella_Int | 0.428 |
| IL_5 | Measles_OD_DB_Int | -0.474 | | IL_5 | Measles_OD_DB_Int | -0.997 |
| IL_5 | Measles_Int | 0.000 | | IL_5 | Measles_Int | 0.000 |
| IL_5 | HepA_Int | -0.526 | | IL_5 | HepA_Int | -0.569 |
| IL_5 | Tetanus_Int | 0.000 | | IL_5 | Tetanus_Int | 0.000 |
| IL_5 | Diptheria_Int | 0.000 | | IL_5 | Diptheria_Int | 0.000 |
| IL_5 | Rubella_Int | 0.000 | | IL_5 | Rubella_Int | 0.997 |
| IL_5 | CMV_Int | 0.000 | | IL_5 | CMV_Int | -0.997 |
| IL_5 | HepB_cAb_Int | -1.000 | | IL_5 | HepB_cAb_Int | 0.000 |
| IL_5 | HepB_eAb_Int | 0.000 | | IL_5 | HepB_eAb_Int | 0.000 |

FIG. 21I10-C

| | | | | | | |
|---|---|---|---|---|---|---|
| IL_5 | HepB_eAg_Int | 0.000 | | IL_5 | HepB_eAg_Int | 0.000 |
| IL_5 | HepC_Int | 0.000 | | IL_5 | HepC_Int | 0.000 |
| IL_5 | Schistosoma_int | 0.000 | | IL_5 | Schistosoma_int | 0.000 |
| IL_5 | Strongyloides_Int | 0.526 | | IL_5 | Strongyloides_Int | 0.000 |
| IL_5 | Filaria_Int | -0.526 | | IL_5 | Filaria_Int | 0.000 |
| IL_6 | IL_1_alpha | 0.610 | | IL_6 | IL_1_alpha | 0.962 |
| IL_6 | IL_1_beta | 1.000 | | IL_6 | IL_1_beta | 0.777 |
| IL_6 | IL_2 | 0.829 | | IL_6 | IL_2 | 0.998 |
| IL_6 | IL_4 | 0.997 | | IL_6 | IL_4 | 0.605 |
| IL_6 | IL_5 | 0.907 | | IL_6 | IL_5 | 0.788 |
| IL_6 | IL_6 | 1.000 | | IL_6 | IL_6 | 1.000 |
| IL_6 | IL_8 | 0.960 | | IL_6 | IL_8 | 0.415 |
| IL_6 | IL_10 | 0.996 | | IL_6 | IL_10 | 0.484 |
| IL_6 | IL_12p70 | 0.994 | | IL_6 | IL_12p70 | -0.944 |
| IL_6 | IL_13 | 0.993 | | IL_6 | IL_13 | -0.295 |
| IL_6 | IL_15 | 0.993 | | IL_6 | IL_15 | 0.614 |
| IL_6 | IL_17 | 1.000 | | IL_6 | IL_17 | 0.041 |
| IL_6 | IL_23 | 0.970 | | IL_6 | IL_23 | -0.879 |
| IL_6 | IFN_gamma | 0.000 | | IL_6 | IFN_gamma | 0.000 |
| IL_6 | TNF_alpha | 0.991 | | IL_6 | TNF_alpha | 0.482 |
| IL_6 | TNF_beta | 0.996 | | IL_6 | TNF_beta | 1.000 |
| IL_6 | Varicella_Int | 0.000 | | IL_6 | Varicella_Int | 0.894 |
| IL_6 | Measles_OD_DB_Int | -0.801 | | IL_6 | Measles_OD_DB_Int | -0.835 |
| IL_6 | Measles_Int | 0.000 | | IL_6 | Measles_Int | 0.000 |
| IL_6 | HepA_Int | -0.118 | | IL_6 | HepA_Int | 0.058 |
| IL_6 | Tetanus_Int | 0.000 | | IL_6 | Tetanus_Int | 0.000 |
| IL_6 | Diptheria_Int | 0.000 | | IL_6 | Diptheria_Int | 0.000 |
| IL_6 | Rubella_Int | 0.000 | | IL_6 | Rubella_Int | 0.835 |
| IL_6 | CMV_Int | 0.000 | | IL_6 | CMV_Int | -0.835 |
| IL_6 | HepB_cAb_Int | -0.919 | | IL_6 | HepB_cAb_Int | 0.000 |
| IL_6 | HepB_eAb_Int | 0.000 | | IL_6 | HepB_eAb_Int | 0.000 |
| IL_6 | HepB_eAg_Int | 0.000 | | IL_6 | HepB_eAg_Int | 0.000 |
| IL_6 | HepC_Int | 0.000 | | IL_6 | HepC_Int | 0.000 |
| IL_6 | Schistosoma_int | 0.000 | | IL_6 | Schistosoma_int | 0.000 |
| IL_6 | Strongyloides_Int | 0.118 | | IL_6 | Strongyloides_Int | 0.000 |
| IL_6 | Filaria_Int | -0.118 | | IL_6 | Filaria_Int | 0.000 |
| IL_8 | IL_1_alpha | 0.363 | | IL_8 | IL_1_alpha | 0.646 |
| IL_8 | IL_1_beta | 0.961 | | IL_8 | IL_1_beta | 0.895 |
| IL_8 | IL_2 | 0.639 | | IL_8 | IL_2 | 0.361 |
| IL_8 | IL_4 | 0.936 | | IL_8 | IL_4 | 0.975 |
| IL_8 | IL_5 | 0.752 | | IL_8 | IL_5 | -0.234 |
| IL_8 | IL_6 | 0.960 | | IL_8 | IL_6 | 0.415 |
| IL_8 | IL_8 | 1.000 | | IL_8 | IL_8 | 1.000 |
| IL_8 | IL_10 | 0.982 | | IL_8 | IL_10 | 0.997 |
| IL_8 | IL_12p70 | 0.986 | | IL_8 | IL_12p70 | -0.691 |
| IL_8 | IL_13 | 0.921 | | IL_8 | IL_13 | 0.747 |
| IL_8 | IL_15 | 0.920 | | IL_8 | IL_15 | 0.973 |
| IL_8 | IL_17 | 0.959 | | IL_8 | IL_17 | 0.926 |
| IL_8 | IL_23 | 0.999 | | IL_8 | IL_23 | -0.799 |
| IL_8 | IFN_gamma | 0.000 | | IL_8 | IFN_gamma | 0.000 |
| IL_8 | TNF_alpha | 0.988 | | IL_8 | TNF_alpha | 0.997 |
| IL_8 | TNF_beta | 0.982 | | IL_8 | TNF_beta | 0.431 |
| IL_8 | Varicella_Int | 0.000 | | IL_8 | Varicella_Int | 0.779 |
| IL_8 | Measles_OD_DB_Int | -0.937 | | IL_8 | Measles_OD_DB_Int | 0.154 |
| IL_8 | Measles_Int | 0.000 | | IL_8 | Measles_Int | 0.000 |
| IL_8 | HepA_Int | 0.165 | | IL_8 | HepA_Int | 0.933 |
| IL_8 | Tetanus_Int | 0.000 | | IL_8 | Tetanus_Int | 0.000 |

FIG. 21I10-D

| | | | | | | |
|---|---|---|---|---|---|---|
| IL_8 | Diptheria_Int | 0.000 | | IL_8 | Diptheria_Int | 0.000 |
| IL_8 | Rubella_Int | 0.000 | | IL_8 | Rubella_Int | -0.154 |
| IL_8 | CMV_Int | 0.000 | | IL_8 | CMV_Int | 0.154 |
| IL_8 | HepB_cAb_Int | -0.772 | | IL_8 | HepB_cAb_Int | 0.000 |
| IL_8 | HepB_eAb_Int | 0.000 | | IL_8 | HepB_eAb_Int | 0.000 |
| IL_8 | HepB_eAg_Int | 0.000 | | IL_8 | HepB_eAg_Int | 0.000 |
| IL_8 | HepC_Int | 0.000 | | IL_8 | HepC_int | 0.000 |
| IL_8 | Schistosoma_int | 0.000 | | IL_8 | Schistosoma_int | 0.000 |
| IL_8 | Strongyloides_Int | -0.165 | | IL_8 | Strongyloides_Int | 0.000 |
| IL_8 | Filaria_Int | 0.165 | | IL_8 | Filaria_Int | 0.000 |
| IL_10 | IL_1_alpha | 0.533 | | IL_10 | IL_1_alpha | 0.704 |
| IL_10 | IL_1_beta | 0.996 | | IL_10 | IL_1_beta | 0.927 |
| IL_10 | IL_2 | 0.774 | | IL_10 | IL_2 | 0.432 |
| IL_10 | IL_4 | 0.986 | | IL_10 | IL_4 | 0.990 |
| IL_10 | IL_5 | 0.864 | | IL_10 | IL_5 | -0.157 |
| IL_10 | IL_6 | 0.996 | | IL_10 | IL_6 | 0.484 |
| IL_10 | IL_8 | 0.982 | | IL_10 | IL_8 | 0.997 |
| IL_10 | IL_10 | 1.000 | | IL_10 | IL_10 | 1.000 |
| IL_10 | IL_12p70 | 1.000 | | IL_10 | IL_12p70 | -0.745 |
| IL_10 | IL_13 | 0.978 | | IL_10 | IL_13 | 0.693 |
| IL_10 | IL_15 | 0.978 | | IL_10 | IL_15 | 0.988 |
| IL_10 | IL_17 | 0.995 | | IL_10 | IL_17 | 0.894 |
| IL_10 | IL_23 | 0.989 | | IL_10 | IL_23 | -0.843 |
| IL_10 | IFN_gamma | 0.000 | | IL_10 | IFN_gamma | 0.000 |
| IL_10 | TNF_alpha | 0.999 | | IL_10 | TNF_alpha | 1.000 |
| IL_10 | TNF_beta | 1.000 | | IL_10 | TNF_beta | 0.500 |
| IL_10 | Varicella_Int | 0.000 | | IL_10 | Varicella_Int | 0.825 |
| IL_10 | Measles_OD_DB_Int | -0.853 | | IL_10 | Measles_OD_DB_Int | 0.076 |
| IL_10 | Measles_Int | 0.000 | | IL_10 | Measles_Int | 0.000 |
| IL_10 | HepA_Int | -0.025 | | IL_10 | HepA_Int | 0.902 |
| IL_10 | Tetanus_Int | 0.000 | | IL_10 | Tetanus_Int | 0.000 |
| IL_10 | Diptheria_Int | 0.000 | | IL_10 | Diptheria_Int | 0.000 |
| IL_10 | Rubella_Int | 0.000 | | IL_10 | Rubella_Int | -0.076 |
| IL_10 | CMV_Int | 0.000 | | IL_10 | CMV_Int | 0.076 |
| IL_10 | HepB_cAb_Int | -0.878 | | IL_10 | HepB_cAb_Int | 0.000 |
| IL_10 | HepB_eAb_Int | 0.000 | | IL_10 | HepB_eAb_Int | 0.000 |
| IL_10 | HepB_eAg_Int | 0.000 | | IL_10 | HepB_eAg_Int | 0.000 |
| IL_10 | HepC_Int | 0.000 | | IL_10 | HepC_int | 0.000 |
| IL_10 | Schistosoma_int | 0.000 | | IL_10 | Schistosoma_int | 0.000 |
| IL_10 | Strongyloides_Int | 0.025 | | IL_10 | Strongyloides_Int | 0.000 |
| IL_10 | Filaria_Int | -0.025 | | IL_10 | Filaria_Int | 0.000 |
| IL_12p70 | IL_1_alpha | 0.516 | | IL_12p70 | IL_1_alpha | -0.998 |
| IL_12p70 | IL_1_beta | 0.994 | | IL_12p70 | IL_1_beta | -0.941 |
| IL_12p70 | IL_2 | 0.760 | | IL_12p70 | IL_2 | -0.924 |
| IL_12p70 | IL_4 | 0.982 | | IL_12p70 | IL_4 | -0.833 |
| IL_12p70 | IL_5 | 0.853 | | IL_12p70 | IL_5 | -0.542 |
| IL_12p70 | IL_6 | 0.994 | | IL_12p70 | IL_6 | -0.944 |
| IL_12p70 | IL_8 | 0.986 | | IL_12p70 | IL_8 | -0.691 |
| IL_12p70 | IL_10 | 1.000 | | IL_12p70 | IL_10 | -0.745 |
| IL_12p70 | IL_12p70 | 1.000 | | IL_12p70 | IL_12p70 | 1.000 |
| IL_12p70 | IL_13 | 0.974 | | IL_12p70 | IL_13 | -0.035 |
| IL_12p70 | IL_15 | 0.973 | | IL_12p70 | IL_15 | -0.839 |
| IL_12p70 | IL_17 | 0.993 | | IL_12p70 | IL_17 | -0.367 |
| IL_12p70 | IL_23 | 0.991 | | IL_12p70 | IL_23 | 0.987 |
| IL_12p70 | IFN_gamma | 0.000 | | IL_12p70 | IFN_gamma | 0.000 |
| IL_12p70 | TNF_alpha | 1.000 | | IL_12p70 | TNF_alpha | -0.743 |
| IL_12p70 | TNF_beta | 1.000 | | IL_12p70 | TNF_beta | -0.950 |

FIG. 21I10-E

| | | | | | | |
|---|---|---|---|---|---|---|
| IL_12p70 | Varicella_Int | 0.000 | | IL_12p70 | Varicella_Int | -0.992 |
| IL_12p70 | Measles_OD_DB_Int | -0.864 | | IL_12p70 | Measles_OD_DB_Int | 0.608 |
| IL_12p70 | Measles_Int | 0.000 | | IL_12p70 | Measles_Int | 0.000 |
| IL_12p70 | HepA_Int | -0.005 | | IL_12p70 | HepA_Int | -0.383 |
| IL_12p70 | Tetanus_Int | 0.000 | | IL_12p70 | Tetanus_Int | 0.000 |
| IL_12p70 | Diptheria_Int | 0.000 | | IL_12p70 | Diptheria_Int | 0.000 |
| IL_12p70 | Rubella_Int | 0.000 | | IL_12p70 | Rubella_Int | -0.608 |
| IL_12p70 | CMV_Int | 0.000 | | IL_12p70 | CMV_Int | 0.608 |
| IL_12p70 | HepB_cAb_Int | -0.868 | | IL_12p70 | HepB_cAb_Int | 0.000 |
| IL_12p70 | HepB_eAb_Int | 0.000 | | IL_12p70 | HepB_eAb_Int | 0.000 |
| IL_12p70 | HepB_eAg_Int | 0.000 | | IL_12p70 | HepB_eAg_Int | 0.000 |
| IL_12p70 | HepC_Int | 0.000 | | IL_12p70 | HepC_Int | 0.000 |
| IL_12p70 | Schistosoma_int | 0.000 | | IL_12p70 | Schistosoma_int | 0.000 |
| IL_12p70 | Strongyloides_Int | 0.005 | | IL_12p70 | Strongyloides_Int | 0.000 |
| IL_12p70 | Filaria_Int | -0.005 | | IL_12p70 | Filaria_Int | 0.000 |
| IL_13 | IL_1_alpha | 0.698 | | IL_13 | IL_1_alpha | -0.024 |
| IL_13 | IL_1_beta | 0.993 | | IL_13 | IL_1_beta | 0.373 |
| IL_13 | IL_2 | 0.889 | | IL_13 | IL_2 | -0.350 |
| IL_13 | IL_4 | 0.999 | | IL_13 | IL_4 | 0.582 |
| IL_13 | IL_5 | 0.950 | | IL_13 | IL_5 | -0.821 |
| IL_13 | IL_6 | 0.993 | | IL_13 | IL_6 | -0.295 |
| IL_13 | IL_8 | 0.921 | | IL_13 | IL_8 | 0.747 |
| IL_13 | IL_10 | 0.978 | | IL_13 | IL_10 | 0.693 |
| IL_13 | IL_12p70 | 0.974 | | IL_13 | IL_12p70 | -0.035 |
| IL_13 | IL_13 | 1.000 | | IL_13 | IL_13 | 1.000 |
| IL_13 | IL_15 | 1.000 | | IL_13 | IL_15 | 0.573 |
| IL_13 | IL_17 | 0.994 | | IL_13 | IL_17 | 0.943 |
| IL_13 | IL_23 | 0.935 | | IL_13 | IL_23 | -0.196 |
| IL_13 | IFN_gamma | 0.000 | | IL_13 | IFN_gamma | 0.000 |
| IL_13 | TNF_alpha | 0.970 | | IL_13 | TNF_alpha | 0.695 |
| IL_13 | TNF_beta | 0.978 | | IL_13 | TNF_beta | -0.278 |
| IL_13 | Varicella_Int | 0.000 | | IL_13 | Varicella_Int | 0.165 |
| IL_13 | Measles_OD_DB_Int | -0.726 | | IL_13 | Measles_OD_DB_Int | 0.772 |
| IL_13 | Measles_Int | 0.000 | | IL_13 | Measles_Int | 0.000 |
| IL_13 | HepA_Int | -0.233 | | IL_13 | HepA_Int | 0.937 |
| IL_13 | Tetanus_Int | 0.000 | | IL_13 | Tetanus_Int | 0.000 |
| IL_13 | Diptheria_Int | 0.000 | | IL_13 | Diptheria_Int | 0.000 |
| IL_13 | Rubella_Int | 0.000 | | IL_13 | Rubella_Int | -0.772 |
| IL_13 | CMV_Int | 0.000 | | IL_13 | CMV_Int | 0.772 |
| IL_13 | HepB_cAb_Int | -0.959 | | IL_13 | HepB_cAb_Int | 0.000 |
| IL_13 | HepB_eAb_Int | 0.000 | | IL_13 | HepB_eAb_Int | 0.000 |
| IL_13 | HepB_eAg_Int | 0.000 | | IL_13 | HepB_eAg_Int | 0.000 |
| IL_13 | HepC_Int | 0.000 | | IL_13 | HepC_Int | 0.000 |
| IL_13 | Schistosoma_int | 0.000 | | IL_13 | Schistosoma_int | 0.000 |
| IL_13 | Strongyloides_Int | 0.233 | | IL_13 | Strongyloides_Int | 0.000 |
| IL_13 | Filaria_Int | -0.233 | | IL_13 | Filaria_Int | 0.000 |
| IL_15 | IL_1_alpha | 0.700 | | IL_15 | IL_1_alpha | 0.805 |
| IL_15 | IL_1_beta | 0.992 | | IL_15 | IL_1_beta | 0.974 |
| IL_15 | IL_2 | 0.890 | | IL_15 | IL_2 | 0.567 |
| IL_15 | IL_4 | 0.999 | | IL_15 | IL_4 | 1.000 |
| IL_15 | IL_5 | 0.951 | | IL_15 | IL_5 | -0.003 |
| IL_15 | IL_6 | 0.993 | | IL_15 | IL_6 | 0.614 |
| IL_15 | IL_8 | 0.920 | | IL_15 | IL_8 | 0.973 |
| IL_15 | IL_10 | 0.978 | | IL_15 | IL_10 | 0.988 |
| IL_15 | IL_12p70 | 0.973 | | IL_15 | IL_12p70 | -0.839 |
| IL_15 | IL_13 | 1.000 | | IL_15 | IL_13 | 0.573 |
| IL_15 | IL_15 | 1.000 | | IL_15 | IL_15 | 1.000 |

FIG. 21I10-F

| IL_15 | IL_17 | 0.993 | IL_15 | IL_17 | 0.814 |
|---|---|---|---|---|---|
| IL_15 | IL_23 | 0.934 | IL_15 | IL_23 | -0.916 |
| IL_15 | IFN_gamma | 0.000 | IL_15 | IFN_gamma | 0.000 |
| IL_15 | TNF_alpha | 0.969 | IL_15 | TNF_alpha | 0.987 |
| IL_15 | TNF_beta | 0.978 | IL_15 | TNF_beta | 0.628 |
| IL_15 | Varicella_Int | 0.000 | IL_15 | Varicella_Int | 0.903 |
| IL_15 | Measles_OD_DB_Int | -0.724 | IL_15 | Measles_OD_DB_Int | -0.079 |
| IL_15 | Measles_Int | 0.000 | IL_15 | Measles_Int | 0.000 |
| IL_15 | HepA_Int | -0.235 | IL_15 | HepA_Int | 0.824 |
| IL_15 | Tetanus_Int | 0.000 | IL_15 | Tetanus_Int | 0.000 |
| IL_15 | Diptheria_Int | 0.000 | IL_15 | Diptheria_Int | 0.000 |
| IL_15 | Rubella_Int | 0.000 | IL_15 | Rubella_Int | 0.079 |
| IL_15 | CMV_Int | 0.000 | IL_15 | CMV_Int | -0.079 |
| IL_15 | HepB_cAb_Int | -0.959 | IL_15 | HepB_cAb_Int | 0.000 |
| IL_15 | HepB_eAb_Int | 0.000 | IL_15 | HepB_eAb_Int | 0.000 |
| IL_15 | HepB_eAg_Int | 0.000 | IL_15 | HepB_eAg_Int | 0.000 |
| IL_15 | HepC_Int | 0.000 | IL_15 | HepC_Int | 0.000 |
| IL_15 | Schistosoma_int | 0.000 | IL_15 | Schistosoma_int | 0.000 |
| IL_15 | Strongyloides_Int | 0.235 | IL_15 | Strongyloides_Int | 0.000 |
| IL_15 | Filaria_Int | -0.235 | IL_15 | Filaria_Int | 0.000 |
| IL_17 | IL_1_alpha | 0.613 | IL_17 | IL_1_alpha | 0.311 |
| IL_17 | IL_1_beta | 1.000 | IL_17 | IL_1_beta | 0.661 |
| IL_17 | IL_2 | 0.832 | IL_17 | IL_2 | -0.018 |
| IL_17 | IL_4 | 0.997 | IL_17 | IL_4 | 0.820 |
| IL_17 | IL_5 | 0.909 | IL_17 | IL_5 | -0.583 |
| IL_17 | IL_6 | 1.000 | IL_17 | IL_6 | 0.041 |
| IL_17 | IL_8 | 0.959 | IL_17 | IL_8 | 0.926 |
| IL_17 | IL_10 | 0.995 | IL_17 | IL_10 | 0.894 |
| IL_17 | IL_12p70 | 0.993 | IL_17 | IL_12p70 | -0.367 |
| IL_17 | IL_13 | 0.994 | IL_17 | IL_13 | 0.943 |
| IL_17 | IL_15 | 0.993 | IL_17 | IL_15 | 0.814 |
| IL_17 | IL_17 | 1.000 | IL_17 | IL_17 | 1.000 |
| IL_17 | IL_23 | 0.969 | IL_17 | IL_23 | -0.512 |
| IL_17 | IFN_gamma | 0.000 | IL_17 | IFN_gamma | 0.000 |
| IL_17 | TNF_alpha | 0.991 | IL_17 | TNF_alpha | 0.895 |
| IL_17 | TNF_beta | 0.995 | IL_17 | TNF_beta | 0.058 |
| IL_17 | Varicella_Int | 0.000 | IL_17 | Varicella_Int | 0.485 |
| IL_17 | Measles_OD_DB_Int | -0.798 | IL_17 | Measles_OD_DB_Int | 0.515 |
| IL_17 | Measles_Int | 0.000 | IL_17 | Measles_Int | 0.000 |
| IL_17 | HepA_Int | -0.123 | IL_17 | HepA_Int | 1.000 |
| IL_17 | Tetanus_Int | 0.000 | IL_17 | Tetanus_Int | 0.000 |
| IL_17 | Diptheria_Int | 0.000 | IL_17 | Diptheria_Int | 0.000 |
| IL_17 | Rubella_Int | 0.000 | IL_17 | Rubella_Int | -0.515 |
| IL_17 | CMV_Int | 0.000 | IL_17 | CMV_Int | 0.515 |
| IL_17 | HepB_cAb_Int | -0.921 | IL_17 | HepB_cAb_Int | 0.000 |
| IL_17 | HepB_eAb_Int | 0.000 | IL_17 | HepB_eAb_Int | 0.000 |
| IL_17 | HepB_eAg_Int | 0.000 | IL_17 | HepB_eAg_Int | 0.000 |
| IL_17 | HepC_Int | 0.000 | IL_17 | HepC_Int | 0.000 |
| IL_17 | Schistosoma_int | 0.000 | IL_17 | Schistosoma_int | 0.000 |
| IL_17 | Strongyloides_Int | 0.123 | IL_17 | Strongyloides_Int | 0.000 |
| IL_17 | Filaria_Int | -0.123 | IL_17 | Filaria_Int | 0.000 |
| IL_23 | IL_1_alpha | 0.399 | IL_23 | IL_1_alpha | -0.975 |
| IL_23 | IL_1_beta | 0.971 | IL_23 | IL_1_beta | -0.983 |
| IL_23 | IL_2 | 0.669 | IL_23 | IL_2 | -0.850 |
| IL_23 | IL_4 | 0.949 | IL_23 | IL_4 | -0.912 |
| IL_23 | IL_5 | 0.777 | IL_23 | IL_5 | -0.399 |
| IL_23 | IL_6 | 0.970 | IL_23 | IL_6 | -0.879 |

FIG. 21I10-G

| | | | | | | |
|---|---|---|---|---|---|---|
| IL_23 | IL_8 | 0.999 | | IL_23 | IL_8 | -0.799 |
| IL_23 | IL_10 | 0.989 | | IL_23 | IL_10 | -0.843 |
| IL_23 | IL_12p70 | 0.991 | | IL_23 | IL_12p70 | 0.987 |
| IL_23 | IL_13 | 0.935 | | IL_23 | IL_13 | -0.196 |
| IL_23 | IL_15 | 0.934 | | IL_23 | IL_15 | -0.916 |
| IL_23 | IL_17 | 0.969 | | IL_23 | IL_17 | -0.512 |
| IL_23 | IL_23 | 1.000 | | IL_23 | IL_23 | 1.000 |
| IL_23 | IFN_gamma | 0.000 | | IL_23 | IFN_gamma | 0.000 |
| IL_23 | TNF_alpha | 0.993 | | IL_23 | TNF_alpha | -0.841 |
| IL_23 | TNF_beta | 0.988 | | IL_23 | TNF_beta | -0.887 |
| IL_23 | Varicella_Int | 0.000 | | IL_23 | Varicella_Int | -0.999 |
| IL_23 | Measles_OD_DB_Int | -0.922 | | IL_23 | Measles_OD_DB_Int | 0.472 |
| IL_23 | Measles_Int | 0.000 | | IL_23 | Measles_Int | 0.000 |
| IL_23 | HepA_Int | 0.126 | | IL_23 | HepA_Int | -0.527 |
| IL_23 | Tetanus_Int | 0.000 | | IL_23 | Tetanus_Int | 0.000 |
| IL_23 | Diptheria_Int | 0.000 | | IL_23 | Diptheria_Int | 0.000 |
| IL_23 | Rubella_Int | 0.000 | | IL_23 | Rubella_Int | -0.472 |
| IL_23 | CMV_Int | 0.000 | | IL_23 | CMV_Int | 0.472 |
| IL_23 | HepB_cAb_Int | -0.796 | | IL_23 | HepB_cAb_Int | 0.000 |
| IL_23 | HepB_eAb_Int | 0.000 | | IL_23 | HepB_eAb_Int | 0.000 |
| IL_23 | HepB_eAg_Int | 0.000 | | IL_23 | HepB_eAg_Int | 0.000 |
| IL_23 | HepC_Int | 0.000 | | IL_23 | HepC_Int | 0.000 |
| IL_23 | Schistosoma_int | 0.000 | | IL_23 | Schistosoma_int | 0.000 |
| IL_23 | Strongyloides_Int | -0.126 | | IL_23 | Strongyloides_Int | 0.000 |
| IL_23 | Filaria_Int | 0.126 | | IL_23 | Filaria_Int | 0.000 |
| IFN_gamma | IL_1_alpha | 0.000 | | IFN_gamma | IL_1_alpha | 0.000 |
| IFN_gamma | IL_1_beta | 0.000 | | IFN_gamma | IL_1_beta | 0.000 |
| IFN_gamma | IL_2 | 0.000 | | IFN_gamma | IL_2 | 0.000 |
| IFN_gamma | IL_4 | 0.000 | | IFN_gamma | IL_4 | 0.000 |
| IFN_gamma | IL_5 | 0.000 | | IFN_gamma | IL_5 | 0.000 |
| IFN_gamma | IL_6 | 0.000 | | IFN_gamma | IL_6 | 0.000 |
| IFN_gamma | IL_8 | 0.000 | | IFN_gamma | IL_8 | 0.000 |
| IFN_gamma | IL_10 | 0.000 | | IFN_gamma | IL_10 | 0.000 |
| IFN_gamma | IL_12p70 | 0.000 | | IFN_gamma | IL_12p70 | 0.000 |
| IFN_gamma | IL_13 | 0.000 | | IFN_gamma | IL_13 | 0.000 |
| IFN_gamma | IL_15 | 0.000 | | IFN_gamma | IL_15 | 0.000 |
| IFN_gamma | IL_17 | 0.000 | | IFN_gamma | IL_17 | 0.000 |
| IFN_gamma | IL_23 | 0.000 | | IFN_gamma | IL_23 | 0.000 |
| IFN_gamma | IFN_gamma | 1.000 | | IFN_gamma | IFN_gamma | 1.000 |
| IFN_gamma | TNF_alpha | 0.000 | | IFN_gamma | TNF_alpha | 0.000 |
| IFN_gamma | TNF_beta | 0.000 | | IFN_gamma | TNF_beta | 0.000 |
| IFN_gamma | Varicella_Int | 0.000 | | IFN_gamma | Varicella_Int | 0.000 |
| IFN_gamma | Measles_OD_DB_Int | 0.000 | | IFN_gamma | Measles_OD_DB_Int | 0.000 |
| IFN_gamma | Measles_Int | 0.000 | | IFN_gamma | Measles_Int | 0.000 |
| IFN_gamma | HepA_Int | 0.000 | | IFN_gamma | HepA_Int | 0.000 |
| IFN_gamma | Tetanus_Int | 0.000 | | IFN_gamma | Tetanus_Int | 0.000 |
| IFN_gamma | Diptheria_Int | 0.000 | | IFN_gamma | Diptheria_Int | 0.000 |
| IFN_gamma | Rubella_Int | 0.000 | | IFN_gamma | Rubella_Int | 0.000 |
| IFN_gamma | CMV_Int | 0.000 | | IFN_gamma | CMV_Int | 0.000 |
| IFN_gamma | HepB_cAb_Int | 0.000 | | IFN_gamma | HepB_cAb_Int | 0.000 |
| IFN_gamma | HepB_eAb_Int | 0.000 | | IFN_gamma | HepB_eAb_Int | 0.000 |
| IFN_gamma | HepB_eAg_Int | 0.000 | | IFN_gamma | HepB_eAg_Int | 0.000 |
| IFN_gamma | HepC_Int | 0.000 | | IFN_gamma | HepC_Int | 0.000 |
| IFN_gamma | Schistosoma_int | 0.000 | | IFN_gamma | Schistosoma_int | 0.000 |
| IFN_gamma | Strongyloides_Int | 0.000 | | IFN_gamma | Strongyloides_Int | 0.000 |
| IFN_gamma | Filaria_Int | 0.000 | | IFN_gamma | Filaria_Int | 0.000 |
| TNF_alpha | IL_1_alpha | 0.501 | | TNF_alpha | IL_1_alpha | 0.702 |

FIG. 21I10-H

| | | | | | | |
|---|---|---|---|---|---|---|
| TNF_alpha | IL_1_beta | 0.992 | | TNF_alpha | IL_1_beta | 0.926 |
| TNF_alpha | IL_2 | 0.749 | | TNF_alpha | IL_2 | 0.430 |
| TNF_alpha | IL_4 | 0.979 | | TNF_alpha | IL_4 | 0.989 |
| TNF_alpha | IL_5 | 0.844 | | TNF_alpha | IL_5 | -0.160 |
| TNF_alpha | IL_6 | 0.991 | | TNF_alpha | IL_6 | 0.482 |
| TNF_alpha | IL_8 | 0.988 | | TNF_alpha | IL_8 | 0.997 |
| TNF_alpha | IL_10 | 0.999 | | TNF_alpha | IL_10 | 1.000 |
| TNF_alpha | IL_12p70 | 1.000 | | TNF_alpha | IL_12p70 | -0.743 |
| TNF_alpha | IL_13 | 0.970 | | TNF_alpha | IL_13 | 0.695 |
| TNF_alpha | IL_15 | 0.969 | | TNF_alpha | IL_15 | 0.987 |
| TNF_alpha | IL_17 | 0.991 | | TNF_alpha | IL_17 | 0.895 |
| TNF_alpha | IL_23 | 0.993 | | TNF_alpha | IL_23 | -0.841 |
| TNF_alpha | IFN_gamma | 0.000 | | TNF_alpha | IFN_gamma | 0.000 |
| TNF_alpha | TNF_alpha | 1.000 | | TNF_alpha | TNF_alpha | 1.000 |
| TNF_alpha | TNF_beta | 0.999 | | TNF_alpha | TNF_beta | 0.497 |
| TNF_alpha | Varicella_Int | 0.000 | | TNF_alpha | Varicella_Int | 0.824 |
| TNF_alpha | Measles_OD_DB_Int | -0.872 | | TNF_alpha | Measles_OD_DB_Int | 0.079 |
| TNF_alpha | Measles_Int | 0.000 | | TNF_alpha | Measles_Int | 0.000 |
| TNF_alpha | HepA_Int | 0.012 | | TNF_alpha | HepA_Int | 0.903 |
| TNF_alpha | Tetanus_Int | 0.000 | | TNF_alpha | Tetanus_Int | 0.000 |
| TNF_alpha | Diptheria_Int | 0.000 | | TNF_alpha | Diptheria_Int | 0.000 |
| TNF_alpha | Rubella_Int | 0.000 | | TNF_alpha | Rubella_Int | -0.079 |
| TNF_alpha | CMV_Int | 0.000 | | TNF_alpha | CMV_Int | 0.079 |
| TNF_alpha | HepB_cAb_Int | -0.860 | | TNF_alpha | HepB_cAb_Int | 0.000 |
| TNF_alpha | HepB_eAb_Int | 0.000 | | TNF_alpha | HepB_eAb_Int | 0.000 |
| TNF_alpha | HepB_eAg_Int | 0.000 | | TNF_alpha | HepB_eAg_Int | 0.000 |
| TNF_alpha | HepC_Int | 0.000 | | TNF_alpha | HepC_Int | 0.000 |
| TNF_alpha | Schistosoma_int | 0.000 | | TNF_alpha | Schistosoma_int | 0.000 |
| TNF_alpha | Strongyloides_Int | -0.012 | | TNF_alpha | Strongyloides_Int | 0.000 |
| TNF_alpha | Filaria_Int | 0.012 | | TNF_alpha | Filaria_Int | 0.000 |
| TNF_beta | IL_1_alpha | 0.533 | | TNF_beta | IL_1_alpha | 0.967 |
| TNF_beta | IL_1_beta | 0.996 | | TNF_beta | IL_1_beta | 0.788 |
| TNF_beta | IL_2 | 0.774 | | TNF_beta | IL_2 | 0.997 |
| TNF_beta | IL_4 | 0.986 | | TNF_beta | IL_4 | 0.619 |
| TNF_beta | IL_5 | 0.864 | | TNF_beta | IL_5 | 0.777 |
| TNF_beta | IL_6 | 0.996 | | TNF_beta | IL_6 | 1.000 |
| TNF_beta | IL_8 | 0.982 | | TNF_beta | IL_8 | 0.431 |
| TNF_beta | IL_10 | 1.000 | | TNF_beta | IL_10 | 0.500 |
| TNF_beta | IL_12p70 | 1.000 | | TNF_beta | IL_12p70 | -0.950 |
| TNF_beta | IL_13 | 0.978 | | TNF_beta | IL_13 | -0.278 |
| TNF_beta | IL_15 | 0.978 | | TNF_beta | IL_15 | 0.628 |
| TNF_beta | IL_17 | 0.995 | | TNF_beta | IL_17 | 0.058 |
| TNF_beta | IL_23 | 0.988 | | TNF_beta | IL_23 | -0.887 |
| TNF_beta | IFN_gamma | 0.000 | | TNF_beta | IFN_gamma | 0.000 |
| TNF_beta | TNF_alpha | 0.999 | | TNF_beta | TNF_alpha | 0.497 |
| TNF_beta | TNF_beta | 1.000 | | TNF_beta | TNF_beta | 1.000 |
| TNF_beta | Varicella_Int | 0.000 | | TNF_beta | Varicella_Int | 0.902 |
| TNF_beta | Measles_OD_DB_Int | -0.853 | | TNF_beta | Measles_OD_DB_Int | -0.826 |
| TNF_beta | Measles_Int | 0.000 | | TNF_beta | Measles_Int | 0.000 |
| TNF_beta | HepA_Int | -0.026 | | TNF_beta | HepA_Int | 0.076 |
| TNF_beta | Tetanus_Int | 0.000 | | TNF_beta | Tetanus_Int | 0.000 |
| TNF_beta | Diptheria_Int | 0.000 | | TNF_beta | Diptheria_Int | 0.000 |
| TNF_beta | Rubella_Int | 0.000 | | TNF_beta | Rubella_Int | 0.826 |
| TNF_beta | CMV_Int | 0.000 | | TNF_beta | CMV_Int | -0.826 |
| TNF_beta | HepB_cAb_Int | -0.879 | | TNF_beta | HepB_cAb_Int | 0.000 |
| TNF_beta | HepB_eAb_Int | 0.000 | | TNF_beta | HepB_eAb_Int | 0.000 |
| TNF_beta | HepB_eAg_Int | 0.000 | | TNF_beta | HepB_eAg_Int | 0.000 |

FIG. 21I10-I

| | | | | | | |
|---|---|---|---|---|---|---|
| TNF_beta | HepC_Int | 0.000 | | TNF_beta | HepC_Int | 0.000 |
| TNF_beta | Schistosoma_int | 0.000 | | TNF_beta | Schistosoma_int | 0.000 |
| TNF_beta | Strongyloides_Int | 0.026 | | TNF_beta | Strongyloides_Int | 0.000 |
| TNF_beta | Filaria_Int | -0.026 | | TNF_beta | Filaria_Int | 0.000 |
| Varicella_Int | IL_1_alpha | 0.000 | | Varicella_Int | IL_1_alpha | 0.982 |
| Varicella_Int | IL_1_beta | 0.000 | | Varicella_Int | IL_1_beta | 0.977 |
| Varicella_Int | IL_2 | 0.000 | | Varicella_Int | IL_2 | 0.866 |
| Varicella_Int | IL_4 | 0.000 | | Varicella_Int | IL_4 | 0.898 |
| Varicella_Int | IL_5 | 0.000 | | Varicella_Int | IL_5 | 0.428 |
| Varicella_Int | IL_6 | 0.000 | | Varicella_Int | IL_6 | 0.894 |
| Varicella_Int | IL_8 | 0.000 | | Varicella_Int | IL_8 | 0.779 |
| Varicella_Int | IL_10 | 0.000 | | Varicella_Int | IL_10 | 0.825 |
| Varicella_Int | IL_12p70 | 0.000 | | Varicella_Int | IL_12p70 | -0.992 |
| Varicella_Int | IL_13 | 0.000 | | Varicella_Int | IL_13 | 0.165 |
| Varicella_Int | IL_15 | 0.000 | | Varicella_Int | IL_15 | 0.903 |
| Varicella_Int | IL_17 | 0.000 | | Varicella_Int | IL_17 | 0.485 |
| Varicella_Int | IL_23 | 0.000 | | Varicella_Int | IL_23 | -0.999 |
| Varicella_Int | IFN_gamma | 0.000 | | Varicella_Int | IFN_gamma | 0.000 |
| Varicella_Int | TNF_alpha | 0.000 | | Varicella_Int | TNF_alpha | 0.824 |
| Varicella_Int | TNF_beta | 0.000 | | Varicella_Int | TNF_beta | 0.902 |
| Varicella_Int | Varicella_Int | 1.000 | | Varicella_Int | Varicella_Int | 1.000 |
| Varicella_Int | Measles_OD_DB_Int | 0.000 | | Varicella_Int | Measles_OD_DB_Int | -0.500 |
| Varicella_Int | Measles_Int | 0.000 | | Varicella_Int | Measles_Int | 0.000 |
| Varicella_Int | HepA_Int | 0.000 | | Varicella_Int | HepA_Int | 0.500 |
| Varicella_Int | Tetanus_Int | 0.000 | | Varicella_Int | Tetanus_Int | 0.000 |
| Varicella_Int | Diptheria_Int | 0.000 | | Varicella_Int | Diptheria_Int | 0.000 |
| Varicella_Int | Rubella_Int | 0.000 | | Varicella_Int | Rubella_Int | 0.500 |
| Varicella_Int | CMV_Int | 0.000 | | Varicella_Int | CMV_Int | -0.500 |
| Varicella_Int | HepB_cAb_Int | 0.000 | | Varicella_Int | HepB_cAb_Int | 0.000 |
| Varicella_Int | HepB_eAb_Int | 0.000 | | Varicella_Int | HepB_eAb_Int | 0.000 |
| Varicella_Int | HepB_eAg_Int | 0.000 | | Varicella_Int | HepB_eAg_Int | 0.000 |
| Varicella_Int | HepC_Int | 0.000 | | Varicella_Int | HepC_Int | 0.000 |
| Varicella_Int | Schistosoma_int | 0.000 | | Varicella_Int | Schistosoma_int | 0.000 |
| Varicella_Int | Strongyloides_Int | 0.000 | | Varicella_Int | Strongyloides_Int | 0.000 |
| Varicella_Int | Filaria_Int | 0.000 | | Varicella_Int | Filaria_Int | 0.000 |
| Measles_OD_DB_Int | IL_1_alpha | -0.014 | | Measles_OD_DB_Int | IL_1_alpha | -0.655 |
| Measles_OD_DB_Int | IL_1_beta | -0.804 | | Measles_OD_DB_Int | IL_1_beta | -0.302 |
| Measles_OD_DB_Int | IL_2 | -0.329 | | Measles_OD_DB_Int | IL_2 | -0.866 |
| Measles_OD_DB_Int | IL_4 | -0.753 | | Measles_OD_DB_Int | IL_4 | -0.068 |
| Measles_OD_DB_Int | IL_5 | -0.474 | | Measles_OD_DB_Int | IL_5 | -0.997 |
| Measles_OD_DB_Int | IL_6 | -0.801 | | Measles_OD_DB_Int | IL_6 | -0.835 |
| Measles_OD_DB_Int | IL_8 | -0.937 | | Measles_OD_DB_Int | IL_8 | 0.154 |
| Measles_OD_DB_Int | IL_10 | -0.853 | | Measles_OD_DB_Int | IL_10 | 0.076 |
| Measles_OD_DB_Int | IL_12p70 | -0.864 | | Measles_OD_DB_Int | IL_12p70 | 0.608 |
| Measles_OD_DB_Int | IL_13 | -0.726 | | Measles_OD_DB_Int | IL_13 | 0.772 |
| Measles_OD_DB_Int | IL_15 | -0.724 | | Measles_OD_DB_Int | IL_15 | -0.079 |
| Measles_OD_DB_Int | IL_17 | -0.798 | | Measles_OD_DB_Int | IL_17 | 0.515 |
| Measles_OD_DB_Int | IL_23 | -0.922 | | Measles_OD_DB_Int | IL_23 | 0.472 |
| Measles_OD_DB_Int | IFN_gamma | 0.000 | | Measles_OD_DB_Int | IFN_gamma | 0.000 |
| Measles_OD_DB_Int | TNF_alpha | -0.872 | | Measles_OD_DB_Int | TNF_alpha | 0.079 |
| Measles_OD_DB_Int | TNF_beta | -0.853 | | Measles_OD_DB_Int | TNF_beta | -0.826 |
| Measles_OD_DB_Int | Varicella_Int | 0.000 | | Measles_OD_DB_Int | Varicella_Int | -0.500 |
| Measles_OD_DB_Int | Measles_OD_DB_Int | 1.000 | | Measles_OD_DB_Int | Measles_OD_DB_Int | 1.000 |
| Measles_OD_DB_Int | Measles_Int | 0.000 | | Measles_OD_DB_Int | Measles_Int | 0.000 |
| Measles_OD_DB_Int | HepA_Int | -0.500 | | Measles_OD_DB_Int | HepA_Int | 0.500 |
| Measles_OD_DB_Int | Tetanus_Int | 0.000 | | Measles_OD_DB_Int | Tetanus_Int | 0.000 |
| Measles_OD_DB_Int | Diptheria_Int | 0.000 | | Measles_OD_DB_Int | Diptheria_Int | 0.000 |

FIG. 21I10-J

| | | | | | | |
|---|---|---|---|---|---|---|
| Measles_OD_DB_Int | Rubella_Int | 0.000 | | Measles_OD_DB_Int | Rubella_Int | -1.000 |
| Measles_OD_DB_Int | CMV_Int | 0.000 | | Measles_OD_DB_Int | CMV_Int | 1.000 |
| Measles_OD_DB_Int | HepB_cAb_Int | 0.500 | | Measles_OD_DB_Int | HepB_cAb_Int | 0.000 |
| Measles_OD_DB_Int | HepB_eAb_Int | 0.000 | | Measles_OD_DB_Int | HepB_eAb_Int | 0.000 |
| Measles_OD_DB_Int | HepB_eAg_Int | 0.000 | | Measles_OD_DB_Int | HepB_eAg_Int | 0.000 |
| Measles_OD_DB_Int | HepC_Int | 0.000 | | Measles_OD_DB_Int | HepC_Int | 0.000 |
| Measles_OD_DB_Int | Schistosoma_int | 0.000 | | Measles_OD_DB_Int | Schistosoma_int | 0.000 |
| Measles_OD_DB_Int | Strongyloides_Int | 0.500 | | Measles_OD_DB_Int | Strongyloides_Int | 0.000 |
| Measles_OD_DB_Int | Filaria_Int | -0.500 | | Measles_OD_DB_Int | Filaria_Int | 0.000 |
| Measles_Int | IL_1_alpha | 0.000 | | Measles_Int | IL_1_alpha | 0.000 |
| Measles_Int | IL_1_beta | 0.000 | | Measles_Int | IL_1_beta | 0.000 |
| Measles_Int | IL_2 | 0.000 | | Measles_Int | IL_2 | 0.000 |
| Measles_Int | IL_4 | 0.000 | | Measles_Int | IL_4 | 0.000 |
| Measles_Int | IL_5 | 0.000 | | Measles_Int | IL_5 | 0.000 |
| Measles_Int | IL_6 | 0.000 | | Measles_Int | IL_6 | 0.000 |
| Measles_Int | IL_8 | 0.000 | | Measles_Int | IL_8 | 0.000 |
| Measles_Int | IL_10 | 0.000 | | Measles_Int | IL_10 | 0.000 |
| Measles_Int | IL_12p70 | 0.000 | | Measles_Int | IL_12p70 | 0.000 |
| Measles_Int | IL_13 | 0.000 | | Measles_Int | IL_13 | 0.000 |
| Measles_Int | IL_15 | 0.000 | | Measles_Int | IL_15 | 0.000 |
| Measles_Int | IL_17 | 0.000 | | Measles_Int | IL_17 | 0.000 |
| Measles_Int | IL_23 | 0.000 | | Measles_Int | IL_23 | 0.000 |
| Measles_Int | IFN_gamma | 0.000 | | Measles_Int | IFN_gamma | 0.000 |
| Measles_Int | TNF_alpha | 0.000 | | Measles_Int | TNF_alpha | 0.000 |
| Measles_Int | TNF_beta | 0.000 | | Measles_Int | TNF_beta | 0.000 |
| Measles_Int | Varicella_Int | 0.000 | | Measles_Int | Varicella_Int | 0.000 |
| Measles_Int | Measles_OD_DB_Int | 0.000 | | Measles_Int | Measles_OD_DB_Int | 0.000 |
| Measles_Int | Measles_Int | 1.000 | | Measles_Int | Measles_Int | 1.000 |
| Measles_Int | HepA_Int | 0.000 | | Measles_Int | HepA_Int | 0.000 |
| Measles_Int | Tetanus_Int | 0.000 | | Measles_Int | Tetanus_Int | 0.000 |
| Measles_Int | Diptheria_Int | 0.000 | | Measles_Int | Diptheria_Int | 0.000 |
| Measles_Int | Rubella_Int | 0.000 | | Measles_Int | Rubella_Int | 0.000 |
| Measles_Int | CMV_Int | 0.000 | | Measles_Int | CMV_Int | 0.000 |
| Measles_Int | HepB_cAb_Int | 0.000 | | Measles_Int | HepB_cAb_Int | 0.000 |
| Measles_Int | HepB_eAb_Int | 0.000 | | Measles_Int | HepB_eAb_Int | 0.000 |
| Measles_Int | HepB_eAg_Int | 0.000 | | Measles_Int | HepB_eAg_Int | 0.000 |
| Measles_Int | HepC_Int | 0.000 | | Measles_Int | HepC_Int | 0.000 |
| Measles_Int | Schistosoma_int | 0.000 | | Measles_Int | Schistosoma_int | 0.000 |
| Measles_Int | Strongyloides_Int | 0.000 | | Measles_Int | Strongyloides_Int | 0.000 |
| Measles_Int | Filaria_Int | 0.000 | | Measles_Int | Filaria_Int | 0.000 |
| HepA_Int | IL_1_alpha | -0.859 | | HepA_Int | IL_1_alpha | 0.327 |
| HepA_Int | IL_1_beta | -0.114 | | HepA_Int | IL_1_beta | 0.674 |
| HepA_Int | IL_2 | -0.653 | | HepA_Int | IL_2 | -0.000 |
| HepA_Int | IL_4 | -0.194 | | HepA_Int | IL_4 | 0.830 |
| HepA_Int | IL_5 | -0.526 | | HepA_Int | IL_5 | -0.569 |
| HepA_Int | IL_6 | -0.118 | | HepA_Int | IL_6 | 0.058 |
| HepA_Int | IL_8 | 0.165 | | HepA_Int | IL_8 | 0.933 |
| HepA_Int | IL_10 | -0.025 | | HepA_Int | IL_10 | 0.902 |
| HepA_Int | IL_12p70 | -0.005 | | HepA_Int | IL_12p70 | -0.383 |
| HepA_Int | IL_13 | -0.233 | | HepA_Int | IL_13 | 0.937 |
| HepA_Int | IL_15 | -0.235 | | HepA_Int | IL_15 | 0.824 |
| HepA_Int | IL_17 | -0.123 | | HepA_Int | IL_17 | 1.000 |
| HepA_Int | IL_23 | 0.126 | | HepA_Int | IL_23 | -0.527 |
| HepA_Int | IFN_gamma | 0.000 | | HepA_Int | IFN_gamma | 0.000 |
| HepA_Int | TNF_alpha | 0.012 | | HepA_Int | TNF_alpha | 0.903 |
| HepA_Int | TNF_beta | -0.026 | | HepA_Int | TNF_beta | 0.076 |
| HepA_Int | Varicella_Int | 0.000 | | HepA_Int | Varicella_Int | 0.500 |

FIG. 21I10-K

| | | | | | | |
|---|---|---|---|---|---|---|
| HepA_Int | Measles_OD_DB_Int | -0.500 | | HepA_Int | Measles_OD_DB_Int | 0.500 |
| HepA_Int | Measles_Int | 0.000 | | HepA_Int | Measles_Int | 0.000 |
| HepA_Int | HepA_Int | 1.000 | | HepA_Int | HepA_Int | 1.000 |
| HepA_Int | Tetanus_Int | 0.000 | | HepA_Int | Tetanus_Int | 0.000 |
| HepA_Int | Diptheria_Int | 0.000 | | HepA_Int | Diptheria_Int | 0.000 |
| HepA_Int | Rubella_Int | 0.000 | | HepA_Int | Rubella_Int | -0.500 |
| HepA_Int | CMV_Int | 0.000 | | HepA_Int | CMV_Int | 0.500 |
| HepA_Int | HepB_cAb_Int | 0.500 | | HepA_Int | HepB_cAb_Int | 0.000 |
| HepA_Int | HepB_eAb_Int | 0.000 | | HepA_Int | HepB_eAb_Int | 0.000 |
| HepA_Int | HepB_eAg_Int | 0.000 | | HepA_Int | HepB_eAg_Int | 0.000 |
| HepA_Int | HepC_Int | 0.000 | | HepA_Int | HepC_Int | 0.000 |
| HepA_Int | Schistosoma_int | 0.000 | | HepA_Int | Schistosoma_int | 0.000 |
| HepA_Int | Strongyloides_Int | -1.000 | | HepA_Int | Strongyloides_Int | 0.000 |
| HepA_Int | Filaria_Int | 1.000 | | HepA_Int | Filaria_Int | 0.000 |
| Tetanus_Int | IL_1_alpha | 0.000 | | Tetanus_Int | IL_1_alpha | 0.000 |
| Tetanus_Int | IL_1_beta | 0.000 | | Tetanus_Int | IL_1_beta | 0.000 |
| Tetanus_Int | IL_2 | 0.000 | | Tetanus_Int | IL_2 | 0.000 |
| Tetanus_Int | IL_4 | 0.000 | | Tetanus_Int | IL_4 | 0.000 |
| Tetanus_Int | IL_5 | 0.000 | | Tetanus_Int | IL_5 | 0.000 |
| Tetanus_Int | IL_6 | 0.000 | | Tetanus_Int | IL_6 | 0.000 |
| Tetanus_Int | IL_8 | 0.000 | | Tetanus_Int | IL_8 | 0.000 |
| Tetanus_Int | IL_10 | 0.000 | | Tetanus_Int | IL_10 | 0.000 |
| Tetanus_Int | IL_12p70 | 0.000 | | Tetanus_Int | IL_12p70 | 0.000 |
| Tetanus_Int | IL_13 | 0.000 | | Tetanus_Int | IL_13 | 0.000 |
| Tetanus_Int | IL_15 | 0.000 | | Tetanus_Int | IL_15 | 0.000 |
| Tetanus_Int | IL_17 | 0.000 | | Tetanus_Int | IL_17 | 0.000 |
| Tetanus_Int | IL_23 | 0.000 | | Tetanus_Int | IL_23 | 0.000 |
| Tetanus_Int | IFN_gamma | 0.000 | | Tetanus_Int | IFN_gamma | 0.000 |
| Tetanus_Int | TNF_alpha | 0.000 | | Tetanus_Int | TNF_alpha | 0.000 |
| Tetanus_Int | TNF_beta | 0.000 | | Tetanus_Int | TNF_beta | 0.000 |
| Tetanus_Int | Varicella_Int | 0.000 | | Tetanus_Int | Varicella_Int | 0.000 |
| Tetanus_Int | Measles_OD_DB_Int | 0.000 | | Tetanus_Int | Measles_OD_DB_Int | 0.000 |
| Tetanus_Int | Measles_Int | 0.000 | | Tetanus_Int | Measles_Int | 0.000 |
| Tetanus_Int | HepA_Int | 0.000 | | Tetanus_Int | HepA_Int | 0.000 |
| Tetanus_Int | Tetanus_Int | 1.000 | | Tetanus_Int | Tetanus_Int | 1.000 |
| Tetanus_Int | Diptheria_Int | 0.000 | | Tetanus_Int | Diptheria_Int | 0.000 |
| Tetanus_Int | Rubella_Int | 0.000 | | Tetanus_Int | Rubella_Int | 0.000 |
| Tetanus_Int | CMV_Int | 0.000 | | Tetanus_Int | CMV_Int | 0.000 |
| Tetanus_Int | HepB_cAb_Int | 0.000 | | Tetanus_Int | HepB_cAb_Int | 0.000 |
| Tetanus_Int | HepB_eAb_Int | 0.000 | | Tetanus_Int | HepB_eAb_Int | 0.000 |
| Tetanus_Int | HepB_eAg_Int | 0.000 | | Tetanus_Int | HepB_eAg_Int | 0.000 |
| Tetanus_Int | HepC_Int | 0.000 | | Tetanus_Int | HepC_Int | 0.000 |
| Tetanus_Int | Schistosoma_int | 0.000 | | Tetanus_Int | Schistosoma_int | 0.000 |
| Tetanus_Int | Strongyloides_Int | 0.000 | | Tetanus_Int | Strongyloides_Int | 0.000 |
| Tetanus_Int | Filaria_Int | 0.000 | | Tetanus_Int | Filaria_Int | 0.000 |
| Diptheria_Int | IL_1_alpha | 0.000 | | Diptheria_Int | IL_1_alpha | 0.000 |
| Diptheria_Int | IL_1_beta | 0.000 | | Diptheria_Int | IL_1_beta | 0.000 |
| Diptheria_Int | IL_2 | 0.000 | | Diptheria_Int | IL_2 | 0.000 |
| Diptheria_Int | IL_4 | 0.000 | | Diptheria_Int | IL_4 | 0.000 |
| Diptheria_Int | IL_5 | 0.000 | | Diptheria_Int | IL_5 | 0.000 |
| Diptheria_Int | IL_6 | 0.000 | | Diptheria_Int | IL_6 | 0.000 |
| Diptheria_Int | IL_8 | 0.000 | | Diptheria_Int | IL_8 | 0.000 |
| Diptheria_Int | IL_10 | 0.000 | | Diptheria_Int | IL_10 | 0.000 |
| Diptheria_Int | IL_12p70 | 0.000 | | Diptheria_Int | IL_12p70 | 0.000 |
| Diptheria_Int | IL_13 | 0.000 | | Diptheria_Int | IL_13 | 0.000 |
| Diptheria_Int | IL_15 | 0.000 | | Diptheria_Int | IL_15 | 0.000 |
| Diptheria_Int | IL_17 | 0.000 | | Diptheria_Int | IL_17 | 0.000 |

FIG. 21I10-L

| | | | | | | |
|---|---|---|---|---|---|---|
| Diptheria_Int | IL_23 | 0.000 | | Diptheria_Int | IL_23 | 0.000 |
| Diptheria_Int | IFN_gamma | 0.000 | | Diptheria_Int | IFN_gamma | 0.000 |
| Diptheria_Int | TNF_alpha | 0.000 | | Diptheria_Int | TNF_alpha | 0.000 |
| Diptheria_Int | TNF_beta | 0.000 | | Diptheria_Int | TNF_beta | 0.000 |
| Diptheria_Int | Varicella_Int | 0.000 | | Diptheria_Int | Varicella_Int | 0.000 |
| Diptheria_Int | Measles_OD_DB_Int | 0.000 | | Diptheria_Int | Measles_OD_DB_Int | 0.000 |
| Diptheria_Int | Measles_Int | 0.000 | | Diptheria_Int | Measles_Int | 0.000 |
| Diptheria_Int | HepA_Int | 0.000 | | Diptheria_Int | HepA_Int | 0.000 |
| Diptheria_Int | Tetanus_Int | 0.000 | | Diptheria_Int | Tetanus_Int | 0.000 |
| Diptheria_Int | Diptheria_Int | 1.000 | | Diptheria_Int | Diptheria_Int | 1.000 |
| Diptheria_Int | Rubella_Int | 0.000 | | Diptheria_Int | Rubella_Int | 0.000 |
| Diptheria_Int | CMV_Int | 0.000 | | Diptheria_Int | CMV_Int | 0.000 |
| Diptheria_Int | HepB_cAb_Int | 0.000 | | Diptheria_Int | HepB_cAb_Int | 0.000 |
| Diptheria_Int | HepB_eAb_Int | 0.000 | | Diptheria_Int | HepB_eAb_Int | 0.000 |
| Diptheria_Int | HepB_eAg_Int | 0.000 | | Diptheria_Int | HepB_eAg_Int | 0.000 |
| Diptheria_Int | HepC_Int | 0.000 | | Diptheria_Int | HepC_Int | 0.000 |
| Diptheria_Int | Schistosoma_int | 0.000 | | Diptheria_Int | Schistosoma_int | 0.000 |
| Diptheria_Int | Strongyloides_Int | 0.000 | | Diptheria_Int | Strongyloides_Int | 0.000 |
| Diptheria_Int | Filaria_Int | 0.000 | | Diptheria_Int | Filaria_Int | 0.000 |
| Rubella_Int | IL_1_alpha | 0.000 | | Rubella_Int | IL_1_alpha | 0.655 |
| Rubella_Int | IL_1_beta | 0.000 | | Rubella_Int | IL_1_beta | 0.302 |
| Rubella_Int | IL_2 | 0.000 | | Rubella_Int | IL_2 | 0.866 |
| Rubella_Int | IL_4 | 0.000 | | Rubella_Int | IL_4 | 0.068 |
| Rubella_Int | IL_5 | 0.000 | | Rubella_Int | IL_5 | 0.997 |
| Rubella_Int | IL_6 | 0.000 | | Rubella_Int | IL_6 | 0.835 |
| Rubella_Int | IL_8 | 0.000 | | Rubella_Int | IL_8 | -0.154 |
| Rubella_Int | IL_10 | 0.000 | | Rubella_Int | IL_10 | -0.076 |
| Rubella_Int | IL_12p70 | 0.000 | | Rubella_Int | IL_12p70 | -0.608 |
| Rubella_Int | IL_13 | 0.000 | | Rubella_Int | IL_13 | -0.772 |
| Rubella_Int | IL_15 | 0.000 | | Rubella_Int | IL_15 | 0.079 |
| Rubella_Int | IL_17 | 0.000 | | Rubella_Int | IL_17 | -0.515 |
| Rubella_Int | IL_23 | 0.000 | | Rubella_Int | IL_23 | -0.472 |
| Rubella_Int | IFN_gamma | 0.000 | | Rubella_Int | IFN_gamma | 0.000 |
| Rubella_Int | TNF_alpha | 0.000 | | Rubella_Int | TNF_alpha | -0.079 |
| Rubella_Int | TNF_beta | 0.000 | | Rubella_Int | TNF_beta | 0.826 |
| Rubella_Int | Varicella_Int | 0.000 | | Rubella_Int | Varicella_Int | 0.500 |
| Rubella_Int | Measles_OD_DB_Int | 0.000 | | Rubella_Int | Measles_OD_DB_Int | -1.000 |
| Rubella_Int | Measles_Int | 0.000 | | Rubella_Int | Measles_Int | 0.000 |
| Rubella_Int | HepA_Int | 0.000 | | Rubella_Int | HepA_Int | -0.500 |
| Rubella_Int | Tetanus_Int | 0.000 | | Rubella_Int | Tetanus_Int | 0.000 |
| Rubella_Int | Diptheria_Int | 0.000 | | Rubella_Int | Diptheria_Int | 0.000 |
| Rubella_Int | Rubella_Int | 1.000 | | Rubella_Int | Rubella_Int | 1.000 |
| Rubella_Int | CMV_Int | 0.000 | | Rubella_Int | CMV_Int | -1.000 |
| Rubella_Int | HepB_cAb_Int | 0.000 | | Rubella_Int | HepB_cAb_Int | 0.000 |
| Rubella_Int | HepB_eAb_Int | 0.000 | | Rubella_Int | HepB_eAb_Int | 0.000 |
| Rubella_Int | HepB_eAg_Int | 0.000 | | Rubella_Int | HepB_eAg_Int | 0.000 |
| Rubella_Int | HepC_Int | 0.000 | | Rubella_Int | HepC_Int | 0.000 |
| Rubella_Int | Schistosoma_int | 0.000 | | Rubella_Int | Schistosoma_int | 0.000 |
| Rubella_Int | Strongyloides_Int | 0.000 | | Rubella_Int | Strongyloides_Int | 0.000 |
| Rubella_Int | Filaria_Int | 0.000 | | Rubella_Int | Filaria_Int | 0.000 |
| CMV_Int | IL_1_alpha | 0.000 | | CMV_Int | IL_1_alpha | -0.655 |
| CMV_Int | IL_1_beta | 0.000 | | CMV_Int | IL_1_beta | -0.302 |
| CMV_Int | IL_2 | 0.000 | | CMV_Int | IL_2 | -0.866 |
| CMV_Int | IL_4 | 0.000 | | CMV_Int | IL_4 | -0.068 |
| CMV_Int | IL_5 | 0.000 | | CMV_Int | IL_5 | -0.997 |
| CMV_Int | IL_6 | 0.000 | | CMV_Int | IL_6 | -0.835 |
| CMV_Int | IL_8 | 0.000 | | CMV_Int | IL_8 | 0.154 |

FIG. 21I10-M

| | | | | | | |
|---|---|---|---|---|---|---|
| CMV_Int | IL_10 | 0.000 | | CMV_Int | IL_10 | 0.076 |
| CMV_Int | IL_12p70 | 0.000 | | CMV_Int | IL_12p70 | 0.608 |
| CMV_Int | IL_13 | 0.000 | | CMV_Int | IL_13 | 0.772 |
| CMV_Int | IL_15 | 0.000 | | CMV_Int | IL_15 | -0.079 |
| CMV_Int | IL_17 | 0.000 | | CMV_Int | IL_17 | 0.515 |
| CMV_Int | IL_23 | 0.000 | | CMV_Int | IL_23 | 0.472 |
| CMV_Int | IFN_gamma | 0.000 | | CMV_Int | IFN_gamma | 0.000 |
| CMV_Int | TNF_alpha | 0.000 | | CMV_Int | TNF_alpha | 0.079 |
| CMV_Int | TNF_beta | 0.000 | | CMV_Int | TNF_beta | -0.826 |
| CMV_Int | Varicella_Int | 0.000 | | CMV_Int | Varicella_Int | -0.500 |
| CMV_Int | Measles_OD_DB_Int | 0.000 | | CMV_Int | Measles_OD_DB_Int | 1.000 |
| CMV_Int | Measles_Int | 0.000 | | CMV_Int | Measles_Int | 0.000 |
| CMV_Int | HepA_Int | 0.000 | | CMV_Int | HepA_Int | 0.500 |
| CMV_Int | Tetanus_Int | 0.000 | | CMV_Int | Tetanus_Int | 0.000 |
| CMV_Int | Diptheria_Int | 0.000 | | CMV_Int | Diptheria_Int | 0.000 |
| CMV_Int | Rubella_Int | 0.000 | | CMV_Int | Rubella_Int | -1.000 |
| CMV_Int | CMV_Int | 1.000 | | CMV_Int | CMV_Int | 1.000 |
| CMV_Int | HepB_cAb_Int | 0.000 | | CMV_Int | HepB_cAb_Int | 0.000 |
| CMV_Int | HepB_eAb_Int | 0.000 | | CMV_Int | HepB_eAb_Int | 0.000 |
| CMV_Int | HepB_eAg_Int | 0.000 | | CMV_Int | HepB_eAg_Int | 0.000 |
| CMV_Int | HepC_Int | 0.000 | | CMV_Int | HepC_Int | 0.000 |
| CMV_Int | Schistosoma_int | 0.000 | | CMV_Int | Schistosoma_int | 0.000 |
| CMV_Int | Strongyloides_Int | 0.000 | | CMV_Int | Strongyloides_Int | 0.000 |
| CMV_Int | Filaria_Int | 0.000 | | CMV_Int | Filaria_Int | 0.000 |
| HepB_cAb_Int | IL_1_alpha | -0.873 | | HepB_cAb_Int | IL_1_alpha | 0.000 |
| HepB_cAb_Int | IL_1_beta | -0.917 | | HepB_cAb_Int | IL_1_beta | 0.000 |
| HepB_cAb_Int | IL_2 | -0.982 | | HepB_cAb_Int | IL_2 | 0.000 |
| HepB_cAb_Int | IL_4 | -0.947 | | HepB_cAb_Int | IL_4 | 0.000 |
| HepB_cAb_Int | IL_5 | -1.000 | | HepB_cAb_Int | IL_5 | 0.000 |
| HepB_cAb_Int | IL_6 | -0.919 | | HepB_cAb_Int | IL_6 | 0.000 |
| HepB_cAb_Int | IL_8 | -0.772 | | HepB_cAb_Int | IL_8 | 0.000 |
| HepB_cAb_Int | IL_10 | -0.878 | | HepB_cAb_Int | IL_10 | 0.000 |
| HepB_cAb_Int | IL_12p70 | -0.868 | | HepB_cAb_Int | IL_12p70 | 0.000 |
| HepB_cAb_Int | IL_13 | -0.959 | | HepB_cAb_Int | IL_13 | 0.000 |
| HepB_cAb_Int | IL_15 | -0.959 | | HepB_cAb_Int | IL_15 | 0.000 |
| HepB_cAb_Int | IL_17 | -0.921 | | HepB_cAb_Int | IL_17 | 0.000 |
| HepB_cAb_Int | IL_23 | -0.796 | | HepB_cAb_Int | IL_23 | 0.000 |
| HepB_cAb_Int | IFN_gamma | 0.000 | | HepB_cAb_Int | IFN_gamma | 0.000 |
| HepB_cAb_Int | TNF_alpha | -0.860 | | HepB_cAb_Int | TNF_alpha | 0.000 |
| HepB_cAb_Int | TNF_beta | -0.879 | | HepB_cAb_Int | TNF_beta | 0.000 |
| HepB_cAb_Int | Varicella_Int | 0.000 | | HepB_cAb_Int | Varicella_Int | 0.000 |
| HepB_cAb_Int | Measles_OD_DB_Int | 0.500 | | HepB_cAb_Int | Measles_OD_DB_Int | 0.000 |
| HepB_cAb_Int | Measles_Int | 0.000 | | HepB_cAb_Int | Measles_Int | 0.000 |
| HepB_cAb_Int | HepA_Int | 0.500 | | HepB_cAb_Int | HepA_Int | 0.000 |
| HepB_cAb_Int | Tetanus_Int | 0.000 | | HepB_cAb_Int | Tetanus_Int | 0.000 |
| HepB_cAb_Int | Diptheria_Int | 0.000 | | HepB_cAb_Int | Diptheria_Int | 0.000 |
| HepB_cAb_Int | Rubella_Int | 0.000 | | HepB_cAb_Int | Rubella_Int | 0.000 |
| HepB_cAb_Int | CMV_Int | 0.000 | | HepB_cAb_Int | CMV_Int | 0.000 |
| HepB_cAb_Int | HepB_cAb_Int | 1.000 | | HepB_cAb_Int | HepB_cAb_Int | 1.000 |
| HepB_cAb_Int | HepB_eAb_Int | 0.000 | | HepB_cAb_Int | HepB_eAb_Int | 0.000 |
| HepB_cAb_Int | HepB_eAg_Int | 0.000 | | HepB_cAb_Int | HepB_eAg_Int | 0.000 |
| HepB_cAb_Int | HepC_Int | 0.000 | | HepB_cAb_Int | HepC_Int | 0.000 |
| HepB_cAb_Int | Schistosoma_int | 0.000 | | HepB_cAb_Int | Schistosoma_int | 0.000 |
| HepB_cAb_Int | Strongyloides_Int | -0.500 | | HepB_cAb_Int | Strongyloides_Int | 0.000 |
| HepB_cAb_Int | Filaria_Int | 0.500 | | HepB_cAb_Int | Filaria_Int | 0.000 |
| HepB_eAb_Int | IL_1_alpha | 0.000 | | HepB_eAb_Int | IL_1_alpha | 0.000 |
| HepB_eAb_Int | IL_1_beta | 0.000 | | HepB_eAb_Int | IL_1_beta | 0.000 |

FIG. 21I10-N

| HepB_eAb_Int | IL_2 | 0.000 | HepB_eAb_Int | IL_2 | 0.000 |
|---|---|---|---|---|---|
| HepB_eAb_Int | IL_4 | 0.000 | HepB_eAb_Int | IL_4 | 0.000 |
| HepB_eAb_Int | IL_5 | 0.000 | HepB_eAb_Int | IL_5 | 0.000 |
| HepB_eAb_Int | IL_6 | 0.000 | HepB_eAb_Int | IL_6 | 0.000 |
| HepB_eAb_Int | IL_8 | 0.000 | HepB_eAb_Int | IL_8 | 0.000 |
| HepB_eAb_Int | IL_10 | 0.000 | HepB_eAb_Int | IL_10 | 0.000 |
| HepB_eAb_Int | IL_12p70 | 0.000 | HepB_eAb_Int | IL_12p70 | 0.000 |
| HepB_eAb_Int | IL_13 | 0.000 | HepB_eAb_Int | IL_13 | 0.000 |
| HepB_eAb_Int | IL_15 | 0.000 | HepB_eAb_Int | IL_15 | 0.000 |
| HepB_eAb_Int | IL_17 | 0.000 | HepB_eAb_Int | IL_17 | 0.000 |
| HepB_eAb_Int | IL_23 | 0.000 | HepB_eAb_Int | IL_23 | 0.000 |
| HepB_eAb_Int | IFN_gamma | 0.000 | HepB_eAb_Int | IFN_gamma | 0.000 |
| HepB_eAb_Int | TNF_alpha | 0.000 | HepB_eAb_Int | TNF_alpha | 0.000 |
| HepB_eAb_Int | TNF_beta | 0.000 | HepB_eAb_Int | TNF_beta | 0.000 |
| HepB_eAb_Int | Varicella_Int | 0.000 | HepB_eAb_Int | Varicella_Int | 0.000 |
| HepB_eAb_Int | Measles_OD_DB_Int | 0.000 | HepB_eAb_Int | Measles_OD_DB_Int | 0.000 |
| HepB_eAb_Int | Measles_Int | 0.000 | HepB_eAb_Int | Measles_Int | 0.000 |
| HepB_eAb_Int | HepA_Int | 0.000 | HepB_eAb_Int | HepA_Int | 0.000 |
| HepB_eAb_Int | Tetanus_Int | 0.000 | HepB_eAb_Int | Tetanus_Int | 0.000 |
| HepB_eAb_Int | Diptheria_Int | 0.000 | HepB_eAb_Int | Diptheria_Int | 0.000 |
| HepB_eAb_Int | Rubella_Int | 0.000 | HepB_eAb_Int | Rubella_Int | 0.000 |
| HepB_eAb_Int | CMV_Int | 0.000 | HepB_eAb_Int | CMV_Int | 0.000 |
| HepB_eAb_Int | HepB_cAb_Int | 0.000 | HepB_eAb_Int | HepB_cAb_Int | 0.000 |
| HepB_eAb_Int | HepB_eAb_Int | 1.000 | HepB_eAb_Int | HepB_eAb_Int | 1.000 |
| HepB_eAb_Int | HepB_eAg_Int | 0.000 | HepB_eAb_Int | HepB_eAg_Int | 0.000 |
| HepB_eAb_Int | HepC_Int | 0.000 | HepB_eAb_Int | HepC_Int | 0.000 |
| HepB_eAb_Int | Schistosoma_int | 0.000 | HepB_eAb_Int | Schistosoma_int | 0.000 |
| HepB_eAb_Int | Strongyloides_Int | 0.000 | HepB_eAb_Int | Strongyloides_Int | 0.000 |
| HepB_eAb_Int | Filaria_Int | 0.000 | HepB_eAb_Int | Filaria_Int | 0.000 |
| HepB_eAg_Int | IL_1_alpha | 0.000 | HepB_eAg_Int | IL_1_alpha | 0.000 |
| HepB_eAg_Int | IL_1_beta | 0.000 | HepB_eAg_Int | IL_1_beta | 0.000 |
| HepB_eAg_Int | IL_2 | 0.000 | HepB_eAg_Int | IL_2 | 0.000 |
| HepB_eAg_Int | IL_4 | 0.000 | HepB_eAg_Int | IL_4 | 0.000 |
| HepB_eAg_Int | IL_5 | 0.000 | HepB_eAg_Int | IL_5 | 0.000 |
| HepB_eAg_Int | IL_6 | 0.000 | HepB_eAg_Int | IL_6 | 0.000 |
| HepB_eAg_Int | IL_8 | 0.000 | HepB_eAg_Int | IL_8 | 0.000 |
| HepB_eAg_Int | IL_10 | 0.000 | HepB_eAg_Int | IL_10 | 0.000 |
| HepB_eAg_Int | IL_12p70 | 0.000 | HepB_eAg_Int | IL_12p70 | 0.000 |
| HepB_eAg_Int | IL_13 | 0.000 | HepB_eAg_Int | IL_13 | 0.000 |
| HepB_eAg_Int | IL_15 | 0.000 | HepB_eAg_Int | IL_15 | 0.000 |
| HepB_eAg_Int | IL_17 | 0.000 | HepB_eAg_Int | IL_17 | 0.000 |
| HepB_eAg_Int | IL_23 | 0.000 | HepB_eAg_Int | IL_23 | 0.000 |
| HepB_eAg_Int | IFN_gamma | 0.000 | HepB_eAg_Int | IFN_gamma | 0.000 |
| HepB_eAg_Int | TNF_alpha | 0.000 | HepB_eAg_Int | TNF_alpha | 0.000 |
| HepB_eAg_Int | TNF_beta | 0.000 | HepB_eAg_Int | TNF_beta | 0.000 |
| HepB_eAg_Int | Varicella_Int | 0.000 | HepB_eAg_Int | Varicella_Int | 0.000 |
| HepB_eAg_Int | Measles_OD_DB_Int | 0.000 | HepB_eAg_Int | Measles_OD_DB_Int | 0.000 |
| HepB_eAg_Int | Measles_Int | 0.000 | HepB_eAg_Int | Measles_Int | 0.000 |
| HepB_eAg_Int | HepA_Int | 0.000 | HepB_eAg_Int | HepA_Int | 0.000 |
| HepB_eAg_Int | Tetanus_Int | 0.000 | HepB_eAg_Int | Tetanus_Int | 0.000 |
| HepB_eAg_Int | Diptheria_Int | 0.000 | HepB_eAg_Int | Diptheria_Int | 0.000 |
| HepB_eAg_Int | Rubella_Int | 0.000 | HepB_eAg_Int | Rubella_Int | 0.000 |
| HepB_eAg_Int | CMV_Int | 0.000 | HepB_eAg_Int | CMV_Int | 0.000 |
| HepB_eAg_Int | HepB_cAb_Int | 0.000 | HepB_eAg_Int | HepB_cAb_Int | 0.000 |
| HepB_eAg_Int | HepB_eAb_Int | 0.000 | HepB_eAg_Int | HepB_eAb_Int | 0.000 |
| HepB_eAg_Int | HepB_eAg_Int | 1.000 | HepB_eAg_Int | HepB_eAg_Int | 1.000 |
| HepB_eAg_Int | HepC_Int | 0.000 | HepB_eAg_Int | HepC_Int | 0.000 |

FIG. 21I10-O

| | | | | | | |
|---|---|---|---|---|---|---|
| HepB_eAg_Int | Schistosoma_int | 0.000 | | HepB_eAg_Int | Schistosoma_int | 0.000 |
| HepB_eAg_Int | Strongyloides_Int | 0.000 | | HepB_eAg_Int | Strongyloides_Int | 0.000 |
| HepB_eAg_Int | Filaria_Int | 0.000 | | HepB_eAg_Int | Filaria_Int | 0.000 |
| HepC_Int | IL_1_alpha | 0.000 | | HepC_Int | IL_1_alpha | 0.000 |
| HepC_Int | IL_1_beta | 0.000 | | HepC_Int | IL_1_beta | 0.000 |
| HepC_Int | IL_2 | 0.000 | | HepC_Int | IL_2 | 0.000 |
| HepC_Int | IL_4 | 0.000 | | HepC_Int | IL_4 | 0.000 |
| HepC_Int | IL_5 | 0.000 | | HepC_Int | IL_5 | 0.000 |
| HepC_Int | IL_6 | 0.000 | | HepC_Int | IL_6 | 0.000 |
| HepC_Int | IL_8 | 0.000 | | HepC_Int | IL_8 | 0.000 |
| HepC_Int | IL_10 | 0.000 | | HepC_Int | IL_10 | 0.000 |
| HepC_Int | IL_12p70 | 0.000 | | HepC_Int | IL_12p70 | 0.000 |
| HepC_Int | IL_13 | 0.000 | | HepC_Int | IL_13 | 0.000 |
| HepC_Int | IL_15 | 0.000 | | HepC_Int | IL_15 | 0.000 |
| HepC_Int | IL_17 | 0.000 | | HepC_Int | IL_17 | 0.000 |
| HepC_Int | IL_23 | 0.000 | | HepC_Int | IL_23 | 0.000 |
| HepC_Int | IFN_gamma | 0.000 | | HepC_Int | IFN_gamma | 0.000 |
| HepC_Int | TNF_alpha | 0.000 | | HepC_Int | TNF_alpha | 0.000 |
| HepC_Int | TNF_beta | 0.000 | | HepC_Int | TNF_beta | 0.000 |
| HepC_Int | Varicella_Int | 0.000 | | HepC_Int | Varicella_Int | 0.000 |
| HepC_Int | Measles_OD_DB_Int | 0.000 | | HepC_Int | Measles_OD_DB_Int | 0.000 |
| HepC_Int | Measles_Int | 0.000 | | HepC_Int | Measles_Int | 0.000 |
| HepC_Int | HepA_Int | 0.000 | | HepC_Int | HepA_int | 0.000 |
| HepC_Int | Tetanus_Int | 0.000 | | HepC_Int | Tetanus_Int | 0.000 |
| HepC_Int | Diptheria_Int | 0.000 | | HepC_Int | Diptheria_Int | 0.000 |
| HepC_Int | Rubella_Int | 0.000 | | HepC_Int | Rubella_Int | 0.000 |
| HepC_Int | CMV_Int | 0.000 | | HepC_Int | CMV_Int | 0.000 |
| HepC_Int | HepB_cAb_Int | 0.000 | | HepC_Int | HepB_cAb_Int | 0.000 |
| HepC_Int | HepB_eAb_Int | 0.000 | | HepC_Int | HepB_eAb_Int | 0.000 |
| HepC_Int | HepB_eAg_Int | 0.000 | | HepC_Int | HepB_eAg_Int | 0.000 |
| HepC_Int | HepC_Int | 1.000 | | HepC_Int | HepC_Int | 1.000 |
| HepC_Int | Schistosoma_int | 0.000 | | HepC_Int | Schistosoma_int | 0.000 |
| HepC_Int | Strongyloides_Int | 0.000 | | HepC_Int | Strongyloides_Int | 0.000 |
| HepC_Int | Filaria_Int | 0.000 | | HepC_Int | Filaria_Int | 0.000 |
| Schistosoma_int | IL_1_alpha | 0.000 | | Schistosoma_int | IL_1_alpha | 0.000 |
| Schistosoma_int | IL_1_beta | 0.000 | | Schistosoma_int | IL_1_beta | 0.000 |
| Schistosoma_int | IL_2 | 0.000 | | Schistosoma_int | IL_2 | 0.000 |
| Schistosoma_int | IL_4 | 0.000 | | Schistosoma_int | IL_4 | 0.000 |
| Schistosoma_int | IL_5 | 0.000 | | Schistosoma_int | IL_5 | 0.000 |
| Schistosoma_int | IL_6 | 0.000 | | Schistosoma_int | IL_6 | 0.000 |
| Schistosoma_int | IL_8 | 0.000 | | Schistosoma_int | IL_8 | 0.000 |
| Schistosoma_int | IL_10 | 0.000 | | Schistosoma_int | IL_10 | 0.000 |
| Schistosoma_int | IL_12p70 | 0.000 | | Schistosoma_int | IL_12p70 | 0.000 |
| Schistosoma_int | IL_13 | 0.000 | | Schistosoma_int | IL_13 | 0.000 |
| Schistosoma_int | IL_15 | 0.000 | | Schistosoma_int | IL_15 | 0.000 |
| Schistosoma_int | IL_17 | 0.000 | | Schistosoma_int | IL_17 | 0.000 |
| Schistosoma_int | IL_23 | 0.000 | | Schistosoma_int | IL_23 | 0.000 |
| Schistosoma_int | IFN_gamma | 0.000 | | Schistosoma_int | IFN_gamma | 0.000 |
| Schistosoma_int | TNF_alpha | 0.000 | | Schistosoma_int | TNF_alpha | 0.000 |
| Schistosoma_int | TNF_beta | 0.000 | | Schistosoma_int | TNF_beta | 0.000 |
| Schistosoma_int | Varicella_Int | 0.000 | | Schistosoma_int | Varicella_Int | 0.000 |
| Schistosoma_int | Measles_OD_DB_Int | 0.000 | | Schistosoma_int | Measles_OD_DB_Int | 0.000 |
| Schistosoma_int | Measles_Int | 0.000 | | Schistosoma_int | Measles_Int | 0.000 |
| Schistosoma_int | HepA_Int | 0.000 | | Schistosoma_int | HepA_Int | 0.000 |
| Schistosoma_int | Tetanus_Int | 0.000 | | Schistosoma_int | Tetanus_Int | 0.000 |
| Schistosoma_int | Diptheria_Int | 0.000 | | Schistosoma_int | Diptheria_Int | 0.000 |
| Schistosoma_int | Rubella_Int | 0.000 | | Schistosoma_int | Rubella_Int | 0.000 |

FIG. 21I10-P

| | | | | | | |
|---|---|---|---|---|---|---|
| Schistosoma_int | CMV_Int | 0.000 | | Schistosoma_int | CMV_Int | 0.000 |
| Schistosoma_int | HepB_cAb_Int | 0.000 | | Schistosoma_int | HepB_cAb_Int | 0.000 |
| Schistosoma_int | HepB_eAb_Int | 0.000 | | Schistosoma_int | HepB_eAb_Int | 0.000 |
| Schistosoma_int | HepB_eAg_Int | 0.000 | | Schistosoma_int | HepB_eAg_Int | 0.000 |
| Schistosoma_int | HepC_Int | 0.000 | | Schistosoma_int | HepC_Int | 0.000 |
| Schistosoma_int | Schistosoma_int | 1.000 | | Schistosoma_int | Schistosoma_int | 1.000 |
| Schistosoma_int | Strongyloides_Int | 0.000 | | Schistosoma_int | Strongyloides_Int | 0.000 |
| Schistosoma_int | Filaria_Int | 0.000 | | Schistosoma_int | Filaria_Int | 0.000 |
| Strongyloides_Int | IL_1_alpha | 0.859 | | Strongyloides_Int | IL_1_alpha | 0.000 |
| Strongyloides_Int | IL_1_beta | 0.114 | | Strongyloides_Int | IL_1_beta | 0.000 |
| Strongyloides_Int | IL_2 | 0.653 | | Strongyloides_Int | IL_2 | 0.000 |
| Strongyloides_Int | IL_4 | 0.194 | | Strongyloides_Int | IL_4 | 0.000 |
| Strongyloides_Int | IL_5 | 0.526 | | Strongyloides_Int | IL_5 | 0.000 |
| Strongyloides_Int | IL_6 | 0.118 | | Strongyloides_Int | IL_6 | 0.000 |
| Strongyloides_Int | IL_8 | -0.165 | | Strongyloides_Int | IL_8 | 0.000 |
| Strongyloides_Int | IL_10 | 0.025 | | Strongyloides_Int | IL_10 | 0.000 |
| Strongyloides_Int | IL_12p70 | 0.005 | | Strongyloides_Int | IL_12p70 | 0.000 |
| Strongyloides_Int | IL_13 | 0.233 | | Strongyloides_Int | IL_13 | 0.000 |
| Strongyloides_Int | IL_15 | 0.235 | | Strongyloides_Int | IL_15 | 0.000 |
| Strongyloides_Int | IL_17 | 0.123 | | Strongyloides_Int | IL_17 | 0.000 |
| Strongyloides_Int | IL_23 | -0.126 | | Strongyloides_Int | IL_23 | 0.000 |
| Strongyloides_Int | IFN_gamma | 0.000 | | Strongyloides_Int | IFN_gamma | 0.000 |
| Strongyloides_Int | TNF_alpha | -0.012 | | Strongyloides_Int | TNF_alpha | 0.000 |
| Strongyloides_Int | TNF_beta | 0.026 | | Strongyloides_Int | TNF_beta | 0.000 |
| Strongyloides_Int | Varicella_Int | 0.000 | | Strongyloides_Int | Varicella_Int | 0.000 |
| Strongyloides_Int | Measles_OD_DB_Int | 0.500 | | Strongyloides_Int | Measles_OD_DB_Int | 0.000 |
| Strongyloides_Int | Measles_Int | 0.000 | | Strongyloides_Int | Measles_Int | 0.000 |
| Strongyloides_Int | HepA_Int | -1.000 | | Strongyloides_Int | HepA_Int | 0.000 |
| Strongyloides_Int | Tetanus_Int | 0.000 | | Strongyloides_Int | Tetanus_Int | 0.000 |
| Strongyloides_Int | Diptheria_Int | 0.000 | | Strongyloides_Int | Diptheria_Int | 0.000 |
| Strongyloides_Int | Rubella_Int | 0.000 | | Strongyloides_Int | Rubella_Int | 0.000 |
| Strongyloides_Int | CMV_Int | 0.000 | | Strongyloides_Int | CMV_Int | 0.000 |
| Strongyloides_Int | HepB_cAb_Int | -0.500 | | Strongyloides_Int | HepB_cAb_Int | 0.000 |
| Strongyloides_Int | HepB_eAb_Int | 0.000 | | Strongyloides_Int | HepB_eAb_Int | 0.000 |
| Strongyloides_Int | HepB_eAg_Int | 0.000 | | Strongyloides_Int | HepB_eAg_Int | 0.000 |
| Strongyloides_Int | HepC_Int | 0.000 | | Strongyloides_Int | HepC_Int | 0.000 |
| Strongyloides_Int | Schistosoma_int | 0.000 | | Strongyloides_Int | Schistosoma_int | 0.000 |
| Strongyloides_Int | Strongyloides_Int | 1.000 | | Strongyloides_Int | Strongyloides_Int | 1.000 |
| Strongyloides_Int | Filaria_Int | -1.000 | | Strongyloides_Int | Filaria_Int | 0.000 |
| Filaria_Int | IL_1_alpha | -0.859 | | Filaria_Int | IL_1_alpha | 0.000 |
| Filaria_Int | IL_1_beta | -0.114 | | Filaria_Int | IL_1_beta | 0.000 |
| Filaria_Int | IL_2 | -0.653 | | Filaria_Int | IL_2 | 0.000 |
| Filaria_Int | IL_4 | -0.194 | | Filaria_Int | IL_4 | 0.000 |
| Filaria_Int | IL_5 | -0.526 | | Filaria_Int | IL_5 | 0.000 |
| Filaria_Int | IL_6 | -0.118 | | Filaria_Int | IL_6 | 0.000 |
| Filaria_Int | IL_8 | 0.165 | | Filaria_Int | IL_8 | 0.000 |
| Filaria_Int | IL_10 | -0.025 | | Filaria_Int | IL_10 | 0.000 |
| Filaria_Int | IL_12p70 | -0.005 | | Filaria_Int | IL_12p70 | 0.000 |
| Filaria_Int | IL_13 | -0.233 | | Filaria_Int | IL_13 | 0.000 |
| Filaria_Int | IL_15 | -0.235 | | Filaria_Int | IL_15 | 0.000 |
| Filaria_Int | IL_17 | -0.123 | | Filaria_Int | IL_17 | 0.000 |
| Filaria_Int | IL_23 | 0.126 | | Filaria_Int | IL_23 | 0.000 |
| Filaria_Int | IFN_gamma | 0.000 | | Filaria_Int | IFN_gamma | 0.000 |
| Filaria_Int | TNF_alpha | 0.012 | | Filaria_Int | TNF_alpha | 0.000 |
| Filaria_Int | TNF_beta | -0.026 | | Filaria_Int | TNF_beta | 0.000 |
| Filaria_Int | Varicella_Int | 0.000 | | Filaria_Int | Varicella_Int | 0.000 |
| Filaria_Int | Measles_OD_DB_Int | -0.500 | | Filaria_Int | Measles_OD_DB_Int | 0.000 |

FIG. 21I10-Q

| | | |
|---|---|---|
| Filaria_Int | Measles_Int | 0.000 |
| Filaria_Int | HepA_Int | 1.000 |
| Filaria_Int | Tetanus_Int | 0.000 |
| Filaria_Int | Diptheria_Int | 0.000 |
| Filaria_Int | Rubella_Int | 0.000 |
| Filaria_Int | CMV_Int | 0.000 |
| Filaria_Int | HepB_cAb_Int | 0.500 |
| Filaria_Int | HepB_eAb_Int | 0.000 |
| Filaria_Int | HepB_eAg_Int | 0.000 |
| Filaria_Int | HepC_Int | 0.000 |
| Filaria_Int | Schistosoma_int | 0.000 |
| Filaria_Int | Strongyloides_Int | -1.000 |
| Filaria_Int | Filaria_Int | 1.000 |

| | | |
|---|---|---|
| Filaria_Int | Measles_Int | 0.000 |
| Filaria_Int | HepA_int | 0.000 |
| Filaria_Int | Tetanus_Int | 0.000 |
| Filaria_Int | Diptheria_Int | 0.000 |
| Filaria_Int | Rubella_Int | 0.000 |
| Filaria_Int | CMV_Int | 0.000 |
| Filaria_Int | HepB_cAb_Int | 0.000 |
| Filaria_Int | HepB_eAb_Int | 0.000 |
| Filaria_Int | HepB_eAg_Int | 0.000 |
| Filaria_Int | HepC_int | 0.000 |
| Filaria_Int | Schistosoma_int | 0.000 |
| Filaria_Int | Strongyloides_Int | 0.000 |
| Filaria_Int | Filaria_Int | 1.000 |

FIG. 21I10-R

| 0.14% - Region_of_Origin=6, Sex=Male, IFN_gamma=7.5-22.5 | | | 0.14% - Region_of_Origin=6, Sex=Female, IFN_gamma=7.5-22.5 | | |
|---|---|---|---|---|---|
| Property 1 | Property 2 | Corr. Coefficient | Property 1 | Property 2 | Corr. Coefficient |
| IL_1_alpha | IL_1_alpha | 1.000 | IL_1_alpha | IL_1_alpha | 1.000 |
| IL_1_alpha | IL_1_beta | -1.000 | IL_1_alpha | IL_1_beta | -1.000 |
| IL_1_alpha | IL_2 | -1.000 | IL_1_alpha | IL_2 | 0.000 |
| IL_1_alpha | IL_4 | 1.000 | IL_1_alpha | IL_4 | 0.000 |
| IL_1_alpha | IL_5 | -1.000 | IL_1_alpha | IL_5 | 1.000 |
| IL_1_alpha | IL_6 | -1.000 | IL_1_alpha | IL_6 | -1.000 |
| IL_1_alpha | IL_8 | 1.000 | IL_1_alpha | IL_8 | -1.000 |
| IL_1_alpha | IL_10 | -1.000 | IL_1_alpha | IL_10 | -1.000 |
| IL_1_alpha | IL_12p70 | -1.000 | IL_1_alpha | IL_12p70 | -1.000 |
| IL_1_alpha | IL_13 | -1.000 | IL_1_alpha | IL_13 | -1.000 |
| IL_1_alpha | IL_15 | -1.000 | IL_1_alpha | IL_15 | -1.000 |
| IL_1_alpha | IL_17 | -1.000 | IL_1_alpha | IL_17 | 1.000 |
| IL_1_alpha | IL_23 | -1.000 | IL_1_alpha | IL_23 | -1.000 |
| IL_1_alpha | IFN_gamma | 0.000 | IL_1_alpha | IFN_gamma | 0.000 |
| IL_1_alpha | TNF_alpha | -1.000 | IL_1_alpha | TNF_alpha | -1.000 |
| IL_1_alpha | TNF_beta | 1.000 | IL_1_alpha | TNF_beta | 1.000 |
| IL_1_alpha | Varicella_Int | 0.000 | IL_1_alpha | Varicella_Int | 0.000 |
| IL_1_alpha | Measles_OD_DB_Int | -1.000 | IL_1_alpha | Measles_OD_DB_Int | -1.000 |
| IL_1_alpha | Measles_Int | 0.000 | IL_1_alpha | Measles_Int | 0.000 |
| IL_1_alpha | HepA_Int | -1.000 | IL_1_alpha | HepA_Int | 0.000 |
| IL_1_alpha | Tetanus_Int | 0.000 | IL_1_alpha | Tetanus_Int | 0.000 |
| IL_1_alpha | Diptheria_Int | 0.000 | IL_1_alpha | Diptheria_Int | 0.000 |
| IL_1_alpha | Rubella_Int | 1.000 | IL_1_alpha | Rubella_Int | 0.000 |
| IL_1_alpha | CMV_Int | 0.000 | IL_1_alpha | CMV_Int | 0.000 |
| IL_1_alpha | HepB_cAb_Int | -1.000 | IL_1_alpha | HepB_cAb_Int | 0.000 |
| IL_1_alpha | HepB_eAb_Int | 0.000 | IL_1_alpha | HepB_eAb_Int | 0.000 |
| IL_1_alpha | HepB_eAg_Int | 0.000 | IL_1_alpha | HepB_eAg_Int | 0.000 |
| IL_1_alpha | HepC_Int | 0.000 | IL_1_alpha | HepC_Int | 0.000 |
| IL_1_alpha | Schistosoma_int | 0.000 | IL_1_alpha | Schistosoma_int | 1.000 |
| IL_1_alpha | Strongyloides_Int | 1.000 | IL_1_alpha | Strongyloides_Int | 1.000 |
| IL_1_alpha | Filaria_Int | 0.000 | IL_1_alpha | Filaria_Int | 0.000 |
| IL_1_beta | IL_1_alpha | -1.000 | IL_1_beta | IL_1_alpha | -1.000 |
| IL_1_beta | IL_1_beta | 1.000 | IL_1_beta | IL_1_beta | 1.000 |
| IL_1_beta | IL_2 | 1.000 | IL_1_beta | IL_2 | 0.000 |
| IL_1_beta | IL_4 | -1.000 | IL_1_beta | IL_4 | 0.000 |
| IL_1_beta | IL_5 | 1.000 | IL_1_beta | IL_5 | -1.000 |
| IL_1_beta | IL_6 | 1.000 | IL_1_beta | IL_6 | 1.000 |
| IL_1_beta | IL_8 | -1.000 | IL_1_beta | IL_8 | 1.000 |
| IL_1_beta | IL_10 | 1.000 | IL_1_beta | IL_10 | 1.000 |
| IL_1_beta | IL_12p70 | 1.000 | IL_1_beta | IL_12p70 | 1.000 |

FIG. 21I11-A

| IL_1_beta | IL_13 | 1.000 | | IL_1_beta | IL_13 | 1.000 |
|---|---|---|---|---|---|---|
| IL_1_beta | IL_15 | 1.000 | | IL_1_beta | IL_15 | 1.000 |
| IL_1_beta | IL_17 | 1.000 | | IL_1_beta | IL_17 | -1.000 |
| IL_1_beta | IL_23 | 1.000 | | IL_1_beta | IL_23 | 1.000 |
| IL_1_beta | IFN_gamma | 0.000 | | IL_1_beta | IFN_gamma | 0.000 |
| IL_1_beta | TNF_alpha | 1.000 | | IL_1_beta | TNF_alpha | 1.000 |
| IL_1_beta | TNF_beta | -1.000 | | IL_1_beta | TNF_beta | -1.000 |
| IL_1_beta | Varicella_Int | 0.000 | | IL_1_beta | Varicella_Int | 0.000 |
| IL_1_beta | Measles_OD_DB_Int | 1.000 | | IL_1_beta | Measles_OD_DB_Int | 1.000 |
| IL_1_beta | Measles_Int | 0.000 | | IL_1_beta | Measles_Int | 0.000 |
| IL_1_beta | HepA_Int | 1.000 | | IL_1_beta | HepA_Int | 0.000 |
| IL_1_beta | Tetanus_Int | 0.000 | | IL_1_beta | Tetanus_Int | 0.000 |
| IL_1_beta | Diptheria_Int | 0.000 | | IL_1_beta | Diptheria_Int | 0.000 |
| IL_1_beta | Rubella_Int | -1.000 | | IL_1_beta | Rubella_Int | 0.000 |
| IL_1_beta | CMV_Int | 0.000 | | IL_1_beta | CMV_Int | 0.000 |
| IL_1_beta | HepB_cAb_Int | 1.000 | | IL_1_beta | HepB_cAb_Int | 0.000 |
| IL_1_beta | HepB_eAb_Int | 0.000 | | IL_1_beta | HepB_eAb_Int | 0.000 |
| IL_1_beta | HepB_eAg_Int | 0.000 | | IL_1_beta | HepB_eAg_Int | 0.000 |
| IL_1_beta | HepC_Int | 0.000 | | IL_1_beta | HepC_Int | 0.000 |
| IL_1_beta | Schistosoma_int | 0.000 | | IL_1_beta | Schistosoma_int | -1.000 |
| IL_1_beta | Strongyloides_Int | -1.000 | | IL_1_beta | Strongyloides_Int | -1.000 |
| IL_1_beta | Filaria_Int | 0.000 | | IL_1_beta | Filaria_Int | 0.000 |
| IL_2 | IL_1_alpha | -1.000 | | IL_2 | IL_1_alpha | 0.000 |
| IL_2 | IL_1_beta | 1.000 | | IL_2 | IL_1_beta | 0.000 |
| IL_2 | IL_2 | 1.000 | | IL_2 | IL_2 | 1.000 |
| IL_2 | IL_4 | -1.000 | | IL_2 | IL_4 | 0.000 |
| IL_2 | IL_5 | 1.000 | | IL_2 | IL_5 | 0.000 |
| IL_2 | IL_6 | 1.000 | | IL_2 | IL_6 | 0.000 |
| IL_2 | IL_8 | -1.000 | | IL_2 | IL_8 | 0.000 |
| IL_2 | IL_10 | 1.000 | | IL_2 | IL_10 | 0.000 |
| IL_2 | IL_12p70 | 1.000 | | IL_2 | IL_12p70 | 0.000 |
| IL_2 | IL_13 | 1.000 | | IL_2 | IL_13 | 0.000 |
| IL_2 | IL_15 | 1.000 | | IL_2 | IL_15 | 0.000 |
| IL_2 | IL_17 | 1.000 | | IL_2 | IL_17 | 0.000 |
| IL_2 | IL_23 | 1.000 | | IL_2 | IL_23 | 0.000 |
| IL_2 | IFN_gamma | 0.000 | | IL_2 | IFN_gamma | 0.000 |
| IL_2 | TNF_alpha | 1.000 | | IL_2 | TNF_alpha | 0.000 |
| IL_2 | TNF_beta | -1.000 | | IL_2 | TNF_beta | 0.000 |
| IL_2 | Varicella_Int | 0.000 | | IL_2 | Varicella_Int | 0.000 |
| IL_2 | Measles_OD_DB_Int | 1.000 | | IL_2 | Measles_OD_DB_Int | 0.000 |
| IL_2 | Measles_int | 0.000 | | IL_2 | Measles_Int | 0.000 |
| IL_2 | HepA_Int | 1.000 | | IL_2 | HepA_Int | 0.000 |
| IL_2 | Tetanus_Int | 0.000 | | IL_2 | Tetanus_Int | 0.000 |
| IL_2 | Diptheria_Int | 0.000 | | IL_2 | Diptheria_Int | 0.000 |
| IL_2 | Rubella_Int | -1.000 | | IL_2 | Rubella_Int | 0.000 |
| IL_2 | CMV_Int | 0.000 | | IL_2 | CMV_Int | 0.000 |
| IL_2 | HepB_cAb_Int | 1.000 | | IL_2 | HepB_cAb_Int | 0.000 |
| IL_2 | HepB_eAb_Int | 0.000 | | IL_2 | HepB_eAb_Int | 0.000 |
| IL_2 | HepB_eAg_Int | 0.000 | | IL_2 | HepB_eAg_Int | 0.000 |
| IL_2 | HepC_Int | 0.000 | | IL_2 | HepC_Int | 0.000 |
| IL_2 | Schistosoma_int | 0.000 | | IL_2 | Schistosoma_int | 0.000 |
| IL_2 | Strongyloides_Int | -1.000 | | IL_2 | Strongyloides_Int | 0.000 |
| IL_2 | Filaria_Int | 0.000 | | IL_2 | Filaria_Int | 0.000 |
| IL_4 | IL_1_alpha | 1.000 | | IL_4 | IL_1_alpha | 0.000 |
| IL_4 | IL_1_beta | -1.000 | | IL_4 | IL_1_beta | 0.000 |
| IL_4 | IL_2 | -1.000 | | IL_4 | IL_2 | 0.000 |
| IL_4 | IL_4 | 1.000 | | IL_4 | IL_4 | 1.000 |

FIG. 21I11-B

| | | | | | | |
|---|---|---|---|---|---|---|
| IL_4 | IL_5 | -1.000 | | IL_4 | IL_5 | 0.000 |
| IL_4 | IL_6 | -1.000 | | IL_4 | IL_6 | 0.000 |
| IL_4 | IL_8 | 1.000 | | IL_4 | IL_8 | 0.000 |
| IL_4 | IL_10 | -1.000 | | IL_4 | IL_10 | 0.000 |
| IL_4 | IL_12p70 | -1.000 | | IL_4 | IL_12p70 | 0.000 |
| IL_4 | IL_13 | -1.000 | | IL_4 | IL_13 | 0.000 |
| IL_4 | IL_15 | -1.000 | | IL_4 | IL_15 | 0.000 |
| IL_4 | IL_17 | -1.000 | | IL_4 | IL_17 | 0.000 |
| IL_4 | IL_23 | -1.000 | | IL_4 | IL_23 | 0.000 |
| IL_4 | IFN_gamma | 0.000 | | IL_4 | IFN_gamma | 0.000 |
| IL_4 | TNF_alpha | -1.000 | | IL_4 | TNF_alpha | 0.000 |
| IL_4 | TNF_beta | 1.000 | | IL_4 | TNF_beta | 0.000 |
| IL_4 | Varicella_Int | 0.000 | | IL_4 | Varicella_Int | 0.000 |
| IL_4 | Measles_OD_DB_Int | -1.000 | | IL_4 | Measles_OD_DB_Int | 0.000 |
| IL_4 | Measles_Int | 0.000 | | IL_4 | Measles_Int | 0.000 |
| IL_4 | HepA_Int | -1.000 | | IL_4 | HepA_Int | 0.000 |
| IL_4 | Tetanus_Int | 0.000 | | IL_4 | Tetanus_Int | 0.000 |
| IL_4 | Diptheria_Int | 0.000 | | IL_4 | Diptheria_Int | 0.000 |
| IL_4 | Rubella_Int | 1.000 | | IL_4 | Rubella_Int | 0.000 |
| IL_4 | CMV_Int | 0.000 | | IL_4 | CMV_Int | 0.000 |
| IL_4 | HepB_cAb_Int | -1.000 | | IL_4 | HepB_cAb_Int | 0.000 |
| IL_4 | HepB_eAb_Int | 0.000 | | IL_4 | HepB_eAb_Int | 0.000 |
| IL_4 | HepB_eAg_Int | 0.000 | | IL_4 | HepB_eAg_Int | 0.000 |
| IL_4 | HepC_Int | 0.000 | | IL_4 | HepC_Int | 0.000 |
| IL_4 | Schistosoma_int | 0.000 | | IL_4 | Schistosoma_int | 0.000 |
| IL_4 | Strongyloides_Int | 1.000 | | IL_4 | Strongyloides_Int | 0.000 |
| IL_4 | Filaria_Int | 0.000 | | IL_4 | Filaria_Int | 0.000 |
| IL_5 | IL_1_alpha | -1.000 | | IL_5 | IL_1_alpha | 1.000 |
| IL_5 | IL_1_beta | 1.000 | | IL_5 | IL_1_beta | -1.000 |
| IL_5 | IL_2 | 1.000 | | IL_5 | IL_2 | 0.000 |
| IL_5 | IL_4 | -1.000 | | IL_5 | IL_4 | 0.000 |
| IL_5 | IL_5 | 1.000 | | IL_5 | IL_5 | 1.000 |
| IL_5 | IL_6 | 1.000 | | IL_5 | IL_6 | -1.000 |
| IL_5 | IL_8 | -1.000 | | IL_5 | IL_8 | -1.000 |
| IL_5 | IL_10 | 1.000 | | IL_5 | IL_10 | -1.000 |
| IL_5 | IL_12p70 | 1.000 | | IL_5 | IL_12p70 | -1.000 |
| IL_5 | IL_13 | 1.000 | | IL_5 | IL_13 | -1.000 |
| IL_5 | IL_15 | 1.000 | | IL_5 | IL_15 | -1.000 |
| IL_5 | IL_17 | 1.000 | | IL_5 | IL_17 | 1.000 |
| IL_5 | IL_23 | 1.000 | | IL_5 | IL_23 | -1.000 |
| IL_5 | IFN_gamma | 0.000 | | IL_5 | IFN_gamma | 0.000 |
| IL_5 | TNF_alpha | 1.000 | | IL_5 | TNF_alpha | -1.000 |
| IL_5 | TNF_beta | -1.000 | | IL_5 | TNF_beta | 1.000 |
| IL_5 | Varicella_Int | 0.000 | | IL_5 | Varicella_Int | 0.000 |
| IL_5 | Measles_OD_DB_Int | 1.000 | | IL_5 | Measles_OD_DB_Int | -1.000 |
| IL_5 | Measles_Int | 0.000 | | IL_5 | Measles_Int | 0.000 |
| IL_5 | HepA_Int | 1.000 | | IL_5 | HepA_Int | 0.000 |
| IL_5 | Tetanus_Int | 0.000 | | IL_5 | Tetanus_Int | 0.000 |
| IL_5 | Diptheria_Int | 0.000 | | IL_5 | Diptheria_Int | 0.000 |
| IL_5 | Rubella_Int | -1.000 | | IL_5 | Rubella_Int | 0.000 |
| IL_5 | CMV_Int | 0.000 | | IL_5 | CMV_Int | 0.000 |
| IL_5 | HepB_cAb_Int | 1.000 | | IL_5 | HepB_cAb_Int | 0.000 |
| IL_5 | HepB_eAb_Int | 0.000 | | IL_5 | HepB_eAb_Int | 0.000 |
| IL_5 | HepB_eAg_Int | 0.000 | | IL_5 | HepB_eAg_Int | 0.000 |
| IL_5 | HepC_Int | 0.000 | | IL_5 | HepC_Int | 0.000 |
| IL_5 | Schistosoma_int | 0.000 | | IL_5 | Schistosoma_int | 1.000 |
| IL_5 | Strongyloides_Int | -1.000 | | IL_5 | Strongyloides_Int | 1.000 |

FIG. 21I11-C

| | | | | | |
|---|---|---|---|---|---|
| IL_5 | Filaria_Int | 0.000 | IL_5 | Filaria_Int | 0.000 |
| IL_6 | IL_1_alpha | -1.000 | IL_6 | IL_1_alpha | -1.000 |
| IL_6 | IL_1_beta | 1.000 | IL_6 | IL_1_beta | 1.000 |
| IL_6 | IL_2 | 1.000 | IL_6 | IL_2 | 0.000 |
| IL_6 | IL_4 | -1.000 | IL_6 | IL_4 | 0.000 |
| IL_6 | IL_5 | 1.000 | IL_6 | IL_5 | -1.000 |
| IL_6 | IL_6 | 1.000 | IL_6 | IL_6 | 1.000 |
| IL_6 | IL_8 | -1.000 | IL_6 | IL_8 | 1.000 |
| IL_6 | IL_10 | 1.000 | IL_6 | IL_10 | 1.000 |
| IL_6 | IL_12p70 | 1.000 | IL_6 | IL_12p70 | 1.000 |
| IL_6 | IL_13 | 1.000 | IL_6 | IL_13 | 1.000 |
| IL_6 | IL_15 | 1.000 | IL_6 | IL_15 | 1.000 |
| IL_6 | IL_17 | 1.000 | IL_6 | IL_17 | -1.000 |
| IL_6 | IL_23 | 1.000 | IL_6 | IL_23 | 1.000 |
| IL_6 | IFN_gamma | 0.000 | IL_6 | IFN_gamma | 0.000 |
| IL_6 | TNF_alpha | 1.000 | IL_6 | TNF_alpha | 1.000 |
| IL_6 | TNF_beta | -1.000 | IL_6 | TNF_beta | -1.000 |
| IL_6 | Varicella_Int | 0.000 | IL_6 | Varicella_Int | 0.000 |
| IL_6 | Measles_OD_DB_Int | 1.000 | IL_6 | Measles_OD_DB_Int | 1.000 |
| IL_6 | Measles_Int | 0.000 | IL_6 | Measles_Int | 0.000 |
| IL_6 | HepA_Int | 1.000 | IL_6 | HepA_Int | 0.000 |
| IL_6 | Tetanus_Int | 0.000 | IL_6 | Tetanus_Int | 0.000 |
| IL_6 | Diptheria_Int | 0.000 | IL_6 | Diptheria_Int | 0.000 |
| IL_6 | Rubella_Int | -1.000 | IL_6 | Rubella_Int | 0.000 |
| IL_6 | CMV_Int | 0.000 | IL_6 | CMV_Int | 0.000 |
| IL_6 | HepB_cAb_Int | 1.000 | IL_6 | HepB_cAb_Int | 0.000 |
| IL_6 | HepB_eAb_Int | 0.000 | IL_6 | HepB_eAb_Int | 0.000 |
| IL_6 | HepB_eAg_Int | 0.000 | IL_6 | HepB_eAg_Int | 0.000 |
| IL_6 | HepC_Int | 0.000 | IL_6 | HepC_Int | 0.000 |
| IL_6 | Schistosoma_int | 0.000 | IL_6 | Schistosoma_int | -1.000 |
| IL_6 | Strongyloides_Int | -1.000 | IL_6 | Strongyloides_Int | -1.000 |
| IL_6 | Filaria_Int | 0.000 | IL_6 | Filaria_Int | 0.000 |
| IL_8 | IL_1_alpha | 1.000 | IL_8 | IL_1_alpha | -1.000 |
| IL_8 | IL_1_beta | -1.000 | IL_8 | IL_1_beta | 1.000 |
| IL_8 | IL_2 | -1.000 | IL_8 | IL_2 | 0.000 |
| IL_8 | IL_4 | 1.000 | IL_8 | IL_4 | 0.000 |
| IL_8 | IL_5 | -1.000 | IL_8 | IL_5 | -1.000 |
| IL_8 | IL_6 | -1.000 | IL_8 | IL_6 | 1.000 |
| IL_8 | IL_8 | 1.000 | IL_8 | IL_8 | 1.000 |
| IL_8 | IL_10 | -1.000 | IL_8 | IL_10 | 1.000 |
| IL_8 | IL_12p70 | -1.000 | IL_8 | IL_12p70 | 1.000 |
| IL_8 | IL_13 | -1.000 | IL_8 | IL_13 | 1.000 |
| IL_8 | IL_15 | -1.000 | IL_8 | IL_15 | 1.000 |
| IL_8 | IL_17 | -1.000 | IL_8 | IL_17 | -1.000 |
| IL_8 | IL_23 | -1.000 | IL_8 | IL_23 | 1.000 |
| IL_8 | IFN_gamma | 0.000 | IL_8 | IFN_gamma | 0.000 |
| IL_8 | TNF_alpha | -1.000 | IL_8 | TNF_alpha | 1.000 |
| IL_8 | TNF_beta | 1.000 | IL_8 | TNF_beta | -1.000 |
| IL_8 | Varicella_Int | 0.000 | IL_8 | Varicella_Int | 0.000 |
| IL_8 | Measles_OD_DB_Int | -1.000 | IL_8 | Measles_OD_DB_Int | 1.000 |
| IL_8 | Measles_Int | 0.000 | IL_8 | Measles_Int | 0.000 |
| IL_8 | HepA_Int | -1.000 | IL_8 | HepA_Int | 0.000 |
| IL_8 | Tetanus_Int | 0.000 | IL_8 | Tetanus_Int | 0.000 |
| IL_8 | Diptheria_Int | 0.000 | IL_8 | Diptheria_Int | 0.000 |
| IL_8 | Rubella_Int | 1.000 | IL_8 | Rubella_Int | 0.000 |
| IL_8 | CMV_Int | 0.000 | IL_8 | CMV_Int | 0.000 |
| IL_8 | HepB_cAb_Int | -1.000 | IL_8 | HepB_cAb_Int | 0.000 |

FIG. 21I11-D

| | | | | | | |
|---|---|---|---|---|---|---|
| IL_8 | HepB_eAb_Int | 0.000 | | IL_8 | HepB_eAb_Int | 0.000 |
| IL_8 | HepB_eAg_Int | 0.000 | | IL_8 | HepB_eAg_Int | 0.000 |
| IL_8 | HepC_Int | 0.000 | | IL_8 | HepC_Int | 0.000 |
| IL_8 | Schistosoma_int | 0.000 | | IL_8 | Schistosoma_int | -1.000 |
| IL_8 | Strongyloides_Int | 1.000 | | IL_8 | Strongyloides_Int | -1.000 |
| IL_8 | Filaria_Int | 0.000 | | IL_8 | Filaria_Int | 0.000 |
| IL_10 | IL_1_alpha | -1.000 | | IL_10 | IL_1_alpha | -1.000 |
| IL_10 | IL_1_beta | 1.000 | | IL_10 | IL_1_beta | 1.000 |
| IL_10 | IL_2 | 1.000 | | IL_10 | IL_2 | 0.000 |
| IL_10 | IL_4 | -1.000 | | IL_10 | IL_4 | 0.000 |
| IL_10 | IL_5 | 1.000 | | IL_10 | IL_5 | -1.000 |
| IL_10 | IL_6 | 1.000 | | IL_10 | IL_6 | 1.000 |
| IL_10 | IL_8 | -1.000 | | IL_10 | IL_8 | 1.000 |
| IL_10 | IL_10 | 1.000 | | IL_10 | IL_10 | 1.000 |
| IL_10 | IL_12p70 | 1.000 | | IL_10 | IL_12p70 | 1.000 |
| IL_10 | IL_13 | 1.000 | | IL_10 | IL_13 | 1.000 |
| IL_10 | IL_15 | 1.000 | | IL_10 | IL_15 | 1.000 |
| IL_10 | IL_17 | 1.000 | | IL_10 | IL_17 | -1.000 |
| IL_10 | IL_23 | 1.000 | | IL_10 | IL_23 | 1.000 |
| IL_10 | IFN_gamma | 0.000 | | IL_10 | IFN_gamma | 0.000 |
| IL_10 | TNF_alpha | 1.000 | | IL_10 | TNF_alpha | 1.000 |
| IL_10 | TNF_beta | -1.000 | | IL_10 | TNF_beta | -1.000 |
| IL_10 | Varicella_Int | 0.000 | | IL_10 | Varicella_Int | 0.000 |
| IL_10 | Measles_OD_DB_Int | 1.000 | | IL_10 | Measles_OD_DB_Int | 1.000 |
| IL_10 | Measles_Int | 0.000 | | IL_10 | Measles_Int | 0.000 |
| IL_10 | HepA_Int | 1.000 | | IL_10 | HepA_Int | 0.000 |
| IL_10 | Tetanus_Int | 0.000 | | IL_10 | Tetanus_Int | 0.000 |
| IL_10 | Diptheria_Int | 0.000 | | IL_10 | Diptheria_Int | 0.000 |
| IL_10 | Rubella_Int | -1.000 | | IL_10 | Rubella_Int | 0.000 |
| IL_10 | CMV_Int | 0.000 | | IL_10 | CMV_Int | 0.000 |
| IL_10 | HepB_cAb_Int | 1.000 | | IL_10 | HepB_cAb_Int | 0.000 |
| IL_10 | HepB_eAb_Int | 0.000 | | IL_10 | HepB_eAb_Int | 0.000 |
| IL_10 | HepB_eAg_Int | 0.000 | | IL_10 | HepB_eAg_Int | 0.000 |
| IL_10 | HepC_Int | 0.000 | | IL_10 | HepC_Int | 0.000 |
| IL_10 | Schistosoma_int | 0.000 | | IL_10 | Schistosoma_int | -1.000 |
| IL_10 | Strongyloides_Int | -1.000 | | IL_10 | Strongyloides_Int | -1.000 |
| IL_10 | Filaria_Int | 0.000 | | IL_10 | Filaria_Int | 0.000 |
| IL_12p70 | IL_1_alpha | -1.000 | | IL_12p70 | IL_1_alpha | -1.000 |
| IL_12p70 | IL_1_beta | 1.000 | | IL_12p70 | IL_1_beta | 1.000 |
| IL_12p70 | IL_2 | 1.000 | | IL_12p70 | IL_2 | 0.000 |
| IL_12p70 | IL_4 | -1.000 | | IL_12p70 | IL_4 | 0.000 |
| IL_12p70 | IL_5 | 1.000 | | IL_12p70 | IL_5 | -1.000 |
| IL_12p70 | IL_6 | 1.000 | | IL_12p70 | IL_6 | 1.000 |
| IL_12p70 | IL_8 | -1.000 | | IL_12p70 | IL_8 | 1.000 |
| IL_12p70 | IL_10 | 1.000 | | IL_12p70 | IL_10 | 1.000 |
| IL_12p70 | IL_12p70 | 1.000 | | IL_12p70 | IL_12p70 | 1.000 |
| IL_12p70 | IL_13 | 1.000 | | IL_12p70 | IL_13 | 1.000 |
| IL_12p70 | IL_15 | 1.000 | | IL_12p70 | IL_15 | 1.000 |
| IL_12p70 | IL_17 | 1.000 | | IL_12p70 | IL_17 | -1.000 |
| IL_12p70 | IL_23 | 1.000 | | IL_12p70 | IL_23 | 1.000 |
| IL_12p70 | IFN_gamma | 0.000 | | IL_12p70 | IFN_gamma | 0.000 |
| IL_12p70 | TNF_alpha | 1.000 | | IL_12p70 | TNF_alpha | 1.000 |
| IL_12p70 | TNF_beta | -1.000 | | IL_12p70 | TNF_beta | -1.000 |
| IL_12p70 | Varicella_Int | 0.000 | | IL_12p70 | Varicella_Int | 0.000 |
| IL_12p70 | Measles_OD_DB_Int | 1.000 | | IL_12p70 | Measles_OD_DB_Int | 1.000 |
| IL_12p70 | Measles_Int | 0.000 | | IL_12p70 | Measles_Int | 0.000 |
| IL_12p70 | HepA_Int | 1.000 | | IL_12p70 | HepA_Int | 0.000 |

FIG. 21I11-E

| | | | | | | |
|---|---|---|---|---|---|---|
| IL_12p70 | Tetanus_Int | 0.000 | | IL_12p70 | Tetanus_Int | 0.000 |
| IL_12p70 | Diptheria_Int | 0.000 | | IL_12p70 | Diptheria_Int | 0.000 |
| IL_12p70 | Rubella_Int | -1.000 | | IL_12p70 | Rubella_Int | 0.000 |
| IL_12p70 | CMV_Int | 0.000 | | IL_12p70 | CMV_Int | 0.000 |
| IL_12p70 | HepB_cAb_Int | 1.000 | | IL_12p70 | HepB_cAb_Int | 0.000 |
| IL_12p70 | HepB_eAb_Int | 0.000 | | IL_12p70 | HepB_eAb_Int | 0.000 |
| IL_12p70 | HepB_eAg_Int | 0.000 | | IL_12p70 | HepB_eAg_Int | 0.000 |
| IL_12p70 | HepC_Int | 0.000 | | IL_12p70 | HepC_Int | 0.000 |
| IL_12p70 | Schistosoma_int | 0.000 | | IL_12p70 | Schistosoma_int | -1.000 |
| IL_12p70 | Strongyloides_Int | -1.000 | | IL_12p70 | Strongyloides_Int | -1.000 |
| IL_12p70 | Filaria_Int | 0.000 | | IL_12p70 | Filaria_Int | 0.000 |
| IL_13 | IL_1_alpha | -1.000 | | IL_13 | IL_1_alpha | -1.000 |
| IL_13 | IL_1_beta | 1.000 | | IL_13 | IL_1_beta | 1.000 |
| IL_13 | IL_2 | 1.000 | | IL_13 | IL_2 | 0.000 |
| IL_13 | IL_4 | -1.000 | | IL_13 | IL_4 | 0.000 |
| IL_13 | IL_5 | 1.000 | | IL_13 | IL_5 | -1.000 |
| IL_13 | IL_6 | 1.000 | | IL_13 | IL_6 | 1.000 |
| IL_13 | IL_8 | -1.000 | | IL_13 | IL_8 | 1.000 |
| IL_13 | IL_10 | 1.000 | | IL_13 | IL_10 | 1.000 |
| IL_13 | IL_12p70 | 1.000 | | IL_13 | IL_12p70 | 1.000 |
| IL_13 | IL_13 | 1.000 | | IL_13 | IL_13 | 1.000 |
| IL_13 | IL_15 | 1.000 | | IL_13 | IL_15 | 1.000 |
| IL_13 | IL_17 | 1.000 | | IL_13 | IL_17 | -1.000 |
| IL_13 | IL_23 | 1.000 | | IL_13 | IL_23 | 1.000 |
| IL_13 | IFN_gamma | 0.000 | | IL_13 | IFN_gamma | 0.000 |
| IL_13 | TNF_alpha | 1.000 | | IL_13 | TNF_alpha | 1.000 |
| IL_13 | TNF_beta | -1.000 | | IL_13 | TNF_beta | -1.000 |
| IL_13 | Varicella_Int | 0.000 | | IL_13 | Varicella_Int | 0.000 |
| IL_13 | Measles_OD_DB_Int | 1.000 | | IL_13 | Measles_OD_DB_Int | 1.000 |
| IL_13 | Measles_Int | 0.000 | | IL_13 | Measles_Int | 0.000 |
| IL_13 | HepA_Int | 1.000 | | IL_13 | HepA_Int | 0.000 |
| IL_13 | Tetanus_Int | 0.000 | | IL_13 | Tetanus_Int | 0.000 |
| IL_13 | Diptheria_Int | 0.000 | | IL_13 | Diptheria_Int | 0.000 |
| IL_13 | Rubella_Int | -1.000 | | IL_13 | Rubella_Int | 0.000 |
| IL_13 | CMV_Int | 0.000 | | IL_13 | CMV_Int | 0.000 |
| IL_13 | HepB_cAb_Int | 1.000 | | IL_13 | HepB_cAb_Int | 0.000 |
| IL_13 | HepB_eAb_Int | 0.000 | | IL_13 | HepB_eAb_Int | 0.000 |
| IL_13 | HepB_eAg_Int | 0.000 | | IL_13 | HepB_eAg_Int | 0.000 |
| IL_13 | HepC_Int | 0.000 | | IL_13 | HepC_Int | 0.000 |
| IL_13 | Schistosoma_int | 0.000 | | IL_13 | Schistosoma_int | -1.000 |
| IL_13 | Strongyloides_Int | -1.000 | | IL_13 | Strongyloides_Int | -1.000 |
| IL_13 | Filaria_Int | 0.000 | | IL_13 | Filaria_Int | 0.000 |
| IL_15 | IL_1_alpha | -1.000 | | IL_15 | IL_1_alpha | -1.000 |
| IL_15 | IL_1_beta | 1.000 | | IL_15 | IL_1_beta | 1.000 |
| IL_15 | IL_2 | 1.000 | | IL_15 | IL_2 | 0.000 |
| IL_15 | IL_4 | -1.000 | | IL_15 | IL_4 | 0.000 |
| IL_15 | IL_5 | 1.000 | | IL_15 | IL_5 | -1.000 |
| IL_15 | IL_6 | 1.000 | | IL_15 | IL_6 | 1.000 |
| IL_15 | IL_8 | -1.000 | | IL_15 | IL_8 | 1.000 |
| IL_15 | IL_10 | 1.000 | | IL_15 | IL_10 | 1.000 |
| IL_15 | IL_12p70 | 1.000 | | IL_15 | IL_12p70 | 1.000 |
| IL_15 | IL_13 | 1.000 | | IL_15 | IL_13 | 1.000 |
| IL_15 | IL_15 | 1.000 | | IL_15 | IL_15 | 1.000 |
| IL_15 | IL_17 | 1.000 | | IL_15 | IL_17 | -1.000 |
| IL_15 | IL_23 | 1.000 | | IL_15 | IL_23 | 1.000 |
| IL_15 | IFN_gamma | 0.000 | | IL_15 | IFN_gamma | 0.000 |
| IL_15 | TNF_alpha | 1.000 | | IL_15 | TNF_alpha | 1.000 |

FIG. 21I11-F

| | | | | | | |
|---|---|---|---|---|---|---|
| IL_15 | TNF_beta | -1.000 | | IL_15 | TNF_beta | -1.000 |
| IL_15 | Varicella_Int | 0.000 | | IL_15 | Varicella_Int | 0.000 |
| IL_15 | Measles_OD_DB_Int | 1.000 | | IL_15 | Measles_OD_DB_Int | 1.000 |
| IL_15 | Measles_Int | 0.000 | | IL_15 | Measles_Int | 0.000 |
| IL_15 | HepA_Int | 1.000 | | IL_15 | HepA_Int | 0.000 |
| IL_15 | Tetanus_Int | 0.000 | | IL_15 | Tetanus_Int | 0.000 |
| IL_15 | Diptheria_Int | 0.000 | | IL_15 | Diptheria_Int | 0.000 |
| IL_15 | Rubella_Int | -1.000 | | IL_15 | Rubella_Int | 0.000 |
| IL_15 | CMV_Int | 0.000 | | IL_15 | CMV_Int | 0.000 |
| IL_15 | HepB_cAb_Int | 1.000 | | IL_15 | HepB_cAb_Int | 0.000 |
| IL_15 | HepB_eAb_Int | 0.000 | | IL_15 | HepB_eAb_Int | 0.000 |
| IL_15 | HepB_eAg_Int | 0.000 | | IL_15 | HepB_eAg_Int | 0.000 |
| IL_15 | HepC_Int | 0.000 | | IL_15 | HepC_Int | 0.000 |
| IL_15 | Schistosoma_int | 0.000 | | IL_15 | Schistosoma_int | -1.000 |
| IL_15 | Strongyloides_Int | -1.000 | | IL_15 | Strongyloides_Int | -1.000 |
| IL_15 | Filaria_Int | 0.000 | | IL_15 | Filaria_Int | 0.000 |
| IL_17 | IL_1_alpha | -1.000 | | IL_17 | IL_1_alpha | 1.000 |
| IL_17 | IL_1_beta | 1.000 | | IL_17 | IL_1_beta | -1.000 |
| IL_17 | IL_2 | 1.000 | | IL_17 | IL_2 | 0.000 |
| IL_17 | IL_4 | -1.000 | | IL_17 | IL_4 | 0.000 |
| IL_17 | IL_5 | 1.000 | | IL_17 | IL_5 | 1.000 |
| IL_17 | IL_6 | 1.000 | | IL_17 | IL_6 | -1.000 |
| IL_17 | IL_8 | -1.000 | | IL_17 | IL_8 | -1.000 |
| IL_17 | IL_10 | 1.000 | | IL_17 | IL_10 | -1.000 |
| IL_17 | IL_12p70 | 1.000 | | IL_17 | IL_12p70 | -1.000 |
| IL_17 | IL_13 | 1.000 | | IL_17 | IL_13 | -1.000 |
| IL_17 | IL_15 | 1.000 | | IL_17 | IL_15 | -1.000 |
| IL_17 | IL_17 | 1.000 | | IL_17 | IL_17 | 1.000 |
| IL_17 | IL_23 | 1.000 | | IL_17 | IL_23 | -1.000 |
| IL_17 | IFN_gamma | 0.000 | | IL_17 | IFN_gamma | 0.000 |
| IL_17 | TNF_alpha | 1.000 | | IL_17 | TNF_alpha | -1.000 |
| IL_17 | TNF_beta | -1.000 | | IL_17 | TNF_beta | 1.000 |
| IL_17 | Varicella_Int | 0.000 | | IL_17 | Varicella_Int | 0.000 |
| IL_17 | Measles_OD_DB_Int | 1.000 | | IL_17 | Measles_OD_DB_Int | -1.000 |
| IL_17 | Measles_Int | 0.000 | | IL_17 | Measles_Int | 0.000 |
| IL_17 | HepA_Int | 1.000 | | IL_17 | HepA_Int | 0.000 |
| IL_17 | Tetanus_Int | 0.000 | | IL_17 | Tetanus_Int | 0.000 |
| IL_17 | Diptheria_Int | 0.000 | | IL_17 | Diptheria_Int | 0.000 |
| IL_17 | Rubella_Int | -1.000 | | IL_17 | Rubella_Int | 0.000 |
| IL_17 | CMV_Int | 0.000 | | IL_17 | CMV_Int | 0.000 |
| IL_17 | HepB_cAb_Int | 1.000 | | IL_17 | HepB_cAb_Int | 0.000 |
| IL_17 | HepB_eAb_Int | 0.000 | | IL_17 | HepB_eAb_Int | 0.000 |
| IL_17 | HepB_eAg_Int | 0.000 | | IL_17 | HepB_eAg_Int | 0.000 |
| IL_17 | HepC_Int | 0.000 | | IL_17 | HepC_Int | 0.000 |
| IL_17 | Schistosoma_int | 0.000 | | IL_17 | Schistosoma_int | 1.000 |
| IL_17 | Strongyloides_Int | -1.000 | | IL_17 | Strongyloides_Int | 1.000 |
| IL_17 | Filaria_Int | 0.000 | | IL_17 | Filaria_Int | 0.000 |
| IL_23 | IL_1_alpha | -1.000 | | IL_23 | IL_1_alpha | -1.000 |
| IL_23 | IL_1_beta | 1.000 | | IL_23 | IL_1_beta | 1.000 |
| IL_23 | IL_2 | 1.000 | | IL_23 | IL_2 | 0.000 |
| IL_23 | IL_4 | -1.000 | | IL_23 | IL_4 | 0.000 |
| IL_23 | IL_5 | 1.000 | | IL_23 | IL_5 | -1.000 |
| IL_23 | IL_6 | 1.000 | | IL_23 | IL_6 | 1.000 |
| IL_23 | IL_8 | -1.000 | | IL_23 | IL_8 | 1.000 |
| IL_23 | IL_10 | 1.000 | | IL_23 | IL_10 | 1.000 |
| IL_23 | IL_12p70 | 1.000 | | IL_23 | IL_12p70 | 1.000 |
| IL_23 | IL_13 | 1.000 | | IL_23 | IL_13 | 1.000 |

FIG. 21I11-G

| | | | | | | |
|---|---|---|---|---|---|---|
| IL_23 | IL_15 | 1.000 | | IL_23 | IL_15 | 1.000 |
| IL_23 | IL_17 | 1.000 | | IL_23 | IL_17 | -1.000 |
| IL_23 | IL_23 | 1.000 | | IL_23 | IL_23 | 1.000 |
| IL_23 | IFN_gamma | 0.000 | | IL_23 | IFN_gamma | 0.000 |
| IL_23 | TNF_alpha | 1.000 | | IL_23 | TNF_alpha | 1.000 |
| IL_23 | TNF_beta | -1.000 | | IL_23 | TNF_beta | -1.000 |
| IL_23 | Varicella_Int | 0.000 | | IL_23 | Varicella_Int | 0.000 |
| IL_23 | Measles_OD_DB_Int | 1.000 | | IL_23 | Measles_OD_DB_Int | 1.000 |
| IL_23 | Measles_Int | 0.000 | | IL_23 | Measles_Int | 0.000 |
| IL_23 | HepA_Int | 1.000 | | IL_23 | HepA_Int | 0.000 |
| IL_23 | Tetanus_Int | 0.000 | | IL_23 | Tetanus_Int | 0.000 |
| IL_23 | Diptheria_Int | 0.000 | | IL_23 | Diptheria_Int | 0.000 |
| IL_23 | Rubella_Int | -1.000 | | IL_23 | Rubella_Int | 0.000 |
| IL_23 | CMV_Int | 0.000 | | IL_23 | CMV_Int | 0.000 |
| IL_23 | HepB_cAb_Int | 1.000 | | IL_23 | HepB_cAb_Int | 0.000 |
| IL_23 | HepB_eAb_Int | 0.000 | | IL_23 | HepB_eAb_Int | 0.000 |
| IL_23 | HepB_eAg_Int | 0.000 | | IL_23 | HepB_eAg_Int | 0.000 |
| IL_23 | HepC_Int | 0.000 | | IL_23 | HepC_Int | 0.000 |
| IL_23 | Schistosoma_int | 0.000 | | IL_23 | Schistosoma_int | -1.000 |
| IL_23 | Strongyloides_Int | -1.000 | | IL_23 | Strongyloides_Int | -1.000 |
| IL_23 | Filaria_Int | 0.000 | | IL_23 | Filaria_Int | 0.000 |
| IFN_gamma | IL_1_alpha | 0.000 | | IFN_gamma | IL_1_alpha | 0.000 |
| IFN_gamma | IL_1_beta | 0.000 | | IFN_gamma | IL_1_beta | 0.000 |
| IFN_gamma | IL_2 | 0.000 | | IFN_gamma | IL_2 | 0.000 |
| IFN_gamma | IL_4 | 0.000 | | IFN_gamma | IL_4 | 0.000 |
| IFN_gamma | IL_5 | 0.000 | | IFN_gamma | IL_5 | 0.000 |
| IFN_gamma | IL_6 | 0.000 | | IFN_gamma | IL_6 | 0.000 |
| IFN_gamma | IL_8 | 0.000 | | IFN_gamma | IL_8 | 0.000 |
| IFN_gamma | IL_10 | 0.000 | | IFN_gamma | IL_10 | 0.000 |
| IFN_gamma | IL_12p70 | 0.000 | | IFN_gamma | IL_12p70 | 0.000 |
| IFN_gamma | IL_13 | 0.000 | | IFN_gamma | IL_13 | 0.000 |
| IFN_gamma | IL_15 | 0.000 | | IFN_gamma | IL_15 | 0.000 |
| IFN_gamma | IL_17 | 0.000 | | IFN_gamma | IL_17 | 0.000 |
| IFN_gamma | IL_23 | 0.000 | | IFN_gamma | IL_23 | 0.000 |
| IFN_gamma | IFN_gamma | 1.000 | | IFN_gamma | IFN_gamma | 1.000 |
| IFN_gamma | TNF_alpha | 0.000 | | IFN_gamma | TNF_alpha | 0.000 |
| IFN_gamma | TNF_beta | 0.000 | | IFN_gamma | TNF_beta | 0.000 |
| IFN_gamma | Varicella_Int | 0.000 | | IFN_gamma | Varicella_Int | 0.000 |
| IFN_gamma | Measles_OD_DB_Int | 0.000 | | IFN_gamma | Measles_OD_DB_Int | 0.000 |
| IFN_gamma | Measles_Int | 0.000 | | IFN_gamma | Measles_Int | 0.000 |
| IFN_gamma | HepA_Int | 0.000 | | IFN_gamma | HepA_Int | 0.000 |
| IFN_gamma | Tetanus_Int | 0.000 | | IFN_gamma | Tetanus_Int | 0.000 |
| IFN_gamma | Diptheria_Int | 0.000 | | IFN_gamma | Diptheria_Int | 0.000 |
| IFN_gamma | Rubella_Int | 0.000 | | IFN_gamma | Rubella_Int | 0.000 |
| IFN_gamma | CMV_Int | 0.000 | | IFN_gamma | CMV_Int | 0.000 |
| IFN_gamma | HepB_cAb_Int | 0.000 | | IFN_gamma | HepB_cAb_Int | 0.000 |
| IFN_gamma | HepB_eAb_Int | 0.000 | | IFN_gamma | HepB_eAb_Int | 0.000 |
| IFN_gamma | HepB_eAg_Int | 0.000 | | IFN_gamma | HepB_eAg_Int | 0.000 |
| IFN_gamma | HepC_Int | 0.000 | | IFN_gamma | HepC_Int | 0.000 |
| IFN_gamma | Schistosoma_int | 0.000 | | IFN_gamma | Schistosoma_int | 0.000 |
| IFN_gamma | Strongyloides_Int | 0.000 | | IFN_gamma | Strongyloides_Int | 0.000 |
| IFN_gamma | Filaria_Int | 0.000 | | IFN_gamma | Filaria_Int | 0.000 |
| TNF_alpha | IL_1_alpha | -1.000 | | TNF_alpha | IL_1_alpha | -1.000 |
| TNF_alpha | IL_1_beta | 1.000 | | TNF_alpha | IL_1_beta | 1.000 |
| TNF_alpha | IL_2 | 1.000 | | TNF_alpha | IL_2 | 0.000 |
| TNF_alpha | IL_4 | -1.000 | | TNF_alpha | IL_4 | 0.000 |
| TNF_alpha | IL_5 | 1.000 | | TNF_alpha | IL_5 | -1.000 |

FIG. 21I11-H

| | | | | | | |
|---|---|---|---|---|---|---|
| TNF_alpha | IL_6 | 1.000 | | TNF_alpha | IL_6 | 1.000 |
| TNF_alpha | IL_8 | -1.000 | | TNF_alpha | IL_8 | 1.000 |
| TNF_alpha | IL_10 | 1.000 | | TNF_alpha | IL_10 | 1.000 |
| TNF_alpha | IL_12p70 | 1.000 | | TNF_alpha | IL_12p70 | 1.000 |
| TNF_alpha | IL_13 | 1.000 | | TNF_alpha | IL_13 | 1.000 |
| TNF_alpha | IL_15 | 1.000 | | TNF_alpha | IL_15 | 1.000 |
| TNF_alpha | IL_17 | 1.000 | | TNF_alpha | IL_17 | -1.000 |
| TNF_alpha | IL_23 | 1.000 | | TNF_alpha | IL_23 | 1.000 |
| TNF_alpha | IFN_gamma | 0.000 | | TNF_alpha | IFN_gamma | 0.000 |
| TNF_alpha | TNF_alpha | 1.000 | | TNF_alpha | TNF_alpha | 1.000 |
| TNF_alpha | TNF_beta | -1.000 | | TNF_alpha | TNF_beta | -1.000 |
| TNF_alpha | Varicella_Int | 0.000 | | TNF_alpha | Varicella_Int | 0.000 |
| TNF_alpha | Measles_OD_DB_Int | 1.000 | | TNF_alpha | Measles_OD_DB_Int | 1.000 |
| TNF_alpha | Measles_Int | 0.000 | | TNF_alpha | Measles_Int | 0.000 |
| TNF_alpha | HepA_Int | 1.000 | | TNF_alpha | HepA_Int | 0.000 |
| TNF_alpha | Tetanus_Int | 0.000 | | TNF_alpha | Tetanus_Int | 0.000 |
| TNF_alpha | Diptheria_Int | 0.000 | | TNF_alpha | Diptheria_Int | 0.000 |
| TNF_alpha | Rubella_Int | -1.000 | | TNF_alpha | Rubella_Int | 0.000 |
| TNF_alpha | CMV_Int | 0.000 | | TNF_alpha | CMV_Int | 0.000 |
| TNF_alpha | HepB_cAb_Int | 1.000 | | TNF_alpha | HepB_cAb_Int | 0.000 |
| TNF_alpha | HepB_eAb_Int | 0.000 | | TNF_alpha | HepB_eAb_Int | 0.000 |
| TNF_alpha | HepB_eAg_Int | 0.000 | | TNF_alpha | HepB_eAg_Int | 0.000 |
| TNF_alpha | HepC_Int | 0.000 | | TNF_alpha | HepC_Int | 0.000 |
| TNF_alpha | Schistosoma_int | 0.000 | | TNF_alpha | Schistosoma_int | -1.000 |
| TNF_alpha | Strongyloides_Int | -1.000 | | TNF_alpha | Strongyloides_Int | -1.000 |
| TNF_alpha | Filaria_Int | 0.000 | | TNF_alpha | Filaria_Int | 0.000 |
| TNF_beta | IL_1_alpha | 1.000 | | TNF_beta | IL_1_alpha | 1.000 |
| TNF_beta | IL_1_beta | -1.000 | | TNF_beta | IL_1_beta | -1.000 |
| TNF_beta | IL_2 | -1.000 | | TNF_beta | IL_2 | 0.000 |
| TNF_beta | IL_4 | 1.000 | | TNF_beta | IL_4 | 0.000 |
| TNF_beta | IL_5 | -1.000 | | TNF_beta | IL_5 | 1.000 |
| TNF_beta | IL_6 | -1.000 | | TNF_beta | IL_6 | -1.000 |
| TNF_beta | IL_8 | 1.000 | | TNF_beta | IL_8 | -1.000 |
| TNF_beta | IL_10 | -1.000 | | TNF_beta | IL_10 | -1.000 |
| TNF_beta | IL_12p70 | -1.000 | | TNF_beta | IL_12p70 | -1.000 |
| TNF_beta | IL_13 | -1.000 | | TNF_beta | IL_13 | -1.000 |
| TNF_beta | IL_15 | -1.000 | | TNF_beta | IL_15 | -1.000 |
| TNF_beta | IL_17 | -1.000 | | TNF_beta | IL_17 | 1.000 |
| TNF_beta | IL_23 | -1.000 | | TNF_beta | IL_23 | -1.000 |
| TNF_beta | IFN_gamma | 0.000 | | TNF_beta | IFN_gamma | 0.000 |
| TNF_beta | TNF_alpha | -1.000 | | TNF_beta | TNF_alpha | -1.000 |
| TNF_beta | TNF_beta | 1.000 | | TNF_beta | TNF_beta | 1.000 |
| TNF_beta | Varicella_Int | 0.000 | | TNF_beta | Varicella_Int | 0.000 |
| TNF_beta | Measles_OD_DB_Int | -1.000 | | TNF_beta | Measles_OD_DB_Int | -1.000 |
| TNF_beta | Measles_Int | 0.000 | | TNF_beta | Measles_Int | 0.000 |
| TNF_beta | HepA_Int | -1.000 | | TNF_beta | HepA_Int | 0.000 |
| TNF_beta | Tetanus_Int | 0.000 | | TNF_beta | Tetanus_Int | 0.000 |
| TNF_beta | Diptheria_Int | 0.000 | | TNF_beta | Diptheria_Int | 0.000 |
| TNF_beta | Rubella_Int | 1.000 | | TNF_beta | Rubella_Int | 0.000 |
| TNF_beta | CMV_Int | 0.000 | | TNF_beta | CMV_Int | 0.000 |
| TNF_beta | HepB_cAb_Int | -1.000 | | TNF_beta | HepB_cAb_Int | 0.000 |
| TNF_beta | HepB_eAb_Int | 0.000 | | TNF_beta | HepB_eAb_Int | 0.000 |
| TNF_beta | HepB_eAg_Int | 0.000 | | TNF_beta | HepB_eAg_Int | 0.000 |
| TNF_beta | HepC_Int | 0.000 | | TNF_beta | HepC_Int | 0.000 |
| TNF_beta | Schistosoma_int | 0.000 | | TNF_beta | Schistosoma_int | 1.000 |
| TNF_beta | Strongyloides_Int | 1.000 | | TNF_beta | Strongyloides_Int | 1.000 |
| TNF_beta | Filaria_Int | 0.000 | | TNF_beta | Filaria_Int | 0.000 |

FIG. 21I11-I

| Col1 | Col2 | Col3 |
|---|---|---|
| Varicella_Int | IL_1_alpha | 0.000 |
| Varicella_Int | IL_1_beta | 0.000 |
| Varicella_Int | IL_2 | 0.000 |
| Varicella_Int | IL_4 | 0.000 |
| Varicella_Int | IL_5 | 0.000 |
| Varicella_Int | IL_6 | 0.000 |
| Varicella_Int | IL_8 | 0.000 |
| Varicella_Int | IL_10 | 0.000 |
| Varicella_Int | IL_12p70 | 0.000 |
| Varicella_Int | IL_13 | 0.000 |
| Varicella_Int | IL_15 | 0.000 |
| Varicella_Int | IL_17 | 0.000 |
| Varicella_Int | IL_23 | 0.000 |
| Varicella_Int | IFN_gamma | 0.000 |
| Varicella_Int | TNF_alpha | 0.000 |
| Varicella_Int | TNF_beta | 0.000 |
| Varicella_Int | Varicella_Int | 1.000 |
| Varicella_Int | Measles_OD_DB_Int | 0.000 |
| Varicella_Int | Measles_Int | 0.000 |
| Varicella_Int | HepA_Int | 0.000 |
| Varicella_Int | Tetanus_Int | 0.000 |
| Varicella_Int | Diptheria_Int | 0.000 |
| Varicella_Int | Rubella_Int | 0.000 |
| Varicella_Int | CMV_Int | 0.000 |
| Varicella_Int | HepB_cAb_Int | 0.000 |
| Varicella_Int | HepB_eAb_Int | 0.000 |
| Varicella_Int | HepB_eAg_Int | 0.000 |
| Varicella_Int | HepC_Int | 0.000 |
| Varicella_Int | Schistosoma_int | 0.000 |
| Varicella_Int | Strongyloides_Int | 0.000 |
| Varicella_Int | Filaria_Int | 0.000 |
| Measles_OD_DB_Int | IL_1_alpha | -1.000 |
| Measles_OD_DB_Int | IL_1_beta | 1.000 |
| Measles_OD_DB_Int | IL_2 | 1.000 |
| Measles_OD_DB_Int | IL_4 | -1.000 |
| Measles_OD_DB_Int | IL_5 | 1.000 |
| Measles_OD_DB_Int | IL_6 | 1.000 |
| Measles_OD_DB_Int | IL_8 | -1.000 |
| Measles_OD_DB_Int | IL_10 | 1.000 |
| Measles_OD_DB_Int | IL_12p70 | 1.000 |
| Measles_OD_DB_Int | IL_13 | 1.000 |
| Measles_OD_DB_Int | IL_15 | 1.000 |
| Measles_OD_DB_Int | IL_17 | 1.000 |
| Measles_OD_DB_Int | IL_23 | 1.000 |
| Measles_OD_DB_Int | IFN_gamma | 0.000 |
| Measles_OD_DB_Int | TNF_alpha | 1.000 |
| Measles_OD_DB_Int | TNF_beta | -1.000 |
| Measles_OD_DB_Int | Varicella_Int | 0.000 |
| Measles_OD_DB_Int | Measles_OD_DB_Int | 1.000 |
| Measles_OD_DB_Int | Measles_Int | 0.000 |
| Measles_OD_DB_Int | HepA_Int | 1.000 |
| Measles_OD_DB_Int | Tetanus_Int | 0.000 |
| Measles_OD_DB_Int | Diptheria_Int | 0.000 |
| Measles_OD_DB_Int | Rubella_Int | -1.000 |
| Measles_OD_DB_Int | CMV_Int | 0.000 |
| Measles_OD_DB_Int | HepB_cAb_Int | 1.000 |
| Measles_OD_DB_Int | HepB_eAb_Int | 0.000 |

| Col1 | Col2 | Col3 |
|---|---|---|
| Varicella_Int | IL_1_alpha | 0.000 |
| Varicella_Int | IL_1_beta | 0.000 |
| Varicella_Int | IL_2 | 0.000 |
| Varicella_Int | IL_4 | 0.000 |
| Varicella_Int | IL_5 | 0.000 |
| Varicella_Int | IL_6 | 0.000 |
| Varicella_Int | IL_8 | 0.000 |
| Varicella_Int | IL_10 | 0.000 |
| Varicella_Int | IL_12p70 | 0.000 |
| Varicella_Int | IL_13 | 0.000 |
| Varicella_Int | IL_15 | 0.000 |
| Varicella_Int | IL_17 | 0.000 |
| Varicella_Int | IL_23 | 0.000 |
| Varicella_Int | IFN_gamma | 0.000 |
| Varicella_Int | TNF_alpha | 0.000 |
| Varicella_Int | TNF_beta | 0.000 |
| Varicella_Int | Varicella_Int | 1.000 |
| Varicella_Int | Measles_OD_DB_Int | 0.000 |
| Varicella_Int | Measles_Int | 0.000 |
| Varicella_Int | HepA_Int | 0.000 |
| Varicella_Int | Tetanus_Int | 0.000 |
| Varicella_Int | Diptheria_Int | 0.000 |
| Varicella_Int | Rubella_Int | 0.000 |
| Varicella_Int | CMV_Int | 0.000 |
| Varicella_Int | HepB_cAb_Int | 0.000 |
| Varicella_Int | HepB_eAb_Int | 0.000 |
| Varicella_Int | HepB_eAg_Int | 0.000 |
| Varicella_Int | HepC_Int | 0.000 |
| Varicella_Int | Schistosoma_int | 0.000 |
| Varicella_Int | Strongyloides_Int | 0.000 |
| Varicella_Int | Filaria_Int | 0.000 |
| Measles_OD_DB_Int | IL_1_alpha | -1.000 |
| Measles_OD_DB_Int | IL_1_beta | 1.000 |
| Measles_OD_DB_Int | IL_2 | 0.000 |
| Measles_OD_DB_Int | IL_4 | 0.000 |
| Measles_OD_DB_Int | IL_5 | -1.000 |
| Measles_OD_DB_Int | IL_6 | 1.000 |
| Measles_OD_DB_Int | IL_8 | 1.000 |
| Measles_OD_DB_Int | IL_10 | 1.000 |
| Measles_OD_DB_Int | IL_12p70 | 1.000 |
| Measles_OD_DB_Int | IL_13 | 1.000 |
| Measles_OD_DB_Int | IL_15 | 1.000 |
| Measles_OD_DB_Int | IL_17 | -1.000 |
| Measles_OD_DB_Int | IL_23 | 1.000 |
| Measles_OD_DB_Int | IFN_gamma | 0.000 |
| Measles_OD_DB_Int | TNF_alpha | 1.000 |
| Measles_OD_DB_Int | TNF_beta | -1.000 |
| Measles_OD_DB_Int | Varicella_Int | 0.000 |
| Measles_OD_DB_Int | Measles_OD_DB_Int | 1.000 |
| Measles_OD_DB_Int | Measles_Int | 0.000 |
| Measles_OD_DB_Int | HepA_Int | 0.000 |
| Measles_OD_DB_Int | Tetanus_Int | 0.000 |
| Measles_OD_DB_Int | Diptheria_Int | 0.000 |
| Measles_OD_DB_Int | Rubella_Int | 0.000 |
| Measles_OD_DB_Int | CMV_Int | 0.000 |
| Measles_OD_DB_Int | HepB_cAb_Int | 0.000 |
| Measles_OD_DB_Int | HepB_eAb_Int | 0.000 |

FIG. 21I11-J

| | | | | | | |
|---|---|---|---|---|---|---|
| Measles_OD_DB_Int | HepB_eAg_Int | 0.000 | | Measles_OD_DB_Int | HepB_eAg_Int | 0.000 |
| Measles_OD_DB_Int | HepC_Int | 0.000 | | Measles_OD_DB_Int | HepC_Int | 0.000 |
| Measles_OD_DB_Int | Schistosoma_int | 0.000 | | Measles_OD_DB_Int | Schistosoma_int | -1.000 |
| Measles_OD_DB_Int | Strongyloides_Int | -1.000 | | Measles_OD_DB_Int | Strongyloides_Int | -1.000 |
| Measles_OD_DB_Int | Filaria_Int | 0.000 | | Measles_OD_DB_Int | Filaria_Int | 0.000 |
| Measles_Int | IL_1_alpha | 0.000 | | Measles_Int | IL_1_alpha | 0.000 |
| Measles_Int | IL_1_beta | 0.000 | | Measles_Int | IL_1_beta | 0.000 |
| Measles_Int | IL_2 | 0.000 | | Measles_Int | IL_2 | 0.000 |
| Measles_Int | IL_4 | 0.000 | | Measles_Int | IL_4 | 0.000 |
| Measles_Int | IL_5 | 0.000 | | Measles_Int | IL_5 | 0.000 |
| Measles_Int | IL_6 | 0.000 | | Measles_Int | IL_6 | 0.000 |
| Measles_Int | IL_8 | 0.000 | | Measles_Int | IL_8 | 0.000 |
| Measles_Int | IL_10 | 0.000 | | Measles_Int | IL_10 | 0.000 |
| Measles_Int | IL_12p70 | 0.000 | | Measles_Int | IL_12p70 | 0.000 |
| Measles_Int | IL_13 | 0.000 | | Measles_Int | IL_13 | 0.000 |
| Measles_Int | IL_15 | 0.000 | | Measles_Int | IL_15 | 0.000 |
| Measles_Int | IL_17 | 0.000 | | Measles_Int | IL_17 | 0.000 |
| Measles_Int | IL_23 | 0.000 | | Measles_Int | IL_23 | 0.000 |
| Measles_Int | IFN_gamma | 0.000 | | Measles_Int | IFN_gamma | 0.000 |
| Measles_Int | TNF_alpha | 0.000 | | Measles_Int | TNF_alpha | 0.000 |
| Measles_Int | TNF_beta | 0.000 | | Measles_Int | TNF_beta | 0.000 |
| Measles_Int | Varicella_Int | 0.000 | | Measles_Int | Varicella_Int | 0.000 |
| Measles_Int | Measles_OD_DB_Int | 0.000 | | Measles_Int | Measles_OD_DB_Int | 0.000 |
| Measles_Int | Measles_Int | 1.000 | | Measles_Int | Measles_Int | 1.000 |
| Measles_Int | HepA_Int | 0.000 | | Measles_Int | HepA_int | 0.000 |
| Measles_Int | Tetanus_Int | 0.000 | | Measles_Int | Tetanus_Int | 0.000 |
| Measles_Int | Diptheria_Int | 0.000 | | Measles_Int | Diptheria_Int | 0.000 |
| Measles_Int | Rubella_Int | 0.000 | | Measles_Int | Rubella_Int | 0.000 |
| Measles_Int | CMV_Int | 0.000 | | Measles_Int | CMV_Int | 0.000 |
| Measles_Int | HepB_cAb_Int | 0.000 | | Measles_Int | HepB_cAb_Int | 0.000 |
| Measles_Int | HepB_eAb_Int | 0.000 | | Measles_Int | HepB_eAb_Int | 0.000 |
| Measles_Int | HepB_eAg_Int | 0.000 | | Measles_Int | HepB_eAg_Int | 0.000 |
| Measles_Int | HepC_Int | 0.000 | | Measles_Int | HepC_Int | 0.000 |
| Measles_Int | Schistosoma_int | 0.000 | | Measles_Int | Schistosoma_int | 0.000 |
| Measles_Int | Strongyloides_Int | 0.000 | | Measles_Int | Strongyloides_Int | 0.000 |
| Measles_Int | Filaria_Int | 0.000 | | Measles_Int | Filaria_Int | 0.000 |
| HepA_Int | IL_1_alpha | -1.000 | | HepA_Int | IL_1_alpha | 0.000 |
| HepA_Int | IL_1_beta | 1.000 | | HepA_Int | IL_1_beta | 0.000 |
| HepA_Int | IL_2 | 1.000 | | HepA_Int | IL_2 | 0.000 |
| HepA_Int | IL_4 | -1.000 | | HepA_Int | IL_4 | 0.000 |
| HepA_Int | IL_5 | 1.000 | | HepA_Int | IL_5 | 0.000 |
| HepA_Int | IL_6 | 1.000 | | HepA_Int | IL_6 | 0.000 |
| HepA_Int | IL_8 | -1.000 | | HepA_Int | IL_8 | 0.000 |
| HepA_Int | IL_10 | 1.000 | | HepA_Int | IL_10 | 0.000 |
| HepA_Int | IL_12p70 | 1.000 | | HepA_Int | IL_12p70 | 0.000 |
| HepA_Int | IL_13 | 1.000 | | HepA_Int | IL_13 | 0.000 |
| HepA_Int | IL_15 | 1.000 | | HepA_Int | IL_15 | 0.000 |
| HepA_Int | IL_17 | 1.000 | | HepA_Int | IL_17 | 0.000 |
| HepA_Int | IL_23 | 1.000 | | HepA_Int | IL_23 | 0.000 |
| HepA_Int | IFN_gamma | 0.000 | | HepA_Int | IFN_gamma | 0.000 |
| HepA_Int | TNF_alpha | 1.000 | | HepA_Int | TNF_alpha | 0.000 |
| HepA_Int | TNF_beta | -1.000 | | HepA_Int | TNF_beta | 0.000 |
| HepA_Int | Varicella_Int | 0.000 | | HepA_Int | Varicella_Int | 0.000 |
| HepA_Int | Measles_OD_DB_Int | 1.000 | | HepA_Int | Measles_OD_DB_Int | 0.000 |
| HepA_Int | Measles_Int | 0.000 | | HepA_Int | Measles_Int | 0.000 |
| HepA_Int | HepA_Int | 1.000 | | HepA_Int | HepA_Int | 1.000 |
| HepA_Int | Tetanus_Int | 0.000 | | HepA_Int | Tetanus_Int | 0.000 |

FIG. 21I11-K

| | | | | | | |
|---|---|---|---|---|---|---|
| HepA_Int | Diptheria_Int | 0.000 | | HepA_Int | Diptheria_Int | 0.000 |
| HepA_Int | Rubella_Int | -1.000 | | HepA_Int | Rubella_Int | 0.000 |
| HepA_Int | CMV_Int | 0.000 | | HepA_Int | CMV_Int | 0.000 |
| HepA_Int | HepB_cAb_Int | 1.000 | | HepA_Int | HepB_cAb_Int | 0.000 |
| HepA_Int | HepB_eAb_Int | 0.000 | | HepA_Int | HepB_eAb_Int | 0.000 |
| HepA_Int | HepB_eAg_Int | 0.000 | | HepA_Int | HepB_eAg_Int | 0.000 |
| HepA_Int | HepC_Int | 0.000 | | HepA_Int | HepC_Int | 0.000 |
| HepA_Int | Schistosoma_int | 0.000 | | HepA_Int | Schistosoma_int | 0.000 |
| HepA_Int | Strongyloides_Int | -1.000 | | HepA_Int | Strongyloides_Int | 0.000 |
| HepA_Int | Filaria_Int | 0.000 | | HepA_Int | Filaria_Int | 0.000 |
| Tetanus_Int | IL_1_alpha | 0.000 | | Tetanus_Int | IL_1_alpha | 0.000 |
| Tetanus_Int | IL_1_beta | 0.000 | | Tetanus_Int | IL_1_beta | 0.000 |
| Tetanus_Int | IL_2 | 0.000 | | Tetanus_Int | IL_2 | 0.000 |
| Tetanus_Int | IL_4 | 0.000 | | Tetanus_Int | IL_4 | 0.000 |
| Tetanus_Int | IL_5 | 0.000 | | Tetanus_Int | IL_5 | 0.000 |
| Tetanus_Int | IL_6 | 0.000 | | Tetanus_Int | IL_6 | 0.000 |
| Tetanus_Int | IL_8 | 0.000 | | Tetanus_Int | IL_8 | 0.000 |
| Tetanus_Int | IL_10 | 0.000 | | Tetanus_Int | IL_10 | 0.000 |
| Tetanus_Int | IL_12p70 | 0.000 | | Tetanus_Int | IL_12p70 | 0.000 |
| Tetanus_Int | IL_13 | 0.000 | | Tetanus_Int | IL_13 | 0.000 |
| Tetanus_Int | IL_15 | 0.000 | | Tetanus_Int | IL_15 | 0.000 |
| Tetanus_Int | IL_17 | 0.000 | | Tetanus_Int | IL_17 | 0.000 |
| Tetanus_Int | IL_23 | 0.000 | | Tetanus_Int | IL_23 | 0.000 |
| Tetanus_Int | IFN_gamma | 0.000 | | Tetanus_Int | IFN_gamma | 0.000 |
| Tetanus_Int | TNF_alpha | 0.000 | | Tetanus_Int | TNF_alpha | 0.000 |
| Tetanus_Int | TNF_beta | 0.000 | | Tetanus_Int | TNF_beta | 0.000 |
| Tetanus_Int | Varicella_Int | 0.000 | | Tetanus_Int | Varicella_Int | 0.000 |
| Tetanus_Int | Measles_OD_DB_Int | 0.000 | | Tetanus_Int | Measles_OD_DB_Int | 0.000 |
| Tetanus_Int | Measles_Int | 0.000 | | Tetanus_Int | Measles_Int | 0.000 |
| Tetanus_Int | HepA_Int | 0.000 | | Tetanus_Int | HepA_Int | 0.000 |
| Tetanus_Int | Tetanus_Int | 1.000 | | Tetanus_Int | Tetanus_Int | 1.000 |
| Tetanus_Int | Diptheria_Int | 0.000 | | Tetanus_Int | Diptheria_Int | 0.000 |
| Tetanus_Int | Rubella_Int | 0.000 | | Tetanus_Int | Rubella_Int | 0.000 |
| Tetanus_Int | CMV_Int | 0.000 | | Tetanus_Int | CMV_Int | 0.000 |
| Tetanus_Int | HepB_cAb_Int | 0.000 | | Tetanus_Int | HepB_cAb_Int | 0.000 |
| Tetanus_Int | HepB_eAb_Int | 0.000 | | Tetanus_Int | HepB_eAb_Int | 0.000 |
| Tetanus_Int | HepB_eAg_Int | 0.000 | | Tetanus_Int | HepB_eAg_Int | 0.000 |
| Tetanus_Int | HepC_Int | 0.000 | | Tetanus_Int | HepC_Int | 0.000 |
| Tetanus_Int | Schistosoma_int | 0.000 | | Tetanus_Int | Schistosoma_int | 0.000 |
| Tetanus_Int | Strongyloides_Int | 0.000 | | Tetanus_Int | Strongyloides_Int | 0.000 |
| Tetanus_Int | Filaria_Int | 0.000 | | Tetanus_Int | Filaria_Int | 0.000 |
| Diptheria_Int | IL_1_alpha | 0.000 | | Diptheria_Int | IL_1_alpha | 0.000 |
| Diptheria_Int | IL_1_beta | 0.000 | | Diptheria_Int | IL_1_beta | 0.000 |
| Diptheria_Int | IL_2 | 0.000 | | Diptheria_Int | IL_2 | 0.000 |
| Diptheria_Int | IL_4 | 0.000 | | Diptheria_Int | IL_4 | 0.000 |
| Diptheria_Int | IL_5 | 0.000 | | Diptheria_Int | IL_5 | 0.000 |
| Diptheria_Int | IL_6 | 0.000 | | Diptheria_Int | IL_6 | 0.000 |
| Diptheria_Int | IL_8 | 0.000 | | Diptheria_Int | IL_8 | 0.000 |
| Diptheria_Int | IL_10 | 0.000 | | Diptheria_Int | IL_10 | 0.000 |
| Diptheria_Int | IL_12p70 | 0.000 | | Diptheria_Int | IL_12p70 | 0.000 |
| Diptheria_Int | IL_13 | 0.000 | | Diptheria_Int | IL_13 | 0.000 |
| Diptheria_Int | IL_15 | 0.000 | | Diptheria_Int | IL_15 | 0.000 |
| Diptheria_Int | IL_17 | 0.000 | | Diptheria_Int | IL_17 | 0.000 |
| Diptheria_Int | IL_23 | 0.000 | | Diptheria_Int | IL_23 | 0.000 |
| Diptheria_Int | IFN_gamma | 0.000 | | Diptheria_Int | IFN_gamma | 0.000 |
| Diptheria_Int | TNF_alpha | 0.000 | | Diptheria_Int | TNF_alpha | 0.000 |
| Diptheria_Int | TNF_beta | 0.000 | | Diptheria_Int | TNF_beta | 0.000 |

FIG. 21I11-L

| | | | | | | |
|---|---|---|---|---|---|---|
| Diptheria_Int | Varicella_Int | 0.000 | | Diptheria_Int | Varicella_Int | 0.000 |
| Diptheria_Int | Measles_OD_DB_Int | 0.000 | | Diptheria_Int | Measles_OD_DB_Int | 0.000 |
| Diptheria_Int | Measles_Int | 0.000 | | Diptheria_Int | Measles_Int | 0.000 |
| Diptheria_Int | HepA_Int | 0.000 | | Diptheria_Int | HepA_Int | 0.000 |
| Diptheria_Int | Tetanus_Int | 0.000 | | Diptheria_Int | Tetanus_Int | 0.000 |
| Diptheria_Int | Diptheria_Int | 1.000 | | Diptheria_Int | Diptheria_Int | 1.000 |
| Diptheria_Int | Rubella_Int | 0.000 | | Diptheria_Int | Rubella_Int | 0.000 |
| Diptheria_Int | CMV_Int | 0.000 | | Diptheria_Int | CMV_Int | 0.000 |
| Diptheria_Int | HepB_cAb_Int | 0.000 | | Diptheria_Int | HepB_cAb_Int | 0.000 |
| Diptheria_Int | HepB_eAb_Int | 0.000 | | Diptheria_Int | HepB_eAb_Int | 0.000 |
| Diptheria_Int | HepB_eAg_Int | 0.000 | | Diptheria_Int | HepB_eAg_Int | 0.000 |
| Diptheria_Int | HepC_Int | 0.000 | | Diptheria_Int | HepC_Int | 0.000 |
| Diptheria_Int | Schistosoma_int | 0.000 | | Diptheria_Int | Schistosoma_int | 0.000 |
| Diptheria_Int | Strongyloides_Int | 0.000 | | Diptheria_Int | Strongyloides_Int | 0.000 |
| Diptheria_Int | Filaria_Int | 0.000 | | Diptheria_Int | Filaria_Int | 0.000 |
| Rubella_Int | IL_1_alpha | 1.000 | | Rubella_Int | IL_1_alpha | 0.000 |
| Rubella_Int | IL_1_beta | -1.000 | | Rubella_Int | IL_1_beta | 0.000 |
| Rubella_Int | IL_2 | -1.000 | | Rubella_Int | IL_2 | 0.000 |
| Rubella_Int | IL_4 | 1.000 | | Rubella_Int | IL_4 | 0.000 |
| Rubella_Int | IL_5 | -1.000 | | Rubella_Int | IL_5 | 0.000 |
| Rubella_Int | IL_6 | -1.000 | | Rubella_Int | IL_6 | 0.000 |
| Rubella_Int | IL_8 | 1.000 | | Rubella_Int | IL_8 | 0.000 |
| Rubella_Int | IL_10 | -1.000 | | Rubella_Int | IL_10 | 0.000 |
| Rubella_Int | IL_12p70 | -1.000 | | Rubella_Int | IL_12p70 | 0.000 |
| Rubella_Int | IL_13 | -1.000 | | Rubella_Int | IL_13 | 0.000 |
| Rubella_Int | IL_15 | -1.000 | | Rubella_Int | IL_15 | 0.000 |
| Rubella_Int | IL_17 | -1.000 | | Rubella_Int | IL_17 | 0.000 |
| Rubella_Int | IL_23 | -1.000 | | Rubella_Int | IL_23 | 0.000 |
| Rubella_Int | IFN_gamma | 0.000 | | Rubella_Int | IFN_gamma | 0.000 |
| Rubella_Int | TNF_alpha | -1.000 | | Rubella_Int | TNF_alpha | 0.000 |
| Rubella_Int | TNF_beta | 1.000 | | Rubella_Int | TNF_beta | 0.000 |
| Rubella_Int | Varicella_Int | 0.000 | | Rubella_Int | Varicella_Int | 0.000 |
| Rubella_Int | Measles_OD_DB_Int | -1.000 | | Rubella_Int | Measles_OD_DB_Int | 0.000 |
| Rubella_Int | Measles_Int | 0.000 | | Rubella_Int | Measles_Int | 0.000 |
| Rubella_Int | HepA_Int | -1.000 | | Rubella_Int | HepA_Int | 0.000 |
| Rubella_Int | Tetanus_Int | 0.000 | | Rubella_Int | Tetanus_Int | 0.000 |
| Rubella_Int | Diptheria_Int | 0.000 | | Rubella_Int | Diptheria_Int | 0.000 |
| Rubella_Int | Rubella_Int | 1.000 | | Rubella_Int | Rubella_Int | 1.000 |
| Rubella_Int | CMV_Int | 0.000 | | Rubella_Int | CMV_Int | 0.000 |
| Rubella_Int | HepB_cAb_Int | -1.000 | | Rubella_Int | HepB_cAb_Int | 0.000 |
| Rubella_Int | HepB_eAb_Int | 0.000 | | Rubella_Int | HepB_eAb_Int | 0.000 |
| Rubella_Int | HepB_eAg_Int | 0.000 | | Rubella_Int | HepB_eAg_Int | 0.000 |
| Rubella_Int | HepC_Int | 0.000 | | Rubella_Int | HepC_Int | 0.000 |
| Rubella_Int | Schistosoma_int | 0.000 | | Rubella_Int | Schistosoma_int | 0.000 |
| Rubella_Int | Strongyloides_Int | 1.000 | | Rubella_Int | Strongyloides_Int | 0.000 |
| Rubella_Int | Filaria_Int | 0.000 | | Rubella_Int | Filaria_Int | 0.000 |
| CMV_Int | IL_1_alpha | 0.000 | | CMV_Int | IL_1_alpha | 0.000 |
| CMV_Int | IL_1_beta | 0.000 | | CMV_Int | IL_1_beta | 0.000 |
| CMV_Int | IL_2 | 0.000 | | CMV_Int | IL_2 | 0.000 |
| CMV_Int | IL_4 | 0.000 | | CMV_Int | IL_4 | 0.000 |
| CMV_Int | IL_5 | 0.000 | | CMV_Int | IL_5 | 0.000 |
| CMV_Int | IL_6 | 0.000 | | CMV_Int | IL_6 | 0.000 |
| CMV_Int | IL_8 | 0.000 | | CMV_Int | IL_8 | 0.000 |
| CMV_Int | IL_10 | 0.000 | | CMV_Int | IL_10 | 0.000 |
| CMV_Int | IL_12p70 | 0.000 | | CMV_Int | IL_12p70 | 0.000 |
| CMV_Int | IL_13 | 0.000 | | CMV_Int | IL_13 | 0.000 |
| CMV_Int | IL_15 | 0.000 | | CMV_Int | IL_15 | 0.000 |

FIG. 21I11-M

| | | | | | | |
|---|---|---|---|---|---|---|
| CMV_Int | IL_17 | 0.000 | | CMV_Int | IL_17 | 0.000 |
| CMV_Int | IL_23 | 0.000 | | CMV_Int | IL_23 | 0.000 |
| CMV_Int | IFN_gamma | 0.000 | | CMV_Int | IFN_gamma | 0.000 |
| CMV_Int | TNF_alpha | 0.000 | | CMV_Int | TNF_alpha | 0.000 |
| CMV_Int | TNF_beta | 0.000 | | CMV_Int | TNF_beta | 0.000 |
| CMV_Int | Varicella_Int | 0.000 | | CMV_Int | Varicella_Int | 0.000 |
| CMV_Int | Measles_OD_DB_Int | 0.000 | | CMV_Int | Measles_OD_DB_Int | 0.000 |
| CMV_Int | Measles_Int | 0.000 | | CMV_Int | Measles_Int | 0.000 |
| CMV_Int | HepA_Int | 0.000 | | CMV_Int | HepA_Int | 0.000 |
| CMV_Int | Tetanus_Int | 0.000 | | CMV_Int | Tetanus_Int | 0.000 |
| CMV_Int | Diptheria_Int | 0.000 | | CMV_Int | Diptheria_Int | 0.000 |
| CMV_Int | Rubella_Int | 0.000 | | CMV_Int | Rubella_Int | 0.000 |
| CMV_Int | CMV_Int | 1.000 | | CMV_Int | CMV_Int | 1.000 |
| CMV_Int | HepB_cAb_Int | 0.000 | | CMV_Int | HepB_cAb_Int | 0.000 |
| CMV_Int | HepB_eAb_Int | 0.000 | | CMV_Int | HepB_eAb_Int | 0.000 |
| CMV_Int | HepB_eAg_Int | 0.000 | | CMV_Int | HepB_eAg_Int | 0.000 |
| CMV_Int | HepC_Int | 0.000 | | CMV_Int | HepC_Int | 0.000 |
| CMV_Int | Schistosoma_int | 0.000 | | CMV_Int | Schistosoma_int | 0.000 |
| CMV_Int | Strongyloides_Int | 0.000 | | CMV_Int | Strongyloides_Int | 0.000 |
| CMV_Int | Filaria_Int | 0.000 | | CMV_Int | Filaria_Int | 0.000 |
| HepB_cAb_Int | IL_1_alpha | -1.000 | | HepB_cAb_Int | IL_1_alpha | 0.000 |
| HepB_cAb_Int | IL_1_beta | 1.000 | | HepB_cAb_Int | IL_1_beta | 0.000 |
| HepB_cAb_Int | IL_2 | 1.000 | | HepB_cAb_Int | IL_2 | 0.000 |
| HepB_cAb_Int | IL_4 | -1.000 | | HepB_cAb_Int | IL_4 | 0.000 |
| HepB_cAb_Int | IL_5 | 1.000 | | HepB_cAb_Int | IL_5 | 0.000 |
| HepB_cAb_Int | IL_6 | 1.000 | | HepB_cAb_Int | IL_6 | 0.000 |
| HepB_cAb_Int | IL_8 | -1.000 | | HepB_cAb_Int | IL_8 | 0.000 |
| HepB_cAb_Int | IL_10 | 1.000 | | HepB_cAb_Int | IL_10 | 0.000 |
| HepB_cAb_Int | IL_12p70 | 1.000 | | HepB_cAb_Int | IL_12p70 | 0.000 |
| HepB_cAb_Int | IL_13 | 1.000 | | HepB_cAb_Int | IL_13 | 0.000 |
| HepB_cAb_Int | IL_15 | 1.000 | | HepB_cAb_Int | IL_15 | 0.000 |
| HepB_cAb_Int | IL_17 | 1.000 | | HepB_cAb_Int | IL_17 | 0.000 |
| HepB_cAb_Int | IL_23 | 1.000 | | HepB_cAb_Int | IL_23 | 0.000 |
| HepB_cAb_Int | IFN_gamma | 0.000 | | HepB_cAb_Int | IFN_gamma | 0.000 |
| HepB_cAb_Int | TNF_alpha | 1.000 | | HepB_cAb_Int | TNF_alpha | 0.000 |
| HepB_cAb_Int | TNF_beta | -1.000 | | HepB_cAb_Int | TNF_beta | 0.000 |
| HepB_cAb_Int | Varicella_Int | 0.000 | | HepB_cAb_Int | Varicella_Int | 0.000 |
| HepB_cAb_Int | Measles_OD_DB_Int | 1.000 | | HepB_cAb_Int | Measles_OD_DB_Int | 0.000 |
| HepB_cAb_Int | Measles_Int | 0.000 | | HepB_cAb_Int | Measles_Int | 0.000 |
| HepB_cAb_Int | HepA_Int | 1.000 | | HepB_cAb_Int | HepA_Int | 0.000 |
| HepB_cAb_Int | Tetanus_Int | 0.000 | | HepB_cAb_Int | Tetanus_Int | 0.000 |
| HepB_cAb_Int | Diptheria_Int | 0.000 | | HepB_cAb_Int | Diptheria_Int | 0.000 |
| HepB_cAb_Int | Rubella_Int | -1.000 | | HepB_cAb_Int | Rubella_Int | 0.000 |
| HepB_cAb_Int | CMV_Int | 0.000 | | HepB_cAb_Int | CMV_Int | 0.000 |
| HepB_cAb_Int | HepB_cAb_Int | 1.000 | | HepB_cAb_Int | HepB_cAb_Int | 1.000 |
| HepB_cAb_Int | HepB_eAb_Int | 0.000 | | HepB_cAb_Int | HepB_eAb_Int | 0.000 |
| HepB_cAb_Int | HepB_eAg_Int | 0.000 | | HepB_cAb_Int | HepB_eAg_Int | 0.000 |
| HepB_cAb_Int | HepC_Int | 0.000 | | HepB_cAb_Int | HepC_Int | 0.000 |
| HepB_cAb_Int | Schistosoma_int | 0.000 | | HepB_cAb_Int | Schistosoma_int | 0.000 |
| HepB_cAb_Int | Strongyloides_Int | -1.000 | | HepB_cAb_Int | Strongyloides_Int | 0.000 |
| HepB_cAb_Int | Filaria_Int | 0.000 | | HepB_cAb_Int | Filaria_Int | 0.000 |
| HepB_eAb_Int | IL_1_alpha | 0.000 | | HepB_eAb_Int | IL_1_alpha | 0.000 |
| HepB_eAb_Int | IL_1_beta | 0.000 | | HepB_eAb_Int | IL_1_beta | 0.000 |
| HepB_eAb_Int | IL_2 | 0.000 | | HepB_eAb_Int | IL_2 | 0.000 |
| HepB_eAb_Int | IL_4 | 0.000 | | HepB_eAb_Int | IL_4 | 0.000 |
| HepB_eAb_Int | IL_5 | 0.000 | | HepB_eAb_Int | IL_5 | 0.000 |
| HepB_eAb_Int | IL_6 | 0.000 | | HepB_eAb_Int | IL_6 | 0.000 |

FIG. 21I11-N

| | | | | | | |
|---|---|---|---|---|---|---|
| HepB_eAb_Int | IL_8 | 0.000 | | HepB_eAb_Int | IL_8 | 0.000 |
| HepB_eAb_Int | IL_10 | 0.000 | | HepB_eAb_Int | IL_10 | 0.000 |
| HepB_eAb_Int | IL_12p70 | 0.000 | | HepB_eAb_Int | IL_12p70 | 0.000 |
| HepB_eAb_Int | IL_13 | 0.000 | | HepB_eAb_Int | IL_13 | 0.000 |
| HepB_eAb_Int | IL_15 | 0.000 | | HepB_eAb_Int | IL_15 | 0.000 |
| HepB_eAb_Int | IL_17 | 0.000 | | HepB_eAb_Int | IL_17 | 0.000 |
| HepB_eAb_Int | IL_23 | 0.000 | | HepB_eAb_Int | IL_23 | 0.000 |
| HepB_eAb_Int | IFN_gamma | 0.000 | | HepB_eAb_Int | IFN_gamma | 0.000 |
| HepB_eAb_Int | TNF_alpha | 0.000 | | HepB_eAb_Int | TNF_alpha | 0.000 |
| HepB_eAb_Int | TNF_beta | 0.000 | | HepB_eAb_Int | TNF_beta | 0.000 |
| HepB_eAb_Int | Varicella_Int | 0.000 | | HepB_eAb_Int | Varicella_Int | 0.000 |
| HepB_eAb_Int | Measles_OD_DB_Int | 0.000 | | HepB_eAb_Int | Measles_OD_DB_Int | 0.000 |
| HepB_eAb_Int | Measles_Int | 0.000 | | HepB_eAb_Int | Measles_Int | 0.000 |
| HepB_eAb_Int | HepA_Int | 0.000 | | HepB_eAb_Int | HepA_Int | 0.000 |
| HepB_eAb_Int | Tetanus_Int | 0.000 | | HepB_eAb_Int | Tetanus_Int | 0.000 |
| HepB_eAb_Int | Diptheria_Int | 0.000 | | HepB_eAb_Int | Diptheria_Int | 0.000 |
| HepB_eAb_Int | Rubella_Int | 0.000 | | HepB_eAb_Int | Rubella_Int | 0.000 |
| HepB_eAb_Int | CMV_Int | 0.000 | | HepB_eAb_Int | CMV_Int | 0.000 |
| HepB_eAb_Int | HepB_cAb_Int | 0.000 | | HepB_eAb_Int | HepB_cAb_Int | 0.000 |
| HepB_eAb_Int | HepB_eAb_Int | 1.000 | | HepB_eAb_Int | HepB_eAb_Int | 1.000 |
| HepB_eAb_Int | HepB_eAg_Int | 0.000 | | HepB_eAb_Int | HepB_eAg_Int | 0.000 |
| HepB_eAb_Int | HepC_Int | 0.000 | | HepB_eAb_Int | HepC_Int | 0.000 |
| HepB_eAb_Int | Schistosoma_int | 0.000 | | HepB_eAb_Int | Schistosoma_int | 0.000 |
| HepB_eAb_Int | Strongyloides_Int | 0.000 | | HepB_eAb_Int | Strongyloides_Int | 0.000 |
| HepB_eAb_Int | Filaria_Int | 0.000 | | HepB_eAb_Int | Filaria_Int | 0.000 |
| HepB_eAg_Int | IL_1_alpha | 0.000 | | HepB_eAg_Int | IL_1_alpha | 0.000 |
| HepB_eAg_Int | IL_1_beta | 0.000 | | HepB_eAg_Int | IL_1_beta | 0.000 |
| HepB_eAg_Int | IL_2 | 0.000 | | HepB_eAg_Int | IL_2 | 0.000 |
| HepB_eAg_Int | IL_4 | 0.000 | | HepB_eAg_Int | IL_4 | 0.000 |
| HepB_eAg_Int | IL_5 | 0.000 | | HepB_eAg_Int | IL_5 | 0.000 |
| HepB_eAg_Int | IL_6 | 0.000 | | HepB_eAg_Int | IL_6 | 0.000 |
| HepB_eAg_Int | IL_8 | 0.000 | | HepB_eAg_Int | IL_8 | 0.000 |
| HepB_eAg_Int | IL_10 | 0.000 | | HepB_eAg_Int | IL_10 | 0.000 |
| HepB_eAg_Int | IL_12p70 | 0.000 | | HepB_eAg_Int | IL_12p70 | 0.000 |
| HepB_eAg_Int | IL_13 | 0.000 | | HepB_eAg_Int | IL_13 | 0.000 |
| HepB_eAg_Int | IL_15 | 0.000 | | HepB_eAg_Int | IL_15 | 0.000 |
| HepB_eAg_Int | IL_17 | 0.000 | | HepB_eAg_Int | IL_17 | 0.000 |
| HepB_eAg_Int | IL_23 | 0.000 | | HepB_eAg_Int | IL_23 | 0.000 |
| HepB_eAg_Int | IFN_gamma | 0.000 | | HepB_eAg_Int | IFN_gamma | 0.000 |
| HepB_eAg_Int | TNF_alpha | 0.000 | | HepB_eAg_Int | TNF_alpha | 0.000 |
| HepB_eAg_Int | TNF_beta | 0.000 | | HepB_eAg_Int | TNF_beta | 0.000 |
| HepB_eAg_Int | Varicella_Int | 0.000 | | HepB_eAg_Int | Varicella_Int | 0.000 |
| HepB_eAg_Int | Measles_OD_DB_Int | 0.000 | | HepB_eAg_Int | Measles_OD_DB_Int | 0.000 |
| HepB_eAg_Int | Measles_Int | 0.000 | | HepB_eAg_Int | Measles_Int | 0.000 |
| HepB_eAg_Int | HepA_Int | 0.000 | | HepB_eAg_Int | HepA_Int | 0.000 |
| HepB_eAg_Int | Tetanus_Int | 0.000 | | HepB_eAg_Int | Tetanus_Int | 0.000 |
| HepB_eAg_Int | Diptheria_Int | 0.000 | | HepB_eAg_Int | Diptheria_Int | 0.000 |
| HepB_eAg_Int | Rubella_Int | 0.000 | | HepB_eAg_Int | Rubella_Int | 0.000 |
| HepB_eAg_Int | CMV_Int | 0.000 | | HepB_eAg_Int | CMV_Int | 0.000 |
| HepB_eAg_Int | HepB_cAb_Int | 0.000 | | HepB_eAg_Int | HepB_cAb_Int | 0.000 |
| HepB_eAg_Int | HepB_eAb_Int | 0.000 | | HepB_eAg_Int | HepB_eAb_Int | 0.000 |
| HepB_eAg_Int | HepB_eAg_Int | 1.000 | | HepB_eAg_Int | HepB_eAg_Int | 1.000 |
| HepB_eAg_Int | HepC_Int | 0.000 | | HepB_eAg_Int | HepC_Int | 0.000 |
| HepB_eAg_Int | Schistosoma_int | 0.000 | | HepB_eAg_Int | Schistosoma_int | 0.000 |
| HepB_eAg_Int | Strongyloides_Int | 0.000 | | HepB_eAg_Int | Strongyloides_Int | 0.000 |
| HepB_eAg_Int | Filaria_Int | 0.000 | | HepB_eAg_Int | Filaria_Int | 0.000 |
| HepC_Int | IL_1_alpha | 0.000 | | HepC_Int | IL_1_alpha | 0.000 |

FIG. 21I11-O

| | | | | | | |
|---|---|---|---|---|---|---|
| HepC_Int | IL_1_beta | 0.000 | | HepC_Int | IL_1_beta | 0.000 |
| HepC_Int | IL_2 | 0.000 | | HepC_Int | IL_2 | 0.000 |
| HepC_Int | IL_4 | 0.000 | | HepC_Int | IL_4 | 0.000 |
| HepC_Int | IL_5 | 0.000 | | HepC_Int | IL_5 | 0.000 |
| HepC_Int | IL_6 | 0.000 | | HepC_Int | IL_6 | 0.000 |
| HepC_Int | IL_8 | 0.000 | | HepC_Int | IL_8 | 0.000 |
| HepC_Int | IL_10 | 0.000 | | HepC_Int | IL_10 | 0.000 |
| HepC_Int | IL_12p70 | 0.000 | | HepC_Int | IL_12p70 | 0.000 |
| HepC_Int | IL_13 | 0.000 | | HepC_Int | IL_13 | 0.000 |
| HepC_Int | IL_15 | 0.000 | | HepC_Int | IL_15 | 0.000 |
| HepC_Int | IL_17 | 0.000 | | HepC_Int | IL_17 | 0.000 |
| HepC_Int | IL_23 | 0.000 | | HepC_Int | IL_23 | 0.000 |
| HepC_Int | IFN_gamma | 0.000 | | HepC_Int | IFN_gamma | 0.000 |
| HepC_Int | TNF_alpha | 0.000 | | HepC_Int | TNF_alpha | 0.000 |
| HepC_Int | TNF_beta | 0.000 | | HepC_Int | TNF_beta | 0.000 |
| HepC_Int | Varicella_Int | 0.000 | | HepC_Int | Varicella_Int | 0.000 |
| HepC_Int | Measles_OD_DB_Int | 0.000 | | HepC_Int | Measles_OD_DB_Int | 0.000 |
| HepC_Int | Measles_Int | 0.000 | | HepC_Int | Measles_Int | 0.000 |
| HepC_Int | HepA_Int | 0.000 | | HepC_Int | HepA_Int | 0.000 |
| HepC_Int | Tetanus_Int | 0.000 | | HepC_Int | Tetanus_Int | 0.000 |
| HepC_Int | Diptheria_Int | 0.000 | | HepC_Int | Diptheria_Int | 0.000 |
| HepC_Int | Rubella_Int | 0.000 | | HepC_Int | Rubella_Int | 0.000 |
| HepC_Int | CMV_Int | 0.000 | | HepC_Int | CMV_Int | 0.000 |
| HepC_Int | HepB_cAb_Int | 0.000 | | HepC_Int | HepB_cAb_Int | 0.000 |
| HepC_Int | HepB_eAb_Int | 0.000 | | HepC_Int | HepB_eAb_Int | 0.000 |
| HepC_Int | HepB_eAg_Int | 0.000 | | HepC_Int | HepB_eAg_Int | 0.000 |
| HepC_Int | HepC_Int | 1.000 | | HepC_Int | HepC_Int | 1.000 |
| HepC_Int | Schistosoma_int | 0.000 | | HepC_Int | Schistosoma_int | 0.000 |
| HepC_Int | Strongyloides_Int | 0.000 | | HepC_Int | Strongyloides_Int | 0.000 |
| HepC_Int | Filaria_Int | 0.000 | | HepC_Int | Filaria_Int | 0.000 |
| Schistosoma_int | IL_1_alpha | 0.000 | | Schistosoma_int | IL_1_alpha | 1.000 |
| Schistosoma_int | IL_1_beta | 0.000 | | Schistosoma_int | IL_1_beta | -1.000 |
| Schistosoma_int | IL_2 | 0.000 | | Schistosoma_int | IL_2 | 0.000 |
| Schistosoma_int | IL_4 | 0.000 | | Schistosoma_int | IL_4 | 0.000 |
| Schistosoma_int | IL_5 | 0.000 | | Schistosoma_int | IL_5 | 1.000 |
| Schistosoma_int | IL_6 | 0.000 | | Schistosoma_int | IL_6 | -1.000 |
| Schistosoma_int | IL_8 | 0.000 | | Schistosoma_int | IL_8 | -1.000 |
| Schistosoma_int | IL_10 | 0.000 | | Schistosoma_int | IL_10 | -1.000 |
| Schistosoma_int | IL_12p70 | 0.000 | | Schistosoma_int | IL_12p70 | -1.000 |
| Schistosoma_int | IL_13 | 0.000 | | Schistosoma_int | IL_13 | -1.000 |
| Schistosoma_int | IL_15 | 0.000 | | Schistosoma_int | IL_15 | -1.000 |
| Schistosoma_int | IL_17 | 0.000 | | Schistosoma_int | IL_17 | 1.000 |
| Schistosoma_int | IL_23 | 0.000 | | Schistosoma_int | IL_23 | -1.000 |
| Schistosoma_int | IFN_gamma | 0.000 | | Schistosoma_int | IFN_gamma | 0.000 |
| Schistosoma_int | TNF_alpha | 0.000 | | Schistosoma_int | TNF_alpha | -1.000 |
| Schistosoma_int | TNF_beta | 0.000 | | Schistosoma_int | TNF_beta | 1.000 |
| Schistosoma_int | Varicella_Int | 0.000 | | Schistosoma_int | Varicella_Int | 0.000 |
| Schistosoma_int | Measles_OD_DB_Int | 0.000 | | Schistosoma_int | Measles_OD_DB_Int | -1.000 |
| Schistosoma_int | Measles_Int | 0.000 | | Schistosoma_int | Measles_Int | 0.000 |
| Schistosoma_int | HepA_Int | 0.000 | | Schistosoma_int | HepA_Int | 0.000 |
| Schistosoma_int | Tetanus_Int | 0.000 | | Schistosoma_int | Tetanus_Int | 0.000 |
| Schistosoma_int | Diptheria_Int | 0.000 | | Schistosoma_int | Diptheria_Int | 0.000 |
| Schistosoma_int | Rubella_Int | 0.000 | | Schistosoma_int | Rubella_Int | 0.000 |
| Schistosoma_int | CMV_Int | 0.000 | | Schistosoma_int | CMV_Int | 0.000 |
| Schistosoma_int | HepB_cAb_Int | 0.000 | | Schistosoma_int | HepB_cAb_Int | 0.000 |
| Schistosoma_int | HepB_eAb_Int | 0.000 | | Schistosoma_int | HepB_eAb_Int | 0.000 |
| Schistosoma_int | HepB_eAg_Int | 0.000 | | Schistosoma_int | HepB_eAg_Int | 0.000 |

FIG. 21I11-P

| | | | | | | |
|---|---|---|---|---|---|---|
| Schistosoma_int | HepC_Int | 0.000 | | Schistosoma_int | HepC_Int | 0.000 |
| Schistosoma_int | Schistosoma_int | 1.000 | | Schistosoma_int | Schistosoma_int | 1.000 |
| Schistosoma_int | Strongyloides_Int | 0.000 | | Schistosoma_int | Strongyloides_Int | 1.000 |
| Schistosoma_int | Filaria_Int | 0.000 | | Schistosoma_int | Filaria_Int | 0.000 |
| Strongyloides_Int | IL_1_alpha | 1.000 | | Strongyloides_Int | IL_1_alpha | 1.000 |
| Strongyloides_Int | IL_1_beta | -1.000 | | Strongyloides_Int | IL_1_beta | -1.000 |
| Strongyloides_Int | IL_2 | -1.000 | | Strongyloides_Int | IL_2 | 0.000 |
| Strongyloides_Int | IL_4 | 1.000 | | Strongyloides_Int | IL_4 | 0.000 |
| Strongyloides_Int | IL_5 | -1.000 | | Strongyloides_Int | IL_5 | 1.000 |
| Strongyloides_Int | IL_6 | -1.000 | | Strongyloides_Int | IL_6 | -1.000 |
| Strongyloides_Int | IL_8 | 1.000 | | Strongyloides_Int | IL_8 | -1.000 |
| Strongyloides_Int | IL_10 | -1.000 | | Strongyloides_Int | IL_10 | -1.000 |
| Strongyloides_Int | IL_12p70 | -1.000 | | Strongyloides_Int | IL_12p70 | -1.000 |
| Strongyloides_Int | IL_13 | -1.000 | | Strongyloides_Int | IL_13 | -1.000 |
| Strongyloides_Int | IL_15 | -1.000 | | Strongyloides_Int | IL_15 | -1.000 |
| Strongyloides_Int | IL_17 | -1.000 | | Strongyloides_Int | IL_17 | 1.000 |
| Strongyloides_Int | IL_23 | -1.000 | | Strongyloides_Int | IL_23 | -1.000 |
| Strongyloides_Int | IFN_gamma | 0.000 | | Strongyloides_Int | IFN_gamma | 0.000 |
| Strongyloides_Int | TNF_alpha | -1.000 | | Strongyloides_Int | TNF_alpha | -1.000 |
| Strongyloides_Int | TNF_beta | 1.000 | | Strongyloides_Int | TNF_beta | 1.000 |
| Strongyloides_Int | Varicella_Int | 0.000 | | Strongyloides_Int | Varicella_Int | 0.000 |
| Strongyloides_Int | Measles_OD_DB_Int | -1.000 | | Strongyloides_Int | Measles_OD_DB_Int | -1.000 |
| Strongyloides_Int | Measles_Int | 0.000 | | Strongyloides_Int | Measles_Int | 0.000 |
| Strongyloides_Int | HepA_Int | -1.000 | | Strongyloides_Int | HepA_Int | 0.000 |
| Strongyloides_Int | Tetanus_Int | 0.000 | | Strongyloides_Int | Tetanus_Int | 0.000 |
| Strongyloides_Int | Diptheria_Int | 0.000 | | Strongyloides_Int | Diptheria_Int | 0.000 |
| Strongyloides_Int | Rubella_Int | 1.000 | | Strongyloides_Int | Rubella_Int | 0.000 |
| Strongyloides_Int | CMV_Int | 0.000 | | Strongyloides_Int | CMV_Int | 0.000 |
| Strongyloides_Int | HepB_cAb_Int | -1.000 | | Strongyloides_Int | HepB_cAb_Int | 0.000 |
| Strongyloides_Int | HepB_eAb_Int | 0.000 | | Strongyloides_Int | HepB_eAb_Int | 0.000 |
| Strongyloides_Int | HepB_eAg_Int | 0.000 | | Strongyloides_Int | HepB_eAg_Int | 0.000 |
| Strongyloides_Int | HepC_Int | 0.000 | | Strongyloides_Int | HepC_Int | 0.000 |
| Strongyloides_Int | Schistosoma_int | 0.000 | | Strongyloides_Int | Schistosoma_int | 1.000 |
| Strongyloides_Int | Strongyloides_Int | 1.000 | | Strongyloides_Int | Strongyloides_Int | 1.000 |
| Strongyloides_Int | Filaria_Int | 0.000 | | Strongyloides_Int | Filaria_Int | 0.000 |
| Filaria_Int | IL_1_alpha | 0.000 | | Filaria_Int | IL_1_alpha | 0.000 |
| Filaria_Int | IL_1_beta | 0.000 | | Filaria_Int | IL_1_beta | 0.000 |
| Filaria_Int | IL_2 | 0.000 | | Filaria_Int | IL_2 | 0.000 |
| Filaria_Int | IL_4 | 0.000 | | Filaria_Int | IL_4 | 0.000 |
| Filaria_Int | IL_5 | 0.000 | | Filaria_Int | IL_5 | 0.000 |
| Filaria_Int | IL_6 | 0.000 | | Filaria_Int | IL_6 | 0.000 |
| Filaria_Int | IL_8 | 0.000 | | Filaria_Int | IL_8 | 0.000 |
| Filaria_Int | IL_10 | 0.000 | | Filaria_Int | IL_10 | 0.000 |
| Filaria_Int | IL_12p70 | 0.000 | | Filaria_Int | IL_12p70 | 0.000 |
| Filaria_Int | IL_13 | 0.000 | | Filaria_Int | IL_13 | 0.000 |
| Filaria_Int | IL_15 | 0.000 | | Filaria_Int | IL_15 | 0.000 |
| Filaria_Int | IL_17 | 0.000 | | Filaria_Int | IL_17 | 0.000 |
| Filaria_Int | IL_23 | 0.000 | | Filaria_Int | IL_23 | 0.000 |
| Filaria_Int | IFN_gamma | 0.000 | | Filaria_Int | IFN_gamma | 0.000 |
| Filaria_Int | TNF_alpha | 0.000 | | Filaria_Int | TNF_alpha | 0.000 |
| Filaria_Int | TNF_beta | 0.000 | | Filaria_Int | TNF_beta | 0.000 |
| Filaria_Int | Varicella_Int | 0.000 | | Filaria_Int | Varicella_Int | 0.000 |
| Filaria_Int | Measles_OD_DB_Int | 0.000 | | Filaria_Int | Measles_OD_DB_Int | 0.000 |
| Filaria_Int | Measles_Int | 0.000 | | Filaria_Int | Measles_Int | 0.000 |
| Filaria_Int | HepA_Int | 0.000 | | Filaria_Int | HepA_Int | 0.000 |
| Filaria_Int | Tetanus_Int | 0.000 | | Filaria_Int | Tetanus_Int | 0.000 |
| Filaria_Int | Diptheria_Int | 0.000 | | Filaria_Int | Diptheria_Int | 0.000 |

FIG. 21I11-Q

| | | |
|---|---|---|
| Filaria_Int | Rubella_Int | 0.000 |
| Filaria_Int | CMV_Int | 0.000 |
| Filaria_Int | HepB_cAb_Int | 0.000 |
| Filaria_Int | HepB_eAb_Int | 0.000 |
| Filaria_Int | HepB_eAg_Int | 0.000 |
| Filaria_Int | HepC_Int | 0.000 |
| Filaria_Int | Schistosoma_int | 0.000 |
| Filaria_Int | Strongyloides_Int | 0.000 |
| Filaria_Int | Filaria_Int | 1.000 |

| | | |
|---|---|---|
| Filaria_Int | Rubella_Int | 0.000 |
| Filaria_Int | CMV_Int | 0.000 |
| Filaria_Int | HepB_cAb_Int | 0.000 |
| Filaria_Int | HepB_eAb_Int | 0.000 |
| Filaria_Int | HepB_eAg_Int | 0.000 |
| Filaria_Int | HepC_Int | 0.000 |
| Filaria_Int | Schistosoma_int | 0.000 |
| Filaria_Int | Strongyloides_Int | 0.000 |
| Filaria_Int | Filaria_Int | 1.000 |

FIG. 21I11-R

| 0.14% - Region_of_Origin=1, Sex=Male, IFN_gamma=7.5-22.5 | | |
|---|---|---|
| Property 1 | Property 2 | Corr. Coefficient |
| IL_1_alpha | IL_1_alpha | 1.000 |
| IL_1_alpha | IL_1_beta | -1.000 |
| IL_1_alpha | IL_2 | -1.000 |
| IL_1_alpha | IL_4 | 1.000 |
| IL_1_alpha | IL_5 | -1.000 |
| IL_1_alpha | IL_6 | 1.000 |
| IL_1_alpha | IL_8 | 1.000 |
| IL_1_alpha | IL_10 | -1.000 |
| IL_1_alpha | IL_12p70 | 1.000 |
| IL_1_alpha | IL_13 | -1.000 |
| IL_1_alpha | IL_15 | -1.000 |
| IL_1_alpha | IL_17 | -1.000 |
| IL_1_alpha | IL_23 | 1.000 |
| IL_1_alpha | IFN_gamma | 0.000 |
| IL_1_alpha | TNF_alpha | -1.000 |
| IL_1_alpha | TNF_beta | 1.000 |
| IL_1_alpha | Varicella_Int | 0.000 |
| IL_1_alpha | Measles_OD_DB_Int | 0.000 |
| IL_1_alpha | Measles_Int | 0.000 |
| IL_1_alpha | HepA_Int | 0.000 |
| IL_1_alpha | Tetanus_Int | 0.000 |
| IL_1_alpha | Diptheria_Int | 0.000 |
| IL_1_alpha | Rubella_Int | -1.000 |
| IL_1_alpha | CMV_Int | 0.000 |
| IL_1_alpha | HepB_cAb_Int | 0.000 |
| IL_1_alpha | HepB_eAb_Int | 0.000 |
| IL_1_alpha | HepB_eAg_Int | 0.000 |
| IL_1_alpha | HepC_Int | 0.000 |
| IL_1_alpha | Schistosoma_int | 0.000 |
| IL_1_alpha | Strongyloides_Int | 1.000 |
| IL_1_alpha | Filaria_Int | 0.000 |
| IL_1_beta | IL_1_alpha | -1.000 |
| IL_1_beta | IL_1_beta | 1.000 |
| IL_1_beta | IL_2 | 1.000 |
| IL_1_beta | IL_4 | -1.000 |
| IL_1_beta | IL_5 | 1.000 |
| IL_1_beta | IL_6 | -1.000 |
| IL_1_beta | IL_8 | -1.000 |
| IL_1_beta | IL_10 | 1.000 |
| IL_1_beta | IL_12p70 | -1.000 |
| IL_1_beta | IL_13 | 1.000 |
| IL_1_beta | IL_15 | 1.000 |
| IL_1_beta | IL_17 | 1.000 |
| IL_1_beta | IL_23 | -1.000 |

| 0.07% - Region_of_Origin=2, Sex=Female, IFN_gamma=22.5-37.5 | | |
|---|---|---|
| Property 1 | Property 2 | Corr. Coefficient |
| IL_1_alpha | IL_1_alpha | 1.000 |
| IL_1_alpha | IL_1_beta | 0.000 |
| IL_1_alpha | IL_2 | 0.000 |
| IL_1_alpha | IL_4 | 0.000 |
| IL_1_alpha | IL_5 | 0.000 |
| IL_1_alpha | IL_6 | 0.000 |
| IL_1_alpha | IL_8 | 0.000 |
| IL_1_alpha | IL_10 | 0.000 |
| IL_1_alpha | IL_12p70 | 0.000 |
| IL_1_alpha | IL_13 | 0.000 |
| IL_1_alpha | IL_15 | 0.000 |
| IL_1_alpha | IL_17 | 0.000 |
| IL_1_alpha | IL_23 | 0.000 |
| IL_1_alpha | IFN_gamma | 0.000 |
| IL_1_alpha | TNF_alpha | 0.000 |
| IL_1_alpha | TNF_beta | 0.000 |
| IL_1_alpha | Varicella_Int | 0.000 |
| IL_1_alpha | Measles_OD_DB_Int | 0.000 |
| IL_1_alpha | Measles_Int | 0.000 |
| IL_1_alpha | HepA_int | 0.000 |
| IL_1_alpha | Tetanus_Int | 0.000 |
| IL_1_alpha | Diptheria_Int | 0.000 |
| IL_1_alpha | Rubella_Int | 0.000 |
| IL_1_alpha | CMV_Int | 0.000 |
| IL_1_alpha | HepB_cAb_Int | 0.000 |
| IL_1_alpha | HepB_eAb_Int | 0.000 |
| IL_1_alpha | HepB_eAg_Int | 0.000 |
| IL_1_alpha | HepC_Int | 0.000 |
| IL_1_alpha | Schistosoma_int | 0.000 |
| IL_1_alpha | Strongyloides_Int | 0.000 |
| IL_1_alpha | Filaria_Int | 0.000 |
| IL_1_beta | IL_1_alpha | 0.000 |
| IL_1_beta | IL_1_beta | 1.000 |
| IL_1_beta | IL_2 | 0.000 |
| IL_1_beta | IL_4 | 0.000 |
| IL_1_beta | IL_5 | 0.000 |
| IL_1_beta | IL_6 | 0.000 |
| IL_1_beta | IL_8 | 0.000 |
| IL_1_beta | IL_10 | 0.000 |
| IL_1_beta | IL_12p70 | 0.000 |
| IL_1_beta | IL_13 | 0.000 |
| IL_1_beta | IL_15 | 0.000 |
| IL_1_beta | IL_17 | 0.000 |
| IL_1_beta | IL_23 | 0.000 |

FIG. 21I12-A

| | | | | | | |
|---|---|---|---|---|---|---|
| IL_1_beta | IFN_gamma | 0.000 | | IL_1_beta | IFN_gamma | 0.000 |
| IL_1_beta | TNF_alpha | 1.000 | | IL_1_beta | TNF_alpha | 0.000 |
| IL_1_beta | TNF_beta | -1.000 | | IL_1_beta | TNF_beta | 0.000 |
| IL_1_beta | Varicella_Int | 0.000 | | IL_1_beta | Varicella_Int | 0.000 |
| IL_1_beta | Measles_OD_DB_Int | 0.000 | | IL_1_beta | Measles_OD_DB_Int | 0.000 |
| IL_1_beta | Measles_Int | 0.000 | | IL_1_beta | Measles_Int | 0.000 |
| IL_1_beta | HepA_Int | 0.000 | | IL_1_beta | HepA_Int | 0.000 |
| IL_1_beta | Tetanus_Int | 0.000 | | IL_1_beta | Tetanus_Int | 0.000 |
| IL_1_beta | Diptheria_Int | 0.000 | | IL_1_beta | Diptheria_Int | 0.000 |
| IL_1_beta | Rubella_Int | 1.000 | | IL_1_beta | Rubella_Int | 0.000 |
| IL_1_beta | CMV_Int | 0.000 | | IL_1_beta | CMV_Int | 0.000 |
| IL_1_beta | HepB_cAb_Int | 0.000 | | IL_1_beta | HepB_cAb_Int | 0.000 |
| IL_1_beta | HepB_eAb_Int | 0.000 | | IL_1_beta | HepB_eAb_Int | 0.000 |
| IL_1_beta | HepB_eAg_Int | 0.000 | | IL_1_beta | HepB_eAg_Int | 0.000 |
| IL_1_beta | HepC_Int | 0.000 | | IL_1_beta | HepC_Int | 0.000 |
| IL_1_beta | Schistosoma_int | 0.000 | | IL_1_beta | Schistosoma_int | 0.000 |
| IL_1_beta | Strongyloides_Int | -1.000 | | IL_1_beta | Strongyloides_Int | 0.000 |
| IL_1_beta | Filaria_Int | 0.000 | | IL_1_beta | Filaria_Int | 0.000 |
| IL_2 | IL_1_alpha | -1.000 | | IL_2 | IL_1_alpha | 0.000 |
| IL_2 | IL_1_beta | 1.000 | | IL_2 | IL_1_beta | 0.000 |
| IL_2 | IL_2 | 1.000 | | IL_2 | IL_2 | 1.000 |
| IL_2 | IL_4 | -1.000 | | IL_2 | IL_4 | 0.000 |
| IL_2 | IL_5 | 1.000 | | IL_2 | IL_5 | 0.000 |
| IL_2 | IL_6 | -1.000 | | IL_2 | IL_6 | 0.000 |
| IL_2 | IL_8 | -1.000 | | IL_2 | IL_8 | 0.000 |
| IL_2 | IL_10 | 1.000 | | IL_2 | IL_10 | 0.000 |
| IL_2 | IL_12p70 | -1.000 | | IL_2 | IL_12p70 | 0.000 |
| IL_2 | IL_13 | 1.000 | | IL_2 | IL_13 | 0.000 |
| IL_2 | IL_15 | 1.000 | | IL_2 | IL_15 | 0.000 |
| IL_2 | IL_17 | 1.000 | | IL_2 | IL_17 | 0.000 |
| IL_2 | IL_23 | -1.000 | | IL_2 | IL_23 | 0.000 |
| IL_2 | IFN_gamma | 0.000 | | IL_2 | IFN_gamma | 0.000 |
| IL_2 | TNF_alpha | 1.000 | | IL_2 | TNF_alpha | 0.000 |
| IL_2 | TNF_beta | -1.000 | | IL_2 | TNF_beta | 0.000 |
| IL_2 | Varicella_Int | 0.000 | | IL_2 | Varicella_Int | 0.000 |
| IL_2 | Measles_OD_DB_Int | 0.000 | | IL_2 | Measles_OD_DB_Int | 0.000 |
| IL_2 | Measles_Int | 0.000 | | IL_2 | Measles_Int | 0.000 |
| IL_2 | HepA_Int | 0.000 | | IL_2 | HepA_Int | 0.000 |
| IL_2 | Tetanus_Int | 0.000 | | IL_2 | Tetanus_Int | 0.000 |
| IL_2 | Diptheria_Int | 0.000 | | IL_2 | Diptheria_Int | 0.000 |
| IL_2 | Rubella_Int | 1.000 | | IL_2 | Rubella_Int | 0.000 |
| IL_2 | CMV_Int | 0.000 | | IL_2 | CMV_Int | 0.000 |
| IL_2 | HepB_cAb_Int | 0.000 | | IL_2 | HepB_cAb_Int | 0.000 |
| IL_2 | HepB_eAb_Int | 0.000 | | IL_2 | HepB_eAb_Int | 0.000 |
| IL_2 | HepB_eAg_Int | 0.000 | | IL_2 | HepB_eAg_Int | 0.000 |
| IL_2 | HepC_Int | 0.000 | | IL_2 | HepC_Int | 0.000 |
| IL_2 | Schistosoma_int | 0.000 | | IL_2 | Schistosoma_int | 0.000 |
| IL_2 | Strongyloides_Int | -1.000 | | IL_2 | Strongyloides_Int | 0.000 |
| IL_2 | Filaria_Int | 0.000 | | IL_2 | Filaria_Int | 0.000 |
| IL_4 | IL_1_alpha | 1.000 | | IL_4 | IL_1_alpha | 0.000 |
| IL_4 | IL_1_beta | -1.000 | | IL_4 | IL_1_beta | 0.000 |
| IL_4 | IL_2 | -1.000 | | IL_4 | IL_2 | 0.000 |
| IL_4 | IL_4 | 1.000 | | IL_4 | IL_4 | 1.000 |
| IL_4 | IL_5 | -1.000 | | IL_4 | IL_5 | 0.000 |
| IL_4 | IL_6 | 1.000 | | IL_4 | IL_6 | 0.000 |
| IL_4 | IL_8 | 1.000 | | IL_4 | IL_8 | 0.000 |
| IL_4 | IL_10 | -1.000 | | IL_4 | IL_10 | 0.000 |

FIG. 21I12-B

| | | | | | | |
|---|---|---|---|---|---|---|
| IL_4 | IL_12p70 | 1.000 | | IL_4 | IL_12p70 | 0.000 |
| IL_4 | IL_13 | -1.000 | | IL_4 | IL_13 | 0.000 |
| IL_4 | IL_15 | -1.000 | | IL_4 | IL_15 | 0.000 |
| IL_4 | IL_17 | -1.000 | | IL_4 | IL_17 | 0.000 |
| IL_4 | IL_23 | 1.000 | | IL_4 | IL_23 | 0.000 |
| IL_4 | IFN_gamma | 0.000 | | IL_4 | IFN_gamma | 0.000 |
| IL_4 | TNF_alpha | -1.000 | | IL_4 | TNF_alpha | 0.000 |
| IL_4 | TNF_beta | 1.000 | | IL_4 | TNF_beta | 0.000 |
| IL_4 | Varicella_Int | 0.000 | | IL_4 | Varicella_Int | 0.000 |
| IL_4 | Measles_OD_DB_Int | 0.000 | | IL_4 | Measles_OD_DB_Int | 0.000 |
| IL_4 | Measles_Int | 0.000 | | IL_4 | Measles_Int | 0.000 |
| IL_4 | HepA_Int | 0.000 | | IL_4 | HepA_Int | 0.000 |
| IL_4 | Tetanus_Int | 0.000 | | IL_4 | Tetanus_Int | 0.000 |
| IL_4 | Diptheria_Int | 0.000 | | IL_4 | Diptheria_Int | 0.000 |
| IL_4 | Rubella_Int | -1.000 | | IL_4 | Rubella_Int | 0.000 |
| IL_4 | CMV_Int | 0.000 | | IL_4 | CMV_Int | 0.000 |
| IL_4 | HepB_cAb_Int | 0.000 | | IL_4 | HepB_cAb_Int | 0.000 |
| IL_4 | HepB_eAb_Int | 0.000 | | IL_4 | HepB_eAb_Int | 0.000 |
| IL_4 | HepB_eAg_Int | 0.000 | | IL_4 | HepB_eAg_Int | 0.000 |
| IL_4 | HepC_Int | 0.000 | | IL_4 | HepC_Int | 0.000 |
| IL_4 | Schistosoma_int | 0.000 | | IL_4 | Schistosoma_int | 0.000 |
| IL_4 | Strongyloides_Int | 1.000 | | IL_4 | Strongyloides_Int | 0.000 |
| IL_4 | Filaria_Int | 0.000 | | IL_4 | Filaria_Int | 0.000 |
| IL_5 | IL_1_alpha | -1.000 | | IL_5 | IL_1_alpha | 0.000 |
| IL_5 | IL_1_beta | 1.000 | | IL_5 | IL_1_beta | 0.000 |
| IL_5 | IL_2 | 1.000 | | IL_5 | IL_2 | 0.000 |
| IL_5 | IL_4 | -1.000 | | IL_5 | IL_4 | 0.000 |
| IL_5 | IL_5 | 1.000 | | IL_5 | IL_5 | 1.000 |
| IL_5 | IL_6 | -1.000 | | IL_5 | IL_6 | 0.000 |
| IL_5 | IL_8 | -1.000 | | IL_5 | IL_8 | 0.000 |
| IL_5 | IL_10 | 1.000 | | IL_5 | IL_10 | 0.000 |
| IL_5 | IL_12p70 | -1.000 | | IL_5 | IL_12p70 | 0.000 |
| IL_5 | IL_13 | 1.000 | | IL_5 | IL_13 | 0.000 |
| IL_5 | IL_15 | 1.000 | | IL_5 | IL_15 | 0.000 |
| IL_5 | IL_17 | 1.000 | | IL_5 | IL_17 | 0.000 |
| IL_5 | IL_23 | -1.000 | | IL_5 | IL_23 | 0.000 |
| IL_5 | IFN_gamma | 0.000 | | IL_5 | IFN_gamma | 0.000 |
| IL_5 | TNF_alpha | 1.000 | | IL_5 | TNF_alpha | 0.000 |
| IL_5 | TNF_beta | -1.000 | | IL_5 | TNF_beta | 0.000 |
| IL_5 | Varicella_Int | 0.000 | | IL_5 | Varicella_Int | 0.000 |
| IL_5 | Measles_OD_DB_Int | 0.000 | | IL_5 | Measles_OD_DB_Int | 0.000 |
| IL_5 | Measles_Int | 0.000 | | IL_5 | Measles_Int | 0.000 |
| IL_5 | HepA_Int | 0.000 | | IL_5 | HepA_Int | 0.000 |
| IL_5 | Tetanus_Int | 0.000 | | IL_5 | Tetanus_Int | 0.000 |
| IL_5 | Diptheria_Int | 0.000 | | IL_5 | Diptheria_Int | 0.000 |
| IL_5 | Rubella_Int | 1.000 | | IL_5 | Rubella_Int | 0.000 |
| IL_5 | CMV_Int | 0.000 | | IL_5 | CMV_Int | 0.000 |
| IL_5 | HepB_cAb_Int | 0.000 | | IL_5 | HepB_cAb_Int | 0.000 |
| IL_5 | HepB_eAb_Int | 0.000 | | IL_5 | HepB_eAb_Int | 0.000 |
| IL_5 | HepB_eAg_Int | 0.000 | | IL_5 | HepB_eAg_Int | 0.000 |
| IL_5 | HepC_Int | 0.000 | | IL_5 | HepC_Int | 0.000 |
| IL_5 | Schistosoma_int | 0.000 | | IL_5 | Schistosoma_int | 0.000 |
| IL_5 | Strongyloides_Int | -1.000 | | IL_5 | Strongyloides_Int | 0.000 |
| IL_5 | Filaria_Int | 0.000 | | IL_5 | Filaria_Int | 0.000 |
| IL_6 | IL_1_alpha | 1.000 | | IL_6 | IL_1_alpha | 0.000 |
| IL_6 | IL_1_beta | -1.000 | | IL_6 | IL_1_beta | 0.000 |
| IL_6 | IL_2 | -1.000 | | IL_6 | IL_2 | 0.000 |

FIG. 21I12-C

| | | | | | | |
|---|---|---|---|---|---|---|
| IL_6 | IL_4 | 1.000 | | IL_6 | IL_4 | 0.000 |
| IL_6 | IL_5 | -1.000 | | IL_6 | IL_5 | 0.000 |
| IL_6 | IL_6 | 1.000 | | IL_6 | IL_6 | 1.000 |
| IL_6 | IL_8 | 1.000 | | IL_6 | IL_8 | 0.000 |
| IL_6 | IL_10 | -1.000 | | IL_6 | IL_10 | 0.000 |
| IL_6 | IL_12p70 | 1.000 | | IL_6 | IL_12p70 | 0.000 |
| IL_6 | IL_13 | -1.000 | | IL_6 | IL_13 | 0.000 |
| IL_6 | IL_15 | -1.000 | | IL_6 | IL_15 | 0.000 |
| IL_6 | IL_17 | -1.000 | | IL_6 | IL_17 | 0.000 |
| IL_6 | IL_23 | 1.000 | | IL_6 | IL_23 | 0.000 |
| IL_6 | IFN_gamma | 0.000 | | IL_6 | IFN_gamma | 0.000 |
| IL_6 | TNF_alpha | -1.000 | | IL_6 | TNF_alpha | 0.000 |
| IL_6 | TNF_beta | 1.000 | | IL_6 | TNF_beta | 0.000 |
| IL_6 | Varicella_Int | 0.000 | | IL_6 | Varicella_Int | 0.000 |
| IL_6 | Measles_OD_DB_Int | 0.000 | | IL_6 | Measles_OD_DB_Int | 0.000 |
| IL_6 | Measles_Int | 0.000 | | IL_6 | Measles_Int | 0.000 |
| IL_6 | HepA_Int | 0.000 | | IL_6 | HepA_Int | 0.000 |
| IL_6 | Tetanus_Int | 0.000 | | IL_6 | Tetanus_Int | 0.000 |
| IL_6 | Diptheria_Int | 0.000 | | IL_6 | Diptheria_Int | 0.000 |
| IL_6 | Rubella_Int | -1.000 | | IL_6 | Rubella_Int | 0.000 |
| IL_6 | CMV_Int | 0.000 | | IL_6 | CMV_Int | 0.000 |
| IL_6 | HepB_cAb_Int | 0.000 | | IL_6 | HepB_cAb_Int | 0.000 |
| IL_6 | HepB_eAb_Int | 0.000 | | IL_6 | HepB_eAb_Int | 0.000 |
| IL_6 | HepB_eAg_Int | 0.000 | | IL_6 | HepB_eAg_Int | 0.000 |
| IL_6 | HepC_Int | 0.000 | | IL_6 | HepC_Int | 0.000 |
| IL_6 | Schistosoma_int | 0.000 | | IL_6 | Schistosoma_int | 0.000 |
| IL_6 | Strongyloides_Int | 1.000 | | IL_6 | Strongyloides_Int | 0.000 |
| IL_6 | Filaria_Int | 0.000 | | IL_6 | Filaria_Int | 0.000 |
| IL_8 | IL_1_alpha | 1.000 | | IL_8 | IL_1_alpha | 0.000 |
| IL_8 | IL_1_beta | -1.000 | | IL_8 | IL_1_beta | 0.000 |
| IL_8 | IL_2 | -1.000 | | IL_8 | IL_2 | 0.000 |
| IL_8 | IL_4 | 1.000 | | IL_8 | IL_4 | 0.000 |
| IL_8 | IL_5 | -1.000 | | IL_8 | IL_5 | 0.000 |
| IL_8 | IL_6 | 1.000 | | IL_8 | IL_6 | 0.000 |
| IL_8 | IL_8 | 1.000 | | IL_8 | IL_8 | 1.000 |
| IL_8 | IL_10 | -1.000 | | IL_8 | IL_10 | 0.000 |
| IL_8 | IL_12p70 | 1.000 | | IL_8 | IL_12p70 | 0.000 |
| IL_8 | IL_13 | -1.000 | | IL_8 | IL_13 | 0.000 |
| IL_8 | IL_15 | -1.000 | | IL_8 | IL_15 | 0.000 |
| IL_8 | IL_17 | -1.000 | | IL_8 | IL_17 | 0.000 |
| IL_8 | IL_23 | 1.000 | | IL_8 | IL_23 | 0.000 |
| IL_8 | IFN_gamma | 0.000 | | IL_8 | IFN_gamma | 0.000 |
| IL_8 | TNF_alpha | -1.000 | | IL_8 | TNF_alpha | 0.000 |
| IL_8 | TNF_beta | 1.000 | | IL_8 | TNF_beta | 0.000 |
| IL_8 | Varicella_Int | 0.000 | | IL_8 | Varicella_Int | 0.000 |
| IL_8 | Measles_OD_DB_Int | 0.000 | | IL_8 | Measles_OD_DB_Int | 0.000 |
| IL_8 | Measles_Int | 0.000 | | IL_8 | Measles_Int | 0.000 |
| IL_8 | HepA_Int | 0.000 | | IL_8 | HepA_Int | 0.000 |
| IL_8 | Tetanus_Int | 0.000 | | IL_8 | Tetanus_Int | 0.000 |
| IL_8 | Diptheria_Int | 0.000 | | IL_8 | Diptheria_Int | 0.000 |
| IL_8 | Rubella_Int | -1.000 | | IL_8 | Rubella_Int | 0.000 |
| IL_8 | CMV_Int | 0.000 | | IL_8 | CMV_Int | 0.000 |
| IL_8 | HepB_cAb_Int | 0.000 | | IL_8 | HepB_cAb_Int | 0.000 |
| IL_8 | HepB_eAb_Int | 0.000 | | IL_8 | HepB_eAb_Int | 0.000 |
| IL_8 | HepB_eAg_Int | 0.000 | | IL_8 | HepB_eAg_Int | 0.000 |
| IL_8 | HepC_Int | 0.000 | | IL_8 | HepC_Int | 0.000 |
| IL_8 | Schistosoma_int | 0.000 | | IL_8 | Schistosoma_int | 0.000 |

FIG. 21I12-D

| | | | | | | |
|---|---|---|---|---|---|---|
| IL_8 | Strongyloides_Int | 1.000 | | IL_8 | Strongyloides_Int | 0.000 |
| IL_8 | Filaria_Int | 0.000 | | IL_8 | Filaria_Int | 0.000 |
| IL_10 | IL_1_alpha | -1.000 | | IL_10 | IL_1_alpha | 0.000 |
| IL_10 | IL_1_beta | 1.000 | | IL_10 | IL_1_beta | 0.000 |
| IL_10 | IL_2 | 1.000 | | IL_10 | IL_2 | 0.000 |
| IL_10 | IL_4 | -1.000 | | IL_10 | IL_4 | 0.000 |
| IL_10 | IL_5 | 1.000 | | IL_10 | IL_5 | 0.000 |
| IL_10 | IL_6 | -1.000 | | IL_10 | IL_6 | 0.000 |
| IL_10 | IL_8 | -1.000 | | IL_10 | IL_8 | 0.000 |
| IL_10 | IL_10 | 1.000 | | IL_10 | IL_10 | 1.000 |
| IL_10 | IL_12p70 | -1.000 | | IL_10 | IL_12p70 | 0.000 |
| IL_10 | IL_13 | 1.000 | | IL_10 | IL_13 | 0.000 |
| IL_10 | IL_15 | 1.000 | | IL_10 | IL_15 | 0.000 |
| IL_10 | IL_17 | 1.000 | | IL_10 | IL_17 | 0.000 |
| IL_10 | IL_23 | -1.000 | | IL_10 | IL_23 | 0.000 |
| IL_10 | IFN_gamma | 0.000 | | IL_10 | IFN_gamma | 0.000 |
| IL_10 | TNF_alpha | 1.000 | | IL_10 | TNF_alpha | 0.000 |
| IL_10 | TNF_beta | -1.000 | | IL_10 | TNF_beta | 0.000 |
| IL_10 | Varicella_Int | 0.000 | | IL_10 | Varicella_Int | 0.000 |
| IL_10 | Measles_OD_DB_Int | 0.000 | | IL_10 | Measles_OD_DB_Int | 0.000 |
| IL_10 | Measles_Int | 0.000 | | IL_10 | Measles_Int | 0.000 |
| IL_10 | HepA_Int | 0.000 | | IL_10 | HepA_Int | 0.000 |
| IL_10 | Tetanus_Int | 0.000 | | IL_10 | Tetanus_Int | 0.000 |
| IL_10 | Diptheria_Int | 0.000 | | IL_10 | Diptheria_Int | 0.000 |
| IL_10 | Rubella_Int | 1.000 | | IL_10 | Rubella_Int | 0.000 |
| IL_10 | CMV_Int | 0.000 | | IL_10 | CMV_Int | 0.000 |
| IL_10 | HepB_cAb_Int | 0.000 | | IL_10 | HepB_cAb_Int | 0.000 |
| IL_10 | HepB_eAb_Int | 0.000 | | IL_10 | HepB_eAb_Int | 0.000 |
| IL_10 | HepB_eAg_Int | 0.000 | | IL_10 | HepB_eAg_Int | 0.000 |
| IL_10 | HepC_Int | 0.000 | | IL_10 | HepC_Int | 0.000 |
| IL_10 | Schistosoma_int | 0.000 | | IL_10 | Schistosoma_int | 0.000 |
| IL_10 | Strongyloides_Int | -1.000 | | IL_10 | Strongyloides_Int | 0.000 |
| IL_10 | Filaria_Int | 0.000 | | IL_10 | Filaria_Int | 0.000 |
| IL_12p70 | IL_1_alpha | 1.000 | | IL_12p70 | IL_1_alpha | 0.000 |
| IL_12p70 | IL_1_beta | -1.000 | | IL_12p70 | IL_1_beta | 0.000 |
| IL_12p70 | IL_2 | -1.000 | | IL_12p70 | IL_2 | 0.000 |
| IL_12p70 | IL_4 | 1.000 | | IL_12p70 | IL_4 | 0.000 |
| IL_12p70 | IL_5 | -1.000 | | IL_12p70 | IL_5 | 0.000 |
| IL_12p70 | IL_6 | 1.000 | | IL_12p70 | IL_6 | 0.000 |
| IL_12p70 | IL_8 | 1.000 | | IL_12p70 | IL_8 | 0.000 |
| IL_12p70 | IL_10 | -1.000 | | IL_12p70 | IL_10 | 0.000 |
| IL_12p70 | IL_12p70 | 1.000 | | IL_12p70 | IL_12p70 | 1.000 |
| IL_12p70 | IL_13 | -1.000 | | IL_12p70 | IL_13 | 0.000 |
| IL_12p70 | IL_15 | -1.000 | | IL_12p70 | IL_15 | 0.000 |
| IL_12p70 | IL_17 | -1.000 | | IL_12p70 | IL_17 | 0.000 |
| IL_12p70 | IL_23 | 1.000 | | IL_12p70 | IL_23 | 0.000 |
| IL_12p70 | IFN_gamma | 0.000 | | IL_12p70 | IFN_gamma | 0.000 |
| IL_12p70 | TNF_alpha | -1.000 | | IL_12p70 | TNF_alpha | 0.000 |
| IL_12p70 | TNF_beta | 1.000 | | IL_12p70 | TNF_beta | 0.000 |
| IL_12p70 | Varicella_Int | 0.000 | | IL_12p70 | Varicella_Int | 0.000 |
| IL_12p70 | Measles_OD_DB_Int | 0.000 | | IL_12p70 | Measles_OD_DB_Int | 0.000 |
| IL_12p70 | Measles_Int | 0.000 | | IL_12p70 | Measles_Int | 0.000 |
| IL_12p70 | HepA_Int | 0.000 | | IL_12p70 | HepA_Int | 0.000 |
| IL_12p70 | Tetanus_Int | 0.000 | | IL_12p70 | Tetanus_Int | 0.000 |
| IL_12p70 | Diptheria_Int | 0.000 | | IL_12p70 | Diptheria_Int | 0.000 |
| IL_12p70 | Rubella_Int | -1.000 | | IL_12p70 | Rubella_Int | 0.000 |
| IL_12p70 | CMV_Int | 0.000 | | IL_12p70 | CMV_Int | 0.000 |

FIG. 21I12-E

| | | | | | | |
|---|---|---|---|---|---|---|
| IL_12p70 | HepB_cAb_Int | 0.000 | | IL_12p70 | HepB_cAb_Int | 0.000 |
| IL_12p70 | HepB_eAb_Int | 0.000 | | IL_12p70 | HepB_eAb_Int | 0.000 |
| IL_12p70 | HepB_eAg_Int | 0.000 | | IL_12p70 | HepB_eAg_Int | 0.000 |
| IL_12p70 | HepC_Int | 0.000 | | IL_12p70 | HepC_Int | 0.000 |
| IL_12p70 | Schistosoma_int | 0.000 | | IL_12p70 | Schistosoma_int | 0.000 |
| IL_12p70 | Strongyloides_Int | 1.000 | | IL_12p70 | Strongyloides_Int | 0.000 |
| IL_12p70 | Filaria_Int | 0.000 | | IL_12p70 | Filaria_Int | 0.000 |
| IL_13 | IL_1_alpha | -1.000 | | IL_13 | IL_1_alpha | 0.000 |
| IL_13 | IL_1_beta | 1.000 | | IL_13 | IL_1_beta | 0.000 |
| IL_13 | IL_2 | 1.000 | | IL_13 | IL_2 | 0.000 |
| IL_13 | IL_4 | -1.000 | | IL_13 | IL_4 | 0.000 |
| IL_13 | IL_5 | 1.000 | | IL_13 | IL_5 | 0.000 |
| IL_13 | IL_6 | -1.000 | | IL_13 | IL_6 | 0.000 |
| IL_13 | IL_8 | -1.000 | | IL_13 | IL_8 | 0.000 |
| IL_13 | IL_10 | 1.000 | | IL_13 | IL_10 | 0.000 |
| IL_13 | IL_12p70 | -1.000 | | IL_13 | IL_12p70 | 0.000 |
| IL_13 | IL_13 | 1.000 | | IL_13 | IL_13 | 1.000 |
| IL_13 | IL_15 | 1.000 | | IL_13 | IL_15 | 0.000 |
| IL_13 | IL_17 | 1.000 | | IL_13 | IL_17 | 0.000 |
| IL_13 | IL_23 | -1.000 | | IL_13 | IL_23 | 0.000 |
| IL_13 | IFN_gamma | 0.000 | | IL_13 | IFN_gamma | 0.000 |
| IL_13 | TNF_alpha | 1.000 | | IL_13 | TNF_alpha | 0.000 |
| IL_13 | TNF_beta | -1.000 | | IL_13 | TNF_beta | 0.000 |
| IL_13 | Varicella_Int | 0.000 | | IL_13 | Varicella_Int | 0.000 |
| IL_13 | Measles_OD_DB_Int | 0.000 | | IL_13 | Measles_OD_DB_Int | 0.000 |
| IL_13 | Measles_Int | 0.000 | | IL_13 | Measles_Int | 0.000 |
| IL_13 | HepA_Int | 0.000 | | IL_13 | HepA_Int | 0.000 |
| IL_13 | Tetanus_Int | 0.000 | | IL_13 | Tetanus_Int | 0.000 |
| IL_13 | Diptheria_Int | 0.000 | | IL_13 | Diptheria_Int | 0.000 |
| IL_13 | Rubella_Int | 1.000 | | IL_13 | Rubella_Int | 0.000 |
| IL_13 | CMV_Int | 0.000 | | IL_13 | CMV_Int | 0.000 |
| IL_13 | HepB_cAb_Int | 0.000 | | IL_13 | HepB_cAb_Int | 0.000 |
| IL_13 | HepB_eAb_Int | 0.000 | | IL_13 | HepB_eAb_Int | 0.000 |
| IL_13 | HepB_eAg_Int | 0.000 | | IL_13 | HepB_eAg_Int | 0.000 |
| IL_13 | HepC_Int | 0.000 | | IL_13 | HepC_Int | 0.000 |
| IL_13 | Schistosoma_int | 0.000 | | IL_13 | Schistosoma_int | 0.000 |
| IL_13 | Strongyloides_Int | -1.000 | | IL_13 | Strongyloides_Int | 0.000 |
| IL_13 | Filaria_Int | 0.000 | | IL_13 | Filaria_Int | 0.000 |
| IL_15 | IL_1_alpha | -1.000 | | IL_15 | IL_1_alpha | 0.000 |
| IL_15 | IL_1_beta | 1.000 | | IL_15 | IL_1_beta | 0.000 |
| IL_15 | IL_2 | 1.000 | | IL_15 | IL_2 | 0.000 |
| IL_15 | IL_4 | -1.000 | | IL_15 | IL_4 | 0.000 |
| IL_15 | IL_5 | 1.000 | | IL_15 | IL_5 | 0.000 |
| IL_15 | IL_6 | -1.000 | | IL_15 | IL_6 | 0.000 |
| IL_15 | IL_8 | -1.000 | | IL_15 | IL_8 | 0.000 |
| IL_15 | IL_10 | 1.000 | | IL_15 | IL_10 | 0.000 |
| IL_15 | IL_12p70 | -1.000 | | IL_15 | IL_12p70 | 0.000 |
| IL_15 | IL_13 | 1.000 | | IL_15 | IL_13 | 0.000 |
| IL_15 | IL_15 | 1.000 | | IL_15 | IL_15 | 1.000 |
| IL_15 | IL_17 | 1.000 | | IL_15 | IL_17 | 0.000 |
| IL_15 | IL_23 | -1.000 | | IL_15 | IL_23 | 0.000 |
| IL_15 | IFN_gamma | 0.000 | | IL_15 | IFN_gamma | 0.000 |
| IL_15 | TNF_alpha | 1.000 | | IL_15 | TNF_alpha | 0.000 |
| IL_15 | TNF_beta | -1.000 | | IL_15 | TNF_beta | 0.000 |
| IL_15 | Varicella_Int | 0.000 | | IL_15 | Varicella_Int | 0.000 |
| IL_15 | Measles_OD_DB_Int | 0.000 | | IL_15 | Measles_OD_DB_Int | 0.000 |
| IL_15 | Measles_Int | 0.000 | | IL_15 | Measles_Int | 0.000 |

FIG. 21I12-F

| Col1 | Col2 | Col3 | Col4 | Col5 | Col6 |
|---|---|---|---|---|---|
| IL_15 | HepA_Int | 0.000 | IL_15 | HepA_Int | 0.000 |
| IL_15 | Tetanus_Int | 0.000 | IL_15 | Tetanus_Int | 0.000 |
| IL_15 | Diptheria_Int | 0.000 | IL_15 | Diptheria_Int | 0.000 |
| IL_15 | Rubella_Int | 1.000 | IL_15 | Rubella_Int | 0.000 |
| IL_15 | CMV_Int | 0.000 | IL_15 | CMV_Int | 0.000 |
| IL_15 | HepB_cAb_Int | 0.000 | IL_15 | HepB_cAb_Int | 0.000 |
| IL_15 | HepB_eAb_Int | 0.000 | IL_15 | HepB_eAb_Int | 0.000 |
| IL_15 | HepB_eAg_Int | 0.000 | IL_15 | HepB_eAg_Int | 0.000 |
| IL_15 | HepC_Int | 0.000 | IL_15 | HepC_Int | 0.000 |
| IL_15 | Schistosoma_int | 0.000 | IL_15 | Schistosoma_int | 0.000 |
| IL_15 | Strongyloides_Int | -1.000 | IL_15 | Strongyloides_Int | 0.000 |
| IL_15 | Filaria_Int | 0.000 | IL_15 | Filaria_Int | 0.000 |
| IL_17 | IL_1_alpha | -1.000 | IL_17 | IL_1_alpha | 0.000 |
| IL_17 | IL_1_beta | 1.000 | IL_17 | IL_1_beta | 0.000 |
| IL_17 | IL_2 | 1.000 | IL_17 | IL_2 | 0.000 |
| IL_17 | IL_4 | -1.000 | IL_17 | IL_4 | 0.000 |
| IL_17 | IL_5 | 1.000 | IL_17 | IL_5 | 0.000 |
| IL_17 | IL_6 | -1.000 | IL_17 | IL_6 | 0.000 |
| IL_17 | IL_8 | -1.000 | IL_17 | IL_8 | 0.000 |
| IL_17 | IL_10 | 1.000 | IL_17 | IL_10 | 0.000 |
| IL_17 | IL_12p70 | -1.000 | IL_17 | IL_12p70 | 0.000 |
| IL_17 | IL_13 | 1.000 | IL_17 | IL_13 | 0.000 |
| IL_17 | IL_15 | 1.000 | IL_17 | IL_15 | 0.000 |
| IL_17 | IL_17 | 1.000 | IL_17 | IL_17 | 1.000 |
| IL_17 | IL_23 | -1.000 | IL_17 | IL_23 | 0.000 |
| IL_17 | IFN_gamma | 0.000 | IL_17 | IFN_gamma | 0.000 |
| IL_17 | TNF_alpha | 1.000 | IL_17 | TNF_alpha | 0.000 |
| IL_17 | TNF_beta | -1.000 | IL_17 | TNF_beta | 0.000 |
| IL_17 | Varicella_Int | 0.000 | IL_17 | Varicella_Int | 0.000 |
| IL_17 | Measles_OD_DB_Int | 0.000 | IL_17 | Measles_OD_DB_Int | 0.000 |
| IL_17 | Measles_Int | 0.000 | IL_17 | Measles_Int | 0.000 |
| IL_17 | HepA_Int | 0.000 | IL_17 | HepA_Int | 0.000 |
| IL_17 | Tetanus_Int | 0.000 | IL_17 | Tetanus_Int | 0.000 |
| IL_17 | Diptheria_Int | 0.000 | IL_17 | Diptheria_Int | 0.000 |
| IL_17 | Rubella_Int | 1.000 | IL_17 | Rubella_Int | 0.000 |
| IL_17 | CMV_Int | 0.000 | IL_17 | CMV_Int | 0.000 |
| IL_17 | HepB_cAb_Int | 0.000 | IL_17 | HepB_cAb_Int | 0.000 |
| IL_17 | HepB_eAb_Int | 0.000 | IL_17 | HepB_eAb_Int | 0.000 |
| IL_17 | HepB_eAg_Int | 0.000 | IL_17 | HepB_eAg_Int | 0.000 |
| IL_17 | HepC_Int | 0.000 | IL_17 | HepC_Int | 0.000 |
| IL_17 | Schistosoma_int | 0.000 | IL_17 | Schistosoma_int | 0.000 |
| IL_17 | Strongyloides_Int | -1.000 | IL_17 | Strongyloides_Int | 0.000 |
| IL_17 | Filaria_Int | 0.000 | IL_17 | Filaria_Int | 0.000 |
| IL_23 | IL_1_alpha | 1.000 | IL_23 | IL_1_alpha | 0.000 |
| IL_23 | IL_1_beta | -1.000 | IL_23 | IL_1_beta | 0.000 |
| IL_23 | IL_2 | -1.000 | IL_23 | IL_2 | 0.000 |
| IL_23 | IL_4 | 1.000 | IL_23 | IL_4 | 0.000 |
| IL_23 | IL_5 | -1.000 | IL_23 | IL_5 | 0.000 |
| IL_23 | IL_6 | 1.000 | IL_23 | IL_6 | 0.000 |
| IL_23 | IL_8 | 1.000 | IL_23 | IL_8 | 0.000 |
| IL_23 | IL_10 | -1.000 | IL_23 | IL_10 | 0.000 |
| IL_23 | IL_12p70 | 1.000 | IL_23 | IL_12p70 | 0.000 |
| IL_23 | IL_13 | -1.000 | IL_23 | IL_13 | 0.000 |
| IL_23 | IL_15 | -1.000 | IL_23 | IL_15 | 0.000 |
| IL_23 | IL_17 | -1.000 | IL_23 | IL_17 | 0.000 |
| IL_23 | IL_23 | 1.000 | IL_23 | IL_23 | 1.000 |
| IL_23 | IFN_gamma | 0.000 | IL_23 | IFN_gamma | 0.000 |

FIG. 21I12-G

| IL_23 | TNF_alpha | -1.000 | IL_23 | TNF_alpha | 0.000 |
|---|---|---|---|---|---|
| IL_23 | TNF_beta | 1.000 | IL_23 | TNF_beta | 0.000 |
| IL_23 | Varicella_Int | 0.000 | IL_23 | Varicella_Int | 0.000 |
| IL_23 | Measles_OD_DB_Int | 0.000 | IL_23 | Measles_OD_DB_Int | 0.000 |
| IL_23 | Measles_Int | 0.000 | IL_23 | Measles_Int | 0.000 |
| IL_23 | HepA_Int | 0.000 | IL_23 | HepA_Int | 0.000 |
| IL_23 | Tetanus_Int | 0.000 | IL_23 | Tetanus_Int | 0.000 |
| IL_23 | Diptheria_Int | 0.000 | IL_23 | Diptheria_Int | 0.000 |
| IL_23 | Rubella_Int | -1.000 | IL_23 | Rubella_Int | 0.000 |
| IL_23 | CMV_Int | 0.000 | IL_23 | CMV_Int | 0.000 |
| IL_23 | HepB_cAb_Int | 0.000 | IL_23 | HepB_cAb_Int | 0.000 |
| IL_23 | HepB_eAb_Int | 0.000 | IL_23 | HepB_eAb_Int | 0.000 |
| IL_23 | HepB_eAg_Int | 0.000 | IL_23 | HepB_eAg_Int | 0.000 |
| IL_23 | HepC_Int | 0.000 | IL_23 | HepC_Int | 0.000 |
| IL_23 | Schistosoma_int | 0.000 | IL_23 | Schistosoma_int | 0.000 |
| IL_23 | Strongyloides_Int | 1.000 | IL_23 | Strongyloides_Int | 0.000 |
| IL_23 | Filaria_Int | 0.000 | IL_23 | Filaria_Int | 0.000 |
| IFN_gamma | IL_1_alpha | 0.000 | IFN_gamma | IL_1_alpha | 0.000 |
| IFN_gamma | IL_1_beta | 0.000 | IFN_gamma | IL_1_beta | 0.000 |
| IFN_gamma | IL_2 | 0.000 | IFN_gamma | IL_2 | 0.000 |
| IFN_gamma | IL_4 | 0.000 | IFN_gamma | IL_4 | 0.000 |
| IFN_gamma | IL_5 | 0.000 | IFN_gamma | IL_5 | 0.000 |
| IFN_gamma | IL_6 | 0.000 | IFN_gamma | IL_6 | 0.000 |
| IFN_gamma | IL_8 | 0.000 | IFN_gamma | IL_8 | 0.000 |
| IFN_gamma | IL_10 | 0.000 | IFN_gamma | IL_10 | 0.000 |
| IFN_gamma | IL_12p70 | 0.000 | IFN_gamma | IL_12p70 | 0.000 |
| IFN_gamma | IL_13 | 0.000 | IFN_gamma | IL_13 | 0.000 |
| IFN_gamma | IL_15 | 0.000 | IFN_gamma | IL_15 | 0.000 |
| IFN_gamma | IL_17 | 0.000 | IFN_gamma | IL_17 | 0.000 |
| IFN_gamma | IL_23 | 0.000 | IFN_gamma | IL_23 | 0.000 |
| IFN_gamma | IFN_gamma | 1.000 | IFN_gamma | IFN_gamma | 1.000 |
| IFN_gamma | TNF_alpha | 0.000 | IFN_gamma | TNF_alpha | 0.000 |
| IFN_gamma | TNF_beta | 0.000 | IFN_gamma | TNF_beta | 0.000 |
| IFN_gamma | Varicella_Int | 0.000 | IFN_gamma | Varicella_Int | 0.000 |
| IFN_gamma | Measles_OD_DB_Int | 0.000 | IFN_gamma | Measles_OD_DB_Int | 0.000 |
| IFN_gamma | Measles_Int | 0.000 | IFN_gamma | Measles_Int | 0.000 |
| IFN_gamma | HepA_Int | 0.000 | IFN_gamma | HepA_Int | 0.000 |
| IFN_gamma | Tetanus_Int | 0.000 | IFN_gamma | Tetanus_Int | 0.000 |
| IFN_gamma | Diptheria_Int | 0.000 | IFN_gamma | Diptheria_Int | 0.000 |
| IFN_gamma | Rubella_Int | 0.000 | IFN_gamma | Rubella_Int | 0.000 |
| IFN_gamma | CMV_Int | 0.000 | IFN_gamma | CMV_Int | 0.000 |
| IFN_gamma | HepB_cAb_Int | 0.000 | IFN_gamma | HepB_cAb_Int | 0.000 |
| IFN_gamma | HepB_eAb_Int | 0.000 | IFN_gamma | HepB_eAb_Int | 0.000 |
| IFN_gamma | HepB_eAg_Int | 0.000 | IFN_gamma | HepB_eAg_Int | 0.000 |
| IFN_gamma | HepC_Int | 0.000 | IFN_gamma | HepC_Int | 0.000 |
| IFN_gamma | Schistosoma_int | 0.000 | IFN_gamma | Schistosoma_int | 0.000 |
| IFN_gamma | Strongyloides_Int | 0.000 | IFN_gamma | Strongyloides_Int | 0.000 |
| IFN_gamma | Filaria_Int | 0.000 | IFN_gamma | Filaria_Int | 0.000 |
| TNF_alpha | IL_1_alpha | -1.000 | TNF_alpha | IL_1_alpha | 0.000 |
| TNF_alpha | IL_1_beta | 1.000 | TNF_alpha | IL_1_beta | 0.000 |
| TNF_alpha | IL_2 | 1.000 | TNF_alpha | IL_2 | 0.000 |
| TNF_alpha | IL_4 | -1.000 | TNF_alpha | IL_4 | 0.000 |
| TNF_alpha | IL_5 | 1.000 | TNF_alpha | IL_5 | 0.000 |
| TNF_alpha | IL_6 | -1.000 | TNF_alpha | IL_6 | 0.000 |
| TNF_alpha | IL_8 | -1.000 | TNF_alpha | IL_8 | 0.000 |
| TNF_alpha | IL_10 | 1.000 | TNF_alpha | IL_10 | 0.000 |
| TNF_alpha | IL_12p70 | -1.000 | TNF_alpha | IL_12p70 | 0.000 |

FIG. 21I12-H

| | | | | | | |
|---|---|---|---|---|---|---|
| TNF_alpha | IL_13 | 1.000 | | TNF_alpha | IL_13 | 0.000 |
| TNF_alpha | IL_15 | 1.000 | | TNF_alpha | IL_15 | 0.000 |
| TNF_alpha | IL_17 | 1.000 | | TNF_alpha | IL_17 | 0.000 |
| TNF_alpha | IL_23 | -1.000 | | TNF_alpha | IL_23 | 0.000 |
| TNF_alpha | IFN_gamma | 0.000 | | TNF_alpha | IFN_gamma | 0.000 |
| TNF_alpha | TNF_alpha | 1.000 | | TNF_alpha | TNF_alpha | 1.000 |
| TNF_alpha | TNF_beta | -1.000 | | TNF_alpha | TNF_beta | 0.000 |
| TNF_alpha | Varicella_Int | 0.000 | | TNF_alpha | Varicella_Int | 0.000 |
| TNF_alpha | Measles_OD_DB_Int | 0.000 | | TNF_alpha | Measles_OD_DB_Int | 0.000 |
| TNF_alpha | Measles_Int | 0.000 | | TNF_alpha | Measles_Int | 0.000 |
| TNF_alpha | HepA_Int | 0.000 | | TNF_alpha | HepA_Int | 0.000 |
| TNF_alpha | Tetanus_Int | 0.000 | | TNF_alpha | Tetanus_Int | 0.000 |
| TNF_alpha | Diptheria_Int | 0.000 | | TNF_alpha | Diptheria_Int | 0.000 |
| TNF_alpha | Rubella_Int | 1.000 | | TNF_alpha | Rubella_Int | 0.000 |
| TNF_alpha | CMV_Int | 0.000 | | TNF_alpha | CMV_Int | 0.000 |
| TNF_alpha | HepB_cAb_Int | 0.000 | | TNF_alpha | HepB_cAb_Int | 0.000 |
| TNF_alpha | HepB_eAb_Int | 0.000 | | TNF_alpha | HepB_eAb_Int | 0.000 |
| TNF_alpha | HepB_eAg_Int | 0.000 | | TNF_alpha | HepB_eAg_Int | 0.000 |
| TNF_alpha | HepC_Int | 0.000 | | TNF_alpha | HepC_Int | 0.000 |
| TNF_alpha | Schistosoma_int | 0.000 | | TNF_alpha | Schistosoma_int | 0.000 |
| TNF_alpha | Strongyloides_Int | -1.000 | | TNF_alpha | Strongyloides_Int | 0.000 |
| TNF_alpha | Filaria_Int | 0.000 | | TNF_alpha | Filaria_Int | 0.000 |
| TNF_beta | IL_1_alpha | 1.000 | | TNF_beta | IL_1_alpha | 0.000 |
| TNF_beta | IL_1_beta | -1.000 | | TNF_beta | IL_1_beta | 0.000 |
| TNF_beta | IL_2 | -1.000 | | TNF_beta | IL_2 | 0.000 |
| TNF_beta | IL_4 | 1.000 | | TNF_beta | IL_4 | 0.000 |
| TNF_beta | IL_5 | -1.000 | | TNF_beta | IL_5 | 0.000 |
| TNF_beta | IL_6 | 1.000 | | TNF_beta | IL_6 | 0.000 |
| TNF_beta | IL_8 | 1.000 | | TNF_beta | IL_8 | 0.000 |
| TNF_beta | IL_10 | -1.000 | | TNF_beta | IL_10 | 0.000 |
| TNF_beta | IL_12p70 | 1.000 | | TNF_beta | IL_12p70 | 0.000 |
| TNF_beta | IL_13 | -1.000 | | TNF_beta | IL_13 | 0.000 |
| TNF_beta | IL_15 | -1.000 | | TNF_beta | IL_15 | 0.000 |
| TNF_beta | IL_17 | -1.000 | | TNF_beta | IL_17 | 0.000 |
| TNF_beta | IL_23 | 1.000 | | TNF_beta | IL_23 | 0.000 |
| TNF_beta | IFN_gamma | 0.000 | | TNF_beta | IFN_gamma | 0.000 |
| TNF_beta | TNF_alpha | -1.000 | | TNF_beta | TNF_alpha | 0.000 |
| TNF_beta | TNF_beta | 1.000 | | TNF_beta | TNF_beta | 1.000 |
| TNF_beta | Varicella_Int | 0.000 | | TNF_beta | Varicella_Int | 0.000 |
| TNF_beta | Measles_OD_DB_Int | 0.000 | | TNF_beta | Measles_OD_DB_Int | 0.000 |
| TNF_beta | Measles_Int | 0.000 | | TNF_beta | Measles_Int | 0.000 |
| TNF_beta | HepA_Int | 0.000 | | TNF_beta | HepA_Int | 0.000 |
| TNF_beta | Tetanus_Int | 0.000 | | TNF_beta | Tetanus_Int | 0.000 |
| TNF_beta | Diptheria_Int | 0.000 | | TNF_beta | Diptheria_Int | 0.000 |
| TNF_beta | Rubella_Int | -1.000 | | TNF_beta | Rubella_Int | 0.000 |
| TNF_beta | CMV_Int | 0.000 | | TNF_beta | CMV_Int | 0.000 |
| TNF_beta | HepB_cAb_Int | 0.000 | | TNF_beta | HepB_cAb_Int | 0.000 |
| TNF_beta | HepB_eAb_Int | 0.000 | | TNF_beta | HepB_eAb_Int | 0.000 |
| TNF_beta | HepB_eAg_Int | 0.000 | | TNF_beta | HepB_eAg_Int | 0.000 |
| TNF_beta | HepC_Int | 0.000 | | TNF_beta | HepC_Int | 0.000 |
| TNF_beta | Schistosoma_int | 0.000 | | TNF_beta | Schistosoma_int | 0.000 |
| TNF_beta | Strongyloides_Int | 1.000 | | TNF_beta | Strongyloides_Int | 0.000 |
| TNF_beta | Filaria_Int | 0.000 | | TNF_beta | Filaria_Int | 0.000 |
| Varicella_Int | IL_1_alpha | 0.000 | | Varicella_Int | IL_1_alpha | 0.000 |
| Varicella_Int | IL_1_beta | 0.000 | | Varicella_Int | IL_1_beta | 0.000 |
| Varicella_Int | IL_2 | 0.000 | | Varicella_Int | IL_2 | 0.000 |
| Varicella_Int | IL_4 | 0.000 | | Varicella_Int | IL_4 | 0.000 |

FIG. 21I12-I

| | | | | | | |
|---|---|---|---|---|---|---|
| Varicella_Int | IL_5 | 0.000 | | Varicella_Int | IL_5 | 0.000 |
| Varicella_Int | IL_6 | 0.000 | | Varicella_Int | IL_6 | 0.000 |
| Varicella_Int | IL_8 | 0.000 | | Varicella_Int | IL_8 | 0.000 |
| Varicella_Int | IL_10 | 0.000 | | Varicella_Int | IL_10 | 0.000 |
| Varicella_Int | IL_12p70 | 0.000 | | Varicella_Int | IL_12p70 | 0.000 |
| Varicella_Int | IL_13 | 0.000 | | Varicella_Int | IL_13 | 0.000 |
| Varicella_Int | IL_15 | 0.000 | | Varicella_Int | IL_15 | 0.000 |
| Varicella_Int | IL_17 | 0.000 | | Varicella_Int | IL_17 | 0.000 |
| Varicella_Int | IL_23 | 0.000 | | Varicella_Int | IL_23 | 0.000 |
| Varicella_Int | IFN_gamma | 0.000 | | Varicella_Int | IFN_gamma | 0.000 |
| Varicella_Int | TNF_alpha | 0.000 | | Varicella_Int | TNF_alpha | 0.000 |
| Varicella_Int | TNF_beta | 0.000 | | Varicella_Int | TNF_beta | 0.000 |
| Varicella_Int | Varicella_Int | 1.000 | | Varicella_Int | Varicella_Int | 1.000 |
| Varicella_Int | Measles_OD_DB_Int | 0.000 | | Varicella_Int | Measles_OD_DB_Int | 0.000 |
| Varicella_Int | Measles_Int | 0.000 | | Varicella_Int | Measles_Int | 0.000 |
| Varicella_Int | HepA_Int | 0.000 | | Varicella_Int | HepA_Int | 0.000 |
| Varicella_Int | Tetanus_Int | 0.000 | | Varicella_Int | Tetanus_Int | 0.000 |
| Varicella_Int | Diptheria_Int | 0.000 | | Varicella_Int | Diptheria_Int | 0.000 |
| Varicella_Int | Rubella_Int | 0.000 | | Varicella_Int | Rubella_Int | 0.000 |
| Varicella_Int | CMV_Int | 0.000 | | Varicella_Int | CMV_Int | 0.000 |
| Varicella_Int | HepB_cAb_Int | 0.000 | | Varicella_Int | HepB_cAb_Int | 0.000 |
| Varicella_Int | HepB_eAb_Int | 0.000 | | Varicella_Int | HepB_eAb_Int | 0.000 |
| Varicella_Int | HepB_eAg_Int | 0.000 | | Varicella_Int | HepB_eAg_Int | 0.000 |
| Varicella_Int | HepC_Int | 0.000 | | Varicella_Int | HepC_Int | 0.000 |
| Varicella_Int | Schistosoma_int | 0.000 | | Varicella_Int | Schistosoma_int | 0.000 |
| Varicella_Int | Strongyloides_Int | 0.000 | | Varicella_Int | Strongyloides_Int | 0.000 |
| Varicella_Int | Filaria_Int | 0.000 | | Varicella_Int | Filaria_Int | 0.000 |
| Measles_OD_DB_Int | IL_1_alpha | 0.000 | | Measles_OD_DB_Int | IL_1_alpha | 0.000 |
| Measles_OD_DB_Int | IL_1_beta | 0.000 | | Measles_OD_DB_Int | IL_1_beta | 0.000 |
| Measles_OD_DB_Int | IL_2 | 0.000 | | Measles_OD_DB_Int | IL_2 | 0.000 |
| Measles_OD_DB_Int | IL_4 | 0.000 | | Measles_OD_DB_Int | IL_4 | 0.000 |
| Measles_OD_DB_Int | IL_5 | 0.000 | | Measles_OD_DB_Int | IL_5 | 0.000 |
| Measles_OD_DB_Int | IL_6 | 0.000 | | Measles_OD_DB_Int | IL_6 | 0.000 |
| Measles_OD_DB_Int | IL_8 | 0.000 | | Measles_OD_DB_Int | IL_8 | 0.000 |
| Measles_OD_DB_Int | IL_10 | 0.000 | | Measles_OD_DB_Int | IL_10 | 0.000 |
| Measles_OD_DB_Int | IL_12p70 | 0.000 | | Measles_OD_DB_Int | IL_12p70 | 0.000 |
| Measles_OD_DB_Int | IL_13 | 0.000 | | Measles_OD_DB_Int | IL_13 | 0.000 |
| Measles_OD_DB_Int | IL_15 | 0.000 | | Measles_OD_DB_Int | IL_15 | 0.000 |
| Measles_OD_DB_Int | IL_17 | 0.000 | | Measles_OD_DB_Int | IL_17 | 0.000 |
| Measles_OD_DB_Int | IL_23 | 0.000 | | Measles_OD_DB_Int | IL_23 | 0.000 |
| Measles_OD_DB_Int | IFN_gamma | 0.000 | | Measles_OD_DB_Int | IFN_gamma | 0.000 |
| Measles_OD_DB_Int | TNF_alpha | 0.000 | | Measles_OD_DB_Int | TNF_alpha | 0.000 |
| Measles_OD_DB_Int | TNF_beta | 0.000 | | Measles_OD_DB_Int | TNF_beta | 0.000 |
| Measles_OD_DB_Int | Varicella_Int | 0.000 | | Measles_OD_DB_Int | Varicella_Int | 0.000 |
| Measles_OD_DB_Int | Measles_OD_DB_Int | 1.000 | | Measles_OD_DB_Int | Measles_OD_DB_Int | 1.000 |
| Measles_OD_DB_Int | Measles_Int | 0.000 | | Measles_OD_DB_Int | Measles_Int | 0.000 |
| Measles_OD_DB_Int | HepA_Int | 0.000 | | Measles_OD_DB_Int | HepA_Int | 0.000 |
| Measles_OD_DB_Int | Tetanus_Int | 0.000 | | Measles_OD_DB_Int | Tetanus_Int | 0.000 |
| Measles_OD_DB_Int | Diptheria_Int | 0.000 | | Measles_OD_DB_Int | Diptheria_Int | 0.000 |
| Measles_OD_DB_Int | Rubella_Int | 0.000 | | Measles_OD_DB_Int | Rubella_Int | 0.000 |
| Measles_OD_DB_Int | CMV_Int | 0.000 | | Measles_OD_DB_Int | CMV_Int | 0.000 |
| Measles_OD_DB_Int | HepB_cAb_Int | 0.000 | | Measles_OD_DB_Int | HepB_cAb_Int | 0.000 |
| Measles_OD_DB_Int | HepB_eAb_Int | 0.000 | | Measles_OD_DB_Int | HepB_eAb_Int | 0.000 |
| Measles_OD_DB_Int | HepB_eAg_Int | 0.000 | | Measles_OD_DB_Int | HepB_eAg_Int | 0.000 |
| Measles_OD_DB_Int | HepC_Int | 0.000 | | Measles_OD_DB_Int | HepC_Int | 0.000 |
| Measles_OD_DB_Int | Schistosoma_int | 0.000 | | Measles_OD_DB_Int | Schistosoma_int | 0.000 |
| Measles_OD_DB_Int | Strongyloides_Int | 0.000 | | Measles_OD_DB_Int | Strongyloides_Int | 0.000 |

FIG. 21I12-J

| | | | | | | |
|---|---|---|---|---|---|---|
| Measles_OD_DB_Int | Filaria_Int | 0.000 | | Measles_OD_DB_Int | Filaria_Int | 0.000 |
| Measles_Int | IL_1_alpha | 0.000 | | Measles_Int | IL_1_alpha | 0.000 |
| Measles_Int | IL_1_beta | 0.000 | | Measles_Int | IL_1_beta | 0.000 |
| Measles_Int | IL_2 | 0.000 | | Measles_Int | IL_2 | 0.000 |
| Measles_Int | IL_4 | 0.000 | | Measles_Int | IL_4 | 0.000 |
| Measles_Int | IL_5 | 0.000 | | Measles_Int | IL_5 | 0.000 |
| Measles_Int | IL_6 | 0.000 | | Measles_Int | IL_6 | 0.000 |
| Measles_Int | IL_8 | 0.000 | | Measles_Int | IL_8 | 0.000 |
| Measles_Int | IL_10 | 0.000 | | Measles_Int | IL_10 | 0.000 |
| Measles_Int | IL_12p70 | 0.000 | | Measles_Int | IL_12p70 | 0.000 |
| Measles_Int | IL_13 | 0.000 | | Measles_Int | IL_13 | 0.000 |
| Measles_Int | IL_15 | 0.000 | | Measles_Int | IL_15 | 0.000 |
| Measles_Int | IL_17 | 0.000 | | Measles_Int | IL_17 | 0.000 |
| Measles_Int | IL_23 | 0.000 | | Measles_Int | IL_23 | 0.000 |
| Measles_Int | IFN_gamma | 0.000 | | Measles_Int | IFN_gamma | 0.000 |
| Measles_Int | TNF_alpha | 0.000 | | Measles_Int | TNF_alpha | 0.000 |
| Measles_Int | TNF_beta | 0.000 | | Measles_Int | TNF_beta | 0.000 |
| Measles_Int | Varicella_Int | 0.000 | | Measles_Int | Varicella_Int | 0.000 |
| Measles_Int | Measles_OD_DB_Int | 0.000 | | Measles_Int | Measles_OD_DB_Int | 0.000 |
| Measles_Int | Measles_Int | 1.000 | | Measles_Int | Measles_Int | 1.000 |
| Measles_Int | HepA_Int | 0.000 | | Measles_Int | HepA_Int | 0.000 |
| Measles_Int | Tetanus_Int | 0.000 | | Measles_Int | Tetanus_Int | 0.000 |
| Measles_Int | Diptheria_Int | 0.000 | | Measles_Int | Diptheria_Int | 0.000 |
| Measles_Int | Rubella_Int | 0.000 | | Measles_Int | Rubella_Int | 0.000 |
| Measles_Int | CMV_Int | 0.000 | | Measles_Int | CMV_Int | 0.000 |
| Measles_Int | HepB_cAb_Int | 0.000 | | Measles_Int | HepB_cAb_Int | 0.000 |
| Measles_Int | HepB_eAb_Int | 0.000 | | Measles_Int | HepB_eAb_Int | 0.000 |
| Measles_Int | HepB_eAg_Int | 0.000 | | Measles_Int | HepB_eAg_Int | 0.000 |
| Measles_Int | HepC_Int | 0.000 | | Measles_Int | HepC_Int | 0.000 |
| Measles_Int | Schistosoma_int | 0.000 | | Measles_Int | Schistosoma_int | 0.000 |
| Measles_Int | Strongyloides_Int | 0.000 | | Measles_Int | Strongyloides_Int | 0.000 |
| Measles_Int | Filaria_Int | 0.000 | | Measles_Int | Filaria_Int | 0.000 |
| HepA_Int | IL_1_alpha | 0.000 | | HepA_Int | IL_1_alpha | 0.000 |
| HepA_Int | IL_1_beta | 0.000 | | HepA_Int | IL_1_beta | 0.000 |
| HepA_Int | IL_2 | 0.000 | | HepA_Int | IL_2 | 0.000 |
| HepA_Int | IL_4 | 0.000 | | HepA_Int | IL_4 | 0.000 |
| HepA_Int | IL_5 | 0.000 | | HepA_Int | IL_5 | 0.000 |
| HepA_Int | IL_6 | 0.000 | | HepA_Int | IL_6 | 0.000 |
| HepA_Int | IL_8 | 0.000 | | HepA_Int | IL_8 | 0.000 |
| HepA_Int | IL_10 | 0.000 | | HepA_Int | IL_10 | 0.000 |
| HepA_Int | IL_12p70 | 0.000 | | HepA_Int | IL_12p70 | 0.000 |
| HepA_Int | IL_13 | 0.000 | | HepA_Int | IL_13 | 0.000 |
| HepA_Int | IL_15 | 0.000 | | HepA_Int | IL_15 | 0.000 |
| HepA_Int | IL_17 | 0.000 | | HepA_Int | IL_17 | 0.000 |
| HepA_Int | IL_23 | 0.000 | | HepA_Int | IL_23 | 0.000 |
| HepA_Int | IFN_gamma | 0.000 | | HepA_Int | IFN_gamma | 0.000 |
| HepA_Int | TNF_alpha | 0.000 | | HepA_Int | TNF_alpha | 0.000 |
| HepA_Int | TNF_beta | 0.000 | | HepA_Int | TNF_beta | 0.000 |
| HepA_Int | Varicella_Int | 0.000 | | HepA_Int | Varicella_Int | 0.000 |
| HepA_Int | Measles_OD_DB_Int | 0.000 | | HepA_Int | Measles_OD_DB_Int | 0.000 |
| HepA_Int | Measles_Int | 0.000 | | HepA_Int | Measles_Int | 0.000 |
| HepA_Int | HepA_Int | 1.000 | | HepA_Int | HepA_Int | 1.000 |
| HepA_Int | Tetanus_Int | 0.000 | | HepA_Int | Tetanus_Int | 0.000 |
| HepA_Int | Diptheria_Int | 0.000 | | HepA_Int | Diptheria_Int | 0.000 |
| HepA_Int | Rubella_Int | 0.000 | | HepA_Int | Rubella_Int | 0.000 |
| HepA_Int | CMV_Int | 0.000 | | HepA_Int | CMV_Int | 0.000 |
| HepA_Int | HepB_cAb_Int | 0.000 | | HepA_Int | HepB_cAb_Int | 0.000 |

FIG. 21I12-K

| | | | | | | |
|---|---|---|---|---|---|---|
| HepA_Int | HepB_eAb_Int | 0.000 | | HepA_Int | HepB_eAb_Int | 0.000 |
| HepA_Int | HepB_eAg_Int | 0.000 | | HepA_Int | HepB_eAg_Int | 0.000 |
| HepA_Int | HepC_Int | 0.000 | | HepA_Int | HepC_Int | 0.000 |
| HepA_Int | Schistosoma_int | 0.000 | | HepA_Int | Schistosoma_int | 0.000 |
| HepA_Int | Strongyloides_Int | 0.000 | | HepA_Int | Strongyloides_Int | 0.000 |
| HepA_Int | Filaria_Int | 0.000 | | HepA_Int | Filaria_Int | 0.000 |
| Tetanus_Int | IL_1_alpha | 0.000 | | Tetanus_Int | IL_1_alpha | 0.000 |
| Tetanus_Int | IL_1_beta | 0.000 | | Tetanus_Int | IL_1_beta | 0.000 |
| Tetanus_Int | IL_2 | 0.000 | | Tetanus_Int | IL_2 | 0.000 |
| Tetanus_Int | IL_4 | 0.000 | | Tetanus_Int | IL_4 | 0.000 |
| Tetanus_Int | IL_5 | 0.000 | | Tetanus_Int | IL_5 | 0.000 |
| Tetanus_Int | IL_6 | 0.000 | | Tetanus_Int | IL_6 | 0.000 |
| Tetanus_Int | IL_8 | 0.000 | | Tetanus_Int | IL_8 | 0.000 |
| Tetanus_Int | IL_10 | 0.000 | | Tetanus_Int | IL_10 | 0.000 |
| Tetanus_Int | IL_12p70 | 0.000 | | Tetanus_Int | IL_12p70 | 0.000 |
| Tetanus_Int | IL_13 | 0.000 | | Tetanus_Int | IL_13 | 0.000 |
| Tetanus_Int | IL_15 | 0.000 | | Tetanus_Int | IL_15 | 0.000 |
| Tetanus_Int | IL_17 | 0.000 | | Tetanus_Int | IL_17 | 0.000 |
| Tetanus_Int | IL_23 | 0.000 | | Tetanus_Int | IL_23 | 0.000 |
| Tetanus_Int | IFN_gamma | 0.000 | | Tetanus_Int | IFN_gamma | 0.000 |
| Tetanus_Int | TNF_alpha | 0.000 | | Tetanus_Int | TNF_alpha | 0.000 |
| Tetanus_Int | TNF_beta | 0.000 | | Tetanus_Int | TNF_beta | 0.000 |
| Tetanus_Int | Varicella_Int | 0.000 | | Tetanus_Int | Varicella_Int | 0.000 |
| Tetanus_Int | Measles_OD_DB_Int | 0.000 | | Tetanus_Int | Measles_OD_DB_Int | 0.000 |
| Tetanus_Int | Measles_Int | 0.000 | | Tetanus_Int | Measles_Int | 0.000 |
| Tetanus_Int | HepA_Int | 0.000 | | Tetanus_Int | HepA_Int | 0.000 |
| Tetanus_Int | Tetanus_Int | 1.000 | | Tetanus_Int | Tetanus_Int | 1.000 |
| Tetanus_Int | Diptheria_Int | 0.000 | | Tetanus_Int | Diptheria_Int | 0.000 |
| Tetanus_Int | Rubella_Int | 0.000 | | Tetanus_Int | Rubella_Int | 0.000 |
| Tetanus_Int | CMV_Int | 0.000 | | Tetanus_Int | CMV_Int | 0.000 |
| Tetanus_Int | HepB_cAb_Int | 0.000 | | Tetanus_Int | HepB_cAb_Int | 0.000 |
| Tetanus_Int | HepB_eAb_Int | 0.000 | | Tetanus_Int | HepB_eAb_Int | 0.000 |
| Tetanus_Int | HepB_eAg_Int | 0.000 | | Tetanus_Int | HepB_eAg_Int | 0.000 |
| Tetanus_Int | HepC_Int | 0.000 | | Tetanus_Int | HepC_Int | 0.000 |
| Tetanus_Int | Schistosoma_int | 0.000 | | Tetanus_Int | Schistosoma_int | 0.000 |
| Tetanus_Int | Strongyloides_Int | 0.000 | | Tetanus_Int | Strongyloides_Int | 0.000 |
| Tetanus_Int | Filaria_Int | 0.000 | | Tetanus_Int | Filaria_Int | 0.000 |
| Diptheria_Int | IL_1_alpha | 0.000 | | Diptheria_Int | IL_1_alpha | 0.000 |
| Diptheria_Int | IL_1_beta | 0.000 | | Diptheria_Int | IL_1_beta | 0.000 |
| Diptheria_Int | IL_2 | 0.000 | | Diptheria_Int | IL_2 | 0.000 |
| Diptheria_Int | IL_4 | 0.000 | | Diptheria_Int | IL_4 | 0.000 |
| Diptheria_Int | IL_5 | 0.000 | | Diptheria_Int | IL_5 | 0.000 |
| Diptheria_Int | IL_6 | 0.000 | | Diptheria_Int | IL_6 | 0.000 |
| Diptheria_Int | IL_8 | 0.000 | | Diptheria_Int | IL_8 | 0.000 |
| Diptheria_Int | IL_10 | 0.000 | | Diptheria_Int | IL_10 | 0.000 |
| Diptheria_Int | IL_12p70 | 0.000 | | Diptheria_Int | IL_12p70 | 0.000 |
| Diptheria_Int | IL_13 | 0.000 | | Diptheria_Int | IL_13 | 0.000 |
| Diptheria_Int | IL_15 | 0.000 | | Diptheria_Int | IL_15 | 0.000 |
| Diptheria_Int | IL_17 | 0.000 | | Diptheria_Int | IL_17 | 0.000 |
| Diptheria_Int | IL_23 | 0.000 | | Diptheria_Int | IL_23 | 0.000 |
| Diptheria_Int | IFN_gamma | 0.000 | | Diptheria_Int | IFN_gamma | 0.000 |
| Diptheria_Int | TNF_alpha | 0.000 | | Diptheria_Int | TNF_alpha | 0.000 |
| Diptheria_Int | TNF_beta | 0.000 | | Diptheria_Int | TNF_beta | 0.000 |
| Diptheria_Int | Varicella_Int | 0.000 | | Diptheria_Int | Varicella_Int | 0.000 |
| Diptheria_Int | Measles_OD_DB_Int | 0.000 | | Diptheria_Int | Measles_OD_DB_Int | 0.000 |
| Diptheria_Int | Measles_Int | 0.000 | | Diptheria_Int | Measles_Int | 0.000 |
| Diptheria_Int | HepA_Int | 0.000 | | Diptheria_Int | HepA_Int | 0.000 |

FIG. 21I12-L

| | | | | | | |
|---|---|---|---|---|---|---|
| Diptheria_Int | Tetanus_Int | 0.000 | | Diptheria_Int | Tetanus_Int | 0.000 |
| Diptheria_Int | Diptheria_Int | 1.000 | | Diptheria_Int | Diptheria_Int | 1.000 |
| Diptheria_Int | Rubella_Int | 0.000 | | Diptheria_Int | Rubella_Int | 0.000 |
| Diptheria_Int | CMV_Int | 0.000 | | Diptheria_Int | CMV_Int | 0.000 |
| Diptheria_Int | HepB_cAb_Int | 0.000 | | Diptheria_Int | HepB_cAb_Int | 0.000 |
| Diptheria_Int | HepB_eAb_Int | 0.000 | | Diptheria_Int | HepB_eAb_Int | 0.000 |
| Diptheria_Int | HepB_eAg_Int | 0.000 | | Diptheria_Int | HepB_eAg_Int | 0.000 |
| Diptheria_Int | HepC_Int | 0.000 | | Diptheria_Int | HepC_Int | 0.000 |
| Diptheria_Int | Schistosoma_int | 0.000 | | Diptheria_Int | Schistosoma_int | 0.000 |
| Diptheria_Int | Strongyloides_Int | 0.000 | | Diptheria_Int | Strongyloides_Int | 0.000 |
| Diptheria_Int | Filaria_Int | 0.000 | | Diptheria_Int | Filaria_Int | 0.000 |
| Rubella_Int | IL_1_alpha | -1.000 | | Rubella_Int | IL_1_alpha | 0.000 |
| Rubella_Int | IL_1_beta | 1.000 | | Rubella_Int | IL_1_beta | 0.000 |
| Rubella_Int | IL_2 | 1.000 | | Rubella_Int | IL_2 | 0.000 |
| Rubella_Int | IL_4 | -1.000 | | Rubella_Int | IL_4 | 0.000 |
| Rubella_Int | IL_5 | 1.000 | | Rubella_Int | IL_5 | 0.000 |
| Rubella_Int | IL_6 | -1.000 | | Rubella_Int | IL_6 | 0.000 |
| Rubella_Int | IL_8 | -1.000 | | Rubella_Int | IL_8 | 0.000 |
| Rubella_Int | IL_10 | 1.000 | | Rubella_Int | IL_10 | 0.000 |
| Rubella_Int | IL_12p70 | -1.000 | | Rubella_Int | IL_12p70 | 0.000 |
| Rubella_Int | IL_13 | 1.000 | | Rubella_Int | IL_13 | 0.000 |
| Rubella_Int | IL_15 | 1.000 | | Rubella_Int | IL_15 | 0.000 |
| Rubella_Int | IL_17 | 1.000 | | Rubella_Int | IL_17 | 0.000 |
| Rubella_Int | IL_23 | -1.000 | | Rubella_Int | IL_23 | 0.000 |
| Rubella_Int | IFN_gamma | 0.000 | | Rubella_Int | IFN_gamma | 0.000 |
| Rubella_Int | TNF_alpha | 1.000 | | Rubella_Int | TNF_alpha | 0.000 |
| Rubella_Int | TNF_beta | -1.000 | | Rubella_Int | TNF_beta | 0.000 |
| Rubella_Int | Varicella_Int | 0.000 | | Rubella_Int | Varicella_Int | 0.000 |
| Rubella_Int | Measles_OD_DB_Int | 0.000 | | Rubella_Int | Measles_OD_DB_Int | 0.000 |
| Rubella_Int | Measles_int | 0.000 | | Rubella_Int | Measles_Int | 0.000 |
| Rubella_Int | HepA_Int | 0.000 | | Rubella_Int | HepA_Int | 0.000 |
| Rubella_Int | Tetanus_Int | 0.000 | | Rubella_Int | Tetanus_Int | 0.000 |
| Rubella_Int | Diptheria_Int | 0.000 | | Rubella_Int | Diptheria_Int | 0.000 |
| Rubella_Int | Rubella_Int | 1.000 | | Rubella_Int | Rubella_Int | 1.000 |
| Rubella_Int | CMV_Int | 0.000 | | Rubella_Int | CMV_Int | 0.000 |
| Rubella_Int | HepB_cAb_Int | 0.000 | | Rubella_Int | HepB_cAb_Int | 0.000 |
| Rubella_Int | HepB_eAb_Int | 0.000 | | Rubella_Int | HepB_eAb_Int | 0.000 |
| Rubella_Int | HepB_eAg_Int | 0.000 | | Rubella_Int | HepB_eAg_Int | 0.000 |
| Rubella_Int | HepC_Int | 0.000 | | Rubella_Int | HepC_Int | 0.000 |
| Rubella_Int | Schistosoma_int | 0.000 | | Rubella_Int | Schistosoma_int | 0.000 |
| Rubella_Int | Strongyloides_Int | -1.000 | | Rubella_Int | Strongyloides_Int | 0.000 |
| Rubella_Int | Filaria_Int | 0.000 | | Rubella_Int | Filaria_Int | 0.000 |
| CMV_Int | IL_1_alpha | 0.000 | | CMV_Int | IL_1_alpha | 0.000 |
| CMV_Int | IL_1_beta | 0.000 | | CMV_Int | IL_1_beta | 0.000 |
| CMV_Int | IL_2 | 0.000 | | CMV_Int | IL_2 | 0.000 |
| CMV_Int | IL_4 | 0.000 | | CMV_Int | IL_4 | 0.000 |
| CMV_Int | IL_5 | 0.000 | | CMV_Int | IL_5 | 0.000 |
| CMV_Int | IL_6 | 0.000 | | CMV_Int | IL_6 | 0.000 |
| CMV_Int | IL_8 | 0.000 | | CMV_Int | IL_8 | 0.000 |
| CMV_Int | IL_10 | 0.000 | | CMV_Int | IL_10 | 0.000 |
| CMV_Int | IL_12p70 | 0.000 | | CMV_Int | IL_12p70 | 0.000 |
| CMV_Int | IL_13 | 0.000 | | CMV_Int | IL_13 | 0.000 |
| CMV_Int | IL_15 | 0.000 | | CMV_Int | IL_15 | 0.000 |
| CMV_Int | IL_17 | 0.000 | | CMV_Int | IL_17 | 0.000 |
| CMV_Int | IL_23 | 0.000 | | CMV_Int | IL_23 | 0.000 |
| CMV_Int | IFN_gamma | 0.000 | | CMV_Int | IFN_gamma | 0.000 |
| CMV_Int | TNF_alpha | 0.000 | | CMV_Int | TNF_alpha | 0.000 |

FIG. 21I12-M

| | | | | | | |
|---|---|---|---|---|---|---|
| CMV_Int | TNF_beta | 0.000 | | CMV_Int | TNF_beta | 0.000 |
| CMV_Int | Varicella_Int | 0.000 | | CMV_Int | Varicella_Int | 0.000 |
| CMV_Int | Measles_OD_DB_Int | 0.000 | | CMV_Int | Measles_OD_DB_Int | 0.000 |
| CMV_Int | Measles_Int | 0.000 | | CMV_Int | Measles_Int | 0.000 |
| CMV_Int | HepA_Int | 0.000 | | CMV_Int | HepA_Int | 0.000 |
| CMV_Int | Tetanus_Int | 0.000 | | CMV_Int | Tetanus_Int | 0.000 |
| CMV_Int | Diptheria_Int | 0.000 | | CMV_Int | Diptheria_Int | 0.000 |
| CMV_Int | Rubella_Int | 0.000 | | CMV_Int | Rubella_Int | 0.000 |
| CMV_Int | CMV_Int | 1.000 | | CMV_Int | CMV_Int | 1.000 |
| CMV_Int | HepB_cAb_Int | 0.000 | | CMV_Int | HepB_cAb_Int | 0.000 |
| CMV_Int | HepB_eAb_Int | 0.000 | | CMV_Int | HepB_eAb_Int | 0.000 |
| CMV_Int | HepB_eAg_Int | 0.000 | | CMV_Int | HepB_eAg_Int | 0.000 |
| CMV_Int | HepC_Int | 0.000 | | CMV_Int | HepC_Int | 0.000 |
| CMV_Int | Schistosoma_int | 0.000 | | CMV_Int | Schistosoma_int | 0.000 |
| CMV_Int | Strongyloides_Int | 0.000 | | CMV_Int | Strongyloides_Int | 0.000 |
| CMV_Int | Filaria_Int | 0.000 | | CMV_Int | Filaria_Int | 0.000 |
| HepB_cAb_Int | IL_1_alpha | 0.000 | | HepB_cAb_Int | IL_1_alpha | 0.000 |
| HepB_cAb_Int | IL_1_beta | 0.000 | | HepB_cAb_Int | IL_1_beta | 0.000 |
| HepB_cAb_Int | IL_2 | 0.000 | | HepB_cAb_Int | IL_2 | 0.000 |
| HepB_cAb_Int | IL_4 | 0.000 | | HepB_cAb_Int | IL_4 | 0.000 |
| HepB_cAb_Int | IL_5 | 0.000 | | HepB_cAb_Int | IL_5 | 0.000 |
| HepB_cAb_Int | IL_6 | 0.000 | | HepB_cAb_Int | IL_6 | 0.000 |
| HepB_cAb_Int | IL_8 | 0.000 | | HepB_cAb_Int | IL_8 | 0.000 |
| HepB_cAb_Int | IL_10 | 0.000 | | HepB_cAb_Int | IL_10 | 0.000 |
| HepB_cAb_Int | IL_12p70 | 0.000 | | HepB_cAb_Int | IL_12p70 | 0.000 |
| HepB_cAb_Int | IL_13 | 0.000 | | HepB_cAb_Int | IL_13 | 0.000 |
| HepB_cAb_Int | IL_15 | 0.000 | | HepB_cAb_Int | IL_15 | 0.000 |
| HepB_cAb_Int | IL_17 | 0.000 | | HepB_cAb_Int | IL_17 | 0.000 |
| HepB_cAb_Int | IL_23 | 0.000 | | HepB_cAb_Int | IL_23 | 0.000 |
| HepB_cAb_Int | IFN_gamma | 0.000 | | HepB_cAb_Int | IFN_gamma | 0.000 |
| HepB_cAb_Int | TNF_alpha | 0.000 | | HepB_cAb_Int | TNF_alpha | 0.000 |
| HepB_cAb_Int | TNF_beta | 0.000 | | HepB_cAb_Int | TNF_beta | 0.000 |
| HepB_cAb_Int | Varicella_Int | 0.000 | | HepB_cAb_Int | Varicella_Int | 0.000 |
| HepB_cAb_Int | Measles_OD_DB_Int | 0.000 | | HepB_cAb_Int | Measles_OD_DB_Int | 0.000 |
| HepB_cAb_Int | Measles_Int | 0.000 | | HepB_cAb_Int | Measles_Int | 0.000 |
| HepB_cAb_Int | HepA_Int | 0.000 | | HepB_cAb_Int | HepA_Int | 0.000 |
| HepB_cAb_Int | Tetanus_Int | 0.000 | | HepB_cAb_Int | Tetanus_Int | 0.000 |
| HepB_cAb_Int | Diptheria_Int | 0.000 | | HepB_cAb_Int | Diptheria_Int | 0.000 |
| HepB_cAb_Int | Rubella_Int | 0.000 | | HepB_cAb_Int | Rubella_Int | 0.000 |
| HepB_cAb_Int | CMV_Int | 0.000 | | HepB_cAb_Int | CMV_Int | 0.000 |
| HepB_cAb_Int | HepB_cAb_Int | 1.000 | | HepB_cAb_Int | HepB_cAb_Int | 1.000 |
| HepB_cAb_Int | HepB_eAb_Int | 0.000 | | HepB_cAb_Int | HepB_eAb_Int | 0.000 |
| HepB_cAb_Int | HepB_eAg_Int | 0.000 | | HepB_cAb_Int | HepB_eAg_Int | 0.000 |
| HepB_cAb_Int | HepC_Int | 0.000 | | HepB_cAb_Int | HepC_Int | 0.000 |
| HepB_cAb_Int | Schistosoma_int | 0.000 | | HepB_cAb_Int | Schistosoma_int | 0.000 |
| HepB_cAb_Int | Strongyloides_Int | 0.000 | | HepB_cAb_Int | Strongyloides_Int | 0.000 |
| HepB_cAb_Int | Filaria_Int | 0.000 | | HepB_cAb_Int | Filaria_Int | 0.000 |
| HepB_eAb_Int | IL_1_alpha | 0.000 | | HepB_eAb_Int | IL_1_alpha | 0.000 |
| HepB_eAb_Int | IL_1_beta | 0.000 | | HepB_eAb_Int | IL_1_beta | 0.000 |
| HepB_eAb_Int | IL_2 | 0.000 | | HepB_eAb_Int | IL_2 | 0.000 |
| HepB_eAb_Int | IL_4 | 0.000 | | HepB_eAb_Int | IL_4 | 0.000 |
| HepB_eAb_Int | IL_5 | 0.000 | | HepB_eAb_Int | IL_5 | 0.000 |
| HepB_eAb_Int | IL_6 | 0.000 | | HepB_eAb_Int | IL_6 | 0.000 |
| HepB_eAb_Int | IL_8 | 0.000 | | HepB_eAb_Int | IL_8 | 0.000 |
| HepB_eAb_Int | IL_10 | 0.000 | | HepB_eAb_Int | IL_10 | 0.000 |
| HepB_eAb_Int | IL_12p70 | 0.000 | | HepB_eAb_Int | IL_12p70 | 0.000 |
| HepB_eAb_Int | IL_13 | 0.000 | | HepB_eAb_Int | IL_13 | 0.000 |

FIG. 21I12-N

| | | | | | | |
|---|---|---|---|---|---|---|
| HepB_eAb_Int | IL_15 | 0.000 | | HepB_eAb_Int | IL_15 | 0.000 |
| HepB_eAb_Int | IL_17 | 0.000 | | HepB_eAb_Int | IL_17 | 0.000 |
| HepB_eAb_Int | IL_23 | 0.000 | | HepB_eAb_Int | IL_23 | 0.000 |
| HepB_eAb_Int | IFN_gamma | 0.000 | | HepB_eAb_Int | IFN_gamma | 0.000 |
| HepB_eAb_Int | TNF_alpha | 0.000 | | HepB_eAb_Int | TNF_alpha | 0.000 |
| HepB_eAb_Int | TNF_beta | 0.000 | | HepB_eAb_Int | TNF_beta | 0.000 |
| HepB_eAb_Int | Varicella_Int | 0.000 | | HepB_eAb_Int | Varicella_Int | 0.000 |
| HepB_eAb_Int | Measles_OD_DB_Int | 0.000 | | HepB_eAb_Int | Measles_OD_DB_Int | 0.000 |
| HepB_eAb_Int | Measles_Int | 0.000 | | HepB_eAb_Int | Measles_Int | 0.000 |
| HepB_eAb_Int | HepA_Int | 0.000 | | HepB_eAb_Int | HepA_Int | 0.000 |
| HepB_eAb_Int | Tetanus_Int | 0.000 | | HepB_eAb_Int | Tetanus_Int | 0.000 |
| HepB_eAb_Int | Diptheria_Int | 0.000 | | HepB_eAb_Int | Diptheria_Int | 0.000 |
| HepB_eAb_Int | Rubella_Int | 0.000 | | HepB_eAb_Int | Rubella_Int | 0.000 |
| HepB_eAb_Int | CMV_Int | 0.000 | | HepB_eAb_Int | CMV_Int | 0.000 |
| HepB_eAb_Int | HepB_cAb_Int | 0.000 | | HepB_eAb_Int | HepB_cAb_Int | 0.000 |
| HepB_eAb_Int | HepB_eAb_Int | 1.000 | | HepB_eAb_Int | HepB_eAb_Int | 1.000 |
| HepB_eAb_Int | HepB_eAg_Int | 0.000 | | HepB_eAb_Int | HepB_eAg_Int | 0.000 |
| HepB_eAb_Int | HepC_Int | 0.000 | | HepB_eAb_Int | HepC_Int | 0.000 |
| HepB_eAb_Int | Schistosoma_int | 0.000 | | HepB_eAb_Int | Schistosoma_int | 0.000 |
| HepB_eAb_Int | Strongyloides_Int | 0.000 | | HepB_eAb_Int | Strongyloides_Int | 0.000 |
| HepB_eAb_Int | Filaria_Int | 0.000 | | HepB_eAb_Int | Filaria_Int | 0.000 |
| HepB_eAg_Int | IL_1_alpha | 0.000 | | HepB_eAg_Int | IL_1_alpha | 0.000 |
| HepB_eAg_Int | IL_1_beta | 0.000 | | HepB_eAg_Int | IL_1_beta | 0.000 |
| HepB_eAg_Int | IL_2 | 0.000 | | HepB_eAg_Int | IL_2 | 0.000 |
| HepB_eAg_Int | IL_4 | 0.000 | | HepB_eAg_Int | IL_4 | 0.000 |
| HepB_eAg_Int | IL_5 | 0.000 | | HepB_eAg_Int | IL_5 | 0.000 |
| HepB_eAg_Int | IL_6 | 0.000 | | HepB_eAg_Int | IL_6 | 0.000 |
| HepB_eAg_Int | IL_8 | 0.000 | | HepB_eAg_Int | IL_8 | 0.000 |
| HepB_eAg_Int | IL_10 | 0.000 | | HepB_eAg_Int | IL_10 | 0.000 |
| HepB_eAg_Int | IL_12p70 | 0.000 | | HepB_eAg_Int | IL_12p70 | 0.000 |
| HepB_eAg_Int | IL_13 | 0.000 | | HepB_eAg_Int | IL_13 | 0.000 |
| HepB_eAg_Int | IL_15 | 0.000 | | HepB_eAg_Int | IL_15 | 0.000 |
| HepB_eAg_Int | IL_17 | 0.000 | | HepB_eAg_Int | IL_17 | 0.000 |
| HepB_eAg_Int | IL_23 | 0.000 | | HepB_eAg_Int | IL_23 | 0.000 |
| HepB_eAg_Int | IFN_gamma | 0.000 | | HepB_eAg_Int | IFN_gamma | 0.000 |
| HepB_eAg_Int | TNF_alpha | 0.000 | | HepB_eAg_Int | TNF_alpha | 0.000 |
| HepB_eAg_Int | TNF_beta | 0.000 | | HepB_eAg_Int | TNF_beta | 0.000 |
| HepB_eAg_Int | Varicella_Int | 0.000 | | HepB_eAg_Int | Varicella_Int | 0.000 |
| HepB_eAg_Int | Measles_OD_DB_Int | 0.000 | | HepB_eAg_Int | Measles_OD_DB_Int | 0.000 |
| HepB_eAg_Int | Measles_Int | 0.000 | | HepB_eAg_Int | Measles_Int | 0.000 |
| HepB_eAg_Int | HepA_Int | 0.000 | | HepB_eAg_Int | HepA_Int | 0.000 |
| HepB_eAg_Int | Tetanus_Int | 0.000 | | HepB_eAg_Int | Tetanus_Int | 0.000 |
| HepB_eAg_Int | Diptheria_Int | 0.000 | | HepB_eAg_Int | Diptheria_Int | 0.000 |
| HepB_eAg_Int | Rubella_Int | 0.000 | | HepB_eAg_Int | Rubella_Int | 0.000 |
| HepB_eAg_Int | CMV_Int | 0.000 | | HepB_eAg_Int | CMV_Int | 0.000 |
| HepB_eAg_Int | HepB_cAb_Int | 0.000 | | HepB_eAg_Int | HepB_cAb_Int | 0.000 |
| HepB_eAg_Int | HepB_eAb_Int | 0.000 | | HepB_eAg_Int | HepB_eAb_Int | 0.000 |
| HepB_eAg_Int | HepB_eAg_Int | 1.000 | | HepB_eAg_Int | HepB_eAg_Int | 1.000 |
| HepB_eAg_Int | HepC_Int | 0.000 | | HepB_eAg_Int | HepC_Int | 0.000 |
| HepB_eAg_Int | Schistosoma_int | 0.000 | | HepB_eAg_Int | Schistosoma_int | 0.000 |
| HepB_eAg_Int | Strongyloides_Int | 0.000 | | HepB_eAg_Int | Strongyloides_Int | 0.000 |
| HepB_eAg_Int | Filaria_Int | 0.000 | | HepB_eAg_Int | Filaria_Int | 0.000 |
| HepC_Int | IL_1_alpha | 0.000 | | HepC_Int | IL_1_alpha | 0.000 |
| HepC_Int | IL_1_beta | 0.000 | | HepC_Int | IL_1_beta | 0.000 |
| HepC_Int | IL_2 | 0.000 | | HepC_Int | IL_2 | 0.000 |
| HepC_Int | IL_4 | 0.000 | | HepC_Int | IL_4 | 0.000 |
| HepC_Int | IL_5 | 0.000 | | HepC_Int | IL_5 | 0.000 |

FIG. 21I12-O

| | | | | | | |
|---|---|---|---|---|---|---|
| HepC_Int | IL_6 | 0.000 | | HepC_Int | IL_6 | 0.000 |
| HepC_Int | IL_8 | 0.000 | | HepC_Int | IL_8 | 0.000 |
| HepC_Int | IL_10 | 0.000 | | HepC_Int | IL_10 | 0.000 |
| HepC_Int | IL_12p70 | 0.000 | | HepC_Int | IL_12p70 | 0.000 |
| HepC_Int | IL_13 | 0.000 | | HepC_Int | IL_13 | 0.000 |
| HepC_Int | IL_15 | 0.000 | | HepC_Int | IL_15 | 0.000 |
| HepC_Int | IL_17 | 0.000 | | HepC_Int | IL_17 | 0.000 |
| HepC_Int | IL_23 | 0.000 | | HepC_Int | IL_23 | 0.000 |
| HepC_Int | IFN_gamma | 0.000 | | HepC_Int | IFN_gamma | 0.000 |
| HepC_Int | TNF_alpha | 0.000 | | HepC_Int | TNF_alpha | 0.000 |
| HepC_Int | TNF_beta | 0.000 | | HepC_Int | TNF_beta | 0.000 |
| HepC_Int | Varicella_Int | 0.000 | | HepC_Int | Varicella_Int | 0.000 |
| HepC_Int | Measles_OD_DB_Int | 0.000 | | HepC_Int | Measles_OD_DB_Int | 0.000 |
| HepC_Int | Measles_Int | 0.000 | | HepC_Int | Measles_Int | 0.000 |
| HepC_Int | HepA_Int | 0.000 | | HepC_Int | HepA_Int | 0.000 |
| HepC_Int | Tetanus_Int | 0.000 | | HepC_Int | Tetanus_Int | 0.000 |
| HepC_Int | Diptheria_Int | 0.000 | | HepC_Int | Diptheria_Int | 0.000 |
| HepC_Int | Rubella_Int | 0.000 | | HepC_Int | Rubella_Int | 0.000 |
| HepC_Int | CMV_Int | 0.000 | | HepC_Int | CMV_Int | 0.000 |
| HepC_Int | HepB_cAb_Int | 0.000 | | HepC_Int | HepB_cAb_Int | 0.000 |
| HepC_Int | HepB_eAb_Int | 0.000 | | HepC_Int | HepB_eAb_Int | 0.000 |
| HepC_Int | HepB_eAg_Int | 0.000 | | HepC_Int | HepB_eAg_Int | 0.000 |
| HepC_Int | HepC_Int | 1.000 | | HepC_Int | HepC_Int | 1.000 |
| HepC_Int | Schistosoma_int | 0.000 | | HepC_Int | Schistosoma_int | 0.000 |
| HepC_Int | Strongyloides_Int | 0.000 | | HepC_Int | Strongyloides_Int | 0.000 |
| HepC_Int | Filaria_Int | 0.000 | | HepC_Int | Filaria_Int | 0.000 |
| Schistosoma_int | IL_1_alpha | 0.000 | | Schistosoma_int | IL_1_alpha | 0.000 |
| Schistosoma_int | IL_1_beta | 0.000 | | Schistosoma_int | IL_1_beta | 0.000 |
| Schistosoma_int | IL_2 | 0.000 | | Schistosoma_int | IL_2 | 0.000 |
| Schistosoma_int | IL_4 | 0.000 | | Schistosoma_int | IL_4 | 0.000 |
| Schistosoma_int | IL_5 | 0.000 | | Schistosoma_int | IL_5 | 0.000 |
| Schistosoma_int | IL_6 | 0.000 | | Schistosoma_int | IL_6 | 0.000 |
| Schistosoma_int | IL_8 | 0.000 | | Schistosoma_int | IL_8 | 0.000 |
| Schistosoma_int | IL_10 | 0.000 | | Schistosoma_int | IL_10 | 0.000 |
| Schistosoma_int | IL_12p70 | 0.000 | | Schistosoma_int | IL_12p70 | 0.000 |
| Schistosoma_int | IL_13 | 0.000 | | Schistosoma_int | IL_13 | 0.000 |
| Schistosoma_int | IL_15 | 0.000 | | Schistosoma_int | IL_15 | 0.000 |
| Schistosoma_int | IL_17 | 0.000 | | Schistosoma_int | IL_17 | 0.000 |
| Schistosoma_int | IL_23 | 0.000 | | Schistosoma_int | IL_23 | 0.000 |
| Schistosoma_int | IFN_gamma | 0.000 | | Schistosoma_int | IFN_gamma | 0.000 |
| Schistosoma_int | TNF_alpha | 0.000 | | Schistosoma_int | TNF_alpha | 0.000 |
| Schistosoma_int | TNF_beta | 0.000 | | Schistosoma_int | TNF_beta | 0.000 |
| Schistosoma_int | Varicella_Int | 0.000 | | Schistosoma_int | Varicella_Int | 0.000 |
| Schistosoma_int | Measles_OD_DB_Int | 0.000 | | Schistosoma_int | Measles_OD_DB_Int | 0.000 |
| Schistosoma_int | Measles_Int | 0.000 | | Schistosoma_int | Measles_Int | 0.000 |
| Schistosoma_int | HepA_Int | 0.000 | | Schistosoma_int | HepA_Int | 0.000 |
| Schistosoma_int | Tetanus_Int | 0.000 | | Schistosoma_int | Tetanus_Int | 0.000 |
| Schistosoma_int | Diptheria_Int | 0.000 | | Schistosoma_int | Diptheria_Int | 0.000 |
| Schistosoma_int | Rubella_Int | 0.000 | | Schistosoma_int | Rubella_Int | 0.000 |
| Schistosoma_int | CMV_Int | 0.000 | | Schistosoma_int | CMV_Int | 0.000 |
| Schistosoma_int | HepB_cAb_Int | 0.000 | | Schistosoma_int | HepB_cAb_Int | 0.000 |
| Schistosoma_int | HepB_eAb_Int | 0.000 | | Schistosoma_int | HepB_eAb_Int | 0.000 |
| Schistosoma_int | HepB_eAg_Int | 0.000 | | Schistosoma_int | HepB_eAg_Int | 0.000 |
| Schistosoma_int | HepC_Int | 0.000 | | Schistosoma_int | HepC_Int | 0.000 |
| Schistosoma_int | Schistosoma_int | 1.000 | | Schistosoma_int | Schistosoma_int | 1.000 |
| Schistosoma_int | Strongyloides_Int | 0.000 | | Schistosoma_int | Strongyloides_Int | 0.000 |
| Schistosoma_int | Filaria_Int | 0.000 | | Schistosoma_int | Filaria_Int | 0.000 |

FIG. 21I12-P

| | | | | | | |
|---|---|---|---|---|---|---|
| Strongyloides_Int | IL_1_alpha | 1.000 | | Strongyloides_Int | IL_1_alpha | 0.000 |
| Strongyloides_Int | IL_1_beta | -1.000 | | Strongyloides_Int | IL_1_beta | 0.000 |
| Strongyloides_Int | IL_2 | -1.000 | | Strongyloides_Int | IL_2 | 0.000 |
| Strongyloides_Int | IL_4 | 1.000 | | Strongyloides_Int | IL_4 | 0.000 |
| Strongyloides_Int | IL_5 | -1.000 | | Strongyloides_Int | IL_5 | 0.000 |
| Strongyloides_Int | IL_6 | 1.000 | | Strongyloides_Int | IL_6 | 0.000 |
| Strongyloides_Int | IL_8 | 1.000 | | Strongyloides_Int | IL_8 | 0.000 |
| Strongyloides_Int | IL_10 | -1.000 | | Strongyloides_Int | IL_10 | 0.000 |
| Strongyloides_Int | IL_12p70 | 1.000 | | Strongyloides_Int | IL_12p70 | 0.000 |
| Strongyloides_Int | IL_13 | -1.000 | | Strongyloides_Int | IL_13 | 0.000 |
| Strongyloides_Int | IL_15 | -1.000 | | Strongyloides_Int | IL_15 | 0.000 |
| Strongyloides_Int | IL_17 | -1.000 | | Strongyloides_Int | IL_17 | 0.000 |
| Strongyloides_Int | IL_23 | 1.000 | | Strongyloides_Int | IL_23 | 0.000 |
| Strongyloides_Int | IFN_gamma | 0.000 | | Strongyloides_Int | IFN_gamma | 0.000 |
| Strongyloides_Int | TNF_alpha | -1.000 | | Strongyloides_Int | TNF_alpha | 0.000 |
| Strongyloides_Int | TNF_beta | 1.000 | | Strongyloides_Int | TNF_beta | 0.000 |
| Strongyloides_Int | Varicella_Int | 0.000 | | Strongyloides_Int | Varicella_Int | 0.000 |
| Strongyloides_Int | Measles_OD_DB_Int | 0.000 | | Strongyloides_Int | Measles_OD_DB_Int | 0.000 |
| Strongyloides_Int | Measles_Int | 0.000 | | Strongyloides_Int | Measles_Int | 0.000 |
| Strongyloides_Int | HepA_Int | 0.000 | | Strongyloides_Int | HepA_Int | 0.000 |
| Strongyloides_Int | Tetanus_Int | 0.000 | | Strongyloides_Int | Tetanus_Int | 0.000 |
| Strongyloides_Int | Diptheria_Int | 0.000 | | Strongyloides_Int | Diptheria_Int | 0.000 |
| Strongyloides_Int | Rubella_Int | -1.000 | | Strongyloides_Int | Rubella_Int | 0.000 |
| Strongyloides_Int | CMV_Int | 0.000 | | Strongyloides_Int | CMV_Int | 0.000 |
| Strongyloides_Int | HepB_cAb_Int | 0.000 | | Strongyloides_Int | HepB_cAb_Int | 0.000 |
| Strongyloides_Int | HepB_eAb_Int | 0.000 | | Strongyloides_Int | HepB_eAb_Int | 0.000 |
| Strongyloides_Int | HepB_eAg_Int | 0.000 | | Strongyloides_Int | HepB_eAg_Int | 0.000 |
| Strongyloides_Int | HepC_Int | 0.000 | | Strongyloides_Int | HepC_Int | 0.000 |
| Strongyloides_Int | Schistosoma_int | 0.000 | | Strongyloides_Int | Schistosoma_int | 0.000 |
| Strongyloides_Int | Strongyloides_Int | 1.000 | | Strongyloides_Int | Strongyloides_Int | 1.000 |
| Strongyloides_Int | Filaria_Int | 0.000 | | Strongyloides_Int | Filaria_Int | 0.000 |
| Filaria_Int | IL_1_alpha | 0.000 | | Filaria_Int | IL_1_alpha | 0.000 |
| Filaria_Int | IL_1_beta | 0.000 | | Filaria_Int | IL_1_beta | 0.000 |
| Filaria_Int | IL_2 | 0.000 | | Filaria_Int | IL_2 | 0.000 |
| Filaria_Int | IL_4 | 0.000 | | Filaria_Int | IL_4 | 0.000 |
| Filaria_Int | IL_5 | 0.000 | | Filaria_Int | IL_5 | 0.000 |
| Filaria_Int | IL_6 | 0.000 | | Filaria_Int | IL_6 | 0.000 |
| Filaria_Int | IL_8 | 0.000 | | Filaria_Int | IL_8 | 0.000 |
| Filaria_Int | IL_10 | 0.000 | | Filaria_Int | IL_10 | 0.000 |
| Filaria_Int | IL_12p70 | 0.000 | | Filaria_Int | IL_12p70 | 0.000 |
| Filaria_Int | IL_13 | 0.000 | | Filaria_Int | IL_13 | 0.000 |
| Filaria_Int | IL_15 | 0.000 | | Filaria_Int | IL_15 | 0.000 |
| Filaria_Int | IL_17 | 0.000 | | Filaria_Int | IL_17 | 0.000 |
| Filaria_Int | IL_23 | 0.000 | | Filaria_Int | IL_23 | 0.000 |
| Filaria_Int | IFN_gamma | 0.000 | | Filaria_Int | IFN_gamma | 0.000 |
| Filaria_Int | TNF_alpha | 0.000 | | Filaria_Int | TNF_alpha | 0.000 |
| Filaria_Int | TNF_beta | 0.000 | | Filaria_Int | TNF_beta | 0.000 |
| Filaria_Int | Varicella_Int | 0.000 | | Filaria_Int | Varicella_Int | 0.000 |
| Filaria_Int | Measles_OD_DB_Int | 0.000 | | Filaria_Int | Measles_OD_DB_Int | 0.000 |
| Filaria_Int | Measles_Int | 0.000 | | Filaria_Int | Measles_Int | 0.000 |
| Filaria_Int | HepA_Int | 0.000 | | Filaria_Int | HepA_Int | 0.000 |
| Filaria_Int | Tetanus_Int | 0.000 | | Filaria_Int | Tetanus_Int | 0.000 |
| Filaria_Int | Diptheria_Int | 0.000 | | Filaria_Int | Diptheria_Int | 0.000 |
| Filaria_Int | Rubella_Int | 0.000 | | Filaria_Int | Rubella_Int | 0.000 |
| Filaria_Int | CMV_Int | 0.000 | | Filaria_Int | CMV_Int | 0.000 |
| Filaria_Int | HepB_cAb_Int | 0.000 | | Filaria_Int | HepB_cAb_Int | 0.000 |
| Filaria_Int | HepB_eAb_Int | 0.000 | | Filaria_Int | HepB_eAb_Int | 0.000 |

FIG. 21I12-Q

| Filaria_Int | HepB_eAg_Int | 0.000 |
|---|---|---|
| Filaria_Int | HepC_Int | 0.000 |
| Filaria_Int | Schistosoma_int | 0.000 |
| Filaria_Int | Strongyloides_Int | 0.000 |
| Filaria_Int | Filaria_Int | 1.000 |

| Filaria_Int | HepB_eAg_Int | 0.000 |
|---|---|---|
| Filaria_Int | HepC_Int | 0.000 |
| Filaria_Int | Schistosoma_int | 0.000 |
| Filaria_Int | Strongyloides_Int | 0.000 |
| Filaria_Int | Filaria_Int | 1.000 |

FIG. 21I12-R

| 0.07% - Region_of_Origin=6, Sex=Female, IFN_gamma=37.5-52.5 | | | 0.07% - Region_of_Origin=3, Sex=Male, IFN_gamma=7.5-22.5 | | |
|---|---|---|---|---|---|
| Property 1 | Property 2 | Corr. Coefficient | Property 1 | Property 2 | Corr. Coefficient |
| IL_1_alpha | IL_1_alpha | 1.000 | IL_1_alpha | IL_1_alpha | 1.000 |
| IL_1_alpha | IL_1_beta | 0.000 | IL_1_alpha | IL_1_beta | 0.000 |
| IL_1_alpha | IL_2 | 0.000 | IL_1_alpha | IL_2 | 0.000 |
| IL_1_alpha | IL_4 | 0.000 | IL_1_alpha | IL_4 | 0.000 |
| IL_1_alpha | IL_5 | 0.000 | IL_1_alpha | IL_5 | 0.000 |
| IL_1_alpha | IL_6 | 0.000 | IL_1_alpha | IL_6 | 0.000 |
| IL_1_alpha | IL_8 | 0.000 | IL_1_alpha | IL_8 | 0.000 |
| IL_1_alpha | IL_10 | 0.000 | IL_1_alpha | IL_10 | 0.000 |
| IL_1_alpha | IL_12p70 | 0.000 | IL_1_alpha | IL_12p70 | 0.000 |
| IL_1_alpha | IL_13 | 0.000 | IL_1_alpha | IL_13 | 0.000 |
| IL_1_alpha | IL_15 | 0.000 | IL_1_alpha | IL_15 | 0.000 |
| IL_1_alpha | IL_17 | 0.000 | IL_1_alpha | IL_17 | 0.000 |
| IL_1_alpha | IL_23 | 0.000 | IL_1_alpha | IL_23 | 0.000 |
| IL_1_alpha | IFN_gamma | 0.000 | IL_1_alpha | IFN_gamma | 0.000 |
| IL_1_alpha | TNF_alpha | 0.000 | IL_1_alpha | TNF_alpha | 0.000 |
| IL_1_alpha | TNF_beta | 0.000 | IL_1_alpha | TNF_beta | 0.000 |
| IL_1_alpha | Varicella_Int | 0.000 | IL_1_alpha | Varicella_Int | 0.000 |
| IL_1_alpha | Measles_OD_DB_Int | 0.000 | IL_1_alpha | Measles_OD_DB_Int | 0.000 |
| IL_1_alpha | Measles_Int | 0.000 | IL_1_alpha | Measles_Int | 0.000 |
| IL_1_alpha | HepA_Int | 0.000 | IL_1_alpha | HepA_Int | 0.000 |
| IL_1_alpha | Tetanus_Int | 0.000 | IL_1_alpha | Tetanus_Int | 0.000 |
| IL_1_alpha | Diptheria_Int | 0.000 | IL_1_alpha | Diptheria_Int | 0.000 |
| IL_1_alpha | Rubella_Int | 0.000 | IL_1_alpha | Rubella_Int | 0.000 |
| IL_1_alpha | CMV_Int | 0.000 | IL_1_alpha | CMV_Int | 0.000 |
| IL_1_alpha | HepB_cAb_Int | 0.000 | IL_1_alpha | HepB_cAb_Int | 0.000 |
| IL_1_alpha | HepB_eAb_Int | 0.000 | IL_1_alpha | HepB_eAb_Int | 0.000 |
| IL_1_alpha | HepB_eAg_Int | 0.000 | IL_1_alpha | HepB_eAg_Int | 0.000 |
| IL_1_alpha | HepC_Int | 0.000 | IL_1_alpha | HepC_Int | 0.000 |
| IL_1_alpha | Schistosoma_int | 0.000 | IL_1_alpha | Schistosoma_int | 0.000 |
| IL_1_alpha | Strongyloides_Int | 0.000 | IL_1_alpha | Strongyloides_Int | 0.000 |
| IL_1_alpha | Filaria_Int | 0.000 | IL_1_alpha | Filaria_Int | 0.000 |
| IL_1_beta | IL_1_alpha | 0.000 | IL_1_beta | IL_1_alpha | 0.000 |
| IL_1_beta | IL_1_beta | 1.000 | IL_1_beta | IL_1_beta | 1.000 |
| IL_1_beta | IL_2 | 0.000 | IL_1_beta | IL_2 | 0.000 |
| IL_1_beta | IL_4 | 0.000 | IL_1_beta | IL_4 | 0.000 |
| IL_1_beta | IL_5 | 0.000 | IL_1_beta | IL_5 | 0.000 |
| IL_1_beta | IL_6 | 0.000 | IL_1_beta | IL_6 | 0.000 |
| IL_1_beta | IL_8 | 0.000 | IL_1_beta | IL_8 | 0.000 |
| IL_1_beta | IL_10 | 0.000 | IL_1_beta | IL_10 | 0.000 |
| IL_1_beta | IL_12p70 | 0.000 | IL_1_beta | IL_12p70 | 0.000 |
| IL_1_beta | IL_13 | 0.000 | IL_1_beta | IL_13 | 0.000 |
| IL_1_beta | IL_15 | 0.000 | IL_1_beta | IL_15 | 0.000 |
| IL_1_beta | IL_17 | 0.000 | IL_1_beta | IL_17 | 0.000 |
| IL_1_beta | IL_23 | 0.000 | IL_1_beta | IL_23 | 0.000 |
| IL_1_beta | IFN_gamma | 0.000 | IL_1_beta | IFN_gamma | 0.000 |
| IL_1_beta | TNF_alpha | 0.000 | IL_1_beta | TNF_alpha | 0.000 |
| IL_1_beta | TNF_beta | 0.000 | IL_1_beta | TNF_beta | 0.000 |
| IL_1_beta | Varicella_Int | 0.000 | IL_1_beta | Varicella_Int | 0.000 |

FIG. 21I13-A

| | | | | | | |
|---|---|---|---|---|---|---|
| IL_1_beta | Measles_OD_DB_Int | 0.000 | | IL_1_beta | Measles_OD_DB_Int | 0.000 |
| IL_1_beta | Measles_Int | 0.000 | | IL_1_beta | Measles_Int | 0.000 |
| IL_1_beta | HepA_Int | 0.000 | | IL_1_beta | HepA_Int | 0.000 |
| IL_1_beta | Tetanus_Int | 0.000 | | IL_1_beta | Tetanus_Int | 0.000 |
| IL_1_beta | Diptheria_Int | 0.000 | | IL_1_beta | Diptheria_Int | 0.000 |
| IL_1_beta | Rubella_Int | 0.000 | | IL_1_beta | Rubella_Int | 0.000 |
| IL_1_beta | CMV_Int | 0.000 | | IL_1_beta | CMV_Int | 0.000 |
| IL_1_beta | HepB_cAb_Int | 0.000 | | IL_1_beta | HepB_cAb_Int | 0.000 |
| IL_1_beta | HepB_eAb_Int | 0.000 | | IL_1_beta | HepB_eAb_Int | 0.000 |
| IL_1_beta | HepB_eAg_Int | 0.000 | | IL_1_beta | HepB_eAg_Int | 0.000 |
| IL_1_beta | HepC_Int | 0.000 | | IL_1_beta | HepC_Int | 0.000 |
| IL_1_beta | Schistosoma_int | 0.000 | | IL_1_beta | Schistosoma_int | 0.000 |
| IL_1_beta | Strongyloides_Int | 0.000 | | IL_1_beta | Strongyloides_Int | 0.000 |
| IL_1_beta | Filaria_Int | 0.000 | | IL_1_beta | Filaria_Int | 0.000 |
| IL_2 | IL_1_alpha | 0.000 | | IL_2 | IL_1_alpha | 0.000 |
| IL_2 | IL_1_beta | 0.000 | | IL_2 | IL_1_beta | 0.000 |
| IL_2 | IL_2 | 1.000 | | IL_2 | IL_2 | 1.000 |
| IL_2 | IL_4 | 0.000 | | IL_2 | IL_4 | 0.000 |
| IL_2 | IL_5 | 0.000 | | IL_2 | IL_5 | 0.000 |
| IL_2 | IL_6 | 0.000 | | IL_2 | IL_6 | 0.000 |
| IL_2 | IL_8 | 0.000 | | IL_2 | IL_8 | 0.000 |
| IL_2 | IL_10 | 0.000 | | IL_2 | IL_10 | 0.000 |
| IL_2 | IL_12p70 | 0.000 | | IL_2 | IL_12p70 | 0.000 |
| IL_2 | IL_13 | 0.000 | | IL_2 | IL_13 | 0.000 |
| IL_2 | IL_15 | 0.000 | | IL_2 | IL_15 | 0.000 |
| IL_2 | IL_17 | 0.000 | | IL_2 | IL_17 | 0.000 |
| IL_2 | IL_23 | 0.000 | | IL_2 | IL_23 | 0.000 |
| IL_2 | IFN_gamma | 0.000 | | IL_2 | IFN_gamma | 0.000 |
| IL_2 | TNF_alpha | 0.000 | | IL_2 | TNF_alpha | 0.000 |
| IL_2 | TNF_beta | 0.000 | | IL_2 | TNF_beta | 0.000 |
| IL_2 | Varicella_Int | 0.000 | | IL_2 | Varicella_Int | 0.000 |
| IL_2 | Measles_OD_DB_Int | 0.000 | | IL_2 | Measles_OD_DB_Int | 0.000 |
| IL_2 | Measles_Int | 0.000 | | IL_2 | Measles_Int | 0.000 |
| IL_2 | HepA_Int | 0.000 | | IL_2 | HepA_Int | 0.000 |
| IL_2 | Tetanus_Int | 0.000 | | IL_2 | Tetanus_Int | 0.000 |
| IL_2 | Diptheria_Int | 0.000 | | IL_2 | Diptheria_Int | 0.000 |
| IL_2 | Rubella_Int | 0.000 | | IL_2 | Rubella_Int | 0.000 |
| IL_2 | CMV_Int | 0.000 | | IL_2 | CMV_Int | 0.000 |
| IL_2 | HepB_cAb_Int | 0.000 | | IL_2 | HepB_cAb_Int | 0.000 |
| IL_2 | HepB_eAb_Int | 0.000 | | IL_2 | HepB_eAb_Int | 0.000 |
| IL_2 | HepB_eAg_Int | 0.000 | | IL_2 | HepB_eAg_Int | 0.000 |
| IL_2 | HepC_Int | 0.000 | | IL_2 | HepC_Int | 0.000 |
| IL_2 | Schistosoma_int | 0.000 | | IL_2 | Schistosoma_int | 0.000 |
| IL_2 | Strongyloides_Int | 0.000 | | IL_2 | Strongyloides_Int | 0.000 |
| IL_2 | Filaria_Int | 0.000 | | IL_2 | Filaria_Int | 0.000 |
| IL_4 | IL_1_alpha | 0.000 | | IL_4 | IL_1_alpha | 0.000 |
| IL_4 | IL_1_beta | 0.000 | | IL_4 | IL_1_beta | 0.000 |
| IL_4 | IL_2 | 0.000 | | IL_4 | IL_2 | 0.000 |
| IL_4 | IL_4 | 1.000 | | IL_4 | IL_4 | 1.000 |
| IL_4 | IL_5 | 0.000 | | IL_4 | IL_5 | 0.000 |
| IL_4 | IL_6 | 0.000 | | IL_4 | IL_6 | 0.000 |
| IL_4 | IL_8 | 0.000 | | IL_4 | IL_8 | 0.000 |
| IL_4 | IL_10 | 0.000 | | IL_4 | IL_10 | 0.000 |
| IL_4 | IL_12p70 | 0.000 | | IL_4 | IL_12p70 | 0.000 |
| IL_4 | IL_13 | 0.000 | | IL_4 | IL_13 | 0.000 |
| IL_4 | IL_15 | 0.000 | | IL_4 | IL_15 | 0.000 |
| IL_4 | IL_17 | 0.000 | | IL_4 | IL_17 | 0.000 |

FIG. 21I13-B

| | | | | | | |
|---|---|---|---|---|---|---|
| IL_4 | IL_23 | 0.000 | | IL_4 | IL_23 | 0.000 |
| IL_4 | IFN_gamma | 0.000 | | IL_4 | IFN_gamma | 0.000 |
| IL_4 | TNF_alpha | 0.000 | | IL_4 | TNF_alpha | 0.000 |
| IL_4 | TNF_beta | 0.000 | | IL_4 | TNF_beta | 0.000 |
| IL_4 | Varicella_Int | 0.000 | | IL_4 | Varicella_Int | 0.000 |
| IL_4 | Measles_OD_DB_Int | 0.000 | | IL_4 | Measles_OD_DB_Int | 0.000 |
| IL_4 | Measles_Int | 0.000 | | IL_4 | Measles_Int | 0.000 |
| IL_4 | HepA_Int | 0.000 | | IL_4 | HepA_Int | 0.000 |
| IL_4 | Tetanus_Int | 0.000 | | IL_4 | Tetanus_Int | 0.000 |
| IL_4 | Diptheria_Int | 0.000 | | IL_4 | Diptheria_Int | 0.000 |
| IL_4 | Rubella_Int | 0.000 | | IL_4 | Rubella_Int | 0.000 |
| IL_4 | CMV_Int | 0.000 | | IL_4 | CMV_Int | 0.000 |
| IL_4 | HepB_cAb_Int | 0.000 | | IL_4 | HepB_cAb_Int | 0.000 |
| IL_4 | HepB_eAb_Int | 0.000 | | IL_4 | HepB_eAb_Int | 0.000 |
| IL_4 | HepB_eAg_Int | 0.000 | | IL_4 | HepB_eAg_Int | 0.000 |
| IL_4 | HepC_Int | 0.000 | | IL_4 | HepC_Int | 0.000 |
| IL_4 | Schistosoma_int | 0.000 | | IL_4 | Schistosoma_int | 0.000 |
| IL_4 | Strongyloides_Int | 0.000 | | IL_4 | Strongyloides_Int | 0.000 |
| IL_4 | Filaria_Int | 0.000 | | IL_4 | Filaria_Int | 0.000 |
| IL_5 | IL_1_alpha | 0.000 | | IL_5 | IL_1_alpha | 0.000 |
| IL_5 | IL_1_beta | 0.000 | | IL_5 | IL_1_beta | 0.000 |
| IL_5 | IL_2 | 0.000 | | IL_5 | IL_2 | 0.000 |
| IL_5 | IL_4 | 0.000 | | IL_5 | IL_4 | 0.000 |
| IL_5 | IL_5 | 1.000 | | IL_5 | IL_5 | 1.000 |
| IL_5 | IL_6 | 0.000 | | IL_5 | IL_6 | 0.000 |
| IL_5 | IL_8 | 0.000 | | IL_5 | IL_8 | 0.000 |
| IL_5 | IL_10 | 0.000 | | IL_5 | IL_10 | 0.000 |
| IL_5 | IL_12p70 | 0.000 | | IL_5 | IL_12p70 | 0.000 |
| IL_5 | IL_13 | 0.000 | | IL_5 | IL_13 | 0.000 |
| IL_5 | IL_15 | 0.000 | | IL_5 | IL_15 | 0.000 |
| IL_5 | IL_17 | 0.000 | | IL_5 | IL_17 | 0.000 |
| IL_5 | IL_23 | 0.000 | | IL_5 | IL_23 | 0.000 |
| IL_5 | IFN_gamma | 0.000 | | IL_5 | IFN_gamma | 0.000 |
| IL_5 | TNF_alpha | 0.000 | | IL_5 | TNF_alpha | 0.000 |
| IL_5 | TNF_beta | 0.000 | | IL_5 | TNF_beta | 0.000 |
| IL_5 | Varicella_Int | 0.000 | | IL_5 | Varicella_Int | 0.000 |
| IL_5 | Measles_OD_DB_Int | 0.000 | | IL_5 | Measles_OD_DB_Int | 0.000 |
| IL_5 | Measles_Int | 0.000 | | IL_5 | Measles_Int | 0.000 |
| IL_5 | HepA_Int | 0.000 | | IL_5 | HepA_Int | 0.000 |
| IL_5 | Tetanus_Int | 0.000 | | IL_5 | Tetanus_Int | 0.000 |
| IL_5 | Diptheria_Int | 0.000 | | IL_5 | Diptheria_Int | 0.000 |
| IL_5 | Rubella_Int | 0.000 | | IL_5 | Rubella_Int | 0.000 |
| IL_5 | CMV_Int | 0.000 | | IL_5 | CMV_Int | 0.000 |
| IL_5 | HepB_cAb_Int | 0.000 | | IL_5 | HepB_cAb_Int | 0.000 |
| IL_5 | HepB_eAb_Int | 0.000 | | IL_5 | HepB_eAb_Int | 0.000 |
| IL_5 | HepB_eAg_Int | 0.000 | | IL_5 | HepB_eAg_Int | 0.000 |
| IL_5 | HepC_Int | 0.000 | | IL_5 | HepC_Int | 0.000 |
| IL_5 | Schistosoma_int | 0.000 | | IL_5 | Schistosoma_int | 0.000 |
| IL_5 | Strongyloides_Int | 0.000 | | IL_5 | Strongyloides_Int | 0.000 |
| IL_5 | Filaria_Int | 0.000 | | IL_5 | Filaria_Int | 0.000 |
| IL_6 | IL_1_alpha | 0.000 | | IL_6 | IL_1_alpha | 0.000 |
| IL_6 | IL_1_beta | 0.000 | | IL_6 | IL_1_beta | 0.000 |
| IL_6 | IL_2 | 0.000 | | IL_6 | IL_2 | 0.000 |
| IL_6 | IL_4 | 0.000 | | IL_6 | IL_4 | 0.000 |
| IL_6 | IL_5 | 0.000 | | IL_6 | IL_5 | 0.000 |
| IL_6 | IL_6 | 1.000 | | IL_6 | IL_6 | 1.000 |
| IL_6 | IL_8 | 0.000 | | IL_6 | IL_8 | 0.000 |

FIG. 21I13-C

| | | | | | | |
|---|---|---|---|---|---|---|
| IL_6 | IL_10 | 0.000 | | IL_6 | IL_10 | 0.000 |
| IL_6 | IL_12p70 | 0.000 | | IL_6 | IL_12p70 | 0.000 |
| IL_6 | IL_13 | 0.000 | | IL_6 | IL_13 | 0.000 |
| IL_6 | IL_15 | 0.000 | | IL_6 | IL_15 | 0.000 |
| IL_6 | IL_17 | 0.000 | | IL_6 | IL_17 | 0.000 |
| IL_6 | IL_23 | 0.000 | | IL_6 | IL_23 | 0.000 |
| IL_6 | IFN_gamma | 0.000 | | IL_6 | IFN_gamma | 0.000 |
| IL_6 | TNF_alpha | 0.000 | | IL_6 | TNF_alpha | 0.000 |
| IL_6 | TNF_beta | 0.000 | | IL_6 | TNF_beta | 0.000 |
| IL_6 | Varicella_Int | 0.000 | | IL_6 | Varicella_Int | 0.000 |
| IL_6 | Measles_OD_DB_Int | 0.000 | | IL_6 | Measles_OD_DB_Int | 0.000 |
| IL_6 | Measles_Int | 0.000 | | IL_6 | Measles_Int | 0.000 |
| IL_6 | HepA_Int | 0.000 | | IL_6 | HepA_Int | 0.000 |
| IL_6 | Tetanus_Int | 0.000 | | IL_6 | Tetanus_Int | 0.000 |
| IL_6 | Diptheria_Int | 0.000 | | IL_6 | Diptheria_Int | 0.000 |
| IL_6 | Rubella_Int | 0.000 | | IL_6 | Rubella_Int | 0.000 |
| IL_6 | CMV_Int | 0.000 | | IL_6 | CMV_Int | 0.000 |
| IL_6 | HepB_cAb_Int | 0.000 | | IL_6 | HepB_cAb_Int | 0.000 |
| IL_6 | HepB_eAb_Int | 0.000 | | IL_6 | HepB_eAb_Int | 0.000 |
| IL_6 | HepB_eAg_Int | 0.000 | | IL_6 | HepB_eAg_Int | 0.000 |
| IL_6 | HepC_Int | 0.000 | | IL_6 | HepC_Int | 0.000 |
| IL_6 | Schistosoma_int | 0.000 | | IL_6 | Schistosoma_int | 0.000 |
| IL_6 | Strongyloides_Int | 0.000 | | IL_6 | Strongyloides_Int | 0.000 |
| IL_6 | Filaria_Int | 0.000 | | IL_6 | Filaria_Int | 0.000 |
| IL_8 | IL_1_alpha | 0.000 | | IL_8 | IL_1_alpha | 0.000 |
| IL_8 | IL_1_beta | 0.000 | | IL_8 | IL_1_beta | 0.000 |
| IL_8 | IL_2 | 0.000 | | IL_8 | IL_2 | 0.000 |
| IL_8 | IL_4 | 0.000 | | IL_8 | IL_4 | 0.000 |
| IL_8 | IL_5 | 0.000 | | IL_8 | IL_5 | 0.000 |
| IL_8 | IL_6 | 0.000 | | IL_8 | IL_6 | 0.000 |
| IL_8 | IL_8 | 1.000 | | IL_8 | IL_8 | 1.000 |
| IL_8 | IL_10 | 0.000 | | IL_8 | IL_10 | 0.000 |
| IL_8 | IL_12p70 | 0.000 | | IL_8 | IL_12p70 | 0.000 |
| IL_8 | IL_13 | 0.000 | | IL_8 | IL_13 | 0.000 |
| IL_8 | IL_15 | 0.000 | | IL_8 | IL_15 | 0.000 |
| IL_8 | IL_17 | 0.000 | | IL_8 | IL_17 | 0.000 |
| IL_8 | IL_23 | 0.000 | | IL_8 | IL_23 | 0.000 |
| IL_8 | IFN_gamma | 0.000 | | IL_8 | IFN_gamma | 0.000 |
| IL_8 | TNF_alpha | 0.000 | | IL_8 | TNF_alpha | 0.000 |
| IL_8 | TNF_beta | 0.000 | | IL_8 | TNF_beta | 0.000 |
| IL_8 | Varicella_Int | 0.000 | | IL_8 | Varicella_Int | 0.000 |
| IL_8 | Measles_OD_DB_Int | 0.000 | | IL_8 | Measles_OD_DB_Int | 0.000 |
| IL_8 | Measles_Int | 0.000 | | IL_8 | Measles_Int | 0.000 |
| IL_8 | HepA_Int | 0.000 | | IL_8 | HepA_Int | 0.000 |
| IL_8 | Tetanus_Int | 0.000 | | IL_8 | Tetanus_Int | 0.000 |
| IL_8 | Diptheria_Int | 0.000 | | IL_8 | Diptheria_Int | 0.000 |
| IL_8 | Rubella_Int | 0.000 | | IL_8 | Rubella_Int | 0.000 |
| IL_8 | CMV_Int | 0.000 | | IL_8 | CMV_Int | 0.000 |
| IL_8 | HepB_cAb_Int | 0.000 | | IL_8 | HepB_cAb_Int | 0.000 |
| IL_8 | HepB_eAb_Int | 0.000 | | IL_8 | HepB_eAb_Int | 0.000 |
| IL_8 | HepB_eAg_Int | 0.000 | | IL_8 | HepB_eAg_Int | 0.000 |
| IL_8 | HepC_Int | 0.000 | | IL_8 | HepC_Int | 0.000 |
| IL_8 | Schistosoma_int | 0.000 | | IL_8 | Schistosoma_int | 0.000 |
| IL_8 | Strongyloides_Int | 0.000 | | IL_8 | Strongyloides_Int | 0.000 |
| IL_8 | Filaria_Int | 0.000 | | IL_8 | Filaria_Int | 0.000 |
| IL_10 | IL_1_alpha | 0.000 | | IL_10 | IL_1_alpha | 0.000 |
| IL_10 | IL_1_beta | 0.000 | | IL_10 | IL_1_beta | 0.000 |

FIG. 21I13-D

| | | | | | | |
|---|---|---|---|---|---|---|
| IL_10 | IL_2 | 0.000 | | IL_10 | IL_2 | 0.000 |
| IL_10 | IL_4 | 0.000 | | IL_10 | IL_4 | 0.000 |
| IL_10 | IL_5 | 0.000 | | IL_10 | IL_5 | 0.000 |
| IL_10 | IL_6 | 0.000 | | IL_10 | IL_6 | 0.000 |
| IL_10 | IL_8 | 0.000 | | IL_10 | IL_8 | 0.000 |
| IL_10 | IL_10 | 1.000 | | IL_10 | IL_10 | 1.000 |
| IL_10 | IL_12p70 | 0.000 | | IL_10 | IL_12p70 | 0.000 |
| IL_10 | IL_13 | 0.000 | | IL_10 | IL_13 | 0.000 |
| IL_10 | IL_15 | 0.000 | | IL_10 | IL_15 | 0.000 |
| IL_10 | IL_17 | 0.000 | | IL_10 | IL_17 | 0.000 |
| IL_10 | IL_23 | 0.000 | | IL_10 | IL_23 | 0.000 |
| IL_10 | IFN_gamma | 0.000 | | IL_10 | IFN_gamma | 0.000 |
| IL_10 | TNF_alpha | 0.000 | | IL_10 | TNF_alpha | 0.000 |
| IL_10 | TNF_beta | 0.000 | | IL_10 | TNF_beta | 0.000 |
| IL_10 | Varicella_Int | 0.000 | | IL_10 | Varicella_Int | 0.000 |
| IL_10 | Measles_OD_DB_Int | 0.000 | | IL_10 | Measles_OD_DB_Int | 0.000 |
| IL_10 | Measles_Int | 0.000 | | IL_10 | Measles_Int | 0.000 |
| IL_10 | HepA_Int | 0.000 | | IL_10 | HepA_Int | 0.000 |
| IL_10 | Tetanus_Int | 0.000 | | IL_10 | Tetanus_Int | 0.000 |
| IL_10 | Diptheria_Int | 0.000 | | IL_10 | Diptheria_Int | 0.000 |
| IL_10 | Rubella_Int | 0.000 | | IL_10 | Rubella_Int | 0.000 |
| IL_10 | CMV_Int | 0.000 | | IL_10 | CMV_Int | 0.000 |
| IL_10 | HepB_cAb_Int | 0.000 | | IL_10 | HepB_cAb_Int | 0.000 |
| IL_10 | HepB_eAb_Int | 0.000 | | IL_10 | HepB_eAb_Int | 0.000 |
| IL_10 | HepB_eAg_Int | 0.000 | | IL_10 | HepB_eAg_Int | 0.000 |
| IL_10 | HepC_Int | 0.000 | | IL_10 | HepC_Int | 0.000 |
| IL_10 | Schistosoma_int | 0.000 | | IL_10 | Schistosoma_int | 0.000 |
| IL_10 | Strongyloides_Int | 0.000 | | IL_10 | Strongyloides_Int | 0.000 |
| IL_10 | Filaria_Int | 0.000 | | IL_10 | Filaria_Int | 0.000 |
| IL_12p70 | IL_1_alpha | 0.000 | | IL_12p70 | IL_1_alpha | 0.000 |
| IL_12p70 | IL_1_beta | 0.000 | | IL_12p70 | IL_1_beta | 0.000 |
| IL_12p70 | IL_2 | 0.000 | | IL_12p70 | IL_2 | 0.000 |
| IL_12p70 | IL_4 | 0.000 | | IL_12p70 | IL_4 | 0.000 |
| IL_12p70 | IL_5 | 0.000 | | IL_12p70 | IL_5 | 0.000 |
| IL_12p70 | IL_6 | 0.000 | | IL_12p70 | IL_6 | 0.000 |
| IL_12p70 | IL_8 | 0.000 | | IL_12p70 | IL_8 | 0.000 |
| IL_12p70 | IL_10 | 0.000 | | IL_12p70 | IL_10 | 0.000 |
| IL_12p70 | IL_12p70 | 1.000 | | IL_12p70 | IL_12p70 | 1.000 |
| IL_12p70 | IL_13 | 0.000 | | IL_12p70 | IL_13 | 0.000 |
| IL_12p70 | IL_15 | 0.000 | | IL_12p70 | IL_15 | 0.000 |
| IL_12p70 | IL_17 | 0.000 | | IL_12p70 | IL_17 | 0.000 |
| IL_12p70 | IL_23 | 0.000 | | IL_12p70 | IL_23 | 0.000 |
| IL_12p70 | IFN_gamma | 0.000 | | IL_12p70 | IFN_gamma | 0.000 |
| IL_12p70 | TNF_alpha | 0.000 | | IL_12p70 | TNF_alpha | 0.000 |
| IL_12p70 | TNF_beta | 0.000 | | IL_12p70 | TNF_beta | 0.000 |
| IL_12p70 | Varicella_Int | 0.000 | | IL_12p70 | Varicella_Int | 0.000 |
| IL_12p70 | Measles_OD_DB_Int | 0.000 | | IL_12p70 | Measles_OD_DB_Int | 0.000 |
| IL_12p70 | Measles_Int | 0.000 | | IL_12p70 | Measles_Int | 0.000 |
| IL_12p70 | HepA_Int | 0.000 | | IL_12p70 | HepA_Int | 0.000 |
| IL_12p70 | Tetanus_Int | 0.000 | | IL_12p70 | Tetanus_Int | 0.000 |
| IL_12p70 | Diptheria_Int | 0.000 | | IL_12p70 | Diptheria_Int | 0.000 |
| IL_12p70 | Rubella_Int | 0.000 | | IL_12p70 | Rubella_Int | 0.000 |
| IL_12p70 | CMV_Int | 0.000 | | IL_12p70 | CMV_Int | 0.000 |
| IL_12p70 | HepB_cAb_Int | 0.000 | | IL_12p70 | HepB_cAb_Int | 0.000 |
| IL_12p70 | HepB_eAb_Int | 0.000 | | IL_12p70 | HepB_eAb_Int | 0.000 |
| IL_12p70 | HepB_eAg_Int | 0.000 | | IL_12p70 | HepB_eAg_Int | 0.000 |
| IL_12p70 | HepC_Int | 0.000 | | IL_12p70 | HepC_Int | 0.000 |

FIG. 21I13-E

| | | | | | | |
|---|---|---|---|---|---|---|
| IL_12p70 | Schistosoma_int | 0.000 | | IL_12p70 | Schistosoma_int | 0.000 |
| IL_12p70 | Strongyloides_Int | 0.000 | | IL_12p70 | Strongyloides_Int | 0.000 |
| IL_12p70 | Filaria_Int | 0.000 | | IL_12p70 | Filaria_Int | 0.000 |
| IL_13 | IL_1_alpha | 0.000 | | IL_13 | IL_1_alpha | 0.000 |
| IL_13 | IL_1_beta | 0.000 | | IL_13 | IL_1_beta | 0.000 |
| IL_13 | IL_2 | 0.000 | | IL_13 | IL_2 | 0.000 |
| IL_13 | IL_4 | 0.000 | | IL_13 | IL_4 | 0.000 |
| IL_13 | IL_5 | 0.000 | | IL_13 | IL_5 | 0.000 |
| IL_13 | IL_6 | 0.000 | | IL_13 | IL_6 | 0.000 |
| IL_13 | IL_8 | 0.000 | | IL_13 | IL_8 | 0.000 |
| IL_13 | IL_10 | 0.000 | | IL_13 | IL_10 | 0.000 |
| IL_13 | IL_12p70 | 0.000 | | IL_13 | IL_12p70 | 0.000 |
| IL_13 | IL_13 | 1.000 | | IL_13 | IL_13 | 1.000 |
| IL_13 | IL_15 | 0.000 | | IL_13 | IL_15 | 0.000 |
| IL_13 | IL_17 | 0.000 | | IL_13 | IL_17 | 0.000 |
| IL_13 | IL_23 | 0.000 | | IL_13 | IL_23 | 0.000 |
| IL_13 | IFN_gamma | 0.000 | | IL_13 | IFN_gamma | 0.000 |
| IL_13 | TNF_alpha | 0.000 | | IL_13 | TNF_alpha | 0.000 |
| IL_13 | TNF_beta | 0.000 | | IL_13 | TNF_beta | 0.000 |
| IL_13 | Varicella_Int | 0.000 | | IL_13 | Varicella_Int | 0.000 |
| IL_13 | Measles_OD_DB_Int | 0.000 | | IL_13 | Measles_OD_DB_Int | 0.000 |
| IL_13 | Measles_Int | 0.000 | | IL_13 | Measles_Int | 0.000 |
| IL_13 | HepA_Int | 0.000 | | IL_13 | HepA_Int | 0.000 |
| IL_13 | Tetanus_Int | 0.000 | | IL_13 | Tetanus_Int | 0.000 |
| IL_13 | Diptheria_Int | 0.000 | | IL_13 | Diptheria_Int | 0.000 |
| IL_13 | Rubella_Int | 0.000 | | IL_13 | Rubella_Int | 0.000 |
| IL_13 | CMV_Int | 0.000 | | IL_13 | CMV_Int | 0.000 |
| IL_13 | HepB_cAb_Int | 0.000 | | IL_13 | HepB_cAb_Int | 0.000 |
| IL_13 | HepB_eAb_Int | 0.000 | | IL_13 | HepB_eAb_Int | 0.000 |
| IL_13 | HepB_eAg_Int | 0.000 | | IL_13 | HepB_eAg_Int | 0.000 |
| IL_13 | HepC_Int | 0.000 | | IL_13 | HepC_Int | 0.000 |
| IL_13 | Schistosoma_int | 0.000 | | IL_13 | Schistosoma_int | 0.000 |
| IL_13 | Strongyloides_Int | 0.000 | | IL_13 | Strongyloides_Int | 0.000 |
| IL_13 | Filaria_Int | 0.000 | | IL_13 | Filaria_Int | 0.000 |
| IL_15 | IL_1_alpha | 0.000 | | IL_15 | IL_1_alpha | 0.000 |
| IL_15 | IL_1_beta | 0.000 | | IL_15 | IL_1_beta | 0.000 |
| IL_15 | IL_2 | 0.000 | | IL_15 | IL_2 | 0.000 |
| IL_15 | IL_4 | 0.000 | | IL_15 | IL_4 | 0.000 |
| IL_15 | IL_5 | 0.000 | | IL_15 | IL_5 | 0.000 |
| IL_15 | IL_6 | 0.000 | | IL_15 | IL_6 | 0.000 |
| IL_15 | IL_8 | 0.000 | | IL_15 | IL_8 | 0.000 |
| IL_15 | IL_10 | 0.000 | | IL_15 | IL_10 | 0.000 |
| IL_15 | IL_12p70 | 0.000 | | IL_15 | IL_12p70 | 0.000 |
| IL_15 | IL_13 | 0.000 | | IL_15 | IL_13 | 0.000 |
| IL_15 | IL_15 | 1.000 | | IL_15 | IL_15 | 1.000 |
| IL_15 | IL_17 | 0.000 | | IL_15 | IL_17 | 0.000 |
| IL_15 | IL_23 | 0.000 | | IL_15 | IL_23 | 0.000 |
| IL_15 | IFN_gamma | 0.000 | | IL_15 | IFN_gamma | 0.000 |
| IL_15 | TNF_alpha | 0.000 | | IL_15 | TNF_alpha | 0.000 |
| IL_15 | TNF_beta | 0.000 | | IL_15 | TNF_beta | 0.000 |
| IL_15 | Varicella_Int | 0.000 | | IL_15 | Varicella_Int | 0.000 |
| IL_15 | Measles_OD_DB_Int | 0.000 | | IL_15 | Measles_OD_DB_Int | 0.000 |
| IL_15 | Measles_Int | 0.000 | | IL_15 | Measles_Int | 0.000 |
| IL_15 | HepA_Int | 0.000 | | IL_15 | HepA_Int | 0.000 |
| IL_15 | Tetanus_Int | 0.000 | | IL_15 | Tetanus_Int | 0.000 |
| IL_15 | Diptheria_Int | 0.000 | | IL_15 | Diptheria_Int | 0.000 |
| IL_15 | Rubella_Int | 0.000 | | IL_15 | Rubella_Int | 0.000 |

FIG. 21I13-F

| | | | | | | |
|---|---|---|---|---|---|---|
| IL_15 | CMV_Int | 0.000 | | IL_15 | CMV_Int | 0.000 |
| IL_15 | HepB_cAb_Int | 0.000 | | IL_15 | HepB_cAb_Int | 0.000 |
| IL_15 | HepB_eAb_Int | 0.000 | | IL_15 | HepB_eAb_Int | 0.000 |
| IL_15 | HepB_eAg_Int | 0.000 | | IL_15 | HepB_eAg_Int | 0.000 |
| IL_15 | HepC_Int | 0.000 | | IL_15 | HepC_Int | 0.000 |
| IL_15 | Schistosoma_int | 0.000 | | IL_15 | Schistosoma_int | 0.000 |
| IL_15 | Strongyloides_Int | 0.000 | | IL_15 | Strongyloides_Int | 0.000 |
| IL_15 | Filaria_Int | 0.000 | | IL_15 | Filaria_Int | 0.000 |
| IL_17 | IL_1_alpha | 0.000 | | IL_17 | IL_1_alpha | 0.000 |
| IL_17 | IL_1_beta | 0.000 | | IL_17 | IL_1_beta | 0.000 |
| IL_17 | IL_2 | 0.000 | | IL_17 | IL_2 | 0.000 |
| IL_17 | IL_4 | 0.000 | | IL_17 | IL_4 | 0.000 |
| IL_17 | IL_5 | 0.000 | | IL_17 | IL_5 | 0.000 |
| IL_17 | IL_6 | 0.000 | | IL_17 | IL_6 | 0.000 |
| IL_17 | IL_8 | 0.000 | | IL_17 | IL_8 | 0.000 |
| IL_17 | IL_10 | 0.000 | | IL_17 | IL_10 | 0.000 |
| IL_17 | IL_12p70 | 0.000 | | IL_17 | IL_12p70 | 0.000 |
| IL_17 | IL_13 | 0.000 | | IL_17 | IL_13 | 0.000 |
| IL_17 | IL_15 | 0.000 | | IL_17 | IL_15 | 0.000 |
| IL_17 | IL_17 | 1.000 | | IL_17 | IL_17 | 1.000 |
| IL_17 | IL_23 | 0.000 | | IL_17 | IL_23 | 0.000 |
| IL_17 | IFN_gamma | 0.000 | | IL_17 | IFN_gamma | 0.000 |
| IL_17 | TNF_alpha | 0.000 | | IL_17 | TNF_alpha | 0.000 |
| IL_17 | TNF_beta | 0.000 | | IL_17 | TNF_beta | 0.000 |
| IL_17 | Varicella_Int | 0.000 | | IL_17 | Varicella_Int | 0.000 |
| IL_17 | Measles_OD_DB_Int | 0.000 | | IL_17 | Measles_OD_DB_Int | 0.000 |
| IL_17 | Measles_Int | 0.000 | | IL_17 | Measles_Int | 0.000 |
| IL_17 | HepA_Int | 0.000 | | IL_17 | HepA_Int | 0.000 |
| IL_17 | Tetanus_Int | 0.000 | | IL_17 | Tetanus_Int | 0.000 |
| IL_17 | Diptheria_Int | 0.000 | | IL_17 | Diptheria_Int | 0.000 |
| IL_17 | Rubella_Int | 0.000 | | IL_17 | Rubella_Int | 0.000 |
| IL_17 | CMV_Int | 0.000 | | IL_17 | CMV_Int | 0.000 |
| IL_17 | HepB_cAb_Int | 0.000 | | IL_17 | HepB_cAb_Int | 0.000 |
| IL_17 | HepB_eAb_Int | 0.000 | | IL_17 | HepB_eAb_Int | 0.000 |
| IL_17 | HepB_eAg_Int | 0.000 | | IL_17 | HepB_eAg_Int | 0.000 |
| IL_17 | HepC_Int | 0.000 | | IL_17 | HepC_Int | 0.000 |
| IL_17 | Schistosoma_int | 0.000 | | IL_17 | Schistosoma_int | 0.000 |
| IL_17 | Strongyloides_Int | 0.000 | | IL_17 | Strongyloides_Int | 0.000 |
| IL_17 | Filaria_Int | 0.000 | | IL_17 | Filaria_Int | 0.000 |
| IL_23 | IL_1_alpha | 0.000 | | IL_23 | IL_1_alpha | 0.000 |
| IL_23 | IL_1_beta | 0.000 | | IL_23 | IL_1_beta | 0.000 |
| IL_23 | IL_2 | 0.000 | | IL_23 | IL_2 | 0.000 |
| IL_23 | IL_4 | 0.000 | | IL_23 | IL_4 | 0.000 |
| IL_23 | IL_5 | 0.000 | | IL_23 | IL_5 | 0.000 |
| IL_23 | IL_6 | 0.000 | | IL_23 | IL_6 | 0.000 |
| IL_23 | IL_8 | 0.000 | | IL_23 | IL_8 | 0.000 |
| IL_23 | IL_10 | 0.000 | | IL_23 | IL_10 | 0.000 |
| IL_23 | IL_12p70 | 0.000 | | IL_23 | IL_12p70 | 0.000 |
| IL_23 | IL_13 | 0.000 | | IL_23 | IL_13 | 0.000 |
| IL_23 | IL_15 | 0.000 | | IL_23 | IL_15 | 0.000 |
| IL_23 | IL_17 | 0.000 | | IL_23 | IL_17 | 0.000 |
| IL_23 | IL_23 | 1.000 | | IL_23 | IL_23 | 1.000 |
| IL_23 | IFN_gamma | 0.000 | | IL_23 | IFN_gamma | 0.000 |
| IL_23 | TNF_alpha | 0.000 | | IL_23 | TNF_alpha | 0.000 |
| IL_23 | TNF_beta | 0.000 | | IL_23 | TNF_beta | 0.000 |
| IL_23 | Varicella_Int | 0.000 | | IL_23 | Varicella_Int | 0.000 |
| IL_23 | Measles_OD_DB_Int | 0.000 | | IL_23 | Measles_OD_DB_Int | 0.000 |

FIG. 21I13-G

| | | | | | | |
|---|---|---|---|---|---|---|
| IL_23 | Measles_Int | 0.000 | | IL_23 | Measles_Int | 0.000 |
| IL_23 | HepA_Int | 0.000 | | IL_23 | HepA_Int | 0.000 |
| IL_23 | Tetanus_Int | 0.000 | | IL_23 | Tetanus_Int | 0.000 |
| IL_23 | Diptheria_Int | 0.000 | | IL_23 | Diptheria_Int | 0.000 |
| IL_23 | Rubella_Int | 0.000 | | IL_23 | Rubella_Int | 0.000 |
| IL_23 | CMV_Int | 0.000 | | IL_23 | CMV_Int | 0.000 |
| IL_23 | HepB_cAb_Int | 0.000 | | IL_23 | HepB_cAb_Int | 0.000 |
| IL_23 | HepB_eAb_Int | 0.000 | | IL_23 | HepB_eAb_Int | 0.000 |
| IL_23 | HepB_eAg_Int | 0.000 | | IL_23 | HepB_eAg_Int | 0.000 |
| IL_23 | HepC_Int | 0.000 | | IL_23 | HepC_Int | 0.000 |
| IL_23 | Schistosoma_int | 0.000 | | IL_23 | Schistosoma_int | 0.000 |
| IL_23 | Strongyloides_Int | 0.000 | | IL_23 | Strongyloides_Int | 0.000 |
| IL_23 | Filaria_Int | 0.000 | | IL_23 | Filaria_Int | 0.000 |
| IFN_gamma | IL_1_alpha | 0.000 | | IFN_gamma | IL_1_alpha | 0.000 |
| IFN_gamma | IL_1_beta | 0.000 | | IFN_gamma | IL_1_beta | 0.000 |
| IFN_gamma | IL_2 | 0.000 | | IFN_gamma | IL_2 | 0.000 |
| IFN_gamma | IL_4 | 0.000 | | IFN_gamma | IL_4 | 0.000 |
| IFN_gamma | IL_5 | 0.000 | | IFN_gamma | IL_5 | 0.000 |
| IFN_gamma | IL_6 | 0.000 | | IFN_gamma | IL_6 | 0.000 |
| IFN_gamma | IL_8 | 0.000 | | IFN_gamma | IL_8 | 0.000 |
| IFN_gamma | IL_10 | 0.000 | | IFN_gamma | IL_10 | 0.000 |
| IFN_gamma | IL_12p70 | 0.000 | | IFN_gamma | IL_12p70 | 0.000 |
| IFN_gamma | IL_13 | 0.000 | | IFN_gamma | IL_13 | 0.000 |
| IFN_gamma | IL_15 | 0.000 | | IFN_gamma | IL_15 | 0.000 |
| IFN_gamma | IL_17 | 0.000 | | IFN_gamma | IL_17 | 0.000 |
| IFN_gamma | IL_23 | 0.000 | | IFN_gamma | IL_23 | 0.000 |
| IFN_gamma | IFN_gamma | 1.000 | | IFN_gamma | IFN_gamma | 1.000 |
| IFN_gamma | TNF_alpha | 0.000 | | IFN_gamma | TNF_alpha | 0.000 |
| IFN_gamma | TNF_beta | 0.000 | | IFN_gamma | TNF_beta | 0.000 |
| IFN_gamma | Varicella_Int | 0.000 | | IFN_gamma | Varicella_Int | 0.000 |
| IFN_gamma | Measles_OD_DB_Int | 0.000 | | IFN_gamma | Measles_OD_DB_Int | 0.000 |
| IFN_gamma | Measles_Int | 0.000 | | IFN_gamma | Measles_Int | 0.000 |
| IFN_gamma | HepA_Int | 0.000 | | IFN_gamma | HepA_Int | 0.000 |
| IFN_gamma | Tetanus_Int | 0.000 | | IFN_gamma | Tetanus_Int | 0.000 |
| IFN_gamma | Diptheria_Int | 0.000 | | IFN_gamma | Diptheria_Int | 0.000 |
| IFN_gamma | Rubella_Int | 0.000 | | IFN_gamma | Rubella_Int | 0.000 |
| IFN_gamma | CMV_Int | 0.000 | | IFN_gamma | CMV_Int | 0.000 |
| IFN_gamma | HepB_cAb_Int | 0.000 | | IFN_gamma | HepB_cAb_Int | 0.000 |
| IFN_gamma | HepB_eAb_Int | 0.000 | | IFN_gamma | HepB_eAb_Int | 0.000 |
| IFN_gamma | HepB_eAg_Int | 0.000 | | IFN_gamma | HepB_eAg_Int | 0.000 |
| IFN_gamma | HepC_Int | 0.000 | | IFN_gamma | HepC_Int | 0.000 |
| IFN_gamma | Schistosoma_int | 0.000 | | IFN_gamma | Schistosoma_int | 0.000 |
| IFN_gamma | Strongyloides_Int | 0.000 | | IFN_gamma | Strongyloides_Int | 0.000 |
| IFN_gamma | Filaria_Int | 0.000 | | IFN_gamma | Filaria_Int | 0.000 |
| TNF_alpha | IL_1_alpha | 0.000 | | TNF_alpha | IL_1_alpha | 0.000 |
| TNF_alpha | IL_1_beta | 0.000 | | TNF_alpha | IL_1_beta | 0.000 |
| TNF_alpha | IL_2 | 0.000 | | TNF_alpha | IL_2 | 0.000 |
| TNF_alpha | IL_4 | 0.000 | | TNF_alpha | IL_4 | 0.000 |
| TNF_alpha | IL_5 | 0.000 | | TNF_alpha | IL_5 | 0.000 |
| TNF_alpha | IL_6 | 0.000 | | TNF_alpha | IL_6 | 0.000 |
| TNF_alpha | IL_8 | 0.000 | | TNF_alpha | IL_8 | 0.000 |
| TNF_alpha | IL_10 | 0.000 | | TNF_alpha | IL_10 | 0.000 |
| TNF_alpha | IL_12p70 | 0.000 | | TNF_alpha | IL_12p70 | 0.000 |
| TNF_alpha | IL_13 | 0.000 | | TNF_alpha | IL_13 | 0.000 |
| TNF_alpha | IL_15 | 0.000 | | TNF_alpha | IL_15 | 0.000 |
| TNF_alpha | IL_17 | 0.000 | | TNF_alpha | IL_17 | 0.000 |
| TNF_alpha | IL_23 | 0.000 | | TNF_alpha | IL_23 | 0.000 |

FIG. 21I13-H

| | | | | | | |
|---|---|---|---|---|---|---|
| TNF_alpha | IFN_gamma | 0.000 | | TNF_alpha | IFN_gamma | 0.000 |
| TNF_alpha | TNF_alpha | 1.000 | | TNF_alpha | TNF_alpha | 1.000 |
| TNF_alpha | TNF_beta | 0.000 | | TNF_alpha | TNF_beta | 0.000 |
| TNF_alpha | Varicella_Int | 0.000 | | TNF_alpha | Varicella_Int | 0.000 |
| TNF_alpha | Measles_OD_DB_Int | 0.000 | | TNF_alpha | Measles_OD_DB_Int | 0.000 |
| TNF_alpha | Measles_Int | 0.000 | | TNF_alpha | Measles_Int | 0.000 |
| TNF_alpha | HepA_Int | 0.000 | | TNF_alpha | HepA_Int | 0.000 |
| TNF_alpha | Tetanus_Int | 0.000 | | TNF_alpha | Tetanus_Int | 0.000 |
| TNF_alpha | Diptheria_Int | 0.000 | | TNF_alpha | Diptheria_Int | 0.000 |
| TNF_alpha | Rubella_Int | 0.000 | | TNF_alpha | Rubella_Int | 0.000 |
| TNF_alpha | CMV_Int | 0.000 | | TNF_alpha | CMV_Int | 0.000 |
| TNF_alpha | HepB_cAb_Int | 0.000 | | TNF_alpha | HepB_cAb_Int | 0.000 |
| TNF_alpha | HepB_eAb_Int | 0.000 | | TNF_alpha | HepB_eAb_Int | 0.000 |
| TNF_alpha | HepB_eAg_Int | 0.000 | | TNF_alpha | HepB_eAg_Int | 0.000 |
| TNF_alpha | HepC_Int | 0.000 | | TNF_alpha | HepC_Int | 0.000 |
| TNF_alpha | Schistosoma_int | 0.000 | | TNF_alpha | Schistosoma_int | 0.000 |
| TNF_alpha | Strongyloides_Int | 0.000 | | TNF_alpha | Strongyloides_Int | 0.000 |
| TNF_alpha | Filaria_Int | 0.000 | | TNF_alpha | Filaria_Int | 0.000 |
| TNF_beta | IL_1_alpha | 0.000 | | TNF_beta | IL_1_alpha | 0.000 |
| TNF_beta | IL_1_beta | 0.000 | | TNF_beta | IL_1_beta | 0.000 |
| TNF_beta | IL_2 | 0.000 | | TNF_beta | IL_2 | 0.000 |
| TNF_beta | IL_4 | 0.000 | | TNF_beta | IL_4 | 0.000 |
| TNF_beta | IL_5 | 0.000 | | TNF_beta | IL_5 | 0.000 |
| TNF_beta | IL_6 | 0.000 | | TNF_beta | IL_6 | 0.000 |
| TNF_beta | IL_8 | 0.000 | | TNF_beta | IL_8 | 0.000 |
| TNF_beta | IL_10 | 0.000 | | TNF_beta | IL_10 | 0.000 |
| TNF_beta | IL_12p70 | 0.000 | | TNF_beta | IL_12p70 | 0.000 |
| TNF_beta | IL_13 | 0.000 | | TNF_beta | IL_13 | 0.000 |
| TNF_beta | IL_15 | 0.000 | | TNF_beta | IL_15 | 0.000 |
| TNF_beta | IL_17 | 0.000 | | TNF_beta | IL_17 | 0.000 |
| TNF_beta | IL_23 | 0.000 | | TNF_beta | IL_23 | 0.000 |
| TNF_beta | IFN_gamma | 0.000 | | TNF_beta | IFN_gamma | 0.000 |
| TNF_beta | TNF_alpha | 0.000 | | TNF_beta | TNF_alpha | 0.000 |
| TNF_beta | TNF_beta | 1.000 | | TNF_beta | TNF_beta | 1.000 |
| TNF_beta | Varicella_Int | 0.000 | | TNF_beta | Varicella_Int | 0.000 |
| TNF_beta | Measles_OD_DB_Int | 0.000 | | TNF_beta | Measles_OD_DB_Int | 0.000 |
| TNF_beta | Measles_Int | 0.000 | | TNF_beta | Measles_Int | 0.000 |
| TNF_beta | HepA_Int | 0.000 | | TNF_beta | HepA_Int | 0.000 |
| TNF_beta | Tetanus_Int | 0.000 | | TNF_beta | Tetanus_Int | 0.000 |
| TNF_beta | Diptheria_Int | 0.000 | | TNF_beta | Diptheria_Int | 0.000 |
| TNF_beta | Rubella_Int | 0.000 | | TNF_beta | Rubella_Int | 0.000 |
| TNF_beta | CMV_Int | 0.000 | | TNF_beta | CMV_Int | 0.000 |
| TNF_beta | HepB_cAb_Int | 0.000 | | TNF_beta | HepB_cAb_Int | 0.000 |
| TNF_beta | HepB_eAb_Int | 0.000 | | TNF_beta | HepB_eAb_Int | 0.000 |
| TNF_beta | HepB_eAg_Int | 0.000 | | TNF_beta | HepB_eAg_Int | 0.000 |
| TNF_beta | HepC_Int | 0.000 | | TNF_beta | HepC_Int | 0.000 |
| TNF_beta | Schistosoma_int | 0.000 | | TNF_beta | Schistosoma_int | 0.000 |
| TNF_beta | Strongyloides_Int | 0.000 | | TNF_beta | Strongyloides_Int | 0.000 |
| TNF_beta | Filaria_Int | 0.000 | | TNF_beta | Filaria_Int | 0.000 |
| Varicella_Int | IL_1_alpha | 0.000 | | Varicella_Int | IL_1_alpha | 0.000 |
| Varicella_Int | IL_1_beta | 0.000 | | Varicella_Int | IL_1_beta | 0.000 |
| Varicella_Int | IL_2 | 0.000 | | Varicella_Int | IL_2 | 0.000 |
| Varicella_Int | IL_4 | 0.000 | | Varicella_Int | IL_4 | 0.000 |
| Varicella_Int | IL_5 | 0.000 | | Varicella_Int | IL_5 | 0.000 |
| Varicella_Int | IL_6 | 0.000 | | Varicella_Int | IL_6 | 0.000 |
| Varicella_Int | IL_8 | 0.000 | | Varicella_Int | IL_8 | 0.000 |
| Varicella_Int | IL_10 | 0.000 | | Varicella_Int | IL_10 | 0.000 |

FIG. 21I13-I

| | | | | | | |
|---|---|---|---|---|---|---|
| Varicella_Int | IL_12p70 | 0.000 | | Varicella_Int | IL_12p70 | 0.000 |
| Varicella_Int | IL_13 | 0.000 | | Varicella_Int | IL_13 | 0.000 |
| Varicella_Int | IL_15 | 0.000 | | Varicella_Int | IL_15 | 0.000 |
| Varicella_Int | IL_17 | 0.000 | | Varicella_Int | IL_17 | 0.000 |
| Varicella_Int | IL_23 | 0.000 | | Varicella_Int | IL_23 | 0.000 |
| Varicella_Int | IFN_gamma | 0.000 | | Varicella_Int | IFN_gamma | 0.000 |
| Varicella_Int | TNF_alpha | 0.000 | | Varicella_Int | TNF_alpha | 0.000 |
| Varicella_Int | TNF_beta | 0.000 | | Varicella_Int | TNF_beta | 0.000 |
| Varicella_Int | Varicella_Int | 1.000 | | Varicella_Int | Varicella_Int | 1.000 |
| Varicella_Int | Measles_OD_DB_Int | 0.000 | | Varicella_Int | Measles_OD_DB_Int | 0.000 |
| Varicella_Int | Measles_Int | 0.000 | | Varicella_Int | Measles_Int | 0.000 |
| Varicella_Int | HepA_Int | 0.000 | | Varicella_Int | HepA_Int | 0.000 |
| Varicella_Int | Tetanus_Int | 0.000 | | Varicella_Int | Tetanus_Int | 0.000 |
| Varicella_Int | Diptheria_Int | 0.000 | | Varicella_Int | Diptheria_Int | 0.000 |
| Varicella_Int | Rubella_Int | 0.000 | | Varicella_Int | Rubella_Int | 0.000 |
| Varicella_Int | CMV_Int | 0.000 | | Varicella_Int | CMV_Int | 0.000 |
| Varicella_Int | HepB_cAb_Int | 0.000 | | Varicella_Int | HepB_cAb_Int | 0.000 |
| Varicella_Int | HepB_eAb_Int | 0.000 | | Varicella_Int | HepB_eAb_Int | 0.000 |
| Varicella_Int | HepB_eAg_Int | 0.000 | | Varicella_Int | HepB_eAg_Int | 0.000 |
| Varicella_Int | HepC_Int | 0.000 | | Varicella_Int | HepC_Int | 0.000 |
| Varicella_Int | Schistosoma_int | 0.000 | | Varicella_Int | Schistosoma_int | 0.000 |
| Varicella_Int | Strongyloides_Int | 0.000 | | Varicella_Int | Strongyloides_Int | 0.000 |
| Varicella_Int | Filaria_Int | 0.000 | | Varicella_Int | Filaria_Int | 0.000 |
| Measles_OD_DB_Int | IL_1_alpha | 0.000 | | Measles_OD_DB_Int | IL_1_alpha | 0.000 |
| Measles_OD_DB_Int | IL_1_beta | 0.000 | | Measles_OD_DB_Int | IL_1_beta | 0.000 |
| Measles_OD_DB_Int | IL_2 | 0.000 | | Measles_OD_DB_Int | IL_2 | 0.000 |
| Measles_OD_DB_Int | IL_4 | 0.000 | | Measles_OD_DB_Int | IL_4 | 0.000 |
| Measles_OD_DB_Int | IL_5 | 0.000 | | Measles_OD_DB_Int | IL_5 | 0.000 |
| Measles_OD_DB_Int | IL_6 | 0.000 | | Measles_OD_DB_Int | IL_6 | 0.000 |
| Measles_OD_DB_Int | IL_8 | 0.000 | | Measles_OD_DB_Int | IL_8 | 0.000 |
| Measles_OD_DB_Int | IL_10 | 0.000 | | Measles_OD_DB_Int | IL_10 | 0.000 |
| Measles_OD_DB_Int | IL_12p70 | 0.000 | | Measles_OD_DB_Int | IL_12p70 | 0.000 |
| Measles_OD_DB_Int | IL_13 | 0.000 | | Measles_OD_DB_Int | IL_13 | 0.000 |
| Measles_OD_DB_Int | IL_15 | 0.000 | | Measles_OD_DB_Int | IL_15 | 0.000 |
| Measles_OD_DB_Int | IL_17 | 0.000 | | Measles_OD_DB_Int | IL_17 | 0.000 |
| Measles_OD_DB_Int | IL_23 | 0.000 | | Measles_OD_DB_Int | IL_23 | 0.000 |
| Measles_OD_DB_Int | IFN_gamma | 0.000 | | Measles_OD_DB_Int | IFN_gamma | 0.000 |
| Measles_OD_DB_Int | TNF_alpha | 0.000 | | Measles_OD_DB_Int | TNF_alpha | 0.000 |
| Measles_OD_DB_Int | TNF_beta | 0.000 | | Measles_OD_DB_Int | TNF_beta | 0.000 |
| Measles_OD_DB_Int | Varicella_Int | 0.000 | | Measles_OD_DB_Int | Varicella_Int | 0.000 |
| Measles_OD_DB_Int | Measles_OD_DB_Int | 1.000 | | Measles_OD_DB_Int | Measles_OD_DB_Int | 1.000 |
| Measles_OD_DB_Int | Measles_Int | 0.000 | | Measles_OD_DB_Int | Measles_Int | 0.000 |
| Measles_OD_DB_Int | HepA_Int | 0.000 | | Measles_OD_DB_Int | HepA_Int | 0.000 |
| Measles_OD_DB_Int | Tetanus_Int | 0.000 | | Measles_OD_DB_Int | Tetanus_Int | 0.000 |
| Measles_OD_DB_Int | Diptheria_Int | 0.000 | | Measles_OD_DB_Int | Diptheria_Int | 0.000 |
| Measles_OD_DB_Int | Rubella_Int | 0.000 | | Measles_OD_DB_Int | Rubella_Int | 0.000 |
| Measles_OD_DB_Int | CMV_Int | 0.000 | | Measles_OD_DB_Int | CMV_Int | 0.000 |
| Measles_OD_DB_Int | HepB_cAb_Int | 0.000 | | Measles_OD_DB_Int | HepB_cAb_Int | 0.000 |
| Measles_OD_DB_Int | HepB_eAb_Int | 0.000 | | Measles_OD_DB_Int | HepB_eAb_Int | 0.000 |
| Measles_OD_DB_Int | HepB_eAg_Int | 0.000 | | Measles_OD_DB_Int | HepB_eAg_Int | 0.000 |
| Measles_OD_DB_Int | HepC_Int | 0.000 | | Measles_OD_DB_Int | HepC_Int | 0.000 |
| Measles_OD_DB_Int | Schistosoma_int | 0.000 | | Measles_OD_DB_Int | Schistosoma_int | 0.000 |
| Measles_OD_DB_Int | Strongyloides_Int | 0.000 | | Measles_OD_DB_Int | Strongyloides_Int | 0.000 |
| Measles_OD_DB_Int | Filaria_Int | 0.000 | | Measles_OD_DB_Int | Filaria_Int | 0.000 |
| Measles_Int | IL_1_alpha | 0.000 | | Measles_Int | IL_1_alpha | 0.000 |
| Measles_Int | IL_1_beta | 0.000 | | Measles_Int | IL_1_beta | 0.000 |
| Measles_Int | IL_2 | 0.000 | | Measles_Int | IL_2 | 0.000 |

FIG. 21I13-J

| | | | | | | |
|---|---|---|---|---|---|---|
| Measles_Int | IL_4 | 0.000 | | Measles_Int | IL_4 | 0.000 |
| Measles_Int | IL_5 | 0.000 | | Measles_Int | IL_5 | 0.000 |
| Measles_Int | IL_6 | 0.000 | | Measles_Int | IL_6 | 0.000 |
| Measles_Int | IL_8 | 0.000 | | Measles_Int | IL_8 | 0.000 |
| Measles_Int | IL_10 | 0.000 | | Measles_Int | IL_10 | 0.000 |
| Measles_Int | IL_12p70 | 0.000 | | Measles_Int | IL_12p70 | 0.000 |
| Measles_Int | IL_13 | 0.000 | | Measles_Int | IL_13 | 0.000 |
| Measles_Int | IL_15 | 0.000 | | Measles_Int | IL_15 | 0.000 |
| Measles_Int | IL_17 | 0.000 | | Measles_Int | IL_17 | 0.000 |
| Measles_Int | IL_23 | 0.000 | | Measles_Int | IL_23 | 0.000 |
| Measles_Int | IFN_gamma | 0.000 | | Measles_Int | IFN_gamma | 0.000 |
| Measles_Int | TNF_alpha | 0.000 | | Measles_Int | TNF_alpha | 0.000 |
| Measles_Int | TNF_beta | 0.000 | | Measles_Int | TNF_beta | 0.000 |
| Measles_Int | Varicella_Int | 0.000 | | Measles_Int | Varicella_Int | 0.000 |
| Measles_Int | Measles_OD_DB_Int | 0.000 | | Measles_Int | Measles_OD_DB_Int | 0.000 |
| Measles_Int | Measles_Int | 1.000 | | Measles_Int | Measles_Int | 1.000 |
| Measles_Int | HepA_Int | 0.000 | | Measles_Int | HepA_Int | 0.000 |
| Measles_Int | Tetanus_Int | 0.000 | | Measles_Int | Tetanus_Int | 0.000 |
| Measles_Int | Diptheria_Int | 0.000 | | Measles_Int | Diptheria_Int | 0.000 |
| Measles_Int | Rubella_Int | 0.000 | | Measles_Int | Rubella_Int | 0.000 |
| Measles_Int | CMV_Int | 0.000 | | Measles_Int | CMV_Int | 0.000 |
| Measles_Int | HepB_cAb_Int | 0.000 | | Measles_Int | HepB_cAb_Int | 0.000 |
| Measles_Int | HepB_eAb_Int | 0.000 | | Measles_Int | HepB_eAb_Int | 0.000 |
| Measles_Int | HepB_eAg_Int | 0.000 | | Measles_Int | HepB_eAg_Int | 0.000 |
| Measles_Int | HepC_Int | 0.000 | | Measles_Int | HepC_Int | 0.000 |
| Measles_Int | Schistosoma_int | 0.000 | | Measles_Int | Schistosoma_int | 0.000 |
| Measles_Int | Strongyloides_Int | 0.000 | | Measles_Int | Strongyloides_Int | 0.000 |
| Measles_Int | Filaria_Int | 0.000 | | Measles_Int | Filaria_Int | 0.000 |
| HepA_Int | IL_1_alpha | 0.000 | | HepA_Int | IL_1_alpha | 0.000 |
| HepA_Int | IL_1_beta | 0.000 | | HepA_Int | IL_1_beta | 0.000 |
| HepA_Int | IL_2 | 0.000 | | HepA_Int | IL_2 | 0.000 |
| HepA_Int | IL_4 | 0.000 | | HepA_Int | IL_4 | 0.000 |
| HepA_Int | IL_5 | 0.000 | | HepA_Int | IL_5 | 0.000 |
| HepA_Int | IL_6 | 0.000 | | HepA_Int | IL_6 | 0.000 |
| HepA_Int | IL_8 | 0.000 | | HepA_Int | IL_8 | 0.000 |
| HepA_Int | IL_10 | 0.000 | | HepA_Int | IL_10 | 0.000 |
| HepA_Int | IL_12p70 | 0.000 | | HepA_Int | IL_12p70 | 0.000 |
| HepA_Int | IL_13 | 0.000 | | HepA_Int | IL_13 | 0.000 |
| HepA_Int | IL_15 | 0.000 | | HepA_Int | IL_15 | 0.000 |
| HepA_Int | IL_17 | 0.000 | | HepA_Int | IL_17 | 0.000 |
| HepA_Int | IL_23 | 0.000 | | HepA_Int | IL_23 | 0.000 |
| HepA_Int | IFN_gamma | 0.000 | | HepA_Int | IFN_gamma | 0.000 |
| HepA_Int | TNF_alpha | 0.000 | | HepA_Int | TNF_alpha | 0.000 |
| HepA_Int | TNF_beta | 0.000 | | HepA_Int | TNF_beta | 0.000 |
| HepA_Int | Varicella_Int | 0.000 | | HepA_Int | Varicella_Int | 0.000 |
| HepA_Int | Measles_OD_DB_Int | 0.000 | | HepA_Int | Measles_OD_DB_Int | 0.000 |
| HepA_Int | Measles_Int | 0.000 | | HepA_Int | Measles_Int | 0.000 |
| HepA_Int | HepA_Int | 1.000 | | HepA_Int | HepA_Int | 1.000 |
| HepA_Int | Tetanus_Int | 0.000 | | HepA_Int | Tetanus_Int | 0.000 |
| HepA_Int | Diptheria_Int | 0.000 | | HepA_Int | Diptheria_Int | 0.000 |
| HepA_Int | Rubella_Int | 0.000 | | HepA_Int | Rubella_Int | 0.000 |
| HepA_Int | CMV_Int | 0.000 | | HepA_Int | CMV_Int | 0.000 |
| HepA_Int | HepB_cAb_Int | 0.000 | | HepA_Int | HepB_cAb_Int | 0.000 |
| HepA_Int | HepB_eAb_Int | 0.000 | | HepA_Int | HepB_eAb_Int | 0.000 |
| HepA_Int | HepB_eAg_Int | 0.000 | | HepA_Int | HepB_eAg_Int | 0.000 |
| HepA_Int | HepC_Int | 0.000 | | HepA_Int | HepC_Int | 0.000 |
| HepA_Int | Schistosoma_int | 0.000 | | HepA_Int | Schistosoma_int | 0.000 |

FIG. 21I13-K

| HepA_Int | Strongyloides_Int | 0.000 | HepA_Int | Strongyloides_Int | 0.000 |
|---|---|---|---|---|---|
| HepA_Int | Filaria_Int | 0.000 | HepA_Int | Filaria_Int | 0.000 |
| Tetanus_Int | IL_1_alpha | 0.000 | Tetanus_Int | IL_1_alpha | 0.000 |
| Tetanus_Int | IL_1_beta | 0.000 | Tetanus_Int | IL_1_beta | 0.000 |
| Tetanus_Int | IL_2 | 0.000 | Tetanus_Int | IL_2 | 0.000 |
| Tetanus_Int | IL_4 | 0.000 | Tetanus_Int | IL_4 | 0.000 |
| Tetanus_Int | IL_5 | 0.000 | Tetanus_Int | IL_5 | 0.000 |
| Tetanus_Int | IL_6 | 0.000 | Tetanus_Int | IL_6 | 0.000 |
| Tetanus_Int | IL_8 | 0.000 | Tetanus_Int | IL_8 | 0.000 |
| Tetanus_Int | IL_10 | 0.000 | Tetanus_Int | IL_10 | 0.000 |
| Tetanus_Int | IL_12p70 | 0.000 | Tetanus_Int | IL_12p70 | 0.000 |
| Tetanus_Int | IL_13 | 0.000 | Tetanus_Int | IL_13 | 0.000 |
| Tetanus_Int | IL_15 | 0.000 | Tetanus_Int | IL_15 | 0.000 |
| Tetanus_Int | IL_17 | 0.000 | Tetanus_Int | IL_17 | 0.000 |
| Tetanus_Int | IL_23 | 0.000 | Tetanus_Int | IL_23 | 0.000 |
| Tetanus_Int | IFN_gamma | 0.000 | Tetanus_Int | IFN_gamma | 0.000 |
| Tetanus_Int | TNF_alpha | 0.000 | Tetanus_Int | TNF_alpha | 0.000 |
| Tetanus_Int | TNF_beta | 0.000 | Tetanus_Int | TNF_beta | 0.000 |
| Tetanus_Int | Varicella_Int | 0.000 | Tetanus_Int | Varicella_Int | 0.000 |
| Tetanus_Int | Measles_OD_DB_Int | 0.000 | Tetanus_Int | Measles_OD_DB_Int | 0.000 |
| Tetanus_Int | Measles_Int | 0.000 | Tetanus_Int | Measles_Int | 0.000 |
| Tetanus_Int | HepA_Int | 0.000 | Tetanus_Int | HepA_Int | 0.000 |
| Tetanus_Int | Tetanus_Int | 1.000 | Tetanus_Int | Tetanus_Int | 1.000 |
| Tetanus_Int | Diptheria_Int | 0.000 | Tetanus_Int | Diptheria_Int | 0.000 |
| Tetanus_Int | Rubella_Int | 0.000 | Tetanus_Int | Rubella_Int | 0.000 |
| Tetanus_Int | CMV_Int | 0.000 | Tetanus_Int | CMV_Int | 0.000 |
| Tetanus_Int | HepB_cAb_Int | 0.000 | Tetanus_Int | HepB_cAb_Int | 0.000 |
| Tetanus_Int | HepB_eAb_Int | 0.000 | Tetanus_Int | HepB_eAb_Int | 0.000 |
| Tetanus_Int | HepB_eAg_Int | 0.000 | Tetanus_Int | HepB_eAg_Int | 0.000 |
| Tetanus_Int | HepC_Int | 0.000 | Tetanus_Int | HepC_Int | 0.000 |
| Tetanus_Int | Schistosoma_int | 0.000 | Tetanus_Int | Schistosoma_int | 0.000 |
| Tetanus_Int | Strongyloides_Int | 0.000 | Tetanus_Int | Strongyloides_Int | 0.000 |
| Tetanus_Int | Filaria_Int | 0.000 | Tetanus_Int | Filaria_Int | 0.000 |
| Diptheria_Int | IL_1_alpha | 0.000 | Diptheria_Int | IL_1_alpha | 0.000 |
| Diptheria_Int | IL_1_beta | 0.000 | Diptheria_Int | IL_1_beta | 0.000 |
| Diptheria_Int | IL_2 | 0.000 | Diptheria_Int | IL_2 | 0.000 |
| Diptheria_Int | IL_4 | 0.000 | Diptheria_Int | IL_4 | 0.000 |
| Diptheria_Int | IL_5 | 0.000 | Diptheria_Int | IL_5 | 0.000 |
| Diptheria_Int | IL_6 | 0.000 | Diptheria_Int | IL_6 | 0.000 |
| Diptheria_Int | IL_8 | 0.000 | Diptheria_Int | IL_8 | 0.000 |
| Diptheria_Int | IL_10 | 0.000 | Diptheria_Int | IL_10 | 0.000 |
| Diptheria_Int | IL_12p70 | 0.000 | Diptheria_Int | IL_12p70 | 0.000 |
| Diptheria_Int | IL_13 | 0.000 | Diptheria_Int | IL_13 | 0.000 |
| Diptheria_Int | IL_15 | 0.000 | Diptheria_Int | IL_15 | 0.000 |
| Diptheria_Int | IL_17 | 0.000 | Diptheria_Int | IL_17 | 0.000 |
| Diptheria_Int | IL_23 | 0.000 | Diptheria_Int | IL_23 | 0.000 |
| Diptheria_Int | IFN_gamma | 0.000 | Diptheria_Int | IFN_gamma | 0.000 |
| Diptheria_Int | TNF_alpha | 0.000 | Diptheria_Int | TNF_alpha | 0.000 |
| Diptheria_Int | TNF_beta | 0.000 | Diptheria_Int | TNF_beta | 0.000 |
| Diptheria_Int | Varicella_Int | 0.000 | Diptheria_Int | Varicella_Int | 0.000 |
| Diptheria_Int | Measles_OD_DB_Int | 0.000 | Diptheria_Int | Measles_OD_DB_Int | 0.000 |
| Diptheria_Int | Measles_Int | 0.000 | Diptheria_Int | Measles_Int | 0.000 |
| Diptheria_Int | HepA_Int | 0.000 | Diptheria_Int | HepA_Int | 0.000 |
| Diptheria_Int | Tetanus_Int | 0.000 | Diptheria_Int | Tetanus_Int | 0.000 |
| Diptheria_Int | Diptheria_Int | 1.000 | Diptheria_Int | Diptheria_Int | 1.000 |
| Diptheria_Int | Rubella_Int | 0.000 | Diptheria_Int | Rubella_Int | 0.000 |
| Diptheria_Int | CMV_Int | 0.000 | Diptheria_Int | CMV_Int | 0.000 |

FIG. 21I13-L

| | | | | | | |
|---|---|---|---|---|---|---|
| Diptheria_Int | HepB_cAb_Int | 0.000 | | Diptheria_Int | HepB_cAb_Int | 0.000 |
| Diptheria_Int | HepB_eAb_Int | 0.000 | | Diptheria_Int | HepB_eAb_Int | 0.000 |
| Diptheria_Int | HepB_eAg_Int | 0.000 | | Diptheria_Int | HepB_eAg_Int | 0.000 |
| Diptheria_Int | HepC_Int | 0.000 | | Diptheria_Int | HepC_Int | 0.000 |
| Diptheria_Int | Schistosoma_int | 0.000 | | Diptheria_Int | Schistosoma_int | 0.000 |
| Diptheria_Int | Strongyloides_Int | 0.000 | | Diptheria_Int | Strongyloides_Int | 0.000 |
| Diptheria_Int | Filaria_Int | 0.000 | | Diptheria_Int | Filaria_Int | 0.000 |
| Rubella_Int | IL_1_alpha | 0.000 | | Rubella_Int | IL_1_alpha | 0.000 |
| Rubella_Int | IL_1_beta | 0.000 | | Rubella_Int | IL_1_beta | 0.000 |
| Rubella_Int | IL_2 | 0.000 | | Rubella_Int | IL_2 | 0.000 |
| Rubella_Int | IL_4 | 0.000 | | Rubella_Int | IL_4 | 0.000 |
| Rubella_Int | IL_5 | 0.000 | | Rubella_Int | IL_5 | 0.000 |
| Rubella_Int | IL_6 | 0.000 | | Rubella_Int | IL_6 | 0.000 |
| Rubella_Int | IL_8 | 0.000 | | Rubella_Int | IL_8 | 0.000 |
| Rubella_Int | IL_10 | 0.000 | | Rubella_Int | IL_10 | 0.000 |
| Rubella_Int | IL_12p70 | 0.000 | | Rubella_Int | IL_12p70 | 0.000 |
| Rubella_Int | IL_13 | 0.000 | | Rubella_Int | IL_13 | 0.000 |
| Rubella_Int | IL_15 | 0.000 | | Rubella_Int | IL_15 | 0.000 |
| Rubella_Int | IL_17 | 0.000 | | Rubella_Int | IL_17 | 0.000 |
| Rubella_Int | IL_23 | 0.000 | | Rubella_Int | IL_23 | 0.000 |
| Rubella_Int | IFN_gamma | 0.000 | | Rubella_Int | IFN_gamma | 0.000 |
| Rubella_Int | TNF_alpha | 0.000 | | Rubella_Int | TNF_alpha | 0.000 |
| Rubella_Int | TNF_beta | 0.000 | | Rubella_Int | TNF_beta | 0.000 |
| Rubella_Int | Varicella_Int | 0.000 | | Rubella_Int | Varicella_Int | 0.000 |
| Rubella_Int | Measles_OD_DB_Int | 0.000 | | Rubella_Int | Measles_OD_DB_Int | 0.000 |
| Rubella_Int | Measles_Int | 0.000 | | Rubella_Int | Measles_Int | 0.000 |
| Rubella_Int | HepA_Int | 0.000 | | Rubella_Int | HepA_Int | 0.000 |
| Rubella_Int | Tetanus_Int | 0.000 | | Rubella_Int | Tetanus_Int | 0.000 |
| Rubella_Int | Diptheria_Int | 0.000 | | Rubella_Int | Diptheria_Int | 0.000 |
| Rubella_Int | Rubella_Int | 1.000 | | Rubella_Int | Rubella_Int | 1.000 |
| Rubella_Int | CMV_Int | 0.000 | | Rubella_Int | CMV_Int | 0.000 |
| Rubella_Int | HepB_cAb_Int | 0.000 | | Rubella_Int | HepB_cAb_Int | 0.000 |
| Rubella_Int | HepB_eAb_Int | 0.000 | | Rubella_Int | HepB_eAb_Int | 0.000 |
| Rubella_Int | HepB_eAg_Int | 0.000 | | Rubella_Int | HepB_eAg_Int | 0.000 |
| Rubella_Int | HepC_Int | 0.000 | | Rubella_Int | HepC_Int | 0.000 |
| Rubella_Int | Schistosoma_int | 0.000 | | Rubella_Int | Schistosoma_int | 0.000 |
| Rubella_Int | Strongyloides_Int | 0.000 | | Rubella_Int | Strongyloides_Int | 0.000 |
| Rubella_Int | Filaria_Int | 0.000 | | Rubella_Int | Filaria_Int | 0.000 |
| CMV_Int | IL_1_alpha | 0.000 | | CMV_Int | IL_1_alpha | 0.000 |
| CMV_Int | IL_1_beta | 0.000 | | CMV_Int | IL_1_beta | 0.000 |
| CMV_Int | IL_2 | 0.000 | | CMV_Int | IL_2 | 0.000 |
| CMV_Int | IL_4 | 0.000 | | CMV_Int | IL_4 | 0.000 |
| CMV_Int | IL_5 | 0.000 | | CMV_Int | IL_5 | 0.000 |
| CMV_Int | IL_6 | 0.000 | | CMV_Int | IL_6 | 0.000 |
| CMV_Int | IL_8 | 0.000 | | CMV_Int | IL_8 | 0.000 |
| CMV_Int | IL_10 | 0.000 | | CMV_Int | IL_10 | 0.000 |
| CMV_Int | IL_12p70 | 0.000 | | CMV_Int | IL_12p70 | 0.000 |
| CMV_Int | IL_13 | 0.000 | | CMV_Int | IL_13 | 0.000 |
| CMV_Int | IL_15 | 0.000 | | CMV_Int | IL_15 | 0.000 |
| CMV_Int | IL_17 | 0.000 | | CMV_Int | IL_17 | 0.000 |
| CMV_Int | IL_23 | 0.000 | | CMV_Int | IL_23 | 0.000 |
| CMV_Int | IFN_gamma | 0.000 | | CMV_Int | IFN_gamma | 0.000 |
| CMV_Int | TNF_alpha | 0.000 | | CMV_Int | TNF_alpha | 0.000 |
| CMV_Int | TNF_beta | 0.000 | | CMV_Int | TNF_beta | 0.000 |
| CMV_Int | Varicella_Int | 0.000 | | CMV_Int | Varicella_Int | 0.000 |
| CMV_Int | Measles_OD_DB_Int | 0.000 | | CMV_Int | Measles_OD_DB_Int | 0.000 |
| CMV_Int | Measles_Int | 0.000 | | CMV_Int | Measles_Int | 0.000 |

FIG. 21I13-M

| | | | | | | |
|---|---|---|---|---|---|---|
| CMV_Int | HepA_Int | 0.000 | | CMV_Int | HepA_Int | 0.000 |
| CMV_Int | Tetanus_Int | 0.000 | | CMV_Int | Tetanus_Int | 0.000 |
| CMV_Int | Diptheria_Int | 0.000 | | CMV_Int | Diptheria_Int | 0.000 |
| CMV_Int | Rubella_Int | 0.000 | | CMV_Int | Rubella_Int | 0.000 |
| CMV_Int | CMV_Int | 1.000 | | CMV_Int | CMV_Int | 1.000 |
| CMV_Int | HepB_cAb_Int | 0.000 | | CMV_Int | HepB_cAb_Int | 0.000 |
| CMV_Int | HepB_eAb_Int | 0.000 | | CMV_Int | HepB_eAb_Int | 0.000 |
| CMV_Int | HepB_eAg_Int | 0.000 | | CMV_Int | HepB_eAg_Int | 0.000 |
| CMV_Int | HepC_Int | 0.000 | | CMV_Int | HepC_Int | 0.000 |
| CMV_Int | Schistosoma_int | 0.000 | | CMV_Int | Schistosoma_int | 0.000 |
| CMV_Int | Strongyloides_Int | 0.000 | | CMV_Int | Strongyloides_Int | 0.000 |
| CMV_Int | Filaria_Int | 0.000 | | CMV_Int | Filaria_Int | 0.000 |
| HepB_cAb_Int | IL_1_alpha | 0.000 | | HepB_cAb_Int | IL_1_alpha | 0.000 |
| HepB_cAb_Int | IL_1_beta | 0.000 | | HepB_cAb_Int | IL_1_beta | 0.000 |
| HepB_cAb_Int | IL_2 | 0.000 | | HepB_cAb_Int | IL_2 | 0.000 |
| HepB_cAb_Int | IL_4 | 0.000 | | HepB_cAb_Int | IL_4 | 0.000 |
| HepB_cAb_Int | IL_5 | 0.000 | | HepB_cAb_Int | IL_5 | 0.000 |
| HepB_cAb_Int | IL_6 | 0.000 | | HepB_cAb_Int | IL_6 | 0.000 |
| HepB_cAb_Int | IL_8 | 0.000 | | HepB_cAb_Int | IL_8 | 0.000 |
| HepB_cAb_Int | IL_10 | 0.000 | | HepB_cAb_Int | IL_10 | 0.000 |
| HepB_cAb_Int | IL_12p70 | 0.000 | | HepB_cAb_Int | IL_12p70 | 0.000 |
| HepB_cAb_Int | IL_13 | 0.000 | | HepB_cAb_Int | IL_13 | 0.000 |
| HepB_cAb_Int | IL_15 | 0.000 | | HepB_cAb_Int | IL_15 | 0.000 |
| HepB_cAb_Int | IL_17 | 0.000 | | HepB_cAb_Int | IL_17 | 0.000 |
| HepB_cAb_Int | IL_23 | 0.000 | | HepB_cAb_Int | IL_23 | 0.000 |
| HepB_cAb_Int | IFN_gamma | 0.000 | | HepB_cAb_Int | IFN_gamma | 0.000 |
| HepB_cAb_Int | TNF_alpha | 0.000 | | HepB_cAb_Int | TNF_alpha | 0.000 |
| HepB_cAb_Int | TNF_beta | 0.000 | | HepB_cAb_Int | TNF_beta | 0.000 |
| HepB_cAb_Int | Varicella_Int | 0.000 | | HepB_cAb_Int | Varicella_Int | 0.000 |
| HepB_cAb_Int | Measles_OD_DB_Int | 0.000 | | HepB_cAb_Int | Measles_OD_DB_Int | 0.000 |
| HepB_cAb_Int | Measles_Int | 0.000 | | HepB_cAb_Int | Measles_Int | 0.000 |
| HepB_cAb_Int | HepA_Int | 0.000 | | HepB_cAb_Int | HepA_Int | 0.000 |
| HepB_cAb_Int | Tetanus_Int | 0.000 | | HepB_cAb_Int | Tetanus_Int | 0.000 |
| HepB_cAb_Int | Diptheria_Int | 0.000 | | HepB_cAb_Int | Diptheria_Int | 0.000 |
| HepB_cAb_Int | Rubella_Int | 0.000 | | HepB_cAb_Int | Rubella_Int | 0.000 |
| HepB_cAb_Int | CMV_Int | 0.000 | | HepB_cAb_Int | CMV_Int | 0.000 |
| HepB_cAb_Int | HepB_cAb_Int | 1.000 | | HepB_cAb_Int | HepB_cAb_Int | 1.000 |
| HepB_cAb_Int | HepB_eAb_Int | 0.000 | | HepB_cAb_Int | HepB_eAb_Int | 0.000 |
| HepB_cAb_Int | HepB_eAg_Int | 0.000 | | HepB_cAb_Int | HepB_eAg_Int | 0.000 |
| HepB_cAb_Int | HepC_Int | 0.000 | | HepB_cAb_Int | HepC_Int | 0.000 |
| HepB_cAb_Int | Schistosoma_int | 0.000 | | HepB_cAb_Int | Schistosoma_int | 0.000 |
| HepB_cAb_Int | Strongyloides_Int | 0.000 | | HepB_cAb_Int | Strongyloides_Int | 0.000 |
| HepB_cAb_Int | Filaria_Int | 0.000 | | HepB_cAb_Int | Filaria_Int | 0.000 |
| HepB_eAb_Int | IL_1_alpha | 0.000 | | HepB_eAb_Int | IL_1_alpha | 0.000 |
| HepB_eAb_Int | IL_1_beta | 0.000 | | HepB_eAb_Int | IL_1_beta | 0.000 |
| HepB_eAb_Int | IL_2 | 0.000 | | HepB_eAb_Int | IL_2 | 0.000 |
| HepB_eAb_Int | IL_4 | 0.000 | | HepB_eAb_Int | IL_4 | 0.000 |
| HepB_eAb_Int | IL_5 | 0.000 | | HepB_eAb_Int | IL_5 | 0.000 |
| HepB_eAb_Int | IL_6 | 0.000 | | HepB_eAb_Int | IL_6 | 0.000 |
| HepB_eAb_Int | IL_8 | 0.000 | | HepB_eAb_Int | IL_8 | 0.000 |
| HepB_eAb_Int | IL_10 | 0.000 | | HepB_eAb_Int | IL_10 | 0.000 |
| HepB_eAb_Int | IL_12p70 | 0.000 | | HepB_eAb_Int | IL_12p70 | 0.000 |
| HepB_eAb_Int | IL_13 | 0.000 | | HepB_eAb_Int | IL_13 | 0.000 |
| HepB_eAb_Int | IL_15 | 0.000 | | HepB_eAb_Int | IL_15 | 0.000 |
| HepB_eAb_Int | IL_17 | 0.000 | | HepB_eAb_Int | IL_17 | 0.000 |
| HepB_eAb_Int | IL_23 | 0.000 | | HepB_eAb_Int | IL_23 | 0.000 |
| HepB_eAb_Int | IFN_gamma | 0.000 | | HepB_eAb_Int | IFN_gamma | 0.000 |

FIG. 21I13-N

| HepB_eAb_Int | TNF_alpha | 0.000 | HepB_eAb_Int | TNF_alpha | 0.000 |
|---|---|---|---|---|---|
| HepB_eAb_Int | TNF_beta | 0.000 | HepB_eAb_Int | TNF_beta | 0.000 |
| HepB_eAb_Int | Varicella_Int | 0.000 | HepB_eAb_Int | Varicella_Int | 0.000 |
| HepB_eAb_Int | Measles_OD_DB_Int | 0.000 | HepB_eAb_Int | Measles_OD_DB_Int | 0.000 |
| HepB_eAb_Int | Measles_Int | 0.000 | HepB_eAb_Int | Measles_Int | 0.000 |
| HepB_eAb_Int | HepA_Int | 0.000 | HepB_eAb_Int | HepA_Int | 0.000 |
| HepB_eAb_Int | Tetanus_Int | 0.000 | HepB_eAb_Int | Tetanus_Int | 0.000 |
| HepB_eAb_Int | Diptheria_Int | 0.000 | HepB_eAb_Int | Diptheria_Int | 0.000 |
| HepB_eAb_Int | Rubella_Int | 0.000 | HepB_eAb_Int | Rubella_Int | 0.000 |
| HepB_eAb_Int | CMV_Int | 0.000 | HepB_eAb_Int | CMV_Int | 0.000 |
| HepB_eAb_Int | HepB_cAb_Int | 0.000 | HepB_eAb_Int | HepB_cAb_Int | 0.000 |
| HepB_eAb_Int | HepB_eAb_Int | 1.000 | HepB_eAb_Int | HepB_eAb_Int | 1.000 |
| HepB_eAb_Int | HepB_eAg_Int | 0.000 | HepB_eAb_Int | HepB_eAg_Int | 0.000 |
| HepB_eAb_Int | HepC_Int | 0.000 | HepB_eAb_Int | HepC_Int | 0.000 |
| HepB_eAb_Int | Schistosoma_int | 0.000 | HepB_eAb_Int | Schistosoma_int | 0.000 |
| HepB_eAb_Int | Strongyloides_Int | 0.000 | HepB_eAb_Int | Strongyloides_Int | 0.000 |
| HepB_eAb_Int | Filaria_Int | 0.000 | HepB_eAb_Int | Filaria_Int | 0.000 |
| HepB_eAg_Int | IL_1_alpha | 0.000 | HepB_eAg_Int | IL_1_alpha | 0.000 |
| HepB_eAg_Int | IL_1_beta | 0.000 | HepB_eAg_Int | IL_1_beta | 0.000 |
| HepB_eAg_Int | IL_2 | 0.000 | HepB_eAg_Int | IL_2 | 0.000 |
| HepB_eAg_Int | IL_4 | 0.000 | HepB_eAg_Int | IL_4 | 0.000 |
| HepB_eAg_Int | IL_5 | 0.000 | HepB_eAg_Int | IL_5 | 0.000 |
| HepB_eAg_Int | IL_6 | 0.000 | HepB_eAg_Int | IL_6 | 0.000 |
| HepB_eAg_Int | IL_8 | 0.000 | HepB_eAg_Int | IL_8 | 0.000 |
| HepB_eAg_Int | IL_10 | 0.000 | HepB_eAg_Int | IL_10 | 0.000 |
| HepB_eAg_Int | IL_12p70 | 0.000 | HepB_eAg_Int | IL_12p70 | 0.000 |
| HepB_eAg_Int | IL_13 | 0.000 | HepB_eAg_Int | IL_13 | 0.000 |
| HepB_eAg_Int | IL_15 | 0.000 | HepB_eAg_Int | IL_15 | 0.000 |
| HepB_eAg_Int | IL_17 | 0.000 | HepB_eAg_Int | IL_17 | 0.000 |
| HepB_eAg_Int | IL_23 | 0.000 | HepB_eAg_Int | IL_23 | 0.000 |
| HepB_eAg_Int | IFN_gamma | 0.000 | HepB_eAg_Int | IFN_gamma | 0.000 |
| HepB_eAg_Int | TNF_alpha | 0.000 | HepB_eAg_Int | TNF_alpha | 0.000 |
| HepB_eAg_Int | TNF_beta | 0.000 | HepB_eAg_Int | TNF_beta | 0.000 |
| HepB_eAg_Int | Varicella_Int | 0.000 | HepB_eAg_Int | Varicella_Int | 0.000 |
| HepB_eAg_Int | Measles_OD_DB_Int | 0.000 | HepB_eAg_Int | Measles_OD_DB_Int | 0.000 |
| HepB_eAg_Int | Measles_Int | 0.000 | HepB_eAg_Int | Measles_Int | 0.000 |
| HepB_eAg_Int | HepA_Int | 0.000 | HepB_eAg_Int | HepA_Int | 0.000 |
| HepB_eAg_Int | Tetanus_Int | 0.000 | HepB_eAg_Int | Tetanus_Int | 0.000 |
| HepB_eAg_Int | Diptheria_Int | 0.000 | HepB_eAg_Int | Diptheria_Int | 0.000 |
| HepB_eAg_Int | Rubella_Int | 0.000 | HepB_eAg_Int | Rubella_Int | 0.000 |
| HepB_eAg_Int | CMV_Int | 0.000 | HepB_eAg_Int | CMV_Int | 0.000 |
| HepB_eAg_Int | HepB_cAb_Int | 0.000 | HepB_eAg_Int | HepB_cAb_Int | 0.000 |
| HepB_eAg_Int | HepB_eAb_Int | 0.000 | HepB_eAg_Int | HepB_eAb_Int | 0.000 |
| HepB_eAg_Int | HepB_eAg_Int | 1.000 | HepB_eAg_Int | HepB_eAg_Int | 1.000 |
| HepB_eAg_Int | HepC_Int | 0.000 | HepB_eAg_Int | HepC_Int | 0.000 |
| HepB_eAg_Int | Schistosoma_int | 0.000 | HepB_eAg_Int | Schistosoma_int | 0.000 |
| HepB_eAg_Int | Strongyloides_Int | 0.000 | HepB_eAg_Int | Strongyloides_Int | 0.000 |
| HepB_eAg_Int | Filaria_Int | 0.000 | HepB_eAg_Int | Filaria_Int | 0.000 |
| HepC_Int | IL_1_alpha | 0.000 | HepC_Int | IL_1_alpha | 0.000 |
| HepC_Int | IL_1_beta | 0.000 | HepC_Int | IL_1_beta | 0.000 |
| HepC_Int | IL_2 | 0.000 | HepC_Int | IL_2 | 0.000 |
| HepC_Int | IL_4 | 0.000 | HepC_Int | IL_4 | 0.000 |
| HepC_Int | IL_5 | 0.000 | HepC_Int | IL_5 | 0.000 |
| HepC_Int | IL_6 | 0.000 | HepC_Int | IL_6 | 0.000 |
| HepC_Int | IL_8 | 0.000 | HepC_Int | IL_8 | 0.000 |
| HepC_Int | IL_10 | 0.000 | HepC_Int | IL_10 | 0.000 |
| HepC_Int | IL_12p70 | 0.000 | HepC_Int | IL_12p70 | 0.000 |

FIG. 21I13-O

| HepC_Int | IL_13 | 0.000 | HepC_Int | IL_13 | 0.000 |
|---|---|---|---|---|---|
| HepC_Int | IL_15 | 0.000 | HepC_Int | IL_15 | 0.000 |
| HepC_Int | IL_17 | 0.000 | HepC_Int | IL_17 | 0.000 |
| HepC_Int | IL_23 | 0.000 | HepC_Int | IL_23 | 0.000 |
| HepC_Int | IFN_gamma | 0.000 | HepC_Int | IFN_gamma | 0.000 |
| HepC_Int | TNF_alpha | 0.000 | HepC_Int | TNF_alpha | 0.000 |
| HepC_Int | TNF_beta | 0.000 | HepC_Int | TNF_beta | 0.000 |
| HepC_Int | Varicella_Int | 0.000 | HepC_Int | Varicella_Int | 0.000 |
| HepC_Int | Measles_OD_DB_Int | 0.000 | HepC_Int | Measles_OD_DB_Int | 0.000 |
| HepC_Int | Measles_Int | 0.000 | HepC_Int | Measles_Int | 0.000 |
| HepC_Int | HepA_Int | 0.000 | HepC_Int | HepA_Int | 0.000 |
| HepC_Int | Tetanus_Int | 0.000 | HepC_Int | Tetanus_Int | 0.000 |
| HepC_Int | Diptheria_Int | 0.000 | HepC_Int | Diptheria_Int | 0.000 |
| HepC_Int | Rubella_Int | 0.000 | HepC_Int | Rubella_Int | 0.000 |
| HepC_Int | CMV_Int | 0.000 | HepC_Int | CMV_Int | 0.000 |
| HepC_Int | HepB_cAb_Int | 0.000 | HepC_Int | HepB_cAb_Int | 0.000 |
| HepC_Int | HepB_eAb_Int | 0.000 | HepC_Int | HepB_eAb_Int | 0.000 |
| HepC_Int | HepB_eAg_Int | 0.000 | HepC_Int | HepB_eAg_Int | 0.000 |
| HepC_Int | HepC_Int | 1.000 | HepC_Int | HepC_Int | 1.000 |
| HepC_Int | Schistosoma_int | 0.000 | HepC_Int | Schistosoma_int | 0.000 |
| HepC_Int | Strongyloides_Int | 0.000 | HepC_Int | Strongyloides_Int | 0.000 |
| HepC_Int | Filaria_Int | 0.000 | HepC_Int | Filaria_Int | 0.000 |
| Schistosoma_int | IL_1_alpha | 0.000 | Schistosoma_int | IL_1_alpha | 0.000 |
| Schistosoma_int | IL_1_beta | 0.000 | Schistosoma_int | IL_1_beta | 0.000 |
| Schistosoma_int | IL_2 | 0.000 | Schistosoma_int | IL_2 | 0.000 |
| Schistosoma_int | IL_4 | 0.000 | Schistosoma_int | IL_4 | 0.000 |
| Schistosoma_int | IL_5 | 0.000 | Schistosoma_int | IL_5 | 0.000 |
| Schistosoma_int | IL_6 | 0.000 | Schistosoma_int | IL_6 | 0.000 |
| Schistosoma_int | IL_8 | 0.000 | Schistosoma_int | IL_8 | 0.000 |
| Schistosoma_int | IL_10 | 0.000 | Schistosoma_int | IL_10 | 0.000 |
| Schistosoma_int | IL_12p70 | 0.000 | Schistosoma_int | IL_12p70 | 0.000 |
| Schistosoma_int | IL_13 | 0.000 | Schistosoma_int | IL_13 | 0.000 |
| Schistosoma_int | IL_15 | 0.000 | Schistosoma_int | IL_15 | 0.000 |
| Schistosoma_int | IL_17 | 0.000 | Schistosoma_int | IL_17 | 0.000 |
| Schistosoma_int | IL_23 | 0.000 | Schistosoma_int | IL_23 | 0.000 |
| Schistosoma_int | IFN_gamma | 0.000 | Schistosoma_int | IFN_gamma | 0.000 |
| Schistosoma_int | TNF_alpha | 0.000 | Schistosoma_int | TNF_alpha | 0.000 |
| Schistosoma_int | TNF_beta | 0.000 | Schistosoma_int | TNF_beta | 0.000 |
| Schistosoma_int | Varicella_Int | 0.000 | Schistosoma_int | Varicella_Int | 0.000 |
| Schistosoma_int | Measles_OD_DB_Int | 0.000 | Schistosoma_int | Measles_OD_DB_Int | 0.000 |
| Schistosoma_int | Measles_Int | 0.000 | Schistosoma_int | Measles_Int | 0.000 |
| Schistosoma_int | HepA_Int | 0.000 | Schistosoma_int | HepA_Int | 0.000 |
| Schistosoma_int | Tetanus_Int | 0.000 | Schistosoma_int | Tetanus_Int | 0.000 |
| Schistosoma_int | Diptheria_Int | 0.000 | Schistosoma_int | Diptheria_Int | 0.000 |
| Schistosoma_int | Rubella_Int | 0.000 | Schistosoma_int | Rubella_Int | 0.000 |
| Schistosoma_int | CMV_Int | 0.000 | Schistosoma_int | CMV_Int | 0.000 |
| Schistosoma_int | HepB_cAb_Int | 0.000 | Schistosoma_int | HepB_cAb_Int | 0.000 |
| Schistosoma_int | HepB_eAb_Int | 0.000 | Schistosoma_int | HepB_eAb_Int | 0.000 |
| Schistosoma_int | HepB_eAg_Int | 0.000 | Schistosoma_int | HepB_eAg_Int | 0.000 |
| Schistosoma_int | HepC_Int | 0.000 | Schistosoma_int | HepC_Int | 0.000 |
| Schistosoma_int | Schistosoma_int | 1.000 | Schistosoma_int | Schistosoma_int | 1.000 |
| Schistosoma_int | Strongyloides_Int | 0.000 | Schistosoma_int | Strongyloides_Int | 0.000 |
| Schistosoma_int | Filaria_Int | 0.000 | Schistosoma_int | Filaria_Int | 0.000 |
| Strongyloides_Int | IL_1_alpha | 0.000 | Strongyloides_Int | IL_1_alpha | 0.000 |
| Strongyloides_Int | IL_1_beta | 0.000 | Strongyloides_Int | IL_1_beta | 0.000 |
| Strongyloides_Int | IL_2 | 0.000 | Strongyloides_Int | IL_2 | 0.000 |
| Strongyloides_Int | IL_4 | 0.000 | Strongyloides_Int | IL_4 | 0.000 |

FIG. 21I13-P

| | | | | | | |
|---|---|---|---|---|---|---|
| Strongyloides_Int | IL_5 | 0.000 | | Strongyloides_Int | IL_5 | 0.000 |
| Strongyloides_Int | IL_6 | 0.000 | | Strongyloides_Int | IL_6 | 0.000 |
| Strongyloides_Int | IL_8 | 0.000 | | Strongyloides_Int | IL_8 | 0.000 |
| Strongyloides_Int | IL_10 | 0.000 | | Strongyloides_Int | IL_10 | 0.000 |
| Strongyloides_Int | IL_12p70 | 0.000 | | Strongyloides_Int | IL_12p70 | 0.000 |
| Strongyloides_Int | IL_13 | 0.000 | | Strongyloides_Int | IL_13 | 0.000 |
| Strongyloides_Int | IL_15 | 0.000 | | Strongyloides_Int | IL_15 | 0.000 |
| Strongyloides_Int | IL_17 | 0.000 | | Strongyloides_Int | IL_17 | 0.000 |
| Strongyloides_Int | IL_23 | 0.000 | | Strongyloides_Int | IL_23 | 0.000 |
| Strongyloides_Int | IFN_gamma | 0.000 | | Strongyloides_Int | IFN_gamma | 0.000 |
| Strongyloides_Int | TNF_alpha | 0.000 | | Strongyloides_Int | TNF_alpha | 0.000 |
| Strongyloides_Int | TNF_beta | 0.000 | | Strongyloides_Int | TNF_beta | 0.000 |
| Strongyloides_Int | Varicella_Int | 0.000 | | Strongyloides_Int | Varicella_Int | 0.000 |
| Strongyloides_Int | Measles_OD_DB_Int | 0.000 | | Strongyloides_Int | Measles_OD_DB_Int | 0.000 |
| Strongyloides_Int | Measles_Int | 0.000 | | Strongyloides_Int | Measles_Int | 0.000 |
| Strongyloides_Int | HepA_Int | 0.000 | | Strongyloides_Int | HepA_Int | 0.000 |
| Strongyloides_Int | Tetanus_Int | 0.000 | | Strongyloides_Int | Tetanus_Int | 0.000 |
| Strongyloides_Int | Diptheria_Int | 0.000 | | Strongyloides_Int | Diptheria_Int | 0.000 |
| Strongyloides_Int | Rubella_Int | 0.000 | | Strongyloides_Int | Rubella_Int | 0.000 |
| Strongyloides_Int | CMV_Int | 0.000 | | Strongyloides_Int | CMV_Int | 0.000 |
| Strongyloides_Int | HepB_cAb_Int | 0.000 | | Strongyloides_Int | HepB_cAb_Int | 0.000 |
| Strongyloides_Int | HepB_eAb_Int | 0.000 | | Strongyloides_Int | HepB_eAb_Int | 0.000 |
| Strongyloides_Int | HepB_eAg_Int | 0.000 | | Strongyloides_Int | HepB_eAg_Int | 0.000 |
| Strongyloides_Int | HepC_Int | 0.000 | | Strongyloides_Int | HepC_Int | 0.000 |
| Strongyloides_Int | Schistosoma_int | 0.000 | | Strongyloides_Int | Schistosoma_int | 0.000 |
| Strongyloides_Int | Strongyloides_Int | 1.000 | | Strongyloides_Int | Strongyloides_Int | 1.000 |
| Strongyloides_Int | Filaria_Int | 0.000 | | Strongyloides_Int | Filaria_Int | 0.000 |
| Filaria_Int | IL_1_alpha | 0.000 | | Filaria_Int | IL_1_alpha | 0.000 |
| Filaria_Int | IL_1_beta | 0.000 | | Filaria_Int | IL_1_beta | 0.000 |
| Filaria_Int | IL_2 | 0.000 | | Filaria_Int | IL_2 | 0.000 |
| Filaria_Int | IL_4 | 0.000 | | Filaria_Int | IL_4 | 0.000 |
| Filaria_Int | IL_5 | 0.000 | | Filaria_Int | IL_5 | 0.000 |
| Filaria_Int | IL_6 | 0.000 | | Filaria_Int | IL_6 | 0.000 |
| Filaria_Int | IL_8 | 0.000 | | Filaria_Int | IL_8 | 0.000 |
| Filaria_Int | IL_10 | 0.000 | | Filaria_Int | IL_10 | 0.000 |
| Filaria_Int | IL_12p70 | 0.000 | | Filaria_Int | IL_12p70 | 0.000 |
| Filaria_Int | IL_13 | 0.000 | | Filaria_Int | IL_13 | 0.000 |
| Filaria_Int | IL_15 | 0.000 | | Filaria_Int | IL_15 | 0.000 |
| Filaria_Int | IL_17 | 0.000 | | Filaria_Int | IL_17 | 0.000 |
| Filaria_Int | IL_23 | 0.000 | | Filaria_Int | IL_23 | 0.000 |
| Filaria_Int | IFN_gamma | 0.000 | | Filaria_Int | IFN_gamma | 0.000 |
| Filaria_Int | TNF_alpha | 0.000 | | Filaria_Int | TNF_alpha | 0.000 |
| Filaria_Int | TNF_beta | 0.000 | | Filaria_Int | TNF_beta | 0.000 |
| Filaria_Int | Varicella_Int | 0.000 | | Filaria_Int | Varicella_Int | 0.000 |
| Filaria_Int | Measles_OD_DB_Int | 0.000 | | Filaria_Int | Measles_OD_DB_Int | 0.000 |
| Filaria_Int | Measles_Int | 0.000 | | Filaria_Int | Measles_Int | 0.000 |
| Filaria_Int | HepA_Int | 0.000 | | Filaria_Int | HepA_Int | 0.000 |
| Filaria_Int | Tetanus_Int | 0.000 | | Filaria_Int | Tetanus_Int | 0.000 |
| Filaria_Int | Diptheria_Int | 0.000 | | Filaria_Int | Diptheria_Int | 0.000 |
| Filaria_Int | Rubella_Int | 0.000 | | Filaria_Int | Rubella_Int | 0.000 |
| Filaria_Int | CMV_Int | 0.000 | | Filaria_Int | CMV_Int | 0.000 |
| Filaria_Int | HepB_cAb_Int | 0.000 | | Filaria_Int | HepB_cAb_Int | 0.000 |
| Filaria_Int | HepB_eAb_Int | 0.000 | | Filaria_Int | HepB_eAb_Int | 0.000 |
| Filaria_Int | HepB_eAg_Int | 0.000 | | Filaria_Int | HepB_eAg_Int | 0.000 |
| Filaria_Int | HepC_Int | 0.000 | | Filaria_Int | HepC_Int | 0.000 |
| Filaria_Int | Schistosoma_int | 0.000 | | Filaria_Int | Schistosoma_int | 0.000 |
| Filaria_Int | Strongyloides_Int | 0.000 | | Filaria_Int | Strongyloides_Int | 0.000 |

FIG. 21I13-Q

| Filaria_Int | Filaria_Int | 1.000 |

| Filaria_Int | Filaria_Int | 1.000 |

FIG. 21I13-R

| 10.89% - Region_of_Origin=6, Sex=Female, IFN_gamma=0-7.5 |||
|---|---|---|
| Property 1 | Property 2 | Corr. Coefficient |
| IL_1_alpha | IL_1_alpha | 1.000 |
| IL_1_alpha | IL_1_beta | 0.389 |
| IL_1_alpha | IL_2 | 0.386 |
| IL_1_alpha | IL_4 | 0.628 |
| IL_1_alpha | IL_5 | 0.474 |
| IL_1_alpha | IL_6 | 0.008 |
| IL_1_alpha | IL_8 | 0.351 |
| IL_1_alpha | IL_10 | 0.472 |
| IL_1_alpha | IL_12p70 | 0.694 |
| IL_1_alpha | IL_13 | 0.375 |
| IL_1_alpha | IL_15 | 0.458 |
| IL_1_alpha | IL_17 | 0.526 |

| 10.53% - Region_of_Origin=1, Sex=Female, IFN_gamma=0-7.5 |||
|---|---|---|
| Property 1 | Property 2 | Corr. Coefficient |
| IL_1_alpha | IL_1_alpha | 1.000 |
| IL_1_alpha | IL_1_beta | 0.542 |
| IL_1_alpha | IL_2 | 0.318 |
| IL_1_alpha | IL_4 | 0.388 |
| IL_1_alpha | IL_5 | 0.398 |
| IL_1_alpha | IL_6 | 0.090 |
| IL_1_alpha | IL_8 | 0.325 |
| IL_1_alpha | IL_10 | 0.278 |
| IL_1_alpha | IL_12p70 | 0.657 |
| IL_1_alpha | IL_13 | 0.272 |
| IL_1_alpha | IL_15 | 0.540 |
| IL_1_alpha | IL_17 | 0.478 |

FIG. 21I4-A

| IL_1_alpha | IL_23 | 0.287 | IL_1_alpha | IL_23 | 0.143 |
|---|---|---|---|---|---|
| IL_1_alpha | IFN_gamma | 0.000 | IL_1_alpha | IFN_gamma | 0.000 |
| IL_1_alpha | TNF_alpha | 0.456 | IL_1_alpha | TNF_alpha | 0.608 |
| IL_1_alpha | TNF_beta | 0.578 | IL_1_alpha | TNF_beta | 0.407 |
| IL_1_alpha | Varicella_Int | -0.049 | IL_1_alpha | Varicella_Int | 0.103 |
| IL_1_alpha | Measles_OD_DB_Int | 0.139 | IL_1_alpha | Measles_OD_DB_Int | -0.056 |
| IL_1_alpha | Measles_Int | 0.083 | IL_1_alpha | Measles_Int | -0.147 |
| IL_1_alpha | HepA_Int | -0.040 | IL_1_alpha | HepA_Int | -0.157 |
| IL_1_alpha | Tetanus_Int | 0.000 | IL_1_alpha | Tetanus_Int | 0.000 |
| IL_1_alpha | Diptheria_Int | 0.000 | IL_1_alpha | Diptheria_Int | 0.000 |
| IL_1_alpha | Rubella_Int | -0.033 | IL_1_alpha | Rubella_Int | 0.176 |
| IL_1_alpha | CMV_Int | 0.065 | IL_1_alpha | CMV_Int | 0.000 |
| IL_1_alpha | HepB_cAb_Int | -0.165 | IL_1_alpha | HepB_cAb_Int | 0.059 |
| IL_1_alpha | HepB_eAb_Int | 0.000 | IL_1_alpha | HepB_eAb_Int | 0.000 |
| IL_1_alpha | HepB_eAg_Int | -0.208 | IL_1_alpha | HepB_eAg_Int | -0.252 |
| IL_1_alpha | HepC_Int | -0.078 | IL_1_alpha | HepC_Int | 0.073 |
| IL_1_alpha | Schistosoma_int | 0.010 | IL_1_alpha | Schistosoma_int | 0.079 |
| IL_1_alpha | Strongyloides_Int | 0.083 | IL_1_alpha | Strongyloides_Int | 0.006 |
| IL_1_alpha | Filaria_Int | 0.116 | IL_1_alpha | Filaria_Int | -0.038 |
| IL_1_beta | IL_1_alpha | 0.389 | IL_1_beta | IL_1_alpha | 0.542 |
| IL_1_beta | IL_1_beta | 1.000 | IL_1_beta | IL_1_beta | 1.000 |
| IL_1_beta | IL_2 | 0.328 | IL_1_beta | IL_2 | 0.415 |
| IL_1_beta | IL_4 | 0.560 | IL_1_beta | IL_4 | 0.471 |
| IL_1_beta | IL_5 | 0.367 | IL_1_beta | IL_5 | 0.421 |
| IL_1_beta | IL_6 | 0.189 | IL_1_beta | IL_6 | 0.397 |
| IL_1_beta | IL_8 | 0.245 | IL_1_beta | IL_8 | 0.319 |
| IL_1_beta | IL_10 | 0.495 | IL_1_beta | IL_10 | 0.394 |
| IL_1_beta | IL_12p70 | 0.435 | IL_1_beta | IL_12p70 | 0.531 |
| IL_1_beta | IL_13 | 0.384 | IL_1_beta | IL_13 | 0.390 |
| IL_1_beta | IL_15 | 0.347 | IL_1_beta | IL_15 | 0.417 |
| IL_1_beta | IL_17 | 0.481 | IL_1_beta | IL_17 | 0.437 |
| IL_1_beta | IL_23 | 0.278 | IL_1_beta | IL_23 | 0.139 |
| IL_1_beta | IFN_gamma | 0.000 | IL_1_beta | IFN_gamma | 0.000 |
| IL_1_beta | TNF_alpha | 0.725 | IL_1_beta | TNF_alpha | 0.525 |
| IL_1_beta | TNF_beta | 0.454 | IL_1_beta | TNF_beta | 0.506 |
| IL_1_beta | Varicella_Int | 0.005 | IL_1_beta | Varicella_Int | -0.056 |
| IL_1_beta | Measles_OD_DB_Int | 0.016 | IL_1_beta | Measles_OD_DB_Int | 0.110 |
| IL_1_beta | Measles_Int | 0.058 | IL_1_beta | Measles_Int | -0.037 |
| IL_1_beta | HepA_Int | 0.033 | IL_1_beta | HepA_Int | -0.255 |
| IL_1_beta | Tetanus_Int | 0.000 | IL_1_beta | Tetanus_Int | 0.000 |
| IL_1_beta | Diptheria_Int | 0.000 | IL_1_beta | Diptheria_Int | 0.000 |
| IL_1_beta | Rubella_Int | 0.025 | IL_1_beta | Rubella_Int | 0.165 |
| IL_1_beta | CMV_Int | 0.021 | IL_1_beta | CMV_Int | 0.000 |
| IL_1_beta | HepB_cAb_Int | -0.025 | IL_1_beta | HepB_cAb_Int | -0.152 |
| IL_1_beta | HepB_eAb_Int | 0.000 | IL_1_beta | HepB_eAb_Int | 0.000 |
| IL_1_beta | HepB_eAg_Int | -0.090 | IL_1_beta | HepB_eAg_Int | 0.159 |
| IL_1_beta | HepC_Int | -0.084 | IL_1_beta | HepC_Int | 0.072 |
| IL_1_beta | Schistosoma_int | 0.183 | IL_1_beta | Schistosoma_int | -0.122 |
| IL_1_beta | Strongyloides_Int | 0.129 | IL_1_beta | Strongyloides_Int | 0.027 |
| IL_1_beta | Filaria_Int | 0.072 | IL_1_beta | Filaria_Int | 0.067 |
| IL_2 | IL_1_alpha | 0.386 | IL_2 | IL_1_alpha | 0.318 |
| IL_2 | IL_1_beta | 0.328 | IL_2 | IL_1_beta | 0.415 |
| IL_2 | IL_2 | 1.000 | IL_2 | IL_2 | 1.000 |
| IL_2 | IL_4 | 0.166 | IL_2 | IL_4 | 0.355 |
| IL_2 | IL_5 | 0.173 | IL_2 | IL_5 | 0.120 |
| IL_2 | IL_6 | 0.568 | IL_2 | IL_6 | 0.151 |
| IL_2 | IL_8 | 0.117 | IL_2 | IL_8 | 0.255 |

FIG. 2114-B

| | | | | | | |
|---|---|---|---|---|---|---|
| IL_2 | IL_10 | 0.222 | | IL_2 | IL_10 | 0.077 |
| IL_2 | IL_12p70 | 0.271 | | IL_2 | IL_12p70 | 0.567 |
| IL_2 | IL_13 | 0.012 | | IL_2 | IL_13 | 0.045 |
| IL_2 | IL_15 | 0.019 | | IL_2 | IL_15 | 0.248 |
| IL_2 | IL_17 | 0.255 | | IL_2 | IL_17 | 0.379 |
| IL_2 | IL_23 | 0.167 | | IL_2 | IL_23 | 0.432 |
| IL_2 | IFN_gamma | 0.000 | | IL_2 | IFN_gamma | 0.000 |
| IL_2 | TNF_alpha | 0.203 | | IL_2 | TNF_alpha | 0.398 |
| IL_2 | TNF_beta | 0.289 | | IL_2 | TNF_beta | 0.547 |
| IL_2 | Varicella_Int | -0.043 | | IL_2 | Varicella_Int | 0.116 |
| IL_2 | Measles_OD_DB_Int | 0.036 | | IL_2 | Measles_OD_DB_Int | 0.067 |
| IL_2 | Measles_Int | -0.070 | | IL_2 | Measles_Int | 0.130 |
| IL_2 | HepA_Int | 0.054 | | IL_2 | HepA_Int | -0.194 |
| IL_2 | Tetanus_Int | 0.000 | | IL_2 | Tetanus_Int | 0.000 |
| IL_2 | Diptheria_Int | 0.000 | | IL_2 | Diptheria_Int | 0.000 |
| IL_2 | Rubella_Int | 0.077 | | IL_2 | Rubella_Int | 0.257 |
| IL_2 | CMV_Int | 0.055 | | IL_2 | CMV_Int | 0.000 |
| IL_2 | HepB_cAb_Int | 0.019 | | IL_2 | HepB_cAb_Int | -0.035 |
| IL_2 | HepB_eAb_Int | 0.000 | | IL_2 | HepB_eAb_Int | 0.000 |
| IL_2 | HepB_eAg_Int | -0.258 | | IL_2 | HepB_eAg_Int | -0.250 |
| IL_2 | HepC_Int | -0.049 | | IL_2 | HepC_Int | 0.197 |
| IL_2 | Schistosoma_Int | -0.026 | | IL_2 | Schistosoma_Int | -0.141 |
| IL_2 | Strongyloides_Int | 0.066 | | IL_2 | Strongyloides_Int | 0.224 |
| IL_2 | Filaria_Int | 0.070 | | IL_2 | Filaria_Int | 0.074 |
| IL_4 | IL_1_alpha | 0.628 | | IL_4 | IL_1_alpha | 0.388 |
| IL_4 | IL_1_beta | 0.560 | | IL_4 | IL_1_beta | 0.471 |
| IL_4 | IL_2 | 0.166 | | IL_4 | IL_2 | 0.355 |
| IL_4 | IL_4 | 1.000 | | IL_4 | IL_4 | 1.000 |
| IL_4 | IL_5 | 0.544 | | IL_4 | IL_5 | 0.287 |
| IL_4 | IL_6 | -0.019 | | IL_4 | IL_6 | 0.101 |
| IL_4 | IL_8 | 0.360 | | IL_4 | IL_8 | 0.282 |
| IL_4 | IL_10 | 0.544 | | IL_4 | IL_10 | 0.253 |
| IL_4 | IL_12p70 | 0.649 | | IL_4 | IL_12p70 | 0.443 |
| IL_4 | IL_13 | 0.628 | | IL_4 | IL_13 | 0.262 |
| IL_4 | IL_15 | 0.504 | | IL_4 | IL_15 | 0.383 |
| IL_4 | IL_17 | 0.615 | | IL_4 | IL_17 | 0.325 |
| IL_4 | IL_23 | 0.405 | | IL_4 | IL_23 | 0.058 |
| IL_4 | IFN_gamma | 0.000 | | IL_4 | IFN_gamma | 0.000 |
| IL_4 | TNF_alpha | 0.607 | | IL_4 | TNF_alpha | 0.452 |
| IL_4 | TNF_beta | 0.546 | | IL_4 | TNF_beta | 0.452 |
| IL_4 | Varicella_Int | 0.050 | | IL_4 | Varicella_Int | -0.151 |
| IL_4 | Measles_OD_DB_Int | 0.047 | | IL_4 | Measles_OD_DB_Int | -0.158 |
| IL_4 | Measles_Int | -0.061 | | IL_4 | Measles_Int | 0.099 |
| IL_4 | HepA_Int | -0.016 | | IL_4 | HepA_Int | -0.109 |
| IL_4 | Tetanus_Int | 0.000 | | IL_4 | Tetanus_Int | 0.000 |
| IL_4 | Diptheria_Int | 0.000 | | IL_4 | Diptheria_Int | 0.000 |
| IL_4 | Rubella_Int | 0.007 | | IL_4 | Rubella_Int | 0.015 |
| IL_4 | CMV_Int | 0.064 | | IL_4 | CMV_Int | 0.000 |
| IL_4 | HepB_cAb_Int | 0.012 | | IL_4 | HepB_cAb_Int | 0.046 |
| IL_4 | HepB_eAb_Int | 0.000 | | IL_4 | HepB_eAb_Int | 0.000 |
| IL_4 | HepB_eAg_Int | -0.272 | | IL_4 | HepB_eAg_Int | -0.339 |
| IL_4 | HepC_Int | -0.064 | | IL_4 | HepC_Int | 0.088 |
| IL_4 | Schistosoma_Int | 0.044 | | IL_4 | Schistosoma_Int | 0.001 |
| IL_4 | Strongyloides_Int | 0.152 | | IL_4 | Strongyloides_Int | -0.045 |
| IL_4 | Filaria_Int | 0.020 | | IL_4 | Filaria_Int | 0.071 |
| IL_5 | IL_1_alpha | 0.474 | | IL_5 | IL_1_alpha | 0.398 |
| IL_5 | IL_1_beta | 0.367 | | IL_5 | IL_1_beta | 0.421 |

FIG. 2114-C

| IL_5 | IL_2 | 0.173 | IL_5 | IL_2 | 0.120 |
|---|---|---|---|---|---|
| IL_5 | IL_4 | 0.544 | IL_5 | IL_4 | 0.287 |
| IL_5 | IL_5 | 1.000 | IL_5 | IL_5 | 1.000 |
| IL_5 | IL_6 | -0.011 | IL_5 | IL_6 | 0.342 |
| IL_5 | IL_8 | 0.156 | IL_5 | IL_8 | 0.384 |
| IL_5 | IL_10 | 0.557 | IL_5 | IL_10 | 0.865 |
| IL_5 | IL_12p70 | 0.628 | IL_5 | IL_12p70 | 0.464 |
| IL_5 | IL_13 | 0.458 | IL_5 | IL_13 | 0.833 |
| IL_5 | IL_15 | 0.366 | IL_5 | IL_15 | 0.396 |
| IL_5 | IL_17 | 0.691 | IL_5 | IL_17 | 0.289 |
| IL_5 | IL_23 | 0.139 | IL_5 | IL_23 | 0.128 |
| IL_5 | IFN_gamma | 0.000 | IL_5 | IFN_gamma | 0.000 |
| IL_5 | TNF_alpha | 0.387 | IL_5 | TNF_alpha | 0.171 |
| IL_5 | TNF_beta | 0.592 | IL_5 | TNF_beta | 0.214 |
| IL_5 | Varicella_Int | 0.066 | IL_5 | Varicella_Int | 0.039 |
| IL_5 | Measles_OD_DB_Int | 0.115 | IL_5 | Measles_OD_DB_Int | 0.011 |
| IL_5 | Measles_Int | 0.045 | IL_5 | Measles_Int | 0.069 |
| IL_5 | HepA_Int | -0.000 | IL_5 | HepA_Int | -0.062 |
| IL_5 | Tetanus_Int | 0.000 | IL_5 | Tetanus_Int | 0.000 |
| IL_5 | Diptheria_Int | 0.000 | IL_5 | Diptheria_Int | 0.000 |
| IL_5 | Rubella_Int | -0.058 | IL_5 | Rubella_Int | 0.089 |
| IL_5 | CMV_Int | 0.091 | IL_5 | CMV_Int | 0.000 |
| IL_5 | HepB_cAb_Int | 0.068 | IL_5 | HepB_cAb_Int | -0.019 |
| IL_5 | HepB_eAb_Int | 0.000 | IL_5 | HepB_eAb_Int | 0.000 |
| IL_5 | HepB_eAg_Int | -0.316 | IL_5 | HepB_eAg_Int | -0.292 |
| IL_5 | HepC_Int | -0.078 | IL_5 | HepC_Int | -0.029 |
| IL_5 | Schistosoma_int | 0.037 | IL_5 | Schistosoma_int | -0.008 |
| IL_5 | Strongyloides_Int | -0.016 | IL_5 | Strongyloides_Int | -0.033 |
| IL_5 | Filaria_Int | -0.038 | IL_5 | Filaria_Int | 0.287 |
| IL_6 | IL_1_alpha | 0.008 | IL_6 | IL_1_alpha | 0.090 |
| IL_6 | IL_1_beta | 0.189 | IL_6 | IL_1_beta | 0.397 |
| IL_6 | IL_2 | 0.568 | IL_6 | IL_2 | 0.151 |
| IL_6 | IL_4 | -0.019 | IL_6 | IL_4 | 0.101 |
| IL_6 | IL_5 | -0.011 | IL_6 | IL_5 | 0.342 |
| IL_6 | IL_6 | 1.000 | IL_6 | IL_6 | 1.000 |
| IL_6 | IL_8 | 0.037 | IL_6 | IL_8 | 0.277 |
| IL_6 | IL_10 | 0.024 | IL_6 | IL_10 | 0.315 |
| IL_6 | IL_12p70 | 0.010 | IL_6 | IL_12p70 | 0.112 |
| IL_6 | IL_13 | 0.053 | IL_6 | IL_13 | 0.385 |
| IL_6 | IL_15 | 0.064 | IL_6 | IL_15 | 0.284 |
| IL_6 | IL_17 | -0.029 | IL_6 | IL_17 | 0.052 |
| IL_6 | IL_23 | -0.063 | IL_6 | IL_23 | -0.055 |
| IL_6 | IFN_gamma | 0.000 | IL_6 | IFN_gamma | 0.000 |
| IL_6 | TNF_alpha | 0.012 | IL_6 | TNF_alpha | 0.049 |
| IL_6 | TNF_beta | 0.025 | IL_6 | TNF_beta | 0.104 |
| IL_6 | Varicella_Int | -0.019 | IL_6 | Varicella_Int | 0.028 |
| IL_6 | Measles_OD_DB_Int | -0.107 | IL_6 | Measles_OD_DB_Int | 0.098 |
| IL_6 | Measles_Int | -0.130 | IL_6 | Measles_Int | 0.066 |
| IL_6 | HepA_Int | 0.106 | IL_6 | HepA_Int | -0.222 |
| IL_6 | Tetanus_Int | 0.000 | IL_6 | Tetanus_Int | 0.000 |
| IL_6 | Diptheria_Int | 0.000 | IL_6 | Diptheria_Int | 0.000 |
| IL_6 | Rubella_Int | 0.207 | IL_6 | Rubella_Int | -0.025 |
| IL_6 | CMV_Int | -0.036 | IL_6 | CMV_Int | 0.000 |
| IL_6 | HepB_cAb_Int | 0.115 | IL_6 | HepB_cAb_Int | -0.094 |
| IL_6 | HepB_eAb_Int | 0.000 | IL_6 | HepB_eAb_Int | 0.000 |
| IL_6 | HepB_eAg_Int | -0.350 | IL_6 | HepB_eAg_Int | -0.292 |
| IL_6 | HepC_Int | -0.044 | IL_6 | HepC_Int | -0.060 |

FIG. 2114-D

| IL_6 | Schistosoma_int | -0.024 | | IL_6 | Schistosoma_int | -0.108 |
|---|---|---|---|---|---|---|
| IL_6 | Strongyloides_Int | -0.159 | | IL_6 | Strongyloides_Int | -0.087 |
| IL_6 | Filaria_Int | -0.095 | | IL_6 | Filaria_Int | -0.040 |
| IL_8 | IL_1_alpha | 0.351 | | IL_8 | IL_1_alpha | 0.325 |
| IL_8 | IL_1_beta | 0.245 | | IL_8 | IL_1_beta | 0.319 |
| IL_8 | IL_2 | 0.117 | | IL_8 | IL_2 | 0.255 |
| IL_8 | IL_4 | 0.360 | | IL_8 | IL_4 | 0.282 |
| IL_8 | IL_5 | 0.156 | | IL_8 | IL_5 | 0.384 |
| IL_8 | IL_6 | 0.037 | | IL_8 | IL_6 | 0.277 |
| IL_8 | IL_8 | 1.000 | | IL_8 | IL_8 | 1.000 |
| IL_8 | IL_10 | 0.116 | | IL_8 | IL_10 | 0.483 |
| IL_8 | IL_12p70 | 0.240 | | IL_8 | IL_12p70 | 0.478 |
| IL_8 | IL_13 | 0.247 | | IL_8 | IL_13 | 0.335 |
| IL_8 | IL_15 | 0.386 | | IL_8 | IL_15 | 0.388 |
| IL_8 | IL_17 | 0.189 | | IL_8 | IL_17 | 0.181 |
| IL_8 | IL_23 | 0.419 | | IL_8 | IL_23 | -0.013 |
| IL_8 | IFN_gamma | 0.000 | | IL_8 | IFN_gamma | 0.000 |
| IL_8 | TNF_alpha | 0.295 | | IL_8 | TNF_alpha | 0.240 |
| IL_8 | TNF_beta | 0.177 | | IL_8 | TNF_beta | 0.239 |
| IL_8 | Varicella_Int | -0.174 | | IL_8 | Varicella_Int | -0.020 |
| IL_8 | Measles_OD_DB_Int | -0.257 | | IL_8 | Measles_OD_DB_Int | -0.045 |
| IL_8 | Measles_Int | 0.098 | | IL_8 | Measles_Int | 0.127 |
| IL_8 | HepA_Int | -0.156 | | IL_8 | HepA_Int | -0.127 |
| IL_8 | Tetanus_Int | 0.000 | | IL_8 | Tetanus_Int | 0.000 |
| IL_8 | Diptheria_Int | 0.000 | | IL_8 | Diptheria_Int | 0.000 |
| IL_8 | Rubella_Int | 0.101 | | IL_8 | Rubella_Int | 0.123 |
| IL_8 | CMV_Int | 0.101 | | IL_8 | CMV_Int | 0.000 |
| IL_8 | HepB_cAb_Int | -0.134 | | IL_8 | HepB_cAb_Int | 0.122 |
| IL_8 | HepB_eAb_Int | 0.000 | | IL_8 | HepB_eAb_Int | 0.000 |
| IL_8 | HepB_eAg_Int | -0.183 | | IL_8 | HepB_eAg_Int | -0.227 |
| IL_8 | HepC_Int | -0.063 | | IL_8 | HepC_Int | 0.298 |
| IL_8 | Schistosoma_int | -0.004 | | IL_8 | Schistosoma_int | 0.019 |
| IL_8 | Strongyloides_Int | 0.031 | | IL_8 | Strongyloides_Int | 0.162 |
| IL_8 | Filaria_Int | -0.099 | | IL_8 | Filaria_Int | 0.010 |
| IL_10 | IL_1_alpha | 0.472 | | IL_10 | IL_1_alpha | 0.278 |
| IL_10 | IL_1_beta | 0.495 | | IL_10 | IL_1_beta | 0.394 |
| IL_10 | IL_2 | 0.222 | | IL_10 | IL_2 | 0.077 |
| IL_10 | IL_4 | 0.544 | | IL_10 | IL_4 | 0.253 |
| IL_10 | IL_5 | 0.557 | | IL_10 | IL_5 | 0.865 |
| IL_10 | IL_6 | 0.024 | | IL_10 | IL_6 | 0.315 |
| IL_10 | IL_8 | 0.116 | | IL_10 | IL_8 | 0.483 |
| IL_10 | IL_10 | 1.000 | | IL_10 | IL_10 | 1.000 |
| IL_10 | IL_12p70 | 0.612 | | IL_10 | IL_12p70 | 0.383 |
| IL_10 | IL_13 | 0.545 | | IL_10 | IL_13 | 0.888 |
| IL_10 | IL_15 | 0.295 | | IL_10 | IL_15 | 0.211 |
| IL_10 | IL_17 | 0.750 | | IL_10 | IL_17 | 0.182 |
| IL_10 | IL_23 | 0.103 | | IL_10 | IL_23 | 0.059 |
| IL_10 | IFN_gamma | 0.000 | | IL_10 | IFN_gamma | 0.000 |
| IL_10 | TNF_alpha | 0.412 | | IL_10 | TNF_alpha | 0.091 |
| IL_10 | TNF_beta | 0.654 | | IL_10 | TNF_beta | 0.172 |
| IL_10 | Varicella_Int | 0.083 | | IL_10 | Varicella_Int | 0.022 |
| IL_10 | Measles_OD_DB_Int | 0.137 | | IL_10 | Measles_OD_DB_Int | 0.062 |
| IL_10 | Measles_Int | -0.037 | | IL_10 | Measles_Int | 0.028 |
| IL_10 | HepA_Int | 0.077 | | IL_10 | HepA_Int | -0.048 |
| IL_10 | Tetanus_Int | 0.000 | | IL_10 | Tetanus_Int | 0.000 |
| IL_10 | Diptheria_Int | 0.000 | | IL_10 | Diptheria_Int | 0.000 |
| IL_10 | Rubella_Int | -0.089 | | IL_10 | Rubella_Int | 0.041 |

FIG. 2114-E

| | | | | | | |
|---|---|---|---|---|---|---|
| IL_10 | CMV_Int | -0.003 | | IL_10 | CMV_Int | 0.000 |
| IL_10 | HepB_cAb_Int | -0.093 | | IL_10 | HepB_cAb_Int | -0.047 |
| IL_10 | HepB_eAb_Int | 0.000 | | IL_10 | HepB_eAb_Int | 0.000 |
| IL_10 | HepB_eAg_Int | -0.366 | | IL_10 | HepB_eAg_Int | -0.200 |
| IL_10 | HepC_Int | -0.095 | | IL_10 | HepC_Int | 0.086 |
| IL_10 | Schistosoma_int | -0.031 | | IL_10 | Schistosoma_int | -0.080 |
| IL_10 | Strongyloides_Int | -0.042 | | IL_10 | Strongyloides_Int | -0.079 |
| IL_10 | Filaria_Int | 0.104 | | IL_10 | Filaria_Int | 0.288 |
| IL_12p70 | IL_1_alpha | 0.694 | | IL_12p70 | IL_1_alpha | 0.657 |
| IL_12p70 | IL_1_beta | 0.435 | | IL_12p70 | IL_1_beta | 0.531 |
| IL_12p70 | IL_2 | 0.271 | | IL_12p70 | IL_2 | 0.567 |
| IL_12p70 | IL_4 | 0.649 | | IL_12p70 | IL_4 | 0.443 |
| IL_12p70 | IL_5 | 0.628 | | IL_12p70 | IL_5 | 0.464 |
| IL_12p70 | IL_6 | 0.010 | | IL_12p70 | IL_6 | 0.112 |
| IL_12p70 | IL_8 | 0.240 | | IL_12p70 | IL_8 | 0.478 |
| IL_12p70 | IL_10 | 0.612 | | IL_12p70 | IL_10 | 0.383 |
| IL_12p70 | IL_12p70 | 1.000 | | IL_12p70 | IL_12p70 | 1.000 |
| IL_12p70 | IL_13 | 0.629 | | IL_12p70 | IL_13 | 0.299 |
| IL_12p70 | IL_15 | 0.401 | | IL_12p70 | IL_15 | 0.598 |
| IL_12p70 | IL_17 | 0.626 | | IL_12p70 | IL_17 | 0.590 |
| IL_12p70 | IL_23 | 0.374 | | IL_12p70 | IL_23 | 0.488 |
| IL_12p70 | IFN_gamma | 0.000 | | IL_12p70 | IFN_gamma | 0.000 |
| IL_12p70 | TNF_alpha | 0.504 | | IL_12p70 | TNF_alpha | 0.491 |
| IL_12p70 | TNF_beta | 0.662 | | IL_12p70 | TNF_beta | 0.528 |
| IL_12p70 | Varicella_Int | 0.041 | | IL_12p70 | Varicella_Int | 0.028 |
| IL_12p70 | Measles_OD_DB_Int | 0.075 | | IL_12p70 | Measles_OD_DB_Int | -0.043 |
| IL_12p70 | Measles_Int | -0.019 | | IL_12p70 | Measles_Int | 0.060 |
| IL_12p70 | HepA_Int | -0.023 | | IL_12p70 | HepA_Int | -0.235 |
| IL_12p70 | Tetanus_Int | 0.000 | | IL_12p70 | Tetanus_Int | 0.000 |
| IL_12p70 | Diptheria_Int | 0.000 | | IL_12p70 | Diptheria_Int | 0.000 |
| IL_12p70 | Rubella_Int | -0.061 | | IL_12p70 | Rubella_Int | 0.371 |
| IL_12p70 | CMV_Int | 0.031 | | IL_12p70 | CMV_Int | 0.000 |
| IL_12p70 | HepB_cAb_Int | -0.058 | | IL_12p70 | HepB_cAb_Int | 0.062 |
| IL_12p70 | HepB_eAb_Int | 0.000 | | IL_12p70 | HepB_eAb_Int | 0.000 |
| IL_12p70 | HepB_eAg_Int | -0.504 | | IL_12p70 | HepB_eAg_Int | -0.320 |
| IL_12p70 | HepC_Int | -0.101 | | IL_12p70 | HepC_Int | 0.106 |
| IL_12p70 | Schistosoma_int | -0.021 | | IL_12p70 | Schistosoma_int | -0.030 |
| IL_12p70 | Strongyloides_Int | 0.020 | | IL_12p70 | Strongyloides_Int | 0.066 |
| IL_12p70 | Filaria_Int | 0.103 | | IL_12p70 | Filaria_Int | 0.099 |
| IL_13 | IL_1_alpha | 0.375 | | IL_13 | IL_1_alpha | 0.272 |
| IL_13 | IL_1_beta | 0.384 | | IL_13 | IL_1_beta | 0.390 |
| IL_13 | IL_2 | 0.012 | | IL_13 | IL_2 | 0.045 |
| IL_13 | IL_4 | 0.628 | | IL_13 | IL_4 | 0.262 |
| IL_13 | IL_5 | 0.458 | | IL_13 | IL_5 | 0.833 |
| IL_13 | IL_6 | 0.053 | | IL_13 | IL_6 | 0.385 |
| IL_13 | IL_8 | 0.247 | | IL_13 | IL_8 | 0.335 |
| IL_13 | IL_10 | 0.545 | | IL_13 | IL_10 | 0.888 |
| IL_13 | IL_12p70 | 0.629 | | IL_13 | IL_12p70 | 0.299 |
| IL_13 | IL_13 | 1.000 | | IL_13 | IL_13 | 1.000 |
| IL_13 | IL_15 | 0.454 | | IL_13 | IL_15 | 0.199 |
| IL_13 | IL_17 | 0.545 | | IL_13 | IL_17 | 0.181 |
| IL_13 | IL_23 | 0.226 | | IL_13 | IL_23 | -0.002 |
| IL_13 | IFN_gamma | 0.000 | | IL_13 | IFN_gamma | 0.000 |
| IL_13 | TNF_alpha | 0.499 | | IL_13 | TNF_alpha | 0.143 |
| IL_13 | TNF_beta | 0.429 | | IL_13 | TNF_beta | 0.162 |
| IL_13 | Varicella_Int | 0.059 | | IL_13 | Varicella_Int | 0.014 |
| IL_13 | Measles_OD_DB_Int | -0.024 | | IL_13 | Measles_OD_DB_Int | 0.005 |

FIG. 2114-F

| | | | | | | |
|---|---|---|---|---|---|---|
| IL_13 | Measles_Int | -0.124 | | IL_13 | Measles_Int | 0.043 |
| IL_13 | HepA_Int | 0.027 | | IL_13 | HepA_Int | -0.098 |
| IL_13 | Tetanus_Int | 0.000 | | IL_13 | Tetanus_Int | 0.000 |
| IL_13 | Diptheria_Int | 0.000 | | IL_13 | Diptheria_Int | 0.000 |
| IL_13 | Rubella_Int | 0.118 | | IL_13 | Rubella_Int | 0.017 |
| IL_13 | CMV_Int | -0.017 | | IL_13 | CMV_Int | 0.000 |
| IL_13 | HepB_cAb_Int | 0.092 | | IL_13 | HepB_cAb_Int | -0.041 |
| IL_13 | HepB_eAb_Int | 0.000 | | IL_13 | HepB_eAb_Int | 0.000 |
| IL_13 | HepB_eAg_Int | -0.357 | | IL_13 | HepB_eAg_Int | -0.235 |
| IL_13 | HepC_Int | -0.106 | | IL_13 | HepC_Int | -0.037 |
| IL_13 | Schistosoma_int | -0.061 | | IL_13 | Schistosoma_int | -0.072 |
| IL_13 | Strongyloides_Int | -0.050 | | IL_13 | Strongyloides_Int | -0.149 |
| IL_13 | Filaria_Int | 0.125 | | IL_13 | Filaria_Int | 0.185 |
| IL_15 | IL_1_alpha | 0.458 | | IL_15 | IL_1_alpha | 0.540 |
| IL_15 | IL_1_beta | 0.347 | | IL_15 | IL_1_beta | 0.417 |
| IL_15 | IL_2 | 0.019 | | IL_15 | IL_2 | 0.248 |
| IL_15 | IL_4 | 0.504 | | IL_15 | IL_4 | 0.383 |
| IL_15 | IL_5 | 0.366 | | IL_15 | IL_5 | 0.396 |
| IL_15 | IL_6 | 0.064 | | IL_15 | IL_6 | 0.284 |
| IL_15 | IL_8 | 0.386 | | IL_15 | IL_8 | 0.388 |
| IL_15 | IL_10 | 0.295 | | IL_15 | IL_10 | 0.211 |
| IL_15 | IL_12p70 | 0.401 | | IL_15 | IL_12p70 | 0.598 |
| IL_15 | IL_13 | 0.454 | | IL_15 | IL_13 | 0.199 |
| IL_15 | IL_15 | 1.000 | | IL_15 | IL_15 | 1.000 |
| IL_15 | IL_17 | 0.334 | | IL_15 | IL_17 | 0.543 |
| IL_15 | IL_23 | 0.217 | | IL_15 | IL_23 | 0.104 |
| IL_15 | IFN_gamma | 0.000 | | IL_15 | IFN_gamma | 0.000 |
| IL_15 | TNF_alpha | 0.349 | | IL_15 | TNF_alpha | 0.444 |
| IL_15 | TNF_beta | 0.293 | | IL_15 | TNF_beta | 0.365 |
| IL_15 | Varicella_Int | -0.112 | | IL_15 | Varicella_Int | 0.096 |
| IL_15 | Measles_OD_DB_Int | -0.037 | | IL_15 | Measles_OD_DB_Int | -0.021 |
| IL_15 | Measles_Int | -0.054 | | IL_15 | Measles_Int | 0.035 |
| IL_15 | HepA_Int | 0.083 | | IL_15 | HepA_Int | -0.095 |
| IL_15 | Tetanus_Int | 0.000 | | IL_15 | Tetanus_Int | 0.000 |
| IL_15 | Diptheria_Int | 0.000 | | IL_15 | Diptheria_Int | 0.000 |
| IL_15 | Rubella_Int | 0.155 | | IL_15 | Rubella_Int | 0.239 |
| IL_15 | CMV_Int | 0.189 | | IL_15 | CMV_Int | 0.000 |
| IL_15 | HepB_cAb_Int | 0.015 | | IL_15 | HepB_cAb_Int | 0.085 |
| IL_15 | HepB_eAb_Int | 0.000 | | IL_15 | HepB_eAb_Int | 0.000 |
| IL_15 | HepB_eAg_Int | -0.262 | | IL_15 | HepB_eAg_Int | -0.347 |
| IL_15 | HepC_Int | -0.108 | | IL_15 | HepC_Int | -0.049 |
| IL_15 | Schistosoma_int | -0.041 | | IL_15 | Schistosoma_int | 0.021 |
| IL_15 | Strongyloides_Int | 0.003 | | IL_15 | Strongyloides_Int | -0.041 |
| IL_15 | Filaria_Int | -0.069 | | IL_15 | Filaria_Int | -0.079 |
| IL_17 | IL_1_alpha | 0.526 | | IL_17 | IL_1_alpha | 0.478 |
| IL_17 | IL_1_beta | 0.481 | | IL_17 | IL_1_beta | 0.437 |
| IL_17 | IL_2 | 0.255 | | IL_17 | IL_2 | 0.379 |
| IL_17 | IL_4 | 0.615 | | IL_17 | IL_4 | 0.325 |
| IL_17 | IL_5 | 0.691 | | IL_17 | IL_5 | 0.289 |
| IL_17 | IL_6 | -0.029 | | IL_17 | IL_6 | 0.052 |
| IL_17 | IL_8 | 0.189 | | IL_17 | IL_8 | 0.181 |
| IL_17 | IL_10 | 0.750 | | IL_17 | IL_10 | 0.182 |
| IL_17 | IL_12p70 | 0.626 | | IL_17 | IL_12p70 | 0.590 |
| IL_17 | IL_13 | 0.545 | | IL_17 | IL_13 | 0.181 |
| IL_17 | IL_15 | 0.334 | | IL_17 | IL_15 | 0.543 |
| IL_17 | IL_17 | 1.000 | | IL_17 | IL_17 | 1.000 |
| IL_17 | IL_23 | 0.236 | | IL_17 | IL_23 | 0.247 |

FIG. 2114-G

| | | | | | | |
|---|---|---|---|---|---|---|
| IL_17 | IFN_gamma | 0.000 | | IL_17 | IFN_gamma | 0.000 |
| IL_17 | TNF_alpha | 0.487 | | IL_17 | TNF_alpha | 0.362 |
| IL_17 | TNF_beta | 0.657 | | IL_17 | TNF_beta | 0.499 |
| IL_17 | Varicella_Int | 0.122 | | IL_17 | Varicella_Int | 0.039 |
| IL_17 | Measles_OD_DB_Int | 0.007 | | IL_17 | Measles_OD_DB_Int | 0.032 |
| IL_17 | Measles_Int | -0.069 | | IL_17 | Measles_Int | 0.074 |
| IL_17 | HepA_Int | 0.044 | | IL_17 | HepA_Int | -0.086 |
| IL_17 | Tetanus_Int | 0.000 | | IL_17 | Tetanus_Int | 0.000 |
| IL_17 | Diptheria_Int | 0.000 | | IL_17 | Diptheria_Int | 0.000 |
| IL_17 | Rubella_Int | -0.043 | | IL_17 | Rubella_Int | 0.264 |
| IL_17 | CMV_Int | 0.025 | | IL_17 | CMV_Int | 0.000 |
| IL_17 | HepB_cAb_Int | -0.017 | | IL_17 | HepB_cAb_Int | 0.022 |
| IL_17 | HepB_eAb_Int | 0.000 | | IL_17 | HepB_eAb_Int | 0.000 |
| IL_17 | HepB_eAg_Int | -0.394 | | IL_17 | HepB_eAg_Int | -0.313 |
| IL_17 | HepC_Int | -0.083 | | IL_17 | HepC_Int | -0.025 |
| IL_17 | Schistosoma_int | -0.012 | | IL_17 | Schistosoma_int | -0.012 |
| IL_17 | Strongyloides_Int | 0.053 | | IL_17 | Strongyloides_Int | -0.019 |
| IL_17 | Filaria_Int | 0.107 | | IL_17 | Filaria_Int | 0.167 |
| IL_23 | IL_1_alpha | 0.287 | | IL_23 | IL_1_alpha | 0.143 |
| IL_23 | IL_1_beta | 0.278 | | IL_23 | IL_1_beta | 0.139 |
| IL_23 | IL_2 | 0.167 | | IL_23 | IL_2 | 0.432 |
| IL_23 | IL_4 | 0.405 | | IL_23 | IL_4 | 0.058 |
| IL_23 | IL_5 | 0.139 | | IL_23 | IL_5 | 0.128 |
| IL_23 | IL_6 | -0.063 | | IL_23 | IL_6 | -0.055 |
| IL_23 | IL_8 | 0.419 | | IL_23 | IL_8 | -0.013 |
| IL_23 | IL_10 | 0.103 | | IL_23 | IL_10 | 0.059 |
| IL_23 | IL_12p70 | 0.374 | | IL_23 | IL_12p70 | 0.488 |
| IL_23 | IL_13 | 0.226 | | IL_23 | IL_13 | -0.002 |
| IL_23 | IL_15 | 0.217 | | IL_23 | IL_15 | 0.104 |
| IL_23 | IL_17 | 0.236 | | IL_23 | IL_17 | 0.247 |
| IL_23 | IL_23 | 1.000 | | IL_23 | IL_23 | 1.000 |
| IL_23 | IFN_gamma | 0.000 | | IL_23 | IFN_gamma | 0.000 |
| IL_23 | TNF_alpha | 0.376 | | IL_23 | TNF_alpha | 0.142 |
| IL_23 | TNF_beta | 0.178 | | IL_23 | TNF_beta | 0.134 |
| IL_23 | Varicella_Int | 0.051 | | IL_23 | Varicella_Int | 0.018 |
| IL_23 | Measles_OD_DB_Int | -0.172 | | IL_23 | Measles_OD_DB_Int | 0.094 |
| IL_23 | Measles_Int | 0.050 | | IL_23 | Measles_Int | 0.042 |
| IL_23 | HepA_Int | -0.112 | | IL_23 | HepA_Int | 0.010 |
| IL_23 | Tetanus_Int | 0.000 | | IL_23 | Tetanus_Int | 0.000 |
| IL_23 | Diptheria_Int | 0.000 | | IL_23 | Diptheria_Int | 0.000 |
| IL_23 | Rubella_Int | 0.068 | | IL_23 | Rubella_Int | 0.091 |
| IL_23 | CMV_Int | 0.045 | | IL_23 | CMV_Int | 0.000 |
| IL_23 | HepB_cAb_Int | -0.015 | | IL_23 | HepB_cAb_Int | 0.077 |
| IL_23 | HepB_eAb_Int | 0.000 | | IL_23 | HepB_eAb_Int | 0.000 |
| IL_23 | HepB_eAg_Int | -0.320 | | IL_23 | HepB_eAg_Int | -0.343 |
| IL_23 | HepC_Int | -0.034 | | IL_23 | HepC_Int | -0.054 |
| IL_23 | Schistosoma_int | -0.025 | | IL_23 | Schistosoma_int | -0.054 |
| IL_23 | Strongyloides_Int | 0.224 | | IL_23 | Strongyloides_Int | 0.036 |
| IL_23 | Filaria_Int | 0.005 | | IL_23 | Filaria_Int | 0.141 |
| IFN_gamma | IL_1_alpha | 0.000 | | IFN_gamma | IL_1_alpha | 0.000 |
| IFN_gamma | IL_1_beta | 0.000 | | IFN_gamma | IL_1_beta | 0.000 |
| IFN_gamma | IL_2 | 0.000 | | IFN_gamma | IL_2 | 0.000 |
| IFN_gamma | IL_4 | 0.000 | | IFN_gamma | IL_4 | 0.000 |
| IFN_gamma | IL_5 | 0.000 | | IFN_gamma | IL_5 | 0.000 |
| IFN_gamma | IL_6 | 0.000 | | IFN_gamma | IL_6 | 0.000 |
| IFN_gamma | IL_8 | 0.000 | | IFN_gamma | IL_8 | 0.000 |
| IFN_gamma | IL_10 | 0.000 | | IFN_gamma | IL_10 | 0.000 |

FIG. 2114-H

| | | | | | | |
|---|---|---|---|---|---|---|
| IFN_gamma | IL_12p70 | 0.000 | | IFN_gamma | IL_12p70 | 0.000 |
| IFN_gamma | IL_13 | 0.000 | | IFN_gamma | IL_13 | 0.000 |
| IFN_gamma | IL_15 | 0.000 | | IFN_gamma | IL_15 | 0.000 |
| IFN_gamma | IL_17 | 0.000 | | IFN_gamma | IL_17 | 0.000 |
| IFN_gamma | IL_23 | 0.000 | | IFN_gamma | IL_23 | 0.000 |
| IFN_gamma | IFN_gamma | 1.000 | | IFN_gamma | IFN_gamma | 1.000 |
| IFN_gamma | TNF_alpha | 0.000 | | IFN_gamma | TNF_alpha | 0.000 |
| IFN_gamma | TNF_beta | 0.000 | | IFN_gamma | TNF_beta | 0.000 |
| IFN_gamma | Varicella_Int | 0.000 | | IFN_gamma | Varicella_Int | 0.000 |
| IFN_gamma | Measles_OD_DB_Int | 0.000 | | IFN_gamma | Measles_OD_DB_Int | 0.000 |
| IFN_gamma | Measles_Int | 0.000 | | IFN_gamma | Measles_Int | 0.000 |
| IFN_gamma | HepA_Int | 0.000 | | IFN_gamma | HepA_Int | 0.000 |
| IFN_gamma | Tetanus_Int | 0.000 | | IFN_gamma | Tetanus_Int | 0.000 |
| IFN_gamma | Diptheria_Int | 0.000 | | IFN_gamma | Diptheria_Int | 0.000 |
| IFN_gamma | Rubella_Int | 0.000 | | IFN_gamma | Rubella_Int | 0.000 |
| IFN_gamma | CMV_Int | 0.000 | | IFN_gamma | CMV_Int | 0.000 |
| IFN_gamma | HepB_cAb_Int | 0.000 | | IFN_gamma | HepB_cAb_Int | 0.000 |
| IFN_gamma | HepB_eAb_Int | 0.000 | | IFN_gamma | HepB_eAb_Int | 0.000 |
| IFN_gamma | HepB_eAg_Int | 0.000 | | IFN_gamma | HepB_eAg_Int | 0.000 |
| IFN_gamma | HepC_Int | 0.000 | | IFN_gamma | HepC_Int | 0.000 |
| IFN_gamma | Schistosoma_int | 0.000 | | IFN_gamma | Schistosoma_int | 0.000 |
| IFN_gamma | Strongyloides_Int | 0.000 | | IFN_gamma | Strongyloides_Int | 0.000 |
| IFN_gamma | Filaria_Int | 0.000 | | IFN_gamma | Filaria_Int | 0.000 |
| TNF_alpha | IL_1_alpha | 0.456 | | TNF_alpha | IL_1_alpha | 0.608 |
| TNF_alpha | IL_1_beta | 0.725 | | TNF_alpha | IL_1_beta | 0.525 |
| TNF_alpha | IL_2 | 0.203 | | TNF_alpha | IL_2 | 0.398 |
| TNF_alpha | IL_4 | 0.607 | | TNF_alpha | IL_4 | 0.452 |
| TNF_alpha | IL_5 | 0.387 | | TNF_alpha | IL_5 | 0.171 |
| TNF_alpha | IL_6 | 0.012 | | TNF_alpha | IL_6 | 0.049 |
| TNF_alpha | IL_8 | 0.295 | | TNF_alpha | IL_8 | 0.240 |
| TNF_alpha | IL_10 | 0.412 | | TNF_alpha | IL_10 | 0.091 |
| TNF_alpha | IL_12p70 | 0.504 | | TNF_alpha | IL_12p70 | 0.491 |
| TNF_alpha | IL_13 | 0.499 | | TNF_alpha | IL_13 | 0.143 |
| TNF_alpha | IL_15 | 0.349 | | TNF_alpha | IL_15 | 0.444 |
| TNF_alpha | IL_17 | 0.487 | | TNF_alpha | IL_17 | 0.362 |
| TNF_alpha | IL_23 | 0.376 | | TNF_alpha | IL_23 | 0.142 |
| TNF_alpha | IFN_gamma | 0.000 | | TNF_alpha | IFN_gamma | 0.000 |
| TNF_alpha | TNF_alpha | 1.000 | | TNF_alpha | TNF_alpha | 1.000 |
| TNF_alpha | TNF_beta | 0.526 | | TNF_alpha | TNF_beta | 0.576 |
| TNF_alpha | Varicella_Int | -0.024 | | TNF_alpha | Varicella_Int | -0.056 |
| TNF_alpha | Measles_OD_DB_Int | -0.028 | | TNF_alpha | Measles_OD_DB_Int | -0.077 |
| TNF_alpha | Measles_Int | -0.034 | | TNF_alpha | Measles_Int | -0.158 |
| TNF_alpha | HepA_Int | -0.023 | | TNF_alpha | HepA_Int | -0.144 |
| TNF_alpha | Tetanus_Int | 0.000 | | TNF_alpha | Tetanus_Int | 0.000 |
| TNF_alpha | Diptheria_Int | 0.000 | | TNF_alpha | Diptheria_Int | 0.000 |
| TNF_alpha | Rubella_Int | 0.110 | | TNF_alpha | Rubella_Int | 0.030 |
| TNF_alpha | CMV_Int | -0.010 | | TNF_alpha | CMV_Int | 0.000 |
| TNF_alpha | HepB_cAb_Int | -0.062 | | TNF_alpha | HepB_cAb_Int | -0.012 |
| TNF_alpha | HepB_eAb_Int | 0.000 | | TNF_alpha | HepB_eAb_Int | 0.000 |
| TNF_alpha | HepB_eAg_Int | -0.090 | | TNF_alpha | HepB_eAg_Int | -0.250 |
| TNF_alpha | HepC_Int | -0.078 | | TNF_alpha | HepC_Int | -0.032 |
| TNF_alpha | Schistosoma_int | 0.133 | | TNF_alpha | Schistosoma_int | -0.001 |
| TNF_alpha | Strongyloides_Int | 0.180 | | TNF_alpha | Strongyloides_Int | 0.071 |
| TNF_alpha | Filaria_Int | 0.133 | | TNF_alpha | Filaria_Int | -0.030 |
| TNF_beta | IL_1_alpha | 0.578 | | TNF_beta | IL_1_alpha | 0.407 |
| TNF_beta | IL_1_beta | 0.454 | | TNF_beta | IL_1_beta | 0.506 |
| TNF_beta | IL_2 | 0.289 | | TNF_beta | IL_2 | 0.547 |

FIG. 2114-I

| | | | | | | |
|---|---|---|---|---|---|---|
| TNF_beta | IL_4 | 0.546 | | TNF_beta | IL_4 | 0.452 |
| TNF_beta | IL_5 | 0.592 | | TNF_beta | IL_5 | 0.214 |
| TNF_beta | IL_6 | 0.025 | | TNF_beta | IL_6 | 0.104 |
| TNF_beta | IL_8 | 0.177 | | TNF_beta | IL_8 | 0.239 |
| TNF_beta | IL_10 | 0.654 | | TNF_beta | IL_10 | 0.172 |
| TNF_beta | IL_12p70 | 0.662 | | TNF_beta | IL_12p70 | 0.528 |
| TNF_beta | IL_13 | 0.429 | | TNF_beta | IL_13 | 0.162 |
| TNF_beta | IL_15 | 0.293 | | TNF_beta | IL_15 | 0.365 |
| TNF_beta | IL_17 | 0.657 | | TNF_beta | IL_17 | 0.499 |
| TNF_beta | IL_23 | 0.178 | | TNF_beta | IL_23 | 0.134 |
| TNF_beta | IFN_gamma | 0.000 | | TNF_beta | IFN_gamma | 0.000 |
| TNF_beta | TNF_alpha | 0.526 | | TNF_beta | TNF_alpha | 0.576 |
| TNF_beta | TNF_beta | 1.000 | | TNF_beta | TNF_beta | 1.000 |
| TNF_beta | Varicella_Int | 0.044 | | TNF_beta | Varicella_Int | 0.063 |
| TNF_beta | Measles_OD_DB_Int | 0.079 | | TNF_beta | Measles_OD_DB_Int | -0.046 |
| TNF_beta | Measles_Int | -0.051 | | TNF_beta | Measles_Int | 0.025 |
| TNF_beta | HepA_Int | 0.029 | | TNF_beta | HepA_Int | -0.299 |
| TNF_beta | Tetanus_Int | 0.000 | | TNF_beta | Tetanus_Int | 0.000 |
| TNF_beta | Diptheria_Int | 0.000 | | TNF_beta | Diptheria_Int | 0.000 |
| TNF_beta | Rubella_Int | -0.010 | | TNF_beta | Rubella_Int | 0.191 |
| TNF_beta | CMV_Int | -0.027 | | TNF_beta | CMV_Int | 0.000 |
| TNF_beta | HepB_cAb_Int | -0.081 | | TNF_beta | HepB_cAb_Int | -0.065 |
| TNF_beta | HepB_eAb_Int | 0.000 | | TNF_beta | HepB_eAb_Int | 0.000 |
| TNF_beta | HepB_eAg_Int | 0.948 | | TNF_beta | HepB_eAg_Int | -0.250 |
| TNF_beta | HepC_Int | -0.057 | | TNF_beta | HepC_Int | 0.078 |
| TNF_beta | Schistosoma_int | 0.032 | | TNF_beta | Schistosoma_int | -0.057 |
| TNF_beta | Strongyloides_Int | 0.056 | | TNF_beta | Strongyloides_Int | 0.167 |
| TNF_beta | Filaria_Int | 0.060 | | TNF_beta | Filaria_Int | -0.001 |
| Varicella_Int | IL_1_alpha | -0.049 | | Varicella_Int | IL_1_alpha | 0.103 |
| Varicella_Int | IL_1_beta | 0.005 | | Varicella_Int | IL_1_beta | -0.056 |
| Varicella_Int | IL_2 | -0.043 | | Varicella_Int | IL_2 | 0.116 |
| Varicella_Int | IL_4 | 0.050 | | Varicella_Int | IL_4 | -0.151 |
| Varicella_Int | IL_5 | 0.066 | | Varicella_Int | IL_5 | 0.039 |
| Varicella_Int | IL_6 | -0.019 | | Varicella_Int | IL_6 | 0.028 |
| Varicella_Int | IL_8 | -0.174 | | Varicella_Int | IL_8 | -0.020 |
| Varicella_Int | IL_10 | 0.083 | | Varicella_Int | IL_10 | 0.022 |
| Varicella_Int | IL_12p70 | 0.041 | | Varicella_Int | IL_12p70 | 0.028 |
| Varicella_Int | IL_13 | 0.059 | | Varicella_Int | IL_13 | 0.014 |
| Varicella_Int | IL_15 | -0.112 | | Varicella_Int | IL_15 | 0.096 |
| Varicella_Int | IL_17 | 0.122 | | Varicella_Int | IL_17 | 0.039 |
| Varicella_Int | IL_23 | 0.051 | | Varicella_Int | IL_23 | 0.018 |
| Varicella_Int | IFN_gamma | 0.000 | | Varicella_Int | IFN_gamma | 0.000 |
| Varicella_Int | TNF_alpha | -0.024 | | Varicella_Int | TNF_alpha | -0.056 |
| Varicella_Int | TNF_beta | 0.044 | | Varicella_Int | TNF_beta | 0.063 |
| Varicella_Int | Varicella_Int | 1.000 | | Varicella_Int | Varicella_Int | 1.000 |
| Varicella_Int | Measles_OD_DB_Int | 0.043 | | Varicella_Int | Measles_OD_DB_Int | 0.205 |
| Varicella_Int | Measles_Int | -0.090 | | Varicella_Int | Measles_Int | -0.042 |
| Varicella_Int | HepA_Int | 0.114 | | Varicella_Int | HepA_Int | -0.048 |
| Varicella_Int | Tetanus_Int | 0.000 | | Varicella_Int | Tetanus_Int | 0.000 |
| Varicella_Int | Diptheria_Int | 0.000 | | Varicella_Int | Diptheria_Int | 0.000 |
| Varicella_Int | Rubella_Int | -0.024 | | Varicella_Int | Rubella_Int | -0.316 |
| Varicella_Int | CMV_Int | 0.041 | | Varicella_Int | CMV_Int | 0.000 |
| Varicella_Int | HepB_cAb_Int | 0.123 | | Varicella_Int | HepB_cAb_Int | 0.213 |
| Varicella_Int | HepB_eAb_Int | 0.000 | | Varicella_Int | HepB_eAb_Int | 0.000 |
| Varicella_Int | HepB_eAg_Int | 0.167 | | Varicella_Int | HepB_eAg_Int | 0.000 |
| Varicella_Int | HepC_Int | 0.034 | | Varicella_Int | HepC_Int | 0.055 |
| Varicella_Int | Schistosoma_int | 0.012 | | Varicella_Int | Schistosoma_int | 0.109 |

FIG. 2114-J

| | | | | | | |
|---|---|---|---|---|---|---|
| Varicella_Int | Strongyloides_Int | -0.139 | | Varicella_Int | Strongyloides_Int | 0.015 |
| Varicella_Int | Filaria_Int | -0.026 | | Varicella_Int | Filaria_Int | -0.057 |
| Measles_OD_DB_Int | IL_1_alpha | 0.139 | | Measles_OD_DB_Int | IL_1_alpha | -0.056 |
| Measles_OD_DB_Int | IL_1_beta | 0.016 | | Measles_OD_DB_Int | IL_1_beta | 0.110 |
| Measles_OD_DB_Int | IL_2 | 0.036 | | Measles_OD_DB_Int | IL_2 | 0.067 |
| Measles_OD_DB_Int | IL_4 | 0.047 | | Measles_OD_DB_Int | IL_4 | -0.158 |
| Measles_OD_DB_Int | IL_5 | 0.115 | | Measles_OD_DB_Int | IL_5 | 0.011 |
| Measles_OD_DB_Int | IL_6 | -0.107 | | Measles_OD_DB_Int | IL_6 | 0.098 |
| Measles_OD_DB_Int | IL_8 | -0.257 | | Measles_OD_DB_Int | IL_8 | -0.045 |
| Measles_OD_DB_Int | IL_10 | 0.137 | | Measles_OD_DB_Int | IL_10 | 0.062 |
| Measles_OD_DB_Int | IL_12p70 | 0.075 | | Measles_OD_DB_Int | IL_12p70 | -0.043 |
| Measles_OD_DB_Int | IL_13 | -0.024 | | Measles_OD_DB_Int | IL_13 | 0.005 |
| Measles_OD_DB_Int | IL_15 | -0.037 | | Measles_OD_DB_Int | IL_15 | -0.021 |
| Measles_OD_DB_Int | IL_17 | 0.007 | | Measles_OD_DB_Int | IL_17 | 0.032 |
| Measles_OD_DB_Int | IL_23 | -0.172 | | Measles_OD_DB_Int | IL_23 | 0.094 |
| Measles_OD_DB_Int | IFN_gamma | 0.000 | | Measles_OD_DB_Int | IFN_gamma | 0.000 |
| Measles_OD_DB_Int | TNF_alpha | -0.028 | | Measles_OD_DB_Int | TNF_alpha | -0.077 |
| Measles_OD_DB_Int | TNF_beta | 0.079 | | Measles_OD_DB_Int | TNF_beta | -0.046 |
| Measles_OD_DB_Int | Varicella_Int | 0.043 | | Measles_OD_DB_Int | Varicella_Int | 0.205 |
| Measles_OD_DB_Int | Measles_OD_DB_Int | 1.000 | | Measles_OD_DB_Int | Measles_OD_DB_Int | 1.000 |
| Measles_OD_DB_Int | Measles_Int | -0.002 | | Measles_OD_DB_Int | Measles_Int | -0.081 |
| Measles_OD_DB_Int | HepA_Int | -0.036 | | Measles_OD_DB_Int | HepA_Int | -0.093 |
| Measles_OD_DB_Int | Tetanus_Int | 0.000 | | Measles_OD_DB_Int | Tetanus_Int | 0.000 |
| Measles_OD_DB_Int | Diptheria_Int | 0.000 | | Measles_OD_DB_Int | Diptheria_Int | 0.000 |
| Measles_OD_DB_Int | Rubella_Int | -0.234 | | Measles_OD_DB_Int | Rubella_Int | -0.089 |
| Measles_OD_DB_Int | CMV_Int | -0.013 | | Measles_OD_DB_Int | CMV_Int | 0.000 |
| Measles_OD_DB_Int | HepB_cAb_Int | -0.021 | | Measles_OD_DB_Int | HepB_cAb_Int | -0.034 |
| Measles_OD_DB_Int | HepB_eAb_Int | 0.000 | | Measles_OD_DB_Int | HepB_eAb_Int | 0.000 |
| Measles_OD_DB_Int | HepB_eAg_Int | 0.420 | | Measles_OD_DB_Int | HepB_eAg_Int | -0.408 |
| Measles_OD_DB_Int | HepC_Int | 0.078 | | Measles_OD_DB_Int | HepC_Int | 0.040 |
| Measles_OD_DB_Int | Schistosoma_Int | 0.018 | | Measles_OD_DB_Int | Schistosoma_Int | 0.027 |
| Measles_OD_DB_Int | Strongyloides_Int | -0.012 | | Measles_OD_DB_Int | Strongyloides_Int | 0.101 |
| Measles_OD_DB_Int | Filaria_Int | 0.143 | | Measles_OD_DB_Int | Filaria_Int | 0.008 |
| Measles_Int | IL_1_alpha | 0.083 | | Measles_Int | IL_1_alpha | -0.147 |
| Measles_Int | IL_1_beta | 0.058 | | Measles_Int | IL_1_beta | -0.037 |
| Measles_Int | IL_2 | -0.070 | | Measles_Int | IL_2 | 0.130 |
| Measles_Int | IL_4 | -0.061 | | Measles_Int | IL_4 | 0.099 |
| Measles_Int | IL_5 | 0.045 | | Measles_Int | IL_5 | 0.069 |
| Measles_Int | IL_6 | -0.130 | | Measles_Int | IL_6 | 0.066 |
| Measles_Int | IL_8 | 0.098 | | Measles_Int | IL_8 | 0.127 |
| Measles_Int | IL_10 | -0.037 | | Measles_Int | IL_10 | 0.028 |
| Measles_Int | IL_12p70 | -0.019 | | Measles_Int | IL_12p70 | 0.060 |
| Measles_Int | IL_13 | -0.124 | | Measles_Int | IL_13 | 0.043 |
| Measles_Int | IL_15 | -0.054 | | Measles_Int | IL_15 | 0.035 |
| Measles_Int | IL_17 | -0.069 | | Measles_Int | IL_17 | 0.074 |
| Measles_Int | IL_23 | 0.050 | | Measles_Int | IL_23 | 0.042 |
| Measles_Int | IFN_gamma | 0.000 | | Measles_Int | IFN_gamma | 0.000 |
| Measles_Int | TNF_alpha | -0.034 | | Measles_Int | TNF_alpha | -0.158 |
| Measles_Int | TNF_beta | -0.051 | | Measles_Int | TNF_beta | 0.025 |
| Measles_Int | Varicella_Int | -0.090 | | Measles_Int | Varicella_Int | -0.042 |
| Measles_Int | Measles_OD_DB_Int | -0.002 | | Measles_Int | Measles_OD_DB_Int | -0.081 |
| Measles_Int | Measles_Int | 1.000 | | Measles_Int | Measles_Int | 1.000 |
| Measles_Int | HepA_Int | -0.160 | | Measles_Int | HepA_Int | 0.070 |
| Measles_Int | Tetanus_Int | 0.000 | | Measles_Int | Tetanus_Int | 0.000 |
| Measles_Int | Diptheria_Int | 0.000 | | Measles_Int | Diptheria_Int | 0.000 |
| Measles_Int | Rubella_Int | 0.057 | | Measles_Int | Rubella_Int | 0.044 |
| Measles_Int | CMV_Int | -0.064 | | Measles_Int | CMV_Int | 0.000 |

FIG. 2114-K

| | | | | | | |
|---|---|---|---|---|---|---|
| Measles_Int | HepB_cAb_Int | -0.050 | | Measles_Int | HepB_cAb_Int | 0.144 |
| Measles_Int | HepB_eAb_Int | 0.000 | | Measles_Int | HepB_eAb_Int | 0.000 |
| Measles_Int | HepB_eAg_Int | 0.000 | | Measles_Int | HepB_eAg_Int | 0.000 |
| Measles_Int | HepC_Int | 0.040 | | Measles_Int | HepC_Int | 0.067 |
| Measles_Int | Schistosoma_int | 0.087 | | Measles_Int | Schistosoma_int | 0.064 |
| Measles_Int | Strongyloides_Int | 0.112 | | Measles_Int | Strongyloides_Int | -0.029 |
| Measles_Int | Filaria_Int | 0.098 | | Measles_Int | Filaria_Int | 0.070 |
| HepA_Int | IL_1_alpha | -0.040 | | HepA_Int | IL_1_alpha | -0.157 |
| HepA_Int | IL_1_beta | 0.033 | | HepA_Int | IL_1_beta | -0.255 |
| HepA_Int | IL_2 | 0.054 | | HepA_Int | IL_2 | -0.194 |
| HepA_Int | IL_4 | -0.016 | | HepA_Int | IL_4 | -0.109 |
| HepA_Int | IL_5 | -0.000 | | HepA_Int | IL_5 | -0.062 |
| HepA_Int | IL_6 | 0.106 | | HepA_Int | IL_6 | -0.222 |
| HepA_Int | IL_8 | -0.156 | | HepA_Int | IL_8 | -0.127 |
| HepA_Int | IL_10 | 0.077 | | HepA_Int | IL_10 | -0.048 |
| HepA_Int | IL_12p70 | -0.023 | | HepA_Int | IL_12p70 | -0.235 |
| HepA_Int | IL_13 | 0.027 | | HepA_Int | IL_13 | -0.098 |
| HepA_Int | IL_15 | 0.083 | | HepA_Int | IL_15 | -0.095 |
| HepA_Int | IL_17 | 0.044 | | HepA_Int | IL_17 | -0.086 |
| HepA_Int | IL_23 | -0.112 | | HepA_Int | IL_23 | 0.010 |
| HepA_Int | IFN_gamma | 0.000 | | HepA_Int | IFN_gamma | 0.000 |
| HepA_Int | TNF_alpha | -0.023 | | HepA_Int | TNF_alpha | -0.144 |
| HepA_Int | TNF_beta | 0.029 | | HepA_Int | TNF_beta | -0.299 |
| HepA_Int | Varicella_Int | 0.114 | | HepA_Int | Varicella_Int | -0.048 |
| HepA_Int | Measles_OD_DB_Int | -0.036 | | HepA_Int | Measles_OD_DB_Int | -0.093 |
| HepA_Int | Measles_Int | -0.160 | | HepA_Int | Measles_Int | 0.070 |
| HepA_Int | HepA_Int | 1.000 | | HepA_Int | HepA_Int | 1.000 |
| HepA_Int | Tetanus_Int | 0.000 | | HepA_Int | Tetanus_Int | 0.000 |
| HepA_Int | Diptheria_Int | 0.000 | | HepA_Int | Diptheria_Int | 0.000 |
| HepA_Int | Rubella_Int | 0.066 | | HepA_Int | Rubella_Int | 0.050 |
| HepA_Int | CMV_Int | 0.137 | | HepA_Int | CMV_Int | 0.000 |
| HepA_Int | HepB_cAb_Int | 0.140 | | HepA_Int | HepB_cAb_Int | 0.224 |
| HepA_Int | HepB_eAb_Int | 0.000 | | HepA_Int | HepB_eAb_Int | 0.000 |
| HepA_Int | HepB_eAg_Int | 0.258 | | HepA_Int | HepB_eAg_Int | 0.000 |
| HepA_Int | HepC_Int | 0.079 | | HepA_Int | HepC_Int | 0.078 |
| HepA_Int | Schistosoma_int | 0.057 | | HepA_Int | Schistosoma_int | 0.062 |
| HepA_Int | Strongyloides_Int | 0.007 | | HepA_Int | Strongyloides_Int | -0.081 |
| HepA_Int | Filaria_Int | -0.044 | | HepA_Int | Filaria_Int | 0.164 |
| Tetanus_Int | IL_1_alpha | 0.000 | | Tetanus_Int | IL_1_alpha | 0.000 |
| Tetanus_Int | IL_1_beta | 0.000 | | Tetanus_Int | IL_1_beta | 0.000 |
| Tetanus_Int | IL_2 | 0.000 | | Tetanus_Int | IL_2 | 0.000 |
| Tetanus_Int | IL_4 | 0.000 | | Tetanus_Int | IL_4 | 0.000 |
| Tetanus_Int | IL_5 | 0.000 | | Tetanus_Int | IL_5 | 0.000 |
| Tetanus_Int | IL_6 | 0.000 | | Tetanus_Int | IL_6 | 0.000 |
| Tetanus_Int | IL_8 | 0.000 | | Tetanus_Int | IL_8 | 0.000 |
| Tetanus_Int | IL_10 | 0.000 | | Tetanus_Int | IL_10 | 0.000 |
| Tetanus_Int | IL_12p70 | 0.000 | | Tetanus_Int | IL_12p70 | 0.000 |
| Tetanus_Int | IL_13 | 0.000 | | Tetanus_Int | IL_13 | 0.000 |
| Tetanus_Int | IL_15 | 0.000 | | Tetanus_Int | IL_15 | 0.000 |
| Tetanus_Int | IL_17 | 0.000 | | Tetanus_Int | IL_17 | 0.000 |
| Tetanus_Int | IL_23 | 0.000 | | Tetanus_Int | IL_23 | 0.000 |
| Tetanus_Int | IFN_gamma | 0.000 | | Tetanus_Int | IFN_gamma | 0.000 |
| Tetanus_Int | TNF_alpha | 0.000 | | Tetanus_Int | TNF_alpha | 0.000 |
| Tetanus_Int | TNF_beta | 0.000 | | Tetanus_Int | TNF_beta | 0.000 |
| Tetanus_Int | Varicella_Int | 0.000 | | Tetanus_Int | Varicella_Int | 0.000 |
| Tetanus_Int | Measles_OD_DB_Int | 0.000 | | Tetanus_Int | Measles_OD_DB_Int | 0.000 |
| Tetanus_Int | Measles_Int | 0.000 | | Tetanus_Int | Measles_Int | 0.000 |

FIG. 2114-L

| | | | | | | |
|---|---|---|---|---|---|---|
| Tetanus_Int | HepA_Int | 0.000 | | Tetanus_Int | HepA_Int | 0.000 |
| Tetanus_Int | Tetanus_Int | 1.000 | | Tetanus_Int | Tetanus_Int | 1.000 |
| Tetanus_Int | Diptheria_Int | 0.000 | | Tetanus_Int | Diptheria_Int | 0.000 |
| Tetanus_Int | Rubella_Int | 0.000 | | Tetanus_Int | Rubella_Int | 0.000 |
| Tetanus_Int | CMV_Int | 0.000 | | Tetanus_Int | CMV_Int | 0.000 |
| Tetanus_Int | HepB_cAb_Int | 0.000 | | Tetanus_Int | HepB_cAb_Int | 0.000 |
| Tetanus_Int | HepB_eAb_Int | 0.000 | | Tetanus_Int | HepB_eAb_Int | 0.000 |
| Tetanus_Int | HepB_eAg_Int | 0.000 | | Tetanus_Int | HepB_eAg_Int | 0.000 |
| Tetanus_Int | HepC_Int | 0.000 | | Tetanus_Int | HepC_Int | 0.000 |
| Tetanus_Int | Schistosoma_int | 0.000 | | Tetanus_Int | Schistosoma_int | 0.000 |
| Tetanus_Int | Strongyloides_Int | 0.000 | | Tetanus_Int | Strongyloides_Int | 0.000 |
| Tetanus_Int | Filaria_Int | 0.000 | | Tetanus_Int | Filaria_Int | 0.000 |
| Diptheria_Int | IL_1_alpha | 0.000 | | Diptheria_Int | IL_1_alpha | 0.000 |
| Diptheria_Int | IL_1_beta | 0.000 | | Diptheria_Int | IL_1_beta | 0.000 |
| Diptheria_Int | IL_2 | 0.000 | | Diptheria_Int | IL_2 | 0.000 |
| Diptheria_Int | IL_4 | 0.000 | | Diptheria_Int | IL_4 | 0.000 |
| Diptheria_Int | IL_5 | 0.000 | | Diptheria_Int | IL_5 | 0.000 |
| Diptheria_Int | IL_6 | 0.000 | | Diptheria_Int | IL_6 | 0.000 |
| Diptheria_Int | IL_8 | 0.000 | | Diptheria_Int | IL_8 | 0.000 |
| Diptheria_Int | IL_10 | 0.000 | | Diptheria_Int | IL_10 | 0.000 |
| Diptheria_Int | IL_12p70 | 0.000 | | Diptheria_Int | IL_12p70 | 0.000 |
| Diptheria_Int | IL_13 | 0.000 | | Diptheria_Int | IL_13 | 0.000 |
| Diptheria_Int | IL_15 | 0.000 | | Diptheria_Int | IL_15 | 0.000 |
| Diptheria_Int | IL_17 | 0.000 | | Diptheria_Int | IL_17 | 0.000 |
| Diptheria_Int | IL_23 | 0.000 | | Diptheria_Int | IL_23 | 0.000 |
| Diptheria_Int | IFN_gamma | 0.000 | | Diptheria_Int | IFN_gamma | 0.000 |
| Diptheria_Int | TNF_alpha | 0.000 | | Diptheria_Int | TNF_alpha | 0.000 |
| Diptheria_Int | TNF_beta | 0.000 | | Diptheria_Int | TNF_beta | 0.000 |
| Diptheria_Int | Varicella_Int | 0.000 | | Diptheria_Int | Varicella_Int | 0.000 |
| Diptheria_Int | Measles_OD_DB_Int | 0.000 | | Diptheria_Int | Measles_OD_DB_Int | 0.000 |
| Diptheria_Int | Measles_Int | 0.000 | | Diptheria_Int | Measles_Int | 0.000 |
| Diptheria_Int | HepA_Int | 0.000 | | Diptheria_Int | HepA_Int | 0.000 |
| Diptheria_Int | Tetanus_Int | 0.000 | | Diptheria_Int | Tetanus_Int | 0.000 |
| Diptheria_Int | Diptheria_Int | 1.000 | | Diptheria_Int | Diptheria_Int | 1.000 |
| Diptheria_Int | Rubella_Int | 0.000 | | Diptheria_Int | Rubella_Int | 0.000 |
| Diptheria_Int | CMV_Int | 0.000 | | Diptheria_Int | CMV_Int | 0.000 |
| Diptheria_Int | HepB_cAb_Int | 0.000 | | Diptheria_Int | HepB_cAb_Int | 0.000 |
| Diptheria_Int | HepB_eAb_Int | 0.000 | | Diptheria_Int | HepB_eAb_Int | 0.000 |
| Diptheria_Int | HepB_eAg_Int | 0.000 | | Diptheria_Int | HepB_eAg_Int | 0.000 |
| Diptheria_Int | HepC_Int | 0.000 | | Diptheria_Int | HepC_Int | 0.000 |
| Diptheria_Int | Schistosoma_int | 0.000 | | Diptheria_Int | Schistosoma_int | 0.000 |
| Diptheria_Int | Strongyloides_Int | 0.000 | | Diptheria_Int | Strongyloides_Int | 0.000 |
| Diptheria_Int | Filaria_Int | 0.000 | | Diptheria_Int | Filaria_Int | 0.000 |
| Rubella_Int | IL_1_alpha | -0.033 | | Rubella_Int | IL_1_alpha | 0.176 |
| Rubella_Int | IL_1_beta | 0.025 | | Rubella_Int | IL_1_beta | 0.165 |
| Rubella_Int | IL_2 | 0.077 | | Rubella_Int | IL_2 | 0.257 |
| Rubella_Int | IL_4 | 0.007 | | Rubella_Int | IL_4 | 0.015 |
| Rubella_Int | IL_5 | -0.058 | | Rubella_Int | IL_5 | 0.089 |
| Rubella_Int | IL_6 | 0.207 | | Rubella_Int | IL_6 | -0.025 |
| Rubella_Int | IL_8 | 0.101 | | Rubella_Int | IL_8 | 0.123 |
| Rubella_Int | IL_10 | -0.089 | | Rubella_Int | IL_10 | 0.041 |
| Rubella_Int | IL_12p70 | -0.061 | | Rubella_Int | IL_12p70 | 0.371 |
| Rubella_Int | IL_13 | 0.118 | | Rubella_Int | IL_13 | 0.017 |
| Rubella_Int | IL_15 | 0.155 | | Rubella_Int | IL_15 | 0.239 |
| Rubella_Int | IL_17 | -0.043 | | Rubella_Int | IL_17 | 0.264 |
| Rubella_Int | IL_23 | 0.068 | | Rubella_Int | IL_23 | 0.091 |
| Rubella_Int | IFN_gamma | 0.000 | | Rubella_Int | IFN_gamma | 0.000 |

FIG. 2114-M

| Rubella_Int | TNF_alpha | 0.110 | Rubella_Int | TNF_alpha | 0.030 |
|---|---|---|---|---|---|
| Rubella_Int | TNF_beta | -0.010 | Rubella_Int | TNF_beta | 0.191 |
| Rubella_Int | Varicella_Int | -0.024 | Rubella_Int | Varicella_Int | -0.316 |
| Rubella_Int | Measles_OD_DB_Int | -0.234 | Rubella_Int | Measles_OD_DB_Int | -0.089 |
| Rubella_Int | Measles_Int | 0.057 | Rubella_Int | Measles_Int | 0.044 |
| Rubella_Int | HepA_Int | 0.066 | Rubella_Int | HepA_Int | 0.050 |
| Rubella_Int | Tetanus_Int | 0.000 | Rubella_Int | Tetanus_Int | 0.000 |
| Rubella_Int | Diptheria_Int | 0.000 | Rubella_Int | Diptheria_Int | 0.000 |
| Rubella_Int | Rubella_Int | 1.000 | Rubella_Int | Rubella_Int | 1.000 |
| Rubella_Int | CMV_Int | 0.050 | Rubella_Int | CMV_Int | 0.000 |
| Rubella_Int | HepB_cAb_Int | 0.039 | Rubella_Int | HepB_cAb_Int | -0.078 |
| Rubella_Int | HepB_eAb_Int | 0.000 | Rubella_Int | HepB_eAb_Int | 0.000 |
| Rubella_Int | HepB_eAg_Int | -0.354 | Rubella_Int | HepB_eAg_Int | 0.000 |
| Rubella_Int | HepC_Int | -0.085 | Rubella_Int | HepC_Int | -0.050 |
| Rubella_Int | Schistosoma_int | 0.055 | Rubella_Int | Schistosoma_int | -0.099 |
| Rubella_Int | Strongyloides_Int | 0.068 | Rubella_Int | Strongyloides_Int | 0.022 |
| Rubella_Int | Filaria_Int | -0.042 | Rubella_Int | Filaria_Int | -0.114 |
| CMV_Int | IL_1_alpha | 0.065 | CMV_Int | IL_1_alpha | 0.000 |
| CMV_Int | IL_1_beta | 0.021 | CMV_Int | IL_1_beta | 0.000 |
| CMV_Int | IL_2 | 0.055 | CMV_Int | IL_2 | 0.000 |
| CMV_Int | IL_4 | 0.064 | CMV_Int | IL_4 | 0.000 |
| CMV_Int | IL_5 | 0.091 | CMV_Int | IL_5 | 0.000 |
| CMV_Int | IL_6 | -0.036 | CMV_Int | IL_6 | 0.000 |
| CMV_Int | IL_8 | 0.101 | CMV_Int | IL_8 | 0.000 |
| CMV_Int | IL_10 | -0.003 | CMV_Int | IL_10 | 0.000 |
| CMV_Int | IL_12p70 | 0.031 | CMV_Int | IL_12p70 | 0.000 |
| CMV_Int | IL_13 | -0.017 | CMV_Int | IL_13 | 0.000 |
| CMV_Int | IL_15 | 0.189 | CMV_Int | IL_15 | 0.000 |
| CMV_Int | IL_17 | 0.025 | CMV_Int | IL_17 | 0.000 |
| CMV_Int | IL_23 | 0.045 | CMV_Int | IL_23 | 0.000 |
| CMV_Int | IFN_gamma | 0.000 | CMV_Int | IFN_gamma | 0.000 |
| CMV_Int | TNF_alpha | -0.010 | CMV_Int | TNF_alpha | 0.000 |
| CMV_Int | TNF_beta | -0.027 | CMV_Int | TNF_beta | 0.000 |
| CMV_Int | Varicella_Int | 0.041 | CMV_Int | Varicella_Int | 0.000 |
| CMV_Int | Measles_OD_DB_Int | -0.013 | CMV_Int | Measles_OD_DB_Int | 0.000 |
| CMV_Int | Measles_Int | -0.064 | CMV_Int | Measles_Int | 0.000 |
| CMV_Int | HepA_Int | 0.137 | CMV_Int | HepA_Int | 0.000 |
| CMV_Int | Tetanus_Int | 0.000 | CMV_Int | Tetanus_Int | 0.000 |
| CMV_Int | Diptheria_Int | 0.000 | CMV_Int | Diptheria_Int | 0.000 |
| CMV_Int | Rubella_Int | 0.050 | CMV_Int | Rubella_Int | 0.000 |
| CMV_Int | CMV_Int | 1.000 | CMV_Int | CMV_Int | 1.000 |
| CMV_Int | HepB_cAb_Int | -0.071 | CMV_Int | HepB_cAb_Int | 0.000 |
| CMV_Int | HepB_eAb_Int | 0.000 | CMV_Int | HepB_eAb_Int | 0.000 |
| CMV_Int | HepB_eAg_Int | 0.000 | CMV_Int | HepB_eAg_Int | 0.000 |
| CMV_Int | HepC_Int | 0.025 | CMV_Int | HepC_Int | 0.000 |
| CMV_Int | Schistosoma_int | 0.059 | CMV_Int | Schistosoma_int | 0.000 |
| CMV_Int | Strongyloides_Int | 0.019 | CMV_Int | Strongyloides_Int | 0.000 |
| CMV_Int | Filaria_Int | -0.283 | CMV_Int | Filaria_Int | 0.000 |
| HepB_cAb_Int | IL_1_alpha | -0.165 | HepB_cAb_Int | IL_1_alpha | 0.059 |
| HepB_cAb_Int | IL_1_beta | -0.025 | HepB_cAb_Int | IL_1_beta | -0.152 |
| HepB_cAb_Int | IL_2 | 0.019 | HepB_cAb_Int | IL_2 | -0.035 |
| HepB_cAb_Int | IL_4 | 0.012 | HepB_cAb_Int | IL_4 | 0.046 |
| HepB_cAb_Int | IL_5 | 0.068 | HepB_cAb_Int | IL_5 | -0.019 |
| HepB_cAb_Int | IL_6 | 0.115 | HepB_cAb_Int | IL_6 | -0.094 |
| HepB_cAb_Int | IL_8 | -0.134 | HepB_cAb_Int | IL_8 | 0.122 |
| HepB_cAb_Int | IL_10 | -0.093 | HepB_cAb_Int | IL_10 | -0.047 |
| HepB_cAb_Int | IL_12p70 | -0.058 | HepB_cAb_Int | IL_12p70 | 0.062 |

FIG. 2114-N

| HepB_cAb_Int | IL_13 | 0.092 | HepB_cAb_Int | IL_13 | -0.041 |
|---|---|---|---|---|---|
| HepB_cAb_Int | IL_15 | 0.015 | HepB_cAb_Int | IL_15 | 0.085 |
| HepB_cAb_Int | IL_17 | -0.017 | HepB_cAb_Int | IL_17 | 0.022 |
| HepB_cAb_Int | IL_23 | -0.015 | HepB_cAb_Int | IL_23 | 0.077 |
| HepB_cAb_Int | IFN_gamma | 0.000 | HepB_cAb_Int | IFN_gamma | 0.000 |
| HepB_cAb_Int | TNF_alpha | -0.062 | HepB_cAb_Int | TNF_alpha | -0.012 |
| HepB_cAb_Int | TNF_beta | -0.081 | HepB_cAb_Int | TNF_beta | -0.065 |
| HepB_cAb_Int | Varicella_Int | 0.123 | HepB_cAb_Int | Varicella_Int | 0.213 |
| HepB_cAb_Int | Measles_OD_DB_Int | -0.021 | HepB_cAb_Int | Measles_OD_DB_Int | -0.034 |
| HepB_cAb_Int | Measles_Int | -0.050 | HepB_cAb_Int | Measles_Int | 0.144 |
| HepB_cAb_Int | HepA_Int | 0.140 | HepB_cAb_Int | HepA_Int | 0.224 |
| HepB_cAb_Int | Tetanus_Int | 0.000 | HepB_cAb_Int | Tetanus_Int | 0.000 |
| HepB_cAb_Int | Diptheria_Int | 0.000 | HepB_cAb_Int | Diptheria_Int | 0.000 |
| HepB_cAb_Int | Rubella_Int | 0.039 | HepB_cAb_Int | Rubella_Int | -0.078 |
| HepB_cAb_Int | CMV_Int | -0.071 | HepB_cAb_Int | CMV_Int | 0.000 |
| HepB_cAb_Int | HepB_cAb_Int | 1.000 | HepB_cAb_Int | HepB_cAb_Int | 1.000 |
| HepB_cAb_Int | HepB_eAb_Int | 0.000 | HepB_cAb_Int | HepB_eAb_Int | 0.000 |
| HepB_cAb_Int | HepB_eAg_Int | 0.000 | HepB_cAb_Int | HepB_eAg_Int | 0.000 |
| HepB_cAb_Int | HepC_Int | 0.144 | HepB_cAb_Int | HepC_Int | 0.184 |
| HepB_cAb_Int | Schistosoma_int | 0.051 | HepB_cAb_Int | Schistosoma_int | 0.190 |
| HepB_cAb_Int | Strongyloides_Int | 0.061 | HepB_cAb_Int | Strongyloides_Int | 0.156 |
| HepB_cAb_Int | Filaria_Int | -0.012 | HepB_cAb_Int | Filaria_Int | 0.120 |
| HepB_eAb_Int | IL_1_alpha | 0.000 | HepB_eAb_Int | IL_1_alpha | 0.000 |
| HepB_eAb_Int | IL_1_beta | 0.000 | HepB_eAb_Int | IL_1_beta | 0.000 |
| HepB_eAb_Int | IL_2 | 0.000 | HepB_eAb_Int | IL_2 | 0.000 |
| HepB_eAb_Int | IL_4 | 0.000 | HepB_eAb_Int | IL_4 | 0.000 |
| HepB_eAb_Int | IL_5 | 0.000 | HepB_eAb_Int | IL_5 | 0.000 |
| HepB_eAb_Int | IL_6 | 0.000 | HepB_eAb_Int | IL_6 | 0.000 |
| HepB_eAb_Int | IL_8 | 0.000 | HepB_eAb_Int | IL_8 | 0.000 |
| HepB_eAb_Int | IL_10 | 0.000 | HepB_eAb_Int | IL_10 | 0.000 |
| HepB_eAb_Int | IL_12p70 | 0.000 | HepB_eAb_Int | IL_12p70 | 0.000 |
| HepB_eAb_Int | IL_13 | 0.000 | HepB_eAb_Int | IL_13 | 0.000 |
| HepB_eAb_Int | IL_15 | 0.000 | HepB_eAb_Int | IL_15 | 0.000 |
| HepB_eAb_Int | IL_17 | 0.000 | HepB_eAb_Int | IL_17 | 0.000 |
| HepB_eAb_Int | IL_23 | 0.000 | HepB_eAb_Int | IL_23 | 0.000 |
| HepB_eAb_Int | IFN_gamma | 0.000 | HepB_eAb_Int | IFN_gamma | 0.000 |
| HepB_eAb_Int | TNF_alpha | 0.000 | HepB_eAb_Int | TNF_alpha | 0.000 |
| HepB_eAb_Int | TNF_beta | 0.000 | HepB_eAb_Int | TNF_beta | 0.000 |
| HepB_eAb_Int | Varicella_Int | 0.000 | HepB_eAb_Int | Varicella_Int | 0.000 |
| HepB_eAb_Int | Measles_OD_DB_Int | 0.000 | HepB_eAb_Int | Measles_OD_DB_Int | 0.000 |
| HepB_eAb_Int | Measles_Int | 0.000 | HepB_eAb_Int | Measles_Int | 0.000 |
| HepB_eAb_Int | HepA_Int | 0.000 | HepB_eAb_Int | HepA_Int | 0.000 |
| HepB_eAb_Int | Tetanus_Int | 0.000 | HepB_eAb_Int | Tetanus_Int | 0.000 |
| HepB_eAb_Int | Diptheria_Int | 0.000 | HepB_eAb_Int | Diptheria_Int | 0.000 |
| HepB_eAb_Int | Rubella_Int | 0.000 | HepB_eAb_Int | Rubella_Int | 0.000 |
| HepB_eAb_Int | CMV_Int | 0.000 | HepB_eAb_Int | CMV_Int | 0.000 |
| HepB_eAb_Int | HepB_cAb_Int | 0.000 | HepB_eAb_Int | HepB_cAb_Int | 0.000 |
| HepB_eAb_Int | HepB_eAb_Int | 1.000 | HepB_eAb_Int | HepB_eAb_Int | 1.000 |
| HepB_eAb_Int | HepB_eAg_Int | 0.000 | HepB_eAb_Int | HepB_eAg_Int | 0.000 |
| HepB_eAb_Int | HepC_Int | 0.000 | HepB_eAb_Int | HepC_Int | 0.000 |
| HepB_eAb_Int | Schistosoma_int | 0.000 | HepB_eAb_Int | Schistosoma_int | 0.000 |
| HepB_eAb_Int | Strongyloides_Int | 0.000 | HepB_eAb_Int | Strongyloides_Int | 0.000 |
| HepB_eAb_Int | Filaria_Int | 0.000 | HepB_eAb_Int | Filaria_Int | 0.000 |
| HepB_eAg_Int | IL_1_alpha | -0.208 | HepB_eAg_Int | IL_1_alpha | -0.252 |
| HepB_eAg_Int | IL_1_beta | -0.090 | HepB_eAg_Int | IL_1_beta | 0.159 |
| HepB_eAg_Int | IL_2 | -0.258 | HepB_eAg_Int | IL_2 | -0.250 |
| HepB_eAg_Int | IL_4 | -0.272 | HepB_eAg_Int | IL_4 | -0.339 |

FIG. 2114-O

| | | | | | | |
|---|---|---|---|---|---|---|
| HepB_eAg_Int | IL_5 | -0.316 | | HepB_eAg_Int | IL_5 | -0.292 |
| HepB_eAg_Int | IL_6 | -0.350 | | HepB_eAg_Int | IL_6 | -0.292 |
| HepB_eAg_Int | IL_8 | -0.183 | | HepB_eAg_Int | IL_8 | -0.227 |
| HepB_eAg_Int | IL_10 | -0.366 | | HepB_eAg_Int | IL_10 | -0.200 |
| HepB_eAg_Int | IL_12p70 | -0.504 | | HepB_eAg_Int | IL_12p70 | -0.320 |
| HepB_eAg_Int | IL_13 | -0.357 | | HepB_eAg_Int | IL_13 | -0.235 |
| HepB_eAg_Int | IL_15 | -0.262 | | HepB_eAg_Int | IL_15 | -0.347 |
| HepB_eAg_Int | IL_17 | -0.394 | | HepB_eAg_Int | IL_17 | -0.313 |
| HepB_eAg_Int | IL_23 | -0.320 | | HepB_eAg_Int | IL_23 | -0.343 |
| HepB_eAg_Int | IFN_gamma | 0.000 | | HepB_eAg_Int | IFN_gamma | 0.000 |
| HepB_eAg_Int | TNF_alpha | -0.090 | | HepB_eAg_Int | TNF_alpha | -0.250 |
| HepB_eAg_Int | TNF_beta | 0.948 | | HepB_eAg_Int | TNF_beta | -0.250 |
| HepB_eAg_Int | Varicella_Int | 0.167 | | HepB_eAg_Int | Varicella_Int | 0.000 |
| HepB_eAg_Int | Measles_OD_DB_Int | 0.420 | | HepB_eAg_Int | Measles_OD_DB_Int | -0.408 |
| HepB_eAg_Int | Measles_Int | 0.000 | | HepB_eAg_Int | Measles_Int | 0.000 |
| HepB_eAg_Int | HepA_Int | 0.258 | | HepB_eAg_Int | HepA_Int | 0.000 |
| HepB_eAg_Int | Tetanus_Int | 0.000 | | HepB_eAg_Int | Tetanus_Int | 0.000 |
| HepB_eAg_Int | Diptheria_Int | 0.000 | | HepB_eAg_Int | Diptheria_Int | 0.000 |
| HepB_eAg_Int | Rubella_Int | -0.354 | | HepB_eAg_Int | Rubella_Int | 0.000 |
| HepB_eAg_Int | CMV_Int | 0.000 | | HepB_eAg_Int | CMV_Int | 0.000 |
| HepB_eAg_Int | HepB_cAb_Int | 0.000 | | HepB_eAg_Int | HepB_cAb_Int | 0.000 |
| HepB_eAg_Int | HepB_eAb_Int | 0.000 | | HepB_eAg_Int | HepB_eAb_Int | 0.000 |
| HepB_eAg_Int | HepB_eAg_Int | 1.000 | | HepB_eAg_Int | HepB_eAg_Int | 1.000 |
| HepB_eAg_Int | HepC_Int | 0.000 | | HepB_eAg_Int | HepC_Int | 0.000 |
| HepB_eAg_Int | Schistosoma_int | -0.200 | | HepB_eAg_Int | Schistosoma_int | 0.000 |
| HepB_eAg_Int | Strongyloides_Int | -0.415 | | HepB_eAg_Int | Strongyloides_Int | 0.000 |
| HepB_eAg_Int | Filaria_Int | 0.000 | | HepB_eAg_Int | Filaria_Int | 0.000 |
| HepC_Int | IL_1_alpha | -0.078 | | HepC_Int | IL_1_alpha | 0.073 |
| HepC_Int | IL_1_beta | -0.084 | | HepC_Int | IL_1_beta | 0.072 |
| HepC_Int | IL_2 | -0.049 | | HepC_Int | IL_2 | 0.197 |
| HepC_Int | IL_4 | -0.064 | | HepC_Int | IL_4 | 0.088 |
| HepC_Int | IL_5 | -0.078 | | HepC_Int | IL_5 | -0.029 |
| HepC_Int | IL_6 | -0.044 | | HepC_Int | IL_6 | -0.060 |
| HepC_Int | IL_8 | -0.063 | | HepC_Int | IL_8 | 0.298 |
| HepC_Int | IL_10 | -0.095 | | HepC_Int | IL_10 | 0.086 |
| HepC_Int | IL_12p70 | -0.101 | | HepC_Int | IL_12p70 | 0.106 |
| HepC_Int | IL_13 | -0.106 | | HepC_Int | IL_13 | -0.037 |
| HepC_Int | IL_15 | -0.108 | | HepC_Int | IL_15 | -0.049 |
| HepC_Int | IL_17 | -0.083 | | HepC_Int | IL_17 | -0.025 |
| HepC_Int | IL_23 | -0.034 | | HepC_Int | IL_23 | -0.054 |
| HepC_Int | IFN_gamma | 0.000 | | HepC_Int | IFN_gamma | 0.000 |
| HepC_Int | TNF_alpha | -0.078 | | HepC_Int | TNF_alpha | -0.032 |
| HepC_Int | TNF_beta | -0.057 | | HepC_Int | TNF_beta | 0.078 |
| HepC_Int | Varicella_Int | 0.034 | | HepC_Int | Varicella_Int | 0.055 |
| HepC_Int | Measles_OD_DB_Int | 0.078 | | HepC_Int | Measles_OD_DB_Int | 0.040 |
| HepC_Int | Measles_Int | 0.040 | | HepC_Int | Measles_Int | 0.067 |
| HepC_Int | HepA_Int | 0.079 | | HepC_Int | HepA_Int | 0.078 |
| HepC_Int | Tetanus_Int | 0.000 | | HepC_Int | Tetanus_Int | 0.000 |
| HepC_Int | Diptheria_Int | 0.000 | | HepC_Int | Diptheria_Int | 0.000 |
| HepC_Int | Rubella_Int | -0.085 | | HepC_Int | Rubella_Int | -0.050 |
| HepC_Int | CMV_Int | 0.025 | | HepC_Int | CMV_Int | 0.000 |
| HepC_Int | HepB_cAb_Int | 0.144 | | HepC_Int | HepB_cAb_Int | 0.184 |
| HepC_Int | HepB_eAb_Int | 0.000 | | HepC_Int | HepB_eAb_Int | 0.000 |
| HepC_Int | HepB_eAg_Int | 0.000 | | HepC_Int | HepB_eAg_Int | 0.000 |
| HepC_Int | HepC_Int | 1.000 | | HepC_Int | HepC_Int | 1.000 |
| HepC_Int | Schistosoma_int | -0.037 | | HepC_Int | Schistosoma_int | -0.062 |
| HepC_Int | Strongyloides_Int | -0.026 | | HepC_Int | Strongyloides_Int | 0.081 |

| | | | | | | |
|---|---|---|---|---|---|---|
| HepC_Int | Filaria_Int | -0.043 | | HepC_Int | Filaria_Int | 0.043 |
| Schistosoma_int | IL_1_alpha | 0.010 | | Schistosoma_int | IL_1_alpha | 0.079 |
| Schistosoma_int | IL_1_beta | 0.183 | | Schistosoma_int | IL_1_beta | -0.122 |
| Schistosoma_int | IL_2 | -0.026 | | Schistosoma_int | IL_2 | -0.141 |
| Schistosoma_int | IL_4 | 0.044 | | Schistosoma_int | IL_4 | 0.001 |
| Schistosoma_int | IL_5 | 0.037 | | Schistosoma_int | IL_5 | -0.008 |
| Schistosoma_int | IL_6 | -0.024 | | Schistosoma_int | IL_6 | -0.108 |
| Schistosoma_int | IL_8 | -0.004 | | Schistosoma_int | IL_8 | 0.019 |
| Schistosoma_int | IL_10 | -0.031 | | Schistosoma_int | IL_10 | -0.080 |
| Schistosoma_int | IL_12p70 | -0.021 | | Schistosoma_int | IL_12p70 | -0.030 |
| Schistosoma_int | IL_13 | -0.061 | | Schistosoma_int | IL_13 | -0.072 |
| Schistosoma_int | IL_15 | -0.041 | | Schistosoma_int | IL_15 | 0.021 |
| Schistosoma_int | IL_17 | -0.012 | | Schistosoma_int | IL_17 | -0.012 |
| Schistosoma_int | IL_23 | -0.025 | | Schistosoma_int | IL_23 | -0.054 |
| Schistosoma_int | IFN_gamma | 0.000 | | Schistosoma_int | IFN_gamma | 0.000 |
| Schistosoma_int | TNF_alpha | 0.133 | | Schistosoma_int | TNF_alpha | -0.001 |
| Schistosoma_int | TNF_beta | 0.032 | | Schistosoma_int | TNF_beta | -0.057 |
| Schistosoma_int | Varicella_Int | 0.012 | | Schistosoma_int | Varicella_Int | 0.109 |
| Schistosoma_int | Measles_OD_DB_Int | 0.018 | | Schistosoma_int | Measles_OD_DB_Int | 0.027 |
| Schistosoma_int | Measles_Int | 0.087 | | Schistosoma_int | Measles_Int | 0.064 |
| Schistosoma_int | HepA_Int | 0.057 | | Schistosoma_int | HepA_Int | 0.062 |
| Schistosoma_int | Tetanus_Int | 0.000 | | Schistosoma_int | Tetanus_Int | 0.000 |
| Schistosoma_int | Diptheria_Int | 0.000 | | Schistosoma_int | Diptheria_Int | 0.000 |
| Schistosoma_int | Rubella_Int | 0.055 | | Schistosoma_int | Rubella_Int | -0.099 |
| Schistosoma_int | CMV_Int | 0.059 | | Schistosoma_int | CMV_Int | 0.000 |
| Schistosoma_int | HepB_cAb_Int | 0.051 | | Schistosoma_int | HepB_cAb_Int | 0.190 |
| Schistosoma_int | HepB_eAb_Int | 0.000 | | Schistosoma_int | HepB_eAb_Int | 0.000 |
| Schistosoma_int | HepB_eAg_Int | -0.200 | | Schistosoma_int | HepB_eAg_Int | 0.000 |
| Schistosoma_int | HepC_Int | -0.037 | | Schistosoma_int | HepC_Int | -0.062 |
| Schistosoma_int | Schistosoma_int | 1.000 | | Schistosoma_int | Schistosoma_int | 1.000 |
| Schistosoma_int | Strongyloides_Int | 0.299 | | Schistosoma_int | Strongyloides_Int | 0.240 |
| Schistosoma_int | Filaria_Int | -0.037 | | Schistosoma_int | Filaria_Int | -0.034 |
| Strongyloides_Int | IL_1_alpha | 0.083 | | Strongyloides_Int | IL_1_alpha | 0.006 |
| Strongyloides_Int | IL_1_beta | 0.129 | | Strongyloides_Int | IL_1_beta | 0.027 |
| Strongyloides_Int | IL_2 | 0.066 | | Strongyloides_Int | IL_2 | 0.224 |
| Strongyloides_Int | IL_4 | 0.152 | | Strongyloides_Int | IL_4 | -0.045 |
| Strongyloides_Int | IL_5 | -0.016 | | Strongyloides_Int | IL_5 | -0.033 |
| Strongyloides_Int | IL_6 | -0.159 | | Strongyloides_Int | IL_6 | -0.087 |
| Strongyloides_Int | IL_8 | 0.031 | | Strongyloides_Int | IL_8 | 0.162 |
| Strongyloides_Int | IL_10 | -0.042 | | Strongyloides_Int | IL_10 | -0.079 |
| Strongyloides_Int | IL_12p70 | 0.020 | | Strongyloides_Int | IL_12p70 | 0.066 |
| Strongyloides_Int | IL_13 | -0.050 | | Strongyloides_Int | IL_13 | -0.149 |
| Strongyloides_Int | IL_15 | 0.003 | | Strongyloides_Int | IL_15 | -0.041 |
| Strongyloides_Int | IL_17 | 0.053 | | Strongyloides_Int | IL_17 | -0.019 |
| Strongyloides_Int | IL_23 | 0.224 | | Strongyloides_Int | IL_23 | 0.036 |
| Strongyloides_Int | IFN_gamma | 0.000 | | Strongyloides_Int | IFN_gamma | 0.000 |
| Strongyloides_Int | TNF_alpha | 0.180 | | Strongyloides_Int | TNF_alpha | 0.071 |
| Strongyloides_Int | TNF_beta | 0.056 | | Strongyloides_Int | TNF_beta | 0.167 |
| Strongyloides_Int | Varicella_Int | -0.139 | | Strongyloides_Int | Varicella_Int | 0.015 |
| Strongyloides_Int | Measles_OD_DB_Int | -0.012 | | Strongyloides_Int | Measles_OD_DB_Int | 0.101 |
| Strongyloides_Int | Measles_Int | 0.112 | | Strongyloides_Int | Measles_Int | -0.029 |
| Strongyloides_Int | HepA_Int | 0.007 | | Strongyloides_Int | HepA_Int | -0.081 |
| Strongyloides_Int | Tetanus_Int | 0.000 | | Strongyloides_Int | Tetanus_Int | 0.000 |
| Strongyloides_Int | Diptheria_Int | 0.000 | | Strongyloides_Int | Diptheria_Int | 0.000 |
| Strongyloides_Int | Rubella_Int | 0.068 | | Strongyloides_Int | Rubella_Int | 0.022 |
| Strongyloides_Int | CMV_Int | 0.019 | | Strongyloides_Int | CMV_Int | 0.000 |
| Strongyloides_Int | HepB_cAb_Int | 0.061 | | Strongyloides_Int | HepB_cAb_Int | 0.156 |

| Strongyloides_Int | HepB_eAb_Int | 0.000 | Strongyloides_Int | HepB_eAb_Int | 0.000 |
|---|---|---|---|---|---|
| Strongyloides_Int | HepB_eAg_Int | -0.415 | Strongyloides_Int | HepB_eAg_Int | 0.000 |
| Strongyloides_Int | HepC_Int | -0.026 | Strongyloides_Int | HepC_Int | 0.081 |
| Strongyloides_Int | Schistosoma_int | 0.299 | Strongyloides_Int | Schistosoma_int | 0.240 |
| Strongyloides_Int | Strongyloides_Int | 1.000 | Strongyloides_Int | Strongyloides_Int | 1.000 |
| Strongyloides_Int | Filaria_Int | 0.223 | Strongyloides_Int | Filaria_Int | 0.169 |
| Filaria_Int | IL_1_alpha | 0.116 | Filaria_Int | IL_1_alpha | -0.038 |
| Filaria_Int | IL_1_beta | 0.072 | Filaria_Int | IL_1_beta | 0.067 |
| Filaria_Int | IL_2 | 0.070 | Filaria_Int | IL_2 | 0.074 |
| Filaria_Int | IL_4 | 0.020 | Filaria_Int | IL_4 | 0.071 |
| Filaria_Int | IL_5 | -0.038 | Filaria_Int | IL_5 | 0.287 |
| Filaria_Int | IL_6 | -0.095 | Filaria_Int | IL_6 | -0.040 |
| Filaria_Int | IL_8 | -0.099 | Filaria_Int | IL_8 | 0.010 |
| Filaria_Int | IL_10 | 0.104 | Filaria_Int | IL_10 | 0.288 |
| Filaria_Int | IL_12p70 | 0.103 | Filaria_Int | IL_12p70 | 0.099 |
| Filaria_Int | IL_13 | 0.125 | Filaria_Int | IL_13 | 0.185 |
| Filaria_Int | IL_15 | -0.069 | Filaria_Int | IL_15 | -0.079 |
| Filaria_Int | IL_17 | 0.107 | Filaria_Int | IL_17 | 0.167 |
| Filaria_Int | IL_23 | 0.005 | Filaria_Int | IL_23 | 0.141 |
| Filaria_Int | IFN_gamma | 0.000 | Filaria_Int | IFN_gamma | 0.000 |
| Filaria_Int | TNF_alpha | 0.133 | Filaria_Int | TNF_alpha | -0.030 |
| Filaria_Int | TNF_beta | 0.060 | Filaria_Int | TNF_beta | -0.001 |
| Filaria_Int | Varicella_Int | -0.026 | Filaria_Int | Varicella_Int | -0.057 |
| Filaria_Int | Measles_OD_DB_Int | 0.143 | Filaria_Int | Measles_OD_DB_Int | 0.008 |
| Filaria_Int | Measles_Int | 0.098 | Filaria_Int | Measles_Int | 0.070 |
| Filaria_Int | HepA_Int | -0.044 | Filaria_Int | HepA_Int | 0.164 |
| Filaria_Int | Tetanus_Int | 0.000 | Filaria_Int | Tetanus_Int | 0.000 |
| Filaria_Int | Diptheria_Int | 0.000 | Filaria_Int | Diptheria_Int | 0.000 |
| Filaria_Int | Rubella_Int | -0.042 | Filaria_Int | Rubella_Int | -0.114 |
| Filaria_Int | CMV_Int | -0.283 | Filaria_Int | CMV_Int | 0.000 |
| Filaria_Int | HepB_cAb_Int | -0.012 | Filaria_Int | HepB_cAb_Int | 0.120 |
| Filaria_Int | HepB_eAb_Int | 0.000 | Filaria_Int | HepB_eAb_Int | 0.000 |
| Filaria_Int | HepB_eAg_Int | 0.000 | Filaria_Int | HepB_eAg_Int | 0.000 |
| Filaria_Int | HepC_Int | -0.043 | Filaria_Int | HepC_Int | 0.043 |
| Filaria_Int | Schistosoma_int | -0.037 | Filaria_Int | Schistosoma_int | -0.034 |
| Filaria_Int | Strongyloides_Int | 0.223 | Filaria_Int | Strongyloides_Int | 0.169 |
| Filaria_Int | Filaria_Int | 1.000 | Filaria_Int | Filaria_Int | 1.000 |

FIG. 2114-R 0.07% - Region_of_Origin=4, Sex=Female, IFN_gamma=127.5-142.5

0.07% - Region_of_Origin=1, Sex=Male, IFN_gamma=142.5-157.5

FIG. 21I15-A

| Property 1 | Property 2 | Corr. Coefficient | Property 1 | Property 2 | Corr. Coefficient |
|---|---|---|---|---|---|
| IL_1_alpha | IL_1_alpha | 1.000 | IL_1_alpha | IL_1_alpha | 1.000 |
| IL_1_alpha | IL_1_beta | 0.000 | IL_1_alpha | IL_1_beta | 0.000 |
| IL_1_alpha | IL_2 | 0.000 | IL_1_alpha | IL_2 | 0.000 |
| IL_1_alpha | IL_4 | 0.000 | IL_1_alpha | IL_4 | 0.000 |
| IL_1_alpha | IL_5 | 0.000 | IL_1_alpha | IL_5 | 0.000 |
| IL_1_alpha | IL_6 | 0.000 | IL_1_alpha | IL_6 | 0.000 |
| IL_1_alpha | IL_8 | 0.000 | IL_1_alpha | IL_8 | 0.000 |
| IL_1_alpha | IL_10 | 0.000 | IL_1_alpha | IL_10 | 0.000 |
| IL_1_alpha | IL_12p70 | 0.000 | IL_1_alpha | IL_12p70 | 0.000 |
| IL_1_alpha | IL_13 | 0.000 | IL_1_alpha | IL_13 | 0.000 |
| IL_1_alpha | IL_15 | 0.000 | IL_1_alpha | IL_15 | 0.000 |
| IL_1_alpha | IL_17 | 0.000 | IL_1_alpha | IL_17 | 0.000 |
| IL_1_alpha | IL_23 | 0.000 | IL_1_alpha | IL_23 | 0.000 |
| IL_1_alpha | IFN_gamma | 0.000 | IL_1_alpha | IFN_gamma | 0.000 |
| IL_1_alpha | TNF_alpha | 0.000 | IL_1_alpha | TNF_alpha | 0.000 |
| IL_1_alpha | TNF_beta | 0.000 | IL_1_alpha | TNF_beta | 0.000 |
| IL_1_alpha | Varicella_Int | 0.000 | IL_1_alpha | Varicella_Int | 0.000 |
| IL_1_alpha | Measles_OD_DB_Int | 0.000 | IL_1_alpha | Measles_OD_DB_Int | 0.000 |
| IL_1_alpha | Measles_Int | 0.000 | IL_1_alpha | Measles_Int | 0.000 |
| IL_1_alpha | HepA_Int | 0.000 | IL_1_alpha | HepA_Int | 0.000 |
| IL_1_alpha | Tetanus_Int | 0.000 | IL_1_alpha | Tetanus_Int | 0.000 |
| IL_1_alpha | Diptheria_Int | 0.000 | IL_1_alpha | Diptheria_Int | 0.000 |
| IL_1_alpha | Rubella_Int | 0.000 | IL_1_alpha | Rubella_Int | 0.000 |
| IL_1_alpha | CMV_Int | 0.000 | IL_1_alpha | CMV_Int | 0.000 |
| IL_1_alpha | HepB_cAb_Int | 0.000 | IL_1_alpha | HepB_cAb_Int | 0.000 |
| IL_1_alpha | HepB_eAb_Int | 0.000 | IL_1_alpha | HepB_eAb_Int | 0.000 |
| IL_1_alpha | HepB_eAg_Int | 0.000 | IL_1_alpha | HepB_eAg_Int | 0.000 |
| IL_1_alpha | HepC_Int | 0.000 | IL_1_alpha | HepC_Int | 0.000 |
| IL_1_alpha | Schistosoma_int | 0.000 | IL_1_alpha | Schistosoma_int | 0.000 |
| IL_1_alpha | Strongyloides_Int | 0.000 | IL_1_alpha | Strongyloides_Int | 0.000 |
| IL_1_alpha | Filaria_Int | 0.000 | IL_1_alpha | Filaria_Int | 0.000 |
| IL_1_beta | IL_1_alpha | 0.000 | IL_1_beta | IL_1_alpha | 0.000 |
| IL_1_beta | IL_1_beta | 1.000 | IL_1_beta | IL_1_beta | 1.000 |
| IL_1_beta | IL_2 | 0.000 | IL_1_beta | IL_2 | 0.000 |
| IL_1_beta | IL_4 | 0.000 | IL_1_beta | IL_4 | 0.000 |
| IL_1_beta | IL_5 | 0.000 | IL_1_beta | IL_5 | 0.000 |
| IL_1_beta | IL_6 | 0.000 | IL_1_beta | IL_6 | 0.000 |
| IL_1_beta | IL_8 | 0.000 | IL_1_beta | IL_8 | 0.000 |
| IL_1_beta | IL_10 | 0.000 | IL_1_beta | IL_10 | 0.000 |
| IL_1_beta | IL_12p70 | 0.000 | IL_1_beta | IL_12p70 | 0.000 |
| IL_1_beta | IL_13 | 0.000 | IL_1_beta | IL_13 | 0.000 |
| IL_1_beta | IL_15 | 0.000 | IL_1_beta | IL_15 | 0.000 |
| IL_1_beta | IL_17 | 0.000 | IL_1_beta | IL_17 | 0.000 |
| IL_1_beta | IL_23 | 0.000 | IL_1_beta | IL_23 | 0.000 |
| IL_1_beta | IFN_gamma | 0.000 | IL_1_beta | IFN_gamma | 0.000 |
| IL_1_beta | TNF_alpha | 0.000 | IL_1_beta | TNF_alpha | 0.000 |
| IL_1_beta | TNF_beta | 0.000 | IL_1_beta | TNF_beta | 0.000 |
| IL_1_beta | Varicella_Int | 0.000 | IL_1_beta | Varicella_Int | 0.000 |
| IL_1_beta | Measles_OD_DB_Int | 0.000 | IL_1_beta | Measles_OD_DB_Int | 0.000 |
| IL_1_beta | Measles_Int | 0.000 | IL_1_beta | Measles_Int | 0.000 |
| IL_1_beta | HepA_Int | 0.000 | IL_1_beta | HepA_Int | 0.000 |
| IL_1_beta | Tetanus_Int | 0.000 | IL_1_beta | Tetanus_Int | 0.000 |
| IL_1_beta | Diptheria_Int | 0.000 | IL_1_beta | Diptheria_Int | 0.000 |
| IL_1_beta | Rubella_Int | 0.000 | IL_1_beta | Rubella_Int | 0.000 |
| IL_1_beta | CMV_Int | 0.000 | IL_1_beta | CMV_Int | 0.000 |
| IL_1_beta | HepB_cAb_Int | 0.000 | IL_1_beta | HepB_cAb_Int | 0.000 |

FIG. 21I15-B

| | | | | | | |
|---|---|---|---|---|---|---|
| IL_1_beta | HepB_eAb_Int | 0.000 | | IL_1_beta | HepB_eAb_Int | 0.000 |
| IL_1_beta | HepB_eAg_Int | 0.000 | | IL_1_beta | HepB_eAg_Int | 0.000 |
| IL_1_beta | HepC_Int | 0.000 | | IL_1_beta | HepC_Int | 0.000 |
| IL_1_beta | Schistosoma_int | 0.000 | | IL_1_beta | Schistosoma_int | 0.000 |
| IL_1_beta | Strongyloides_Int | 0.000 | | IL_1_beta | Strongyloides_Int | 0.000 |
| IL_1_beta | Filaria_Int | 0.000 | | IL_1_beta | Filaria_Int | 0.000 |
| IL_2 | IL_1_alpha | 0.000 | | IL_2 | IL_1_alpha | 0.000 |
| IL_2 | IL_1_beta | 0.000 | | IL_2 | IL_1_beta | 0.000 |
| IL_2 | IL_2 | 1.000 | | IL_2 | IL_2 | 1.000 |
| IL_2 | IL_4 | 0.000 | | IL_2 | IL_4 | 0.000 |
| IL_2 | IL_5 | 0.000 | | IL_2 | IL_5 | 0.000 |
| IL_2 | IL_6 | 0.000 | | IL_2 | IL_6 | 0.000 |
| IL_2 | IL_8 | 0.000 | | IL_2 | IL_8 | 0.000 |
| IL_2 | IL_10 | 0.000 | | IL_2 | IL_10 | 0.000 |
| IL_2 | IL_12p70 | 0.000 | | IL_2 | IL_12p70 | 0.000 |
| IL_2 | IL_13 | 0.000 | | IL_2 | IL_13 | 0.000 |
| IL_2 | IL_15 | 0.000 | | IL_2 | IL_15 | 0.000 |
| IL_2 | IL_17 | 0.000 | | IL_2 | IL_17 | 0.000 |
| IL_2 | IL_23 | 0.000 | | IL_2 | IL_23 | 0.000 |
| IL_2 | IFN_gamma | 0.000 | | IL_2 | IFN_gamma | 0.000 |
| IL_2 | TNF_alpha | 0.000 | | IL_2 | TNF_alpha | 0.000 |
| IL_2 | TNF_beta | 0.000 | | IL_2 | TNF_beta | 0.000 |
| IL_2 | Varicella_Int | 0.000 | | IL_2 | Varicella_Int | 0.000 |
| IL_2 | Measles_OD_DB_Int | 0.000 | | IL_2 | Measles_OD_DB_Int | 0.000 |
| IL_2 | Measles_Int | 0.000 | | IL_2 | Measles_Int | 0.000 |
| IL_2 | HepA_Int | 0.000 | | IL_2 | HepA_Int | 0.000 |
| IL_2 | Tetanus_Int | 0.000 | | IL_2 | Tetanus_Int | 0.000 |
| IL_2 | Diptheria_Int | 0.000 | | IL_2 | Diptheria_Int | 0.000 |
| IL_2 | Rubella_Int | 0.000 | | IL_2 | Rubella_Int | 0.000 |
| IL_2 | CMV_Int | 0.000 | | IL_2 | CMV_Int | 0.000 |
| IL_2 | HepB_cAb_Int | 0.000 | | IL_2 | HepB_cAb_Int | 0.000 |
| IL_2 | HepB_eAb_Int | 0.000 | | IL_2 | HepB_eAb_Int | 0.000 |
| IL_2 | HepB_eAg_Int | 0.000 | | IL_2 | HepB_eAg_Int | 0.000 |
| IL_2 | HepC_Int | 0.000 | | IL_2 | HepC_Int | 0.000 |
| IL_2 | Schistosoma_int | 0.000 | | IL_2 | Schistosoma_int | 0.000 |
| IL_2 | Strongyloides_Int | 0.000 | | IL_2 | Strongyloides_Int | 0.000 |
| IL_2 | Filaria_Int | 0.000 | | IL_2 | Filaria_Int | 0.000 |
| IL_4 | IL_1_alpha | 0.000 | | IL_4 | IL_1_alpha | 0.000 |
| IL_4 | IL_1_beta | 0.000 | | IL_4 | IL_1_beta | 0.000 |
| IL_4 | IL_2 | 0.000 | | IL_4 | IL_2 | 0.000 |
| IL_4 | IL_4 | 1.000 | | IL_4 | IL_4 | 1.000 |
| IL_4 | IL_5 | 0.000 | | IL_4 | IL_5 | 0.000 |
| IL_4 | IL_6 | 0.000 | | IL_4 | IL_6 | 0.000 |
| IL_4 | IL_8 | 0.000 | | IL_4 | IL_8 | 0.000 |
| IL_4 | IL_10 | 0.000 | | IL_4 | IL_10 | 0.000 |
| IL_4 | IL_12p70 | 0.000 | | IL_4 | IL_12p70 | 0.000 |
| IL_4 | IL_13 | 0.000 | | IL_4 | IL_13 | 0.000 |
| IL_4 | IL_15 | 0.000 | | IL_4 | IL_15 | 0.000 |
| IL_4 | IL_17 | 0.000 | | IL_4 | IL_17 | 0.000 |
| IL_4 | IL_23 | 0.000 | | IL_4 | IL_23 | 0.000 |
| IL_4 | IFN_gamma | 0.000 | | IL_4 | IFN_gamma | 0.000 |
| IL_4 | TNF_alpha | 0.000 | | IL_4 | TNF_alpha | 0.000 |
| IL_4 | TNF_beta | 0.000 | | IL_4 | TNF_beta | 0.000 |
| IL_4 | Varicella_Int | 0.000 | | IL_4 | Varicella_Int | 0.000 |
| IL_4 | Measles_OD_DB_Int | 0.000 | | IL_4 | Measles_OD_DB_Int | 0.000 |
| IL_4 | Measles_Int | 0.000 | | IL_4 | Measles_Int | 0.000 |
| IL_4 | HepA_Int | 0.000 | | IL_4 | HepA_Int | 0.000 |

FIG. 21I15-C

| | | | | | | |
|---|---|---|---|---|---|---|
| IL_4 | Tetanus_Int | 0.000 | | IL_4 | Tetanus_Int | 0.000 |
| IL_4 | Diptheria_Int | 0.000 | | IL_4 | Diptheria_Int | 0.000 |
| IL_4 | Rubella_Int | 0.000 | | IL_4 | Rubella_Int | 0.000 |
| IL_4 | CMV_Int | 0.000 | | IL_4 | CMV_Int | 0.000 |
| IL_4 | HepB_cAb_Int | 0.000 | | IL_4 | HepB_cAb_Int | 0.000 |
| IL_4 | HepB_eAb_Int | 0.000 | | IL_4 | HepB_eAb_Int | 0.000 |
| IL_4 | HepB_eAg_Int | 0.000 | | IL_4 | HepB_eAg_Int | 0.000 |
| IL_4 | HepC_Int | 0.000 | | IL_4 | HepC_Int | 0.000 |
| IL_4 | Schistosoma_int | 0.000 | | IL_4 | Schistosoma_int | 0.000 |
| IL_4 | Strongyloides_Int | 0.000 | | IL_4 | Strongyloides_Int | 0.000 |
| IL_4 | Filaria_Int | 0.000 | | IL_4 | Filaria_Int | 0.000 |
| IL_5 | IL_1_alpha | 0.000 | | IL_5 | IL_1_alpha | 0.000 |
| IL_5 | IL_1_beta | 0.000 | | IL_5 | IL_1_beta | 0.000 |
| IL_5 | IL_2 | 0.000 | | IL_5 | IL_2 | 0.000 |
| IL_5 | IL_4 | 0.000 | | IL_5 | IL_4 | 0.000 |
| IL_5 | IL_5 | 1.000 | | IL_5 | IL_5 | 1.000 |
| IL_5 | IL_6 | 0.000 | | IL_5 | IL_6 | 0.000 |
| IL_5 | IL_8 | 0.000 | | IL_5 | IL_8 | 0.000 |
| IL_5 | IL_10 | 0.000 | | IL_5 | IL_10 | 0.000 |
| IL_5 | IL_12p70 | 0.000 | | IL_5 | IL_12p70 | 0.000 |
| IL_5 | IL_13 | 0.000 | | IL_5 | IL_13 | 0.000 |
| IL_5 | IL_15 | 0.000 | | IL_5 | IL_15 | 0.000 |
| IL_5 | IL_17 | 0.000 | | IL_5 | IL_17 | 0.000 |
| IL_5 | IL_23 | 0.000 | | IL_5 | IL_23 | 0.000 |
| IL_5 | IFN_gamma | 0.000 | | IL_5 | IFN_gamma | 0.000 |
| IL_5 | TNF_alpha | 0.000 | | IL_5 | TNF_alpha | 0.000 |
| IL_5 | TNF_beta | 0.000 | | IL_5 | TNF_beta | 0.000 |
| IL_5 | Varicella_Int | 0.000 | | IL_5 | Varicella_Int | 0.000 |
| IL_5 | Measles_OD_DB_Int | 0.000 | | IL_5 | Measles_OD_DB_Int | 0.000 |
| IL_5 | Measles_Int | 0.000 | | IL_5 | Measles_Int | 0.000 |
| IL_5 | HepA_Int | 0.000 | | IL_5 | HepA_Int | 0.000 |
| IL_5 | Tetanus_Int | 0.000 | | IL_5 | Tetanus_Int | 0.000 |
| IL_5 | Diptheria_Int | 0.000 | | IL_5 | Diptheria_Int | 0.000 |
| IL_5 | Rubella_Int | 0.000 | | IL_5 | Rubella_Int | 0.000 |
| IL_5 | CMV_Int | 0.000 | | IL_5 | CMV_Int | 0.000 |
| IL_5 | HepB_cAb_Int | 0.000 | | IL_5 | HepB_cAb_Int | 0.000 |
| IL_5 | HepB_eAb_Int | 0.000 | | IL_5 | HepB_eAb_Int | 0.000 |
| IL_5 | HepB_eAg_Int | 0.000 | | IL_5 | HepB_eAg_Int | 0.000 |
| IL_5 | HepC_Int | 0.000 | | IL_5 | HepC_Int | 0.000 |
| IL_5 | Schistosoma_int | 0.000 | | IL_5 | Schistosoma_int | 0.000 |
| IL_5 | Strongyloides_Int | 0.000 | | IL_5 | Strongyloides_Int | 0.000 |
| IL_5 | Filaria_Int | 0.000 | | IL_5 | Filaria_Int | 0.000 |
| IL_6 | IL_1_alpha | 0.000 | | IL_6 | IL_1_alpha | 0.000 |
| IL_6 | IL_1_beta | 0.000 | | IL_6 | IL_1_beta | 0.000 |
| IL_6 | IL_2 | 0.000 | | IL_6 | IL_2 | 0.000 |
| IL_6 | IL_4 | 0.000 | | IL_6 | IL_4 | 0.000 |
| IL_6 | IL_5 | 0.000 | | IL_6 | IL_5 | 0.000 |
| IL_6 | IL_6 | 1.000 | | IL_6 | IL_6 | 1.000 |
| IL_6 | IL_8 | 0.000 | | IL_6 | IL_8 | 0.000 |
| IL_6 | IL_10 | 0.000 | | IL_6 | IL_10 | 0.000 |
| IL_6 | IL_12p70 | 0.000 | | IL_6 | IL_12p70 | 0.000 |
| IL_6 | IL_13 | 0.000 | | IL_6 | IL_13 | 0.000 |
| IL_6 | IL_15 | 0.000 | | IL_6 | IL_15 | 0.000 |
| IL_6 | IL_17 | 0.000 | | IL_6 | IL_17 | 0.000 |
| IL_6 | IL_23 | 0.000 | | IL_6 | IL_23 | 0.000 |
| IL_6 | IFN_gamma | 0.000 | | IL_6 | IFN_gamma | 0.000 |
| IL_6 | TNF_alpha | 0.000 | | IL_6 | TNF_alpha | 0.000 |

FIG. 21I15-D

| | | | | | | |
|---|---|---|---|---|---|---|
| IL_6 | TNF_beta | 0.000 | | IL_6 | TNF_beta | 0.000 |
| IL_6 | Varicella_Int | 0.000 | | IL_6 | Varicella_Int | 0.000 |
| IL_6 | Measles_OD_DB_Int | 0.000 | | IL_6 | Measles_OD_DB_Int | 0.000 |
| IL_6 | Measles_Int | 0.000 | | IL_6 | Measles_Int | 0.000 |
| IL_6 | HepA_Int | 0.000 | | IL_6 | HepA_Int | 0.000 |
| IL_6 | Tetanus_Int | 0.000 | | IL_6 | Tetanus_Int | 0.000 |
| IL_6 | Diptheria_Int | 0.000 | | IL_6 | Diptheria_Int | 0.000 |
| IL_6 | Rubella_Int | 0.000 | | IL_6 | Rubella_Int | 0.000 |
| IL_6 | CMV_Int | 0.000 | | IL_6 | CMV_Int | 0.000 |
| IL_6 | HepB_cAb_Int | 0.000 | | IL_6 | HepB_cAb_Int | 0.000 |
| IL_6 | HepB_eAb_Int | 0.000 | | IL_6 | HepB_eAb_Int | 0.000 |
| IL_6 | HepB_eAg_Int | 0.000 | | IL_6 | HepB_eAg_Int | 0.000 |
| IL_6 | HepC_Int | 0.000 | | IL_6 | HepC_Int | 0.000 |
| IL_6 | Schistosoma_int | 0.000 | | IL_6 | Schistosoma_int | 0.000 |
| IL_6 | Strongyloides_Int | 0.000 | | IL_6 | Strongyloides_Int | 0.000 |
| IL_6 | Filaria_Int | 0.000 | | IL_6 | Filaria_Int | 0.000 |
| IL_8 | IL_1_alpha | 0.000 | | IL_8 | IL_1_alpha | 0.000 |
| IL_8 | IL_1_beta | 0.000 | | IL_8 | IL_1_beta | 0.000 |
| IL_8 | IL_2 | 0.000 | | IL_8 | IL_2 | 0.000 |
| IL_8 | IL_4 | 0.000 | | IL_8 | IL_4 | 0.000 |
| IL_8 | IL_5 | 0.000 | | IL_8 | IL_5 | 0.000 |
| IL_8 | IL_6 | 0.000 | | IL_8 | IL_6 | 0.000 |
| IL_8 | IL_8 | 1.000 | | IL_8 | IL_8 | 1.000 |
| IL_8 | IL_10 | 0.000 | | IL_8 | IL_10 | 0.000 |
| IL_8 | IL_12p70 | 0.000 | | IL_8 | IL_12p70 | 0.000 |
| IL_8 | IL_13 | 0.000 | | IL_8 | IL_13 | 0.000 |
| IL_8 | IL_15 | 0.000 | | IL_8 | IL_15 | 0.000 |
| IL_8 | IL_17 | 0.000 | | IL_8 | IL_17 | 0.000 |
| IL_8 | IL_23 | 0.000 | | IL_8 | IL_23 | 0.000 |
| IL_8 | IFN_gamma | 0.000 | | IL_8 | IFN_gamma | 0.000 |
| IL_8 | TNF_alpha | 0.000 | | IL_8 | TNF_alpha | 0.000 |
| IL_8 | TNF_beta | 0.000 | | IL_8 | TNF_beta | 0.000 |
| IL_8 | Varicella_Int | 0.000 | | IL_8 | Varicella_Int | 0.000 |
| IL_8 | Measles_OD_DB_Int | 0.000 | | IL_8 | Measles_OD_DB_Int | 0.000 |
| IL_8 | Measles_Int | 0.000 | | IL_8 | Measles_Int | 0.000 |
| IL_8 | HepA_Int | 0.000 | | IL_8 | HepA_Int | 0.000 |
| IL_8 | Tetanus_Int | 0.000 | | IL_8 | Tetanus_Int | 0.000 |
| IL_8 | Diptheria_Int | 0.000 | | IL_8 | Diptheria_Int | 0.000 |
| IL_8 | Rubella_Int | 0.000 | | IL_8 | Rubella_Int | 0.000 |
| IL_8 | CMV_Int | 0.000 | | IL_8 | CMV_Int | 0.000 |
| IL_8 | HepB_cAb_Int | 0.000 | | IL_8 | HepB_cAb_Int | 0.000 |
| IL_8 | HepB_eAb_Int | 0.000 | | IL_8 | HepB_eAb_Int | 0.000 |
| IL_8 | HepB_eAg_Int | 0.000 | | IL_8 | HepB_eAg_Int | 0.000 |
| IL_8 | HepC_Int | 0.000 | | IL_8 | HepC_Int | 0.000 |
| IL_8 | Schistosoma_int | 0.000 | | IL_8 | Schistosoma_int | 0.000 |
| IL_8 | Strongyloides_Int | 0.000 | | IL_8 | Strongyloides_Int | 0.000 |
| IL_8 | Filaria_Int | 0.000 | | IL_8 | Filaria_Int | 0.000 |
| IL_10 | IL_1_alpha | 0.000 | | IL_10 | IL_1_alpha | 0.000 |
| IL_10 | IL_1_beta | 0.000 | | IL_10 | IL_1_beta | 0.000 |
| IL_10 | IL_2 | 0.000 | | IL_10 | IL_2 | 0.000 |
| IL_10 | IL_4 | 0.000 | | IL_10 | IL_4 | 0.000 |
| IL_10 | IL_5 | 0.000 | | IL_10 | IL_5 | 0.000 |
| IL_10 | IL_6 | 0.000 | | IL_10 | IL_6 | 0.000 |
| IL_10 | IL_8 | 0.000 | | IL_10 | IL_8 | 0.000 |
| IL_10 | IL_10 | 1.000 | | IL_10 | IL_10 | 1.000 |
| IL_10 | IL_12p70 | 0.000 | | IL_10 | IL_12p70 | 0.000 |
| IL_10 | IL_13 | 0.000 | | IL_10 | IL_13 | 0.000 |

FIG. 21I15-E

| | | | | | | |
|---|---|---|---|---|---|---|
| IL_10 | IL_15 | 0.000 | | IL_10 | IL_15 | 0.000 |
| IL_10 | IL_17 | 0.000 | | IL_10 | IL_17 | 0.000 |
| IL_10 | IL_23 | 0.000 | | IL_10 | IL_23 | 0.000 |
| IL_10 | IFN_gamma | 0.000 | | IL_10 | IFN_gamma | 0.000 |
| IL_10 | TNF_alpha | 0.000 | | IL_10 | TNF_alpha | 0.000 |
| IL_10 | TNF_beta | 0.000 | | IL_10 | TNF_beta | 0.000 |
| IL_10 | Varicella_Int | 0.000 | | IL_10 | Varicella_Int | 0.000 |
| IL_10 | Measles_OD_DB_Int | 0.000 | | IL_10 | Measles_OD_DB_Int | 0.000 |
| IL_10 | Measles_Int | 0.000 | | IL_10 | Measles_Int | 0.000 |
| IL_10 | HepA_Int | 0.000 | | IL_10 | HepA_Int | 0.000 |
| IL_10 | Tetanus_Int | 0.000 | | IL_10 | Tetanus_Int | 0.000 |
| IL_10 | Diptheria_Int | 0.000 | | IL_10 | Diptheria_Int | 0.000 |
| IL_10 | Rubella_Int | 0.000 | | IL_10 | Rubella_Int | 0.000 |
| IL_10 | CMV_Int | 0.000 | | IL_10 | CMV_Int | 0.000 |
| IL_10 | HepB_cAb_Int | 0.000 | | IL_10 | HepB_cAb_Int | 0.000 |
| IL_10 | HepB_eAb_Int | 0.000 | | IL_10 | HepB_eAb_Int | 0.000 |
| IL_10 | HepB_eAg_Int | 0.000 | | IL_10 | HepB_eAg_Int | 0.000 |
| IL_10 | HepC_Int | 0.000 | | IL_10 | HepC_Int | 0.000 |
| IL_10 | Schistosoma_int | 0.000 | | IL_10 | Schistosoma_int | 0.000 |
| IL_10 | Strongyloides_Int | 0.000 | | IL_10 | Strongyloides_Int | 0.000 |
| IL_10 | Filaria_Int | 0.000 | | IL_10 | Filaria_Int | 0.000 |
| IL_12p70 | IL_1_alpha | 0.000 | | IL_12p70 | IL_1_alpha | 0.000 |
| IL_12p70 | IL_1_beta | 0.000 | | IL_12p70 | IL_1_beta | 0.000 |
| IL_12p70 | IL_2 | 0.000 | | IL_12p70 | IL_2 | 0.000 |
| IL_12p70 | IL_4 | 0.000 | | IL_12p70 | IL_4 | 0.000 |
| IL_12p70 | IL_5 | 0.000 | | IL_12p70 | IL_5 | 0.000 |
| IL_12p70 | IL_6 | 0.000 | | IL_12p70 | IL_6 | 0.000 |
| IL_12p70 | IL_8 | 0.000 | | IL_12p70 | IL_8 | 0.000 |
| IL_12p70 | IL_10 | 0.000 | | IL_12p70 | IL_10 | 0.000 |
| IL_12p70 | IL_12p70 | 1.000 | | IL_12p70 | IL_12p70 | 1.000 |
| IL_12p70 | IL_13 | 0.000 | | IL_12p70 | IL_13 | 0.000 |
| IL_12p70 | IL_15 | 0.000 | | IL_12p70 | IL_15 | 0.000 |
| IL_12p70 | IL_17 | 0.000 | | IL_12p70 | IL_17 | 0.000 |
| IL_12p70 | IL_23 | 0.000 | | IL_12p70 | IL_23 | 0.000 |
| IL_12p70 | IFN_gamma | 0.000 | | IL_12p70 | IFN_gamma | 0.000 |
| IL_12p70 | TNF_alpha | 0.000 | | IL_12p70 | TNF_alpha | 0.000 |
| IL_12p70 | TNF_beta | 0.000 | | IL_12p70 | TNF_beta | 0.000 |
| IL_12p70 | Varicella_Int | 0.000 | | IL_12p70 | Varicella_Int | 0.000 |
| IL_12p70 | Measles_OD_DB_Int | 0.000 | | IL_12p70 | Measles_OD_DB_Int | 0.000 |
| IL_12p70 | Measles_Int | 0.000 | | IL_12p70 | Measles_Int | 0.000 |
| IL_12p70 | HepA_Int | 0.000 | | IL_12p70 | HepA_Int | 0.000 |
| IL_12p70 | Tetanus_Int | 0.000 | | IL_12p70 | Tetanus_Int | 0.000 |
| IL_12p70 | Diptheria_Int | 0.000 | | IL_12p70 | Diptheria_Int | 0.000 |
| IL_12p70 | Rubella_Int | 0.000 | | IL_12p70 | Rubella_Int | 0.000 |
| IL_12p70 | CMV_Int | 0.000 | | IL_12p70 | CMV_Int | 0.000 |
| IL_12p70 | HepB_cAb_Int | 0.000 | | IL_12p70 | HepB_cAb_Int | 0.000 |
| IL_12p70 | HepB_eAb_Int | 0.000 | | IL_12p70 | HepB_eAb_Int | 0.000 |
| IL_12p70 | HepB_eAg_Int | 0.000 | | IL_12p70 | HepB_eAg_Int | 0.000 |
| IL_12p70 | HepC_Int | 0.000 | | IL_12p70 | HepC_Int | 0.000 |
| IL_12p70 | Schistosoma_int | 0.000 | | IL_12p70 | Schistosoma_int | 0.000 |
| IL_12p70 | Strongyloides_Int | 0.000 | | IL_12p70 | Strongyloides_Int | 0.000 |
| IL_12p70 | Filaria_Int | 0.000 | | IL_12p70 | Filaria_Int | 0.000 |
| IL_13 | IL_1_alpha | 0.000 | | IL_13 | IL_1_alpha | 0.000 |
| IL_13 | IL_1_beta | 0.000 | | IL_13 | IL_1_beta | 0.000 |
| IL_13 | IL_2 | 0.000 | | IL_13 | IL_2 | 0.000 |
| IL_13 | IL_4 | 0.000 | | IL_13 | IL_4 | 0.000 |
| IL_13 | IL_5 | 0.000 | | IL_13 | IL_5 | 0.000 |

FIG. 21I15-F

| | | | | | | |
|---|---|---|---|---|---|---|
| IL_13 | IL_6 | 0.000 | | IL_13 | IL_6 | 0.000 |
| IL_13 | IL_8 | 0.000 | | IL_13 | IL_8 | 0.000 |
| IL_13 | IL_10 | 0.000 | | IL_13 | IL_10 | 0.000 |
| IL_13 | IL_12p70 | 0.000 | | IL_13 | IL_12p70 | 0.000 |
| IL_13 | IL_13 | 1.000 | | IL_13 | IL_13 | 1.000 |
| IL_13 | IL_15 | 0.000 | | IL_13 | IL_15 | 0.000 |
| IL_13 | IL_17 | 0.000 | | IL_13 | IL_17 | 0.000 |
| IL_13 | IL_23 | 0.000 | | IL_13 | IL_23 | 0.000 |
| IL_13 | IFN_gamma | 0.000 | | IL_13 | IFN_gamma | 0.000 |
| IL_13 | TNF_alpha | 0.000 | | IL_13 | TNF_alpha | 0.000 |
| IL_13 | TNF_beta | 0.000 | | IL_13 | TNF_beta | 0.000 |
| IL_13 | Varicella_Int | 0.000 | | IL_13 | Varicella_Int | 0.000 |
| IL_13 | Measles_OD_DB_Int | 0.000 | | IL_13 | Measles_OD_DB_Int | 0.000 |
| IL_13 | Measles_Int | 0.000 | | IL_13 | Measles_Int | 0.000 |
| IL_13 | HepA_Int | 0.000 | | IL_13 | HepA_Int | 0.000 |
| IL_13 | Tetanus_Int | 0.000 | | IL_13 | Tetanus_Int | 0.000 |
| IL_13 | Diptheria_Int | 0.000 | | IL_13 | Diptheria_Int | 0.000 |
| IL_13 | Rubella_Int | 0.000 | | IL_13 | Rubella_Int | 0.000 |
| IL_13 | CMV_Int | 0.000 | | IL_13 | CMV_Int | 0.000 |
| IL_13 | HepB_cAb_Int | 0.000 | | IL_13 | HepB_cAb_Int | 0.000 |
| IL_13 | HepB_eAb_Int | 0.000 | | IL_13 | HepB_eAb_Int | 0.000 |
| IL_13 | HepB_eAg_Int | 0.000 | | IL_13 | HepB_eAg_Int | 0.000 |
| IL_13 | HepC_Int | 0.000 | | IL_13 | HepC_Int | 0.000 |
| IL_13 | Schistosoma_int | 0.000 | | IL_13 | Schistosoma_int | 0.000 |
| IL_13 | Strongyloides_Int | 0.000 | | IL_13 | Strongyloides_Int | 0.000 |
| IL_13 | Filaria_Int | 0.000 | | IL_13 | Filaria_Int | 0.000 |
| IL_15 | IL_1_alpha | 0.000 | | IL_15 | IL_1_alpha | 0.000 |
| IL_15 | IL_1_beta | 0.000 | | IL_15 | IL_1_beta | 0.000 |
| IL_15 | IL_2 | 0.000 | | IL_15 | IL_2 | 0.000 |
| IL_15 | IL_4 | 0.000 | | IL_15 | IL_4 | 0.000 |
| IL_15 | IL_5 | 0.000 | | IL_15 | IL_5 | 0.000 |
| IL_15 | IL_6 | 0.000 | | IL_15 | IL_6 | 0.000 |
| IL_15 | IL_8 | 0.000 | | IL_15 | IL_8 | 0.000 |
| IL_15 | IL_10 | 0.000 | | IL_15 | IL_10 | 0.000 |
| IL_15 | IL_12p70 | 0.000 | | IL_15 | IL_12p70 | 0.000 |
| IL_15 | IL_13 | 0.000 | | IL_15 | IL_13 | 0.000 |
| IL_15 | IL_15 | 1.000 | | IL_15 | IL_15 | 1.000 |
| IL_15 | IL_17 | 0.000 | | IL_15 | IL_17 | 0.000 |
| IL_15 | IL_23 | 0.000 | | IL_15 | IL_23 | 0.000 |
| IL_15 | IFN_gamma | 0.000 | | IL_15 | IFN_gamma | 0.000 |
| IL_15 | TNF_alpha | 0.000 | | IL_15 | TNF_alpha | 0.000 |
| IL_15 | TNF_beta | 0.000 | | IL_15 | TNF_beta | 0.000 |
| IL_15 | Varicella_Int | 0.000 | | IL_15 | Varicella_Int | 0.000 |
| IL_15 | Measles_OD_DB_Int | 0.000 | | IL_15 | Measles_OD_DB_Int | 0.000 |
| IL_15 | Measles_Int | 0.000 | | IL_15 | Measles_Int | 0.000 |
| IL_15 | HepA_Int | 0.000 | | IL_15 | HepA_Int | 0.000 |
| IL_15 | Tetanus_Int | 0.000 | | IL_15 | Tetanus_Int | 0.000 |
| IL_15 | Diptheria_Int | 0.000 | | IL_15 | Diptheria_Int | 0.000 |
| IL_15 | Rubella_Int | 0.000 | | IL_15 | Rubella_Int | 0.000 |
| IL_15 | CMV_Int | 0.000 | | IL_15 | CMV_Int | 0.000 |
| IL_15 | HepB_cAb_Int | 0.000 | | IL_15 | HepB_cAb_Int | 0.000 |
| IL_15 | HepB_eAb_Int | 0.000 | | IL_15 | HepB_eAb_Int | 0.000 |
| IL_15 | HepB_eAg_Int | 0.000 | | IL_15 | HepB_eAg_Int | 0.000 |
| IL_15 | HepC_Int | 0.000 | | IL_15 | HepC_Int | 0.000 |
| IL_15 | Schistosoma_int | 0.000 | | IL_15 | Schistosoma_int | 0.000 |
| IL_15 | Strongyloides_Int | 0.000 | | IL_15 | Strongyloides_Int | 0.000 |
| IL_15 | Filaria_Int | 0.000 | | IL_15 | Filaria_Int | 0.000 |

FIG. 21I15-G

| | | | | | | |
|---|---|---|---|---|---|---|
| IL_17 | IL_1_alpha | 0.000 | | IL_17 | IL_1_alpha | 0.000 |
| IL_17 | IL_1_beta | 0.000 | | IL_17 | IL_1_beta | 0.000 |
| IL_17 | IL_2 | 0.000 | | IL_17 | IL_2 | 0.000 |
| IL_17 | IL_4 | 0.000 | | IL_17 | IL_4 | 0.000 |
| IL_17 | IL_5 | 0.000 | | IL_17 | IL_5 | 0.000 |
| IL_17 | IL_6 | 0.000 | | IL_17 | IL_6 | 0.000 |
| IL_17 | IL_8 | 0.000 | | IL_17 | IL_8 | 0.000 |
| IL_17 | IL_10 | 0.000 | | IL_17 | IL_10 | 0.000 |
| IL_17 | IL_12p70 | 0.000 | | IL_17 | IL_12p70 | 0.000 |
| IL_17 | IL_13 | 0.000 | | IL_17 | IL_13 | 0.000 |
| IL_17 | IL_15 | 0.000 | | IL_17 | IL_15 | 0.000 |
| IL_17 | IL_17 | 1.000 | | IL_17 | IL_17 | 1.000 |
| IL_17 | IL_23 | 0.000 | | IL_17 | IL_23 | 0.000 |
| IL_17 | IFN_gamma | 0.000 | | IL_17 | IFN_gamma | 0.000 |
| IL_17 | TNF_alpha | 0.000 | | IL_17 | TNF_alpha | 0.000 |
| IL_17 | TNF_beta | 0.000 | | IL_17 | TNF_beta | 0.000 |
| IL_17 | Varicella_Int | 0.000 | | IL_17 | Varicella_Int | 0.000 |
| IL_17 | Measles_OD_DB_Int | 0.000 | | IL_17 | Measles_OD_DB_Int | 0.000 |
| IL_17 | Measles_Int | 0.000 | | IL_17 | Measles_Int | 0.000 |
| IL_17 | HepA_Int | 0.000 | | IL_17 | HepA_Int | 0.000 |
| IL_17 | Tetanus_Int | 0.000 | | IL_17 | Tetanus_Int | 0.000 |
| IL_17 | Diptheria_Int | 0.000 | | IL_17 | Diptheria_Int | 0.000 |
| IL_17 | Rubella_Int | 0.000 | | IL_17 | Rubella_Int | 0.000 |
| IL_17 | CMV_Int | 0.000 | | IL_17 | CMV_Int | 0.000 |
| IL_17 | HepB_cAb_Int | 0.000 | | IL_17 | HepB_cAb_Int | 0.000 |
| IL_17 | HepB_eAb_Int | 0.000 | | IL_17 | HepB_eAb_Int | 0.000 |
| IL_17 | HepB_eAg_Int | 0.000 | | IL_17 | HepB_eAg_Int | 0.000 |
| IL_17 | HepC_Int | 0.000 | | IL_17 | HepC_Int | 0.000 |
| IL_17 | Schistosoma_int | 0.000 | | IL_17 | Schistosoma_int | 0.000 |
| IL_17 | Strongyloides_Int | 0.000 | | IL_17 | Strongyloides_Int | 0.000 |
| IL_17 | Filaria_Int | 0.000 | | IL_17 | Filaria_Int | 0.000 |
| IL_23 | IL_1_alpha | 0.000 | | IL_23 | IL_1_alpha | 0.000 |
| IL_23 | IL_1_beta | 0.000 | | IL_23 | IL_1_beta | 0.000 |
| IL_23 | IL_2 | 0.000 | | IL_23 | IL_2 | 0.000 |
| IL_23 | IL_4 | 0.000 | | IL_23 | IL_4 | 0.000 |
| IL_23 | IL_5 | 0.000 | | IL_23 | IL_5 | 0.000 |
| IL_23 | IL_6 | 0.000 | | IL_23 | IL_6 | 0.000 |
| IL_23 | IL_8 | 0.000 | | IL_23 | IL_8 | 0.000 |
| IL_23 | IL_10 | 0.000 | | IL_23 | IL_10 | 0.000 |
| IL_23 | IL_12p70 | 0.000 | | IL_23 | IL_12p70 | 0.000 |
| IL_23 | IL_13 | 0.000 | | IL_23 | IL_13 | 0.000 |
| IL_23 | IL_15 | 0.000 | | IL_23 | IL_15 | 0.000 |
| IL_23 | IL_17 | 0.000 | | IL_23 | IL_17 | 0.000 |
| IL_23 | IL_23 | 1.000 | | IL_23 | IL_23 | 1.000 |
| IL_23 | IFN_gamma | 0.000 | | IL_23 | IFN_gamma | 0.000 |
| IL_23 | TNF_alpha | 0.000 | | IL_23 | TNF_alpha | 0.000 |
| IL_23 | TNF_beta | 0.000 | | IL_23 | TNF_beta | 0.000 |
| IL_23 | Varicella_Int | 0.000 | | IL_23 | Varicella_Int | 0.000 |
| IL_23 | Measles_OD_DB_Int | 0.000 | | IL_23 | Measles_OD_DB_Int | 0.000 |
| IL_23 | Measles_Int | 0.000 | | IL_23 | Measles_Int | 0.000 |
| IL_23 | HepA_Int | 0.000 | | IL_23 | HepA_Int | 0.000 |
| IL_23 | Tetanus_Int | 0.000 | | IL_23 | Tetanus_Int | 0.000 |
| IL_23 | Diptheria_Int | 0.000 | | IL_23 | Diptheria_Int | 0.000 |
| IL_23 | Rubella_Int | 0.000 | | IL_23 | Rubella_Int | 0.000 |
| IL_23 | CMV_Int | 0.000 | | IL_23 | CMV_Int | 0.000 |
| IL_23 | HepB_cAb_Int | 0.000 | | IL_23 | HepB_cAb_Int | 0.000 |
| IL_23 | HepB_eAb_Int | 0.000 | | IL_23 | HepB_eAb_Int | 0.000 |

FIG. 21I15-H

| | | | | | | |
|---|---|---|---|---|---|---|
| IL_23 | HepB_eAg_Int | 0.000 | | IL_23 | HepB_eAg_Int | 0.000 |
| IL_23 | HepC_Int | 0.000 | | IL_23 | HepC_Int | 0.000 |
| IL_23 | Schistosoma_int | 0.000 | | IL_23 | Schistosoma_int | 0.000 |
| IL_23 | Strongyloides_Int | 0.000 | | IL_23 | Strongyloides_Int | 0.000 |
| IL_23 | Filaria_Int | 0.000 | | IL_23 | Filaria_Int | 0.000 |
| IFN_gamma | IL_1_alpha | 0.000 | | IFN_gamma | IL_1_alpha | 0.000 |
| IFN_gamma | IL_1_beta | 0.000 | | IFN_gamma | IL_1_beta | 0.000 |
| IFN_gamma | IL_2 | 0.000 | | IFN_gamma | IL_2 | 0.000 |
| IFN_gamma | IL_4 | 0.000 | | IFN_gamma | IL_4 | 0.000 |
| IFN_gamma | IL_5 | 0.000 | | IFN_gamma | IL_5 | 0.000 |
| IFN_gamma | IL_6 | 0.000 | | IFN_gamma | IL_6 | 0.000 |
| IFN_gamma | IL_8 | 0.000 | | IFN_gamma | IL_8 | 0.000 |
| IFN_gamma | IL_10 | 0.000 | | IFN_gamma | IL_10 | 0.000 |
| IFN_gamma | IL_12p70 | 0.000 | | IFN_gamma | IL_12p70 | 0.000 |
| IFN_gamma | IL_13 | 0.000 | | IFN_gamma | IL_13 | 0.000 |
| IFN_gamma | IL_15 | 0.000 | | IFN_gamma | IL_15 | 0.000 |
| IFN_gamma | IL_17 | 0.000 | | IFN_gamma | IL_17 | 0.000 |
| IFN_gamma | IL_23 | 0.000 | | IFN_gamma | IL_23 | 0.000 |
| IFN_gamma | IFN_gamma | 1.000 | | IFN_gamma | IFN_gamma | 1.000 |
| IFN_gamma | TNF_alpha | 0.000 | | IFN_gamma | TNF_alpha | 0.000 |
| IFN_gamma | TNF_beta | 0.000 | | IFN_gamma | TNF_beta | 0.000 |
| IFN_gamma | Varicella_Int | 0.000 | | IFN_gamma | Varicella_Int | 0.000 |
| IFN_gamma | Measles_OD_DB_Int | 0.000 | | IFN_gamma | Measles_OD_DB_Int | 0.000 |
| IFN_gamma | Measles_Int | 0.000 | | IFN_gamma | Measles_Int | 0.000 |
| IFN_gamma | HepA_Int | 0.000 | | IFN_gamma | HepA_Int | 0.000 |
| IFN_gamma | Tetanus_Int | 0.000 | | IFN_gamma | Tetanus_Int | 0.000 |
| IFN_gamma | Diptheria_Int | 0.000 | | IFN_gamma | Diptheria_Int | 0.000 |
| IFN_gamma | Rubella_Int | 0.000 | | IFN_gamma | Rubella_Int | 0.000 |
| IFN_gamma | CMV_Int | 0.000 | | IFN_gamma | CMV_Int | 0.000 |
| IFN_gamma | HepB_cAb_Int | 0.000 | | IFN_gamma | HepB_cAb_Int | 0.000 |
| IFN_gamma | HepB_eAb_Int | 0.000 | | IFN_gamma | HepB_eAb_Int | 0.000 |
| IFN_gamma | HepB_eAg_Int | 0.000 | | IFN_gamma | HepB_eAg_Int | 0.000 |
| IFN_gamma | HepC_Int | 0.000 | | IFN_gamma | HepC_Int | 0.000 |
| IFN_gamma | Schistosoma_int | 0.000 | | IFN_gamma | Schistosoma_int | 0.000 |
| IFN_gamma | Strongyloides_Int | 0.000 | | IFN_gamma | Strongyloides_Int | 0.000 |
| IFN_gamma | Filaria_Int | 0.000 | | IFN_gamma | Filaria_Int | 0.000 |
| TNF_alpha | IL_1_alpha | 0.000 | | TNF_alpha | IL_1_alpha | 0.000 |
| TNF_alpha | IL_1_beta | 0.000 | | TNF_alpha | IL_1_beta | 0.000 |
| TNF_alpha | IL_2 | 0.000 | | TNF_alpha | IL_2 | 0.000 |
| TNF_alpha | IL_4 | 0.000 | | TNF_alpha | IL_4 | 0.000 |
| TNF_alpha | IL_5 | 0.000 | | TNF_alpha | IL_5 | 0.000 |
| TNF_alpha | IL_6 | 0.000 | | TNF_alpha | IL_6 | 0.000 |
| TNF_alpha | IL_8 | 0.000 | | TNF_alpha | IL_8 | 0.000 |
| TNF_alpha | IL_10 | 0.000 | | TNF_alpha | IL_10 | 0.000 |
| TNF_alpha | IL_12p70 | 0.000 | | TNF_alpha | IL_12p70 | 0.000 |
| TNF_alpha | IL_13 | 0.000 | | TNF_alpha | IL_13 | 0.000 |
| TNF_alpha | IL_15 | 0.000 | | TNF_alpha | IL_15 | 0.000 |
| TNF_alpha | IL_17 | 0.000 | | TNF_alpha | IL_17 | 0.000 |
| TNF_alpha | IL_23 | 0.000 | | TNF_alpha | IL_23 | 0.000 |
| TNF_alpha | IFN_gamma | 0.000 | | TNF_alpha | IFN_gamma | 0.000 |
| TNF_alpha | TNF_alpha | 1.000 | | TNF_alpha | TNF_alpha | 1.000 |
| TNF_alpha | TNF_beta | 0.000 | | TNF_alpha | TNF_beta | 0.000 |
| TNF_alpha | Varicella_Int | 0.000 | | TNF_alpha | Varicella_Int | 0.000 |
| TNF_alpha | Measles_OD_DB_Int | 0.000 | | TNF_alpha | Measles_OD_DB_Int | 0.000 |
| TNF_alpha | Measles_Int | 0.000 | | TNF_alpha | Measles_Int | 0.000 |
| TNF_alpha | HepA_Int | 0.000 | | TNF_alpha | HepA_Int | 0.000 |
| TNF_alpha | Tetanus_Int | 0.000 | | TNF_alpha | Tetanus_Int | 0.000 |

FIG. 21I15-I

| | | | | | | |
|---|---|---|---|---|---|---|
| TNF_alpha | Diptheria_Int | 0.000 | | TNF_alpha | Diptheria_Int | 0.000 |
| TNF_alpha | Rubella_Int | 0.000 | | TNF_alpha | Rubella_Int | 0.000 |
| TNF_alpha | CMV_Int | 0.000 | | TNF_alpha | CMV_Int | 0.000 |
| TNF_alpha | HepB_cAb_Int | 0.000 | | TNF_alpha | HepB_cAb_Int | 0.000 |
| TNF_alpha | HepB_eAb_Int | 0.000 | | TNF_alpha | HepB_eAb_Int | 0.000 |
| TNF_alpha | HepB_eAg_Int | 0.000 | | TNF_alpha | HepB_eAg_Int | 0.000 |
| TNF_alpha | HepC_Int | 0.000 | | TNF_alpha | HepC_Int | 0.000 |
| TNF_alpha | Schistosoma_int | 0.000 | | TNF_alpha | Schistosoma_int | 0.000 |
| TNF_alpha | Strongyloides_Int | 0.000 | | TNF_alpha | Strongyloides_Int | 0.000 |
| TNF_alpha | Filaria_Int | 0.000 | | TNF_alpha | Filaria_Int | 0.000 |
| TNF_beta | IL_1_alpha | 0.000 | | TNF_beta | IL_1_alpha | 0.000 |
| TNF_beta | IL_1_beta | 0.000 | | TNF_beta | IL_1_beta | 0.000 |
| TNF_beta | IL_2 | 0.000 | | TNF_beta | IL_2 | 0.000 |
| TNF_beta | IL_4 | 0.000 | | TNF_beta | IL_4 | 0.000 |
| TNF_beta | IL_5 | 0.000 | | TNF_beta | IL_5 | 0.000 |
| TNF_beta | IL_6 | 0.000 | | TNF_beta | IL_6 | 0.000 |
| TNF_beta | IL_8 | 0.000 | | TNF_beta | IL_8 | 0.000 |
| TNF_beta | IL_10 | 0.000 | | TNF_beta | IL_10 | 0.000 |
| TNF_beta | IL_12p70 | 0.000 | | TNF_beta | IL_12p70 | 0.000 |
| TNF_beta | IL_13 | 0.000 | | TNF_beta | IL_13 | 0.000 |
| TNF_beta | IL_15 | 0.000 | | TNF_beta | IL_15 | 0.000 |
| TNF_beta | IL_17 | 0.000 | | TNF_beta | IL_17 | 0.000 |
| TNF_beta | IL_23 | 0.000 | | TNF_beta | IL_23 | 0.000 |
| TNF_beta | IFN_gamma | 0.000 | | TNF_beta | IFN_gamma | 0.000 |
| TNF_beta | TNF_alpha | 0.000 | | TNF_beta | TNF_alpha | 0.000 |
| TNF_beta | TNF_beta | 1.000 | | TNF_beta | TNF_beta | 1.000 |
| TNF_beta | Varicella_Int | 0.000 | | TNF_beta | Varicella_Int | 0.000 |
| TNF_beta | Measles_OD_DB_Int | 0.000 | | TNF_beta | Measles_OD_DB_Int | 0.000 |
| TNF_beta | Measles_Int | 0.000 | | TNF_beta | Measles_Int | 0.000 |
| TNF_beta | HepA_Int | 0.000 | | TNF_beta | HepA_Int | 0.000 |
| TNF_beta | Tetanus_Int | 0.000 | | TNF_beta | Tetanus_Int | 0.000 |
| TNF_beta | Diptheria_Int | 0.000 | | TNF_beta | Diptheria_Int | 0.000 |
| TNF_beta | Rubella_Int | 0.000 | | TNF_beta | Rubella_Int | 0.000 |
| TNF_beta | CMV_Int | 0.000 | | TNF_beta | CMV_Int | 0.000 |
| TNF_beta | HepB_cAb_Int | 0.000 | | TNF_beta | HepB_cAb_Int | 0.000 |
| TNF_beta | HepB_eAb_Int | 0.000 | | TNF_beta | HepB_eAb_Int | 0.000 |
| TNF_beta | HepB_eAg_Int | 0.000 | | TNF_beta | HepB_eAg_Int | 0.000 |
| TNF_beta | HepC_Int | 0.000 | | TNF_beta | HepC_Int | 0.000 |
| TNF_beta | Schistosoma_int | 0.000 | | TNF_beta | Schistosoma_int | 0.000 |
| TNF_beta | Strongyloides_Int | 0.000 | | TNF_beta | Strongyloides_Int | 0.000 |
| TNF_beta | Filaria_Int | 0.000 | | TNF_beta | Filaria_Int | 0.000 |
| Varicella_Int | IL_1_alpha | 0.000 | | Varicella_Int | IL_1_alpha | 0.000 |
| Varicella_Int | IL_1_beta | 0.000 | | Varicella_Int | IL_1_beta | 0.000 |
| Varicella_Int | IL_2 | 0.000 | | Varicella_Int | IL_2 | 0.000 |
| Varicella_Int | IL_4 | 0.000 | | Varicella_Int | IL_4 | 0.000 |
| Varicella_Int | IL_5 | 0.000 | | Varicella_Int | IL_5 | 0.000 |
| Varicella_Int | IL_6 | 0.000 | | Varicella_Int | IL_6 | 0.000 |
| Varicella_Int | IL_8 | 0.000 | | Varicella_Int | IL_8 | 0.000 |
| Varicella_Int | IL_10 | 0.000 | | Varicella_Int | IL_10 | 0.000 |
| Varicella_Int | IL_12p70 | 0.000 | | Varicella_Int | IL_12p70 | 0.000 |
| Varicella_Int | IL_13 | 0.000 | | Varicella_Int | IL_13 | 0.000 |
| Varicella_Int | IL_15 | 0.000 | | Varicella_Int | IL_15 | 0.000 |
| Varicella_Int | IL_17 | 0.000 | | Varicella_Int | IL_17 | 0.000 |
| Varicella_Int | IL_23 | 0.000 | | Varicella_Int | IL_23 | 0.000 |
| Varicella_Int | IFN_gamma | 0.000 | | Varicella_Int | IFN_gamma | 0.000 |
| Varicella_Int | TNF_alpha | 0.000 | | Varicella_Int | TNF_alpha | 0.000 |
| Varicella_Int | TNF_beta | 0.000 | | Varicella_Int | TNF_beta | 0.000 |

FIG. 21I15-J

| | | | | | | |
|---|---|---|---|---|---|---|
| Varicella_Int | Varicella_Int | 1.000 | | Varicella_Int | Varicella_Int | 1.000 |
| Varicella_Int | Measles_OD_DB_Int | 0.000 | | Varicella_Int | Measles_OD_DB_Int | 0.000 |
| Varicella_Int | Measles_Int | 0.000 | | Varicella_Int | Measles_Int | 0.000 |
| Varicella_Int | HepA_Int | 0.000 | | Varicella_Int | HepA_Int | 0.000 |
| Varicella_Int | Tetanus_Int | 0.000 | | Varicella_Int | Tetanus_Int | 0.000 |
| Varicella_Int | Diptheria_Int | 0.000 | | Varicella_Int | Diptheria_Int | 0.000 |
| Varicella_Int | Rubella_Int | 0.000 | | Varicella_Int | Rubella_Int | 0.000 |
| Varicella_Int | CMV_Int | 0.000 | | Varicella_Int | CMV_Int | 0.000 |
| Varicella_Int | HepB_cAb_Int | 0.000 | | Varicella_Int | HepB_cAb_Int | 0.000 |
| Varicella_Int | HepB_eAb_Int | 0.000 | | Varicella_Int | HepB_eAb_Int | 0.000 |
| Varicella_Int | HepB_eAg_Int | 0.000 | | Varicella_Int | HepB_eAg_Int | 0.000 |
| Varicella_Int | HepC_Int | 0.000 | | Varicella_Int | HepC_Int | 0.000 |
| Varicella_Int | Schistosoma_int | 0.000 | | Varicella_Int | Schistosoma_int | 0.000 |
| Varicella_Int | Strongyloides_Int | 0.000 | | Varicella_Int | Strongyloides_Int | 0.000 |
| Varicella_Int | Filaria_Int | 0.000 | | Varicella_Int | Filaria_Int | 0.000 |
| Measles_OD_DB_Int | IL_1_alpha | 0.000 | | Measles_OD_DB_Int | IL_1_alpha | 0.000 |
| Measles_OD_DB_Int | IL_1_beta | 0.000 | | Measles_OD_DB_Int | IL_1_beta | 0.000 |
| Measles_OD_DB_Int | IL_2 | 0.000 | | Measles_OD_DB_Int | IL_2 | 0.000 |
| Measles_OD_DB_Int | IL_4 | 0.000 | | Measles_OD_DB_Int | IL_4 | 0.000 |
| Measles_OD_DB_Int | IL_5 | 0.000 | | Measles_OD_DB_Int | IL_5 | 0.000 |
| Measles_OD_DB_Int | IL_6 | 0.000 | | Measles_OD_DB_Int | IL_6 | 0.000 |
| Measles_OD_DB_Int | IL_8 | 0.000 | | Measles_OD_DB_Int | IL_8 | 0.000 |
| Measles_OD_DB_Int | IL_10 | 0.000 | | Measles_OD_DB_Int | IL_10 | 0.000 |
| Measles_OD_DB_Int | IL_12p70 | 0.000 | | Measles_OD_DB_Int | IL_12p70 | 0.000 |
| Measles_OD_DB_Int | IL_13 | 0.000 | | Measles_OD_DB_Int | IL_13 | 0.000 |
| Measles_OD_DB_Int | IL_15 | 0.000 | | Measles_OD_DB_Int | IL_15 | 0.000 |
| Measles_OD_DB_Int | IL_17 | 0.000 | | Measles_OD_DB_Int | IL_17 | 0.000 |
| Measles_OD_DB_Int | IL_23 | 0.000 | | Measles_OD_DB_Int | IL_23 | 0.000 |
| Measles_OD_DB_Int | IFN_gamma | 0.000 | | Measles_OD_DB_Int | IFN_gamma | 0.000 |
| Measles_OD_DB_Int | TNF_alpha | 0.000 | | Measles_OD_DB_Int | TNF_alpha | 0.000 |
| Measles_OD_DB_Int | TNF_beta | 0.000 | | Measles_OD_DB_Int | TNF_beta | 0.000 |
| Measles_OD_DB_Int | Varicella_Int | 0.000 | | Measles_OD_DB_Int | Varicella_Int | 0.000 |
| Measles_OD_DB_Int | Measles_OD_DB_Int | 1.000 | | Measles_OD_DB_Int | Measles_OD_DB_Int | 1.000 |
| Measles_OD_DB_Int | Measles_Int | 0.000 | | Measles_OD_DB_Int | Measles_Int | 0.000 |
| Measles_OD_DB_Int | HepA_Int | 0.000 | | Measles_OD_DB_Int | HepA_Int | 0.000 |
| Measles_OD_DB_Int | Tetanus_Int | 0.000 | | Measles_OD_DB_Int | Tetanus_Int | 0.000 |
| Measles_OD_DB_Int | Diptheria_Int | 0.000 | | Measles_OD_DB_Int | Diptheria_Int | 0.000 |
| Measles_OD_DB_Int | Rubella_Int | 0.000 | | Measles_OD_DB_Int | Rubella_Int | 0.000 |
| Measles_OD_DB_Int | CMV_Int | 0.000 | | Measles_OD_DB_Int | CMV_Int | 0.000 |
| Measles_OD_DB_Int | HepB_cAb_Int | 0.000 | | Measles_OD_DB_Int | HepB_cAb_Int | 0.000 |
| Measles_OD_DB_Int | HepB_eAb_Int | 0.000 | | Measles_OD_DB_Int | HepB_eAb_Int | 0.000 |
| Measles_OD_DB_Int | HepB_eAg_Int | 0.000 | | Measles_OD_DB_Int | HepB_eAg_Int | 0.000 |
| Measles_OD_DB_Int | HepC_Int | 0.000 | | Measles_OD_DB_Int | HepC_Int | 0.000 |
| Measles_OD_DB_Int | Schistosoma_int | 0.000 | | Measles_OD_DB_Int | Schistosoma_int | 0.000 |
| Measles_OD_DB_Int | Strongyloides_Int | 0.000 | | Measles_OD_DB_Int | Strongyloides_Int | 0.000 |
| Measles_OD_DB_Int | Filaria_Int | 0.000 | | Measles_OD_DB_Int | Filaria_Int | 0.000 |
| Measles_Int | IL_1_alpha | 0.000 | | Measles_Int | IL_1_alpha | 0.000 |
| Measles_Int | IL_1_beta | 0.000 | | Measles_Int | IL_1_beta | 0.000 |
| Measles_Int | IL_2 | 0.000 | | Measles_Int | IL_2 | 0.000 |
| Measles_Int | IL_4 | 0.000 | | Measles_Int | IL_4 | 0.000 |
| Measles_Int | IL_5 | 0.000 | | Measles_Int | IL_5 | 0.000 |
| Measles_Int | IL_6 | 0.000 | | Measles_Int | IL_6 | 0.000 |
| Measles_Int | IL_8 | 0.000 | | Measles_Int | IL_8 | 0.000 |
| Measles_Int | IL_10 | 0.000 | | Measles_Int | IL_10 | 0.000 |
| Measles_Int | IL_12p70 | 0.000 | | Measles_Int | IL_12p70 | 0.000 |
| Measles_Int | IL_13 | 0.000 | | Measles_Int | IL_13 | 0.000 |
| Measles_Int | IL_15 | 0.000 | | Measles_Int | IL_15 | 0.000 |

FIG. 21I15-K

| | | | | | | |
|---|---|---|---|---|---|---|
| Measles_Int | IL_17 | 0.000 | | Measles_Int | IL_17 | 0.000 |
| Measles_Int | IL_23 | 0.000 | | Measles_Int | IL_23 | 0.000 |
| Measles_Int | IFN_gamma | 0.000 | | Measles_Int | IFN_gamma | 0.000 |
| Measles_Int | TNF_alpha | 0.000 | | Measles_Int | TNF_alpha | 0.000 |
| Measles_Int | TNF_beta | 0.000 | | Measles_Int | TNF_beta | 0.000 |
| Measles_Int | Varicella_Int | 0.000 | | Measles_Int | Varicella_Int | 0.000 |
| Measles_Int | Measles_OD_DB_Int | 0.000 | | Measles_Int | Measles_OD_DB_Int | 0.000 |
| Measles_Int | Measles_Int | 1.000 | | Measles_Int | Measles_Int | 1.000 |
| Measles_Int | HepA_Int | 0.000 | | Measles_Int | HepA_Int | 0.000 |
| Measles_Int | Tetanus_Int | 0.000 | | Measles_Int | Tetanus_Int | 0.000 |
| Measles_Int | Diptheria_Int | 0.000 | | Measles_Int | Diptheria_Int | 0.000 |
| Measles_Int | Rubella_Int | 0.000 | | Measles_Int | Rubella_Int | 0.000 |
| Measles_Int | CMV_Int | 0.000 | | Measles_Int | CMV_Int | 0.000 |
| Measles_Int | HepB_cAb_Int | 0.000 | | Measles_Int | HepB_cAb_Int | 0.000 |
| Measles_Int | HepB_eAb_Int | 0.000 | | Measles_Int | HepB_eAb_Int | 0.000 |
| Measles_Int | HepB_eAg_Int | 0.000 | | Measles_Int | HepB_eAg_Int | 0.000 |
| Measles_Int | HepC_Int | 0.000 | | Measles_Int | HepC_Int | 0.000 |
| Measles_Int | Schistosoma_int | 0.000 | | Measles_Int | Schistosoma_int | 0.000 |
| Measles_Int | Strongyloides_Int | 0.000 | | Measles_Int | Strongyloides_Int | 0.000 |
| Measles_Int | Filaria_Int | 0.000 | | Measles_Int | Filaria_Int | 0.000 |
| HepA_Int | IL_1_alpha | 0.000 | | HepA_Int | IL_1_alpha | 0.000 |
| HepA_Int | IL_1_beta | 0.000 | | HepA_Int | IL_1_beta | 0.000 |
| HepA_Int | IL_2 | 0.000 | | HepA_Int | IL_2 | 0.000 |
| HepA_Int | IL_4 | 0.000 | | HepA_Int | IL_4 | 0.000 |
| HepA_Int | IL_5 | 0.000 | | HepA_Int | IL_5 | 0.000 |
| HepA_Int | IL_6 | 0.000 | | HepA_Int | IL_6 | 0.000 |
| HepA_Int | IL_8 | 0.000 | | HepA_Int | IL_8 | 0.000 |
| HepA_Int | IL_10 | 0.000 | | HepA_Int | IL_10 | 0.000 |
| HepA_Int | IL_12p70 | 0.000 | | HepA_Int | IL_12p70 | 0.000 |
| HepA_Int | IL_13 | 0.000 | | HepA_Int | IL_13 | 0.000 |
| HepA_Int | IL_15 | 0.000 | | HepA_Int | IL_15 | 0.000 |
| HepA_Int | IL_17 | 0.000 | | HepA_Int | IL_17 | 0.000 |
| HepA_Int | IL_23 | 0.000 | | HepA_Int | IL_23 | 0.000 |
| HepA_Int | IFN_gamma | 0.000 | | HepA_Int | IFN_gamma | 0.000 |
| HepA_Int | TNF_alpha | 0.000 | | HepA_Int | TNF_alpha | 0.000 |
| HepA_Int | TNF_beta | 0.000 | | HepA_Int | TNF_beta | 0.000 |
| HepA_Int | Varicella_Int | 0.000 | | HepA_Int | Varicella_Int | 0.000 |
| HepA_Int | Measles_OD_DB_Int | 0.000 | | HepA_Int | Measles_OD_DB_Int | 0.000 |
| HepA_Int | Measles_Int | 0.000 | | HepA_Int | Measles_Int | 0.000 |
| HepA_Int | HepA_Int | 1.000 | | HepA_Int | HepA_Int | 1.000 |
| HepA_Int | Tetanus_Int | 0.000 | | HepA_Int | Tetanus_Int | 0.000 |
| HepA_Int | Diptheria_Int | 0.000 | | HepA_Int | Diptheria_Int | 0.000 |
| HepA_Int | Rubella_Int | 0.000 | | HepA_Int | Rubella_Int | 0.000 |
| HepA_Int | CMV_Int | 0.000 | | HepA_Int | CMV_Int | 0.000 |
| HepA_Int | HepB_cAb_Int | 0.000 | | HepA_Int | HepB_cAb_Int | 0.000 |
| HepA_Int | HepB_eAb_Int | 0.000 | | HepA_Int | HepB_eAb_Int | 0.000 |
| HepA_Int | HepB_eAg_Int | 0.000 | | HepA_Int | HepB_eAg_Int | 0.000 |
| HepA_Int | HepC_Int | 0.000 | | HepA_Int | HepC_Int | 0.000 |
| HepA_Int | Schistosoma_int | 0.000 | | HepA_Int | Schistosoma_int | 0.000 |
| HepA_Int | Strongyloides_Int | 0.000 | | HepA_Int | Strongyloides_Int | 0.000 |
| HepA_Int | Filaria_Int | 0.000 | | HepA_Int | Filaria_Int | 0.000 |
| Tetanus_Int | IL_1_alpha | 0.000 | | Tetanus_Int | IL_1_alpha | 0.000 |
| Tetanus_Int | IL_1_beta | 0.000 | | Tetanus_Int | IL_1_beta | 0.000 |
| Tetanus_Int | IL_2 | 0.000 | | Tetanus_Int | IL_2 | 0.000 |
| Tetanus_Int | IL_4 | 0.000 | | Tetanus_Int | IL_4 | 0.000 |
| Tetanus_Int | IL_5 | 0.000 | | Tetanus_Int | IL_5 | 0.000 |
| Tetanus_Int | IL_6 | 0.000 | | Tetanus_Int | IL_6 | 0.000 |

FIG. 21I15-L

| | | | | | | |
|---|---|---|---|---|---|---|
| Tetanus_Int | IL_8 | 0.000 | | Tetanus_Int | IL_8 | 0.000 |
| Tetanus_Int | IL_10 | 0.000 | | Tetanus_Int | IL_10 | 0.000 |
| Tetanus_Int | IL_12p70 | 0.000 | | Tetanus_Int | IL_12p70 | 0.000 |
| Tetanus_Int | IL_13 | 0.000 | | Tetanus_Int | IL_13 | 0.000 |
| Tetanus_Int | IL_15 | 0.000 | | Tetanus_Int | IL_15 | 0.000 |
| Tetanus_Int | IL_17 | 0.000 | | Tetanus_Int | IL_17 | 0.000 |
| Tetanus_Int | IL_23 | 0.000 | | Tetanus_Int | IL_23 | 0.000 |
| Tetanus_Int | IFN_gamma | 0.000 | | Tetanus_Int | IFN_gamma | 0.000 |
| Tetanus_Int | TNF_alpha | 0.000 | | Tetanus_Int | TNF_alpha | 0.000 |
| Tetanus_Int | TNF_beta | 0.000 | | Tetanus_Int | TNF_beta | 0.000 |
| Tetanus_Int | Varicella_Int | 0.000 | | Tetanus_Int | Varicella_Int | 0.000 |
| Tetanus_Int | Measles_OD_DB_Int | 0.000 | | Tetanus_Int | Measles_OD_DB_Int | 0.000 |
| Tetanus_Int | Measles_Int | 0.000 | | Tetanus_Int | Measles_Int | 0.000 |
| Tetanus_Int | HepA_Int | 0.000 | | Tetanus_Int | HepA_Int | 0.000 |
| Tetanus_Int | Tetanus_Int | 1.000 | | Tetanus_Int | Tetanus_Int | 1.000 |
| Tetanus_Int | Diptheria_Int | 0.000 | | Tetanus_Int | Diptheria_Int | 0.000 |
| Tetanus_Int | Rubella_Int | 0.000 | | Tetanus_Int | Rubella_Int | 0.000 |
| Tetanus_Int | CMV_Int | 0.000 | | Tetanus_Int | CMV_Int | 0.000 |
| Tetanus_Int | HepB_cAb_Int | 0.000 | | Tetanus_Int | HepB_cAb_Int | 0.000 |
| Tetanus_Int | HepB_eAb_Int | 0.000 | | Tetanus_Int | HepB_eAb_Int | 0.000 |
| Tetanus_Int | HepB_eAg_Int | 0.000 | | Tetanus_Int | HepB_eAg_Int | 0.000 |
| Tetanus_Int | HepC_Int | 0.000 | | Tetanus_Int | HepC_Int | 0.000 |
| Tetanus_Int | Schistosoma_int | 0.000 | | Tetanus_Int | Schistosoma_int | 0.000 |
| Tetanus_Int | Strongyloides_Int | 0.000 | | Tetanus_Int | Strongyloides_Int | 0.000 |
| Tetanus_Int | Filaria_Int | 0.000 | | Tetanus_Int | Filaria_Int | 0.000 |
| Diptheria_Int | IL_1_alpha | 0.000 | | Diptheria_Int | IL_1_alpha | 0.000 |
| Diptheria_Int | IL_1_beta | 0.000 | | Diptheria_Int | IL_1_beta | 0.000 |
| Diptheria_Int | IL_2 | 0.000 | | Diptheria_Int | IL_2 | 0.000 |
| Diptheria_Int | IL_4 | 0.000 | | Diptheria_Int | IL_4 | 0.000 |
| Diptheria_Int | IL_5 | 0.000 | | Diptheria_Int | IL_5 | 0.000 |
| Diptheria_Int | IL_6 | 0.000 | | Diptheria_Int | IL_6 | 0.000 |
| Diptheria_Int | IL_8 | 0.000 | | Diptheria_Int | IL_8 | 0.000 |
| Diptheria_Int | IL_10 | 0.000 | | Diptheria_Int | IL_10 | 0.000 |
| Diptheria_Int | IL_12p70 | 0.000 | | Diptheria_Int | IL_12p70 | 0.000 |
| Diptheria_Int | IL_13 | 0.000 | | Diptheria_Int | IL_13 | 0.000 |
| Diptheria_Int | IL_15 | 0.000 | | Diptheria_Int | IL_15 | 0.000 |
| Diptheria_Int | IL_17 | 0.000 | | Diptheria_Int | IL_17 | 0.000 |
| Diptheria_Int | IL_23 | 0.000 | | Diptheria_Int | IL_23 | 0.000 |
| Diptheria_Int | IFN_gamma | 0.000 | | Diptheria_Int | IFN_gamma | 0.000 |
| Diptheria_Int | TNF_alpha | 0.000 | | Diptheria_Int | TNF_alpha | 0.000 |
| Diptheria_Int | TNF_beta | 0.000 | | Diptheria_Int | TNF_beta | 0.000 |
| Diptheria_Int | Varicella_Int | 0.000 | | Diptheria_Int | Varicella_Int | 0.000 |
| Diptheria_Int | Measles_OD_DB_Int | 0.000 | | Diptheria_Int | Measles_OD_DB_Int | 0.000 |
| Diptheria_Int | Measles_Int | 0.000 | | Diptheria_Int | Measles_Int | 0.000 |
| Diptheria_Int | HepA_Int | 0.000 | | Diptheria_Int | HepA_Int | 0.000 |
| Diptheria_Int | Tetanus_Int | 0.000 | | Diptheria_Int | Tetanus_Int | 0.000 |
| Diptheria_Int | Diptheria_Int | 1.000 | | Diptheria_Int | Diptheria_Int | 1.000 |
| Diptheria_Int | Rubella_Int | 0.000 | | Diptheria_Int | Rubella_Int | 0.000 |
| Diptheria_Int | CMV_Int | 0.000 | | Diptheria_Int | CMV_Int | 0.000 |
| Diptheria_Int | HepB_cAb_Int | 0.000 | | Diptheria_Int | HepB_cAb_Int | 0.000 |
| Diptheria_Int | HepB_eAb_Int | 0.000 | | Diptheria_Int | HepB_eAb_Int | 0.000 |
| Diptheria_Int | HepB_eAg_Int | 0.000 | | Diptheria_Int | HepB_eAg_Int | 0.000 |
| Diptheria_Int | HepC_Int | 0.000 | | Diptheria_Int | HepC_Int | 0.000 |
| Diptheria_Int | Schistosoma_int | 0.000 | | Diptheria_Int | Schistosoma_int | 0.000 |
| Diptheria_Int | Strongyloides_Int | 0.000 | | Diptheria_Int | Strongyloides_Int | 0.000 |
| Diptheria_Int | Filaria_Int | 0.000 | | Diptheria_Int | Filaria_Int | 0.000 |
| Rubella_Int | IL_1_alpha | 0.000 | | Rubella_Int | IL_1_alpha | 0.000 |

FIG. 21I15-M

| | | | | | | |
|---|---|---|---|---|---|---|
| Rubella_Int | IL_1_beta | 0.000 | | Rubella_Int | IL_1_beta | 0.000 |
| Rubella_Int | IL_2 | 0.000 | | Rubella_Int | IL_2 | 0.000 |
| Rubella_Int | IL_4 | 0.000 | | Rubella_Int | IL_4 | 0.000 |
| Rubella_Int | IL_5 | 0.000 | | Rubella_Int | IL_5 | 0.000 |
| Rubella_Int | IL_6 | 0.000 | | Rubella_Int | IL_6 | 0.000 |
| Rubella_Int | IL_8 | 0.000 | | Rubella_Int | IL_8 | 0.000 |
| Rubella_Int | IL_10 | 0.000 | | Rubella_Int | IL_10 | 0.000 |
| Rubella_Int | IL_12p70 | 0.000 | | Rubella_Int | IL_12p70 | 0.000 |
| Rubella_Int | IL_13 | 0.000 | | Rubella_Int | IL_13 | 0.000 |
| Rubella_Int | IL_15 | 0.000 | | Rubella_Int | IL_15 | 0.000 |
| Rubella_Int | IL_17 | 0.000 | | Rubella_Int | IL_17 | 0.000 |
| Rubella_Int | IL_23 | 0.000 | | Rubella_Int | IL_23 | 0.000 |
| Rubella_Int | IFN_gamma | 0.000 | | Rubella_Int | IFN_gamma | 0.000 |
| Rubella_Int | TNF_alpha | 0.000 | | Rubella_Int | TNF_alpha | 0.000 |
| Rubella_Int | TNF_beta | 0.000 | | Rubella_Int | TNF_beta | 0.000 |
| Rubella_Int | Varicella_Int | 0.000 | | Rubella_Int | Varicella_Int | 0.000 |
| Rubella_Int | Measles_OD_DB_Int | 0.000 | | Rubella_Int | Measles_OD_DB_Int | 0.000 |
| Rubella_Int | Measles_Int | 0.000 | | Rubella_Int | Measles_Int | 0.000 |
| Rubella_Int | HepA_Int | 0.000 | | Rubella_Int | HepA_Int | 0.000 |
| Rubella_Int | Tetanus_Int | 0.000 | | Rubella_Int | Tetanus_Int | 0.000 |
| Rubella_Int | Diptheria_Int | 0.000 | | Rubella_Int | Diptheria_Int | 0.000 |
| Rubella_Int | Rubella_Int | 1.000 | | Rubella_Int | Rubella_Int | 1.000 |
| Rubella_Int | CMV_Int | 0.000 | | Rubella_Int | CMV_Int | 0.000 |
| Rubella_Int | HepB_cAb_Int | 0.000 | | Rubella_Int | HepB_cAb_Int | 0.000 |
| Rubella_Int | HepB_eAb_Int | 0.000 | | Rubella_Int | HepB_eAb_Int | 0.000 |
| Rubella_Int | HepB_eAg_Int | 0.000 | | Rubella_Int | HepB_eAg_Int | 0.000 |
| Rubella_Int | HepC_Int | 0.000 | | Rubella_Int | HepC_Int | 0.000 |
| Rubella_Int | Schistosoma_int | 0.000 | | Rubella_Int | Schistosoma_int | 0.000 |
| Rubella_Int | Strongyloides_Int | 0.000 | | Rubella_Int | Strongyloides_Int | 0.000 |
| Rubella_Int | Filaria_Int | 0.000 | | Rubella_Int | Filaria_Int | 0.000 |
| CMV_Int | IL_1_alpha | 0.000 | | CMV_Int | IL_1_alpha | 0.000 |
| CMV_Int | IL_1_beta | 0.000 | | CMV_Int | IL_1_beta | 0.000 |
| CMV_Int | IL_2 | 0.000 | | CMV_Int | IL_2 | 0.000 |
| CMV_Int | IL_4 | 0.000 | | CMV_Int | IL_4 | 0.000 |
| CMV_Int | IL_5 | 0.000 | | CMV_Int | IL_5 | 0.000 |
| CMV_Int | IL_6 | 0.000 | | CMV_Int | IL_6 | 0.000 |
| CMV_Int | IL_8 | 0.000 | | CMV_Int | IL_8 | 0.000 |
| CMV_Int | IL_10 | 0.000 | | CMV_Int | IL_10 | 0.000 |
| CMV_Int | IL_12p70 | 0.000 | | CMV_Int | IL_12p70 | 0.000 |
| CMV_Int | IL_13 | 0.000 | | CMV_Int | IL_13 | 0.000 |
| CMV_Int | IL_15 | 0.000 | | CMV_Int | IL_15 | 0.000 |
| CMV_Int | IL_17 | 0.000 | | CMV_Int | IL_17 | 0.000 |
| CMV_Int | IL_23 | 0.000 | | CMV_Int | IL_23 | 0.000 |
| CMV_Int | IFN_gamma | 0.000 | | CMV_Int | IFN_gamma | 0.000 |
| CMV_Int | TNF_alpha | 0.000 | | CMV_Int | TNF_alpha | 0.000 |
| CMV_Int | TNF_beta | 0.000 | | CMV_Int | TNF_beta | 0.000 |
| CMV_Int | Varicella_Int | 0.000 | | CMV_Int | Varicella_Int | 0.000 |
| CMV_Int | Measles_OD_DB_Int | 0.000 | | CMV_Int | Measles_OD_DB_Int | 0.000 |
| CMV_Int | Measles_Int | 0.000 | | CMV_Int | Measles_Int | 0.000 |
| CMV_Int | HepA_Int | 0.000 | | CMV_Int | HepA_Int | 0.000 |
| CMV_Int | Tetanus_Int | 0.000 | | CMV_Int | Tetanus_Int | 0.000 |
| CMV_Int | Diptheria_Int | 0.000 | | CMV_Int | Diptheria_Int | 0.000 |
| CMV_Int | Rubella_Int | 0.000 | | CMV_Int | Rubella_Int | 0.000 |
| CMV_Int | CMV_Int | 1.000 | | CMV_Int | CMV_Int | 1.000 |
| CMV_Int | HepB_cAb_Int | 0.000 | | CMV_Int | HepB_cAb_Int | 0.000 |
| CMV_Int | HepB_eAb_Int | 0.000 | | CMV_Int | HepB_eAb_Int | 0.000 |
| CMV_Int | HepB_eAg_Int | 0.000 | | CMV_Int | HepB_eAg_Int | 0.000 |

FIG. 21I15-N

| | | | | | | |
|---|---|---|---|---|---|---|
| CMV_Int | HepC_Int | 0.000 | | CMV_Int | HepC_Int | 0.000 |
| CMV_Int | Schistosoma_int | 0.000 | | CMV_Int | Schistosoma_int | 0.000 |
| CMV_Int | Strongyloides_Int | 0.000 | | CMV_Int | Strongyloides_Int | 0.000 |
| CMV_Int | Filaria_Int | 0.000 | | CMV_Int | Filaria_Int | 0.000 |
| HepB_cAb_Int | IL_1_alpha | 0.000 | | HepB_cAb_Int | IL_1_alpha | 0.000 |
| HepB_cAb_Int | IL_1_beta | 0.000 | | HepB_cAb_Int | IL_1_beta | 0.000 |
| HepB_cAb_Int | IL_2 | 0.000 | | HepB_cAb_Int | IL_2 | 0.000 |
| HepB_cAb_Int | IL_4 | 0.000 | | HepB_cAb_Int | IL_4 | 0.000 |
| HepB_cAb_Int | IL_5 | 0.000 | | HepB_cAb_Int | IL_5 | 0.000 |
| HepB_cAb_Int | IL_6 | 0.000 | | HepB_cAb_Int | IL_6 | 0.000 |
| HepB_cAb_Int | IL_8 | 0.000 | | HepB_cAb_Int | IL_8 | 0.000 |
| HepB_cAb_Int | IL_10 | 0.000 | | HepB_cAb_Int | IL_10 | 0.000 |
| HepB_cAb_Int | IL_12p70 | 0.000 | | HepB_cAb_Int | IL_12p70 | 0.000 |
| HepB_cAb_Int | IL_13 | 0.000 | | HepB_cAb_Int | IL_13 | 0.000 |
| HepB_cAb_Int | IL_15 | 0.000 | | HepB_cAb_Int | IL_15 | 0.000 |
| HepB_cAb_Int | IL_17 | 0.000 | | HepB_cAb_Int | IL_17 | 0.000 |
| HepB_cAb_Int | IL_23 | 0.000 | | HepB_cAb_Int | IL_23 | 0.000 |
| HepB_cAb_Int | IFN_gamma | 0.000 | | HepB_cAb_Int | IFN_gamma | 0.000 |
| HepB_cAb_Int | TNF_alpha | 0.000 | | HepB_cAb_Int | TNF_alpha | 0.000 |
| HepB_cAb_Int | TNF_beta | 0.000 | | HepB_cAb_Int | TNF_beta | 0.000 |
| HepB_cAb_Int | Varicella_Int | 0.000 | | HepB_cAb_Int | Varicella_Int | 0.000 |
| HepB_cAb_Int | Measles_OD_DB_Int | 0.000 | | HepB_cAb_Int | Measles_OD_DB_Int | 0.000 |
| HepB_cAb_Int | Measles_Int | 0.000 | | HepB_cAb_Int | Measles_Int | 0.000 |
| HepB_cAb_Int | HepA_Int | 0.000 | | HepB_cAb_Int | HepA_Int | 0.000 |
| HepB_cAb_Int | Tetanus_Int | 0.000 | | HepB_cAb_Int | Tetanus_Int | 0.000 |
| HepB_cAb_Int | Diptheria_Int | 0.000 | | HepB_cAb_Int | Diptheria_Int | 0.000 |
| HepB_cAb_Int | Rubella_Int | 0.000 | | HepB_cAb_Int | Rubella_Int | 0.000 |
| HepB_cAb_Int | CMV_Int | 0.000 | | HepB_cAb_Int | CMV_Int | 0.000 |
| HepB_cAb_Int | HepB_cAb_Int | 1.000 | | HepB_cAb_Int | HepB_cAb_Int | 1.000 |
| HepB_cAb_Int | HepB_eAb_Int | 0.000 | | HepB_cAb_Int | HepB_eAb_Int | 0.000 |
| HepB_cAb_Int | HepB_eAg_Int | 0.000 | | HepB_cAb_Int | HepB_eAg_Int | 0.000 |
| HepB_cAb_Int | HepC_Int | 0.000 | | HepB_cAb_Int | HepC_Int | 0.000 |
| HepB_cAb_Int | Schistosoma_int | 0.000 | | HepB_cAb_Int | Schistosoma_int | 0.000 |
| HepB_cAb_Int | Strongyloides_Int | 0.000 | | HepB_cAb_Int | Strongyloides_Int | 0.000 |
| HepB_cAb_Int | Filaria_Int | 0.000 | | HepB_cAb_Int | Filaria_Int | 0.000 |
| HepB_eAb_Int | IL_1_alpha | 0.000 | | HepB_eAb_Int | IL_1_alpha | 0.000 |
| HepB_eAb_Int | IL_1_beta | 0.000 | | HepB_eAb_Int | IL_1_beta | 0.000 |
| HepB_eAb_Int | IL_2 | 0.000 | | HepB_eAb_Int | IL_2 | 0.000 |
| HepB_eAb_Int | IL_4 | 0.000 | | HepB_eAb_Int | IL_4 | 0.000 |
| HepB_eAb_Int | IL_5 | 0.000 | | HepB_eAb_Int | IL_5 | 0.000 |
| HepB_eAb_Int | IL_6 | 0.000 | | HepB_eAb_Int | IL_6 | 0.000 |
| HepB_eAb_Int | IL_8 | 0.000 | | HepB_eAb_Int | IL_8 | 0.000 |
| HepB_eAb_Int | IL_10 | 0.000 | | HepB_eAb_Int | IL_10 | 0.000 |
| HepB_eAb_Int | IL_12p70 | 0.000 | | HepB_eAb_Int | IL_12p70 | 0.000 |
| HepB_eAb_Int | IL_13 | 0.000 | | HepB_eAb_Int | IL_13 | 0.000 |
| HepB_eAb_Int | IL_15 | 0.000 | | HepB_eAb_Int | IL_15 | 0.000 |
| HepB_eAb_Int | IL_17 | 0.000 | | HepB_eAb_Int | IL_17 | 0.000 |
| HepB_eAb_Int | IL_23 | 0.000 | | HepB_eAb_Int | IL_23 | 0.000 |
| HepB_eAb_Int | IFN_gamma | 0.000 | | HepB_eAb_Int | IFN_gamma | 0.000 |
| HepB_eAb_Int | TNF_alpha | 0.000 | | HepB_eAb_Int | TNF_alpha | 0.000 |
| HepB_eAb_Int | TNF_beta | 0.000 | | HepB_eAb_Int | TNF_beta | 0.000 |
| HepB_eAb_Int | Varicella_Int | 0.000 | | HepB_eAb_Int | Varicella_Int | 0.000 |
| HepB_eAb_Int | Measles_OD_DB_Int | 0.000 | | HepB_eAb_Int | Measles_OD_DB_Int | 0.000 |
| HepB_eAb_Int | Measles_Int | 0.000 | | HepB_eAb_Int | Measles_Int | 0.000 |
| HepB_eAb_Int | HepA_Int | 0.000 | | HepB_eAb_Int | HepA_Int | 0.000 |
| HepB_eAb_Int | Tetanus_Int | 0.000 | | HepB_eAb_Int | Tetanus_Int | 0.000 |
| HepB_eAb_Int | Diptheria_Int | 0.000 | | HepB_eAb_Int | Diptheria_Int | 0.000 |

FIG. 21I15-O

| | | | | | | |
|---|---|---|---|---|---|---|
| HepB_eAb_Int | Rubella_Int | 0.000 | | HepB_eAb_Int | Rubella_Int | 0.000 |
| HepB_eAb_Int | CMV_Int | 0.000 | | HepB_eAb_Int | CMV_Int | 0.000 |
| HepB_eAb_Int | HepB_cAb_Int | 0.000 | | HepB_eAb_Int | HepB_cAb_Int | 0.000 |
| HepB_eAb_Int | HepB_eAb_Int | 1.000 | | HepB_eAb_Int | HepB_eAb_Int | 1.000 |
| HepB_eAb_Int | HepB_eAg_Int | 0.000 | | HepB_eAb_Int | HepB_eAg_Int | 0.000 |
| HepB_eAb_Int | HepC_Int | 0.000 | | HepB_eAb_Int | HepC_Int | 0.000 |
| HepB_eAb_Int | Schistosoma_int | 0.000 | | HepB_eAb_Int | Schistosoma_int | 0.000 |
| HepB_eAb_Int | Strongyloides_Int | 0.000 | | HepB_eAb_Int | Strongyloides_Int | 0.000 |
| HepB_eAb_Int | Filaria_Int | 0.000 | | HepB_eAb_Int | Filaria_Int | 0.000 |
| HepB_eAg_Int | IL_1_alpha | 0.000 | | HepB_eAg_Int | IL_1_alpha | 0.000 |
| HepB_eAg_Int | IL_1_beta | 0.000 | | HepB_eAg_Int | IL_1_beta | 0.000 |
| HepB_eAg_Int | IL_2 | 0.000 | | HepB_eAg_Int | IL_2 | 0.000 |
| HepB_eAg_Int | IL_4 | 0.000 | | HepB_eAg_Int | IL_4 | 0.000 |
| HepB_eAg_Int | IL_5 | 0.000 | | HepB_eAg_Int | IL_5 | 0.000 |
| HepB_eAg_Int | IL_6 | 0.000 | | HepB_eAg_Int | IL_6 | 0.000 |
| HepB_eAg_Int | IL_8 | 0.000 | | HepB_eAg_Int | IL_8 | 0.000 |
| HepB_eAg_Int | IL_10 | 0.000 | | HepB_eAg_Int | IL_10 | 0.000 |
| HepB_eAg_Int | IL_12p70 | 0.000 | | HepB_eAg_Int | IL_12p70 | 0.000 |
| HepB_eAg_Int | IL_13 | 0.000 | | HepB_eAg_Int | IL_13 | 0.000 |
| HepB_eAg_Int | IL_15 | 0.000 | | HepB_eAg_Int | IL_15 | 0.000 |
| HepB_eAg_Int | IL_17 | 0.000 | | HepB_eAg_Int | IL_17 | 0.000 |
| HepB_eAg_Int | IL_23 | 0.000 | | HepB_eAg_Int | IL_23 | 0.000 |
| HepB_eAg_Int | IFN_gamma | 0.000 | | HepB_eAg_Int | IFN_gamma | 0.000 |
| HepB_eAg_Int | TNF_alpha | 0.000 | | HepB_eAg_Int | TNF_alpha | 0.000 |
| HepB_eAg_Int | TNF_beta | 0.000 | | HepB_eAg_Int | TNF_beta | 0.000 |
| HepB_eAg_Int | Varicella_Int | 0.000 | | HepB_eAg_Int | Varicella_Int | 0.000 |
| HepB_eAg_Int | Measles_OD_DB_Int | 0.000 | | HepB_eAg_Int | Measles_OD_DB_Int | 0.000 |
| HepB_eAg_Int | Measles_Int | 0.000 | | HepB_eAg_Int | Measles_Int | 0.000 |
| HepB_eAg_Int | HepA_Int | 0.000 | | HepB_eAg_Int | HepA_Int | 0.000 |
| HepB_eAg_Int | Tetanus_Int | 0.000 | | HepB_eAg_Int | Tetanus_Int | 0.000 |
| HepB_eAg_Int | Diptheria_Int | 0.000 | | HepB_eAg_Int | Diptheria_Int | 0.000 |
| HepB_eAg_Int | Rubella_Int | 0.000 | | HepB_eAg_Int | Rubella_Int | 0.000 |
| HepB_eAg_Int | CMV_Int | 0.000 | | HepB_eAg_Int | CMV_Int | 0.000 |
| HepB_eAg_Int | HepB_cAb_Int | 0.000 | | HepB_eAg_Int | HepB_cAb_Int | 0.000 |
| HepB_eAg_Int | HepB_eAb_Int | 0.000 | | HepB_eAg_Int | HepB_eAb_Int | 0.000 |
| HepB_eAg_Int | HepB_eAg_Int | 1.000 | | HepB_eAg_Int | HepB_eAg_Int | 1.000 |
| HepB_eAg_Int | HepC_Int | 0.000 | | HepB_eAg_Int | HepC_Int | 0.000 |
| HepB_eAg_Int | Schistosoma_int | 0.000 | | HepB_eAg_Int | Schistosoma_int | 0.000 |
| HepB_eAg_Int | Strongyloides_Int | 0.000 | | HepB_eAg_Int | Strongyloides_Int | 0.000 |
| HepB_eAg_Int | Filaria_Int | 0.000 | | HepB_eAg_Int | Filaria_Int | 0.000 |
| HepC_Int | IL_1_alpha | 0.000 | | HepC_Int | IL_1_alpha | 0.000 |
| HepC_Int | IL_1_beta | 0.000 | | HepC_Int | IL_1_beta | 0.000 |
| HepC_Int | IL_2 | 0.000 | | HepC_Int | IL_2 | 0.000 |
| HepC_Int | IL_4 | 0.000 | | HepC_Int | IL_4 | 0.000 |
| HepC_Int | IL_5 | 0.000 | | HepC_Int | IL_5 | 0.000 |
| HepC_Int | IL_6 | 0.000 | | HepC_Int | IL_6 | 0.000 |
| HepC_Int | IL_8 | 0.000 | | HepC_Int | IL_8 | 0.000 |
| HepC_Int | IL_10 | 0.000 | | HepC_Int | IL_10 | 0.000 |
| HepC_Int | IL_12p70 | 0.000 | | HepC_Int | IL_12p70 | 0.000 |
| HepC_Int | IL_13 | 0.000 | | HepC_Int | IL_13 | 0.000 |
| HepC_Int | IL_15 | 0.000 | | HepC_Int | IL_15 | 0.000 |
| HepC_Int | IL_17 | 0.000 | | HepC_Int | IL_17 | 0.000 |
| HepC_Int | IL_23 | 0.000 | | HepC_Int | IL_23 | 0.000 |
| HepC_Int | IFN_gamma | 0.000 | | HepC_Int | IFN_gamma | 0.000 |
| HepC_Int | TNF_alpha | 0.000 | | HepC_Int | TNF_alpha | 0.000 |
| HepC_Int | TNF_beta | 0.000 | | HepC_Int | TNF_beta | 0.000 |
| HepC_Int | Varicella_Int | 0.000 | | HepC_Int | Varicella_Int | 0.000 |

FIG. 21I15-P

| HepC_Int | Measles_OD_DB_Int | 0.000 | HepC_Int | Measles_OD_DB_Int | 0.000 |
|---|---|---|---|---|---|
| HepC_Int | Measles_Int | 0.000 | HepC_Int | Measles_Int | 0.000 |
| HepC_Int | HepA_Int | 0.000 | HepC_Int | HepA_Int | 0.000 |
| HepC_Int | Tetanus_Int | 0.000 | HepC_Int | Tetanus_Int | 0.000 |
| HepC_Int | Diptheria_Int | 0.000 | HepC_Int | Diptheria_Int | 0.000 |
| HepC_Int | Rubella_Int | 0.000 | HepC_Int | Rubella_Int | 0.000 |
| HepC_Int | CMV_Int | 0.000 | HepC_Int | CMV_Int | 0.000 |
| HepC_Int | HepB_cAb_Int | 0.000 | HepC_Int | HepB_cAb_Int | 0.000 |
| HepC_Int | HepB_eAb_Int | 0.000 | HepC_Int | HepB_eAb_Int | 0.000 |
| HepC_Int | HepB_eAg_Int | 0.000 | HepC_Int | HepB_eAg_Int | 0.000 |
| HepC_Int | HepC_Int | 1.000 | HepC_Int | HepC_Int | 1.000 |
| HepC_Int | Schistosoma_int | 0.000 | HepC_Int | Schistosoma_int | 0.000 |
| HepC_Int | Strongyloides_Int | 0.000 | HepC_Int | Strongyloides_Int | 0.000 |
| HepC_Int | Filaria_Int | 0.000 | HepC_Int | Filaria_Int | 0.000 |
| Schistosoma_int | IL_1_alpha | 0.000 | Schistosoma_int | IL_1_alpha | 0.000 |
| Schistosoma_int | IL_1_beta | 0.000 | Schistosoma_int | IL_1_beta | 0.000 |
| Schistosoma_int | IL_2 | 0.000 | Schistosoma_int | IL_2 | 0.000 |
| Schistosoma_int | IL_4 | 0.000 | Schistosoma_int | IL_4 | 0.000 |
| Schistosoma_int | IL_5 | 0.000 | Schistosoma_int | IL_5 | 0.000 |
| Schistosoma_int | IL_6 | 0.000 | Schistosoma_int | IL_6 | 0.000 |
| Schistosoma_int | IL_8 | 0.000 | Schistosoma_int | IL_8 | 0.000 |
| Schistosoma_int | IL_10 | 0.000 | Schistosoma_int | IL_10 | 0.000 |
| Schistosoma_int | IL_12p70 | 0.000 | Schistosoma_int | IL_12p70 | 0.000 |
| Schistosoma_int | IL_13 | 0.000 | Schistosoma_int | IL_13 | 0.000 |
| Schistosoma_int | IL_15 | 0.000 | Schistosoma_int | IL_15 | 0.000 |
| Schistosoma_int | IL_17 | 0.000 | Schistosoma_int | IL_17 | 0.000 |
| Schistosoma_int | IL_23 | 0.000 | Schistosoma_int | IL_23 | 0.000 |
| Schistosoma_int | IFN_gamma | 0.000 | Schistosoma_int | IFN_gamma | 0.000 |
| Schistosoma_int | TNF_alpha | 0.000 | Schistosoma_int | TNF_alpha | 0.000 |
| Schistosoma_int | TNF_beta | 0.000 | Schistosoma_int | TNF_beta | 0.000 |
| Schistosoma_int | Varicella_Int | 0.000 | Schistosoma_int | Varicella_Int | 0.000 |
| Schistosoma_int | Measles_OD_DB_Int | 0.000 | Schistosoma_int | Measles_OD_DB_Int | 0.000 |
| Schistosoma_int | Measles_Int | 0.000 | Schistosoma_int | Measles_Int | 0.000 |
| Schistosoma_int | HepA_Int | 0.000 | Schistosoma_int | HepA_Int | 0.000 |
| Schistosoma_int | Tetanus_Int | 0.000 | Schistosoma_int | Tetanus_Int | 0.000 |
| Schistosoma_int | Diptheria_Int | 0.000 | Schistosoma_int | Diptheria_Int | 0.000 |
| Schistosoma_int | Rubella_Int | 0.000 | Schistosoma_int | Rubella_Int | 0.000 |
| Schistosoma_int | CMV_Int | 0.000 | Schistosoma_int | CMV_Int | 0.000 |
| Schistosoma_int | HepB_cAb_Int | 0.000 | Schistosoma_int | HepB_cAb_Int | 0.000 |
| Schistosoma_int | HepB_eAb_Int | 0.000 | Schistosoma_int | HepB_eAb_Int | 0.000 |
| Schistosoma_int | HepB_eAg_Int | 0.000 | Schistosoma_int | HepB_eAg_Int | 0.000 |
| Schistosoma_int | HepC_Int | 0.000 | Schistosoma_int | HepC_Int | 0.000 |
| Schistosoma_int | Schistosoma_int | 1.000 | Schistosoma_int | Schistosoma_int | 1.000 |
| Schistosoma_int | Strongyloides_Int | 0.000 | Schistosoma_int | Strongyloides_Int | 0.000 |
| Schistosoma_int | Filaria_Int | 0.000 | Schistosoma_int | Filaria_Int | 0.000 |
| Strongyloides_Int | IL_1_alpha | 0.000 | Strongyloides_Int | IL_1_alpha | 0.000 |
| Strongyloides_Int | IL_1_beta | 0.000 | Strongyloides_Int | IL_1_beta | 0.000 |
| Strongyloides_Int | IL_2 | 0.000 | Strongyloides_Int | IL_2 | 0.000 |
| Strongyloides_Int | IL_4 | 0.000 | Strongyloides_Int | IL_4 | 0.000 |
| Strongyloides_Int | IL_5 | 0.000 | Strongyloides_Int | IL_5 | 0.000 |
| Strongyloides_Int | IL_6 | 0.000 | Strongyloides_Int | IL_6 | 0.000 |
| Strongyloides_Int | IL_8 | 0.000 | Strongyloides_Int | IL_8 | 0.000 |
| Strongyloides_Int | IL_10 | 0.000 | Strongyloides_Int | IL_10 | 0.000 |
| Strongyloides_Int | IL_12p70 | 0.000 | Strongyloides_Int | IL_12p70 | 0.000 |
| Strongyloides_Int | IL_13 | 0.000 | Strongyloides_Int | IL_13 | 0.000 |
| Strongyloides_Int | IL_15 | 0.000 | Strongyloides_Int | IL_15 | 0.000 |
| Strongyloides_Int | IL_17 | 0.000 | Strongyloides_Int | IL_17 | 0.000 |

FIG. 21I15-Q

| | | | | | | |
|---|---|---|---|---|---|---|
| Strongyloides_Int | IL_23 | 0.000 | | Strongyloides_Int | IL_23 | 0.000 |
| Strongyloides_Int | IFN_gamma | 0.000 | | Strongyloides_Int | IFN_gamma | 0.000 |
| Strongyloides_Int | TNF_alpha | 0.000 | | Strongyloides_Int | TNF_alpha | 0.000 |
| Strongyloides_Int | TNF_beta | 0.000 | | Strongyloides_Int | TNF_beta | 0.000 |
| Strongyloides_Int | Varicella_Int | 0.000 | | Strongyloides_Int | Varicella_Int | 0.000 |
| Strongyloides_Int | Measles_OD_DB_Int | 0.000 | | Strongyloides_Int | Measles_OD_DB_Int | 0.000 |
| Strongyloides_Int | Measles_Int | 0.000 | | Strongyloides_Int | Measles_Int | 0.000 |
| Strongyloides_Int | HepA_Int | 0.000 | | Strongyloides_Int | HepA_Int | 0.000 |
| Strongyloides_Int | Tetanus_Int | 0.000 | | Strongyloides_Int | Tetanus_Int | 0.000 |
| Strongyloides_Int | Diptheria_Int | 0.000 | | Strongyloides_Int | Diptheria_Int | 0.000 |
| Strongyloides_Int | Rubella_Int | 0.000 | | Strongyloides_Int | Rubella_Int | 0.000 |
| Strongyloides_Int | CMV_Int | 0.000 | | Strongyloides_Int | CMV_Int | 0.000 |
| Strongyloides_Int | HepB_cAb_Int | 0.000 | | Strongyloides_Int | HepB_cAb_Int | 0.000 |
| Strongyloides_Int | HepB_eAb_Int | 0.000 | | Strongyloides_Int | HepB_eAb_Int | 0.000 |
| Strongyloides_Int | HepB_eAg_Int | 0.000 | | Strongyloides_Int | HepB_eAg_Int | 0.000 |
| Strongyloides_Int | HepC_Int | 0.000 | | Strongyloides_Int | HepC_Int | 0.000 |
| Strongyloides_Int | Schistosoma_int | 0.000 | | Strongyloides_Int | Schistosoma_int | 0.000 |
| Strongyloides_Int | Strongyloides_Int | 1.000 | | Strongyloides_Int | Strongyloides_Int | 1.000 |
| Strongyloides_Int | Filaria_Int | 0.000 | | Strongyloides_Int | Filaria_Int | 0.000 |
| Filaria_Int | IL_1_alpha | 0.000 | | Filaria_Int | IL_1_alpha | 0.000 |
| Filaria_Int | IL_1_beta | 0.000 | | Filaria_Int | IL_1_beta | 0.000 |
| Filaria_Int | IL_2 | 0.000 | | Filaria_Int | IL_2 | 0.000 |
| Filaria_Int | IL_4 | 0.000 | | Filaria_Int | IL_4 | 0.000 |
| Filaria_Int | IL_5 | 0.000 | | Filaria_Int | IL_5 | 0.000 |
| Filaria_Int | IL_6 | 0.000 | | Filaria_Int | IL_6 | 0.000 |
| Filaria_Int | IL_8 | 0.000 | | Filaria_Int | IL_8 | 0.000 |
| Filaria_Int | IL_10 | 0.000 | | Filaria_Int | IL_10 | 0.000 |
| Filaria_Int | IL_12p70 | 0.000 | | Filaria_Int | IL_12p70 | 0.000 |
| Filaria_Int | IL_13 | 0.000 | | Filaria_Int | IL_13 | 0.000 |
| Filaria_Int | IL_15 | 0.000 | | Filaria_Int | IL_15 | 0.000 |
| Filaria_Int | IL_17 | 0.000 | | Filaria_Int | IL_17 | 0.000 |
| Filaria_Int | IL_23 | 0.000 | | Filaria_Int | IL_23 | 0.000 |
| Filaria_Int | IFN_gamma | 0.000 | | Filaria_Int | IFN_gamma | 0.000 |
| Filaria_Int | TNF_alpha | 0.000 | | Filaria_Int | TNF_alpha | 0.000 |
| Filaria_Int | TNF_beta | 0.000 | | Filaria_Int | TNF_beta | 0.000 |
| Filaria_Int | Varicella_Int | 0.000 | | Filaria_Int | Varicella_Int | 0.000 |
| Filaria_Int | Measles_OD_DB_Int | 0.000 | | Filaria_Int | Measles_OD_DB_Int | 0.000 |
| Filaria_Int | Measles_Int | 0.000 | | Filaria_Int | Measles_Int | 0.000 |
| Filaria_Int | HepA_Int | 0.000 | | Filaria_Int | HepA_Int | 0.000 |
| Filaria_Int | Tetanus_Int | 0.000 | | Filaria_Int | Tetanus_Int | 0.000 |
| Filaria_Int | Diptheria_Int | 0.000 | | Filaria_Int | Diptheria_Int | 0.000 |
| Filaria_Int | Rubella_Int | 0.000 | | Filaria_Int | Rubella_Int | 0.000 |
| Filaria_Int | CMV_Int | 0.000 | | Filaria_Int | CMV_Int | 0.000 |
| Filaria_Int | HepB_cAb_Int | 0.000 | | Filaria_Int | HepB_cAb_Int | 0.000 |
| Filaria_Int | HepB_eAb_Int | 0.000 | | Filaria_Int | HepB_eAb_Int | 0.000 |
| Filaria_Int | HepB_eAg_Int | 0.000 | | Filaria_Int | HepB_eAg_Int | 0.000 |
| Filaria_Int | HepC_Int | 0.000 | | Filaria_Int | HepC_int | 0.000 |
| Filaria_Int | Schistosoma_int | 0.000 | | Filaria_Int | Schistosoma_int | 0.000 |
| Filaria_Int | Strongyloides_Int | 0.000 | | Filaria_Int | Strongyloides_Int | 0.000 |
| Filaria_Int | Filaria_Int | 1.000 | | Filaria_Int | Filaria_Int | 1.000 |

FIG. 21I15-R

| 0.07% - Region_of_Origin=5, Sex=Male, IFN_gamma=22.5-37.5 | | |
|---|---|---|
| Property 1 | Property 2 | Corr. Coefficient |
| IL_1_alpha | IL_1_alpha | 1.000 |
| IL_1_alpha | IL_1_beta | 0.000 |
| IL_1_alpha | IL_2 | 0.000 |

| 0.07% - Region_of_Origin=5, Sex=Male, IFN_gamma=7.5-22.5 | | |
|---|---|---|
| Property 1 | Property 2 | Corr. Coefficient |
| IL_1_alpha | IL_1_alpha | 1.000 |
| IL_1_alpha | IL_1_beta | 0.000 |
| IL_1_alpha | IL_2 | 0.000 |

FIG. 21I16-A

| | | | | | | |
|---|---|---|---|---|---|---|
| IL_1_alpha | IL_4 | 0.000 | | IL_1_alpha | IL_4 | 0.000 |
| IL_1_alpha | IL_5 | 0.000 | | IL_1_alpha | IL_5 | 0.000 |
| IL_1_alpha | IL_6 | 0.000 | | IL_1_alpha | IL_6 | 0.000 |
| IL_1_alpha | IL_8 | 0.000 | | IL_1_alpha | IL_8 | 0.000 |
| IL_1_alpha | IL_10 | 0.000 | | IL_1_alpha | IL_10 | 0.000 |
| IL_1_alpha | IL_12p70 | 0.000 | | IL_1_alpha | IL_12p70 | 0.000 |
| IL_1_alpha | IL_13 | 0.000 | | IL_1_alpha | IL_13 | 0.000 |
| IL_1_alpha | IL_15 | 0.000 | | IL_1_alpha | IL_15 | 0.000 |
| IL_1_alpha | IL_17 | 0.000 | | IL_1_alpha | IL_17 | 0.000 |
| IL_1_alpha | IL_23 | 0.000 | | IL_1_alpha | IL_23 | 0.000 |
| IL_1_alpha | IFN_gamma | 0.000 | | IL_1_alpha | IFN_gamma | 0.000 |
| IL_1_alpha | TNF_alpha | 0.000 | | IL_1_alpha | TNF_alpha | 0.000 |
| IL_1_alpha | TNF_beta | 0.000 | | IL_1_alpha | TNF_beta | 0.000 |
| IL_1_alpha | Varicella_Int | 0.000 | | IL_1_alpha | Varicella_Int | 0.000 |
| IL_1_alpha | Measles_OD_DB_Int | 0.000 | | IL_1_alpha | Measles_OD_DB_Int | 0.000 |
| IL_1_alpha | Measles_Int | 0.000 | | IL_1_alpha | Measles_Int | 0.000 |
| IL_1_alpha | HepA_Int | 0.000 | | IL_1_alpha | HepA_Int | 0.000 |
| IL_1_alpha | Tetanus_Int | 0.000 | | IL_1_alpha | Tetanus_Int | 0.000 |
| IL_1_alpha | Diptheria_Int | 0.000 | | IL_1_alpha | Diptheria_Int | 0.000 |
| IL_1_alpha | Rubella_Int | 0.000 | | IL_1_alpha | Rubella_Int | 0.000 |
| IL_1_alpha | CMV_Int | 0.000 | | IL_1_alpha | CMV_Int | 0.000 |
| IL_1_alpha | HepB_cAb_Int | 0.000 | | IL_1_alpha | HepB_cAb_Int | 0.000 |
| IL_1_alpha | HepB_eAb_Int | 0.000 | | IL_1_alpha | HepB_eAb_Int | 0.000 |
| IL_1_alpha | HepB_eAg_Int | 0.000 | | IL_1_alpha | HepB_eAg_Int | 0.000 |
| IL_1_alpha | HepC_Int | 0.000 | | IL_1_alpha | HepC_Int | 0.000 |
| IL_1_alpha | Schistosoma_int | 0.000 | | IL_1_alpha | Schistosoma_int | 0.000 |
| IL_1_alpha | Strongyloides_Int | 0.000 | | IL_1_alpha | Strongyloides_Int | 0.000 |
| IL_1_alpha | Filaria_Int | 0.000 | | IL_1_alpha | Filaria_Int | 0.000 |
| IL_1_beta | IL_1_alpha | 0.000 | | IL_1_beta | IL_1_alpha | 0.000 |
| IL_1_beta | IL_1_beta | 1.000 | | IL_1_beta | IL_1_beta | 1.000 |
| IL_1_beta | IL_2 | 0.000 | | IL_1_beta | IL_2 | 0.000 |
| IL_1_beta | IL_4 | 0.000 | | IL_1_beta | IL_4 | 0.000 |
| IL_1_beta | IL_5 | 0.000 | | IL_1_beta | IL_5 | 0.000 |
| IL_1_beta | IL_6 | 0.000 | | IL_1_beta | IL_6 | 0.000 |
| IL_1_beta | IL_8 | 0.000 | | IL_1_beta | IL_8 | 0.000 |
| IL_1_beta | IL_10 | 0.000 | | IL_1_beta | IL_10 | 0.000 |
| IL_1_beta | IL_12p70 | 0.000 | | IL_1_beta | IL_12p70 | 0.000 |
| IL_1_beta | IL_13 | 0.000 | | IL_1_beta | IL_13 | 0.000 |
| IL_1_beta | IL_15 | 0.000 | | IL_1_beta | IL_15 | 0.000 |
| IL_1_beta | IL_17 | 0.000 | | IL_1_beta | IL_17 | 0.000 |
| IL_1_beta | IL_23 | 0.000 | | IL_1_beta | IL_23 | 0.000 |
| IL_1_beta | IFN_gamma | 0.000 | | IL_1_beta | IFN_gamma | 0.000 |
| IL_1_beta | TNF_alpha | 0.000 | | IL_1_beta | TNF_alpha | 0.000 |
| IL_1_beta | TNF_beta | 0.000 | | IL_1_beta | TNF_beta | 0.000 |
| IL_1_beta | Varicella_Int | 0.000 | | IL_1_beta | Varicella_Int | 0.000 |
| IL_1_beta | Measles_OD_DB_Int | 0.000 | | IL_1_beta | Measles_OD_DB_Int | 0.000 |
| IL_1_beta | Measles_Int | 0.000 | | IL_1_beta | Measles_Int | 0.000 |
| IL_1_beta | HepA_Int | 0.000 | | IL_1_beta | HepA_Int | 0.000 |
| IL_1_beta | Tetanus_Int | 0.000 | | IL_1_beta | Tetanus_Int | 0.000 |
| IL_1_beta | Diptheria_Int | 0.000 | | IL_1_beta | Diptheria_Int | 0.000 |
| IL_1_beta | Rubella_Int | 0.000 | | IL_1_beta | Rubella_Int | 0.000 |
| IL_1_beta | CMV_Int | 0.000 | | IL_1_beta | CMV_Int | 0.000 |
| IL_1_beta | HepB_cAb_Int | 0.000 | | IL_1_beta | HepB_cAb_Int | 0.000 |
| IL_1_beta | HepB_eAb_Int | 0.000 | | IL_1_beta | HepB_eAb_Int | 0.000 |
| IL_1_beta | HepB_eAg_Int | 0.000 | | IL_1_beta | HepB_eAg_Int | 0.000 |
| IL_1_beta | HepC_Int | 0.000 | | IL_1_beta | HepC_Int | 0.000 |
| IL_1_beta | Schistosoma_int | 0.000 | | IL_1_beta | Schistosoma_int | 0.000 |

FIG. 21I16-B

| | | | | | | |
|---|---|---|---|---|---|---|
| IL_1_beta | Strongyloides_Int | 0.000 | | IL_1_beta | Strongyloides_Int | 0.000 |
| IL_1_beta | Filaria_Int | 0.000 | | IL_1_beta | Filaria_Int | 0.000 |
| IL_2 | IL_1_alpha | 0.000 | | IL_2 | IL_1_alpha | 0.000 |
| IL_2 | IL_1_beta | 0.000 | | IL_2 | IL_1_beta | 0.000 |
| IL_2 | IL_2 | 1.000 | | IL_2 | IL_2 | 1.000 |
| IL_2 | IL_4 | 0.000 | | IL_2 | IL_4 | 0.000 |
| IL_2 | IL_5 | 0.000 | | IL_2 | IL_5 | 0.000 |
| IL_2 | IL_6 | 0.000 | | IL_2 | IL_6 | 0.000 |
| IL_2 | IL_8 | 0.000 | | IL_2 | IL_8 | 0.000 |
| IL_2 | IL_10 | 0.000 | | IL_2 | IL_10 | 0.000 |
| IL_2 | IL_12p70 | 0.000 | | IL_2 | IL_12p70 | 0.000 |
| IL_2 | IL_13 | 0.000 | | IL_2 | IL_13 | 0.000 |
| IL_2 | IL_15 | 0.000 | | IL_2 | IL_15 | 0.000 |
| IL_2 | IL_17 | 0.000 | | IL_2 | IL_17 | 0.000 |
| IL_2 | IL_23 | 0.000 | | IL_2 | IL_23 | 0.000 |
| IL_2 | IFN_gamma | 0.000 | | IL_2 | IFN_gamma | 0.000 |
| IL_2 | TNF_alpha | 0.000 | | IL_2 | TNF_alpha | 0.000 |
| IL_2 | TNF_beta | 0.000 | | IL_2 | TNF_beta | 0.000 |
| IL_2 | Varicella_Int | 0.000 | | IL_2 | Varicella_Int | 0.000 |
| IL_2 | Measles_OD_DB_Int | 0.000 | | IL_2 | Measles_OD_DB_Int | 0.000 |
| IL_2 | Measles_Int | 0.000 | | IL_2 | Measles_Int | 0.000 |
| IL_2 | HepA_Int | 0.000 | | IL_2 | HepA_Int | 0.000 |
| IL_2 | Tetanus_Int | 0.000 | | IL_2 | Tetanus_Int | 0.000 |
| IL_2 | Diptheria_Int | 0.000 | | IL_2 | Diptheria_Int | 0.000 |
| IL_2 | Rubella_Int | 0.000 | | IL_2 | Rubella_Int | 0.000 |
| IL_2 | CMV_Int | 0.000 | | IL_2 | CMV_Int | 0.000 |
| IL_2 | HepB_cAb_Int | 0.000 | | IL_2 | HepB_cAb_Int | 0.000 |
| IL_2 | HepB_eAb_Int | 0.000 | | IL_2 | HepB_eAb_Int | 0.000 |
| IL_2 | HepB_eAg_Int | 0.000 | | IL_2 | HepB_eAg_Int | 0.000 |
| IL_2 | HepC_Int | 0.000 | | IL_2 | HepC_Int | 0.000 |
| IL_2 | Schistosoma_int | 0.000 | | IL_2 | Schistosoma_int | 0.000 |
| IL_2 | Strongyloides_Int | 0.000 | | IL_2 | Strongyloides_Int | 0.000 |
| IL_2 | Filaria_Int | 0.000 | | IL_2 | Filaria_Int | 0.000 |
| IL_4 | IL_1_alpha | 0.000 | | IL_4 | IL_1_alpha | 0.000 |
| IL_4 | IL_1_beta | 0.000 | | IL_4 | IL_1_beta | 0.000 |
| IL_4 | IL_2 | 0.000 | | IL_4 | IL_2 | 0.000 |
| IL_4 | IL_4 | 1.000 | | IL_4 | IL_4 | 1.000 |
| IL_4 | IL_5 | 0.000 | | IL_4 | IL_5 | 0.000 |
| IL_4 | IL_6 | 0.000 | | IL_4 | IL_6 | 0.000 |
| IL_4 | IL_8 | 0.000 | | IL_4 | IL_8 | 0.000 |
| IL_4 | IL_10 | 0.000 | | IL_4 | IL_10 | 0.000 |
| IL_4 | IL_12p70 | 0.000 | | IL_4 | IL_12p70 | 0.000 |
| IL_4 | IL_13 | 0.000 | | IL_4 | IL_13 | 0.000 |
| IL_4 | IL_15 | 0.000 | | IL_4 | IL_15 | 0.000 |
| IL_4 | IL_17 | 0.000 | | IL_4 | IL_17 | 0.000 |
| IL_4 | IL_23 | 0.000 | | IL_4 | IL_23 | 0.000 |
| IL_4 | IFN_gamma | 0.000 | | IL_4 | IFN_gamma | 0.000 |
| IL_4 | TNF_alpha | 0.000 | | IL_4 | TNF_alpha | 0.000 |
| IL_4 | TNF_beta | 0.000 | | IL_4 | TNF_beta | 0.000 |
| IL_4 | Varicella_Int | 0.000 | | IL_4 | Varicella_Int | 0.000 |
| IL_4 | Measles_OD_DB_Int | 0.000 | | IL_4 | Measles_OD_DB_Int | 0.000 |
| IL_4 | Measles_Int | 0.000 | | IL_4 | Measles_Int | 0.000 |
| IL_4 | HepA_Int | 0.000 | | IL_4 | HepA_Int | 0.000 |
| IL_4 | Tetanus_Int | 0.000 | | IL_4 | Tetanus_Int | 0.000 |
| IL_4 | Diptheria_Int | 0.000 | | IL_4 | Diptheria_Int | 0.000 |
| IL_4 | Rubella_Int | 0.000 | | IL_4 | Rubella_Int | 0.000 |
| IL_4 | CMV_Int | 0.000 | | IL_4 | CMV_Int | 0.000 |

FIG. 21I16-C

| | | | | | | |
|---|---|---|---|---|---|---|
| IL_4 | HepB_cAb_Int | 0.000 | | IL_4 | HepB_cAb_Int | 0.000 |
| IL_4 | HepB_eAb_Int | 0.000 | | IL_4 | HepB_eAb_Int | 0.000 |
| IL_4 | HepB_eAg_Int | 0.000 | | IL_4 | HepB_eAg_Int | 0.000 |
| IL_4 | HepC_Int | 0.000 | | IL_4 | HepC_Int | 0.000 |
| IL_4 | Schistosoma_int | 0.000 | | IL_4 | Schistosoma_int | 0.000 |
| IL_4 | Strongyloides_Int | 0.000 | | IL_4 | Strongyloides_Int | 0.000 |
| IL_4 | Filaria_Int | 0.000 | | IL_4 | Filaria_Int | 0.000 |
| IL_5 | IL_1_alpha | 0.000 | | IL_5 | IL_1_alpha | 0.000 |
| IL_5 | IL_1_beta | 0.000 | | IL_5 | IL_1_beta | 0.000 |
| IL_5 | IL_2 | 0.000 | | IL_5 | IL_2 | 0.000 |
| IL_5 | IL_4 | 0.000 | | IL_5 | IL_4 | 0.000 |
| IL_5 | IL_5 | 1.000 | | IL_5 | IL_5 | 1.000 |
| IL_5 | IL_6 | 0.000 | | IL_5 | IL_6 | 0.000 |
| IL_5 | IL_8 | 0.000 | | IL_5 | IL_8 | 0.000 |
| IL_5 | IL_10 | 0.000 | | IL_5 | IL_10 | 0.000 |
| IL_5 | IL_12p70 | 0.000 | | IL_5 | IL_12p70 | 0.000 |
| IL_5 | IL_13 | 0.000 | | IL_5 | IL_13 | 0.000 |
| IL_5 | IL_15 | 0.000 | | IL_5 | IL_15 | 0.000 |
| IL_5 | IL_17 | 0.000 | | IL_5 | IL_17 | 0.000 |
| IL_5 | IL_23 | 0.000 | | IL_5 | IL_23 | 0.000 |
| IL_5 | IFN_gamma | 0.000 | | IL_5 | IFN_gamma | 0.000 |
| IL_5 | TNF_alpha | 0.000 | | IL_5 | TNF_alpha | 0.000 |
| IL_5 | TNF_beta | 0.000 | | IL_5 | TNF_beta | 0.000 |
| IL_5 | Varicella_Int | 0.000 | | IL_5 | Varicella_Int | 0.000 |
| IL_5 | Measles_OD_DB_Int | 0.000 | | IL_5 | Measles_OD_DB_Int | 0.000 |
| IL_5 | Measles_Int | 0.000 | | IL_5 | Measles_Int | 0.000 |
| IL_5 | HepA_Int | 0.000 | | IL_5 | HepA_Int | 0.000 |
| IL_5 | Tetanus_Int | 0.000 | | IL_5 | Tetanus_Int | 0.000 |
| IL_5 | Diptheria_Int | 0.000 | | IL_5 | Diptheria_Int | 0.000 |
| IL_5 | Rubella_Int | 0.000 | | IL_5 | Rubella_Int | 0.000 |
| IL_5 | CMV_Int | 0.000 | | IL_5 | CMV_Int | 0.000 |
| IL_5 | HepB_cAb_Int | 0.000 | | IL_5 | HepB_cAb_Int | 0.000 |
| IL_5 | HepB_eAb_Int | 0.000 | | IL_5 | HepB_eAb_Int | 0.000 |
| IL_5 | HepB_eAg_Int | 0.000 | | IL_5 | HepB_eAg_Int | 0.000 |
| IL_5 | HepC_Int | 0.000 | | IL_5 | HepC_Int | 0.000 |
| IL_5 | Schistosoma_int | 0.000 | | IL_5 | Schistosoma_int | 0.000 |
| IL_5 | Strongyloides_Int | 0.000 | | IL_5 | Strongyloides_Int | 0.000 |
| IL_5 | Filaria_Int | 0.000 | | IL_5 | Filaria_Int | 0.000 |
| IL_6 | IL_1_alpha | 0.000 | | IL_6 | IL_1_alpha | 0.000 |
| IL_6 | IL_1_beta | 0.000 | | IL_6 | IL_1_beta | 0.000 |
| IL_6 | IL_2 | 0.000 | | IL_6 | IL_2 | 0.000 |
| IL_6 | IL_4 | 0.000 | | IL_6 | IL_4 | 0.000 |
| IL_6 | IL_5 | 0.000 | | IL_6 | IL_5 | 0.000 |
| IL_6 | IL_6 | 1.000 | | IL_6 | IL_6 | 1.000 |
| IL_6 | IL_8 | 0.000 | | IL_6 | IL_8 | 0.000 |
| IL_6 | IL_10 | 0.000 | | IL_6 | IL_10 | 0.000 |
| IL_6 | IL_12p70 | 0.000 | | IL_6 | IL_12p70 | 0.000 |
| IL_6 | IL_13 | 0.000 | | IL_6 | IL_13 | 0.000 |
| IL_6 | IL_15 | 0.000 | | IL_6 | IL_15 | 0.000 |
| IL_6 | IL_17 | 0.000 | | IL_6 | IL_17 | 0.000 |
| IL_6 | IL_23 | 0.000 | | IL_6 | IL_23 | 0.000 |
| IL_6 | IFN_gamma | 0.000 | | IL_6 | IFN_gamma | 0.000 |
| IL_6 | TNF_alpha | 0.000 | | IL_6 | TNF_alpha | 0.000 |
| IL_6 | TNF_beta | 0.000 | | IL_6 | TNF_beta | 0.000 |
| IL_6 | Varicella_Int | 0.000 | | IL_6 | Varicella_Int | 0.000 |
| IL_6 | Measles_OD_DB_Int | 0.000 | | IL_6 | Measles_OD_DB_Int | 0.000 |
| IL_6 | Measles_Int | 0.000 | | IL_6 | Measles_Int | 0.000 |

FIG. 21I16-D

| | | | | | | |
|---|---|---|---|---|---|---|
| IL_6 | HepA_Int | 0.000 | | IL_6 | HepA_Int | 0.000 |
| IL_6 | Tetanus_Int | 0.000 | | IL_6 | Tetanus_Int | 0.000 |
| IL_6 | Diptheria_Int | 0.000 | | IL_6 | Diptheria_Int | 0.000 |
| IL_6 | Rubella_Int | 0.000 | | IL_6 | Rubella_Int | 0.000 |
| IL_6 | CMV_Int | 0.000 | | IL_6 | CMV_Int | 0.000 |
| IL_6 | HepB_cAb_Int | 0.000 | | IL_6 | HepB_cAb_Int | 0.000 |
| IL_6 | HepB_eAb_Int | 0.000 | | IL_6 | HepB_eAb_Int | 0.000 |
| IL_6 | HepB_eAg_Int | 0.000 | | IL_6 | HepB_eAg_Int | 0.000 |
| IL_6 | HepC_Int | 0.000 | | IL_6 | HepC_Int | 0.000 |
| IL_6 | Schistosoma_int | 0.000 | | IL_6 | Schistosoma_int | 0.000 |
| IL_6 | Strongyloides_Int | 0.000 | | IL_6 | Strongyloides_Int | 0.000 |
| IL_6 | Filaria_Int | 0.000 | | IL_6 | Filaria_Int | 0.000 |
| IL_8 | IL_1_alpha | 0.000 | | IL_8 | IL_1_alpha | 0.000 |
| IL_8 | IL_1_beta | 0.000 | | IL_8 | IL_1_beta | 0.000 |
| IL_8 | IL_2 | 0.000 | | IL_8 | IL_2 | 0.000 |
| IL_8 | IL_4 | 0.000 | | IL_8 | IL_4 | 0.000 |
| IL_8 | IL_5 | 0.000 | | IL_8 | IL_5 | 0.000 |
| IL_8 | IL_6 | 0.000 | | IL_8 | IL_6 | 0.000 |
| IL_8 | IL_8 | 1.000 | | IL_8 | IL_8 | 1.000 |
| IL_8 | IL_10 | 0.000 | | IL_8 | IL_10 | 0.000 |
| IL_8 | IL_12p70 | 0.000 | | IL_8 | IL_12p70 | 0.000 |
| IL_8 | IL_13 | 0.000 | | IL_8 | IL_13 | 0.000 |
| IL_8 | IL_15 | 0.000 | | IL_8 | IL_15 | 0.000 |
| IL_8 | IL_17 | 0.000 | | IL_8 | IL_17 | 0.000 |
| IL_8 | IL_23 | 0.000 | | IL_8 | IL_23 | 0.000 |
| IL_8 | IFN_gamma | 0.000 | | IL_8 | IFN_gamma | 0.000 |
| IL_8 | TNF_alpha | 0.000 | | IL_8 | TNF_alpha | 0.000 |
| IL_8 | TNF_beta | 0.000 | | IL_8 | TNF_beta | 0.000 |
| IL_8 | Varicella_Int | 0.000 | | IL_8 | Varicella_Int | 0.000 |
| IL_8 | Measles_OD_DB_Int | 0.000 | | IL_8 | Measles_OD_DB_Int | 0.000 |
| IL_8 | Measles_Int | 0.000 | | IL_8 | Measles_Int | 0.000 |
| IL_8 | HepA_Int | 0.000 | | IL_8 | HepA_Int | 0.000 |
| IL_8 | Tetanus_Int | 0.000 | | IL_8 | Tetanus_Int | 0.000 |
| IL_8 | Diptheria_Int | 0.000 | | IL_8 | Diptheria_Int | 0.000 |
| IL_8 | Rubella_Int | 0.000 | | IL_8 | Rubella_Int | 0.000 |
| IL_8 | CMV_Int | 0.000 | | IL_8 | CMV_Int | 0.000 |
| IL_8 | HepB_cAb_Int | 0.000 | | IL_8 | HepB_cAb_Int | 0.000 |
| IL_8 | HepB_eAb_Int | 0.000 | | IL_8 | HepB_eAb_Int | 0.000 |
| IL_8 | HepB_eAg_Int | 0.000 | | IL_8 | HepB_eAg_Int | 0.000 |
| IL_8 | HepC_Int | 0.000 | | IL_8 | HepC_Int | 0.000 |
| IL_8 | Schistosoma_int | 0.000 | | IL_8 | Schistosoma_int | 0.000 |
| IL_8 | Strongyloides_Int | 0.000 | | IL_8 | Strongyloides_Int | 0.000 |
| IL_8 | Filaria_Int | 0.000 | | IL_8 | Filaria_Int | 0.000 |
| IL_10 | IL_1_alpha | 0.000 | | IL_10 | IL_1_alpha | 0.000 |
| IL_10 | IL_1_beta | 0.000 | | IL_10 | IL_1_beta | 0.000 |
| IL_10 | IL_2 | 0.000 | | IL_10 | IL_2 | 0.000 |
| IL_10 | IL_4 | 0.000 | | IL_10 | IL_4 | 0.000 |
| IL_10 | IL_5 | 0.000 | | IL_10 | IL_5 | 0.000 |
| IL_10 | IL_6 | 0.000 | | IL_10 | IL_6 | 0.000 |
| IL_10 | IL_8 | 0.000 | | IL_10 | IL_8 | 0.000 |
| IL_10 | IL_10 | 1.000 | | IL_10 | IL_10 | 1.000 |
| IL_10 | IL_12p70 | 0.000 | | IL_10 | IL_12p70 | 0.000 |
| IL_10 | IL_13 | 0.000 | | IL_10 | IL_13 | 0.000 |
| IL_10 | IL_15 | 0.000 | | IL_10 | IL_15 | 0.000 |
| IL_10 | IL_17 | 0.000 | | IL_10 | IL_17 | 0.000 |
| IL_10 | IL_23 | 0.000 | | IL_10 | IL_23 | 0.000 |
| IL_10 | IFN_gamma | 0.000 | | IL_10 | IFN_gamma | 0.000 |

FIG. 21I16-E

| | | | | | | |
|---|---|---|---|---|---|---|
| IL_10 | TNF_alpha | 0.000 | | IL_10 | TNF_alpha | 0.000 |
| IL_10 | TNF_beta | 0.000 | | IL_10 | TNF_beta | 0.000 |
| IL_10 | Varicella_Int | 0.000 | | IL_10 | Varicella_Int | 0.000 |
| IL_10 | Measles_OD_DB_Int | 0.000 | | IL_10 | Measles_OD_DB_Int | 0.000 |
| IL_10 | Measles_Int | 0.000 | | IL_10 | Measles_Int | 0.000 |
| IL_10 | HepA_Int | 0.000 | | IL_10 | HepA_Int | 0.000 |
| IL_10 | Tetanus_Int | 0.000 | | IL_10 | Tetanus_Int | 0.000 |
| IL_10 | Diptheria_Int | 0.000 | | IL_10 | Diptheria_Int | 0.000 |
| IL_10 | Rubella_Int | 0.000 | | IL_10 | Rubella_Int | 0.000 |
| IL_10 | CMV_Int | 0.000 | | IL_10 | CMV_Int | 0.000 |
| IL_10 | HepB_cAb_Int | 0.000 | | IL_10 | HepB_cAb_Int | 0.000 |
| IL_10 | HepB_eAb_Int | 0.000 | | IL_10 | HepB_eAb_Int | 0.000 |
| IL_10 | HepB_eAg_Int | 0.000 | | IL_10 | HepB_eAg_Int | 0.000 |
| IL_10 | HepC_Int | 0.000 | | IL_10 | HepC_Int | 0.000 |
| IL_10 | Schistosoma_int | 0.000 | | IL_10 | Schistosoma_int | 0.000 |
| IL_10 | Strongyloides_Int | 0.000 | | IL_10 | Strongyloides_Int | 0.000 |
| IL_10 | Filaria_Int | 0.000 | | IL_10 | Filaria_Int | 0.000 |
| IL_12p70 | IL_1_alpha | 0.000 | | IL_12p70 | IL_1_alpha | 0.000 |
| IL_12p70 | IL_1_beta | 0.000 | | IL_12p70 | IL_1_beta | 0.000 |
| IL_12p70 | IL_2 | 0.000 | | IL_12p70 | IL_2 | 0.000 |
| IL_12p70 | IL_4 | 0.000 | | IL_12p70 | IL_4 | 0.000 |
| IL_12p70 | IL_5 | 0.000 | | IL_12p70 | IL_5 | 0.000 |
| IL_12p70 | IL_6 | 0.000 | | IL_12p70 | IL_6 | 0.000 |
| IL_12p70 | IL_8 | 0.000 | | IL_12p70 | IL_8 | 0.000 |
| IL_12p70 | IL_10 | 0.000 | | IL_12p70 | IL_10 | 0.000 |
| IL_12p70 | IL_12p70 | 1.000 | | IL_12p70 | IL_12p70 | 1.000 |
| IL_12p70 | IL_13 | 0.000 | | IL_12p70 | IL_13 | 0.000 |
| IL_12p70 | IL_15 | 0.000 | | IL_12p70 | IL_15 | 0.000 |
| IL_12p70 | IL_17 | 0.000 | | IL_12p70 | IL_17 | 0.000 |
| IL_12p70 | IL_23 | 0.000 | | IL_12p70 | IL_23 | 0.000 |
| IL_12p70 | IFN_gamma | 0.000 | | IL_12p70 | IFN_gamma | 0.000 |
| IL_12p70 | TNF_alpha | 0.000 | | IL_12p70 | TNF_alpha | 0.000 |
| IL_12p70 | TNF_beta | 0.000 | | IL_12p70 | TNF_beta | 0.000 |
| IL_12p70 | Varicella_Int | 0.000 | | IL_12p70 | Varicella_Int | 0.000 |
| IL_12p70 | Measles_OD_DB_Int | 0.000 | | IL_12p70 | Measles_OD_DB_Int | 0.000 |
| IL_12p70 | Measles_Int | 0.000 | | IL_12p70 | Measles_Int | 0.000 |
| IL_12p70 | HepA_Int | 0.000 | | IL_12p70 | HepA_Int | 0.000 |
| IL_12p70 | Tetanus_Int | 0.000 | | IL_12p70 | Tetanus_Int | 0.000 |
| IL_12p70 | Diptheria_Int | 0.000 | | IL_12p70 | Diptheria_Int | 0.000 |
| IL_12p70 | Rubella_Int | 0.000 | | IL_12p70 | Rubella_Int | 0.000 |
| IL_12p70 | CMV_Int | 0.000 | | IL_12p70 | CMV_Int | 0.000 |
| IL_12p70 | HepB_cAb_Int | 0.000 | | IL_12p70 | HepB_cAb_Int | 0.000 |
| IL_12p70 | HepB_eAb_Int | 0.000 | | IL_12p70 | HepB_eAb_Int | 0.000 |
| IL_12p70 | HepB_eAg_Int | 0.000 | | IL_12p70 | HepB_eAg_Int | 0.000 |
| IL_12p70 | HepC_Int | 0.000 | | IL_12p70 | HepC_Int | 0.000 |
| IL_12p70 | Schistosoma_int | 0.000 | | IL_12p70 | Schistosoma_int | 0.000 |
| IL_12p70 | Strongyloides_Int | 0.000 | | IL_12p70 | Strongyloides_Int | 0.000 |
| IL_12p70 | Filaria_Int | 0.000 | | IL_12p70 | Filaria_Int | 0.000 |
| IL_13 | IL_1_alpha | 0.000 | | IL_13 | IL_1_alpha | 0.000 |
| IL_13 | IL_1_beta | 0.000 | | IL_13 | IL_1_beta | 0.000 |
| IL_13 | IL_2 | 0.000 | | IL_13 | IL_2 | 0.000 |
| IL_13 | IL_4 | 0.000 | | IL_13 | IL_4 | 0.000 |
| IL_13 | IL_5 | 0.000 | | IL_13 | IL_5 | 0.000 |
| IL_13 | IL_6 | 0.000 | | IL_13 | IL_6 | 0.000 |
| IL_13 | IL_8 | 0.000 | | IL_13 | IL_8 | 0.000 |
| IL_13 | IL_10 | 0.000 | | IL_13 | IL_10 | 0.000 |
| IL_13 | IL_12p70 | 0.000 | | IL_13 | IL_12p70 | 0.000 |

FIG. 21I16-F

| | | | | | | |
|---|---|---|---|---|---|---|
| IL_13 | IL_13 | 1.000 | | IL_13 | IL_13 | 1.000 |
| IL_13 | IL_15 | 0.000 | | IL_13 | IL_15 | 0.000 |
| IL_13 | IL_17 | 0.000 | | IL_13 | IL_17 | 0.000 |
| IL_13 | IL_23 | 0.000 | | IL_13 | IL_23 | 0.000 |
| IL_13 | IFN_gamma | 0.000 | | IL_13 | IFN_gamma | 0.000 |
| IL_13 | TNF_alpha | 0.000 | | IL_13 | TNF_alpha | 0.000 |
| IL_13 | TNF_beta | 0.000 | | IL_13 | TNF_beta | 0.000 |
| IL_13 | Varicella_Int | 0.000 | | IL_13 | Varicella_Int | 0.000 |
| IL_13 | Measles_OD_DB_Int | 0.000 | | IL_13 | Measles_OD_DB_Int | 0.000 |
| IL_13 | Measles_Int | 0.000 | | IL_13 | Measles_Int | 0.000 |
| IL_13 | HepA_Int | 0.000 | | IL_13 | HepA_Int | 0.000 |
| IL_13 | Tetanus_Int | 0.000 | | IL_13 | Tetanus_Int | 0.000 |
| IL_13 | Diptheria_Int | 0.000 | | IL_13 | Diptheria_Int | 0.000 |
| IL_13 | Rubella_Int | 0.000 | | IL_13 | Rubella_Int | 0.000 |
| IL_13 | CMV_Int | 0.000 | | IL_13 | CMV_Int | 0.000 |
| IL_13 | HepB_cAb_Int | 0.000 | | IL_13 | HepB_cAb_Int | 0.000 |
| IL_13 | HepB_eAb_Int | 0.000 | | IL_13 | HepB_eAb_Int | 0.000 |
| IL_13 | HepB_eAg_Int | 0.000 | | IL_13 | HepB_eAg_Int | 0.000 |
| IL_13 | HepC_Int | 0.000 | | IL_13 | HepC_Int | 0.000 |
| IL_13 | Schistosoma_int | 0.000 | | IL_13 | Schistosoma_int | 0.000 |
| IL_13 | Strongyloides_Int | 0.000 | | IL_13 | Strongyloides_Int | 0.000 |
| IL_13 | Filaria_Int | 0.000 | | IL_13 | Filaria_Int | 0.000 |
| IL_15 | IL_1_alpha | 0.000 | | IL_15 | IL_1_alpha | 0.000 |
| IL_15 | IL_1_beta | 0.000 | | IL_15 | IL_1_beta | 0.000 |
| IL_15 | IL_2 | 0.000 | | IL_15 | IL_2 | 0.000 |
| IL_15 | IL_4 | 0.000 | | IL_15 | IL_4 | 0.000 |
| IL_15 | IL_5 | 0.000 | | IL_15 | IL_5 | 0.000 |
| IL_15 | IL_6 | 0.000 | | IL_15 | IL_6 | 0.000 |
| IL_15 | IL_8 | 0.000 | | IL_15 | IL_8 | 0.000 |
| IL_15 | IL_10 | 0.000 | | IL_15 | IL_10 | 0.000 |
| IL_15 | IL_12p70 | 0.000 | | IL_15 | IL_12p70 | 0.000 |
| IL_15 | IL_13 | 0.000 | | IL_15 | IL_13 | 0.000 |
| IL_15 | IL_15 | 1.000 | | IL_15 | IL_15 | 1.000 |
| IL_15 | IL_17 | 0.000 | | IL_15 | IL_17 | 0.000 |
| IL_15 | IL_23 | 0.000 | | IL_15 | IL_23 | 0.000 |
| IL_15 | IFN_gamma | 0.000 | | IL_15 | IFN_gamma | 0.000 |
| IL_15 | TNF_alpha | 0.000 | | IL_15 | TNF_alpha | 0.000 |
| IL_15 | TNF_beta | 0.000 | | IL_15 | TNF_beta | 0.000 |
| IL_15 | Varicella_Int | 0.000 | | IL_15 | Varicella_Int | 0.000 |
| IL_15 | Measles_OD_DB_Int | 0.000 | | IL_15 | Measles_OD_DB_Int | 0.000 |
| IL_15 | Measles_Int | 0.000 | | IL_15 | Measles_Int | 0.000 |
| IL_15 | HepA_Int | 0.000 | | IL_15 | HepA_Int | 0.000 |
| IL_15 | Tetanus_Int | 0.000 | | IL_15 | Tetanus_Int | 0.000 |
| IL_15 | Diptheria_Int | 0.000 | | IL_15 | Diptheria_Int | 0.000 |
| IL_15 | Rubella_Int | 0.000 | | IL_15 | Rubella_Int | 0.000 |
| IL_15 | CMV_Int | 0.000 | | IL_15 | CMV_Int | 0.000 |
| IL_15 | HepB_cAb_Int | 0.000 | | IL_15 | HepB_cAb_Int | 0.000 |
| IL_15 | HepB_eAb_Int | 0.000 | | IL_15 | HepB_eAb_Int | 0.000 |
| IL_15 | HepB_eAg_Int | 0.000 | | IL_15 | HepB_eAg_Int | 0.000 |
| IL_15 | HepC_Int | 0.000 | | IL_15 | HepC_Int | 0.000 |
| IL_15 | Schistosoma_int | 0.000 | | IL_15 | Schistosoma_int | 0.000 |
| IL_15 | Strongyloides_Int | 0.000 | | IL_15 | Strongyloides_Int | 0.000 |
| IL_15 | Filaria_Int | 0.000 | | IL_15 | Filaria_Int | 0.000 |
| IL_17 | IL_1_alpha | 0.000 | | IL_17 | IL_1_alpha | 0.000 |
| IL_17 | IL_1_beta | 0.000 | | IL_17 | IL_1_beta | 0.000 |
| IL_17 | IL_2 | 0.000 | | IL_17 | IL_2 | 0.000 |
| IL_17 | IL_4 | 0.000 | | IL_17 | IL_4 | 0.000 |

FIG. 21I16-G

| IL_17 | IL_5 | 0.000 | | IL_17 | IL_5 | 0.000 |
|---|---|---|---|---|---|---|
| IL_17 | IL_6 | 0.000 | | IL_17 | IL_6 | 0.000 |
| IL_17 | IL_8 | 0.000 | | IL_17 | IL_8 | 0.000 |
| IL_17 | IL_10 | 0.000 | | IL_17 | IL_10 | 0.000 |
| IL_17 | IL_12p70 | 0.000 | | IL_17 | IL_12p70 | 0.000 |
| IL_17 | IL_13 | 0.000 | | IL_17 | IL_13 | 0.000 |
| IL_17 | IL_15 | 0.000 | | IL_17 | IL_15 | 0.000 |
| IL_17 | IL_17 | 1.000 | | IL_17 | IL_17 | 1.000 |
| IL_17 | IL_23 | 0.000 | | IL_17 | IL_23 | 0.000 |
| IL_17 | IFN_gamma | 0.000 | | IL_17 | IFN_gamma | 0.000 |
| IL_17 | TNF_alpha | 0.000 | | IL_17 | TNF_alpha | 0.000 |
| IL_17 | TNF_beta | 0.000 | | IL_17 | TNF_beta | 0.000 |
| IL_17 | Varicella_Int | 0.000 | | IL_17 | Varicella_Int | 0.000 |
| IL_17 | Measles_OD_DB_Int | 0.000 | | IL_17 | Measles_OD_DB_Int | 0.000 |
| IL_17 | Measles_Int | 0.000 | | IL_17 | Measles_Int | 0.000 |
| IL_17 | HepA_Int | 0.000 | | IL_17 | HepA_Int | 0.000 |
| IL_17 | Tetanus_Int | 0.000 | | IL_17 | Tetanus_Int | 0.000 |
| IL_17 | Diptheria_Int | 0.000 | | IL_17 | Diptheria_Int | 0.000 |
| IL_17 | Rubella_Int | 0.000 | | IL_17 | Rubella_Int | 0.000 |
| IL_17 | CMV_Int | 0.000 | | IL_17 | CMV_Int | 0.000 |
| IL_17 | HepB_cAb_Int | 0.000 | | IL_17 | HepB_cAb_Int | 0.000 |
| IL_17 | HepB_eAb_Int | 0.000 | | IL_17 | HepB_eAb_Int | 0.000 |
| IL_17 | HepB_eAg_Int | 0.000 | | IL_17 | HepB_eAg_Int | 0.000 |
| IL_17 | HepC_Int | 0.000 | | IL_17 | HepC_Int | 0.000 |
| IL_17 | Schistosoma_int | 0.000 | | IL_17 | Schistosoma_int | 0.000 |
| IL_17 | Strongyloides_Int | 0.000 | | IL_17 | Strongyloides_Int | 0.000 |
| IL_17 | Filaria_Int | 0.000 | | IL_17 | Filaria_Int | 0.000 |
| IL_23 | IL_1_alpha | 0.000 | | IL_23 | IL_1_alpha | 0.000 |
| IL_23 | IL_1_beta | 0.000 | | IL_23 | IL_1_beta | 0.000 |
| IL_23 | IL_2 | 0.000 | | IL_23 | IL_2 | 0.000 |
| IL_23 | IL_4 | 0.000 | | IL_23 | IL_4 | 0.000 |
| IL_23 | IL_5 | 0.000 | | IL_23 | IL_5 | 0.000 |
| IL_23 | IL_6 | 0.000 | | IL_23 | IL_6 | 0.000 |
| IL_23 | IL_8 | 0.000 | | IL_23 | IL_8 | 0.000 |
| IL_23 | IL_10 | 0.000 | | IL_23 | IL_10 | 0.000 |
| IL_23 | IL_12p70 | 0.000 | | IL_23 | IL_12p70 | 0.000 |
| IL_23 | IL_13 | 0.000 | | IL_23 | IL_13 | 0.000 |
| IL_23 | IL_15 | 0.000 | | IL_23 | IL_15 | 0.000 |
| IL_23 | IL_17 | 0.000 | | IL_23 | IL_17 | 0.000 |
| IL_23 | IL_23 | 1.000 | | IL_23 | IL_23 | 1.000 |
| IL_23 | IFN_gamma | 0.000 | | IL_23 | IFN_gamma | 0.000 |
| IL_23 | TNF_alpha | 0.000 | | IL_23 | TNF_alpha | 0.000 |
| IL_23 | TNF_beta | 0.000 | | IL_23 | TNF_beta | 0.000 |
| IL_23 | Varicella_Int | 0.000 | | IL_23 | Varicella_Int | 0.000 |
| IL_23 | Measles_OD_DB_Int | 0.000 | | IL_23 | Measles_OD_DB_Int | 0.000 |
| IL_23 | Measles_Int | 0.000 | | IL_23 | Measles_Int | 0.000 |
| IL_23 | HepA_Int | 0.000 | | IL_23 | HepA_Int | 0.000 |
| IL_23 | Tetanus_Int | 0.000 | | IL_23 | Tetanus_Int | 0.000 |
| IL_23 | Diptheria_Int | 0.000 | | IL_23 | Diptheria_Int | 0.000 |
| IL_23 | Rubella_Int | 0.000 | | IL_23 | Rubella_Int | 0.000 |
| IL_23 | CMV_Int | 0.000 | | IL_23 | CMV_Int | 0.000 |
| IL_23 | HepB_cAb_Int | 0.000 | | IL_23 | HepB_cAb_Int | 0.000 |
| IL_23 | HepB_eAb_Int | 0.000 | | IL_23 | HepB_eAb_Int | 0.000 |
| IL_23 | HepB_eAg_Int | 0.000 | | IL_23 | HepB_eAg_Int | 0.000 |
| IL_23 | HepC_Int | 0.000 | | IL_23 | HepC_Int | 0.000 |
| IL_23 | Schistosoma_int | 0.000 | | IL_23 | Schistosoma_int | 0.000 |
| IL_23 | Strongyloides_Int | 0.000 | | IL_23 | Strongyloides_Int | 0.000 |

FIG. 21I16-H

| IL_23 | Filaria_Int | 0.000 | IL_23 | Filaria_Int | 0.000 |
|---|---|---|---|---|---|
| IFN_gamma | IL_1_alpha | 0.000 | IFN_gamma | IL_1_alpha | 0.000 |
| IFN_gamma | IL_1_beta | 0.000 | IFN_gamma | IL_1_beta | 0.000 |
| IFN_gamma | IL_2 | 0.000 | IFN_gamma | IL_2 | 0.000 |
| IFN_gamma | IL_4 | 0.000 | IFN_gamma | IL_4 | 0.000 |
| IFN_gamma | IL_5 | 0.000 | IFN_gamma | IL_5 | 0.000 |
| IFN_gamma | IL_6 | 0.000 | IFN_gamma | IL_6 | 0.000 |
| IFN_gamma | IL_8 | 0.000 | IFN_gamma | IL_8 | 0.000 |
| IFN_gamma | IL_10 | 0.000 | IFN_gamma | IL_10 | 0.000 |
| IFN_gamma | IL_12p70 | 0.000 | IFN_gamma | IL_12p70 | 0.000 |
| IFN_gamma | IL_13 | 0.000 | IFN_gamma | IL_13 | 0.000 |
| IFN_gamma | IL_15 | 0.000 | IFN_gamma | IL_15 | 0.000 |
| IFN_gamma | IL_17 | 0.000 | IFN_gamma | IL_17 | 0.000 |
| IFN_gamma | IL_23 | 0.000 | IFN_gamma | IL_23 | 0.000 |
| IFN_gamma | IFN_gamma | 1.000 | IFN_gamma | IFN_gamma | 1.000 |
| IFN_gamma | TNF_alpha | 0.000 | IFN_gamma | TNF_alpha | 0.000 |
| IFN_gamma | TNF_beta | 0.000 | IFN_gamma | TNF_beta | 0.000 |
| IFN_gamma | Varicella_Int | 0.000 | IFN_gamma | Varicella_Int | 0.000 |
| IFN_gamma | Measles_OD_DB_Int | 0.000 | IFN_gamma | Measles_OD_DB_Int | 0.000 |
| IFN_gamma | Measles_Int | 0.000 | IFN_gamma | Measles_Int | 0.000 |
| IFN_gamma | HepA_Int | 0.000 | IFN_gamma | HepA_Int | 0.000 |
| IFN_gamma | Tetanus_Int | 0.000 | IFN_gamma | Tetanus_Int | 0.000 |
| IFN_gamma | Diptheria_Int | 0.000 | IFN_gamma | Diptheria_Int | 0.000 |
| IFN_gamma | Rubella_Int | 0.000 | IFN_gamma | Rubella_Int | 0.000 |
| IFN_gamma | CMV_Int | 0.000 | IFN_gamma | CMV_Int | 0.000 |
| IFN_gamma | HepB_cAb_Int | 0.000 | IFN_gamma | HepB_cAb_Int | 0.000 |
| IFN_gamma | HepB_eAb_Int | 0.000 | IFN_gamma | HepB_eAb_Int | 0.000 |
| IFN_gamma | HepB_eAg_Int | 0.000 | IFN_gamma | HepB_eAg_Int | 0.000 |
| IFN_gamma | HepC_Int | 0.000 | IFN_gamma | HepC_Int | 0.000 |
| IFN_gamma | Schistosoma_int | 0.000 | IFN_gamma | Schistosoma_int | 0.000 |
| IFN_gamma | Strongyloides_Int | 0.000 | IFN_gamma | Strongyloides_Int | 0.000 |
| IFN_gamma | Filaria_Int | 0.000 | IFN_gamma | Filaria_Int | 0.000 |
| TNF_alpha | IL_1_alpha | 0.000 | TNF_alpha | IL_1_alpha | 0.000 |
| TNF_alpha | IL_1_beta | 0.000 | TNF_alpha | IL_1_beta | 0.000 |
| TNF_alpha | IL_2 | 0.000 | TNF_alpha | IL_2 | 0.000 |
| TNF_alpha | IL_4 | 0.000 | TNF_alpha | IL_4 | 0.000 |
| TNF_alpha | IL_5 | 0.000 | TNF_alpha | IL_5 | 0.000 |
| TNF_alpha | IL_6 | 0.000 | TNF_alpha | IL_6 | 0.000 |
| TNF_alpha | IL_8 | 0.000 | TNF_alpha | IL_8 | 0.000 |
| TNF_alpha | IL_10 | 0.000 | TNF_alpha | IL_10 | 0.000 |
| TNF_alpha | IL_12p70 | 0.000 | TNF_alpha | IL_12p70 | 0.000 |
| TNF_alpha | IL_13 | 0.000 | TNF_alpha | IL_13 | 0.000 |
| TNF_alpha | IL_15 | 0.000 | TNF_alpha | IL_15 | 0.000 |
| TNF_alpha | IL_17 | 0.000 | TNF_alpha | IL_17 | 0.000 |
| TNF_alpha | IL_23 | 0.000 | TNF_alpha | IL_23 | 0.000 |
| TNF_alpha | IFN_gamma | 0.000 | TNF_alpha | IFN_gamma | 0.000 |
| TNF_alpha | TNF_alpha | 1.000 | TNF_alpha | TNF_alpha | 1.000 |
| TNF_alpha | TNF_beta | 0.000 | TNF_alpha | TNF_beta | 0.000 |
| TNF_alpha | Varicella_Int | 0.000 | TNF_alpha | Varicella_Int | 0.000 |
| TNF_alpha | Measles_OD_DB_Int | 0.000 | TNF_alpha | Measles_OD_DB_Int | 0.000 |
| TNF_alpha | Measles_Int | 0.000 | TNF_alpha | Measles_Int | 0.000 |
| TNF_alpha | HepA_Int | 0.000 | TNF_alpha | HepA_Int | 0.000 |
| TNF_alpha | Tetanus_Int | 0.000 | TNF_alpha | Tetanus_Int | 0.000 |
| TNF_alpha | Diptheria_Int | 0.000 | TNF_alpha | Diptheria_Int | 0.000 |
| TNF_alpha | Rubella_Int | 0.000 | TNF_alpha | Rubella_Int | 0.000 |
| TNF_alpha | CMV_Int | 0.000 | TNF_alpha | CMV_Int | 0.000 |
| TNF_alpha | HepB_cAb_Int | 0.000 | TNF_alpha | HepB_cAb_Int | 0.000 |

FIG. 21I16-I

| | | | | | | |
|---|---|---|---|---|---|---|
| TNF_alpha | HepB_eAb_Int | 0.000 | | TNF_alpha | HepB_eAb_Int | 0.000 |
| TNF_alpha | HepB_eAg_Int | 0.000 | | TNF_alpha | HepB_eAg_Int | 0.000 |
| TNF_alpha | HepC_Int | 0.000 | | TNF_alpha | HepC_Int | 0.000 |
| TNF_alpha | Schistosoma_int | 0.000 | | TNF_alpha | Schistosoma_int | 0.000 |
| TNF_alpha | Strongyloides_Int | 0.000 | | TNF_alpha | Strongyloides_Int | 0.000 |
| TNF_alpha | Filaria_Int | 0.000 | | TNF_alpha | Filaria_Int | 0.000 |
| TNF_beta | IL_1_alpha | 0.000 | | TNF_beta | IL_1_alpha | 0.000 |
| TNF_beta | IL_1_beta | 0.000 | | TNF_beta | IL_1_beta | 0.000 |
| TNF_beta | IL_2 | 0.000 | | TNF_beta | IL_2 | 0.000 |
| TNF_beta | IL_4 | 0.000 | | TNF_beta | IL_4 | 0.000 |
| TNF_beta | IL_5 | 0.000 | | TNF_beta | IL_5 | 0.000 |
| TNF_beta | IL_6 | 0.000 | | TNF_beta | IL_6 | 0.000 |
| TNF_beta | IL_8 | 0.000 | | TNF_beta | IL_8 | 0.000 |
| TNF_beta | IL_10 | 0.000 | | TNF_beta | IL_10 | 0.000 |
| TNF_beta | IL_12p70 | 0.000 | | TNF_beta | IL_12p70 | 0.000 |
| TNF_beta | IL_13 | 0.000 | | TNF_beta | IL_13 | 0.000 |
| TNF_beta | IL_15 | 0.000 | | TNF_beta | IL_15 | 0.000 |
| TNF_beta | IL_17 | 0.000 | | TNF_beta | IL_17 | 0.000 |
| TNF_beta | IL_23 | 0.000 | | TNF_beta | IL_23 | 0.000 |
| TNF_beta | IFN_gamma | 0.000 | | TNF_beta | IFN_gamma | 0.000 |
| TNF_beta | TNF_alpha | 0.000 | | TNF_beta | TNF_alpha | 0.000 |
| TNF_beta | TNF_beta | 1.000 | | TNF_beta | TNF_beta | 1.000 |
| TNF_beta | Varicella_Int | 0.000 | | TNF_beta | Varicella_Int | 0.000 |
| TNF_beta | Measles_OD_DB_Int | 0.000 | | TNF_beta | Measles_OD_DB_Int | 0.000 |
| TNF_beta | Measles_Int | 0.000 | | TNF_beta | Measles_Int | 0.000 |
| TNF_beta | HepA_Int | 0.000 | | TNF_beta | HepA_Int | 0.000 |
| TNF_beta | Tetanus_Int | 0.000 | | TNF_beta | Tetanus_Int | 0.000 |
| TNF_beta | Diptheria_Int | 0.000 | | TNF_beta | Diptheria_Int | 0.000 |
| TNF_beta | Rubella_Int | 0.000 | | TNF_beta | Rubella_Int | 0.000 |
| TNF_beta | CMV_Int | 0.000 | | TNF_beta | CMV_Int | 0.000 |
| TNF_beta | HepB_cAb_Int | 0.000 | | TNF_beta | HepB_cAb_Int | 0.000 |
| TNF_beta | HepB_eAb_Int | 0.000 | | TNF_beta | HepB_eAb_Int | 0.000 |
| TNF_beta | HepB_eAg_Int | 0.000 | | TNF_beta | HepB_eAg_Int | 0.000 |
| TNF_beta | HepC_Int | 0.000 | | TNF_beta | HepC_Int | 0.000 |
| TNF_beta | Schistosoma_int | 0.000 | | TNF_beta | Schistosoma_int | 0.000 |
| TNF_beta | Strongyloides_Int | 0.000 | | TNF_beta | Strongyloides_Int | 0.000 |
| TNF_beta | Filaria_Int | 0.000 | | TNF_beta | Filaria_Int | 0.000 |
| Varicella_Int | IL_1_alpha | 0.000 | | Varicella_Int | IL_1_alpha | 0.000 |
| Varicella_Int | IL_1_beta | 0.000 | | Varicella_Int | IL_1_beta | 0.000 |
| Varicella_Int | IL_2 | 0.000 | | Varicella_Int | IL_2 | 0.000 |
| Varicella_Int | IL_4 | 0.000 | | Varicella_Int | IL_4 | 0.000 |
| Varicella_Int | IL_5 | 0.000 | | Varicella_Int | IL_5 | 0.000 |
| Varicella_Int | IL_6 | 0.000 | | Varicella_Int | IL_6 | 0.000 |
| Varicella_Int | IL_8 | 0.000 | | Varicella_Int | IL_8 | 0.000 |
| Varicella_Int | IL_10 | 0.000 | | Varicella_Int | IL_10 | 0.000 |
| Varicella_Int | IL_12p70 | 0.000 | | Varicella_Int | IL_12p70 | 0.000 |
| Varicella_Int | IL_13 | 0.000 | | Varicella_Int | IL_13 | 0.000 |
| Varicella_Int | IL_15 | 0.000 | | Varicella_Int | IL_15 | 0.000 |
| Varicella_Int | IL_17 | 0.000 | | Varicella_Int | IL_17 | 0.000 |
| Varicella_Int | IL_23 | 0.000 | | Varicella_Int | IL_23 | 0.000 |
| Varicella_Int | IFN_gamma | 0.000 | | Varicella_Int | IFN_gamma | 0.000 |
| Varicella_Int | TNF_alpha | 0.000 | | Varicella_Int | TNF_alpha | 0.000 |
| Varicella_Int | TNF_beta | 0.000 | | Varicella_Int | TNF_beta | 0.000 |
| Varicella_Int | Varicella_Int | 1.000 | | Varicella_Int | Varicella_Int | 1.000 |
| Varicella_Int | Measles_OD_DB_Int | 0.000 | | Varicella_Int | Measles_OD_DB_Int | 0.000 |
| Varicella_Int | Measles_Int | 0.000 | | Varicella_Int | Measles_Int | 0.000 |
| Varicella_Int | HepA_Int | 0.000 | | Varicella_Int | HepA_Int | 0.000 |

FIG. 21I16-J

| | | | | | | |
|---|---|---|---|---|---|---|
| Varicella_Int | Tetanus_Int | 0.000 | | Varicella_Int | Tetanus_Int | 0.000 |
| Varicella_Int | Diptheria_Int | 0.000 | | Varicella_Int | Diptheria_Int | 0.000 |
| Varicella_Int | Rubella_Int | 0.000 | | Varicella_Int | Rubella_Int | 0.000 |
| Varicella_Int | CMV_Int | 0.000 | | Varicella_Int | CMV_Int | 0.000 |
| Varicella_Int | HepB_cAb_Int | 0.000 | | Varicella_Int | HepB_cAb_Int | 0.000 |
| Varicella_Int | HepB_eAb_Int | 0.000 | | Varicella_Int | HepB_eAb_Int | 0.000 |
| Varicella_Int | HepB_eAg_Int | 0.000 | | Varicella_Int | HepB_eAg_Int | 0.000 |
| Varicella_Int | HepC_Int | 0.000 | | Varicella_Int | HepC_Int | 0.000 |
| Varicella_Int | Schistosoma_int | 0.000 | | Varicella_Int | Schistosoma_int | 0.000 |
| Varicella_Int | Strongyloides_Int | 0.000 | | Varicella_Int | Strongyloides_Int | 0.000 |
| Varicella_Int | Filaria_Int | 0.000 | | Varicella_Int | Filaria_Int | 0.000 |
| Measles_OD_DB_Int | IL_1_alpha | 0.000 | | Measles_OD_DB_Int | IL_1_alpha | 0.000 |
| Measles_OD_DB_Int | IL_1_beta | 0.000 | | Measles_OD_DB_Int | IL_1_beta | 0.000 |
| Measles_OD_DB_Int | IL_2 | 0.000 | | Measles_OD_DB_Int | IL_2 | 0.000 |
| Measles_OD_DB_Int | IL_4 | 0.000 | | Measles_OD_DB_Int | IL_4 | 0.000 |
| Measles_OD_DB_Int | IL_5 | 0.000 | | Measles_OD_DB_Int | IL_5 | 0.000 |
| Measles_OD_DB_Int | IL_6 | 0.000 | | Measles_OD_DB_Int | IL_6 | 0.000 |
| Measles_OD_DB_Int | IL_8 | 0.000 | | Measles_OD_DB_Int | IL_8 | 0.000 |
| Measles_OD_DB_Int | IL_10 | 0.000 | | Measles_OD_DB_Int | IL_10 | 0.000 |
| Measles_OD_DB_Int | IL_12p70 | 0.000 | | Measles_OD_DB_Int | IL_12p70 | 0.000 |
| Measles_OD_DB_Int | IL_13 | 0.000 | | Measles_OD_DB_Int | IL_13 | 0.000 |
| Measles_OD_DB_Int | IL_15 | 0.000 | | Measles_OD_DB_Int | IL_15 | 0.000 |
| Measles_OD_DB_Int | IL_17 | 0.000 | | Measles_OD_DB_Int | IL_17 | 0.000 |
| Measles_OD_DB_Int | IL_23 | 0.000 | | Measles_OD_DB_Int | IL_23 | 0.000 |
| Measles_OD_DB_Int | IFN_gamma | 0.000 | | Measles_OD_DB_Int | IFN_gamma | 0.000 |
| Measles_OD_DB_Int | TNF_alpha | 0.000 | | Measles_OD_DB_Int | TNF_alpha | 0.000 |
| Measles_OD_DB_Int | TNF_beta | 0.000 | | Measles_OD_DB_Int | TNF_beta | 0.000 |
| Measles_OD_DB_Int | Varicella_Int | 0.000 | | Measles_OD_DB_Int | Varicella_Int | 0.000 |
| Measles_OD_DB_Int | Measles_OD_DB_Int | 1.000 | | Measles_OD_DB_Int | Measles_OD_DB_Int | 1.000 |
| Measles_OD_DB_Int | Measles_Int | 0.000 | | Measles_OD_DB_Int | Measles_Int | 0.000 |
| Measles_OD_DB_Int | HepA_Int | 0.000 | | Measles_OD_DB_Int | HepA_Int | 0.000 |
| Measles_OD_DB_Int | Tetanus_Int | 0.000 | | Measles_OD_DB_Int | Tetanus_Int | 0.000 |
| Measles_OD_DB_Int | Diptheria_Int | 0.000 | | Measles_OD_DB_Int | Diptheria_Int | 0.000 |
| Measles_OD_DB_Int | Rubella_Int | 0.000 | | Measles_OD_DB_Int | Rubella_Int | 0.000 |
| Measles_OD_DB_Int | CMV_Int | 0.000 | | Measles_OD_DB_Int | CMV_Int | 0.000 |
| Measles_OD_DB_Int | HepB_cAb_Int | 0.000 | | Measles_OD_DB_Int | HepB_cAb_Int | 0.000 |
| Measles_OD_DB_Int | HepB_eAb_Int | 0.000 | | Measles_OD_DB_Int | HepB_eAb_Int | 0.000 |
| Measles_OD_DB_Int | HepB_eAg_Int | 0.000 | | Measles_OD_DB_Int | HepB_eAg_Int | 0.000 |
| Measles_OD_DB_Int | HepC_Int | 0.000 | | Measles_OD_DB_Int | HepC_Int | 0.000 |
| Measles_OD_DB_Int | Schistosoma_int | 0.000 | | Measles_OD_DB_Int | Schistosoma_int | 0.000 |
| Measles_OD_DB_Int | Strongyloides_Int | 0.000 | | Measles_OD_DB_Int | Strongyloides_Int | 0.000 |
| Measles_OD_DB_Int | Filaria_Int | 0.000 | | Measles_OD_DB_Int | Filaria_Int | 0.000 |
| Measles_Int | IL_1_alpha | 0.000 | | Measles_Int | IL_1_alpha | 0.000 |
| Measles_Int | IL_1_beta | 0.000 | | Measles_Int | IL_1_beta | 0.000 |
| Measles_Int | IL_2 | 0.000 | | Measles_Int | IL_2 | 0.000 |
| Measles_Int | IL_4 | 0.000 | | Measles_Int | IL_4 | 0.000 |
| Measles_Int | IL_5 | 0.000 | | Measles_Int | IL_5 | 0.000 |
| Measles_Int | IL_6 | 0.000 | | Measles_Int | IL_6 | 0.000 |
| Measles_Int | IL_8 | 0.000 | | Measles_Int | IL_8 | 0.000 |
| Measles_Int | IL_10 | 0.000 | | Measles_Int | IL_10 | 0.000 |
| Measles_Int | IL_12p70 | 0.000 | | Measles_Int | IL_12p70 | 0.000 |
| Measles_Int | IL_13 | 0.000 | | Measles_Int | IL_13 | 0.000 |
| Measles_Int | IL_15 | 0.000 | | Measles_Int | IL_15 | 0.000 |
| Measles_Int | IL_17 | 0.000 | | Measles_Int | IL_17 | 0.000 |
| Measles_Int | IL_23 | 0.000 | | Measles_Int | IL_23 | 0.000 |
| Measles_Int | IFN_gamma | 0.000 | | Measles_Int | IFN_gamma | 0.000 |
| Measles_Int | TNF_alpha | 0.000 | | Measles_Int | TNF_alpha | 0.000 |

FIG. 21I16-K

| | | | | | | |
|---|---|---|---|---|---|---|
| Measles_Int | TNF_beta | 0.000 | | Measles_Int | TNF_beta | 0.000 |
| Measles_Int | Varicella_Int | 0.000 | | Measles_Int | Varicella_Int | 0.000 |
| Measles_Int | Measles_OD_DB_Int | 0.000 | | Measles_Int | Measles_OD_DB_Int | 0.000 |
| Measles_Int | Measles_Int | 1.000 | | Measles_Int | Measles_Int | 1.000 |
| Measles_Int | HepA_Int | 0.000 | | Measles_Int | HepA_Int | 0.000 |
| Measles_Int | Tetanus_Int | 0.000 | | Measles_Int | Tetanus_Int | 0.000 |
| Measles_Int | Diptheria_Int | 0.000 | | Measles_Int | Diptheria_Int | 0.000 |
| Measles_Int | Rubella_Int | 0.000 | | Measles_Int | Rubella_Int | 0.000 |
| Measles_Int | CMV_Int | 0.000 | | Measles_Int | CMV_Int | 0.000 |
| Measles_Int | HepB_cAb_Int | 0.000 | | Measles_Int | HepB_cAb_Int | 0.000 |
| Measles_Int | HepB_eAb_Int | 0.000 | | Measles_Int | HepB_eAb_Int | 0.000 |
| Measles_Int | HepB_eAg_Int | 0.000 | | Measles_Int | HepB_eAg_Int | 0.000 |
| Measles_Int | HepC_Int | 0.000 | | Measles_Int | HepC_Int | 0.000 |
| Measles_Int | Schistosoma_int | 0.000 | | Measles_Int | Schistosoma_int | 0.000 |
| Measles_Int | Strongyloides_Int | 0.000 | | Measles_Int | Strongyloides_Int | 0.000 |
| Measles_Int | Filaria_Int | 0.000 | | Measles_Int | Filaria_Int | 0.000 |
| HepA_Int | IL_1_alpha | 0.000 | | HepA_Int | IL_1_alpha | 0.000 |
| HepA_Int | IL_1_beta | 0.000 | | HepA_Int | IL_1_beta | 0.000 |
| HepA_Int | IL_2 | 0.000 | | HepA_Int | IL_2 | 0.000 |
| HepA_Int | IL_4 | 0.000 | | HepA_Int | IL_4 | 0.000 |
| HepA_Int | IL_5 | 0.000 | | HepA_Int | IL_5 | 0.000 |
| HepA_Int | IL_6 | 0.000 | | HepA_Int | IL_6 | 0.000 |
| HepA_Int | IL_8 | 0.000 | | HepA_Int | IL_8 | 0.000 |
| HepA_Int | IL_10 | 0.000 | | HepA_Int | IL_10 | 0.000 |
| HepA_Int | IL_12p70 | 0.000 | | HepA_Int | IL_12p70 | 0.000 |
| HepA_Int | IL_13 | 0.000 | | HepA_Int | IL_13 | 0.000 |
| HepA_Int | IL_15 | 0.000 | | HepA_Int | IL_15 | 0.000 |
| HepA_Int | IL_17 | 0.000 | | HepA_Int | IL_17 | 0.000 |
| HepA_Int | IL_23 | 0.000 | | HepA_Int | IL_23 | 0.000 |
| HepA_Int | IFN_gamma | 0.000 | | HepA_Int | IFN_gamma | 0.000 |
| HepA_Int | TNF_alpha | 0.000 | | HepA_Int | TNF_alpha | 0.000 |
| HepA_Int | TNF_beta | 0.000 | | HepA_Int | TNF_beta | 0.000 |
| HepA_Int | Varicella_Int | 0.000 | | HepA_Int | Varicella_Int | 0.000 |
| HepA_Int | Measles_OD_DB_Int | 0.000 | | HepA_Int | Measles_OD_DB_Int | 0.000 |
| HepA_Int | Measles_Int | 0.000 | | HepA_Int | Measles_Int | 0.000 |
| HepA_Int | HepA_Int | 1.000 | | HepA_Int | HepA_Int | 1.000 |
| HepA_Int | Tetanus_Int | 0.000 | | HepA_Int | Tetanus_Int | 0.000 |
| HepA_Int | Diptheria_Int | 0.000 | | HepA_Int | Diptheria_Int | 0.000 |
| HepA_Int | Rubella_Int | 0.000 | | HepA_Int | Rubella_Int | 0.000 |
| HepA_Int | CMV_Int | 0.000 | | HepA_Int | CMV_Int | 0.000 |
| HepA_Int | HepB_cAb_Int | 0.000 | | HepA_Int | HepB_cAb_Int | 0.000 |
| HepA_Int | HepB_eAb_Int | 0.000 | | HepA_Int | HepB_eAb_Int | 0.000 |
| HepA_Int | HepB_eAg_Int | 0.000 | | HepA_Int | HepB_eAg_Int | 0.000 |
| HepA_Int | HepC_Int | 0.000 | | HepA_Int | HepC_Int | 0.000 |
| HepA_Int | Schistosoma_int | 0.000 | | HepA_Int | Schistosoma_int | 0.000 |
| HepA_Int | Strongyloides_Int | 0.000 | | HepA_Int | Strongyloides_Int | 0.000 |
| HepA_Int | Filaria_Int | 0.000 | | HepA_Int | Filaria_Int | 0.000 |
| Tetanus_Int | IL_1_alpha | 0.000 | | Tetanus_Int | IL_1_alpha | 0.000 |
| Tetanus_Int | IL_1_beta | 0.000 | | Tetanus_Int | IL_1_beta | 0.000 |
| Tetanus_Int | IL_2 | 0.000 | | Tetanus_Int | IL_2 | 0.000 |
| Tetanus_Int | IL_4 | 0.000 | | Tetanus_Int | IL_4 | 0.000 |
| Tetanus_Int | IL_5 | 0.000 | | Tetanus_Int | IL_5 | 0.000 |
| Tetanus_Int | IL_6 | 0.000 | | Tetanus_Int | IL_6 | 0.000 |
| Tetanus_Int | IL_8 | 0.000 | | Tetanus_Int | IL_8 | 0.000 |
| Tetanus_Int | IL_10 | 0.000 | | Tetanus_Int | IL_10 | 0.000 |
| Tetanus_Int | IL_12p70 | 0.000 | | Tetanus_Int | IL_12p70 | 0.000 |
| Tetanus_Int | IL_13 | 0.000 | | Tetanus_Int | IL_13 | 0.000 |

FIG. 21I16-L

| | | | | | | |
|---|---|---|---|---|---|---|
| Tetanus_Int | IL_15 | 0.000 | | Tetanus_Int | IL_15 | 0.000 |
| Tetanus_Int | IL_17 | 0.000 | | Tetanus_Int | IL_17 | 0.000 |
| Tetanus_Int | IL_23 | 0.000 | | Tetanus_Int | IL_23 | 0.000 |
| Tetanus_Int | IFN_gamma | 0.000 | | Tetanus_Int | IFN_gamma | 0.000 |
| Tetanus_Int | TNF_alpha | 0.000 | | Tetanus_Int | TNF_alpha | 0.000 |
| Tetanus_Int | TNF_beta | 0.000 | | Tetanus_Int | TNF_beta | 0.000 |
| Tetanus_Int | Varicella_Int | 0.000 | | Tetanus_Int | Varicella_Int | 0.000 |
| Tetanus_Int | Measles_OD_DB_Int | 0.000 | | Tetanus_Int | Measles_OD_DB_Int | 0.000 |
| Tetanus_Int | Measles_Int | 0.000 | | Tetanus_Int | Measles_Int | 0.000 |
| Tetanus_Int | HepA_Int | 0.000 | | Tetanus_Int | HepA_Int | 0.000 |
| Tetanus_Int | Tetanus_Int | 1.000 | | Tetanus_Int | Tetanus_Int | 1.000 |
| Tetanus_Int | Diptheria_Int | 0.000 | | Tetanus_Int | Diptheria_Int | 0.000 |
| Tetanus_Int | Rubella_Int | 0.000 | | Tetanus_Int | Rubella_Int | 0.000 |
| Tetanus_Int | CMV_Int | 0.000 | | Tetanus_Int | CMV_Int | 0.000 |
| Tetanus_Int | HepB_cAb_Int | 0.000 | | Tetanus_Int | HepB_cAb_Int | 0.000 |
| Tetanus_Int | HepB_eAb_Int | 0.000 | | Tetanus_Int | HepB_eAb_Int | 0.000 |
| Tetanus_Int | HepB_eAg_Int | 0.000 | | Tetanus_Int | HepB_eAg_Int | 0.000 |
| Tetanus_Int | HepC_Int | 0.000 | | Tetanus_Int | HepC_Int | 0.000 |
| Tetanus_Int | Schistosoma_int | 0.000 | | Tetanus_Int | Schistosoma_int | 0.000 |
| Tetanus_Int | Strongyloides_Int | 0.000 | | Tetanus_Int | Strongyloides_Int | 0.000 |
| Tetanus_Int | Filaria_Int | 0.000 | | Tetanus_Int | Filaria_Int | 0.000 |
| Diptheria_Int | IL_1_alpha | 0.000 | | Diptheria_Int | IL_1_alpha | 0.000 |
| Diptheria_Int | IL_1_beta | 0.000 | | Diptheria_Int | IL_1_beta | 0.000 |
| Diptheria_Int | IL_2 | 0.000 | | Diptheria_Int | IL_2 | 0.000 |
| Diptheria_Int | IL_4 | 0.000 | | Diptheria_Int | IL_4 | 0.000 |
| Diptheria_Int | IL_5 | 0.000 | | Diptheria_Int | IL_5 | 0.000 |
| Diptheria_Int | IL_6 | 0.000 | | Diptheria_Int | IL_6 | 0.000 |
| Diptheria_Int | IL_8 | 0.000 | | Diptheria_Int | IL_8 | 0.000 |
| Diptheria_Int | IL_10 | 0.000 | | Diptheria_Int | IL_10 | 0.000 |
| Diptheria_Int | IL_12p70 | 0.000 | | Diptheria_Int | IL_12p70 | 0.000 |
| Diptheria_Int | IL_13 | 0.000 | | Diptheria_Int | IL_13 | 0.000 |
| Diptheria_Int | IL_15 | 0.000 | | Diptheria_Int | IL_15 | 0.000 |
| Diptheria_Int | IL_17 | 0.000 | | Diptheria_Int | IL_17 | 0.000 |
| Diptheria_Int | IL_23 | 0.000 | | Diptheria_Int | IL_23 | 0.000 |
| Diptheria_Int | IFN_gamma | 0.000 | | Diptheria_Int | IFN_gamma | 0.000 |
| Diptheria_Int | TNF_alpha | 0.000 | | Diptheria_Int | TNF_alpha | 0.000 |
| Diptheria_Int | TNF_beta | 0.000 | | Diptheria_Int | TNF_beta | 0.000 |
| Diptheria_Int | Varicella_Int | 0.000 | | Diptheria_Int | Varicella_Int | 0.000 |
| Diptheria_Int | Measles_OD_DB_Int | 0.000 | | Diptheria_Int | Measles_OD_DB_Int | 0.000 |
| Diptheria_Int | Measles_Int | 0.000 | | Diptheria_Int | Measles_Int | 0.000 |
| Diptheria_Int | HepA_Int | 0.000 | | Diptheria_Int | HepA_Int | 0.000 |
| Diptheria_Int | Tetanus_Int | 0.000 | | Diptheria_Int | Tetanus_Int | 0.000 |
| Diptheria_Int | Diptheria_Int | 1.000 | | Diptheria_Int | Diptheria_Int | 1.000 |
| Diptheria_Int | Rubella_Int | 0.000 | | Diptheria_Int | Rubella_Int | 0.000 |
| Diptheria_Int | CMV_Int | 0.000 | | Diptheria_Int | CMV_Int | 0.000 |
| Diptheria_Int | HepB_cAb_Int | 0.000 | | Diptheria_Int | HepB_cAb_Int | 0.000 |
| Diptheria_Int | HepB_eAb_Int | 0.000 | | Diptheria_Int | HepB_eAb_Int | 0.000 |
| Diptheria_Int | HepB_eAg_Int | 0.000 | | Diptheria_Int | HepB_eAg_Int | 0.000 |
| Diptheria_Int | HepC_Int | 0.000 | | Diptheria_Int | HepC_Int | 0.000 |
| Diptheria_Int | Schistosoma_int | 0.000 | | Diptheria_Int | Schistosoma_int | 0.000 |
| Diptheria_Int | Strongyloides_Int | 0.000 | | Diptheria_Int | Strongyloides_Int | 0.000 |
| Diptheria_Int | Filaria_Int | 0.000 | | Diptheria_Int | Filaria_Int | 0.000 |
| Rubella_Int | IL_1_alpha | 0.000 | | Rubella_Int | IL_1_alpha | 0.000 |
| Rubella_Int | IL_1_beta | 0.000 | | Rubella_Int | IL_1_beta | 0.000 |
| Rubella_Int | IL_2 | 0.000 | | Rubella_Int | IL_2 | 0.000 |
| Rubella_Int | IL_4 | 0.000 | | Rubella_Int | IL_4 | 0.000 |
| Rubella_Int | IL_5 | 0.000 | | Rubella_Int | IL_5 | 0.000 |

FIG. 21I16-M

| | | | | | | |
|---|---|---|---|---|---|---|
| Rubella_Int | IL_6 | 0.000 | | Rubella_Int | IL_6 | 0.000 |
| Rubella_Int | IL_8 | 0.000 | | Rubella_Int | IL_8 | 0.000 |
| Rubella_Int | IL_10 | 0.000 | | Rubella_Int | IL_10 | 0.000 |
| Rubella_Int | IL_12p70 | 0.000 | | Rubella_Int | IL_12p70 | 0.000 |
| Rubella_Int | IL_13 | 0.000 | | Rubella_Int | IL_13 | 0.000 |
| Rubella_Int | IL_15 | 0.000 | | Rubella_Int | IL_15 | 0.000 |
| Rubella_Int | IL_17 | 0.000 | | Rubella_Int | IL_17 | 0.000 |
| Rubella_Int | IL_23 | 0.000 | | Rubella_Int | IL_23 | 0.000 |
| Rubella_Int | IFN_gamma | 0.000 | | Rubella_Int | IFN_gamma | 0.000 |
| Rubella_Int | TNF_alpha | 0.000 | | Rubella_Int | TNF_alpha | 0.000 |
| Rubella_Int | TNF_beta | 0.000 | | Rubella_Int | TNF_beta | 0.000 |
| Rubella_Int | Varicella_Int | 0.000 | | Rubella_Int | Varicella_Int | 0.000 |
| Rubella_Int | Measles_OD_DB_Int | 0.000 | | Rubella_Int | Measles_OD_DB_Int | 0.000 |
| Rubella_Int | Measles_Int | 0.000 | | Rubella_Int | Measles_Int | 0.000 |
| Rubella_Int | HepA_Int | 0.000 | | Rubella_Int | HepA_Int | 0.000 |
| Rubella_Int | Tetanus_Int | 0.000 | | Rubella_Int | Tetanus_Int | 0.000 |
| Rubella_Int | Diptheria_Int | 0.000 | | Rubella_Int | Diptheria_Int | 0.000 |
| Rubella_Int | Rubella_Int | 1.000 | | Rubella_Int | Rubella_Int | 1.000 |
| Rubella_Int | CMV_Int | 0.000 | | Rubella_Int | CMV_Int | 0.000 |
| Rubella_Int | HepB_cAb_Int | 0.000 | | Rubella_Int | HepB_cAb_Int | 0.000 |
| Rubella_Int | HepB_eAb_Int | 0.000 | | Rubella_Int | HepB_eAb_Int | 0.000 |
| Rubella_Int | HepB_eAg_Int | 0.000 | | Rubella_Int | HepB_eAg_Int | 0.000 |
| Rubella_Int | HepC_Int | 0.000 | | Rubella_Int | HepC_Int | 0.000 |
| Rubella_Int | Schistosoma_int | 0.000 | | Rubella_Int | Schistosoma_int | 0.000 |
| Rubella_Int | Strongyloides_Int | 0.000 | | Rubella_Int | Strongyloides_Int | 0.000 |
| Rubella_Int | Filaria_Int | 0.000 | | Rubella_Int | Filaria_Int | 0.000 |
| CMV_Int | IL_1_alpha | 0.000 | | CMV_Int | IL_1_alpha | 0.000 |
| CMV_Int | IL_1_beta | 0.000 | | CMV_Int | IL_1_beta | 0.000 |
| CMV_Int | IL_2 | 0.000 | | CMV_Int | IL_2 | 0.000 |
| CMV_Int | IL_4 | 0.000 | | CMV_Int | IL_4 | 0.000 |
| CMV_Int | IL_5 | 0.000 | | CMV_Int | IL_5 | 0.000 |
| CMV_Int | IL_6 | 0.000 | | CMV_Int | IL_6 | 0.000 |
| CMV_Int | IL_8 | 0.000 | | CMV_Int | IL_8 | 0.000 |
| CMV_Int | IL_10 | 0.000 | | CMV_Int | IL_10 | 0.000 |
| CMV_Int | IL_12p70 | 0.000 | | CMV_Int | IL_12p70 | 0.000 |
| CMV_Int | IL_13 | 0.000 | | CMV_Int | IL_13 | 0.000 |
| CMV_Int | IL_15 | 0.000 | | CMV_Int | IL_15 | 0.000 |
| CMV_Int | IL_17 | 0.000 | | CMV_Int | IL_17 | 0.000 |
| CMV_Int | IL_23 | 0.000 | | CMV_Int | IL_23 | 0.000 |
| CMV_Int | IFN_gamma | 0.000 | | CMV_Int | IFN_gamma | 0.000 |
| CMV_Int | TNF_alpha | 0.000 | | CMV_Int | TNF_alpha | 0.000 |
| CMV_Int | TNF_beta | 0.000 | | CMV_Int | TNF_beta | 0.000 |
| CMV_Int | Varicella_Int | 0.000 | | CMV_Int | Varicella_Int | 0.000 |
| CMV_Int | Measles_OD_DB_Int | 0.000 | | CMV_Int | Measles_OD_DB_Int | 0.000 |
| CMV_Int | Measles_int | 0.000 | | CMV_Int | Measles_Int | 0.000 |
| CMV_Int | HepA_Int | 0.000 | | CMV_Int | HepA_Int | 0.000 |
| CMV_Int | Tetanus_Int | 0.000 | | CMV_Int | Tetanus_Int | 0.000 |
| CMV_Int | Diptheria_Int | 0.000 | | CMV_Int | Diptheria_Int | 0.000 |
| CMV_Int | Rubella_Int | 0.000 | | CMV_Int | Rubella_Int | 0.000 |
| CMV_Int | CMV_Int | 1.000 | | CMV_Int | CMV_Int | 1.000 |
| CMV_Int | HepB_cAb_Int | 0.000 | | CMV_Int | HepB_cAb_Int | 0.000 |
| CMV_Int | HepB_eAb_Int | 0.000 | | CMV_Int | HepB_eAb_Int | 0.000 |
| CMV_Int | HepB_eAg_Int | 0.000 | | CMV_Int | HepB_eAg_Int | 0.000 |
| CMV_Int | HepC_Int | 0.000 | | CMV_Int | HepC_Int | 0.000 |
| CMV_Int | Schistosoma_int | 0.000 | | CMV_Int | Schistosoma_int | 0.000 |
| CMV_Int | Strongyloides_Int | 0.000 | | CMV_Int | Strongyloides_Int | 0.000 |
| CMV_Int | Filaria_Int | 0.000 | | CMV_Int | Filaria_Int | 0.000 |

FIG. 21I16-N

| | | | | | | |
|---|---|---|---|---|---|---|
| HepB_cAb_Int | IL_1_alpha | 0.000 | | HepB_cAb_Int | IL_1_alpha | 0.000 |
| HepB_cAb_Int | IL_1_beta | 0.000 | | HepB_cAb_Int | IL_1_beta | 0.000 |
| HepB_cAb_Int | IL_2 | 0.000 | | HepB_cAb_Int | IL_2 | 0.000 |
| HepB_cAb_Int | IL_4 | 0.000 | | HepB_cAb_Int | IL_4 | 0.000 |
| HepB_cAb_Int | IL_5 | 0.000 | | HepB_cAb_Int | IL_5 | 0.000 |
| HepB_cAb_Int | IL_6 | 0.000 | | HepB_cAb_Int | IL_6 | 0.000 |
| HepB_cAb_Int | IL_8 | 0.000 | | HepB_cAb_Int | IL_8 | 0.000 |
| HepB_cAb_Int | IL_10 | 0.000 | | HepB_cAb_Int | IL_10 | 0.000 |
| HepB_cAb_Int | IL_12p70 | 0.000 | | HepB_cAb_Int | IL_12p70 | 0.000 |
| HepB_cAb_Int | IL_13 | 0.000 | | HepB_cAb_Int | IL_13 | 0.000 |
| HepB_cAb_Int | IL_15 | 0.000 | | HepB_cAb_Int | IL_15 | 0.000 |
| HepB_cAb_Int | IL_17 | 0.000 | | HepB_cAb_Int | IL_17 | 0.000 |
| HepB_cAb_Int | IL_23 | 0.000 | | HepB_cAb_Int | IL_23 | 0.000 |
| HepB_cAb_Int | IFN_gamma | 0.000 | | HepB_cAb_Int | IFN_gamma | 0.000 |
| HepB_cAb_Int | TNF_alpha | 0.000 | | HepB_cAb_Int | TNF_alpha | 0.000 |
| HepB_cAb_Int | TNF_beta | 0.000 | | HepB_cAb_Int | TNF_beta | 0.000 |
| HepB_cAb_Int | Varicella_Int | 0.000 | | HepB_cAb_Int | Varicella_Int | 0.000 |
| HepB_cAb_Int | Measles_OD_DB_Int | 0.000 | | HepB_cAb_Int | Measles_OD_DB_Int | 0.000 |
| HepB_cAb_Int | Measles_Int | 0.000 | | HepB_cAb_Int | Measles_Int | 0.000 |
| HepB_cAb_Int | HepA_Int | 0.000 | | HepB_cAb_Int | HepA_Int | 0.000 |
| HepB_cAb_Int | Tetanus_Int | 0.000 | | HepB_cAb_Int | Tetanus_Int | 0.000 |
| HepB_cAb_Int | Diptheria_Int | 0.000 | | HepB_cAb_Int | Diptheria_Int | 0.000 |
| HepB_cAb_Int | Rubella_Int | 0.000 | | HepB_cAb_Int | Rubella_Int | 0.000 |
| HepB_cAb_Int | CMV_Int | 0.000 | | HepB_cAb_Int | CMV_Int | 0.000 |
| HepB_cAb_Int | HepB_cAb_Int | 1.000 | | HepB_cAb_Int | HepB_cAb_Int | 1.000 |
| HepB_cAb_Int | HepB_eAb_Int | 0.000 | | HepB_cAb_Int | HepB_eAb_Int | 0.000 |
| HepB_cAb_Int | HepB_eAg_Int | 0.000 | | HepB_cAb_Int | HepB_eAg_Int | 0.000 |
| HepB_cAb_Int | HepC_Int | 0.000 | | HepB_cAb_Int | HepC_Int | 0.000 |
| HepB_cAb_Int | Schistosoma_int | 0.000 | | HepB_cAb_Int | Schistosoma_int | 0.000 |
| HepB_cAb_Int | Strongyloides_Int | 0.000 | | HepB_cAb_Int | Strongyloides_Int | 0.000 |
| HepB_cAb_Int | Filaria_Int | 0.000 | | HepB_cAb_Int | Filaria_Int | 0.000 |
| HepB_eAb_Int | IL_1_alpha | 0.000 | | HepB_eAb_Int | IL_1_alpha | 0.000 |
| HepB_eAb_Int | IL_1_beta | 0.000 | | HepB_eAb_Int | IL_1_beta | 0.000 |
| HepB_eAb_Int | IL_2 | 0.000 | | HepB_eAb_Int | IL_2 | 0.000 |
| HepB_eAb_Int | IL_4 | 0.000 | | HepB_eAb_Int | IL_4 | 0.000 |
| HepB_eAb_Int | IL_5 | 0.000 | | HepB_eAb_Int | IL_5 | 0.000 |
| HepB_eAb_Int | IL_6 | 0.000 | | HepB_eAb_Int | IL_6 | 0.000 |
| HepB_eAb_Int | IL_8 | 0.000 | | HepB_eAb_Int | IL_8 | 0.000 |
| HepB_eAb_Int | IL_10 | 0.000 | | HepB_eAb_Int | IL_10 | 0.000 |
| HepB_eAb_Int | IL_12p70 | 0.000 | | HepB_eAb_Int | IL_12p70 | 0.000 |
| HepB_eAb_Int | IL_13 | 0.000 | | HepB_eAb_Int | IL_13 | 0.000 |
| HepB_eAb_Int | IL_15 | 0.000 | | HepB_eAb_Int | IL_15 | 0.000 |
| HepB_eAb_Int | IL_17 | 0.000 | | HepB_eAb_Int | IL_17 | 0.000 |
| HepB_eAb_Int | IL_23 | 0.000 | | HepB_eAb_Int | IL_23 | 0.000 |
| HepB_eAb_Int | IFN_gamma | 0.000 | | HepB_eAb_Int | IFN_gamma | 0.000 |
| HepB_eAb_Int | TNF_alpha | 0.000 | | HepB_eAb_Int | TNF_alpha | 0.000 |
| HepB_eAb_Int | TNF_beta | 0.000 | | HepB_eAb_Int | TNF_beta | 0.000 |
| HepB_eAb_Int | Varicella_Int | 0.000 | | HepB_eAb_Int | Varicella_Int | 0.000 |
| HepB_eAb_Int | Measles_OD_DB_Int | 0.000 | | HepB_eAb_Int | Measles_OD_DB_Int | 0.000 |
| HepB_eAb_Int | Measles_Int | 0.000 | | HepB_eAb_Int | Measles_Int | 0.000 |
| HepB_eAb_Int | HepA_Int | 0.000 | | HepB_eAb_Int | HepA_Int | 0.000 |
| HepB_eAb_Int | Tetanus_Int | 0.000 | | HepB_eAb_Int | Tetanus_Int | 0.000 |
| HepB_eAb_Int | Diptheria_Int | 0.000 | | HepB_eAb_Int | Diptheria_Int | 0.000 |
| HepB_eAb_Int | Rubella_Int | 0.000 | | HepB_eAb_Int | Rubella_Int | 0.000 |
| HepB_eAb_Int | CMV_Int | 0.000 | | HepB_eAb_Int | CMV_Int | 0.000 |
| HepB_eAb_Int | HepB_cAb_Int | 0.000 | | HepB_eAb_Int | HepB_cAb_Int | 0.000 |
| HepB_eAb_Int | HepB_eAb_Int | 1.000 | | HepB_eAb_Int | HepB_eAb_Int | 1.000 |

FIG. 21I16-O

| | | | | | | |
|---|---|---|---|---|---|---|
| HepB_eAb_Int | HepB_eAg_Int | 0.000 | | HepB_eAb_Int | HepB_eAg_Int | 0.000 |
| HepB_eAb_Int | HepC_Int | 0.000 | | HepB_eAb_Int | HepC_Int | 0.000 |
| HepB_eAb_Int | Schistosoma_int | 0.000 | | HepB_eAb_Int | Schistosoma_int | 0.000 |
| HepB_eAb_Int | Strongyloides_Int | 0.000 | | HepB_eAb_Int | Strongyloides_Int | 0.000 |
| HepB_eAb_Int | Filaria_Int | 0.000 | | HepB_eAb_Int | Filaria_Int | 0.000 |
| HepB_eAg_Int | IL_1_alpha | 0.000 | | HepB_eAg_Int | IL_1_alpha | 0.000 |
| HepB_eAg_Int | IL_1_beta | 0.000 | | HepB_eAg_Int | IL_1_beta | 0.000 |
| HepB_eAg_Int | IL_2 | 0.000 | | HepB_eAg_Int | IL_2 | 0.000 |
| HepB_eAg_Int | IL_4 | 0.000 | | HepB_eAg_Int | IL_4 | 0.000 |
| HepB_eAg_Int | IL_5 | 0.000 | | HepB_eAg_Int | IL_5 | 0.000 |
| HepB_eAg_Int | IL_6 | 0.000 | | HepB_eAg_Int | IL_6 | 0.000 |
| HepB_eAg_Int | IL_8 | 0.000 | | HepB_eAg_Int | IL_8 | 0.000 |
| HepB_eAg_Int | IL_10 | 0.000 | | HepB_eAg_Int | IL_10 | 0.000 |
| HepB_eAg_Int | IL_12p70 | 0.000 | | HepB_eAg_Int | IL_12p70 | 0.000 |
| HepB_eAg_Int | IL_13 | 0.000 | | HepB_eAg_Int | IL_13 | 0.000 |
| HepB_eAg_Int | IL_15 | 0.000 | | HepB_eAg_Int | IL_15 | 0.000 |
| HepB_eAg_Int | IL_17 | 0.000 | | HepB_eAg_Int | IL_17 | 0.000 |
| HepB_eAg_Int | IL_23 | 0.000 | | HepB_eAg_Int | IL_23 | 0.000 |
| HepB_eAg_Int | IFN_gamma | 0.000 | | HepB_eAg_Int | IFN_gamma | 0.000 |
| HepB_eAg_Int | TNF_alpha | 0.000 | | HepB_eAg_Int | TNF_alpha | 0.000 |
| HepB_eAg_Int | TNF_beta | 0.000 | | HepB_eAg_Int | TNF_beta | 0.000 |
| HepB_eAg_Int | Varicella_Int | 0.000 | | HepB_eAg_Int | Varicella_Int | 0.000 |
| HepB_eAg_Int | Measles_OD_DB_Int | 0.000 | | HepB_eAg_Int | Measles_OD_DB_Int | 0.000 |
| HepB_eAg_Int | Measles_Int | 0.000 | | HepB_eAg_Int | Measles_Int | 0.000 |
| HepB_eAg_Int | HepA_Int | 0.000 | | HepB_eAg_Int | HepA_Int | 0.000 |
| HepB_eAg_Int | Tetanus_Int | 0.000 | | HepB_eAg_Int | Tetanus_Int | 0.000 |
| HepB_eAg_Int | Diptheria_Int | 0.000 | | HepB_eAg_Int | Diptheria_Int | 0.000 |
| HepB_eAg_Int | Rubella_Int | 0.000 | | HepB_eAg_Int | Rubella_Int | 0.000 |
| HepB_eAg_Int | CMV_Int | 0.000 | | HepB_eAg_Int | CMV_Int | 0.000 |
| HepB_eAg_Int | HepB_cAb_Int | 0.000 | | HepB_eAg_Int | HepB_cAb_Int | 0.000 |
| HepB_eAg_Int | HepB_eAb_Int | 0.000 | | HepB_eAg_Int | HepB_eAb_Int | 0.000 |
| HepB_eAg_Int | HepB_eAg_Int | 1.000 | | HepB_eAg_Int | HepB_eAg_Int | 1.000 |
| HepB_eAg_Int | HepC_Int | 0.000 | | HepB_eAg_Int | HepC_Int | 0.000 |
| HepB_eAg_Int | Schistosoma_int | 0.000 | | HepB_eAg_Int | Schistosoma_int | 0.000 |
| HepB_eAg_Int | Strongyloides_Int | 0.000 | | HepB_eAg_Int | Strongyloides_Int | 0.000 |
| HepB_eAg_Int | Filaria_Int | 0.000 | | HepB_eAg_Int | Filaria_Int | 0.000 |
| HepC_Int | IL_1_alpha | 0.000 | | HepC_Int | IL_1_alpha | 0.000 |
| HepC_Int | IL_1_beta | 0.000 | | HepC_Int | IL_1_beta | 0.000 |
| HepC_Int | IL_2 | 0.000 | | HepC_Int | IL_2 | 0.000 |
| HepC_Int | IL_4 | 0.000 | | HepC_Int | IL_4 | 0.000 |
| HepC_Int | IL_5 | 0.000 | | HepC_Int | IL_5 | 0.000 |
| HepC_Int | IL_6 | 0.000 | | HepC_Int | IL_6 | 0.000 |
| HepC_Int | IL_8 | 0.000 | | HepC_Int | IL_8 | 0.000 |
| HepC_Int | IL_10 | 0.000 | | HepC_Int | IL_10 | 0.000 |
| HepC_Int | IL_12p70 | 0.000 | | HepC_Int | IL_12p70 | 0.000 |
| HepC_Int | IL_13 | 0.000 | | HepC_Int | IL_13 | 0.000 |
| HepC_Int | IL_15 | 0.000 | | HepC_Int | IL_15 | 0.000 |
| HepC_Int | IL_17 | 0.000 | | HepC_Int | IL_17 | 0.000 |
| HepC_Int | IL_23 | 0.000 | | HepC_Int | IL_23 | 0.000 |
| HepC_Int | IFN_gamma | 0.000 | | HepC_Int | IFN_gamma | 0.000 |
| HepC_Int | TNF_alpha | 0.000 | | HepC_Int | TNF_alpha | 0.000 |
| HepC_Int | TNF_beta | 0.000 | | HepC_Int | TNF_beta | 0.000 |
| HepC_Int | Varicella_Int | 0.000 | | HepC_Int | Varicella_Int | 0.000 |
| HepC_Int | Measles_OD_DB_Int | 0.000 | | HepC_Int | Measles_OD_DB_Int | 0.000 |
| HepC_Int | Measles_Int | 0.000 | | HepC_Int | Measles_Int | 0.000 |
| HepC_Int | HepA_Int | 0.000 | | HepC_Int | HepA_Int | 0.000 |
| HepC_Int | Tetanus_Int | 0.000 | | HepC_Int | Tetanus_Int | 0.000 |

FIG. 21I16-P

| | | | | | | |
|---|---|---|---|---|---|---|
| HepC_Int | Diptheria_Int | 0.000 | | HepC_Int | Diptheria_Int | 0.000 |
| HepC_Int | Rubella_Int | 0.000 | | HepC_Int | Rubella_Int | 0.000 |
| HepC_Int | CMV_Int | 0.000 | | HepC_Int | CMV_Int | 0.000 |
| HepC_Int | HepB_cAb_Int | 0.000 | | HepC_Int | HepB_cAb_Int | 0.000 |
| HepC_Int | HepB_eAb_Int | 0.000 | | HepC_Int | HepB_eAb_Int | 0.000 |
| HepC_Int | HepB_eAg_Int | 0.000 | | HepC_Int | HepB_eAg_Int | 0.000 |
| HepC_Int | HepC_Int | 1.000 | | HepC_Int | HepC_Int | 1.000 |
| HepC_Int | Schistosoma_int | 0.000 | | HepC_Int | Schistosoma_int | 0.000 |
| HepC_Int | Strongyloides_Int | 0.000 | | HepC_Int | Strongyloides_Int | 0.000 |
| HepC_Int | Filaria_Int | 0.000 | | HepC_Int | Filaria_Int | 0.000 |
| Schistosoma_int | IL_1_alpha | 0.000 | | Schistosoma_int | IL_1_alpha | 0.000 |
| Schistosoma_int | IL_1_beta | 0.000 | | Schistosoma_int | IL_1_beta | 0.000 |
| Schistosoma_int | IL_2 | 0.000 | | Schistosoma_int | IL_2 | 0.000 |
| Schistosoma_int | IL_4 | 0.000 | | Schistosoma_int | IL_4 | 0.000 |
| Schistosoma_int | IL_5 | 0.000 | | Schistosoma_int | IL_5 | 0.000 |
| Schistosoma_int | IL_6 | 0.000 | | Schistosoma_int | IL_6 | 0.000 |
| Schistosoma_int | IL_8 | 0.000 | | Schistosoma_int | IL_8 | 0.000 |
| Schistosoma_int | IL_10 | 0.000 | | Schistosoma_int | IL_10 | 0.000 |
| Schistosoma_int | IL_12p70 | 0.000 | | Schistosoma_int | IL_12p70 | 0.000 |
| Schistosoma_int | IL_13 | 0.000 | | Schistosoma_int | IL_13 | 0.000 |
| Schistosoma_int | IL_15 | 0.000 | | Schistosoma_int | IL_15 | 0.000 |
| Schistosoma_int | IL_17 | 0.000 | | Schistosoma_int | IL_17 | 0.000 |
| Schistosoma_int | IL_23 | 0.000 | | Schistosoma_int | IL_23 | 0.000 |
| Schistosoma_int | IFN_gamma | 0.000 | | Schistosoma_int | IFN_gamma | 0.000 |
| Schistosoma_int | TNF_alpha | 0.000 | | Schistosoma_int | TNF_alpha | 0.000 |
| Schistosoma_int | TNF_beta | 0.000 | | Schistosoma_int | TNF_beta | 0.000 |
| Schistosoma_int | Varicella_Int | 0.000 | | Schistosoma_int | Varicella_Int | 0.000 |
| Schistosoma_int | Measles_OD_DB_Int | 0.000 | | Schistosoma_int | Measles_OD_DB_Int | 0.000 |
| Schistosoma_int | Measles_Int | 0.000 | | Schistosoma_int | Measles_Int | 0.000 |
| Schistosoma_int | HepA_Int | 0.000 | | Schistosoma_int | HepA_Int | 0.000 |
| Schistosoma_int | Tetanus_Int | 0.000 | | Schistosoma_int | Tetanus_Int | 0.000 |
| Schistosoma_int | Diptheria_Int | 0.000 | | Schistosoma_int | Diptheria_Int | 0.000 |
| Schistosoma_int | Rubella_Int | 0.000 | | Schistosoma_int | Rubella_Int | 0.000 |
| Schistosoma_int | CMV_Int | 0.000 | | Schistosoma_int | CMV_Int | 0.000 |
| Schistosoma_int | HepB_cAb_Int | 0.000 | | Schistosoma_int | HepB_cAb_Int | 0.000 |
| Schistosoma_int | HepB_eAb_Int | 0.000 | | Schistosoma_int | HepB_eAb_Int | 0.000 |
| Schistosoma_int | HepB_eAg_Int | 0.000 | | Schistosoma_int | HepB_eAg_Int | 0.000 |
| Schistosoma_int | HepC_Int | 0.000 | | Schistosoma_int | HepC_Int | 0.000 |
| Schistosoma_int | Schistosoma_int | 1.000 | | Schistosoma_int | Schistosoma_int | 1.000 |
| Schistosoma_int | Strongyloides_Int | 0.000 | | Schistosoma_int | Strongyloides_Int | 0.000 |
| Schistosoma_int | Filaria_Int | 0.000 | | Schistosoma_int | Filaria_Int | 0.000 |
| Strongyloides_Int | IL_1_alpha | 0.000 | | Strongyloides_Int | IL_1_alpha | 0.000 |
| Strongyloides_Int | IL_1_beta | 0.000 | | Strongyloides_Int | IL_1_beta | 0.000 |
| Strongyloides_Int | IL_2 | 0.000 | | Strongyloides_Int | IL_2 | 0.000 |
| Strongyloides_Int | IL_4 | 0.000 | | Strongyloides_Int | IL_4 | 0.000 |
| Strongyloides_Int | IL_5 | 0.000 | | Strongyloides_Int | IL_5 | 0.000 |
| Strongyloides_Int | IL_6 | 0.000 | | Strongyloides_Int | IL_6 | 0.000 |
| Strongyloides_Int | IL_8 | 0.000 | | Strongyloides_Int | IL_8 | 0.000 |
| Strongyloides_Int | IL_10 | 0.000 | | Strongyloides_Int | IL_10 | 0.000 |
| Strongyloides_Int | IL_12p70 | 0.000 | | Strongyloides_Int | IL_12p70 | 0.000 |
| Strongyloides_Int | IL_13 | 0.000 | | Strongyloides_Int | IL_13 | 0.000 |
| Strongyloides_Int | IL_15 | 0.000 | | Strongyloides_Int | IL_15 | 0.000 |
| Strongyloides_Int | IL_17 | 0.000 | | Strongyloides_Int | IL_17 | 0.000 |
| Strongyloides_Int | IL_23 | 0.000 | | Strongyloides_Int | IL_23 | 0.000 |
| Strongyloides_Int | IFN_gamma | 0.000 | | Strongyloides_Int | IFN_gamma | 0.000 |
| Strongyloides_Int | TNF_alpha | 0.000 | | Strongyloides_Int | TNF_alpha | 0.000 |
| Strongyloides_Int | TNF_beta | 0.000 | | Strongyloides_Int | TNF_beta | 0.000 |

FIG. 21I16-Q

| | | | | | | |
|---|---|---|---|---|---|---|
| Strongyloides_Int | Varicella_Int | 0.000 | | Strongyloides_Int | Varicella_Int | 0.000 |
| Strongyloides_Int | Measles_OD_DB_Int | 0.000 | | Strongyloides_Int | Measles_OD_DB_Int | 0.000 |
| Strongyloides_Int | Measles_Int | 0.000 | | Strongyloides_Int | Measles_Int | 0.000 |
| Strongyloides_Int | HepA_Int | 0.000 | | Strongyloides_Int | HepA_Int | 0.000 |
| Strongyloides_Int | Tetanus_Int | 0.000 | | Strongyloides_Int | Tetanus_Int | 0.000 |
| Strongyloides_Int | Diptheria_Int | 0.000 | | Strongyloides_Int | Diptheria_Int | 0.000 |
| Strongyloides_Int | Rubella_Int | 0.000 | | Strongyloides_Int | Rubella_Int | 0.000 |
| Strongyloides_Int | CMV_Int | 0.000 | | Strongyloides_Int | CMV_Int | 0.000 |
| Strongyloides_Int | HepB_cAb_Int | 0.000 | | Strongyloides_Int | HepB_cAb_Int | 0.000 |
| Strongyloides_Int | HepB_eAb_Int | 0.000 | | Strongyloides_Int | HepB_eAb_Int | 0.000 |
| Strongyloides_Int | HepB_eAg_Int | 0.000 | | Strongyloides_Int | HepB_eAg_Int | 0.000 |
| Strongyloides_Int | HepC_Int | 0.000 | | Strongyloides_Int | HepC_Int | 0.000 |
| Strongyloides_Int | Schistosoma_int | 0.000 | | Strongyloides_Int | Schistosoma_int | 0.000 |
| Strongyloides_Int | Strongyloides_Int | 1.000 | | Strongyloides_Int | Strongyloides_Int | 1.000 |
| Strongyloides_Int | Filaria_Int | 0.000 | | Strongyloides_Int | Filaria_Int | 0.000 |
| Filaria_Int | IL_1_alpha | 0.000 | | Filaria_Int | IL_1_alpha | 0.000 |
| Filaria_Int | IL_1_beta | 0.000 | | Filaria_Int | IL_1_beta | 0.000 |
| Filaria_Int | IL_2 | 0.000 | | Filaria_Int | IL_2 | 0.000 |
| Filaria_Int | IL_4 | 0.000 | | Filaria_Int | IL_4 | 0.000 |
| Filaria_Int | IL_5 | 0.000 | | Filaria_Int | IL_5 | 0.000 |
| Filaria_Int | IL_6 | 0.000 | | Filaria_Int | IL_6 | 0.000 |
| Filaria_Int | IL_8 | 0.000 | | Filaria_Int | IL_8 | 0.000 |
| Filaria_Int | IL_10 | 0.000 | | Filaria_Int | IL_10 | 0.000 |
| Filaria_Int | IL_12p70 | 0.000 | | Filaria_Int | IL_12p70 | 0.000 |
| Filaria_Int | IL_13 | 0.000 | | Filaria_Int | IL_13 | 0.000 |
| Filaria_Int | IL_15 | 0.000 | | Filaria_Int | IL_15 | 0.000 |
| Filaria_Int | IL_17 | 0.000 | | Filaria_Int | IL_17 | 0.000 |
| Filaria_Int | IL_23 | 0.000 | | Filaria_Int | IL_23 | 0.000 |
| Filaria_Int | IFN_gamma | 0.000 | | Filaria_Int | IFN_gamma | 0.000 |
| Filaria_Int | TNF_alpha | 0.000 | | Filaria_Int | TNF_alpha | 0.000 |
| Filaria_Int | TNF_beta | 0.000 | | Filaria_Int | TNF_beta | 0.000 |
| Filaria_Int | Varicella_Int | 0.000 | | Filaria_Int | Varicella_Int | 0.000 |
| Filaria_Int | Measles_OD_DB_Int | 0.000 | | Filaria_Int | Measles_OD_DB_Int | 0.000 |
| Filaria_Int | Measles_Int | 0.000 | | Filaria_Int | Measles_Int | 0.000 |
| Filaria_Int | HepA_Int | 0.000 | | Filaria_Int | HepA_Int | 0.000 |
| Filaria_Int | Tetanus_Int | 0.000 | | Filaria_Int | Tetanus_Int | 0.000 |
| Filaria_Int | Diptheria_Int | 0.000 | | Filaria_Int | Diptheria_Int | 0.000 |
| Filaria_Int | Rubella_Int | 0.000 | | Filaria_Int | Rubella_Int | 0.000 |
| Filaria_Int | CMV_Int | 0.000 | | Filaria_Int | CMV_Int | 0.000 |
| Filaria_Int | HepB_cAb_Int | 0.000 | | Filaria_Int | HepB_cAb_Int | 0.000 |
| Filaria_Int | HepB_eAb_Int | 0.000 | | Filaria_Int | HepB_eAb_Int | 0.000 |
| Filaria_Int | HepB_eAg_Int | 0.000 | | Filaria_Int | HepB_eAg_Int | 0.000 |
| Filaria_Int | HepC_Int | 0.000 | | Filaria_Int | HepC_int | 0.000 |
| Filaria_Int | Schistosoma_int | 0.000 | | Filaria_Int | Schistosoma_int | 0.000 |
| Filaria_Int | Strongyloides_Int | 0.000 | | Filaria_Int | Strongyloides_Int | 0.000 |
| Filaria_Int | Filaria_Int | 1.000 | | Filaria_Int | Filaria_Int | 1.000 |

FIG. 21I16-R

| Differences Between Groups ||||| 
|---|---|---|---|---|
| Property 1 | Property 2 | Std. Deviation | Correlation Values | Group |
| HepB_eAb_Int | IL_2 | 0.366 | 0 | Region_of_Origin=4, Sex=Female, IFN_gamma=0-7.5 (16.59%) |
| | | | 0 | Region_of_Origin=2, Sex=Male, IFN_gamma=0-7.5 (10.97%) |
| | | | 0 | Region_of_Origin=6, Sex=Female, IFN_gamma=0-7.5 (10.89%) |
| | | | 0 | |
| | | | 0 | |
| | | | -0.965992308985186 | Region_of_Origin=1, Sex=Female, IFN_gamma=0-7.5 (10.53%) |
| | | | 0 | |
| | | | 0 | Region_of_Origin=2, Sex=Female, IFN_gamma=0-7.5 (10.32%) |
| | | | -1 | |
| | | | 0 | Region_of_Origin=3, Sex=Female, IFN_gamma=0-7.5 (8.15%) |
| | | | 0 | |
| | | | | Region_of_Origin=5, Sex=Female, IFN_gamma=0-7.5 (7.14%) |
| | | | | Region_of_Origin=1, Sex=Male, IFN_gamma=0-7.5 (6.42%) |
| | | | | Region_of_Origin=4, Sex=Male, IFN_gamma=0-7.5 (5.99%) |
| | | | | Region_of_Origin=6, Sex=Male, IFN_gamma=0-7.5 (4.26%) |
| | | | | Region_of_Origin=5, Sex=Male, IFN_gamma=0-7.5 (3.17%) |
| | | | | Region_of_Origin=3, Sex=Male, IFN_gamma=0-7.5 (3.03%) |
| HepB_eAg_Int | TNF_beta | 0.360 | 0 | Region_of_Origin=4, Sex=Female, IFN_gamma=0-7.5 (16.59%) |
| | | | 0 | Region_of_Origin=2, Sex=Male, IFN_gamma=0-7.5 (10.97%) |
| | | | 0.948479434050883 | |
| | | | -0.25 | Region_of_Origin=6, Sex=Female, IFN_gamma=0-7.5 (10.89%) |
| | | | 0 | |
| | | | 0 | Region_of_Origin=1, Sex=Female, IFN_gamma=0-7.5 (10.53%) |
| | | | 0.898339035656008 | |
| | | | 0 | Region_of_Origin=2, Sex=Female, IFN_gamma=0-7.5 (10.32%) |
| | | | 0 | |
| | | | 0 | Region_of_Origin=3, Sex=Female, IFN_gamma=0-7.5 (8.15%) |
| | | | 0 | |
| | | | | Region_of_Origin=5, Sex=Female, IFN_gamma=0-7.5 (7.14%) |
| | | | | Region_of_Origin=1, Sex=Male, IFN_gamma=0-7.5 (6.42%) |
| | | | | Region_of_Origin=4, Sex=Male, IFN_gamma=0-7.5 (5.99%) |
| | | | | Region_of_Origin=6, Sex=Male, IFN_gamma=0-7.5 (4.26%) |
| | | | | Region_of_Origin=5, Sex=Male, IFN_gamma=0-7.5 (3.17%) |
| | | | | Region_of_Origin=3, Sex=Male, IFN_gamma=0-7.5 (3.03%) |

FIG. 21I17-A

| Differences Between Groups ||||| 
|---|---|---|---|---|
| Property 1 | Property 2 | Std. Deviation | Correlation Values | Group |
| HepB_eAg_Int | IL_23 | 0.318 | 0<br>0<br>-0.320443911437677<br>-0.343159510576641<br>0<br>0<br>0.999459600450254<br>0<br>0<br>0<br>0<br>0 | Region_of_Origin=4, Sex=Female, IFN_gamma=0-7.5 (16.59%)<br>Region_of_Origin=2, Sex=Male, IFN_gamma=0-7.5 (10.97%)<br>Region_of_Origin=6, Sex=Female, IFN_gamma=0-7.5 (10.89%)<br>Region_of_Origin=1, Sex=Female, IFN_gamma=0-7.5 (10.53%)<br>Region_of_Origin=2, Sex=Female, IFN_gamma=0-7.5 (10.32%)<br>Region_of_Origin=3, Sex=Female, IFN_gamma=0-7.5 (8.15%)<br>Region_of_Origin=5, Sex=Female, IFN_gamma=0-7.5 (7.14%)<br>Region_of_Origin=1, Sex=Male, IFN_gamma=0-7.5 (6.42%)<br>Region_of_Origin=4, Sex=Male, IFN_gamma=0-7.5 (5.99%)<br>Region_of_Origin=6, Sex=Male, IFN_gamma=0-7.5 (4.26%)<br>Region_of_Origin=5, Sex=Male, IFN_gamma=0-7.5 (3.17%)<br>Region_of_Origin=3, Sex=Male, IFN_gamma=0-7.5 (3.03%) |
| IL_2 | IL_6 | 0.306 | -0.102135729647186<br>0.123826939346636<br>0.567608344845003<br>0.150911942897458<br>-0.130285769668379<br>-2.3340945660905e-002<br>-1.38129089973822e-002<br>0.180654586734813<br>0.4399996885339<br>0.318425085779155<br>0.608382632751428<br>0.887675362469668 | Region_of_Origin=4, Sex=Female, IFN_gamma=0-7.5 (16.59%)<br>Region_of_Origin=2, Sex=Male, IFN_gamma=0-7.5 (10.97%)<br>Region_of_Origin=6, Sex=Female, IFN_gamma=0-7.5 (10.89%)<br>Region_of_Origin=1, Sex=Female, IFN_gamma=0-7.5 (10.53%)<br>Region_of_Origin=2, Sex=Female, IFN_gamma=0-7.5 (10.32%)<br>Region_of_Origin=3, Sex=Female, IFN_gamma=0-7.5 (8.15%)<br>Region_of_Origin=5, Sex=Female, IFN_gamma=0-7.5 (7.14%)<br>Region_of_Origin=1, Sex=Male, IFN_gamma=0-7.5 (6.42%)<br>Region_of_Origin=4, Sex=Male, IFN_gamma=0-7.5 (5.99%)<br>Region_of_Origin=6, Sex=Male, IFN_gamma=0-7.5 (4.26%)<br>Region_of_Origin=5, Sex=Male, IFN_gamma=0-7.5 (3.17%)<br>Region_of_Origin=3, Sex=Male, IFN_gamma=0-7.5 (3.03%) |

FIG. 21I17-B

| Differences Between Groups ||||| 
|---|---|---|---|---|
| Property 1 | Property 2 | Std. Deviation | Correlation Values | Group |
| HepB_eAg_Int | IL_5 | 0.301 | 0 | Region_of_Origin=4, Sex=Female, IFN_gamma=0-7.5 (16.59%) |
| | | | 0 | Region_of_Origin=2, Sex=Male, IFN_gamma=0-7.5 (10.97%) |
| | | | -0.31617660420346 | |
| | | | -0.29198782330768 | Region_of_Origin=6, Sex=Female, IFN_gamma=0-7.5 (10.89%) |
| | | | 0 | |
| | | | 0 | Region_of_Origin=1, Sex=Female, IFN_gamma=0-7.5 (10.53%) |
| | | | 0.953683698889925 | |
| | | | 0 | Region_of_Origin=2, Sex=Female, IFN_gamma=0-7.5 (10.32%) |
| | | | 0 | |
| | | | 0 | Region_of_Origin=3, Sex=Female, IFN_gamma=0-7.5 (8.15%) |
| | | | 0 | Region_of_Origin=5, Sex=Female, IFN_gamma=0-7.5 (7.14%) |
| | | | | Region_of_Origin=1, Sex=Male, IFN_gamma=0-7.5 (6.42%) |
| | | | | Region_of_Origin=4, Sex=Male, IFN_gamma=0-7.5 (5.99%) |
| | | | | Region_of_Origin=6, Sex=Male, IFN_gamma=0-7.5 (4.26%) |
| | | | | Region_of_Origin=5, Sex=Male, IFN_gamma=0-7.5 (3.17%) |
| | | | | Region_of_Origin=3, Sex=Male, IFN_gamma=0-7.5 (3.03%) |
| IL_2 | HepB_eAg_Int | 0.295 | 0 | Region_of_Origin=4, Sex=Female, IFN_gamma=0-7.5 (16.59%) |
| | | | 0 | Region_of_Origin=2, Sex=Male, IFN_gamma=0-7.5 (10.97%) |
| | | | -0.258070524289817 | |
| | | | -0.25 | Region_of_Origin=6, Sex=Female, IFN_gamma=0-7.5 (10.89%) |
| | | | 0 | |
| | | | 0 | Region_of_Origin=1, Sex=Female, IFN_gamma=0-7.5 (10.53%) |
| | | | 0.965992308985186 | |
| | | | 0 | Region_of_Origin=2, Sex=Female, IFN_gamma=0-7.5 (10.32%) |
| | | | 0 | |
| | | | 0 | Region_of_Origin=3, Sex=Female, IFN_gamma=0-7.5 (8.15%) |
| | | | 0 | Region_of_Origin=5, Sex=Female, IFN_gamma=0-7.5 (7.14%) |
| | | | | Region_of_Origin=1, Sex=Male, IFN_gamma=0-7.5 (6.42%) |
| | | | | Region_of_Origin=4, Sex=Male, IFN_gamma=0-7.5 (5.99%) |
| | | | | Region_of_Origin=6, Sex=Male, IFN_gamma=0-7.5 (4.26%) |
| | | | | Region_of_Origin=5, Sex=Male, IFN_gamma=0-7.5 (3.17%) |
| | | | | Region_of_Origin=3, Sex=Male, IFN_gamma=0-7.5 (3.03%) |

FIG. 21I17-C

| Differences Between Groups |||||
|---|---|---|---|---|
| Property 1 | Property 2 | Std. Deviation | Correlation Values | Group |
| Measles_Int | HepB_eAb_Int | 0.287 | 0<br>0<br>0<br>0<br>0<br>0<br>1<br>0<br>0<br>-0.2<br>0<br>0 | Region_of_Origin=4, Sex=Female, IFN_gamma=0-7.5 (16.59%)<br>Region_of_Origin=2, Sex=Male, IFN_gamma=0-7.5 (10.97%)<br>Region_of_Origin=6, Sex=Female, IFN_gamma=0-7.5 (10.89%)<br>Region_of_Origin=1, Sex=Female, IFN_gamma=0-7.5 (10.53%)<br>Region_of_Origin=2, Sex=Female, IFN_gamma=0-7.5 (10.32%)<br>Region_of_Origin=3, Sex=Female, IFN_gamma=0-7.5 (8.15%)<br>Region_of_Origin=5, Sex=Female, IFN_gamma=0-7.5 (7.14%)<br>Region_of_Origin=1, Sex=Male, IFN_gamma=0-7.5 (6.42%)<br>Region_of_Origin=4, Sex=Male, IFN_gamma=0-7.5 (5.99%)<br>Region_of_Origin=6, Sex=Male, IFN_gamma=0-7.5 (4.26%)<br>Region_of_Origin=5, Sex=Male, IFN_gamma=0-7.5 (3.17%)<br>Region_of_Origin=3, Sex=Male, IFN_gamma=0-7.5 (3.03%) |
| IL_23 | HepB_eAb_Int | 0.282 | 0<br>0<br>0<br>0<br>0<br>0<br>-0.999459600450254<br>0<br>0<br>0.128002735074172<br>0<br>0 | Region_of_Origin=4, Sex=Female, IFN_gamma=0-7.5 (16.59%)<br>Region_of_Origin=2, Sex=Male, IFN_gamma=0-7.5 (10.97%)<br>Region_of_Origin=6, Sex=Female, IFN_gamma=0-7.5 (10.89%)<br>Region_of_Origin=1, Sex=Female, IFN_gamma=0-7.5 (10.53%)<br>Region_of_Origin=2, Sex=Female, IFN_gamma=0-7.5 (10.32%)<br>Region_of_Origin=3, Sex=Female, IFN_gamma=0-7.5 (8.15%)<br>Region_of_Origin=5, Sex=Female, IFN_gamma=0-7.5 (7.14%)<br>Region_of_Origin=1, Sex=Male, IFN_gamma=0-7.5 (6.42%)<br>Region_of_Origin=4, Sex=Male, IFN_gamma=0-7.5 (5.99%)<br>Region_of_Origin=6, Sex=Male, IFN_gamma=0-7.5 (4.26%)<br>Region_of_Origin=5, Sex=Male, IFN_gamma=0-7.5 (3.17%)<br>Region_of_Origin=3, Sex=Male, IFN_gamma=0-7.5 (3.03%) |

FIG. 21I17-D

Differences Between Groups

| Property 1 | Property 2 | Std. Deviation | Correlation Values | Group |
|---|---|---|---|---|
| Strongyloides_Int | HepB_eAg_Int | 0.278 | 0<br>0<br>-0.4152273992687<br>0<br>0<br>0<br>0.87831006565368<br>0<br>0<br>0<br>0<br>0 | Region_of_Origin=4, Sex=Female, IFN_gamma=0-7.5 (16.59%)<br>Region_of_Origin=2, Sex=Male, IFN_gamma=0-7.5 (10.97%)<br>Region_of_Origin=6, Sex=Female, IFN_gamma=0-7.5 (10.89%)<br>Region_of_Origin=1, Sex=Female, IFN_gamma=0-7.5 (10.53%)<br>Region_of_Origin=2, Sex=Female, IFN_gamma=0-7.5 (10.32%)<br>Region_of_Origin=3, Sex=Female, IFN_gamma=0-7.5 (8.15%)<br>Region_of_Origin=5, Sex=Female, IFN_gamma=0-7.5 (7.14%)<br>Region_of_Origin=1, Sex=Male, IFN_gamma=0-7.5 (6.42%)<br>Region_of_Origin=4, Sex=Male, IFN_gamma=0-7.5 (5.99%)<br>Region_of_Origin=6, Sex=Male, IFN_gamma=0-7.5 (4.26%)<br>Region_of_Origin=5, Sex=Male, IFN_gamma=0-7.5 (3.17%)<br>Region_of_Origin=3, Sex=Male, IFN_gamma=0-7.5 (3.03%) |
| HepB_eAg_Int | IL_4 | 0.277 | 0<br>0<br>-0.271928269577898<br>-0.339189370171922<br>0<br>0<br>0.859521930048767<br>0<br>0<br>0<br>0<br>0 | Region_of_Origin=4, Sex=Female, IFN_gamma=0-7.5 (16.59%)<br>Region_of_Origin=2, Sex=Male, IFN_gamma=0-7.5 (10.97%)<br>Region_of_Origin=6, Sex=Female, IFN_gamma=0-7.5 (10.89%)<br>Region_of_Origin=1, Sex=Female, IFN_gamma=0-7.5 (10.53%)<br>Region_of_Origin=2, Sex=Female, IFN_gamma=0-7.5 (10.32%)<br>Region_of_Origin=3, Sex=Female, IFN_gamma=0-7.5 (8.15%)<br>Region_of_Origin=5, Sex=Female, IFN_gamma=0-7.5 (7.14%)<br>Region_of_Origin=1, Sex=Male, IFN_gamma=0-7.5 (6.42%)<br>Region_of_Origin=4, Sex=Male, IFN_gamma=0-7.5 (5.99%)<br>Region_of_Origin=6, Sex=Male, IFN_gamma=0-7.5 (4.26%)<br>Region_of_Origin=5, Sex=Male, IFN_gamma=0-7.5 (3.17%)<br>Region_of_Origin=3, Sex=Male, IFN_gamma=0-7.5 (3.03%) |

FIG. 21I17-E

| Differences Between Groups ||||| 
|---|---|---|---|---|
| Property 1 | Property 2 | Std. Deviation | Correlation Values | Group |
| Measles_Int | HepB_eAg_Int | 0.276 | 0<br>0<br>0<br>0<br>0<br>0<br>-1<br>0<br>0<br>0<br>0<br>0 | Region_of_Origin=4, Sex=Female, IFN_gamma=0-7.5 (16.59%)<br>Region_of_Origin=2, Sex=Male, IFN_gamma=0-7.5 (10.97%)<br>Region_of_Origin=6, Sex=Female, IFN_gamma=0-7.5 (10.89%)<br>Region_of_Origin=1, Sex=Female, IFN_gamma=0-7.5 (10.53%)<br>Region_of_Origin=2, Sex=Female, IFN_gamma=0-7.5 (10.32%)<br>Region_of_Origin=3, Sex=Female, IFN_gamma=0-7.5 (8.15%)<br>Region_of_Origin=5, Sex=Female, IFN_gamma=0-7.5 (7.14%)<br>Region_of_Origin=1, Sex=Male, IFN_gamma=0-7.5 (6.42%)<br>Region_of_Origin=4, Sex=Male, IFN_gamma=0-7.5 (5.99%)<br>Region_of_Origin=6, Sex=Male, IFN_gamma=0-7.5 (4.26%)<br>Region_of_Origin=5, Sex=Male, IFN_gamma=0-7.5 (3.17%)<br>Region_of_Origin=3, Sex=Male, IFN_gamma=0-7.5 (3.03%) |
| HepB_eAb_Int | HepB_eAg_Int | 0.276 | 0<br>0<br>0<br>0<br>0<br>0<br>-1<br>0<br>0<br>0<br>0<br>0 | Region_of_Origin=4, Sex=Female, IFN_gamma=0-7.5 (16.59%)<br>Region_of_Origin=2, Sex=Male, IFN_gamma=0-7.5 (10.97%)<br>Region_of_Origin=6, Sex=Female, IFN_gamma=0-7.5 (10.89%)<br>Region_of_Origin=1, Sex=Female, IFN_gamma=0-7.5 (10.53%)<br>Region_of_Origin=2, Sex=Female, IFN_gamma=0-7.5 (10.32%)<br>Region_of_Origin=3, Sex=Female, IFN_gamma=0-7.5 (8.15%)<br>Region_of_Origin=5, Sex=Female, IFN_gamma=0-7.5 (7.14%)<br>Region_of_Origin=1, Sex=Male, IFN_gamma=0-7.5 (6.42%)<br>Region_of_Origin=4, Sex=Male, IFN_gamma=0-7.5 (5.99%)<br>Region_of_Origin=6, Sex=Male, IFN_gamma=0-7.5 (4.26%)<br>Region_of_Origin=5, Sex=Male, IFN_gamma=0-7.5 (3.17%)<br>Region_of_Origin=3, Sex=Male, IFN_gamma=0-7.5 (3.03%) |

FIG. 21I17-F

Differences Between Groups

| Property 1 | Property 2 | Std. Deviation | Correlation Values | Group |
|---|---|---|---|---|
| HepB_eAb_Int | IL_5 | 0.275 | 0<br>0<br>0<br>0<br>0<br>0<br>-0.953683698889925<br>0<br>0<br>0.206092232485585<br>0<br>0 | Region_of_Origin=4, Sex=Female, IFN_gamma=0-7.5 (16.59%)<br>Region_of_Origin=2, Sex=Male, IFN_gamma=0-7.5 (10.97%)<br>Region_of_Origin=6, Sex=Female, IFN_gamma=0-7.5 (10.89%)<br>Region_of_Origin=1, Sex=Female, IFN_gamma=0-7.5 (10.53%)<br>Region_of_Origin=2, Sex=Female, IFN_gamma=0-7.5 (10.32%)<br>Region_of_Origin=3, Sex=Female, IFN_gamma=0-7.5 (8.15%)<br>Region_of_Origin=5, Sex=Female, IFN_gamma=0-7.5 (7.14%)<br>Region_of_Origin=1, Sex=Male, IFN_gamma=0-7.5 (6.42%)<br>Region_of_Origin=4, Sex=Male, IFN_gamma=0-7.5 (5.99%)<br>Region_of_Origin=6, Sex=Male, IFN_gamma=0-7.5 (4.26%)<br>Region_of_Origin=5, Sex=Male, IFN_gamma=0-7.5 (3.17%)<br>Region_of_Origin=3, Sex=Male, IFN_gamma=0-7.5 (3.03%) |
| IL_4 | HepB_eAb_Int | 0.271 | 0<br>0<br>0<br>0<br>0<br>0<br>-0.859521930048767<br>0<br>0<br>0.402263418202181<br>0<br>0 | Region_of_Origin=4, Sex=Female, IFN_gamma=0-7.5 (16.59%)<br>Region_of_Origin=2, Sex=Male, IFN_gamma=0-7.5 (10.97%)<br>Region_of_Origin=6, Sex=Female, IFN_gamma=0-7.5 (10.89%)<br>Region_of_Origin=1, Sex=Female, IFN_gamma=0-7.5 (10.53%)<br>Region_of_Origin=2, Sex=Female, IFN_gamma=0-7.5 (10.32%)<br>Region_of_Origin=3, Sex=Female, IFN_gamma=0-7.5 (8.15%)<br>Region_of_Origin=5, Sex=Female, IFN_gamma=0-7.5 (7.14%)<br>Region_of_Origin=1, Sex=Male, IFN_gamma=0-7.5 (6.42%)<br>Region_of_Origin=4, Sex=Male, IFN_gamma=0-7.5 (5.99%)<br>Region_of_Origin=6, Sex=Male, IFN_gamma=0-7.5 (4.26%)<br>Region_of_Origin=5, Sex=Male, IFN_gamma=0-7.5 (3.17%)<br>Region_of_Origin=3, Sex=Male, IFN_gamma=0-7.5 (3.03%) |

FIG. 21I17-G

| Differences Between Groups ||||||
|---|---|---|---|---|
| Property 1 | Property 2 | Std. Deviation | Correlation Values | Group |
| IL_6 | IL_10 | 0.289 | 8.3031749334545e-002<br>0.529778344153521<br>2.41586654992975e-002<br>0.314988249523674<br>8.11900402879371e-002<br>4.30013460000942e-002<br>0.138626960696986<br>0.937130728110766<br>0.374857386690803<br>0.463921389270159<br>0.537018398632813<br>6.52695436633052e-002 | Region_of_Origin=4, Sex=Female, IFN_gamma=0-7.5 (16.59%)<br>Region_of_Origin=2, Sex=Male, IFN_gamma=0-7.5 (10.97%)<br>Region_of_Origin=6, Sex=Female, IFN_gamma=0-7.5 (10.89%)<br>Region_of_Origin=1, Sex=Female, IFN_gamma=0-7.5 (10.53%)<br>Region_of_Origin=2, Sex=Female, IFN_gamma=0-7.5 (10.32%)<br>Region_of_Origin=3, Sex=Female, IFN_gamma=0-7.5 (8.15%)<br>Region_of_Origin=5, Sex=Female, IFN_gamma=0-7.5 (7.14%)<br>Region_of_Origin=1, Sex=Male, IFN_gamma=0-7.5 (6.42%)<br>Region_of_Origin=4, Sex=Male, IFN_gamma=0-7.5 (5.99%)<br>Region_of_Origin=6, Sex=Male, IFN_gamma=0-7.5 (4.26%)<br>Region_of_Origin=5, Sex=Male, IFN_gamma=0-7.5 (3.17%)<br>Region_of_Origin=3, Sex=Male, IFN_gamma=0-7.5 (3.03%) |
| TNF_beta | HepB_eAb_Int | 0.288 | 0<br>0<br>0<br>0<br>0<br>0<br>-0.898339035656008<br>0<br>0<br>0.293976697261863<br>0<br>0 | Region_of_Origin=4, Sex=Female, IFN_gamma=0-7.5 (16.59%)<br>Region_of_Origin=2, Sex=Male, IFN_gamma=0-7.5 (10.97%)<br>Region_of_Origin=6, Sex=Female, IFN_gamma=0-7.5 (10.89%)<br>Region_of_Origin=1, Sex=Female, IFN_gamma=0-7.5 (10.53%)<br>Region_of_Origin=2, Sex=Female, IFN_gamma=0-7.5 (10.32%)<br>Region_of_Origin=3, Sex=Female, IFN_gamma=0-7.5 (8.15%)<br>Region_of_Origin=5, Sex=Female, IFN_gamma=0-7.5 (7.14%)<br>Region_of_Origin=1, Sex=Male, IFN_gamma=0-7.5 (6.42%)<br>Region_of_Origin=4, Sex=Male, IFN_gamma=0-7.5 (5.99%)<br>Region_of_Origin=6, Sex=Male, IFN_gamma=0-7.5 (4.26%)<br>Region_of_Origin=5, Sex=Male, IFN_gamma=0-7.5 (3.17%)<br>Region_of_Origin=3, Sex=Male, IFN_gamma=0-7.5 (3.03%) |

FIG. 21I17-H

| Differences Between Groups ||||| 
|---|---|---|---|---|
| Property 1 | Property 2 | Std. Deviation | Correlation Values | Group |
| IL_6 | IL_13 | 0.266 | 0.335382515494212<br>0.538921508225337<br>5.34885849381608e-002<br>0.385361286205321<br>0.262310954529893<br>0.548030688643396<br>1.01009441728548e-002<br>0.913487950604778<br>0.377149641745368<br>0.677022778674797<br>0.622725906395306<br>4.88388842731266e-002 | Region_of_Origin=4, Sex=Female, IFN_gamma=0-7.5 (16.59%)<br>Region_of_Origin=2, Sex=Male, IFN_gamma=0-7.5 (10.97%)<br>Region_of_Origin=6, Sex=Female, IFN_gamma=0-7.5 (10.89%)<br>Region_of_Origin=1, Sex=Female, IFN_gamma=0-7.5 (10.53%)<br>Region_of_Origin=2, Sex=Female, IFN_gamma=0-7.5 (10.32%)<br>Region_of_Origin=3, Sex=Female, IFN_gamma=0-7.5 (8.15%)<br>Region_of_Origin=5, Sex=Female, IFN_gamma=0-7.5 (7.14%)<br>Region_of_Origin=1, Sex=Male, IFN_gamma=0-7.5 (6.42%)<br>Region_of_Origin=4, Sex=Male, IFN_gamma=0-7.5 (5.99%)<br>Region_of_Origin=6, Sex=Male, IFN_gamma=0-7.5 (4.26%)<br>Region_of_Origin=5, Sex=Male, IFN_gamma=0-7.5 (3.17%)<br>Region_of_Origin=3, Sex=Male, IFN_gamma=0-7.5 (3.03%) |
| TNF_alpha | IL_6 | 0.263 | -6.62443080763697e-002<br>0.313419216284368<br>1.17878775459949e-002<br>4.92386740934867e-002<br>2.68981960276361e-002<br>-6.97937972679993e-003<br>1.81268720580535e-002<br>0.633994444308831<br>0.229069172332975<br>0.319552237507304<br>0.783162186841331<br>-3.48181483642027e-003 | Region_of_Origin=4, Sex=Female, IFN_gamma=0-7.5 (16.59%)<br>Region_of_Origin=2, Sex=Male, IFN_gamma=0-7.5 (10.97%)<br>Region_of_Origin=6, Sex=Female, IFN_gamma=0-7.5 (10.89%)<br>Region_of_Origin=1, Sex=Female, IFN_gamma=0-7.5 (10.53%)<br>Region_of_Origin=2, Sex=Female, IFN_gamma=0-7.5 (10.32%)<br>Region_of_Origin=3, Sex=Female, IFN_gamma=0-7.5 (8.15%)<br>Region_of_Origin=5, Sex=Female, IFN_gamma=0-7.5 (7.14%)<br>Region_of_Origin=1, Sex=Male, IFN_gamma=0-7.5 (6.42%)<br>Region_of_Origin=4, Sex=Male, IFN_gamma=0-7.5 (5.99%)<br>Region_of_Origin=6, Sex=Male, IFN_gamma=0-7.5 (4.26%)<br>Region_of_Origin=5, Sex=Male, IFN_gamma=0-7.5 (3.17%)<br>Region_of_Origin=3, Sex=Male, IFN_gamma=0-7.5 (3.03%) |

FIG. 21I17-I

Differences Between Groups

| Property 1 | Property 2 | Std. Deviation | Correlation Values | Group |
|---|---|---|---|---|
| Measles_Int | HepA_Int | 0.254 | 1.41050953713674e-002<br>0.704761478602412<br>-0.159724524044029<br>7.02263130548267e-002<br>-2.14913829665635e-002<br>-4.57868546495628e-002<br>0.182944401388574<br>0.570751763692042<br>-5.4630190114603e-002<br>-4.77008907862002e-002<br>-1.61374306091976e-002<br>0 | Region_of_Origin=4, Sex=Female, IFN_gamma=0-7.5 (16.59%)<br>Region_of_Origin=2, Sex=Male, IFN_gamma=0-7.5 (10.97%)<br>Region_of_Origin=6, Sex=Female, IFN_gamma=0-7.5 (10.89%)<br>Region_of_Origin=1, Sex=Female, IFN_gamma=0-7.5 (10.53%)<br>Region_of_Origin=2, Sex=Female, IFN_gamma=0-7.5 (10.32%)<br>Region_of_Origin=3, Sex=Female, IFN_gamma=0-7.5 (8.15%)<br>Region_of_Origin=5, Sex=Female, IFN_gamma=0-7.5 (7.14%)<br>Region_of_Origin=1, Sex=Male, IFN_gamma=0-7.5 (6.42%)<br>Region_of_Origin=4, Sex=Male, IFN_gamma=0-7.5 (5.99%)<br>Region_of_Origin=6, Sex=Male, IFN_gamma=0-7.5 (4.26%)<br>Region_of_Origin=5, Sex=Male, IFN_gamma=0-7.5 (3.17%)<br>Region_of_Origin=3, Sex=Male, IFN_gamma=0-7.5 (3.03%) |
| Strongyloides_Int | HepB_eAb_Int | 0.254 | 0<br>0<br>0<br>0<br>0<br>0<br>-0.87831006565368<br>0<br>0<br>0.2<br>0<br>0 | Region_of_Origin=4, Sex=Female, IFN_gamma=0-7.5 (16.59%)<br>Region_of_Origin=2, Sex=Male, IFN_gamma=0-7.5 (10.97%)<br>Region_of_Origin=6, Sex=Female, IFN_gamma=0-7.5 (10.89%)<br>Region_of_Origin=1, Sex=Female, IFN_gamma=0-7.5 (10.53%)<br>Region_of_Origin=2, Sex=Female, IFN_gamma=0-7.5 (10.32%)<br>Region_of_Origin=3, Sex=Female, IFN_gamma=0-7.5 (8.15%)<br>Region_of_Origin=5, Sex=Female, IFN_gamma=0-7.5 (7.14%)<br>Region_of_Origin=1, Sex=Male, IFN_gamma=0-7.5 (6.42%)<br>Region_of_Origin=4, Sex=Male, IFN_gamma=0-7.5 (5.99%)<br>Region_of_Origin=6, Sex=Male, IFN_gamma=0-7.5 (4.26%)<br>Region_of_Origin=5, Sex=Male, IFN_gamma=0-7.5 (3.17%)<br>Region_of_Origin=3, Sex=Male, IFN_gamma=0-7.5 (3.03%) |

FIG. 21I17-J

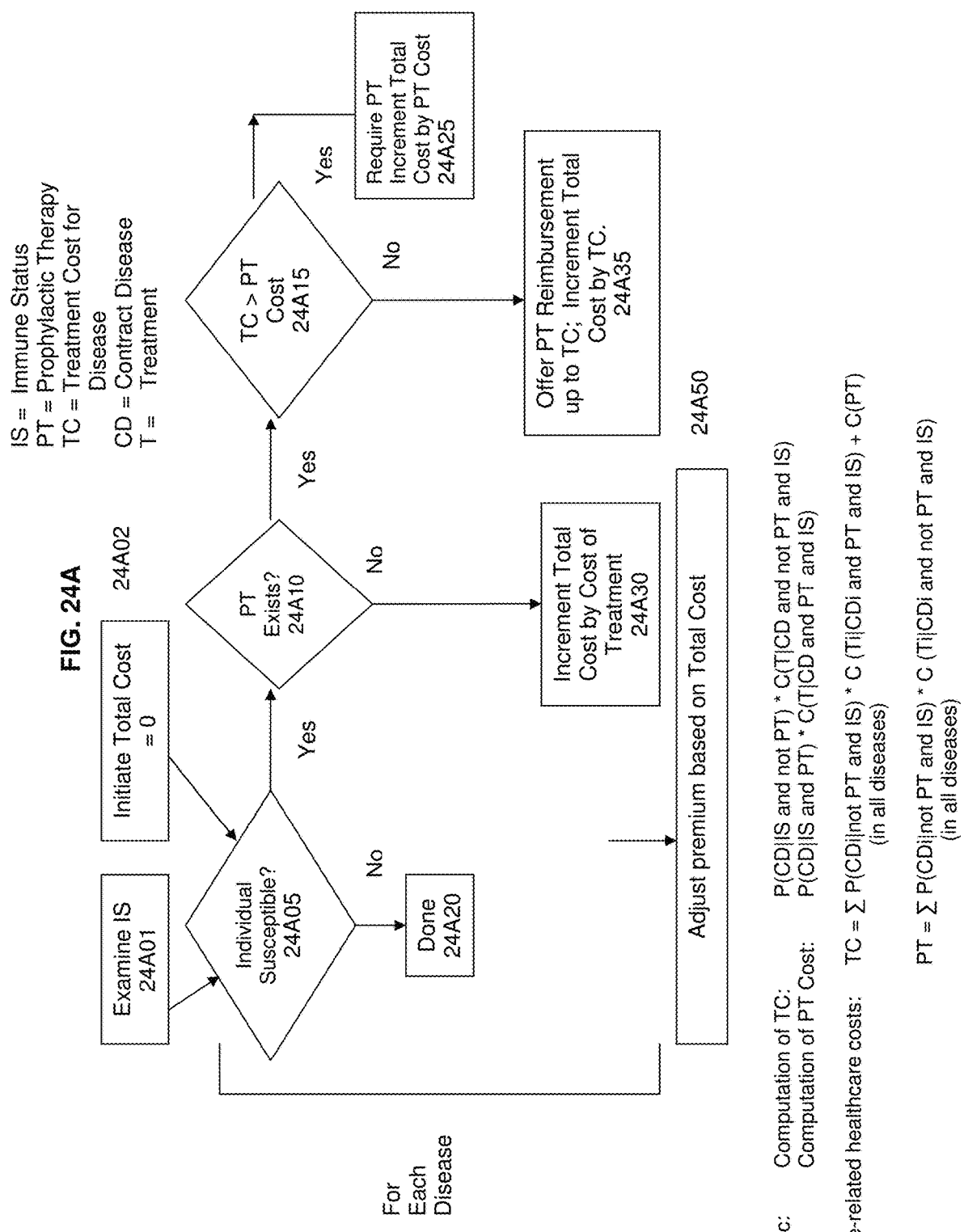

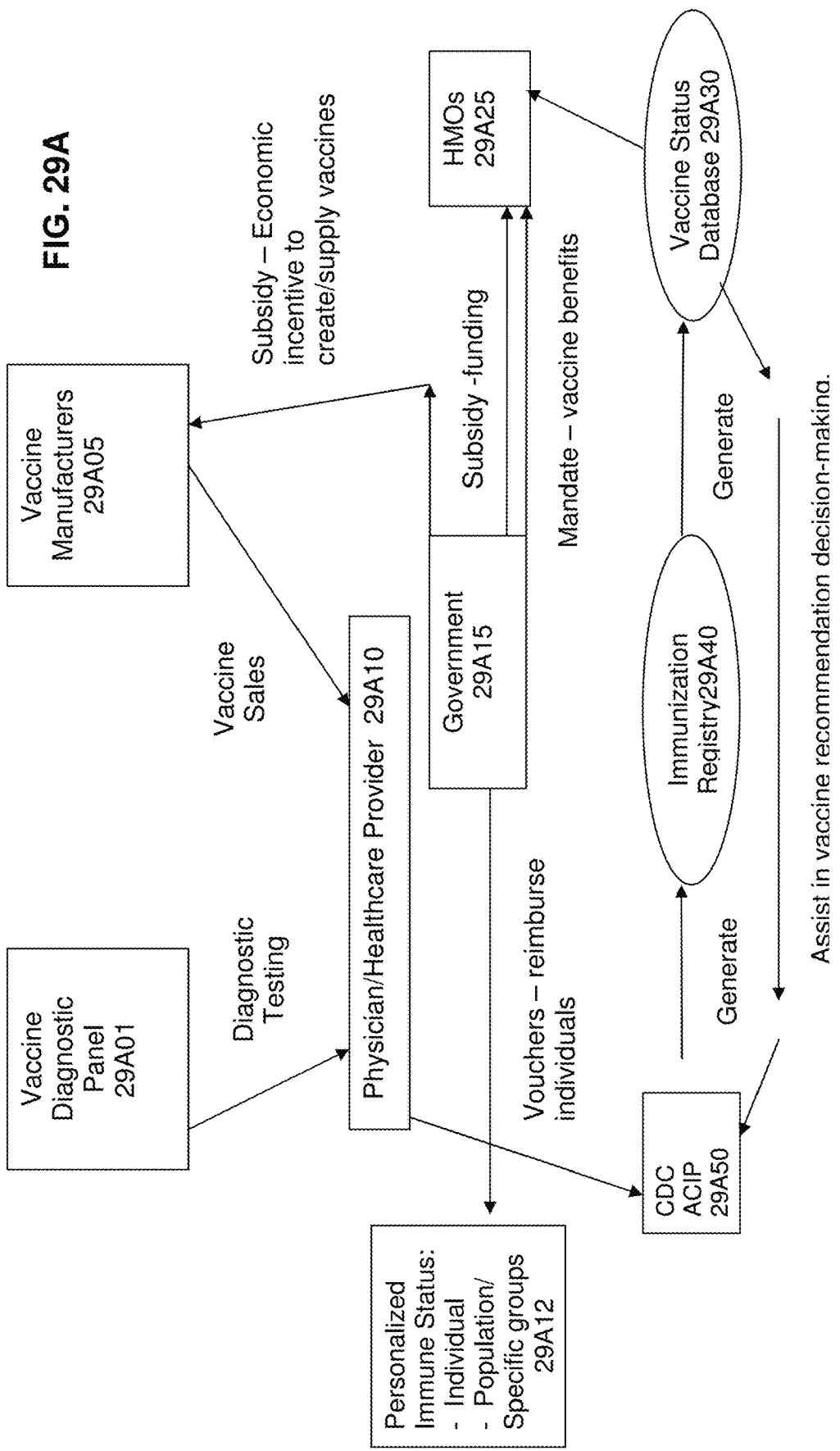

AUTOMATED SYSTEMS AND METHODS FOR OBTAINING, STORING, PROCESSING AND UTILIZING IMMUNOLOGIC INFORMATION OF AN INDIVIDUAL OR POPULATION FOR VARIOUS USES

TECHNICAL FIELD

The present invention relates to individualized health care, immunology and medical informatics, and more particularly to automated systems and methods for acquiring, storing, processing and utilizing immunologic and other information of individuals and populations for decision making in various public health, medical and health care related applications.

BACKGROUND OF THE INVENTION

Personalized medicine is considered by many to be the wave of the future. A personalized medicine approach seeks to identify whether a given individual needs a given treatment or intervention prior to administering it, rather than relying on "standards" representing an average person in a group or population.

This approach is based on the well known fact that some individuals in a demographic population have naturally low or naturally high values which are not best measured against a statistical mean for the demographic population, but against that individual's own measured history.

Determination of the immune status of individuals to, for example, vaccine-preventable diseases requires an assay system that can detect antibodies that may be present at very low levels, especially when natural or vaccine exposure may have been many years previously. In addition, such an assay system could be used more generally to assess an individual's immune competence at different stages of that individual's life, as well as to also measure the vaccine status of individuals with varying special needs and requirements (e.g., military personnel or travelers).

What is thus needed in the art is a system and method for measuring and processing immunologic information of individuals and populations through various points in time of their lives so as to better track each individual's immune status and make appropriate diagnostic, prophylactic and therapeutic recommendations.

What is further needed in the art is a supporting structure to conveniently store the results of such screenings for easy access and processing, for data mining purposes as well as for use in a variety of commercial, research and governmental applications where a knowledge of the immunological indicia of customers, subjects and citizens can create efficiencies and optimizations, as well as allow for the exploitation of commercial opportunities and improve the quality of life.

SUMMARY OF THE INVENTION

A system and method for assessing the immunological status of one or more individuals in a patient population is presented. The method includes establishing a database comprising a plurality of records of information each representative of the immune status of an individual in the population, each of said records including (1) current information from one or more assays for the presence of a biochemical, and (2) individual specific information comprising one or more of said individual's medical history, said individual's doctors' observations and historical, demographic, lifestyle, and familial information relating to said individual. The method further includes processing the information in said database to find trends or patterns relating to the immune status of individuals in said patient population; and using the said trends or patterns as part of a health care related decision making process. In exemplary embodiments of the present invention, processing the information in the database includes generating a list of correlations between variables or fields in the database. The correlations in the list can be further refined automatically, and a set of hypotheses or literature citations can be linked to the final correlations. The correlations, the processing, their associated hypotheses can then be reported to a user or automatically fed into another system component to generate a medical or health related decision. In exemplary embodiments of the present invention, a first assay panel containing a plurality of cytokine assays can be administered and the results processed. Based on automatic analyses of the cytokine data, a second tier or set of assays can be run on the same individual. The cytokine assay results being used to inform the contents of a second assay panel.

BRIEF DESCRIPTION OF THE DRAWINGS

Section I Figures

FIG. 5F depicts a model of the development of the immune response in schitosome infection;

Section II Figures

Figure 21A:
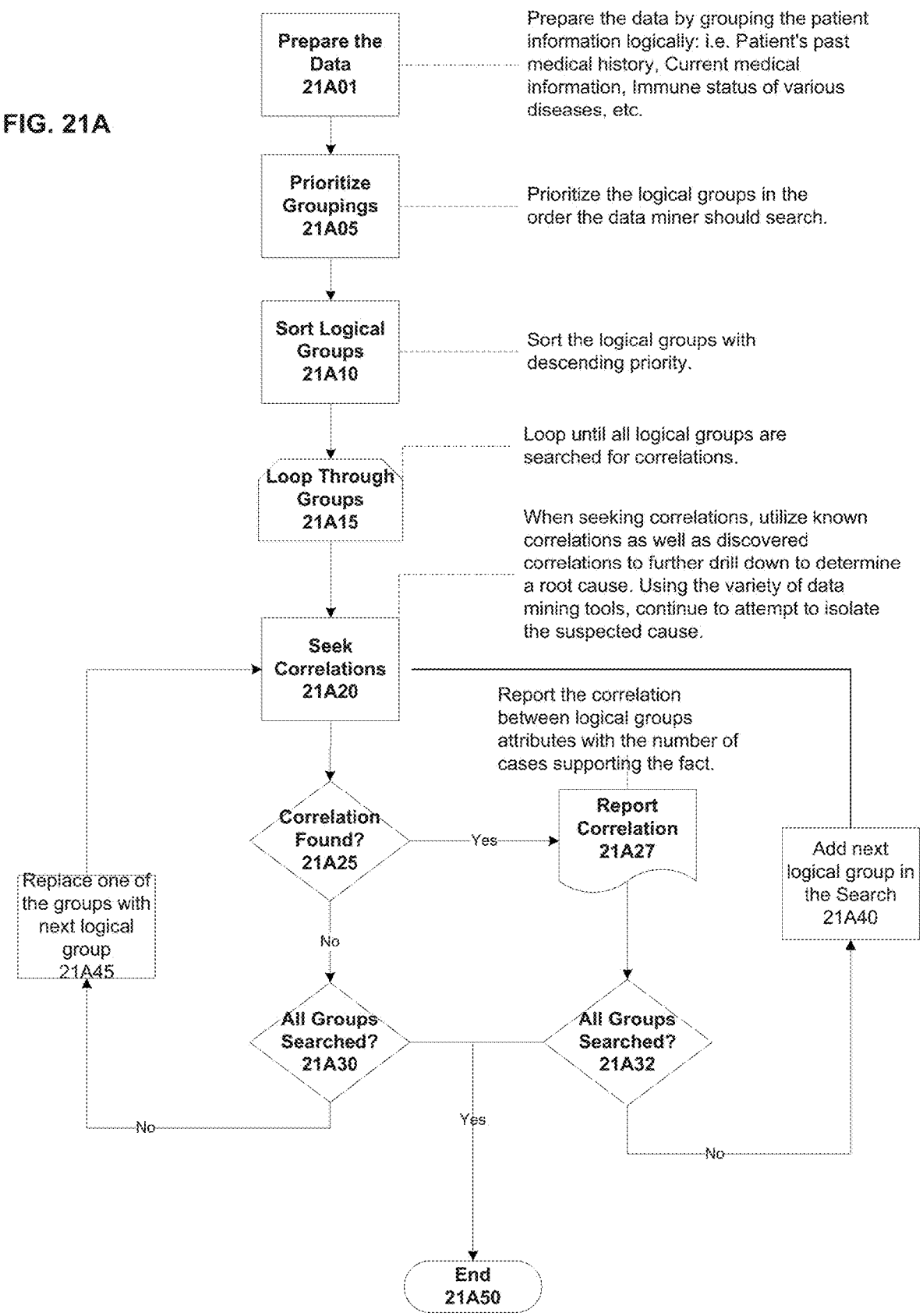
Figure 21B:
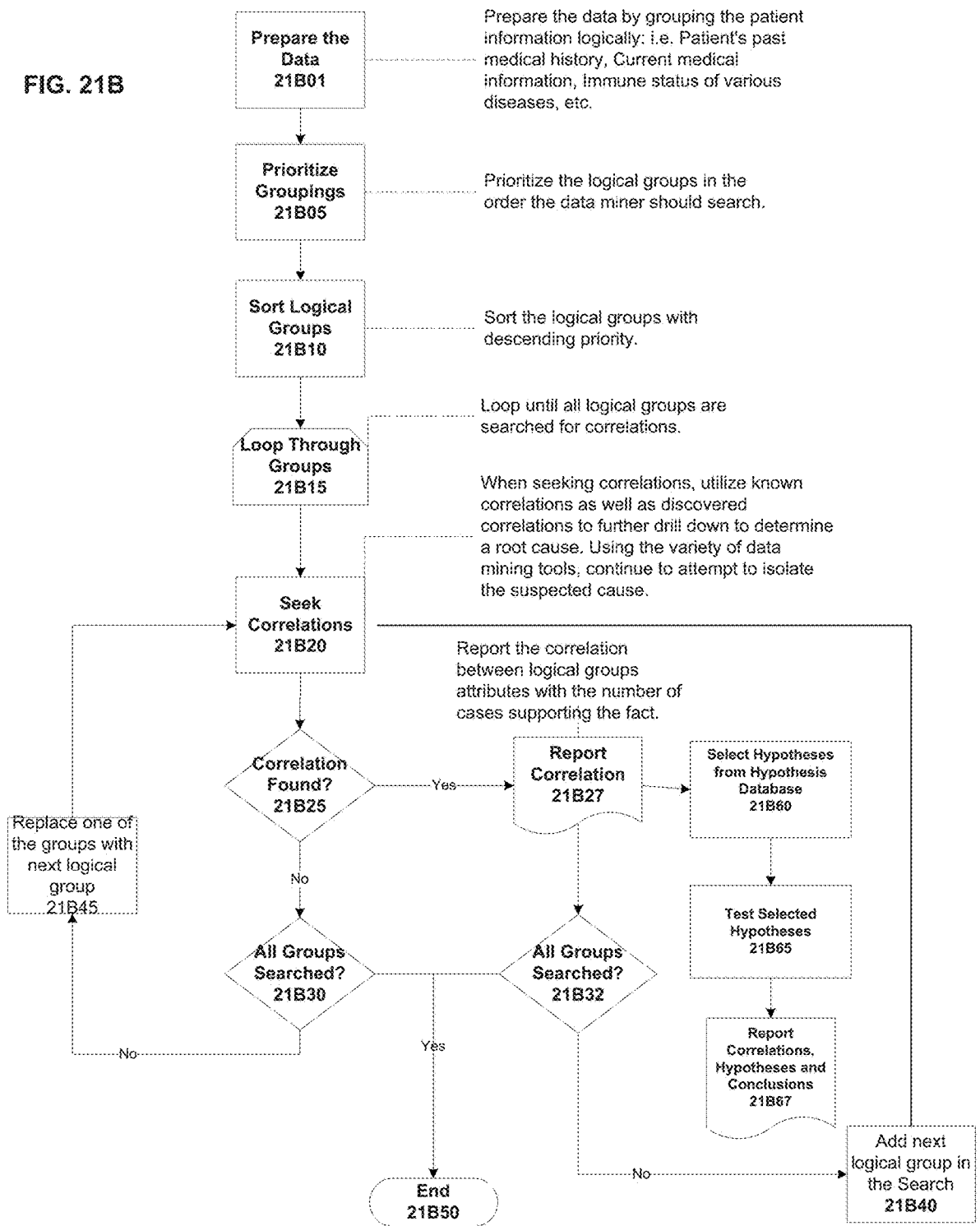
Figure 21C:
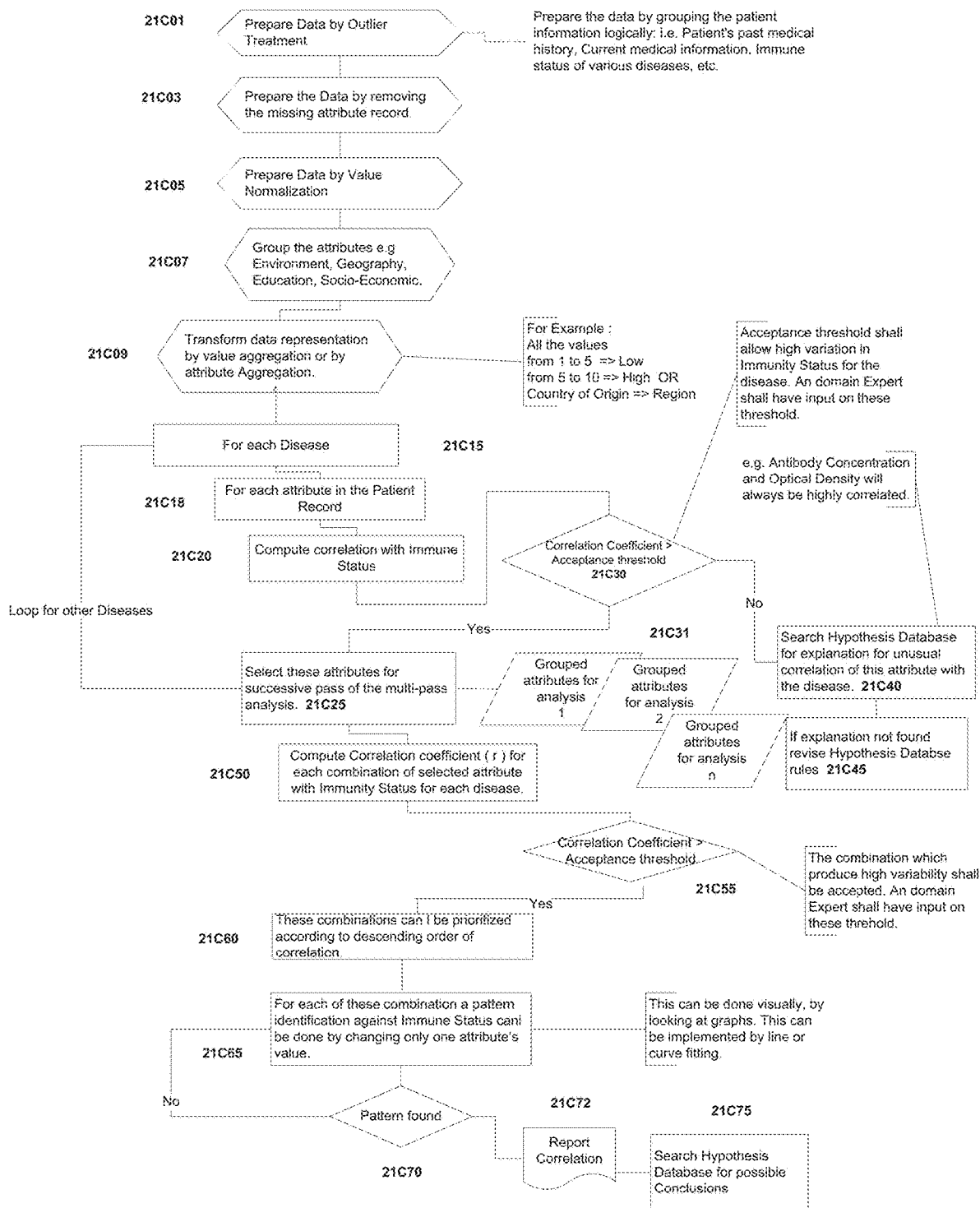
Figures 5B, 21E:
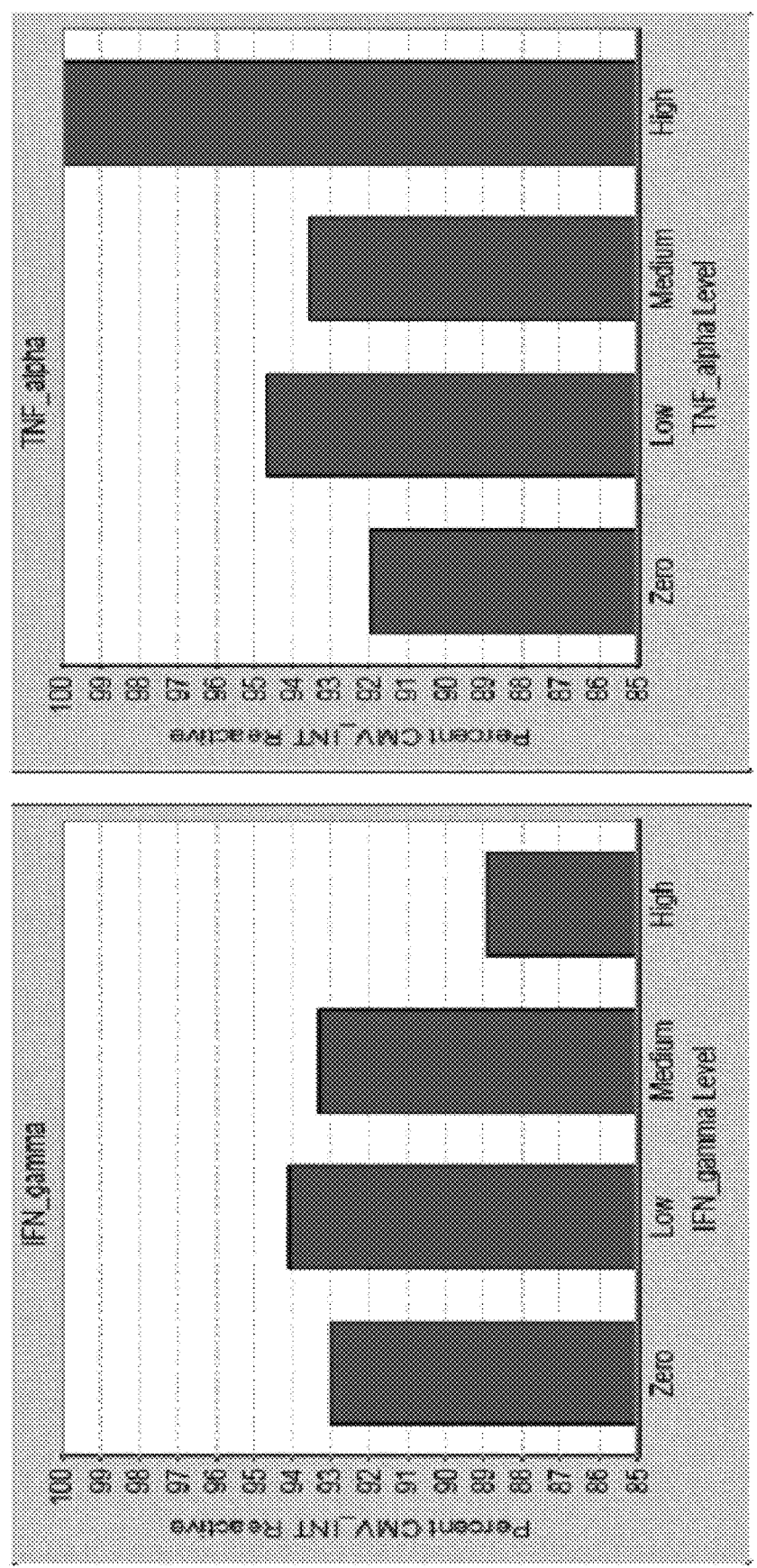
Figures 5C, 21E:
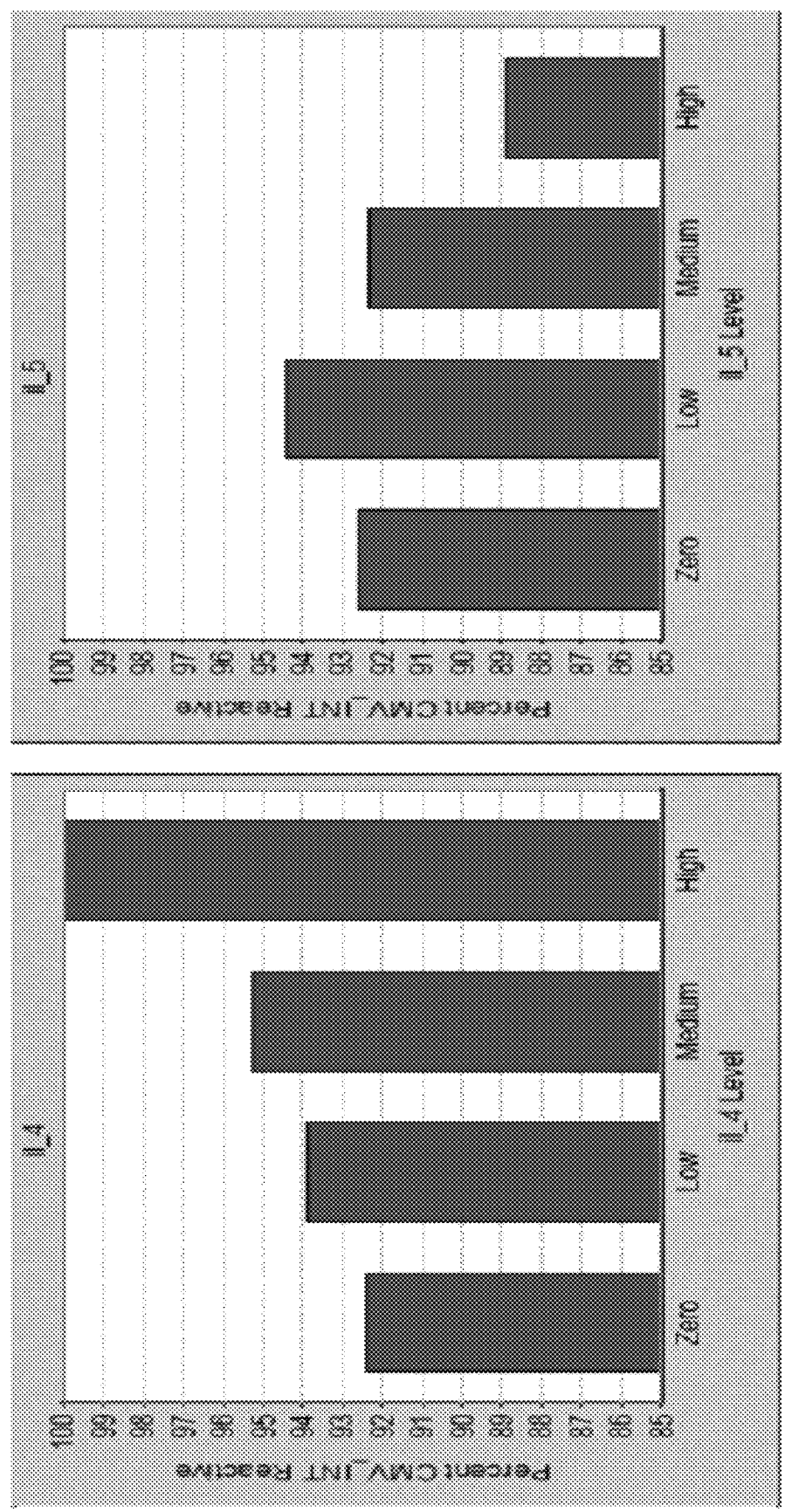
Figures 5D, 21E:
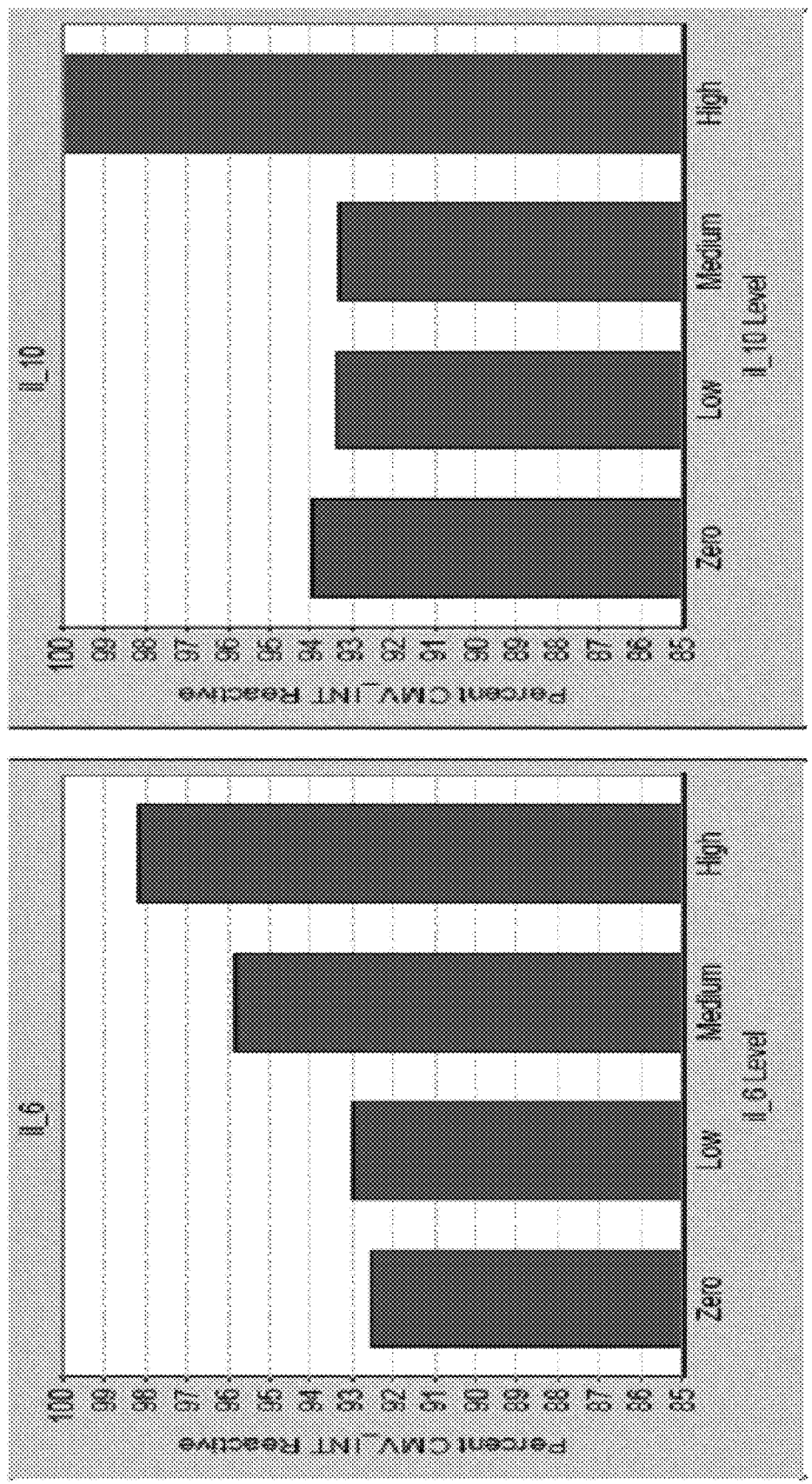
Figures 1H, 21G:
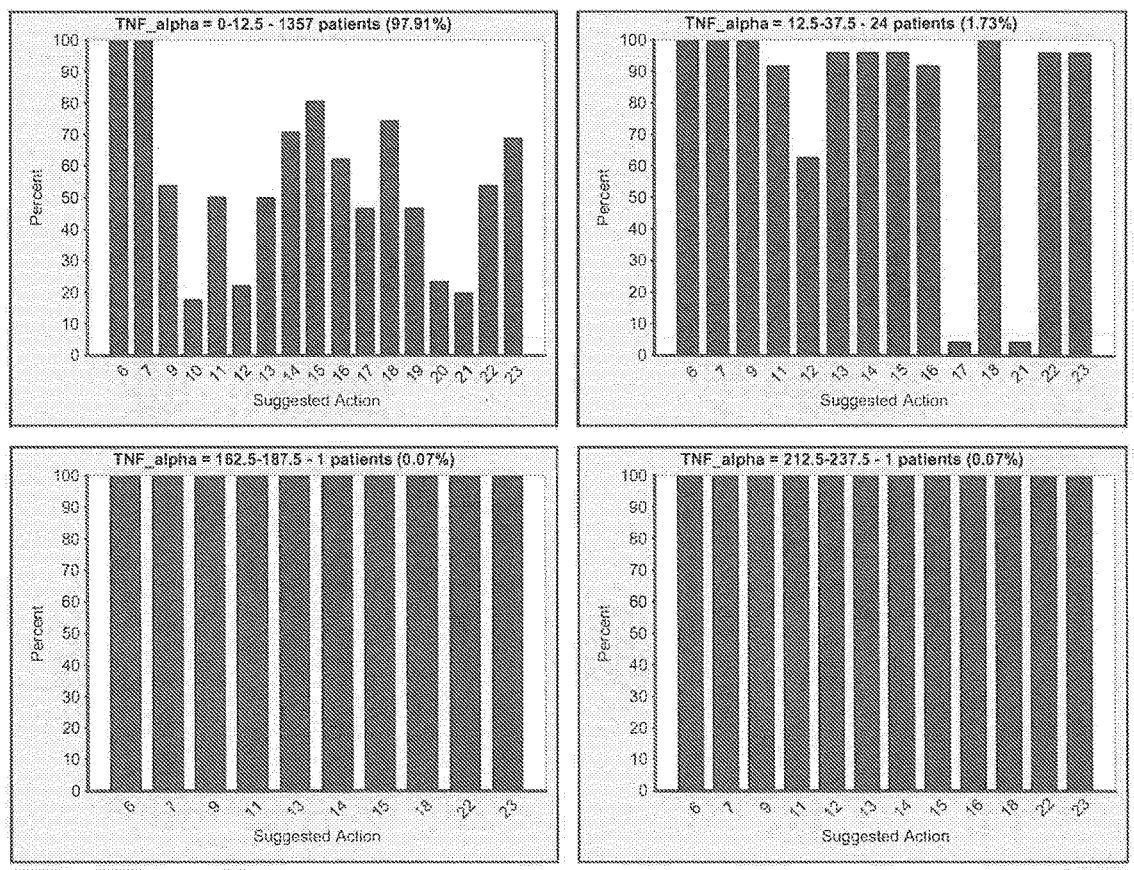
Figures 1I, 21G:
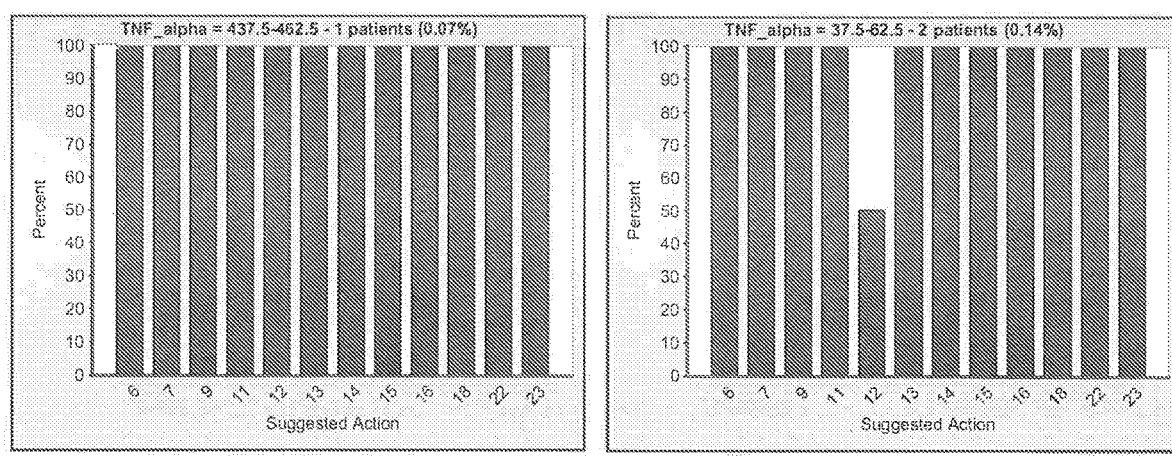
Figures 2H, 21G:
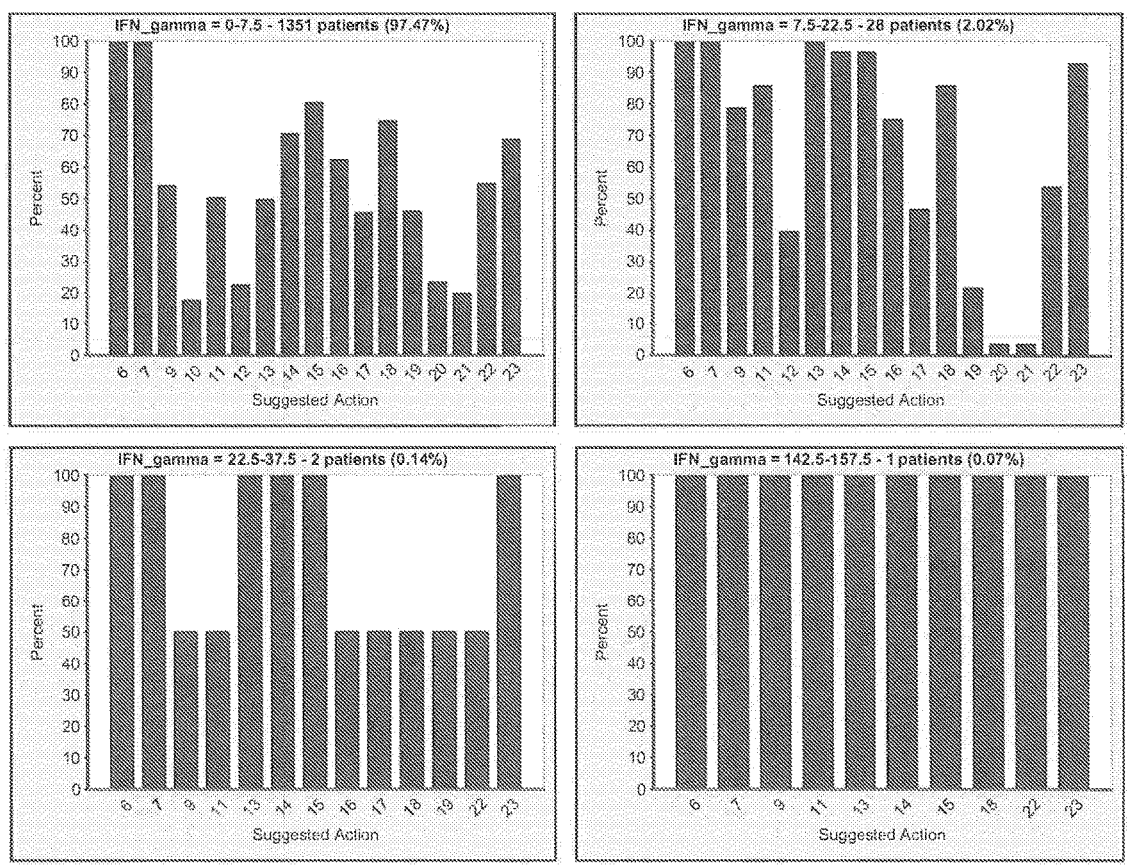
Figures 2I, 21G:
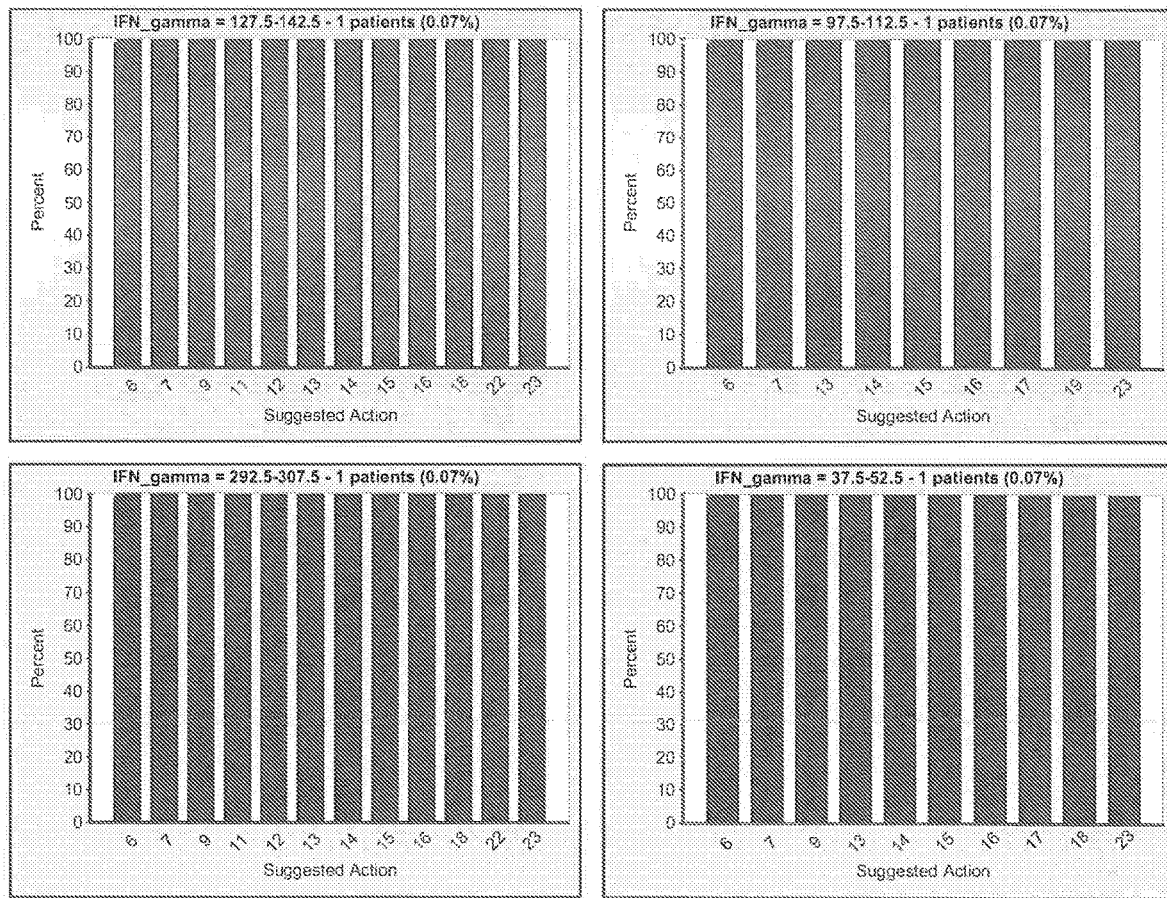
Figures 3, 21G:
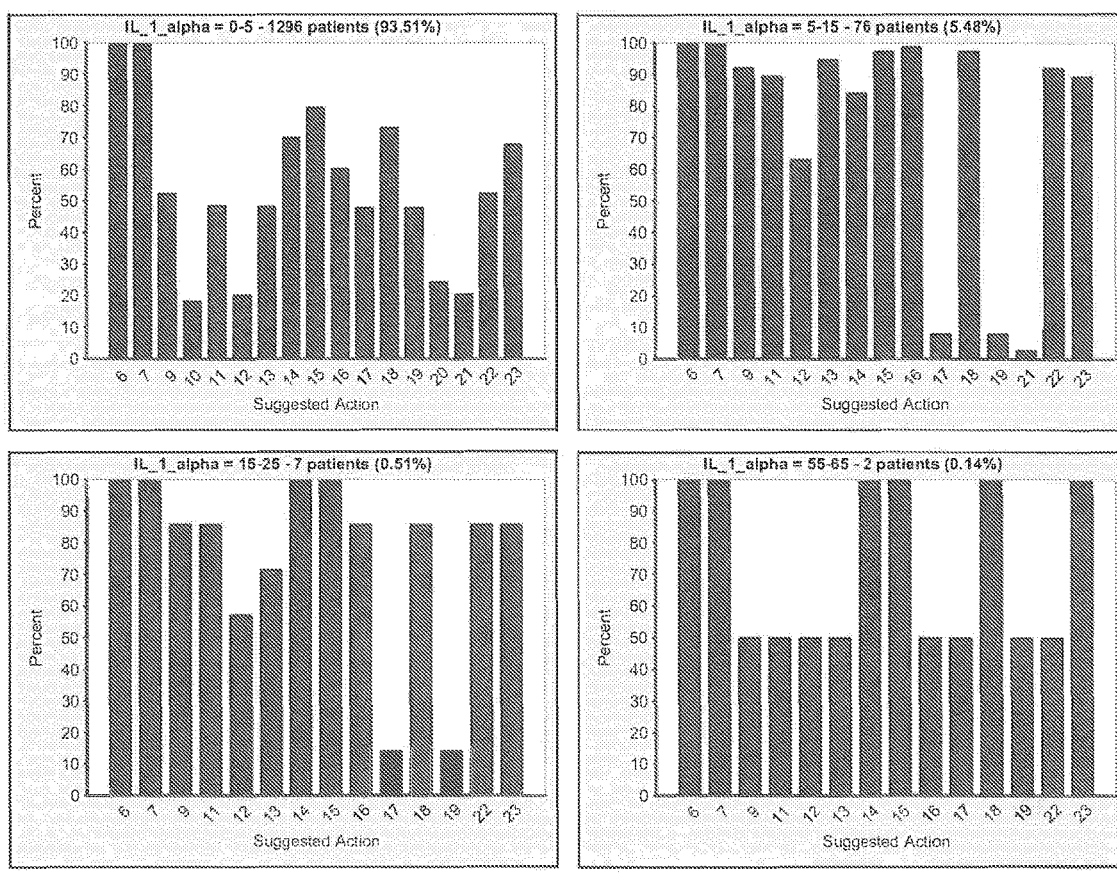
FIGS. 3 and 4 depict various exemplary configurations for assaying a patient sample according to an exemplary embodiment of the present invention.
Figures 21, 21G, 22, 23, 24, 25, 26, 27, 28, 29, 30, 31:
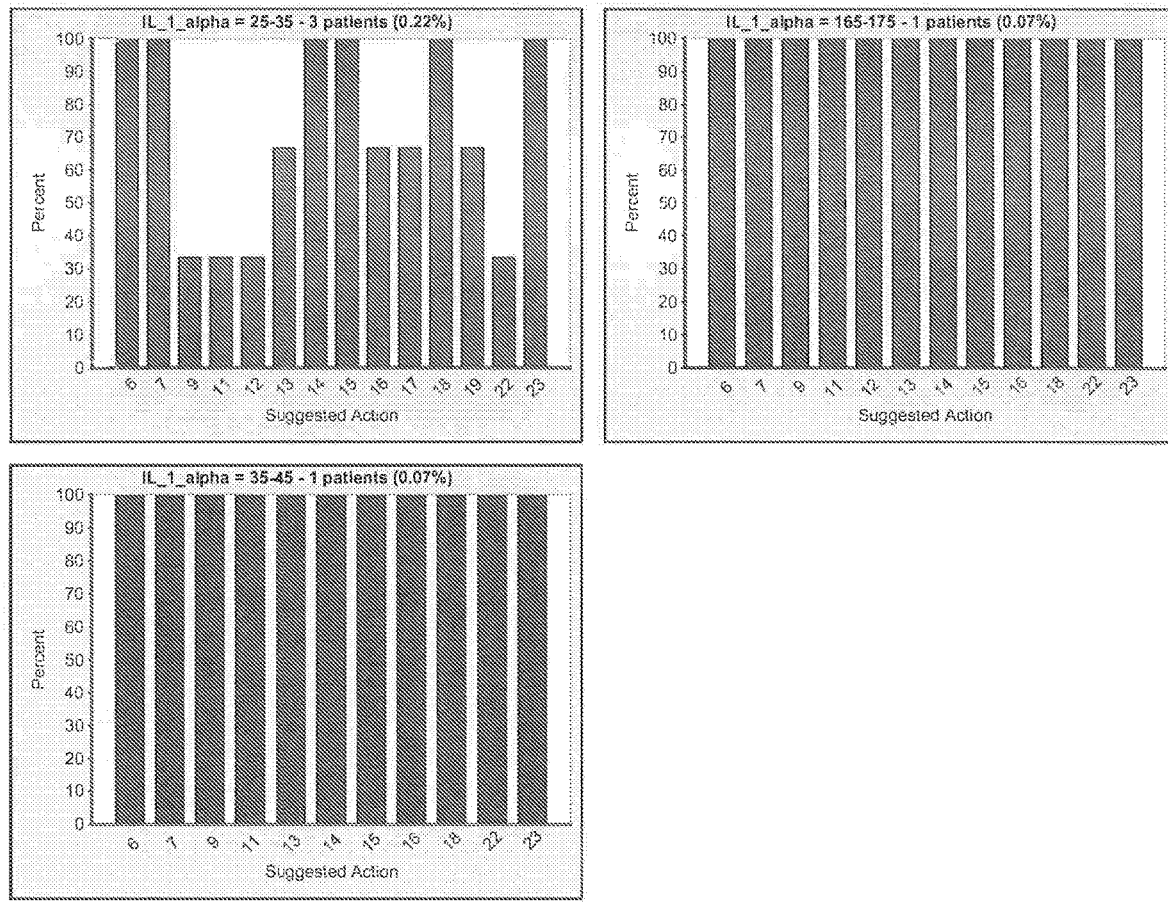
Figures 4, 21G:
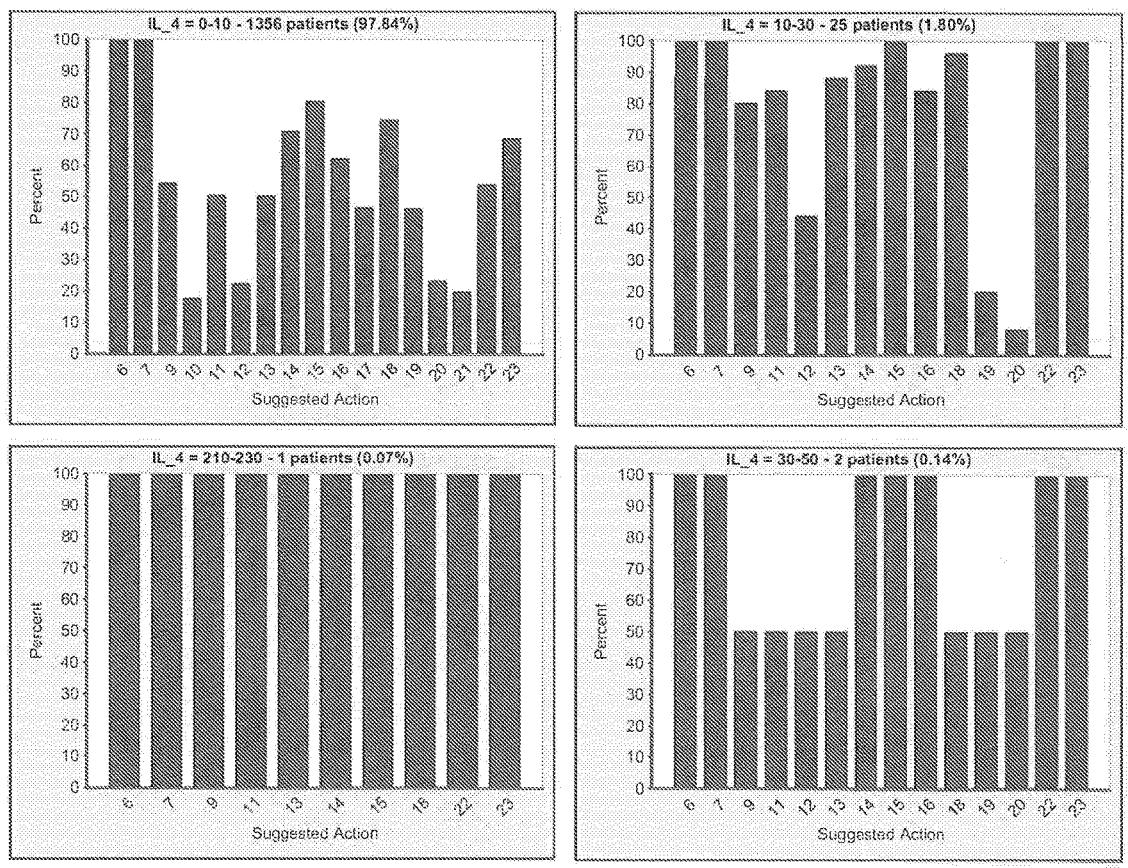
Figures 21, 21G, 22, 23, 24, 25, 26, 27, 28, 29, 30, 31, 32, 33, 34, 35, 36, 37, 38, 39, 40, 41:
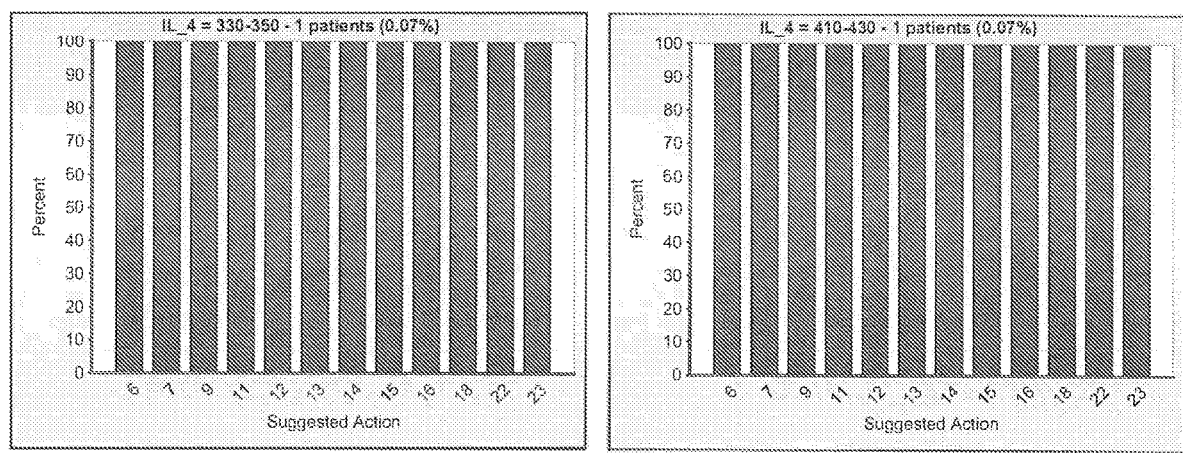
Figures 5, 21G:
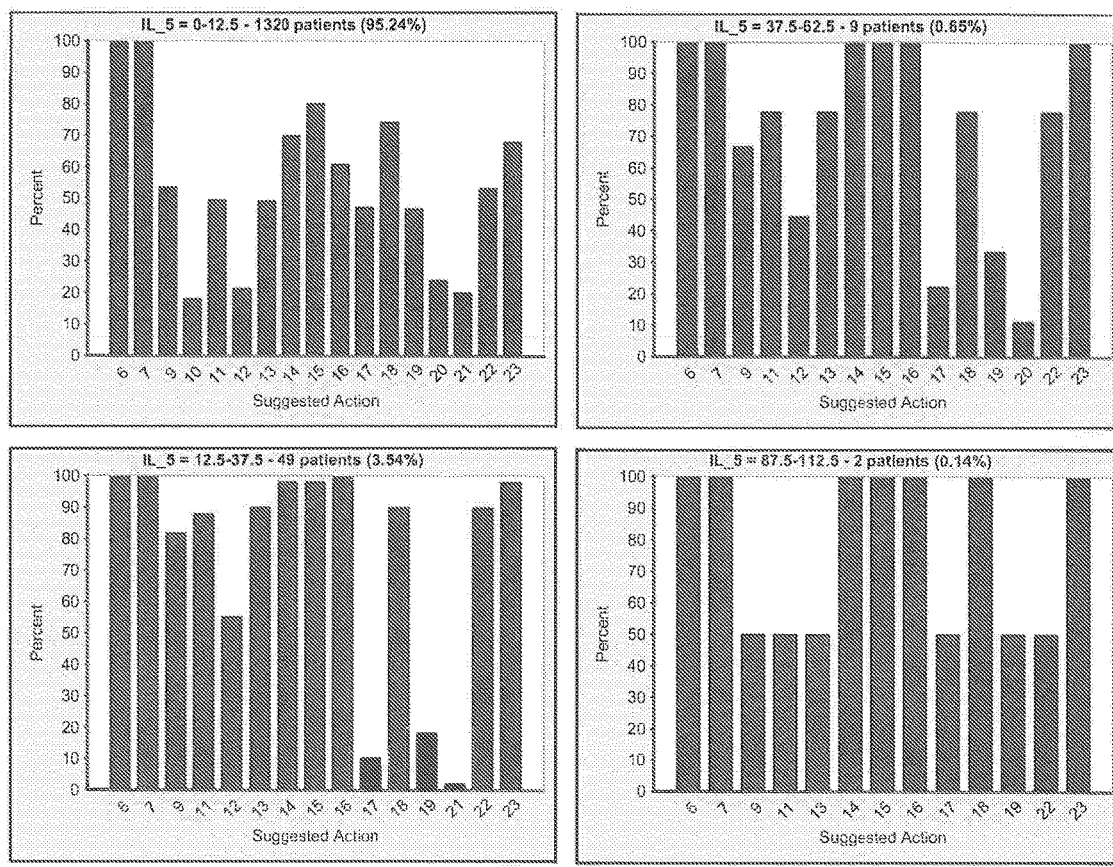
Figures 21, 21G, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51:
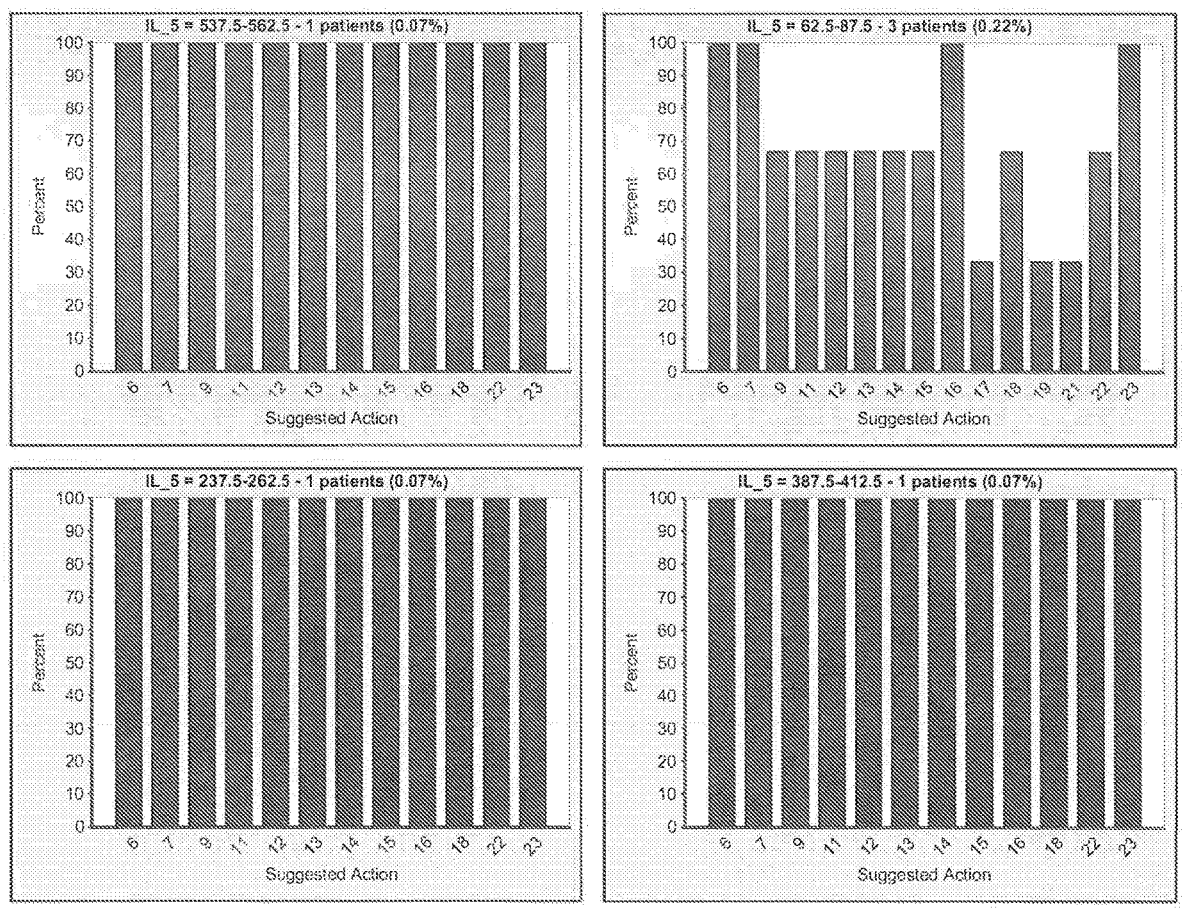
Figures 21, 21G, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61:
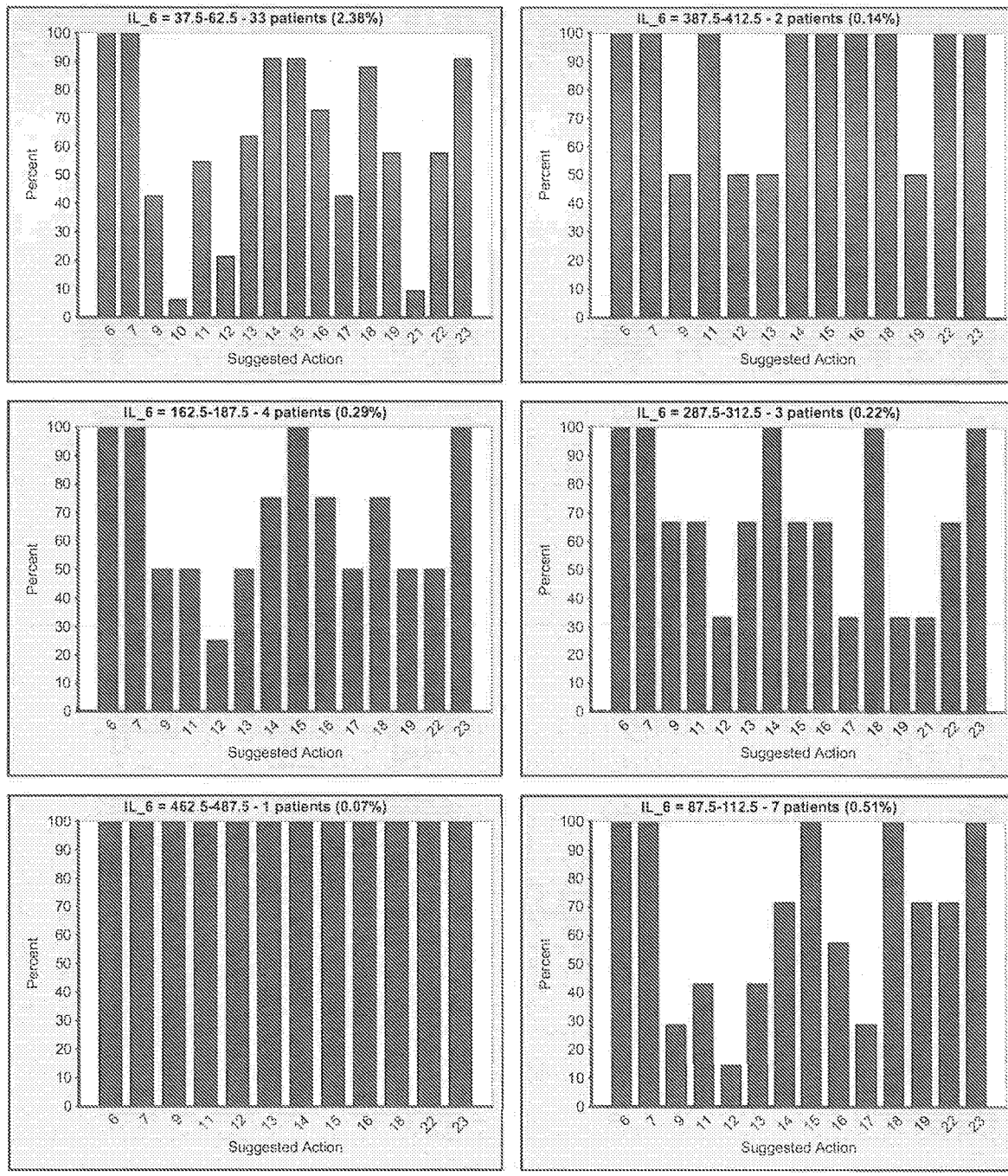
Figures 6J, 21G:
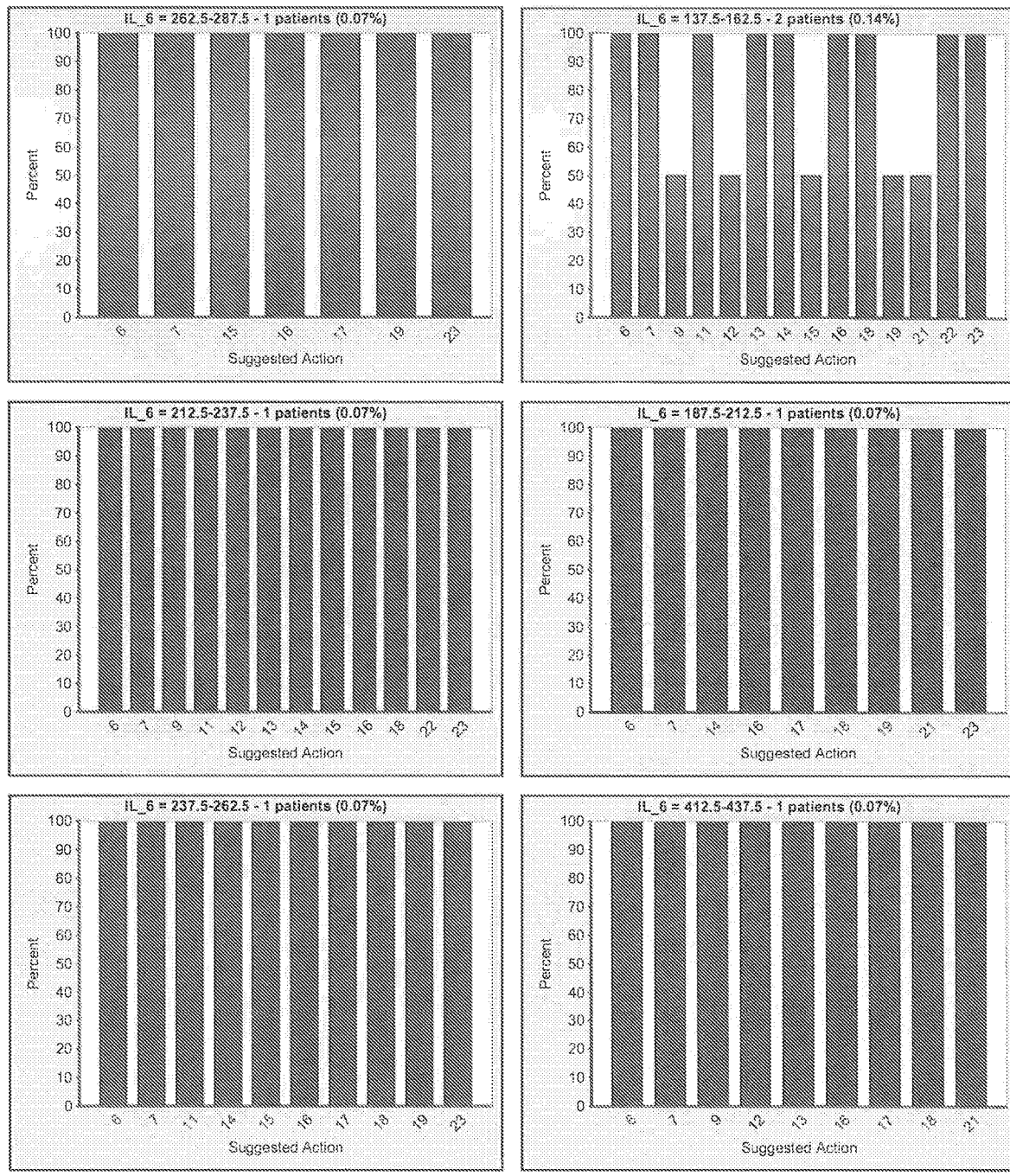
Figures 7, 21G:
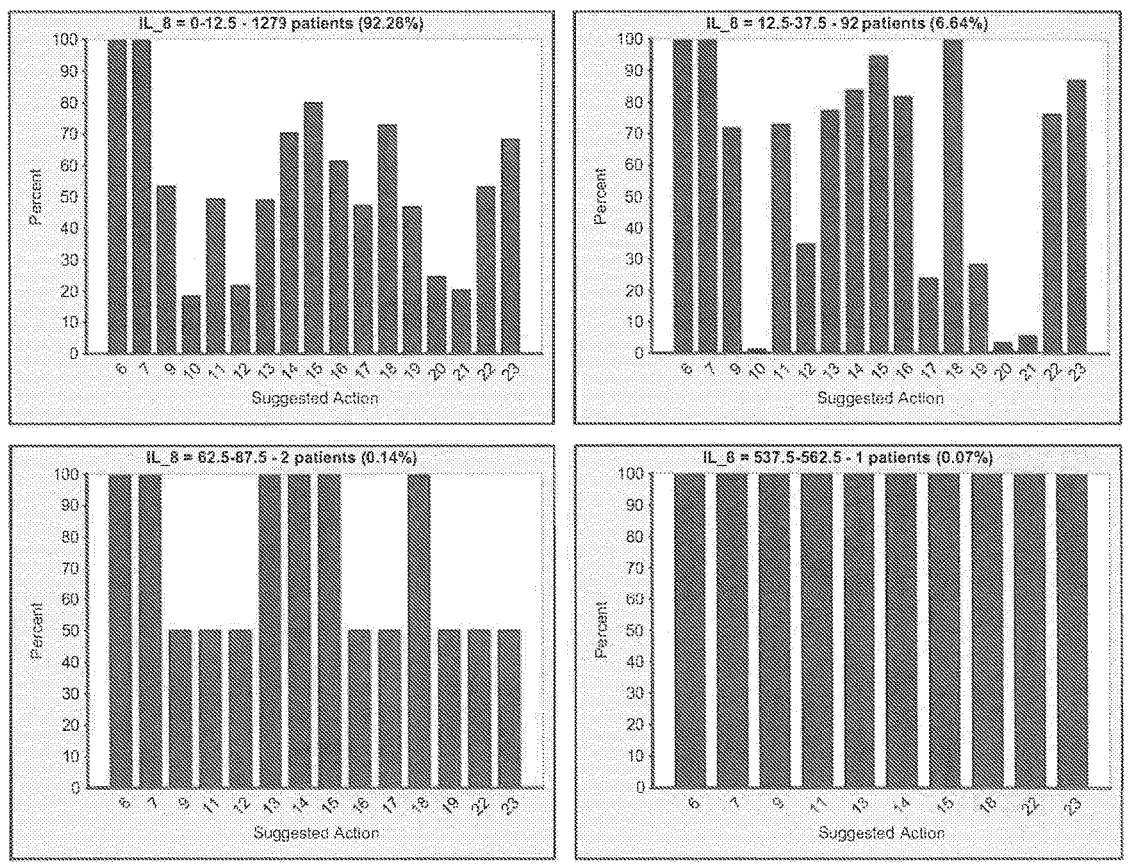
Figures 21, 21G, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71:
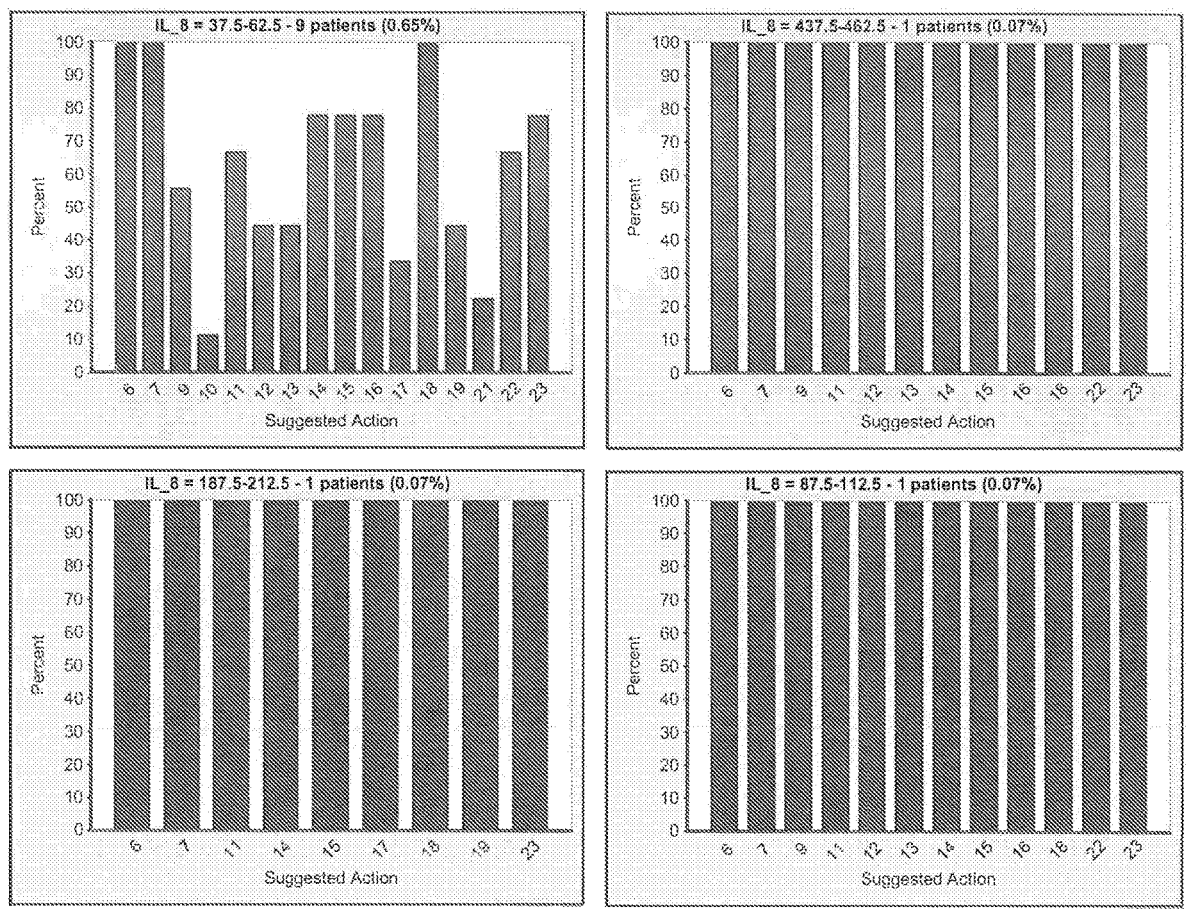
Figures 8, 21G:
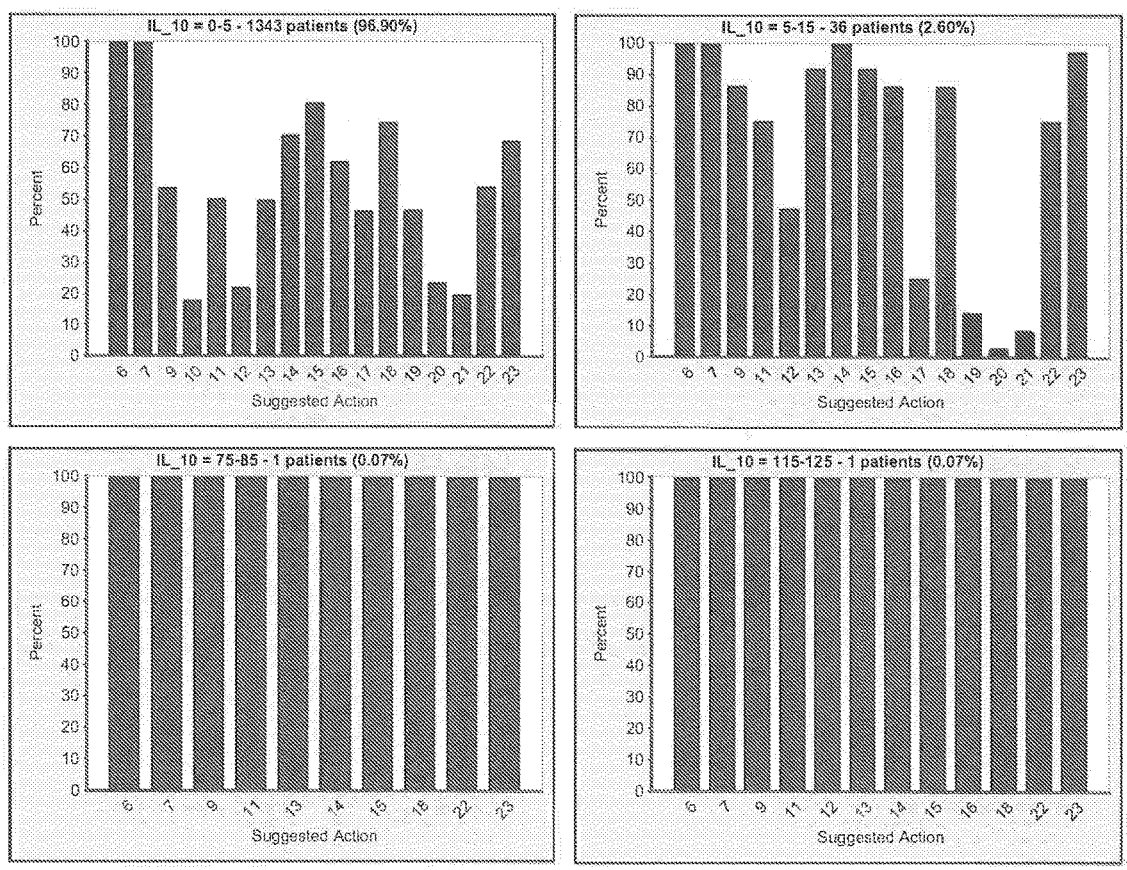
Figures 21G, 81:
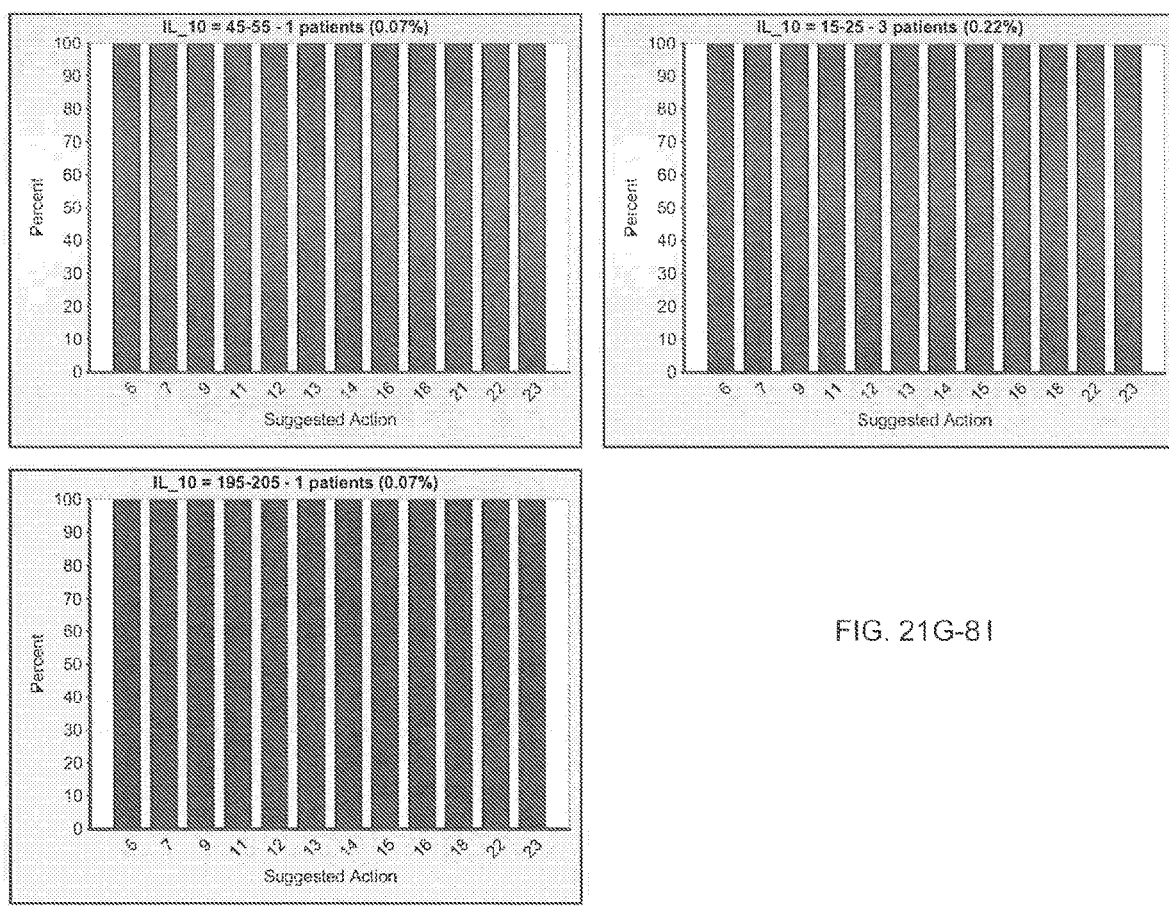
Figures 9, 21G:
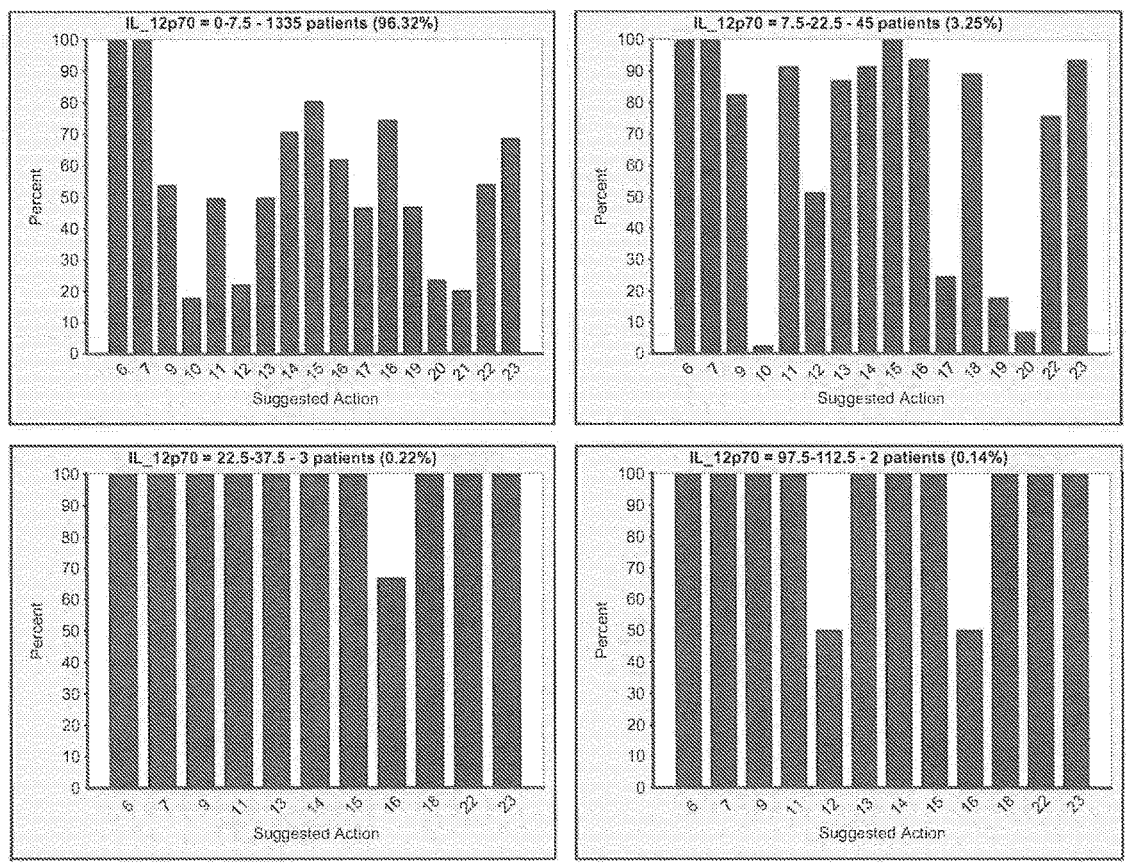
Figures 21G, 91:
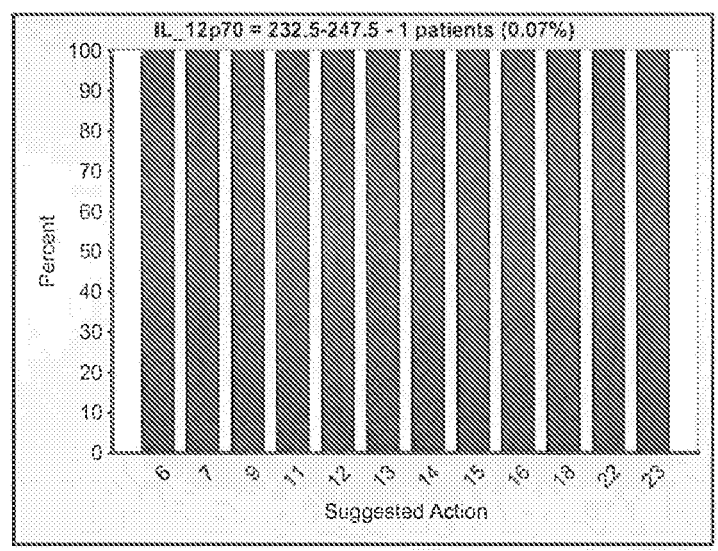
Figures 10, 21G:
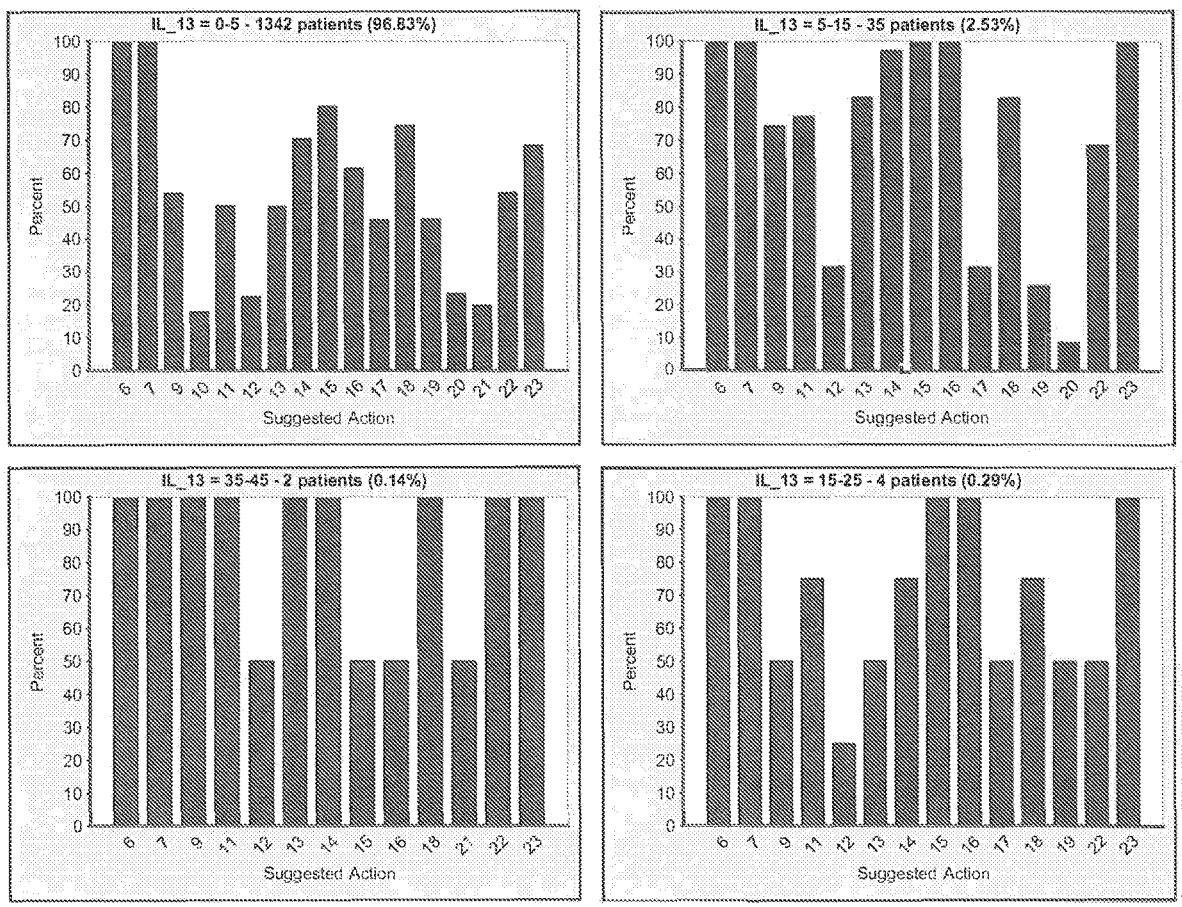
Figures 10I, 21G:
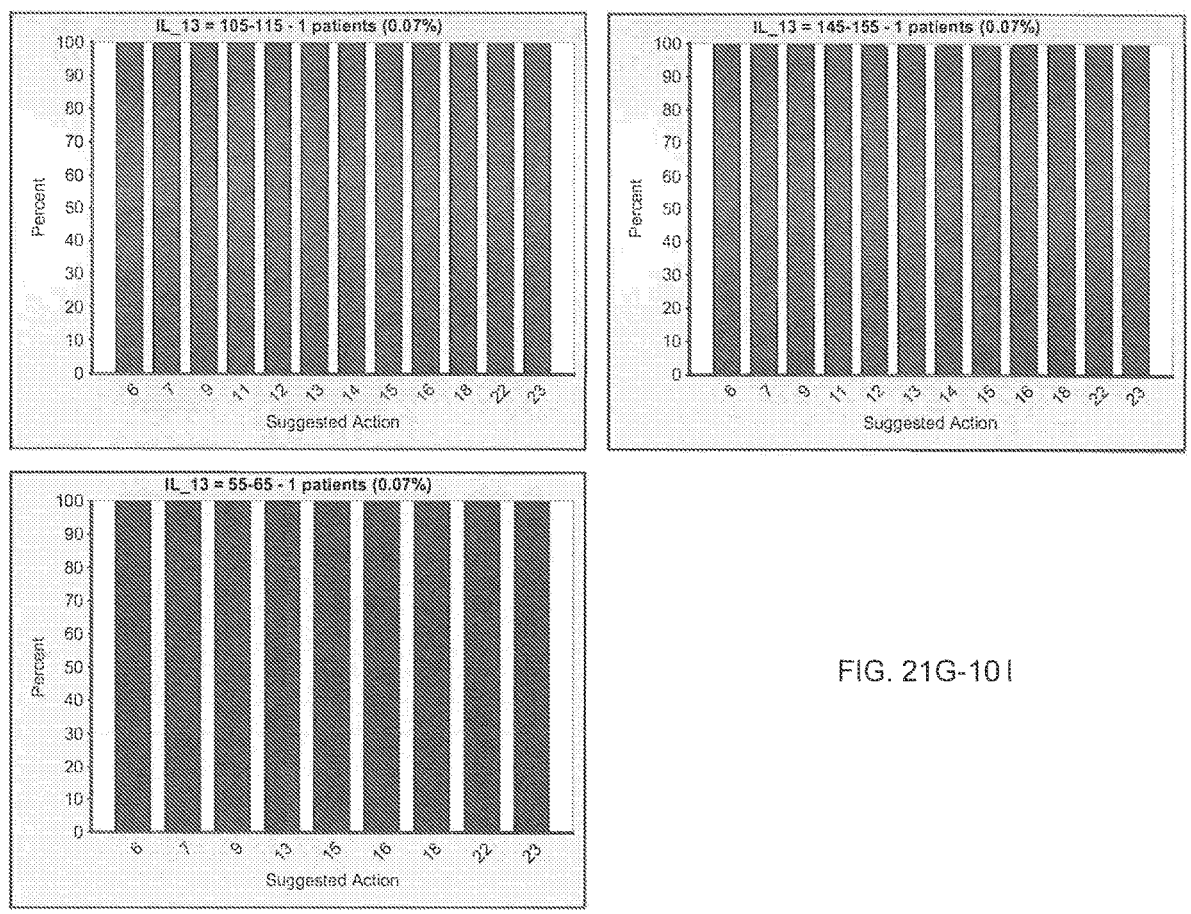
Figure 21:
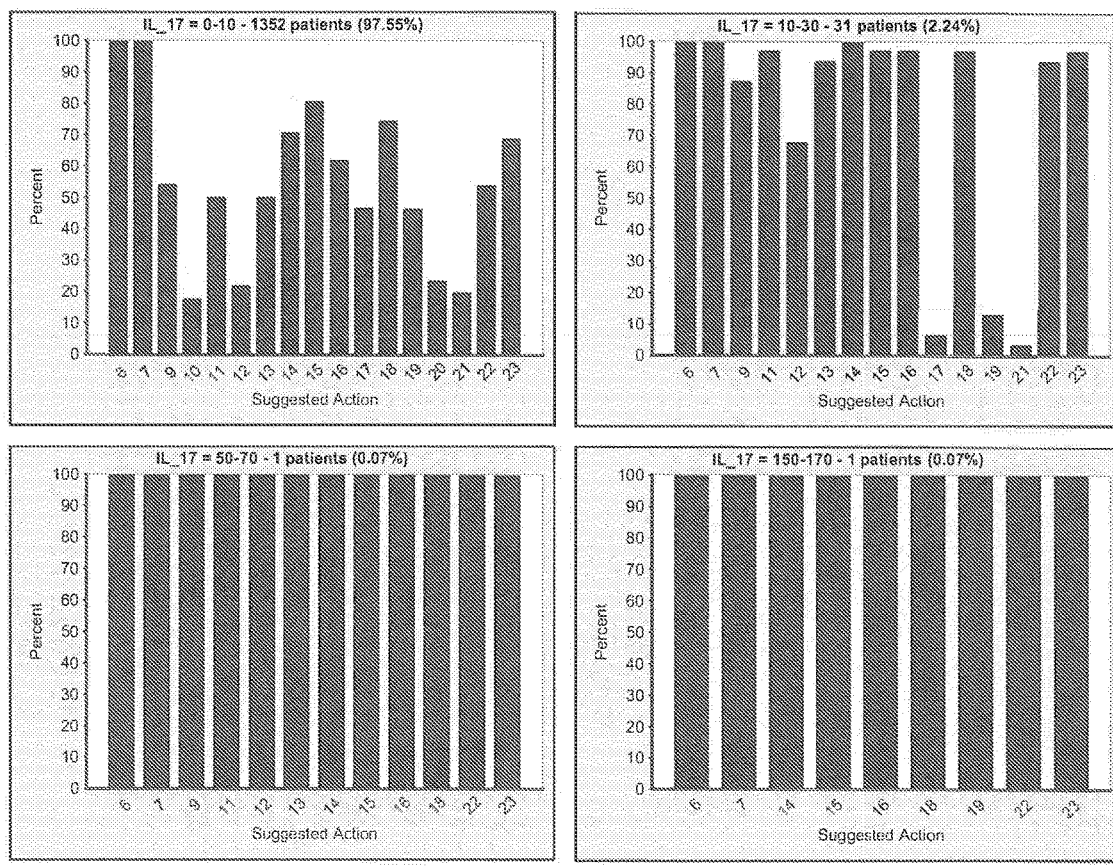
Figures 11, 21G:
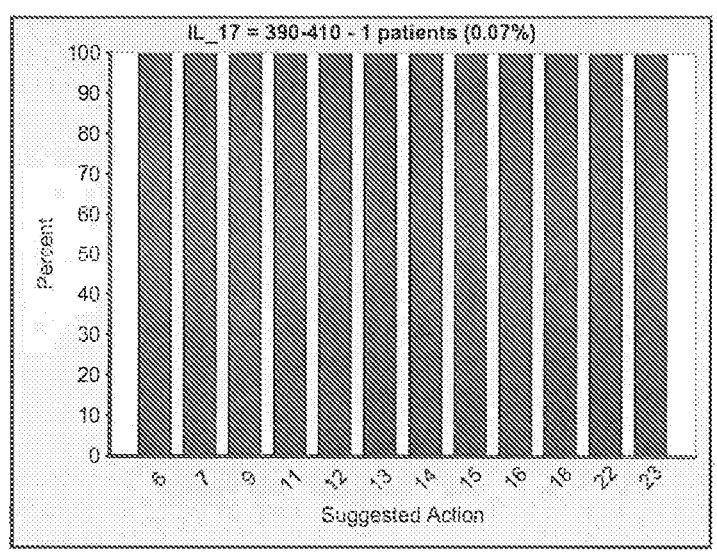
Figures 12, 21G:
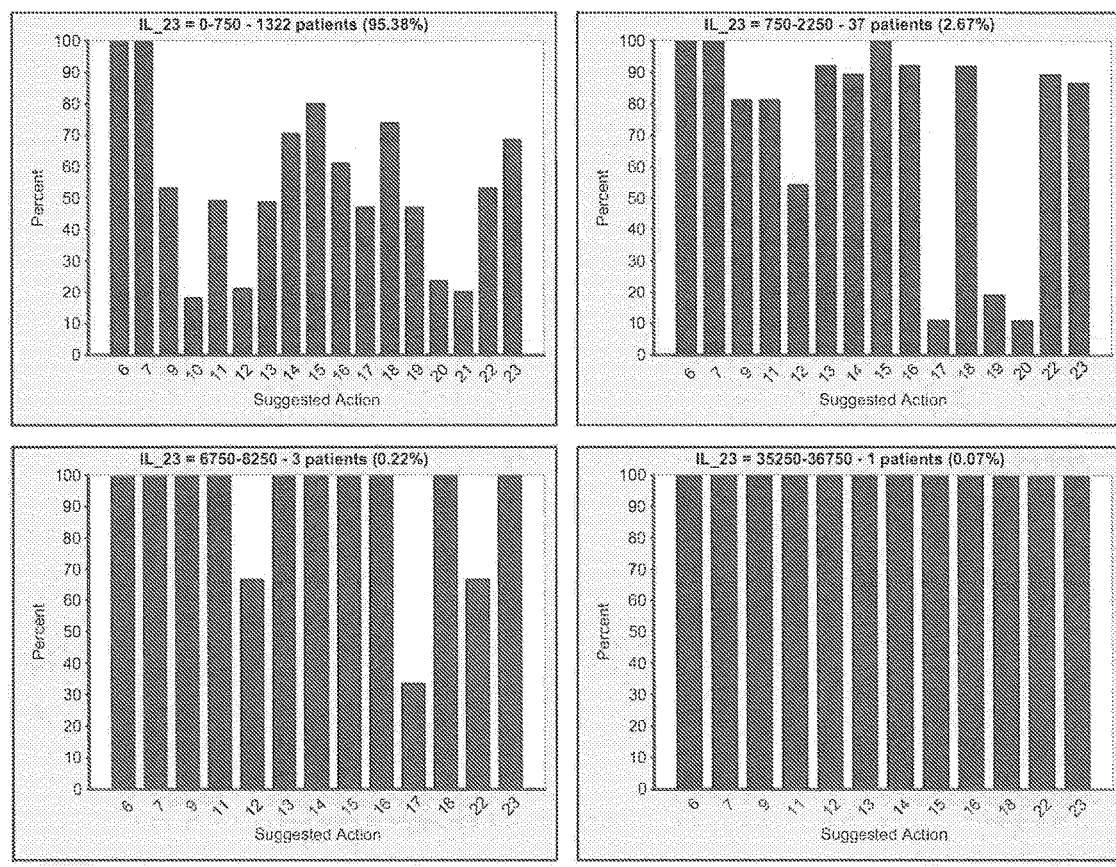
Figures 12, 21G:
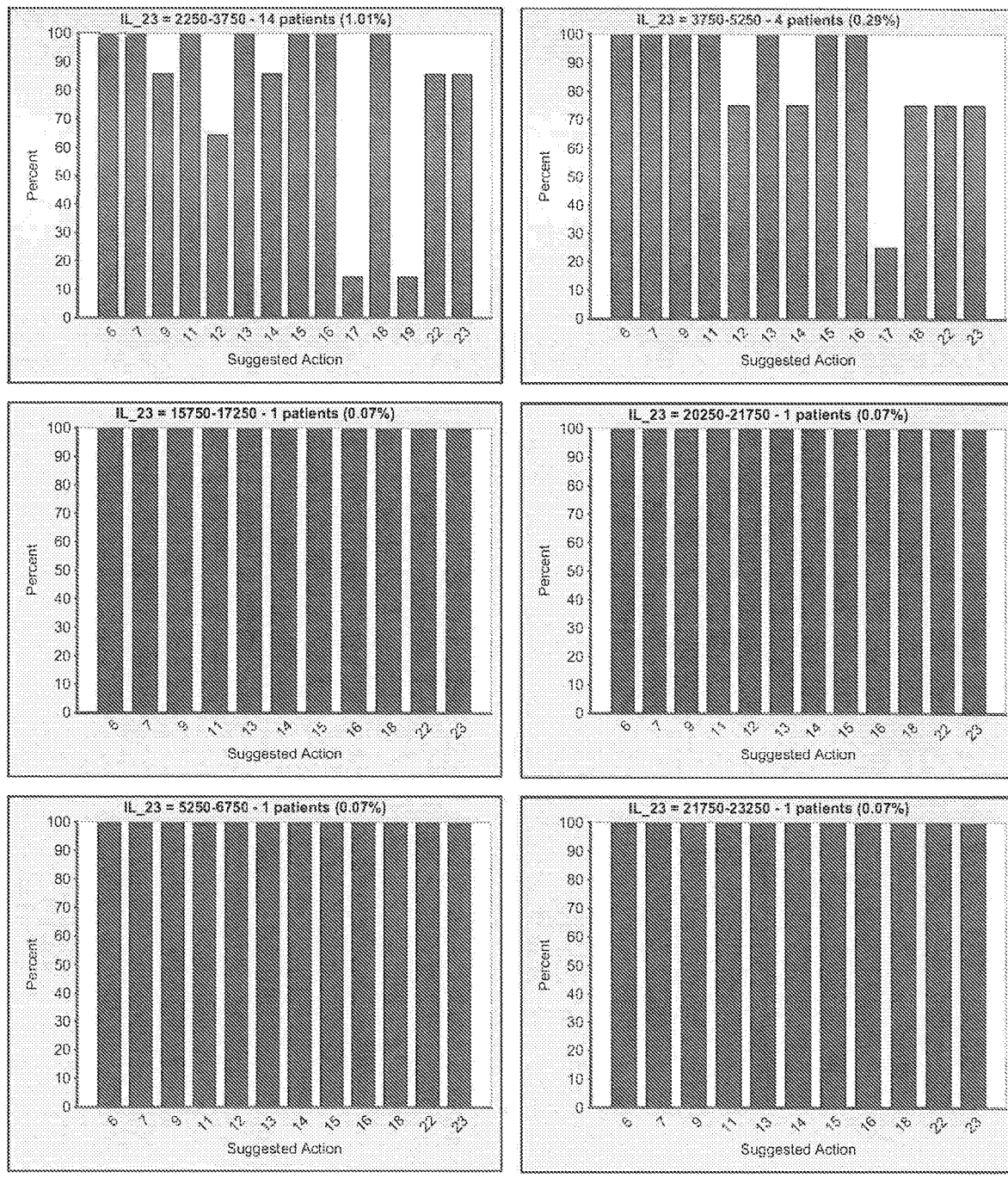
Figures 12, 21G:
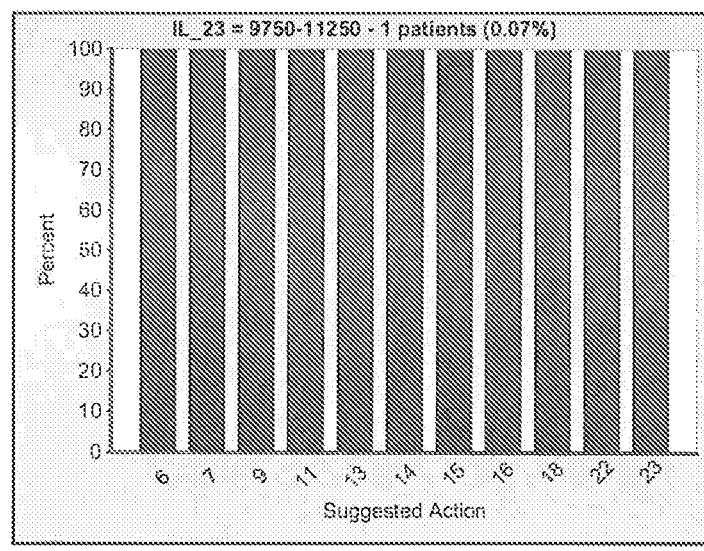
Figure 22:
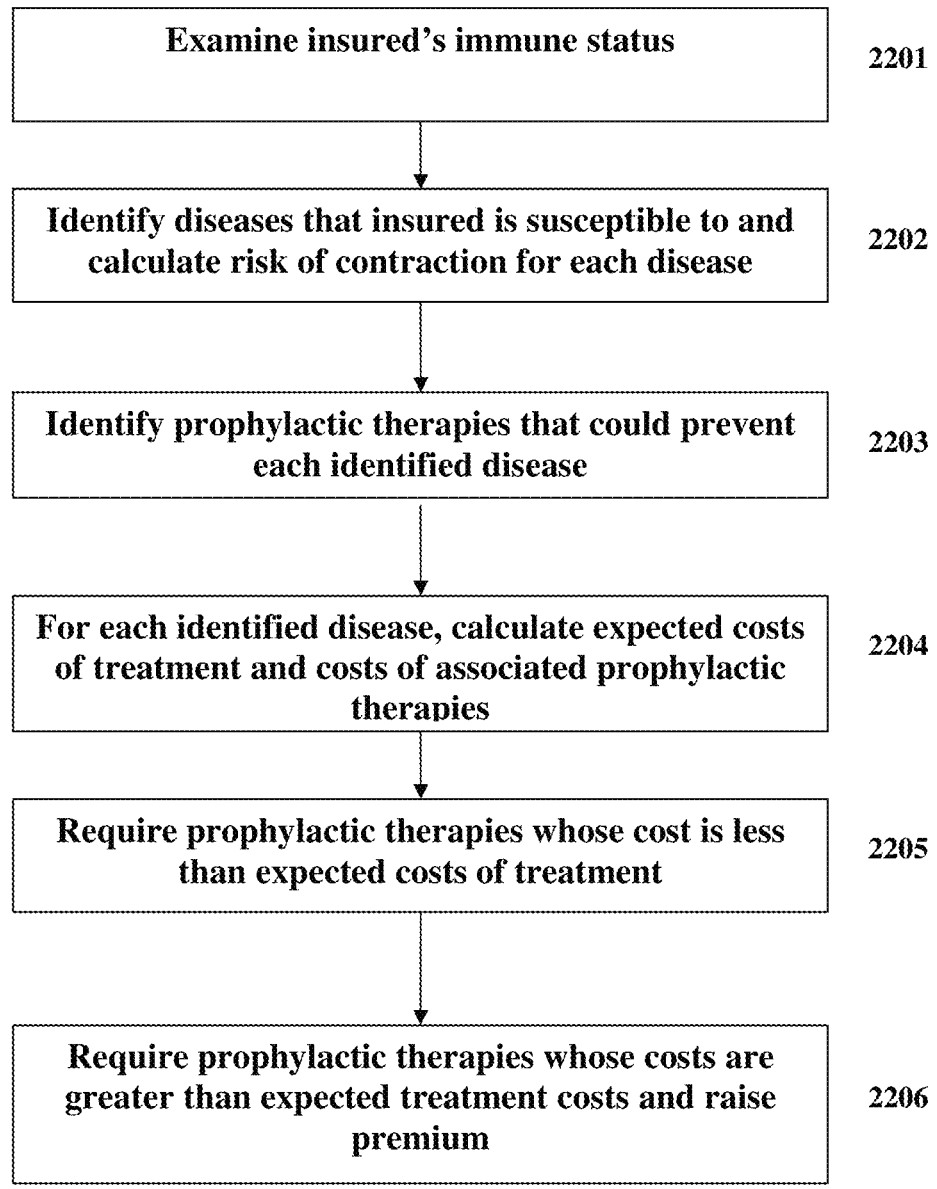
Figure 23:
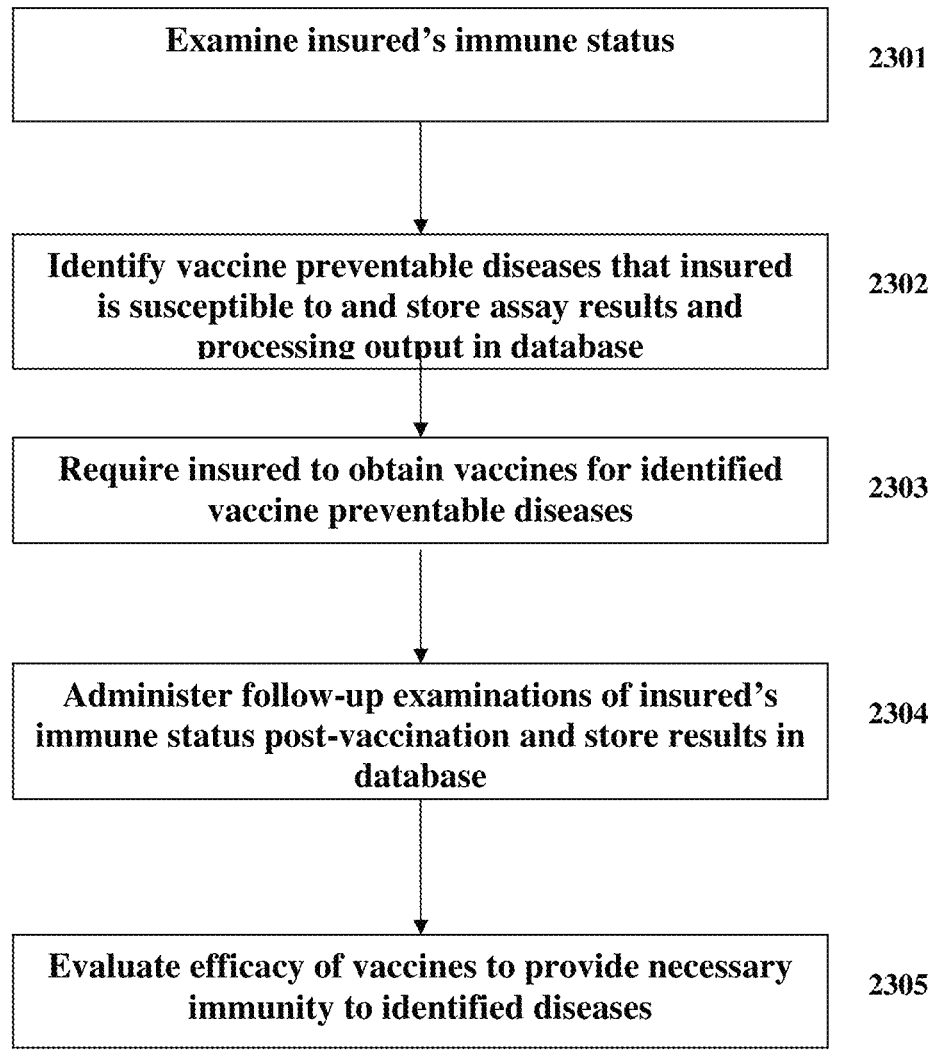
Figure 24:
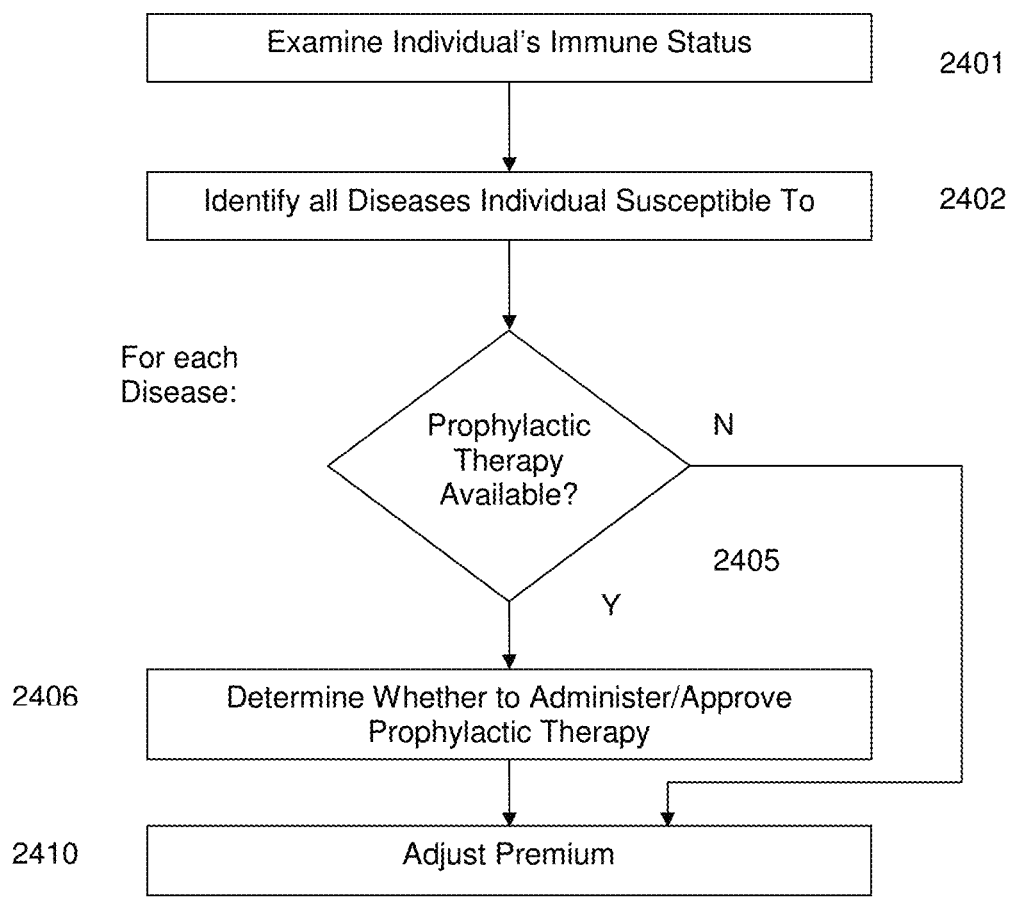

FIG. 6 depicts exemplary assay results in an exemplary database according to the present invention;

FIG. 7 depicts exemplary diagnostic module recommendation types according to an exemplary embodiment of the present invention;

FIG. 8 illustrates an exemplary perceptron network which implements a rule for a normal individual using as inputs the results of an exemplary menigicoccal diagnostic panel;

FIG. 8A illustrates the exemplary perceptron network of FIG. 8 implementing a similar rule for an abnormal individual;

FIG. 9 depicts an XML representation of the exemplary perceptron networks of FIGS. 8 and 8A;

FIG. 10 depicts an exemplary symbology for diagnostic goals which can be used to articulate diagnostic goals in an exemplary embodiment of the present invention;

FIG. 11 illustrates exemplary diagnostic goals using the symbology of FIG. 10;

FIG. 12 illustrates an exemplary database schema for patient information according to an exemplary embodiment of the present invention;

FIG. 13 illustrates an exemplary database schema for visit information according to an exemplary embodiment of the present invention;

FIG. 14 illustrates an exemplary database schema for test results according to an exemplary embodiment of the present invention;

FIG. 15 depicts exemplary patient age intervals used in an exemplary database according to an exemplary embodiment of the present invention;

FIG. 16 is a plot of an exemplary female antibody comparison over a number of years according to an exemplary embodiment of the present invention.

Figure 1:
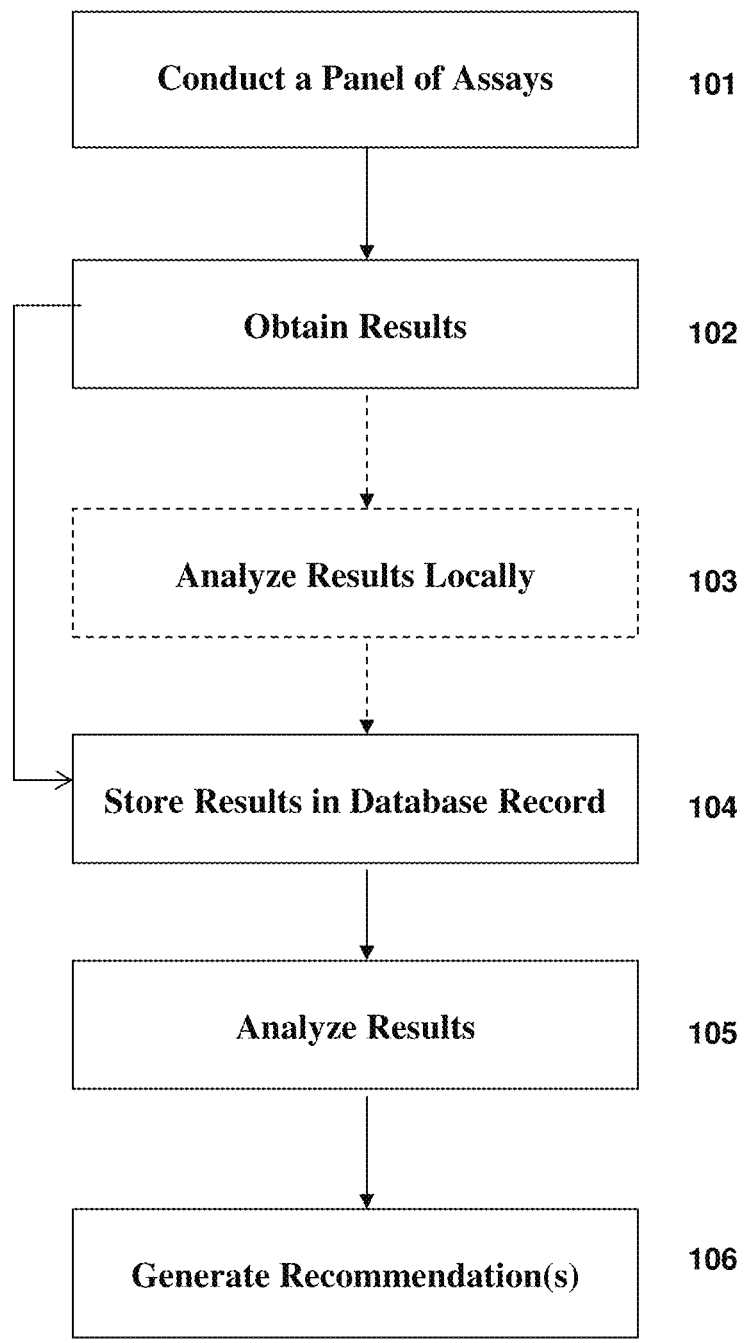
FIG. 1 depicts a generalized exemplary process flow according to exemplary embodiments of the present invention.
Figure 20A:
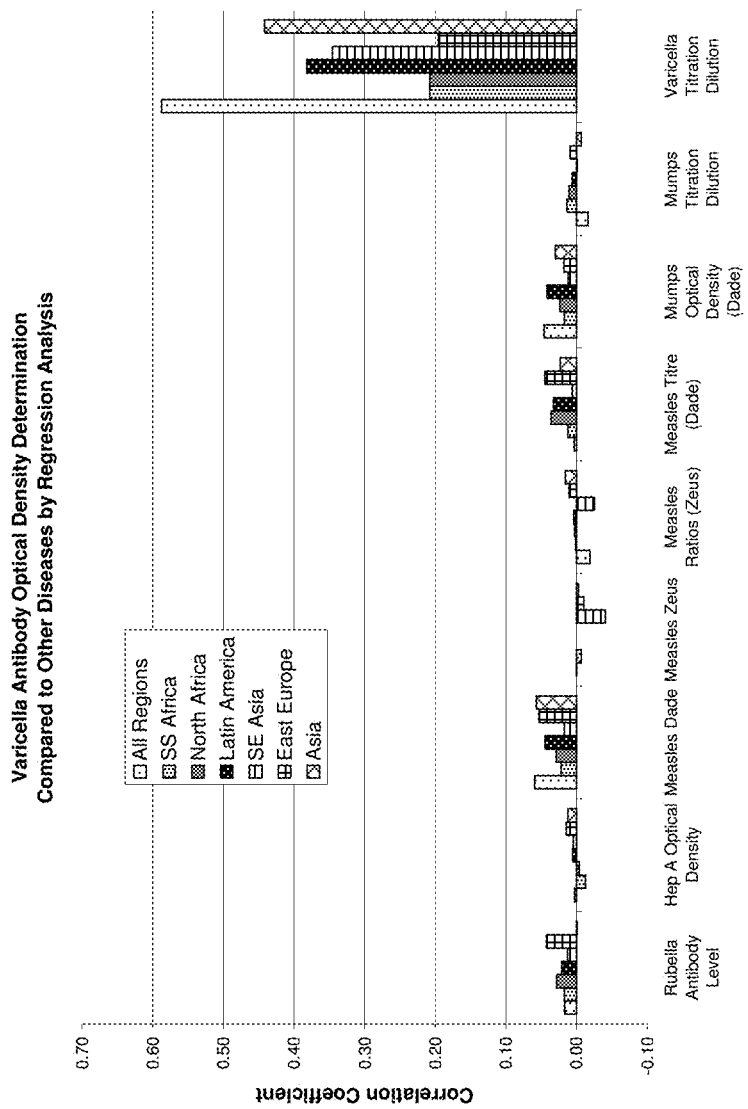
Figure 20B:
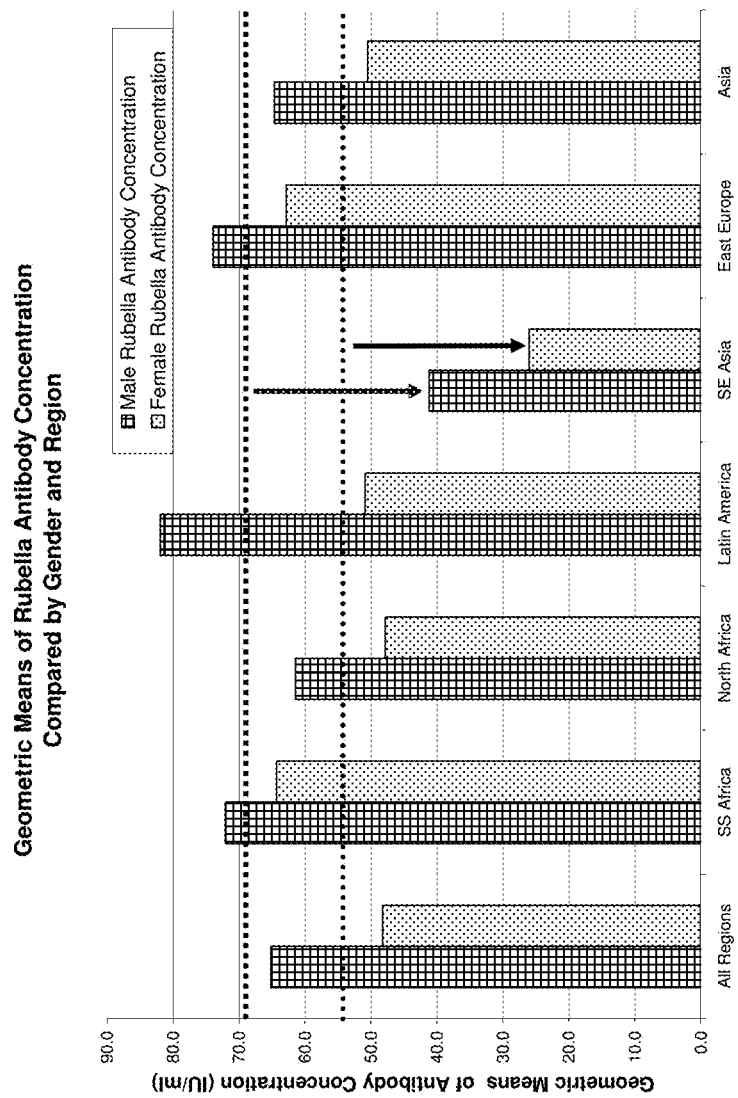
Figure 20C:
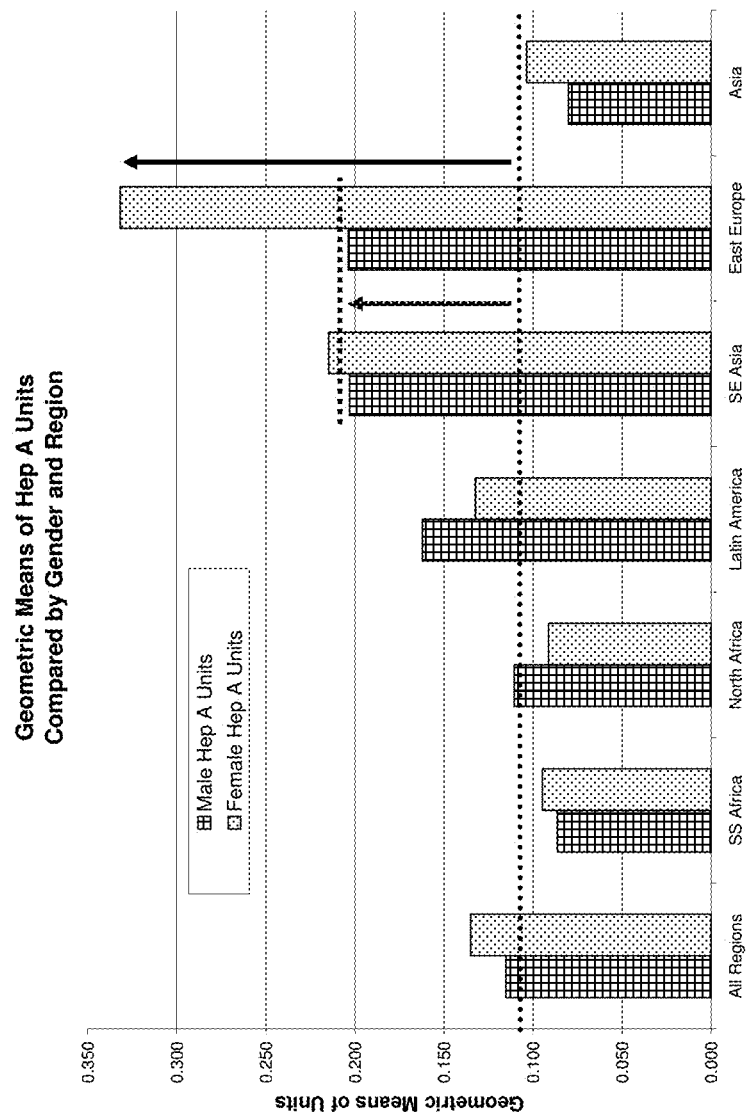
Figure 20D:
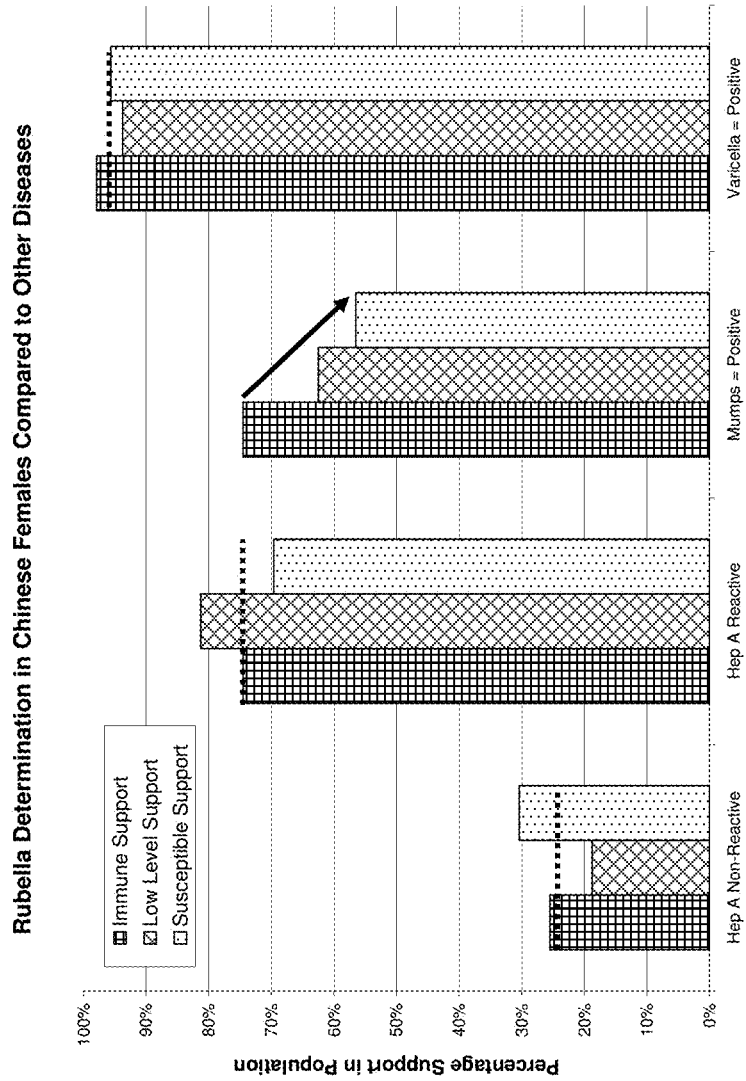
Figure 20E:
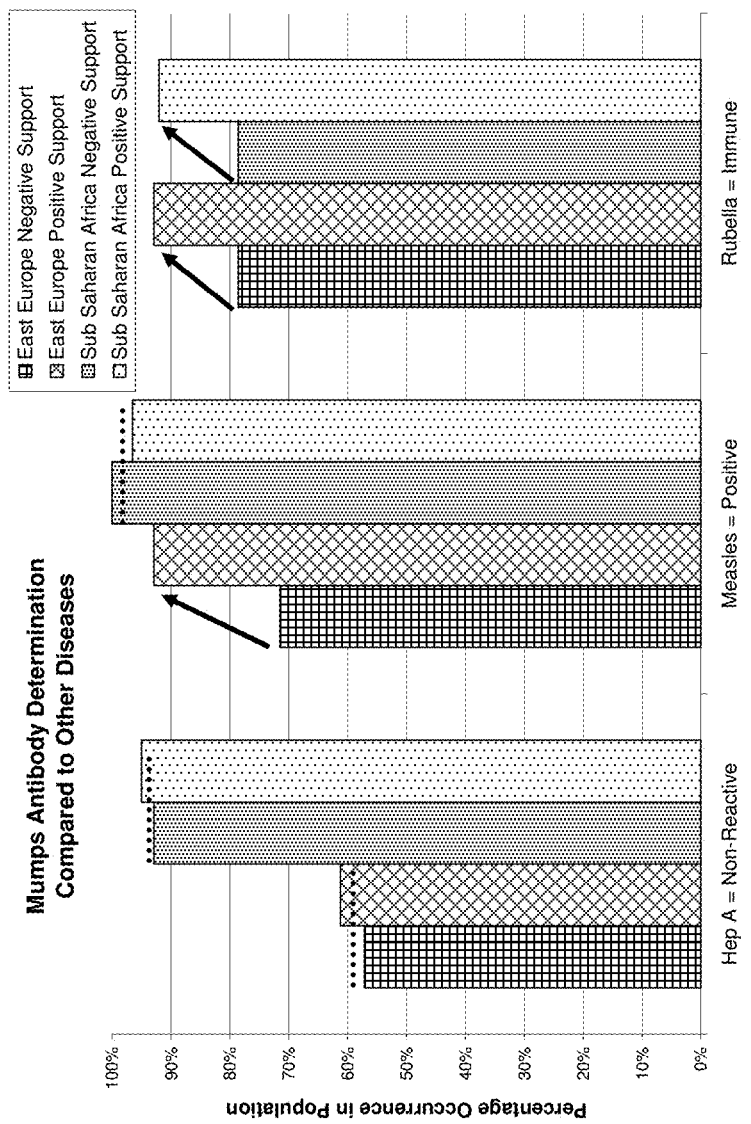
Figure 20F:
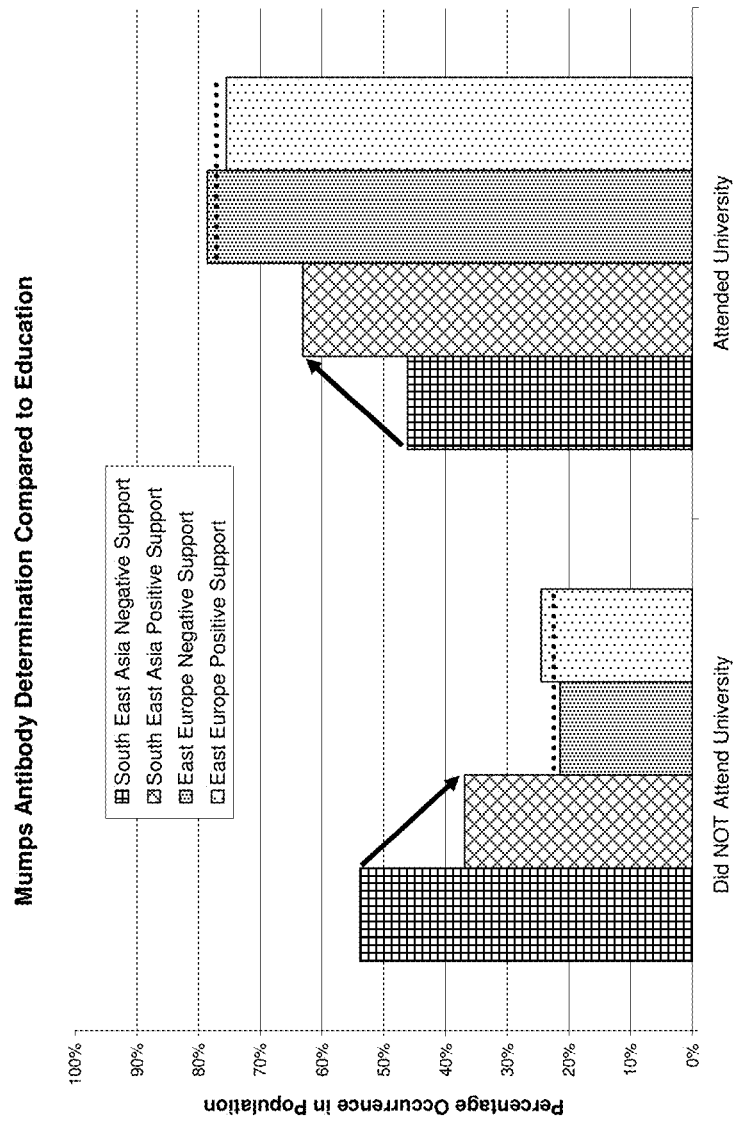

FIG. 17 is a plot of an exemplary comparison of two individual females, one vaccinated and one not vaccinated, according to an exemplary embodiment of the present invention;

FIG. 18 is a plot of exemplary antibody levels in a compliment-deficient individual according to an exemplary embodiment of the present invention;

FIG. 19 is a plot of exemplary antibody levels in a healthy individual according to an exemplary embodiment of the present invention;

FIG. 19A is an example SQL query according to an exemplary embodiment of the present invention; and FIG. 19B is a table illustrating the correlation among antibody levels in an exemplary female population according to an exemplary embodiment of the present invention;

FIGS. 20 through 20F illustrate exemplary data mining results obtained from operating on an exemplary database according to an exemplary embodiment of the present invention;

FIG. 21A illustrates an exemplary pattern detection process flow according to an exemplary embodiment of the present invention;

FIG. 21B illustrates an exemplary pattern detection process flow with hypothesis generation according to an exemplary embodiment of the present invention;

FIG. 21C illustrates an exemplary automatic pattern detection process flow according to an exemplary embodiment of the present invention;

FIGS. 21D-1 through 21D-37 illustrate automated data mining protocols according to an exemplary embodiment of the present invention;

FIGS. 21D-38 through 21D-40 respectively illustrate exemplary algorithms for Hepatitis A Virus (HAV), Hepatitis B Virus (HBV), and Hepatitis C Virus (HCV) Testing according to an exemplary embodiment of the present invention;

FIGS. 21E-1 through 21E-12 depict exemplary data analysis results obtained using an exemplary embodiment of the present invention. In FIG. 21E-4 the following reason of origin code is used: (1) Sub-Saharan Africa, (2) Southern Asia, (3) North Africa, (4) Latin America/Caribbean, (5) Eastern Europe, (6) Southeast Asia. In FIG. 21E-9, IL-6:IL-2 ratio examined vs. antibody levels to CMV (top panel) and hepatitis B (bottom panel). Color denotes age of individual patients.

FIGS. 21F-1 through 21F-6 depict the results of predictive models built using cytokine data according to an exemplary embodiment of the present invention;

FIGS. 21G-1 through 21G-12 depict the results of running an exemplary patient population rule mining protocol according to an exemplary embodiment of the present invention;

FIGS. 21H-1 through 21H-10 depict the results of running an exemplary individual patient vaccine recommendation protocol according to an exemplary embodiment of the present invention;

FIG. 21I is an exemplary output from an exemplary automated data mining protocol according to an exemplary embodiment of the present invention, segmenting an exemplary database by Region of origin, Sex and the cytokine assay IFN-gamma;

Section III Figures

Figure 25:
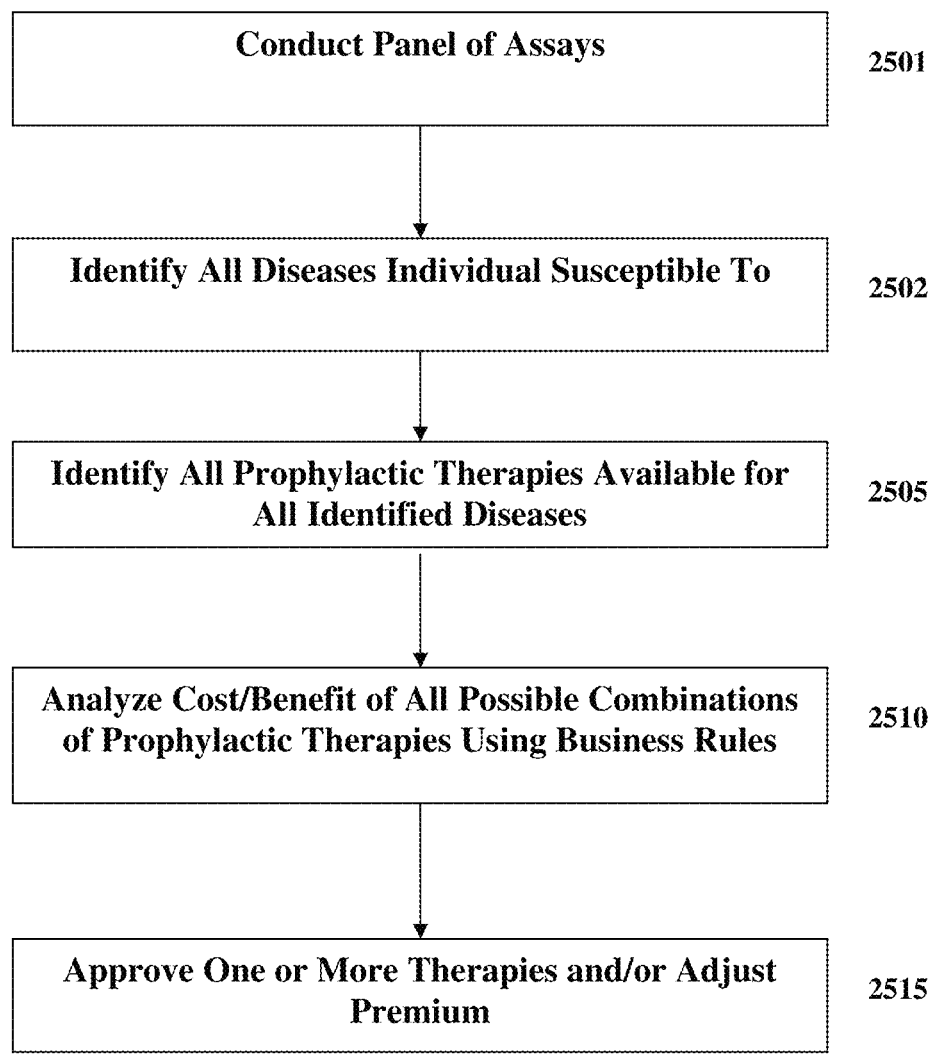
Figure 25A:
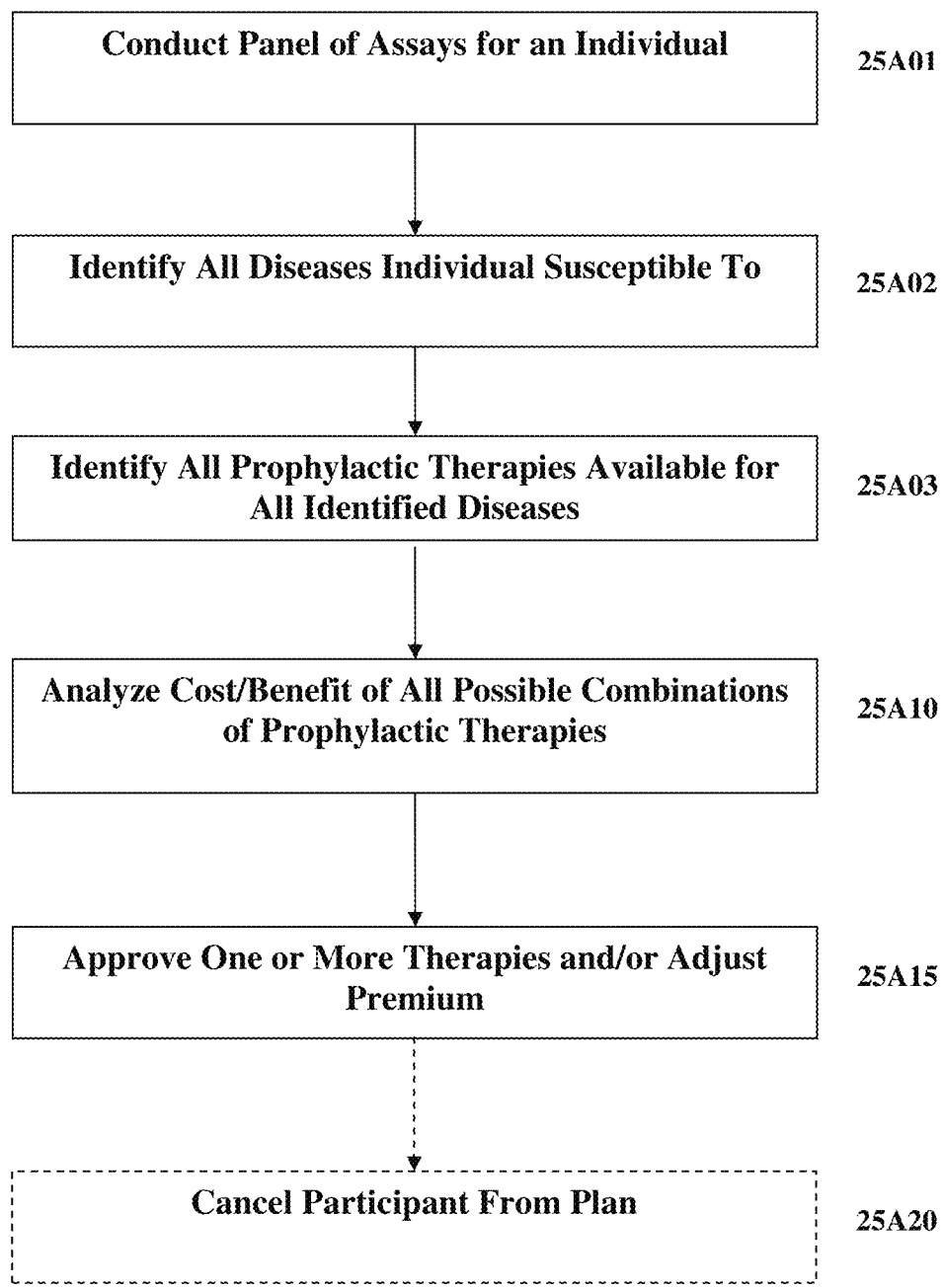
Figure 26:
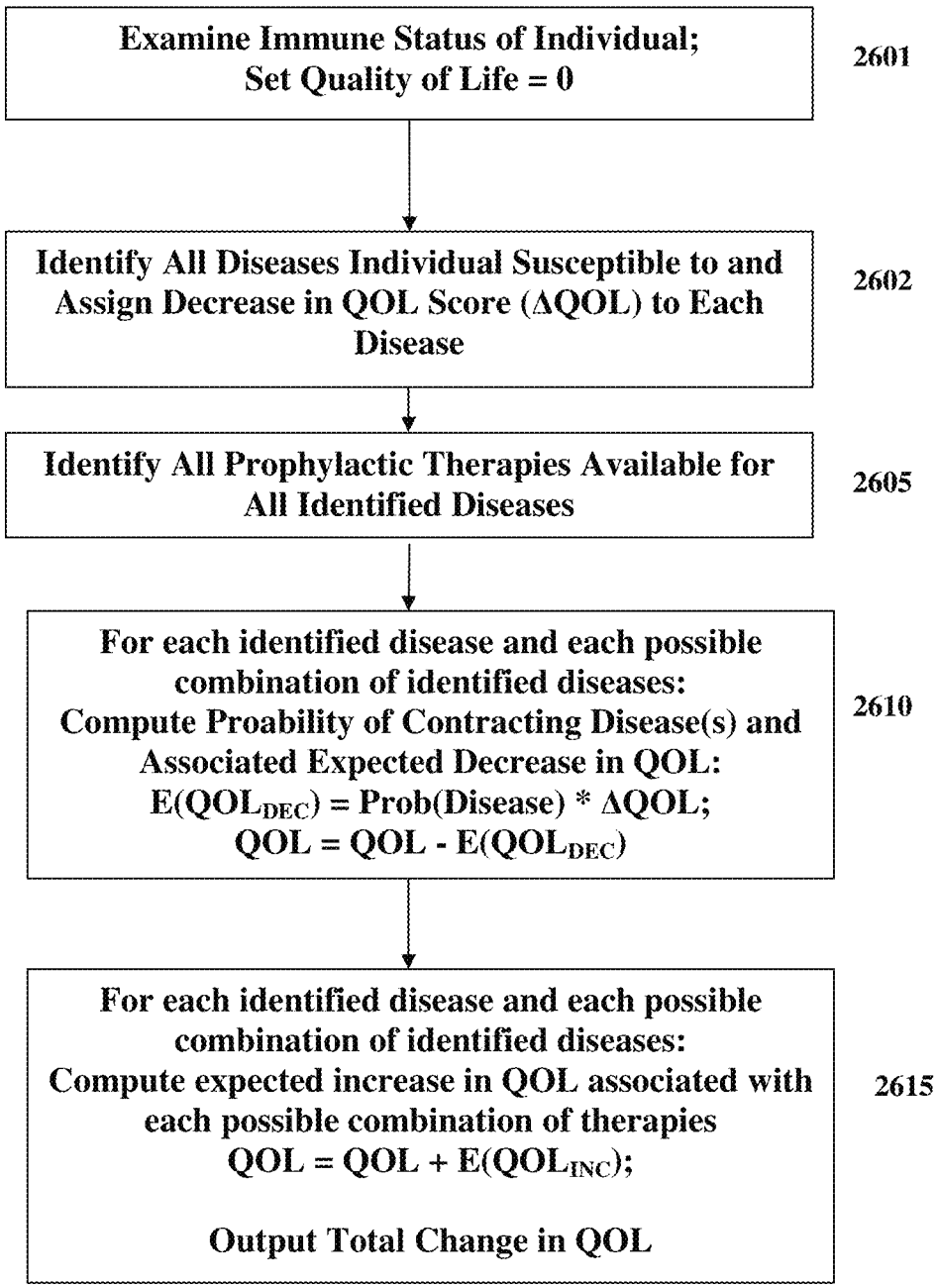
Figure 26A:
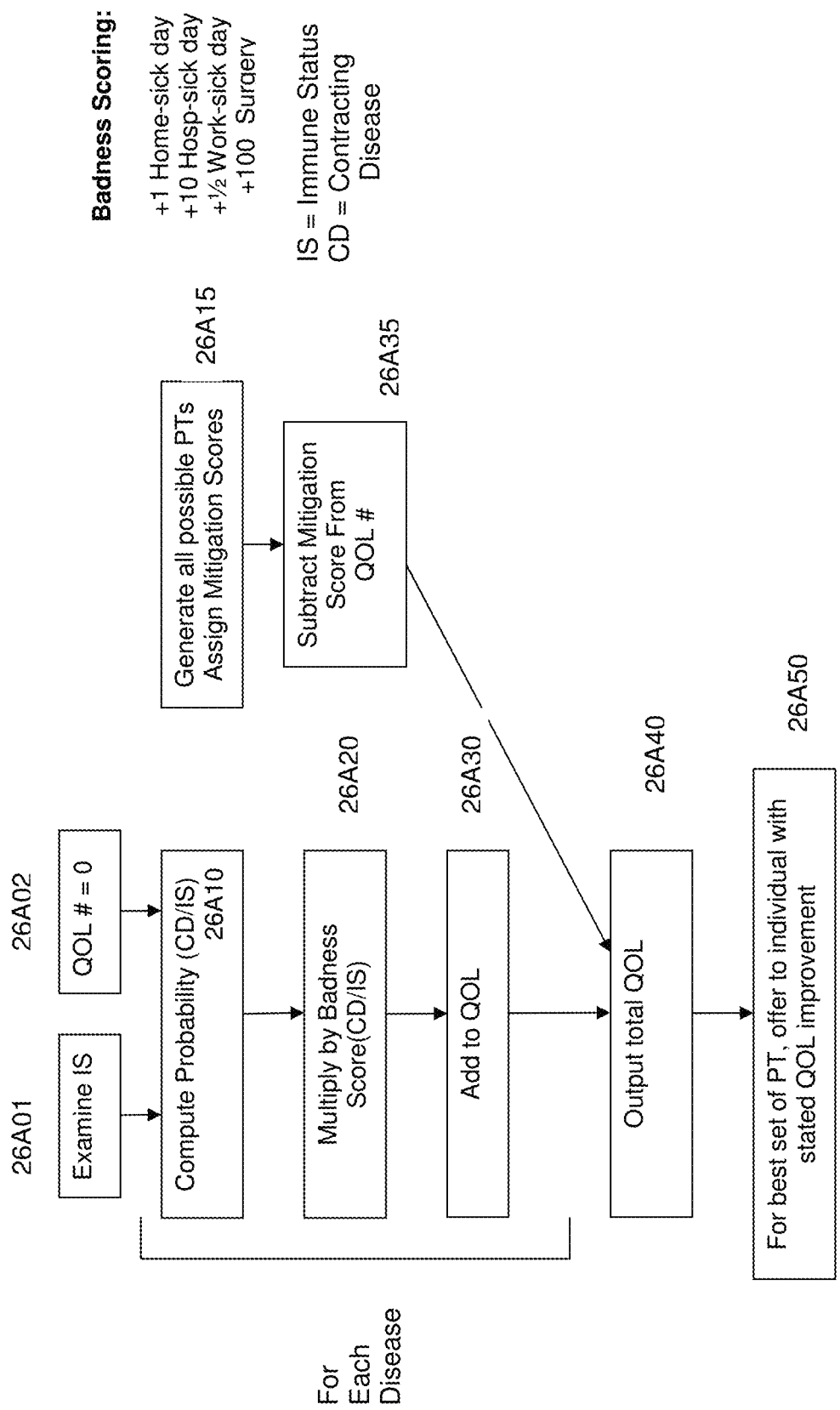
Figure 27:
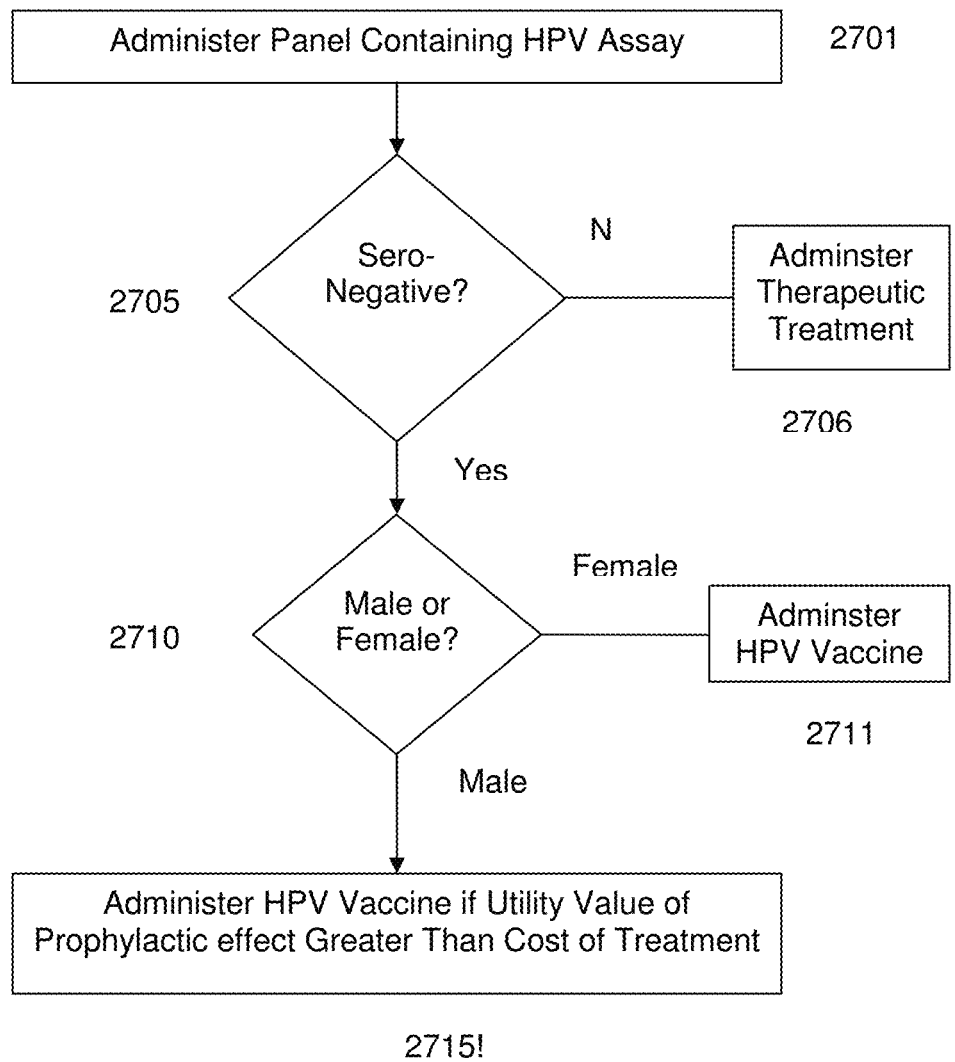
Figure 28:
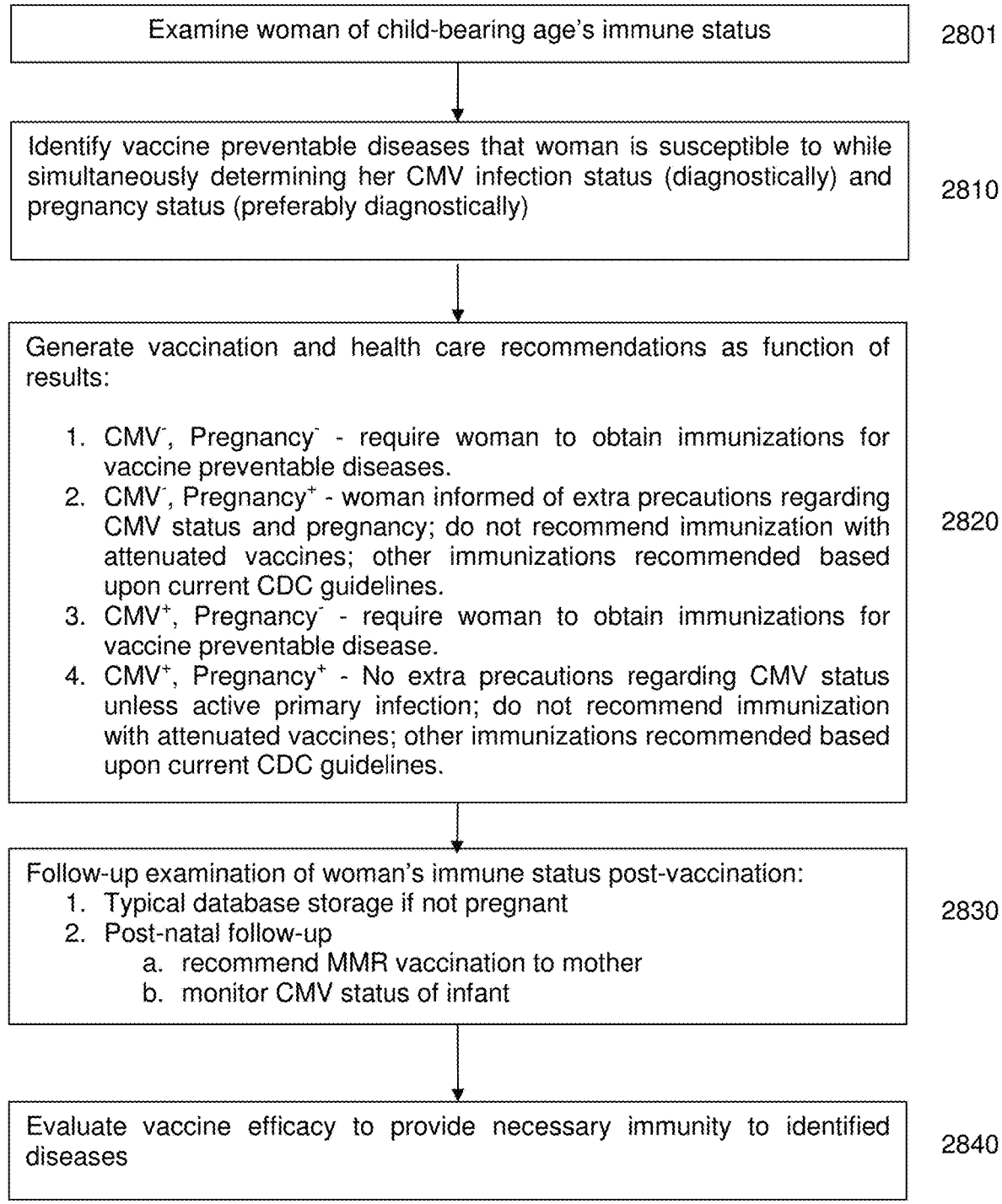
Figure 29:
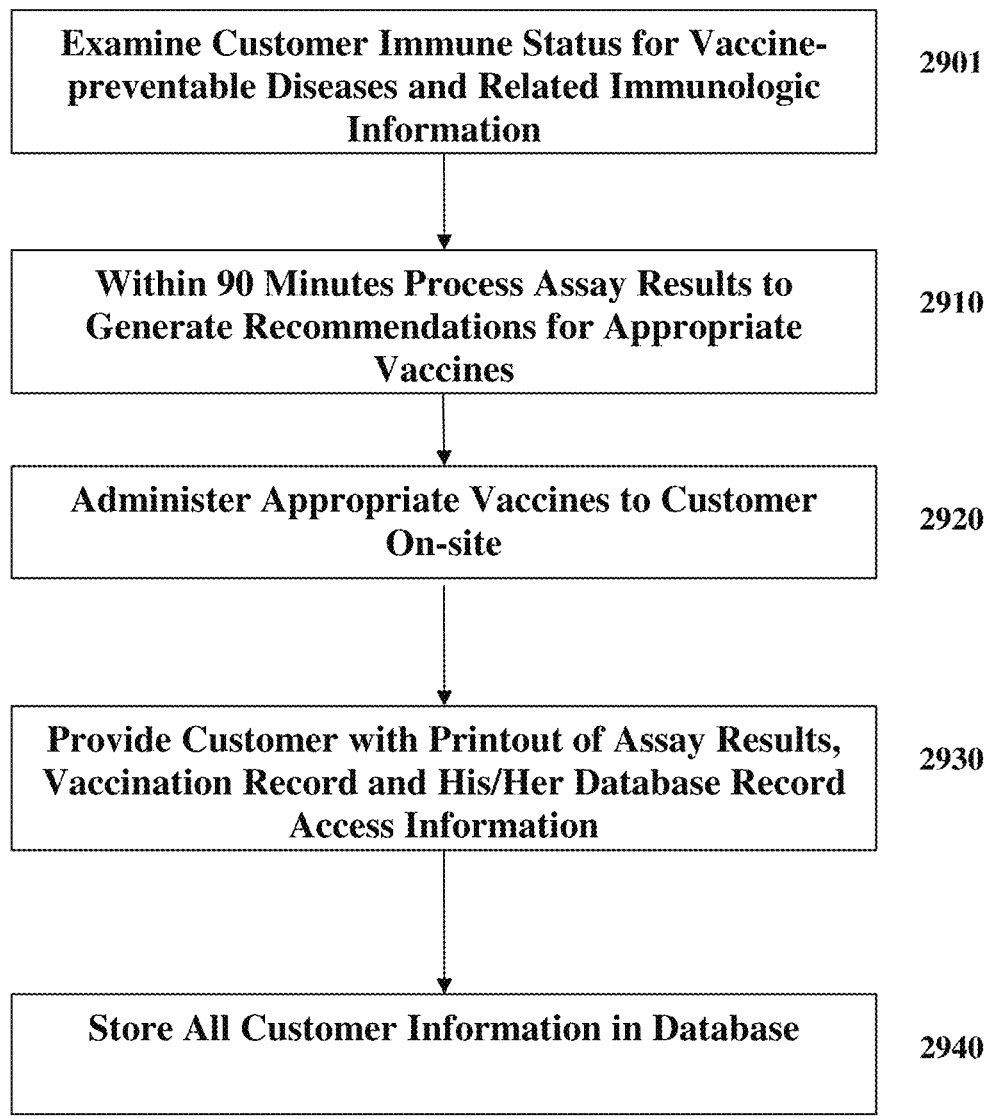
Figure 29B:
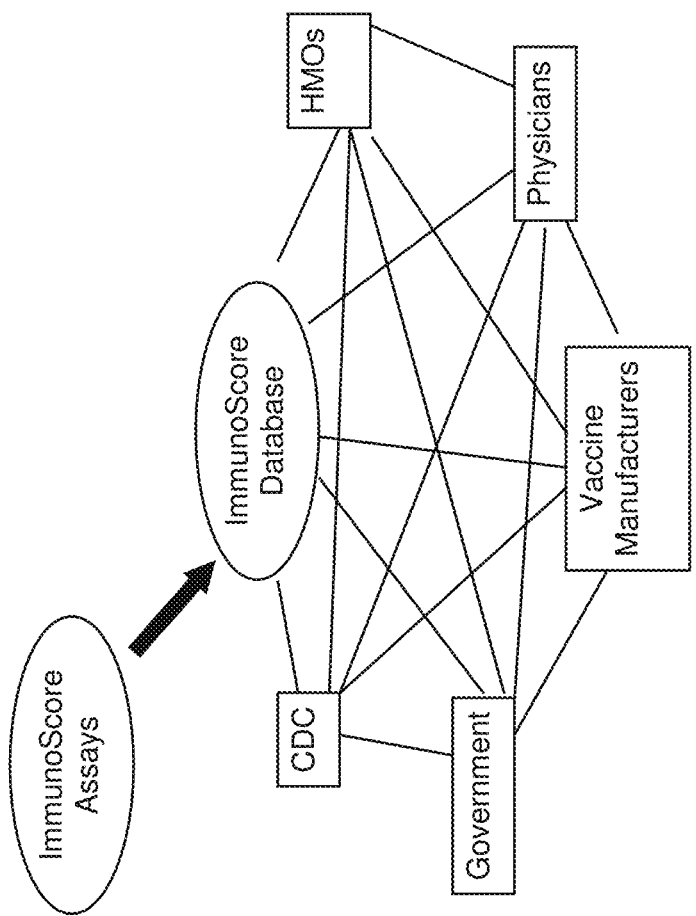
Figure 29C:
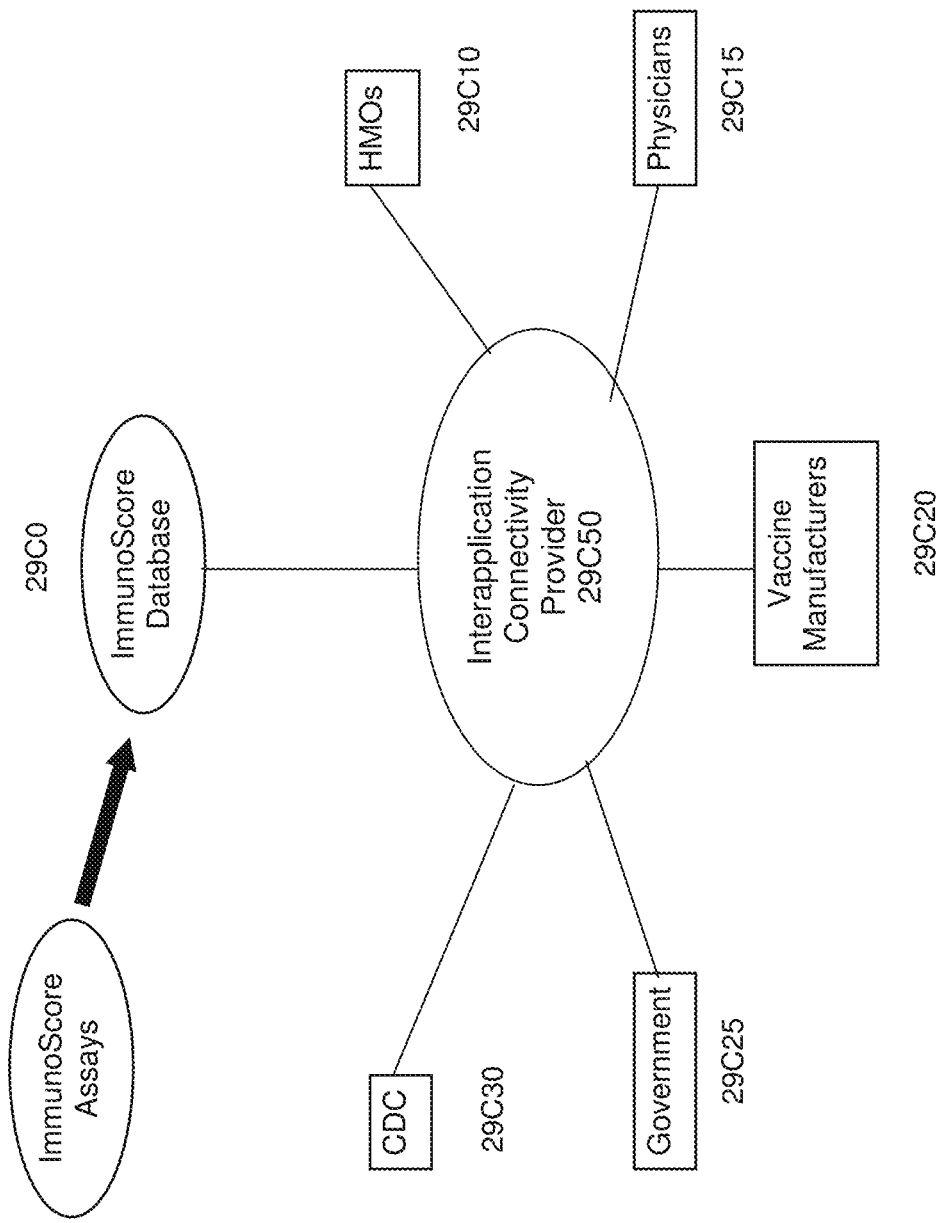
Figure 30:
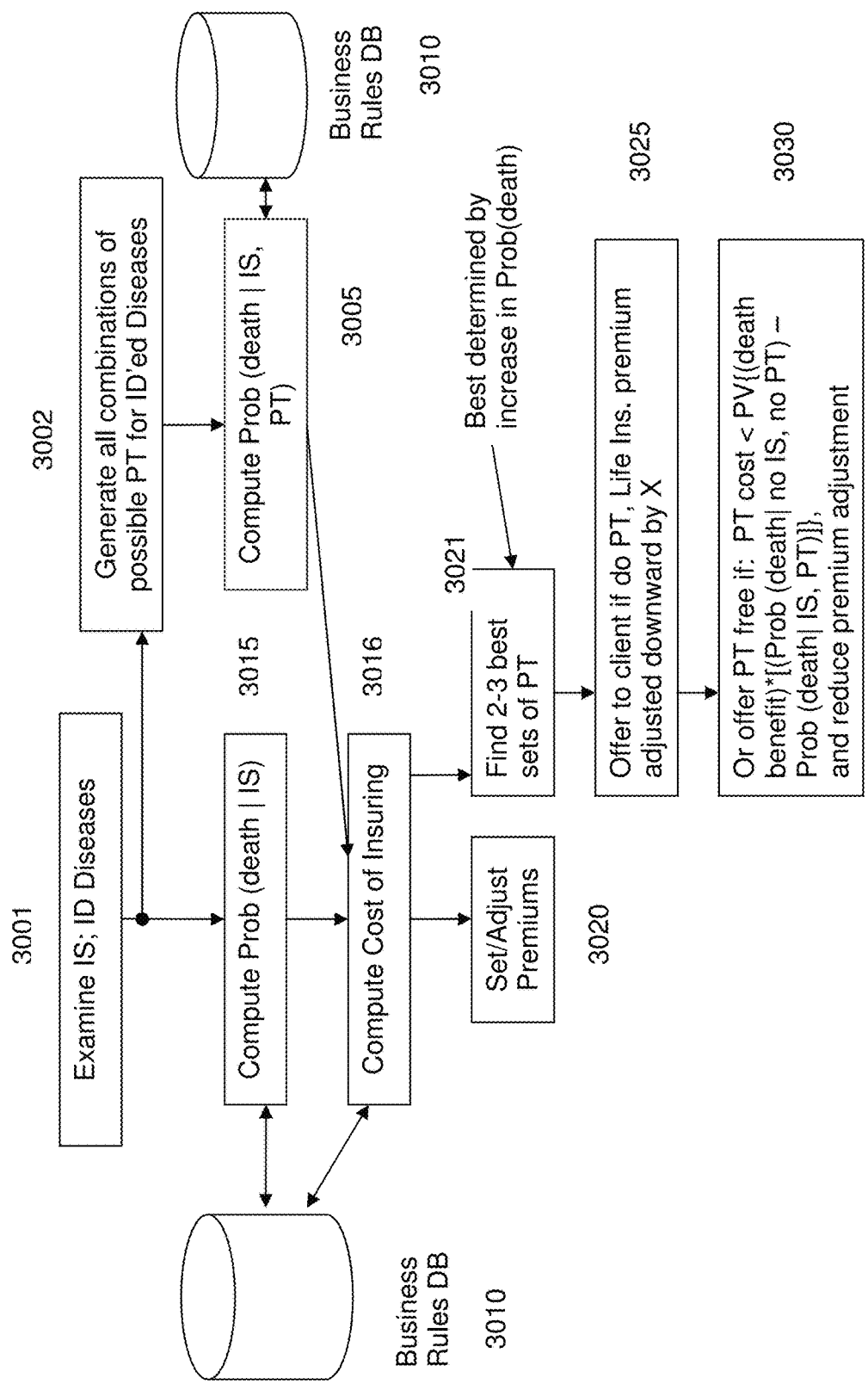
Figure 31:
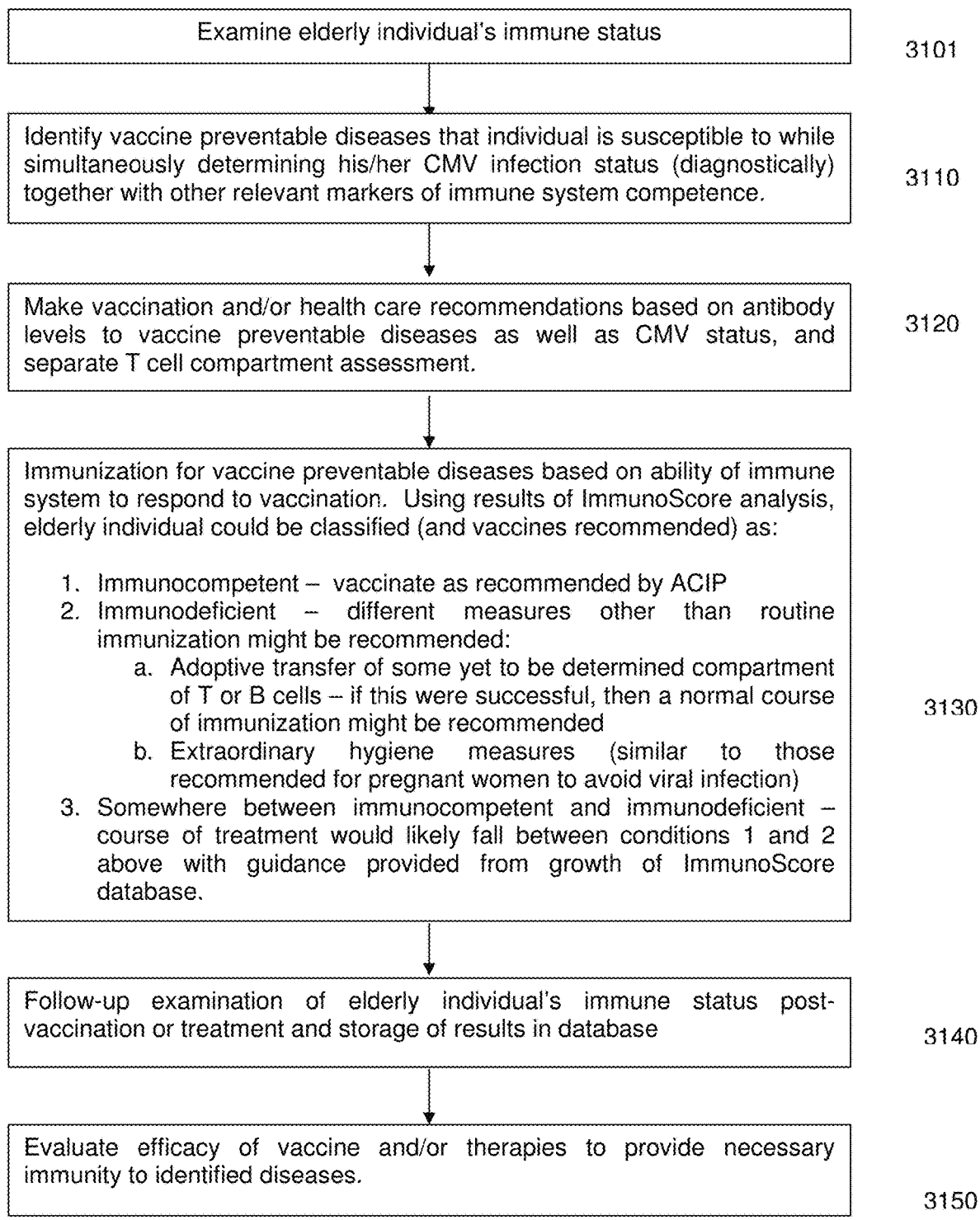
Figure 32:
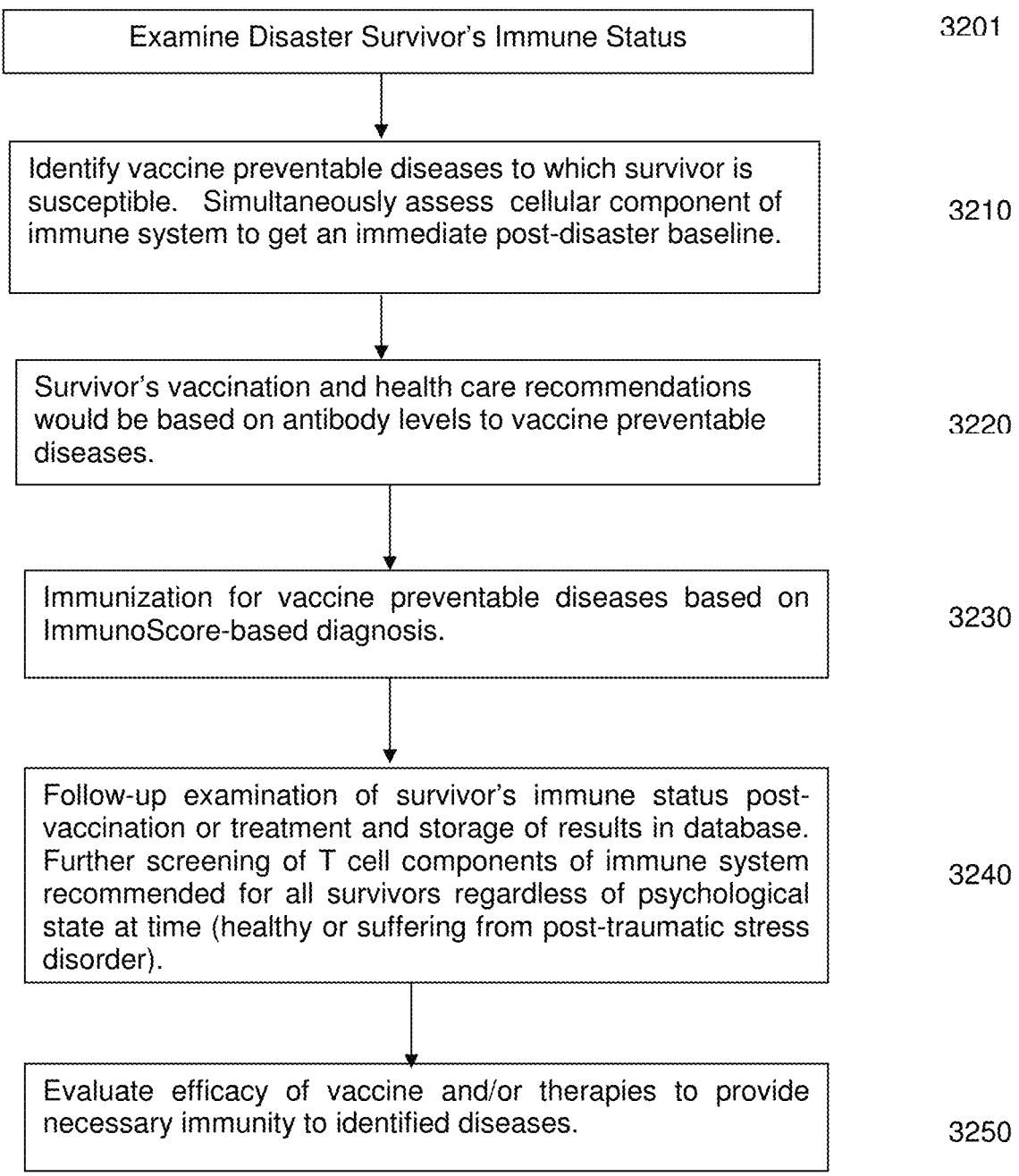
Figure 33:
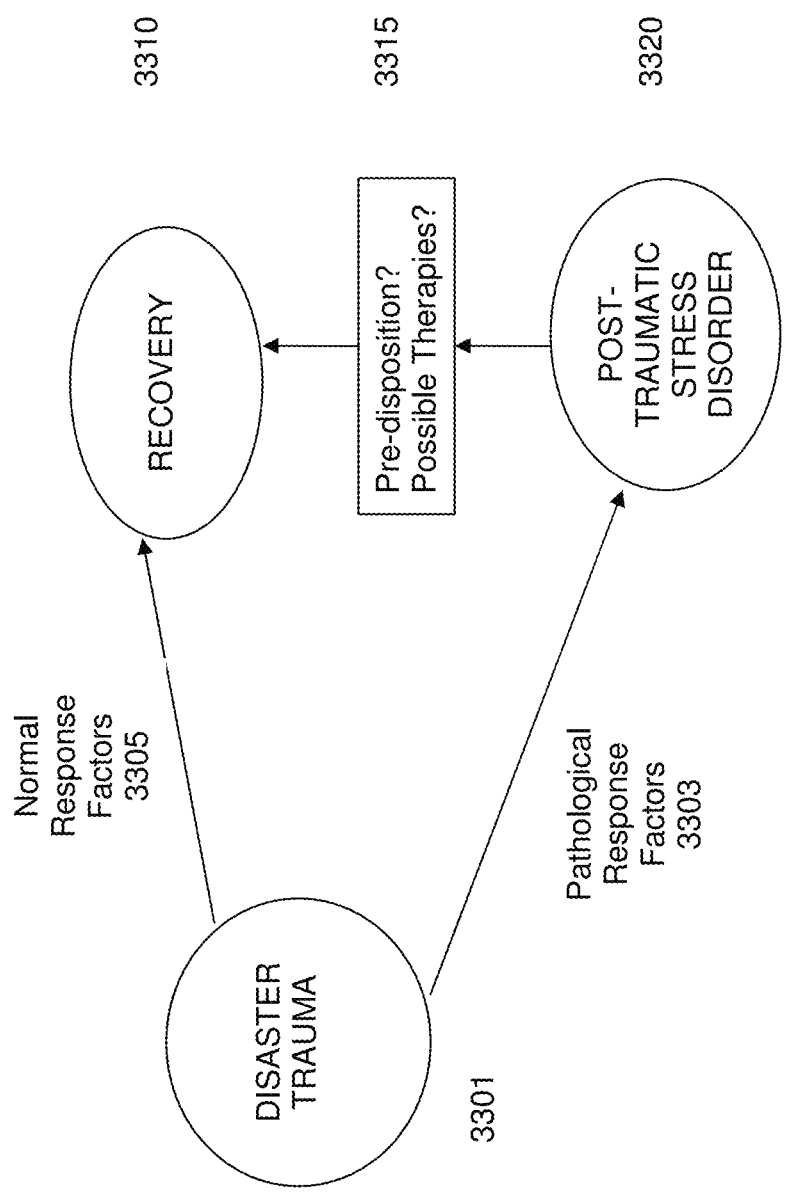
Figure 34:
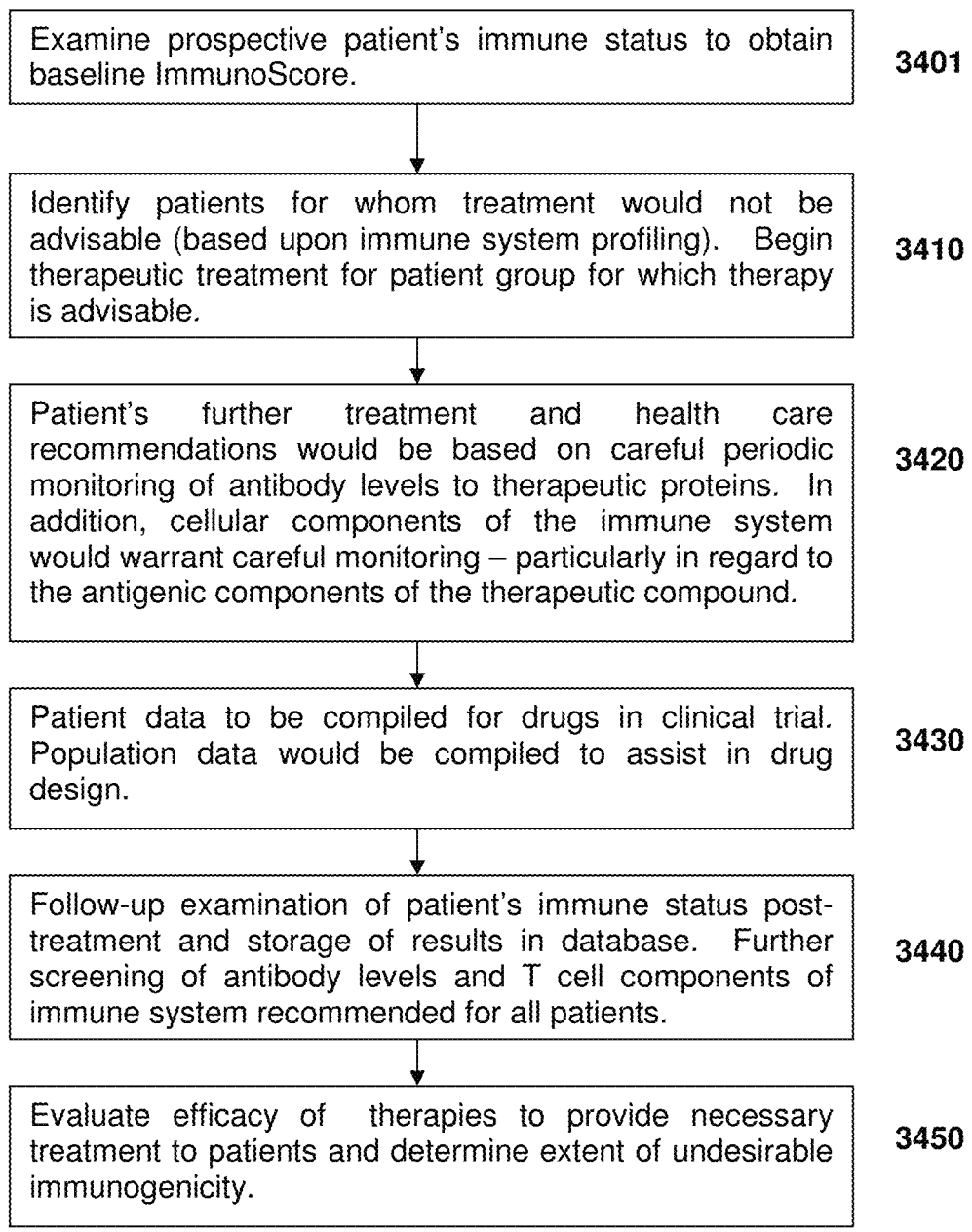
Figure 35:
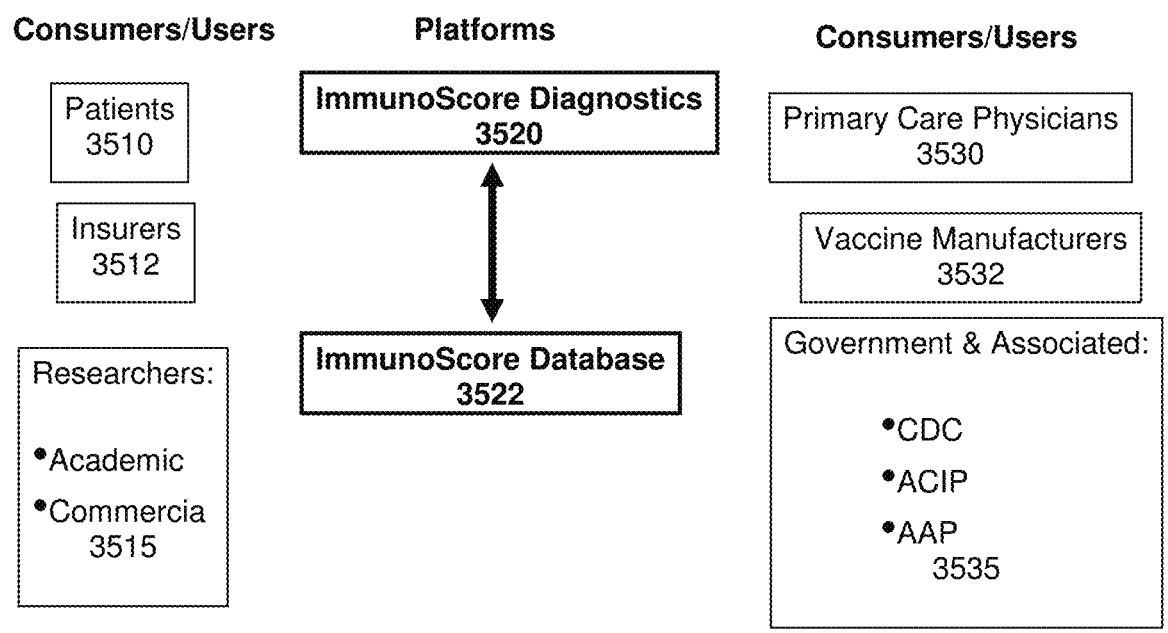
Figure 36:
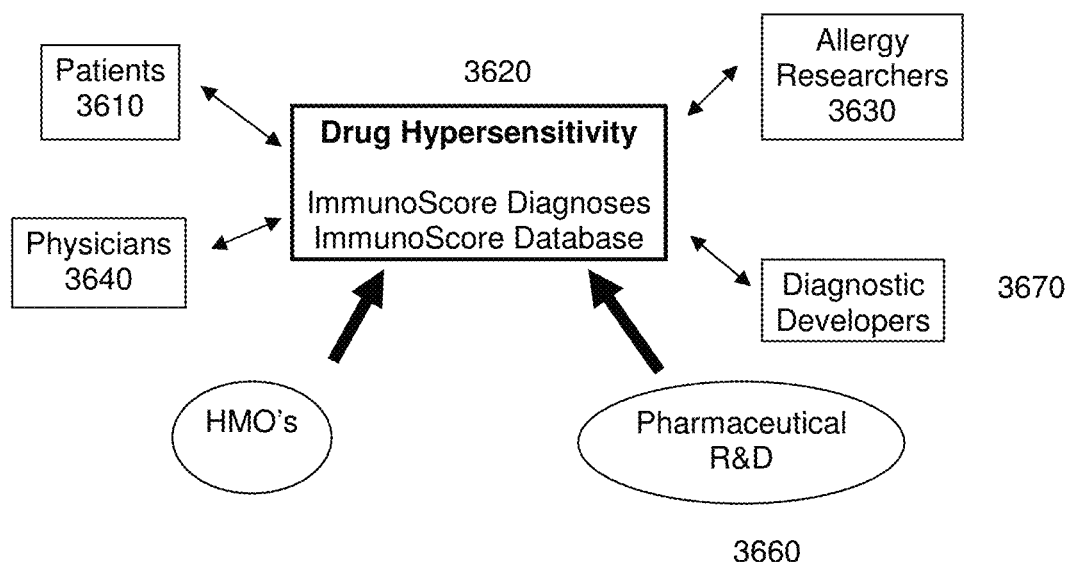

FIG. 22 is a process flow diagram for use in a healthcare management embodiment according to the present invention;

FIG. 23 is a subset of the process flow depicted in FIG. 22;

FIG. 24 is an alternative process flow chart for healthcare management according to the exemplary embodiment of the present invention;

FIG. 24A is a more detailed process flow chart similar to that of FIG. 22;

FIG. 25 is an alternative process flow chart for managing healthcare according the exemplary embodiment of the present invention;

FIG. 25A is the process flow chart of FIG. 25 with an additional optional element;

FIG. 26 is an alternative process flow chart for managing healthcare according to the exemplary embodiment of the present invention;

FIG. 26A is an alternative version of the process flow of FIG. 26 with greater detail;

FIG. 27 is a process flow chart for cervical cancer prevention according to the exemplary embodiment of the present invention;

FIG. 28 is a process flow chart for managing the care of women of childbearing age according to the exemplary embodiment of the present invention;

FIG. 29 is a process flow chart for an exemplary "Vaccine-O-Mat" application according to an exemplary embodiment of the present invention;

FIG. 29A is a system diagram of entities involved in the vaccine distribution application according to an exemplary embodiment of the present invention;

FIG. 29B illustrates the necessary connectivity for the vaccine distribution application illustrated in FIG. 29A;

FIG. 29C is the connectivity displayed in that FIG. 29B recast by use of an interapplication connectivity provider according to an exemplary embodiment of the present invention;

FIG. 30 is an exemplary flow chart for use in a life insurance optimization application according to an exemplary embodiment of the present invention;

FIG. 31 is an exemplary process flow chart for use in an immunosenescence management application according to an exemplary embodiment of the present invention;

FIG. 32 is an exemplary process flow chart for a disaster management application according to an exemplary embodiment of the present invention;

FIG. 33 is an alternative process flow chart for the psychological aspects of disaster response for a disaster response application according to an exemplary embodiment of the present invention;

FIG. 34 depicts exemplary process flow in an immunogenicity discovery application according to an exemplary embodiment of the present invention;

FIG. 35 illustrates components of an exemplary two-sided market application according to an exemplary embodiment of the present invention; and FIG. 36 illustrates components of an exemplary drug hypersensitivity two-sided market application according to an exemplary embodiment of the present invention.

TABLE OF CONTENTS

TECHNICAL FIELD
SUMMARY OF THE INVENTION
BRIEF DESCRIPTION OF THE DRAWINGS
DETAILED DESCRIPTION OF THE INVENTION
EXEMPLARY ASSAY PANELS
  A. COLLEGE STUDENT DIAGNOSTIC PANELS
    1. Meningococcal Diagnostic Panel
    2. Sexually Transmitted Diseases Assay Panel
    3. Persistent Immunity Induced by Childhood Vaccines
  B. ADULT DIAGNOSTIC PANELS
    1. Measurment of Immunity Induced By Vaccines for Military Personnel
    2. ImmunoScore Measurement of Vaccine-Induced Immunity for Travelers
    3. Cytokine Measurement in ImmunoScore
    4. Quantitation
IMMUNOSCORE EXEMPLARY SUPERPANELS
    1. ImmunoScore Diagnostic Panel and Preventive Therapy for Autoimmune Disease
    2. ImmuneScore Diagnostic Panel: Aging, Longevity, Cancer and Human Cytomegalovirus
  D. EXEMPLARY IMMUNOSCORE SUPERPANELS
    1. Middle School Student ImmunoPrint Super Diagnostic Panel
    2. Exemplary ImmunoScore Diagnostic Panels for Women of Child-Bearing Years
EXEMPLARY IMMUNOSCORE SYSTEM DATABASES
  A. General Overview
  B. Exemplary Illustrative Database
    1. Overall Description
    2. Impact of Data Mining
    3. Diagnostic Module
    4. Data Mining Module
  C. Exemplary Canadian Immigrant Project Database Used to Illustrate Data Mining and Hypothesis Generation
  D. Data Mining—Analyses and Conclusions
    1. Linear regression analysis—correlation coefficiants
    2. Geometric mean values
    3. Percent support between variables
    4. Possible Conclusions
  E. PATTERN DETECTION AND HYPOTHESIS GENERATION
    1. Initial Exemplary Analysis: Data Mining Steps
  F. AUTOMATED DATA MINING
    1. Exempary Software Development Environment
    2. Client-Server Computing
    3. Third-party Applications
    4. Extending Pipeline Pilot
    5. Integrating Protocols
    6. Data Mining Tool
    7. Single Patient Vaccine Recommendations
    8. Patient Population Rule Mining
    9. Age Binned with Differences
    10. Automated Data Mining
    11. Data Files Used in Pipeline Protocols Described Above
    12. Complete Copy of Exemplary Pipeline Pilot Code
  G. EXEMPLARY INTERNAL HYPOTHESIS DATABASE
  H. EXPLANATION AND BASIS OF EXEMPLARY RULES CREATED FOR PROCESSING CIP DATABASE
  I. INTERPRETATION OF CERTAIN RESULTS OF AUTOMATED DATA MINING
  J. EXTENSION OF DATABASE AND AUTOMATIC DATA MINING FUNCTIONALITY
  K. EXEMPLARY ANALYSIS PERFORMED ON CIP DATABASE
  L. EXEMPLARY RESULTS USING DATA MINING PROTOCOLS ON CIP DATABASE
USES OF IMMUNOSCORE INFORMATION AND AUTOMATED DATA MINING RESULTS IN VARIOUS COMMERCIAL, RESEARCH AND GOVERNMENTAL CONTEXTS
  A. Health Insurance Underwriting and Management
  B. Health Care/Health Insurance Credit Exchange
  C. Veterans Health Care Management (Variant of Health Care)
  D. Socialized Medicine Management
  E. Supplemental Insurance (AFLAC Model)
  F. ImmunoScore and the Wellness Industry
  G. Women of Childbearing Age/Screening of Pregnant Women
  H. Vaccine-o-Mat/Vaccine Distribution Network I. Consumer Accessibility to Immunologic Information
J. Immunoscore Connectivity Via Interapplication Translator/Data Integrator
K. Immunologic Informatics Based Life Insurance Underwriting
L. Diagnosing and Managing Immunosenescence in the Elderly
M. Frozen Storage of Naive Immune Cells (IRP Considerations)
N. Vaccine Use Outcome/Design
O. Research Services
P. Immigration Consulting
Q. Disaster Survivors: Immunizations, Recovery, Prognosis and Treatment
R. Monitor Adoptive Immunotherapy/Transplants
S. Elective Surgery
T. Services to Charitable Foundations Promoting Immunological Well Being
U. Discovery of Unwanted Immunogenicity of Therapeutics
V. Two-Sided Market Applications
W. Drug Hypersensitivity
   1. Consistent high quality
   2. Lower cost—follows from high quality
   3. Available to all—for ethical, political, systemic, and business reasons, health care must be available to everyone
   4. Single model—every provider in the system must compete to offer the best product at the best price
   5. Shaped by market forces—the consumer market has the sustained systemic power to bring consumers more for less
   6. Practical—the solution must arise from present realities
   7. Progressive—dramatic change can not occur all at once
   8. Self-reinforcing—as any part of the health care system moves toward a new reality, that movement must allow and encourage other parts to move forward as well
Y. User Access Via Data Networks and On-line Advertising
Z. Prophylactic therapies during surgery
AA. Contraindications for biological active therapeutics
WHAT IS CLAIMED:

DETAILED DESCRIPTION OF THE INVENTION

General Overview

In what follows, systems and methods of the present invention will be often referred to as the "ImmunoScore" system, method and/or database, as the case may be.

"ImmunoScore" is a trademark and/or service mark currently envisioned by the assignee hereof to be utilized in connection with exemplary embodiments of the present invention.

The present invention is directed to the collection, processing, and use of immunologic information. Immunologic information is to be understood in a broad sense, including any information which may be useful as an indicator of any immunological function of a mammalian body. More specifically, the present invention includes acquiring information that is indicative of the immune status of an individual, processing that information, storing the raw information as well as the outputs from the processing stage, and of that information at various times and in various ways to recommend various actions such as prophylactic or further diagnostic interventions, or abstention from action, for individuals or population. The present invention exploits a number of advances in technology as well as advances in how people think about medical treatment. In exemplary embodiments of the present invention, a number of immunological or immunological related (in a broad sense) assays can be administered to an individual. Using modern technology such as, for example, the M1M Analyzer marketed by BioVeris™ Corporation of Gaithersburg, Md., one can run a large number of assays, such as, for example 20, 40 or 60, and obtain results therefrom in a relatively short period of time. Moreover, these assay results can be stored in a memory, either locally or at one or more central servers or in associated databases, and can be operated upon by various algorithms or rules which can generate information as to that individual's immune status as well as recommendations for further augmenting that immune status or taking further action in response to the information acquired, from the assays and their processing. This information can be used in a variety of commercial, research, and healthcare contexts. Thus a variety of business methods or opportunities can be created or facilitated using the information obtained according to the methods of the present invention.

The present invention is described in three distinct sections. The first section describes the scientific background and motivation for creating various assay panels to be administered, singularly or in combination with other assay panels, to different individuals in different populations at different times in each individual's life cycle. This discussion culminates in suggested or exemplary assay super panels which can be administered in various contexts to various individuals.

A second section describes how information obtained from results of the administered assays can be stored, processed, and utilized. This discussion comprises, inter alia, a description of an exemplary database in which (i) results from numerous assays can be stored along with (ii) individual-specific information and (iii) the outputs of various algorithms which operate upon the assay results of that individual. This section also presents an exemplary database upon which immunologic data mining was performed according to the techniques of the present invention, and summarizes interesting and illustrative results form that exercise.

In a third and final section, a variety of business and commercial methods are described in which information from the assay panels as stored in the database and further processed can be used to increase business efficiencies, create new markets and opportunities, and/or provide useful tools for research and development.

Before describing each of these three areas in detail, a brief overview of a generalized method and system according to exemplary embodiments of the present invention is presented with reference to FIGS. 1, 2, 2A and 2B.

FIG. 1 depicts an exemplary process flow according to an exemplary embodiment of the present invention. Beginning at 101, an assay or panel of assays can be conducted on a biological sample, e.g., blood, urine, etc., which has been taken from an individual. Such individual can simply be an individual or he or she can be a member of a population or sub-population whose immunologic informatics are of use to some entity or enterprise. For example, the individual could be an insured of a health insurance company that is using the techniques of the present invention to efficiently manage the healthcare of its insureds so as to minimize costs. Or, alternatively, such an individual could be an immigrant whose vaccination history is unknown but whose immune status is of interest to his new country's immigration service. Such exemplary embodiments are described more fully below in Section III.

In FIG. 1, at 102 the results of the assay or assays conducted at 101 can be obtained, and at 103 there can be an optional step of analyzing the assay results locally. In exemplary embodiments of the present invention assays can be conducted and read in a variety of assay reading devices. There are many assays available using known techniques. Some of them are more sophisticated and some less sophisticated. In exemplary embodiments of the present invention, an assay reading device can, for example, obtain results at 102, store those results and analyze them locally, for example, in a processor communicably connected to the assay reading device. Alternatively, if only raw assay results are obtained from a less sophisticated technology, those results can, for example, be sent over a data network and stored in a database record. This is illustrated at 104. At 105, the results can be analyzed by accessing the particular record associated with the particular individual to whom the assay panel or panels were administered at a given time. Such analysis can involve a variety of algorithms ranging from a simplistic look at quantity of antibodies per defined unit of blood or other bodily fluid, or it can also, for example, include a complex analysis where a variety of assay results are input and combined in linear and non-linear ways to produce some metric of immunologic significance. Such algorithms are described more fully below in Section II. Finally, at 106, based on the results of the above described analysis, recommendations can be generated. Such recommendations can include, for example, that the individual obtain one or more vaccines, that the individual be administered prophylactic therapies to boost his or her immune system, or that the individual be administered gene therapy to correct the genetic defect which places him or her at risk of communicating a certain disease or condition, to name a few.

In general, in many exemplary embodiments according to the present invention process flow will be equivalent to or substantially similar to the process flow depicted in FIG. 1. In each of those exemplary embodiments, one or more panels of assays can be conducted with respect to one or more individuals. Results can be obtained, stored and analyzed, and based on such analysis, recommendations for action (or inaction, such as, for example, in cases of over-vaccination, as described above) can be recommended.

Figure 2:
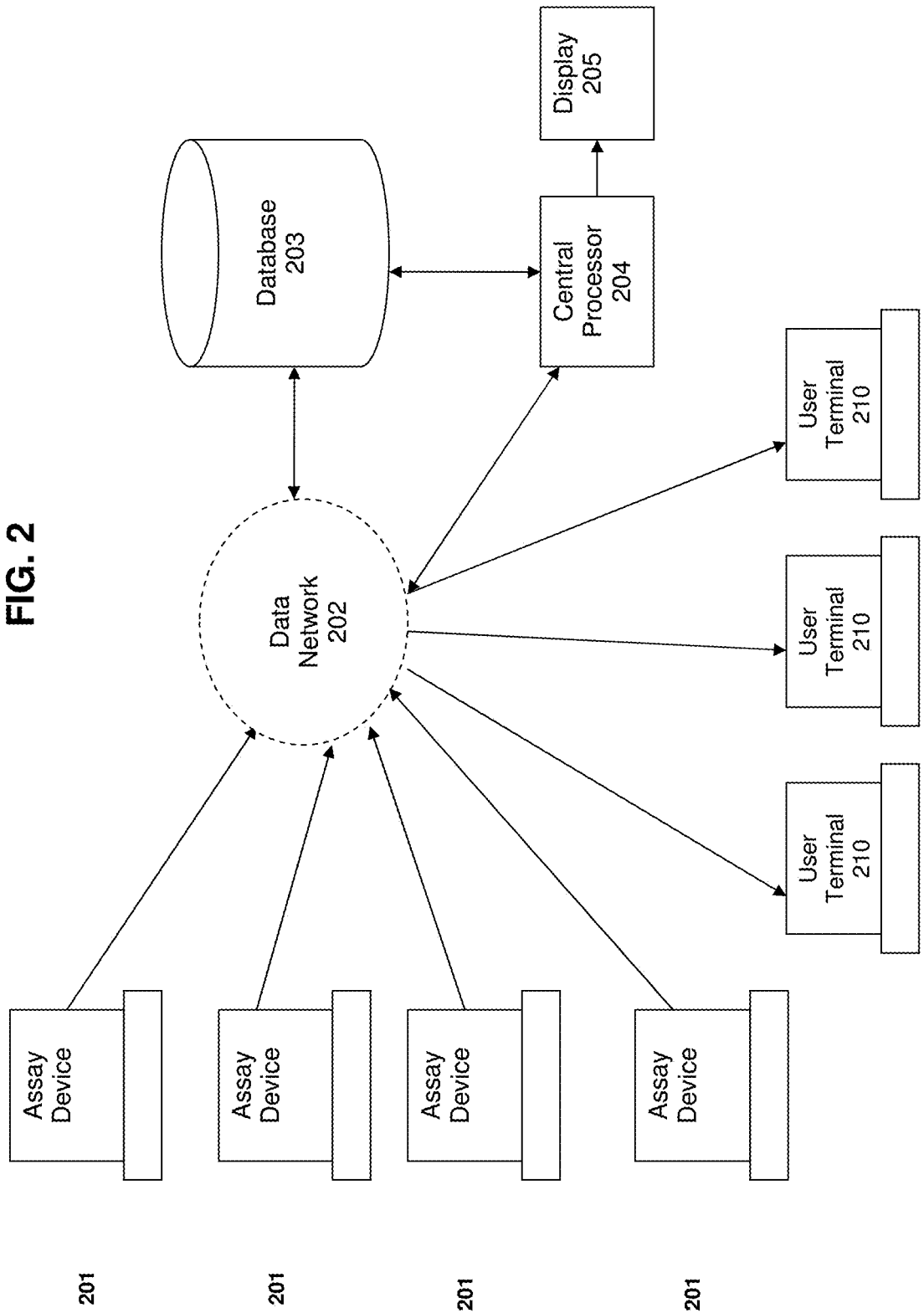
FIG. 2 depicts an exemplary system overview according to exemplary embodiments of the present invention.

FIG. 2 is an exemplary generalized system diagram which correlates to the generalized method depicted in FIG. 1. With reference to FIG. 2, there can be seen a number of assay devices 201. These assay devices include one or more assay panels which have been conducted with respect to an individual or individuals and for which results have been obtained. The results obtained from the assay devices can, as described in connection with the generalized method in FIG. 1, be locally analyzed at each assay device, provided that such assay device has a data processor and memory and the results can be stored locally at the assay device. Alternatively, the assay device results can, for example, be communicated over a data network 202 to a central processor 204 and stored in a central database 203. The central processor 204 can access the records which it has received and analyze them by implementing a number of analytic algorithms as described more fully below.

Central processor 204, based on its analysis, can generate recommendations based on decision trees and criteria embedded in the various analytic algorithms it implements. These recommendations can be displayed locally at the central processor at display 205 and can there be printed in a tangible medium for distribution to interested persons. Alternatively, the central processor 204 can, for example, send the results of its analysis over a data network to various users who can access the results at user terminals 210.

Figure 2A:
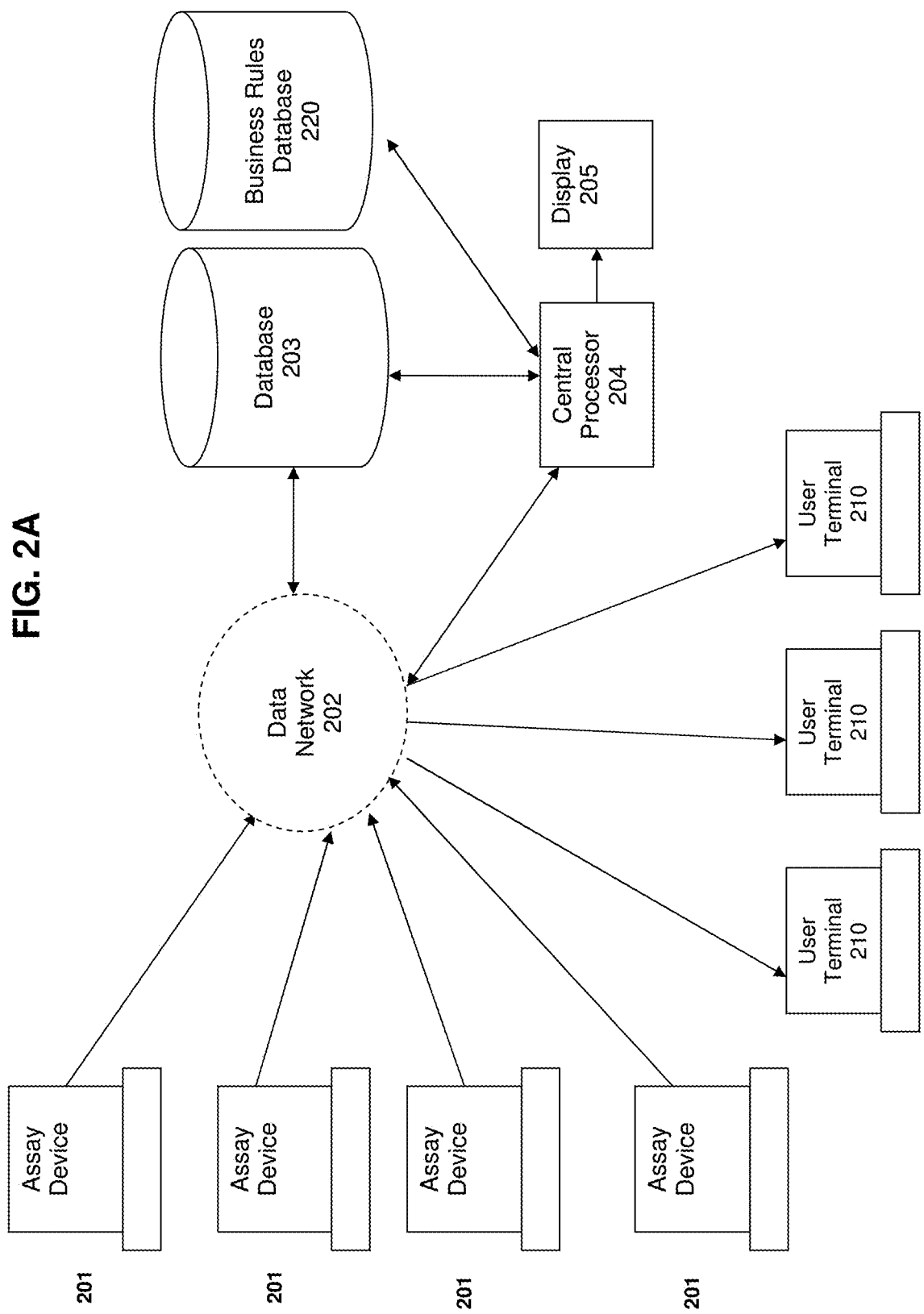
FIG. 2A depicts an alternate exemplary system overview according to exemplary embodiments of the present invention.

FIG. 2A presents an alternative generalized system diagram similar to FIG. 2. However, as can be seen in FIG. 2A, there is an additional database, the business rules database 220, communicably connected to central processor 204. In such an exemplary system the central processor can implement algorithms to operate on stored assay data which can, for example, also take as inputs various business rules in generating a decision regarding a recommendation. For example, as described more fully below in Section III, an exemplary embodiment of the present invention can be utilized to help a health insurance underwriter manage its population of insureds. There can, for example, be an annual or semi-annual requirement of all insureds to have assays for various immunological components conducted on their blood or other bodily fluids. After analysis of the results of such assays, an insurance company can determine whether a particular insured is susceptible to one or more given diseases or other ailments which would result in increased expenditures for medical treatment. The insurance company could then decide if it was not more economical to require the insured to undergo certain prophylactic treatments, such as, for example, vaccines or immune system boosting therapies, etc., where the cost of such prophylactic therapies is less than, as determined by some user determined factor, the expected exposure for medical care if the insured contracts one or more of the diseases or ailments to which he or she is susceptible.

In such context, there would need to be a number of business rules where such user defined quantities, threshold levels, cost functions or metrics, figures of merit, expected risks, etc., can be input and articulated or incorporated in a number of rules. Such rules can then be taken into account by the central processor in implementing algorithms which take as inputs data from business rules database 220 as well as a primary ImmunoScore database 203.

Figure 2B:
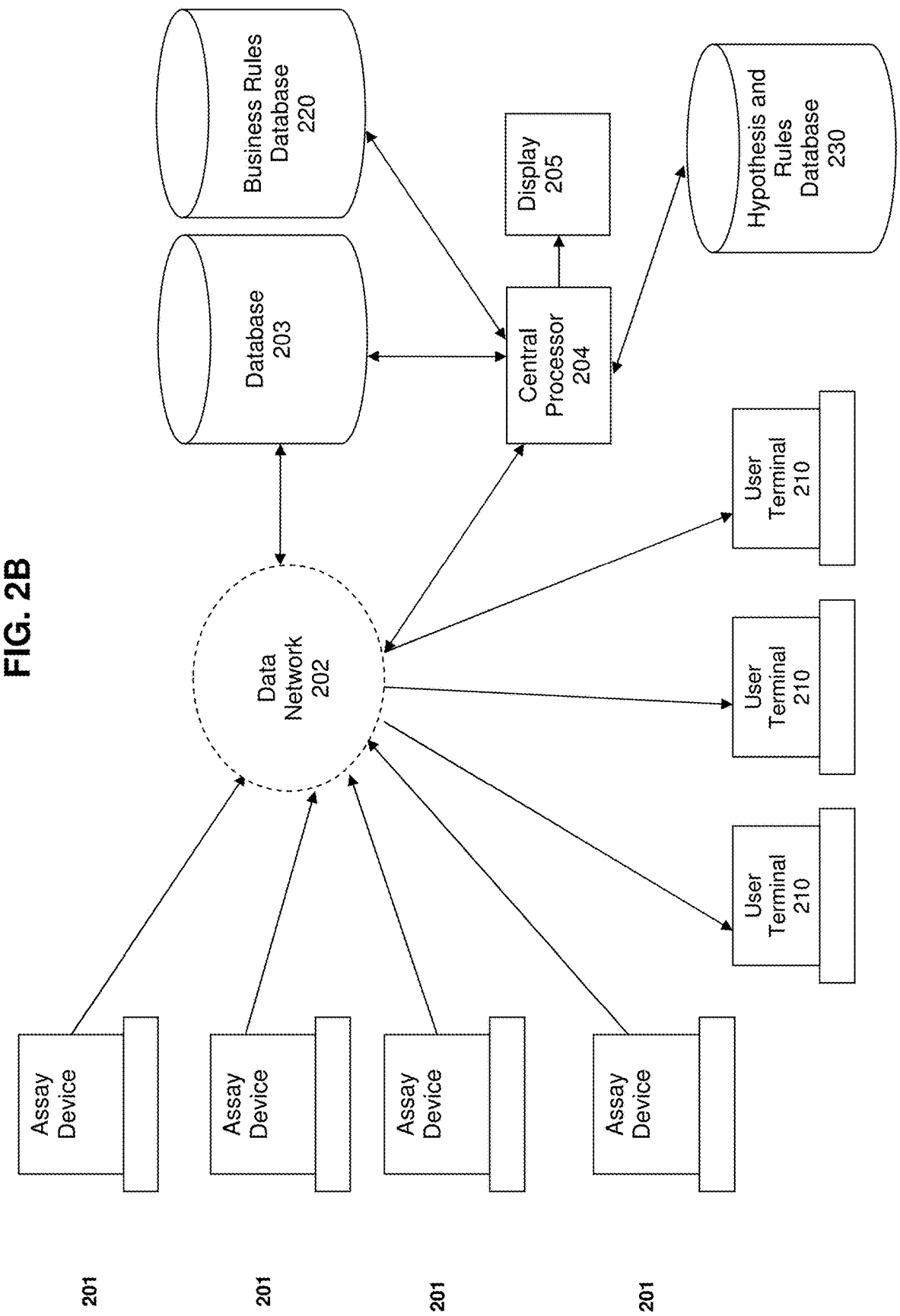
FIG. 2B depicts yet another alternate exemplary system overview according to exemplary embodiments of the present invention.

FIG. 2B presents an alternative generalized system diagram similar to FIGS. 2A and 2B. However, as can be seen in FIG. 2B, there is shown yet another additional database, a hypothesis and rules database 250, communicably connected to central processor 204. In such an exemplary system a central processor can, for example, implement data mining algorithms to operate on stored immunologic and background data to find a set of correlations. Such data mining algorithms can for example, be used to corroborate known or expected relationships, such as, for example, a correlation in antibody levels for measles, mumps and rubella in persons born in the United States after 1960, where the three vaccines were given simultaneously. In fact, an interesting follow-up would be to track if the rates of antibody levels for each of these three diseases change in the individual at a similar or a different rate, and if different, determine why.

Alternatively, for example, such data mining algorithms can be used to find counter-intuitive, or generally unknowns connections between variables or fields in the database.

In either case, once a set of correlations is obtained, intelligence in an exemplary system can be used to automatically generate a set of hypotheses to explain such correlations (or, if known, any follow-up data related thereto, as described above) and proceed to test the viability of each hypothesis using the data in the database. Or, alternatively, such intelligence can inform a user that additional data is needed to vet a hypothesis.

This process is explained more fully in Section II below.

Further, using such correlations, an exemplary system can, for example, also take as inputs various business rules in generating a decision regarding a recommendation. For example, as described more fully below in Section III, an exemplary embodiment of the present invention can be utilized to help a health insurance underwriter manage its population of insureds. There can, for example, be an annual or semi-annual requirement of all insureds to have assays for various immunological components conducted on their blood or other bodily fluids. After analysis of the results of such assays, an insurance company can determine whether a particular insured is susceptible to one or more given diseases or other ailments which would result in increased expenditures for medical treatment. The insurance company could then decide if it was more economical to require the insured to undergo certain prophylactic treatments, such as, for example, vaccines or immune system boosting therapies, etc., where the cost of such prophylactic therapies is less than, as determined by some user determined factor, the expected exposure for medical care if the insured contracts one or more of the diseases or ailments to which he or she is susceptible.

In such context, there would need to be a number of business rules where such user defined quantities, threshold levels, cost functions or metrics, figures of merit, expected risks, etc., can be input and articulated or incorporated in a number of rules. Such rules can then be taken into account by the central processor in implementing algorithms which take as inputs data from business rules database 220 as well as a primary ImmunoScore database 203.

Given the generalized exemplary method of FIG. 1 and the generalized exemplary systems of FIGS. 2, 2A and 2B, what is next described are a number of exemplary assay panels which can be administered to an individual or members of a population according to exemplary embodiments of the present invention. The scientific background behind the various exemplary assay panel, as well as which segments of the general population such panels are best administered to, are also described.

Exemplary Assay Panels

The present invention is, inter alia, concerned with assessing the "protective immune status" or "immunologic status" of an individual or population. A "protective immune status" is understood to be represented by an array of detectable components (phenotypic and/or genotypic) of an immune system (adaptive and/or innate) that comprise its protective capacity against harmful substances and/or cells (such as, for example, microorganisms or cancer). Such components can, for example, consist of genes as well as gene products. Genes can include, for example, those which encode immunologic receptors (such as, for example, toll-like receptors ("TLR"s) and chemoattractant receptors) as well as effector molecules (such as, for example, cytokines and chemokines) which may also, for example, exist as genetic polymorphisms capable of deleterious and/or beneficial effects. Gene products can include, for example, antibodies, complements, cytokines, chemokines, chemoattractant receptors, TLRs, lectins, and other immune-related ligands. Harmful substances can consist of, for example, chemicals and/or toxins originating from the environment, microorganisms, or one's self.

Once diagnostic information is acquired from an individual regarding his or her immune status, this information can be, for example, added to a system database. Such a database can contain, for example, not only the results of ImmunoScore diagnostic testing but a wide variety of demographic data and patient history information as well. Such a system database can, for example, be used to record adverse events occurring coincident with immunizations. Such information can be invaluable to, for example, the ACIP for making recommendations regarding immunization scheduling, as well as help discover unsuspected patterns and correlations relevant to immune status and immune response.

ImmunoScore diagnostic testing can be, for example, tailored to meet an individual's specific immunization status needs. In addition, each individual can, for example, receive their own personal ImmunoScore card that they could carry with them to health care office visits, and the database information can be easily transferable in the ever-increasingly likely event that they change physicians or other primary health care providers. Additionally, ImmunoScore data, analysis of such data and relevant database information can, for example, be stored as part of a person's totality of health information and medical records, in electronic formats such as, for example, entries in electronic health information databases, or computer chips embedded in, for example, "smart" cards or "smart driver's licenses."

For economy of description, most of the references cited herein are provided in full citation in Appendix A to the Immunologic Informatics Patent. Throughout the text citations are made to author and year of publication alone.

One component of ImmunoScore data can be, for example, the raw as well as processed results of diagnostic tests or assays relating to immune status, as described below. ImmunoScore diagnostic testing is envisioned to be done on a small assay device or testing instrument that can be located, for example, in a doctor's office. The testing can be done, for example, with a sample of an individual's whole blood, plasma, serum, saliva, milk, semen, tears, or urine. In the case of blood, for example, the sample can be obtained by a finger prick, heel stick, ear stick, other skin prick, capillary draw, venous draw, or an arterial draw. The instrument can, for example, take assay panels and the patient sample. Patient information can also be input. The resulting information can be, for example, displayed to a user, printed, stored in a removal medium, stored in the instrument, and/or transmitted (wired or wireless) to other devices such as via an intranet, a VPN or the Internet, for example.

Numerous systems and methods have been developed for the detection and quantitation of analytes of interest in biochemical and biological substances that can be used, for example, in such an instrument. Such methods and systems which are capable of measuring trace amounts of microorganisms, pharmaceuticals, hormones, viruses, antibodies, nucleic acids and other proteins can be of great value to researchers and clinicians.

A substantial body of art has been developed based upon well known binding reactions, such as, for example, antigen-antibody reactions, nucleic acid hybridization techniques, and protein-ligand systems. The high degree of specificity in many biochemical and biological binding systems has led to many assay methods and systems of value in research and diagnostics. Typically, the existence of an analyte of interest is indicated by the presence or absence of an observable "label" attached to one or more of the binding materials. Of particular interest are labels which can be made to luminesce through photochemical, chemical, and/or electrochemical means. "Photoluminescence" is the process whereby a material is induced to luminesce when it absorbs electromagnetic radiation. Fluorescence and phosphorescence are types of photoluminescence. "Chemiluminescent" processes entail the creation of luminescent species by chemical transfer of energy. "Electrochemiluminescence" entails creation of luminescent species electrochemically.

Electrochemiluminescent (ECL) assay techniques are an improvement over chemiluminescent techniques. They can, for example, provide a sensitive and precise measurement of the presence and concentration of an analyte of interest. In such techniques, the incubated sample is exposed to a voltammetric working electrode in order to trigger luminescence. In the proper chemical environment, such electrochemiluminescence is triggered by a voltage impressed on the working electrode at a particular time and in a particular manner. The light produced by the label is measured and indicates the presence or quantity of the analyte. For a fuller description of such ECL techniques, exemplary reference is made to U.S. Pat. Nos. 5,221,605; 5,705,402; 6,140,138; 6,325,973; and 6,451,225. The disclosures of the aforesaid patents are hereby incorporated herein by reference.

Amplification techniques for nucleic acids may be combined with the above assay techniques. For example, U.S. Pat. No. 6,048,687 discloses how NASBA can be combined with an ECL technique; and U.S. Pat. No. 6,174,709 discloses how PCR can be combined with an ECL technique. The disclosures of the aforesaid patents are also hereby incorporated herein by reference.

An assay instrument can, for example, be, or be similar to, the BioVeris Corporation M1R or M1M instruments with an added sample processing front end [ Roche products]. Aspects of these instruments are disclosed in pending U.S. patent application Ser. Nos. 10/600,165 and 10/841,569, each under common assignment herewith. The disclosures of these patent applications are hereby incorporated herein by reference.

In exemplary embodiments of the present invention, an assay instrument can include, for example, amplification techniques such as PCR or NASBA. In exemplary embodiments of the present invention, the instrument can use fluorescence, chemiluminescence, or ECL assay techniques. In exemplary embodiments, multiple measurements can be done simultaneously; in other exemplary embodiments of the present invention, multiple measurements can be done sequentially. In exemplary embodiments of the present invention, an assay instrument can, for example, contain self-test and/or self-calibration components.

In exemplary embodiments of the present invention, a sample can be added to an assay panel, and the combination then inserted into the test instrument, as shown in FIG. 3. In alternate exemplary embodiments, the sample and assay panel can be separately inserted into the test instrument, as shown, for example, in FIG. 4.

As described below, entries to an exemplary master ImmunoScore database can be, for example, coded so as to protect patient confidentiality. A patient could, however, be able to learn from their physician in real time, for example, which vaccines he or she might need to ensure protection from vaccine-preventable illnesses. The physician can, for example, offer the vaccine, or other therapy, during the same visit, or shortly thereafter. Any possible adverse effects from any delivered vaccinations could be subsequently entered into an ImmunoS core database and that information could be shared with the ACIP or other agencies or bodies, as described more fully below.

The actual assays can be performed, for example, based upon the needs of the individual or individuals being examined. Age, occupation, travel plans, immigration status, military status, and previous health status can all be considered prior to initiation of ImmunoScore diagnostic analyses in exemplary embodiments. In exemplary embodiments of the present invention, the following exemplary broad categories can, for example, be utilized as focal points for test panels:

1. Entry to primary school.
2. College entry.
3. Age 19-49 years.
4. Age 50-64 years.
5. Age>65 years.
6. Health-care professionals.
7. Military personnel:
    recruits and officer accessions;
    alert forces;
    individualized according to occupational or personal needs; and
    veterans.
8. Travelers.
9. Immigrants.
10. Individuals with identifiable health risks (not necessarily exclusively):
    a. Complement-deficient individuals (e.g. meningococcal disease susceptibility);
    b. Genetically identified (e.g. HLA haplotype, sepsis susceptibility) disease-susceptible individuals;
    c. Mannose-binding lectin-deficient individuals;
    d. Hepatitis B vaccine poor/non-responders; and
    e. Ethnic groups and others known to respond poorly to polysaccharide, conjugate, or other vaccines.

A. College Student Diagnostic Panels

1. Meningococcal Diagnostic Panel

In exemplary embodiments of the present invention, the following tests can be included in a meningococcal diagnostic panel:

1. Antibody (Ig) to (4 tests):
    Group A Meningococcal Polysaccharide (GAMP)
    Group C Meningococcal Polysaccharide (GCMP)
    Group Y Meningococcal Polysaccharide (GYMP)
    Group W-135 Meningococcal Polysaccharide (GWMP)
2. Antibody (IgM) to Group B Meningococcal Polysaccharide (GBMP) (1 test)
3. Serum levels of complement components (7 tests):
    C5
    C6
    C7
    C8
    C9
    Properdin
    MBL
4. Measurement of genetic polymorphisms (5 tests):
    FcγRIIa receptor
    IL-1
    IL-1R
    IL-6
    IL-10

2. Sexually Transmitted Diseases Assay Panel

In exemplary embodiments of the present invention, the following tests can, for example, be used for ImmunoScore measurement of immunity to STDs:
    Antibodies to *Chlamydia*—IgG, IgA, and IgM (3)
    Antibodies to HSV—IgG to HSV-1 and HSV-2 (2)
    DNA analyses of HPV types—particular emphasis on high-risk
    Antibody to *N. gonorrhoeae* (1)
    Antibody to *T. pallidum* (1)
    T-cell related response to *T. pallidum*
    Antibody to HIV T-cell related response to HIV
Antibodies to GBS serotypes (at least 3)
Measurement of Th1/Th2 cytokines (many as current evolving definitions)

3. Persistent Immunity Induced by Childhood Vaccines

In exemplary embodiments according to the present invention, the following tests for measurement of immunity to childhood vaccines can be included in an exemplary ImmunoScore panel directed to college students, or in other exemplary embodiments, to adults in general:

Antibody to HBs (1)
Antibody to diphtheria toxin (1)
Antibody to tetanus toxin (1)
Pertusis antibodies (4):
Antibody to pertussis toxin (PT)
Antibody to pertactin (PRN)
Antibody to filamentous hemagglutinin (FHA)
Antibody to fimbriae
Antibody to PRP (Hib) (1)
Antibodies to poliovirus serotypes P1, P2, and P3 (3)
Antibody to measles (1)
Antibody to mumps (1)
Antibody to rubella (1)
Antibody to varicella (1)
Antibody to pneumococcal serotypes (7)

B. Adult Diagnostic Panels

1. Measurement of Immunity Induced by Vaccines for Military Personnel

In exemplary embodiments of the present invention military personnel can be administered the following diagnostic panels:

1. College Student ImmunoScore Panels consisting of:
   Meningococcal Diagnostic Panel;
   Sexually Transmitted Disease Diagnostic Panel;
   Persistent Immunity Induced by Childhood Vaccine Diagnostic Panel; and as described above; and in addition
2. Military personnel can have specific vaccination needs as outlined in Table 3 below depending on their assignments and type of deployment. Specific branches of the service may also have specific vaccination needs and permutations of the basic diagnostic panels. Thus, in exemplary embodiments, military personnel can be administered one or more of the following tests:

TABLE 3

Vaccine Diagnostic Panels Exclusive to the Military:

| Vaccine | Antibody Marker |
| --- | --- |
| Adenovirus 4 & 7 | Neutralizing antibody |
| Anthrax | PA |
| Cholera | LPS IgG |
| Plague | Fraction I Capsular Antigen |
| Smallpox | Neutralizing antibody |
| Lyme disease | OspA |

2. ImmunoScore Measurement of Vaccine-Induced Immunity for Travelers

In exemplary embodiments of the present invention, an ImmunoScore traveler's assay panel can, for example, include the following:

Antibody to HAV (1)
Antibody to HBs (1)
Antibody to Japanese Encephalitis (1)
Antibody to rabies (1)
   other rabies related cytokine assays (as necessary)
Antibody to Typhoid fever (1)
Antibody to yellow fever (1)
Antibody to diphtheria toxin (1)
Antibody to tetanus toxin (1)
Pertusis antibodies (4):
   Antibody to pertussis toxin (PT)
   Antibody to pertactin (PRN)
   Antibody to filamentous hemagglutinin (FHA)
   Antibody to fimbriae
Antibodies to poliovirus serotypes P1, P2, and P3 (3)
Antibody to measles (1)
Antibody to mumps (1)
Antibody to rubella (1)

3. Cytokine Measurement in ImmunoScore

Introduction

An individual's immune system functions as an informational system that is shaped during that person's life after exposure to pathogens. Immune interventions, such as vaccines, that manipulate the "knowledge" of the immune system are among the most cost effective in modern medicine. Currently, globally immunotherapy for non-communicable diseases is not showing the same success achieved in fighting infection. Despite considerable experimental advances in understanding immune tolerance, autoimmune diseases continue to be treated by non-specific immunosuppression. The substantial experimental data generated with animal models remain limited in their capacity to allow predictions and guide clinical interventions (Lage, 2008).

The immune system should be considered a complex network, given that it consists of more than 200 cytokines and chemokines and contains millions of lymphocyte clones and its macroscopic activity is dictated by the interactions of all these components. How complexity influences immunology is demonstrated by the almost universal failure to predict the outcome of gene-inactivation experiments, the absence of effective vaccines for malaria and other parasites, tuberculosis or HIV, and the context dependent effects of some immunotherapy interventions (which induce either tolerance or immunity).

Over recent decades the immune system has been subject to a great deal of investigation. Growing complexity has often been a major byproduct of the discoveries reported, and subsequently models such as the Th1/Th2 paradigm, were developed to cope with such complexity. Regarding autoimmune diseases, verifying and expanding such models is desirable, because it has proven difficult to extrapolate findings to existing models that were often developed in different contexts (Delaleu, et al. 2008). Recent technological advances have greatly increased the amount of information and the number of proteins that can be investigated in any given system and put into a scientific context simultaneously.

By studying the immune system through the application of reductioninst principles, its mediators have been thoroughly analyzed over recent decades. This has yielded tremendous scientific advances. However, studying the properties of the immune system's isolated components is limited in terms of elucidating how system properties emerge, because they may strongly rely on and arise from interactions between numerous system components. The complexity of the immune system should not paralyze immunology research. The realization that the immune system is a complex network has led to wider use of mathematical models for simulating its activity and testing hypotheses in silico. ImmunoScore technology represents a novel way to analyze the implications of multiple molecules in a specific condition and provide insight into the inter-relationships that define a specific immune system status.

Cytokines are a large and diverse group of plasma-membrane associated or secreted proteins that bind cell-surface receptors and thereby regulate many important biological processes. These processes include development, hematopoesis, inflammation, immune responses, and tissue repair. Whether in a healthy individual or in an acute or chronic disease situation, cytokines act in concert rather than in isolation, and no single cytokine in a cross-sectional model is adequate to serve as an absolute screening marker. It is essential to understand the regulation of cytokine production in healthy individuals as well as individuals with distinct disease states. The application of ImmunoScore technology to cytokine analyses will help to establish the viability and merits of a multi-marker approach for clinical risk stratification. ImmunoScore technology will examine expressed levels of cytokines as serum markers, as correlation between mRNA levels and protein expression has previously been demonstrated to be poor in a model of autoimmune disease (Hu, et al. 2007).

Introduction: T-Helper Cell Subsets

Uncommitted CD4+ T helper cells can be induced to differentiate towards T helper 1 (Th1), Th2, Th17, and regulatory (Treg) phenotypes according to the local cytokine milieu (FIG. 1). Th1 cells secrete (among others) IFN-γ and TNF-α, which allow these cells to be particularly effective in protecting against intracellular infections by viruses and bacteria that grow in macrophages, as well as eliminating cancerous cells (Kidd, 2003). Th2 cells secrete IL-4, IL-5, IL-10, and IL-13 which upregulate antibody production and target parasitic organisms. Th2 cells activate B cells, which are adapted for defense against parasites that are vulnerable to IL-4 switched IgE production, IL-5 induced eosinophilia, and IL-3 and IL-4 stimulated mast cell proliferation and degranulation (Kaiko, et al. 2007). Th17 cells secrete IL-17, IL-17F, IL-6, IL-22, and TNF-α and appear to play a role in both tissue inflammation and activation of neutrophils to combat extracellular bacteria. Treg cells secrete IL-10 and TGF-β, which modify helper T cell activity and suppress some of their functions, inducing tolerance to antigens.

Anomalous T cell responses bolster a range of diseases, including asthma, allergy, and autoimmune disease. Fundamental immune elements of these diseases are the development of antigen-specific T-helper cells. Th1, Th2, and Th17 cells are associated with the clinical features and disease progression. The phenotypes of these polarized T cells that differentiate from naive precursors is determined by the complex interaction of antigen presenting cells with naive T cells and involves myriad factors, including the dominant cytokine environment, co-stimulatory molecules, the type and amount of antigen presented, and a wide variety of signaling cascades. The decision to take the immune response in a certain direction is not made by one signal alone, but rather through many different elements acting synergistically, antagonistically, and through positive and negative feedback loops to activate a Th1, Th2, or Th17 immune response, or combination thereof (Kaiko, et al. 2007).

Cytokines are the most influential factors that modulate T cell phenotype, and their mechanism of action involves intracellular signals transmitted through cytokine receptors expressed on the surface of T cells. In essence, any cell that differentially secretes or consumes key cytokines can regulate the function of other effector cells that are activated in close proximity (Sojka, et al. 2008).

Evolution of Th1/Th2 Paradigm to Include Th17 and Treg Cells

The initial concept of the Th1/Th2 paradigm is depicted in FIG. 2, where the T helper cell immune response was balanced on opposite sides of a teeter-totter. Cytokines produced during one type of response were imagined to be counter-productive to the other type of response in this model, expression of the Th1 response would cause a dampening of the Th2 response, and vice versa. Chronic over-expression of either type response would be undesirable to the individual, with a chronic Th1 response seen to cause autoimmunity and graft rejection, among others, and a chronic over-expression of the Th2 response to be the cause of atopic diseases and allergies.

With the discovery of Th17 and the re-discovery of Treg cells, it became apparent that the teeter totter model depicted in FIG. 2 was too simplistic, and the newer models now include the Th17 and Treg arms to accommodate these cell types (FIG. 3). In the recent past, inflammatory responses were assigned as an over-expression of Th1 cells, while at the same time allowing that inflammation could occur in the absence of the signature cytokine of Th1 cells, IFN-γ. Now, the Th17 cell pool is seen as having a significant contribution to inflammation. Th17 responses in the presence of a Th1 response can presumably lead to autoimmune disease, while Th17 responses in the presence of a Th2 response can lead to allergic or atopic disease. Treg cells are envisioned as the cells that dampen the immune response to avoid autoimmune and allergic reactions, however, over-expression of the Treg cell population is also not desirable as this can lead to chronic infection, or more strikingly, acute, fatal infection.

Th1 Cytokine Signals

Th1 cell development begins with the secretion of IL-12 and type 1 IFNs (IFN-α and IFN-β). These cytokines are released by macrophages and dendritic cells (DCs) upon activation by intracellular pathogens (Farrar, et al. 2002). IL-12 induces the production of IFN-γ from the Th1 cells, which then acts in an autocrine manner to generate a positive feedback loop, producing more IL-12. IFN-γ acts as an inhibitor of the Th2 pathway by preventing Th2 cell proliferation. Once the IL-12 receptor is expressed, IL-12 is then able to bind its receptor and further reinforce the differentiation of Th1 cells. IL-12 signaling activates the transcription factors STAT-3, STAT-4 and nuclear factor-κB to promote the production of cytokines associated with the Th1 phenotype (Kaiko, et al. 2007). The IFN-γ secreted by Th1 cells as they develop stimulates surrounding naive Th cells to begin polarization into more Th1 cells, in a self-renewing paracrine loop (Kidd, 2003). Other proposed Th1 polarizing factors include IL-27, and the intercellular adhesion molecule-1 (ICAM-1) binding its receptor (Salomon and Bluestone, 1998).

Th1 Effector Cell Signature:
  Induced by: IL-12
  Produce: IFN-γ, TNF-α, IL-2
  Suppressed by: IL-10, TGF-β, IL-23

Th2 Cytokine Signals

The production of Th2 effector cells primarily involves the action of cytokines IL-4, IL-6, IL-10, and IL-11. IL-4 induces the production of STAT-6 in naive T cells, which in turn activates the expression of the zinc finger transcription factor GATA-3 (Ouyang, et al. 1998). GATA-3 augments promoter activity or reverses chromatin structure based suppression of regions that are responsible for controlling Th2 cytokine gene expression. This results in the release of cytokines characteristic of the Th2 phenotype: IL-4, IL-5, IL-9, IL-10, and IL-13. Another result is the inhibition of expression of IL-12 receptor and therefore Th1 development (Farrar, et al. 2002). As Th2 cells mature, they produce increasing levels of IL-4, which generates a paracrine loop and induces neighboring naive T cells to develop to Th2 cells (Kidd, 2003). IL-6 is also released early in Th2 cell development, and up-regulates IL-4 and inhibits STAT-1 phosphorylation, thereby preventing IFN-γ synthesis (Dodge, et al. 2003). IL-6 also plays an integral role in Th17 differentiation. IL-11 released by myeloid cells acts directly on T cells to stimulate IL-4 and IL-5 synthesis and also to inhibit IFN-γ production.

The induction of mast cell degranulation and the release of histamine have been demonstrated to polarize the function of DCs and Th cells towards a Th2 phenotype (Mazzoni, et al. 2006). Degranulation reduced the capacity of DCs to induce Th1 cells and instead promoted the development of increased numbers of IL-4 secreting T cells. This indicates that mast cells may have a critical function in the development of the antigen specific Th2 cell phenotype in mast cell-mediated diseases, such as asthma.

It seems likely that the inducible co-stimulator (ICOS) is capable of co-stimulating distinct effector functions, depending on the density of surface expression and tissue localization of the immune response. There appears to be a relationship between ICOS cell-surface density and the type of cytokines produced (Kaiko, et al. 2007). There is a strong association between intermediate expression of ICOS and secretion of Th2 cytokines, and high levels of ICOS expression and release of the regulatory cytokine IL-10 (Lohning, et al. 2003).

Th2 Effector Cell Signature:
  Induced by: IL-4
  Produce: IL-4, IL-5, IL-13, IL-10
  Suppressed by: IL-10, TGF-β
Th17 Cytokine Signals Th17 cells represent a subset of CD4+ cells that is both distinct from and antagonized by cells of the Th1 and Th2 lineages. Although found throughout the body, Th17 cells are predominantly found in the lung and digestive mucosa suggesting a homeostatic role in those tissues (Kryczek, et al. 2007). The generation of Th17 cells is inhibited by IL-4 and IFN-γ potentially by down-regulation of the IL-23 receptor (Harrington, et al. 2005). IL-23 appears to be essential for the production of a robust Th17 response, but is not responsible for the initial induction of the Th17 phenotype. Rather, Th17 cells appear to be induced by a combination of IL-6 and TGF-β. The combination of these cytokines induces the predominant generation of Th17 cells with minimal numbers of Tregs in a mutually exclusive pattern (Veldhoen, et al. 2006; Bettelli, et al. 2006). As TGF-β is involved in the development of both Tregs and Th17 cells, which may occur through the inhibition of IL-4- and IFN-γ-dependent pathways, it appears that IL-6, a known inhibitor of Treg development, plays an integral role in switching between these inflammatory and suppressive cell types (Kaiko, 2007). Neutralizing IL-17 in cultures of Th17 cells alters the balance in favor of Tregs, suggesting an important inhibitory action of IL-17 on Treg cells (Nardelli, et al. 2004).

Th17 Effector Cells Signature:
  Induced by: TGF-β, IL-6
  Produce: IL-17, IL-21, IL-22
  Maintained by: IL-23
  Suppressed by: IL-4, IFN-γ, IL-2, IFN-α
Treg Cytokine Signals Every adaptive immune response involves recruitment and activation of not only effector T and B cells but also Tregs, and that the balance between the two populations is critical for the proper control of the quality and magnitude of adaptive immune responses and for establishing or breaching tolerance to self- and non-self antigens (Sakaguchi, et al. 2008). The exact mechanism by which the Tregs exert their effect is currently unknown, although it is believed that their suppressive function may be contact-dependent (Afzali, et al. 2007). Other studies show an important role for TGF-β and IL-10 production as mediators of Treg activity that is contact-independent (Dieckmann, et al. 2002; Longhi, et al. 2006). Both TGF-β and IL-2 are important for the development of Tregs (Afzali, et al. 2007; Malek and Bayer, 2004). Foxp3 expression as a complex leads to Treg cell-mediated suppression in a cell-cell contact-dependent or -independent manner (Li and Greene, 2008). In humans, disruption of Foxp3 function leads to an immune dysfunction, polyendocrinopathy, enteropathy, X-linked (IPEX) syndrome characterized by autoimmune disease, allergy, and inflammatory bowel disease (Bennett, et al. 2001). In the absence of cell-cell contact, Tregs can suppress T cell activity by either directly secreting IL-10, TGF-β, and IL-35, or competing for cytokines via receptors that contain the common γ-chain, which binds to IL-2, IL-4, and IL-7 (Sojka, et al. 2008).

Given the diverse array of suppressive mechanisms, Treg activity needs to be attenuated to mount effective immune responses to infection. Treg function can be modulated by a variety of pro-inflammatory signals including Toll-like receptor triggering and direct inhibition by tumor necrosis factor-α (TNF-α) (Liu and Zhao, 2007; Valencia, et al. 2006). The up-regulation of B7 expression (CD80 and CD86) by antigen-presenting cells represents a central event in the activation of naive T cells and may serve as a mechanism to disrupt regulatory T cell tolerance by rendering effector T cells unresponsive to suppression (Sojka, et al. 2008). B cells with their lower expression of CD80/CD86 appear to be more efficient antigen-presenting cells than dendritic cells for inducing effector Treg cells (Benson, et al. 2007).

Treg Cell Signature:
  Induced by: TGF-β, IL-2
  Produce: IL-10, TGF-β, IL-35
  Suppressed by: IL-6, IL-17, IL-31
Dendritic Cells Dendritic cells are recognized as one of the most important cell types for initiating the priming of naive CD4+ helper T (Th) cells and for inducing CD8+ cell differentiation into killer cells (Banchereau, et al. 2000). Immature dendritic cells are found at strategic anatomical sites throughout the body, thereby allowing them to respond rapidly to microbial invasion (Pashine, et al. 2005). Activation of lymphoid dendritic cells, because of their preponderance to secrete IL-12, may be important for priming Th1-like responses, while early activation of myeloid dendritic cells may lead to Th2-like responses (Pulendran, 2004). It has also been suggested that the production of Il-6 by dendritic cells may be reponsible for inhibiting the suppressor activity of Treg cells (Pasare and Medzhitov, 2004). This production of IL-6 might also reasonably be assumed to enable the activation of Th17 cells.

B Cells and Success of Vaccinations

The most dramatic health problem of the aged immune system is the increaing rates of morbidity and mortality from recurrent and invasive infections of the respiratory tract caused by encapsulated bacteria such as Streptococcus pneumoniae (Sankilampi, et al. 1997). It has been reported that increased susceptibility to secondary pneumococcal pneumonia is at least in part caused by excessive Il-10 production and reduced neutrophil function in the lung (van der Sluijs, et al. 2004). Two populations of B cells have been identified in human peripheral blood: mature and memory B cells. IgD-CD27+ memory B cells can produce IgG, IgM, and IgA, while IgD+CD27+ IgM memory B cells predominantly produce IgM (Shi, et al. 2003). The presence of IgM memory B cells in the blood correlates with protection from pnuemococcal infection (Kruetzmann, et al. 2003). Natural antibodies make up most of the IgM in the serum and have the function to limit the growth and dissemination of pathogens during the early phases of infection and potentiate the immune response (Ochsenbein, et al. 1999). Physiological and transient disposition to pneumococcal infection of young children (under 2 years of age) is associated with the lack of circulating IgM memory cells and of serum anti-polysaccharide IgM (Kruetzmann, et al. 2003). Decline of splenic functions may reflect diminished numbers of aged IgM memory B cells. Effectiveness of pneumococcal polysaccharide vaccine in older adults on protection against pneumococcal infections may be associated with the increase and activation of circulating IgM memory B cells, resulting in rapid synthesis of anti-polysaccharide IgM antibodies (Shi, et al. 2005).

Regulatory B Cells

The maintenance of tolerance is an absolute requirement of a sophisticated regulatory apparatus to prevent or dampen overzealous immune responses. In addition to the ability of B cells to prime and activate the immune system, B cells with regulatory function (Bregs) have been identified in experimental models of autoimmunity, infections, and cancer, supporting the notion that, similar to Tregs, Breg-mediated suppression is an important means for the maintenance of peripheral tolerance. This regulatory function appears to be directly mediated by the production of IL-10 and TGF-β and by the ability of the B cells to interact with pathogenic T cells to inhibit harmful immune responses (Mauri and Ehrenstein, 2008). B cells are typically characterized by their ability to produce antibodies. However, B cells possess additional immune functions, including the production of cytokines and the ability to function as secondary antigen presenting cells. As with T cells, the B cell population contains functionally distinct subsets capable of performing both pathogenic and regulatory functions (Mizoguchi and Bhan, 2006). B cells can play a pathogenic role in acquired immune responses by producing autoantibodies that contribute to the development of autoimmune diseases (Murakami and Honjo, 1997; Korganow, et al. 1999; Fields, et al. 2003). The existence of an immunoregulatory B cell subset that plays a role in immune regulation resulting in complete recovery from experimental autoimmune encephalomyelitis was reported in a murine model of that disease (Wolf, et al. 1996).

IL-10 from regulatory B cells can repress the production of IL-6 and IL-12 by DCs, thereby inhibiting the differentiation of Th17 and Th1 cells, respectively (Lampropoulou, et al. 2008).

Like their T cell counterparts, B cells can be divided into functionally distinct regulatory subsets capable of inhibiting inflammatory responses and inducing immune tolerance (Mizoguchi and Bhan, 2006).

Role of Basophils

Basophils activated by IL-3 or antibody to FcεRI induce B cell proliferation and the production of IgM and IgG1 in the presence of activated CD4+ T cells; this B cell proliferation and immunoglobulin production requires IL-6, IL-4 and cell contact (Kawakami, 2008). Activated basophils enhance the humoral memory response by secreting IL-6 and by altering the phenotype of CD4+ cells (that is, by inducing CD4+ T cell up-regulation of IL-4, IL-5, IL-10, IL-13, and the transcription factor GATA-3 and down-regulation of IFN-γ and IL-2) (Denzel, et al. 2008).

Trauma and Cytokines

The immune system undergoes numerous changes after traumatic injuries, including a down-regulation of the Th1 response and up-regulation of the Th2 response (Miller, et al. 2007). They Th1 response is suppressed as illustrated by diminished IL-2, IFN-γ, and IL-12 levels after major injury. The enhancement of the Th2 profile is marked by elevated IL-10 and IL-4. Certain cytokine profiles, ratios, and polymorphisms may help identify patients at increased risk of systemic inflammatory response syndrome (SIRS), sepsis, multiple organ failure (MOF), and deep venous thrombosis. Some provocative indications for individuals more susceptible to complications include (Miller, et al. 2007):

- decreased IL-12
- increased IL-10
- increased sIL-2Ra
- increased IL-18
- IL-18 promoter genetic polymorphisms
- IL-6: IL-10 ratio Identification of those Th1/Th2 cytokine profiles associated with worse prognosis may one day allow clinicians to risk stratify injured patients and identify those at increased risk of developing SIRS, sepsis, MOF, and deep venous thrombosis.

Stress and Cytokines

Recent evidence indicates that the major stress hormones, glucocorticoids and catecholamines, systemically inhibit IL-12, TNF-α, and IFN-γ, while simultaneously upregulating IL-10, IL-4, and TGF-β production indicating a generic Th1 to Th2 shift (Calcagni and Elenkov, 2006). However, in certain local responses and under certain conditions, stress hormones may actually facilitate inflammation through induction of IL-1, IL-6, IL-8, IL-18, TNF-α, and CRP production. Autoimmunity, chronic infections, major depression, and atherosclerosis are characterized by a dysregulation of the pro/anti-inflammatory and Th1/Th2 cytokine balance (Calcagni and Elenkov, 2006). These authors stated that conditions that are associated with significant changes in stress system activity, such as acute or chronic stress, cessation of chronic stress, pregnancy and the post-partum period, or rheumatoid arthritis through modulation of the systemic or local pro-anti-inflammatory and Th1/Th2 cytokine balance, may suppress or potentiate disease activity and/or progression. Stress-hormones induced inhibition or up-regulation of innate and Th cytokine production may represent an important mechanism by which stress affects disease susceptibility, activity, and outcome of various immune-related diseases.

Inflammatory Bowel Disease (IBD) and Cytokines

Traditional dogma has had different viewpoints of inflammatory bowel disease and cytokines: Crohn's disease (CD) has been thought to have a Th1 motif, while ulcerative colitis (UC) was thought to have given rise to a Th2 expression (Mudter and Neurath, 2007). CD has been associated with elevated expression of IFN-γ, TNF-α, and IL-12. In UC, the pattern is less clear; there is a modified Th2 response associated with cytokines such as IL-15 and IL-10 (Torres and Rios, 2008). Other publications have reported that the IL-17/IL-23 pathway may have a pivotal role in intestinal inflammation (Hue, et al. 2006; Kullberg, et al. 2006).

Atherosclerosis

Atherosclerosis historically was considered to be mainly a degenerative disease, but it is now well ascertained that its pathogenesis is inflammatory (Jawien, 2008). Serum levels of the IL-1 family of cytokines (including IL-18 and IL-33) have been correlated with various aspects of cardiovascular disease and their outcomes (Apostolakis, et al. 2008). IL-1Ra, a natural antagonist of IL-1, possesses anti-inflammatory properties, mainly through the endogenous inhibition of IL-1 signaling (Apostalakis, et al. 2008).

Oxidized low density lipoprotein (OxLDL) is not only pro-inflammatory and pro-atherogenic, but several of the neoepitopes generated during oxidation are highly immunogenic and result in the generation of auto-antibodies. The overall evidence supports the notion that IgG auto-antibodies to OxLDL are associated with pro-atherogenic properties, and that IgM auto-antibodies to OxLDL are associated with atheroprotective properties (Gounopoulos, et al. 2007). ImmunoScore would track trends in anti-OxLDL antibody levels in patients over time and add this information to the ImmunoScore database. Similarly, antibody levels to Hsp 60 would be tracked to determine if these antibodies are beneficial or detrimental to patients.

One researcher proposed that in general, it is believed that the Th1 response and its mediators: IFN-γ, TNF-α, IL-1, IL-12, and IL-18 enhance atherogenesis, while a Th2 response and its mediators: IL-4, IL-5, IL-10 and IL-13 inhibit the development of atherosclerosis (Jawien, 2008). Another group put the atherosclerosis profile onto the Th17/Treg axis by stating that acute coronary syndrome was associated with an increase in Th17 cytokines (IL-17, IL-6, and IL-23) and a decrease in Treg cytokines (TGF-β and IL-10) (Cheng, et al. 2008). By measuring all the associated cytokines over time and various demographics, the ImmunoScore technology would be able to specifically enumerate and assign significance to these assays and relate the results to the individuals being tested.

Another study found that in patients with an inflammatory response, as demonstrated by elevated levels of IL-6 in serum, CMV seropositivity was a strong and independent predictor for cardiac death (Blankenberg, et al. 2001). High CMV antibody titers may be associated with a chronic inflammatory response resulting in increased IL-6 levels. This in turn, can lead to an increase in CRP levels and a poor prognosis for coronary artery disease outcome. It has been shown that statins can reduce the inflammatory response. Periodic ImmunoScore measurements in a treated patient population would assist physicians regarding course and effectiveness of statin treatments, as serum CMV positivity without inflammatory response is not indicative of fatal cardiovascular events (Blankenberg, et al. 2001).

Another group proposed classifying cytokines related to both atherosclerosis and diabetes in the following categories: "noxious" comprising IL-1, IL-2, IL-6, IL-7, IL-8, IL-15, IL-17, and IL-18; "protective" comprising IL-4, IL-10, IL-11, IL-12, and IL-13; and "aloof" comprising IL-5, IL-9, IL-14, IL-16, and IL-19 through IL-29 (Fisman, et al. 2008).

Proposed ImmunoScore Atherosclerotic Disease Panel
  Indicators for Poor Prognosis (Th1/Th17 axis)
    IL-6
    IL-12
    IL-18
    IL-33
    IFN-γ
    TNF-α
    CRP
    Antibody to CMV
  Indicators for Improved Prognosis (Th2/Treg axis)
    IL-10 (with exception of transplant patients)
    TGF-β
    IL-5
  Indeterminate Prognostic Value (Th2)
    IL-4
    Antibody to OxLDL
    Antibody to Hsp 60
  Th17 Autoimmune Pathogenesis Th17 may play an essential role against certain extracellular pathogens. However, Th17 cells with specificity for self-antigens are highly pathogenic and lead to the development of inflammation and severe autoimmunity. Interleukin (IL)-17 was originally named cytotoxic T lymphocyte-associated antigen-8 (CTLA-8) (Paradowska, et al. 2007). There are six members of the IL-17 protein family (IL-17A through IL-17F). The IL-17 family plays a key role in the regulation of immune and inflammatory response, in the homeostasis of several tissues, and the progression of autoimmune diseases (Paradowska, et al. 2007).

IL-23 and IL-17 are associated with a number of human autoimmune disorders. Th17 cells are likely to be highly pathogenic in rheumatoid arthritis (McGeachy and Cua, 2008). IL-17+, CD4+ and CD8+ T cells have been identified in active lesions in the brain of multiple sclerosis patients (Tzartos, et al. 2008). Psoriasis has also been linked to inappropriate Th17 cell responses. IL-17, IL-23, and 11-22 are all elevated in psoriatic lesional skin (Lee, et al. 2004; Wilson, et al. 2007; Wolk, et al. 2004).

As the Th1 and Th2 cell subsets cross-regulate the differentiation of the other cell type, they also appear to negatively regulate the differentiation of Th17 cells (McGeach and Cua, 2008). Addition of IL-2, IFN-γ, or IL-4 to cultures inhibits either IL23- or TGF-β plus IL-6-stimulated differentiation of mouse and human Th17 cells (Annunziato, et al. 2007; Harrington, et al. 2005; Murphy et al. 2003; Park, et al. 2005; Wilson, et al. 2007).

Foxp3+ regulatory T cells (Treg) are necessary and sufficient to prevent autoimmunity throughout the lifespan of an individual. TGF-β induces Foxp3 in naïve T cells, but TGF-β and IL-6 together drive the generation of Th17 cells (Korn, et al. 2007). A group found that in humans, IL-23 and IL-1β are able to drive naive CD4+ T cells toward the Th17 phenotype (Wilson, et al. 2007).

Th17 cells probably have a specific role in normal immune function through the coordinated action of their effector cytokines and chemokines, similar to the well established functions of Th1 and Th2 cells in regulating cellular immunity and antibody production. The signature cytokine and chemokine profile of Th17 cells suggests that these cells regulate the immune function of epithelial cells rather than cells of the classical immune system (Wilson, et al. 2007).

When mucosal immunity is not countered by anti-inflammatory mediators, excessive pro-inflammatory responses result in chronic inflammatory bowel disease (IBD) (Braegger, 1994). One study demonstrated that IL-23 was essential for the manifestation of chronic intestinal inflammation, whereas IL-12 was not. A critical target of IL-23 was shown to be a unique subset of tissue-homing memory T cells, that were specifically activated by IL-23 to produce IL-17 and IL-6. They concluded that this pathway might be responsible for chronic intestinal inflammation as well as other chronic autoimmune inflammatory diseases (Yen, et al. 2006).

Th17 differentiation
    TGF-β (may inhibit in humans?—Chen and O'Shea, 2008)
    IL-1β (Toh and Miossec, 2007; Chen and O'Shea, 2008)

IL-6
IL-23
Th17 amplification
   IL-21 (produced by Th17 cells)
Th17 stabilization
   IL-23

Thymus-produced self-reactive T cells, which become activated in the periphery by recognition of major histocompatibility complex/self-peptide complexes, stimulate antigen presenting cells (APCs) to secrete IL-6. APC-derived IL-6, together with T cell-derived IL-6, drives naïve self-reactive T cells to differentiate into arthritogenic Th17 cells. In mice, deficiency of either IL-17 or IL-6 completely inhibits the development of arthritis, while IFN-γ deficiency exacerbates the development of arthritis (Hirota, et al. 2007). In humans, it is not yet clear whether rheumatoid arthritis is a Th1 or a Th17 mediated disease (Lubberts, 2008).

The IL-17 family of cytokines has been implicated in the pathogenesis of rheumatoid arthritis (RA) and juvenile idiopathic arthritis (JIA) (Nistala, et al. 2008). In JIA, IL-17 is increased in patients with active disease as compared to those in remission (de Jager, et al. 2007). Conversely, Treg cells are present at significantly higher numbers in patients with a milder clinical phenotype than in those with a more severe form of arthritis (De Kleer, et al. 2004).

Th17 cell cytokine production (Lubberts, 2008):
   IL-17A
   IL-17F
   IL-6
   TNF-α
   GM-CSF
   IL-21
   IL-22
   IL-26

IL-6

The pleiotropic cytokine IL-6, previously called B cell stimulatory factor-2 (Bcl-2 or BSF-2) or IFN-β2, has emerged in recent years as a key regulator of the transition from innate to adaptive immunity through its ability to modulate leukocyte recruitment at inflammatory sites (Kishimoto, 2006; Ohsugi, 2007). It has been found that there is a thermally-sensitive alert system utilizing IL-6 signaling that promotes immune surveillance, thus shedding light on the benefits of mounting a febrile reaction during inflammation (Vardam, et al. 2007).

One of the most important systemic actions of IL-6 is induction of the acute phase response. Acute phase proteins are produced primarily by the liver and include proteins that promote the immune response through activation of complement, induction of pro-inflammatory cytokines, and stimulation of neutrophil chemotaxis (Cronstein, 2007). In humans, tow of the most prominent acute phase proteins are CRP and serum amyloid A (Van Snick, 1990).

IL-6 exerts a significant influence on the course of inflammation in humans. There is evidence that IL-6 is capable of mediating both pro-inflammatory effects, including the induction of intercellular adhesion molecules and the recruitment of leukocytes, and anti-inflammatory effects, such as the suppression of the pro-inflammatory cytokines, TNF-α and IL-1 (Wong, et al. 2003).

IL-6 in combination with its soluble receptor, sIL-6Rα, influences the transition from acute to chronic inflammation (Gabay, 2006). Prospective studies have shown that long-term IL-6 levels are associated with coronary heart disease (CHD) risk as strongly as are some major established risk factors (Danesh, et al. 2008). This group pointed out the pressing need for paired studies of individuals, in that owing to fluctuations in IL-6 values over time, comparisons using only baseline values may yield biased estimates of the true association between Il-6 and CHD, which can be corrected, for the most part, by using data from paired measurements. In addition, given the central role of IL-6 levels in inflammatory pathways and its continuous association with CHD risk, it warrants further investigation as a plausible potential therapeutic target. The ImmunoScore database will serve to hold an individual's paired measurements of various cytokines and enable future prospective studies for many diseases, as well as enable the study of CHD. In addition, ImmunoScore diagnostic applications could track fundamental immune parameters in individuals undergoing IL-6 directed therapy.

Cardiovascular disease is a leading cause of mortality in rheumatoid arthritis (RA). Endothelial dysfunction often precedes manifest atherosclerosis. Among immunological and metabolic laboratory markers, anticyclic citrullinated peptide antibodies, IgM rheumatoid factor, circulating immune complexes, pro-inflammatory cytokines including TNF-α and IL-6, Th0/Th1 cells, homocysteine, dyslipidemia, decreased folate and vitamin B production, and paraoxonase activity may all be involved in the development of vascular disease in RA (Szekanecz, et al. 2007). The early diagnosis of endothelial dysfunction and atherosclerosis, active immunosuppressive treatment, the use of drugs that control atherosclerosis, changes in sedentary lifestyle, and the close follow-up of RA patients may help to minimize cardiovascular risk in these individuals.

High serum levels of IL-6 have been linked to risks for several conditions, such as cardiovascular disease, type 2 diabetes, mental health complications, and some cancers. Stress-induced immune dysregulation has been shown to be significant enough to result in health consequences, including reducing the immune response to vaccines, slowing wound healing, reactivating latent viruses, and enhancing the risk for more severe infectious disease. There is evidence that psychological stress promotes immune dysfunction that negatively impacts human health (Godbout and Glaser, 2006).

Local cellular environmental factors and an individual's genetic susceptibility play a role in the transduction of IL-6 signals. Depending on the expression of CD45 on multiple myeloma cells, IL-6 can either result in proliferation or apoptosis of CD45+ cells depending on circumstantial stimuli (Ishikawa, et al. 2006). Chronic obstructive pulmonary disease (COPD) is a multicomponent disease characterized by abnormal inflammatory response of the lungs to noxious particles, accompanied by systemic effects like weight loss, muscle wasting, reduced functional capacity, and impaired health status. A persistent low-grade systemic inflammatory response, determined in part by genetic components, is present in a portion of the COPD population (Yanbaeva, et al. 2006).

IL-22

Elevated serum and plasma levels of IL-22 are indicative of Crohn's disease. Normal population mean level are approximately 2 pg/mL, while mean levels in Crohn's disease patients reach 24 pg/mL, and are higher with flares of the disease (Wolk, et al. 2007).

IL-23

Interleukin-23 is composed of the IL-12p40 subunit and a novel p19 subunit. It can enhance the proliferation of memory T cells and the production of IFN-γ, IL-12, and TNF-α from activated T cells. IL-23 can also act directly on dendritic cells and possesses potent anti-tumor and anti-metastatic activity in murine models of cancer (Hao and Shan, 2006).

IL-23 possesses unique roles in the differentiation and expansion of memory T cells. IL-23 is also associated with Th17 responses and the cytokine produced by the antigen presenting cells (i.e. IL-12 vs. IL-23) determines in part if a response is Th1 or Th17 (Tan, et al. 2008).

IL-23 is an inflammatory cytokine that plays a key role in the pathogenesis of several autoimmune and inflammatory diseases. It orchestrates innate and T cell mediated inflammatory pathways and can promote Th17 cell responses (Izcue, et al. 2008). IL-23 has been associated with several inflammatory disease including rheumatoid arthritis, inflammatory bowel disease, and *Helicobacter pylori* associated gastritis. The immune response in the intestine is typically a delicate balance between effector and regulatory T cell responses, and IL-23 plays a key role in this balance. Factors may promote inflammation not only by direct effects on inflammatory mediators, but also indirectly by impeding regulatory mechanisms (Izcue, et al. 2008). IL-6 has been identified as an inflammatory mediator that desensitizes T cells to Treg cell mediated suppression (Pasare and Medzhitov, 2003). IL-23, via its ability to impede Treg cell responses in the intestine, may promote host protective immunity at this site.

Cytokines and Autoimmunity

The presence of IL-17 mRNA or IL-17 protein in tissues and biological fluids of patients has been associated with rheumatoid arthritis (Kotake, et al. 1999; Honorati, et al. 2001), multiple sclerosis (Matusevicius, et al. 1999; Kurasawa, et al. 2000), systemic lupus erythematosus (Wong, et al. 2000), inflammatory bowel disease (Nielsen, et al. 2003; Fujino, et al. 2003), atopic dermatitis (Koga, et al. 2008), Lyme arthritis (Infante-Duarte, et al. 2000), and psoriasis (Albanesi, et al. 2000).

In autoimmunity, IFN-γ does not appear to be pathogenic, but rather protective, as inhibition of IFN-γ signaling enhances the development of pathogenic Th17 and exacerbates autoimmunity (Harrington, et al. 2005). Also, the neutralization of IL-4, produced by Th2 cells is critical to in neutralizing the development of IL-17; however, neither IFN-γ nor IL-4 seem to be effective on already established Th17 pathogenesis (Harrington, et al. 2005).

In organ-specific autoimmunity, the balance of cytokines is a key determinant of resistance or susceptibility. Animal models of experimental autoimmune encephalomyelitis (EAE) are considered to mirror conditions of multiple sclerosis (MS) in humans. In EAE, disease susceptibility is thought to correlate with the expression of pro-inflammatory cytokines such as IL-17, IFN-γ, TNF-α, IL-6, and IL-1β. On the other hand, Th2 cytokines such as IL-4 and IL-13 have been shown to be important for preventing or easing disease symptoms (Cash, et al. 1994; Olsson, 1995). IL-25 is expressed in organ systems where regulation of inflammation is of critical importance (Kleinschek, et al. 2007). In healthy digestive and respiratory tracts, an anti-inflammatory environment must be maintained due to constant exposure to commensal microbes.

Although IL-25 and IL-17 are members of the same cytokine family, they play opposing roles in the regulation of organ-specific autoimmunity. The type 2 responses promoted by IL-25 drive a novel regulatory mechanism for controlling Th17 responses. This regulation relies on IL-13 and not IL-4, suggesting that IL-13 may be secreted at higher levels in the target organs during autoimmune inflammation (Kleinschek, et al. 2007).

In mice, IL-25 is expressed by lung epithelial cells as a result of innate immune responses to allergens. IL-25 promotes Th2 cell differentiation in an IL-4-dependent manner and has been shown to be a critical factor regulating the initiation of innate and adaptive pro-allergic responses (Angkasekwinai, et al. 2007).

Human patients with IBD have elevated IL-17 and IL-22 in affected colonic tissue and serum, depending on disease activity and severity (Fujino, et al. 2003; Nielsen, et al. 2003; to Velde, et al. 2007). Patients with rheumatoid arthritis have elevated Il-17 and IL-22 in synovial fluid (Kotake, et al. 1999; Ikeuchi, et al. 2005). Il-22 is increased in psoriatric serum and high levels of IL-23 have been detected in psoriasis lesions (Wolk, et al. 2006; Piskin, et al. 2006).

Etanercept is a TNFR-Ig fusion protein that has been used clinically to block TNF at molecular and cellular levels. A group studying the effect of this drug on psoriasis patients found that improvement in psoriasis disease correlated with the rapid down-modulation of DC and Th17 cell products and downstream effector molecules. Final disease resolution correlated with later down-modulation of Th1 cells (Zaba, et al. 2007).

Although many patients have been treated with immunomodulatory drugs, there are surprisingly limited data on therapeutic mechanisms in human inflammatory disease. Consistent monitoring of serum cytokines during therapies for autoimmune disease with ImmunoScore technology will provide benefit to physicians, patients, and pharmaceutical researchers. In the case of etanercept treatment of psoriasis described above, it was found that first DC and Th17 effects in lesions were lessened, but disease was not completely resolved until Th1 effects were also ameliorated. For other inhibitors of TNF (of which there are three currently in clinical use), there may be different mechanisms as yet undiscovered. Careful monitoring of the progress of autoimmune diseases and treatments to ease disease symptoms are to be a hallmark of ImmunoScore implementation. Based upon current understanding of autoimmune disease flares, the following cytokines are to be monitored in patients suffering from autoimmune disease symptoms. Progressive spikes of each of these cytokine groupings are to be expected. Effective therapeutic treatment should be indicated by faster cycling of each stage.

1. When expressed together, these cytokines indicate a "highly aggressive" Th17 profile:
   IL-17
   IL-22
2. For Th17 induction and stability:
   IL-23
   IL-6
   TGF-β
3. Cytokines indicative of impending flare resolution:
   IFN-γ (Th1 cytokine—interferes with long term Th17 cell survival)
   IL-4 (Th2 cytokine—interferes with long term Th17 survival)
   IL-27
4. Treg cytokines:
   IL-10
   TGF-β

It has been proposed that there is a reciprocal relationship between pathogenic Th17 cells and Foxp3+ Treg cells, in which IL-6, an acute phase protein induced during inflammation, acts as a pivot to determine whether the immune response is dominated by the highly inflammatory Th17 cells or protective Treg cells (Bettelli, et al. 2007).

Cytokines and Cancer

Immunosuppressive networks mediated by IL-10 and TGF-β seem to inhibit cell-mediated immune responses against cancer cells (Zou, 2005). Clinical data show a decreased ratio of circulating Th1 cells to circulating Th2 cells and their associated cytokines in different cancer types and also in chronic inflammatory conditions that are associated with increased risk of cancer (Tan and Coussens, 2007).

Increased levels of circulating cytokines and their receptors (most often of the pro-inflammatory cytokine IL-6) have been found in observational studies of patients with various types of cancer, both at the diagnosis of the primary disease and in those with metastases, compared with healthy people and people with benign tumors (Seruga, et al. 2008).

Various specific cancer treatments can stimulate the immune system to produce pro-inflammatory cytokines that are associated with toxic effects of treatment such as cancer-related fatigue, flu-like systemic effects and bone loss. They can lead to impaired quality of life of patients with cancer and poor compliance with treatments (Seruga, et al. 2008). Stimulation of the immune system by specific cancer treatments might also have a substantial role in producing anti-cancer effects. Cancer drugs might differentially effect the secretion of cytokines in humans with cancer, and this secretion might be a tool with which to monitor the therapeutic indices of drugs. Periodic ImmunoScore diagnostic measurements of cytokines relevant to specific cancer types would be invaluable to doctors and their patients.

Cancer patients frequently suffer from fatigue and some suffer from cognitive impairment during and after treatment for cancer (Lawrence, et al. 2004; Vardy and Tannock, 2007). An animal study has indicated the likely importance of IL-6 in the development of cognitive impairment (Sparkman, et al. 2006). IL-10 has been shown to counteract the production of IL-6 in microglial cells (Heyen, et al. 2000). In another study, patients with myeloid leukemia or myelodysplastic syndrome who had higher serum IL-6 levels were found to have poorer executive function, whereas higher levels of IL-8 were associated with better memory (Myers, et al. 2005).

Many cancer patients, during both treatment and long-term follow-up, experience psychological distress including anxiety and depression (Zabora, et al. 2001). Studies of chronic and acute stress showed increased circulating levels of Il-6 and TNF-α compared with controls (Kuecolt-Glaser, et al. 2003; Graham, et al. 2006). Cancer-related fatigue is strongly associated with a depressed mood (Bower, et al. 2006). Clinical studies have also shown an association between circulating levels of IL-6 and resistance to chemotherapy (De Vita, et al. 1998; Zhang and Adachi, 1999). Il-6 is one of the most ubiquitously deregulated cytokines in cancer patients and high levels of circulating IL-6 most commonly predicted poor outcome in observational studies (Hong, et al. 2007). Stage is an important prognostic factor in every cancer type and in observational studies there is a consistent trend of higher levels of circulating cytokines in more advanced stages of various cancers than in early stages, which further supports an association with the outcome of cancer (Seruga, et al. 2008). A study of oral squamous cell carcinoma found significant contributions of IL-6 and TNF-α to disease (Vairaktaris, et al. 2008).

Some immunomodulatory cytokines have been demonstrated to have anti-tumor activity. These include TNF-α, IFN-γ, IFN-α, IL-2, IL-12, IL-15, and IL-18. Others with promise of anti-tumor activity include IL-21, IL-23, and IL-27 (Weiss, et al. 2007).

Pro-inflammatory cytokines are involved in the development and progression of cancer and are also associated with fatigue, depression, cognitive impairment, anorexia, and pain, which all affect the quality of life of the patient. Sustained production of some cytokines may also be associated with cancer recurrence and progression. Strategies to monitor and inhibit the effects of such cytokines might therefore have profound effects on quality of life and survival.

Proposed ImmunoScore Cancer Cytokine Panel
  IL1-RA
  sIL2R
  IL-6
  IL-8
  IL-10
  TNF-α
  M-CSF
  VEGF Treg Manipulation Depletion of naturally arising Tregs not only elicits autoimmunity, but also augments immune responses to non-self antigens (Sakaguchi, et al. 2008). Treg depletion produces inflammatory bowel disease, which likely results from excessive immune responses to commensal bacteria in the intestine (Singh, et al. 2001). Removal or reduction of CD4+CD25+ Tregs also provokes effective tumor immunity in otherwise non-responding animals and augments microbial immunity in chronic infection, leading to eradication of tumors or microbes (Wang and Wang, 2007; Belkaid and Rouse, 2005). Conversely, CD4+CD25+ T cells enriched from normal mice suppress allergy, establish tolerance to organ grafts, prevent graft versus host disease after bone marrow transplantation, and promote fetal-maternal tolerance (Sakaguchi, 2005).

Several key concepts have been formulated regarding dominant self-tolerance and immune regulation (Sakaguchi, et al. 2008). First, the normal immune system generates Tregs that are engaged in suppressing immune responses towards self, quasi-self (such as autologous tumor cells), and non-self (such as microbes and allografts). Second, the normal thymus produces potentially pathogenic self-reactive T cells as well as functionally mature Tregs; mature Tregs persist in the periphery and exert dominant control over the self-reactive T cells. Third, Treg deficiency in the periphery is sufficient to evoke chronic T cell-mediated autoimmunity and immunopathology.

In vitro, Tregs suppress the proliferation and cytokine production (particularly IL-2) of responder T cells in the presence of antigen presenting cells (Takahashi, et al. 2000). Several mechanisms of Treg mediated suppression have been proposed, and these include secretion by the Treg of immunosuppressive cytokines, cell contact dependent suppression, and functional modification or killing of antigen presenting cells. IL-10 and TGF-β contribute to suppression of inflammatory bowel disease by Treg depletion (Read, et al. 2000). TGF-β may act as a direct mediator of suppression, and/or maintain Foxp3 expression and suppressive activity in Tregs (von Boehmer, 2005). A recent study has shown that Foxp3 natural Tregs predominantly produce immunosuppressive IL-35: ectopic expression of IL-35 confers regulatory activity on naive T cells, whereas recombinant IL-35 suppresses T cell proliferation (Collison, et al. 2007).

Foxp3 Tregs are abundant in tumors. Natural Tregs that promote self tolerance may act to impede immune surveillance against cancers in normal individuals and suppress potential responsiveness to autologous tumors in cancer patients. Targeting Tregs is a promising approach for cancer immunotherapy. Such approaches could include local depletion of Tregs in the tumor mass, attenuation of Treg function at the time of therapeutic vaccination with tumor antigen, and ex vivo expansion of tumor infiltrating lymphocytes after the depletion of Tregs (Sakaguchi, et al. 2008).

Role(s) of TGF-β

TGF-β is well known as an important cytokine that promotes the differentiation of anti-inflammatory Foxp3+ Treg cells. The finding that TGF-β is also required for the differentiation of pro-inflammatory Th17 cells was unexpected (Veldhoen, et al. 2006; Bettelli, et al. 2006). A model has been proposed wherein Th17 and Treg cell subsets may work together to either elicit or restrain tissue inflammation (Cua and Kastelein, 2006). The gut mucosa has high concentrations of TGF-β, which may induce a local population of Foxp3+ Treg cells to maintain homeostasis in an environment filled with commensal bacteria. The gut lamia propria also naturally contains a considerable number of IL-17 producing cells that may help to maintain the mucosal barrier (Mangan, et al. 2006). When there is a breach of the protective mucosa, dendritic cells secrete copious amounts of IL-6 and IL-23. This then, likely activates Th17 cells to release IL-17, TNF-α, and GM-CSF which recruit neutrophils to protect the host from invading pathogens (Cuan and Kastelein, 2006). In the final phase of infection, this model predicts that microbe-specific Th1 and Th2 cells would enter the inflamed mucosa. These cells secrete pro-inflammatory factors, which activate macrophage killing functions and promote anti-microbial antibody responses, respectively. They also repress the differentiation and function of Th17 cells. As the infection subsides, IL-6 and IL-23 production is reduced and the balance swings toward favoring the development of TGF-β-dependent Treg cells, essential for maintaining mucosal homeostasis.

Role of IL-2

IL-2 has multiple targets. It facilitates differentiation of CD4+ T cells to Th1 and Th2 cells and expands CD8+ memory T cells and natural killer cells. On the other hand, IL-2 promotes apoptosis in antigen activated T cells. IL-2 also maintains Foxp3+ natural Tregs, expands them at high doses and facilitates TGF-β-dependent differentiation of naive T cells to inflammatory Th17 cells (Laurence, et al. 2007). Thus, assuming that the main source of IL-2 is activated T cells, there is a negative feedback control of immune responses via IL-2; that is, IL-2 produced by activated non-regulatory T cells contributes to the maintenance, expansion and activation of natural Tregs, which in turn limits the expansion of non-regulatory T cells (Sakaguchi, et al. 2008). Disruption of this IL-2 mediated feedback loop at any step promotes the development of autoimmune/inflammatory disease. Further, manipulation of this feedback loop is instrumental in tuning the intensity of Treg mediated suppression, hence the strength of a variety of immune responses.

IL-2 is an essential cytokine for both generating and then limiting T cell-dependent immune responses. IL-2 has potent T cell growth factor activity (Smith, 1980). The strongest support for a crucial role for IL-2 in the generation of the immune response is that T cell proliferation and function in vitro can be substantially inhibited using monoclonal antibodies specific for either IL-2 or IL-2R (Malek and Bayer, 2004). The third key activity of IL-2 is its ability to sensitize activated T cells to undergo apoptosis by a tumor necrosis factor (TNF) dependent pathway (Lenardo, 1991).

Impaired production of Treg cells is sufficient to account for the lethal autoimmunity that is associated with IL-2 and IL-2R deficient mice. The main function of IL-2 seems to be the production of Treg cells and the maintenance of peripheral T cell tolerance (Malek and Bayer, 2004). In therapeutic settings, manipulation of Treg cell number or function might be accomplished by targeting IL-2 or IL-2R.

Relevant to Canadian Immigrant Population

As described below, an exemplary database comprised of records of bioassay and patient history information was obtained and used to illustrate various algorithms according to exemplary embodiments of the present invention. The individuals whose records were obtained were all immigrants to Canada. Accordingly, that database is sometimes referred to herein as the "CIP Database."

Treg cells appear to play a crucial role in controlling the threshold for T-cell activation via dendritic cell co-stimulation. When Treg cell activity is high, as is postulated to occur in response to infection in the developing world, dendritic cell expression of co-stimulatory molecule is low (like that on B cells) and production of potentially harmful but relatively low affinity self-reactive effector T cells is inhibited. Conversely, as occurs in the developed world where Treg activity is lower, T cells are more readily activated by dendritic cells expressing high levels of co-stimulatory molecules in addition to otherwise harmless antigens, like self determinants and allergens, resulting in the generation of Th1 and Th2 effector T cells, respectively. This way of thinking is attractive because it provides a rational explanation for the inverse relationship between the incidence of autoimmune and allergic diseases on the one hand and infectious diseases on the other hand in the developed world (FIG. 4—Basten and de St Groth, 2008).

Infections Relevant to the Canadian Immigrant Population Database

There is increasing awareness that helminth infections can ameliorate pro-inflammatory conditions. The outcome of shistosomal infection in mice depends on Th2 polarization (Belkaid and Rouse, 2005). The inhibitory effects of natural Treg cells on the Th1 response have been shown to promote Th2 polarization and to protect the host from lethal inflammatory pathology ((McKee and Pearce, 2004).

Natural Treg cells also seem to be important in the disease caused by hepatitis C virus. A chief complication of this chronic infection is massive liver damage that often requires organ transplant (Belkaid and Rouse, 2005). Liver biopsies obtained at the time of transplants show an inverse correlation between the number of natural Treg cells in the periphery and the histological inflammatory score. These Treg cells were actively secreting IL-10 and TGF-β (Cabrera, et al. 2004). People chronically infected with hepatitis C virus have more circulating natural Treg cells than do uninfected people, and depletion of Treg cells enhances antigen-specific CD8+ T cell responses in vitro (Sugimoto, et al. 2003).

*Schistosomiasis* and the Canadian Immigrant Population Database

Figure 5:
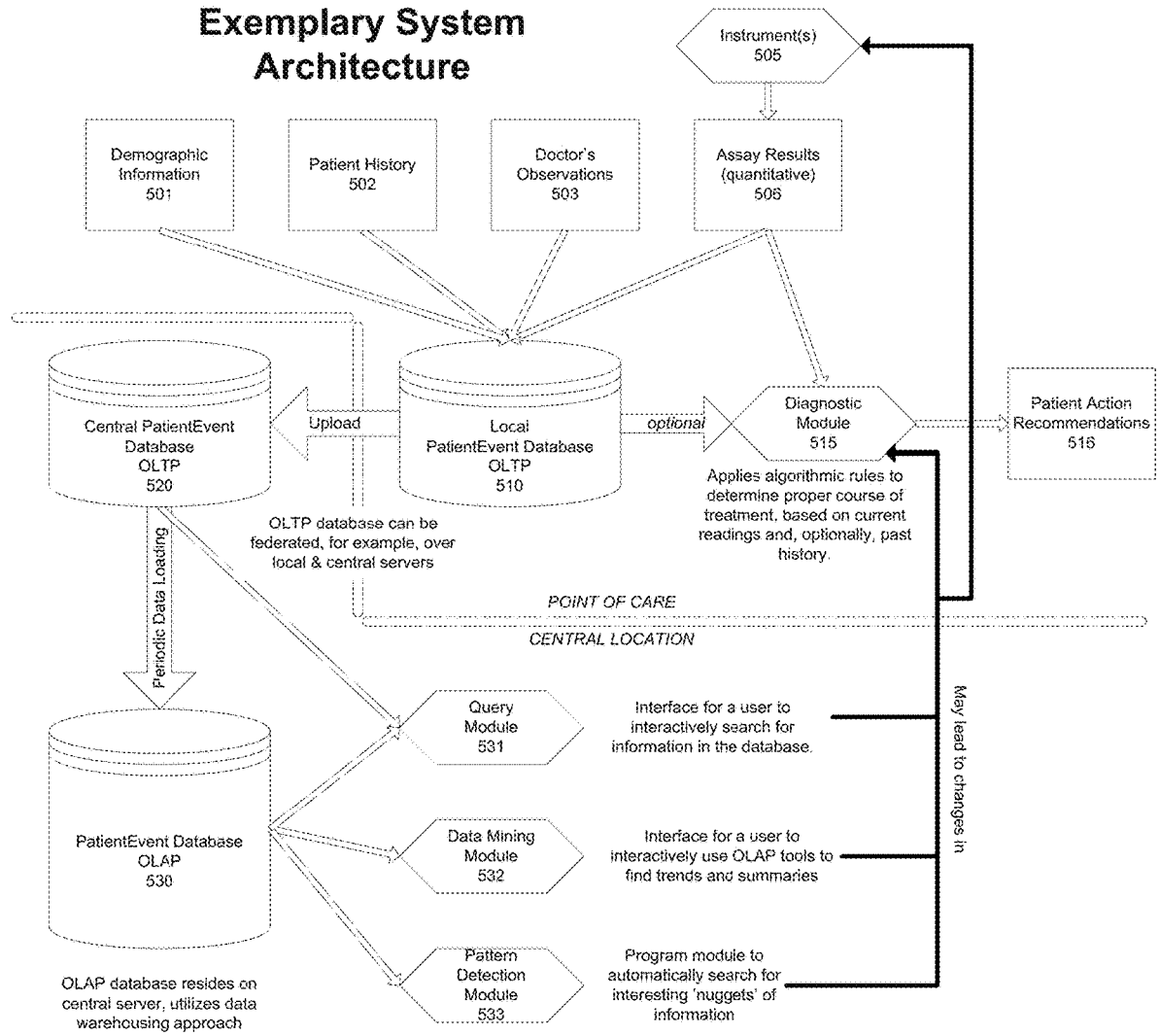
FIG. 5 depicts a detailed system diagram according to an exemplary embodiment of the present invention.

The estimated mortality owing to *Schistosoma mansoni* and *Schistosoma haematobium* in sub-Saharan Africa is 280,000 each year (van der Werf, et al. in press). *Schistosomiasis* causes a range of morbidities, the development of which seems to be influenced to a large extent by the nature of the induced immune response and its effects on granuloma formation and associated pathologies in target organs (Pearce and MacDonald, 2002). The development of the immune response in infection is shown in FIG. 5. In the course of the infection, the immune response progresses through at least three phases. In the first three to five weeks, during which the host is exposed to migrating immature parasites, the dominant response is Th1-like. As the parasites mature, mate, and begin to produce eggs at weeks 5-6, the response changes; the Th1 component decreases and this is associated with the emergence of a strong Th2 response. This response is induced primarily by egg antigens. During the chronic phase of infection, the Th2 response is modulated and granulomas that form around newly deposited eggs are smaller than at earlier times during infection. During acute illness, there is a measurable level of TNF-α in the plasma, and PBMCs produce large quantities of IL-1 and IL-6 (de Jesus, et al. 2002). At the end of the Th1 phase, the production of IL-10 is likely at least partly responsible for the down-regulation of the inflammatory functions (Montenegro, et al. 1999). In the chronic phase, prolonged Th2 responses contribute to the development of hepatic fibrosis and chronic morbidity (Cheever, et al. 2000). The main Th2 cytokine responsible for fibrosis is IL-13 (Pearce and MacDonald, 2002). Mediators associated with Th1 responses, such as IFN-γ, TNF-α, and IL-12 can prevent IL-13 mediated fibrosis (Hesse, et al. 2001).

Expression of Il-25 (IL-17E) is critical for immunity against helmith infections (Owyang, et al. 2006). Il-25 protein administration in an animal model results in elevated expression of Th2 cytokines, IL-4, IL-5, and IL-13 (Fort, et al. 2001). IL-25 also regulates the development of autoimmune inflammation mediated by IL-17-producing T cells (Kleinschek, et al. 2007).

Helminth infections in patients with multiple sclerosis (MS) created a B cell population producing high levels of IL-10, dampening harmful autoimmune responses. One group concluded that increased production of B cell-derived IL-10 and of neurotrophic factors are part of the parasite's regulation of host immunity and can alter the course of MS, potentially explaining environmental-related MS suppression observed in areas of low disease prevalence (Correale, et al. 2008).

The burden and chronicity of helminth infections is an important variable that may determine whether helminths act as a risk factor for, or confer protection against, allergic diseases (Yazdanbakhsh, et al. 2002). The over-riding view is that heavy helminth infections protect against allergy (Lynch, et al. 1997). Moreover, it has been proposed that alterations of commensal bacteria influences intestinal immune homeostasis by direct regulation of the IL-25/IL-23/IL-17 axis (Zaph, et al. 2008).

Additional Cytokine Assays—CIP Database
IL-1

IL-1 is a pleiotropic cytokine the primarily affects inflammatory responses, immune reactivity, and hematopoiesis (Dinarello, 2005; Apte and Voronov, 2002). Its potency stems from inducing cytokine, chemokine, pro-inflammatory molecule secretion, and adhesion molecule expression in diverse cells, thereby amplifying and sustaining the response. Membrane-associated IL-1α is immunostimulatory. Low level secreted IL-1β induces limited inflammatory responses followed by T cell activation. High levels of Il-1β are accompanied by broad inflammation with tissue damage (Dinarello, 2005; Apte and Voronov, 2002; Mariathasan and Monack. 2007).

Interleukin-1 includes a family of closely related genes; the two major agonistic proteins, IL-1α and IL-1β, are pleiotropic and affect mainly inflammation, immunity and hemopoiesis (Apte, et al. 2006). These IL-1 molecules bind to the same receptors and induce the same biological functions. As such, they have been considered identical in normal homeostasis and disease. However, the IL-1 molecules differ in their compartmentalization within the cell. IL-1β is active in its secreted form, while IL-1α is active in cell-associated forms—either as the intracellular precursor or as membrane-bound IL-1α. It has been proposed that membrane associated IL-1α expressed on malignant cells stimulates anti-tumor immunity, while secretable IL-1β, derived from the microenvironment or malignant cells, activates inflammation that promotes invasiveness and also induces tumor-mediated suppression (Apte, et al. 2006). Both sarcoma cell-derived IL-1α and IL-1β promote tumor growth. However, IL-1α exerts regulatory authority on the tumor cell-matrix cross-talk, and only IL-1β initiates systemic inflammation (Nazarenko, et al. 2008).

IL-1 is also an important mediator of inflammation and a major cause of tissue damage in rheumatoid arthritis (RA). In a mouse model of vaccination to prevent RA, it was found that immunization with IL-1β was strongly protective against the development of arthritis, while immunization with a similarly constructed IL-1α vaccine had no effect (Spohn, et al. 2008). Another group examining genetic polymorphisms in genes coding for IL-1α and IL-1β in RA found that in a majority of cases, genetic polymorphisms in these genes were not a major contributor to genetic susceptibility (Johnsen, et al. 2008), strengthening the argument for ImmunoScore based analyses which measures phenotypic expression of protein components.

IL-8

Interleukin-8 (IL-8 or CXCL8) is a chemokine known to possess tumorigenic and pro-angiogenic properties as well as leukocyte chemotactic activity (Brat, et al. 2005). Il-8 has been found to play an important role in autoimmune, inflammatory, and infectious diseases (Harada, et al 1994; Koch, et al. 1992; Smyth, et al. 1991). Because of its potent pro-inflammatory properties, IL-8 is tightly regulated, and its expression is low or undetectable in normal tissues. Expression of IL-8 can be induced by IL-1, TNF-α, IL-6, and IFN-γ (Baggiolini, et al. 1994; DeForge, et al. 1993). Potent inhibitors of IL-8 production include IL-4 and IL-10 (Mukaida, et al. 1994; Xie, 2001).

There is evidence that IL-8 is involved in tumor formation and malignant progression (Brat, et al. 2005). Mast cell mediators including fibroblast growth factor-2 and IL-8 are mitogenic to melanoma cells. Current evidence supports an accessory role for mast cells in the development and progression of cutaneous malignancies, but it is currently unclear whether the mast cells have promoting or inhibitory effects on tumors (Ch'ng, et al. 2006).

IL-8 is expressed in working muscles. The small transient release of IL-8 by working muscle is likely used for local angiogenesis, whereas systemic increase of plasma IL-8 is likely indicative of a tumor disease state (Akerstrom, et al. 2005). Other cytokines, including Il-6 and IL-15 are released locally by working muscle (Nielsen and Pedersen, 2007). Interestingly, anti-oxidant vitamins, C and E, have been shown to inhibit the release of pro-inflammatory cytokines from human skeletal muscle (Fischer, et al. 2004).

The use of biochemical markers in neonatal infection has remained an important area of research. Many infection markers are components of the inflammatory cascade and IL-6 and IL-8 have been demonstrated to have good diagnostic utility as early phase markers, while CRP and procalcitonin have superior diagnostic properties during the later phases (Lam and Ng, 2008).

IL-17

Interleukin-17, described extensively above, is a pro-inflammatory cytokine which induces differentiation and migration of neutrophils through induction of cytokines and chemokines including granulocyte-colony stimulating factor and CXCL8/IL-8. IL-17 producing T cells have a pivotal role in the pathogenesis of autoimmune diseases. IL-17 is also involved in protective immunity against extracellular bacterial or fungal pathogens such as *Klebsiella pneumoniae* and *Candida albicans* (Matsuzaki and Umemura, 2007).

IL-13

Interleukin-13 plays a major role in various inflammatory diseases including cancer, asthma, and allergy. It mediates a variety of different effects on various cell types including B cells, monocytes, natural killer cells, and fibroblasts (Joshi, et al. 2006).

Bronchial asthma is a complex disorder that is thought to arise as a result of aberrant T cell responses to non-infectious environmental antigens. In particular, asthma symptoms are closely associated with the presence of activated Th2 cytokine-producing cells making IL-4, IL-5, and IL-13 in the airway wall (Nakajima and Takatsu, 2007). Animal models of disease have provided compelling evidence that IL-13, independent of the other Th2 cytokines, is both necessary and sufficient to induce all features of allergic asthma (Wills-Karp, 2004). IL-13 has been described as a target for therapeutics, as it is involved in the pathogenesis of bronchial asthma and therapeutic agents have been described that block IL-13 signals (Izuhara, et al. 2006). Biological agents directed against the IL-13 pathway and new immunoregulatory agents that modulate functions of Treg and Th17 cells are likely to be successful against asthma (Adcock, et al. 2008).

Th2 cells, producing IL-4 and IL-13 have also been implicated in systemic sclerosis which is characterized by extensive fibrosis, microvascular stenosis, and autoantibody production (Sakkas, et al. 2006).

Receptors for IL-4 and IL-13 are overexpressed on malignant cells from brain tumors. These cells have been experimentally targeted by using a chimeric IL-13 constructed with a mutated form of *pseudomonas* exotoxin (Shimamura, et al. 2006). ImmunoScore technology would be useful monitoring clinical therapies and overall health of the immune system during the course of such treatments.

In tuberculosis, IL-4 and IL-13 can undermine effective Th1-mediated immunity and make an individual more susceptible to TB infection (Rook, 2007). It has been postulated that for a TB vaccine to be effective, not only must the Th1 axis be promoted, the Th2 axis must be suppressed. Understanding the balance between Il-12, IL-13, Il-23, and IL-27 is crucial to the development of immune intervention in tuberculosis (Cooper, et al. 2007).

IL-13 levels have been shown to be elevated in patients with gastrointestinal nematode and helminth infections of the liver (Grencis and Bancroft, 2004; Hirayam, 2004). In patients with *schistosomiasis*, both IL-13 and IFN-γ were shown to be elevated, suggesting a compartmentalization of the anti-schistosome immune response (Dessein, et al. 2004).

IL-15

Interleukin-15 is a pleiotropic cytokine that plays an important role in both the innate and adaptive immune system. IL-15 promotes the activation of neutrophils and macrophages, and is critical to DC function. In addition, IL-15 is essential to the development, homeostasis, function, and survival of natural killer and CD8+ T cells (Diab, et al. 2005). Abnormalities of IL-15 expression have been described in patients with rheumatoid arthritis or inflammatory bowel disease (Waldmann, 2002). In contrast to the role of IL-2 which is in the elimination of self-reactive T cells to prevent autoimmunity, IL-15 is dedicated to the prolonged maintenance of memory T cell responses to invading pathogens (Waldmann, 2006). IL-15 has been proposed as having anti-cancer properties, in addition to triggering innate immunity (Shanmugham, et al. 2006).

TNFβ (Lymphotoxin β)

Lymphotoxin β is implicated in lymphoid follicle development, production of pro-inflammatory cytokines, and can enhance the production of fibroblasts and synoviocytes. The expression of lymphotoxin β is significantly increased in RA patients (O'Rourke, et al. 2008). It was speculated that lymphotoxin β may play a role in RA disease pathogenesis by contributing to a more intense inflammatory reaction in the synovium. Important to the concept of immunosenescence, in a mouse model, over-expression of lymphotoxin was shown to induce fulminant thymic involution (Heikenwalder, et al. 2008). Host responses to cytomegalovirus (CMV) infections include early initial production of interferons. New data indicate that, preceding the induction of type I interferons, an earlier critical type I interferon elicited in primary infected stromal cells via the lymphotoxin β receptor system and mediated by B cells is necessary to kick-start an efficient antiviral response (Fodil-Cornu and Vidal, 2008).

In addition, signaling through the lymphotoxin pathway is a crucial element in the maintenance of the organized microenvironment. Inhibitors of the lymphotoxin pathway have been shown to reduce disease in a wide range of autoimmune models (Gommerman and Browning, 2003).

ImmunoScore Total Immunoglobulin Assays

IgG (g/L)
 IgG1 (normal range=4.9-11.4 g/L)
 IgG2 (normal range=1.5-6.4 g/L)
 IgG3 (normal range=0.2-1.10 g/L)
 IgG4 (normal range=0.08-1.4 g/L)
IgM (g/L)
IgA (g/L)
IgE (g/L)

ImmunoScore Cytokine Assay Panel

Th1
 IL-12 (induction)
 IL-27 (induction)
 IFN-γ (produced by Th1)
 TNF-α (produced by Th1)
 IL-2 (produced by Th1 late in cycle?)
 IL-10 (Th1 suppressed by)
 TGF-β (Th1 suppressed by)

Th2
 IL-4 (induction and production by Th2)
 IL-5 (produced by Th2)
 IL-13 (produced by Th2)
 IL-10 (produced by Th2 to dampen Th1 response?)
 IL-10 (suppressed by)
 TGF-β (suppressed by)

Th17
 TGF-β (induced by—with IL-6)
 IL-6 (induced by—with TGF-β)
 IL-1β (induced by)
 IL-17A (produced by Th17)
 IL-17F (produced by Th17)
 IL-21 (produced by Th17)
 IL-22 (produced by Th17—seen as both inflammatory and anti-inflammatory)
 IL-23 (Th17 response maintained by presence of IL-23)
 IL-1 (Th17 response maintained by IL-1 which is produced by Th1 cells)
 IL-4 (suppressed by IL-4 which is produced by Th2 cells)
 IFN-γ (suppressed by IFN-γ which is produced by Th1 cells)

Figure 5A:
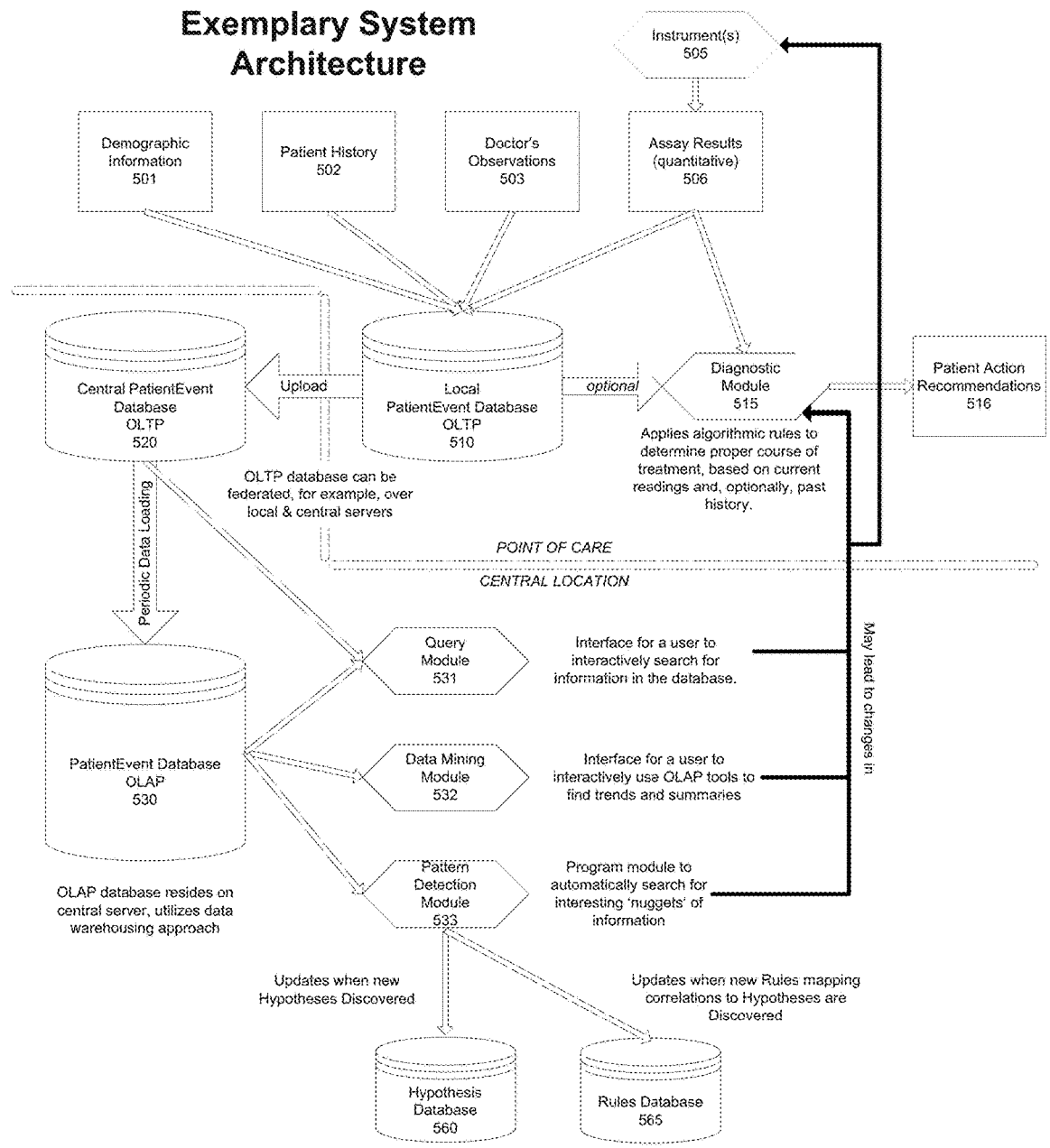
FIG. 5A depicts a detailed system diagram according to an alternate exemplary embodiment of the present invention.
Figure 5B:
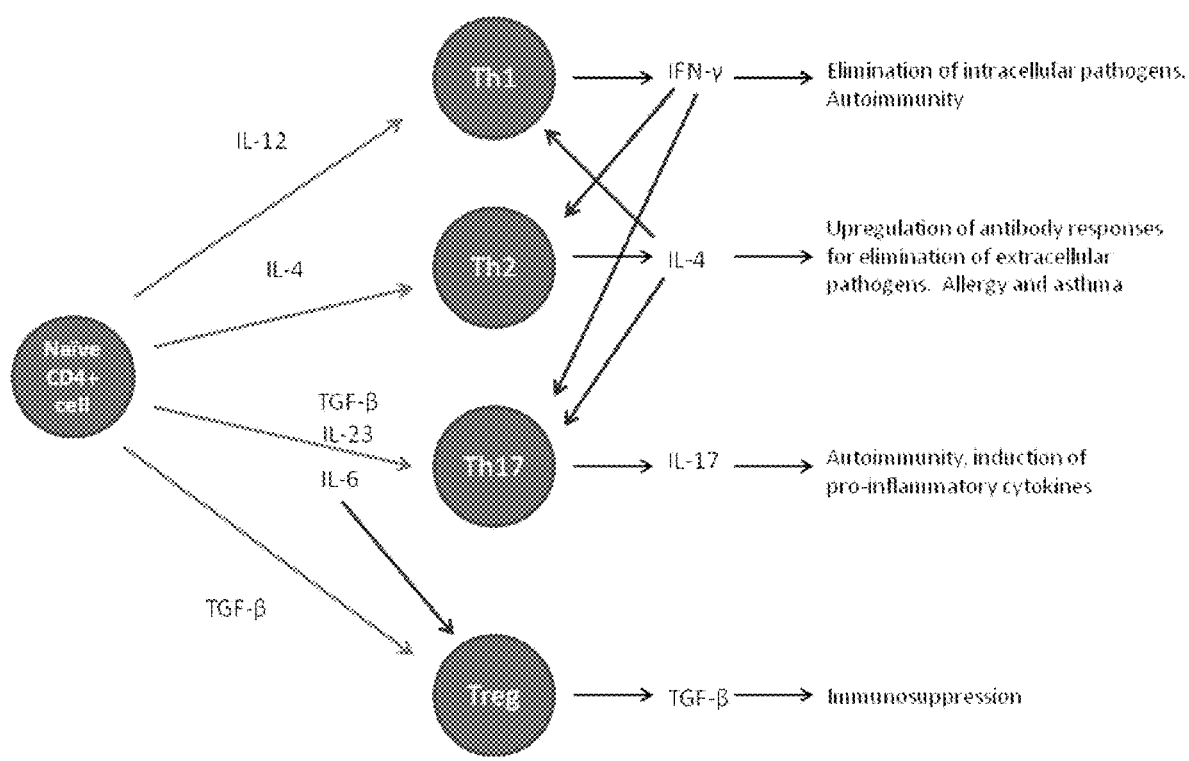
FIG. 5B depicts T helper cell commitment towards specific lineages. Depending on local cytokine milieu, naïve CD4+ cells can differentiate to one of three types of CD4+ T effector cells (Th1, Th2, or Th17) or CD4+ immunosuppressive Treg cells. Green arrows indicate positive cytokine signals for differentiation, while red arrows indicate suppressive effects of cytokines on particular cell types. This simplified diagram captures only the cytokines of major influence as the state of the art currently stands.

IFN-α (suppressed by)
IL-2 (suppressed by)
IL-27 (suppressed by)
Treg
    TGF-β (induced by—in the absence of IL-6)
    IL-10 (produced by—suppress Th1 and Th2 responses)
    TGF-β (produced by—suppress Th1 and Th2, expand Th17 together with IL-6)
    IL-6 (suppressed by)
    IL-21 (suppressed by)
    IL-31 (suppressed by)
B Cell Differentiation and Regulation
    IL-2
    IL-4
    IL-7 (important in aging immune system)
    IL-9
    IL-10
    IL-15
    IL-21
Canadian Immigrant Population Database Cytokine Assays
    IL-1α—inflammatory; likely stimulates Th17 response locally
    IL-1β—inflammatory; likely stimulates Th17 response more systemically
    IL-2—produced by Th1—induce Treg
    IL-4—produced by Th2
    IL-5—produced by Th2
    IL-6—pro-inflammatory—together with TGF-β induce Th17
    IL-8—pro-inflammatory
    IL-10—anti-inflammatory; produced by Treg
    IL-12—induce Th1
    IL-13—produced by Th2
    IL-15—trigger of innate immunity; anti-tumor role
    IL-17—pro-inflammatory; produced by Th17
    IL-23'maintenance of Th17
    IFN-γ—produced by Th1
    TNF-α—pro-inflammatory; produced by Th17 and Th1
    TNF-β—pro-inflammatory; increased levels signal autoimmune disease flares FIG. 5B depicts T helper cell commitment towards specific lineages. Depending on local cytokine milieu, naive CD4+ cells can differentiate to one of three types of CD4+ T effector cells (Th1, Th2, or Th17) or CD4+ immunosuppressive Treg cells. Green arrows indicate positive cytokine signals for differentiation, while red arrows indicate suppressive effects of cytokines on particular cell types. This simplified diagram captures only the cytokines of major influence as the state of the art currently stands.

Figure 5C:
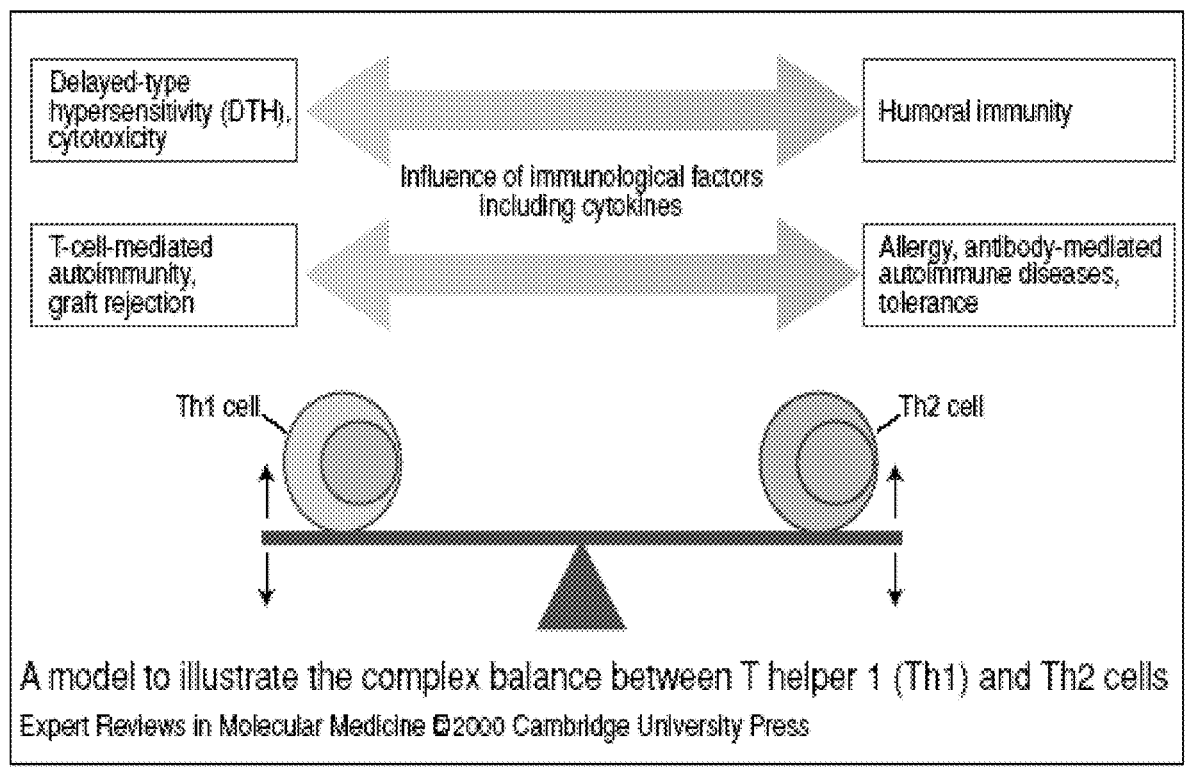
FIG. 5C depicts an exemplary Th1/Th2 Paradigm model as it existed circa 2000. Th1 cells known for important role in cell mediated immunity, whilst Th2 cells acknowledged to be important for humoral immunity. At this time, it was thought that Th1 over-response was solely responsible for autoimmune disease. The story has proven to be more complicated with the current understanding of the role of Th17 cells.

FIG. 5C depicts Th1/Th2 Paradigm. Model of paradigm as it existed circa 2000. Th1 cells known for important role in cell mediated immunity, whilst Th2 cells acknowledged to be important for humoral immunity. At this time, it was thought that Th1 over-response was solely responsible for autoimmune disease. The story has proven to be more complicated with the current understanding of the role of Th17 cells.

Figure 5D:
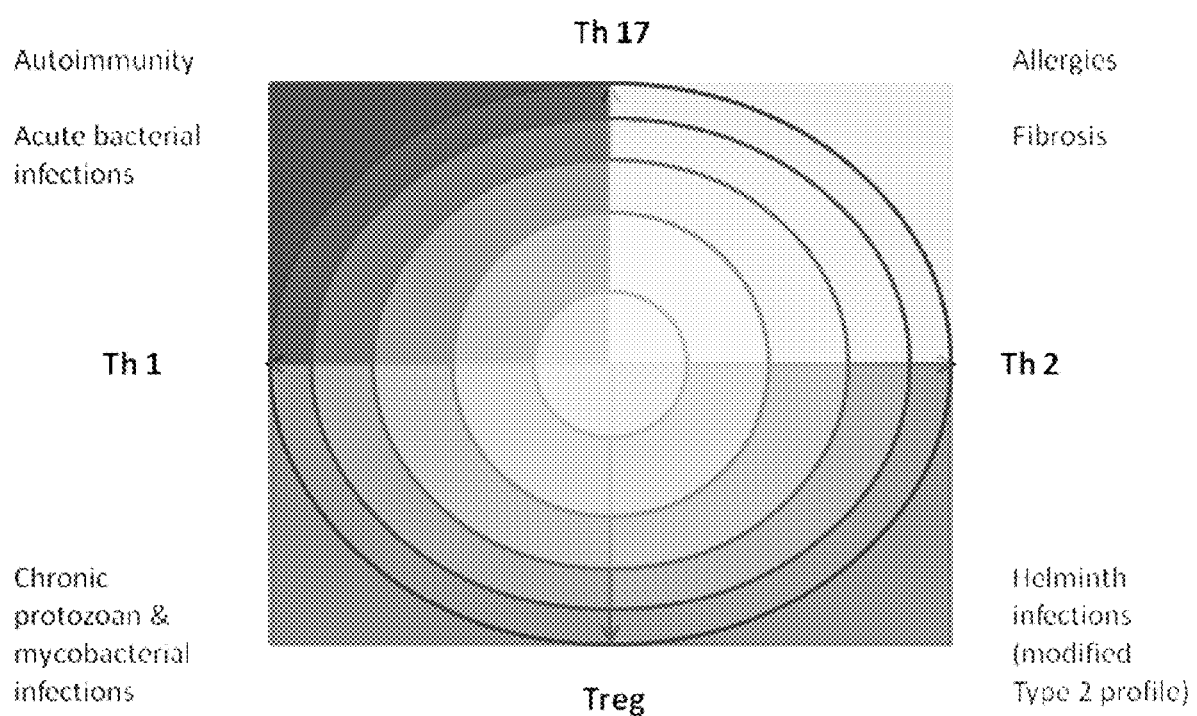
FIG. 5D depicts an exemplary evolving Th1/Th2/Th17/Treg paradigm, which now includes arms that recognize the importance of Th17 and Treg cells. Rather than balance on one fulcrum between two opposite sides, the model now encompasses more complicated interactions whilst tilting on at least two axes. Over-expression of any one of the four arms of the T cell immune response without response of the opposite functions can lead to undesirable complications and over-reaction of the immune system. Th17 responses coupled with Th1 responses can lead to autoimmune reactions, while Th17 coupled to Th2 responses can lead to allergic reactions. Over-expression of regulatory responses with Th1 reactions can lead to chronic microbial or viral infection, while coupled with Th2 responses can lead to chronic parasitic infections.

FIG. 5D depicts an evolving Th1/Th2/Th17/Treg paradigm. The Th1/Th2 paradigm now includes arms that recognize the importance of Th17 and Treg cells. Rather than balance on one fulcrum between two opposite sides, the model now encompasses more complicated interactions whilst tilting on at least two axes. Over-expression of any one of the four arms of the T cell immune response without response of the opposite functions can lead to undesirable complications and over-reaction of the immune system. Th17 responses coupled with Th1 responses can lead to autoimmune reactions, while Th17 coupled to Th2 responses can lead to allergic reactions. Over-expression of regulatory responses with Th1 reactions can lead to chronic microbial or viral infection, while coupled with Th2 responses can lead to chronic parasitic infections.

Figure 5E:
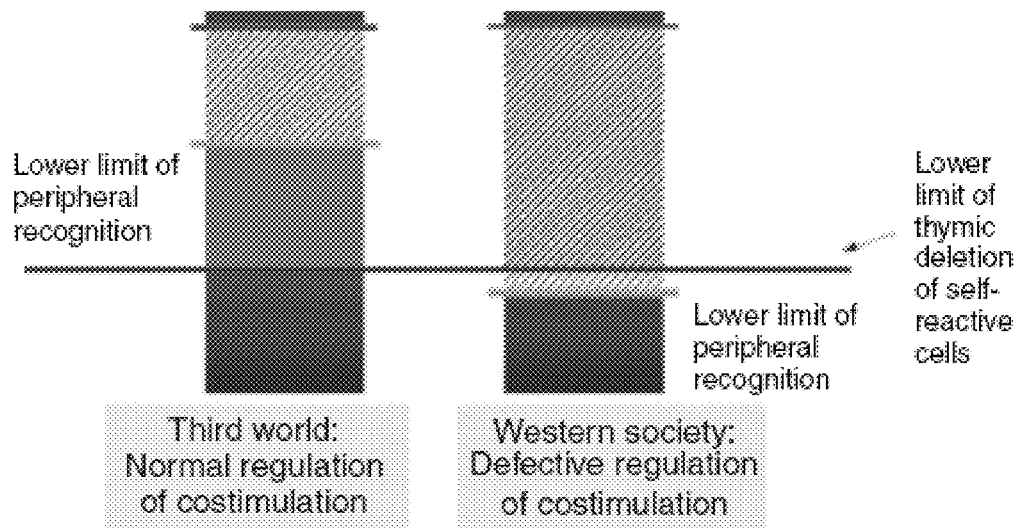
FIG. 5E depicts an exemplary model illustrating how Treg-mediated control of CD80/CD86 expression may control the threshold of antigen recognition, crucial for preventing the activation of low avidity self-reactive T cells that are below the cut-off imposed during thymic selection. Treg cells stimulated during high affinity responses to microbes would increase the threshold (indicated by green line) by reducing dendritic cell expression of co-stimulatory molecules. Conversely, in the absence of strong Treg cell activity, the threshold of self antigen recognition may drop below the thymic cut-off (indicated by black line), allowing activation of low avidity anti-self T cells (Basten, et al. 2008).

FIG. 5E depicts an exemplary model illustrating how Treg-mediated control of CD80/CD86 expression may control the threshold of antigen recognition, crucial for preventing the activation of low avidity self-reactive T cells that are below the cut-off imposed during thymic selection. Treg cells stimulated during high affinity responses to microbes would increase the threshold (indicated by green line) by reducing dendritic cell expression of co-stimulatory molecules. Conversely, in the absence of strong Treg cell activity, the threshold of self antigen recognition may drop below the thymic cut-off (indicated by black line), allowing activation of low avidity anti-self T cells (Basten, et al. 2008).

FIG. 5F depicts the development of the immune response in schitosome infection (Pearce and MacDonald, 2002).

4. Quantitation

As part of the ImmunoScore technology, immune responses can be quantitated. For example, Th1, Th2, Th17, and Treg responses can be quantitated. These quantitative values can be used in at one point in time, or can be trended over time to help determine a person's immune status. These values and/or their time responses can also be used with other factors such as antibody concentrations to help determine a person's immune status.

Immune responses such as Th1, Th2, Th17, Treg, and the like can be quantitated using a collection of blood measurements; for example, a collection of cytokine concentrations. Some of cytokines suppress an immune response; suppression can be, for example, quantitatively characterized by negative coefficients in a function relating concentrations to response. Because cytokine concentrations can vary by many orders of magnitude, immune response quantitation may be related to the logarithm of the concentrations rather than the concentration. Because basal concentrations of cytokines are not always the same, the ratio of the cytokine concentration to its basal concentration (or the logarithm of the ratio) can be used in the quantitation.

As more particular examples, the Th1 quantitation can be a function of cytokine concentrations; the Th1 quantitation can be a function of the concentrations of IFN-γ, TNF-α, IL-2, IL-12, IL-10, TGF-β, and IL-23; the Th1 quantitation can be a polynomial function of the concentrations (or the logarithm of the concentrations) of IFN-γ, TNF-α, IL-2, IL-12, IL-10, TGF-β, and IL-23; the Th1 quantitation can be a linear function of the concentrations (or the logarithm of the concentrations) of IFN-γ, TNF-α, IL-2, IL-12, IL-10, TGF-β, and IL-23. As a second set of examples, the Th2 quantitation can be a function of cytokine concentrations; the Th2 quantitation can be a function of the concentrations of IL-4, IL5, IL-13, IL-10, and TGF-β; the Th2 quantitation can be a polynomial function of the concentrations (or the logarithm of the concentrations) of IL-4, IL5, IL-13, IL-10, and TGF-β; the Th2 quantitation can be a linear function of the concentrations (or the logarithm of the concentrations) of IL-4, IL5, IL-13, IL-10, and TGF-β. As a third set of examples, the Th17 quantitation can be a function of cytokine concentrations; the Th17 quantitation can be a function of the concentrations of TGF-β, IL-2, IL-4, IL-6, IL-17, IL-21, IL-22, IL-23, IFN-α, and IFN-γ; the Th17 quantitation can be a polynomial function of the concentrations (or the logarithm of the concentrations) of TGF-β, IL-2, IL-4, IL-6, IL-17, IL-21, IL-22, IL-23, IFN-α, and IFN-γ; the Th17 quantitation can be a linear function of the concentrations (or the logarithm of the concentrations) of TGF-β, IL-2, IL-4, IL-6, IL-17, IL-21, IL-22, IL-23, IFN-α, and IFN-γ.

As a fourth set of examples, Treg quantitation can be a function of cytokine concentrations; the Treg quantitation can be a function of the concentrations of IL-2, IL-6, IL-10, IL-31, IL-35, and TGF-β; the Treg quantitation can be a polynomial function of the concentrations (or the logarithm of the concentrations) of IL-2, IL-6, IL-10, IL-31, IL-35, and TGF-β; the Treg quantitation can be a linear function of the concentrations (or the logarithm of the concentrations) of IL-2, IL-6, IL-10, IL-31, IL-35, and TGF-β.

Combining the quantitative measurements for Th1 and Th2 responses to form a Th1|Th2 response is another aspect of ImmunoScore technology. In some embodiments, Th1|Th2 is simply the difference between the Th2 quantitation and the Th1 quantitation. For example, a positive Th1|Th2 value can be indicative of a Th2 response, while a negative Th1|Th2 value can be indicative of a Th1 response.

Combining the quantitative measurements for Th17 and Treg responses to form a Th17|Treg response is another aspect of ImmunoScore technology. In some embodiments, Th17|Treg is simply the difference between the Th17 quantitation and the Treg quantitation. For example, a positive Th17|Treg value can be indicative of a Th17 response, while a negative Th17|Treg value can be indicative of a Treg response.

Further distillation of immune response information can be done, for example, by combining the Th1|Th2 response and the Th17|Treg response. By considering Th1|Th2 and Th17|Treg as two dimensions of an immune response, a magnitude and direction can be computed. A small magnitude can be interpreted as the immune system being in balance. For large magnitudes, the direction can indicate the type of immune response. For example, if 0° represents a Th2 response; 90° a Th17 response; 180°, a Th1 response; and 270°, a Treg response; then a direction of 45° can be indicative of allergies and/or fibrosis. Continuing this example, 135° can be indicative of autoimmunity and/or an acute bacterial infection; 225° can be indicative of chronic protozoan & mycobacterial infections; 315° can be indicative of Helminth infections. Trend tracking magnitude and direction over time can be used to differentiate between acute and chronic immune issues, such as the 135° direction that may represent autoimmunity or an acute bacterial infection.

As additional knowledge about the immune system is learned, additional dimensions can be added to the two dimensional Th1|Th2, Th17|Treg example above. Small magnitudes can still represent a balanced immune system, and for large magnitudes the direction can indicate the type of imbalance.

Example 1

Let $\overline{Th1}$ be the quantitative measurement of the Th1 response.

$$\overline{Th1} = \alpha_0 + \sum_i \alpha_i \ln c_i$$

In the above equation, $c_i$ represents the concentration of the $i^{th}$ cytokine, $\alpha_i$ is the coefficient relating the magnitude and sign of the amount the $i^{th}$ cytokine affects the Th1 response, and $\alpha_0$ is a weighted sum of the logarithm of the basal concentrations. Cytokines that do not affect the Th1 response can either be excluded from the summation or use a coefficient of 0. To simplify notation when combining responses, the coefficient of 0 method will be used. This equation is a linear function of logarithm of the ratio of the cytokine concentration to the basal concentration. To change the equation to a linear function of logarithm of the cytokine concentration, set $\alpha_0=0$.

Similar equations can be generated for the Th2 response, Th17 response, and the Treg response:

$$\overline{Th2} = \beta_0 + \sum_i \beta_i \ln c_i$$

$$\overline{Th17} = \gamma_0 + \sum_i \gamma_i \ln c_i$$

$$\overline{Treg} = \delta_0 + \sum_i \delta_i \ln c_i$$

The Th1|Th2 response can then be computed as $\overline{Th2}-\overline{Th1}=\beta_0-\alpha_0+\Sigma_i(\beta_i-\alpha_i)\ln c_i$. The Th17|Treg response can be computed as $\overline{Th17}-\overline{Treg}=\gamma_0-\delta_0+\Sigma_i(\gamma_i-\delta_i)\ln c_i$. The magnitude of the combined response can be computed as $$\sqrt{\left(\beta_0 - \alpha_0 + \sum_i (\beta_i - \alpha_i)\ln c_i\right)^2 + \left(\gamma_0 - \delta_0 + \sum_i (\gamma_i - \delta_i)\ln c_i\right)^2}$$

The direction of the combined response can be computed as $$\tan^{-1}\frac{\gamma_0 - \delta_0 + \sum_i (\gamma_i - \delta_i)\ln c_i}{\beta_0 - \alpha_0 + \sum_i (\beta_i - \alpha_i)\ln c_i}$$

When tracking the direction over time, the solution to the arctangent that minimizes the magnitude of the direction change can be selected: for example, if the first direction is 1° and the direction changes by 2° in the clockwise direction, −1° should be chosen rather than 359°.

B. Immunoscore Exemplary Superpanels

1. ImmunoScore Diagnostic Panel and Preventive Therapy for Autoimmune Disease

In exemplary embodiments of the present invention, some or all of the following assays can be included in an ImmunoScore Autoimmune Screening/Diagnostic Panel:

1. Antibody Assays
    anti-myelin oligodendrocyte glycoprotein (MOG) antibody
    anti-measles virus antibodies
    anti-21-hydroxylase antibody
    anti-adrenal cortex antibody
    anti-*Klebsiella* antibodies
    anti-cardiolipin antibody
    anti-lupus anticoagulant antibody
    anti-beta-2-glycoprotein antibody
    anti-hematopoietic precursor cell antibodies
    anti-soluble liver antigen antibody
    anti-RO/SSA antibody
    anti-endomysial antibody (AEA)
    anti-tissue transglutaminase (anti-tTG)

anti-*Saccharomyces cerevisiae* antibody (ASCA)
anti-neutrophil antibody (pANCA)
anti-porin protein C of *E. coli* antibody (anti-OmpC)
anti-glutamic acid decarboxylase antibody (GADA)
  particularly anti-65 kDa isoform
anti-protein tyrosine phosphatase-like molecule antibody (IA-2A)
anti-glomerular basement membrane (GBM) antibody
anti-neutrophil cytoplasmic antigens (ANCA)
anti-GD1a/GD1b complex antibody
anti-LM1 antibody
anti-GM1 antibody
anti-thyroglobulin antibody
anti-nuclear antibodies (ANA)
  lupus anticoagulant (LA) antibody
  anti-phospholipid (aPL)
  anti-SS/A antibody
  anti-SS/B antibody
  anti-Sm antibody
  anti-RNP antibody
  anti-Jo1 antibody
  anti-Scl-70 antibody
  anti-dsDNA antibody
  anti-Centromere B antibody
  anti-Histone antibody
anti-alphaIIbbeta 3 IgM
anti-acetylcholine receptor (anti-AChR) antibody
anti-muscle-specific tyrosine kinase (MuSK) antibody
anti-neuroleukin antibody
anti-gliadin antibody
anti-CV 2 antibody
anti-GQ1b IgG
anti-GQ1b IgM
anti-thyroid peroxidase antibody
keratinocyte cell-surface antibodies
  anti-BP 180 (bullous pemphigoid antigen 2)
  anti-BP 230 (bullous pemphigoid antigen 1)
anti-intrinsic factor antibody
anti-parietal cell antibodies
anti-mitochondrial antibodies
  in particular, anti-E2 component of pyruvate dehydrogenase complex (PDC) antibody
anti-cyclic citrullinated peptide (CCP) antibody
anti-heat shock protein (HSP) 65 antibody
anti-HSP 90 antibody
anti-DnaJ antibody
anti-BiP antibody
anti-heterogeneous nuclear RNP A2/B1 antibody
anti-heterogeneous nuclear RNP D antibody
anti-annexin V antibody
anti-calpastatin antibody
anti-type II collagen antibody
anti-glucose-6-phosphate (GPI) antibody
anti-elongation factor
anti-human cartilage gp39 antibody
anti-*Chlamydia* antibodies
anti-La/SSB antibody
anti-fodrine antibody
anti-salivary duct antibodies
anti-Red Blood Cell (RBC) IgM
anti-neutrophil cytoplasmic antibodies
anti-thyroid microsomal antibody (ATMA)
anti-smooth muscle antibody (SMA)
anti-mitochondrial antibody (AMA)
anti-extractable nuclear antigens (ENA) antibody
anti-actin antibody (AAA)
anti-hair follicle antibodies
anti-anagen matrix antibody
anti-cuticle antibody
anti-cortex keratinocytes antibody
anti-melanocyte nuclear antigen
anti-human dermal microvascular endothelial cells (HD-MEC) antibodies
  anti-81 kDa HDMEC antigen, in particular
anti-*Trypanosoma cruzi* antibodies
anti-oleic acid IgM
anti-palmitic acid IgM
anti-myristic acid IgM
anti-azelaic acid IgM
anti-malondialdehyde IgM
anti-aceylcholine IgM
anti-S-farnesyl-L-cysteine IgM
anti-ganglionic nicotinic acetylcholine receptor antibody
anti-follicle-stimulating hormone (FSH) IgA
anti-V14D IgA
anti-V14D IgG
anti-cytoskeleton-associated protein 4/p63 (CKA4/p63)-specific antibody
anti-cytokeratin 10 antibody
anti-Voltage-Gated Potassium Channels (VGKCs) antibodies
anti-*Chlamydia pneumoniae* antibodies
anti-human cytomegalovirus (CMV) antibodies
anti-*Toxoplasma gondii* antibodies
anti-CENP-A antibody
anti-CENP-B antibody 2. Cytokine Assays
  Interleukin-1α (IL-1α)
  IL-1β
  IL-2
  IL-4
  IL-5
  IL-6
  IL-7
  IL-8
  IL-10
  IL-12
  IL-13
  IL-15
  IL-18
  Interferon α (IFN-α)
  IFN-γ
  TNF-α
  G-CSF
  MCP-1
  MIP-1α
  MIP-1β
  MIP-3α
  MIP-3β
  EGF
  VEGF
  TNFRII
  EGFR 3. Toll-Like Receptor (TLR) Genetic Variants
  TLR 2
  TLR 3
  TLR 4
  TLR 7
  TLR 8
  TLR 9

4. HLA Haplotype Screening
  HLA A24
  HLA B8
  HLA B18

HLA B27
HLA B51
HLA B60
HLA B62
HLA DR2
HLA DR3
HLA DR4
HLA DR5
HLA DR7

5. Protein Isoforms/Genetic Polymorphisms/Serum Protein Levels

Apolipoprotein E isoforms
    apo E2
    apo E3
    apo E4
  Serum Apolipoprotein A-IV level
  Mannose-binding lectin (MBL) polymorphism
  Serum Haptoglobin level
  Serum Transthyretin level
  Serum Fibrinogen level
  Serum Vitamin B12 level
  Serum Folic acid level 2. ImmunoScore Diagnostic Panel: Aging, Longevity, Cancer and Human Cytomegalovirus Old age is accompanied by an increased incidence of infection and poorer responses to vaccination. A progressive decline in the integrity of the immune system is one of the physiologic changes during mammalian aging. Perhaps the most profound clinical impact of age on the immune system concerns the response of the elderly to vaccination (Pawelec, 2005). An immune risk phenotype (IRP) was described wherein individuals possessed high CD8 and low CD4 numbers and poor proliferative response (Wikby, et al. 2005). Characteristics of the IRP are listed in Table I (Vasto, et al. 2007). The IRP consists of a cluster of these parameters, not each parameter individually. Which are the most important and which additional factors are involved remains to be determined.

Lifelong and chronic antigenic load may represent the major driving force for immunosenescence, which impacts on human lifespan by reducing the number of virgin antigen-non experienced T cells, and results in their replacement by expanded clones of antigen-experienced effector and memory T cells which display a late differentiation phenotype. Gradually, the T cell population shifts to a lower ratio of naïve cells to memory cells, the thymus releases fewer naïve T cells with age and those T cells remaining, especially the $CD8^+$ subset, also show increased oligoclonality with age. Presumably, the repertoire of cells available to respond to antigenic challenge from previously encountered pathogens shrinks. In addition, older organisms often are overrun by memory cells that carry a single type of T cell receptor, i.e. the clonal expansion referred to above. Therefore, the memory cells from old individuals might recognize a limited set of antigens despite being plentiful in number, and in addition, are likely to show various degrees of dysfunctionality. Many of the clonal expansions filling the individual's immune system seem to result from previous infections by persistent viruses, especially CMV (Ouyang, et al. 2003b), but also, to a lesser extent EBV (Ouyang, et al. 2003a) and possibly other herpes viruses (Vasto, et al. 2007). A high number of $CD8^+$ cells are found to be specific for a single CMV epitope (Pawelec, et al. 2005; Pawelec, et al. 2004). In humans, the accumulation of CMV-specific T cells has been observed to reduce T cell immunity toward EBV infection (Khan, et al. 2004) and influenza vaccination (Trzonkowski, et al. 2003). Functional analyses performed with T cells from nonagenarians demonstrated that they were characterized by decreased functional capacity when compared with similar cells isolated from middle aged individuals (Hadrup, et al. 2006). This suggests that increased numbers of CMV-specific T cells could be the result of a compensatory mechanism enabling control of CMV despite lower functional capacity (Hadrup, et al. 2006). The biology of CMV infection in humans can be conceptualized as an evolutionary "negotiated" balance between viral mechanisms of pathogenesis, persistence, and immune evasion and the host cellular immune response (Sylwester, et al. 2005).

One of the immunodominant viral antigens recognized by CMV-specific $CD8^+$ T cells is derived from the 65-kDa phosphoprotein (pp65). Samples from octogenarian and nonagenarian populations revealed that a large number of $CD8^+CD28^-$ cells were specific for the pp65 antigen. These findings imply a co-dominant role of CMV as a cause for a compromised immunity in old age (Vasto, et al. 2007). A second immunodominant antigen is the IE-1 antigen. Epitope specificity and immunodominance of CD8 T cells against IE-1 and pp65 are comparable in acute infection and long-term memory often with marked focusing of responses that are probably established very early on. However, the kinetics of CD8 T cell responses for these antigens expressed at opposite ends of the replicative cycle of the virus reflect the different modes of antigen presentation, which probably depend on levels of viral activity occurring over the lifetime of the host (Khan, et al. 2007). Other studies have suggested an extraordinary complexity of CMV-specific T cell responses to chronic infection (Sylwester, et al. 2005). This complexity complicates efforts to understand the basis of the CMV immune balance and, in clinical practice, to determine the thresholds that define the boundary between controlled vs. progressive CMV infection in immunocompromised subjects and between normal and excessive CMV-specific immunity in the elderly (Sylwester, et al. 2005).

There are a suggested sequence of stages for IRP individuals that begin with the acquisition of CMV infection in earlier life, followed by generation of $CD8^+CD28^-$ cells to control persistent CMV infection, and eventually the development of an IRP. Recently, a group of rare individuals was discovered who moved out of the IRP category by a process of immune suppression, including increases in IL-6 and IL-10 and decreases in the number of $CD3^+CD8^+CD28^-$ cells (Wikby, et al. 2006).

There are two theories regarding the evolution of senescence—mutation accumulation and antagonistic pleiotropy. The mutation accumulation theory of senescence postulates that there are numerous loci subject to mutation to deleterious alleles, whose effects on survival or other components of fitness are restricted to narrow bands of ages (Rose, 1991). The equilibrium frequencies of such deleterious alleles will be higher the later in life in which they act (Charlesworth, 1994). The alternative path involves antagonistic pleiotropy, according to which genes that increase early performance are likely to become established in a population even if they have adverse effects on later performance (Williams, 1957; Rose, 1991). Antagonistic pleiotropy was originally defined as meaning opposite effects of the same allele at different ages (Williams, 1957). Antagonistic pleiotropy in evolutionary theory usually refers to opposite effects of a genotype on fecundity and survival. The existence of trade-offs between these two components of Darwinian fitness was proposed to explain the evolution of senescence and the maintenance, via the creation of the heterozygous advantage, of polymorphism at loci involved in the determination of both traits (Kirkwood and Rose, 1991). In a later model, antagonistic pleiotropy involved, instead, relative survival values of a genotype at different ages (Toupance, et al. 1998). The two theories are not mutually exclusive, and modeling exercises have examined the validity of each (Charlesworth and Hughes, 1996).

An example of antagonistic pleiotropy would be the high expression of testosterone in a male gorilla, which could lead to increased aggression and strength that would allow the male to become dominant and mate more frequently, but may eventually lead to a shortened lifespan due to increased atherosclerosis. Recent studies at the molecular level have suggested that cellular senescence may be antagonistically pleiotropic because it prevents tumorigenesis, but also contributes to organismic aging (Troen, 2003).

In one study, it was suggested that cellular senescence was antagonistically pleiotropic, protecting from cancer early in life, but promoting carcinogenesis in aged organisms (Krtolica, et al. 2001). Another study (Hughes, et al. 2002) found the AP (antagonistic pleiotropy) model is consistent with the existence of a few genes with individually large effects on late-life fitness, whereas the MA (mutation accumulation) process should lead to the maintenance of may deleterious alleles at intermediate frequencies within populations and these alleles can have individually small effects on late-life performance and health. Current methods of identifying aging genes (such as mutation studies and quantitative trait locus-mapping experiments) are most effective in finding alleles of large effect, and even well designed studies will probably miss genes with small effects. Novel approaches are needed to find such genes.

Cancer rates also increase sharply with age in both sexes, and the majority of cases of cancer occur in patients over the age of 65. Tumor progression is a complex process that depends on interactions between tumor cells and host cells. The inflammatory aspect of the host response is of particular interest because it includes the release of pro-inflammatory cytokines, some of which may promote tumor growth and hence influence survival. Some kinds of solid tumors are likely affected by regulatory cytokine genotypes. In particular, pro-inflammatory genotypes characterized by a low IL-10 or a high IL-6 producer seem to be associated with a worse clinical outcome (Caruso, et al. 2004). On the other hand, recent evidence has linked IL-10 and IL-6 cytokine polymorphisms to longevity. In fact, individuals who are genetically predisposed to produce high levels of IL-6 have a reduced capacity to reach the extreme limits of human life, whereas the high IL-10 producer genotype is increased among centenarians (Caruso, et al. 2004). The opposite effect of IL-6 and IL-10 in cancer and longevity is intriguing. Inflammatory genotypes may be both friends and enemies. The immune system has evolved to control pathogens, therefore pro-inflammatory responses are likely to be evolutionarily programmed to resist fatal infections, and a high IL-6 or a low IL-10 production is associated with increased resistance to pathogens. However, decreased level of IL-6 or increased level of IL-10 might better control inflammatory responses and cancer development. These conditions might result in an increased chance of long life survival in an environment with reduced pathogen loads (Caruso, et al. 2004).

Most tumor supressor genes can be classified as either caretakers or gatekeepers (Kinzler and Voglestein, 1997). Caretaker tumor suppressor genes prevent cancer by protecting the genome from mutations. They generally act by preventing DNA damage or optimizing DNA repair. In addition to preventing cancer, genes that help maintain genomic integrity also prevent or retard the development of other aging phenotypes and age-related pathologies (Hasty, et al. 2003). Gatekeeper tumor suppressors, by contrast, prevent cancer by acting on intact cells—specifically, mitotic cells that are at risk for neoplastic transformation. Gatekeepers can virtually eliminate potential cancer cells by inducing programmed cell death (apoptosis). Alternatively, they can prevent potential cancer cells from proliferating by inducing permanent withdrawal from the cell cycle (cellular senescence). Although little is known about how cells choose between apoptotic and senescence responses, there is little doubt that both responses are crucial for suppressing cancer (Campisi, 2001; Green and Evan, 2002).

Increasing evidence suggests that the rise in cancer with age results from a synergy between the accumulation of mutations and age-related, pro-oncogenic changes in the tissue milieu. Most age related cancers derive from epithelial cells. Epithelial tissues are supported by a stroma, which is composed of extracellular matrix and several cell types. One age-related change that occurs in epithelial tissues is the accumulation of senescent cells. Cellular senescence is a potent tumor suppressive mechanism that irreversibly arrests proliferation in response to damage or stimuli that put cells at risk for neoplastic transformation. Senescent cells secrete factors that can disrupt tissue architecture and stimulate neighboring cells to proliferate. The suggestion has been made that senescent cells can create a tissue environment that synergizes with oncogenic mutations to promote the progression of age-related cancers (Krtolica and Campisi, 2003). The recent evidence indicates that cellular senescence may be an example of evolutionary antagonistic pleiotropy.

A major difference between microbial pathogens and tumors as potential vaccine targets is that cancer cells are derived from the host, and most of their macromolecules are normal self-antigens present in normal cells. To take advantage of the immune system's specificity, antigens must be found that clearly mark the cancer cells as different from host cells. An area generating much interest is the possibility of overcoming mechanisms that downregulate or attenuate the immune response, as is depicted in FIG. 5D (Berzofsky, et al. 2004b). With reference thereto, FIG. 5D illustrates negative regulation of tumor immunosurveillance and anti-tumor immune responses. FIG. 5D(A) depicts $CD4^+CD25^+$ T regulatory cells, induced by peptide presented by class II MHC molecules in the presence of IL-2, may inhibit induction of effector $CD4^+$ or $CD8^+$ T cells by a contact-dependent mechanism, possibly involving cell surface and/or secreted TGF-$\beta$, and FIG. 5D(B) illustrates how $CD4^+$ NKT cells may be induced by tumor glycolipid presented by CD1d to secrete IL-13, which stimulates $Gr-1^+CD11b^+$ myeloid cells to produce TGF-$\beta$, which inhibits induction of $CD8^+$ CTLs mediating tumor immunosurveillance. TGF-$\beta$ may also inhibit CD4+ T cells (not shown). Blockade of other mechanisms can improve immunosurveillance and the response to vaccines. Other suppressor or negative regulatory cells have been described in other contexts, but not as well study in the context of cancer (Berzofsky, et al.). Such mechanisms may have evolved to reduce inflammation and immunopathology or to prevent autoimmunity. Tumors have co-opted these mechanisms to evade immunosurveillance.

Thus, it has been postulated that the excess of dysfunctional CD8 T cells is indirectly immunosuppressive by filling the "immunologic space" and shrinking the T-cell repertoire for new antigens, as well as directly suppressive via cytokine secretion. It is associated with the IRP predicting two and four year mortality in longitudinal studies of very old people. It is hypothesized that deletion of such accumulations of dysfunctional cells would be beneficial to the individual. It may be possible to distinguish functional CMV-specific cells (which are essential to maintain immunosurveillance) from dysfunctional ones by their expression of certain surface molecules. This, coupled with methods directed at reinvigorating the thymus (such as, for example, the use of interleukin 7), and targeting CMV by pharmacologic and immunotherapeutic interventions might result in the immunorejuvenation sufficient to take elderly individuals out of the risk category and thereby extend healthy longevity (Pawelec, et al. 2006). Animal models suggest that IL-7 improves immune reconstitution through increasing thymic output and, perhaps more importantly, through antigen-independent homeostatic driven proliferation in the periphery (Sasson, et al. 2006). A study in old Rhesus macaques showed that treatment of the elderly with IL-7 may provide an effective therapy to improve the immune system (Aspinall, et al. 2007).

In rural Gambians, the season of birth strongly predicts adult mortality. Those born during the harvest season have longer life spans than do those born during the hungry season, and the deaths associated with infectious diseases suggest permanent early-life influences on immunity (Ngom, et al. 2004). One group studied thymic size and output in Gambian infants born in either the hungry or the harvest season by measuring signal-joint T cell receptor-rearrangement circles (sjTRECs) at birth and at 8 weeks of age.

They found that by 8 weeks of age, those born in the hungry season had significantly lower sjTREC counts (indicating poor immune function) than did those born in the harvest season. These results correlated directly with lower ELISA measurements of IL-7 in mothers' breast milk (Ngom, et al. 2004). This research group speculated that these data show a plausible pathway linking external season insults to mothers with thymic development in their infants, which suggests possible implications for long-term programming of immunity.

ImmunoScore Measurements and Applications. Thus, there is a balance between viral mechanisms of pathogenesis, persistence, and immune evasion and the host cellular immune response. The immunologic basis of this balance has not been completely characterized. The nature and threshold of CMV-specific T cell responses required for long-term CMV containment yet remain to be defined. This information would facilitate identification of highly susceptible individuals and provide a specific target for immunotherapeutic approaches designed to establish, maintain, or restore immunologic protection (Sylwester, et al. 2005). There seem to be clinical consequences to an overly robust CMV-specific T cell response. An obvious prerequisite for a better understanding of what constitutes insufficient or excessive CMV-specific T cell immunity is the ability to evaluate the overall CMV-specific T cell response in infected individuals. Future longitudinal studies would benefit from combining data on viral reactivation and primary infection with immunological monitoring (Hadrup, et al. 2006). The ImmunoScore diagnostic and database systems would provide just such an opportunity for data collection and monitoring longitudinal data collection.

Although CMV seropositivity appears to be one of the driving forces for induction of CD8 T cell clonality, this is not currently detectable in the middle-age population (Hadrup, et al. 2006). The influence of CMV on clonality only becomes relevant at a detectable level in the elderly. Superior detection capabilities available through the ImmunoScore technology might lead to earlier detection of possible immune depletion as individuals pass through middle age.

ImmunoScore technology by its nature of compiling individual patient data would offer the opportunity for longitudinal design of research studies. The longitudinal design is a superior alternative to the cross-sectional method for conducting ageing research, but it has seldom been used due to extensive costs as studies are currently conducted. The ImmunoScore system would naturally build a longitudinal component into patient care at no increased initial cost. The database would yield important insights into ageing and all its implications at a lower cost and dramatically improve healthcare.

Questions have been raised concerning CMV infection and its relationship to the IRP (Vasto, et al. 2007). Uncertainties that require clarification are: Is there an immunogenetic component influencing the IRP phenotype that might explain the different degree of CMV clonal expansion vs. non-IRP phenotype? May this difference depend on social and/or environmental factors? Might the genetic or environmental component affect the degree of clonal expansion of CMV in IRP individuals? What can be the main cause of death in IRP? Can IRP selection be predictive in young as well as in old individuals? Is it possible to revert/prevent accumulation of CMV-specific cells? These are all questions that can, in exemplary embodiments of the present invention, be addressed by the application of ImmunoScore diagnostic and database technologies.

Immunogenetic components can, for example, be monitored using unique technology designed to investigate single nucleotide polymorphisms (SNPs) rapidly and those data could be stored in the ImmunoScore central database. Additionally, social and environmental factors can be part of the ImmunoScore demographic data collected at routine patient visits to their physicians. The accumulation of these data on the ImmunoScore database would yield potential relationships regarding environmental and social factors to the IRP.

Careful monitoring of the ImmunoScore database would shed more light onto environmental and/or genetic factors contributing to the clonal expansion of CMV T cells in IRP individuals and the non-IRP individuals.

As the ImmunoScore data collection system is envisaged as a cradle-to-grave system of healthcare, the cause of death in IRP individuals can be collected and collated. Preliminary indications are that IRP selection is likely to be predictive in the young as well as in the very elderly. The ImmunoScore cradle-to-grave philosophy of patient data tracking can be invaluable in assessing these issues. Additionally, prevention/reversion of the accumulation of CMV-specific T cells would seem an issue of paramount importance. Preliminary studies in animal models regarding judicious use of IL-7 have been promising. ImmunoScore can, for example, track treatments and even shed light on when such treatments should commence in the life of the afflicted individuals.

CMV Vaccine and Vaccines Against Chronic Viral Infections and Cancer. In a recent review of priorities for vaccine development, CMV was ranked in the highest of five tiers by the Institute of Medicine in the United States as a potentially cost-saving vaccine target (Stratton, et al. 2000). In general, CMV is acquired earlier in life in developing countries and among the lower socioeconomic strata of the developed countries (Stagno and Cloud, 1990). Recently, the seroepidemiology of CMV was examined in Australia (Seale, et al. 2006). The pattern of age-specific seroprevalence of CMV antibody, as provided in FIG. 5C, closely matched the pattern found from analysis of the exemplary OP database described in Section II, below. Indeed, a review of CMV seroprevalence studies conducted around the world revealed that residents of developing countries have higher rates of CMV seropositivity than those of developed countries (Enright and Prober, 2004). The potential benefits of a CMV vaccine would include reduced transmission to pregnant women and less CMV disease due to primary infection or reactivation in organ transplant recipients and the immunosuppressed (Griffiths, et al. 2000).

It is possible that the development of a vaccine that is effective against viruses that cause chronic infection may require consideration of a paradigm different than those previously used for organisms causing acute infection (Berzofsky et al. 2004). In most cases of chronic viral infection, the immune response to the natural infection is not sufficient to eradicate that infection. The challenge for the $21^{st}$ century is to apply the latest fundamental knowledge in molecular biology, virology, and immunology to developing vaccines that are more effective at eliciting immunity than the natural infections and consequently, effective against chronic viral and other infectious diseases in addition to cancer, which do not fit the classic paradigm. ImmunoScore diagnostic and database tracking would be invaluable in analyzing the efficacy of a CMV vaccine, as well as vaccines developed against HIV, hepatitis C virus (HCV), human papilloma virus (HPV) and Epstein-Barr virus (EBV), among others.

As prophylaxis against acute infectious diseases, vaccines have been among the most cost-effective agents, saving many millions of lives. However, for treatment of chronic infections and cancer, vaccines have yet to achieve widespread success. Increased understanding of the immune system has raised new hope of harnessing the exquisite specificity of the immune system to attack cancer (Berzofsky, et al. 2004b). In exemplary embodiments of the present invention exemplary ImmunoScore diagnostic panels and database systems can add considerably to this knowledge base and can, for example, assist in intelligent vaccine design and monitoring of the efficacy of the vaccines as they are developed.

TABLE I

Characteristics of the Immune Risk Phenotype (IRP)

CD4:CD8 ratio < 1
Poor T cell proliferative responses to mitogens
Increased $CD8^+CD28^-$ and $CD8^+CD57^+$ cells
Low B cell count
CMV seropositivity
Clonal expansion of CD8 cells carrying receptors for CMV
High proportion of dysfunctional cells amongst the CMV-specific CD8 cells D. Exemplary Immunoscore Superpanels
1. Middle School Student ImmunoPrint Super Diagnostic Panel In exemplary embodiments of the present invention, a middle school superpanel can, for example, comprise the following exemplary panels:
1.1. Persistent Immunity Induced by Childhood Vaccines
  This panel is described above in section A3.
1.2. Sexually Transmitted Disease (STD) Diagnostic Panel
  For children entering middle school (grades six through eight) a baseline determination for antibody levels to STDs is advisable. Recommended tests for ImmunoPrint measurement of immunity to STDs:
    Antibodies to *Chlamydia*—IgG, IgA, and IgM (3)
    Antibodies to HSV—IgG to HSV-1 and HSV-2 (2)
    DNA analyses of HPV types—particular emphasis on high-risk
    Antibody to *N. gonorrhoeae* (1)
    Antibody to *T. pallidum* (1)
    T-cell related response to *T. pallidum*
    Antibody to HIV
    T-cell related response to HIV
    Antibodies to GBS serotypes (at least 3)
    Measurement of Th1/Th2 cytokines (many as current evolving definitions)
    Antibodies to organisms that cause Urinary Tract Infection (UTIs)
      *Escherichia coli*
      *Staphylococcus saprophyticus*
      *Proteus mirabilis*
      *Klebsiella pneumoniae*
      *Enterococcus* species
      *Pseudomonas aeruginosa*

Currently, there are no vaccines available for any of these STDs, with the exception of the Merck HPV vaccine. Until this situation is ameliorated as to a particular vaccine preventable disease, an ImmunoScore STD diagnostic panel would thus be to recommend treatments, track immunological response or provide other analyses, and not be used to recommend a vaccine or track the persistence of immunity conferred by it. Thus, in exemplary embodiments of the present invention an exemplary ImmunoScore database can, for example, generate correlates of protection information for all disease-causing organisms. As vaccines are developed, ImmunoScore diagnoses could, for example, be designed to examine antibody and other related immune responses to vaccine components.

*Chlamydia trachomatis* infection is the most commonly reported sexually transmitted disease in the United States, with the highest rates among adolescent females and young women. Because up to 70% of chlamydial infections in women are asymptomatic, routine screening and treatment of infected persons is essential to prevent pelvic inflammatory disease, infertility, ectopic pregnancy, and perinatal infections. The third U.S. Preventive Services Task Force (USPSTF) recommends that primary care physicians routinely screen all women whether or not they are pregnant if they:
  Are sexually active and aged 25 or younger.
  Have more than one sexual partner, regardless of age.
  Have had an STD in the past, regardless of age.
  Do not use condoms consistently and correctly, regardless of age.
According to studies reviewed by the third USPSTF:
  The cost of screening women who are not pregnant and who are at risk for chlamydial infection may be less than the cost of treating *Chlamydia* and its complications.
  Screening patients at greatest risk is more cost effective than screening all patients.
  DNA or RNA amplification tests are more sensitive than culture.
A low cost diagnostic test for *Chlamydia* infection or immune response to a *Chlamydia* vaccine would be a welcome addition to immune status determination by ImmunoPrint diagnostic testing.

Herpes simplex virus type 2 (HSV-2) is the primary cause of genital herpes, a common sexually transmitted disease with at least 40 to 60 million infected individuals in the U. S. Medically serious complications of HSV are rare but constitute a significant burden, given the high rates of HSV seropositivity in the population.

Many prophylactic and therapeutic vaccination approaches have been explored for the prevention or treatment of HSV infection. Infection induces both humoral and T-cell immunity. Vaccine candidates for HSV-2 infection include subunit vaccines, killed and live attenuated virus vaccines, and viral DNA vaccines.

Human papillomaviruses (HPV) are small double-stranded DNA viruses that are responsible for pathological conditions ranging from benign skin warts to invasive cervical carcinomas. Cervical cancer is the second leading cause of cancer death among women worldwide, and more than 99% of cervical cancers contain HPV, particularly the high-risk HRP type 16 (HPV-16). Two HPV oncoproteins, E6 and E7, are consistently expressed in HPV-associated cancer cells and are responsible for their malignant transformation. These oncogenic proteins represent ideal target antigens for developing vaccines and immunotherapeutic strategies against HPV-associated neoplasms. More than 10,000 American women a year are diagnosed with cancer or precancerous cells caused by HPV, and 3,700 of them will die. Eighty times that number will die worldwide. An effective vaccine could prevent nearly all of those deaths. The CDC is currently considering an HPV vaccine for all children aged 12 years. A positive recommendation by the ACIP could start states thinking of requiring the vaccine for entry into middle school.

*Neisseria gonorrhoeae*, the causative agent or gonorrhea, is one of the most common sexually transmitted pathogens worldwide. Although a robust inflammatory response ensues during symptomatic infection, no apparent protective immunity is developed following infection, as shown in a male human challenge study and by the high incidence of recidivism among patients attending sexually transmitted disease clinics. The search for a vaccine against gonorrhea has been largely disappointing. In human vaccine trials, partially lysed gonococci, purified pilin, and purified porin were shown to be immunogenic, but all failed to elicit protection upon subsequent natural exposure. The lack of protective immunity is likely due, in part, to the capacity of many gonococcal surface antigens to undergo high-frequency phase and antigenic variation.

Individuals infected with *Treponema pallidum* subsp. *pallidum* develop specific immune responses that are able to clear millions of treponemes from sites of primary and secondary syphilis. Despite the fact that humans develop robust immune responses against *T. pallidum*, they can be infected multiple times. The response is a T-cell mediated delayed-type hypersensitivity response in which T cells infiltrate syphilitic lesions and activate macrophages to phagocytose antibody-opsonized treponemes. How treponemes from heterologous isolates can evade the recall response of a previously infected individual is unknown. Data from animal studies suggest that both antibodies and T cells play a role in protection but neither alone prevents infection. It is possible that antigenic diversity of *T. pallidum* accounts for the lack of heterologous protection. The *T. pallidum* repeat protein K (TprK) is a strong candidate for a treponemal factor involved in immune evasion. Epitope mapping studies revealed that, during experimental infection, T cells are directed to the conserved regions of TprK, while the antibodies are directed to the variable regions.

A safe, effective prophylactic human immunodeficiency virus (HIV) vaccine is urgently needed to curb the current AIDS epidemic. There are currently 40 million individuals in the world infected with HIV, and nearly 16,000 new infections occur worldwide each day. Effective HIV-1 vaccines must be capable of protecting immunized individuals from infection with a broad array of diverse viral variants. Attempts to develop a safe and effective AIDS vaccine have been slowed, in part, by the difficulty in clearly defining specific immune responses that can prevent infection and limit disease progression. This is in part due to the poor immunogenicity of the envelope glycoprotein, the tremendous variability of the virus, its ability to evade and impair the host's immune system, and its ability to persist by integrating into the host's immune system, and its ability to persist by integrating into the host's genome of a number of different cell types. It is generally believed that an effective HIV-1 vaccine must be capable of inducing neutralizing antibodies as well as strong cell-mediated immune responses in outbred populations.

Group B Streptococci (GBS) emerged dramatically in the 1970s as the leading cause of neonatal infection and as an important cause of maternal uterine infection. The burden from GBS disease in elderly persons has also increased. In 1996, the first national consensus guidelines were released. Since then, there has been a 70% reduction in early-onset neonatal GBS infection. In 2002, new national guidelines were released recommending:

solely a screen-based prevention strategy
a new algorithm for patients with penicillin allergy
more specific practices in certain clinical scenarios
Yet clinical issues remain, including implementation of new diagnostic techniques, management of preterm rupture of membranes, use of alternative antibiotic approaches, improvement of compliance, prevention of low birth weight infants, emergence of resistant organisms, and vaccine development.

Urinary tract infections (UTIs) are a leading cause of morbidity and mortality and health care expenditures in persons of all ages. Sexually active young women are disproportionately affected, but several other populations, including elderly persons and those undergoing genitourinary instrumentation and catheterization, are also at risk. UTIs are the leading cause of gram-negative bacteremia (Orenstein and Wong, 1999).

Lymphocytes are the effector cells of acquired immunity. Two T helper subsets are Th1 and Th2, based on two distinct cytokine profiles that resulted in the overall regulation of the immune response. The Th1 cell (with its associated cytokines: INF-γ, TNF-α, IL-2, IL-12) is biased towards the cell-mediated side of immunity, effective against intracellular parasites, and its down regulation of Th2 can provide relief from allergic reactions due to IgE; but detrimental effects may result in autoimmunity and graft rejection. On the other hand, the Th2 cell (with its associated cytokines IL-4, IL-5, IL-6, IL-10, IL-13) favors humoral immunity, providing an effective correlate of protection for most vaccines, and its down regulation of Th1 can result in some benefit of tolerance to prevent cellular autoimmune reactions; but certain harmful characteristics related to IgE-based allergies and autoimmunity may result. In order to diagnose or predict an immunologic disease and/or provide therapy or prophylaxis, the Th polarization status must be determined; this should also be applied to measure susceptibility to infectious and neoplastic diseases. Th status is measurable in terms of cytokine profiles, chemokine/chemoattractant receptors, specific effector cell products, or gene expression profiles. An exemplary diagnostic panel is described in the table below:

| Th1 | | Th2 | |
|---|---|---|---|
| Cytokines | Receptors | Cytokines | Receptors |
| INF-γ | CCR5 | IL-4 | CCR3 |
| TNF-α | CXCR3 | IL-5 | CCR4 |
| IL-2 | CCR1 | IL-6 | CCR8 |
| IL-12 | | IL-10 | CRTh2 |
| | | IL-13 | |

2. Exemplary ImmunoScore Diagnostic Panels for Women of Child-Bearing Years

Adult immunization rates have fallen short of national goals partly because of misconceptions about the safety and benefits of current vaccines. The danger of misconceptions is magnified during pregnancy when concerned physicians are hesitant to administer vaccines and patients are reluctant to receive them. Routine vaccines that are generally safe to administer during pregnancy include diphtheria, tetanus, influenza, and hepatitis B. Other vaccines, such as meningococcal and rabies, may be considered. Vaccines that are contraindicated, because of the theoretical risk of fetal transmission, include measles, mumps and rubella; varicella; and BCG. A number of other vaccines have not yet been adequately studied; therefore, theoretic risks of vaccination must be weighed against the risks of disease to mother and fetus.

The administration of vaccines during pregnancy poses a number of concerns to physicians and patients about the risk of transmitting a virus to a developing fetus. This risk is primarily theoretical. No evidence exists of risk from vaccinating pregnant women with inactivated virus or bacterial vaccines or toxoids (CDC, 2002). Physicians should consider vaccinating pregnant women on the basis of the risks of vaccination versus the benefits of protection in each particular situation, regardless of whether live or inactivated vaccines are used (Sur, et al. 2003). Generally, live-virus vaccines are contraindicated for pregnant women because of the theoretical risk of transmission of vaccine virus to the fetus. The following table summarizes recommendations for vaccines commonly administered and their indication for use during pregnancy.

TABLE 11

Immunizations During Pregnancy

| Considered safe if otherwise indicated | Contraindicated during pregnancy or safety not established | Special recommendations pertain |
|---|---|---|
| Tetanus and diphtheria toxoids (Td) | BCG* | Anthrax |
| Hepatitis B | Measles* | Hepatitis A |
| Influenza | Mumps* | Japanese encephalitis |
| Meningococcal | Rubella* | Pneumococcal |
| Rabies | Varicella* | Polio (IPV) |
| | | Typhoid |
| | | Vaccinia* |
| | | Yellow fever* |

* = Live, attenuated vaccine

Women in their second and third trimesters of pregnancy have an increased risk of influenza-related complications including pneumonia and a four-fold risk of hospitalization (Neuzil, et al. 1998). The CDC has recommended that women who will be in the second or third trimester during influenza season and all pregnant women with additional high-risk medical conditions should receive vaccination in the fall. Despite publication of these guidelines, rates of vaccination among high-risk patients remain low (Silverman and Greif, 2001; Schrag, et al. 2003). Many possible explanations exist for this discrepancy, including vaccine unavailability, logistical concerns, poor reimbursement, fear of side effects, and lack of adequate patient or physician education (Wallis, et al. 2004).

A number of maternal conditions were perceived as potential contraindications to influenza vaccination during pregnancy. The most common of these were the first trimester, history of preterm labor, history of intrauterine fetal demise, and pregnancy induced hypertension; none of these are listed by the CDC as contraindications (Wallis, et al. 2004). According to this group, another potentially significant obstacle to influenza vaccination during pregnancy was physician reimbursement. Several responders remarked that reimbursement from insurance companies played a part in whether they stocked the vaccine in their offices and whether it was administered to pregnant patients. Although they acknowledged the indications for the vaccine, some obstetricians stated that insurance plans have refused reimbursement for vaccination because they were not the patient's primary care provider for this "preventive" service. Although patients may still be instructed to obtain vaccination elsewhere, this additional obstacle to recommended obstetrical care may result in lower immunization rates. These authors concluded by stating that further research is needed to determine effective methods of increasing vaccination rates in this high-risk population.

Cytomegalovirus (CMV) is found universally throughout all geographic locations and socioeconomic groups, and infects between 50-80% of adults in the United States by 40 years of age. CMV is also the virus most frequently transmitted to a developing child before birth. The incidence of primary CMV infection in pregnant women in the U.S. varies from 1-3%. Healthy pregnant women are not at special risk for disease from CMV infection. When infected with CMV, most women have no symptoms and very few have a disease resembling mononucleosis. It is their unborn babies that may be at risk for congenital CMV disease. CMV remains the most important cause of congenital viral infection in the U.S. For infants who are infected by their mothers before birth, two potential problems exist:

1. Generalized infection may occur in the infant, and symptoms may range from moderate enlargement of the liver and spleen (with jaundice) to fatal illness. With supportive treatment most infants with CMV disease usually survive. However, from 80-90% will have complications within the first few years of life that may include hearing loss, vision impairment, and varying degrees of mental retardation.
2. Another 5-10% of infants who are infected but without symptoms at birth will subsequently have varying degrees of hearing and mental or coordination problems.

However, these risks appear to be almost exclusively associated with women who previously have not been infected with CMV and who are having their first infection during pregnancy. There appears to be little risk of CMV-related complications for women who have been infected at least six months prior to conception. The current recommendations from the CDC for pregnant women with regard to CMV infection are:
1. Throughout the pregnancy, practice good personal hygiene, especially hand washing with soap and water, after contact with diapers or oral secretions (particularly with a child who is in day care).
2. Women who develop a mononucleosis-like illness during pregnancy should be evaluated for CMV infection and counseled about the possible risks to the unborn child.
3. Laboratory testing for antibody to CMV can be performed to determine if a woman already had a CMV infection.
4. Recovery of CMV from the cervix or urine of women at or before the time of delivery does not warrant a cesarean section.
5. The demonstrated benefits of breast-feeding outweigh the minimal risk of acquiring CMV infection from the breast-feeding mother.
6. There is no need to either screen for CMV or exclude CMV-excreting children from schools or institutions because the virus is frequently found in many healthy children and adults.

Recently, it was found that hyperimmune globulin therapy in pregnant women was associated with a significantly lower risk of congenital CMV disease (Nigro, et al. 2005). This group concluded that treatment of pregnant women with CMV-specific hyperimmune globulin is sage, and their findings suggested that it may be effective in the treatment and prevention of congenital CMV infection.

Specific ImmunoScore diagnostic panel recommendations must take into account the woman of child-bearing years status with regard to pregnancy. Ideally, an ImmunoScore screening of a young women prior to child-bearing years would give an appropriate "baseline" reading of that individual. In this instance, for example, a positive serologic test for CMV would be an indication that CMV-like illness during pregnancy would not be a cause of concern regarding transmission to that mother's infant during a pregnancy later in that woman's life.

Clearly, women of child-bearing years that are not pregnant, or not planning to get pregnant in the six months following ImmunoScore screening would have different recommendations than pregnant women. An ideal location and time for ImmunoScore diagnostic screening women of child-bearing years would be during their annual recommended visit to the OB/GYN. An early baseline could be achieved for each patient and the Specialist could make use of the specific recommendations without confusion as to which immunizations would be appropriate. It is very important to assure immunity to the components of the measles-mumps-rubella vaccine prior to pregnancy and the ImmunoScore service would enable that assurance.

Accordingly, in exemplary embodiments of the present invention a Women of Child-Bearing Years ImmunoScore superpanel can be defined as follows.

2.1. Recommended tests for ImmunoScore Measurement of Immunity:
  Antibody to Cytomegalovirus (1)
    History of CMV infection needs to be captured to complete ImmunoScore database and add relevance to pregnancy.
  Pregnancy test (1)
  A pregnancy test is critical to making the correct decisions regarding administration of vaccines to women of this age group. There are, of course, other considerations here, but the status of the woman in question regarding pregnancy must be resolved in order to make accurate therapeutic decisions. In addition to CMV antibody, the physician(s) of women of child bearing years need to be aware of the recommendations of the CDC regarding immunizing pregnant women and the risks of immunization vs. the risks of foregoing immunizations. In addition, physicians should be aware that following appropriate immunization protocols and assuring a competent immune status is extremely important for women of child-bearing years.

2.2. Persistent Immunity Induced by Childhood Vaccines Diagnostic Panel
  Described above.
2.3. Sexually Transmitted Disease (STD) Diagnostic Panel
  Described above.

Exemplary Immunoscore System Databases
  A. General Overview

In exemplary embodiments of the present invention the results of immunologic and other assays of an individual together with additional medical, lifestyle, environmental and other demographic information can be collected at the same time as, or derived from, the collected data, and can, for example, be stored in a system database. Such a database can, for example, serve as an electronic record of immune status and other data over a period of time, both for individuals as well as for populations or sub-populations, as described below. Additionally, for example, such a database can be augmented with information regarding diagnoses received, treatments administered, pharmaceuticals prescribed, costs of medical services performed, insurance re-imbursements, metrics as to the efficacy of treatments and/or pharmaceuticals administered, as well other relevant information to facilitate evaluation of the efficacy and efficiency of medical services rendered, as described more fully below.

Thus, for example, for each run of an exemplary ImmunoScore assay within an exemplary system, various categories of data can be collected. Data can, for example, be stored in an electronic database using standard techniques as are known in the art. An example of data which can be stored and the manner in which it can be stored is next described. It is understood that this example is not intended to preclude the storage of additional collected or derived data as may prove useful for the purposes of trending, data mining, evaluation or diagnostic improvement, as described below, or as may be needed in or useful to any of the exemplary applications described in Section III below.

For each assay an exemplary system can record a unique assay ID, which can incorporate, for example, among other information, an identifier for the assay instrument. This ID can be unique over the universe of instruments, ensuring that when data is aggregated into a central system no two assay result records will have the same identifier. A possible implementation of this functionality is given, for example, by Microsoft's use of the GUID (Globally Unique Identifier), a 16 byte identifier generated by a computer and guaranteed to be unique across all computers.

Each record can include the time and date that the assay was performed, stored to a time resolution of, for example, one second. As is known, there are a variety of standard means of storing time and date information in a database. One simple means is, for example, to record the number of seconds from an arbitrary start time, such as, for example, Jan. 1, 1900 at midnight.

Each record can, for example, also include an indication of the location where the sample was processed. This can include, for example, an identifier of the instrument used, as well as real-world location information, such as, for example, the name and address of the facility where the instrument has been installed.

The aforementioned exemplary fields comprise identification information which is important to maintain for all samples. In addition, information about the sample and patient can be stored in the database as well. Patient information can, for example, be stored in a form which is separate from the bulk of the data, and referenced by a data link. Patient information, which can include, for example, name, social security number, birth date or other information (such as is described below in detail), can be maintained with emphasis on security standards are known in the art. The storage of identifiable individual patient information in a separate virtual location from the remaining data can help to maintain such a high level of security.

In exemplary embodiments of the present invention, a system can, for each assay result, also store an identifier indicating exactly which assay was performed on the sample. This can indicate not only the analyte to be determined, but also information regarding the production of the reagents used in the assay. This information can be used to distinguish between, and compensate for, for example, lot-to-lot variations in assay manufacture. It can also allow for converting different assays for the same analyte into a normalized value, so that trends across geography as well as time can be obtained.

The measurement of an immune response to a particular disease or other analyte can involve the collection of a large quantity of low level data generated by an instrument. For an ECL instrument, for example, an instrument can measure the light emitted from the electrochemiluminescence over some time period as well as other information such as voltages and currents used to induce the electrochemiluminescence and the temperature near the electrodes through which the electrical energy is delivered to drive the electrochemiluminescent reaction. From this "raw data" and possibly instrument calibration information, a single number, for example, can be computed to represent an ECL signal for that measurement. Additional information can be computed from the raw data and instrument calibration information that indicates the quality of the ECL signal, for example, whether the instrument was operating in an appropriate environmental condition, whether sample was present, or whether the instrument was operating as expected. The raw data and such derived data can, for example, be stored in an exemplary ImmunoScore system database. In general the size of the storage required for this raw data can vary depending upon the resolution at which the data is captured. It is possible that a finer-grained resolution, resulting in a larger data storage requirement, will yield more useful analysis for some assays rather than others. Storage of both the raw data and the derived values can be done, for example, using industry-standard methods for the persistence of floating point numbers. For example, four (4) bytes of storage, yielding approximately six (6) significant digits, can be used for each stored value.

The quantity of greatest interest in an assay is the concentration of the analyte under evaluation. This concentration can be determined by converting a computed ECL signal to a concentration. This conversion can be done, for example, by backfitting the ECL signal through a calibration curve that relates ECL signal to analyte concentration. In general, such a calibration curve can vary from assay to assay, and can change over time for a given assay as that assay is refined.

Calibration curves enable both interpolation and extrapolation of ECL signal measurements for samples with known analyte concentrations for ECL signal measurements of samples of unknown amounts of analyte. The form of the mathematical functions used in a curve fit can, for example, make assumptions regarding the continuity and/or smoothness of the underlying relation such as through interpolating the measurements with functions such as piecewise constant, piecewise linear, cubic spline, or for example, by throughfitting all the data with linear, quadratic, cubic, or quartic polynomials. For overconstrained systems, parameters can be computed by minimizing an error function such as, for example, least squares (e.g., Press et al. 1992) or total least squares (e.g., Van Huffel et al. 1991). The form of the mathematical function may make assumptions about the assay mechanism, such as a one site saturation, two site saturation, one site saturation with nonspecific binding, two site saturations with nonspecific binding, a sigmoidal dose response curve with or without a variable slope, one-site competition, two-site competition, or a four-parameter logistic. Generation of a calibration curve entails selecting the form of the mathematical function and then fitting the parameters of the function with measurements. The measurements can, for example, be done on the test instrument or can be done in whole or in part elsewhere (e.g., at the place the assay is manufactured). The measurements can either perfectly constrain or over-constrain the mathematical function. As noted, for overconstrained systems, model parameters can be computed by minimizing an error function such as least squares.

In exemplary embodiments of the present invention, for each analyte the form of the mathematical function or model (stored, for example, as an index into a table of known models), the computed model parameters, as well as the data used to compute the model parameters, can be associated with each measurement of the analyte. To reduce the amount of redundant information stored in the database, the association for each measurement can be a link to the calibration data rather than the calibration data itself. Instruments can be re-calibrated at any time, such as, for example, on a weekly basis or with every measurement. The quality of the calibration can also be assessed, for example, through the running of controls or by computing the residual error from an overconstrained curve fit.

Thus, a calculated concentration can be stored by the system. This can be, in exemplary embodiments of the present invention, the primary input to analysis recommendation algorithms employed by the remainder of the system. It is noted that not all assays will result in a quantitative concentration. For example, some assays, due to the shape of their calibration curve, may yield two different concentrations for the same measured signal. Such assays are said to "hook." In such cases the most an exemplary system can store is an indicator that the measured concentration is above a certain level, the lower of the two returned calculated values. Other assays, for various reasons, may return only qualitative results rather than true quantitative results. In all cases, a system database can be capable of storing and retrieving the result. For this reason, in exemplary embodiments of the present invention, the result of an assay can be stored not as a simple floating point number, but as a complex object which can take into account the various scenarios described above. Such an object can have, for example, several fields of its own.

A compressed version of the database can, in exemplary embodiments of the present invention, consist of only the initial ID information, patient ID information, test ID information, and the calculated concentration of analyte. This is a minimal set of data which can prove productive for data mining and trending analysis, as detailed below. The additional data described herein can, for example, be used to enhance the value of this analysis.

Algorithms encoded or implemented or implemented in an exemplary system can be used, for example, to determine a recommendation for action. This recommendation can be based upon a calculated concentration of, for example, antibody response. Other information can also be considered, including, for example, the results of other assays upon the same sample within a given assay panel.

Regardless of the means of determining the recommended action, as described above, a final recommendation can be stored in the database. A system database can, for example, also store the "reasoning" behind the recommendation, allowing a human to later query the database to determine why a given course of action was recommended. Given that the number of recommended courses of action can be broad, these actions can be categorized and encoded. For example, a recommendation to administer a particular vaccination may be encoded with one byte to indicate "give vaccination" and two additional bytes to indicate the particular vaccination that is warranted. A field for comments can also be included, to allow the capture of the system's reasoning—in this case, an explanation of how algorithms and rules were applied to determine the stated conclusion.

A system database according to an exemplary embodiment of the present invention can be implemented, for example, as a shared resource spread over multiple computer platforms. For purposes of trending and analysis, it may be necessary to accumulate the data from a large number of systems into a central repository as depicted in FIG. 2, or, for example, in the case of having only decentralized information, by using a mechanism or process to locate and query the distributed sources. The individual databases can therefore require the capability to link up with a defined central database and upload their contents. This can occur on a periodic basis, or as may be triggered by a user of the system. Additionally, there can be multiple central servers, so that a given enterprise may choose to aggregate their data at any level. Unique IDs associated with sample and panel records can serve to allow for the combination of data from disparate sources without data "collision."

The linkage between local databases and a central database can be implemented, for example, across a local area network (LAN), a private data network, a VPN, an intranet or across the Internet. It is also possible to link databases on a periodic basis using physical media, such as CD-ROMs. Similarly, various users such as, for example, health care providers, individuals, insurance executives, consumers of research services, health care management personnel, etc., can access an exemplary system via a web based interface across a local area network (LAN), a private data network, a VPN, an intranet or across the Internet.

Once data has been accumulated into a central repository, a separate system can be used to perform data mining and data trending analysis upon the stored data. There are many valuable sorts of analyses which can be performed on the accumulated data in an exemplary system according to the present invention.

Given that each data record can, for example, be identified with a particular individual or patient and a particular time and date, it becomes possible to perform trending analysis of a patient's (or a population's) ImmunoScore profile over time. In many cases an individual's absolute measured value of an analyte is not as important as the trending of that value over a time. Some individuals may have naturally low or naturally high values which are not best measured against a statistical mean for their demographic population, but rather against that individual's own measured history.

As described above, each patient can, for example, also be placed within certain demographic categories. It can be useful to compare a patient's measured ImmunoScore profile against the corresponding profile for the demographic groups to which he or she belongs. Deviation from the measured means for a demographic slice of the population can prove more meaningful than can a comparison to a total threshold. Thus, in exemplary embodiments of the present invention, collected data can be used to continually modify the demographic profile averages known to the system, taking care to not pollute the system with outlying data points. For example, it may prove useful to produce separate ImmunoScore demographic profiles for patients who are known to have experienced vaccinations versus those for whom there is no known immunization record. Alternatively, as is described below in Section III, such an immunization record can be inferred and reconstructed, as in the provision of ImmunoScore services to national immigration services or authorities or bodies dealing with such concerns.

Trending information in a demographic profile, for example, can also be useful. For example, tracking an indication of a typical person (e.g., mean, median, or mode), or an indication of the spread amongst people (e.g., standard deviation, interquartile range, or range) over time can enable an exemplary system to assess the relationship between immune status indicia and external factors, such as, for example, seasonal effects. Eating habits, sleeping habits, time aboard ship, etc. can be found to affect immune status in groups where these external factors are partially controllable (such as, for example, in military personnel). Comparing immune status indicators of differing demographic profiles can have important epidemiological significance.

Finally, it is expected that the collection of ImmunoScore data from a large number of individuals and/or populations can eventually lead to the improvement of diagnostic tests, thus forming a feedback loop. These improved diagnostic tests can then, for example, be deployed to field instruments, resulting in more accurate measurements and diagnoses. Such exemplary embodiments having feedback loops can be implemented, for example, with respect to particular populations or demographic groups, such as, for example, the military, college students, immigrants or any other group or combination thereof as described above.

B. Exemplary Illustrative Database

1. Overall Description

To illustrate the systems and methods of the present invention, a database system was constructed to serve as a testbed for the exercise of the business models described below. Such an exemplary database system was used to demonstrate the tools and techniques that might be used in a full scale system according to the present invention. Accordingly, a large data set was constructed using statistical techniques. The data was produced according to match existing knowledge about the distribution of immune response values among the general population.

The exemplary database system has two primary components. These two components represent the algorithmically interesting sections that can be, for example, present in a full-scale operational system according to an embodiment of the present invention. Such a full system could, for example, contain other modules as well, along the lines of industry standard large scale database systems. Such an exemplary system is depicted in FIG. 5 and is next generally described.

With reference to FIG. 5, an exemplary system architecture can be constructed. The exemplary system architecture can be, for example, divided into two sub-systems, one relatively local to "point of care" or locations where the individuals or patients whose immune status is to be analyzed are located. The other subsystem can be in a central location where complex data mining and analysis can occur. Thus, with reference to FIG. 5, an upper portion of the figure contains components which can be located at the point of care and a lower portion of the figure contains components which can be, for example, located at a system central location. The point of care is divided from the central location in the figure by a double dotted and dashed line for ease of identification.

With reference to the point of care sub-system, there can be one or more Instruments 505 which are devices which can read immunologic assays. Instruments 505 yield Assay Results 506. Assay Results 506, along with Doctor's Observations 503, Patient History 502 and Demographic Information 501 regarding the individual or patient can all be stored in Local PatientEvent Database 510. Database 510 can be, for example, an online transaction processing database. Because the point of care sub-system is generally directed to generating a recommendation in a relatively short time, there are two pathways to Diagnostic Module 515. Diagnostic Module 515 applies algorithmic rules to the assay results to determine a proper course of treatment or action based on current readings and optionally on past history. Thus, there is a flow of information from Assay Results 506 to Diagnostic Module 515. Alternatively, Diagnostic Module 515 can implement algorithms having other inputs besides the current Assay Results 506, such as, for example, Demographic Information 501, Patient History 502, and Doctor's Observations 503 (understood to include any observations by any health care provider, or the like, in a general sense) which can be stored in Local PatientEvent Database 510. Thus, in FIG. 5, there is an arrow labeled "optional" running from Local PatientEvent Database 510 to Diagnostic Module 515. Regardless of which source of information Diagnostic Module 515 draws upon, it can, for example, output the patient action recommendation 516 as indicated.

Returning to the central location sub-system of FIG. 5, a connection exists between Local PatientEvent Database 510 and a Central PatientEvent Database 520. This connects the two sub-systems. It is contemplated that at regular intervals data from Local PatientEvent Database 510 can be uploaded to Central PatientEvent Database 520. Moreover, although the central location sub-system could be mirrored in a number of distributed central location subsystems, the point of care sub-system is contemplated to take data from numerous instruments and in fact have numerous local patient event databases in those locales. In short, the point of care sub-system is found wherever potential customers or patients are found. It is noted that there can be a myriad of such locations, given the various and sundry applications and business models that exemplary embodiments of the present invention contemplate. Examples of such applications are described more fully in Section III, below. Therefore, there could be a great number of local patient event databases all of which feed into Central PatientEvent Database 520. None of these additional point of care sub-systems are shown in FIG. 5, for reasons of ease of illustration.

Returning again to Central PatientEvent Database 520, it is noted that this database can, for example, also be an online transaction processing database or OLTP. It is contemplated that this database can, for example, periodically load data to an online analytic processing database, or OLAP in the form of PatientEvent Database 530. PatientEvent Database 530 can be, for example, adapted to provide inputs to complicated algorithms dealing with data mining and pattern detection, as next described.

PatientEvent Database 530 can, for example, reside on a central server and utilize a data warehouse approach. There can be a variety of connections to PatientEvent Database 530 such as, for example, a Query Module 531, a Data Mining Module 532 and a Pattern Detection Module 533. Query Module 531 can be, for example, an interface by which a user can interactively search for information in database 530. Query Module 531 can also access Central PatientEvent Database 520 implement a variety of operations on the data there as well. Data Mining Module 532 can be an interface by which a user can interactively use OLAP tools to finds trends and summaries in the stored data. Finally, Pattern Detection Module 533 can be a program module which can be used to automatically search for patterns or other "hidden" correlations between various data points in a database. It is contemplated that in exemplary embodiments of the present invention Pattern Detection Module 533 can regularly sort through all of the stored data looking for patterns using various algorithms. Some of such algorithms can, for example, articulate some hunch or a correlative assumption provided by a panel of immunological experts for which they do not have hard data. Pattern Detection Module 533 is thus an important feature in exemplary embodiments of the present invention. Additional exemplary databases which Patter Detection Module 533 can utilize are described below in connection with FIG. 5A.

The exemplary system depicted in FIG. 5 will next be described in greater detail. A first module of interest is termed Diagnostic Module 515. The function of this software module is to input a set of assay results 506 obtained through measurements by instruments 505, and to make one or more recommendations 516 based upon the analysis of assay results 506. Diagnostic Module 515 can be designed in such a way that additional assay panels can be slotted into an existing system as they are developed. Some exemplary algorithms used to make recommendations as a function of assay results are described in more detail below, including descriptions both of algorithms used in the exemplary database as well as additional algorithms that could be implemented in various exemplary embodiments of the present invention.

Diagnostic Module 515 can rest upon a Local Database 510 containing Assay Results 506 obtained from Instruments 505. These results are pertinent to an individual patient. Local Database 510 can also, for example, contain background medical history 502 for that patient, demographic information 501 pertinent to the patient, and a summary of other medical observations 503 made by medical professionals or persons fulfilling a similar function. Local Database 510 can also, for example, contain statistical information obtained from a larger central database, as described below.

A second exemplary module of interest is Data Mining Module 532. Whereas Diagnostic Module 515 is intended for the analysis of a particular individual's data at a particular point in time, Data Mining module 532 can, for example, look at a broader range of data collected from many individuals over a range, or interval, of time. Through analysis of this collected data a system can, for example, be used to support various business methods and other applications by deducing trends and patterns within an immunological landscape. A particular result could be fed back into the Diagnostic Module's algorithms, improving their effectiveness by providing additional specificity with regard to an individual's background, possibly in terms of background or demographic information such as, for example, gender, racial background, geographic origin, lifestyle, economic circumstances social circumstances, or age.

As can be seen from FIG. 5, while the Diagnostic Module's functionalities are primarily local in nature and patient-specific, the Data Mining Module's functionalities are primarily central, and system-wide. As noted, this structure is reflected in the division of FIG. 5 into two zones, the "Point of Care" zone, shown at the top of the figure, and the "Central Location" zone, shown at the bottom of the figure.

Data Mining Module 532 depends upon the existence of a large central database containing records from a wide variety of individuals over a long span of time. Thus, the local databases described above can, for example, exist in a federated state with the central database, uploading their information on a regular basis, where this information can, for example, be integrated into the full system.

2. Impact of Data Mining

Patterns can be detected within the data in an exemplary database which are related to demographic and other non-immunologic information such as, for example, gender, age, ethnicity, geographic origin, employment, etc. These patterns may not be obvious until large numbers of individuals are assessed, using a computer that can be by nature much more efficient, unbiased, and precise in pattern recognition.

From such patterns, new correlates can, for example, can be established, and old correlates can be changed. For example, in immunization related applications, it may be proposed, based on previous data, that a serum antibody concentration of 2 micrograms per ml should be used to represent a threshold of protection against meningococcal disease, so that anyone with less antibody would be recommended for immunization. Subsequent and continued analysis, however, may show that this threshold value should be reduced or raised for given individuals, depending on, for example, age or ethnic background, or some other undefined parameter. In turn, an ethnicity evaluation could lead to the discovery of a specific biological or genetic marker. For example, the functional activity of *Haemophilus influenzae* type b (Hib) antibodies may vary with different individuals, where the same antibody concentration may not possess the same level of bacteriocidal activity due to differences in antibody avidity. For example, regarding age, Hib polysaccharides have been shown to be poorly immunogenic in children less than 2 years of age (Granoff D M, 1985, J Pediatr 107:330-36). Similarly, regarding ethnicity it has been shown from previous studies that Eskimos and Apaches are more susceptible to Hib meningitis because they possess a less effective antibody repertoire to the Hib polysaccharide capsule, based on the presence or absence of certain variable region genes used in the production of the polysaccharide-specific antibodies.

Additionally, variations in host factors can lead to significant differences in the immune response to vaccines, which can also be discerned by data mining. For example, late-stage complement deficiency may have no impact on antibody production, but would certainly reduce the effectiveness of those antibodies in killing bacteria, thereby lowering their activity. In such case, the antibody threshold for protection may need to be raised in order to achieve the same level of protection in this subpopulation.

As previously described for Hib, the capacity for protective antibody production is the direct result of variable region gene haplotypes. In this case, ethnic differences were first observed as a gross marker, but the presence of specific genes was later determined to be responsible. In a similar but different manner, HLA haplotypes have also been correlated with the susceptibility to certain infections, as well as the unresponsiveness to certain vaccines. For example, certain HLA antigens appear to be correlated with chronic hepatitis B virus (HBV) infections and HBV vaccine nonresponsiveness. In such cases, in exemplary embodiments, of the present invention, subpopulations can be identified, initially by ethnicity, then later by genetics, to evolve a more specific and appropriate diagnostic outcome.

Another example of the influence of ethnicity on responsiveness to treatment is the case of NitroMed's BiDil™, which was approved by the U.S. FDA in 2005 for the treatment of heart failure in African Americans. BiDil™ is an orally administered, nitric oxide-enhancing drug that was shown to have clearly different effects on blacks versus whites in clinical trials, where the "differences may be related to environmental, social, lifestyle, or genetic factors or to interactions among all of these." (see http://www.fda.gov/fdac/features/2005/505_BiDil.html). In exemplary embodiments of the present invention, data mining can, for example, be used to observe and identify these kinds of effects and correlations, and then be later used to determine the specific underlying mechanisms.

Data mining can also be used, for example, to change or reverse previously held dogma(s) concerning long-term protection from vaccination. For example, immunity resulting from the smallpox vaccine, used extensively during the previous century, was originally thought to last for less than a decade. Recent analyses however, have shown that "more than 90% of volunteers vaccinated 25-75 years ago still maintain substantial humoral or cellular immunity (or both) against vaccinia, the virus used to vaccinate against smallpox." (Hammarlund E et al., 2003, Nature Medicine 9:1131-37). The same study further showed that "Antiviral antibody responses remained stable between 1-75 years after vaccination, whereas antiviral T-cell responses declined slowly, with a half-life of 8-15 years." While it is not clear what level and combination of responses is required for protection, the authors concluded that "the morbidity and mortality associated with an intentional smallpox outbreak would be substantially reduced because of pre-existing immunity in a large number of previously vaccinated individuals." This is exactly the type of information that could be obtained through data mining over time on large populations, as contemplated in exemplary embodiments of the present invention.

As noted above, an exemplary system similar to that depicted in FIG. 5 was built using standard software development tools and packages. The algorithms were encoded using the XML data description language. The engine for executing the algorithms was built using the Java programming language. An Oracle database was used for data storage and data mining querying. Excel spreadsheets were used for data construction and analysis. Details of the construction are given below.

3. Diagnostic Module 3.1. Overview

Diagnostic Module 515 forms the heart of an exemplary ImmunoScore decision system. At a basic level, the diagnostic module exists to provide relevant information and/or to suggest courses of recommended action (for various purposes, depending upon the application; see Section III below) based upon an individual's immune status, as measured by instrumentation or obtained from elsewhere, in combination with other supporting data. There are many different ways that such a determination could be made. Next described are some exemplary algorithms that were used in the example system as well as other exemplary decision support algorithms which could be implemented using the same techniques.

One essential function of a diagnostic module can be, for example, to assist a medical or other professional in making decisions regarding which actions to take with a specific individual, making use of data regarding that person's immune status. As noted, in exemplary embodiments of the present invention, an individual's immune status can be determined by conducting a panel of assays, each of which assays can produce an element of data. For purposes of the example database, information presumed to be obtainable through such assays is summarized in FIG. 6. It should be noted that in practice some of this information may not yet be obtainable, although it is expected that assays could be developed along the lines of existing tests in order to complete this spectrum.

In addition to immune status information obtained from assays, a diagnostic module can make use of other information specific to the patient being examined. This information falls into two principal categories: demographic information, such as, for example, age and gender, and patient medical history. Most demographic information can be simply expressed in a database. Patient medical history is more problematic, although there are many existing healthcare database systems which do this adequately. The difficulty with patient medical history, however, is in devising algorithms which can make use of this qualitative data. It is expected that particular care can be taken to use algorithmic techniques which have proven adept in dealing with inconsistent or unreliable data, such as, for example, neural networks, described in greater detail below. This is due to the inherent unreliability of self-reported medical history data, along with the historic problems found in the transfer of medical records. If a system with built-in reliability checks is implemented, then it can be possible to rely more strongly upon historical data.

Thus, the exemplary system described below can store both demographic and past medical history information for individual patients, but does not make use of these factors in performing diagnostic assessments or recommendations of courses of action. However, the algorithms implemented can easily be extended into these realms once more information becomes available.

The output of Diagnostic Module 515 can be, for example, a series of recommendations. A recommendation is simply defined as any discernible bit of data which might be of interest to a medical professional, health care or life insurer, medical services analyst, researcher or other user of the present invention in determining a given course of action. In the case of a patient's immune status, a common recommendation could be, for example, to recommend a particular vaccination, to conclude whether the individual is in an overall sense healthy, to conclude that certain potential hypotheses need further data to be fully explored, to tag the individual as being potentially immunosenescent, or to grant a health insurance credit or debit relative to a health insurance policy or HMO membership fee. Or, for example, a recommendation not to vaccinate, to reduce the over-vaccination of the populace. A summary of some exemplary types recommendations that can be offered by an exemplary Diagnostic Module are provided in FIG. 7.

In exemplary embodiments of the present invention a Diagnostic Module can be capable of producing a set of recommendations for each analysis. For example, it might recommend that both vaccine V be administered and that the individual be retested in three weeks to monitor his or her response to such vaccine. For each recommendation, an exemplary Diagnostic Module can, for example, also provide a confidence level, which is a measure of the system's support for any given conclusion. A user can take this confidence level into account when deciding upon a course of action. A course of action with a low confidence level but a high financial cost, for example, could be delayed until additional data could be gathered to more strongly support the course of action.

In exemplary embodiments of the present invention a Diagnostic Module can, for example, be constructed in a manner to allow the deployment of many different algorithms within its basic shell. For the exemplary system, an algorithmic approach based upon perceptrons was used. This approach is detailed below. Additionally described are alternative algorithmic approaches, each of which has different strengths and weaknesses. It is noted that some of these approaches are realistically infeasible until such time as large-scale data collection of immune status informatics becomes available.

3.2. Perceptron Algorithms

A perceptron is a simple neural network, a computer science representation based upon an analogy with the operation of human neurons. Perceptrons were invented by Frank Rosenblatt in 1957, and have been used in artificial intelligence research since that time. A perceptron is simplistic, but adequate for the computation of algorithmic diagnostic results within the exemplary system of the invention. More importantly, there is a clear progression between perceptrons and more sophisticated artificial intelligence techniques, which may be of use in more complex embodiments of the invention.

An example of a perceptron is given in FIGS. 8 and 8A. These networks encode the decision making process for the running of a Meningococcal Diagnostic Panel, as described above. There are seventeen inputs to the algorithm, one for each of the measurements that can be taken in an exemplary meningococcal assay panel. Five inputs are for the meningococcal serogroups, seven for the complement components, and five for the genetic poymorphisms. There are two output recommendations from this panel R1 810 (or in FIG. 8A, R2 810) and R3 840. R1/R2 is a recommendation to vaccinate an individual with a meningococcal vaccine. R3 840 is a recommendation to monitor the individual on a stricter interval schedule than normal, because the individual may be more susceptible to this condition than the average individual in the populace. FIGS. 8 and 8A depict the same prerceptron, with different values for the various nodes upon firing.

With reference to FIG. 8, serum IgG levels for vaccine-preventable serogroups (A, C, W-135, and Y) of *Neisseria Meningitis* can be assessed. As seen in the fifth input to R1, the panel also has a built-in facility to measure and consider serogroup B, but there is no currently available vaccine or clearly known threshold of protection for this serogroup, so it was left blank. A serum IgG level exceeding 2.0 ug/mL for all four serogroups would be presumptive of protection in an otherwise healthy individual, i.e., an individual (i) found not deficient in serum levels of measured complement components, and (ii) having no deleterious genetic polymorphisms as indicated in the CC Test 820 and Genetic Polymorphism Test 830. There would be no immediate recommendation for meningococcal vaccination for these individuals.

The following is a description of rule execution flow for the exemplary perceptron of FIGS. 8 and 8A.

R1—Recommend Vaccination. With reference to FIG. 8. If the CC Test 820 and the Genetic Poly Test 830 show the person is normal, both of them will fire, giving a minimal total of 2.0 at R3. Then no contribution at R1 from R3, and if any of the serogourps is deficient, R1 will be at least=1.0 and R1 will fire. If the CC Test 820 or the Genetic Poly Test 830 show that the person is not normal, R3 840 will fire, giving a base total of −4.0. Nothing will be contributed from the R3 conclusion as even if the inputs to R1 810 from the four serogroup assays are all 1.0 (all deficient), this added to −4.0=0, which is <1.0, and R1 needs to be >=1.0 to fire. Thus FIG. 8 only operates as to normal individuals vis-à-vis the CC and Genetic Poly tests.

R3—Recommend Flagging. If the total at R3 840 is less than 2.0, the individual is not normal, R3 fires and the recommendation will be to flag this individual for monitoring.

FIG. 8A is similar to FIG. 8, except that it applies a different recommend vaccination rule, R2 at 810, for a different immunological context. The perceptron is modified as to values, but the nodes are identical.

R2—Recommend Vaccination. With reference to FIG. 8A, if deficiencies were to be revealed in any of an individual's complement components, or if any unfavorable genetic polymorphisms were shown to exist, then it is likely that a serum IgG level of >5.0 ug/mL (not the >2.0 UG level as in the rule of FIG. 8) for the vaccine-preventable serogroups would be desirable in these individuals. If these individuals had IgG levels exceeding 5.0 ug/mL for all four serogroups, no vaccination would be recommended. If the level of antibody to any of the four serogroups were to be below 5.0 ug/mL, then a vaccination would be recommended. If the CC Test or the Genetic Poly Test show the person is not normal, one of them will fire, giving a minimal total of 10 at R2. Then, all that is required is for one of the serogroups to be deficient (i.e., <5.0 ug/ml) in order for the recommendation at R2 to evaluate to true.

R3—Recommend Flagging. If the CC Test and the Genetic Poly Test show the person is normal, both of them will fire, giving a minimal total of 2.0. If the total is less than 2.0, R3 fires, they are not normal and the recommendation will be to flag this individual for monitoring.

Because al perceptrons operate on the data in parallel, an abnormal individual can, for example, be captured in the perceptron of FIG. 8A and can thus receive no vaccination recommendation from the perceptron of FIG. 8.

A perceptron operates through software by simulating the "firing" of nodes based upon numerical conditions being met. As each node fires, it can contribute to the firing of other nodes, in some cases positively and in some cases in an inhibitory fashion. The network as a whole has completed execution when the rightmost nodes, representing diagnostic recommendations, have either fired or have come to rest.

The perceptrons in the exemplary system were encoded manually based upon existing knowledge of diagnostic recommendations in use today. Each perceptron can be represented either graphically, as in FIG. 8, or textually, as in FIG. 9. FIG. 9 is thus a textual representation of the perceptron network using a language called XML, or eXtensible Markup Language. In the exemplary these XML files can be deployed to the diagnostic module as discrete packets. An exemplary Diagnostic Module connected to an instrument, or bank of instruments, could, for example, be configured with only those perceptron algorithms required for that site.

In addition, updated versions of these algorithms could be deployed as the algorithms are improved over time in a continuous process of system learning or iteration. Thus, in exemplary embodiments of the present invention, knowledge gained through use of the data mining module, detailed below, can be fed back into the individual diagnostic modules, thus improving the accuracy of the entire system. For example, it may be deduced through data mining of an exemplary database that the level of antibody activity which is a strong indication of the need for vaccination is lower in men than in women. A new perceptron algorithm could then be deployed, for example, including the gender of the patient as a new input node, with a link to the vaccination recommendation node.

More subtly, a perceptron can include within it a series of weights which can, for example, correspond to the importance of each bit of evidence to the recommendation procedure. Over time these weights can be continually adjusted and redeployed to reflect increased understanding of the role of each of the immunological factors being measured.

3.3. Alternate Algorithmic Approaches

There are a number of alternate algorithmic approaches which can be used within a Diagnostic Module. Each has varying strengths and weaknesses. An exemplary system can, for example, include a combination of these approaches in order to come up with the most complete recommendation for a course of action.

The process of evaluating algorithmic approaches involves a consideration of the goals which are to be met. A Diagnostic Module can, for example, be configured to optimize for any one of a number of different criteria. Possible goals can include, for example, optimizing the welfare of the patient, minimizing costs for the patient related to the disease in question, minimizing overall patient healthcare costs, and minimizing life insurance costs. The decision algorithm used in the diagnostic module can thus vary depending on how these goals are prioritized.

A key difference between a system according to the present invention and existing systems is the use of an individual's immune status information and associated data as inputs to the decision procedure. This allows the system to provide more tailored and individualized recommendations instead of relying upon aggregate statistical measures. A second key difference is the introduction of historical patient immune status and other data. It is possible, for example, that a given individual's antibody level is below some computed norm, but is in fact high in relation to that individual's past results. This might conventionally be, for example, a contraindication for vaccination, a recommendation which would not be made if the individual's immune status were only to be compared to the population standards.

Using the exemplary symbology laid out in FIG. 10, various diagnostic goals as shown in FIG. 11 can be summarized.

3.4. Additional Input Data

This section describes additional data which could be incorporated into a diagnostic module in exemplary embodiments of the present invention.

As noted above, historical immune status information can be a useful addition. Basing a recommendation solely upon an individual's status at the current point in time is an adequate approach, but it risks making incorrect recommendations for those patients who do not fall within the average range of the population at large. A simple extension to the system would be to move away from absolute measures of, for example, antibody level and antibody activity level, and to substitute instead relative measures based upon the percent change in these values since the last historical measurement, or in comparison to the individual's historical averages. The same decision procedures could be applied, but retooled so that a decision rule such as "the level is greater than 30" becomes "the level is greater than 15% above the patient's baseline". In order for this to occur, an exemplary system can either maintain a central record of the patient's immune status over time, or provide means to allow the portable storage and transfer of this historical record, perhaps under the patient's control. Various forms of "smartcard" or electronic storage technologies as are known could be used for this purpose.

A second type of additional input data relates to demographic information. Current decision procedures do little to distinguish treatment recommendations based upon an individual's age, gender or racial background, although it is known that these factors have a considerable effect on the interpretation of immune status information. Thus, an exemplary system could make use of such demographic information, customizing the diagnostic algorithms to take into account observed patterns. Additional research would be required to deduce these patterns in the population as a whole in order to make reasonable modifications to the decision procedures.

3.5. Decision Rule Algorithms

A clear successor to the perceptron approach could be to extend the system to full neural networks. The distinction between perceptrons and more complex neural networks is the incorporation into the latter of feedback links from later nodes to earlier nodes in the network. This not only increases the complexity of the algorithms which can be implemented, but allows for algorithms which improve over time through a learning mechanism. Neural networks are a well-established domain of artificial research. The primary impediment to neural networks is that they are difficult to construct by hand. A typical neural network is instead evolved through the use of training algorithms. These training algorithms require as input a set of training data. In an exemplary embodiment of the present invention, the training data could consist of immune status data from a large population of people coupled with data about the eventual onset of diseases in that population. Were such a database to exist, neural networks could be constructed which could predict the onset of disease based upon features in an individual's immune status information. An advantage to using neural networks is that they could be a simple drop-in replacement to the current Diagnostic Module in terms of inputs and outputs.

4. Data Mining Module 4.1. Overview

The Data Mining Module is the large-scale component of exemplary systems according to the present invention. As noted above, while the Diagnostic Module focuses upon obtaining results specific to a particular individual, the Data Mining Module can be, for example, designed to examine trends in large data sets assembled for many individuals and with many readings per individual. This capability is necessary to support business models in which information is deduced about immune status patterns, as well as to improve the functionality of the Diagnostic Module over time.

As noted, an exemplary system was constructed using an Oracle database server. The schema for the database system is given in FIGS. 12 through 14. The schema used is termed a 'star schema', which is a database layout optimized for online analytical processing. This is a standard concept in data mining. More information about the data storage is given below.

4.2. Sample Data

A sample database was intended to represent actual immune status information which could be collected from a large population over a large span of time. The test measurements contained within the database are randomly generated within the constraints detailed below.

The exemplary database contains three distinct sorts of information.

The first block of information is individual immune status information. As an example, the individual is assumed to be a patient in some healthcare context. The schema for the patient information table is given in FIG. 12. To summarize, the database contains information on the patient's birthdate, gender, racial background and geographic location. All of this information can potentially be used for data mining efforts related to immune status. The database also contains other information strictly for identification purposes, such as name and ID.

In the exemplary database, patient information was randomly generated. Gender was split evenly, and geographic placement was divided among four test cities. Racial backgrounds were assigned to match latest U.S. census figures available.

The second block of information is patient visit information. A schema for the patient visit information table is given in FIG. 13. To summarize, this information covers data that could, for example, be collected by a physician at the time of a patient's visit. There can be multiple visit information records for each patient. The majority of this information covers various symptoms present in the patient at the time of the visit. This information can be used within the Diagnostic Module, above, as part of an algorithm which takes into account diagnostic information other than the immune status assay results. This information can also be used in data mining to discover correlations between physical symptoms, immune status indicator levels, and subsequent onset of disease. The visit information section of the database is also used to store recommendations from the Diagnostic Module.

In the exemplary database, symptomatic information was assigned randomly. The example Diagnostic Module did not make use of symptomatic information.

The third block of information is the actual results of immune status assays. In the exemplary database there are 48 distinct simulated measured quantities, although this can be expanded, for example, to any reasonable number in a straightforward manner. The schema for this data block is given in FIG. 14.

In the exemplary database, assay test results are generated with care. The distribution of antibody levels are randomly generated based upon a log-normal distribution with an average of 50 micrograms per milliliter, as is consistent with measured antibody levels in practice. These values are used as initial baseline levels for the patients in the database. New values are then entered to simulate readings taken at set time intervals in the exemplary patients' lives, as indicated in FIG. 15. At each age, the antibody levels were perturbed using a small normal distribution, to simulate variation in the population over time. Results are biased to match the observed behavior of antibody activity in populations as they age, as shown in FIG. 16. All data in FIG. 16 is from simulated vaccinated patients.

Half of the sample population was treated as if they had received a standard vaccination schedule at age 5; the other half was left untreated. Antibody levels were adjusted to suit, as shown in FIG. 17. In addition, a subset of patients were given artificially lowered complement levels and antibody activity levels with no change to the measured antibody levels, simulating the effect of complement-deficient patients on the data mining procedure. This is shown in FIGS. 18 and 19.

The intent behind this production of sample data was to produce a population with interesting characteristics that could be highlighted in the data mining module. Although the exact features used may not be strictly representative of the population as a whole, they represent the type of correlation that a system such as this could detect within real patient data. It could easily be imagined, for example, that individuals of a particular racial background might naturally have elevated levels of a particular antibody. The system being described could be used to deduce that fact, which may have implications for the immunological care that such individuals would receive.

It is noted that all assay results, such as antibody levels, such as, for example, "Gcmp AVG" in FIG. 16, may be measured and quantified as units (U) per volume (e.g., ml), where U may be defined as some arbitrary unit of a particular assay for the purpose of relative comparisons. In addition, U may be replaced by a more precise measurement of mass, such as micrograms, where possible and appropriate. Antibody activity, such as, for example, "Gcmp AVG" in FIG. 16, refers to the functional activity of an antibody, which may consist of, but not necessarily be restricted to, bactericidal or bacterial killing properties. In these specific examples, assay results from individuals may be processed for statistical purposes in the evaluation of a population, as in FIG. 16, where individuals may be averaged (AVG) by appropriate statistical formulas. Where statistical processing assumes a normal distribution, geometric means may be used to average the results from different individuals, thereby requiring a log transformation of data sets, since it is generally found that only the log values of immune responses will follow a normal distribution.

4.3. Exemplary Use of the Patent Event Database

In exemplary embodiments of the present invention, a database used for data mining can, for example, be accessed in three different modes, as indicated in FIG. 5.

A first mode can be, for example, an interactive query mode. A user can interactively search for results in the database. Typically queries might include the retrieval of a single individual's immune status over time, or the comparison of two such individuals, as shown in FIG. 19. Queries can be submitted, for example, using either a graphical query tool or through the use of Structured Query Language (SQL), a computer language for the querying of databases. An exemplary SQL query is shown in FIG. 19A. Both of these methods of access are well-known in the industry. With reference to FIG. 5, a user can use the query mode via Query Module 531.

A second exemplary mode is the use of Online Analytical Processing tools, or OLAP tools, to find patterns within the database. A simple example of this is the production of aggregate statistics for subpopulations within the whole. In FIG. 19B, for example, a query for correlation coefficients to GCMP levels is restricted to female patients. A similar query might look at only patients from a distinct geographical area or racial background. Correlation statistics can also be generated, to test hypotheses about possible causal links among measured antibodies, between antibody measurements and physical symptoms, or correlations between any of these and demographic information. The utility of such a tool depends directly on the quantity and quality of data that is input into the system. For the exemplary system, trends that were deliberately introduced into the sample data can be "discovered", but other correlations are simply a function of random noise. In a real system, a variety of interesting patterns can be deduced. For the exemplary database, standard OLAP tools were used. With reference to FIG. 5, a user can use the data mining mode via Data Mining Module 532.

A third exemplary mode that is anticipated is the construction of a pattern detection module. This can, for example, comprise software programmed to sift through the accumulated immune status and other data and search for patterns that might not be evident to a human observer. It is generally true that there are statistically significant patterns in the underlying data which are too subtle or too complex for simple detection schemes. Such an automated detection system can, for example, rely upon one or more of the artificial intelligence pattern recognition techniques as described above and in the standard literature. In exemplary embodiments of the present invention both neural networks and genetic algorithms can, for example, be used to perform this task. With reference to FIG. 5, a user can use the pattern detection mode via Pattern Detection Module 533.

FIG. 5A illustrates an alternative exemplary system architecture to that of FIG. 5. FIG. 5A has a few additions, namely, Hypothesis Database 560 and Rules Database 565. Each of these databases can be used, for example, when pattern detection module 533 discovers a correlation between database variables. When that occurs, a list of such correlations can, for example, be reported to a human expert or group of experts for review. Or, for example, an intelligent system can attempt to recognize the characteristics of such a correlation and associate possible hypotheses to explain it. These can be generated, for example, from a Hypothesis Database 560, and the rules by which a given correlation can, for example, be mapped to one or more hypotheses can be stored, for example, in a Rules Database 565. In such exemplary embodiments, once a set of hypotheses is generated, an exemplary system itself can go back and mine the data to either rule out, corroborate, or confirm that there is insufficient data to either confirm or rule out, each hypothesis in the set. In the latter case the system can recommend that further information be collected, such as, for example, via additional assay panels known to the system, lab tests, additional patient history items, etc. This process is described in greater detail below.

C. Exemplary Canadian Immigrant Project Database Used to Illustrate Data Mining and Hypothesis Generation Appendix A contains selections (i.e. an initial set of records) from an exemplary database which was used to illustrate various data mining functionalities according to exemplary embodiments of the present invention. The database was created from data obtained in interviews with and by performing tests on blood obtained from a number of newly arrived immigrants to Canada under the auspices of Dr. Chris Greenaway (Assistant Professor in the Department of Medicine, McGill University, and a staff physician in the Departments of Microbiology and Internal Medicine, Sir Mortimer B. Davis Jewish General Hospital, Montréal, Quebec). As can be seen from the initial pages of the database, there are entries for assay results for each of measles, mumps, varicella, rubella, hepatitis A, hepatitis B, hepatitis C, tetanus, diphtheria, cytomegalovirus, strongoloides, *schistosoma*, filarial, and sixteen cytokines (IL-1α, IL-1β, IL-2, IL-4, IL-5, IL-6, IL-8, IL-10, IL-12p70, IL-13, IL-15, IL-17, IL-23, IFN-γ, TNF-α, TNF-β), as well as other factors such as age, gender, region/country of origin, socioeconomic status, etc. In the descriptions that follow, this database will sometimes be referred to as the CIP database (for Canadian Immigration Project). The entire CIP database has approximately 1500 records. The database contains, specifically, the following data:
Immunological Tests:
Hepatitis A
Measles (two different manufacturers for diagnostic testing)
Mumps
Rubella
Varicella
Tetanus
Diphtheria
Cytomegalovirus
Hepatitis B
Hepatitis C
CMV
Strongoloides
*Schistosoma*
Filaria
IL-1α
IL-1β
IL-2
IL-4
IL-5
IL-6
IL-8
IL-10
IL-12p70
IL-13
IL-15
IL-17
IL-23
IFN-γ
TNF-α
TNF-β
Historical/Demographic Data:
Region of Origin, being one of:
Sub-Saharan Africa
Latin America and South America
Caribbean
Europe
Eastern Europe
South Asia
Southeast Asia
North Africa/Middle East
Demographic information:
Date recruited
Gender
Age (all participants were adults ≥18 years of age)
Whether the interview was taken through an interpreter
Country of origin, being one of:
India
Bangladesh
Sri Lanka
Pakistan
Morocco
Vietnam
Congo
Other
Date moved to Canada
Citizenship status, being one of
Refugee claimant
Refugee
Immigrant
Other
Pregnancy
History of vaccine-preventable diseases
Participant had written vaccination record?
Participant's residence in home country had indoor toilet/no indoor toilet
If indoor toilet,
Flush?
Other?
Participant's residence in home country had outdoor toilet/no outdoor toilet
If outdoor toilet,
Outhouse?
Covered pit latrine?
Other?
Participant's residence in home country water supply
Tap inside?
Tap outside?
Closed well?
Public stand pipe?
Bottle?
Pump?
River?
Pump earth system?
Tap inside and closed well?
Other?
University education?
Participant's residence in home country degree of crowding (number of individuals/room)?
Participant's residence in home country had electricity/no electricity?

The CIP database could be augmented to facilitate a broader scope of data mining. In such embodiments results of the following assays could be added: Tuberculosis, Avian (H5N1) flu, Pandemic flu (not necessarily H5N1), Chronic infectious diseases other than CMV EBV, Herpes/Type?, Zoster outbreak/varicella antibody level following outbreak?, HPV, HIV HTLV I, *Helicobacter pylori*, Lyme disease, Tularemia, Parasite infections, Malaria, *Strongyloides*, Hantavirus, Leishmaniasis, Toxoplasmosis (particularly among pregnant women), Antibody levels to other infectious diseases currently on vaccination schedules: Hib, Pneumococcal (conjugate vs. PS vaccines); Meningococcal (conjugate vs. PS vaccines); Poliovirus; Traveler's vaccines; Japanese encephalitis; Cholera; Yellow fever; Military-specific vaccines: Anthrax, Smallpox, Plague, Rabies; Other infectious agents not currently vaccinated for, including: *Staphylococcus aureus, Moraxella catarrhalis.*

In exemplary embodiments of the present invention, the following non-immunologic data can, for example, also be obtained and stored in an individual's exemplary Immunoscore database record:
Environmental considerations
Zip/Postal code
Rural/Urban home environment
Working environment
many interactions with many people
few interactions with few people
Interactions with types of people at home/work:
adults
children/age of children
interactions with local travelers
interactions with global travelers
Commute to work
public transport/drive?
duration?
crowded/stressful?
Power source
proximity to power lines
type of fuel proximity to power plant
Water
source
well
city
nature of treatment
Nutrition
Diet
high/low fat
meat/vegetable intake
Common food infections
*Salmonella*
Cholera
Hepatitis A
Typhoid
Alcohol consumption/volume
Vitamin supplements
Fitness
Regular exercise/sedentary
Cardiac/blood pressure assessment
History of smoking
Second hand smoking
School(s) attended
Day school/boarding school
Crowding at school?
Work environment
high/low/intermediate stress
job satisfaction
occupation
work described as physical/mental/combination?
safety considerations at work?
infectious organisms present
nosocomial infections a concern?
chemical agents?
Air quality
home
work
Animal exposure
pets
work
farm
lab
leisure
wooded environment?
horseback riding?
Family/personal history:
Chronic disease/nature?
Cancer/type?
Heart disease
Diabetes
Known immunodeficiency
Asthma
Kidney disease
Liver disease
Lung disease
Allergies/type?
Mental illness
Back problems
Joint pain/injury?
Chronic fatigue
Osteoporosis
Arthritis
Epilepsy
Education level
highest grade achieved
Education type
public/private?
education environment
crowding?
stress
quality of school (measured objectively, of course)
Military service?
Nature of deployment
Service branch?
Rank It is understood that an exemplary database according to the present invention can contain records for various individuals from different countries and locales, being managed under various health care systems, and that various types of assays can be used to obtain assay results. Thus, in exemplary embodiments of the present invention, the data stored in the database can, for example, be normalized to some database wide standard defined for each data field used in the database, or, for example, can be stored in its original form and any algorithm that seeks to access data first performs normalizing of the various records which are input to that algorithm. It is for the purposes of such normalizing that information regarding assay manufacturer, type, and curve that maps an OD or other assay raw result to IUs of an antibody or other measured biochemical needs, in general, to be stored in the database.

Next described are the results of data mining and hypothesis generation studies performed on the exemplary CIP database. These examples illustrate methods and techniques that can be used in exemplary embodiments of the present invention.

D. Data Mining—Analyses and Conclusions

In exemplary embodiments of the present invention, immunologic information stored in an exemplary database (such as, for example, the CIP database, described above) can, for example, be analyzed in various ways and related to other variables in the database. Three useful examples of such analysis can, for example, include: (1) linear regression analysis on two variables to determine whether a positive or a negative correlation exists; (2) comparison of geometric mean immune values (obtained, for example, as antibody concentration, optical density, etc.) for both genders by geographical regions; and (3) percentage of positive or negative support within a population for one variable with respect to another. Examples of such analyses are described below using data from the CIP database.

1. Linear Regression Analysis—Correlation Coefficients

In exemplary embodiments of the present invention, tables of correlation coefficients (r) can, for example, be generated when comparing one particular immunologic variable (such as, for example, varicella antibody optical density) against other disease-related immune measurements, either for both genders together or separately. For example, FIG. 20 presents the correlation coefficients between Varicella OD and various other variables in the CIP database. FIG. 20 presents three tables. The top table is the correlation of Varicella OD with each of nine other variables from the CIP database for all persons in the CIP database. The second and third tables present this information segregating males and females. For example, in FIG. 20, r values have been highlighted by shading when they are either >0.05 or <−0.05, as a means of readily identifying patterns of relatedness (where |r|≥0.05 is considered as "related").

With reference to FIG. 20, Varicella optical density is obviously highly positively correlated with Varicella titration dilution, inasmuch as one is calculated from the other, but other relationships also appear, although somewhat less pronounced. If the genders are separated, then the relationships appear even more strongly, as expected, since scatter is thus reduced. From the tables presented in FIG. 20, Measles and Mumps immunity (Dade assay) appear to be slightly correlated with Varicella immunity.

The r values in the tables can also, for example, be graphed in such a way so as to better visualize any condition patterns, as is shown, for example, in FIG. 20A. Again, the Measles and Mumps relationship to Varicella stands out above the others (not considering the Varicella titration dilution data, which is obviously correlated to Varicella OD).

2. Geometric Mean Values

In exemplary embodiments of the present invention, immune data can, for example, be statistically analyzed for the purpose of characterizing populations of different geographical regions, as well as for comparing results across genders. Such mean values can thus be graphically compared by gender and region to visualize population dynamics. For example, the geometric means of Rubella antibody concentrations for different regions can be graphically analyzed by gender, as shown in FIG. 20B. With reference thereto, a trend can be seen where males have higher antibody levels than females across all populations in the database. It is also apparent that persons from Southeast Asia show a lower antibody level relative to the other regions in this study. To help facilitate this assessment, dotted lines were drawn on FIG. 20B to indicate the mean of the means (geometric) from all of the populations (excluding Southeast Asia) separately for males and females. The arrows above the bars for the Southeast Asia data show the difference between the mean values for Southeast Asia compared with such mean of the means for all other regions. It would thus appear that Southeast Asia has a lower immune profile for Rubella. This can, for example, be explained as the effect of (i) no specific Rubella vaccine program; and (ii) a possibly a lower exposure rate compared with the rest of the world, making Southeast Asians more susceptible to this disease when traveling to other geographic regions.

This finding highlights one of the many potential uses of the present invention. As described below in Section III, exemplary embodiments of the present invention can be directed to health insurance underwriting. Here, for example, knowledge of the fact that Southeast Asians tend to be vulnerable to Rubella would indicate that such persons, as a condition of maintaining insured status under a health plan or HMO, could be required to obtain Rubella vaccination.

In a similar manner, the geometric means of Hep A units in the OP database (which are inversely proportional to antibody concentrations and derived from immunoassays), were plotted in FIG. 20C for different geographical regions, again separately for each gender. In this case, it appears that there is no significant difference between males and females across all populations except one, Eastern Europe. Also, once again, Southeast Asia appears to be different from the other regions, where the Hep A antibodies are lower, as shown by higher assay units which, as noted, are inversely related to antibody concentration. In addition, persons from Eastern Europe are also seen as being generally lower in antibodies, and the Eastern European females (dotted bars) are seen as having particularly lower antibodies than the males. Again, in FIG. 20C a dotted line has been drawn to represent the mean of the means (geometric) from all of the populations, excluding Southeast Asia and East Europe, but combining males and females. Another dotted line has been drawn to represent the mean of the means from the excluded populations, except for the Eastern European females, which are noticeably higher in units (and thus lower in antibodies).

The arrows in FIG. 20C highlight the differences between (i) the overall population mean of means and the mean for Southease Asians and Eastern European males; and (ii) the overall population mean of means and the unit levels for Eastern European females. Overall, there appears to be less Hep A reactivity for Southeast Asia and Eastern Europe when compared with other regions; this is especially so among East European females. This may, for example, indicate no vaccination and possibly less exposure, with greater disease susceptibility. Thus, from a health insurance/ health management perspective, an adult female from Eastern Europe should have a Hep A vaccination.

3. Percent Support Between Variables

In exemplary embodiments of the present invention, the percentage of a population that demonstrates a positive or negative relationship for one variable with respect to another variable can, for example, be determined and graphically analyzed. For example, using data from the CIP database, Rubella antibody levels were measured in females from China, and the results were grouped according to immune status: immune support (protective high antibody level), low level support (equivocal antibody level), or susceptible support (non-immune antibody level). The percentage of each of these groups that supports an association with another immune variable, either positively or negatively, for various different diseases was then plotted in FIG. 20D. It is apparent that there is no significant difference in support for Rubella with Hep A (non-reactive or reactive) or with Varicella (positive); once again, in FIG. 20D dotted lines have been drawn to help visualize that the Rubella immune levels show no clear trend from immune to lower immunity to susceptible in these specific cases of other diseases. However, as regards Mumps, there is a clear trend for Rubella immune support when compared with Mumps. The arrow shows that there is a greater percentage of Rubella immune support for positive mumps, i.e., immune response for Rubella is correlated with that for Mumps.

The immune support of Mumps for other immune variables can, for example, also be used to compare different geographical regions, as is shown, for example, in FIG. 20E. In FIG. 20E, only the positive and negative Mumps support groups are plotted (leaving out the equivocal "low level support" group) for each of Eastern Europe and Sub Saharan Africa with respect to Hep A=non-reactive, measles=positive, and Rubella=immune. Dotted lines have been drawn to illustrate that there is no difference in Mumps immune support for Hep A=non-reactive in both regions, but the arrows show that there is a difference for Measles=positive in Eastern Europe only, and a difference for Rubella=immune in both regions. Thus, a higher percentage of Mumps immunity is seen with Measles immunity in East Europe, and with Rubella immunity in both East Europe and Sub Saharan Africa.

In exemplary embodiments of the present invention, immune support can also be related to other variables that do not measure immune status, such as, for example, education. An example of such a correlation analysis is shown in FIG. 20F. In this example, the positive and negative Mumps support groups are plotted for Southeast Asia and East Europe with respect to university attendance. From these results it appears that for Southeast Asia, a higher percentage of negative Mumps immune support occurs when there is less university attendance, and in the expected reciprocal way, a higher percentage of positive Mumps immune support occurs with university attendance. For Eastern Europe, however, there is no relationship seen between Mumps immune support and university attendance.

4. Possible Conclusions

The data mining examples described above demonstrate the usefulness, in exemplary embodiments of the present invention, of an analysis of relationships among different variables, both immunologic and otherwise in an unbiased mathematical manner. Regression analysis can, for example, be performed to just look for correlations at random, but the relationships may be weak and difficult to see. Additionally, for example, population means can be used to detect broad population differences or similarities. Also, percentage support analysis between different variables can, for example, allow for a greater focus on specific relationships between different immune status results and other factors that may affect them.

The examples described above point towards interesting correlations, some of which can be explained based on known immunization practices, and others which may, for example, indicate previously unforeseen relationships involving exposure to disease. For example, in countries where MMR (Measles, Mumps, Rubella) vaccines are administered, one might expect to see a clear correlation of immunity for all three diseases; but this would usually occur only in developed countries such as the U.S., Canada, and parts of Europe. Also, in some cases, there may only be single immunizations for Measles. The immigrant populations used in the examples discussed above, however, were most likely not immunized for the diseases under analysis, and thus most of the observed immunity would be due to environmental exposure to the infectious agents of disease, or possibly some other agents or substances that cross-react with these disease agents.

Due to socioeconomic conditions in these regions, it is possible that exposure to one disease might also indicate exposure to others, particularly in crowded areas, or areas where diseases are known to be endemic. It is therefore not surprising to see positive correlations between Mumps and Measles or Rubella, as seen in the China and Eastern Europe data. In certain circumstances, however, the disease exposure may be so prevalent (>90% of population) that there would be no way to establish correlations to other factors since everyone has it; this might be the case, for example, for Mumps support with Measles in Sub Saharan Africa as shown in FIG. 20E. Increased immunity for Mumps in Southeast Asia for those who attend a university could be the result of these more fortunate people being allowed greater access to vaccines, or, for example, it could be due to greater disease exposure in crowded dormitories. No difference in Mumps for university attendance in Eastern Europe might mean that there is greater disease incidence, or, for example, that there is greater university attendance, since both positive and negative support percentages are high. No difference in Rubella support for Hep A reactivity or positive Varicella in China may be, for example, the result of higher disease prevalence and exposure overall. A trend towards higher Rubella antibodies in males for all regions might indicate an unforeseen gender preference that could warrant further epidemiological studies in relation genetic polymorphism if this is not the result of broad cultural practices regarding vaccinations or disease exposure. The significantly lower Hep A antibody levels (higher assay units) only for females in Eastern Europe may, for example, might indicate a cultural phenomenon for further study.

These examples merely scratch the surface of what can be explored in terms of epidemiology, immunity, socioeconomics, and genetic polymorphism in exemplary embodiments of the present invention. Such exemplary analyses, can be used, for example, to design more focused studies on specific areas of interest or, for example, to test specific relationships that are only hinted at in the beginning. It is also useful to remember that the data in these examples only represent immigrants entering Canada; it may therefore be important, in exemplary embodiments of the present invention, to collect more samples and expand the database to other population segments, and/or to follow the same persons through time taking samples of each participant annually for an extended period of time.

As can be seen from the above description, in exemplary embodiments of the present invention, once a list of correlations has been obtained by analysis of a given set of records in an exemplary database, either humans or intelligent systems are needed to postulate explanatory hypothesis, which can then be verified, or at least can be attempted to be verified, excluded or determined as inconclusive.

E. Pattern Detection and Hypothesis Generation

FIG. 21A illustrates an exemplary process flow for pattern detection according to exemplary embodiments of the present invention. With reference thereto, at 21A01 patient information attributes can be collected and then grouped together into separate logical groupings. The following table illustrates such an exemplary grouping.

| Logical group | Attributes Example |
|---|---|
| Patient Information | Patient's information that never changes e.g. Gender, Birth Date |
| Current medical information | Visit date, female patient is pregnant or not at the time of visit, patient is taking medication or not etc. |
| Geography | Patient's country of origin, region of origin |
| Immune Status | Optical density of various diseases like HepA, Rubella etc and also the immune interpretation i.e. Positive, negative or susceptible for a disease. |
| Environmental conditions | Patients education level, Type of toilet, water supply, average people in house hold, number of rooms in house hold, type of water supply etc. |
| Patients medical history | Has patient been hospitalized before? If the patient had diseases like measles, mumps etc and at what age, patient has vaccine record. |
| Miscellaneous | Information that does not fall into any of the above |

Next, at 21A05, the logical groups can be prioritized in an order in which they are to be correlated. For example, one could choose the highest priority logical groups that you want to find correlations between (e.g. Immune Status v. Geography of the patient). This can be done, for example, at 21A15, for all the logical groups. At 21A20, correlations can be sought. This can be done, for example, as follows:

1. obtain the percentage of people in the same geographical regions that are immune, not immune or susceptible to diseases.
2. try to find a region where the patient population has variation in immunity status towards a disease. The reason for this is that if 89% of the people are Immune to Mumps in, say, N. America, this means that there is not enough data for people who are not immune to Mumps for evaluation. Whereas in South East Asia 67% are immune to Rubella, therefore there is a large percentage of the population (33%) that are either susceptible to Rubella or not immune. Thus when there is difference in immune status in population in the same region the remaining data can be explored to attempt to determine the cause.
3. Try to evaluate the above results by next logical group (i.e. patient information—does the immunity status of a region differ by gender?). Obtain the percentage of population by region and gender that are immune, not immune or susceptible to the disease. If there is a major variation in the percentage of male-female population for same region that are immune or not immune, then there is a discrepancy and the other data can then be explored to attempt to determine a cause.

4. Use a data mining tool to find the correlations of the next logical group (i.e., for example environmental conditions on the patients within the same region and gender and same immune status).

5. Obtain the geometric means of the optical density of the various diseases by geography and gender. This can determine if there is a difference in the antibody level between genders living in the same geographical regions. After seeking correlations at 21A20, if a correlation is found at 21A25, it can be reported at 21A27. The process can continue until all groups have been searched, and process flow ends, at 21A50.

In exemplary embodiments of the present invention, Oracle Data Miner can be used, for example, as a tool for finding patterns in a database.

Using this tool, for example, there are different ways of finding correlations in the data.

Association Rules:

Oracle data miner uses an a priori algorithm to find these association rules.

A priori Algorithm Details

Oracle Data Miner calculates the following two properties of association rules:

Support: Support of an associating pattern is the percentage of task-relevant data transactions for which the data is true.

If A=>B

Support (A=>B)=Number of tuples containing both A and B

Total number of tuples

Confidence: Confidence is defined as the measure of certainty or trustworthiness associated with each discovered pattern.

If A=>B

Confidence (A=>B)=Number of tuples containing both A and B

Number of tuples containing A

Associations can be calculated in 3 steps:
1. Find all combinations of items, called frequent itemsets, whose support is greater than minimum support.
2. Decide the minimum support and minimum confidence required for choosing the rules. As the data set under consideration was small we kept the minimum support=0.1 and minimum confidence as 0.1 so that we do not miss any data that might have any inverse co relation or strong co relation.
3. Use the frequent itemsets to generate the desired rules. Rules that satisfy both minimum support threshold and minimum confidence threshold are called strong rules. Reading the confidence and support get the rules that are correlated.

For example, association rules generated for Chinese females who are immune to rubella.

Some exemplary rules that can be generated can be, for example:

| Confidence | Support |
|---|---|
| 1.00000 | 0.25532 |
| 1.00000 | 0.74468 |
| 1.00000 | 0.17021 |

-continued

| Confidence | Support |
|---|---|
| 1.00000 | 0.80851 |
| 1.00000 | 0.97872 |

Rules

If Hep A Non-Reactive then Rubella Immune

If Hep A Reactive then Rubella Immune

If Measles=Negative then Rubella Immune

If Measles=Positive then Rubella Immune

If Varicella=Positive then Rubella Immune

Conclusions can be derived, for example, from the rules generated by data miner.

Thus, Rule 1 means that 25% of the Chinese females who are immune to Rubella are Hep A non reactive. The trustworthiness of this statement is 100%.

Regression:

Regression creates predictive models. The difference between regression and classification is that regression deals with numerical/continuous target attributes, whereas classification deals with discrete/categorical target attributes. In other words, if the target attribute contains continuous (floating-point) values, a regression technique is required. If the target attribute contains categorical (string or discrete integer) values, a classification technique is called for.

The most common form of regression is linear regression, in which a line that best fits the data is calculated, that is, the line that minimizes the average distance of all the points from the line.

This line becomes a predictive model when the value of the dependent variable is not known; its value is predicted by the point on the line that corresponds to the values of the independent variables for that record. Oracle Data Mining provides both linear and non-linear regression models.

Algorithm options: Support Vector Machines (SVM)

Support Vector Machine (SVM) is a classification and regression prediction tool that uses machine learning theory to maximize predictive accuracy while automatically avoiding over fit of the data.

Geometric Mean:

$$GM_y = \sqrt[n]{y_1 y_2 y_3 \ldots y_n}$$

The geometric mean of a set of positive data is defined as the $n^{th}$ root of the product of all the members of the set, where n is the number of members.

Another way to calculate the geometric mean, which may aid in statistical analyses, is to define it as the antilog of the mean of the log values for a set of numbers.

Exemplary Data Mining Algorithm

Using the CIP database, the following exemplary algorithm was performed:
1. The logical groups were prioritized so that the immune status (immune assay results) could be shown according to geography, followed by Gender. This is shown in all examples of the data mining (regression analysis, geometric means, and percent support). All other logical groups could be examined later for possible relationships that might help explain the observed correlations.

2. Regression analyses were performed between all immune variables at each geographic location, and by gender. Varying cut-offs could be set to detect patterns of correlations from tabulated correlation coefficients. For example, r values were highlighted in the table where they were >0.05 or <−0.05, is described above in connection with FIG. 20. This resulted a possible association of Varicella with Measles and Mumps. These r values were also graphed to facilitate any visualization, as demonstrated.
3. Geometric means of immune assay results were calculated for all geographic regions, and by gender. Graphic analyses were performed, as demonstrated, to detect differences or similarities between regions, as well as gender. For example, there appeared to be a gender difference globally for Rubella immunity in favor of males, and a lower immunity overall in Southeast Asia. Hep A showed this gender difference only for East Europe, with lower overall reactivity in both Southeast Asia and East Europe.
4. Setting the confidence at 100% for different immune subsets of a disease, different geographical regions were examined for the percent support of the association with other variables. For example, in each immune subset of Rubella (immune, low level, susceptible) for Chinese females, the percent support was determined for each of the other disease immune variables. The graph (FIG. 20D) shows that there is a greater association of Rubella immune support for positive Mumps, when compared with Rubella low level or susceptible support. In another graph (FIG. 20E), positive and negative Mumps support was associated with other diseases in different geographical locations. In this case, there was a greater percent positive Mumps support for Measles and Rubella in both East Europe and Sub Saharan Africa.
5. To enhance the chances of seeing meaningful associations, regions where there was a lower incidence of immune status result (e.g., <80%) were looked at, so that associations were not just based on the fact that everyone has a particular status. For example, if 95% of a population has a particular status, then that status could likely be associated with anything; however, as noted above, since there is 67% immunity for Rubella in Southeast Asia, then there was enough non-immunity to allow some possibility of detecting meaningful associations.
6. Other logical groups were then now be examined for other possible associations and explanations of previous associations. For example, an association was graphically demonstrated between positive Mumps support and university attendance in Southeast Asia (FIG. 20F).

FIG. 21B depicts the exemplary pattern detection process flow of FIG. 21A with additional expert system functionalities. Thus, at 21B60, for each correlation, the hypothesis database can be searched for possible explanations of the given correlation. In general, this can be done, for example, by using a Rules Database and Hypothesis as shown in FIG. 5A (and FIG. 2B) to map correlations to hypotheses according to defined rules. Once a set of hypotheses is generated, for example, at 21B65 each hypothesis can be tested, to the extent possible, automatically, using data in the system database. Finally, at 21B67, a report can be generated which lists the generated hypothesis and states, based on system data, if that hypothesis is corroborated, ruled out, or inconclusive, as next described.

Thus, in exemplary embodiments of the present invention, a Hypothesis Database (and associated Rules Database) can function as a repository for expert knowledge. When correlations are discovered by the system, these databases can be consulted to provide possible explanations as to why certain correlations may exist. A Rules Database can, for example, map—as a function of its conditions on attributes, such as, for example, the database variables involved in the correlation—correlations to hypothesis already stored in a Hypothesis Database. For example, a possible sequence may occur as follows:
1. Database Searched.
2. Correlation found between Rubella and Varicella where Antibody levels are directly proportional.
3. Consult Hypotheses Database for possible explanations.
4. Possible explanations:
   a. Cross Reactivity (when exposed to one disease, build up resistance to the other)
   b. Multiple disease vaccinations; and
   c. Patient living in an area where risk of exposure is great.
5. System can automatically seek to verify whether each hypothesis generated by the system, using the Rules Database and Hypothesis Database, as above, is valid. For example, the database records for the individuals involved in the correlation can be checked for (i) vaccinations for either or both of Rubella and Varicella, and for (ii) living and/or socioeconomic conditions conducive to exposure.
   Next, the hypothesis and the support/nonsupport/nonconclusiveness of each hypothesis can be reported to humans, as shown in 21B67 of FIG. 21B.
6. After receiving a report, each correlation can be analyzed by a human to determine if a new hypothesis should be added and fed back into the Hypotheses Database; or if an existing hypothesis is operative in the given context.

An example of this process can be illustrated with reference to FIG. 20B, which presents levels of Rubella antibody concentration across various regions using data form the CIP database. First, the data was grouped by gender and region to determine if any trends were discovered.

As noted above, it was discovered that the females in Southeast Asia had especially low levels of Rubella antibodies. Upon further, lower level, geographic analysis it was found that the individuals from China were the ones with low levels.

Possible hypotheses for this occurrence are, for example:
1. The females tested were never vaccinated for Rubella.
2. The females tested were not exposed to Rubella via the general populace.

As above, data already in the system can be used to examine the validity of each of these hypotheses.

In this way future correlations can, for example, be analyzed by the system itself to suggest possible reasons as to why trends or patterns have emerged.

Exemplary Automatic Pattern Detection Module

FIG. 21C depicts exemplary process flow for an exemplary automated pattern detection module according to an exemplary embodiment of the present invention. With general reference thereto, the following exemplary process can be implemented in exemplary embodiments of the present invention for such a module:
1. Prepare data for data mining. Most data mining algorithms require data to be suitably transformed in order to produce good results. Some common data transformations are: binning, normalization, missing value imputation, and outlier removal. In exemplary embodiments of the present invention, techniques used for transforming the data can be, for example, selected based on attribute data type, attribute value range, attribute cardinality, and percentage of missing values for an attribute or a record. (21C01, 21C03, 21C05)
2. Group the attributes of the data into different logical groups like patient current immune status, patient history, environmental conditions they lived in, geography, etc. (21C07)
3. As this is a data centric data mining system for diseases, a focal point is to get the disease immune status relativity. The attribute importance of each attribute can be found to rank them in an ascending order to determine which attributes effect patient's immune status to a particular disease. Attribute Importance ranks the predictive attributes by eliminating redundant, irrelevant, or uninformative attributes and identifying those predictor attributes that may have the most influence in making predictions. (21C07)
Example For rubella interpretation attribute the following was found:
Attribute Importance Order

| | |
|---|---|
| RUBELLA_ANTIBODY_LEVEL | 1 |
| MEASLES_OPD_ZEUS | 2 |
| ELECTRICITY | 3 |
| PT_GENDER | 4 |

4. For each disease immune status (21C15) find a correlation with all possible combinations of identified set of attributes found in Step 3. (21C1B), (21C20) For example, a correlation between Rubella interpretation and Rubella antibody level and gender was found.
5. For each correlation a threshold can be with the help of a (human) domain expert (21C30)
6. Compare the correlation found by the data miner with the thresholds set. Verify the combination of attributes resulting correlation with the disease immunity status with acceptable threshold with the hypotheses database. If such relation already exists remove this combination from further investigation.
7. If the correlation can not be explained by existing hypotheses, analyze this attribute combination further for each attribute's contribution to the correlation of the whole set of attributes with disease immune status.
8. Derive association rules for the correlated attribute set found from Step 7.
9. Check rules with the discovered set of rules for its existence.
10. Analyze the Rules for determining the patterns in the data set using line or curve fitting.
11. Report discovered pattern and verify with existing hypotheses database.

For an initial exemplary analyses of the CIP database described above, where data was received in the form of an Excel spreadsheet, and data mining was accomplished using Oracle software, the following processes were utilized. Similar processes can be implemented in exemplary embodiments of the present invention. As described below in detail, in a follow-up series of analyses on the CIP database, fully automated protocols using the PipelinePilot™ software environment were created.

1. Initial Exemplary Analysis: Data Mining Steps
1.1. Data Preparation:
  1. The data is received in .xls format.
  2. The data then needs to be scrutinized for each column and modified. Example: some columns have data like ">250". That needs to be changed to some number greater than 250 (Scientist discretion) since the data needs to be imported into the database as a number and ">250" is not a number.
  3. All the data is checked for valid values in the .xls sheet before importing into the database.
  4. Save the data.xls file as data.csv file (Comma separated file).
  5. Create the table using the data received using the script createtable.sql.
  6. Import the data from the .xls sheet into the new table using the Immnoscore.ctl file.
1.2. Association Rules:
  Association Rules provide the ability to show relationships that exist in the data.
  To find the association rules between the attributes of the data use the Oracle Data Miner (ODM). For example, obtain association rules for everyone that has a Measles Interpretation which is positive.
  1. Create a view of records that have the attribute value "measles interpretation" as "positive".
  2. Next go to Oracle Data Miner.
  3. Click on Models>Association Rules>Build.
  4. Name your Model and Click Next to continue.
  5. Specify the location of the data used to build the model.
    a. Schema: Select the schema containing the input table.
    b. Input table: Select the table or view to use.
    c. Records per Case: Select Single Record per case. (As each patient record is 1 record in your view).
    Click Next to continue.
  6. ODM supports Apriori Algorithm to build Association Rules. You can change the defaults.
    Minimum Support: A real number between 0-1.Ask the scientist for details.
    Minimum Confidence: A real number between 0-1.Ask the scientist for details.
    Limit Number of Attributes in Each Rule: Number between 2-100.
  After specifying the values Click Next to continue.
  7. Select data preparation if any is required. Click Next to continue.
  8. Choose the attribute to include in your model. Click Next to continue
  9. Click Finish to queue your mining activity.
  10. Once the mining activity is executed without error, get the rules based on Rule Length Ascending, Support Descending and Confidence Descending.
  11. Export the rules to an .xls sheets.
1.3. Regression:
  Regression Models provide the ability to predict numerical attributes about data entities.
  Steps:
  1. Create an Oracle View from the main table with all the numerical fields that you want in your regression model.
  2. Click on ODM.
  3. Click Model>Regression>Build
  4. Name your Model. Click Next to continue.
  5. Specify the location of the data used to build the model.
    Schema: Select the schema containing the input table.
    Input table: Select the table or view to use.

Records per Case: Select Single Record per case. (As each patient record is 1 record in your view).
Click Next to continue.
6. ODM uses the Support Vector Machine algorithm for regression. Change the values of the defaults by asking the scientists. Currently defaults given by ODM are used.
7. Click Next to Continue.
8. Select Automatic Preparation option for your Model. Click Next to continue.
9. Select the attribute you want to predict. Click Next to continue.
10. Select all the attributes that must be in your model. Click Next to continue.
11. Click Finish to queue the mining task on the server.
12. Once the task is done export the results to an .xls sheet.

F. Automated Data Mining

In exemplary embodiments of the present invention, partially or fully automated processing of the data in an exemplary database can be implemented in various ways. The following describes five exemplary software tools that can be used in exemplary embodiments of the present invention. These tools were created and then used to analyze an expanded version of the CIP database. As noted above, approximately 20% of the records of the CIP database (i.e., the first 330 records) are provided in Appendix A hereto for easy reference.

1. Exemplary Software Development Environment

The below described software tools have been implemented using Scitegic Software's Pipeline Pilot™ programming tool. The Scitegic approach, known as data pipelining, uses a data flow framework to describe the processing of data. FIGS. 21D-1 through 21D-37 illustrate the following discussion.

Data pipelining is the rapid, independent processing of data records through a branching network of computational steps. It has several advantages over conventional technologies, including:

Flexibility: Each data record is processed independently, allowing processing to be tailored to each record.
Speed: Highly optimized methods allow rapid analysis of thousands (or millions) of data records.
Efficiency: Individual processing of data records limits memory use so that many protocols can be executed simultaneously.
Ease of use: Protocols are easy to construct, with visualization that exposes key data processing steps.
Integration: Data pipelining is a powerful tool for connecting the different data sources, databases, and applications required in the drug-discovery enterprise.

Thus, Pipeline Pilot provides environments to design, test, and deploy data processing procedures called protocols. A protocol is made up of a set of components that perform operations such as data reading, calculation, merging, filtering, and viewing. The connections between components define the sequence in which data is processed. Data from files, databases, user input, and the Internet is merged, compared, and processed, according to the logic of the protocol.

Protocols are constructed with a graphical drag-and-drop interface. The work environment is divided into windows. On the left, the Explorer shows the contents of the database of available components and prebuilt protocols. Additionally, a user can save new protocols in the database of components and publish them for enterprise-wide sharing and reuse. On the right, the workspace provides a way to create new protocols by dropping and connecting components.

The visual representation makes it simple to understand critical data processing steps in a potentially complicated procedure. Components are displayed as function-specific icons clearly identified with descriptive labels. Data records are passed between components through pipes represented by gray lines.

2. Client-Server Computing

Pipeline Pilot employs the client-server model of computing FIG. 21D-1. The professional client provides a way to create and edit components and protocols, which are stored on the server. All protocols are executed on the server. The server can also connect to resources on other machines, including files, databases and third party applications. This architecture provides a convenient way to integrate Pipeline Pilot and distribute resources efficiently across different locations.

3. Third-Party Applications

Many Pipeline Pilot components integrate with third-party applications such as, for example, Microsoft Word and Excel, Spotfire Decision Site, and Accelrys DS ViewerPro. A user can use these applications to read from, write to, and view data.

4. Extending Pipeline Pilot

Pipeline Pilot includes the following types of components that extend the program's functionality:

Open Database Connectivity (ODBC): A user can access databases such as Oracle, SQL Server, and MS Access that reside anywhere on the user's network. ODBC components allow a user to select, insert, delete, and update data.
Run Program Components: A user can execute an operating system command on the server or on a user's client and extend the functionality of a protocol to include any operation that a user can invoke from a command line. For example, a user can write out one or more data files, invoke the command line program to work on these files, and then read the results back into the protocol when the command execution is completed.
Simple Object Access Protocol (SOAP) services: A user can make requests to a calculator or service that resides on Unix, Linux, and other remote machines. The SOAP component sends the necessary data to the SOAP server, collects the results, and adds the data to the current record.
Scripting: A user can write scripts in one of the supported syntaxes (VBScript, Perl, Java and Python) and use them in protocols. The script has access to the contents of each data record passed to the script component and to the relevant protocol properties. This allows a user to write components such as data readers, data writers, data filters, and calculators.
Visualization tools: Standard visualization tools such as Internet Explorer, Excel, Spotfire, and Accelrys' viewer software are integrated with Pipeline Pilot. Additional third party viewers can be created by exporting the appropriate data file and executing an operating system command to start up the visualization software and read in the data file.

5. Integrating Protocols

Pipeline Pilot works with data and computer services that commonly exist on user networks. After writing and publishing a protocol, a user can access the functionality of the protocol from environments other than Pipeline Pilot. For example, a user can run protocols on the Pipeline Pilot server from Internet Explorer, integrate a protocol into a third-party application such as Excel or Spotfire Decision Site, run protocols from SOAP clients or from the command line on any computer where a Pipeline Pilot client or server is installed.

Next described are five exemplary automated data mining tools that were implemented in Pipeline Pilot, and that were used to analyze the CIP database described above.

6. Data Mining Tool

This tool is designed to find correlations between variables, or fields in a database, across populations.

Run Application From:

Webport is the out of the box web-based client for Pipeline Pilot. Protocols can be deployed to Webport by saving them in the Protocols\Web Services folder within Pipeline Pilot. Webport users simply go to a web page and from this location protocols can be run. Users do not even need to know that Pipeline Pilot is being used; to the user it is simply a web page where information can be obtained.

This paradigm is used for all protocols deployed via Webport.

Protocols

Protocols|Web Services\Wellstat_v3\Data Mining Tool
    Protocols|Web Services\Wellstat_v3\Utilites\Filter Form with Binning
    Protocols|Web Services\Wellstat_v3\Utilites\Filtered Graph with Binning From Webport, all protocols are visible, except those protocols stored in a folder called Utilities. Because of this, all of the protocols that are performing queries and calculations are "hidden" in the Utilities folder. The Data Mining Tool protocol is outside of the Utilities folder and thus it is visible from Webport. This protocol is merely a shell that points to the first protocol that needs to be run. On the protocol's Implementation tab, the Protocol Form parameter points to the protocol which will actually be run when the user clicks on the Data Mining Tool in Webport. For the Data Mining Tool, this protocol is the Filter Form with Binning protocol. The data entered into the form created by Filter Form with Binning is passed to Filtered Graph with Binning.

A protocol is composed of components, which are the building blocks within Pipeline Pilot. In general a component performs a particular task. Multiple components can be collapsed into a Subprotocol. In this case, multiple components appear to be a single component as one looks at the protocol. When a user double-clicks on a subprotocol, it opens to show the components that make up the subprotocol. In this way, a subprotocol can hide more complex logic.

Input:

Below is a screen shot of an exemplary embodiment of a data mining tool and its user interface. It is via this interface that a user can input information that will be passed to the data mining tool. As can be seen from the figure, this particular version of the data mining tool is called "Data Munger With Binning."

As can be seen from the exemplary screenshot in FIG. 21D-2, a user can select which properties to group by, including the bin size for any groups for which binning is desired. It is often convenient to bin by age in 5 or 10 year increments. An upper and lower correlation threshold can also be set. Options regarding output format can include, for example, selecting to show the Value Table for each heat map and/or to create a PDF version of the output.

Lower and upper values for the standard deviations across groups can also be specified. This is used to determine which attribute pairs appear in the Difference Between Groups output tab. This allows the user to set the cutoff values for which attribute pairs are "interesting" based on how much variation there is between the groups.

The protocol is set up to point to the necessary data files. The parameter that points to the full data file is at the top level of the protocol, so that the administrator of this application can easily set the path to the full data source. The Full Data Source parameter is accessed by clicking on the white space of the protocol, as illustrated in FIG. 21D-3.

Output:

There are up to 4 output tabs for this application:
Filters
PDF of Filters (optional)
Differences Between Groups
Whole Data Set Pie Charts for Each Group The first output tab includes a Pie Chart showing the percentage of the population that makes up each group for which a Heat Map was created. One correlation matrix and heat map are created for each data group, including only the selected attributes (such selected attributes are selected from the interface at the "Attributes to Include in Heat Map" field). Only correlation values within the specified range will be shown. If the Show Value Table option is selected, the values for the heat map are also displayed in a table. If the Create PDF option is selected, a second tab is created for a PDF version of the report.

FIG. 21D-4 depicts an exemplary data set distribution pie chart, an exemplary correlation matrix visualized as a heat map corresponding to the segment of the database represented by the pink upper left piece of the pie, and a list of all the cells in the heat map and their actual correlation values.

In addition, a tab displaying the differences between groups for each pair of attributes can be created as illustrated in FIG. 21D-5. Only attribute pairs that have a standard deviation within the upper and lower standard deviation thresholds will be displayed. The table can, for example, be sorted by decreasing standard deviation values, as shown below. This report allows the user to assess which attribute pairs may be interesting based on the differences between the groups. For example, attribute pairs which have a larger standard deviation can be used to create different patient suggestion rules for different groups within the populations.

A final results tab can show the distribution of the data set for each of the properties the data has been grouped by, as separate pie charts. Taking both properties together results in the two property pie chart shown in FIG. 21D-6.

Application Design:

As shown in FIG. 21D-7, there are three major steps involved in this application:
Data preparation and grouping (red)
Creation of Correlation Matrices and Heat Maps (purple)
Creation of Reports (green)

FIG. 21D-8 illustrates the Data Mining Tool protocol, which includes subprotocols, illustrated in FIG. 21D-9, for Data Prep, Filtered Heat Maps and Difference Table creation and the creation of the Distribution Pie Charts. The components shown are actually subprotocols, which are composed of multiple components to carry out the described tasks.

The data set is grouped so that each group (i.e., each segment of the database that resulted from the "Group By" choices made via the interface) of data can be acted on independently. For each group, a correlation matrix is calculated and a Heat Map is used to display this data.

The correlation value for each attribute pair is then compared across all of the groups and the standard deviation is calculated. This can be used to determine whether the correlation is "universal" across the database, or only seen within certain defined segments.

The various pieces of information that are created are then placed into the appropriate report outputs.

7. Single Patient Vaccine Recommendations

Run Application From:

Webport

Protocols

Protocols|Web Services\Single Patient Vaccine Recommendations

Protocols|Web Services\Utilites\Single Patient Form

Protocols|Web Services\Utilites\Single Patient Treatment Suggestions

Protocols|Web Services\Utilites\Create Learn Models (to be run only once prior to these protocols)

The Single Patient Vaccine Recommendations protocol is outside of the Utilities folder and thus it is visible from Webport. This protocol is merely a shell that points to the protocols that do the work. On the protocol's Implementation tab, the Protocol Form parameter points to the protocol which will actually be run when the user clicks on Single Patient Vaccine Recommendations in Webport. For the Single Patient Vaccine Recommendations, this protocol is the Single Patient Form. The data entered into the form created by Single Patient Form is passed to Single Patient Treatment Suggestions. Create Learn Models must be run prior to using the Single Patient protocols.

Input:

A user browses to locate a file with a patient's data. An exemplary Webport user interface is shown in FIG. 21D-10.

The protocol is set up to point to the necessary data files. These parameters are at the top level of the protocol, so that the administrator of this application can easily set the paths to the specified sources. These parameters are accessed by clicking on the white space of the protocol.

The Rules database is comprised of several files. Rules Source contains the information about the Rule_ID and the Suggested Action. The Rules Definition Source contains information about which conditions must be met for each rule. And Conditions Source contains information about conditions that are used to describe the rules, for example, Pregnancy=1.

There are also files for internal and external references. The Keyword Source file documents the keywords for a each rule. The Literature Source file contains information about published documents, including a field containing Keywords that are used to link the document to rules via the Keyword Source file.

Output:

The result page has two sections. The Results table shows which rules the patient satisfies, including the Conditions, Suggested Action, Internal References and External References.

The Patient Data table shows the results for each assay, including predicted values. The percentiles for the entire data set, the patient's sex, the patient's age group and the patient's region of origin are also included for all OD and TITRE properties.

Below is an image of an exemplary output for an exemplary individual in the database, the first record of the CIP database provided in Appendix A below. In this exemplary embodiment, each rule in the Rule Database is compared to the patient's test values. If the patient matches all of the conditions for the rule, the rule is considered "satisfied" and will appear in the Results Table, illustrated in FIG. 21D-12, including the conditions, suggested action, internal and external references for that rule.

Application Design:

As can be seen in FIG. 21D-13, there are three major steps involved in this application:

Data prep (red)

Determining Satisfied Rules (purple)

Create Tables for Report (green)

As part of the data preparation, the patient's data is read in and any properties that are missing can be predicted using learn models created using the Create Learn Models protocol (which must be run once prior to running this protocol). This protocol, illustrated in FIG. 21D-14, creates a Learn Model for each property that is specified as a property that should be predicted. These Learn Models can be called from other protocols in order to calculate values for properties for patients that are missing values.

The percentiles for the patient are calculated relative to the total population, his or her age bin, his or her sex and his or her region of origin.

The patient's results are then used to determine which of the rules in the Rules Database are satisfied, as illustrated in FIG. 21D-15. The patient data table includes all values in the original patient data file, any predicted values, and the various percentile calculations.

For any rule that is satisfied, the information about the suggested action, internal and external references are joined in from the appropriate files. This information is displayed in the Results table.

8. Patient Population Rule Mining

Run Application From:

Webport

Protocols

Protocols|Web Services\Wellstat_v3\Patient Population Rule Mining

Protocols|Web Services\Wellstat_v3\Utilites\Multiple Patient Form

Protocols|Web Services\Wellstat_v3\Utilites\Multiple Patient Treatment

Protocols|Web Services\Wellstat_v3\Utilites\Multiple Patient Data Link Table

The Patient Population Rule Mining protocol is outside of the Utilities folder and thus it is visible from Webport. This protocol is merely a shell that points to the protocols that do the work. On the protocol's Implementation tab, the Protocol Form parameter points to the protocol which will actually be run when the user clicks on Patient Population Rule Mining in Webport. For the Patient Population Rule Mining, this protocol is the Multiple Patient Form. The data entered into the form created by Multiple Patient Form is passed to Multiple Patient Treatment. The Multiple Patient Data Link protocol is run when the user clicks on a bar in any of the output graphs.

Input:

A user browses to locate file with patient's data and selects what property to bin on. For properties that require binning, the bin size is also entered. An exemplary interface appears below, which allows a user to select a file to read, and select the variable to graph by (with or without binning). In the example shown in FIG. 21D-16, the graphs are drawn according to age, in bins of 20 years.

The protocol is set up to point to the necessary data files for the Rules Database. parameters are at the top level of the protocol, so that the administrator of this application can easily set the paths to the specified sources. These parameters are accessed by clicking on the white space of the protocol, as illustrated in FIG. 21D-17.

A description of the files that make up the Rules database can be found in the section describing the Single Patient Vaccine Recommendations.

Output:

As shown in FIG. 21D-18, the output of the Patient Population Rule Mining protocol consists of bar charts and a summary table with information about the standard deviation for each rule across the groups.

The Bar Chart in FIG. 21D-18 shows the percent of the data set that satisfies each rule. There is also a table that shows the standard deviation for each rule between the groups of data (for example the different age bins). Rules that have a standard deviation greater than 5% are highlighted. For each data group there is a Bar Chart showing the percent of the data set that satisfies each rule. One patient can be included in multiple bars within each chart; the bars do not add up to 100%. For example, if a patient satisfies both Rule 1 and Rule 2, that patient is included in both bars. There is also a bar displaying patients that did not satisfy any of the rules. This is useful for understanding what percent of the patients have no suggested actions. As illustrated in FIG. 19, clicking on a bar creates a new window that shows the data records that make up that bar.

Application Design:

As can be seen in FIG. 21D-20, there are three major steps involved in this application:

Get Rule Definitions and Calculate Rules for Each Patient (red)

Grouping of Patients and Calculation of Standard Deviation (purple)

Creating tables and charts for reporting (green)

The determination of which rules are satisfied for each patient is done in the same way that the Single Patient rule determination is done. A Bar Chart is created showing how many patients in the full data set satisfy the criteria for each rule. There is also a table showing the standard deviation for each rule across the patient groups.

Each patient is placed in the appropriate bin and the number of patients satisfying each rule in each bin is calculated. Bar Charts are created showing the percent of patients within each group that satisfy each rule. Clicking on a bar in any of the Bar Charts creates a new HTML page showing the data that makes up the bar.

9. Age Binned with Differences

Run Application From:

Pipeline Pilot Client

This protocol can also be deployed from Webport if desired. A user can then run the protocol without having to install the Pipeline Pilot client.

Protocols

Protocols|Web Services\Wellstat_v3\Utilites\Age Binned with Differences

Input:

The protocol can be set up to point to the Full Data Source. Also the property to bin on, and the bin size can be entered via the protocol's top level parameters, illustrated in FIG. 21D-22. These are accessed by clicking on the white space of the protocol. To have this report use a different property and bin size, the user can simply change the prop_list_bin parameter to the property of interest and the bin_size parameter to the desired bin size. Different bin sizes and/or properties can be selected and the protocol can be run multiple times, in order to illuminate how different groupings can affect the correlation values. In exemplary embodiments of the present invention, a "brute force" binning by every binnable property of interest can be automatically launched via multiple copies of this protocol operating in parallel and all the correlations thereby obtained out put to a cache or a list. Corresponding correlations can then be compared as to correlation values to isolate the best grouping relative to maximizing each such correlation.

A user can also, set the upper and lower threshold for the standard deviation to be used to filter the results. These parameters can be changed to any desired values. In this example, the lower standard deviation threshold is set to 0.50 which will limit the output to only those attribute pairs that have this level of deviation. The upper deviation level is set at 2, which is the maximum deviation (−1 to 1).

Output:

As illustrated in FIG. 21D-23, each chart displays the correlation values for a pair of attributes across all of the bins, in this example, age with a bin size of 5 years. One XY Chart is created for each pair of attributes. Each chart displays the correlation value for a different attribute pair across the entire age spectrum (or whichever property the user specifies). This output allows the user to quickly identify which bins of the data have significantly lower or higher correlation values. Also, patterns of differences across groups can be identified by looking at the output graphs as a whole.

Application Design:

As seen in FIG. 21D-24, there are three major steps involved in this application:

Data prep and creation of correlation matrices

Calculating the Standard Deviation of the correlation values for each Attribute Pairs Creation of XY Charts The entire data set is read in and the data binned on the specified property, in this example age binned with a bin size of 5, giving 12 bins ranging from age 20-75. A correlation matrix is created for the data for each age bin.

The correlation value for each pair of attributes can then be compared over the entire age range and the standard deviation calculated. Also, the percent of the population contained within each bin is listed. This information can be used to identify bins with only a very small sample size.

Attribute pairs can be, for example, filtered out if the standard deviation of the correlation values across the age bins (value_StdDev) is not within the lower and upper stddev thresholds. Attribute pairs that are not filtered out, are plotted in an XY Chart, as shown above.

10. Automated Data Mining

Run Application From:

Pipeline Pilot Client

This protocol could also be deployed from Webport if desired. This would allow users to be able to run the protocol without having to install the Pipeline Pilot client.

Protocols

Protocols|Web Services\Wellstat_v3\Utilites\Automated Data Mining

Protocols|Web Services\Wellstat_v3\Utilites\Automated Run—Parallel

The Automated Run—Parallel protocol can be used to create a data cache of the correlation value, attribute pair and group information for all possible groups: The list of groups can be generated using a nested loop script, as described below. Automated Data Mining can then use this cache (described above) to create a report showing what grouping gives the highest correlation value for a particular attribute pair. In an exemplary implementation, the Automated Run—Parallel protocol was run to create all the data caches that are then used by Automated Data Mining as inputs. This was done because running Automated Run—Parallel on a PC takes approximately three hours with the CIP data base as an input. Thus Automated Run—Parallel is assumed to have been already been pre-run as a data prep step by Automated Data Mining. Accordingly, pre processing the database and creating the cache allows for running Automated Data Mining in real time. With more computational power, Automated Run—Parallel can simply be connected to Automated Data Mining and both protocols can run from start to finish in an automated fashion.

Input:

The protocol is set up to point to the Full Data Source. This parameter can be, for example, accessed by clicking on the white space of the protocol, as illustrated in FIG. 21D-25.

Output:

FIG. 21D-26 illustrates the two outputs generated by this application. A tabular output shows all of the correlation values for a particular attribute pair across all groups, above the specified correlation threshold and standard deviation threshold. An absolute correlation value threshold can be set by the user. This report allows users to quickly identify how best to maximize the correlation value for a particular attribute pair.

The second output is created by starting with a particular group, for example Measles_OD_DB_Int=0 and looking at what additional grouping can be added to increase the correlation values for a particular attribute pair. The graphs show the original correlation value as a green line and the improved correlation values as red dots, one dot for each new grouping. Each point on the graph has a mouse-over tooltip showing the grouping and correlation value. A table is also created displaying the data for each point on the graph.

Application Design:

As seen in FIG. 21D-27, there are four major steps involved in this application:
 Generation of all possible groups (blue)
 Creation of one correlation matrix per group
 Organization of the data by Attribute Pairs
 Creation of tables and XY charts Because generating the correlation matrix data is more time consuming than the other data manipulation and generation of the reports, this application has been broken into two protocols. However, this is not a requirement. The Automated Run—Parallel protocol performs the first two steps. Automated data Mining performs the last two steps. Automated Run—Parallel generates a correlation matrix for each possible grouping, from single property groups (such as, for example, sex or age) to as many groups as desired.

After the Automated Run—Parallel protocol is used to create correlation matrices, the Automated Data Mining protocols can perform an analysis and generation of the reports. The Automated Run—Parallel protocol is designed to create one correlation matrix for each possible group. This data can be used in a variety of ways.

A simple nested loop, illustrated in FIG. 21D-28, can be used, for example, to create all of the possible data groups, including any binning necessary. This nested looping script adds all unique data groups to the prop_list property and the associated bin size information to the bin_size property.

A file can be used to store the information about bin size for these groups. The file is composed of two fields, one for the name of the property and one for the bin size of that property. The grouping and creation of the correlation matrices can be done in the same way as for the other protocols listed above. Once the correlation matrix is created, the data contained in the table can be manipulated and displayed in a variety of ways.

In the example illustrated in FIG. 21D-29, this was implemented for up to a grouping of two properties, but any additional number of properties can be added as desired. For each possible group, the data can be used to create a correlation matrix and the data is added to a data cache which is used in the report creation. Since there are many possible ways to work with the correlation matrix data once it is created, the cache makes the correlation data accessible without having to rerun the part of the application that creates this information.

As can be seen, the Automated Run—Parallel protocol has a subprotocol, namely Subprotocol 1, at the end of pipe 2 (pipe 2 snakes around for ease of viewing). This subprotocol is where a correlation matrix is created for a group. Subprotocol 1 detail is illustrated in FIG. 21D-30.

Detail of Filtered Heat Maps, a subprotocol in the third pipe of Subprotocol 1, is illustrated in FIG. 21D-31.

Finally, subprotocol "for HTML", illustrated in FIG. 32, (in the fourth pipe of the "Filtered Heat Maps" subprotocol of Subprotocol 1 of pipe 2 of Automated Run—Parallel), is where the correlation matrix for each group is created. The data is stored in a data cache so it can be accessed by the Automated Data Mining protocol.

As noted, after Automated Run—Parallel has preprocessed the data, then Automated Data Mining begins processing. FIG. 21D-33 illustrates its high level processes. The Data Prep subprotocol takes the data from the cache created by Automated Run—Parallel and groups and cleans up the data in preparation for creation of the report. This step could be moved to Automated Run—Parallel in order for all data preparation to be done in that protocol. Detail of the Data Prep subprotocol of Automated Data Mining is illustrated in FIG. 21D-34.

The two subprotocols belonging to the Data Prep subprotocol of Automated Data Mining are illustrated in FIG. 21D-35.

In the exemplary implementation the data is displayed in two ways, in HTML output and in a PDF file. The protocols to do this, Create Graphs and Create Tables, are illustrated in FIG. 21D-36.

11. Data Files Used in Pipeline Protocols Described Above

As noted above, to run the above described protocols a number of data files are drawn from. The exemplary files used were a set of Excel spreadsheets placed in a data folder, as illustrated in FIG. 21D-37.

As can be seen from the screen shot of the Data\Wellstat folder, the files used were CIP_data.xls, Conditions.xls, Literature.xls, Rule_Definition.xls, Rules.xls, and Rules_Keywords.xls. These files, their contents, and their functions are next described.

CIP_data.xls

This is the complete CIP database described above, the first 330 records of which are provided below in Appendix A.

Literature.xls

This is an internal database created to capture known information from literature and other sources regarding any conditions, diseases or symptoms that a particular bioassay result, or a combination of such results, may be a marker for. An exemplary literature database was constructed to catalog the indications of bioassay results provided in the CIP database Copies of the Conditions.xls, Rules.xls, Rules_keywords.xls, and Rule_Defininition.xls spreadsheets are provided in Exhibit A as well.

Conditions.xls

The Conditions.xls spreadsheet was used in applying defined rules to the Single Patient Vaccine Recommendations protocol. It can also be used, for example, in Patient Population Rule Mining embodiments.

Rules.xls

The Rules.xls spreadsheet was used in applying defined rules to the Single Patient Vaccine Recommendations protocol. It can also be used, for example, in Patient Population Rule Mining embodiments.

Rule_Definition.xls

The Rule_Definition.xls spreadsheet was used in applying defined rules to the Single Patient Vaccine Recommendations protocol. It can also be used, for example, in Patient Population Rule Mining embodiments.

Rules_keywords.xls

The Rules_keywords.xls spreadsheet was used in applying defined rules to the Single Patient Vaccine Recommendations protocol. It can also be used, for example, in Patient Population Rule Mining embodiments.

12. Complete Copy of Exemplary Pipeline Pilot Code (Provided on CD)

A complete copy of the Pipeline Pilot code is provided in Appendix C hereto, which is submitted on a CD for ease of viewing. Further information regarding the contents of the CD is provided in Appendix C below.

G. Exemplary Internal Hypothesis Database

Appendix B exemplifies the type of hypothesis database that can be constructed using scientific articles and other literature regarding antibody markers to assist an ImmunoScore database user in building serological correlates for immunologic and other information stored in an exemplary database (such as, for example, the CIP database). So named as a "hypothesis database," the database can provide a user with all available information regarding two variables found to be correlated. The known information may, but often may not, explain the observed correlation. If it cannot, it can at least marshal whatever is known regarding the variables implicated in the correlation.

In exemplary embodiments of the present invention, a hypothesis database can be constructed using a software spreadsheet application, such as, for example, Microsoft Excel, Word Perfect Quattro Pro® or Lotus 1-2-3®. Spreadsheet columns can be set up to record data obtained from the scientific articles as follows, for example:

| Spreadsheet Column | Information Recorded |
| --- | --- |
| A | Assay (or Marker) |
| B | Assay Family |
| C | Assay Code |
| D | Assay Test Type |
| E | Sample Size |
| F | Percent (%) Support |
| G | P Value/Confidence Interval (CI) |
| H | Interpretation |
| I | Disease/Condition |
| J | Source |
| K | Notes |

Upon reviewing a scientific article about an assay or marker, and making a determination that it contains data suitable for entry into the database (i.e., for example, that the study is not based on just one or only a few study subjects, that the study reports P values and/or confidence intervals, that the study provides numerical data supporting the results reported), each specific assay or marker discussed by the article can be entered in a separate row of Column A of the spreadsheet. The assay family to which the assay or marker belongs can be entered in Column B of the spreadsheet. Each specific assay (or marker) can be assigned an assay code, which can be entered in Column C of the spreadsheet. The specific kind of test performed to identify the assay (or marker), such as, for example, enzyme-linked immunoassay (ELISA), particle agglutination, sandwich enzyme immunoassay, neutralization assay, solid phase enzyme immunoassay, molecular enzyme immunoassay, can be entered in Column D. The total study sample size (including controls) can be entered in Column E of the spreadsheet. Numerical data supporting the study results reported, such as, for example, the number of study subjects out of the total subjects exhibiting the specific assay (or marker), the percentage of study subjects exhibiting the specific assay (or marker), the number of study subjects having serum concentration levels less than, equal to, or greater than a certain amount, can be entered in Column F of the spreadsheet. P values and/or 95% Confidence Interval values correlating with the numerical data supporting the study results can be entered in Column G, such as where only one study result is entered in Column F. Where more than one study result is entered in Column F, p values and/or 95% Confidence Interval values, can be included in Column F together with the study results to which each such value pertains. The interpretation of the study results by the scientific article's author(s), such as, for example, a particular antibody level may indicate an active infection with a particular disease or acquired resistance to reinfection with a particular disease or may be associated with the presence of another disease, can be entered in Column H. The particular disease or condition in connection with which the assay (or marker) has been detected, such as, for example the detection of anti-diphtheria antibodies in HIV-1 infected subjects, can be entered in Column I. The source of the data entered in Columns A through I and in Column K, such as, for example, the author(s) and title of the scientific article from which the data was obtained, as well as the name of the journal, volume number, issue number (if available), page numbers and year in which the article was published, can be entered in Column J. Other data reported in the specific scientific study identified in Column J, such as, for example, the geographical location where the study was conducted, the nationality of the study subjects, the gender breakdown of the study subjects, whether the study examined more than one assay (or marker), and the age of the study subjects, may be entered in Column K.

Appendix B, attached hereto, is a printout of the exemplary CIP hypothesis database created using Microsoft Excel. Because of printing constraints, Columns A-H of each row of the database can be found on odd-numbered pages, while Columns I-K of each row of the database can be found on even-numbered pages.

The various automated data mining protocols described above (and whose complete code is provided in Appendix D), can, for example, draw upon the information captured in the exemplary CIP hypothesis database, as next described.

In one embodiment, an exemplary system can retrieve data entered in the exemplary CIP hypothesis database to perform a single patient analysis. For example, if serological assays indicate that an individual patient has both filarial antibodies and *strongyloides* antibodies, the exemplary system can retrieve the data from the exemplary CIP hypothesis database rows 2, 3, and 5. Row 2, for example, contains data captured from an article entitled "Predictive markers for development of *strongyloidiasis* in patient infect with both *Strongyloidiasis stercoralis* and HTLV-1," by M. Satoh et al., and published in *Clinical Experimental Immunology* Vol. 133: 291096 (2003) (Column J). The captured data includes, for example, that particle agglutination (Column D) was used to test HTLV-1 (a retrovirus, in the same class of virus as the AIDS virus, and is associated with a rare form of blood dsycrasia known as Adult T-cell Leukemia/lymphoma (ATLL) and a myelopathy, tropical spastic paresis) antibody titer (Column A) in 44 (Column E) patients infected with *Strongyloides stercoralis* (a nematode) in Okinawa, Japan, and that 31 patients (18 males, 13 females) were HTLV-1-positive and 11 patients (7 males, 4 females) were HTLV-1-negative (Column K). Antibody titer in the direct fecal smear-positive group (8,192 median ranging up to 28,672) was higher than in the direct fecal smear-negative group (4,096 median ranging up to 15,360) (P<0.05) (Column F). There was a significant correlation (p=+0.566, P<0.01) between the HTLV-1 proviral load and the antibody titer, and an inverse correlation between HTLV-1 proviral load and EBNA (Epstein-Barr Virus) antibody titer (detected by anti-complement immunofluorescence) (p=−0.387, P<0.05) indicating that increased HTLV-1 proviral load was especially related to lowering of immune status perhaps resulting in an increase of *S. stercoralis* load via immunity impairment (Column K). The authors concluded, inter alia, that the activity of HTLV-1 infection influences the results of direct fecal method of measuring HTLV-1 antibody titer in patients infected with both *S. stercoralis* and HTLV-1 (Column H). Row 3, for example, contains data captured from an article entitled "L3 antigen-specific antibody isotype responses in human *strongyloidiasis*: correlations with larval output," by N. S. Atkins, et al., and published in *Parasite Immunology*, Vol. 21: 517-26 (1999) (Column J). The captured data includes, for example, that immunoblotting (Column D) was used to test for IgA antibody (Column A) in 34 patients (Column E) consisting of two groups of chronically infected (for more than 30 years) ex-Far East Prisoners of War with and without detectable *Strongyloides stercoralis* larvae (Column K). IgA reactivity with six immunodominant *S. stercoralis* antigens was significantly elevated in individuals with undetectable larval output (Column F) (P<0.05 for three antigens and P<0.01 for one antigen) (Column G), and IgE recognition of four *S. stercoralis* antigens was significantly higher among individuals with larval output (Column F). The authors concluded, inter alia, that the results were consistent with an IgA-mediated immune effector mechanism in modulating larval output (i.e., inhibiting worm fecundity and egg viability) and IgE playing a prominent role in acquired resistance to reinfection (Columns H and K). The authors postulated that parallel upregulation of IgE and IgG4 responses to certain antigenic components suggests IgG4 blockage of IgE-mediated allergic responses and may be central to establishment and persistence of asymptomatic chronic *strongyloidiasis* (Column K). Row 5, for example, contains data captured from an article entitled "Detection of filaria-specific IgG4 antibodies and filarial DNA, for the screening of blood spots for *Brugia timori*," by P. Fischer, et al., and published in *Annals of Tropical Medicine & Parasitology* 99(1): 53-60 (2005) (Column J). The captured data includes, for example, that *Brugia* rapid (BR) (an antibody-detection dipstick test) and PCR (polymerase chain reaction)-based assays (Column D) were used to test for IgG4 antibody (Column A) in 66 individuals (Column E) from Alor island, East Nusa Tenggara, Indonesia (which is an area highly endemic for *Brugia timori*) (Column K). Thirty-seven (37) of the 66 individuals (56.1%) of filter-paper blood spot eluates were positive using the BR test (32 strongly and 5 weakly), while the plasma samples of 47 of the 66 individuals (71.2%) were positive; 9 (23.4%) of the BR filter-paper blood spot eluates positives were PCR-positive (Column F). The authors concluded, inter alia, that, in general, the presence of microfilaremia is associated with relatively high titers of anti-filarial IgG4 (Column H).

In another embodiment, the analysis of population heat maps can be supplemented by drawing upon the information captured regarding the assays (or markers) implicated in a given correlation from the exemplary CIP hypothesis database. For example, if analysis of population heat maps generated by the Pipeline Pilot software reveals a correlation between hepatitis C virus (HCV) and *schistosomiasis*, as is described below, the exemplary system can retrieve the data from the exemplary CIP hypothesis database on *schistosomiasis* from row 4 and on hepatitis C from rows 44, 47-48, 51, 61-124, 136, and 148-150. Row 4, for example, contains data captured from an article entitled "The antibody responses to adult-worm antigens of *Schistosomiasis haematobium*, among infected and resistant individuals from an endemic community in southern Ghana," by Y. Osada, et al., and published in *Annals of Tropical Medicine & Parasitology*, Volume 97(8): 817-26 (2003) (Column J). The captured data includes, for example, that enzyme-linked immunoassay (ELISA) (Column D) was used to test for IgE, IgG, IgA and IgM antibodies (Column A) in 27 individuals (Column E) infected with *Schistosoma haematobium* (11 endemic normal subjects; 16 patently infected subjects) in Okyerko, the Gomoa district of Ghana, where *S. haematobium* is endemic (Column K). Endemic normal subjects were generally older than patently infected individuals (P<0.001); the male-female ratio was higher in patently infected individuals than in endemic normal individuals, although the difference was not statistically significant (P>0.05); and for patently infected individuals and for patently infected and endemic normal individuals combined, *S. haematobium* egg output was negatively correlated with the water-contact index (Column K). Endemic normals have similar levels of IgM antibody, higher levels of IgA (P<0.05) and lower levels of IgE (P<0.01) and IgG (P<0.05) than patently infected individuals; for combined endemic normals and patently infected individuals, males had levels of IgM, IgA and IgE similar to that of females, but significantly higher levels of IgG (P<0.01); when the patently infected and endemic normals were considered as a single group, *S. haematobium* egg outputs positively correlated with levels IgE (P 0.01) and IgG (P<0.001); in the patently infected group alone, only the correlation with IgG was statistically significant (P<0.01); the P values for the positive correlation of IgG and IgE in endemic normals only, patently infected only, and endemic normals and patently infected combined were 0.01, 0.05 and 0.001, respectively; positive correlations between levels of specific IgG and IgE were statistically significant only when data for endemic normals and patently infected individuals was pooled (P<0.05); levels of specific IgA and IgE were positively correlated in the patently infected group (P<0.01), but not in the combined group; and levels of specific IgA and IgG were positively correlated in the endemic normals (P<0.05), but not in the combined endemic normal and patently infected group (Column F). The authors concluded, inter alia, that the relatively high levels of IgG and IgE may directly reflect "active" current infection or that the high level of specific IgG seen in the patented infected group may reflect the presence of blocking antibodies; and that IgE and IgG antigens can be used as markers to reflect current infection intensity and that anti-worm antibodies do not act as protective antibodies in the natural course of urinary *schistosomiasis* (Column H).

A sampling of the kind of data regarding hepatitis C captured from the articles in rows 44, 47-48, 51, 61-124, 136, and 148-150, is exemplified by the data from, for example, rows 44 and 51. Row 44, for example, contains data captured from an article entitled "Viral markers and use of factor products among Finnish patients with bleeding disorders," by F. Ebeling, et al., and published in *Haemophilia* 7: 42-46 (2001) (Column J). The captured data includes, for example, that ELISA (Column D) was used to test for hepatitis C antibody (Column A) in 193 patients (Column E) with bleeding disorders (hemophilia A or B, type 3 von Willebrand disease or factor XIII deficiency) in Finland, 179 (93%) of whom were males (Column K). Fifty-one percent (51%) of the patients were anti-HCV positive (Column F), and the authors interpreted this positivity as being associated with blood transfusions (Column H). Row 51, for example, contains data captured from an article entitled "The clinical epidemiology and course of the spectrum of renal diseases associated with HIV infection," by Lynda A. Szczech, et al., and published in *Kidney International*, Volume 66: 1145-52 (2004). The captured data includes, for example, that hepatitis C antibody (Column A) was identified in 89 HIV-infected patients who underwent renal biopsy during the course of clinical care at six major medical centers in the United States, 47 of whom had lesions other than HIV-associated nephropathy (HIVAN) and 42 of whom had HIVAN lesions (Column K). Patients with lesions other than HIVAN were less likely to be black (37/47 vs. 42/42, P=+0.02), less likely to have hypertension (24/26 vs. 31/24, P=0.03), more likely to have greater creatinine clearance at the time of biopsy (60.6 vs. 39.0 mL/min, P=0.008), and have greater CD4 lymphocyte count at time of biopsy (287 vs. 187 cells/mL, P-0.04); all patients with HIVAN were black (Column K). Unadjusted survival curves demonstrated better renal survival among patients with non-HIVAN lesions (P=0.002) (Column K). Patients with lesions other than HIVAN tended toward being more likely to be infected with hepatitis C (25/41 vs. 17/41, P=0.08); and the presence of hepatitis C antibody was associated with a faster time to the institution of renal replacement therapy (HR 2.60, P=0.01) (Column F). The authors concluded, inter alia, that patients with nephropathy other than HIV-associated nephropathy were more likely to have hepatitis C antibodies (Column H).

In another example, if analysis of population heat maps generated by the Pipeline Pilot software reveals a correlation between measles and hepatitis, as is described below, the exemplary system can retrieve the data from the exemplary CIP hypothesis database on measles from rows 9, 12, 27-31, and 34 and on hepatitis from rows 44-53, and 55-157.

A sampling of the kind of data regarding measles captured from the articles in rows 9, 12, 27-31, and 34, is exemplified by the data from, for example, rows 27 and 34. Row 27, for example, contains data captured from an article entitled "Measles antibody in vaccinated human immunodeficiency virus type 1-infected children," by Stephen M. Arpardi, et al., and published in *Pediatrics*, Volume 97(5): 653-57 (1996) (Column J). The captured data includes, for example, that ELISA (Column D) was used to test for measles antibody (Column A) in 81 perinatally HIV-infected children with prior documented receipt of measles vaccine (i.e., monovalent measles or combination measles-mumps-rubella), with a median age of 42 months at the time of study, and a median age of 14 months at first vaccination (Column K). Overall, 58 subjects (72%) had measles neutralization assay antibody titers >1:5 (Column K). Children studied within 1 year of vaccination were significantly more likely to have detectable measles antibodies than those studied more than 1 year after vaccination (83% vs. 52%, P<0.01), and the proportion of children with detectable measles antibody was greatest for children with no evidence of immunosuppression and lowest for children with severe immunosuppression (Column F). The proportion of children with detectable measles antibody was significantly lower for children with CD8 greater than the $95^{th}$ percentile for their age and for children with lower CD4/CD8 ratios (Column F). The authors concluded, inter alia, that the prevalence of measles antibody in vaccinated HIV-infected children was considerably lower than in healthy children (only 72% of previously vaccinated children had measles antibody detected by neutralization assay, in contrast to 95% among healthy children), that the proportion of children with detectable measles antibody declined over time, and that revaccination for seronegative HIV-infected children was not likely to be effective once immunodeficiency was established (Column H). Row 34, for example, contains data captured from an article entitled "Clinical presentation of subacute sclerosing panencephalitis in Papua New Guinea," by Charles S. Mgone, et al., and published in *Tropical Medicine & International Health*, Volume 8(3): 219-27 (2003) (Column J). The captured data includes, for example, that enzyme immunoassay (EIA) (Column D) was used to test both serum and cerebrospinal fluid for measles-specific IgG antibody (Column A) in 95 children with a clinical diagnosis of subacute sclerosing panencephalitis (SSPE) from within Eastern Highlands province of Papua, New Guinea (Column K). Twenty-eight children had had measles, 28 had not and 14 were uncertain; the verified mean age for contracting measles was 8.8±2.7 months, the majority of children who had measles had contracted the infection in the first year of life, the mean age at which SSPE was manifested was 7.9±2.6 years, and the time between the measles illness and the onset of SSPE was 6.2±1.9 years (Column F). The authors concluded, inter alia, that high titers of measles antibodies are found in the serum (>200,000) and/or cerebrospinal fluid (>2000) of SSPE children (Column H), and that, although the pathogenesis of SSPE is not fully understood, the accumulated evidence suggests that it arises from persistence of altered measles virus in the brain (Column K).

A sampling of the kind of data regarding hepatitis captured from the articles in rows 44-53, and 55-157, is exemplified by the data from, for example, row 133. Row 133, for example, contains data captured from an article entitled "A Seroprevalence Survey of Hepatitis B Markers among Haitians in a Southwest Florida Farming Community," by Michael D. Malsion, et al., and published in *American Journal of Public Health*, Volume 75(9): 1094-95 (1985). The captured data includes, for example, that radioimmunoassays (Column D) were used to test for HBsAg (hepatitis B surface antigen), anti-HBc (antibody to hepatitis B core antigen) and anti-HBs (antibody to hepatitis B surface antigen) (Column A) in 123 Haitian women attending a prenatal clinic in Immokalee, Fla., a small, migrant farmworker community during a 12-month period (Column K). Twenty-eight out of 51 (55%) Haitian mothers had one or more HBV markers; 2/51 (4%) asymptomatic mothers were HBsAg positive and children of these women (aged 1 to 3 years) were negative for all HBV markers; 4/7 (57%) of the infants less than 6 months old and their mothers were antibody positive, but none were HBsAg positive; 3/54 (6%) of the children 1-4 years old were antibody positive and none were HBsAg-positive (Column F). The authors concluded, inter alia, that a large proportion of the Haitian women in Immokalee have been previously infected with HBV, and a small percentage are probably chronic HBsAg carriers; of the 7 HBsAg-positive women identified, only 1 was HBeAg positive; the infants of 2 HBsAg-positive women were negative for HBV markers, suggesting that the risk of perinatal transmission of hepatitis for infants born to HBeAg-negative women is low; and the small portion of children 1-4 years old with HBV markers suggests the risk for sib-to-sib transmission in this age group is also low (Column H).

If a correlation is found that is hitherto unknown (and thus interesting), a user will want to try to best explain the correlation as well as why it is or is not uniform across various segments of a given population. Providing such a user with both information from internal databases, as well as information obtained from external databases, is thus very useful. Such internal database could include, for example, the exemplary CIP hypothesis database. External databases can include all known sources of immunological, medical, epidemiological, and related information, such as NIH, Medline, PubMed, patent databases, etc. An external database search can be launched, for example, using a real time external text analytics tool, such as is provided as a protocol in the Pipeline Pilot Software described above.

Thus, in exemplary embodiments of the present invention, after running an automatic data mining program on a given database, the results in the form of a set of "interesting" correlations can, for example, be generated. These correlations can then be further automatically processed, by running an internal as well as external text search on them to associate with each variable in the correlation known information that hypothesizes a basis for the correlation found. If no such hypothesis is available, which is generally the case for truly counter-intuitive and novel correlations, such information as is then known regarding each of the variables in the correlation can be marshalled via such searching, and can be output in a report of a user. This can assist such a user in formulating a hypothesis or in ruling one out.

H. Explanation and Basis of Exemplary Rules Created for Processing CIP Database

As described in the Automated Data Mining section above, a rules database was created for processing individual records or populations from the CIP database. This was called "Rules.xls" and is provided in Appendix A below. The following describes the rationale and basis for various ones of these rules.

For example, Table 1 displays an exemplary set of the exemplary Canadian Immigrant Population assays and their interpretations.

TABLE 1

| CIP Assays and Possible Interpretations | |
|---|---|
| CIP Assay | Possible Interpretation |
| Measles | +/−/equivocal |
| Mumps | +/−/equivocal |
| Rubella | +/−/equivocal |
| Varicella | +/−/equivocal |
| Tetanus | OD → IU → no interpretation |
| Diphtheria | OD → IU → no interpretation |
| Cytomegalovirus (CMV) | +/− |
| Strongyloides | +/−/equivocal |
| Filaria | +/−/equivocal |
| Schistosoma | +/− |
| Hepatitis A | +/− |

TABLE 1-continued

| CIP Assays and Possible Interpretations | |
|---|---|
| CIP Assay | Possible Interpretation |
| Hepatitis B | |
| HBc Ab | +/− |
| HBs Ab | + (not apparent) |
| HBs Ag | reactive/non-reactive |
| HBe Ab | reactive/non-reactive |
| HBe Ag | reactive/non-reactive |
| Hepatitis C | |
| HCV Ab | +/−/"grayzone" = equivocal |
| HCV PCR | +/− |
| HCV LIA | +/− |
| IL-1 alpha | reactive/non-reactive |
| IL-1 beta | reactive/non-reactive |
| IL-2 | reactive/non-reactive |
| IL-4 | reactive/non-reactive |
| IL-5 | reactive/non-reactive |
| IL-6 | reactive/non-reactive |
| IL-8 | reactive/non-reactive |
| IL-10 | reactive/non-reactive |
| IL-12p70 | reactive/non-reactive |
| IL-13 | reactive/non-reactive |
| IL-15 | reactive/non-reactive |
| IL-17 | reactive/non-reactive |
| IL-23 | reactive/non-reactive |
| IFN-gamma | reactive/non-reactive |
| TNF-alpha | reactive/non-reactive |
| TNF-beta | reactive/non-reactive |

Exemplary Rules for Measles-Mumps-Rubella (MMR) Testing

All patients are tested for measles-mumps-rubella antibodies. Positive results require no further action. Negative or equivocal results in any one of these assays would indicate need for immunization with MMR vaccine. Equivocal results in any one assay should require a booster immunization, while negative results would indicate a series of two immunizations.

As with all live virus vaccines, women known to be pregnant should not receive the MMR vaccine, and pregnancy should be avoided for four weeks following vaccination with MMR. However, women who are breast-feeding can be vaccinated. Children and other household contacts of pregnant women should be vaccinated according to the recommended schedule.

Severely immunocompromised persons should not be given MMR vaccine. This includes persons with conditions such as congenital immunodeficiency, AIDS, leukemia, lymphoma, generalized malignancy, and those receiving treatment for cancer with drugs, radiation, or large doses of corticosteroids. Household contacts of immunocompromised people should be vaccinated according to the recommended schedule.

Although persons with AIDS or HIV infection with signs of serious immunosuppression should not be given MMR, persons with HIV infection without symptoms can and should be vaccinated against measles.

Exemplary Rules for Varicella Testing

All patients are tested for varicella antibody. Positive results require no further action. Children under the age of 13 with no history of chicken pox and negative results should receive two immunizations four to eight weeks apart. Children with equivocal results and no history of disease should receive one booster immunization and be retested after one year.

Herpes zoster (shingles) is a currently a risk for patients over 60 years of age. Patients in that age category, who do not have an immunodeficiency, and have a negative or equivocal result, should receive one dose of zoster vaccine specifically formulated for adults. An immunodeficiency in these individuals would include a history of primary or acquired immunodeficiency states including leukemia; lymphomas of any type, or other malignant neoplasms affecting the bone marrow or lymphatic system; or AIDS or other clinical manifestations of infection with human immunodeficiency viruses. This vaccine is not indicated for women of child-bearing age and should not be administered to pregnant females.

Exemplary Rules for Tetanus Testing

All patients should be tested for tetanus antibody. Patients with less than the minimum protective level of 0.01 International Units (IU)/mL should be given a booster dose of tetanus vaccine. Individuals over seven years of age receive the vaccine in combination with diphtheria vaccine (Td). Those children younger than seven years of age can be boosted with a vaccine containing a pertussis component (DTaP). People who had a serious allergic reaction to one dose of tetanus toxoid should not receive another. Persons with a moderate or severe acute illness should postpone receiving the vaccine until they are improved.

Exemplary Rules for Diphtheria Testing

All patients should be tested for diphtheria antibody. Patients with less than the minimum protective level of 0.01 IU/mL should be given a booster dose of diphtheria vaccine. Individuals over seven years of age receive the vaccine in combination with tetanus vaccine (Td). Those children younger than seven can be boosted with a vaccine containing the pertussis component as with the tetanus vaccine described above. People who have had a serious allergic reaction to one dose of DTaP, DT, Td, or Tdap vaccine should not receive another. Persons with a moderate or severe illness should postpone receiving the vaccine until their condition has improved.

Exemplary Rules for Cytomegalovirus (CMV) Testing

All patients should be tested for CMV antibody. A negative result would require no specific action.

As previously described, a positive result may be indicative of possible immunosuppression in these individuals as they age. Periodic diagnostic monitoring of these patients with positive antibody levels should be triggered and furthermore, increase in frequency as they age.

As annual flu immunizations and periodic booster immunizations against pneumococcal infection have little effect in the elderly with high CMV titers, patients with very high levels of CMV antibody potentially may have different vaccine recommendations than the general population:

Patients over 65 years of age with repeatedly high CMV levels should have their younger contacts (children and grandchildren) vaccinated annually against influenza. In addition, these same contact individuals should have their pneumococcal vaccinations up-to-date. Depending on recommendations by the ACIP and AAP, these individuals may possibly be recommended to not receive the annual influenza immunization.

Patients over 65 years of age with repeatedly high CMV antibody levels should also be regularly screened for routine Th1/Th2/Treg/Th17 cytokine levels to assess immune balance and any autoimmune diseases should be closely monitored by regular ImmunoScore diagnostic screening.

Patients 50-65 years of age with repeatedly high CMV levels should have regular influenza vaccinations and be checked every 2-5 years for antibody levels to pneumococcal polysaccharides used in vaccines currently marketed. Similar to the elderly group, patient contacts (children and grandchildren) should also have up-to-date influenza and pneumococcal immunizations.

Patients 50-65 years of age with repeatedly high CMV antibody levels should also be regularly screened for cytokine levels as described above. Onset of autoimmune disease and flares should be monitored closely by the health care providers.

Patients younger than 50 years of age with repeatedly high CMV antibody levels should be regularly immunized against influenza, and should be examined every 2-5 years for antibody levels to pneumococcal polysaccharides used in current vaccines.

Patients younger than 50 years of age with repeatedly high CMV antibody levels should be regularly screened for cytokine levels.

Patients younger than 50 years of age with repeatedly high CMV antibody levels may be an ideal group to test with immunotherapeutics under development.

Exemplary Rules for *Strongyloides* Testing

All patients should be tested for *Strongyloides stercoralis* antibody. Negative tests require no follow-up action. A positive or equivocal result would indicate the further examination of stool samples. Microscopic examination of stool specimens is insensitive; estimates for a single positive stool examination in cases of uncomplicated infection range from 0 to 66%. To overcome this lack of sensitivity, investigators have recommended examination of up to seven stool specimens; use of more sensitive and labor-intensive methods of stool examination; use of agar plate cultures; and collection of alternate specimens, such as duodenal aspirates.

Due to these difficulties in diagnosing the progress of *strongyloides* infections, reported efficacies of drugs used to treat *strongyloides* infection vary widely. Chemotherapy is advocated and considered an effective control measure for the reduction of morbidity resulting from intestinal nematode infection. The current drug of choice for *strongyloides* is the benzimidazole compound, thiabendazole. This drug requires a three day regimen. Another drug being considered is ivermectin, which may be preferable, because it requires only one dose. Post-treatment follow-up testing recommendations would require stool sampling 30 days post-treatment.

Exemplary Rules for Filaria Testing

All patients should be tested for antibody to filarial worms, *Wuchereria bancrofti* and *Brugia malayi*. Negative tests require no follow-up action.

Filarial worms reside in the lymphatic system, and therefore likely have a great impact on the body's immune defense systems. Though infection is usually acquired early in childhood, filarial disease can take years to manifest. Many infected individuals develop no clinical symptoms underscoring the need for routine diagnostic testing in endemic areas.

Individuals that are positive for filaria antibody should be treated with a combination of albendazole with either diethylcarbamazine or ivermectin. This treatment has been shown to be over 99% effective in removing microfilariae from the blood for a full year after treatment. Seropositive individuals should be screened one year after treatment.

Patients that have equivocal antibody levels should be re-tested after several weeks to determine if they are in the early stages of infection. If they then have a positive result, they should be treated as above. If negative, no further action is required.

Exemplary Rules for *Schistosoma* Testing

All patients should be tested for worms that cause *schistosomiasis*. Patients that have negative tests require no follow-up action.

Patients are infected by contact with water used in normal daily activities such as personal or domestic hygiene and swimming, or by professional activities such as fishing, rice cultivation and irrigation. *Schistosomiasis* is endemic in 74 tropical developing countries. Some 600 million people are at risk of becoming infected. Population movements and refugees in unstable regions contribute to the transmission of *schistosomiasis*.

Patients who have a positive antibody result should be treated depending on the manifestation of illness. Praziquantel is used to treat all forms of *schistosomiasis*. Oxamniquine is used exclusively to treat intestinal *schistosomiasis*, and metrifonate is effective for the treatment of urinary *schistosomiasis*. No further intervention is typically needed following treatment for 2-5 years. According to the World Health Organization (WHO), treatment of *schistosomiasis* must be accompanied by health education to preclude re-infection.

Exemplary Rules for Hepatitis A Virus (HAV) Testing

All patients should be tested for total antibody to HAV. HAV testing evaluates total antibody levels to HAV among patients. If a patient tests positive for anti-HAV, a further test for anti-HAV IgM is performed to determine presence of acute infection. Currently approved assays do not detect less than 100 mIU/mL of antibody, yet levels as low as 10 to 20 mIU/mL are thought to confer protection. The CDC does not currently recommend revaccination of healthy individuals with undetectable antibody levels.

The most likely time for an HAV-infected person to spread HAV to others is during the two weeks before the infected person develops symptoms. Clearly, if a person doesn't even know that he or she is infected, it makes it difficult to protect others from getting the infection. The risk of spreading HAV becomes smaller over time and can still be present one week or longer after symptoms develop (e.g., yellowing of skin and eyes). Infants are more likely to be capable of spreading HAV for longer periods of time.

If an unvaccinated person thinks that he or she might have been exposed, he or she should call their health professional immediately to schedule an appointment to determine whether a real exposure has occurred and whether Ig should be administered. Ig is a concentrated dose of human antibodies that includes anti-HAV. In most cases, this preparation can protect an exposed person from developing HAV infection.

People at increased risk for exposure to HAV infection or those who are more likely to get seriously ill if infected with HAV should be vaccinated. According to CDC recommendations, these individuals include All children at age 1 year (12-23 months)
People aged 12 months or older who are traveling to or working in any area of the world except the United States, Canada, Western Europe, Japan, New Zealand, and Australia
Men who have sex with men
Illegal drug users, both oral and injecting
People who have blood clotting disorders
People who work with HAV-infected primates or with HAV in a research laboratory setting. No other groups have been shown to be at increased risk for HAV infection because of occupational exposure.

People with chronic liver disease are not at increased risk of getting infected, but are at risk for developing serious complications if they get infected.
Any person who wishes to be immune to hepatitis A Hepatitis A vaccine is NOT routinely recommended for healthcare workers, sewage workers, or daycare providers. Children who are not vaccinated by age two years should be vaccinated as soon as feasible.

Exemplary Rules for Hepatitis B Virus (HBV) Testing

All patients are tested for anti-HBs (antibody to hepatitis B surface antigen) and anti-HBc (antibody to hepatitis B core antigen). Depending on the results of these two tests, additional testing will be performed as follows (FIG. 1):

POSITIVE/POSITIVE If the patient has positive results for both tests, the HbsAg (hepatitis B surface antigen) is measured. This test is done to determine whether patients are chronic carriers of HBV infection. In cases in which the HBsAg test is negative, no further tests are performed, and the results are interpreted as indicating a patient exposed to hepatitis B virus that has cleared the virus. If the HBsAg test is positive, the person is identified as a chronic carrier of hepatitis B. Patients positive for HBsAg are further tested for the presence of antibody for hepatitis B core antigen IgM (IgM anti-HBc), hepatitis B e antigen (HBeAg), and antibody to hepatitis B e antigen (anti-HBe) to evaluate the level of viral replication.

POSITIVE/NEGATIVE Patients testing positive for anti-HBc only are then tested for HBsAg. Whether the HBsAg test is positive or negative, the plasma is further tested for IgM anti-HBc, HBeAg, and anti-HBe to evaluate the level of viral replication. Any positive result in this series of tests indicates that the patient is a chronic HBV carrier.

NEGATIVE/POSITIVE Patients testing negative for anti-HBc but positive for anti-HBs may have been either vaccinated or exposed naturally to HBV, or this may represent a false-positive result (no exposure). These individuals will be retested the following year.

NEGATIVE/NEGATIVE Patients testing negative for both anti-HBs and anti-HBc have not been exposed to HBV and will be retested the next year.

It is estimated that about 1 out of 3 of the nearly 1 million Americans with chronic HBV infection acquired their infection as infants or young children. Those with chronic HBV infection are most likely to spread the infection to others. Infants and children who become chronically infected have an increased risk of dying prematurely from liver cancer or cirrhosis.

In contrast to other vaccine-preventable diseases of childhood, HBV infection in infants and young children usually produces no symptoms. Thus, the small number of reported cases of hepatitis B among children represents the tip of the iceberg of all HBV infections in children. For every child with symptoms of hepatitis B, there are at least 100 HBV-infected children with no symptoms—hence the increased risk to spread the infection to others without knowing it.

Second, early childhood infection occurs. About 16,000 children under 10 years of age were infected with HBV every year in the United States before routine infant hepatitis B vaccination was recommended. Although these infections represented few of all HBV infections in the United States, it is estimated that 18 out of 100 people with chronic HBV infection in the United States acquired their infection during early childhood. Clearly, infections occur among unvaccinated infants born to mothers who are not HBV-infected. In addition, unvaccinated foreign-born children account for a high proportion of infections. More effort needs to be placed on vaccinating these unprotected children.

Hepatitis B vaccine, usually a three-dose series, is recommended for all children 0-18 years of age. It is recommended for infants beginning at birth in the hospital. All older children who did not get all the recommended doses of hepatitis B vaccine as an infant should complete their vaccine series as soon as possible. Most states require hepatitis B vaccine for school entry. Adolescents who are just starting their series will need two or three doses, depending on their age and the brand of vaccine used. Adults at increased risk of acquiring HBV infection should also be vaccinated. In addition, the vaccine can be given to any person who desires protection from hepatitis B.

- Groups of adults at increased risk of HBV infection
- Healthcare workers and public safety workers with reasonably anticipated risk for exposure to blood or blood-contaminated body fluids
- Men who have sex with men
- Sexually active people who are not in long-term, mutually monogamous relationships
- People seeking evaluation or treatment for a sexually transmitted disease
- Current or recent injection drug users
- Inmates of long-term correctional facilities
- People with end-stage kidney disease, including predialysis, hemodialysis, peritoneal dialysis, and home dialysis patients
- Staff and residents of institutions or group homes for the developmentally challenged
- Household members and sex partners of people with chronic HBV infection
- Susceptible (non-infected) people from United States populations known to previously or currently have high rates of childhood HBV infection, including Alaska Natives, Pacific Islanders, and immigrants or refugees from countries with intermediate or high rates of chronic HBV infection.
- International travelers to regions with high or intermediate rates of HBV infection.

In addition, any adult who wishes to be protected from HBV infection should be vaccinated without having to acknowledge a specific risk factor.

Exemplary Rules for Hepatitis C Virus (HCV) Testing

Testing protocol begins with screening patient sera for the presence of antibody to HCV.

POSITIVE If the patient tests positive for anti-HCV with a ratio of optical density of sample signal to optical density of cutoff signal (S/C ratio) between 1.0 and 3.0, a confirmatory test is done to rule out a false positive anti-HCV result. Confirmatory tests are usually both performed (either PCR and LIA as in the OP study, or PCR and RIBA). If the PCR result is positive, then positive anti-HCV will be considered a true positive. If both the confirmatory tests are negative, the antibody result is considered to be a false positive. If the RIBA is indeterminate and the PCR is negative, then the interpretation of the positive anti-HCV result is uncertain. It could be a false positive, or the person could be chronically infected with HCV or in the process of seroconversion.

All patients who are found to have no or questionable evidence of past exposure to HCV (FIG. 3) will be retested the following year.

NEGATIVE If the anti-HCV test is negative, PCR testing for the presence of HCV RNA is conducted to rule out a false negative anti-HCV test. If the PCR test is positive, the patient is considered HCV infected and no further testing need be performed. If the PCR result is negative, the patient will be retested the following year.

FIG. 21D-38 depicts an exemplary algorithm for Hepatitis A Virus (HAV) testing, FIG. 21D-39 depicts an exemplary algorithm for Hepatitis B Virus Testing, and FIG. 21D-40 depicts an exemplary algorithm for Hepatitis C Virus (HCV) Testing, according to an exemplary embodiment of the present invention.

I. Interpretation of Certain Results of Automated Data Mining

Heat Map Correlations

Parasitic Worms and Hepatitis C

The various automated data mining protocols described above (and whose complete code is provided in Appendix D), can, for example, create population heat maps from the exemplary CIP database. These population heat maps may show positive, negative or no correlation between and among various assays (or markers) or between and among assays and other variables within the CIP population. For example, the population heat maps revealed a correlation between antibody reactivity to parasitic worms and hepatitis C viruses. To explain this an exemplary system could, for example, automatically consult an internal hypothesis database to search for possible explanations for the correlation. As can be seen from the CIP hypothesis database described above and provided in Appendix B, none of the parasitic worm references discuss hepatitis and none of the hepatitis C references discuss parasitic worms. Thus, in exemplary embodiments of the present invention, the exemplary system could, for example, then launch an internet search and access various internet databases, such as, for example, PubMed, MedLine, Science Direct, and NIH, as well as the Internet in general, to find any information that might offer an explanation regarding the observed correlation. In the present example, a search of scientific articles available in the PubMed database provided a basis for this observed worms-hepatitis C correlation as described below.

Hepatitis C virus (HCV) infection is the main cause of chronic liver disease in Egypt and is largely associated with *schistosomiasis*. Concomitant infection with HCV and schistosomes can cause aggravation of liver damage. These two infectious agents have been shown to have similar adverse effects on the immune system, as manifested by their action on cytokine production by Th1 and Th2 cells. Patients coinfected with hepatitis C virus and *Schistosoma mansoni* show high incidence of viral persistence and accelerated fibrosis. It is possible that enhancement of a Th2 response in co-infected individuals plays a role in persistence and severity of HCV infection in patients concomitantly infected with *S. mansoni*.

Patients infected with schistomsoma frequently show a high seroprevalence of anti-hepatitis C virus (anti-HCV) antibodies. The exact underlying mechanism by which *schistosomiasis* enhances HCV seropositivity is unknown. In Egypt, evidence suggests that individuals over the age of 40 have been exposed more to the risk of HCV infection through inadequately sterilized needles used in mass antischistosomal treatment campaigns conducted from the 1960s through the 1980s. Some researchers have postulated that patients designated low positive for HCV antibody perhaps were falsely positive due to the generation of autoantibodies in connection with *Schistosoma mansoni* infection.

A striking clinical feature of HCV infection is that more than 50% of patients with acute HCV develop chronic infection. It has been noted that activation of Th2 responses seems to play a role in the development of chronicity in these patients. However, the possibility of helminth or nematode co-infection in these patients was not examined.

Another research group investigating the possible diagnostic role of IL-10 measurement, postulated that elevated IL-10 correlated in HCV-positive schistosomal patients with the development of morbidity. Co-infected individuals appear to have increased Th2-related cytokines, and *schistosomiasis* may down regulate the normal stimulatory effect that HCV infection would have on Th1 cytokines, leading to the chronicity of HCV infection and playing a role in unresponsiveness to interferon therapy in co-infected patients. The same group of researchers found that HCV infection correlated with an alteration of serum immunoglobulins in patients with chronic liver disease.

A murine model of *schistosoma*/hepatitis co-infection demonstrated that suppression of the antiviral type I interferon response by schistosome egg Ags in vivo predisposed the liver to enhanced viral replication with ensuing immunopathological consequences. It is though that this model might be paralleled in human schistosome/hepatotropic virus co-infections, including hepatitis B and hepatitis C viruses.

During the time of egg deposition, schistosome-infected mice exhibit a down regulation of interleukin 2 and gamma interferon production toward parasitic antigens, mitogens, and foreign non-parasite protein antigens. A group of researchers found that mice infected with virus alone rapidly cleared the virus, while in animals co-infected with virus and *S. mansoni*, viral clearance was delayed by as much as 3 weeks in the liver and by several days in the spleen and lungs. These observations suggest that helminth infection may influence immune responses to concurrent viral infections.

A cohort study conducted in the Philippines found that males infected with schistosomes consistently produced higher levels of Th2 cytokines, and also had a higher prevalence of liver fibrosis.

A case-controlled study was recently undertaken to describe the prevalence of *Strongyloides stercoralis* infection among patients with autoimmune liver disease, such as primary biliary cirrhosis, autoimmune hepatitis, and primary sclerosing cholangitis. The authors of that study hypothesized that immunomodulation by *S. stercoralis* infection may lower the incidence of autoimmune liver disease.

*Strongyloides stercoralis* infection has been shown to be related to increased risk in alcoholic cirrhosis. The same study found no increased risk for non-alcoholic cirrhosis.

Measles and Hepatitis

In another example, the population heat maps revealed a correlation between antibody reactivity for measles and hepatitis viruses. The exemplary system first would automatically consult the internal CIP hypothesis database to search for possible explanations for the correlation. As can be seen from the CIP hypothesis database described in Appendix B, none of the measles references discuss hepatitis and none of the hepatitis references discuss measles. In exemplary embodiments of the present invention, the exemplary system would then launch an internet search and access various internet databases, such as, for example, PubMed, MedLine, Science Direct, and NIH, as well as the internet in general, to find any information that might offer an explanation regarding the observed correlation. In the present example, a search of scientific articles available in the PubMed database, provided a basis for this observed correlation as described below.

The hepatotropic viruses, measles and herpes viruses have been shown to act presumably as a trigger in patients with autoimmune hepatitis.

Adult syncytial giant cell hepatitis (GCH) is an uncommon and often fulminant form of hepatitis that may be caused by infection with a novel paramyxo-like virus. In situ hybridization studies showed that the disease agent was genetically related to the measles virus. One group of researchers concluded that paramyxoviruses should be considered in patients with severe sporadic hepatitis.

Epstein-Barr virus has a seroprevalence of more than 80% worldwide and is known to be associated with hepatitis. However, little is known about the underlying pathogenesis and immune system mechanisms and there are no standard diagnostic criteria for diagnosing EBV-hepatitis available.

Viral infections of the mesenteric microvascular endothelium have been hypothesized as pathogenic factors in inflammatory bowel disease. The detection of anti-measles virus IgM in the majority of patients with Crohn's disease and in about one-half of ulcerative colitis patients as compared to a very low prevalence in patients with other chronic inflammatory disease is consistent with the hypothesis that the measles virus has pathogenic implications in inflammatory bowel diseases.

J. Extension of Database and Automatic Data Mining Functionality

In exemplary embodiments of the present invention, the database could be augmented by utilizing electronic medical records, such as Google's Personal Health Record, for example, to supply the non-assay information. In such embodiments, an individuals health records could be automatically downloaded to his database record each time they are updated.

In exemplary embodiments according to the present invention, a database and analysis system can be fully integrated with any computer system used to perform any of the applications described below in Section III, supplying, as it were, the back office number crunching conclusions to be operated upon by any scoring, decision making, or other application system or software as may be useful.

Additionally, using the correlation matrix and data mining techniques described above, algorithms designed to operate on images, such as, for example, pattern recognition algorithms and other image processing algorithms, such as, for example, edge detection and morphology, could be used to refine correlation regions in a "variable space" to automatically further process the data to find correlations of interest, as well as to find the precise segmentation in said variable space to maximize the value of the correlation and thus find the group of individuals that has the most in most common as to that correlation. By repeating this process for every identified correlation and comparing the results, i.e., the different optimal segmentations of the database for each correlation, the most can be learned about what is driving the correlation.

Finally, derived variables, such as the rate of change of antibody levels through time, the ratio of various bioassay results, etc., can be added to the database and correlations identified with respect to these derived "second order" variables. It may be that a connection or phenomenon only manifests at the level of such secondary, or tertiary or nary variables, and only an automated process that methodically processes the data over and over with complex algorithms can bring to light all the information buried therein.

In exemplary embodiments of the present invention, the time rate of change of an assay variable over time, as well as the second derivative with respect to time of that assay variable. Algorithms can easily be crafted that track any changes in the assay values over time, as well as the second derivative of such assays with respect to time. This can be especially useful in analyzing cytokine data, which tends to fluctuate with inflammations, colds and flu, but which often exhibits a baseline balance between Th1 and Th2 categories, for example.

K. Exemplary Analyses Performed on CIP Database

In exemplary embodiments of the present invention, a sample can be first analyzed by assaying all or a plurality of cytokines, and then, based on the individual's "cytokine signature" automatically spawning an additional panel or superpanel of assays to perform. Such an exemplary embodiment utilizes the cytokine's systemic immunological qualities to predict or locate potential areas for further study. Such a predictive algorithm can be based, for example, upon where an individual's cytokine signature lies within the Th1-Th2-Th17-Treg two dimensional space shown n FIG. 5D. For example, an individual with a high Th1 and high Th17 profile could have his serum automatically tested for autoimmune markers, or for example, antibodies to bacterial infections. Another individual with a high Th2 and high Th17 profile could have his serum automatically tested for markers of allergy or atopic disease. Yet another individual with high Th1 and Treg profile could automatically be tested for a chronic mycobacterial infection, while another individual with high Th2 and Treg could be tested automatically for parasitic infection.

FIG. 21E-1 shows the interpretation of immunoassay results of a random sampling of the Canadian Immigrant Population (CIP) database by Pipeline Pilot, categorizing the results as either reactive (positive), non-reactive (negative), or equivocal (marginal results interpreted as neither positive nor negative). Significant percentages (18-20% of total) of the results of two of the immunoassays for parasites from the panel (filaria and *strongyloides*) were classified as equivocal, possibly indicating a nascent infection in these individuals with these parasites.

FIG. 21E-2 shows several signature Th2 cytokine assays compared with results from parasite antibody assays. For filaria (FIG. 21E-2a), the highest amount of reactive results for both IL-4 and IL-5 occur in the filaria equivocal patients. The same is true for IL-5 assay results for *strongyloides* equivocal patients (FIG. 21E-2b). If we are to logically assume that equivocal results for these assays were to become positive results in the near future for these patients, the increased levels of IL-4 and IL-5 as signature Th2 cytokines may be indicative of early stages of infection with both of these parasites. It is conceivable that as the ImmunoScore database grows, results such as this might be seen as indicative of early intervention against parasitic infection in areas where such infections are endemic. A patient with an equivocal filaria result might not ordinarily be treated, but elevated Th2 cytokine levels in individual patients might call for treatment in patients that are equivocal for filaria and have elevated levels of both IL-4 and IL-5, for instance. In *strongyloides* patients, the initial flare of Th2 cytokines seems counterbalanced by increased expression of inflammatory cytokines, IL-6 and TNF-α as shown in FIG. 21E-2c. An increased percentage of patient population positive for these cytokines is seen in samples that are not negative (e.g. reactive and equivocal *strongyloides* assay results).

Patients with serum antibody reactive to Hepatitis B core antigen are considered to have an active hepatitis B infection. This patient population had higher levels of inflammatory cytokine TNF-α than did patients non-reactive to core antigen (FIG. 21E-3).

Seropositivity to cytomegalovirus (CMV) has been linked to an aging immune system, and inability to deal with debilitating infection in the elderly (e.g. influenza and Streptococcus pneumoniae). FIG. 21E-4 shows the CIP database examined for seropositivity to CMV, drawing a distinction between very high seropositivity (>250) and lower serum antibody levels. It can be observed that females are more likely than males to have very high serum antibody levels to CMV, likely due to more interactions with very small children. Examination of the region of origin of the CIP draws clear distinctions in this population. Individuals from sub-Saharan Africa, Southern Asia, and North Africa are more likely than not to have very high levels of serum antibody to CMV, while individuals from the Latin America/Caribbean region, Eastern Europe, or Southeast Asia are more likely to have fewer serum antibodies to CMV. Examination of the age of the total population shows a clear increase in CMV seropositivity correlated with advancing age.

FIG. 21E-5 examines the trend for increased serum cytokine levels plotted against CMV reactivity. The general trend for six of the eight cytokines examined is for increased serum levels of cytokines correlated with increased levels of CMV. One notable significant exception in this population is observed in the levels of IFN-γ, which are inversely correlated with CMV seropositivity. It has been noted that elderly individuals are more prone to viral infection, and decreased levels of IFN-γ in these individuals could be highly significant.

Serum cytokine levels were similarly examined vs. percent of CIP that had serum antibodies to filaria (FIG. 21E-6). These results indicated higher levels of IL-4, IL-10, TNF-α, IL-17, and TNF-β to be associated with filarial infection, with no notable increases in the other cytokines. The increased level of IL-4 might be expected based upon reports of parasitic infections being correlated with overall increase in Th2 cytokines. IL-10 is associated with Treg cells and could also be expected as a regulatory factor in dampening the Th2 response. The increased levels of TNF-α, TNF-β, and IL-17 could be indicative of inflammation and could also be a cause for the increased levels of IL-10. It is interesting that the apparent patterns of IL-17 and IL-23 are somewhat incongruous, seeing that it is reported that IL-23 expression is necessary to maintain a TH17 response. Other cytokines, reported to be pro-inflammatory, such as IL-8, IL-1, and IL-15 are not remarkable in their pattern of expression as related to filarial infection. FIG. 21E-7 shows a decrease in IFN-γ levels in individuals seropositive for hepatitis A. This is somewhat unexpected in that IFN-γ is considered crucial for the combat of viral disease. Similar results were seen with individual positive for hepatitis B core antigen (data not shown).

An interesting cytokine profile is presented in FIG. 21E-8 of individuals possessing serum antibodies to *Strongyloides*. These individuals show decreasing levels of TNF-α, TNF-β, IL-6, IL-17, IL-15, IL-8, IL-2, and IL-5, with a concomitant increase in IFN-γ, IL-23, IL-10 and IL-4 levels. The IL-4 increase could be due to increased Th2 expression, but this leaves the decrease in IL-5 expression more difficult to explain. The IL-10 increase with the concomitant decrease in many other cytokines could possibly be a demonstration of the suppressive effects of Treg cells expressing increased amounts of IL-10. Many of the pro-inflammatory cytokines are decreasing correspondent to *Strongyloides* antibody positivity, but there is an increase in IFN-γ and IL-23. Clearly the pattern of cytokine expression is complicated and worthy of further study.

FIG. 21E-9 shows a multi-variate analysis of components of the CIP database incorporating the IL-6:IL-2 cytokine ratio vs. serum levels of anti-CMV antibody (top panel) and anti-hepatitis B antibody (bottom panel) and color coded by age. This particular representation is not necessarily informative, but rather demonstrative of the types of analyses that can be accomplished by ImmunoScore technology.

CMV Reactivity/Non-Reactivity

FIG. 21E-11, Table 1, shows the percentages of the CIP that are positive for at least one cytokine in the four cytokine categories previously described—Th1, Th2, Treg, and Th17, and analyzes this positivity in relationship to positive serological tests for disease-specific antibodies. The mean values of the entire population are indicated in green, and significant deviations from the mean of the entire population greater than 1.0 are indicated in yellow. Thus, FIG. 21E-11, Table 1, shows that patients that are non-reactive for CMV antibody have significantly lower levels of Th1, Th2, and Th17 cytokines than do subjects that are seropositive for anti-CMV antibody. Also significantly, these same patients that are non-reactive to CMV have higher levels of Treg cytokines. Taken together, these results indicate that these patients are far less likely to suffer from chronic inflammatory conditions based upon their cytokine profiles. Patients that are seropositive or CMV antibody show the opposite— that is, they have elevated levels of TH1, Th2, and Th17 cytokines and reduced levels of Treg cytokines. Due to the large number of CMV positive individuals (94% of OP database), however, these results do not rise to the level of significance.

Hygiene Hypothesis Revisited

The hygiene hypothesis has described a state wherein parasitic infections in third world countries help prevent patients from atopic/allergic conditions like asthma by tipping the Th1/Th2 balance toward a more Th2-like state in those individuals. According to the hypothesis, we would expect to see a relative boost in the levels of Th2 cytokines in patients that are seropostive for infections with filaria, *strongyloides* and *schistosoma*. The results in FIG. 21E-11 indicate that while there are increases in levels of Th2 cytokines for patients infected with *strongyloides* and filaria, those patients with filarial infections do not rise to the level of significance. Curiously, patients infected with *schistosoma* actually show a decrease in the level of Th2 cytokines that also does not rise to the level of significance. Also counter to the stated hygiene hypothesis, the levels of Th1 cytokines are increased in patients seropostive for *strongyloides* (significantly) and filaria. Levels of Th17 cytokines are increased in patients seropositive for filaria (significantly) and *strongyloides*. Perhaps the most striking of the observations is that all three parasitic infections showed increases in the levels of Treg cytokines, with patients seropositive for filaria and *strongyloides* showing significantly higher increases than the rest of the CIP database. It is likely that the story behind the hygiene hypothesis is more complicated that a shift in Th1/Th2 cytokine balance and needs to consider the contributions of Th17 and Treg cytokine-producing cells.

Mining the CIP Database

The Canadian Immigrant Population Database is organized by large geographic regions of origin of the subjects. These regions are defined as follows:
Region 1=Sub-Saharan Africa
Region 2=South Asia
Region 3=North Africa
Region 4=Latin America/Caribbean
Region 5=Eastern Europe
Region 6=Southeast Asia The Data Mining Tool was used to examine cytokine levels together with antibody levels to vaccine-preventable diseases, three parasitic infections (filaria, *schistosoma*, and *strongyloides*), viral hepatitis infections (A, B, and C), and infection with cytomegalovirus. Patients were grouped according to region of origin and gender, and place in bins based upon their ages, separated by 20 year increments. The age categories in this instance were from 10-30 years of age, 30 through 50, 50 through 70, and 70 through 90. The tool generated 39 separate heat maps (FIGS. 21E-10.1 through 21E-10.21) based upon these classifications. The heat maps produced by the data mining tool display very interesting patterns of correlation based upon region of origin, gender, and age. Heat maps produced by population analyses with inadequate sample size produce very predictable, and uninteresting heat maps. These would include those heat maps in FIGS. 21E-10.3 (top), 21E-10.4, 21E-10.8, 21E-10.12 (top), 21E-10.15, 21E-10.18, and 21E-10.21.

Individuals in the CIP database originating from Sub-Saharan Africa are shown in FIGS. 21E-10.1 through 21E-10.4. Discounting those patients in FIG. 21E-10.4 due to small sample size, the other individuals show very interesting patterns of correlation between cytokine expression and antibodies to the various antigens tested. In the female population under 30 years of age, cytokine patterns are largely inversely correlated with antibody reactivity to measles, hepatitis A, and hepatitis B core antigen. Male subjects in this same age category show some negative correlations with some cytokines and varicella, and a separate group of cytokines and antibody to hepatitis B core antigen. As the population ages, these heat maps change dramatically (FIGS. 21E-10.2 and 21E-10.3). By the time the males reach middle age and older (50-70), there is a striking inverse correlation between all cytokine levels and parasitic exposure (e.g. filaria, *schistosoma*, and *strongyloides* shown in the bottom panel of FIG. 21E-10.3). This same group of individuals has a high degree of correlation among the parasitic infections themselves (red grouping at very bottom right of the bottom panel of FIG. 21E-10.3).

In addition, there are interesting negative correlation patterns among the cytokine expression in this group itself—in particular, IL-8 and IL-5 expression are inversely correlated with a number of the other cytokines. Curiously, IL-8 (a pro-inflammatory cytokine) is inversely correlated with a number of other inflammatory cytokines (IL-1. IL-17 and IL-23), as well as anti-inflammatory cytokines IL-10, IL-4, and IL-5.

Individuals in the CIP database originating from southern Asia display very different heat maps (FIGS. 21E-10.5 through 21E-10.7). The gender differences in heat map profiles as the population ages are striking. Isolating on the upper left quadrants (or "cytokine quadrant") in the six heat maps, one can see that the younger males (under age 50) have better correlation values for the cytokine expression in general than do the females. From the total population analysis, it is not certain which of the genders would be considered more fit immunologically, but the differences are striking. Both of the older groups (FIG. 21E-10.7) show many areas of negative correlation among the cytokine quadrant, particularly the females. At this point, it is unclear what the uncoupling of cytokine correlations mean for an aging population. Further study and analyses may yield important information regarding aging immune systems. It is possible that the uncoupling of cytokine correlations is a sign of immune health in this population—there is a wealth of information that could possibly be gleaned from ImmunoScore population analyses.

Regional geographic differences in population immune profiling can be seen when analyzing those individuals in the CIP database originating from North Africa (FIGS. 21E-10.9 through 21E-10.11). The data in FIG. 21E-10.11 is likely not as reliable due to small sample size, but the younger individuals show striking cytokine profiles. The younger individuals (FIG. 21E-10.9) are remarkable for their lack of overall positive cytokine correlation. Again, this may or may not be a sign of decreased immune health, but the profile changes in the older individuals in this population. Particularly in the males, there is much more positive correlation in the cytokine quadrant than in the younger group. The females from North Africa show very minor positive correlations in the cytokine quadrant when compared to other regions around the globe. This becomes obvious when examining the female populations from Latin America/Caribbean (FIGS. 21E-10.12 through 21E-10.14). The females in this group have striking positive correlations in the cytokine quadrant particularly in the 10-30 and 30-50 age groups, but the positive correlations are still prevalent in the 50-70 age group. In addition to the across the board positive correlation for cytokine values, there is a very noticeable negative correlation among cytokine values and hepatitis A infection in 30-50 year old Latin American females (FIG. 21E-10.13—top). The younger Latin American males show some interesting negative correlations between cytokine values and filaria infection, and to a lesser extent, rubella, hepatitis A, measles, tetanus, and varicella (FIG. 21E-10.12—bottom).

The demographic groups from Eastern Europe and Southeast Asia were smaller, but interesting nonetheless. In the younger groups from Eastern Europe (FIG. 21E-10.16), there were interesting negative correlations between the cytokine assays and the CMV antibody assay. CMV infection is not as prevalent in Eastern Europe as some other areas of the world, and it would be interesting to investigate this relationship further, particularly in the light of the role CMV infection plays in immune senescence. Hepatitis A and rubella also appear to have significant areas of negative correlation with cytokine expression profiles in these groups. Finally, in the group from Southeast Asia, the younger males (FIG. 21E-10.19—bottom) showed an interesting pattern of reactivity between the cytokine assays and the hepatitis B_e antigen assays. There were areas of strong positive correlation (e.g. IL-1, IL-4, IL-5, IL-6, and IL-17) and also areas of strong negative correlation (IL-2, IL-8, and IL-23). There is an interesting un-coupling of the Th17 cytokines in this instance, namely the pattern of IL-23 is vastly different from that of IL-17 and IL-6.

L. Exemplary Results Using Data Mining Protocols on CIP Database

Using the various automated analysis and data mining protocols described above, various analyses of the CIP database were performed. In a first set of analyses, a series of cytokine based searches were run, using a library of cytokine analysis protocols that were created for this purpose. These include the cytokine analyses described in the previous section, as well as the creation of predictive models, based on bayesian modeling, that take as inputs a plurality of cytokine assay values and out put a prediction for various non-cytokine immunological virus, parasite or other exposures.

FIGS. 21F-1 through 21F-6 depict the results of predictive models built using cytokine data according to an exemplary embodiment of the present invention;

FIGS. 21G-1 through 21G-12 depict the results of running an exemplary patient population rule mining protocol according to an exemplary embodiment of the present invention;

In exemplary embodiments of the present invention, a first assay panel containing a plurality of cytokine assays can be administered and the results processed. Based on automatic analyses of the cytokine data, a second tier or set of assays can then be run on the same individual. The cytokine assay results being used to inform the contents of a second assay panel. In this manner, it is not necessary to fund the assay of entire superpanels unless and until the expense is justified. This exemplary embodiment can be particularly useful in a health care management or insurance embodiment, as described below, especially where assay costs are high or must be carefully controlled. The cytokine data can be analyzed in a variety of ways, and a "cytokine signature" can be generated and stored in the database. Such a cytokine signature can then be an input to a series of algorithms, the output of the totality of which is a set of secondary assays to be run for that individual (or population). The secondary assays and the cytokines can then together be processed, for example, in any of the ways described or disclosed above, or in the code provided herewith in Appendix D.

Also very useful in an insurance underwriting or health care management application, is the exemplary single patient vaccine recommendation protocol. Although originally named for its vaccine recommendation capabilities, it actually tallys all of an individual's assay results, calculates and presents where within the database they fall percentage wise, and displays therapeutic, diagnostic and other recommendations or observations based on the assay and other variable values in that individuals' record.

Such a protocol can be used, for example, to calculate an immunoscore, an overall immune status, with one or more sub-immunoscores, and an underwriter can use such a protocol from their desktop computer to immediately look up the electronic file on any patient or insured, and can approve health care procedures, intelligently audit for premium or rating purposes, and generally have command of the individual's entire health picture at a glance, all assisted by the system intelligence.

FIGS. 21H-1 through 21H-10 depict the results of running an exemplary individual patient vaccine recommendation protocol according to an exemplary embodiment of the present invention for 10 randomly selected individuals' within the database.

Exemplary Automated Data Mining Complete Output

FIG. 21I is an exemplary output from an exemplary automated data mining protocol according to an exemplary embodiment of the present invention, segmenting an exemplary database by Region of origin, Sex and the cytokine assay IFN-gamma. The output includes an overview of the data set distribution, a heat map for each of the twenty-eight data sets plotting correlations of features in each data set, and a listing of the complete cell by cell (feature by feature) data for each set.

Uses of Immunoscore Information and Automated Data Mining Results in Various Commercial, Research and Governmental Contexts In exemplary embodiments of the present invention, ImmunoScore information (including, for example, results of assay panels, individual history and records of health care visits and treatments administered or undergone) processed in an exemplary system and stored in an exemplary database can be used in a variety of commercial, research and governmental applications. These uses can range from optimizing the health care costs of a medical insurance underwriter to facilitating immunogenicity studies for a pharmaceutical manufacturer, or, for example, to tracking the incoming and subsequent immune status of immigrants. In what follows, descriptions of several exemplary business methods which leverage or exploit the use of ImmunoScore informatics are presented.

A. Health Insurance Underwriting and Management

In exemplary embodiments of the present invention, systems and methods according to the present invention can be used, for example, to optimize the business of health insurers as well as healthcare providers, who are essentially self insurers. In general, a health insurance underwriter or a health insurance provider has a population of individuals, generally called insureds or plan members, whose medical care costs are reimbursed or paid for directly by the healthcare insurer or the healthcare plan. In such contexts, it is useful to monitor the health of the population of insureds or plan members, especially those who are older and in those years, generally, for example, starting at age 60, when individuals begin to encounter greater health and medical problems.

In exemplary embodiments of the present invention, each plan member or insured, or, for example, each plan member or insured above a certain age, can be assayed, and the results can be used to determine whether any prophylactic therapy should be administered to these individuals. Sometimes the decision is as simple as identifying vaccine preventable diseases for which the individual does not have sufficient levels of antibodies. In that case, the prophylactic therapy would be the administration of the vaccine in question. More complicated decisions could include identification of diseases or of biochemical markers therefor, that an insured or plan member is susceptible to that do not have a direct and economical prophylactic therapy. In that case, there can be, for example, a more complex algorithm which decides what to do given (i) assay results and (ii) the relative costs of assuming the risk that the insured will contract the disease versus the costs of prophylactic therapies to prevent the disease or diseases implicated. Such algorithms could, for example, be implemented in a system such as is depicted in FIG. 2A, where, for example, in addition to database 203 where the results of assays conducted on individuals are stored, there can also be a business rules database 220 which can also supply inputs to a central processor 204 which implements such analysis and algorithms. The inputs to such algorithms can then be, for example, not just assay results, medical history and demographic information, but also a set of business rules allowing a decision to be made or facilitated, taking into account the relative costs and benefits of administering prophylactic therapies. Such benefits to be considered can, for example, be those inuring to the individual as well as those inuring to the members of the health care plan as a whole, or, those which seek to maximize profits or efficiencies. In exemplary embodiments of the present invention such a healthcare insurance optimization method could be implemented as is illustrated in process flow diagrams FIGS. 22 and 23.

As can be envisioned from the CIP database, it appears that the level of anti-Rubella antibody is uniformly lower in those individuals from SE Asia. Rubella is a generally a mild, self-resolving infection except in pregnant females, in which instance there are undue complications to the newborn, known as Chronic Rubella Syndrome (CRS). In an immigrant population such as the one documented in the CIP database, if women of child-bearing age from SE Asia were demonstrated to be susceptible to Rubella infection, health care authorities, as well as those underwriting insurance policies would benefit from such information. Not only are those women more at risk during pregnancy, but this particular immigrant population would be more likely to infect native Canadians of child-bearing age (assuming that their own antibody levels had waned). The general health of the population, therefore, would be well-served making sure that these individuals were appropriately vaccinated to avoid Rubella infection and possible complications to child-bearing women. These data reveal that Canadian authorities (and by extension, those in the United States) could, for example, be well served and fiscally responsible in the long run by testing and immunizing the immigrant population against Rubella and other vaccine-preventable diseases.

FIG. 22 depicts an exemplary process flow for a health care management application. With reference thereto, at 2201 an insured's immune status can be examined, for example by conducting one or more assays or panels of assays such as, for example, those that are described above. At 2202, for example, the results of those assays can be used to identify diseases that the insured is susceptible to, and moreover, the risk of contraction of each disease for that individual can be calculated. At 2203, prophylactic therapies that could prevent each identified disease can be identified, and at 2204, for each identified disease a decision can be made by calculating the expected costs of treatment (such as, for example, by taking the known costs of treatment multiplied by the probability of contraction) and the costs of associated prophylactic therapies. Finally, at 2205, prophylactic therapies that cost less than the expected costs of treatment can be required for the insured as a condition of maintaining his or her insurance coverage or membership in the health plan. For those prophylactic therapies whose costs are greater than expected treatment costs but nevertheless desired by the insured, the cost differential can be born by the insured rather than the health insurer.

FIG. 23 depicts a particular subset of the process flow illustrated in FIG. 22 where the prophylactic therapies are simple and the ailments identified are vaccine preventable diseases. Beginning at 2301, an insured or plan member's immune status is examined by conducting one or more assays or panels of assays such as those described above. At 2302, vaccine preventable diseases to which the insured is susceptible are identified based on an analysis of the results of the immune status from 2301. At 2303, the insured can be, for example, required to obtain vaccines for the identified vaccine preventable diseases. At 2304, follow-up examinations of the insured's immune status post-vaccination can be made, again by conducting one or more assays or panels of assays, and these results can also be stored in the database. At 2305, the follow-up examination results can be used to evaluate the efficacy of any administered vaccines to provide the necessary immunity to the identified diseases for this individual. When extended to an entire population, such as, for example, the insureds of a health insurance company or the members of a health plan, this can, for example, provide a means of evaluating the efficacy of vaccines in an aging population. This can also be very useful in the context of measuring and dealing with immunosenescense, as described below.

Next described are a number of process flow charts which illustrate exemplary process flow according to various embodiments of the present invention applied to healthcare management applications. FIG. 24 is an alternative process flow to that depicted in FIG. 22, and is concerned with adjusting an insurance premium or an HMO participation fee for an individual based upon identification of potential diseases that an individual is susceptible to using ImmunoScore diagnostics.

The context of FIG. 24 could arise, for example, where an insurance company or HMO requiring an annual ImmunoScore diagnostic panel as a condition of maintaining insurance coverage or participation under a healthcare plan. Such annual requirement would be akin to the annual information questionnaires that automobile insurance companies require of all of their insureds wherein an insured must state if he has had any serious health problems, if he has been involved in any accidents, or if other out of the ordinary events have occurred. With reference to FIG. 24 at 2401, the individual's immune status can be examined and at 2402, based upon the results of such examination, all diseases to which the individual is susceptible can be identified. 2405 is a decision tree which is applied to each disease identified at 2402. Thus, at 2405, for each disease a decision is made as to whether a prophylactic therapy is available. If there is no such available therapy, the flow terminates at 2410 where the insured's premium is adjusted upward, to account for the additional risk the insurance company is taking in continuing to cover this individual. If, at 2405 there is a prophylactic therapy available then the flow moves to 2406 where it is determined whether to administer or approve the prophylactic therapy. Based upon this decision, the premium can also be adjusted.

FIG. 24A is a more detailed version of the analyses described in connection with FIGS. 22 and 24. With reference to FIG. 24A, at 24A01 the immune status of an individual can be examined, and at 24A02 the initial total cost can be set to zero. 24A02 through 24A35 are then applied in a loop which cycles over all of the diseases for which an individual is tested in the examination at 24A01. Such identified diseases can be, for example, those indicated by analyzing the results of assays conducted and other data associated with the individual or various populations to which he/she belongs, as described above. For each potential disease, at 24A05 it can be determined whether the individual is susceptible or not based upon the assay results. If the individual is not susceptible, process flow can terminate as to that disease at 24A20 and no incrementation of cost occurs. If the individual is susceptible, the flow moves to 24A10 where it is determined whether a prophylactic therapy exists. If a prophylactic therapy does not exist, at 24A30 the total cost is incremented by the cost of treatment. If such a therapy does exist, at 24A05 it can be determined whether the treatment cost from the disease is greater than the cost of the prophylactic therapy. If the treatment cost is greater than the cost of such therapy, then at 24A35 the prophylactic therapy can be offered to be reimbursed up to the treatment cost and the total cost can be incremented by the treatment cost. If the cost of prophylatic therapy is greater than treatment cost, then at 24A25 the individual is required to take the prophylactic therapy and the total cost can be incremented by the prophylactic therapy's cost. After looping through all of the potentially relevant diseases, at 24A50 the premium can be adjusted based upon the total cost. The computation of total cost and prophylactic therapy cost at both the disease specific level and the over-all levels can be given by the following rules:

Disease Specific:
Computation of TC: $P(CD|IS \text{ and not } PT)*C(T|CD \text{ and not } PT \text{ and } IS)$
Computation of PT Cost: $P(CD|IS \text{ and } PT)*C(T|CD \text{ and } PT \text{ and } IS)$ Overall Disease-Related Healthcare Costs:
$TC=\Sigma P(CDi|\text{not } PT \text{ and } IS)*C(Ti|CDi \text{ and } PT \text{ and } IS)+C(PT)$ (in all diseases)
$PT=\Sigma P(CDi|\text{not } PT \text{ and } IS)*C(Ti|CDi \text{ and not } PT \text{ and } IS)$ The various exemplary implementations of healthcare management described above have considered each disease individually. FIG. 25 addresses a more complicated situation where all of the potential diseases are identified and all prophylactic therapies available for all of the identified diseases are also identified in all possible combinations of diseases and prophylactic therapies are analyzed using a cost benefit approach. Thus, with reference to FIG. 25, at 2501 a panel of assays can be conducted. At 2502, based upon the results of such assays all diseases the individuals are susceptible to are identified. At 2505 all prophylactic therapies which are available for each of the identified diseases can also be identified, and at 2510 a cost benefit analysis of all possible combinations of prophylactic therapies and diseases can be, for example, undertaken using business rules. Implementation of this functionality represents a much more complex level of analysis as it is necessary to first define all possible combinations of diseases and prophylactic therapies. For example, if the individual is susceptible to five diseases and a prophylactic therapy exists for each of them but these prophylactic therapies vary widely in cost, it can be, for example, useful to a healthcare manager or a healthcare insurance underwriter to know whether it may be more economical to only administer some of the identified prophylactic therapies and run the risk of the individual contracting the diseases for which prophylactic therapies are not administered. For each of the possible combinations a cost in terms of cost of administering the prophylactic therapy and expected cost of treatment without the therapy is assessed and at 2515 one or more therapies can be approved and/or the insured's premium or the individual's insurance premium adjusted.

It is understood that in the description of the various possible algorithms which can be used in an ImmunoScore analysis for healthcare management that the term individual, insured, and healthcare plan participant are functionally equivalent. While some algorithms are expressed in terms of health insurance context, the same analysis represented by them can easily be applied to HMO management or management of other healthcare plans. As will be described below, the same techniques can be applied where the entire population is covered under a healthcare plan, such as, for example, in a socialized medicine jurisdiction. Alternatively, the same techniques can be applied where a large population of some mutual affinity is covered by a single healthcare plan such as, for example, United States Veterans whose healthcare is provided by the U.S. Veterans Administration. Thus, it is understood that any particular algorithm or method described in one context also applies to any other contexts.

FIG. 25A is identical to FIG. 25 except that it offers an additional option. At 25A20, if, in fact, the minimum cost, which is simply the total cost of the least costly permutation at 25A10, is, for example, too great for underwriting limits or healthcare management criteria at 25A20, the participant can, for example, be canceled from the plan.

FIG. 26 depicts an exemplary process flow for use in healthcare management applications. FIG. 26 is not concerned with dollar costs but rather cost in terms of quality of life. Such an analysis would be useful where dollar cost is less important than quality of life, such as, for example, in exemplary embodiments where a supplemental insurance company insures a minimum quality of life and undertakes to provide for whatever healthcare costs are necessary to maintain that quality of life. Additionally, a socialized medicine jurisdiction, for example, could have a minimum quality of life which it seeks to provide to each citizen as a basic human right which that jurisdiction sees all of its citizens as having. With reference to FIG. 26, at 2601, an immune status of an individual can be examined and the quality of life can be set to zero. For the purposes of FIG. 26, a higher quality of life score translates to a higher quality of life. At 2602 all diseases to which the individual is susceptible are identified and a decrease in QOL score can, for example, be assigned to each disease. The scoring data (i.e., a map of identified health scenarios to some QOL metric) can, for example, be stored in a business rules database such as is depicted in FIG. 2A. Such a decrease in quality of life score can be, for example, a measure of unexpected pain and suffering, a measure of how many sick days are generally associated with it, or, for example, whether the sick days are at home, taken at the hospital, or taken while still at work, and finally whether surgery is involved. At 2605, all prophylactic therapies which are available for all of the identified diseases at 2602 can also be identified. At 2610 for each identified disease and each possible combination of identified diseases (assuming that the individual could contract more than one disease, either simultaneously or in succession) the probability of contracting the disease can be computed and from that probability an associated expected decrease in quality of life can be, for example, computed. As provided in FIG. 26, an exemplary formula which can be used in this context:

$$E(QOL_{DEC}) = \text{Prob(Disease)} * \Delta QOL;$$

$$QOL = QOL - E(QOL_{DEC})$$

At 2615 an increase in quality of life can be assessed for each identified disease or combination of identified diseases for which either prophylactic therapies or therapeutic therapies exist. Thus, in exemplary embodiments of the present invention, the quality of life score can be incremented by looping through each disease and adding the expected increase in quality of life associated with either (i) providing a prophylactic therapy or (ii) a therapeutic measure to mitigate the loss and quality of life due to contracting the disease. For example, not every disease for which there is a prophylactic therapy can be totally obviated. Some diseases to which individuals are susceptible can be mitigated but not prevented by prophylactic therapies. For example, when people feel the onset of a cold they often take echinacea. Echinacea tends to lower the amount of time one is symptomatic but rarely totally prevents contracting the cold. Alternatively, if a prophylactic therapy completely obviates the individual from contracting the disease then the $E(QOL_{inc})$ should exactly equal the $E(QOL_{dec})$. If the prophylactic therapy happens, for example, to bestow other benefits besides preventing the disease, then the expected increase in the QOL associated with undergoing the prophylactic therapy would exceed the $E(QOL_{dec})$. Similar computations would apply to various possibilities. At the end of process flow in FIG. 26 a net quality of life figure can thus be computed.

FIG. 26A is a more detailed process flow for the example illustrated in FIG. 26 with the exception that in FIG. 26 an improved QOL is indicated by a more positive score and in FIG. 26A an improved QOL is indicated by a more negative score. At 26A01 immune status can be examined and at 26A02 the quality of life can be set to zero. At 26A10 the probability of contracting a disease given the immune status obtained in at 26A01 can, for example, be computed. At 26A20 the probability of contracting the disease given the immune status can be multiplied by a "badness" score. At 26A30 this product can be added to the quality of life score. 26A10 through 26A35 can then be repeated for each disease for which susceptibility could be examined, given the assays administered at 26A01. In this exemplary process flow a better quality of life is associated with a lower number which is the opposite convention of that adopted in the process flow of FIG. 26. It is for this reason that a "badness" score is assigned to each disease and an expected "badness" is added to the quality of life at 26A30. Additionally, at 26A15, all possible prophylactic therapies for the identified disease (it is noted that 26A15 and 26A35 are within the for-each-disease loop as well) can be generated and mitigation scores can be assigned for each physical therapy or combination thereof. At 26A35, the mitigation score can be, for example, subtracted from the quality of life score and once flow is looped from 26A10 through 26A35 for each disease, at 26A40 a total quality of life score can, for example, be output. Using this total quality of life score, at 26A50 the best set of prophylactic therapies in terms of higher quality of life can be offered to the individual with the stated quality of life improvement.

It is noted that in the schema of FIG. 26A a badness score is associated with each contracted identified disease. An exemplary badness scoring system is presented in the upper right of FIG. 26A and comprises, for example, +1 for a home sick day, +10 for a hospital sick day, +½ for a work sick day, and +100 for a surgery. Accordingly, the quality of life score would dramatically decrease if the individual was found to susceptible to a number of diseases each of which required surgery if contracted.

FIG. 27 is a final healthcare management exemplary process flow chart. FIG. 27 addresses a newly discovered HPV vaccine that is 100% effective in preventing cervical cancer in women. The question is who should receive the vaccine and when should they be tested. From the point of view of society as a whole, perhaps everybody who has not contracted HPV should be vaccinated to prevent them from ever contracting it and thus prevent the females amongst them, and females in contact with the males amongst them, from ever contracting cervical cancer. Of course, this has a greater cost than simply vaccinating women prior to their exposure to HPV. Therefore, the decision as to who receives the HPV vaccine will often depend upon who is managing the healthcare of the population in question. This will be described in connection with the final decision at 2715.

With reference to FIG. 27, beginning at 2701, an assay panel containing an HPV assay can, for example, be conducted relative to one or more individuals. At 2705 it can be determined whether that individual is seronegative or seropositive to the HPV virus. If seronegative, the individual has not yet contracted HPV and flow moves to 2710, where the decision as to the individual's gender is made. If the individual is a male, is not seronegative, and is seropositive to HPV, then flow can terminate at 2706 and any therapeutic treatments that are available can be administered. Continuing at 2710, if the individual is a female flow terminates at 2711 and the HPV vaccine is always administered. Whether the healthcare manager is an insurance company, an HMO, a socialized medicine jurisdiction or a large scale healthcare management entity such as the Veterans Administration, any female whose healthcare is being managed should be vaccinated to prevent any healthcare expenditure in treatment for cervical cancer. However, what about males? The only utility derived from vaccinating males is that females in sexual contact with them will not contract HPV. If those females are managed by a different healthcare entity there is little utility in protecting "our" men. If those females are protected in the same healthcare management entity, then there is utility in protecting them. Alternatively, even if the females are not provided healthcare or healthcare insurance under a given plan, a government regulating that plan may see a social benefit in wiping out cervical cancer, or at least those cervical cancers caused by HPV, which are the vast majority of such cancers. Accordingly, given all of these concerns, at 2715, the HPV vaccine can be administered if the utility value of the prophylactic effect is greater than the cost of treatment, which is simply the cost of the vaccine. The utility value will, as noted above, be a complicated function of a number of factors, the most prominent of which being who is responsible (financially, politically or morally) for the healthcare of the females that this male may come in contact with.

B. Health Care/Health Insurance Credit Exchange

The applications that have been described thus far relating to healthcare management all assume that in the cost benefit analysis, additional costs can be passed to an insured, or, for example, if too high, the insured or member of a health plan (such as an HMO) can be canceled. While this may maximize profits for the health plan or the health insurance company in the short run, it can result in dissatisfied insureds and eventually loss of a certain percentage of the insured base of individuals. Loss of customers is never a good thing, even if under certain analyses they are unprofitable customers. One way of solving this problem is, instead of passing costs through to consumers, i.e., to insureds or health plan members, to set up a means by which they can procure credits in years when they are predominately healthy and use those credits when not costs but—debits—are assessed against them as per the exemplary analyses described above in connection with FIGS. 22 through 27. Thus, in exemplary embodiments of the present invention, a health care provider, a health care insurance company, or other financial intermediary in conjunction with the health insurance provider or health care provider, such as an HMO, can set up a health insurance credit exchange. Such an exchange can operate in a fashion similar to those government programs which have rules against excessive energy use or excessive pollution derived from an entity's activities. An entity which is a polluter, or an "excessive" user of energy or a natural resource such as water, for example, can purchase credits from other individuals or entities who have a low energy use, low water use or are low polluters. In this fashion, those individuals or entities who exceed a certain threshold of some desirable metric, such as, for example, low energy use, low water use, or other "green" factors, can purchase, negotiate, trade or otherwise procure credits from those who are below such a threshold so as to avoid fines or negative consequences from violating the environmental or natural resource use standards.

Thus, in the health care context there are always some individuals who are sick more than others. Individuals do not know whether they will be in the underwriting bin of more sickly than average or less sickly than average. Insurance companies try to spread the risk of the more sickly amongst a larger population which obviously includes those who are less sickly, and charge an essentially average health insurance premium to everyone. However, as underwriting becomes more granular, using exemplary embodiments of the present invention, it can be predicted, even decades in advance whether a particular individual is more or less likely to contract a disease, such as for example, autoimmune diseases as described above. For example, as described above in Section I, certain autoimmune diseases have markers which are harbingers 7-10 years in advance of their eventual symtomology. Thus, using exemplary embodiments of the present invention, health care plans, health care administrators and health care insurers will be able to divide the population into many more bins of insureds and associate with each of them a more accurate health insurance premium cost. This can cause those in the more risky bins to have a much greater insurance cost. One way of ameliorating this is to encourage people to join health care plans early in their lives when they are healthy and before even the onset of eventual disease emerges, such as via a marker or predictor in an Immunoscore assay result marker context. In so doing, people who are healthy can receive credits which they can bank within the system or buy, sell or trade. If regular Immunoscore audits of individuals reveal that someone is moving from a less risky bin into a more risky bin, and a cost would be added to their health insurance premium (i.e., a debit), instead of paying an extra premium they can procure a credit through a health care credit exchange either from their own account which they banked in earlier years or from other healthy peoples' accounts which are presently available for exchange.

Thus, in exemplary embodiments of the present invention, an insurance company could, by setting up and maintaining such a healthcare credit exchange, retain more customers as well as encourage customers to join its ranks of insureds early on in their lives so as to be able to bank for the future and/or sell credits for being healthy. By acting as intermediary, an exemplary system can make a market for such health care credits, and not have to wait for a particular debit holder to find a particular credit holder willing to exchange. Acting in some ways as a securities market maker, an Immunoscore based third party can buy credits and sell debits.

Thus, in exemplary embodiments of the present invention, insureds can thus be induced to pay higher premiums when they are younger and more healthy which would therefore give them extra protection against being assessed debits later on should they become sick. This results in a net flow of capital to the health insurers, or the HMOs, because they can charge higher premiums than the "true" or correct "premium" with the full consent of the insured in exchange for allowing and facilitating participation in the health care credits exchange. On the other hand, they can also retain more customers because people who are subject to debits as a result of more granular analyses of their overall health via Immunoscore diagnostics can simply use credits they have accumulated earlier in their lives or procure credits from other insureds which would ultimately be cheaper for them than having to find substandard coverage. Additionally, the insurance company is not faced with canceling bad insureds and then having to spend client development money to procure new "good" insureds, rather, it can more or less retain its insured base as well as generate additional profits from the maintenance of the healthcare credit exchange.

Further, if a healthcare management entity sets up a health care credit exchange it can, in exemplary embodiments of the present invention, require immunoscore diagnostics, such as set forth in Section 1 above, at various significant life points in each insured's lifetime. This can have the effect of positive feedback in the amount of data that an immunoscore database has available and thus, an improvement and greater accuracy and predictive value that the algorithms of the Immunoscore analysis can provide to the insurer. Over the course of time an insurer will tend to make more money and have more accurate predictive models than its competitors who do not use such an Immunoscore system.

Finally, ImmunoScore databases lend themselves to storing health care credit and debit information as part of an individual's record, making it nearly seamless to create algorithms to track such credits/debits and manage the exchange. After all, ImmunoScore is the tool being used to generate the very granularity that assigns the credits/debits and makes the entire business possible.

C. Veterans Health Care Management (Variant of Health Care)

A special instance of health care management relates to veterans care. In the United States, the Veterans Health Administration (VHA) provides a broad spectrum of medical, surgical, and rehabilitative care to its customers. Individuals that qualify for veterans healthcare services include, for example, returning Active Duty, National Guard and Reserve service members of Operation Enduring Freedom (OEF) and Operation Iraqi Freedom (OIF). The vision statement of the VHA states that it needs to be a comprehensive, integrated healthcare system that provides excellence in health care value, excellence in service as defined by its customers, and excellence in education and research, and needs to be an organization characterized by exceptional accountability and by being an employer of choice.

In exemplary embodiments of the present invention, veterans, with their special requirements based on service, can be well served by ImmunoScore diagnostics and data management. As previously described in Section I, soldiers have very specific vaccination requirements based on their deployment and area of expertise. ImmunoScore diagnostic panels can be tailored to the needs and context of the individual soldier based upon his or her previous exposure to immunization and also to different infectious agents depending on the relevant theater of deployment. In addition to immune response to infectious agents, veterans are likely candidates for measurement of immune system perturbations induced by, for example, Post Traumatic Stress Disorder (PTSD), exposure to unique chemical agents (e.g., Agent Orange), Gulf War Syndrome, and recovery from injuries sustained in service.

As described above in connection with the CIP database, linear regression analysis of a patient database could yield valuable information pertinent to appropriate treatment of veterans after their years of service. Those analyses displayed possible correlations between, for example, measles and mumps immunity and immunity to varicella infection. Any possible associations between service locale and adverse agents could be documented and analyzed by an exemplary ImmunoScore data mining process in similar fashion.

The VA Research and Development program (The Office of Research and Development) aspires to lead the Veterans Health Administration in providing unequaled health care value to veterans. The ImmunoScore technology can help contain healthcare costs for veterans by monitoring and analyzing immunologic information.

D. Socialized Medicine Management

A socialized medicine jurisdiction is essentially a health care provider or insurer for an entire population. Thus, the health care management applications of ImmunoScore described above can also be implemented in a socialized medicine jurisdiction. Countries with socialized medicine, such as the UK, New Zealand, and particularly Canada, present opportunities to stress preventive medicine for the good of the populace (i.e., by maximizing QOL for a given health care budget) and the advantages of lower cost healthcare as represented by ImmunoScore managed healthcare. These governments could be provided with healthcare management services via an implementation of the ImmunoScore system.

The CIP database discussed in Section II above, has revealed the utility of an exemplary ImmunoScore database for a country with an immigrant population. There has been much concern regarding outbreaks of mumps in the United States and Europe. This disease has clearly been shown to spread from contact with travelers (CDC, 2006). The CIP database indicates a degree of relatedness between patients that have antibodies to both Rubella and Mumps. If this type of analysis were to be extended to geographic regions and associated with specific genders, a government that supported socialized medicine could, for example, be very much in favor of assuring that an immigrant population was properly immunized, for the protection of that immigrant population, as well as the native population.

E. Supplemental Insurance (AFLAC Model)

AFLAC is the leading provider of supplemental insurance, which provides help with expenses not covered by an individual's major medical plan. The company is the number one provider of guaranteed-renewable insurance in the United States and Japan. Its products provide protection to more than 40 million people and go beyond the traditional insurance by directly paying claimants with cash benefits.

With the cost of health care rising, the challenge for most employers is to satisfy the specialized needs of each employee without having to fund expensive new plans. AFLAC provides products including, for example, the following: Accident Disability; Short Term; Disability; Cancer Benefit; Hospital Indemnity.

ImmunoScore diagnostic testing and database storage can provide information for use in just such supplemental insurance programs. ImmunoScore can, for example, provide an individual with immune status testing that could be monitored over time and offer the peace of mind that would come from knowing that that patient had a "healthy" immune system. In addition, an insurer would be better able to underwrite premiums for supplemental health insurance with a sounder understanding of the patient's health status.

Additionally, in exemplary embodiments of the present invention, a "immunological insurance plan" could be offered. Such a plan could provide all immunological monitoring and therapeutics to each insured for a fixed annual premium and guarantee a certain defined quality of life to each insured. Such a plan could utilize one or more of the health care management processes described above.

To be able to effectively underwrite such supplemental insurance, supplemental insurance firms need to be aware of relatedness between immune parameters as revealed by database analyses. For instance, the CIP database revealed tendencies for Hepatitis A antibody to be present in individuals from certain geographic regions. Supplemental insurance coverage could benefit from insuring that travelers to these regions were assured of their own immune system's ability to combat Hepatitis A infections in regions where the disease is endemic. Or, for example, the CIP database revealed a possible suspension of Tetanus immunity amongst individuals reactive to CMV. In exemplary embodiments of the present invention, a health insurer (whether supplemental or primary) would take special care to take such a factor into account.

F. Immunoscore and the Wellness Industry

In 1994, the U.S. Congress laid the groundwork for the Wellness Industry by passing the Dietary Supplement Health and Education Act (DSHEA). This Act set new standards for the manufacturing, testing and marketing of nutritional products. Products that meet strict government standards earn the title of nutraceuticals. Blurring the line between conventional foods and drugs, nutraceuticals are defined as foods or parts of food that confer health or medicinal value, including the prevention and treatment of disease.

The Food Policy Institute (http://www.foodpolicyinstitute.org) has defined drivers of nutraceutical industry growth. The nutraceutical market was once viewed as largely a counter-culture "back to nature" phenomenon, but is now buoyed by a number of solid fundamentals.

Changing consumer demographics. Americans are living longer and emphasizing the importance of quality of life in their later years. As the baby boomers approach ages where personal health becomes more paramount, the demand for mechanisms for conveying health will grow.

Increasing ethnic diversification. The mainstream U.S. nutraceuticals industry is a relatively new phenomenon. However, the use of foods, herbals, and other natural products to convey health and medicinal values has a long history of acceptance by many of the world's cultures.

Paradigm shift in personal health. Americans are taking more responsibility for their personal health, embracing the concept of health maintenance and wellness. Thus, the paradigm is shifting away from disease treatment and towards disease prevention.

Dissatisfaction with Western healthcare. Americans are becoming more reticent about accepting the side effects of synthetic drugs and remedies. Similarly, rising healthcare costs are encouraging Americans to explore alternatives to traditional orthodox medicine.

Increasing acceptance of alternative healthcare practices. There is a growing acceptance among Americans of alternative or complementary therapies and wellness modalities. Recent years have witnessed increased use, for example, of chiropractic care, vitamin therapy, aromatherapy, meditation and relaxation techniques, and acupuncture.

Increased understanding and awareness of diet-disease relationships. Many of the leading causes of premature death in the U.S. are diet-related. Examples include heart disease, diabetes, and many types of cancer. The USDA estimates that diet-related disease and death costs the U.S. in excess of $250 billion each year.

The Food Policy Institute has identified challenges facing the nutraceutical industry.

Few farmers are producing herbals and other botanical inputs (due to limited market knowledge, technical requirements and other obstacles.

Limited access to finance and capital constrains industry development and expansion.

Ambiguous regulatory framework for ensuring product standardization and efficacy.

Regulatory restrictions on marketing products via health claims impede retail efforts.

Raw material supply issues (consistency of quality and availability) for botanical manufacturers.

Limited endorsement by traditional healthcare practitioners.

Consumers can not differentiate between high and low quality products and are not sufficiently educated to make informed decisions about proper product use.

ImmunoScore diagnoses and database could provide the answers to these challenges. Individuals and populations could be studied with respect to the efficacy of a nutraceutical diet. ImmunoScore would either pave the way for more growth in curtain nutraceuticals, or perhaps point out the sale of "snake oil." Individual products, or product lines could be endorsed as valid by ImmunoScore measurements.

The Wellness Industry is expected to grow. The Wellness Industry includes the concept of "wellness insurance" to lower health care costs to individuals. This may provide yet another opportunity to leverage ImmunoScore testing and data storage into the insurance industry.

In addition, workplace wellness as a concept has been used extensively in recent years by management in business and industry, health professionals, fitness experts, and others. Well-designed and administered programs deliver positive outcomes for employers as well as employees. Because healthy employees cost less than employees suffering from illness, ImmunoScore can be a part of employee insurance offered by employers wanting the best and most affordable health care for their employees.

Analyses of the CIP database have shown the development of positive and negative relationships for one variable with respect to another variable (for example, Rubella antibody and Hepatitis A antibody levels as is illustrated in FIG. 20D, and for example, Mumps antibody vis-a-vis Hep A, Measles and Rubella, as shown in FIG. 20E). This type of analysis could be extended to other variables regarding "wellness." For example, fitness measurements could be incorporated (body mass index, cardiac function, etc.) into an overall immune fitness relationship.

Virtual Physicals™—Incorporate ImmunoScore Diagnostic and Database

The Virtual Physical™ is a comprehensive diagnostic screening procedure that uses state-of-the-art technology to take a global look at a patient's body and identify a variety of conditions at early stages where intervention can be most helpful. A Virtual Physical™ may also be viewed as an integral component of a holistic, behavioral medicine program, where the body, and one's diet, exercise, and lifestyle habits are viewed as a whole, determining where problems may exist and where changes might be required.

The Virtual Physical's™ early detection capability can uncover asymptomatic and often life-threatening diseases generally not detectable by physical exam or standard screening tests. This allows the management of disease in early stages, where medical therapy and treatment options are typically less costly, less invasive and more effective.

Virtual Physical's™ comprehensive scan of an individual's body is significantly more detailed than an X-ray. It covers: (a) the heart and arteries, identifying near microscopic amounts of plaque; (b) the lungs at the air cell level showing the earliest stages of smoke damage, emphysema, or lung cancer; (c) the spine, evaluating for osteoporosis, disc disease and other back problems; (d) internal organs for detection of tumors, stones and cysts of all sizes; (e) aneurysms in the abdominal and chest cavities; (f) thyroid and parathyroid disease; (g) joint disease; and (h) uterine, ovarian, and prostate disease.

In the interest of determining a patient's "totality of health," ImmunoScore screening could accompany a Virtual Physical™ to add an immune health component to the virtual screening. It is possible that insurance will cover a Virtual Physical™ in the future, and ImmunoScore testing and data storage could be incorporated into the patient's records that could be transferred to the patient's primary care physician or specialist.

G. Women of Childbearing Age/Screening of Pregnant Women

A superpanel for women of childbearing age was described above in Section I.

In light thereof, ImmunoScore diagnostic tests and database storage availability in the offices of obstetricians would greatly enable appropriate immunization of pregnant women as well as find correlates of prenatal interest. In addition to screening pregnant women for their immune status regarding vaccine preventable diseases, ImmunoScore diagnoses and data management could also be of value in determining the immune status of pregnant women regarding, for example, group B streptococcal infection, cytomegalovirus (CMV) infection, and other infectious diseases that may adversely affect the newborn, yet are treatable prenatally. Early onset GBS infection has been the leading cause of death attributable to infection in newborn infants for over three decades, with over 6,000 cases a year in the United States (Vallejo, et al. 1994). Antibiotics have been used to good effect to prevent newborn GBS infection. There is also promising preliminary data on an effective intervention to prevent CMV infection in newborns in pregnant women that has been published recently (Nigro, et al. 2005). All these treatments can be more advantageously administered using ImmunoScore technology.

FIG. 28. depicts an exemplary process flow for managing the immune status of women of child-bearing age. Beginning at 2801 the immune status of a women of child-bearing age is examined. At 2810 the vaccine preventable diseases to which the woman is susceptible are identified as well as the woman CMV infection status and pregnancy status. At 2820 these three variables are used to generate healthcare recommendations, as follows. If the woman has not been infected with CMV and is not pregnant, she is advised to obtain immunizations for the identified vaccine preventable diseases. If she is an insured under a healthcare insurance plan, or her healthcare is provided by an HMV or socialized medicine entity she can be, for example, required to obtain these immunizations to save future treatment costs as well as to serve the utility of having a healthy population. If she has not been infected with CMV but is pregnant, she can be informed of extra precautions regarding CMV status and pregnancy. Moreover, no immunization with attenuated vaccines is recommended or should be performed. However, other immunizations should be recommended based upon current CDC guidelines. If the woman is seropositive to CMV and is not pregnant, she can be advised or required, as the case may be, to obtain immunizations for the identified vaccine preventable disease. Finally, if she seropositive for CMV and pregnant, no extra precautions should be taken regarding the CMV status unless there is an active primary infection. Moreover, no attenuated vaccine should be recommended or administered. However, other immunizations can be recommended or required based upon current CDC guidelines. At 2830 a follow-up examination of the women's immune status post-vaccination can be conducted, and, if she is not pregnant, the information can simply be stored in a system database. If she is pregnant, a post-natal follow-up can be recommended or required, as the case may be, comprising MMR vaccination of the mother and monitoring of CMV status of the child. Finally, at 2840, based upon the post-vaccination follow-up at 2830 the efficacy of the administered vaccines can be evaluated as to whether they provide the necessary immunity to the vaccine preventable diseases identified at 2810.

The CIP clearly points out the need for antibody measurements in women of child-bearing years. The obvious antibody to be examined is that for Rubella, to which the women of SE Asia were shown to have levels below average. Other important antibodies in women of child bearing years are, of course, those to group B Streptococcal organisms and others that affect fetal development or those associated with neonatal illnesses. From an insurance and public health perspective, these are extremely important issues.

H. Vaccine-O-Mat/Vaccine Distribution Network

In exemplary embodiments of the present invention, ImmunoScore technologies can be used to facilitate the easy dispensing of vaccines to the public as well as giving the public access to their immunologic information. Therefore, in exemplary embodiments of the present invention a business analogous to the "Fotomat" photograph finishing stores, once located in malls and strip malls across America, can be created. For purposes of the present description, this exemplary embodiment of the present invention can be called "Vaccine-o-Mat." Vaccine-o-Mats can be located in small buildings in corners of malls and strip malls, as concessions in large chain stores such as Target or Wal-Mart, or they can be located almost anywhere in appropriate markets and one day be as ubiquitous as Starbucks Coffee centers. At a Vaccine-o-Mat a member of the public can have his or her immune status checked and can receive any vaccines that he or she may be deficient in. If an individual steps on a rusty nail and doesn't remember the last time he or she had a tetanus booster he or she can simply drive to the nearest Vaccine-o-Mat, have a panel of assays containing tetanus and any related compliments as conducted and determine then and there whether he or she needs a vaccine. What makes the Vaccine-o-Mat business possible is instruments which can process large numbers of assays in a relatively short period of time, as noted above. One such instrument is the cobase 411 analyzer (Roche Diagnostics).

FIG. 29 depicts an exemplary process flow for use at a Vaccine-o-Mat. At 2901, the customer's immune status is examined for vaccine preventable diseases and related immunologic information. It is further contemplated that a particular customer may want to have his or her bodily fluids assayed for a wide variety of immunologic tests and not have them restricted to vaccine preventable diseases. Therefore 2901 need not to be strictly directed towards vaccine preventable diseases. At 2910, within 90 minutes the assay results can be processed to generate recommendations for appropriate vaccines. This functionality depends upon, as noted above, instruments which can process a large number of assays in a relatively short amount of time. This concept allows for partnering with large chain stores or malls where customers could make their first stop at the Vaccine-o-Mat to have their blood tested. They could then continue shopping and then return at the end of their shopping excursion to receive any necessary vaccines and report regarding their immune status. At 2920 appropriate vaccines can be administered to the customer on site, and at 2930 the customer can be provided with a printout of the assay results the updated vaccination record and his or her database record from the ImmunoScore database along with instructions on how to access that information in the future. Finally, at 2940 all of the additionally required customer information resulting from that particular visit is stored in the database for future reference.

One of the benefits of the ImmunoScore technology is the ability to link diagnostic testing of the immune system with rapid delivery of medication at the point of care (ideally, during the course of an office visit). Thus, in exemplary embodiments of the present invention a vaccine distribution network can be set up, for example, to link vaccine manufacturers to physicians' offices—or other authorized vaccine dispensing personnel equipped with diagnostic facilities. Vaccine distribution can also, for example, become part of the ImmunoScore database tracking specific manufacturers' lots numbers to points of sale. This can be important in getting timely information incorporated into the Vaccine Adverse Event Reporting System (VAERS).

FIG. 29A depicts exemplary envisioned interactions between various parties according to an exemplary embodiment of the present invention directed towards vaccine distribution. Information gathered to an exemplary ImmunoScore database can, for example, be shared with the various agencies responsible for dictating vaccination decisions. Unsuspected or unknown relationships regarding immune health or function can be, for example, "fished" or "mined" from a system database using appropriate queries and analysis. In addition, in exemplary embodiments of the present invention, suspected adverse events from vaccination could be addressed and acknowledged or dismissed, based upon information gleaned from the system database.

With reference to FIG. 29A, various entities and institutions which can, for example, be involved in vaccine distribution or vaccine distribution network are depicted. They include any vaccine manufacturers 29A05 who through vaccine sales provide vaccines to physicians or healthcare providers 29A10. The physicians or healthcare providers 29A10 also receive diagnostic testing kits and research services, such as, for example, ImmunoScore vaccine diagnostic panels 29A01. The government 29A15 has a variety of roles in a vaccine distribution network, including subsidizing or providing economic incentives to create or build a supply of vaccines by a transfer of funds to, or via tax incentives to, vaccine manufacturers 29A05. The government can further subsidize or fund HMOs 29A25 and in this context the Veteran's Administration, described above can be considered one of them. Additionally, the government 29A15 can mandate vaccine benefits to certain segments of the population and those can be provided by HMO 29A25 or equivalents. Finally, the government 29A15 can itself access personalized immune status data as to individuals or populations or sub-populations 29A12 for a variety of research or health management purposes. The CDC and ACIP 29A50 can receive input from Physicians/Healthcare Providers 29A10 as well as from a vaccine status database 29A30. Vaccine status database 29A30 can be generated from an Immunization Registry 29A40 set up by the CDC, ACIP or other similar institutions or bodies to maintain immunization records for the population so as to better know who should be vaccinated. FIGS. 29B and 29C, described below illustrate improving connectivity between entities and organizations who could access and utilize ImmunoScore information in this context, allowing the benefits of ImmunoScore to be ubiquitously available.

I. Consumer Accessibility to Immunologic Information

Americans are playing a risky game of sexual roulette, according to a new poll finding that only 39 percent of respondents always ask a new lover if they are infected with HIV. The poll, taken by Zogby for MSNBC.com also found that 73 percent of respondents were involved in a monogamous relationship, and that 66 percent of those surveyed had had unprotected sex while under the influence of alcohol. While 39 percent of respondents said they always asked whether a new partner is infected with HIV or other sexually transmitted diseases, 31 percent said they never discuss the touchy issue with a new partner. Moreover, the survey found that 15 percent of Americans had paid for sex, 35 percent of respondents said they had been with between one and five sexual partners, and 19 percent said they had had more than 25 partners.

In exemplary embodiments of the present invention this "risky business" can be ameliorated. Accordingly, at the Vaccine-o-Mat described above, individuals can have their immune status tested by conducting, for example, an STD assay panel, as described in Section I above, which can then be shown to potential sexual partners to fully disclose the immunologic risks that may be involved in any proposed liaison. For example, a couple can stop at a Vaccine-o-Mat near a romantic restaurant of their choice. They can have the assays conducted and go off to dine. If things are going well, by the time their coffee has arrived they can obtain each other's immune status and be off—either alone or together—depending upon the ImmunoScore results.

Alternatively, for example, someone worried by past promiscuities can routinely procure his or her immune status at the local Vaccine-o-Mat in 90 minutes, and put any worries to rest, or at least know what they are facing.

J. Immunoscore Connectivity Via Interapplication Translator/Data Integrator

In many exemplary embodiments according to the present invention, the power of an ImmunoScore diagnosis and database lies in the interaction of the database with many different organizations, as shown in FIG. 29B. Use of a web services interconnector to provide this connectivity is illustrated in FIG. 29C, next described. The CDC, the government (or governments, for that matter), health maintenance organizations, vaccine manufacturers, and physicians would all be able to interact with the database and each other to make the best possible decisions regarding the health and welfare of the citizenry.

With reference to FIGS. 29B and 29C, a number of entities and organizations who could access and utilize ImmunScore information are shown. FIG. 29B shows a complicated information exchange structure wherein each entity involved has to set up a separate communications line or pathway to each of the other entities in the network. This can easily be remedied, as shown in FIG. 29C, by utilization of an Interapplication Connectivity Provider 29C50 which can interconnect the various individual and sometimes proprietary computer systems, computer networks, databases, and applications of each of the individual entities participating in the vaccine distribution/creation network so that they can talk to each other. This technology is often referred to as interapplication connectivity or interapplication translation. One example of such a interapplication connectivity provider is the IBM, in particular the IBM Web Services Centers Of Excellence. Additionally, Enterprise Computing service companies, such as, for example, EDS also provide products which link different and disparate computing platforms so that they can exchange data and information in an efficient manner.

The CIP database has only scratched the surface of what can be captured and shared by a large ImmunoScore database, but important information can be gleaned from this database, such as it is, of use to government sources, patients, physicians, and insurers. Demographic information regarding crowding and sanitary facilities has been shown to correlate to degrees of protection to vaccine-preventable diseases in the populations examined. If the database were to also include information regarding the movement of patients (for instance), much useful information could be shared among these concerned groups.

K. Immunologic Informatics Based Life Insurance Underwriting

In the exemplary embodiments of the present invention ImmunoScore data can be used to optimize the underwriting of life insurance. Additionally, assuming that regulatory restrictions are not preclusive, ImmunoScore data can be used by companies which provide both life and health insurance to the same clientele. The use of ImmunoScore technology for these purposes is depicted in the exemplary process flow chart of FIG. 30.

With reference to FIG. 30, at 3001 an individual's immune status can be examined and any diseases to which he or she is susceptible identified. At 3015, by accessing Business Rules Database 3010, the probability of death of the individual given the immune status identified at 3001 can be computed. At 3016 the cost of insuring that individual, based on the probability of death of years to death calculated in at 3015 can be computed and premiums can be set at 3020. It is noted that the term "death" appearing in FIG. 30 is shorthand for "years remaining until death."

Additionally, at 3002 all combinations of possible prophylactic therapies can be generated given the immune status obtained at 3001. From these combinations, at 3005, the probability of time (generally in years) to death given the immune status and the various combinations of prophylactic therapies can be computed. Such computation, at 3005, exchanges data with Business Rule Database 3010. For convenience, two Business Rules Databases 3010 are depicted in FIG. 30; in exemplary embodiments of the present invention there could be one or many Business Rules Databases each devoted to a specific informational domain. In the depicted exemplary embodiment of FIG. 30 they could most likely be combined inasmuch as they are providing information which allows a system to compute the probable time to death given an immune status. However, the Business Rules Database on the right side of the figure may require more complex information in order to also factor in the available set of possible preventive therapies for each identified disease.

At 3016, the outputs of 3015 and 3005 are input to allow the exemplary system to compute the cost of insuring the given individual. At 3021 the system can select the two or three best sets of prophylactic therapies from the information generated at 3002, and at 3025 it can offer these prophylactic therapies to the client with a proviso that the life insurance premium set at 3020 in absence of factoring in prophylactic therapies could be lower by (x) if the client chooses to undertake the prophylactic therapies. Alternatively, at 3030 it may be in an insurance company's interest to pay for the prophylactic therapies, i.e., offering them to the insured for free, if the cost of the prophylactic therapies is less than the present value of the expected savings to the life insurance companies by the insured having the prophylactic therapies performed. This can be expressed, for example, as:

$$PT\ cost < PV\{(death\ benefit)*[(Prob(death|no\ IS, no\ PT) - Prob(death|IS, PT)]\}$$

Thus, if at 3030 such an offer is made, any premium adjustment at 3020 can be diminished or completely reduced. The function of 3030 is to increase the profits to the life insurance company by not only identifying the premium which it would charge the insured but also, based on the immune status data obtained during the underwriting process (or during an annual audit process), to identify prophylactic treatments that could be offered to increase the time to death for the same individual thus allowing the insurance company to continue to earn the return on the cumulative premiums prior to having to pay the death benefit to the survivors.

It is also noted that at 3021 where the 2-3 best sets of prophylactic therapies are found the term best is really a function of how much the probable time to death is increased. Finally, the availability of probable time to death given a certain immune status and certain prophylactic therapy can be computed using the following equation as noted in FIG. 30:

$$Prob(death|IS\ and\ PT) = P(CD|PT\ and\ IS)*P(D|CD\ and\ IS) + P(not\ CD|PT\ and\ IS)*P(D|not\ CD\ and\ PT\ IS)$$

When offering prophylactic therapies to an insured, unique opportunities arise for insurance companies providing both life and health benefits. A healthier insured lives longer and uses less health care, resulting in twofold savings for an insurer. Because such a life insurance company also approves health care expenditures, there is no red tape or customer effort spent on securing approval for any offered or recommended prophylactic therapies. Thus, in such contexts, the real world optimizations can actually converge on the theoretical optimizations calculated by an ImmunoScore analysis as depicted in FIG. 30. This can, in exemplary embodiments, increase QOL for insureds and profits for the insurers, as well, hopefully.

Patient commonalities, as revealed by analyses of the OP database, could be visualized. For example, if a population immigrating from Eastern Europe were shown, in general, to have lower protection against a specific disease or diseases, that information could, for example, be of interest to health/life insurance companies.

Described below is a second exemplary embodiment of the present invention wherein ImmunoScore data can be used to optimize the underwriting of life insurance. The second embodiment can be used in combination with or separate from the method described above.

The underlying concept of this method involves ascertaining an individual's likelihood of surviving an unknown, unanticipated, or otherwise unaccounted for disease. For example, the disease may be one that is not considered at step 3001. For example, new diseases emerge (e.g., HIV in the 1980's) or old diseases become resistant to therapies (e.g., antibiotic resistant forms). Thus, ImmunoScore is used to assess the ability of an individual's immune system to react favorably to one of these challenges.

For example, the magnitude and direction of the combined response of Th1, Th2, Th17, and Treg can be used to assess an individual's ability to resist new diseases. In some embodiments, the probability of death given an immune status (Prob(death|IS)) is inversely related to the magnitude of the combined response. The larger the magnitude of the combined response (as trended over time or at one time point), the more out-of-balance the immune system is, increasing the chances the individual will contract diseases, thereby increasing the appropriate life insurance premium.

This use of ImmunoScore technology may be easier to implement than the other life insurance model, because less information is required regarding diseases, prophylactic therapies, and how they affect the individual's remaining lifetime. Nevertheless, this second method can still improve the stratification of individuals to set and/or adjust premium levels. The two methods can be used in combination. The first method can be used on all known diseases or on a subset (perhaps only 1-10 diseases) to improve the results obtained from only using the second method.

L. Diagnosing and Managing Immunosenescence in the Elderly

Human aging is associated with progressive decline in immune functions and increased frequency of infections. Morbidity and mortality due to infectious disease is greater in the elderly than in the young, at least partly because of age-associated decreased immune competence, which renders individuals more susceptible to pathogens (Pawelec, et al. 2005). A decline in immune function is a hallmark of aging that affects the ability to resist influenza and respond to vaccination. An accumulation of dysfunctional T cells may be detrimental under conditions of chronic antigenic stress (chronic infection, cancer, autoimmunity). The most important changes occur in T-cell immunity, and are manifested particularly as altered clonal expansion of cells of limited antigen specificity (Fulop, et al. 2005). This is most marked in the $CD8^+$ T cell subset, which displays a decrease in both responsiveness and normal function. Normally, $CD8^+$ T cells appear to be strongly associated with cytolytic activity, either by direct killing of antigen-bearing target cells by granule-mediated exocytosis or Fas-mediated cytotoxic mechanisms. In addition, it is suggested that antigen-activated $CD8^+$ T lymphocytes can eliminate or control viral infection by secretion of antiviral cytokines, such as gamma interferon (IFN-γ) and tumor necrosis factor alpha (TNF-α). IFN-γ production by $CD8^+$ T cells can have both local and systemic consequences, whereas cytotoxins such as perforin are cytolytic for the cells that come in direct contact with the cytolytic T lymphocytes (CTL).

The output of the T cell pool is governed by output from the thymus and not by replication (Aspinall and Andrew, 2000). As thymic T cell production diminishes with age, a decline in contribution made by thymic emigrants to the naive T cell pool occurs (Mackall, et al. 1995). Diminution in the size of the naive T cell pool is a common finding with aging, and is a consequence of reduced thymic output (Kurashima, et al. 1995). Thymic atrophy is thought to result from a failure of the thymic microenvironment to support thymopoiesis in old age and recent evidence suggests that a decline in interleukin-7 (IL-7) expression may limit thymocyte development by restricting combinations of survival, proliferation and rearrangement of the beta chain of the T cell receptor (Andrew and Aspinall, 2002). Therapeutic intervention with IL-7 and derivatives has been shown to reverse thymic atrophy in old animals and also lead to improved immune function compared with age and sex matched control animals (Aspinall, 2005).

The $CD8^+$ T cell repertoire becomes less diverse in old age due to reduced thymic output and the accumulation of clonally expanded memory $CD8^+$ T cells as a consequence of prolonged antigenic stimulation. Clonally expanded T cells are usually CD8+ and show an increased incidence with age, so far it seems that clonal expansion is not due to malignancy but may follow antigen stimulation. It has been suggested that repeated or persistent infections with viruses such as influenza, cytomegalovirus (CMV), and Epstein-Barr virus (EBV) may drive responses that result in large T cell clones. Longitudinal studies suggest that a set of immune parameters including high percentages of peripheral $CD8^+CD28^-CD57^+$ T cells, low $CD4^+$ and B cell counts, and poor T cell proliferative responses to mitogens is associated with decreased remaining longevity in the free-living very elderly (>85 years). CMV seropositivity is closely associated with increases in the size of the $CD57^+$ $CD8^+$ T cell pool, which is thought to represent a highly differentiated population of late memory cells. Furthermore, CMV seropositivity is associated with increases in $CD8^+$ count in old age and has been documented to have negative influences on immune parameters in the very elderly. A group concluded that the "obsession" of a large fraction of the entire $CD8^+$ T cell subset with one single viral epitope may contribute to the increased incidence of infectious disease in the elderly by shrinking the T cell repertoire for responses to other antigens. Like CMV, EBV manages to persist for the lifetime of the infected host. During chronic asymptomatic infection in healthy individuals, EBV resides in memory T cells. Expansion of peripheral CD8+ CD28– T cells in response to chronic EBV infection has been linked to rheumatoid arthritis. The clinical consequences of these changes are as yet not well defined, except for their extremely important negative impact on defense against infections. Considering the public health consequences of decreased immune competence in old age, strategies for immune response modulation are desirable to decrease the health burden for the elderly and improve their quality of life.

Features of successful aging have been associated with well-preserved immune function while poor survival is predicted by high CTL counts, low numbers of B cells and poor responses by T cells to polyclonal stimulation. The phenomenon of replicative sensescence has been associated with these changes and relates to a finite number of doublings (25-30 cycles) after which cell cycle arrest occurs. In CTLs, this growth arrest is associated with increased production of several pro-inflammatory cytokines, resistance to apoptosis and loss of the co-stimulatory molecule, CD28, required for optimal stimulation of CTLs. In older adults, greater than 50% of CTLs fail to express CD28 and these cells are resistant to apoptosis.

The loss of CD28 expression due to replicative senescence has been associated with a number of the adverse effects of aging on immune function. Although the frequency of influenza virus-specific CTLs does not appreciably change with age, the decline in CTL activity against influenza may be due to a loss of antigen-specific proliferation and/or diminished lytic activity. Normal loss of CD28 expression during CTL activation and the potential for these cells to undergo activation-induced cell death, may be confused with the loss of CD28 with replicative senescence and resistance of CTLs to apoptosis. Furthermore, the role of cytokines (such as, for example, IL-2, IL-7, and IL-15) in preventing activation-induced cell death and age-related changes in the production of these cytokines create a complex array of interactions that may confound the interpretation of in vitro experiments. Understanding the complexity will provide an opportunity to optimize the CTL response to vaccination by manipulating CTLs that retain their replicative capacity in response to appropriate antigenic stimuli.

Currently, influenza vaccination of elderly individuals is recommended worldwide. A recent study looked retrospectively at influenza vaccine efficacy in individuals aged 65 years or older. They found that in homes for elderly individuals, that vaccines were not significantly effective against influenza, influenza-like illness, or pneumonia. More encouragingly, vaccine performance was improved for admissions to the hospital for influenza or pneumonia, respiratory diseases, and cardiac disease. This group concluded that the usefulness of influenza and pneumococcal vaccines was modest. On the same day the Jefferson report was published online, the American Medical Directors Association released a special announcement regarding the Jefferson study and influenza vaccine recommendations for the elderly (http://www.amda.com/newsroom/092205_vaccines.htm). While not disagreeing with the tenets of the study, they continued to recommend for vaccination of the elderly because influenza vaccination is effective at preventing severe illness, secondary complications, and deaths. They also reiterated that the CDC recommends influenza vaccination for people age 65 years and over and for all persons in long-term care facilities (http://www.amda.com/newsroom/092205_vaccines.htm). Both groups concluded that better influenza vaccines that offer more protection in older persons are desirable and a high priority of influenza researchers.

The threat of pandemic influenza has increased with the direct transmission of highly pathogenic avian H5N1 viruses to humans. Continued reliance in killed virus or subunit vaccines will leave adults at significantly higher risk of illness, disability and death in the event of an influenza pandemic. Research that increases our understanding of how immunosenescence affects the cell-mediated response to influenza and vaccine responsiveness is critical to the development of effective pandemic influenza vaccines for older people. In the absence of influenza vaccines that target these defects, an influenza pandemic will have a significant impact on older people and quickly overwhelm the health care system.

On Aug. 8, 2005 the CDC has stated that the effectiveness of inactivated influenza vaccine depends primarily on the age and the immunocompetence of the vaccine recipient and the degree of similarity between the viruses in the vaccine and those in circulation. When the vaccine and circulating viruses are antigenically similar, influenza vaccine prevents influenza illness among approximately 70-90% of healthy adults aged <65 years. Children aged ≥6 months can develop protective levels of anti-influenza antibody against specific influenza virus strains after vaccination, although the antibody response among children at high risk for influenza-related complications might be lower than among healthy children. In addition, no efficacy was demonstrated among children who had received only one dose of influenza vaccine, illustrating the importance of administering two doses of vaccine to previously unvaccinated children aged <9 years. Older persons and persons with certain chronic diseases might develop lower post-vaccination antibody titers than healthy young adults and thus remain susceptible to influenza infection and influenza-related upper respiratory tract illness (http://www.cdc.gov/flu/professionals/vaccination/efficacy.htm). While current vaccines are cost-saving, new influenza vaccines will likely be needed to avoid the crisis anticipated in health care related to the general aging of the population.

Another component to the aging immune system is the relationship between innate immunity and inflammation. During evolution the human was set to live 40 or 50 years; today, however, the immune system must remain active for a much longer time. This very long activity leads to a chronic inflammation that slowly but inexorably damages one or several organs. This is a typical phenomenon linked to aging and it is considered the major risk factor for age-related chronic diseases. Alzheimer's disease, atherosclerosis, diabetes, sarcopenia, and cancer to name several, all have an important inflammatory component, though disease progression seems also dependent on the genetic background of individuals Inflammatory genotypes are an important and necessary part of the normal host response to pathogens in early life, but the overproduction of inflammatory molecules might also cause immune-related inflammatory diseases and eventual death later.

Most age-related diseases have complex etiology and pathogenic mechanisms. The clinical diagnosis and therapy of these diseases requires a multidisciplinary approach with progressively increased costs. A body of experimental and clinical evidence suggest that the immune system is implicated, with a variable degree of importance, in almost all age-related or associated diseases. Both the innate and the clonotypic immune systems are usually involved in the pathogenesis of these chronic diseases (Caruso, et al. 2004; Pawelec, et al. 2002). Several functional markers of the immune system may be used either as markers of successful aging or conversely as markers of unsuccessful aging. A combination of high $CD8^+$ and low $CD4^+$ and poor T cell proliferation has been associated with higher mortality in very old subjects. Old men carrying an anti-inflammatory IL-10 high-producer genotype or a pro-inflammatory IL-2 low-producer genotype show the lowest values of CD8+ cells. This study, however, did not do a functional assessment of T cells.

In a mouse model looking at T cell subset patterns, researchers found that a composite combination of subset values was a significant predictor of longevity among genetically heterogeneous mice, with a strength of association higher in older mice than among the young. Developing useful biomarkers of aging has proven to be remarkable difficult, in part because many age-sensitive variables tested as candidate biomarkers are sensitive to genetic and nongenetic influences other than aging. Any individual assay, for example a test of a specific T cell subset in a single blood sample, is likely to have a good deal of uncertainty, but the combination of results from related tests may increase the signal-to-noise ratio and thus provide stronger predictive power than any single assay by itself. In humans, ImmunoScore testing would help build the models of T cell subset patterns. Possible courses of therapy would then be ideally tailored to meet the needs of the individual and not a "best guess, one size fits all" course of treatment.

Clearly, the population aged ≥65 years would be better served by ImmunoScore diagnostics rather than the current state of affairs. A blanket recommendation for an influenza or pneumococcal vaccination for the entire elderly population may not be in the best interest of an individual being immunized. ImmunoScore diagnostic tests could, for example, first reveal levels of protective antibody to vaccine-preventable diseases. Of particular interest would be antibody levels against influenza, pneumococcal infection, tetanus, diphtheria, pertussis, hepatitis, varicella, CMV, and EBV. Just as important as determination of antibody levels in elderly patient sera, ImmunoScore diagnostic tests could reveal the status of cellular components of the immune system. The proportion of naive/committed T and B cells would be crucial for further recommendations by the attending medical staff. As therapeutic interventions are developed for dealing with immunosenescence, the ImmunoScore diagnostic information regarding individuals and compiled database information will shed valuable light onto the effects of treatments on the immune system. As the population ages, strategies for immune response modulation are desirable to decrease the health burden for the elderly and improve their quality of life.

A preliminary immune risk phenotype (IRP) has been developed from longitudinal studies of the elderly. Immune system measurements consisted of determinations of T-cell subsets, plasma IL-6, IL-2 responsiveness to conconavalin A, and CMV and EBV serology. Regression analyses indicated that the IRP and cognitive impairment together predicted 58% of observed deaths. This type of analysis would be a valuable adjunct to assessing insurance premiums.

The following table captures exemplary desirable analytes to monitor in the population as individuals age. A database storing the results of such assays could ensure that a given individual's analyte levels could be tracked over time rather than merely captured as a snapshot.

TABLE 1

Alterations in the T-cell compartment with age

| Alteration | Analyte |
|---|---|
| ↑ | CD45RO+ cells |
| ↑ | CD95+ cells |
| ↓ | CD28 expression |
| ↑ | CD152 expression |
| ↑ | killer cell lectin-like receptor G1 |
| ↓ | apoptosis of CD8 cells |
| ↑ | apoptosis of CD4 cells |
| ↓ | IFN-γ production |
| ↓ | IL-2 production |
| ↓ | telomere lengths |
| ↓ | telomerase induction |
| ↑ | DNA damage |
| ↓ | DNA repair |
| ↓ | stress resistance and heat-shock protein expression |

Thus, in exemplary embodiments of the present invention an Immunosenescence superpanel can be defined, comprising the following panels:
Meningococcal Diagnostic Panel;
Persistent Immunity Induced by Childhood Vaccines; and
Immunosenescence Diagnostic Panel The first two panels are defined in Sections IA1 and IA3 of the Immunologic Information Patent, and an Immunosenesence panel can, for example, be defined as follows.

Human aging is associated with progressive decline in immune functions and increased frequency of infections. A decline in immune function is a hallmark of aging that affects the ability to resist influenza and respond to vaccination. The most important changes occur in T cell immunity. An accumulation of dysfunctional T cells may be detrimental under conditions of chronic antigenic stress (chronic infection, cancer, autoimmunity).

Exemplary Alterations in T-Cell Compartment to Monitor

| Typical Alteration | Analyte |
|---|---|
| Increased | CD45RO+ cells |
| Increased | CD95+ cells |
| Decreased | CD 28 expression |
| Increased | CD152 expression |
| Increased | Killer cell lectin-like receptor G1 |
| Decreased | Apoptosis of CD8+ cells |
| Increased | Apoptosis of CD4+ cells |
| Decreased | IFN-γ production |
| Decreased | IL-2 production |
| Decreased | Telomere lengths |
| Decreased | Telomerase induction |
| Increased | DNA damage |
| Decreased | DNA repair |
| Decreased | Stress resistance and heat-shock protein expression |

Other analytes of particular interest in an immunosenescence assay panel can, for example, include:
Antibody to CMV
Antibody to EBV
Antibody to influenza
Antibody to pneumococcal disease
Antibody to pertussis
Antibody to tetanus
Antibody to diphtheria
Plasma levels of IL-6
Th1/Th2 components as described below:

| TH1 | | TH2 | |
|---|---|---|---|
| Cytokines | Receptors | Cytokines | Receptors |
| INF-γ | CCR5 | IL-4 | CCR3 |
| TNF-α | CXCR3 | IL-5 | CCR4 |
| IL-2 | CCR1 | IL-6 | CCR8 |
| IL-12 | | IL-10 | CRTh2 |
| | | IL-13 | |

FIG. 31 depicts an exemplary process flow for managing immunosenescent individuals, either in a health care provider or a health care insurer context.

In exemplary embodiments of the present invention immunosenescense in an individual can be managed using the process exemplary flow depicted in FIG. 31. With reference thereto, at 3101, an elderly individual's immune status can be examined. This can be accomplished by conducting one or more assay panels as described above in Section I. At 3110, the vaccine preventable diseases that the elderly individual is susceptible to can be identified at the same time the individual's CMV infection status together with other relevant markers of an immune system competence can also be determined. At 3120 vaccine and/or other healthcare recommendations can be made based upon the immune status examined at 3101. Additionally, a separate T cell compartment can be assessed. At 3130, the individual can be immunized for vaccine preventable disease based upon his or her immune system's ability to response to vaccination. Using the ImmunoScore data, the individual can be classified as either (1) immunocompetent (2) immuno-deficient or (3) somewhere inbetween immunocompetent or immuno-deficient. At 3130 an immunocompetent individual can be vaccinated as recommended by current ACIP recommendations. An immuno-deficient individual would need to be managed using different measures than routine vaccination. Such measures could include, for example, adoptive transfer of a compartment of T or B cells or extraordinary hygiene measures. The individuals who fall somewhere between immunocompetence and immunodeficiency need some kind of hybrid health management between standard vaccination and immunoadjuvant therapies such as adoptive transfer of T or B cells and extraordinary hygiene measures. At 3140, the elderly individual's immune status can be followed up post vaccination or post treatment and these results stored in the system database. At 3150, this information can be used to evaluate the efficacy of the vaccination or other therapies as to their abilities to provide the necessary immunity to the identified diseases.

M. Frozen Storage of Naive Immune Cells (IRP Considerations)

As previously described, the immune risk phenotype (IRP) is an emerging concept—predicting mortality based on CMV seropositivity (Pawelec, et al. 2005). Pawelec, et al. maintained that the manner in which CMV and the host immune system interact is critical in determining the IRP and is hence predictive of mortality. The consequences of IRP is early expression of immunosenescence. Immunosenescence leads to: a) decreased T- and B-cell responses to foreign antigen; b) increased responses to self antigens; c) increased morbidity and mortality to infectious disease; and d) decreased response to vaccine antigens.

Greater elucidation of the IRP and its consequences is to be expected in the future. Genetic screening at a very early age could be predictive of immune health at a much more advanced age. The ImmunoScore diagnostic screen could be performed from a heel stick done at birth, and a child's baseline immune status could almost instantaneously be generated. Pre-natal screening tests could also be developed in the future as an immunodiagnostic tool.

Concerned parents may wish to store their child's cord blood as a source of hematopoietic progenitor cells that could be stored (at a cost to the parents or the insurers) for that child for treatment of developing IRP symptoms much later in life. Umbilical cord blood (UCB) is currently used as a source of these hematopoietic progenitor cells as an alternative to the bone marrow or peripheral blood for treatment of several onco-hematological diseases (Adami, et al. 2005).

On Apr. 18, 2005 the Institute of Medicine (TOM) issued a report recommending that a new cord blood coordinating center—similar to the existing National Marrow Donor Program—be set up to ensure a standardized and interconnected national system to cost-effectively store and distribute these cells.

ImmunoScore diagnostics shows the need for storing cord blood.

Another application for ImmunoScore diagnostics is to link storage and analysis of naive cells of the immune system (innate or adaptive), as next described.

T cells currently used for adaptive immunotherapy trials are selected for their capacity to produce high levels of IFN-γ and for their ability to efficiently and specifically lyse relevant target cells (Dudley and Rosenburg, 2003; Yee, et al. 2002). However, it was found that $CD8^+$ T cells that acquire complete effector properties and exhibit increased anti-tumor activity in vitro are less effective at triggering tumor regressions and cures in vivo (Gattinoni, et al. 2005). While the progressive acquisition of terminal effector properties is characterized by pronounced in vitro tumor killing, in vivo T cell activation, proliferation, and survival are progressively impaired. These findings suggest that the current methodology for selecting T cells for transfer is inadequate (Gattinoni, et al. 2005). It is clear that new solutions are needed to generate more effective anti-tumor T cells for the development of experimental human adoptive transfer-based therapies.

The indication is that storage of naive T and B cells is important for individuals who will become immunocompromised later in life, whether those cells come from that individual or from another source. Naive cells would also not necessarily be isolated from cord blood, but could also be isolated from bone marrow or peripheral blood. In addition, screening methods can be used to characterize those immune cells regarding cell surface characteristics and cytokine expression. Here too, ImmunoScore can be used to a distinct advantage.

N. Vaccine Use Outcome/Design

Currently, what the public considers vaccines are designed as a prophylactic means to avoid illness caused by infectious disease. In practice, agents used to promote an immune response as a therapeutic course of action for cancer or immunotherapy have also been termed "vaccines." It is the intent of the ImmunoScore design to be able to monitor changes in an individual's immune system in relation to a prophylactic or therapeutic vaccine and enable the individual patient and his physician to make the best possible decisions regarding the patient's immune system health regarding prophylactic vaccination, therapeutic vaccination, or other therapeutic treatment in attempt to "shift" the immune system of that patient. In addition, the ImmunoScore database will compile important population data regarding demographics and population genetics.

O. Research Services

In exemplary embodiments of the present invention ImmunoScore technologies can be used to provide research services, such as, for example, for clinical trials in the following areas:

1. vaccines;
2. transplants;
3. adaptive immunotherapy;
4. population modeling; and
5. government applications.

P. Immigration Consulting

Testing the immigrant population for vaccine-preventable diseases is another embodiment of the invention. Governments are very interested in the immunization status of individuals and families immigrating into their countries. The invention can rapidly provide the results of assays to governmental authorities for all required immunizations. There would be no need to rely on paperwork—a diagnostic examination would yield more suitable data regarding immune status. The current vaccination requirements for immigration into the United States are for measles, mumps, rubella, polio, tetanus, diphtheria, pertussis, influenza, hepatitis B and any other vaccinations recommended by the Advisory Committee for Immunization Practices (ACIP). Current recommendations of the ACIP also include varicella, *Haemophilus influenzae* type B, and pneumococcal vaccines. The current law requires all individuals applying for status as a lawful permanent resident (either by applying for an immigrant visa abroad or for adjustment of status in the United States) to establish that they have been vaccinated. Nonimmigrant (temporary) visa applicants are not required to comply with the vaccination requirements as a condition of visa issuance, but must comply if they apply for adjustment of status at a later date (Immigration and Naturalization Services, 2001).

One or more exemplary ImmunoScore diagnostic panels could, for example, be provided to INS or other immigration authorities as a means to determine the immune status of immigrants. In practice, ImmunoScore diagnostic testing can be more cost-effective than a paper record trail and more likely to be reliable as an accurate assessment of immune status of individuals relocating to the United States.

Additionally, the Institute of Medicine (IOM) has concluded that the United States quarantine system is in need of a strategic overhaul. The IOM reports that the United States once had 55 federal quarantine stations, but the perception that microbial threats had been controlled led to dismantling of most of the system in the 1970s. However, nearly 40 new infectious diseases have been identified since 1973, and bioterrorism has become a serious concern. The 25 stations that will make up the expanded quarantine station system now receive more than 75 million international travelers a year, according to IOM reports. The stations screen travelers, refugees, immigrants, animals, and cargo for disease agents shortly before and during their arrival. However, the quarantine system relies on a much broader network that includes local public health agencies, hospitals, customs agents, agricultural inspectors, and others, the IOM said.

The IOM recommended the following:

The quarantine stations, the CDC, and the DGMQ (called the quarantine core) should lead the effort by developing a national strategic plan with uniform principles and outcomes. The quarantine core should shift its main focus from inspecting people and cargo at ports to leading the activities of the overall quarantine system. The strategic plan should help participating government agencies and other groups in the system to prioritize activities and focus resources on the greatest risks.

The quarantine core should work with partners in the quarantine network to define or redefine each group's roles, authority, and communication channels.

The quarantine system needs enhanced skills, more people, more training, more space, and better use of technology to fulfill its evolving role. An example of technology cited in the news release was targeted use of passenger locator cards that could be used on flights to and from countries with disease outbreaks. The cards would log passenger seat numbers and contact information in a scannable format. This could simplify tracking of passengers potentially exposed to disease, such as those who flew to the United States from Sierra Leone in 2004 with a man who later died of Lassa fever.

The quarantine core must review its methodology periodically to ensure stations are in the best places and appropriately staffed.

The quarantine core must have plans, capacity, resources, and "clear and sufficient legal authority" to respond quickly to surges in activity at one or more ports.

The core must define and fund a research agenda to measure the effectiveness of its procedures. The committee found that many routines at quarantine stations are based on experience and tradition and lack a scientific basis.

The core must use scientifically sound methods to measure the effectiveness and quality of its operations, including assessing performance of critical functions throughout the system. It must also address any shortfalls that come to light. (http://www.nap.edu/books/030909951X/html).

ImmunoScore technology could be useful at such immigration port of entry screening points. There is a need for global health that can not be understated. The cost of failure could be extremely high. There are people moving around the globe and among the states with clear health needs, and they are currently moving without the ability of government authorities to track them.

Additionally, ImmunoScore technologies can be used to discover links between immunological phenomena. For example, from the results of Greenway (discussed above in Section I regarding the immigrant panel) a possible link between TB infection and HepB prevalence can be investigated by analyzing sera from an immigrant population for both active TB and HepB seropositivity. It is possible that more than one co-infection may be found in this manner. For example, in the following study, A high prevalence of hepatitis B virus infection among tuberculosis patients with and without HIV in Rio de Janeiro, Brazil, Blal C A et al Eur J Clin Microbiol Infect Dis. 2005 January; 24(1):41-3, such a correlation was in fact found.

The Blal study sought to investigate the prevalence and exposure factors associated with hepatitis B infection in tuberculosis patients with and without HIV type 1 co-infection. The presence of hepatitis B virus serological markers was investigated in a retrospective study. The seroprevalence of hepatitis B virus in patients with tuberculosis only was 14.6%, and in tuberculosis patients co-infected with HIV it increased to 35.8%. In patients with HIV and tuberculosis co-infection, homosexuality constituted the principal exposure factor, while in tuberculosis patients without HIV, a gradual increase in hepatitis B virus seroprevalence was noted along with increasing age. These results demonstrate that hepatitis B infection is highly prevalent in tuberculosis patients in Brazil and suggest that a vaccination program for the general population should be considered in order to prevent further hepatitis B infections.

Q. Disaster Survivors: Immunizations, Recovery, Prognosis and Treatment

In exemplary embodiments of the present invention, rapid response services to disaster survivors can be provided. FIG. 32 depicts an exemplary process flow for such an application.

At 3201 a disaster survivors' immune status can be examined using one or more ImmunoScore assay panels as described above in Section I. At 3210 the vaccine preventable diseases to which the survivor is susceptible can be identified and simultaneously the cellular component of his or her immune system can be assessed to get an immediate post disaster baseline. At 3220 vaccination and healthcare recommendations can be generated based upon antibody levels to the identified to the assay vaccine preventable diseases. At 3230 immunization can be carried out and at 3240 follow-up examination of the survivor's immune status can be administered and the results stored in the system database. Further screening of T cell components of the immune system is recommended for all survivors regardless of their psychological state at the time in order to develop data regarding post-traumatic stress disorder. Finally, at 3250 the efficacy of the vaccine and/or therapies can be evaluated as to their ability to provide necessary immunity to the identified diseases.

There are many different possible responses of an individual to an event perceived as potentially life-threatening. It is difficult to predict long-term responses to trauma based on the acute response to a traumatic event. If physiological risk factors are important in understanding how psychopathology develops, then ImmunoScore measurements can provide invaluable research information and possibly identify treatments yet to be defined. This could pave the way to personalized medicine. FIG. 33 illustrates possible responses to trauma.

With reference thereto, at 3301 a Disaster Trauma occurs. There are two pathways leading from 3301, namely, Normal Response Factors 3305 and Pathological Response Factors 3303. A Normal Response Factors 3305 pathway from Disaster Trauma 3301 leads to Recovery at 3310. However, Pathological Response Factors 3303 lead an individual from Disaster Trauma 3301 to Post-Traumatic Stress Disorder 3320. It is the job of healthcare personnel to put the individual on a Pathway to Recovery 3310. In exemplary embodiments of the present invention ImmunoScore technologies can be used to determine possible therapies 3315, as well as to track immunological correlates of PTSD to verify diagnosis and evaluate therapeutic efficacies.

In the immediate aftermath of a traumatic event, most people experience a combination of the following symptoms: (a) difficulty sleeping, (b) difficulty concentrating, (c) irritability, (d) nightmares, (e) recurrent thoughts of the trauma, and (f) distress at the reminder of the traumatic event. The question in the determination of a pathological response is when does the continuation of these "normal" responses become pathological, and have serious effect on the health of the individual's immune system?

There are different possible outcomes of trauma exposure. There is an increased risk of: (a) Post-Traumatic Stress Disorder (PTSD), (b) major depression, (c) panic disorder, (d) generalized anxiety disorder, (e) substance abuse, and (f) other somatic symptoms or expressions of physical illness including hypertension, asthma, and chronic pain syndromes. The differential outcomes may rely on different physiological parameters.

Pre-existing cognitive factors may or may not be the cause, result, or correlate of pre-existing biological alterations, either or both setting the stage for an extreme response to the trauma. Clarifying the precise nature and biological correlates of symptoms that appear in the immediate aftermath of a trauma will assist in developing models for potential prophylactic interventions and early treatments. In this regard the ImmunoScore diagnostic panel could initially be used in a research application to track immune system markers and relate them to specific conditions. As a system database evolves, ImmunoScore panels can, for example, be used as a guide to therapeutic treatment.

Individuals currently at the greatest risk for developing PTSD following trauma are those individuals with (a) a family history of psychopathology, (b) a history of childhood abuse, (c) prior trauma exposure, and (d) the cognitive factors of lower IQ, female gender, and poor social support. There is increased concordance for PTSD in monozygotic twins compared with dizygotic twins lending support to the genetic pre-disposition argument of PTSD.

R. Monitor Adoptive Immunotherapy/Transplants

After adaptive transfer, several events must occur for T cells to cause the regression of established tumors. T cells must be activated in vivo through antigen-specific vaccination. They must then vigorously expand to levels capable of causing the destruction of significant tumor burdens. Finally, anti-tumor T cells must survive long enough to complete the eradication of all tumor cells (Overwijk, et al. 2003). It has been found in an animal model that the progressive differentiation of T cells to a terminal differentiated effector stage results in a series of phenotypic and functional changes that make them less "fit" to perform these functions (Gattinoni, et al. 2005).

In patients under consideration for adaptive immunotherapy and/or transplantation, history and analyses of exposure to CMV, EBV, West Nile Virus, and viral hepatitis in both the donor and recipient are crucial. ImmunoScore diagnoses of both the donor and recipient would examine the immune history of both individuals.

S. Elective Surgery

Many patients opt for elective surgery—plastic surgery, facial plastic surgery, dermatology, cosmetic dentistry, vision, urology, and infertility among others. Whenever undergoing surgery, there is a risk of nosocomial infection. Common organisms that cause nosocomial infections are *Apergillus, Candida, Staphylococcus aureus, Staphylococcus epidermidis, Pseudomonas aeruginosa*, and *Bordetella pertusis*. Prior to elective surgery, it would benefit the patient and the attending surgeon to know the level of antibody protection to these infectious agents. An ImmunoScore panel could be tailored to meet these diagnostic needs and immunizations could be provided to those agents with available vaccines. If the patient's immune status is sufficiently poor, a recommendation not to have the surgery may be given. In these cases, the expected value of costs of complications rising from infections outweighes the expected value of the benefits from the surgery. In addition, following surgery patients could be screened for c reactive protein (CRP), tumor necrosis factor-alpha (TNF-α), IL-6, and soluble IL-2 receptor (sIL-2R) as possible early indicators of inflammation leading to sepsis. It is important to screen for a panel of analytes indicating sepsis, as one analyte is often not enough to get a proper diagnosis.

T. Services to Charitable Foundations Promoting Immunological Well Being

Currently, the lack of accurate, affordable, and accessible diagnostic tests significantly impedes global health efforts. The Global Alliance for Vaccines and Immunizations (GAVI) was created in 1999 to protect health and save children's lives throughout the widespread use of modern vaccines. GAVI is a partnership of governments, international organizations, major philanthropists, research institutions, and the private sector that work together to: (a) improve access to sustainable immunization services, (b) expand the safe use of all needed cost-effective vaccines, (c) accelerate research and development efforts for new vaccines needed in developing countries, (d) make immunization coverage a key indicator of development, (e) promote sustainability by adequate financing, and (f) reinforce global and national immunization goals including eradicating polio, eliminating maternal and neonatal tetanus, reducing measles, and increasing access to vitamin A.

Underlying all health care tools—including therapeutic products, vaccines, and other preventative tools—are "platform" technologies that define and facilitate their use. For example, immunochromatography is a technology platform that has enabled the development of affordable, easy-to-use dipstick format diagnostic tools. The ImmunoScore diagnostic panel, a platform technology, can be used to great advantage by GAVI to improve global health efforts GAVI issues requests for proposal (RFPs) to support research efforts to create diagnostic technology platforms and tolls that enable improved prevention, treatment, and surveillance in developing country settings. The foundation issues RFPs to support the systemic evaluation of sets of genes, proteins, and cellular pathways to determine their potential role in contributing to the development of new vaccines, diagnostics, and drugs for GAVI's priority diseases and conditions. One area of concern is population genetics and how to design drugs and vaccines to discourage the emergence of resistance and to discover how genetics affects the efficacy of drugs and other interventions. The ImmunoScore database would be an ideal tool for GAVI to use to evaluate genetic parameters and immune response to vaccines and drugs under consideration. A second area is applied immunology. Here systematic approaches, such as that provided by the ImmunoScore technology, are needed to measure the human immune response to guide vaccine design and define biological signs that identify early or latent infection.

U. Discovery of Unwanted Immunogenicity of Therapeutics

There is potential of the human immune system to identify biological therapeutic products as foreign and mount an immune response. There are three main areas of concern with the production of antibodies against biological therapeutics in humans:

Safety—assurance of safety involves the assessment of whether antibodies induced could have adverse clinical implications.

Efficacy—can be affected by the presence of antibodies binding to the product and reducing its potency.

Measurement of phamacokinetic/pharmacodynamic parameters—the presence of antibodies can alter these clinical parameters and also interfere in the assays used in their assessment (Koren, et al. 2002).

The immunogenicity of therapeutic proteins can be influenced by many factors, including the genetic background of the patient, the type of disease, the type of protein (human or nonhuman), the presence of conjugates or fragments, the route of administration, dose frequency, and duration of treatment (Schellekens, 2002). Manufacturing, handling, and storage can introduce contaminants, or alter the three dimensional structure of the protein via oxidation or aggregate formation. Various means have been suggested by which therapeutic proteins might be modified to reduce their immunogenicity, including PEGylation, site-specific mutagenesis, exon shuffling, and humanization of monoclonal antibodies (Schellekens, 2002). In the future, it may be possible to predict the immunogenicity of new therapeutic proteins more accurately, using specifically designed animal models, including nonhuman primates and transgenic mice.

ImmunoScore diagnoses and database storage could be instrumental in the development of analytical techniques to monitor both the drugs and the patient population. An individual's tendency to mount an immune challenge to a protein therapeutic could be revealed prior to initiation of the treatment based upon the patient's ImmunoScore profile. In addition, once therapeutic treatment began, ImmunoScore diagnoses and database management could track a patient's immune response to the drug. The drug manufacturers would be able to use the ImmunoScore technology to conduct clinical trials and also to select an appropriate population in which to test the drug. Based upon ImmunoScore population data, the drug could be designated for use based upon the genotype of the individual being treated.

FIG. 34 depicts an exemplary process flow for an ImmunoScore immunogenicity study in exemplary embodiments of the present invention. The exemplary study is directed to immunogenicity of therapeutic proteins.

With reference thereto, at 3401 a prospective patient's immune status can be examined to obtain a baseline ImmunoScore. At 3410 patients for whom treatment would not be advisable (based upon immune system profiling) can be identified, and therapeutic treatment for a patient group for which therapy is advisable can be initiated. At 3420 patients' further treatment and health care recommendations can be made, based on careful periodic monitoring of antibody levels to therapeutic proteins. In addition, cellular components of the immune system would warrant careful monitoring—particularly in regard to the antigenic components of the therapeutic compound. At 3430 patient data can be compiled for drugs in clinical trial. Population data can also be compiled to assist in drug design. At 3440, follow-up examinations of patients' immune status post-treatment can be implemented and the results stored in a system database. Further screening of antibody levels and T-cell components of the immune system can be implemented for all patients. Finally, at 3450 the efficacy of therapies to provide necessary treatment to patients can be evaluated, and the extent of undesirable immunogenicity can be determined.

V. Two-Sided Market Applications

A two-sided market is a market wherein there are two sets (at least) of customers that, in effect, need each other. Each type of customer values the market more if the other type of customer also buys the service. Businesses service such markets by acting as "matchmakers."

Examples of two-sided markets:
computer operating systems
  software developers write applications
  computer users run applications
video game console manufacturers serve
  video game players
  video game designers
payment card companies
  consumers
  merchants These businesses all produce platforms that make matches between two or more distinct groups of consumers.

The description of two-sided markets likely came about from payment card companies and legal ramifications of what may have been perceived as monopolistic business practices, but was actually the demonstration of two-sided marketing practices. A key aspect to the business model for most of these industries involves the optimal pricing structure: the division of revenues between the two sides of the market that gets both sides on board. The need for pricing structure as well as pricing level distinguishes industries based on a two-sided market from the industries ordinarily studied by economists. In two-sided markets, the product may not exist at all if the business does not get the pricing structure right. Currently, there is no appreciable market for adult vaccines, other than those for influenza and pneumococcus. ImmunoScore diagnostics can, for example, likely reveal lapses in protection for vaccine preventable diseases, such as pertussis, tetanus, diphtheria, mumps, measles, and others. Diagnostic testing can thus reveal a large marketing potential for vaccine manufacturers.

Both the ImmunoScore diagnostic application and the ImmunoScore database management modules can be considered as two-sided marketing opportunities, in that none of the participants (patients, insurers, researchers, primary care physicians, vaccine manufacturers, or government entities) may necessarily be willing to enter into a beneficial marketing alliance without direction provided by the ImmunoScore platforms, as illustrated in FIG. 35. ImmunoScore can act as a "matchmaker" for these different groups of consumers. An ImmunoScore diagnostic platform can, for example, serve to link patients, physicians, and vaccine manufacturers and help to illustrate the need for continuing vaccine coverage in adults and children at risk. As an ImmunoScore database module grows from an ImmunoScore diagnostic module, insurers, research groups (both academic and commercial), and groups responsible for vaccine decision-making (ACIP and AAP) and tracking (CDC and VAERS) can be able to take advantage of the data generated from assessing the immune status of patients.

Network effects. A network effect arises when the value that one user receives from a product increases with the number of other users of that product. It goes without saying that the value to governmental decision-making, insuring, and research interests can expand enormously with the increase in size of an ImmunoScore patient database. Health insurers can also be involved at ImmunoScore diagnostic platform level. Insurers that would be interested in providing insurance based upon an individual patient's ImmunoScore would benefit most from the ImmunoScore database platform. Most network effects arise because a product tends to be two-sided. ImmunoScore, having more than two interactive sides, would demonstrate large network effects that should benefit society as a whole, with better health for the population at large and decreased costs for the insurers. Information garnered from an ImmunoScore Database can enable the performance of vaccine researchers and the vaccine decision-makers in the government tremendously.

Survey of Two-Sided Markets
Diverse industries:
  credit cards
  computer operating systems
  video games
  corporate bond trading
  residential real estate Firms in these industries have adopted similar business models and pricing strategies for solving the problem they have in common—getting and keeping two sides of a market on board. The intermediary helps customers complete a transaction by providing a platform. The transaction occurs when both sides get together. Currently, there is a real need to get adult patients and vaccine manufacturers together for the betterment of public health. ImmunoScore diagnostics will be an effective facilitator of this interaction, with the medical insurance companies being a third beneficiary. The intermediaries succeed in the businesses by figuring out how a pricing structure internalizes the externalities between the two sides. In the case of ImmunoScore Diagnostics, the health insurers should be willing to pay for the diagnostic testing as well as the cost of vaccination, as those costs would be less than those to treat debilitating diseases otherwise preventable by judicious use of vaccination.

A market is two-sided if at any point in time there are:

two distinct groups of customers—with ImmunoScore diagnostic and ImmunoScore database platforms, there would be patients, vaccine manufacturers, health insurers, vaccine researchers, and vaccine decision-making organizations that would benefit from the two-sided ImmunoScore platforms.

the value obtained by one kind of customer increases with the number of the other kind of customers—as the number of patients are added to the database, the database would increase in potential utility to researchers, vaccine decision-makers, insurers, and vaccine manufacturers. The more the database grows, the better it would be for the patient population as physicians would better be able to determine individual patient's immune status based on knowledge accumulated over the entire patient population.

the intermediary is necessary for internalizing the externalities created by one group for the other group—there is currently no real push for adults or older children to have diagnostic screening related to vaccine-preventable diseases. As ImmunoScore data accumulate, there should be an added impetus for adult and adolescent vaccination coverage.

Researchers have examined the pricing and production strategy of a firm in a two-sided market. Consider the case in which both sides of the market are buying a "transaction" and in which the seller incurs a marginal cost for consummating that transaction. The prices charged to the buyers and sellers are two prices. The buyer's demand depends only on the price faced by the buyer and the seller's demand depends only on the price faced by the seller. The demands can be thought of, roughly speaking, as the number of buyers and sellers using the system. The transactions that a seller engages in, and its benefits from those transactions, increase proportionally with the number of buyers on the system. The same holds for an individual buyer. Total demand equals the product of the two demands. Thus, if there were 500 sellers and 100 buyers, there would be 50,000 transactions. The assumption of a multiplicative demand between the two sides actually understates the importance of the indirect network effects. It ignores the fact that the value each side obtains from the other side increases with the number of customers on the other side. In the cases of ImmunoScore diagnostics and an ImmunoScore database, the benefit to all sides of the market could increase dramatically (presumably something more than a multiplicative effect) as the number of consumers grows. Feeding information to the database can only assist patients, physicians, vaccine decision-making bodies, vaccine manufacturers, and health insurers.

None of the conditions for determining the price level or the price structure in two-sided markets corresponds to marginal revenue equaling marginal costs on either side of the market. Such conditions have no meaning in two-sided markets because there is no way to allocate the increases in revenues from changes in prices to one side or the other. Changes in prices result in more "transactions" from which each side jointly benefits.

Business Models in Two-Sided Markets. Both sides need to be brought on board. For instance, there would be no demand by households for payment cards is they could not be used anywhere, and no demand by retailers if no one had them to use. Investment and pricing strategies are key to getting both sides on board. Even with both sides on board, businesses have to carefully balance their two demands. They have to consider how changes on one side of the market will impact the other side of the market. The need to balance the needs of the various consumers will be of utmost importance to the careful development of ImmunoScore diagnostics and ImmunoScore database management as two-sided markets. Currently, patients, physicians, and vaccine manufacturers seem painfully unaware of the need for diagnostic testing and boosting for vaccine-preventable diseases.

Getting both sides on board. One way to get both sides on board is to obtain a critical mass of users on one side of the market by giving them the service for free or even paying them to take it. Another way to solve the chicken-and-egg problem is to invest in one side of the market to lower the costs to consumers on that side of participating in the market. Providing low prices or transfers to one side of the market helps the platform solve the chicken-and-egg problem by encouraging the benefited group's participation—which in turn, due to network effects, encourages the non-benefited group's participation. Another effect of providing benefits to one side is that this assistance can discourage use of competing two-sided firms. In the case of the ImmunoScore diagnostic and database platforms, initially the medical insurance industry would likely bear the burden of any associated costs, but the benefit to this industry in increased wellness of their clientele should offset any up-front costs. In addition, to those patients who are seen to have an unfavorable ImmunoScore the supplemental insurance industry should be available and able to come in and insure those individuals with special needs.

Pricing strategies and balancing interests. Firms in mature two-sided markets still have to devise and maintain an optimal pricing structure. In most observed two-sided markets, companies seem to settle on pricing structures that are heavily skewed towards one side of the market. Certain customers on one side of the market may be extremely valuable to customers on the other side of the market—"marquee buyers." In the case of the ImmunoScore diagnostic and database platforms, the "marquee buyers" could be seen as large HMOs that would in truth benefit from having a healthier patient population. The existence of marquee buyers tends to reduce the price to all buyers and increase it to its sellers. Acceptance of ImmunoScore platforms by large insurance organizations and government agencies would enable "bringing on board" smaller insurance agencies. A similar phenomenon occurs when certain customers are extremely loyal to the two-sided firm—perhaps because of long-term contracts or sunk-cost investments.

Multihoming. Most two-sided markets in the real world appear to have several competing two-sided firms and at least one side appears to multihome. Multihoming affects both the price level and the pricing structure. Not surprisingly the price level tends to be lower with multihoming. The possibility of multihoming may encourage firms to lower their prices on the side of the market in which multihoming could occur. By lowering their prices, firms discourage customers on that side from affiliating with other two-sided firms. The firm can then charge more to customers on the other side, for whom fewer substitutes are available.

Two-Sided Markets and Social Welfare. A relatively small number of firms tend to compete in two-sided markets. That is because these markets have network effects and usually incur substantial fixed costs for getting one or both sides on board. Larger firms have advantages over smaller firms because larger size delivers more value—a bigger network—to consumers. Firms in concentrated two-sided markets may have opportunities to earn supra-competitive profits—i.e., profits that exceed those necessary to attract capital to the industry after accounting for risk. Several factors affect the extent to which this can happen over time.

7. The extent to which firms are competing to become established in a two-sided market. This results in investment to court customers, to provide them with subsidies in the form of equipment, and to offer them low or negative prices. Vaccine manufacturers and physicians offices might initially need to be coaxed into the ImmunoScore diagnostic and database markets, but should see the benefits as the structure grows.

8. The extent to which there are first mover advantages in getting either side of the market on board Then, the competition to make these investments should reduce the opportunities to earn significant supra-competitive returns. Savvy Health Maintenance Organizations could be the first to realize the benefits to their coverage that ImmunoScore diagnostics and database platforms could provide, and as such may be eager to get into this opportunity at the ground level. The governmental organizations could also be made to see the benefits of diagnosing and cataloging lapses in vaccine-preventable disease conditions.

The consequences of having relatively few competitors in two-sided markets, and the existence of network effects, raise familiar issues concerning the efficacy of competitive markets and the possible roles for government intervention. The pricing and investment strategies that firms in two-sided markets use to get both sides on board and balance the interests of both sides raise novel questions. These pricing and other business strategies are needed to solve a fundamental economic problem arising from the interdependency of demand on both sides of the market. In some cases, the product could not even exist without efforts to subsidize one side of the market or the other. In the case of the ImmunoScore platforms, the patients would likely need to be subsidized by the participation of health insurers.

Researchers have compared the pricing structure adopted by firms in two-sided markets to the pricing structure that would maximize social welfare. Interestingly, they find that a monopoly firm, a firm with competition, and a benevolent social planner would adopt similar pricing structures. The precise relative prices would differ somewhat. They found that the pricing structure adopted by the market is not biased towards one side of the market or the other side of the market compared to the pricing structure that would be adopted by the benevolent social planner. ImmunoScore diagnostic and database platforms may be thought of as a benevolent social plan. The welfare of the patients is paramount, and there would be additional benefits presented to vaccine manufacturers, research groups, and government organizations.

Two-sided markets are an increasingly important part of the global economy. Firms that provide platforms for multiple consumer groups are a critical part of many interrelated segments of the computer industry. In most industrialized countries a large fraction of payments takes place through firms and associations that provide platforms for merchants and customers to exchange money. The increased importance of the Internet for household-to-household, business-to-household, and business-to-business transactions and the emergence of e-pay systems on the Internet will increase the fraction of payments going through commercial payment platforms. ImmunoScore diagnostic and database platforms would help bring health care into the $21^{st}$ century. There is a tremendous need for portability in health care record-keeping, and the ImmunoScore database platform would be instrumental in the transfer of health care records from primary care physician to specialist.

Two-sided firms have to come up with the right price structure and the right investment strategy for balancing the demands of the customer groups they must get and keep on their platforms.

In many industries, platforms court two (or more) sides that use the platform to interact with each other. The platform may charge interaction-independent fixed fees. For example, American Express charges yearly fees to cardholders. In the case of video games, platforms charge game developers fees for development kits on top of royalties per copy sold, and they charge gamers for the console. In the case of the ImmunoScore database platform, it might be appropriate to charge academic and commercial research groups for use of the information captured by the database modules.

Managers devote considerable time and resources to figure out which side should bear the pricing burden, and commonly end up making little money on one side (or even using this side as a loss-leader) and recouping their costs on the other side. Marketing managers for the ImmunoScore platforms will need to carefully balance many consumers' needs and the applications of fees.

Pricing Principles for Two-Sided Platforms. Departures from standard business strategies that result from the platform's internalization of the other side's welfare (the linkage between the two sides from the platform's viewpoint). This linkage is most apparent when the platform makes no or loses money on one side. A factor that is conducive to a high price on one side, to the extent that it raises the platform's margin on that side, tends also to call for a low price on the other side as attracting members on that other side becomes more profitable. In the case of the ImmunoScore platforms, it is imperative to bring patients on board, but their participation might be encouraged by the dual factors of their curiosity as to their personal ImmunoScore and also the participation of their insurer in the platform.

Platforms must perform a balancing act with respect to their price structure as well as other policy dimensions; quite generally, they encourage positive externalities and discourage negative ones and to do so usually constrain one side to the benefit of the other. While asymmetric information and the concomitant rent extraction concerns keep the platform's price structure neutral, it is nonetheless a source of suboptimal trade among end-users. The platform has an incentive to cap or alter through a subsidy the price charged to buyers so as to boost buyer's surplus and their willingness to join the platform. Then the platform behaves pretty much like a public utility commission that addresses a market power problem by setting a price cap or by subsidizing some services through a fund levied from other services.

The rationale for constraining the price charged by the seller to the buyer would vanish if the industry were organized according to the vertical view: were the platform not to deal directly with buyers, the platform would want to provide sellers with the maximal profit in their relationship with buyers and therefore would grant them maximal commercial freedom. It is only because the platform can extract surplus on the buyer side that it is willing to displease the seller side by constraining it.

End-users often care not only about the price (that they pay to the platform and to the other side), but also about the quality of the interaction. In health care, the quality of the physician-patient interaction assumes particular importance. An ImmunoScore Diagnostic platform will help nurture the doctor-patient relationship and focus on the patient's "wellness" rather than strictly on "treatment."

While price regulation is complex or inefficient, the platform may still make itself attractive to one side of the market by encouraging competition on the other side. Competition on the other side brings prices closer to marginal cost, and the volume of interactions closer to the efficient volume; it also protects against the hold-up of one's specific investments. An ImmunoScore diagnostic platform could encourage competition among vaccine manufacturers on behalf of the patient population. The manufacturers should still realize greater sales, but their prices should remain competitive for the insurers and patient population. Accordingly, a two-sided platform benefits from allowing competition on a given side as it can at least partly recoup benefits on the other side.

Dynamics. To create a two-sided market, a "chicken or egg" problem has to be solved: to convince some buyers to adopt a certain intermediation platform, it is necessary to first convince some sellers; but, to convince the sellers, there must be some buyers on the market. In most models, this problem is avoided by assuming the simultaneous arrival of agents on the two market sides, in a rational expectations equilibrium. However, there are circumstances in which one market side has to intervene before the other one. The most cited case is the one of videogame consoles which, to get customers, must appear on the market already equipped with a complete range of games and complementary applications. There appears to be a growing need for the determination of a patient's immune status. There is a current outbreak of mumps disease in the Midwest in individuals that have received two MMR immunizations. The incidence of pertussis continues to increase. Travel has now been related to the spread of Severe Acute Respiratory Syndrome (SARS), influenza, measles, tuberculosis, and mumps. The time is appropriate for the introduction of the measurement of the immune status of individual patients, and the tracking of information regarding each individual's immune status. ImmunoScore diagnostic and database platforms can tip the balance from a display of need to a mode of action going forward.

W. Drug Hypersensitivity
Incorporating Drug Hypersensitivity into a Two-Sided Business Model Adverse drug reactions are common. Identifying true drug allergy, however, can be challenging. Drug hypersensitivity is a clinical diagnosis based upon available data. Drug hypersensitivity is defined as an immune-mediated response to a drug agent in a sensitized patient. Identifiable risk factors for drug hypersensitivity reactions include age, female gender, concurrent illnesses, and previous hypersensitivity to related drugs. Monitoring drug hypersensitivity in patients and incorporating those data into an ImmunoScore database platform is another example of a two-sided market opportunity. As with the other examples of two-sided markets, the medical insurance organizations would likely initially cover most of the expenditures to bring the other market components into the market that would be beneficial to all participants. Other "sides" of the market would involve patients, physicians, researchers for both the pharmaceutical industry and allergy specialists.

The Gel and Coombs classification system describes the predominant immune mechanisms that lead to clinical symptoms of drug hypersensitivity (Table 1). This classification system includes IgE-mediated Type I reactions, cytotoxic Type II reactions, Type III reactions involving the formation of immune complexes, and the delayed, cell-mediated Type IV reactions. However, some drug hypersensitivity reactions are difficult to classify because of a lack of evidence supporting a predominant immunologic mechanism. These include certain cutaneous drug reactions and specific drug hypersensitivity syndromes.

Diagnostic testing for these reactions remains somewhat problematic. The current types of tests and therapeutic considerations are for each of the four types of hypersensitivity reactions described in Table 2 below. Confirmation of suspected Type I hypersensitivity reactions requires the detection of antigen-specific IgE. Currently, skin testing is a useful diagnostic procedure for reactivity to penicillin. With other drug agents, a negative skin test does not effectively rule out the presence of specific IgE. Further IgE tests for other agents await development. The sensitivity of ECL technology as embodied in an exemplary ImmunoScore diagnostic platform can be a very effective tool to enable researchers to better study IgE populations specific for drug component antigens. Currently, the diagnosis of drug hypersensitivity is usually based upon clinical judgment because definitive, confirmatory drug-specific testing is often difficult.

Once the diagnosis has been established, appropriate documentation should be included in the medical record specifying the causative drug and the nature of the adverse effect. Immune-mediated drug hypersensitivity reactions typically pose a predictable, more serious health risk with re-exposure to the drug. In this application of the technology, an exemplary ImmunoScore database platform can, for example, capture all pertinent information related to any adverse drug reaction. This would not only be of benefit to the patient, but also as data was accrued, pharmaceutical companies would benefit from statistical information gathered from mining the database. Real drug hypersensitivity would also be separated from reactions that may not be hypersensitivity. Instead of relying on patient recall and a faulty data collection system, an exemplary ImmunoScore database can only include documented case histories. Patient medications can, for example, be tracked via an ImmunoScore database and real hypersensitivity can be officially documented.

The most important drug-related risk factors for drug hypersensitivity concern the chemical properties and molecular weight of a drug. Larger drugs with greater structural complexity are more likely to be immunogenic. Heterologous antisera, streptokinase and insulin are examples of complex antigens capable of eliciting hypersensitivity reactions. Another factor affecting the frequency of hypersensitivity drug reactions is the route of drug administration; topical, intramuscular, and intravenous administrations are more likely to cause hypersensitivity reactions. These effects are caused by the efficiency of antigen presentation in the skin, the adjuvant effects of repository drug preparations, and the high concentrations of circulating drug antigen rapidly achieved with intravenous therapy. Oral medications are less likely to result in drug hypersensitivity.

Most medications, because of their small molecular size, are unable to elicit an immune response independently. Drugs must first covalently bind to larger carrier molecules such as tissue or serum proteins to act as complete multivalent antigens. This process is called haptenation, and the drugs act as haptens. The elicited immune response may be humoral, with the production of specific antibodies, cellular, with the generation of specific T lymphocytes, or both. Frequently, the identity of the metabolites is unknown, making it impossible to develop accurate diagnostic tests for drug allergy (Solensky, 2006).

A thorough history is an essential component of the evaluation of patients with suspected drug allergies. The history helps guide the clinician in the choice of diagnostic tests and the decision whether it is safe to reintroduce the medication. Typically, years or decades have passed since reactions occurred, and, as a result, these records are usually unavailable at the time of consultation.

Patients labeled penicillin-allergic are more likely to be treated with more expensive and broad-spectrum antibiotics, a practice that leads to the development and spread of multiple drug-resistant bacteria and higher direct and indirect health care costs. Among patients with a reported history of penicillin allergy, 80-90% have no evidence of IgE antibodies to penicillin on skin testing and thus avoid penicillin unnecessarily. The discrepancy between claimed and real penicillin allergies probably results from several factors. The reaction may have been predictable or due to the underlying illness and hence may have been mislabeled as allergic from the onset. Another contributor to the discrepancy is the tendency of patients with type 1 penicillin allergy to lose penicillin-specific IgE antibodies over time. Insight into the immunochemistry of penicillin has allowed for the development of validated skin-test reagents to detect penicillin-specific IgE.

Together with penicillin, cephalosporins are the antibiotics most widely used for treating common infections, and like penicillin, can cause immediate reactions. Manifested clinically by urticaria, angio-edema, rhinitis, brochospasm, and anaphylactic shock, such reactions are generally IgE-mediated and are among the most dangerous. Although the incidence of severe immediate reactions to cephalosporins does not seem to be much different from that to penicillin, studies of cephalosporins as allergens are not nearly as numerous or thorough as those on penicillin, and very few have been dedicated to the still little known determinants responsible for allergic reactions.

Unpredictable adverse reactions to aspirin and NSAIDS fall into several major categories. Respiratory reactions occur in patients with underlying asthma, non-allergic rhinitis, and nasal polyposis. The preferred term for this disorder is aspirin-exacerbated respiratory disease (AERD). The reactions typically involve the entire respiratory tract, with symptoms of rhinitis, conjunctivitis, and bronchospasm. Patients who have AERD exhibit cross-reactivity with all non-steroidal anti-inflammatory drugs (NSAIDS), but they can tolerate cyclo-oxygenase 2 enzyme (COX-2) selective inhibitors. No in vitro tests to detect aspirin sensitivity exist, and oral challenge remains the gold standard diagnostic test for AERD.

True hypersensitivity reactions to local anesthetics are uncommon and usually consist of delayed contact dermatitis; anaphylaxis from local anesthetics occurs rarely if ever. Most adverse reactions are vasovagal, psychogenic, toxic, or predictable side effects of epinephrine that is often used in combination with local anesthetics. Large-scale studies have found that, following full evaluation, virtually all patients with a history of allergy to local anesthetics are able to tolerate these drugs. Unfortunately, patients who experience any adverse reaction to local anesthetics are frequently labeled allergic and told to avoid all "-caines" in the future. Because evaluation of these patients invariably finds them able to receive a local anesthetic, such evaluation prevents them from being subjected to the increased risk of general anesthesia or, alternatively, to pain from the absence of anesthesia. Evaluation of patients with a supposed allergy to local anesthetics is also important because it serves to alleviate dentists' or physicians' legal (malpractice-related) concerns regarding use of a drug to which the patient is listed as being allergic.

Allergic drug reactions compose a small percentage of adverse drug reactions, yet they are commonly encountered in clinical practice, and physicians are taught to routinely question patients about these reactions during history taking. Medical history taking is critical in the evaluation of antibiotic allergy and in distinguishing allergic reactions from other adverse reactions. This information is important, since over-diagnosis of allergic reactions can lead to unnecessary use of more costly antimicrobial agents and may promote the development of resistant microorganisms. Whenever possible, patients who are being evaluated for possible antibiotic allergy should be encouraged to provide all medical records related to previous adverse drug reactions.

Treatment. For drugs that are presumed to be mediated by IgE, drug desensitization my be performed if the implicated agent is required for treatment. Desensitization involves the administration of increasing amounts of the antibiotic slowly over a period of hours until a therapeutic dose is reached. The mechanism by which clinical tolerance is achieved is unclear, but it is thought to involve antigen-specific mast-cell desensitization. Since maintenance of a desensitized state requires the continuous presence of the drug, desensitization must be repeated if the antibiotic is required again later.

For reactions that are not considered to be mediated by IgE, management depends on the clinical manifestations of the previous reaction. For macropapular eruptions, the specialist may consider a graded drug challenge, which is equivalent to provocation testing. Initial starting doses are generally higher than those used for desensitization, and the interval between doses varies, ranging from hours to days or weeks. The decision whether to discontinue an antibiotic if a reaction occurs depends on the nature of the reaction; bullous lesions or those involving mucous membranes warrant withdrawal of the drug, whereas it may be reasonable to treat through milder reactions, such as maculopapular eruptions, with the use of antihistamines, corticosteroids, or both as needed.

Cephalosporin in patients with penicillin allergy. Penicillins and cephalosporins share a β-lactam ring structure, making cross-reactivity a concern. Whereas most patients who have a history of penicillin allergy will tolerate cephalosporins, indiscriminate administration cannot be recommended, especially for patients who have had life-threatening reactions. For patients with a history of penicillin allergy who require a cephalosporin, treatment depends on whether the previous reaction was mediated by IgE. If testing is positive and a cephalosporin is considered necessary, then desensitization should be performed with the use of the particular cephalosporin chosen for treatment.

Areas of Uncertainty. (Gruchalla and Pirmohamed, 2006) The mechanisms underlying antibiotic allergy have not been clearly elucidated. This understanding is needed to facilitate the development of better diagnostic tools and drugs then are less immunogenic. Better understanding is needed of factors mediating individual susceptibility to allergic reactions to antibiotics. Some patients have reported adverse reactions to many chemically unrelated antibiotics. The existence of the so-called multiple drug allergy syndrome is controversial, and accepted diagnostic tests are needed to document drug allergy in these patients.

Recommendations. Patients who report a history of antibiotic allergy require a careful assessment of the nature of the reaction to determine if the likelihood that it was immunologically mediated. For patients whose history suggests and IgE-mediated reaction to penicillin, skin testing is indicated. If the test results are negative, the β-lactam agent may be administered. If the test results are positive or testing cannot be done, the drug should be avoided or a desensitization procedure should be performed.

ImmunoScore and Drug Hypersensitivity. Exemplary ImmunoScore diagnostic and ImmunoScore database platforms can be seen as examples of two-sided markets in both the diagnoses of drug hypersensitivity as well as in the retention of an individual patient's drug hypersensitivity testing and records for future health care medication decisions as shown in FIG. 36. In such cases, it would be predicted that the health maintenance organizations and pharmaceutical manufacturers (seen at the base of the diagram, propping up the platform structure) would belong to the side(s) of the market most eager to subsidize the other partners. Patients, physicians, and allergy specialists are natural partners to exemplary ImmunoScore diagnostic and database platforms regarding drug hypersensitivity. Because the diagnoses of drug hypersensitivity reactions are in their infancy from a scientific standpoint, research groups developing diagnostic assays are also natural customers for the two ImmunoScore platforms.

Initial patient histories should include a recording of all prescription and non-prescription drugs taken within the last month, including dates of administration and dosage. This is a real example of the proposed utility of the ImmunoScore database platform, wherein patient medications could be tracked and also easily transferable from primary care physicians to specialists.

For the HMOs and other insurers, drug hypersensitivity diagnoses and cataloging by ImmunoScore are a natural marriage. There are dual concerns in health care regarding the expense of exotic antibiotics and the development of antibiotic-resistant strains of organisms. Real patient information regarding drug hypersensitivity (as opposed to patient recall and limited health records) would certainly be welcomed by the medical and insurance professions.

TABLE 1

Gell and Coombs Classification of Drug Hypersensitivity Reactions (Riedl and Casillas, 2003)

| Immune reaction | Mechanism | Clinical manifestations | Timing of reactions |
|---|---|---|---|
| Type I (IgE mediated) | Drug-IgE complex binding to mast cells with release of histamine, inflammatory mediators | Urticaria, angioedema, bronchospasm, pruritus, vomiting, diarrhea, anaphylaxis | Minutes to hours after drug exposure |
| Type II (cytotoxic) | Specific IgG or IgM antibodies directed at drug-hapten coated cells | Hemolytic anemia, neutropenia, thrombocytopenia | Variable |
| Type III (immune complex) | Tissue deposition of drug-antibody complexes with complement activation and inflammation | Serum sickness, fever, rash, arthralgias, lymphoadenopathy, urticaria, glomerulonephritis, vasculitis | 1 to 3 weeks after drug exposure |
| Type IV (delayed, cell-mediated) | MHC presentation of drug molecules to T cells with cytokine and inflammatory mediator release | Allergic contact dermatitis, maculopapular drug rash | 2 to 7 days after cutaneous drug exposure |

TABLE 2

Diagnostic Testing and Therapy for Drug Hypersensitivity (Solensky, 2005)

| Immune reaction | Laboratory tests | Therapeutic considerations |
|---|---|---|
| Type I (IgE-mediated) | Skin testing<br>Radioallergosorbent test (RAST)<br>Serum trypase | Discontinue drug<br>Consider epinephrine, antihistamines, systemic corticosteroids, bronchodilators<br>Inpatient monitoring, if severe |
| Type II (cytotoxic) | Direct or indirect Coombs' test | Discontinue drug<br>Consider systemic corticosteroids<br>Transfusion in severe cases |
| Type III (immune complex) | Erythrocyte sedimentation rate (ESR)<br>Complement studies<br>Antinuclear antibody, antihistone antibody<br>Tissue biopsy for immunofluorescence studies | Discontinue drug<br>Consider NSAIDS, antihistamines, or systemic coricosteroids; or plasmapheresis, if severe |
| Type IV (delayed, cell-mediated) | Patch testing<br>Lymphocyte proliferation assay | Discontinue drug<br>Consider topical corticosteroids, antihistamines, or systemic corticosteroids, if severe |

X. Health Care Transparency and Competition

Currently, health care in the United States consumes $2 trillion per year. Out-of-pocket costs for those who have insurance have nearly tripled in the last six years, and 46 million Americans are uninsured. Unpaid and unpayable health care bills account for the majority of all personal bankruptcies in the country. Eight criteria for improving health care can be articulated as:

1. Consistent High Quality
2. Lower cost—follows from high quality. Higher quality is often naturally less expensive. Providers improve quality by honing their organizational processes to become more efficient and effective—to avoid error and to do things right the first time.
3. Available to all—for ethical, political, systemic, and business reasons, health care must be available to everyone.

4. Single model—every provider in the system must compete to offer the best product at the best price.
5. Shaped by market forces—the consumer market has the sustained systemic power to bring consumers more for less.
6. Practical—the solution must arise from present realities.
7. Progressive—dramatic change can not occur all at once.
8. Self-reinforcing—as any part of the health care system moves toward a new reality, that movement must allow and encourage other parts to move forward as well.

Competition thus far has failed to work the same wonders in health care that it has in so many other industries. In Redefining Health Care: Creating Value-Based Competition on Results, Michael Porter and Elizabeth Teisberg argue that this is because competition has taken place at the wrong level and over the wrong goals. Further exacerbating the problem is the complete absence of feedback loops. Very little in health care has a real price or a real measurable result. Competition in health care has consisted of health plans' and providers' attempts to push cost and risk of themselves and onto each other or onto employers—and now, onto the consumers. Consumers are not looking to embrace an institution, but are looking for a solution for a particular problem. One can envision a world in which health care is organized mainly around products tailored to particular medical conditions. Such products can be delivered by medically integrated practice units made up of teams that work together on the same medical condition over long periods of time. In this particular vision, transparency drives quality. Health plans could steer patients toward the providers who offer the best results for the least money. Referring physicians could refuse to recommend any specialist or package with quality scores in the lower quintiles, for fear of being sued for malpractice themselves. When health care providers compete at the level of the medical condition, on real prices and real results, feedback loops can become extremely compelling. Offering the highest possible quality at the lowest possible price will no longer be voluntary, and health plans will also be forced to compete on the basis of real results and genuine customer service at the lowest price, rather than at their current modus operandi—which can include denying coverage and shifting cost and risk to employers, consumers, and providers.

New structures for public reporting of medical results are popping up on federal, state and regional levels. In many of these initiatives, process measures are starting to give way to results measures. In a number of regions, new tiered payment models use co-payments and other means to encourage patients to use the providers with the lowest cost and highest quality scores. Such models also reward more efficient systems, those that beat their risk-adjusted cost targets, with higher reimbursements, and punish those less efficient providers with lower reimbursements.

The pieces—transparency, integrated products, and true measurement—are coming into play in the health care marketplace. Once it becomes common for health care providers to post actual prices and actual results in standardized ways that produce comparable data, it is hard to see how consumers, insurance companies, and referring physicians would ever choose low quality at high prices.

In exemplary embodiments of the present invention, ImmunoScore diagnostics and database management can, for example, keep score not only of patient's immune data, but effectiveness of treatments/vaccine tie records of physician recommendations relating immune status to fiscal responsibility and patient well-being provide data for insurers provide data for providers provide data for consumers Major decisions about health care in the U.S. have traditionally been made by employers, who determine for their employees which benefits and forms of coverage are needed, what types of providers are included in the network, and which organizations administer the benefits. But this paternalistic approach effectively allowed the consumer to be a passive participant in his or her own health care. The consumer to this point has had no economic incentive to seek the best care at the fairest price, or to give up unhealthy habits. It has been written (Knott, et al. 2007) that new health care formats and competitors are gaining traction, with MinuteClinics and RediClinics—low cost walk-in health care centers for common ailments at one end of the spectrum, and highly personalized "concierge care" at the other. In addition, companies that are not traditional health care players are leveraging their capabilities to create entirely new offerings that enable and encourage the move toward health care consumerism. Fidelity, for example, is developing products and tools that exploit the emerging health-wealth intersection, such as a calculator that helps predict out-of-pocket health care costs. Standardized data on cost, service, and outcomes has the power to establish a new basis of competition. Payers are also pushing for new payment mechanisms, such as pay-for-performance, that base reimbursement on outcomes or adherence to broadly accepted clinical guidelines, known as evidence based medicine.

To make competition and innovation among payers and suppliers possible, an exemplary system could include the following:

consumers who live healthy lives and plan for their future health care needs a fundamentally restructured supply side that provides consumers all the information they need to make wise choices and is quick to respond to changing consumer demands new kinds of intermediaries to help align the supply and demand sides and help consumers navigate the complex system Much of what is needed on the demand side is in place today or likely to emerge in the near term. Consumer-directed health plan (CDHP) enrollees offer an early glimpse of subtle changes in a retail market. CDHP enrollees are more likely to be aware of price and quality differences in products and services and more likely to have seen information and shop around; they are more likely to ask for prices up front, more likely to negotiate prices, and more willing to trade convenience for lower prices. They are also more likely to plan ahead when making health care decisions and to invest dollars now to prevent problems later.

The overall design of the ImmunoScore technology is one in which preventative medicine takes the forefront in treatment options. Vaccine status is the most obvious application, and patients lacking protective antibody levels can be vaccinated. Other levels of immune preparedness would also be similarly assessed and preventative measures could be undertaken prior to clinical manifestations of autoimmune disease, cancer, or immunosenescence. Similarly, evaluations of physicians and health plans could be readily facilitated using the ImmunoScore database. ImmunoScore can be used to discover and define fundamental relationships, such as, for example, (i) optimal Th1/Th2 balances, or (ii)

lack of any members for immunosenescense or autoimmune disease, that can serve as indicators of overall immune system harmony. Such relationships can, for example, be quantified as one or more "ImmunoScores." Patients with healthy ImmunoScores would point to their primary care physicians and their insurers as providers of admirable health care practices. Prevention being much more cost-effective than treatment would provide the best of all worlds to the patients, physicians and insurers. Physicians whose patients had consistently lower ImmunoScores would raise a cautionary flag and those doctors and practices could be scrutinized for provision of first rate health care (or something less). If the records were transparent, patients as consumers would use their dollars to pay for the best possible health care rather than pay for poor care at high cost. For example, in 2005, Aetna began testing tools that allow consumers to compare physicians on actual cost, so that they can gauge their out-of-pocket expenses. WellPoint has embarked on a pilot program at the suggestion of General Motors to provide complete comparative cost data for hospitals on "episodes of care." A number of employers are also finding success with wellness programs. Typical wellness programs feature free or low-cost health screenings and other sorts of preventive care.

It has been approved proposed that additional investments in health information technology and greater connectivity among providers will be needed to ease sharing of patient information and enable consumers to better manage their own health. ImmunoScore database management can, for example, serve as an excellent tool to address connectivity issues that patients, physicians, and insurers would have. Thus, ImmunoScore technology proposes to be a new intermediary in health care connectivity. Patients would have more control over their own health care decisions—spending as well as courses of treatment.

Public health and data collection. In public health, the current underlying assumption is that good data will lead to better decisions, which will result in enhanced population health. In practice, no necessary linear sequence exists from good data to better health (AbouZahr, et al. 2007). Various types of data are obtained at different levels of the health system, to be used by several actors for many reasons. Providers generate and use information in the context of patients' care; managers need data to enhance efficiency and effectiveness; planners rely on statistics for operational decisions; and policymakers use information for prioritization and resource allocation (AbouZahr, et al. 2007). There are different data sources currently used to formulate public policy—each with advantages and disadvantages:

Routinely reported service data. Routine and administrative reports are generated as a by-product of patient-provider interactions and health facility functioning. Health facilities are a primary source of data for notifiable diseases and are at the heart of a country's surveillance and response programs, although facility case reporting needs to be complemented by active case seeking strategies to generate a complete picture of epidemic risk. No matter how many data elements are routinely reported, information is inevitably biased by patterns of service use and non-use, and the extent or direction of bias is impossible to ascertain without recourse to other sources of data. Services delivered (number of immunizations, antenatal visits, outpatients seen, etc) do not necessarily equate to population need.

Population based data. Mistrust of service-based statistics has fuelled interest in household surveys that can generate unbiased data for populations as a whole rather than just the sections that use available health services. These household surveys have several disadvantages. They need large investments in human and financial resources and therefore are usually funded externally, resulting in bias towards the interests of donors or well-sponsored programs. They are also time-consuming and are undertaken only occasionally, and generate results spanning a period, rather than the immediate past. Samples are rarely of sufficient size to deliver nationally valid results. Growth in surveys to generate health related data has been fuelled by their ability to deliver statistics on child mortality, population coverage, and certain risk factors. In the past few years, scope for measurement of health status with household surveys has greatly expanded owing to cheap and reliable diagnostic tests that can be used in the research setting to generate population-based estimates of disease prevalence. But surveys are not as effective for measurement of adult mortality, which is a relatively rare event compared with child mortality.

ImmunoScore would relieve much of the concern regarding public health and data collection. As stated above, there has been concern regarding bias in the routinely reported service data. As ImmunoScore grows in size and popular usage, concerns about bias can be alleviated. Services delivered to any individual patient would be based solely upon the needs of that particular patient, and tailored to that individual patient's immunologic needs, with no regard for social stratum. Political justifications for mis-representation of data would be eliminated by the automatic and mechanical nature of the data acquisition.

The tremendous requirement for human and financial resources for collecting population based data would also be alleviated by ImmunoScore technology. Data can be collected at hundreds of remote locations and transferred back to an exemplary ImmunoScore central database. There would be no need for third party human resources—data collection would occur at the hospital, clinic, or physician's office and stored for future use.

ImmunoScore Tracking of Medical Services (ImmunoScoreKeeping)

As has been described, heath care processes are very complex, involving both clinical and administrative tasks, large volumes of data, and a large number of patients and personnel. Health care processes are also very dynamic. As new processes are initiated, changes in health care treatments, drugs, and protocols can invalidate current methodologies, requiring reparative actions. ImmunoScoreKeeping can, for example, capture all of such complicated dynamic components and provide accurate performance measurements ("ImmunoScoreCards") not only for individual patients, but also as a means of tracking relative efficiencies of other complex components of the health care system.

For example, upon a visit to a provider using an ImmunoScore system, the patient's data can be captured by an "ImmunoScoreKeeper." (an exemplary POC assay reader connected to a system database, as described above). Not only demographic and test data, but also treatments/drugs prescribed, physician's ID number, and insurer can be stored. Any additional testing or measurements (blood chemistry, X-rays, physical therapy, etc.) can be entered into the remote ImmunoScore data collection system at, for example, the physician's office. A critical requirement for efficient management of health care is the management of the quality of service. Appropriate control of quality of service leads to the creation of quality care services; these, in turn, can fulfill patient satisfaction.

Traditionally, health care services have been managed using limited forms of workflow. Some examples of these are clinical and administrative protocols. However, these protocols have remained limited in their usefulness in part because developers have rarely incorporated both clinical and administrative activities into one comprehensive care protocol. This lack of integration hinders the delivery of care, as the effectiveness of protocols is often dependent on many administrative tasks being properly executed at the correct time.

Thus, in exemplary embodiments of the present invention, ImmunoScoreKeeping can enable medical practices to provide better quality care at reduced costs. ImmunoScore can, for example, maintain keep ImmunoScoreCards on:
- individual patients
- physicians
- groups of physicians/managed care organizations
- insurers In addition, as vaccines, drugs, and therapies prescribed can all be monitored and tracked, an ImmunoScoreKeeper can also monitor the efficacy of the vaccines, drugs, and treatments prescribed. As these data are compiled, they can be shared and submitted to appropriate oversight organizations (FDA, CDC, ACIP, Physician's organizations, drug and vaccine manufacturers, etc.) to better enable these groups to make clear decisions and/or recommendations. Such organizations would be consumers of ImmunoScore data.

Thus, an ImmunoScoreKeeper can allow insurers to rate physicians and enable their customers (the patients) to make better informed decisions regarding their choice of physician. An ImmunoScoreKeeper can track effectiveness of treatments to patient outcomes. Prescription drug and vaccine efficacies can be monitored not only in population-based samplings, but longitudinally in individual patients with repeated ImmunoScore diagnostic testing protocols. Physicians can thus monitor the efficiency of the practice that they are associated with, and thereby make the best career choices to advance their careers in the most efficient practices. Hospitals could be measured for effectiveness in patient care against other hospitals and groups of physicians. Types of hospital settings could be evaluated prospectively. Causes of nosocomial infections might be tracked, for example, to certain types of hospital environments. Insurers can be measured against common metrics and be forced to compete for business via accurate ImmunoScoreKeeping.

In exemplary embodiments of the present invention, an ImmunoScoreKeeper can, for example, provide a means of integrated monitoring of individual patient treatment and also administration of both physicians and insurers practices. The ImmunoScoreKeeper can, for example, generate a numerical value for each component of the health care system upon which real competition among providers and insurers could be generated. This competition would thereby provide substantial increases in health care quality and decreases in health care costs.

Y. User Access Via Data Networks and On-Line Advertising

In exemplary embodiments of the present invention, users can, for example, access an ImmunoScore Database via computer data networks. Such networks can include, for example, VPN's or the Internet. In exemplary embodiments of the present invention, an ImmunoScore database can be accessed, updated and queried via one or more web page portals. With a substantial ImmunoScore subscriber base of clinicians, health care management professionals, individuals, health insurance managers and executives, and pharmaceutical company researchers and management personnel, a given ImmunoScore embodiment can serve as an indispensable portal for anyone involved in the health care, health insurance, life sciences and related industries. This creates an opportunity for targeted on-line advertising.

Online advertising is growing quickly. Recent research predicts that global spending on Internet ads will overtake radio in 2008. It has also been predicted that the rate of spending on Internet ads will grow six times faster than that for traditional media between 2006 and 2009, a trend already taking shape in the Middle East and Europe. Even companies that do not engage in e-commerce, such as, for example, Unilever, nonetheless want to create better user experiences for people online. They want to improve their brand presence.

Many other companies have started to use Web 2.0 technologies, such as, for example, blogging and video clips, to increase brand awareness. Last year (2006) in China, Pepsi invited people to write screenplays for company spokesmen and a famous pop singer. And when it launched its Qashqai car in the UK last month, Nissan offered a game website where people could try to shoot the car; it broadcast video clips of the car, which could be linked to blogs and social networking sites; and it ran banners over some Yahoo sites.

This summer, two companies, Joost and BabelGum, will start to broadcast entire TV programs free over the Internet. The content owners in effect have their own channels and advertising will pay the way. In effect, "people will watch Friends on a website. We may thus see the death of the TV station and the birth of the network station.

Given this state of affairs, in exemplary embodiments of the present invention an exemplary system according to the present invention can be used as an Internet portal for everyone associated with health care in the broadest system (thus encompassing any consumers or providers of any of the business models described above). In the same sense that individuals utilize online search engines, such as, for example, Google or answer.com, to research a topic, anyone remotely connected to health care, can, for example, access an exemplary ImmunoScore webportal. Whether the individual is simply an individual who has records in an ImmunoScore database, whether the individual is an executive of a health insurance company or an HMO, whether the individual in question is a physician or hospital administrator, or whether the individual is a researcher or someone who works in sales or the technical side of pharmaceutical developments, an exemplary ImmunoScore system and an associated ImmunoScore web interface can become a ubiquitous tool used each and every day by millions of people. Targeted online advertising can then be used to deliver business to business, or business to individual in the case of individual to consumers, advertising to a market which is already attuned to the benefits of technology which is applied to healthcare and understands the value of preventive medicine, individualized medicine, and a granular approach to health care provision and analysis and follow-up as to efficiency and efficacy of health care.

For example, individuals whose ImmunoScore record, after the appropriate analysis, has disclosed a potential likelihood of having an autoimmune disease can be provided literature, products, news of new drugs, experimental clinical trials, etc., for their review and potential participation and/or purchase. Similarly, health insurance companies offering a healthcare credit exchange program, as described above, can also advertise such programs and enhancements to such programs to a target audience of sophisticated health care consumers. An interested third party operator of an exemplary system according to the present invention could even, for example, offer to create and operate a health care exchange program to all health care insurance companies using ImmunoScore! All of these examples list just a few of the possibilities. Thus, the more data that an exemplary ImmunoScore database obtains and learns how to best process to extract all of the information latent therein, the greater impact Immunoscore technology can have and the greater draw an ImmunoScore based web portal can provide.

Z. Prophylatic Therapies During Surgery

Before a surgical procedure, the patient's ImmunoScore can be used to aid in the execution of the surgery. For example, if the patient's ImmunoScore indicates that the patient's immune system is in good balance, fewer or less powerful prophylactic antibiotics may be prescribed and/or administered. Benefits include reducing costs, and maintaining the patient's natural gut flora (which for example, may avoid Clostridium difficile infections). Conversely, if the patient's immune system is weak, additional or more powerful antibiotics may be help prevent a surgically-induced infection. As another example, if the patient's ImmunoScore indicates substantial allergies, additional testing may be useful to determine if the patient is allergic to certain surgical materials (e.g., latex) so that alternates can be used.

AA. Contraindications for Biological Active Therapeutics

Biologically active therapeutics may present new issues for patients. These therapeutics include priobiotics. These therapeutics include viruses that have been engineered to selectively attack only some cells in the body (e.g., cancerous cells). When administering these biologically active therapeutics, there is some chance of unexpected consequences. By examining an individual's ImmunoScore, unexpected consequences may be avoided by contradindicating the biologically active therapeutic.

The present invention has been described in connection with exemplary embodiments and implementations, as examples only. It will be understood by those having ordinary skill in the pertinent art that modifications to any of the embodiments may be easily made without materially departing from the scope and spirit of the present invention which is defined by the appended claims. Such modifications can include, for example, using other appropriate assays or tests, other rules or analyses of the results thereof, as may be known in the art to assess the immune status of individuals or populations. Additionally, such modifications can include, for example, using various assay devices and techniques as may be known, using various available methods of storing and analyzing data (including various "data mining" techniques) as may be available, and defining various alternative demographic groups and various sets of ImmunoScore test panels to be administered thereto.

What is claimed is:

1. A method of optimizing the management of health care for an individual in a population, comprising:
examining the individual's immune status;
identifying diseases that the insured may be susceptible to;
calculating the risk of contraction for each disease;
identifying all prophylactic therapies that could prevent each identified disease;
calculating, for all possible combinations of diseases and prophylactic therapies,
expected costs of treatment and costs of associated prophylactic therapies; and
requiring prophylactic therapies optimized for overall cost,
wherein at least one of said examining immune status and identifying diseases that the individual may be susceptible to includes:
(a) establishing a database comprising a plurality of records of information each representative of the immune status of an individual in the population, to one or more vaccine-preventable diseases, each of said records including
(1) current information from one or more assays to determine the immunity of said individual to one or more vaccine-preventable diseases, and
(2) patient-specific information comprising one or more of said patient's medical history, said patient's doctors observations and/or demographic information relating to said patient;
(b) processing the information in said database to find trends or patterns relating to the immune status of individuals in said patient population; and
(c) using the said trends or patterns found in (b) in deciding whether or not to vaccinate an individual;
wherein said processing the information in said database includes:
generating a list of correlations between variables or fields in the database;
for each correlation in the list:
generating a set of hypotheses that may explain said correlation; and
as to each hypothesis in the set, automatically refuting, supporting or stating that there is insufficient data to analyze said hypothesis by further processing of the database.

2. The method of claim 1, further comprising assessing, as a condition of continued coverage, an additional premium charge if the overall cost places the insured into a higher risk bin.

3. The method of claim 2, wherein a debit that is exchangeable on a health care credit/debit exchange is issued in lieu of an additional premium.

4. A computer program product comprising a computer usable medium having computer readable program code means embodied therein, the computer readable program code means in said computer program product comprising means for causing a computer to:
examine the individual's immune status;
identify diseases that the insured may be susceptible to;
calculate the risk of contraction for each disease;
identify all prophylactic therapies that could prevent each identified disease;
calculate, for all possible combinations of diseases and prophylactic therapies,
expected costs of treatment and costs of associated prophylactic therapies; and
require prophylactic therapies optimized for overall cost,
wherein at least one of said examine immune status and identify diseases that the individual may be susceptible to includes:
(a) establishing a database comprising a plurality of records of information each representative of the immune status of an individual in the population, to one or more vaccine-preventable diseases, each of said records including
(1) current information from one or more assays to determine the immunity of said individual to one or more vaccine-preventable diseases, and
(2) patient-specific information comprising one or more of said patient's medical history, said patient's doctors observations and/or demographic information relating to said patient;
(b) processing the information in said database to find trends or patterns relating to the immune status of individuals in said patient population; and
(c) using the said trends or patterns found in (b) in deciding whether or not to vaccinate an individual;
wherein said processing the information in said database includes:
generating a list of correlations between variables or fields in the database;
for each correlation in the list:
  generating a set of hypotheses that may explain said correlation; and
  as to each hypothesis in the set, automatically refuting, supporting or stating that there is insufficient data to analyze said hypothesis by further processing of the database.

* * * * *